(12) United States Patent
Kobayashi et al.

(10) Patent No.: US 8,187,494 B2
(45) Date of Patent: May 29, 2012

(54) FOUR- OR FIVE-RING LIQUID CRYSTAL COMPOUND HAVING LATERAL FLUORINE, LIQUID CRYSTAL COMPOSITION, AND LIQUID CRYSTAL DISPLAY DEVICE

(75) Inventors: Masahide Kobayashi, Chiba (JP); Teru Shimada, Chiba (JP)

(73) Assignees: JNC Corporation, Tokyo (JP); Chisso Petrochemical Corporation, Tokyo (JP)

( * ) Notice: Subject to any disclaimer, the term of this patent is extended or adjusted under 35 U.S.C. 154(b) by 23 days.

(21) Appl. No.: 12/676,328

(22) PCT Filed: Aug. 26, 2008

(86) PCT No.: PCT/JP2008/065187
§ 371 (c)(1),
(2), (4) Date: Mar. 3, 2010

(87) PCT Pub. No.: WO2009/031437
PCT Pub. Date: Mar. 12, 2009

(65) Prior Publication Data
US 2010/0309402 A1    Dec. 9, 2010

(30) Foreign Application Priority Data

Sep. 6, 2007 (JP) ................... 2007-231610
Apr. 25, 2008 (JP) ................... 2008-114727

(51) Int. Cl.
C09K 19/00 (2006.01)
C09K 19/06 (2006.01)
C09K 19/32 (2006.01)
C09K 19/52 (2006.01)

(52) U.S. Cl. ........... 252/299.6; 252/299.01; 252/299.61; 252/299.62; 252/299.63; 252/299.66; 430/20; 428/1.1; 570/128; 570/129; 349/1; 349/56; 549/427; 549/428; 549/374; 549/416; 568/642; 568/643

(58) Field of Classification Search ............. 252/299.01, 252/299.6, 299.61–299.63, 299.66; 430/20; 428/1.1; 570/128–129; 349/1, 56; 549/427–428, 549/374, 416; 568/642–643; 544/335
See application file for complete search history.

(56) References Cited

U.S. PATENT DOCUMENTS

| | | | |
|---|---|---|---|
| 5,198,149 A | 3/1993 | Reiffenrath et al. | |
| 5,279,764 A | 1/1994 | Reiffenrath et al. | |
| 7,425,355 B2 * | 9/2008 | Klasen-Memmer et al. | .. 428/1.1 |
| 2004/0006235 A1 | 1/2004 | Pauluth et al. | |
| 2004/0106798 A1 | 6/2004 | Bremer et al. | |
| 2006/0263544 A1 | 11/2006 | Klasen-Memmer et al. | |
| 2008/0063814 A1 | 3/2008 | Shimada | |

FOREIGN PATENT DOCUMENTS

| | | |
|---|---|---|
| DE | 3839213 | 5/1990 |
| DE | 101 57 670 | 6/2002 |
| EP | 0949231 | 10/1999 |
| JP | H11-116512 | 4/1999 |
| JP | 2007-002132 | 1/2007 |

OTHER PUBLICATIONS

European Search Report of International PCT Application No. PCT/JP2008/065187, dated May 20, 2011.

* cited by examiner

*Primary Examiner* — Geraldina Visconti
(74) *Attorney, Agent, or Firm* — J.C. Patents

(57) ABSTRACT

The invention provides a liquid crystal compound having stability to heat, light and so forth, a wide temperature range of a nematic phase, a small viscosity, a suitable optical anisotropy, and a suitable elastic constant $K_{33}$, and further having a suitable and negative dielectric anisotropy and an excellent compatibility with other liquid crystal compounds, and a liquid crystal composition having stability to heat, light and so forth, a low viscosity, a large optical anisotropy, a suitable and negative dielectric anisotropy, and a suitable elastic constant $K_{33}$, a low threshold voltage, a high maximum temperature (phase-transition temperature on a nematic phase-isotropic phase) of a nematic phase, and a low minimum temperature of the nematic phase. The liquid crystal compound which has a specific structure having fluorine at a lateral position and also having phenylene in which hydrogen on the benzene ring is replaced by fluorine, and a liquid crystal composition containing the compound are prepared.

17 Claims, No Drawings

FOUR- OR FIVE-RING LIQUID CRYSTAL COMPOUND HAVING LATERAL FLUORINE, LIQUID CRYSTAL COMPOSITION, AND LIQUID CRYSTAL DISPLAY DEVICE

FIELD OF THE INVENTION

The invention relates to a liquid crystal compound, a liquid crystal composition, and a liquid crystal display device. The invention relates more specifically to a fluorobenzene derivative which is a liquid crystal compound, having fluorine at a lateral position, a liquid crystal composition with a nematic phase comprising this compound, and a liquid crystal display device comprising this composition.

BACKGROUND OF THE INVENTION

A liquid crystal display device typified by a liquid crystal display panel, a liquid crystal display module and so forth utilizes optical anisotropy, dielectric anisotropy and so forth which are possessed by a liquid crystal compound (in this invention a liquid crystal compound means a generic term for a compound having a nematic phase, a smectic phase and so forth, and a compound having no liquid crystal phases but useful as a component of a liquid crystal composition.). As operation modes of this liquid crystal display device, a variety of modes are known, such as PC (phase change), TN (twisted nematic), STN (super twisted nematic), BTN (bistable twisted nematic), ECB (electrically controlled birefringence), OCB (optically compensated bend), IPS (in-plane switching), and VA (vertical alignment) modes.

It is known that among these operation modes, the ECB mode, the IPS mode, the VA mode and so forth are utilizing a homeotropic property of liquid crystal molecules, and that a limited-viewing angle which is a disadvantage of the conventional display modes such as the TN and STN modes can be improved especially by use of the IPS and VA modes.

A large number of liquid crystal compounds in which hydrogen on the benzene-ring is replaced by fluorine have been examined conventionally as components for a liquid crystal composition having a negative dielectric anisotropy which is useable to the liquid crystal display device with these operation modes (for example, refer to the patent documents Nos. 1 to 6.).

For example, the compounds (A) and (B) in which hydrogen on the benzene-ring is replaced by fluorine have been examined (refer to the patent documents Nos. 1 and 2). However, such compounds do not have a high clearing point.

The terphenyl compound (C) having fluorine at a lateral position has been examined (refer to the patent document No. 3). However, this compound has a high melting point and its clearing point is low.

The quaterphenyl compound (D) which has fluorine at a lateral position has been examined (refer to the patent document No. 4). However, this compound has a poor compatibility and its transition temperature on a nematic phase is high.

The compound (E) having a bonding group and a lateral fluorine has been examined (refer to the patent documents No. 5). However, the compound (E) has a low clearing point because of having the bonding group.

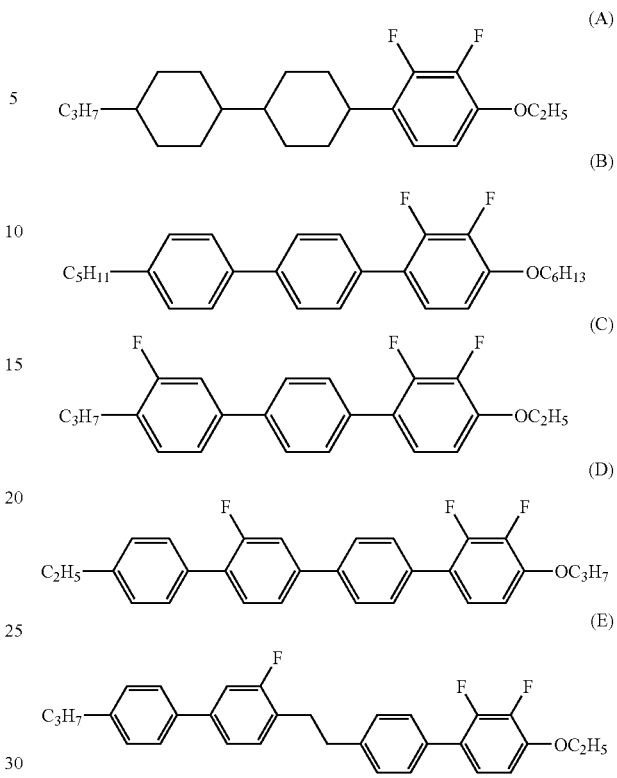

The patent documents cited herein are No. 1: JP H02-503441 A (1990); No. 2: WO 1989/02425 A; No. 3: JP H11-116512 A (1999); No. 4: JP 2003-286208 A; and No. 5: JP 2007-002132 A.

DISCLOSURE OF THE INVENTION

Subjects to be Solved by the Invention

In view of the circumstances described above, even liquid crystal display devices by means of operation modes such as the IPS and VA modes are more problematic than CRTs for use of display devices, and, for example, an improvement of a response speed, an improvement of contrast, and a decrease in driving voltage are required.

The display device operated by means of the IPS mode or VA mode described above is composed of a liquid crystal composition mainly having a negative dielectric anisotropy. In order to further improve these characteristics and so forth, it is required for liquid crystal compounds contained in this liquid crystal composition to have characteristics shown in items (1) to (8) below. That is to say:
(1) being chemically stable and physically stable,
(2) having a high clearing point (transition temperature on a liquid crystal phase-an isotropic phase),
(3) being low in a minimum temperature of liquid crystal phases (a nematic phase, a smectic phase and so forth), especially of the nematic phase,
(4) being low in viscosity,
(5) having an suitable optical anisotropy,
(6) having a suitable and negative dielectric anisotropy,
(7) having an suitable elastic constant $K_{33}$ ($K_{33}$: bend elastic constant), and
(8) being excellent in compatibility with other liquid crystal compounds.

A voltage holding ratio can be increased by use of a composition containing a chemically and physically stable liquid crystal compound as described in item (1) for a display device. The temperature range of a nematic phase can be widened in a composition which contains a liquid crystal compound having a high clearing point or a low minimum temperature of liquid crystal phases as described in items (2) and (3), and thus a display device is usable in a wide temperature range.

Furthermore, when a composition containing a compound with a small viscosity as described in item (4) and a compound having a large elastic constant $K_{33}$ as described in item (7) are used for a display device, response speed can be improved, and in the case of a display device using a composition which contains a compound having suitable optical anisotropy as described in item (5), an improvement of the contrast in a display device can be expected. Optical anisotropy is required in a range of small to large values according to the design of a device. Recently, a method for improving the response speed by means of a smaller cell thickness has been investigated, whereby a liquid crystal composition having a large optical anisotropy has also been required.

Moreover, when a liquid crystal compound has a large negative dielectric anisotropy, the threshold voltage of the liquid crystal composition containing this compound can be decreased. Hence, the driving voltage of a display device can be decreased and electric power consumption can also be decreased in the case of a display device using a composition containing a compound which has a suitable and negative dielectric anisotropy as described in item (6). Further, the driving voltage of a display device can be decreased and the electric power consumption can also decreased by use of a composition containing a compound with a small elastic constant $K_{33}$ as described in item (7).

The liquid crystal compound is generally used as a composition prepared by being mixed with many other liquid crystal compounds in order to exhibit characteristics which cannot be attained with a single compound. Accordingly, it is desirable that a liquid crystal compound used for a display device has an excellent compatibility with other liquid crystal compounds and so forth, as described in item (8). Since the display device may also be used in a wide temperature range including a lower temperature than the freezing point, a compound which exhibits an excellent compatibility even in a low temperature region may be desirable.

The first aim of the invention is to provide a liquid crystal compound having stability to heat, light and so forth, a nematic phase in a wide temperature range, a small viscosity, a suitable optical anisotropy, and a suitable elastic constant $K_{33}$, and further having a suitable and negative dielectric anisotropy and an excellent compatibility with other liquid crystal compounds.

The second aim of the invention is to provide a liquid crystal composition which satisfies stability to heat, light and so forth, a small viscosity, a suitable optical anisotropy, a suitable elastic constant $K_{33}$, and a low threshold voltage by comprising this compound, and further satisfies at least one characteristic in the characteristics such as a high maximum temperature of a nematic phase (phase-transition temperature on a nematic phase-an isotropic phase) and a low minimum temperature of the nematic phase. It is also the aim to provide a liquid crystal composition having a suitable balance with respect to at least two characteristics.

The third aim of the invention is to provide a liquid crystal display device, which comprises the composition described above, having a short response time, a small power consumption, a low driving voltage, a large contrast, and a wide and usable temperature range.

Means to Solve the Subjects

The inventors have keenly studied on these subjects and thus found that a four- or five-ring liquid crystal compound having fluorine at a lateral position, in a specific structure having phenylene in which hydrogen on the benzene ring is replaced by fluorine, has stability to heat, light and so forth, a nematic phase in a wide temperature range, a small viscosity, a suitable optical anisotropy, and a suitable elastic constant $K_{33}$, and further has a suitable and negative dielectric anisotropy and an excellent compatibility with other liquid crystal compounds. They also found that a liquid crystal composition comprising this compound has stability to heat, light and so forth, a small viscosity, a suitable optical anisotropy, a suitable elastic constant $K_{33}$, a suitable and negative dielectric anisotropy, and a low threshold voltage, and further has a high maximum temperature of a nematic phase, and a low minimum temperature of the nematic phase. They further found that a liquid crystal display device comprising this composition has a short response time, a small electric power consumption, a small driving voltage, a large contrast ratio, and a wide and usable temperature range. On the basis of the above findings, the invention has been completed.

The invention has items 1 to 16 described below.

[Item 1] A compound represented by formula (a):

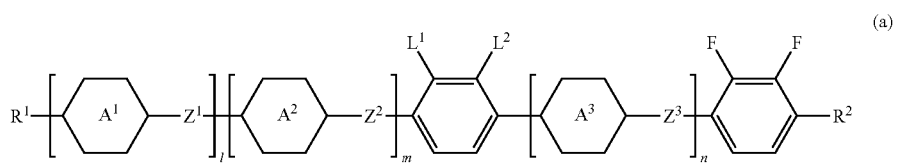

In formula (a), $R^1$ and $R^2$ are each independently hydrogen, alkyl having 1 to 10 carbons, or alkenyl having 2 to 10 carbons, and in these groups, —$CH_2$— may be nonadjacently replaced by —O— or —S— and hydrogen may be replaced by fluorine;

ring $A^1$ and ring $A^2$ are each independently trans-1,4-cyclohexylene, cyclohexene-1,4-diyl, 1,3-dioxane-2,5-diyl, tetrahydropyran-2,5-diyl, pyrimidine-2,5-diyl, pyridine-2,5-diyl, naphthalene-2,6-diyl, decahydronaphthalene-2,6-diyl, or 1,2,3,4-tetrahydronaphthalene-2,6-diyl, and in these rings, hydrogen may be replaced by fluorine;

ring $A^3$ is trans-1,4-cyclohexylene, cyclohexene-1,4-diyl, 1,3-dioxane-2,5-diyl, tetrahydropyran-2,5-diyl, pyrimidine-2,5-diyl, pyridine-2,5-diyl, 1,4-phenylene, naphthalene-2,6-diyl, decahydronaphthalene-2,6-diyl, or 1,2,3,4-tetrahydronaphthalene-2,6-diyl, and in these rings, hydrogen may be replaced by fluorine;

$L^1$ and $L^2$ are each independently hydrogen or fluorine, and at least one of $L^1$ and $L^2$ is fluorine;

$Z^1$, $Z^2$, and $Z^3$ are each independently a single bond, —(CH$_2$)$_2$—, —(CH$_2$)$_4$—, —CH=CH—, —C≡C—, —CH$_2$O—, —OCH$_2$—, —COO—, —COO—, —CF$_2$O—, or —OCF$_2$—; and l and m are each independently 0, 1, or 2, n is 1 or 2, and l+m+n is 2 or 3.

[Item 2] The compound according to item 1, wherein in formula (a), $R^1$ is hydrogen, alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons; and $R^2$ is alkyl having 1 to 10 carbons, alkoxy having 1 to 9 carbons, or alkenyloxy having 2 to 9 carbons.

[Item 3] The compound according to item 1, which is represented by formula (a-1):

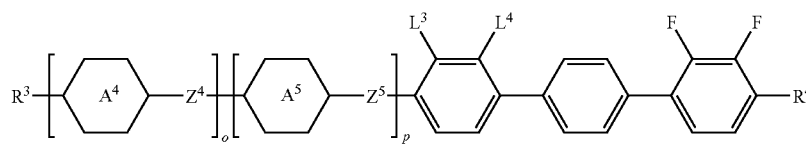

In formula (a-1), $R^3$ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

$R^4$ is alkoxy having 1 to 9 carbons or alkenyloxy having 2 to 9 carbons;

rings $A^4$ and $A^5$ are each independently trans-1,4-cyclohexylene, cyclohexene-1,4-diyl, 1,3-dioxane-2,5-diyl, tetrahydropyran-2,5-diyl, pyrimidine-2,5-diyl, or pyridine-2,5-diyl;

$L^3$ and $L^4$ are each independently hydrogen or fluorine, and at least one of $L^3$ and $L^4$ is fluorine;

$Z^4$ and $Z^5$ are each independently a single bond, —(CH$_2$)$_2$—, —(CH$_2$)$_4$—, —CH=CH—, —C≡C—, —CH$_2$O—, —OCH$_2$—, —COO—, or —OCO—; and o and p are each independently 0 or 1, and o+p is 1 or 2.

[Item 4] The compound according to item 3, which is represented by formula (a-2):

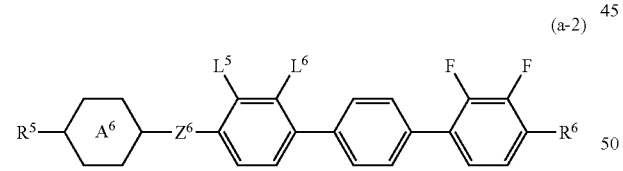

In formula (a-2), $R^5$ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

$R^6$ is alkoxy having 1 to 9 carbons or alkenyloxy having 2 to 9 carbons;

ring $A^6$ is trans-1,4-cyclohexylene, cyclohexene-1,4-diyl, 1,3-dioxane-2,5-diyl, or tetrahydropyran-2-5-diyl;

$L^5$ and $L^6$ are each independently hydrogen or fluorine, and at least one of $L^5$ and $L^6$ is fluorine; and $Z^6$ is a single bond, —(CH$_2$)$_2$—, —CH$_2$O—, —OCH$_2$—, —COO—, or —OCO—.

[Item 5] The compound according to item 3, which is represented by formula (a-3):

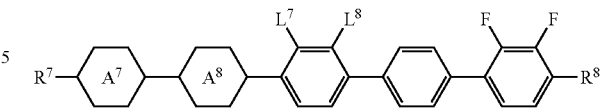

In formula (a-3), $R^7$ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

$R^8$ is alkoxy having 1 to 9 carbons or alkenyloxy having 2 to 9 carbons;

rings $A^7$ and $A^8$ are each independently trans-1,4-cyclohexylene, cyclohexene-1,4-diyl, 1,3-dioxane-2,5-diyl, or tetrahydropyran-2,5-diyl; and $L^7$ and $L^8$ are simultaneously fluorine, or one of $L^7$ and $L^8$ is hydrogen and the other is fluorine.

[Item 6] The compound according to item 4, which is represented by formulas (a-4) to (a-6):

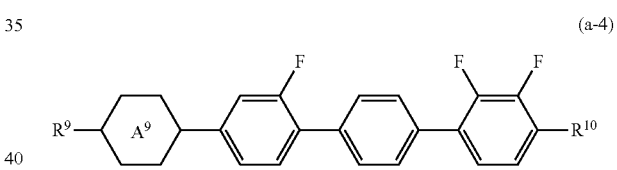

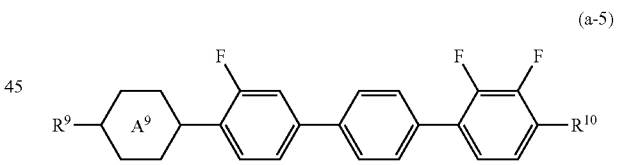

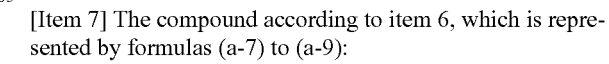

In formulas (a-4) to (a-6), $R^9$ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

$R^{10}$ is alkoxy having 1 to 9 carbons or alkenyloxy having 2 to 9 carbons; and ring $A^9$ is trans-1,4-cyclohexylene, cyclohexene-1,4-diyl, 1,3-dioxane-2,5-diyl, or tetrahydropyran-2,5-diyl.

[Item 7] The compound according to item 6, which is represented by formulas (a-7) to (a-9):

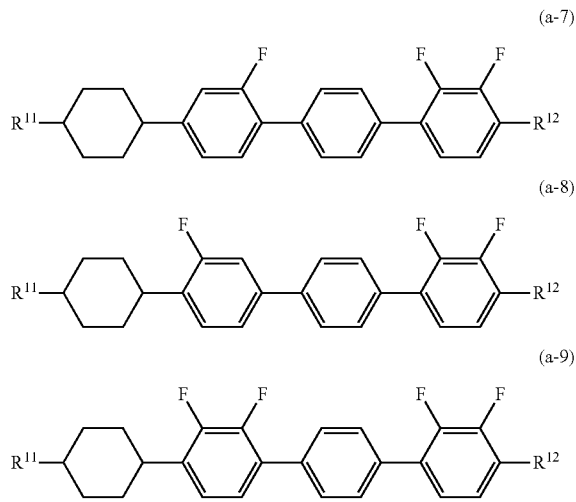

In formulas (a-7) to (a-9), $R^{11}$ is alkyl having 1 to 10 carbons, alkenyl having 2 to 10 carbons, or alkoxy having 1 to 9 carbons; and $R^{12}$ is alkoxy having 1 to 9 carbons or alkenyloxy having 2 to 9 carbons.

[Item 8] The compound according to item 6, which is represented by formulas (a-10) to (a-12):

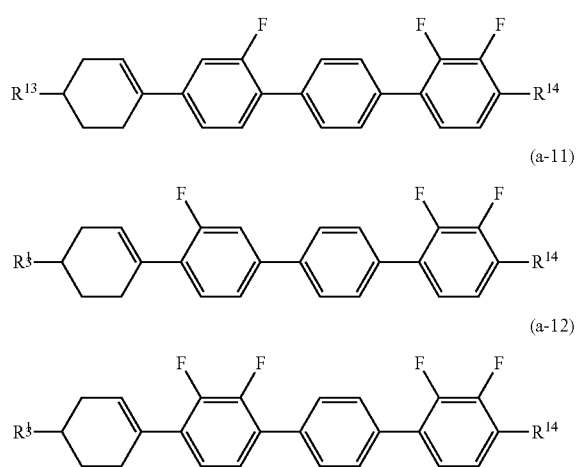

In formulas (a-10) to (a-12), $R^{13}$ is alkyl having 1 to 10 carbons, alkenyl having 2 to 10 carbons, or alkoxy having 1 to 9 carbons; and $R^{14}$ is alkoxy having 1 to 9 carbons or alkenyloxy having 2 to 9 carbons.

[Item 9] The compound according to item 6, which is represented by formulas (a-13) to (a-18):

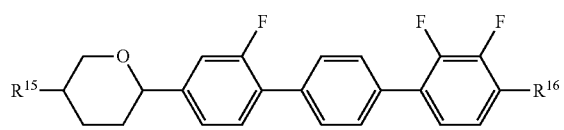

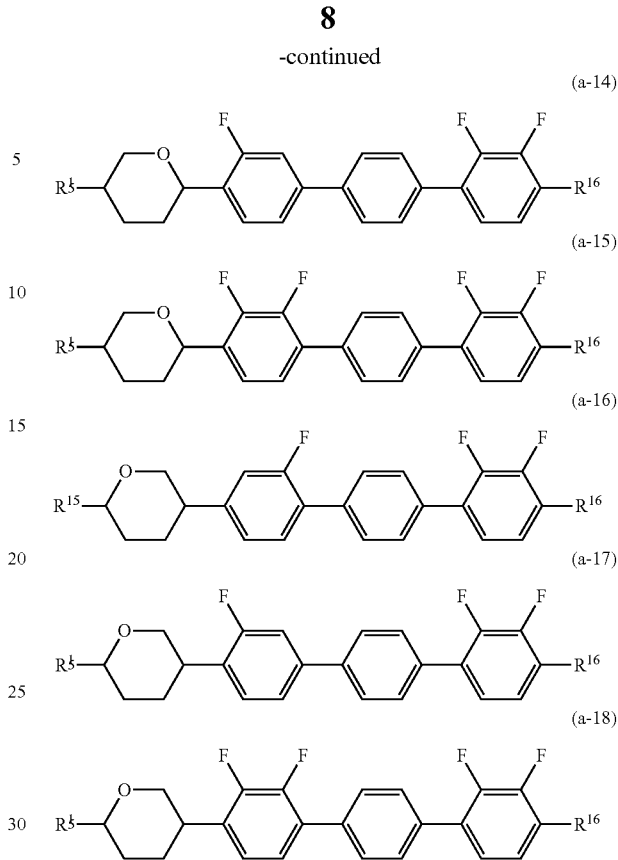

In formulas (a-13) to (a-18), $R^{15}$ is alkyl having 1 to 10 carbons, alkenyl having 2 to 10 carbons, or alkoxy having 1 to 9 carbons; and $R^{16}$ is alkoxy having 1 to 9 carbons or alkenyloxy having 2 to 9 carbons.

[Item 10] The compound according to item 6, which is represented by formulas (a-19) to (a-24):

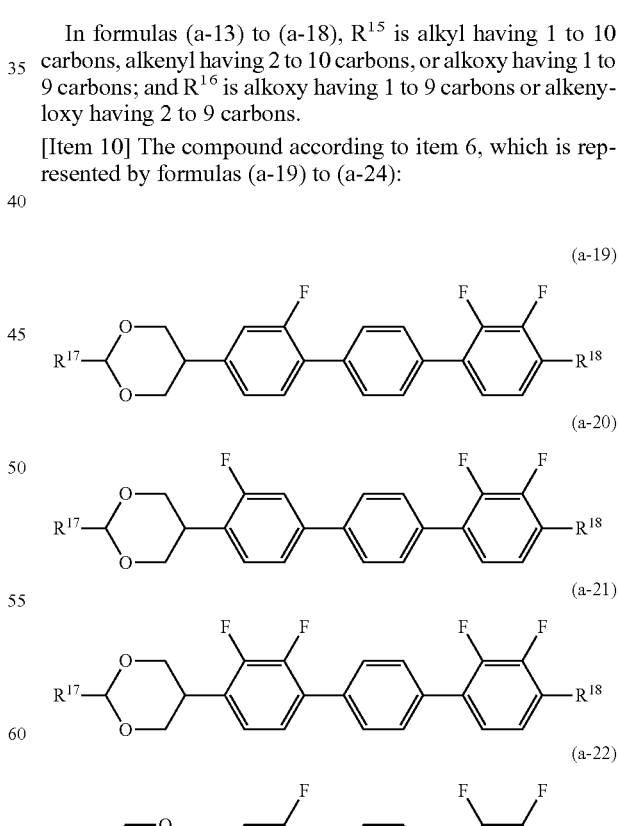

(a-23)

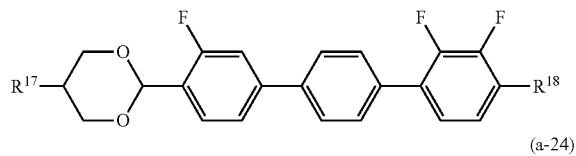

(a-24)

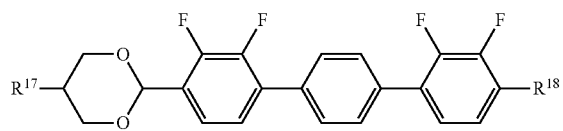

In formulas (a-19) to (a-24), $R^{17}$ is alkyl having 1 to 10 carbons, alkenyl having 2 to 10 carbons or alkoxy having 1 to 9 carbons; and $R^{18}$ is alkoxy having 1 to 9 carbons or alkenyloxy having 2 to 9 carbons.

[Item 11] A liquid crystal composition which has a negative dielectric anisotropy, comprising a first component which is at least one compound selected from compounds according to any one of items 1 to 10, and a second component which is at least one compound selected from the group of compounds represented by formula (e-1), formula (e-2), and formula (e-3).

(e-1)

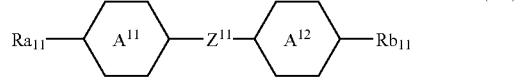

(e-2)

(e-3)

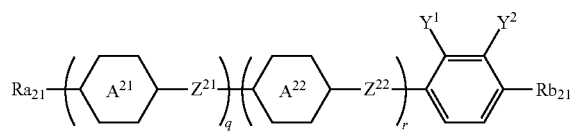

In the formula, $Ra_{11}$ and $R_{11}$ are each independently alkyl having 1 to 10 carbons, and in the alkyl, —$CH_2$— may be nonadjacently replaced by —O—, —$(CH_2)_2$— may be nonadjacently replaced by —CH=CH—, and hydrogen may be replaced by fluorine;

ring $A^{11}$, ring $A^{12}$, ring $A^{13}$, and ring $A^{14}$ are each independently trans-1,4-cyclohexylene, 1,4-phenylene, 2-fluoro-1,4-phenylene, 3-fluoro-1,4-phenylene, pyrimidine-2,5-diyl, 1,3-dioxane-2,5-diyl, or tetrahydropyran-2,5-diyl; and, $Z^{11}$, $Z^{12}$, and $Z^{13}$ are each independently a single bond, —$CH_2$—$CH_2$—, —CH=CH—, —C≡C—, —COO—, or —$CH_2O$—.

[Item 12] A liquid crystal composition which has a negative dielectric anisotropy, comprising a first component which is at least one compound selected from the group of compounds according to item 6, and a second component which is at least one compound selected from the group of compounds represented by formula (e-1), formula (e-2), and formula (e-3).

[Item 13] The liquid crystal composition according to item 12, wherein the content ratio of the first component is in the range of 5% to 60% by weight and the content ratio of the second component is in the range of 40% to 95% by weight, based on the total weight of the liquid crystal composition.

[Item 14] The liquid crystal composition according to item 11 or 12, comprising, in addition to the first component and the second component, a third component which is at least one compound selected from the group of compounds represented by formulas (g-1) to (g-6):

(g-1)

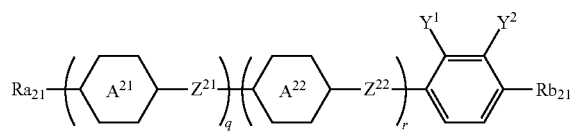

(g-2)

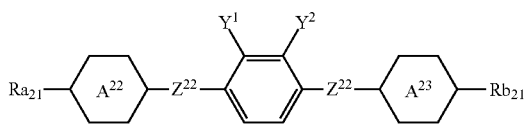

(g-3)

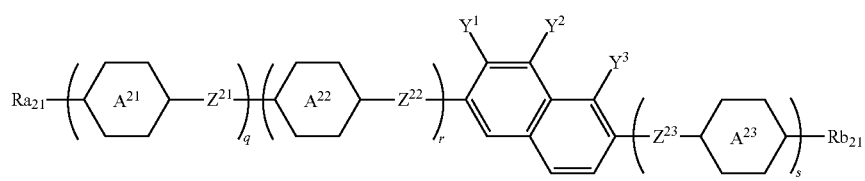

(g-4)

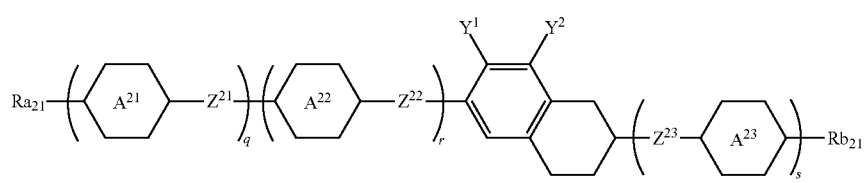

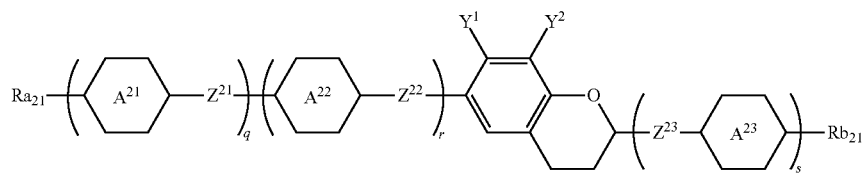
(g-5)

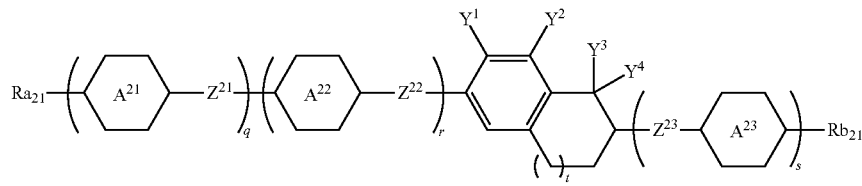
(g-6)

In formulas (g-1) to (g-6), $Ra_{21}$ and $Rb_{21}$ are each independently hydrogen or alkyl having 1 to 10 carbons, and in the alkyl, —$CH_2$— may be nonadjacently replaced by —O—, and —$(CH_2)_2$— may be nonadjacently replaced by —CH=CH—, and hydrogen may be replaced by fluorine;

ring $A^{21}$, ring $A^{22}$, and ring $A^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, 1,3-dioxane-2,5-diyl, or tetrahydropyran-2,5-diyl;

$Z^{21}$, $Z^{22}$, and $Z^{23}$ are each independently a single bond, —$CH_2$—$CH_2$—, —CH=CH—, —C≡C—, —$OCF_2$—, —$CF_2O$—, —$OCF_2CH_2CH_2$—, —$CH_2CH_2CF_2O$—, —COO—, —OCO—, —$OCH_2$—, or —$CH_2O$—;

$Y^1$, $Y^2$, $Y^3$, and $Y^4$ are each independently fluorine or chlorine;

q, r, and s are each independently 0, 1 or 2, q+r is 1 or 2, q+r+s is 1, 2 or 3; and t is 0, 1 or 2.

[Item 15] The liquid crystal composition according to item 11 or 12, comprising, in addition to the first component and the second component, a third component which is at least one compound selected from the group of compounds represented by formulas (h-1) to (h-7).

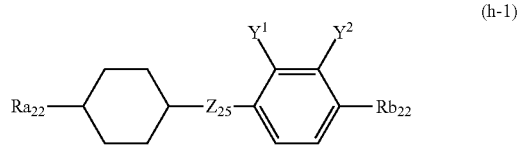
(h-1)

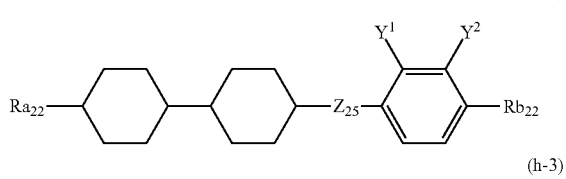
(h-2)

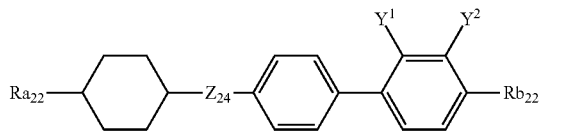
(h-3)

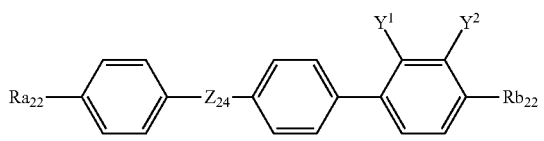
(h-4)

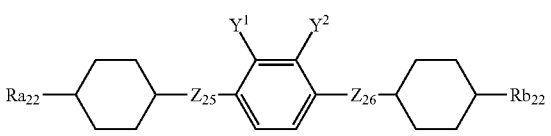
(h-5)

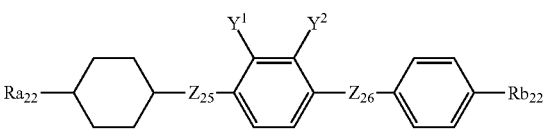
(h-6)

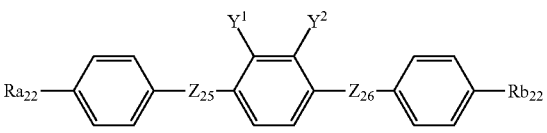
(h-7)

In formulas (h-1) to (h-7), $Ra_{22}$ and $Rb_{22}$ are each independently a straight-chain alkyl having 1 to 8 carbons, a straight-chain alkenyl having 2 to 8 carbons, or alkoxy having 1 to 7 carbons;

$Z^{24}$, $Z^{25}$, and $Z^{26}$ are a single bond, —$CH_2CH_2$—, —$CH_2O$—, or —$OCH_2$—; and $Y^1$ and $Y^2$ are simultaneously fluorine, or one of $Y^1$ and $Y^2$ is fluorine and the other is chlorine.

[Item 16] A liquid crystal composition which has a negative dielectric anisotropy, comprising a first component which is at least one compound selected from the group of compounds according to Item 6, a second component which is at least one compound selected from the group of compounds represented by formula (e-1), formula (e-2), and formula (e-3) according to item 11, and a third component which is at least one compound selected from the group of compounds represented by formulas (h-1) to (h-7) according to item 15.

[Item 17] The liquid crystal composition according to any one of items 14 to 16, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

[Item 18] A liquid crystal display device comprising the liquid crystal composition according to any one of items 11 to 17.

[Item 19] The liquid crystal display device according to item 18, wherein the operation mode thereof is a VA mode or a IPS mode, and the driving mode thereof is an active matrix mode.

Effect of the Invention

The liquid crystal compound of the invention has stability to heat, light and so forth, a nematic phase in a wide temperature range, a small viscosity, a suitable optical anisotropy, and a suitable elastic constant $K_{33}$ ($K_{33}$: bend elastic constant), and further has a suitable and negative dielectric anisotropy and an excellent compatibility with other liquid crystal compounds. Moreover, the liquid crystal compound of the invention is quite excellent in a tendency of increasing optical anisotropy without decreasing a maximum temperature of a nematic phase or increasing viscosity.

The liquid crystal compound of the invention has a small viscosity, a suitable optical anisotropy, a suitable elastic constant $K_{33}$, a suitable and negative dielectric anisotropy, and a low threshold voltage, and further has a high maximum temperature of a nematic phase and a low minimum temperature of the nematic phase. Since the liquid crystal composition of the invention has a suitable optical anisotropy, it is particularly effective in a device which requires a suitable optical anisotropy.

The liquid crystal display device of the invention is characterized by comprising this liquid crystal composition, and consequently has a short response time, a small power consumption, a small driving voltage, a large contrast ratio, and a wide and usable temperature range, and can be suitably used as a liquid crystal display device with the display mode such as a PC, TN, STN, ECB, OCB, IPS, or VA mode. It can be suitably used especially as a liquid crystal display device with a IPS or VA mode.

BEST EMBODIMENT TO CARRY OUT THE INVENTION

Hereinafter, the invention is explained in more detail. In the following description, the amount of a compound which is expressed in percentage means the weight percentage (% by weight) based on the total weight of the composition unless otherwise noted.

[Liquid Crystal Compound (a)]

The liquid crystal compound of the invention has a structure represented by formula (a) (hereinafter the compound is also referred to as "the compound (a)").

In formula (a), $R^1$ and $R^2$ are each independently hydrogen, alkyl having 1 to 10 carbons or alkenyl having 2 to 10 carbons, and in these groups, —CH$_2$— may be replaced by —O— and/or —S—, but —O— and/or —S— are not successive and hydrogen may be replaced by fluorine.

Ring $A^1$ and ring $A^2$ are trans-1,4-cyclohexylene, cyclohexane-1,4-diyl, 1,3-dioxane-2,5-diyl, tetrahydropyran-2,5-diyl, pyrimidine-2,5-diyl, pyridine-2,5-diyl, naphthalene-2,6-diyl, decahydronaphthalene-2,6-diyl, or 1,2,3,4-tetrahydronaphthalene-2,6-diyl, and in these rings, hydrogen may be replaced by fluorine.

Ring $A^3$ is trans-1,4-cyclohexylene, cyclohexene-1,4-diyl, 1,3-dioxane-2,5-diyl, tetrahydropyran-2,5-diyl, pyrimidine-2,5-diyl, pyridine-2,5-diyl, 1,4-phenylene, naphthalene-2,6-diyl, decahydronaphthalene-2,6-diyl, or 1,2,3,4-tetrahydronaphthalene-2,6-diyl, and in these rings, hydrogen may be replaced by fluorine.

$L^1$ and $L^2$ are each independently a hydrogen atom or a fluorine atom, and at least one of $L^1$ and $L^2$ is a fluorine atom;

$Z^1$, $Z^2$, and $Z^3$ are each independently a single bond, —(CH$_2$)$_2$—, —(CH$_2$)$_4$—, —CH=CH—, —C≡C—, —CH$_2$O—, —OCH$_2$—, —COO—, —OCO—, —CF$_2$O—, or —OCF$_2$—; and l and m are each independently 0, 1 or 2, n is 1 or 2, and l+m+n is 2 or 3.

The compound (a), as described above, has a ring other than 1,4-phenylene, and 1,4-phenylene in which hydrogen at the 2- or 3-position is replaced by fluorine, and 1,4-phenylene in which hydrogen at 2- and 3-positions are replaced by fluorine. The compound (a) exhibits a nematic phase in a wide temperature range, a small viscosity, a suitable optical anisotropy, a suitable elastic constant $K_{33}$, a suitable and negative dielectric anisotropy, and an excellent compatibility with other liquid crystal compounds because of having such a structure. In particular, the compound (a) is quite excellent in view of a large optical anisotropy, without decreasing a maximum temperature of a nematic phase and without increasing the viscosity.

In the formula, $R^1$ and $R^2$ are hydrogen, alkyl having 1 to 10 carbons, or alkenyl having 2 to 10 carbons. When the alkyl is CH$_3$(CH$_2$)$_3$—, for example, $R^1$ and $R^2$ may be CH$_3$ (CH$_2$)$_2$O—, CH$_3$—O—(CH$_2$)$_2$—, CH$_3$—O—CH$_2$—O—; H$_2$C=CH—(CH$_2$)$_2$—, CH$_3$—CH=CH—CH$_2$—, or CH$_3$—CH=CH—O—, wherein —CH$_2$— was replaced by —O—, or —(CH$_2$)$_2$— was replaced by —CH=CH—.

However, a group such as CH$_3$—O—O—CH$_2$— in which oxygen and another oxygen are adjacent and a group such as CH$_3$—CH=CH—CH=CH— in which double bond parts are adjacent are undesirable in consideration for the stability of the compound.

More specifically, $R^1$ and $R^2$ include hydrogen, alkyl, alkoxy, alkoxyalkyl, alkoxyalkoxy, alkenyl, alkenyloxy, alkenyloxyalkyl, and alkoxyalkenyl.

At least one hydrogen in these groups may be replaced by fluorine. It is desirable that the chain of the carbon-carbon

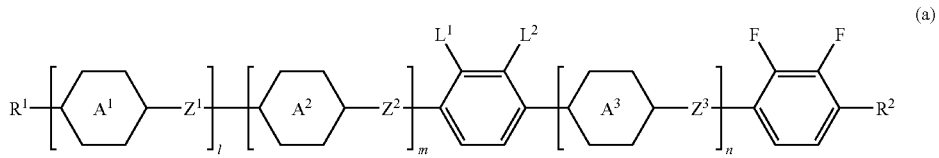

(a)

bonds in these groups is straight. If the chain of carbon-carbon bonds is straight, temperature ranges of liquid crystal phases can be widened and viscosity can be decreased. If either $R^1$ or $R^2$ is an optically active group, the compound is useful as a chiral dopant and a reverse twist domain which will occur in a liquid crystal display device can be prevented by adding the compound to a liquid crystal composition.

The $R^1$ and $R^2$ are preferably alkyl, alkoxy, alkoxyalkyl, alkenyl, fluoroalkyl, and fluoroalkoxy, more preferably alkyl, alkoxy, alkoxyalkyl, alkenyl, —CH$_2$F, and —OCH$_2$F, and still more preferably alkyl, alkoxy, and alkenyl.

If the $R^1$ and $R^2$ are alkyl, alkoxy, and alkenyl, temperature ranges of liquid crystal phases on the liquid crystal compounds can be widened. A desirable configuration of —CH=CH— in the alkenyl depends on the position of a double bond.

A trans-configuration is desirable in the alkenyl having a double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$, and —C$_2$H$_4$CH=CHC$_2$H$_5$.

On the other hand, a cis-configuration is desirable in the alkenyl having a double bond at an even-numbered position, such as —CH$_2$CH=CHCH$_3$, —CH$_2$CH=CHC$_2$H$_5$, and —CH$_2$CH=CHC$_3$H$_3$. The alkenyl compound bearing the desirable configuration described above has a wide temperature range of liquid crystal phases, a large elastic constant ratio $K_{33}/K_{11}$ ($K_{33}$: bend elastic constant, $K_{11}$: spray elastic constant), and a decreased viscosity of the compound. Furthermore, if this liquid crystal compound is added to a liquid crystal composition, the maximum temperature ($T_{NI}$) of a nematic phase can be increased.

Specific examples of the alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_9$H$_{17}$, —C$_9$H$_{19}$, and —C$_{10}$H$_{21}$; specific examples of the alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, and —OC$_9$H$_{19}$; specific examples of the alkoxyalkyl include —CH$_2$OCH$_3$, —CH$_2$OC$_2$H$_5$, —CH$_2$OC$_3$H$_7$, —(CH$_2$)$_2$OCH$_3$, —(CH$_2$)$_2$OC$_2$H$_5$, —(CH$_2$)$_2$OCH$_3$H$_3$, —(CH$_2$)$_3$OCH$_3$, —(CH$_2$)$_4$OCH$_3$, and —(CH$_2$)$_5$OCH$_3$; specific examples of the alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$CH=CH$_2$, —CH=CHC$_3$H$_7$, —CH$_2$CH=CHC$_2$H$_5$, —(CH$_2$)$_2$CH=CHCH$_3$, and —(CH$_2$)$_3$CH=CH$_2$; and specific examples of the alkenyloxy include —OCH$_2$CH=CH$_2$, —OCH$_2$CH=CHCH$_3$, and —OCH$_2$CH=CHC$_2$H$_5$.

Specific examples of alkyl in which hydrogen is replaced by halogen include —CH$_2$F, —CHF$_2$, —CF$_3$, —(CH$_2$)$_2$F, —CF$_2$CH$_2$F, —CF$_2$CHF$_2$, —CH$_2$CF$_3$, —CF$_2$CF$_3$, —(CH$_2$)$_3$F, —(CF$_2$)$_2$CF$_3$, —CF$_2$CHFCF$_3$, and —CHFCF$_2$CF$_3$; specific examples of alkoxy in which hydrogen is replaced by halogen include —OCF$_3$, —OCHF$_2$, —OCH$_2$F, —OCF$_2$CF$_3$, —OCF$_2$CHF$_2$, —OCF$_2$CH$_2$F, —OCF$_2$CF$_2$CF$_3$, —OCF$_2$CHFCF$_3$, and —OCHFCF$_2$CF$_3$; and specific examples of alkenyl in which hydrogen is replaced by halogen include —CH=CHF, —CH=CF$_2$, —CF=CHF, —CH=CHCH$_2$F, —CH=CHCF$_3$, and —(CH$_2$)$_2$CH=CF$_2$.

Thus, among the specific examples, $R^1$ and $R^2$ are preferably —CH$_3$, —C$_2$H$_5$, —C$_3$H$_7$, —C$_4$H$_9$, —C$_5$H$_{11}$, —OCH$_3$, —OC$_2$H$_5$, OC$_3$H$_7$, —OC$_4$H$_9$, —OC$_5$H$_{11}$, —CH$_2$OCH$_3$, —(CH$_2$)$_2$OCH$_3$— (CH$_2$)$_3$OCH$_3$, —CH$_2$CH=CH$_2$, —CH$_2$CH=CHCH$_3$, —(CH$_2$)$_2$CH=CH$_2$, —CH$_2$CH=CHC$_2$H$_5$, —(CH$_2$)$_2$CH=CHCH$_3$, —(CH$_2$)$_3$CH=CH$_2$, —(CH$_2$)$_3$CH=CHCH$_3$ —(CH$_2$)$_3$CH=CHC$_2$H$_5$— (CH$_2$)$_3$CH=CHC$_3$H$_7$, —OCH$_2$CH=CH$_2$, —OCH$_2$CH=CHCH$_3$, —OCH$_2$CH=CHC$_2$H$_5$, —CF$_3$, —CHF$_2$, —CH$_2$F, —OCF$_3$, —OCHF$_2$, —OCH$_2$F, —OCF$_2$CF$_3$, —OCF$_2$CHF$_2$, —OCF$_2$CH$_2$F, —OCF$_2$CF$_2$CF$_3$, —OCF$_2$CHFCF$_3$, and —OCHFCF$_2$CF$_3$ and more preferably —CH$_3$, —C$_2$H$_5$, —C$_3$H$_7$, —OCH$_3$, —OC$_2$H$_5$, —OC$_3$H$_7$, —OC$_4$H$_9$, —(CH$_2$)$_2$ CH=CH$_2$, —(CH$_2$)$_2$CH=CHCH$_3$, and —(CH$_2$)$_2$ CH=CHC$_3$H$_7$.

The ring $A^1$ and ring $A^2$ are trans-1,4-cyclohexylene, cyclohexane-1,4-diyl, trans-1,3-dioxane-2,5-diyl, trans-tetrahydropyran-2,5-diyl, pyrimidine-2,5-diyl, pyridine-2,5-diyl, naphthalene-2,6-diyl, decahydronaphthalene-2,6-diyl, or 1,2,3,4-tetrahydronaphthalene-2,6-diyl, and in these rings, hydrogen may be replaced by fluorine.

The ring $A^1$ and ring $A^2$ are preferably trans-1,4-cyclohexylene, cyclohexene-1,4-diyl, trans-1,3-dioxane-2,5-diyl, trans-tetrahydropyran-2,5-diyl, pyridine-2,5-diyl, and 6-fluoropyridine-2,5-diyl.

Among these, the rings are more preferably trans-1,4-cyclohexylene, cyclohexene-1,4-diyl, trans-1,3-dioxane-2,5-diyl, trans-tetrahydropyran-2,5-diyl, and trans-1,4-cyclohexylene, and most preferably cyclohexene-1,4-diyl.

In particular, viscosity can be decreased if at least one of these rings is trans-1,4-cyclohexylene, and if this liquid crystal compound is added to a liquid crystal composition, the maximum temperature ($T_{NI}$) of a nematic phase can be increased.

The ring $A^3$ is trans-1,4-cyclohexylene, cyclohexene-1,4-diyl, 1,3-dioxane-2,5-diyl, tetrahydropyran-2,5-diyl, 1,4-phenylene, pyrimidine-2,5-diyl, pyridine-2,5-diyl, naphthalene-2,6-diyl, decahydronaphthalene-2,6-diyl, or 1,2,3,4-tetrahydronaphthalene-2,6-diyl, and in these rings, hydrogen may be replaced by fluorine.

The ring $A^3$ is preferably trans-1,4-cyclohexylene, cyclohexane-1,4-diyl, 1,4-phenylene, pyrimidine-2,5-diyl, pyridine-2,5-diyl, naphthalene-2,6-diyl, 1,4-phenylene, pyridine-2,5-diyl, and 6-fluoropyridine-2,5-diyl.

Among these, the ring is more preferably 1,4-phenylene, pyrimidine-2,5-diyl, pyridine-2,5-diyl, and naphthalene-2,6-diyl, and most preferably 1,4-phenylene.

If the ring $A^3$ is 1,4-phenylene, the viscosity can be decreased, the optical anisotropy ($\Delta n$) tends to be increased, and the orientational order parameter can be increased.

The $L^1$ and $L^2$ are each independently a hydrogen atom or a fluorine atom, and at least one of them is a fluorine atom.

It is desirable that one of $L^1$ and $L^2$ is hydrogen and the other is fluorine in order to decrease the melting point of the compound.

The $Z^1$, $Z^2$, and $Z^3$ are independently a single bond, —(CH$_2$)$_2$—, —(CH$_2$)$_4$—, —CH=CH—, —C≡C—, —CH$_2$O—, —OCH$_2$—, —COO—, —OCO—, —CF$_2$O—, or —OCF$_2$—.

The $Z^1$, $Z^2$, and $Z^3$ are preferably a single bond, —(CH$_2$)$_2$—, or —CH=CH—, since the viscosity of the compound can be decreased. They are preferably a single bond, —(CH$_2$)$_2$—, and —CH=CH—, and more preferably a single bond and —(CH$_2$)$_2$— in consideration for the stability of the compound.

When the $Z^1$, $Z^2$ and $Z^3$ are —CH=CH—, the configuration of other groups bonded to the double bond is preferably trans. The temperature range of the liquid crystal phases of this liquid crystal compound can be widen due to such configuration, and when this liquid crystal compound is added to a liquid crystal composition, the maximum temperature ($T_{NI}$) of a nematic phase can be increased.

If the $Z^1$, $Z^2$ and $Z^3$ contain —CH=CH—, the temperature range of liquid crystal phases can be widen, the elastic constant ratio $K_{33}/K_{11}$ ($K_{33}$: bend elastic constant, $K_{11}$: spray elastic constant) can be increased, and the viscosity of the compound can be decreased, and when this liquid crystal compound is added to a liquid crystal composition, the maximum temperature ($T_{NI}$) of a nematic phase can be increased.

Incidentally, the liquid crystal compound (a) may also contain isotopes such as $^2H$ (deuterium), $^{13}C$ and so forth in a larger amount than the amount of the natural abundance, since such isotopes do not cause a large difference in physical properties of the compound.

In these liquid crystal compounds (a), it is possible to adjust physical properties such as the dielectric anisotropy, to desired physical properties by suitably selecting $R^1$, $R^2$, ring $A^1$, ring $A^2$, ring $A^3$, $Z^1$, $Z^2$, and $Z^3$.

Examples of desirable compounds among compounds represented by the compound (a) include the compound (a-1).

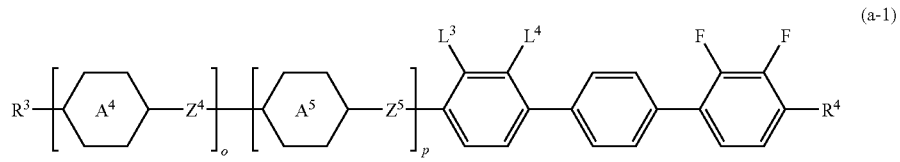
(a-1)

In formula (a-1), $R^3$ is alkyl having 1 to 10 carbons or alkenyl having 2 to 10 carbons, alkoxy having 1 to 9 carbons, alkoxyalkenyl having 2 to 9 carbons, or alkenyloxy having 2 to 9 carbons;

$R^4$ is alkoxy having 1 to 9 carbons or alkenyloxy having 2 to 9 carbons;

rings $A^4$ and $A^5$ are each independently trans-1,4-cyclohexylene, cyclohexene-1,4-diyl, 1,3-dioxane-2,5-diyl, tetrahydropyran-2,5-diyl, or pyrimidine-2,5-diyl, pyridine-2,5-diyl;

$L^3$ and $L^4$ are each independently hydrogen or fluorine, and at least one of them is fluorine;

$Z^4$ and $Z^5$ are each independently a single bond, —(CH$_2$)$_2$—, —(CH$_2$)$_4$—, —CH=CH—, —C≡C—, —CH$_2$O—, —OCH$_2$—, —COO—, or —OCO—; and o and p are each independently 0 or 1, and o+p is 1 or 2.

The liquid crystal compound represented by the compound (a-1) has a large negative dielectric anisotropy, stability to heat or light, a nematic phase in a wide temperature range, a suitable optical anisotropy, and a suitable elastic constant $K_{33}$. Among these, the compound where $Z^4$ and $Z^5$ are single bonds and o+p is 1 is more desirable in view of a lower minimum temperature of liquid crystal phases, a higher maximum temperature of a nematic phase, and a smaller viscosity. Furthermore, the compound in which o+p is 2 has a nematic phase in a very wide temperature range, a suitable optical anisotropy, and a suitable elastic constant $K_{33}$. The compound is more desirable especially in view of a still higher maximum temperature of a nematic phase.

Examples of more desirable compounds among the compounds represented by the compound (a-1) include the compounds (a-7) to (a-24).

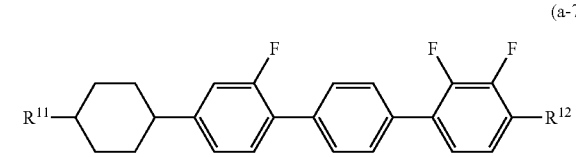
(a-7)

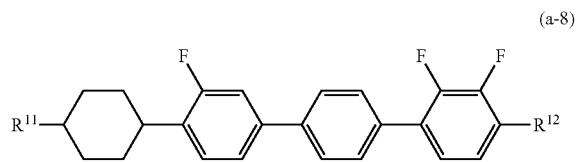
(a-8)

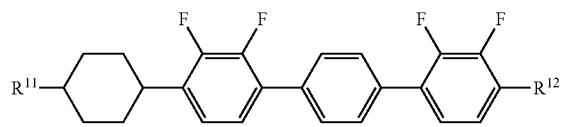
(a-9)

In formulas (a-7) to (a-9), $R^{11}$ is alkyl having 1 to 10 carbons, alkenyl having 2 to 10 carbons, or alkoxy having 1 to 9 carbons; and $R^{12}$ is alkoxy having 1 to 9 carbons or alkenyloxy having 2 to 9 carbons.

Since the liquid crystal compounds represented by the compounds (a-7) to (a-9) have a trans-1,4-cyclohexylene group, they are more desirable in view of stability to heat or light, a lower minimum temperature of liquid crystal phases, a higher maximum temperature of a nematic phase, a suitable optical anisotropy, a suitable elastic constant $K_{33}$, and a smaller viscosity.

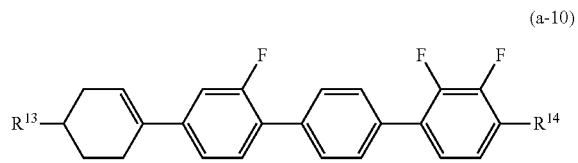
(a-10)

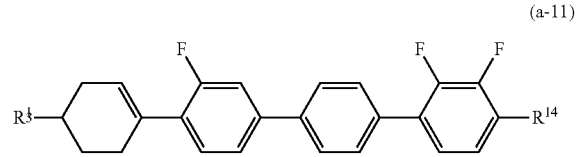
(a-11)

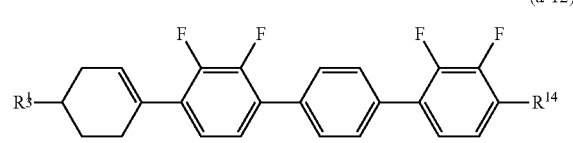
(a-12)

In formulas (a-10) to (a-12), $R^{13}$ is alkyl having 1 to 10 carbons, alkenyl having 2 to 10 carbons, or alkoxy having 1 to 9 carbons; and $R^{14}$ is alkoxy having 1 to 9 carbons or alkenyloxy having 2 to 9 carbons.

Since the liquid crystal compounds represented by formulas (a-10) to (a-12) have a cyclohexene-1,4-diyl group, they are more desirable in view of a low viscosity without decreasing mostly the maximum temperatures of nematic phases.

(a-13)
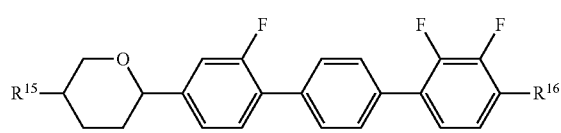

(a-14)
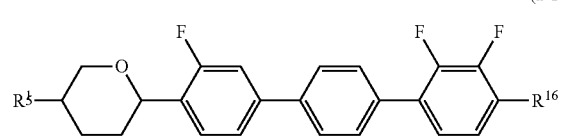

(a-15)
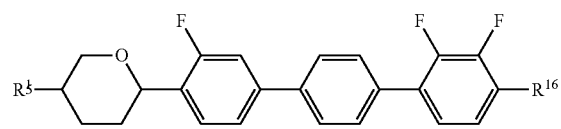

(a-16)
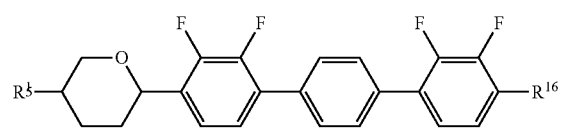

(a-17)
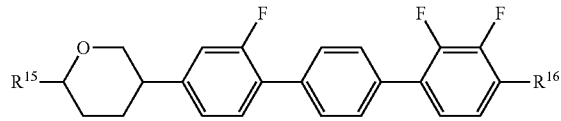

(a-18)
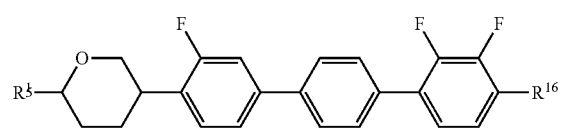

In formulas (a-13) to (a-18), $R^{15}$ is alkyl having 1 to 10 carbons, alkenyl having 2 to 10 carbons, or alkoxy having 1 to 9 carbons; and $R^{16}$ is alkoxy having 1 to 9 carbons or alkenyloxy having 2 to 9 carbons.

Since the liquid crystal compounds represented by the compounds (a-13) to (a-18) have a tetrahydropyran-2,5-diyl group, they are more desirable in view of a suppressed exhibition of a smectic phase, a lower minimum temperature of liquid crystal phases without decreasing mostly the maximum temperature of a nematic phase, and a higher compatibility.

(a-19)
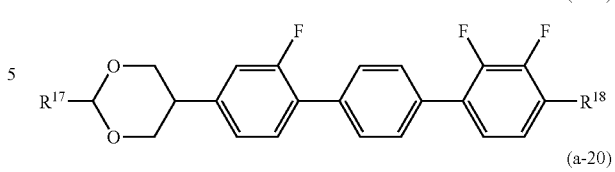

(a-20)
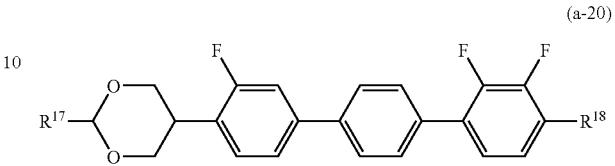

(a-21)
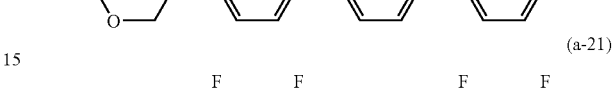

(a-22)
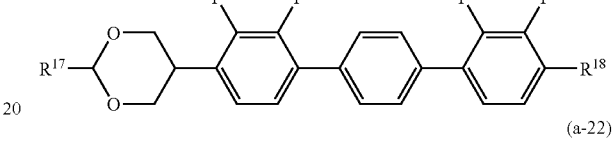

(a-23)
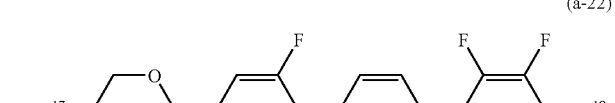

(a-24)
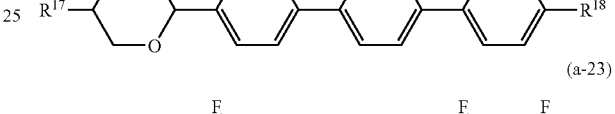

(a-23)
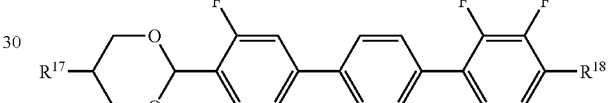

(a-24)
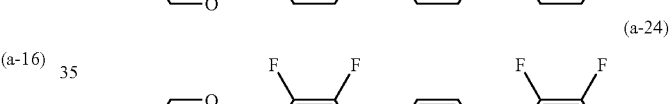

In formulas (a-19) to (a-24), $R^{17}$ is alkyl having 1 to 10 carbons, alkenyl having 2 to 10 carbons, or alkoxy having 1 to 9 carbons; and $R^{18}$ is alkoxy having 1 to 9 carbons or alkenyloxy having 2 to 9 carbons.

Since the liquid crystal compounds represented by the compounds (a-19) to (a-24) have a 1,3-dioxane-2,5-diyl group, they are more desirable in view of a peculiar dielectric anisotropy.

When liquid crystal compounds have the structure represented by the liquid crystal compounds (a-7) to (a-24), they have a suitable and negative dielectric anisotropy and an excellent compatibility with other liquid crystal compounds. Furthermore, they have stability to heat, light and so forth, a nematic phase in a wide temperature range, a small viscosity, a suitable optical anisotropy, and a suitable elastic constant $K_{33}$. A liquid crystal composition comprising this liquid crystal compound (a) is stable under conditions in which a liquid crystal display device is usually used, and this compound does not deposit its crystals (or its smectic phase) even when the composition is kept at low temperature.

Hence, the liquid crystal compound (a) is suitably applied to a liquid crystal composition used for liquid crystal display devices with display modes such as PC, TN, STN, ECB, OCB, IPS, and VA, and is quite suitably applied to a liquid crystal composition used for liquid crystal display devices with display modes such as IPS and VA.

[Synthesis of the Liquid Crystal Compound (a)]

The liquid crystal compound (a) can be synthesized by suitably combining techniques in synthetic organic chemistry. Methods of introducing objective terminal groups, rings and bonding groups into starting materials are described, for example, in ORGANIC SYNTHESES (John Wiley & Sons, Inc), ORGANIC REACTIONS (John Wiley & Sons, Inc), COMPREHENSIVE ORGANIC SYNTHESIS (Pergamon Press), NEW EXPERIMENTAL CHEMISTRY COURSE (Shin Jikken Kagaku Kouza, in Japanese title) (Maruzen), and so forth.

<Formation of the Bonding Groups $Z^1$, $Z^2$, or $Z^3$>

One example of methods for forming the bonding groups $Z^1$, $Z^2$, or $Z^3$ is shown. Schemes for forming the bonding groups is illustrated as follows. In the schemes, $MSG^1$ or $MSG^2$ is a monovalent organic group. A plurality of the $MSG^1$ (or $MSG^2$) used in the schemes may be identical or different. The compounds (1A) to (1H) correspond to the liquid crystal compound (a).

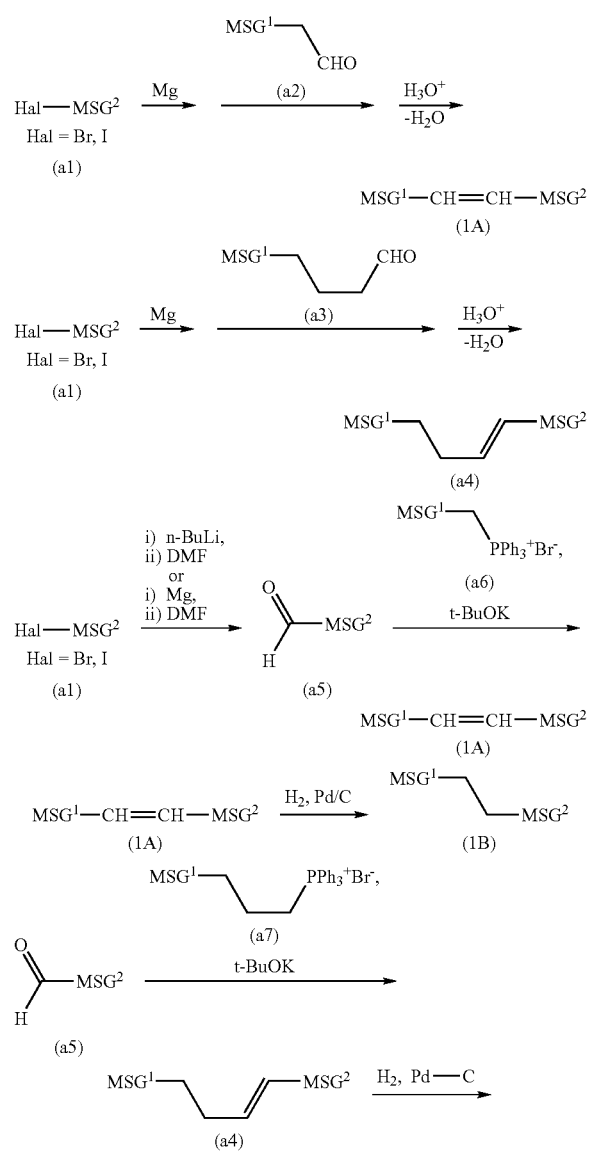

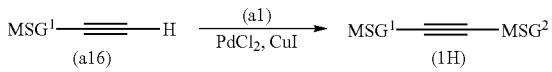

<Formation of Double Bonds>

A Grignard reagent is prepared by reacting the organohalogen compound (a1) having the monovalent organic group, $MSG^2$, with magnesium. A corresponding alcohol derivative is synthesized by reacting the Grignard reagent thus prepared or a lithium salt with the aldehyde derivative (a2) or (a3). Then, the corresponding compound (1A) or (a4) can be synthesized by dehydrating the alcohol derivative obtained, in the presence of an acid catalyst such as p-toluenesulfonic acid.

The organohalogen compound (a1) is treated with butyllithium or magnesium and then reacted with a formamide such as N,N-dimethylformamide (DMF) giving the aldehyde derivative (a5). The compound (1A) having a corresponding double bond can be synthesized by reacting the aldehyde (a6) obtained with phosphorus ylide that is obtained by the treatment of the phosphonium salt (a7) with a base such as potassium t-butoxide. Since a cis-isomer may be formed depending on reaction conditions, the cis-isomer is isomerized to a trans-isomer according to any known method as required.

<Formation of —$(CH_2)_2$—>

The compound (1B) is synthesized by hydrogenating the compound (1A) in the presence of a catalyst such as palladium on carbon (Pd/C).

<Formation of —$(CH_2)_4$—>

The compound (a-4) having a corresponding double bond is synthesized by reacting the aldehyde derivative (a5) with phosphorus ylide that is obtained by the treatment of the phosphonium salt (a7) with a base such as potassium t-butoxide. Then, the compound (1C) can be synthesized by hydrogenating the compound (a-4) in the presence of a catalyst such as Pd/C.

<Formation of Single Bonds>

A Grignard reagent or a lithium salt is prepared by reacting the organohalogen compound (a1) with magnesium or butyllithium. The dihydroxyborane derivative (a8) is synthesized by reacting the Grignard reagent or the lithium salt prepared with a boric acid ester such as trimethyl borate, and then by hydrolyzing with an acid such as hydrochloric acid. The compound (1D) can be synthesized by reacting the dihydroxyborane derivative (a8) with the organohalogen compound (a9) in the presence of a catalyst, for example, composed of an aqueous carbonate solution and tetrakis(triphenylphosphine)palladium ($Pd(PPh_3)_4$).

The organohalogen compound (a9) having the monovalent organic group $MSG^1$ is reacted with butyllithium and then with zinc chloride giving an intermediate. The compound (1D) can be synthesized by reacting the intermediate with the compound (a1), for example, in the presence of a bistriphenylphosphinedichloropalladium ($Pd(PPh_3)_2Cl_2$) catalyst.

<Formation of —$CH_2O$— or —$OCH_2$—>

The alcohol derivative (a10) is obtained by oxidizing the dihydroxyborane derivative (a8) with an oxidizing agent such as hydrogen peroxide. Separately, the alcohol derivative (a10) is obtained by reducing the aldehyde derivative (a5) with a reducing agent such as sodium borohydride. The organohalogen compound (a12) is obtained by halogenating the alcohol derivative (a10) obtained with hydrobromic acid or the like. The compound (1E) can be synthesized by reacting the alcohol derivative (a10) thus obtained with the organohalogen compound (a12) in the presence of potassium carbonate or the like.

<Formation of —COO— and —OCO—>

The compound (a9) is reacted with n-butyllithium and then with carbon dioxide giving the carboxylic acid derivative (a13). The compound (1F) having —COO— can be synthesized by dehydrating the carboxylic acid derivative (a13) with the phenol derivative (a14) in the presence of DDC (1,3-dicyclohexylcarbodiimide) and DMAP (4-dimethylaminopyridine).

The compounds having —COO— can also be synthesized according to this method.

<Formation of —$CF_2O$— and —$OCF_2$—>

The compound (a15) is obtained by treating the compound (1F) with a thionating agent such as Lawesson's reagent. The compound (1G) having —$CF_2O$— is synthesized by fluorinating the compound (a15) by use of a hydrogen fluoride-pyridine complex and N-bromosuccinimide (NBS). Refer to M. Kuroboshi, et al., Chem. Lett., 1992, 827. The compound (1G) is also synthesized by fluorinating the compound (a15) with (diethylamino)sulfur trifluoride (DAST). Refer to W. H. Bunnelle, et al., J. Org. Chem. 1990, 55, 768. The compounds having —$OCF_2$— are also synthesized according to this method. These bonding groups can also be formed according to the method described in Peer. Kirsch, et al., Angew. Chem. Int. Ed. 2001, 40, 1480.

<Formation of —C≡C—>

The compound (a16) is obtained by reacting the compound (a9) with 2-methyl-3-butyne-2-ol in the presence of a catalyst of dichloropalladium and copper halide, and then deprotecting the resulting product under a basic condition. The compound (1H) is synthesized by reacting the compound (a16) with the compound (a1) in the presence of a catalyst of dichloropalladium and copper halide.

<Formation of Ring $A^1$, $A^2$, or $A^3$>

Starting materials are commercially available or methods for their syntheses are well known with regard to rings, such as trans-1,4-cyclohexylene, cyclohexene-1,4-diyl, 1,3-dioxane-2,5-diyl, tetrahydropyran-2,5-diyl, 1,4-phenylene, pyrimidine-2,5-diyl, pyridine-2,5-diyl, and naphthalene-2,6-diyl.

[Method for Producing the Liquid Crystal Compound (a)]

Synthetic examples for the liquid crystal compound (a), that is to say, the liquid crystal compound represented by the general formula (a), are shown as follows.

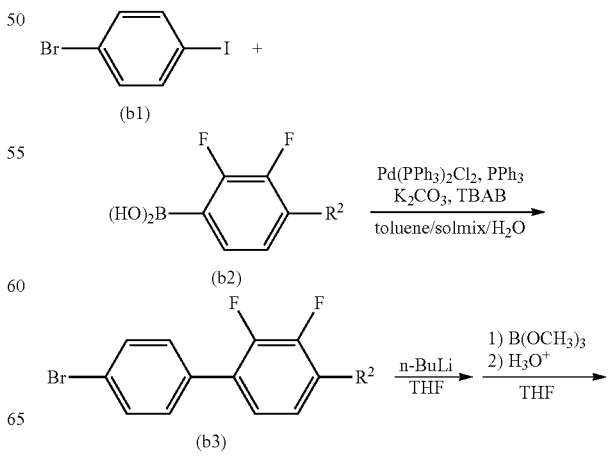

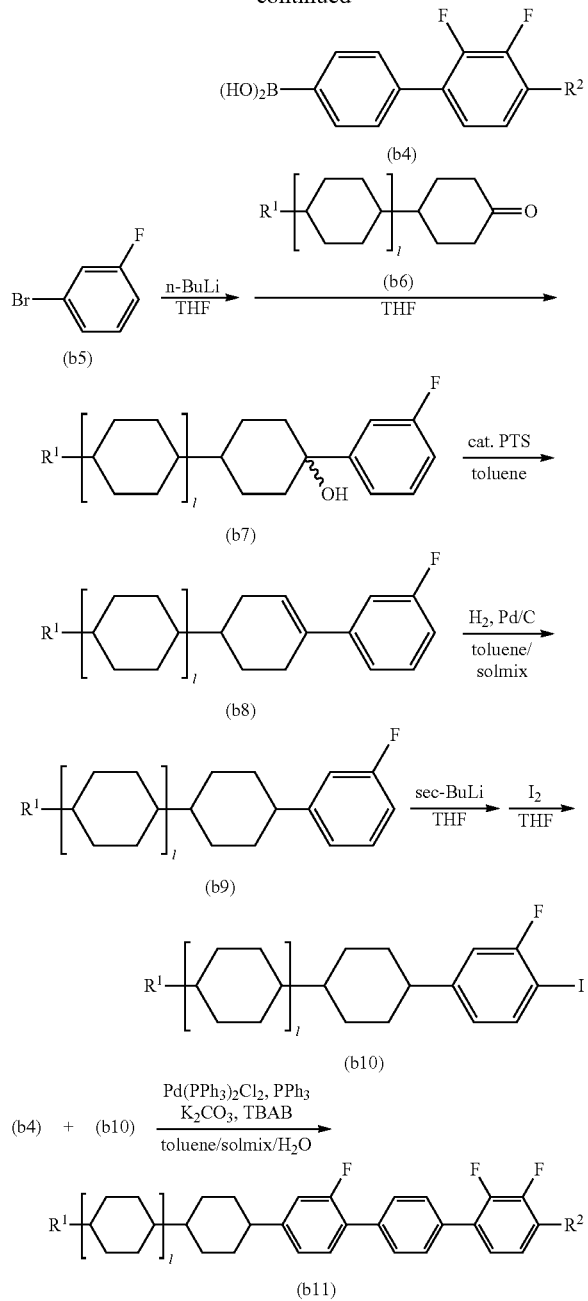

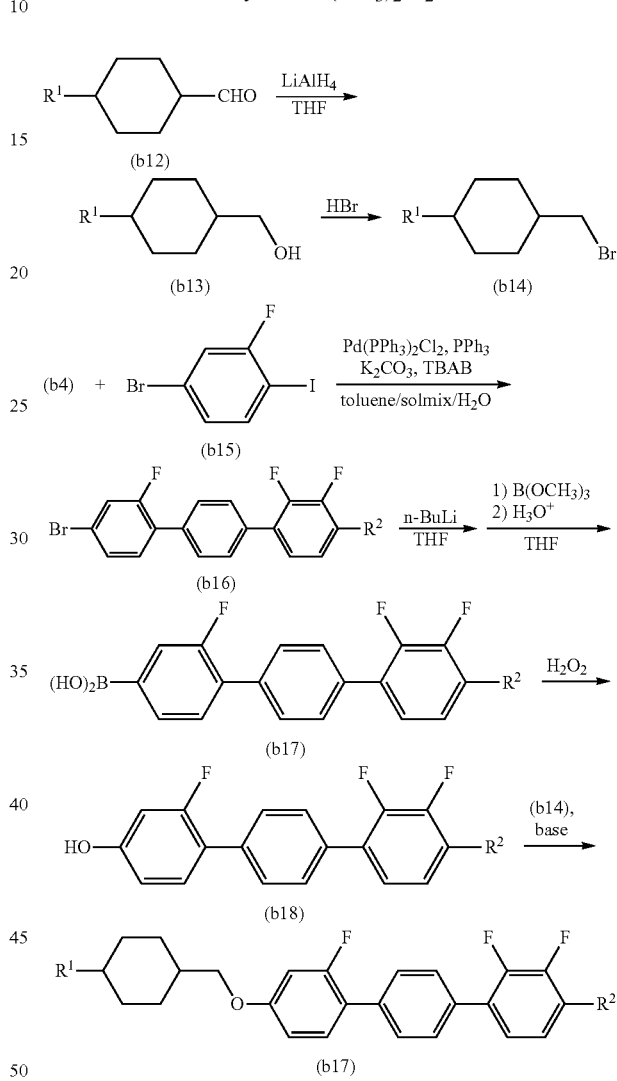

In these formulas, $R^1$ and $R^2$ have the meanings identical to those described above.

The compound (b3) is obtained by reacting the compound (b1) with the dihydroxyborane derivative (b2) in the presence of a catalyst of potassium carbonate, Pd $(PPh_3)_2Cl_2$, or the like. Then, a lithium salt is prepared by reacting the compound (b3) with n-BuLi. The dihydroxyborane derivative (b4) is obtained by reacting this lithium salt with trimethoxyborane. Separately, a lithium salt is prepared by reacting the compound (b5) with n-BuLi. The alcohol derivative (b7) is obtained by reacting this lithium salt with the carbonyl derivative (b6). The cyclohexene derivative (b8) is obtained by dehydrating the alcohol derivative (b7) obtained in the presence of an acid catalyst of p-toluenesulfonic acid or the like. The compound (b9) is obtained by hydrogenating this compound (b8) in the presence of a catalyst, such as Pd/C. A lithium salt is prepared by reacting the compound (b9) obtained with sec-BuLi. The iodine derivative (b10) is obtained by reacting this lithium salt with iodine. The compound (b11), which is one example of the liquid crystal compound (a) of the invention, can be synthesized by reacting the iodine derivative (b10) obtained with the dihydroxyborane derivative (b4) in the presence of a base such as potassium carbonate and a catalyst of $Pd(PPh_3)_2Cl_2$ or the like.

The compound (b13) is obtained by reducing the compound (b12) with lithium hydride aluminum or the like. Then, the compound (b14) is obtained by brominating the compound (b13) with hydrobromic acid or the like. Separately, the compound (b16) is obtained by reacting the dihydroxyborane derivative (b4) with the compound (b15) in the presence of a base such as potassium carbonate and a catalyst of $Pd(PPh_3)_2Cl_{12}$ or the like. Then, a lithium salt is prepared by reacting this compound (b16) with n-BuLi. The dihydroxyborane derivative (b17) is obtained by reacting this lithium salt with a boric acid ester, and then hydrolyzing the reaction product in acidic conditions. The phenol derivative (b18) is obtained by oxidizing this dihydroxyborane derivative (b17) with an oxidizing agent such as hydrogen peroxide. The compound (b19), which is one example of the liquid crystal compound (a) of the invention, can be synthesized by etherifying the compound (b14) obtained by use of the above procedure with the phenol derivative (b18) in the presence of a base such as potassium carbonate.

[Liquid Crystal Compositions]

The liquid crystal composition of the invention is explained as follows. The components of this liquid crystal composition are characterized by containing at least one kind of the liquid crystal compound (a), and the component may contain two or more kinds of the liquid crystal compounds (a), and may be composed of the liquid crystal compound (a) alone. When the liquid crystal composition of the invention is prepared, its components can also be selected, for example, by taking into consideration the dielectric anisotropy of the liquid crystal compound (a). The liquid crystal composition containing selected components has a low viscosity, a suitable and negative dielectric anisotropy, a suitable elastic constant $K_{33}$, a low threshold voltage, a high maximum temperature of a nematic phase (phase-transition temperature on a nematic phase-a isotropic phase), and a low minimum temperature of the nematic phase.

[Liquid Crystal Composition (1)]

It is desirable that the liquid crystal composition of the invention (hereinafter also referred to as the liquid crystal composition (1)) further comprises at least one liquid crystal compound selected from the group of compounds represented by formulas (e-1) to (e-3) as a second component (hereinafter also referred to as the compounds (e-1) to (e-3), respectively) in addition to the liquid crystal compound (a).

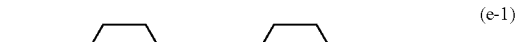
(e-1)

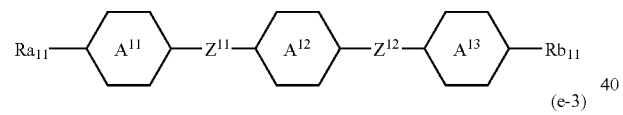
(e-2)

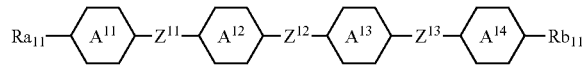
(e-3)

In formulas (e-1) to (e-3), $Ra_{11}$ and $Rb_{11}$ are each independently alkyl having 1 to 10 carbons, and in the alkyl, —$CH_2$— may be nonadjacently replaced by —O—, and —$(CH_2)_2$— may be nonadjacently replaced by —CH=CH—, and hydrogen may be replaced by fluorine.

In formulas (e-1) to (e-3), ring $A^{11}$, ring $A^{12}$, ring $A^{13}$, and ring $A^{14}$ are each independently trans-1,4-cyclohexylene, 1,4-phenylene, 2-fluoro-1,4-phenylene, 3-fluoro-1,4-phenylene, pyrimidine-2,5-diyl, 1,3-dioxane-2,5-diyl, or tetrahydropyran-2,5-diyl.

In formulas (e-1) to (e-3), $Z^{11}$, $Z^{12}$, and $Z^{13}$ are each independently a single bond, —$CH_2$—$CH_2$—, —CH=CH—, —C≡C—, —COO—, or $CH_2O$—.

Viscosity of a liquid crystal composition can be decreased and the minimum temperature of a nematic phase can be decreased by adding a second component to the liquid crystal compound (a). Since the dielectric anisotropy of the compounds (e-1) to (e-3) are nearly 0, the dielectric anisotropy of the liquid crystal composition containing the compounds can be adjusted so as to approach 0.

The compound (e-1) or (e-2) is effective in decreasing the viscosity of the liquid crystal composition comprising the compound and increasing the voltage holding ratio. The compound (e-3) is effective in increasing the maximum temperature of a nematic phase of the liquid crystal composition containing the compound, and increasing the voltage holding ratio.

If two or more rings are trans-1,4-cyclohexylene in the ring $A^{11}$, ring $A^{12}$, ring $A^{13}$, and ring $A^{14}$, the maximum temperature of a nematic phase in the liquid crystal composition containing the rings can be increased. If two or more rings are 1,4-phenylene, the optical anisotropy of the liquid crystal composition containing the rings can be increased.

More desirable compounds for the second components are represented by formulas (2-1) to (2-74) (hereinafter also referred to as the compounds (2-1) to (2-74), respectively). In these compounds, $Ra_{11}$ and $Rb_{11}$ have the meanings identical to those described for the compounds (e-1) to (e-3).

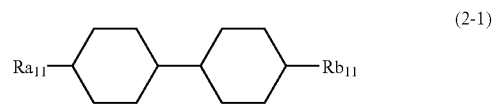
(2-1)

(2-2)

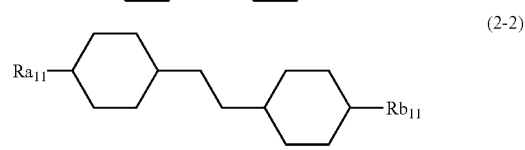
(2-3)

(2-4)

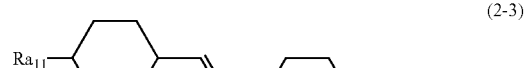

(2-5)

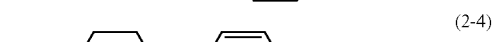

(2-6)

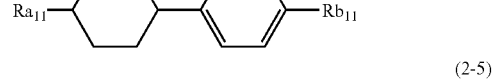

(2-7)


(2-8)


(2-9)

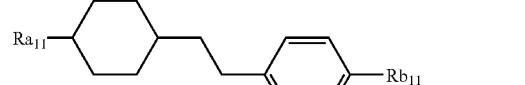

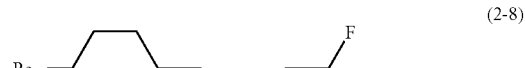

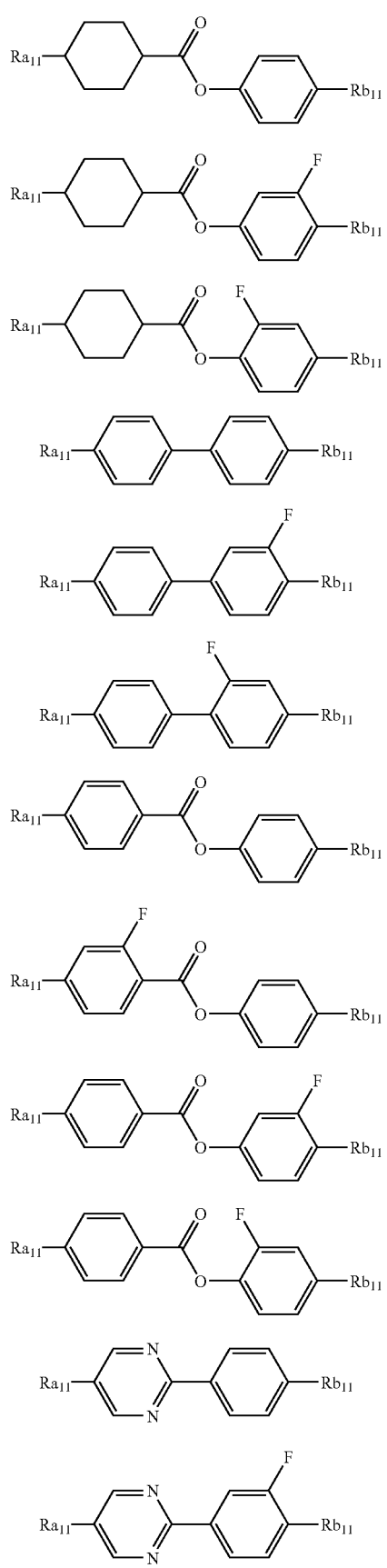
(2-10)
(2-11)
(2-12)
(2-13)
(2-14)
(2-15)
(2-16)
(2-17)
(2-18)
(2-19)
(2-20)
(2-21)
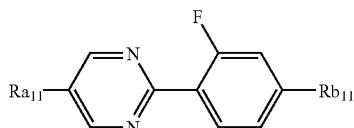
(2-22)
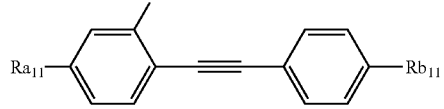
(2-23)
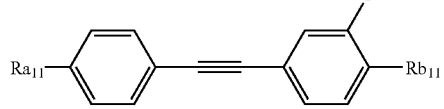
(2-24)
(2-25)
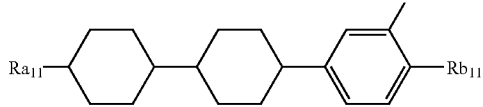
(2-26)
(2-27)
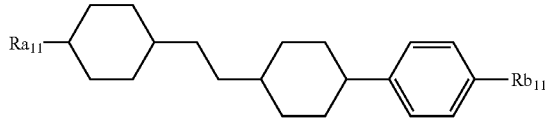
(2-28)
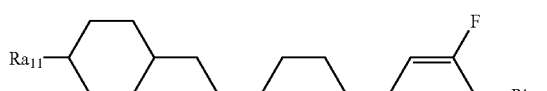
(2-29)
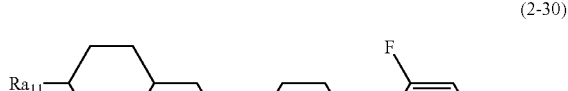
(2-30)
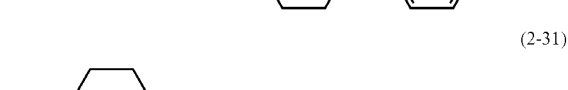
(2-31)
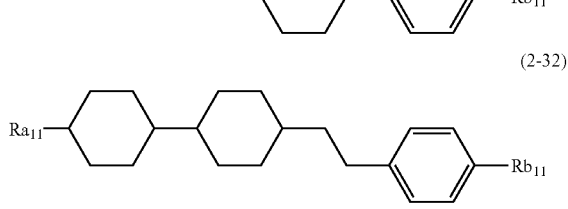
(2-32)

(2-33) 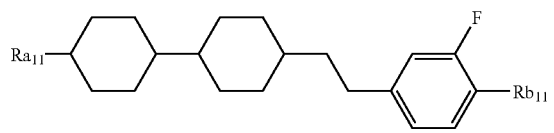
(2-34) 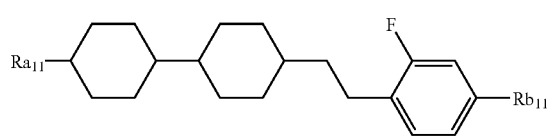
(2-35) 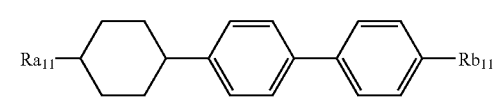
(2-36) 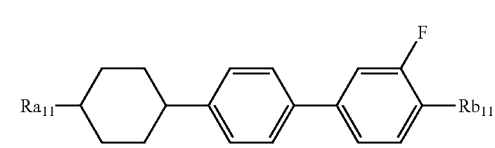
(2-37) 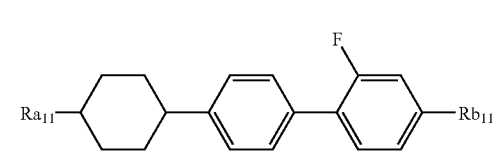
(2-38) 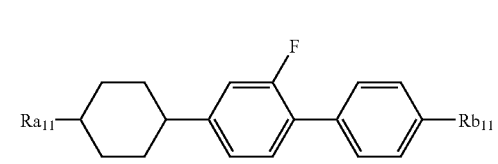
(2-39) 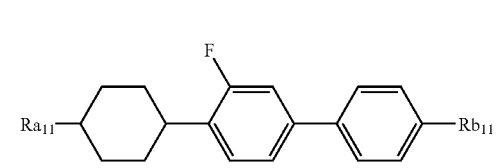
(2-40) 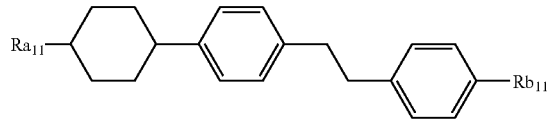
(2-41) 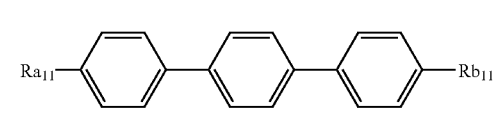
(2-42) 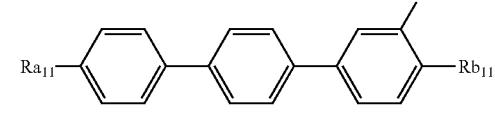
(2-43) 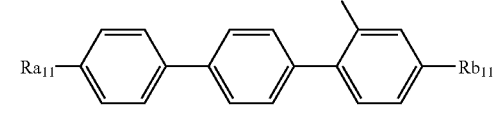
(2-44) 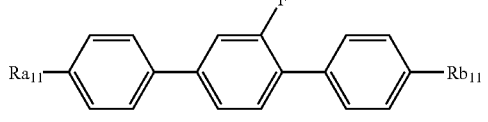
(2-45) 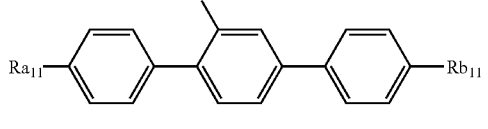
(2-46) 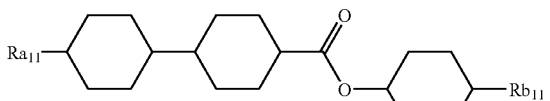
(2-47) 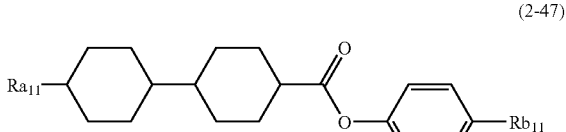
(2-48) 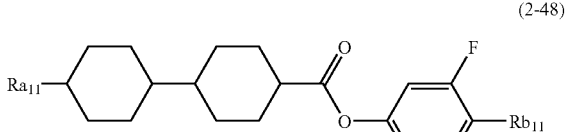
(2-49) 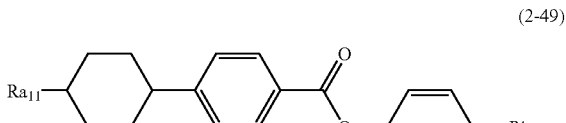
(2-50) 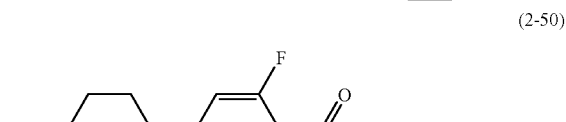
(2-51) 
(2-52) 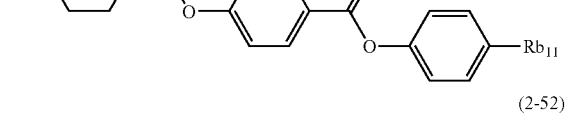
(2-53) 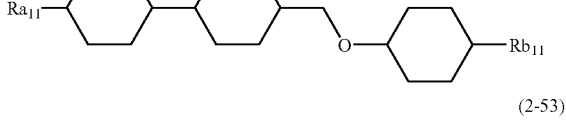

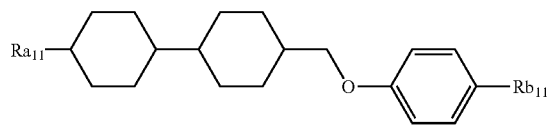
(2-54)

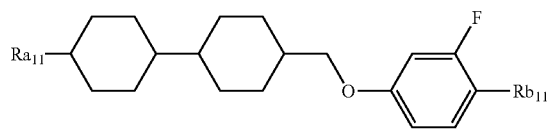
(2-55)

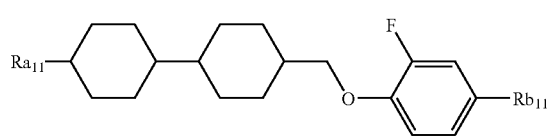
(2-56)

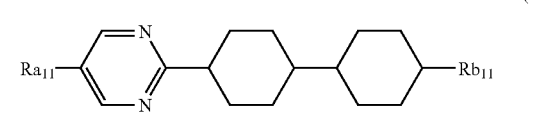
(2-57)

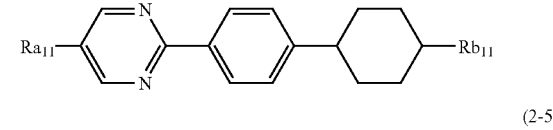
(2-58)

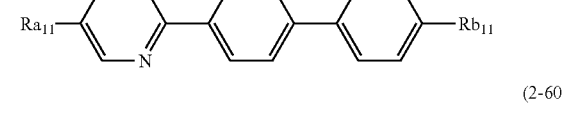
(2-59)

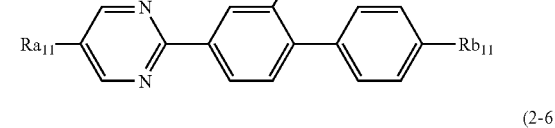
(2-60)

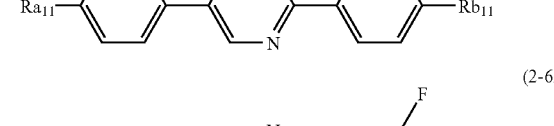
(2-61)

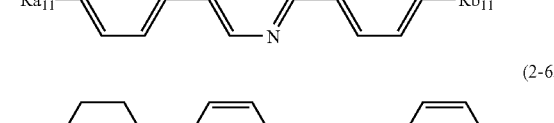
(2-62)

(2-63)

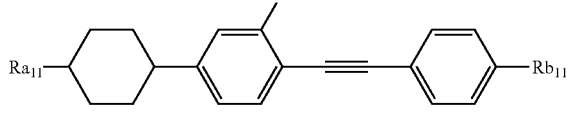
(2-64)

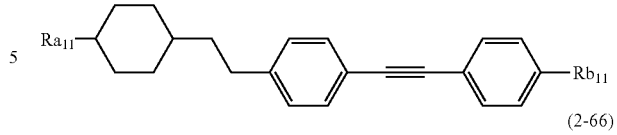
(2-65)

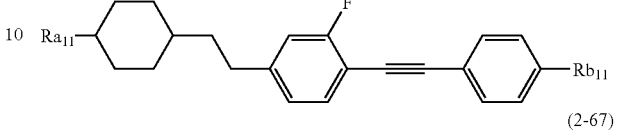
(2-66)

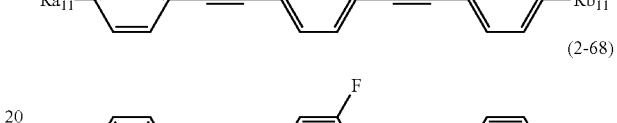
(2-67)

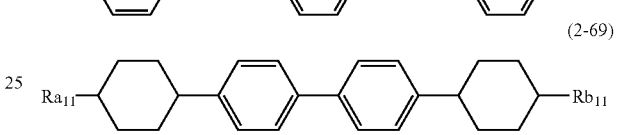
(2-68)

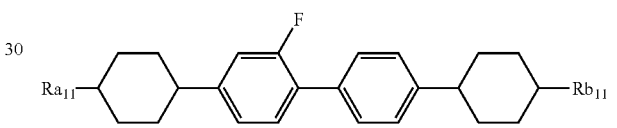
(2-69)

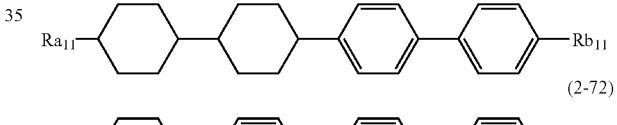
(2-70)

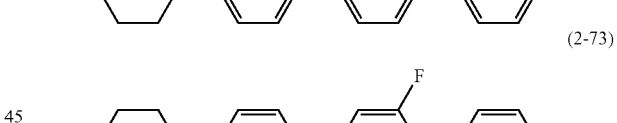
(2-71)

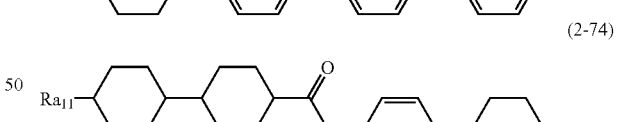
(2-72)

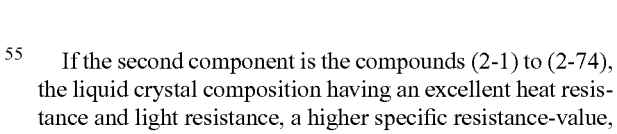
(2-73)

(2-74)

If the second component is the compounds (2-1) to (2-74), the liquid crystal composition having an excellent heat resistance and light resistance, a higher specific resistance-value, and a nematic phase in a wide range can be prepared.

In particular, the liquid crystal composition (1), wherein the first component of the liquid crystal composition (1) is at least one compound selected from the group of compounds represented by formulas (a-1-1) to (a-1-6) and formulas (a-2-1) to (a-2-6), and the second component is at least one compound selected from the group of compounds represented by formulas (e-1) to (e-3), has an excellent heat resistance and light resistance, and further has a wider range of a nematic phase, a larger voltage holding ratio, a smaller viscosity, and a suitable elastic constant $K_{33}$.

Although the content of the second component in the liquid crystal composition (1) of the invention is not limited particularly, it is desirable to increase the content in view of a lower viscosity. Since the threshold voltage of a liquid crystal composition tends to increase with an increase of the content of the second component, when the liquid crystal composition of the invention is used, for example, for a liquid crystal device with the VA mode, the content of the second component is in the range of 45% to 95% by weight based on the total weight of the liquid crystal compounds contained in the liquid crystal composition (1), and the content of the first component is more preferably in the range of 5% to 60% by weight based on the total weight of the liquid crystal compounds contained in the liquid crystal composition (1).

[Liquid Crystal Composition (2)]

A liquid crystal composition comprising at least one compound selected from the group of the liquid crystal compounds represented by formulas (g-1) to (g-4) (hereinafter also referred to as the compounds (g-1) to (g-4), respectively) as a third component, in addition to the first component and the second component is also desirable (hereinafter also referred to as the liquid crystal composition (2)) as the liquid crystal composition of the invention.

In formulas (g-1) to (g-6), $Ra_{21}$ and $Rb_{21}$ are each independently hydrogen or alkyl having 1 to 10 carbons, and in the alkyl, —$CH_2$— may be nonadjacently replaced by —O—, and —$(CH_2)_2$— may be nonadjacently replaced by —CH=CH—, and hydrogen may be replaced by fluorine.

In formula (g-1) to (g-6), rings $A^{21}$, $A^{22}$, and $A^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, 1,3-dioxane-2,5-diyl, or tetrahydropyran-2,5-diyl.

In formula (g-1) to (g-6), $Z^{21}$, $Z^{22}$, and $Z^{23}$ are each independently a single bond, —$CH_2$—$CH_2$—, —CH=CH—, —C≡C'—, —$OCF_2$—, —$CF_2O$—, —$OCF_2CH_2CH_2$—, —$CH_2CH_2CF_2O$—, —COO—, —OCO—, —$OCH_2$—, or —$CH_2O$—, and $Y^1$, $Y^2$, $Y^3$, and $Y^4$ are each independently fluorine or chlorine.

In formula (g-1) to (g-6), q, r, and s are each independently 0, 1, or 2, q+r is 1 or 2, q+r+s is 1, 2, or 3, and t is 0, 1, or 2. The liquid crystal composition (2) which further comprises the third component has a large negative dielectric anisotropy.

The liquid crystal composition having a wide temperature range of a nematic phase, a small viscosity, a large negative dielectric anisotropy, and a large specific resistance-value can be obtained and the liquid crystal composition in which these physical properties are suitably balanced is obtained.

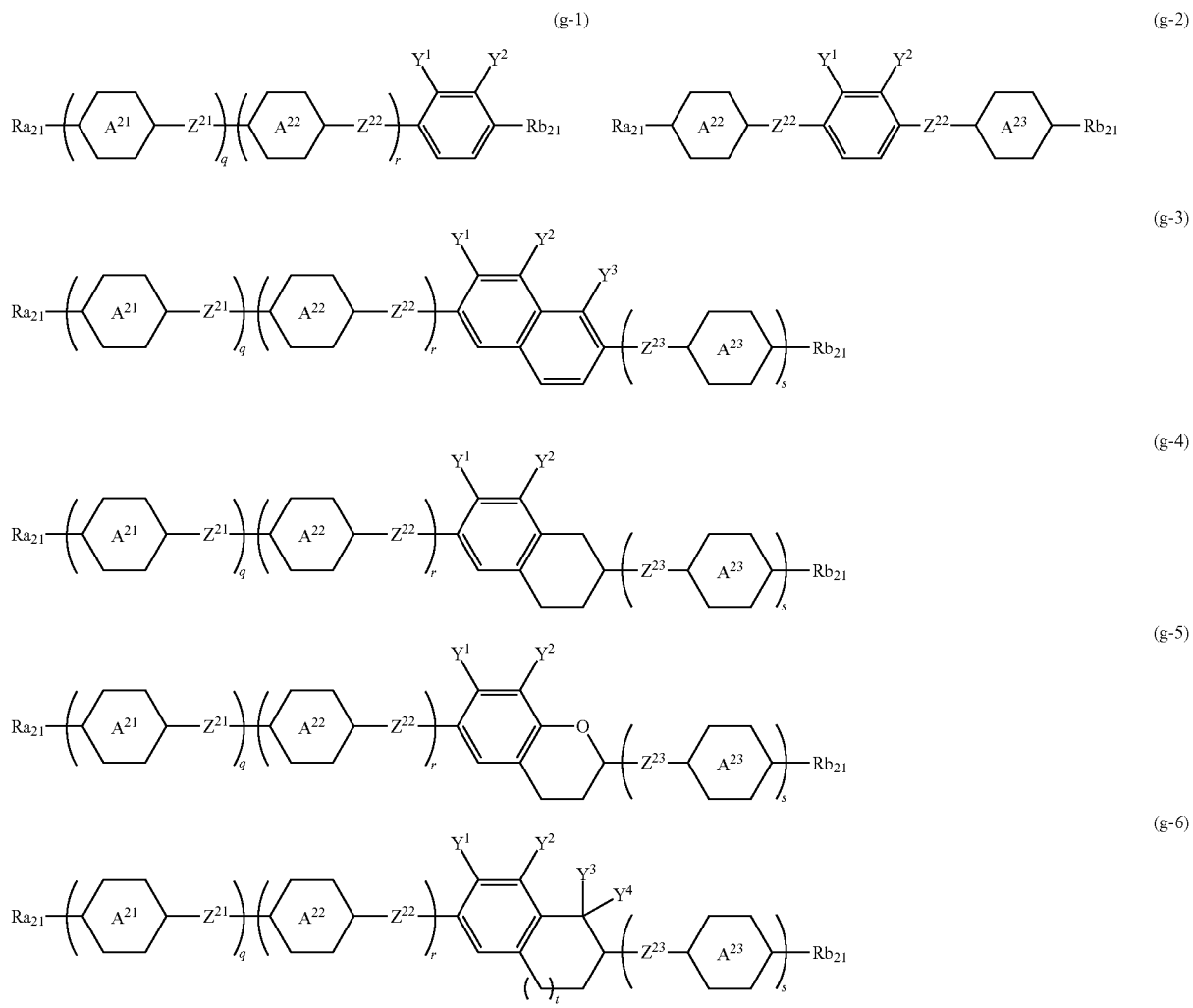

Among the third components, at least one compound selected from the group of compounds represented by formulas (h-1) to (h-7) (hereinafter also referred to as the compounds (h-1) to (h-7), respectively) are desirable in view of a low viscosity, heat resistance, and light resistance are desirable.

The compounds (h-3) and (h-6) can increase optical anisotropy and the compounds (h-4) and (h-7) can further increase optical anisotropy.

The compounds (h-5), (h-6), and (h-7) can decrease a minimum temperature of a nematic phase in the liquid crystal composition comprising them.

Among the liquid crystal compositions (2), in particular, a liquid crystal composition which comprises first, second, and third components has an excellent heat resistance and light resistance, a wide temperature range of a nematic phase, a small viscosity, a high voltage holding ratio, a suitable optical anisotropy, a suitable dielectric anisotropy, and a suitable elastic constant $K_{33}$, wherein the first component is at least one compound selected from the group of compounds represented by formulas (a-1-1) to (a-1-6) and formulas (a-2-1) to (a-2-6), the second component is at least one compound selected from the group of compounds represented by formulas (e-1) to (e-3), and the third component is at least one compound selected from the group of compounds represented by formulas (h-1) to (h-7). Furthermore, the liquid crystal composition is desirable in view of these physical properties suitably balanced.

Among the third components, more desirable compounds are the compounds (3-1) to (3-118). In these compounds, $Rb_{22}$ and $Rb_{22}$ have the meanings identical to those described for the compounds (h-1) to (h-7).

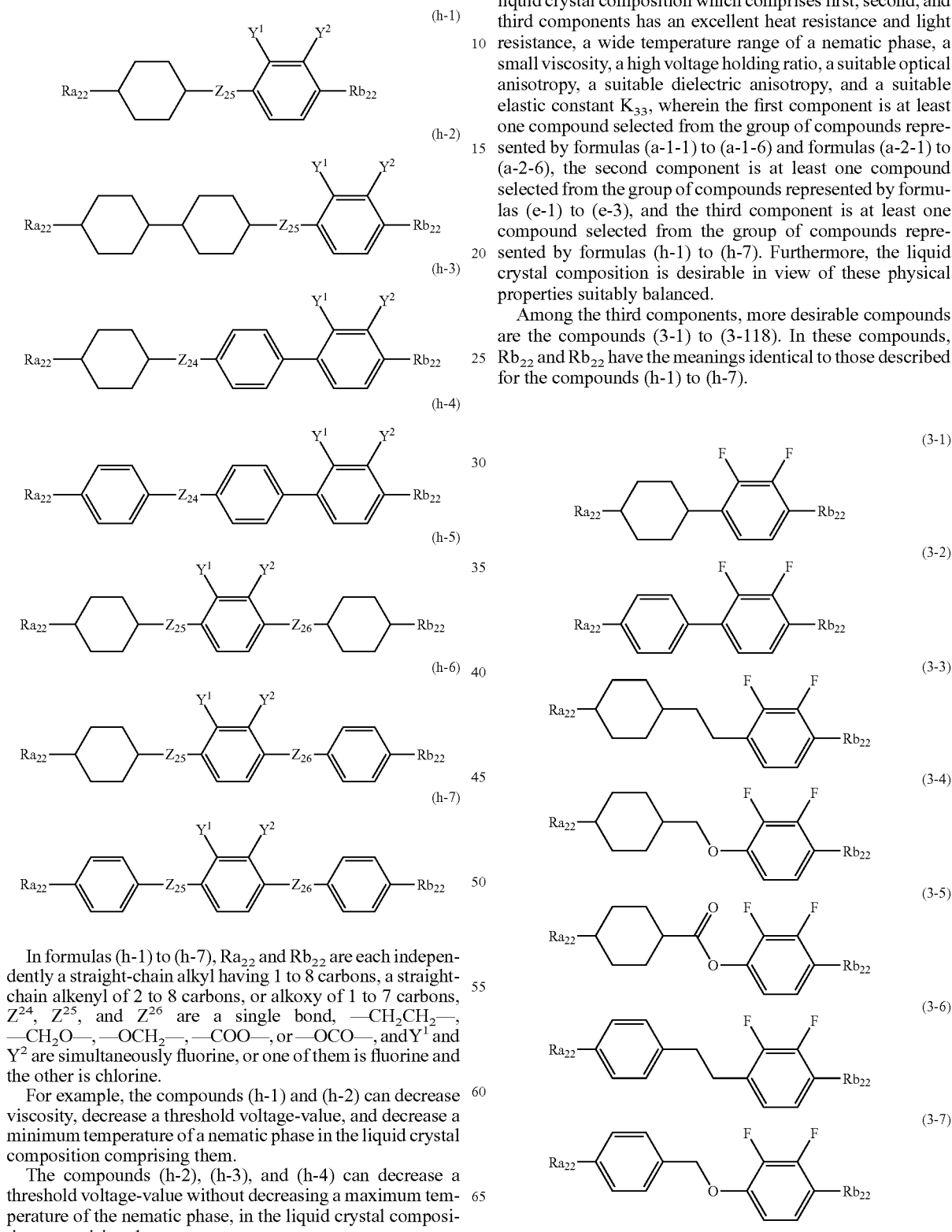

In formulas (h-1) to (h-7), $Ra_{22}$ and $Rb_{22}$ are each independently a straight-chain alkyl having 1 to 8 carbons, a straight-chain alkenyl of 2 to 8 carbons, or alkoxy of 1 to 7 carbons, $Z^{24}$, $Z^{25}$, and $Z^{26}$ are a single bond, —$CH_2CH_2$—, —$CH_2O$—, —$OCH_2$—, —COO—, or —OCO—, and $Y^1$ and $Y^2$ are simultaneously fluorine, or one of them is fluorine and the other is chlorine.

For example, the compounds (h-1) and (h-2) can decrease viscosity, decrease a threshold voltage-value, and decrease a minimum temperature of a nematic phase in the liquid crystal composition comprising them.

The compounds (h-2), (h-3), and (h-4) can decrease a threshold voltage-value without decreasing a maximum temperature of the nematic phase, in the liquid crystal composition comprising them.

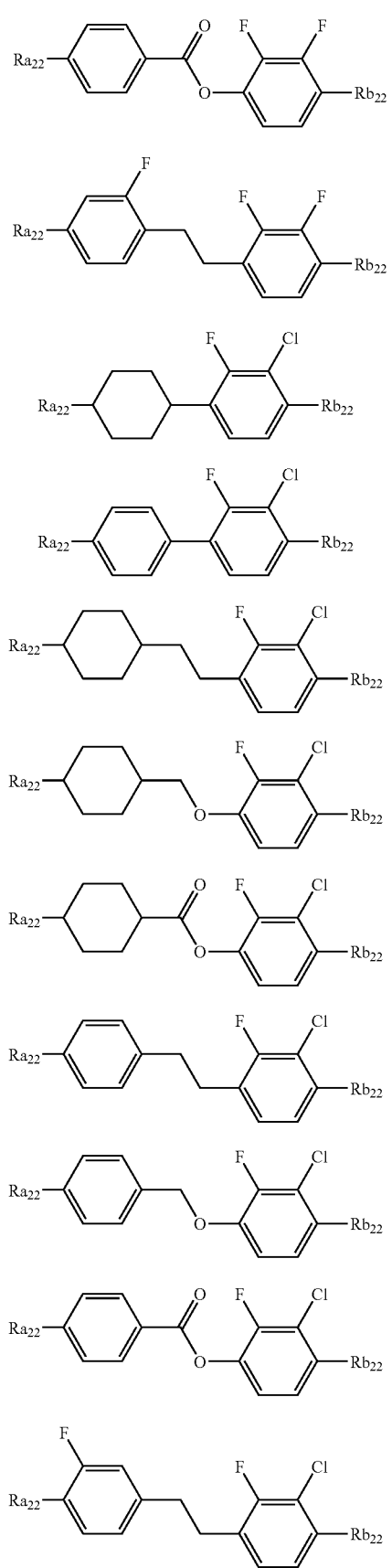
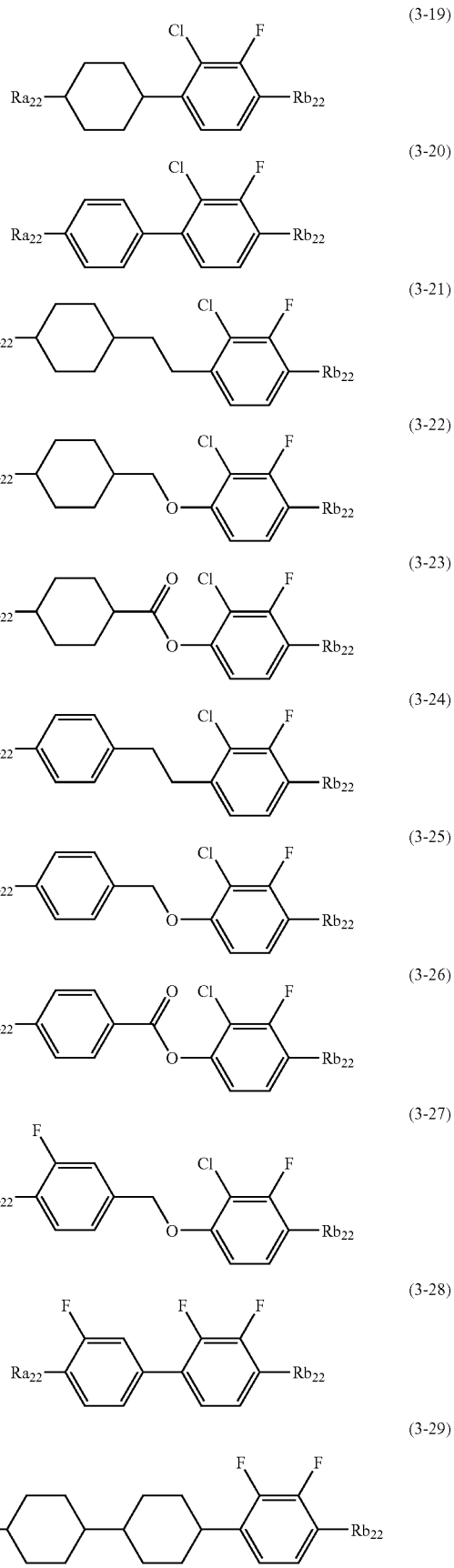

(3-30)
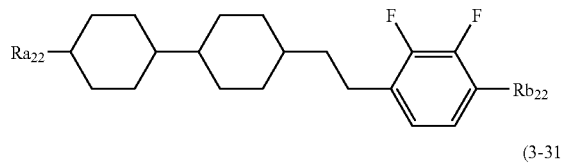
(3-31)
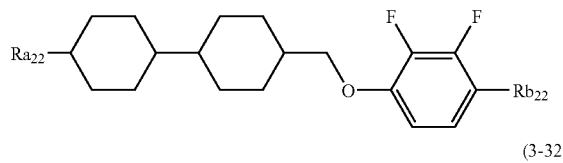
(3-32)
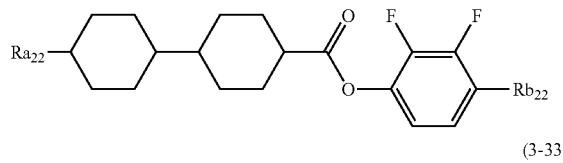
(3-33)
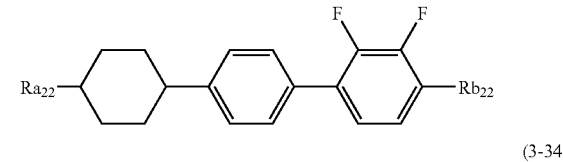
(3-34)
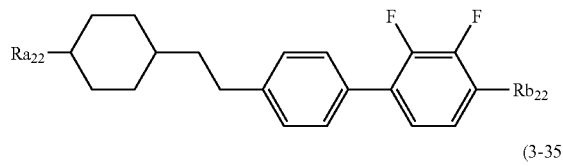
(3-35)
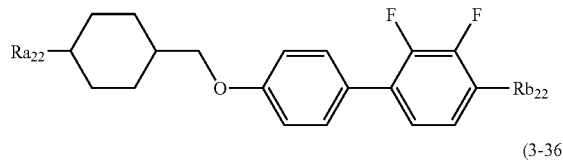
(3-36)
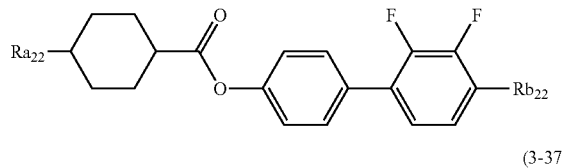
(3-37)
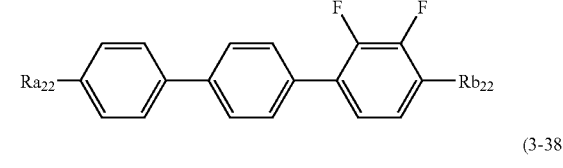
(3-38)
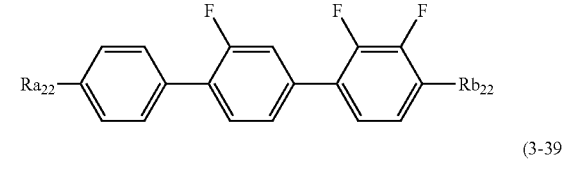
(3-39)
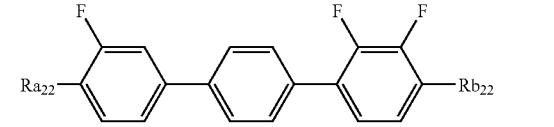
(3-40)
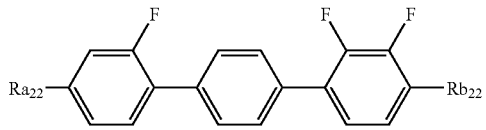
(3-41)
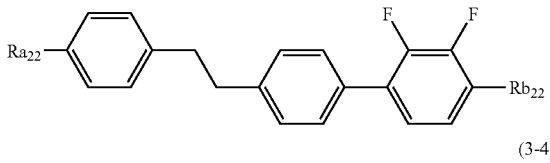
(3-42)
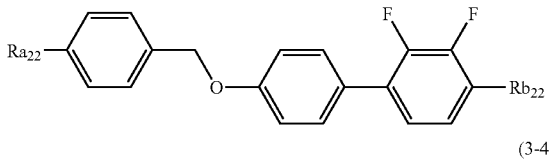
(3-43)
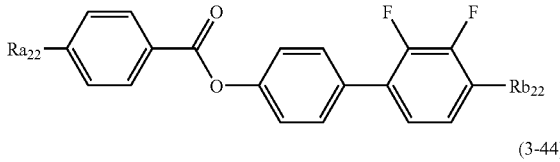
(3-44)
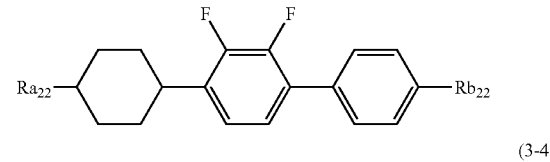
(3-45)
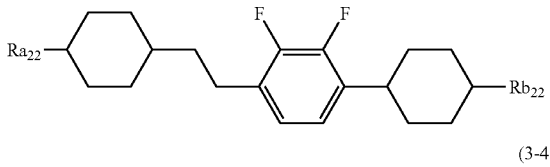
(3-46)
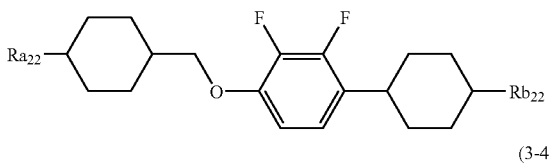
(3-47)
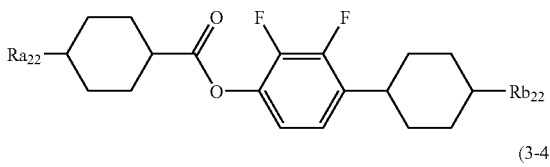
(3-48)
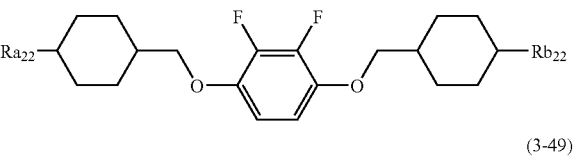
(3-49)

(3-50)
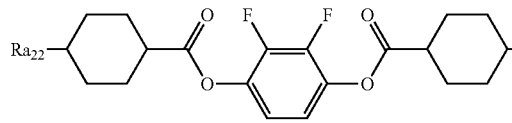
(3-51)
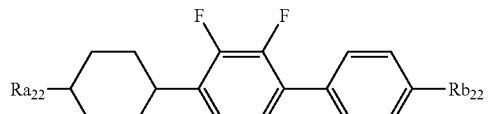
(3-52)
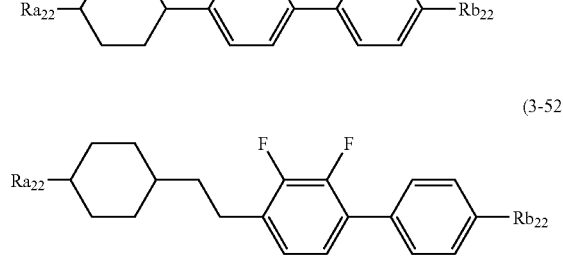
(3-53)
(3-54)
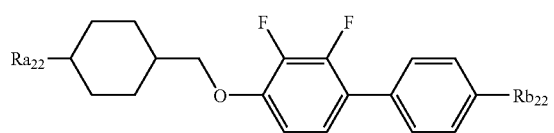
(3-55)
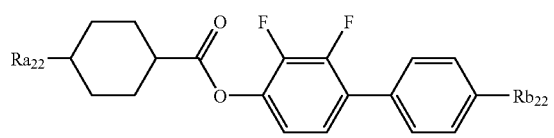
(3-56)
(3-57)
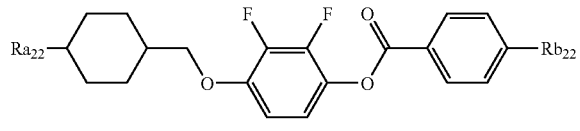
(3-58)
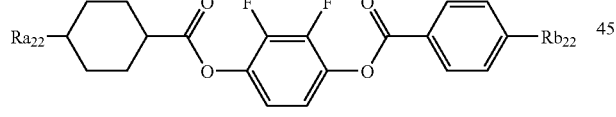
(3-59)
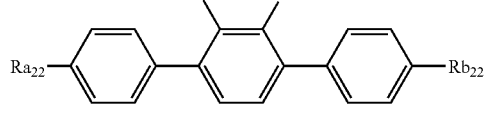
(3-60)
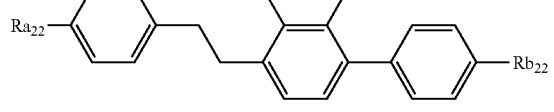
(3-61)
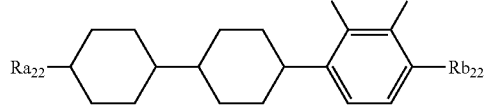
(3-62)
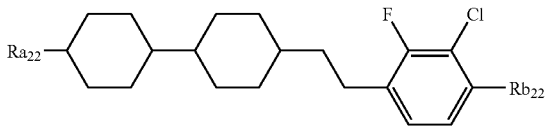
(3-63)
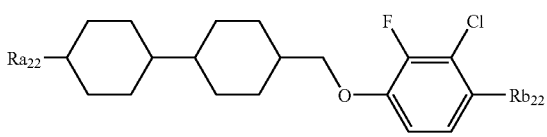
(3-64)
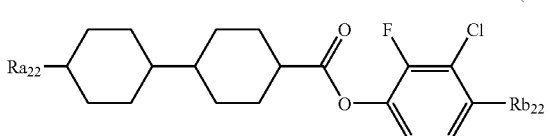
(3-65)
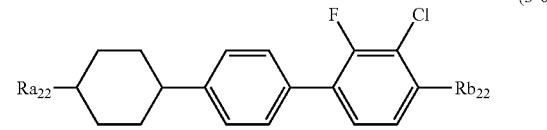
(3-66)
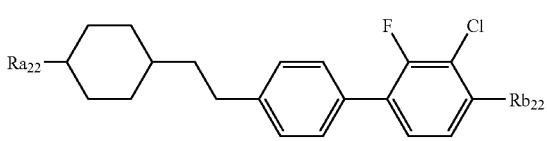
(3-67)
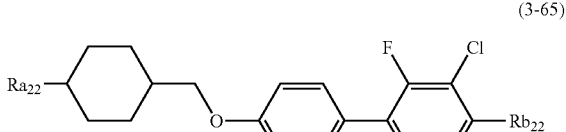
(3-68)
(3-69)

(3-70) through (3-89): chemical structures.

(3-90)
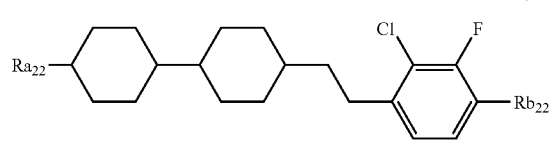
(3-91)
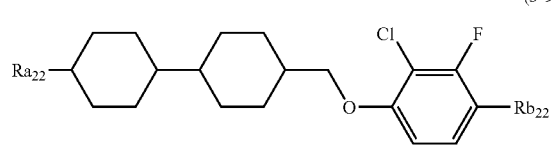
(3-92)
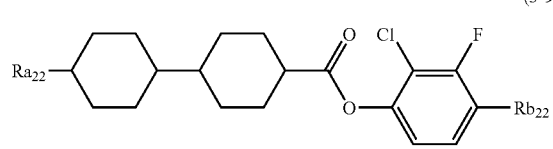
(3-93)
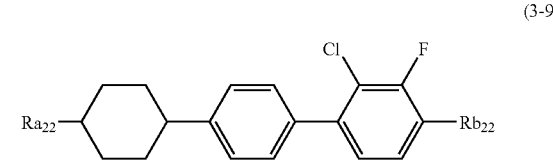
(3-94)
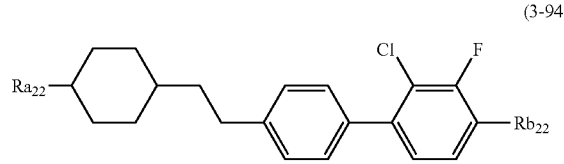
(3-95)
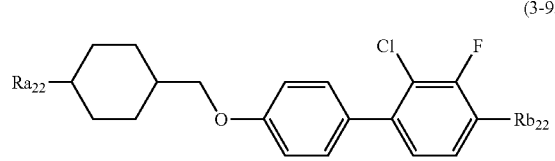
(3-96)
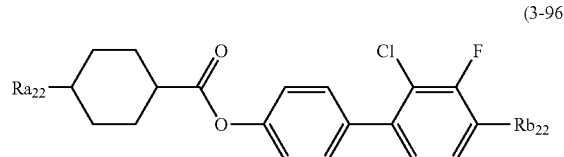
(3-97)
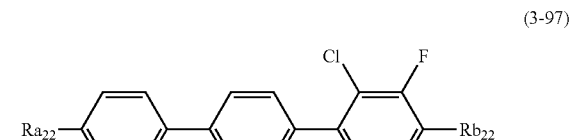
(3-98)
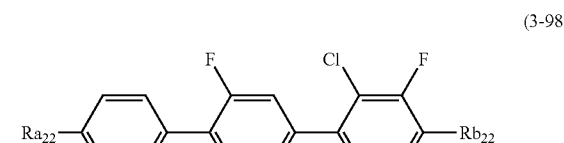
(3-99)
(3-100)
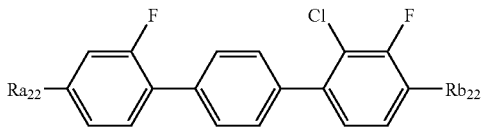
(3-101)
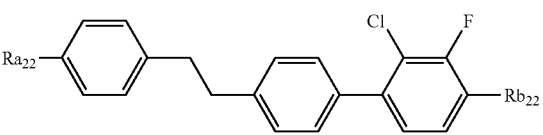
(3-102)
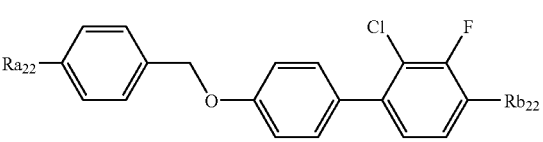
(3-103)
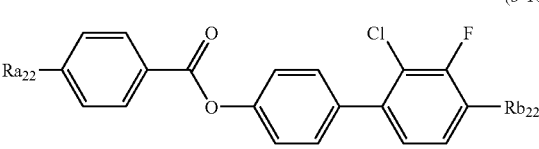
(3-104)
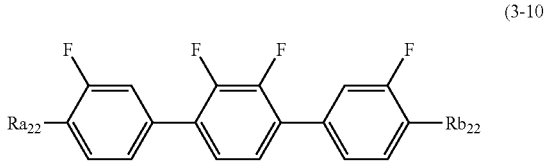
(3-105)
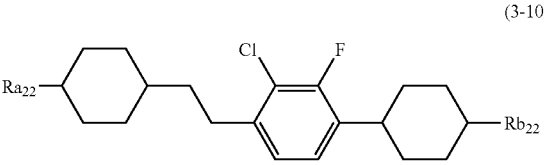
(3-106)
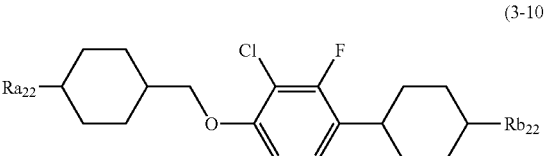
(3-107)
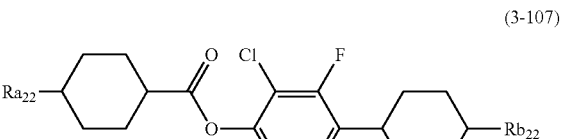
(3-108)
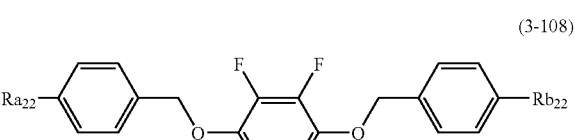
(3-109)
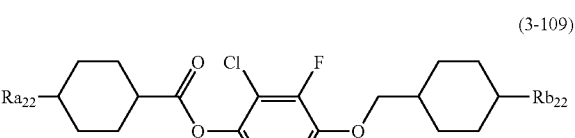

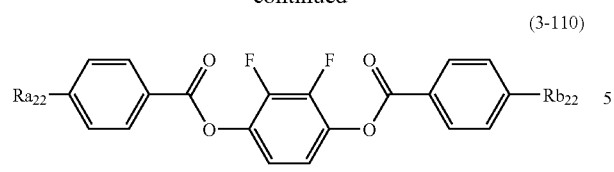
(3-110)
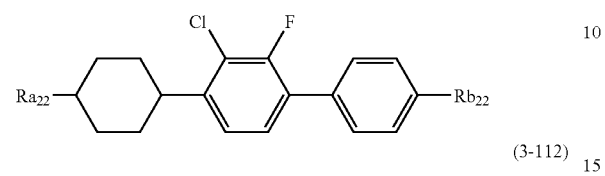
(3-111)
(3-112)
(3-113)
(3-114)
(3-115)
(3-116)
(3-117)
(3-118)
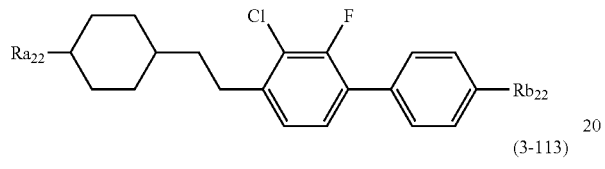

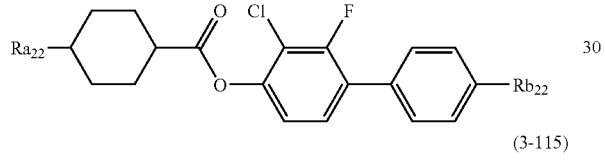

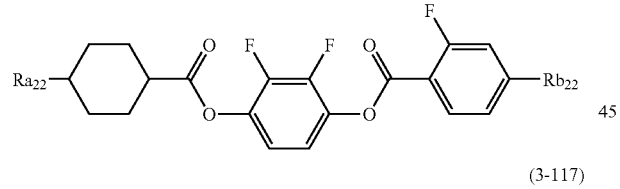

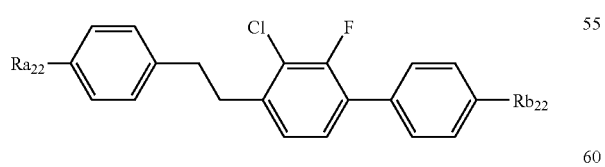

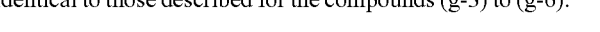

(3-119)
(3-120)
(3-121)
(3-122)
(3-123)
(3-124)
(3-125)
(3-126)
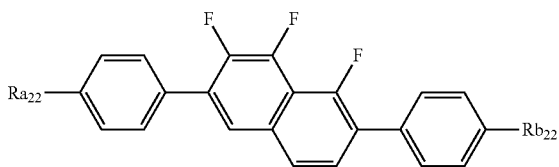
For example, compounds having a condensed ring, such as the compounds (g-3) to (g-6) are desirable in view of decreasing a threshold voltage-value, and the compounds (3-119) to (3-143) are desirable in view of heat resistance or light resistance. In these compounds, $Ra_{22}$ and $Rb_{22}$ have the meanings identical to those described for the compounds (g-3) to (g-6).

-continued (3-127)
(3-128)
(3-129)
(3-130)
(3-131)
(3-132)
(3-133)
(3-134)

-continued (3-135)
(3-136)
(3-137)
(3-138)
(3-139)
(3-139)
(3-140)
(3-141)

(3-142)

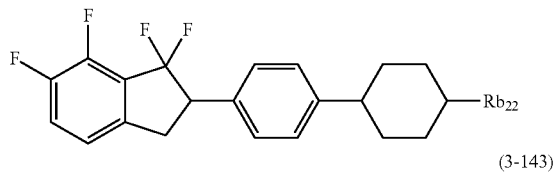

(3-143)

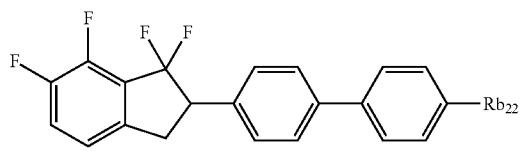

Although the content of the third component in the liquid crystal composition of the invention is not limited particularly, it is desirable to increase the content in view of preventing a decrease in the absolute value of a negative dielectric anisotropy. Although the content ratios of the first component, second component, and third component of the liquid crystal composition (2) of the invention are not limited particularly, it is desirable that the content ratio of the liquid crystal compound (a) is in the range of 5% to 60% by weight, the content ratio of the second component is in the range of 20% to 75% by weight, and the content ratio of the third component is in the range of 20% to 75% by weight based on the total weight of the liquid crystal composition (2).

When the ratios of the contents of the first component, second component, and third component of the liquid crystal composition (2) are in these ranges, the composition (2) has an excellent heat resistance and light resistance, a wide temperature range of a nematic phase, a small viscosity, a high voltage holding ratio, and a suitable optical anisotropy, a suitable dielectric anisotropy, a suitable elastic constant $K_{33}$. Furthermore, a liquid crystal composition in which these physical properties are more suitably balanced is obtained.

[Aspects and so forth of the Liquid Crystal Composition]

In one aspect on the liquid crystal composition of the invention, other liquid crystal compounds, in addition to the liquid crystal compounds composed of the first components, the second components, and the third component which is added as required, may be added and used for the purpose of further adjusting, for example, characteristics of the liquid crystal composition. In another aspect on the liquid crystal composition of the invention, other liquid crystal compounds except the liquid crystal compounds composed of the first and second components and the third component which is added as required may not be added and used, for example, in view of their cost.

Additives, such as an optically active compound, dye, antifoaming agent, ultraviolet absorber, and antioxidant may further be added to the liquid crystal composition of the invention. When the optically active compound is added to the liquid crystal composition of the invention, it may induce a helical structure of liquid crystals imparting a twist angle and so forth.

A known chiral doping agent is added as the optically active compound. This chiral doping agent is effective in inducing a helical structure of liquid crystals, adjusting a twist angle required and then preventing a reverse twist. An example of the chiral doping agent includes the optically active compounds (Op-1) to (Op-13).

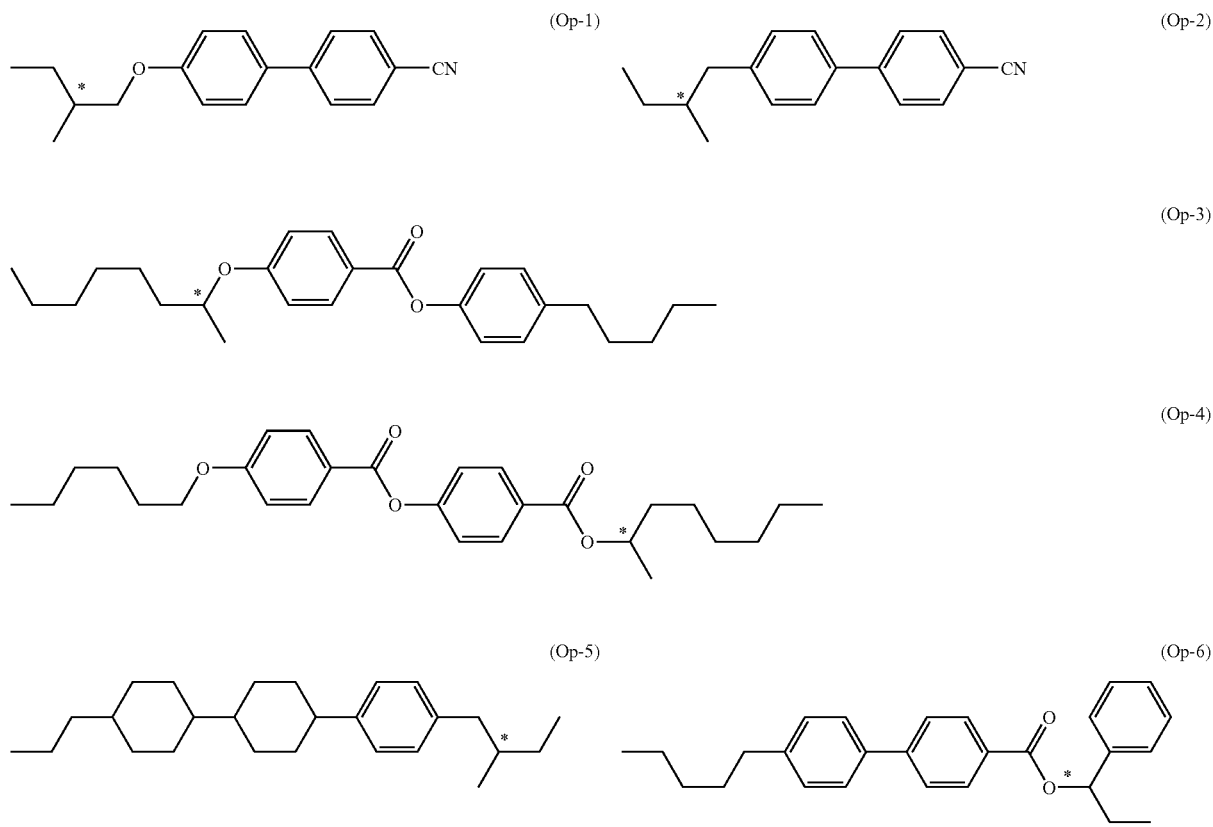

-continued

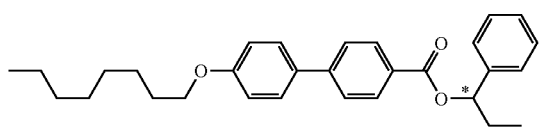
(Op-7)

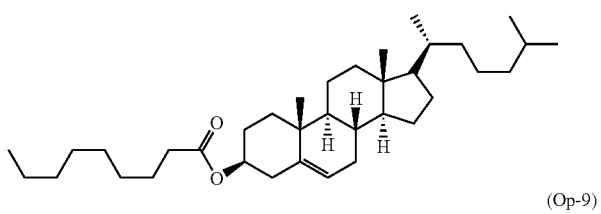
(Op-8)

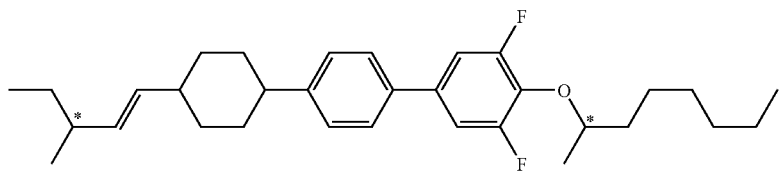
(Op-9)

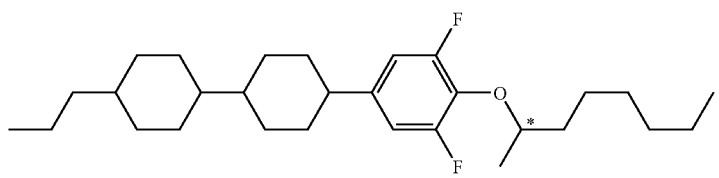
(Op-10)

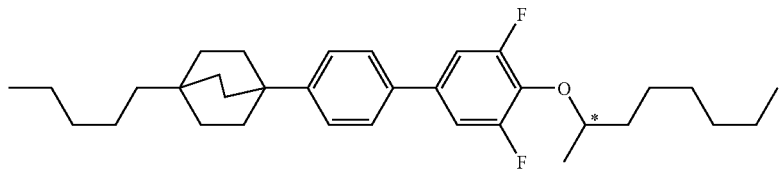
(Op-11)

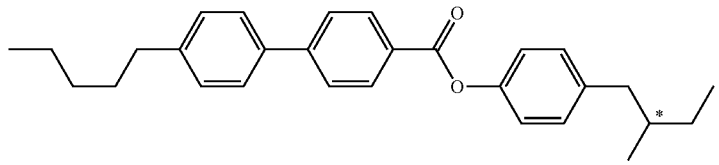
(Op-12)

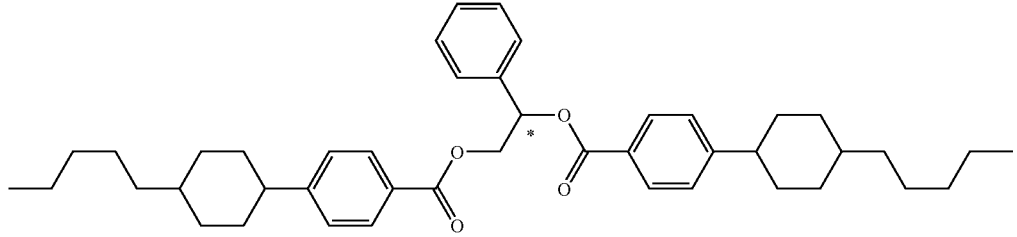
(Op-13)

When a dye is added to the liquid crystal composition of the invention, the liquid crystal composition can be applied to the liquid crystal display device which has a GH (Guest host) mode. When an antifoaming agent is added to the liquid crystal composition of the invention, it is possible to suppress the formation of foam during the transportation of the liquid crystal composition or in a process of manufacturing liquid crystal display devices using this liquid crystal composition.

When an ultraviolet absorber or an antioxidant is added to the liquid crystal composition of the invention, it is possible to prevent degradation of the liquid crystal composition and of the liquid crystal display device containing the liquid crystal composition. For example, the antioxidant can suppress a decrease in a specific resistance-value, when the liquid crystal composition is heated.

Ultraviolet absorbers include a benzophenone-based ultraviolet absorber, a benzoate-based ultraviolet absorber, a triazole-based ultraviolet absorber, and so forth. A specific example of the benzophenone-based ultraviolet absorber is 2-hydroxy-4-n-octoxybenzophenone.

A specific example of the benzoate-based ultraviolet absorber is 2,4-di-t-butylphenyl-3,5-di-t-butyl-4-hydroxybenzoate. Specific examples of the triazole-based ultraviolet absorber are 2-(2-hydroxy-5-methylphenyl)benzotriazole, 2-[2-hydroxy-3-(3,4,5,6-tetrahydroxyphthalimido-methyl)-5-methylphenyl]benzotriazole, and 2-(3-t-butyl-2-hydroxy-5-methylphenyl)-5-chlorobenzotriazole.

Antioxidants include a phenol-based antioxidant, an organosulfur-based antioxidant and so forth. An antioxidant represented by formula (1) is desirable especially in view of a large effect on antioxidation without changing the physical property-values of a liquid crystal composition.

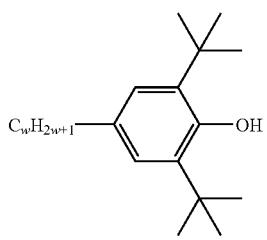
(I)

In formula (1), w is an integer of 1 to 15.

Specific examples of the phenol-based antioxidant are 2,6-di-t-butyl-4-methylphenol, 2,6-di-t-butyl-4-ethylphenol, 2,6-di-t-butyl-4-propylphenol, 2,6-di-t-butyl-4-butylphenol, 2,6-di-t-butyl-4-pentylphenol, 2,6-di-t-butyl-4-hexylphenol, 2,6-di-t-butyl-4-heptylphenol, 2,6-di-t-butyl-4-octylphenol, 2,6-di-t-butyl-4-nonylphenol, 2,6-di-t-butyl-4-decylphenol, 2,6-di-t-butyl-4-undecylphenol, 2,6-di-t-butyl-4-dodecylphenol, 2,6-di-t-butyl-4-tridecylphenol, 2,6-di-t-butyl-4-tetra-decylphenol, 2,6-di-t-butyl-4-pentadecylphenol, 2,2'-methylenebis(6-t-butyl 4-methylphenol), 4,4'-butylidenebis(6-t-butyl-3-methylphenol), 2,6-di-t-butyl-4-(2-octadecyloxycarbonyl)ethylphenol, and pentaerythritol tetrakis[3-(3,5-di-t-butyl-4-hydroxyphenyl)propionate].

Specific examples of the organosulfur-based antioxidant are dilauryl-3,3'-thiopropionate, dimyristyl-3,3'-thiopropionate, distearyl-3,3'-thiopropionate, pentaerythritoltetrakis (3-laurylthiopropionate), and 2-mercaptobenzimidazole.

Additives typified by an ultraviolet absorber, antioxidant and so forth may be added and used in the range of amounts which do not prevent the purpose of the invention and can attain the purpose of the addition of the additives.

When an ultraviolet absorber or an antioxidant is added, for example, its content ratio is usually in the range of 10 ppm to 500 ppm, preferably in the range of 30 ppm to 300 ppm, and more preferably in the range of 40 ppm to 200 ppm based on the total weight of the liquid crystal composition of the present invention.

Incidentally, in another aspect, the liquid crystal composition of the invention may contain impurities of starting materials, by-products, solvents used for reactions, catalysts for syntheses and so forth, which have been contaminated in the process such as for synthesizing each compound constituting a liquid crystal composition and for preparing the liquid crystal composition.

[Method for Producing Liquid Crystal Compositions]

When each of the compounds which constitute the components of the liquid crystal composition of the invention is a liquid, for example, the composition is prepared by mixing and shaking the compounds. When solids are included, the composition is prepared by mixing and then shaking the compounds, after the compounds have been heated and liquefied. Moreover, the liquid crystal composition of the invention can also be prepared by the use of other known methods.

[Characteristics of Liquid Crystal Compositions]

Since the maximum temperature of a nematic phase can be adjusted to 70° C. or above and the minimum temperature of the nematic phase can be adjusted to −20° C. or below in the liquid crystal composition of the invention, the temperature range of the nematic phase is wide. Accordingly, the liquid crystal display device containing this liquid crystal composition can be used in a wide temperature range.

In the liquid crystal composition of the invention, the optical anisotropy can be normally in the range of −0.05 to 0.18, preferably in the range of 0.10 to 0.13, by suitably adjusting the composition ratio and so forth. The dielectric anisotropy can be normally in the range of −5.0 to −2.0, and preferably in the range of −4.5 to −2.5 in the liquid crystal composition of the invention. The liquid crystal composition having the dielectric anisotropy of the range of −4.5 to −2.5 can be suitably used for a liquid crystal display device which operates by means of the IPS and VA modes.

[Liquid Crystal Display Devices]

The liquid crystal composition of the invention can be used not only for the liquid crystal display devices with operation modes such as the PC, TN, STN, and OCB modes which are driven by means of the AM mode, but also for liquid crystal display devices with operation modes such as the PC, TN, STN, OCB, VA, and IPS modes which are driven by means of the passive matrix (PM) mode.

The liquid crystal display devices with the AM and PM modes can be applied to liquid crystal displays and so forth having any of a reflection type, transmission type, and semi-transmission type. Moreover, the liquid crystal composition of the invention can also be used for a DS (dynamic scattering) mode-device having the liquid crystal composition to which an conducting agent is added, and a NCAP (nematic curvilinear aligned phase) device having the liquid crystal composition microencapsulated, and a PD (polymer dispersed) device having a three-dimensional network polymer formed in the liquid crystal composition, for example, a PN (polymer network) device.

Since the liquid crystal composition of the present invention has the characteristics described above, it can be suitably used for the liquid crystal display device with a AM mode which is driven by means of operation modes such as the VA and IPS modes, wherein the liquid crystal composition having a negative dielectric anisotropy is used, especially for the liquid crystal display device with the AM mode which is driven by means of the VA mode.

The direction of an electric field is perpendicular to liquid crystal layers in a liquid crystal display device which is driven by means of the TN mode, the VA mode or the like. On the other hand, the direction of an electric field is parallel to liquid crystal layers in a liquid crystal display device which is driven by means of the IPS mode or the like. The structure of the liquid crystal display device which is driven by means of the VA mode is reported by K. Ohmuro, S. Kataoka, T. Sasaki and Y. Koike, SID '97 Digest of Technical Papers, 28, 845 (1997), and the structure of the liquid crystal display device which is driven by means of the IPS mode is reported in WO 1991/10936 A (patent family: U.S. Pat. No. 5,576,867).

EXAMPLES

Example of the Liquid Crystal Compound (a)

The invention will be explained below in more detail based on examples. However, the invention is not limited to the examples. The term "%" means "% by weight", unless otherwise specified.

Since the compounds obtained herein were identified on the basis of nuclear magnetic resonance spectra obtained by means of $^1$H-NMR analysis, gas chromatograms obtained by means of gas chromatography (GC) analysis, and so forth, the analytical methods will be explained first.

$^1$H-NMR Analysis:

A model DRX-500 apparatus (made by Bruker BioSpin Corporation) was used for measurement. Samples prepared in examples and so forth were dissolved in deuterated solvents such as $CDCl_3$ in which the samples were soluble, and measurement was carried out under the conditions of room temperature, thirty two times of accumulation, and 500 MHz. In the explanation of the nuclear magnetic resonance spectra obtained, symbols s, d, t, q, m, and br stand for a singlet, doublet, triplet, quartet, multiplet, and broad, respectively. Tetramethylsilane (TMS) was used as a standard reference material for a zero-point on a chemical shift δ value.

GC Analysis:

A Gas Chromatograph Model GC-14B made by Shimadzu Corporation was used for measurement. A capillary column CBP1-M25-025 (length 25 m, bore 0.22 mm, film thickness 0.25 μm; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 280° C. and the temperature of the detector (FID) was set at 300° C.

A sample was dissolved in toluene giving a 1% by weight solution, and then 1 μl of the solution obtained was injected into the sample injector. Chromatopac Model C-R6A made by Shimadzu Corporation or its equivalent was used as a recorder. The resulting gas chromatogram indicated the retention time of peaks and the values of peak areas corresponding to component compounds.

Chloroform or hexane, for example, may also be used as a solvent for diluting the sample. The following capillary columns may also be used: DB-1 (length 30 m, bore 0.32 mm, film thickness 0.25 μm) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd, and so forth.

The ratio of peak areas in the gas chromatogram corresponds to the ratio of component compounds. In general, the percentage by weight of each component compound in an analytical sample is not completely the same with the percentage of each peak area in the analytical sample. In the invention, however, the percentage by weight of the component compound in the analytical sample corresponds substantially to the percentage of the peak area in the analytical sample, because the correction coefficient is essentially 1 when the columns described above are used. This is because there is no significant difference among the correction coefficients of liquid crystal compounds as components. An internal standard method by use of gas chromatograms is used in order to determine the composition ratio of the liquid crystal compounds in the liquid crystal composition more accurately by means of gas chromatograms. The component of each liquid crystal compound (test-component) weighed accurately in a fixed amount and a liquid crystal compound serving as a standard (standard reference material) are analyzed simultaneously by means of gas chromatography, and the relative intensity on the ratio of the peak area of the test-component to that of the standard reference material is calculated in advance. Next, the composition ratio of the liquid crystal compounds in the liquid crystal composition can be determined more accurately by means of the gas-chromatographic analysis using the correction based on the relative intensity of the peak area of each component to that of the standard reference material.

[Samples for Measuring Physical Property-Values of Liquid Crystal Compounds and So Forth]

Two kinds of samples are used for measuring the physical property-values of a liquid crystal compound: one is a compound itself, and the other is a mixture of the compound and mother liquid crystals.

In the latter case using a sample in which a compound is mixed with mother liquid crystals, measurement is carried out according to the following method. First, the sample is prepared by mixing 15% by weight of the liquid crystal compound obtained and 85% by weight of the mother liquid crystals. Then, extrapolated values are calculated from the measured values of the resulting sample by means of an extrapolation method based on the following formula. The extrapolated values are regarded as the physical property-values of the compound.

<Extrapolated Value>=(100×<Measured value of sample>−<% by weight of mother liquid crystals>×<Measured value of mother liquid crystals>)/<% by weight of liquid crystal compound>

When a smectic phase or crystals are deposited even at this ratio of the liquid crystal compound to the mother liquid crystals at 25° C., the ratio of the liquid crystal compound to the mother liquid crystals is changed in the order of (10% by weight: 90% by weight), (5% by weight: 95% by weight), and (1% by weight: 99% by weight). The physical property-values of the sample are measured at the ratio in which the smectic phase or the crystals are not deposited at 25° C. Extrapolated values are determined according to the above equation, and regarded as the physical property-values of the liquid crystal compound.

There are a variety of mother liquid crystals used for the measurement and, for example, the composition ratio (% by weight) of the mother liquid crystals (i) is as shown below.

Mother Liquid Crystals (i):

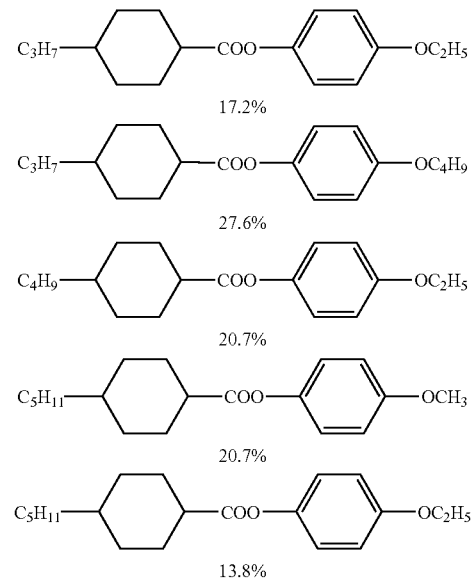

A liquid crystal composition itself was used as a sample for measuring the physical property-values of the liquid crystal composition.

[Method for Measuring Physical Property-Values of Liquid Crystal Compounds and So Forth]

Physical property-values were measured according to the following methods. Most of the measurement methods were described in the Standard of Electronic Industries Association of Japan, EIAJ•ED-2521A, or those with some modifications. No TFT was attached to a TN device used for measurement.

In the measured values, values obtained by use of a sample of a liquid crystal compound itself and values obtained by use of a sample of a liquid crystal composition itself, as they were, were reported herein as experimental data. Values obtained by extrapolating measured values of a sample in which a compound was mixed to mother liquid crystals were reported herein as experimental data.

Phase Structure and Transition Temperature (° C.):

Measurement was carried out according to the following methods (1) and (2).

(1) A compound was placed on a hot plate of a melting point apparatus (Hot Stage Model FP-52 made by Mettler Toledo International Inc.) equipped with a polarizing microscope, and phase conditions and their changes were observed with the polarizing microscope, specifying the kinds of liquid crystal phases while the compound was heated at the rate of 3° C. per minute.

(2) A sample was heated and then cooled at a rate of 3° C. per minute by use of a Perkin-Elmer differential scanning calorimeter, a DSC-7 System or a Diamond DSC System. A starting point of an endothermic peak or an exothermic peak caused by a phase change of the sample was obtained by means of the extrapolation (on set) and the phase transition temperature was determined.

Hereinafter, the symbol C stood for crystals, which were expressed by $C_1$ or $C_2$ when the kinds of crystals were distinguishable. The symbols S and N stood for a smectic phase and a nematic phase, respectively. The symbol I stood for a liquid (isotropic). When a smectic B phase, or a smectic A phase was distinguishable in the smectic phases, they were expressed as $S_B$, or $S_A$ respectively. Transition temperatures were expressed as, for example, "C 50.0 N 100.0 I", which means that the transition temperature from crystals to a nematic phase (CN) is 50.0° C., and the transition temperature from the nematic phase to a liquid (NI) is 100.0° C. The same applied to other transition temperatures.

Maximum Temperature of Nematic Phase ($T_{NI}$; ° C.):

A sample (a liquid crystal composition, or a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. A maximum temperature meant a temperature measured when part of the sample began to change from a nematic phase to an isotropic liquid. Hereinafter, the maximum temperature of a nematic phase may simply be abbreviated to "maximum temperature".

Compatibility at Low Temperature:

Samples were prepared by mixing a compound with mother liquid crystals so that the amount of the liquid crystal compound became 20% by weight, 15% by weight, 10% by weight, 5% by weight, 3% by weight, and 1% by weight, and placed in glass vials. After these glass vials had been kept in a freezer at −10° C. or −20° C. for a certain period, they were observed whether or not crystals or a smectic phase had been deposited.

Viscosity (η; measured at 20° C.; mPa·s):

Viscosity was measured by use of an E-type viscometer.

Rotational Viscosity (γ1; measured at 25° C.; mPa·s)

Measurement was carried out according to the method described in M. Imai, et al., Molecular Crystals and Liquid Crystals, Vol. 259, 37 (1995). A sample (a liquid crystal composition, or a mixture of a liquid crystal compound and mother liquid crystals) was put in a VA device in which a distance between two glass substrates (cell gap) was 20 μm. Voltage was applied to the device stepwise with an increment of 1 volt in the range of 30 to 50 volts. After 0.2 second without the voltage applied, applied voltage was repeated under the conditions of only one rectangular wave (rectangular pulse; 0.2 second) and no voltage applied (2 seconds). The peak current and the peak time of a transient current generated by the applied voltage were measured. The value of rotational viscosity was obtained from the measured values and the calculating equation (8) in page 40 of the paper presented by M. Imai, et al. The value of dielectric anisotropy necessary for the calculation was available from the section on dielectric anisotropy described below.

Optical Anisotropy (Refractive Index Anisotropy; measured at 25° C.; Δn).

Measurement was carried out by use of an Abbe refractometer with a polarizing plate attached to the ocular, using light at a wavelength of 589 nm. The surface of a main prism was rubbed in one direction, and then a sample (a liquid crystal composition, or a mixture of a liquid crystal compound and mother liquid crystals) was dropped onto the main prism. A refractive index (n∥) was measured when the direction of polarized light was parallel to that of the rubbing. A refractive index (n⊥) was measured when the direction of polarized light was perpendicular to that of the rubbing. The value of optical anisotropy was calculated from the equation: Δn=n∥−n⊥.

Dielectric Anisotropy (Δ∈; measured at 25° C.):

Dielectric anisotropy was measured by the following method. An ethanol solution (20 mL) of octadecyltriethoxysilane (0.16 mL) was applied to well-washed glass substrates. The glass substrates were rotated with a spinner, and then heated at 150° C. for 1 hour. A VA device in which a distance (cell gap) was 20 μm was assembled from the two glass substrates.

A polyimide alignment film was prepared on glass substrates in a similar manner. After a rubbing-treatment to the alignment film obtained on the glass substrates, a TN device in which a distance between the two glass substrates was 9 μm and the twist angle was 80 degrees was assembled.

A sample (a liquid crystal composition, or a mixture of a liquid crystal compound and mother liquid crystals) was put in the VA device obtained, applied with a voltage of 0.5 V (1 kHz, sine waves), and then a dielectric constant (∈∥) in a major axis direction of liquid crystal molecules was measured.

The sample (the liquid crystal composition, or the mixture of the liquid crystal compound and the mother liquid crystals) was put in the TN device obtained, applied with a voltage of 0.5 V (1 kHz, sine waves), and then a dielectric constant (∈⊥) in a minor axis direction of liquid crystal molecules was measured. The value of dielectric anisotropy was calculated from the equation of ∈=∈∥−∈⊥.

Voltage Holding Ratio (VHR; measured at 25° C.; %):

A TN device used for measurement had a polyimide-alignment film and a distance between two glass substrates (cell gap) of 6 μm. A sample was put in the device, and then the device was sealed with an adhesive polymerizable under ultraviolet radiation. The TN device was charged at 25° C. by applying pulse voltage (60 microseconds at 5 V). Decaying voltage was measured for 16.7 milliseconds with a High Speed Voltmeter, and the area A between a voltage curve and a horizontal axis in a unit period was measured. The area B was an area without the voltage decay. The voltage holding ratio was the percentage of the area A to the area B.

Elastic Constant ($K_{11}$ and $K_{33}$; measured at 25° C.):

Elastic Constant Measurement System Model EC-1 made by Toyo Corporation was used for measurement. A sample was put in a homeotropic cell in which a distance between two glass substrates (cell gap) was 20 μm. An electric charge of 20 volts to 0 volts was applied to the cell, and electrostatic capacity and applied voltage were measured. The measured values of the electric capacity (C) and the applied voltage (V) were fitted to formula (2.98) and formula (2.101) in page 75 of the "Liquid crystal device handbook" (Nikkan Kogyo Shimbun) and the value of the elastic constant was obtained from formula (2.100).

Example 1

Synthesis of 4-ethoxy-2,3,2"-trifluoro-4"-(trans-4-propylcyclohexyl)-1,1'-terphenyl (No. 12)

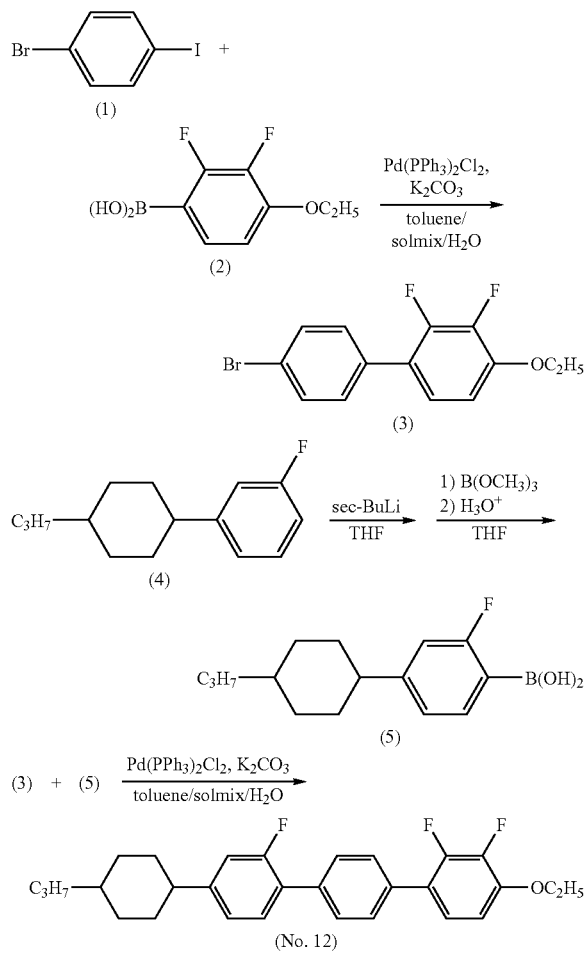

First Step:

4-Bromoiodobenzene (1) (20.0 g), 4-ethoxy-2,3-difluorophenylboronic acid (2) (14.4 g), potassium carbonate (29.3 g), $Pd(Ph_3P)_2Cl_2$ (1.49 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. The mixture was then allowed to stand until it had separated into two phases of organic and aqueous phases, and an extractive operation to an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The product was further purified by means of recrystallization from Solmix A-11 and dried, giving 20.8 g of 4-ethoxy-4'-bromo-2,3-difluoro-1,1'-biphenyl (3). The yield based on the compound (1) was 94.0%.

Second Step:

4-Propyl-1-(3-fluorophenyl)-cyclohexane (4) (10.0 g) and THF (100 ml) were put in a reaction vessel under a nitrogen atmosphere, and cooled to −74° C. Then, sec-butyllithium (1.00 M, in a cyclohexane and n-hexane solution; 49.9 ml) was added dropwise thereto in the temperature range of −74° C. to −70° C., and the mixture was stirred for another 2 hours. Subsequently, trimethyl borate (5.2 g) in a THF (50 ml) solution was added dropwise thereto in the temperature range of −74° C. to −65° C., and the mixture was stirred for another 8 hours while allowing the temperature to come to 25° C. Then, the reaction mixture was poured into a vessel containing 1N-hydrochloric acid (100 ml) and ice-water (500 ml), and mixed. Ethyl acetate (300 ml) was added thereto and the mixture was allowed to be separated into organic and aqueous phases, and then an extractive operation was carried out. The organic phase was fractionated, washed sequentially with a saturated aqueous solution of sodium hydrogencarbonate and brine, and then dried over anhydrous magnesium sulfate. The solvent was then distilled off under reduced pressure, giving 11.9 g of 2-fluoro-4-(4-propylcyclohexyl)-boronic acid (5). The yield based on the compound (4) was 99.0%.

Third Step:

The compound (3)(7.2 g), the boronic acid derivative (5) (6.0 g), potassium carbonate (7.8 g), $Pd(Ph_3P)_2Cl_2$ (0.4 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (300 ml) and toluene (200 ml), and mixed. The mixture was then allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The product was further purified by means of recrystallization from a mixed solvent of ethyl acetate and Solmix A-11 (volume ratio; ethyl acetate: Solmix A-11=2:1) and dried, giving 5.5 g of 4-ethoxy-2,3,2"-trifluoro-4"-(trans-4-propylcyclohexyl)-1,1'-terphenyl (No. 12). The yield based on the compound (3) was 53.1%.

The chemical shift δ (ppm) in $^1$H-NMR analysis was described below, and the compound obtained was identified as 4-ethoxy-2,3,2"-trifluoro-4"-(trans-4-propylcyclohexyl)-1,1'-terphenyl. The solvent for measurement was $CDCl_3$.

Chemical shift δ (ppm); 7.58 (dd, 4H), 7.38 (t, 1H), 7.13 (td, 1H), 7.06 (dd, 1H), 7.01 (dd, 1H), 6.80 (t, 1H), 4.17 (q, 2H), 2.51 (dd, 1H), 1.90 (dd, 4H), 1.52-1.42 (m, 5H), 1.41-1.27 (m, 3H), 1.27-1.20 (m, 2H), 1.13-1.02 (m, 2H), and 0.91 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 12) were as follows.

Transition temperature: C 118.1, N 304.9, I.
$T_{NI}$=238.6° C., $\Delta\varepsilon$=−7.22, $\Delta n$=0.271.

Example 2

Synthesis of 4-ethoxy-2,3,2″-trifluoro-4″-(trans-4-pentylcyclohexyl)-1,1′-terphenyl (No. 32)

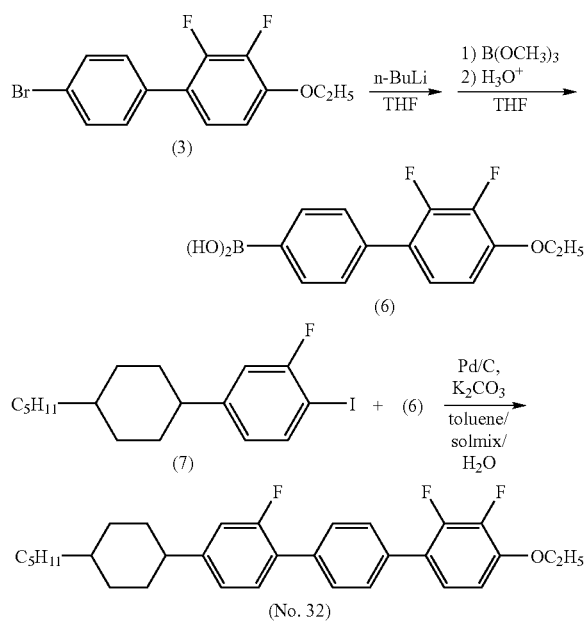

First Step:

The compound (3) (10.0 g) and THF (100 ml) were put in a reaction vessel under a nitrogen atmosphere, and cooled to −74° C. n-Butyllithium (1.57 M in a n-hexane solution; 22.4 ml) was added dropwise thereto in the temperature range of −74° C. to −70° C., and the mixture obtained was stirred for another 2 hours. Subsequently, trimethyl borate (4.0 g) in a THF (50 ml) solution was added dropwise thereto in the temperature range of −74° C. to −65° C., and the mixture was stirred for another 8 hours while allowing the temperature to come to 25° C. Then, the reaction mixture was poured into a vessel containing 1N-hydrochloric acid (100 ml) and ice-water (500 ml), and mixed. Ethyl acetate (300 ml) was added thereto and the mixture was allowed to be separated into organic and aqueous phases, and then an extractive operation was carried out. The organic phase obtained was fractionated, washed sequentially with a saturated aqueous solution of sodium hydrogencarbonate and brine, and then dried over anhydrous magnesium sulfate. The solvent was then distilled off under reduced pressure, giving 11.7 g of 4-ethoxy-2,3-difluoro-1,1′-biphenyl-4′-boronic acid (6). The yield based on the compound (3) was 81.1%.

Second Step:

4-Pentyl-1-(3-fluoro-4-iodinephenyl)-cyclohexane (7) (3.0 g), the dihydroxyborane derivative (6) (2.7 g), potassium carbonate (3.3 g), palladium carbon catalyst (NX type of 5% Pd/C; 50% wet; made by N. E. Chemcat; hereinafter referred to as Pd/C(NX type)) (0.03 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (300 ml) and toluene (300 ml), and mixed. The mixture was then allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The product was further purified by means of recrystallization from a mixed solvent of ethyl acetate/Solmix A-11 (volume ratio; ethyl acetate: Solmix A-11=1:1) and dried, giving 3.5 g of 4-ethoxy-2,3,2″-trifluoro-4″-(trans-4-pentylcyclohexyl)-1,1′-terphenyl (No. 32). The yield based on the compound (7) was 90.9%.

The chemical shift δ (ppm) in $^1$H-NMR analysis was described below, and the compound obtained was identified as 4-ethoxy-2,3,2″-trifluoro-4″-(trans-4-pentylcyclohexyl)-1,1′-terphenyl. The solvent for measurement was CDCl$_3$.

The chemical shift δ (ppm); 7.59 (dd, 4H), 7.39 (t, 1H), 7.14 (td, 1H), 7.07 (dd, 1H), 7.02 (dd, 1H), 6.81 (t, 1H), 4.17 (q, 2H), 2.51 (dd, 1H), 1.92 (dd, 4H), 1.53-1.42 (m, 5H), 1.37-1.20 (m, 9H), 1.10-1.01 (m, 2H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy ($\Delta\varepsilon$), and the optical anisotropy ($\Delta n$). The physical property-values of the compound (No. 32) were as follows.

Transition temperature: C 107.8 N 299.3 I.
$T_{NI}$=238.6° C., $\Delta\varepsilon$=−5.54, $\Delta n$=0.257.

Example 3

Synthesis of 4-ethoxy-2,3,2″-trifluoro-4″-(trans-4-heptylcyclohexyl)-1,1′-terphenyl (No. 52)

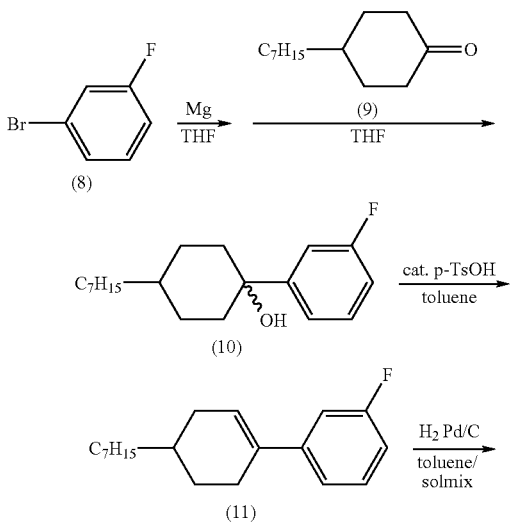

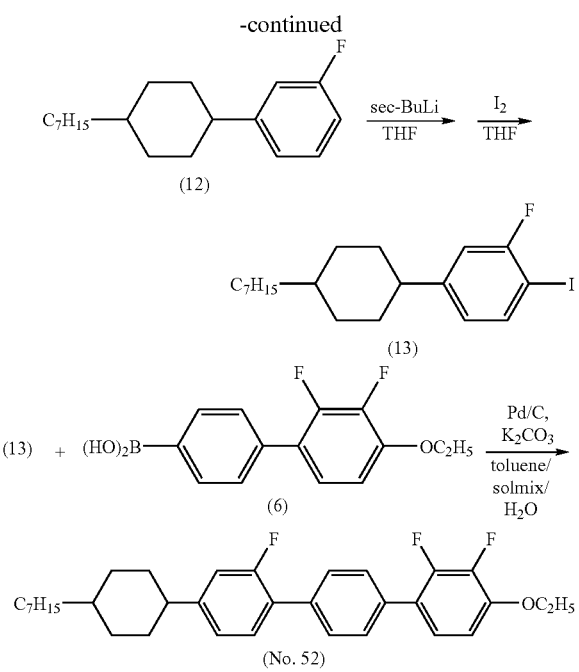

First Step:

Well-dried magnesium (8.3 g) and THF (20 ml) were put in a reaction vessel under a nitrogen atmosphere, and heated to 50° C. 3-Fluorobromobenzene (8) (60.0 g) dissolved in THF (300 ml) was slowly added dropwise thereto in the temperature range of 40° C. to 60° C., and the mixture was stirred for another 60 minutes. Then, 4-heptylcyclohexanone (9) (50.0 g) dissolved in THF (150 ml) was slowly added dropwise thereto in the temperature range of 50° C. to 60° C., and the mixture was stirred for another 60 minutes. The reaction mixture obtained was cooled to 30° C., and then poured into a vessel containing an aqueous 1N—HCl solution (900 ml) and ethyl acetate (500 ml), and mixed. The mixture was then allowed to stand until it had separated into two phases of organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was distilled off under reduced pressure, giving 80.0 g of 4-heptyl-1-(3-fluorophenyl)-cyclohexanol (10). The compound (10) obtained was a yellow oil.

Second Step:

The compound (10) (80.0 g), p-toluenesulfonic acid (2.4 g) and toluene (250 ml) were mixed, and the mixture was heated under reflux for 2 hours while water being distilled was removed. The reaction mixture obtained was cooled to 30° C., and then water (500 ml) and toluene (900 ml) were added and mixed thereto. The mixture was then allowed to stand until it had separated into two phases of organic and aqueous phases, and an extractive operation into an organic phase was carried out. The organic phase obtained was fractionated, washed with a saturated aqueous solution of sodium hydrogencarbonate and water, and then dried over anhydrous magnesium sulfate. The solution obtained was purified with a fractional operation by means of column chromatography using heptane as the eluent and silica gel as the stationary phase powder, and dried, giving 70.3 g of 4-heptyl-1-(3-fluorophenyl)-3-cyclohexene (11). The yield based on the compound (11) was 94.0%.

Third Step:

The compound (11) was dissolved in a mixed solvent of toluene (150 ml) and Solmix A-11 (150 ml), and 0.86 g of Pd/C(NX type) was added thereto. The mixture was stirred at room temperature under a hydrogen atmosphere until hydrogen absorption had ceased. After the reaction had been completed, Pd/C was removed and then the solvent was distilled off. The residue obtained was purified with a fractional operation by means of column chromatography using heptane as the eluent and silica gel as the stationary phase powder, and further purified by means of recrystallization from Solmix A-11, and dried, giving 44.7 g of 4-heptyl-1-(3-fluorophenyl)-cyclohexane (12). The yield based on the compound (12) was 75.8%.

Fourth Step:

The compound (12) (5.0 g) and THF (100 ml) were put in a reaction vessel under a nitrogen atmosphere, and cooled to −74° C. sec-Butyllithium (1.00 M, in a n-hexane and cyclohexane solution; 20.0 ml) was added dropwise thereto in the temperature range of −74° C. to −70° C., and the mixture was stirred for another 2 hours. Subsequently, iodine (5.1 g) in a THF (20 ml) solution was added dropwise thereto in the temperature range of −75° C. to −70° C., and the mixture was stirred for another 8 hours while allowing the temperature to come to 25° C. The reaction mixture obtained was poured into an aqueous solution of sodium thiosulfate (500 ml), and mixed. Toluene (300 ml) was added thereto and the mixture was allowed to be separated into organic and aqueous phases, and an extractive operation was carried out. The organic phase obtained was fractionated, washed with brine, and then dried over anhydrous magnesium sulfate. The solution obtained was concentrated under reduced pressure, and the residue obtained was purified with a fractional operation by means of column chromatography using heptane as the eluent and silica gel as the stationary phase powder, the solvent was distilled off, and then the residue was dried, giving 5.7 g of 4-heptyl-1-(4-iodine-3-fluorophenyl)-cyclohexane (13). The yield based on the compound (12) was 78.3%.

Fifth Step:

The compound (13) (5.7 g), the dihydroxyborane derivative (6) (4.7 g), potassium carbonate (5.9 g), Pd/C(NX type) (0.05 g), toluene (100 ml), Solmix A-11 (100 ml), and water (100 ml) were put in a reaction vessel under a nitrogen atmosphere, and heated under reflux for 2 hours. The reaction mixture was cooled to 25° C., poured into water (300 ml) and toluene (300 ml), and then mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The product was further purified by means of recrystallization from a mixed solvent of ethyl acetate/Solmix A-11 (volume ratio; ethyl acetate: Solmix A-11=2:1) and dried, giving 4.6 g of 4-ethoxy-2,3,2"-trifluoro-4"-(trans-4-heptylcyclohexyl)-1, 1'-terphenyl (No. 52). The yield based on the compound (13) was 63.6%.

The chemical shift δ (ppm) in $^1$H-NMR analysis was described below, and the compound obtained was identified as 4-ethoxy-2,3,2"-trifluoro-4"-(trans-4-heptylcyclohexyl)-1,1'-terphenyl. The solvent for measurement was $CDCl_3$.

Chemical shift δ (ppm); 7.59 (dd, 4H), 7.39 (t, 1H), 7.15 (td, 1H), 7.07 (dd, 1H), 7.02 (dd, 1H), 6.82 (t, 1H), 4.17 (q, 2H), 2.51 (dd, 1H), 1.91 (dd, 4H), 1.52-1.42 (m, 5H), 1.37-1.20 (m, 13H), 1.10-1.01 (m, 2H), and 0.89 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy ($\Delta\varepsilon$), and the optical anisotropy ($\Delta n$). The physical property-values of the compound (No. 52) were as follows.

Transition temperature: C 116.6 $S_A$ 175.0 N 281.2 I.
$T_{NI}$=236.6° C., $\Delta\varepsilon$=-4.88, $\Delta n$=0.227.

Example 4

Synthesis of 4-(4-ethoxy-2,3,3"-trifluoro-1,1'-terphenyl)-1-propylcyclohexyl-3-ene (No. 652)

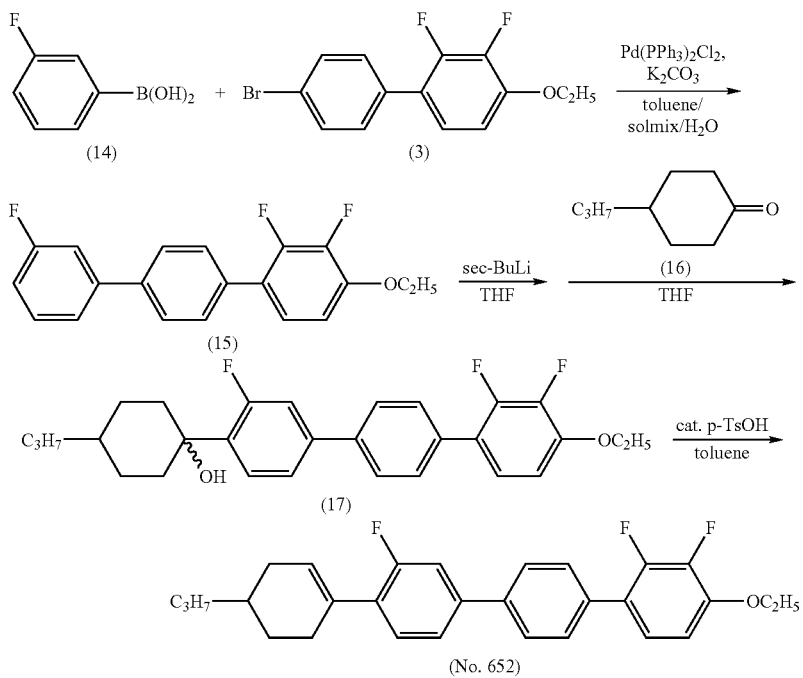

First Step:

4-Ethoxy-4'-bromo-2,3-difluoro-1,1'-biphenyl (3) (10.0 g), 3-fluorophenylboronic acid (14) (4.5 g), potassium carbonate (13.2 g), Pd(Ph$_3$P)$_2$Cl$_2$ (0.7 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The product was further purified by means of recrystallization from a mixed solvent of ethyl acetate/Solmix A-11 (volume ratio; ethyl acetate: Solmix A-11=2:1), and dried, giving 9.3 g of 4-ethoxy-2,3,3"-trifluoro-1,1'-terphenyl (15). The yield based on the compound (3) was 88.7%.

Second Step:

The compound (15) (5.0 g) and THF (100 ml) were put in a reaction vessel under a nitrogen atmosphere, and cooled to -74° C. sec-Butyllithium (1.00 M, in a n-hexane and cyclohexane solution; 16.8 ml) was added dropwise thereto in the temperature range of -74° C. to -70° C., and the mixture was stirred for another 2 hours. Subsequently, 4-propylhexanone (16) (2.4 g) in a THF (20 ml) solution was added dropwise thereto in the temperature range of -75° C. to -70° C., and the mixture was stirred for another 8 hours while allowing the temperature to come to 25° C. The reaction mixture obtained was poured into a vessel containing an aqueous 1N—HCl solution (200 ml) and ethyl acetate (300 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. Subsequently, the solvent was distilled off under reduced pressure, giving 7.0 g of 4-(4-ethoxy-2,3, 3"-trifluoro-1,1'-terphenyl)-1-propylcyclohexanol (17). The compound (17) obtained was white solids.

Third Step:

The compound (17) (7.0 g), p-toluenesulfonic acid (0.2 g), and toluene (250 ml) were mixed, and the mixture was heated under reflux for 2 hours while water being distilled was removed. The reaction mixture was cooled to 30° C., and then water (300 ml) and toluene (500 ml) were added and mixed thereto. The mixture was then allowed to stand until it had separated into two phases of organic and aqueous phases, and an extractive operation was carried out. The organic phase obtained was fractionated, washed with a saturated aqueous solution of sodium hydrogencarbonate and water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene:heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 6.0 g of 4-(4-ethoxy-2,3,3"-trifluoro-1,1'-terphenyl)-1-propylcyclohexyl-3-ene (No. 652). The yield based on the compound (17) was 89.1%.

The chemical shift δ (ppm) in $^1$H-NMR analysis was described below, and the compound obtained was identified as 4-(4-ethoxy-2,3,3"-trifluoro-1,1'-terphenyl)-1-propylcyclohexyl-3-ene. The solvent for measurement was $CDCl_3$.

Chemical shift δ (ppm); 7.62 (dd, 4H), 7.38-7.28 (m, 3H), 7.14 (td, 1H), 6.82 (t, 1H), 6.01 (m, 1H), 4.17 (q, 2H), 2.56-2.47 (m, 1H), 2.47-2.38 (m, 1H), 2.34 (dt, 1H), 1.93-1.80 (m, 2H), 1.70-1.61 (m, 1H), 1.50 (t, 3H), 1.45-1.35 (m, 3H), 1.35-1.28 (m, 2H), and 0.94 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 652) were as follows.

Transition temperature: C 102.1 $S_A$ 136.8 N 299.0 I.
$T_{NI}$=247.6° C., Δ∈=−5.12, Δn=0.298.

Example 5

Synthesis of 4-(4-ethoxy-2,3,3"-trifluoro-1,1'-terphenyl)-1-propylcyclohexane (No. 172)

trifluoro-1,1'-terphenyl)-1-propylcyclohexane (No. 172). The yield based on the compound (No. 652) was 19.0%.

Chemical shift δ (ppm) in $^1$H-NMR analysis was described below, and the compound obtained was identified as 4-(4-ethoxy 2,3,3"-trifluoro-1,1'-terphenyl)-1-propylcyclohexane. The solvent for measurement was $CDCl_3$.

Chemical shift δ (ppm); 7.59 (dd, 4H), 7.38-7.27 (m, 3H), 7.13 (td, 1H), 6.81 (t, 1H), 4.17 (q, 2H), 2.85 (dd, 1H), 1.90 (dd, 4H), 1.58-1.45 (m, 5H), 1.42-1.28 (m, 3H), 1.28-1.20 (m, 2H), 1.16-1.05 (m, 2H), and 0.91 (t, 3H)

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 172) were as follows.

Transition temperature: C 129.1 N 311.7 I.
$T_{NI}$=246.6° C., Δ∈=−6.62, Δn=0.271.

Example 6

Synthesis of 4-(4-ethoxy-2,3,2"-trifluoro-1,1'-terphenyl)-1-propylcyclohexyl-3-ene (No. 492)

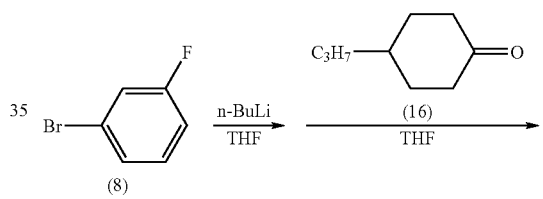

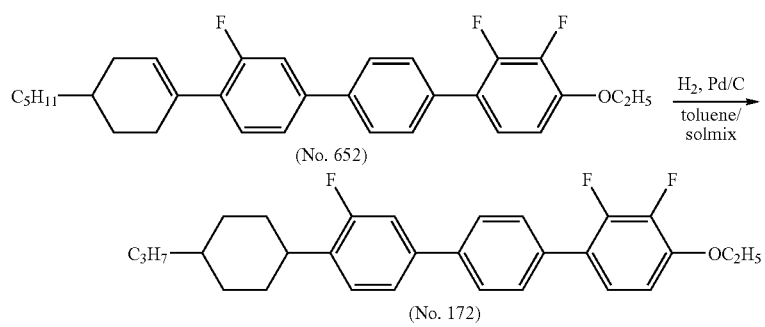

First Step:

The compound (No. 652) (3.3 g) was dissolved in a mixed solvent of toluene (150 ml) and Solmix A-11 (150 ml), and Pd/C (NX type) (0.02 g) was added thereto. The mixture was stirred at room temperature under a hydrogen atmosphere until hydrogen absorption had ceased. After the reaction had been completed, Pd/C was removed and then the solvent was distilled off. The residue obtained was purified with a fractional operation by means of column chromatography using heptane as the eluent and silica gel as the stationary phase powder, further purified by means of recrystallization from Solmix A-11 and dried, giving 0.6 g of 4-(4-ethoxy-2,3,3"-

-continued

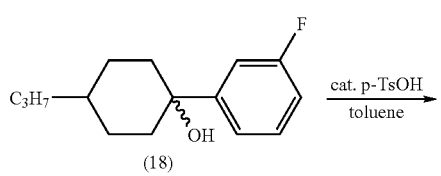

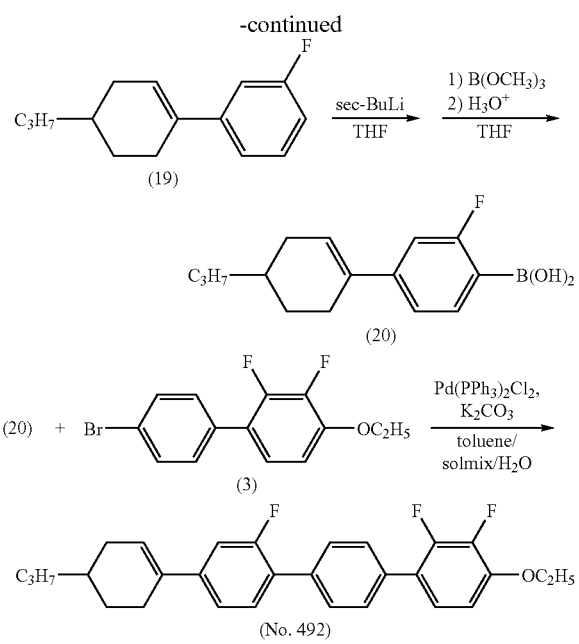

First Step:

3-Fluorobromobenzene (8) (10.0 g) and THF (100 ml) were put in a reaction vessel under a nitrogen atmosphere, and cooled to −74° C. n-Butyllithium (1.57 M, in a n-hexane solution; 40.0 ml) was added dropwise thereto in the temperature range of −74° C. to −70° C., and the mixture was stirred for another 2 hours. Subsequently, 4-propylhexanone (16) (12.0 g) in a THF (50 ml) solution was added dropwise thereto in the temperature range of −74° C. to −65° C., and the mixture was stirred for another 8 hours while allowing the temperature to come to 25° C. The reaction mixture obtained was poured into a vessel containing a 1N—HCl solution (500 ml) and ethyl acetate (300 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. Subsequently, the solvent was distilled off under reduced pressure, giving 13.5 g of 4-propyl-1-(3-fluorophenyl)-cyclohexanol (18). The compound (18) obtained was a yellow oil.

Second Step:

The compound (18) (13.5 g), p-toluenesulfonic acid (0.4 g) and toluene (250 ml) were mixed, and the mixture was heated under reflux for 2 hours while water being distilled was removed. The reaction mixture was cooled to 30° C., and then water (300 ml) and toluene (500 ml) were added and mixed thereto. The mixture was then allowed to stand until it had separated into organic and aqueous phases, and an extractive operation was carried out. The organic phase obtained was fractionated, washed with a saturated aqueous solution of sodium hydrogencarbonate and water, and then dried over anhydrous magnesium sulfate. The solution obtained was purified with a fractional operation by means of column chromatography using heptane as the eluent and silica gel as the stationary phase powder and dried, giving 7.7 g of 4-propyl-1-(3-fluorophenyl)-3-cyclohexene (19). The yield based on the compound (18) was 61.7%.

Third Step:

4-Propyl-1-(3-fluorophenyl)-3-cyclohexene (19) (7.7 g) and THF (100 ml) were put in a reaction vessel under a nitrogen atmosphere, and cooled to −74° C. sec-Butyllithium (1.00 M, in a n-hexane and cyclohexane solution; 42.3 ml) was added dropwise thereto in the temperature range of −74° C. to −70° C., and the mixture was stirred for another 2 hours. Subsequently, trimethyl borate (5.5 g) in a THF (50 ml) solution was added dropwise thereto in the temperature range of −74° C. to −65° C., and the mixture was stirred for another 8 hours while allowing the temperature to come to 25° C. Then, the reaction mixture was poured into a vessel containing 1N-hydrochloric acid (100 ml) and ice-water (500 ml), and mixed. Ethyl acetate (300 ml) was added thereto and the mixture was allowed to be separated into organic and aqueous phases, and then an extractive operation was carried out. The organic phase obtained was fractionated, washed with water, a saturated aqueous solution of sodium hydrogencarbonate and brine, and then dried over anhydrous magnesium sulfate. The solvent was then distilled off under reduced pressure, giving 6.4 g of 2-fluoro-4-(4-propyl-3-cyclohexenyl)-boronic acid (20). The yield based on the compound (19) was 69.2%.

Fourth Step:

4-Ethoxy-4'-bromo-2,3-difluoro-1,1'-biphenyl (3) (2.0 g), the boronic acid derivative (20) (2.5 g), potassium carbonate (2.7 g), Pd(Ph$_3$P)$_2$Cl$_2$ (0.1 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 2.5 g of 4-(4-ethoxy-2,3,2''-trifluoro-1,1'-terphenyl)-1-propylcyclohexyl-3-ene (No. 492). The yield based on the compound (3) was 85.1%.

The chemical shift δ (ppm) in $^1$H-NMR analysis was described below, and the compound obtained was identified as 4-(4-ethoxy-2,3,2''-trifluoro-1,1'-terphenyl)-1-propyl-cyclohexyl-3-ene. The solvent for measurement was CDCl$_3$.

Chemical shift δ (ppm); 7.60 (dd, 4H), 7.40 (t, 1H), 7.26 (dd, 1H), 7.19 (dd, 1H), 7.14 (td, 1H), 6.81 (t, 1H), 6.22 (br, 1H), 4.16 (q, 2H), 2.46 (br, 2H), 2.35 (dt, 1H), 1.94 (m, 1H), 1.85 (m, 1H), 1.67-1.57 (m, 1H), 1.49 (t, 3H), 1.44-1.25 (m, 5H), and 0.93 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 92) were as follows.

Transition temperature: C 117.6 N 294.9 I.
$T_{NI}$=252.6° C., Δ∈=−6.29, Δn=0.307.

Example 7

Synthesis of 4-(4-ethoxy-2,3,2"-trifluoro-1,1'-terphenyl)-1-pentylcyclohexyl-3-ene (No. 512)

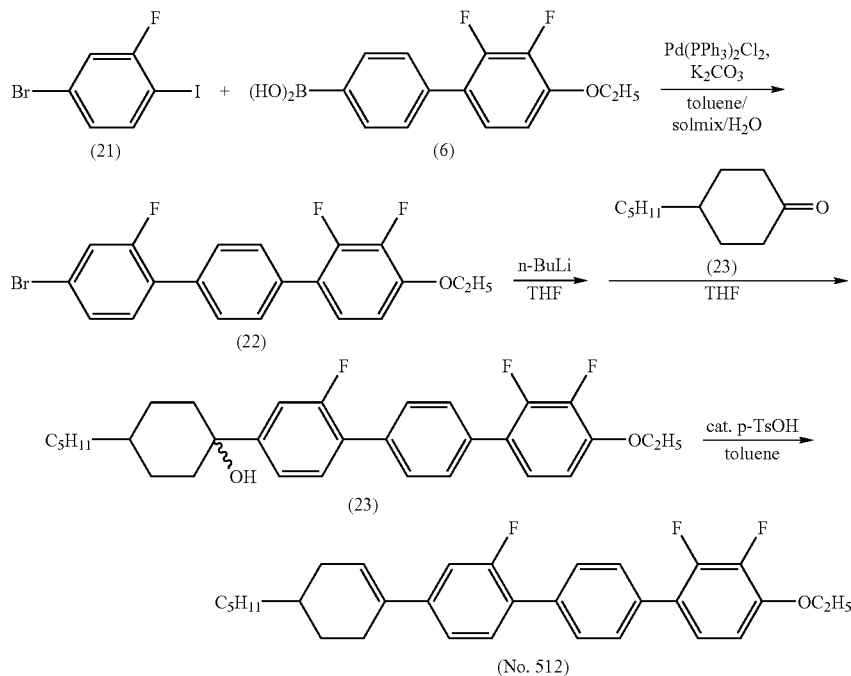

First Step:

4-Bromo-2-fluoro-iodobenzene (21) (5.0 g), 4-ethoxy-2,3-difluoro-1,1'-biphenyl-4'-boronic acid (6) (4.7 g), potassium carbonate (6.9 g), Pd(Ph$_3$P)$_2$Cl$_2$ (0.4 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 5.6 g of 4'-bromo-4-ethoxy-2,3,2"-trifluoro-1,1'-terphenyl (22). The yield based on a compound (21) was 82.8%.

Second Step:

The compound (22) (10.0 g) and THF (100 ml) were put in a reaction vessel under a nitrogen atmosphere, and cooled to −74° C. n-Butyllithium (1.57 M, in a n-hexane solution; 17.2 ml) was added dropwise thereto in the temperature range of −74° C. to −70° C., and the mixture was stirred for another 2 hours. Subsequently, 4-pentylcyclohexanone (23) (6.2 g) in a THF (50 ml) solution was added dropwise thereto in the temperature range of −75° C. to −70° C., and the mixture was stirred for another 8 hours while allowing the temperature to come to 25° C. The reaction mixture obtained was poured into a vessel containing a 1N—HCl solution (200 ml) and ethyl acetate (300 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was then distilled off under reduced pressure, giving 12.0 g of 4-(4-ethoxy-2,3,2"-trifluoro-1,1'-terphenyl)-1-pentylcyclohexanol (23). The compound (23) obtained was white solids.

Third Step:

The compound (23) (12.0 g), p-toluenesulfonic acid (0.4 g), and toluene (250 ml) were mixed, and the mixture was heated under reflux for 2 hours while water being distilled was removed. The reaction mixture was cooled to 30° C., and then water (300 ml) and toluene (500 ml) were added thereto. The mixture was mixed, and then allowed to stand until it had separated into organic and aqueous phases, and an extractive operation was carried out. The organic phase obtained was fractionated, washed with a saturated aqueous solution of sodium hydrogencarbonate and water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 7.2 g of 4-(4-ethoxy-2,3,2"-trifluoro-1,1'-terphenyl)-1-pentylcyclohexyl-3-ene (No. 512). The yield based on the compound (23) was 62.2%.

The chemical shift δ (ppm) in $^1$H-NMR analysis was described below, and the compound obtained was identified as 4-(4-ethoxy-2,3,2"-trifluoro-1,1'-terphenyl)-1-pentylcyclohexyl-3-ene. The solvent for measurement was CDCl$_3$.

Chemical shift δ (ppm); 7.60 (dd, 4H), 7.42 (t, 1H), 7.26 (dd, 1H), 7.19 (dd, 1H), 7.14 (td, 1H), 6.81 (t, 1H), 6.22 (br, 1H), 4.16 (q, 2H), 2.46 (br, 2H), 2.35 (dt, 1H), 1.94 (m, 1H), 1.86 (m, 1H), 1.65-1.54 (m, 1H), 1.49 (t, 3H), 1.43-1.24 (m, 9H), and 0.91 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature (T$_{NI}$), the dielectric anisotropy (Δ∈), and the optical anisotropy (Δn). The physical property-values of the compound (No. 512) were as follows.

Transition temperature: C 94.7 N 289.8 I.
T$_{NI}$=250.6° C., Δ∈=−6.43, Δn=0.287.

Example 8

Synthesis of 4-(4-ethoxy-2,3,2"-trifluoro-1,1'-terphenyl)-1-heptylcyclohexyl-3-ene (No. 532)

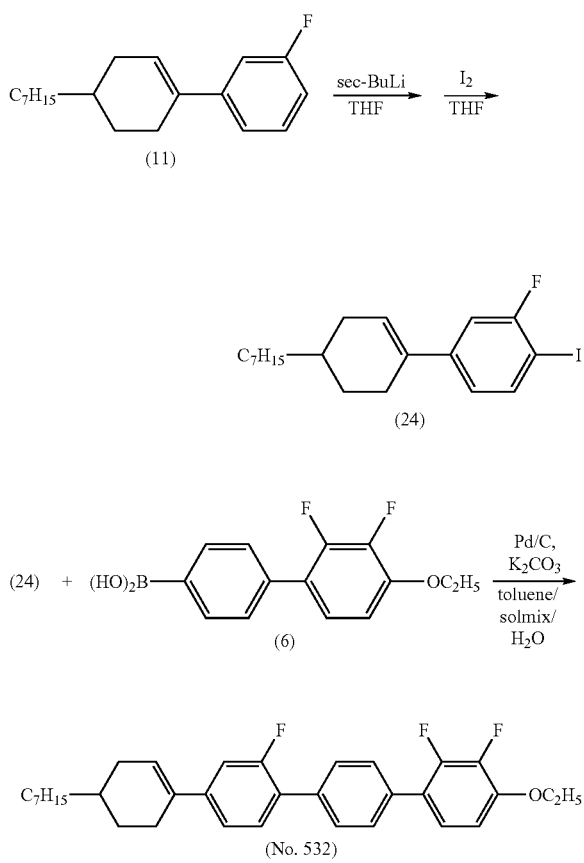

First Step:

4-Heptyl-1-(3-fluorophenyl)-3-cyclohexene (11) (10.0 g) and THF (100 ml) were put in a reaction vessel under a nitrogen atmosphere, and cooled to −74° C. sec-Butyllithium (1.00 M, in a n-hexane and cyclohexane solution; 40.1 ml) was added dropwise thereto in the temperature range of −74° C. to −70° C., and the mixture was stirred for another 2 hours. Subsequently, iodine (9.3 g) in a THF (100 ml) solution was added dropwise thereto in the temperature range of −75° C. to −70° C., and the mixture was stirred for another 8 hours while allowing the temperature to come to 25° C. The reaction mixture obtained was poured into an aqueous solution of sodium thiosulfate (500 ml), and mixed. Toluene (500 ml) was added thereto and the mixture was allowed to be separated into organic and aqueous phases, and an extractive operation was carried out. The organic phase obtained was fractionated, washed with brine, and then dried over anhydrous magnesium sulfate. The solution obtained was concentrated under reduced pressure, and the residue obtained was purified with a fractional operation by means of column chromatography using heptane as the eluent and silica gel as the stationary phase powder, the solvent was distilled off and the residue was dried, giving 13.8 g of 4-heptyl-1-(4-iodine-3-fluorophenyl)-cyclohexyl-3-ene (24). The yield based on the compound (11) was 85.9%.

Second Step:

The compound (24) (5.0 g), the dihydroxyborane derivative (6) (4.2 g), potassium carbonate (5.2 g), Pd/C (NX type) (0.05 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (300 ml) and toluene (300 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 2.8 g of 4-(4-ethoxy-2,3,2"-trifluoro-1,1'-terphenyl)-1-heptylcyclohexyl-3-ene (No. 532). The yield based on the compound (11) was 43.5%.

The chemical shift δ (ppm) in $^1$H-NMR analysis was described below, and the compound obtained was identified as 4-(4-ethoxy-2,3,2"-trifluoro-1,1'-terphenyl)-1-heptylcyclohexyl-3-ene. The solvent for measurement was CDCl$_3$.

Chemical shift δ (ppm); 7.60 (dd, 4H), 7.42 (t, 1H), 7.26 (dd, 1H), 7.19 (dd, 1H), 7.14 (td, 1H), 6.81 (t, 1H), 6.21 (m, 1H), 4.17 (q, 2H), 2.51-2.42 (m, 2H), 2.35 (dt, 1H), 1.98-1.90 (m, 1H), 1.89-1.80 (m, 1H), 1.64-1.54 (m, 1H), 1.49 (t, 3H), 1.43-1.23 (m, 13H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature (T$_{NI}$), the dielectric anisotropy (Δ∈), and the optical anisotropy (Δn). The physical property-values of the compound (No. 532) were as follows.

Transition temperature: C 95.0 S$_A$ 208.6 N 275.2 I.
T$_{NI}$=244.6° C., Δ∈=−5.81, Δn=0.294.

Example 9

Synthesis of 4-(4-ethoxy-2,3,3"-trifluoro-1,1'-terphenyl)-1-pentylcyclohexyl-3-ene (No. 672)

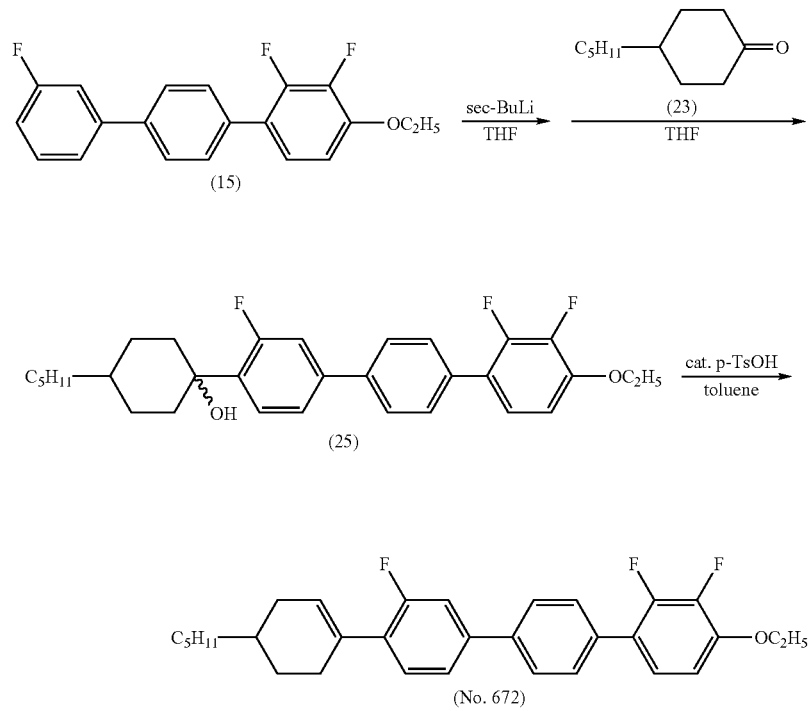

First Step:

The compound (15) (10.0 g) and THF (100 ml) were put in a reaction vessel under a nitrogen atmosphere, and cooled to −74° C. sec-Butyllithium (1.00 M, in a n-hexane and cyclohexane solution; 36.6 ml) was added dropwise thereto in the temperature range of −74° C. to −70° C., and the mixture was stirred for another 2 hours. Subsequently, 4-pentylcyclohexanone (16) (5.1 g) in a THF (50 ml) solution was added dropwise thereto in the temperature range of −75° C. to −70° C., and the mixture was stirred for another 8 hours while allowing the temperature to come to 25° C. The reaction mixture obtained was poured into a vessel containing a 1N—HCl solution (200 ml) and ethyl acetate (300 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was then distilled off under reduced pressure, giving 13.4 g of 4-(4-ethoxy-2,3, 3"-trifluoro-1,1'-terphenyl)-1-pentylcyclohexanol (25). The compound (25) obtained was white solids.

Second Step:

The compound (17) (13.4 g), p-toluenesulfonic acid (0.4 g), and toluene (250 ml) are mixed, and the mixture was heated under reflux for 2 hours while water being distilled was removed. The reaction mixture was cooled to 30° C., and then water (300 ml) and toluene (500 ml) were added and mixed thereto. The mixture was then allowed to stand until it had separated into organic and aqueous phases, and an extractive operation was carried out. The organic phase obtained was fractionated, washed with a saturated aqueous solution of sodium hydrogencarbonate and water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 10.8 g of 4-(4-ethoxy-2,3,3"-trifluoro-1,1'-terphenyl)-1-pentylcyclohexyl-3-ene (No. 672). The yield based on the compound (25) was 83.6%.

The chemical shift δ (ppm) in $^1$H-NMR analysis was described below, and the compound obtained was identified as 4-(4-ethoxy-2,3,3"-trifluoro-1,1'-terphenyl)-1-pentylcyclohexyl-3-ene. The solvent for measurement was CDCl$_3$.

Chemical shift δ (ppm); 7.61 (dd, 4H), 7.38-7.28 (m, 3H), 7.14 (td, 1H), 6.80 (td, 1H), 6.00 (m, 1H), 4.18 (q, 2H), 2.54-2.38 (m, 2H), 2.33 (dt, 1H), 1.94-1.80 (m, 2H), 1.70-1.58 (m, 1H), 1.49 (t, 3H), 1.43-1.25 (m, 9H), and 0.91 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 672) were as follows.

Transition temperature: C 88.3 S$_A$ 196.9 N 287.3 I.
$T_{NI}$=245.3° C., Δ∈=−5.23, Δn=0.294.

Example 10

Synthesis of Trans-2-(4-ethoxy-2,3,2"-trifluoro-1,1'-terphenyl)-5-pentyltetrahydropyran (No. 992)

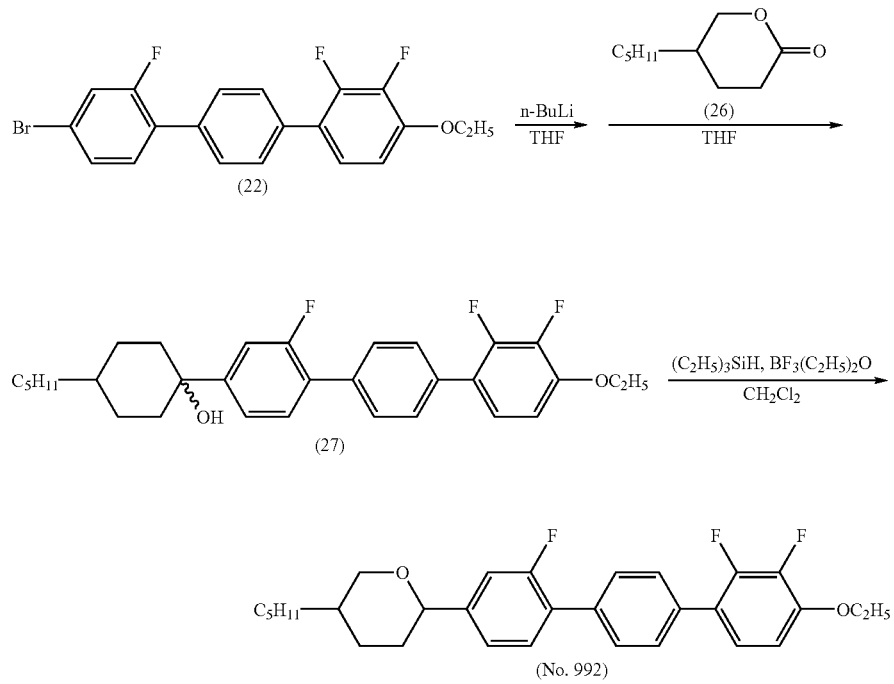

First Step:

The compound (22) (3.0 g) and THF (100 ml) were put in a reaction vessel under a nitrogen atmosphere, and cooled to −74° C. n-Butyllithium (1.57 M, in a n-hexane solution; 5.2 ml) was added dropwise thereto in the temperature range of −74° C. to −70° C., and the mixture was stirred for another 2 hours. Subsequently, 4-pentyl-tetrahydro-2-pyron (26) (1.4 g) in a THF (20 ml) solution was added dropwise thereto in the temperature range of −74° C. to −70° C., and the mixture was stirred for another 8 hours while allowing the temperature to come to 25° C. The reaction mixture obtained was poured into a vessel containing ice-water (200 ml) and ethyl acetate (100 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was then distilled off under reduced pressure, giving 3.6 g of 2-(4-ethoxy-2,3,2"-trifluoro-1,1'-terphenyl)-2-hydroxy-5-pentyl tetrahydropyran (27). The compound (27) obtained was white solids.

Second Step:

The compound (27) (3.6 g), boron trifluoride-diethyl ether complex (1.8 ml), and methylene chloride (100 ml) were put in a reaction vessel under a nitrogen atmosphere, and cooled to −60° C. Triethylsilane (2.3 ml) was added dropwise thereto in the temperature range of −60° C. to −58° C., and the mixture was stirred at the same temperature for 2 hours, and further stirred for 8 hours while allowing the temperature to come to 25° C. The reaction mixture obtained was poured into a vessel containing ice-water (200 ml) and ethyl acetate (100 ml), and mixed. The mixture was then allowed to stand until it had separated into organic and aqueous phases, and then an extractive operation was carried out. The organic phase obtained was fractionated, washed with water, and then dried over anhydrous magnesium sulfate. The solvent was then distilled off under reduced pressure, and the residue obtained was purified with a fractional operation by means of column chromatography using toluene as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 0.81 g of trans-2-(4-ethoxy-2,3,2"-trifluoro-1,1'-terphenyl)-5-pentyltetrahydropyran (No. 992). The yield based on the compound (27) was 23.2%.

The chemical shift δ (ppm) in $^1$H-NMR analysis was described below, and the compound obtained was identified as trans-2-(4-ethoxy-2,3,2"-trifluoro-1,1'-terphenyl)-5-pentyltetrahydropyran. The solvent for measurement was CDCl$_3$.

Chemical shift δ (ppm); 7.60 (dd, 4H), 7.44 (t, 1H), 7.21 (m, 1H), 7.19 (dd, 1H), 7.14 (td, 1H), 6.82 (td, 1H), 4.30 (d, 1H), 4.17 (q, 2H), 4.10 (dd, 1H), 3.23 (t, 1H), 2.01 (m, 1H), 1.92 (m, 1H), 1.72-1.57 (m, 2H), 1.49 (t, 3H), 1.40-1.24 (m, 7H), 1.24-1.09 (m, 2H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 992) were as follows.

Transition temperature: C 97.3 N 282.0 I.
$T_{NI}$=232.6° C., Δ∈=−4.62, Δn=0.247.

Example 11

Synthesis of Trans-2-(4-ethoxy-2,3,3"-trifluoro-1,1'-terphenyl)-5-pentyltetrahydropyran (No. 1152)

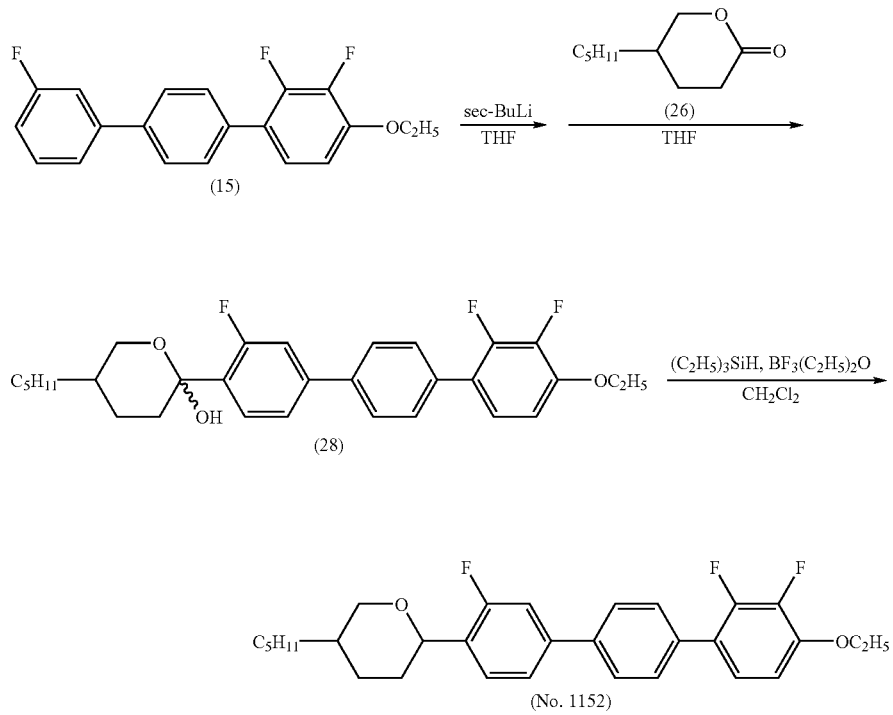

First Step:

The compound (15) (3.0 g) and THF (100 ml) were put in a reaction vessel under a nitrogen atmosphere, and cooled to −74° C. sec-Butyllithium (1.00 M, in a n-hexane and cyclohexane solution; 11.1 ml) was added dropwise thereto in the temperature range of −74° C. to −70° C., and the mixture was stirred for another 2 hours. Subsequently, 4-pentyl-tetrahydro-2-pyron (14) (1.7 g) in a THF (20 ml) solution was added dropwise thereto in the temperature range of −74° C. to −70° C., and the mixture was stirred for another 8 hours while allowing the temperature to come to 25° C. The reaction mixture obtained was poured into a vessel containing ice-water (200 ml) and ethyl acetate (100 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was then distilled off under reduced pressure, giving 4.5 g of 2-(4-ethoxy-2,3,3"-trifluoro-1,1'-terphenyl)-2-hydroxy-5-pentyltetrahydropyran (28). The compound (28) obtained was white solids.

Third Step:

The compound (28) (4.5 g), boron trifluoride-diethyl ether complex (1.7 ml), and methylene chloride (100 ml) were put in a reaction vessel under a nitrogen atmosphere, and cooled to −60° C. Triethylsilane (2.1 ml) was added dropwise thereto in the temperature range of −60° C. to −58° C., and the mixture was stirred at the same temperature for 2 hours, and further stirred for 8 hours while allowing the temperature to come to 25° C. The reaction mixture obtained was poured into a vessel containing ice-water (200 ml) and ethyl acetate (100 ml), and mixed. The mixture was then allowed to stand until it had separated into organic and aqueous phases, and then an extractive operation was carried out. The organic phase obtained was fractionated, washed with water, and then dried over anhydrous magnesium sulfate. The solvent was then distilled off under reduced pressure, and the residue obtained was purified with a fractional operation by means of column chromatography using toluene as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 0.45 g of trans-2-(4-ethoxy-2,3,3"-trifluoro-1,1'-terphenyl)-5-pentyltetrahydropyran (No. 1152). The yield based on the compound (28) was 10.3%.

The chemical shift δ (ppm) in $^1$H-NMR analysis was described below, and the compound obtained was identified as trans-2-(4-ethoxy-2,3,3"-trifluoro-1,1'-terphenyl)-5-pentyltetrahydropyran. The solvent for measurement was $CDCl_3$.

Chemical shift δ (ppm); 7.61 (dd, 4H), 7.56 (t, 1H), 7.42 (dd, 1H), 7.28 (dd, 1H), 7.14 (td, 1H), 6.82 (td, 1H), 4.63 (d, 1H), 4.17 (q, 2H), 4.11 (dd, 1H), 3.26 (t, 1H), 2.00 (td, 1H), 1.95 (td, 1H), 1.75-1.64 (m, 1H), 1.64-1.58 (m, 1H), 1.49 (t, 3H), 1.40-1.24 (m, 7H), 1.24-1.09 (m, 2H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 1152) were as follows.

Transition temperature: C 89.1 N 278.3 I.
$T_{NI}$=224.6° C., $\Delta\varepsilon$=−4.28, $\Delta n$=0.257.

Example 12

Synthesis of 4-ethoxy-2,3,2"-trifluoro-4"-(trans-4-ethenylcyclohexyl)-1,1'-terphenyl (No. 72)

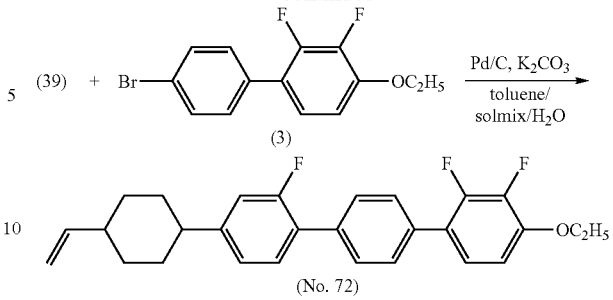

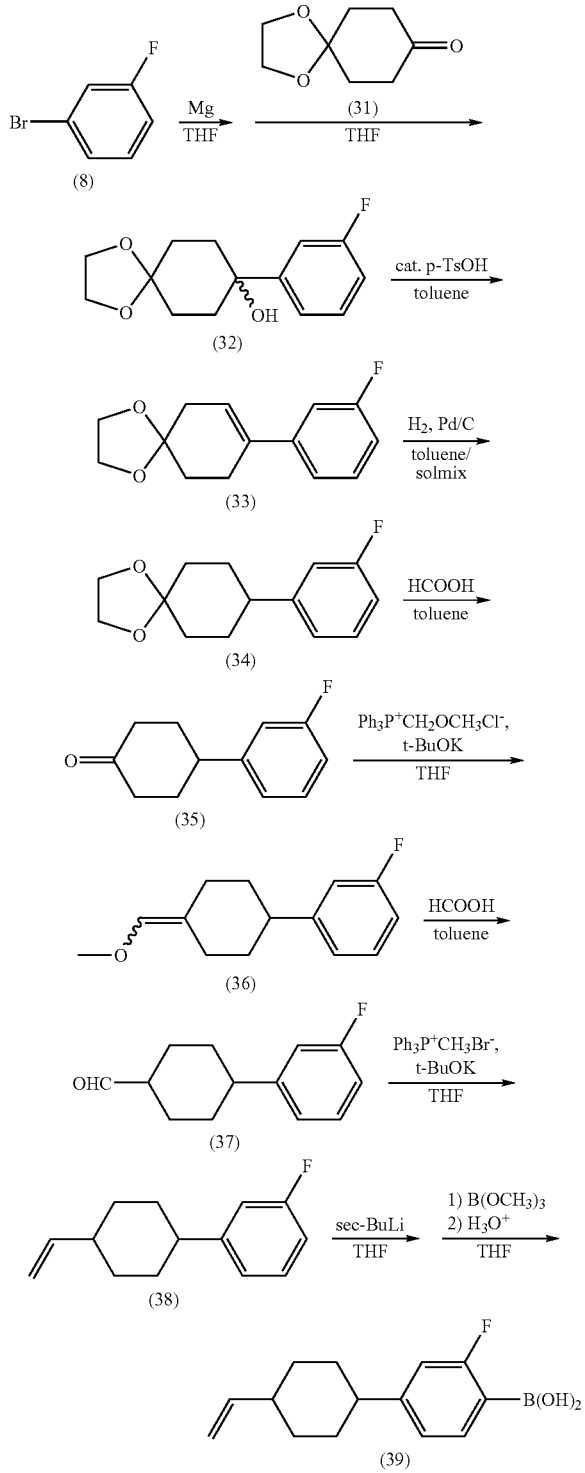

First Step:

Well-dried magnesium (9.3 g) and THF (20 ml) were put in a reaction vessel under a nitrogen atmosphere, and heated to 50° C. 3-Fluorobromobenzene (8) (67.2 g) dissolved in THF (300 ml) was slowly added dropwise thereto in the temperature range of 40° C. to 60° C., and the mixture was stirred for another 60 minutes.

1,4-Dioxaspyro[4.5]decane-8-one (31) (50.0 g) dissolved in THF (150 ml) was slowly added dropwise thereto in the temperature range of 50° C. to 60° C., and the mixture was stirred for another 60 minutes. The reaction mixture obtained was cooled to 30° C., and then poured into a vessel containing an aqueous NH$_4$Cl solution (900 ml) and ethyl acetate (500 ml), and mixed. The mixture was then allowed to stand until it had separated into two phases of organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was distilled off under reduced pressure, giving 73.5 g of 8-(3-fluorophenyl)-1,4-dioxaspyro[4.5]deca-8-ol (32). The compound (32) obtained was a yellow oil.

Second Step:

The compound (32) (73.5 g), p-toluenesulfonic acid (2.2 g), ethylene glycol (3.7 g), and toluene (250 ml) were mixed, and the mixture was heated under reflux for 2 hours while water being distilled was removed. The reaction mixture was cooled to 30° C., and then water (200 ml) and toluene (500 ml) were added and mixed thereto. The mixture was then allowed to stand until it had separated into two phases of organic and aqueous phases, and an extractive operation was carried out. The organic phase obtained was fractionated, washed with a saturated aqueous solution of sodium hydrogencarbonate and water, and then dried over anhydrous magnesium sulfate. The solution obtained was purified with a fractional operation by means of column chromatography using heptane as the eluent and silica gel as the stationary phase powder and dried, giving 60.2 g of 8-(3-fluorophenyl)-1,4-dioxaspyro[4.5]decene (33). The yield based on the compound (8) was 80.0%.

Third Step:

The compound (33) was dissolved in a mixed solvent of toluene (150 ml) and Solmix A-11 (150 ml), and 0.7 g of Pd/C (NX type) was added thereto. The mixture was stirred at room temperature until hydrogen absorption had ceased. After the reaction had been completed, Pd/C was removed and further the solvent was distilled off. The residue obtained was purified with a fractional operation by means of column chromatography using toluene as the eluent and silica gel as the stationary phase powder, and dried, giving 52.3 g of 8-(3-fluorophenyl)-1,4-dioxaspyro[4.5]decane (34). The yield based on the compound (33) was 86.1%.

Fourth Step:

The compound (34) (52.3 g), formic acid (87%; 58.6 ml), and toluene (200 ml) were mixed, and the mixture was heated under reflux for 2 hours. The reaction mixture was cooled to 30° C., and then water (200 ml) and toluene (300 ml) were added and mixed thereto. The mixture was then allowed to stand until it had separated into two phases of organic and aqueous phases, and an extractive operation was carried out. The organic phase obtained was fractionated, washed with water, a saturated aqueous solution of sodium hydrogencarbonate and water, and then dried over anhydrous magnesium sulfate. The solution obtained was purified by means of recrystallization from heptane and dried, giving 41.9 g of 1-(3-fluorophenyl)-cyclohexane-4-one (35). The yield based on a compound (34) was 98.5%.

Fifth Step:

Well-dried methoxymethyltriphenylphosphonium chloride (112.1 g) and THF (1000 ml) were mixed under a nitrogen atmosphere, and cooled to −30° C. Then, potassium t-butoxide (t-BuOK; 36.7 g) was put in thereto in twice in the temperature range of −30° C. to 20° C. After the mixture had been stirred at −20° C. for 30 minutes, the compound (35) (41.9 g) dissolved in THF (200 ml) was added dropwise thereto in the temperature range of −30° C. to −20° C. After the reaction had been stirred at −10° C. for 30 minutes, it was poured into a mixture of water (500 ml) and toluene (500 ml), and mixed. The mixture was then allowed to stand until it had separated into two phases of organic and aqueous phases, and an extractive operation was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The eluent obtained was concentrated under reduced pressure, giving 45.0 g of 1-(3-fluorophenyl)-4-methoxymethylenecyclohexane (36). The yield based on the compound (35) was 93.7%.

Sixth Step:

The compound (36) (45.0 g), formic acid (87%; 54.0 g), and toluene (250 ml) were mixed, and the mixture was heated under reflux for 2 hours. The reaction mixture was cooled to 30° C., and then water (200 ml) and toluene (200 ml) were added and mixed thereto. The mixture was then allowed to stand until it had separated into two phases of organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was distilled off under reduced pressure, and light yellow solids. The residue was dissolved in toluene (50 ml). The solution was added to a mixture of 5.0 g of 95% sodium hydroxide and 200 ml of Solmix A-11 cooled to 7° C., and the solution obtained was stirred at 10° C. for 2 hours. Then, an aqueous 2N-sodium hydroxide solution (100 ml) was added thereto, and the mixture was stirred at 5° C. for 2 hours. The reaction mixture obtained was poured into a mixture of water (200 ml) and toluene (200 ml), and mixed. The mixture was then allowed to stand until it had separated into two phases of organic and aqueous phases, and an extractive operation was carried out. The organic phase obtained was fractionated, washed with water, and then dried over anhydrous magnesium sulfate. Then, the solvent was distilled off under reduced pressure, and the residue obtained was concentrated and purified with a fractional operation by means of column chromatography using toluene as the eluent and silica gel as the stationary phase powder and dried, giving 39.8 g of 1-(3-fluorophenyl)-trans-4-cyclohexanecarboaldehyde (37). The yield based on the compound (36) was 94.5%.

Seventh Step:

Well-dried methoxymethyltriphenylphosphonium bromide (26.0 g) and THF (200 ml) were mixed under a nitrogen atmosphere, and cooled to −30° C. Then, potassium t-butoxide (t-BuOK; 8.2 g) was put in thereto in twice in the temperature range of −30° C. to 20° C. After the mixture had been stirred at −20° C. for 30 minutes, the compound (37) (10.0 g) dissolved in THF (50 ml) was added dropwise thereto in the temperature range of −30° C. to −20° C. After the reaction mixture had been stirred at −10° C. for 30 minutes, it was poured into a mixture of water (200 ml) and toluene (200 ml), and mixed. The mixture was then allowed to stand until it had separated into two phases of organic and aqueous phases, and an extractive operation was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The eluent obtained was concentrated under reduced pressure, giving 9.0 g of 1-(3-fluorophenyl)-trans-4-ethenylcyclohexane (38). The yield based on the compound (37) was 90.9%.

Eighth Step:

The compound (38) (9.0 g) and THF (100 ml) were put in a reaction vessel under a nitrogen atmosphere, and cooled to −74° C. sec-Butyllithium (1.00 M, in a n-hexane and cyclohexane solution; 20.0 ml) was added dropwise thereto in the temperature range of −74° C. to −70° C., and the mixture was stirred for another 2 hours. Subsequently, trimethoxyborane (5.5 g) in a THF (20 ml) solution was added dropwise thereto in the temperature range of −75° C. to −70° C., and the mixture was stirred for 8 hours while allowing the temperature to come to 25° C. The reaction mixture obtained was poured into an aqueous 1N—HCl solution (200 ml), and mixed. Then, toluene (200 ml) was added thereto and the mixture was allowed to be separated into organic and aqueous phases, and an extractive operation was carried out. The organic phase obtained was fractionated, washed with brine, and then dried over anhydrous magnesium sulfate. The solution obtained was washed with heptane and dried, giving 4.9 g of trans-4-(4-ethenylcyclohexyl)-3-fluorophenylboronic acid (39). The yield based on the compound (38) was 44.8%.

Ninth Step:

4-Ethoxy-4'-bromo-2,3-difluoro-1,1'-biphenyl (3) (2.8 g), the boronic acid derivative (39) (2.0 g), potassium carbonate (3.4 g), Pd(Ph$_3$P)$_2$Cl$_2$ (0.15 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 1.4 g of 4-ethoxy-2,3,2"-trifluoro-4"-(trans-4-ethenyl-cyclohexyl)-1,1'-terphenyl (No. 72). The yield based on the compound (39) was 40.6%.

The chemical shift δ (ppm) in $^1$H-NMR analysis was described below, and the compound obtained was identified as 4-ethoxy-2,3,2"-trifluoro-4"-(trans-4-ethenylcyclohexyl)-1,1'-terphenyl (No. 72). The solvent for measurement was $CDCl_3$.

Chemical shift δ (ppm); 7.59 (dd, 4H), 7.40 (t, 1H), 7.14 (td, 1H), 7.07 (dd, 1H), 7.02 (dd, 1H), 6.81 (td, 1H), 5.83 (ddd, 1H), 5.02 (d, 1H), 4.94 (d, 1H), 4.17 (q, 2H), 2.53 (td, 1H), 2.10-1.89 (m, 5H), 1.58-1.44 (m, 6H), and 1.29 (qd, 1H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 72) were as follows.

Transition temperature: C 127.6 N 302.8 I.
$T_{NI}$=238.6° C., Δ∈=−5.60, Δn=0.227.

Example 13

Synthesis of 4-ethoxy-2,3,2"-trifluoro-4"-{trans-4-(1-pentenylcyclohexyl)}-1,1'-terphenyl (No. 112)

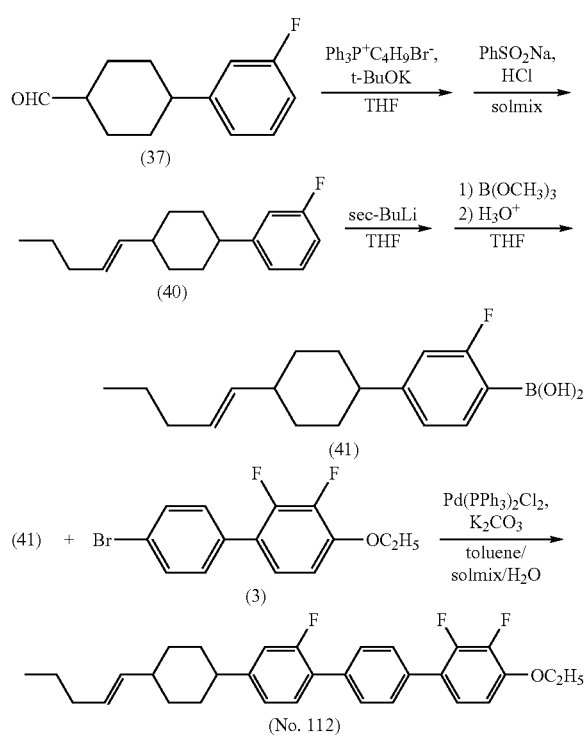

First Step:

Well-dried butoxyltriphenylphosphonium bromide (58.1 g) and THF (200 ml) were mixed under a nitrogen atmosphere and cooled to −30° C. Then, potassium t-butoxide (t-BuOK; 16.3 g) was put in thereto in twice in the temperature range of −30° C. to 20° C. After the mixture had been stirred at −20° C. for 30 minutes, the compound (37) (20.0 g) dissolved in THF (100 ml) was added dropwise thereto in the temperature range of −30° C. to −20° C. After the reaction mixture had been stirred at −10° C. for 30 minutes, it was poured into a mixture of water (400 ml) and toluene (400 ml), and mixed. The mixture was then allowed to stand until it had separated into two phases of organic and aqueous phases, and an extractive operation was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The eluent obtained was concentrated under reduced pressure. The residue was mixed with sodium benzenesulfonate dihydrate (31.0 g) and Solmix A-11 (100 ml), and heated under reflux for 8 hours. The reaction mixture was cooled to 30° C., and then water (200 ml) and toluene (200 ml) were added and mixed thereto. The mixture was then allowed to stand until it had separated into two phases of organic and aqueous phases, and an extractive operation was carried out. The organic phase obtained was fractionated, washed with water, a saturated aqueous solution of sodium hydrogencarbonate and water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from Solmix A-11, and dried, giving 15.8 g of 1-(3-fluorophenyl)-trans-4-(1-pentenyl)cyclohexane (40). The yield based on the compound (37) was 66.2%.

Second Step:

The compound (40) (15.8 g) and THF (100 ml) were put in a reaction vessel under a nitrogen atmosphere, and cooled to −74° C. sec-Butyllithium (1.00 M, in a n-hexane and cyclohexane solution; 20.0 ml) was added dropwise thereto in the temperature range of −74° C. to −70° C., and the mixture was stirred for another 2 hours. Subsequently, trimethoxyborane (7.3 g) in a THF solution (40 ml) was added dropwise thereto in the temperature range of −75° C. to −70° C., and the mixture was stirred for 8 hours while allowing the temperature to come to 25° C. The reaction mixture obtained was poured into an aqueous 1N—HCl solution (200 ml), and mixed. Then, toluene (200 ml) was added thereto and the mixture was allowed to be separated into organic and aqueous phases, and an extractive operation was carried out. The organic phase obtained was fractionated, washed with brine, and then dried over anhydrous magnesium sulfate. The solution obtained was washed with heptane and dried, giving 5.5 g of trans-4-(1-pentenylcyclohexyl)-3-fluorophenylboronic acid (41). The yield based on the compound (40) was 29.6%.

Third Step:

4-Ethoxy-4'-bromo-2,3-difluoro-1,1'-biphenyl (3) (3.0 g), the boronic acid derivative (41) (3.1 g), potassium carbonate (4.0 g), Pd(Ph$_3$P)$_2$Cl$_2$ (0.20 g), toluene (100 ml), Solmix A-11 (100 ml), and water (100 ml) were put in a reaction vessel under a nitrogen atmosphere, and heated under reflux for 2 hours. The reaction mixture was cooled to 25° C., The mixture was then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 2.9 g of 4-ethoxy-2,3,2"-trifluoro-4"-{trans-4-(1-pentenylcyclohexyl)}-1,1'-terphenyl (No. 112). The yield based on the compound (3) was 62.8%.

The chemical shift δ (ppm) in $^1$H-NMR analysis was described below, and the compound obtained was identified as 4-ethoxy-2,3,2"-trifluoro-4"-{trans-4-(1-ethenylcyclohexyl)}-1,1'-terphenyl (No. 112). The solvent for measurement was CDCl$_3$.

Chemical shift δ (ppm); 7.59 (dd, 4H), 7.39 (t, 1H), 7.14 (td, 1H), 7.07 (dd, 1H), 7.02 (dd, 1H), 6.81 (td, 1H), 5.42 (m, 2H), 4.17 (q, 2H), 2.51 (td, 1H), 2.04-1.93 (m, 5H), 1.93-1.84 (m, 2H), 1.56-1.44 (m, 5H), 1.38 (sextet, 2H), 1.29 (qd, 2H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy ($\Delta \in$), and the optical anisotropy (Δn). The physical property-values of the compound (No. 112) were as follows.

Transition temperature: C 110.6 S$_A$ 162.5 N 328.2 I.
$T_{NI}$=253.3° C., $\Delta \in$=-5.07, Δn=0.260.

Example 14

Synthesis of Trans-4'-[4-ethoxy-2,3,2"-trifluoro-4"-1,1'-terphenyl]-trans-4-propylbicyclohexyl (No. 2892)

under a nitrogen atmosphere, and cooled to -74° C. sec-Butyllithium (1.00 M, in a n-hexane and cyclohexane solution; 33.1 ml) was added dropwise thereto in the temperature range of -74° C. to -70° C., and the mixture was stirred for another 2 hours. Subsequently, trimethyl borate (5.2 g) in a THF (50 ml) solution was added dropwise thereto in the temperature range of -74° C. to -65° C., and the mixture was stirred for 8 hours while allowing the temperature to come to 25° C. The reaction mixture obtained was poured into 1N—HCl (100 ml) and ice-water (500 ml), and mixed. Then, ethyl acetate (300 ml) was added thereto and the mixture was allowed to be separated into organic and aqueous phases, and an extractive operation was carried out. The organic phase obtained was fractionated, washed sequentially with water, a saturated aqueous solution of sodium hydrogencarbonate and brine, and then dried over anhydrous magnesium sulfate. The solvent was distilled off under reduced pressure, giving 8.5 g of 2-fluoro-trans-4'-(trans-4-propylbicyclohexyl)-phenylboronic acid (30). The yield based on the compound (29) was 74.2%.

Second Step:

4-Ethoxy-4'-bromo-2,3-difluoro-1,1'-biphenyl (3) (5.0 g), the boronic acid derivative (30) (6.7 g), potassium carbonate (6.6 g), Pd(Ph$_3$P)$_2$Cl$_2$ (0.3 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional opera-

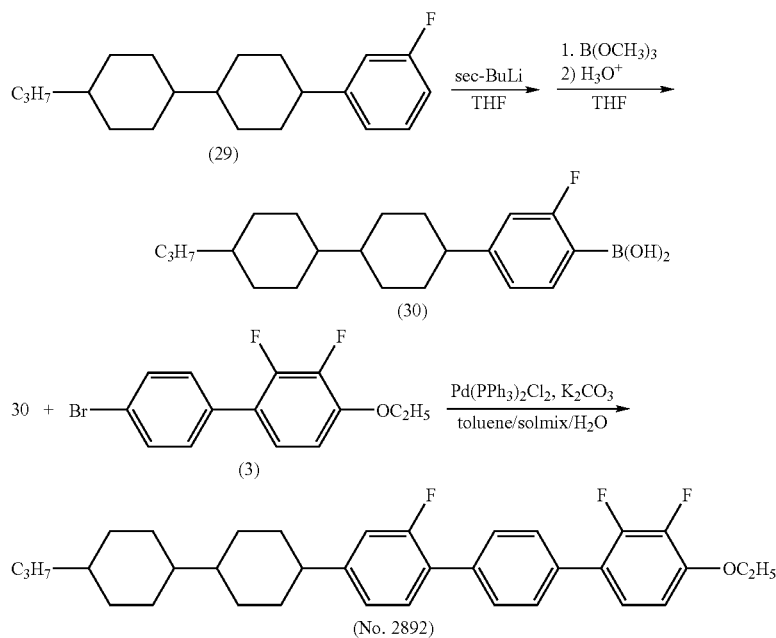

First Step:

Trans-4'-(3-Fluorophenyl)-trans-4-propylbicyclohexyl (29) (10.0 g) and THF (100 ml) were put in a reaction vessel tion by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 6.8 g of trans-4'-[4-ethoxy-2,3,2''-trifluoro-4''-1,1'-terphenyl]-trans-4-propylbicyclohexyl (No. 2892). The yield based on the compound (3) was 79.1%.

The chemical shift δ (ppm) in $^1$H-NMR analysis was described below, and the compound obtained was identified as trans-4'-[4-ethoxy-2,3,2''-trifluoro-4''-1,1'-terphenyl]-trans-4-propylbicyclohexyl. The solvent for measurement was CDCl$_3$.

Chemical shift δ (ppm); 7.59 (dd, 4H), 7.39 (t, 1H), 7.15 (td, 1H), 7.07 (dd, 1H), 7.02 (dd, 1H), 6.82 (t, 1H), 4.17 (q, 2H), 2.50 (td, 1H), 1.97 (d, 2H), 1.87 (m, 2H), 1.76 (t, 4H), 1.49 (t, 3H), 1.47-1.42 (m, 2H), 1.36-1.27 (m, 2H), 1.22-1.12 (m, 6H), 1.10-0.96 (m, 3H), 0.92-0.82 (m, 2H), and 0.88 (t, 3H).

The transition temperature of the compound (No. 2892) obtained was as follows.

Transition temperature: C 246.3 S$_A$ 194.9 N>400 I.

Example 15

Synthesis of 1-(4-ethoxy-2,3,2'',3''-tetrafluoro-1,1'-terphenyl)-trans-4-pentylcyclohexyl-3-ene (No. 832)

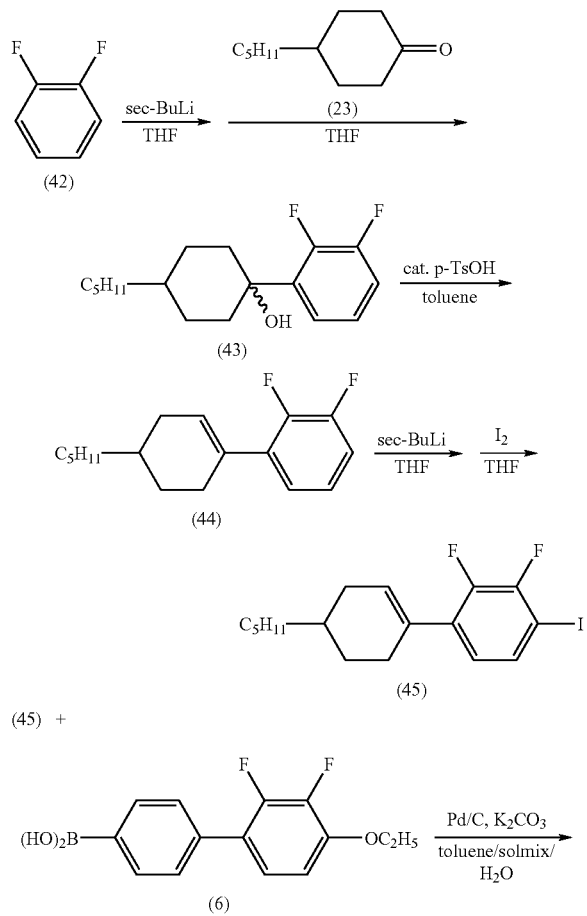

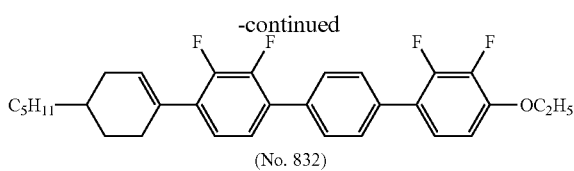

First Step:

1,2-Difluorobenzene (8) (100.0 g) and THF (100 ml) were put in a reaction vessel under a nitrogen atmosphere, and cooled to −74° C. n-Butyllithium (1.57 M, in a n-hexane solution; 876.5 ml) was added dropwise thereto in the temperature range of −74° C. to −70° C., and the mixture was stirred for another 2 hours. Subsequently, 4-pentylcyclohexanone (43) (177.0 g) in a THF (300 ml) solution was added dropwise thereto in the temperature range of −74° C. to −65° C., and the mixture was stirred for another 8 hours while allowing the temperature to come to 25° C. The reaction mixture obtained was poured into a vessel containing an aqueous 1N—HCl solution (500 ml) and ethyl acetate (800 ml), and mixed. The mixture was then allowed to stand until it had separated into organic and aqueous phases, and an extractive operation was carried out. The organic phase obtained was fractionated, washed with water, a saturated aqueous solution of sodium hydrogencarbonate and water, and then dried over anhydrous magnesium sulfate. The solvent was then distilled off under reduced pressure, giving 215.1 g of 4-pentyl-1-(2,3-difluorophenyl)-cyclohexanol (44). The compound (44) obtained was a yellow oil.

Second Step:

The compound (44) (215.1 g), p-toluenesulfonic acid (6.5 g), and toluene (300 ml) were mixed, and the mixture was heated under reflux for 2 hours while water being distilled was removed. The reaction mixture was cooled to 30° C., and then water (500 ml) and toluene (800 ml) were added and mixed thereto. The mixture was allowed to stand until it had separated into organic and aqueous phases, and an extractive operation into an organic phase was carried out. The organic phase obtained was fractionated, washed with a saturated aqueous solution of sodium hydrogencarbonate and water, and then dried over anhydrous magnesium sulfate. The solution obtained was purified with a fractional operation by means of column chromatography using heptane as the eluent and silica gel as the stationary phase powder, and dried, giving 186.6 g of 4-pentyl 1-(2,3-difluorophenyl)-cyclohexyl-3-ene (45). The yield based on the compound (18) was 81.0%.

Third Step:

The compound (45) (10.0 g) and THF (100 ml) were put in a reaction vessel under a nitrogen atmosphere, and cooled to −74° C. sec-Butyllithium (1.00 M, in a n-hexane and cyclohexane solution; 43.3 ml) was added dropwise thereto in the temperature range of −74° C. to −70° C., and the mixture was stirred for another 2 hours. Subsequently, iodine (12.0 g) in a THF solution (100 ml) was added dropwise thereto in the temperature range of −75° C. to −70° C., and the mixture was stirred for 8 hours while allowing the temperature to come to 25° C. The reaction mixture obtained was poured into an aqueous solution of sodium thiosulfate (500 ml), and mixed. Then, toluene (200 ml) was added thereto and the mixture was allowed to be separated into organic and aqueous phases, and an extractive operation was carried out. The organic phase obtained was fractionated, washed with brine, and then dried over anhydrous magnesium sulfate. The solution obtained was concentrated under reduced pressure, and the residue obtained was purified with a fractional operation by means of column chromatography using heptane as the eluent and silica gel as the stationary phase powder. The solvent was distilled off and the residue was dried, giving 13.6 g of 4-pentyl-1-(2,3-difluorophenyl-4-iodine)-cyclohexyl-3-ene (46). The yield based on the compound (45) was 92.1%.

Fourth Step:

The compound (46) (6.0 g), the dihydroxyborane derivative (6) (5.2 g), potassium carbonate (10.6 g), Pd/C (NX type) (0.06 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (300 ml) and toluene (300 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 6.0 g of 1-(4-ethoxy-2,3,2",3"-tetrafluoro-1,1'-terphenyl)-trans-4-pentylcyclohexyl-3-ene (No. 832). The yield based on the compound (46) was 78.1%.

The chemical shift δ (ppm) in $^1$H-NMR analysis was described below, and the compound obtained was identified as 1-(4-ethoxy-2,3,2",3"-tetrafluoro-1,1'-terphenyl)-trans-4-pentylcyclohexyl-3-ene (No. 832). The solvent for measurement was $CDCl_3$ Chemical shift δ (ppm); 7.59 (dd, 4H), 7.15 (td, 1H), 7.14 (td, 1H), 7.06 (td, 1H), 6.82 (td, 1H), 6.03 (br, 1H), 4.17 (q, 2H), 2.44-2.30 (m, 3H), 1.94-1.90 (m, 2H), 1.68-1.58 (m, 1H), 1.48 (t, 3H), 1.44-1.25 (m, 9H), and 0.91 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 832) were as follows.

Transition temperature: C 110.2 N 279.5 I.
$T_{NI}$=192.6° C., Δ∈=−5.24, Δn=0.227.

Example 16

Synthesis of 1-(4-ethoxy-2,3,2",3"-tetrafluoro-1,1'-terphenyl)-trans-4-pentylcyclohexane (No. 352)

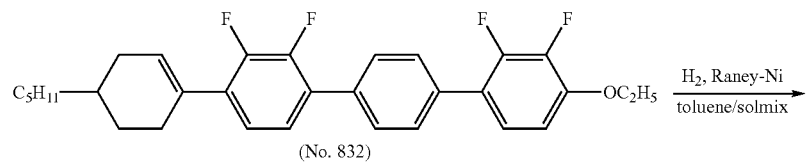

(No. 832)

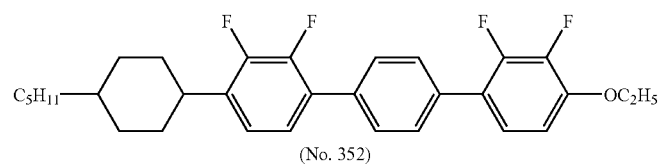

(No. 352)

First Step:

The compound (No. 832) (3.0 g) was dissolved in a mixed solvent of toluene (150 ml) and Solmix A-11 (150 ml), and Raney nickel (0.30 g) was added thereto. The mixture was stirred at room temperature under a hydrogen atmosphere until hydrogen absorption had ceased. After the reaction had been completed, Raney nickel was removed and the solvent was distilled off. The residue obtained was purified with a fractional operation by means of column chromatography using a mixed solvent of heptane and toluene (volume ratio; heptane: toluene=2:3) as the eluent and silica gel as the stationary phase powder. The residue was further purified by means of recrystallization from a mixed solvent of ethyl acetate/Solmix A-11 (volume ratio; ethyl acetate:Solmix A-11=1:2), and dried, giving 2.0 g of 1-(4-ethoxy-2,3,2",3"-tetrafluoro-1,1'-terphenyl)-trans-4-pentylcyclohexane (No. 352). The yield based on the compound (No. 832) was 66.4%.

The chemical shift δ (ppm) in $^1$H-NMR analysis was described below, and the compound obtained was identified as 1-(4-ethoxy-2,3,2",3"-tetrafluoro-1,1'-terphenyl)-trans-4-pentylcyclohexane (No. 352). The solvent for measurement was $CDCl_3$.

Chemical shift δ (ppm); 7.59 (dd, 4H), 7.16 (td, 1H), 7.14 (td, 1H), 7.04 (td, 1H), 6.82 (td, 1H), 4.17 (q, 2H), 2.88 (td, 1H), 1.90 (m, 4H), 1.58-1.45 (m, 5H), 1.48-1.21 (m, 9H), 1.17-1.06 (m, 2H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 352) were as follows.

Transition temperature: C 118.9 N 292.9 I.
$T_{NI}$=228.6° C., Δ∈=−6.14, Δn=0.207.

Example 17

Synthesis of 1-(4-ethoxy-2,3,2",3"-tetrafluoro-1,1'-terphenyl)-trans-4-butoxycyclohexyl-3-ene (No. 912)

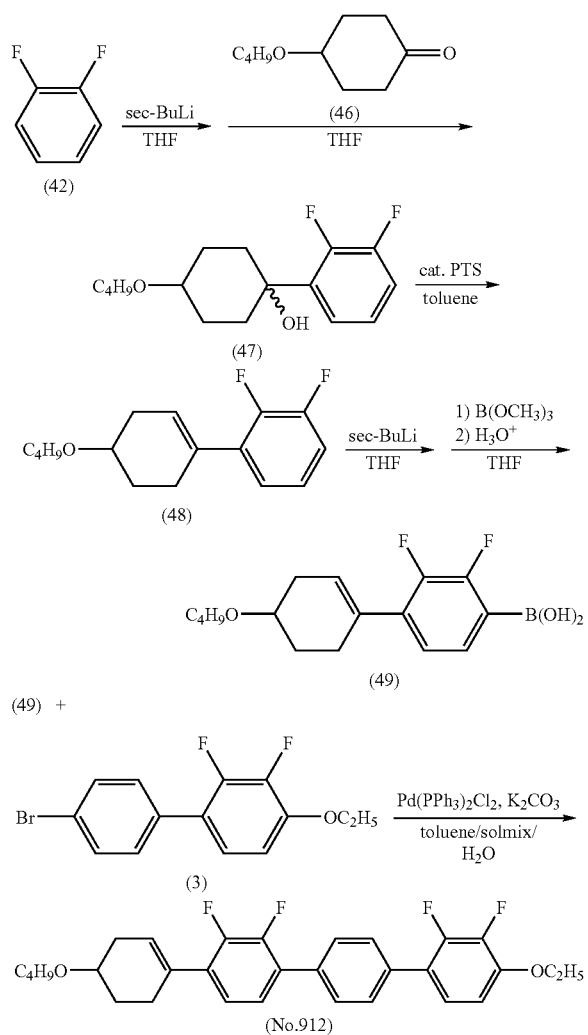

First Step:

1,2-Difluorobenzene (42) (57 g) and THF (100 ml) were put in a reaction vessel under a nitrogen atmosphere, and cooled to −74° C. sec-Butyllithium (1.00 M, in a n-hexane and cyclohexane solution; 500 ml) was added dropwise thereto in the temperature range of −74° C. to −70° C., and the mixture was stirred for another 2 hours. Subsequently, 4-butoxycyclohexanone (22) (85.1 g) in a THF (200 ml) solution was added dropwise thereto in the temperature range of −75° C. to −70° C., and the mixture was stirred for 8 hours while allowing the temperature to come to 25° C. The reaction mixture obtained was added into a vessel containing an aqueous 1N—HCl solution (500 ml) and ethyl acetate (500 ml), and mixed. Subsequently, the mixture was allowed to stand until it had separated into two phases of organic and aqueous phases, and an extractive operation was carried out. The organic phase obtained was fractionated, washed with water, a saturated aqueous solution of sodium hydrogencarbonate and water and then dried over anhydrous magnesium sulfate. Then, the solvent was distilled off under reduced pressure, giving 130.1 g of 4-butoxy-(2,3-difluorophenyl)cyclohexanol (47). The compound (47) obtained was a yellow oily material.

Second Step:

The compound (47) (130.1 g), p-toluenesulfonic acid (1.3 g), and toluene (500 ml) were mixed, and the mixture was heated under reflux for 2 hours while water being distilled was removed. The reaction mixture was cooled to 30° C., and then water (500 ml) and toluene (500 ml) were added, and mixed thereto. The mixture was allowed to stand until it had separated into organic and aqueous phases, and an extractive operation into an organic phase was carried out. The organic phase obtained was fractionated, washed with a saturated aqueous solution of sodium hydrogencarbonate and water, and then dried over anhydrous magnesium sulfate. The solution obtained was purified with a fractional operation by means of column chromatography using toluene as the eluent and silica gel as the stationary phase powder, and dried, giving 71.6 g of 4-butoxy-(2,3-difluorophenyl)cyclohexene (48). The compound (48) obtained was a colorless oil, having the boiling point at 131° C./3 mmHg to 132° C./3 mmHg, and the yield based on the compound (6) was 66.5%.

Third Step:

4-Butoxy-(2,3-difluorophenyl)cyclohexene (48) (11.0 g) and THF (200 ml) were put in a reaction vessel under a nitrogen atmosphere, and cooled to −74° C. sec-Butyllithium (1.00 M, in a n-hexane and cyclohexane solution; 50.0 ml) was added dropwise thereto in the temperature range of −74° C. to −70° C., and the mixture was stirred for another 2 hours. Subsequently, trimethyl borate (5.2 g) in a THF solution (50 ml) was added dropwise thereto in the temperature range of −74° C. to −65° C., and the mixture was stirred for 8 hours while allowing the temperature to come to 25° C. The reaction mixture obtained was added into a vessel containing an aqueous 1N—HCl solution (100 ml) and ice-water (500 ml), and mixed. Then, ethyl acetate (300 ml) was added thereto and the mixture was allowed to be separated into organic and aqueous phases, and an extractive operation was carried out. The organic phase obtained was fractionated, washed with water, a saturated aqueous solution of sodium hydrogencarbonate and brine and then dried over anhydrous magnesium sulfate. Then, the solvent was distilled off under reduced pressure, giving 10.7 g of 4-(4-butoxycyclohexenyl)-2,3-difluorophenyl boronic acid (49). The yield based on the compound (48) was 83.6%.

Fourth Step:

4-Ethoxy 4'-bromo-2,3-difluoro-1,1'-biphenyl (3) (3.0 g), the boronic acid derivative (49) (2.2 g), potassium carbonate (2.65 g), Pd(Ph₃P)₂Cl₂ (0.13 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using a mixed solvent of toluene and heptane (volume ratio; toluene: heptane=1:1) as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 0.91 g of 1-(4-ethoxy-2,3,2",3"-tetrafluoro-1,1'-terphenyl-trans-4-butoxycyclohexyl-3-ene (No. 912). The yield based on the compound (3) was 28.7%.

The chemical shift δ (ppm) in $^1$H-NMR analysis was described below, and the compound obtained was identified as 1-(4-ethoxy-2,3,2",3"-tetrafluoro-1,1'-terphenyl-trans-4-butoxycyclohexyl-3-ene (No. 912). The solvent for measurement was $CDCl_3$.

Chemical shift δ (ppm); 7.59 (dd, 4H), 7.16 (td, 1H), 7.15 (td, 1H), 7.04 (td, 1H), 6.81 (td, 1H), 5.97 (m, 1H), 4.17 (q, 2H), 3.66 (m, 1H), 3.52 (m, 2H), 2.64-2.46 (m, 3H), 2.28-2.20 (m, 1H), 2.11-2.04 (m, 1H), 1.84-1.74 (m, 1H), 1.64-1.56 (m, 2H), 1.49 (t, 3H), 1.41 (sextet, 2H), and 0.95 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 912) were as follows.

Transition temperature: C 121.2 N 250.5 I.
$T_{NI}$=189.6° C., Δ∈=-6.38, Δn=0.267.

Example 18

Synthesis of 1-(4-ethoxy-2,3,2"-trifluoro-1,1'-terphenyl)-trans-4-propyl-2,6-dioxane (No. 1952)

a saturated aqueous solution of sodium hydrogencarbonate and water, and then dried over anhydrous magnesium sulfate. The solvent was then distilled off under reduced pressure, the residue was purified by means of recrystallization from heptane, and dried, giving 11.3 g of 4"-(4-ethoxy-2,3,2"-trifluoro-1,1'-terphenyl)carboaldehyde (50). The yield based on the compound (22) was 64.6%.

Second Step:

The compound (50) (6.3 g), 2-pentylpropyleneglycol (3.7 g), p-toluenesulfonic acid (0.34 g), and toluene (300 ml) were mixed, and the mixture was heated under reflux for 2 hours. The reaction mixture was cooled to 30° C., and then water (300 ml) and toluene (500 ml) were added and mixed thereto. The mixture was then allowed to stand until it had separated into organic and aqueous phases, and an extractive operation into an organic phase was carried out. The organic phase obtained was fractionated, washed with a saturated aqueous solution of sodium hydrogencarbonate and water, and then dried over anhydrous magnesium sulfate. The solution obtained was purified with a fractional operation by means of column chromatography using toluene as the eluent and silica gel as the stationary phase powder. Then, the solvent was distilled off under reduced pressure, and the residue was purified by means of recrystallization from a mixed solvent of ethyl acetate/Solmix A-11 (volume ratio; ethyl acetate: Solmix A-11=2:1), and dried, giving 2.1 g of 1-(4-ethoxy-2,3,2"-trifluoro-1,1'-terphenyl)-trans-4-pentyl-2,6-dioxane (No. 1952). The yield based on the compound (50) was 24.9%.

The chemical shift δ (ppm) in $^1$H-NMR analysis was described below, and the compound obtained was identified

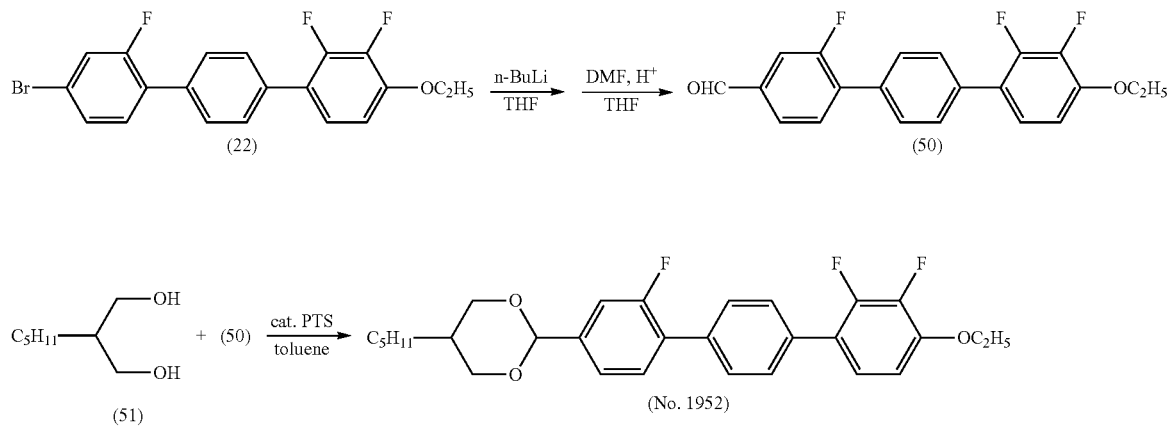

First Step:

4"-Bromo-4-ethoxy-2,3,2"-trifluoro-1,1'-terphenyl (22) (20.0 g) and THF (200 ml) were put in a reaction vessel under a nitrogen atmosphere, and cooled to -74° C. n-Butyllithium (1.55 M, in a n-hexane solution; 54.0 ml) was added dropwise thereto in the temperature range of -74° C. to -70° C., and the mixture was stirred for another 2 hours. Subsequently, N,N-dimethylformamide (5.4 ml) dissolved in THF (20 ml) was added dropwise thereto in the temperature range of 50° C. to 60° C., and the mixture was stirred for another 60 minutes. The reaction mixture obtained was cooled down to 30° C. and poured into a vessel containing an aqueous 1N—HCl solution (200 ml) and ethyl acetate (200 ml), mixed. The mixture was allowed to stand until it had separated into organic and aqueous phases, and an extractive operation was carried out. The organic phase obtained was fractionated, washed with water, as 1-(4-ethoxy-2,3,2",3"-trifluoro-1,1'-terphenyl)-trans-4-pentyl 2,6-dioxane (No. 1952). The solvent for measurement was $CDCl_3$.

Chemical shift δ (ppm); 7.59 (dd, 4H), 7.48 (td, 1H), 7.35 (td, 1H), 7.34 (td, 1H), 7.14 (td, 1H), 6.82 (td, 1H), 5.44 (s, 1H), 4.27 (d, 1H), 4.24 (d, 1H), 4.17 (q, 2H), 2.14 (m, 1H), 1.56 (d, 1H), 1.49 (t, 3H), 1.37-1.24 (m, 7H), 1.15-1.07 (m, 2H), and 0.90 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy (Δ∈), and the optical anisotropy (Δn). The physical property-values of the compound (No. 1952) were as follows.

Transition temperature: $C_1$ 86.1 $C_2$ 119.8 N 260.2 I.
$T_{NI}$=233.6° C., $\Delta\varepsilon$=−3.96, $\Delta n$=0.257.

Example 19

Synthesis of 1-ethoxy-2,3,2"-trifluoro-4"-(trans-4-pentylcyclohexylmethoxy)-1,1'-terphenyl (No. 3921)

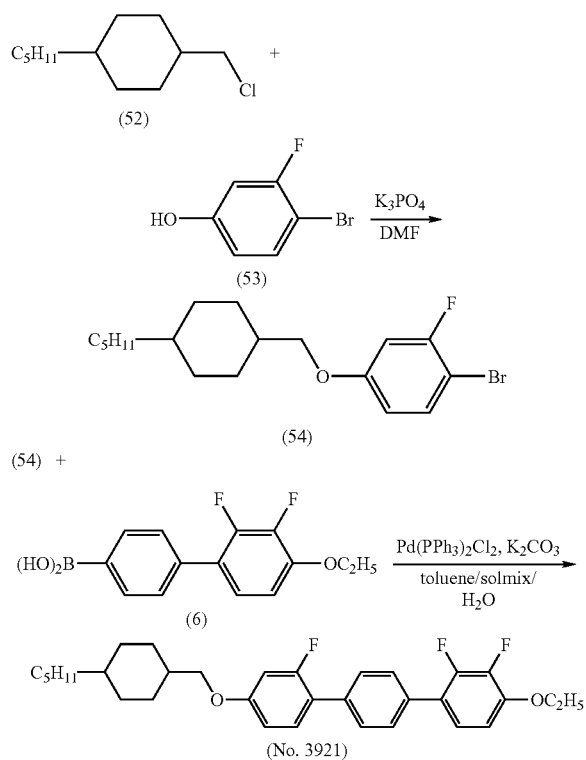

First Step:

4-Bromo-3-fluorophenol (53) (5.7 g) and tripotassium phosphate ($K_3PO_4$) (26.2 g) were added to DMF (100 ml) under a nitrogen atmosphere, and the mixture was stirred at 70° C. trans-4-Chloromethylpentyl cyclohexane (52) (5.0 g) was added thereto and the mixture was stirred at 70° C. for 7 hours. After the reaction mixture obtained had been cooled to 30° C. and separated form solid materials by filtration, toluene (100 ml) and water (100 ml) were added and mixed thereto. The mixture was then allowed to stand until it had separated into organic and aqueous phases, and an extractive operation into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. Further, the residue was purified by means of recrystallization from Solmix A-11, and dried, giving 8.0 g of 4-bromo-3-fluoro-(trans-4-pentylcyclohexylmethoxy)benzene (54). The yield based on the compound (52) was 90.8%.

Second Step:

4-Bromo-3-fluoro-(trans-4-pentylcyclohexylmethoxy) benzene (54) (5.0 g), 4-ethoxy-2,3-difluoro-1,1'-biphenyl-4'-boronic acid (6) (4.3 g), potassium carbonate (5.8 g), $Pd(Ph_3P)_2Cl_2$ (0.3 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. The mixture was then allowed to stand until it had separated into organic and aqueous phases, and an extractive operation into an organic phase was carried out. The organic phase obtained was fractionated, washed with water, and then dried over anhydrous magnesium sulfate. Then, the solvent was concentrated under reduced pressure, and the residue obtained was purified with a fractional operation by means of column chromatography using toluene as the eluent and silica gel as the stationary phase powder. Then, the residue was purified by means of recrystallization from a mixed solvent of ethyl acetate/Solmix A-11 (volume ratio; ethyl acetate: Solmix A-11=2:1), and dried, giving 5.6 g of 1-ethoxy-2,3,2"-trifluoro-4"-(trans-4-pentylcyclohexylmethoxy)-1,1'-terphenyl (No. 3921). The yield based on the compound (54) was 85.4%.

The chemical shift δ (ppm) in $^1$H-NMR analysis was described below, and the compound obtained was identified as 1-ethoxy-2,3,2"-trifluoro-4"-(trans-4-pentylcyclohexylmethoxy)-1,1'-terphenyl (No. 3921). The solvent for measurement was $CDCl_3$.

Chemical shift δ (ppm); 7.56 (dd, 4H), 7.37 (t, 1H), 7.13 (td, 1H), 6.81 (td, 1H), 6.77 (dd, 1H), 6.70 (dd, 1H), 4.17 (q, 2H), 3.78 (d, 2H), 1.90 (d, 2H), 1.82 (d, 2H), 1.76 (m, 1H), 1.48 (t, 3H), 1.35-1.16 (m, 9H), 1.12-1.02 (m, 2H), 1.01-0.93 (m, 2H), and 0.89 (t, 3H).

Measured values of the compound itself were used for the transition temperature, and extrapolated values converted from the measured values of the sample, in which the compound was mixed in the mother liquid crystals (i), by means of the extrapolation method described above were used for the maximum temperature ($T_{NI}$), the dielectric anisotropy ($\Delta\varepsilon$), and the optical anisotropy ($\Delta n$). The physical property-values of the compound (No. 1952) were as follows.

Transition temperature: C 126.2 N 252.9 I.
$T_{NI}$=217.9° C., $\Delta\varepsilon$=−3.43, $\Delta n$=0.287.

Example 20

Synthesis of 1-ethoxy-2,3,3"-trifluoro-4"-(trans-4-pentylcyclohexylmethoxy)-1,1'-terphenyl (No. 3922)

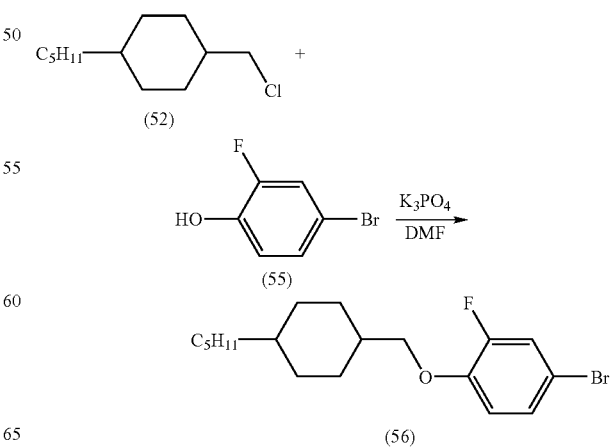

-continued

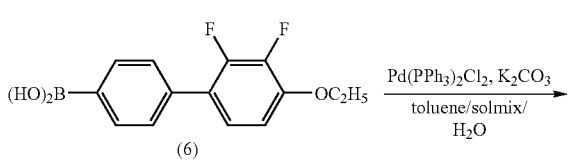

(6)

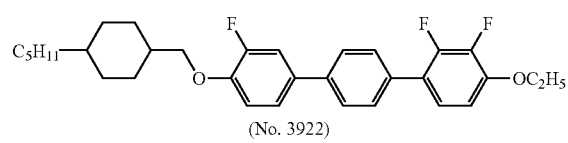

(No. 3922)

First Step:

4-Bromo-2-fluorophenol (55) (14.1 g) and tripotassium phosphate (K$_3$PO$_4$; 52.3 g) were added to DMF (200 ml) under a nitrogen atmosphere, and the mixture was stirred at 70° C. trans-4-Chloromethylpentyl cyclohexane (52) (10.0 g) was added thereto, and stirred at 70° C. for 7 hours. The reaction mixture obtained was cooled to 30° C., and then solids were filtered out. Toluene (200 ml) and water (200 ml) were added and mixed thereto. The mixture was then allowed to stand until it had separated into organic and aqueous phases, and an extractive operation into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. Further, the residue was purified by means of recrystallization from Solmix A-11, and dried, giving 16.5 g of 4-bromo-2-fluoro-(trans-4-pentylcyclohexylmethoxy)benzene (56). The yield based on the compound (55) was 93.6%.

Second Step:

4-Bromo-2-fluoro-(trans-4-pentylcyclohexylmethoxy) benzene (56) (3.0 g), 4-ethoxy-2,3-difluoro-1,1'-biphenyl-4'-boronic acid (6) (3.4 g), potassium carbonate (4.0 g), Pd(Ph$_3$P)$_2$Cl$_2$ (0.2 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. The mixture was then allowed to stand until it had separated into organic and aqueous phases, and an extractive operation into an organic phase was carried out. The organic phase obtained was fractionated, washed with water, and then dried over anhydrous magnesium sulfate. Then, the solvent was concentrated under reduced pressure, and the residue obtained was purified with a fractional operation by means of column chromatography using toluene as the eluent and silica gel as the stationary phase powder. Then, the residue was purified by means of recrystallization from a mixed solvent of ethyl acetate/Solmix A-11 (volume ratio; ethyl acetate: Solmix A-11=2:1), and dried, giving 2.8 g of 1-ethoxy-2,3,3"-trifluoro-4"-(trans-4-pentylcyclohexylmethoxy)-1,1'-terphenyl (No. 3922). The yield based on the compound (56) was 57.6%.

The chemical shift δ (ppm) in $^1$H-NMR analysis was described below, and the compound obtained was identified as 1-ethoxy-2,3,3"-trifluoro-4"-(trans-4-pentylcyclohexylmethoxy)-1,1'-terphenyl (No. 3922). The solvent for measurement was CDCl$_3$.

Chemical shift δ (ppm); 7.59 (dd, 4H), 7.35 (dd, 1H), 7.31 (dd, 1H), 7.12 (td, 1H), 7.02 (t, 1H), 6.81 (td, 1H), 4.17 (q, 2H), 3.87 (d, 2H), 1.97-1.90 (m, 2H), 1.86-1.77 (m, 3H), 1.48 (t, 3H), 1.35-1.16 (m, 9H), 1.08 (qd, 2H), 1.01-0.92 (m, 2H), and 0.89 (t, 3H).

The transition temperature of the compound (No. 3922) obtained was as follows.

Transition temperature: C 143.4 N 259.9 I.

Example 21

Synthesis of 1-ethoxy-2,3,2",3"-tetrafluoro-4"-(trans-4-pentylcyclohexylmethoxy)-1,1'-terphenyl (No. 3923)

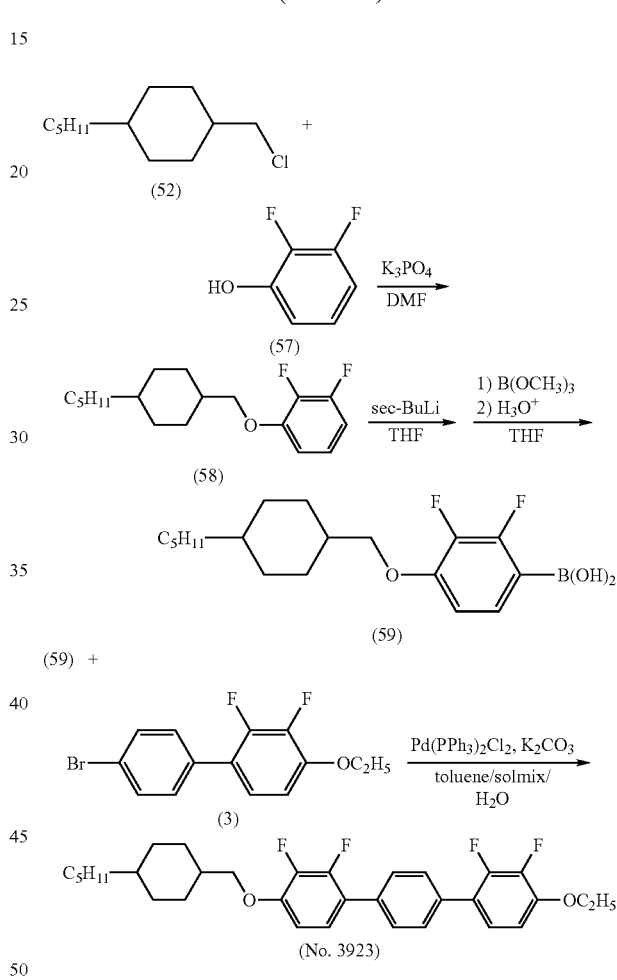

First Step:

2,3-Difluorophenol (57) (9.6 g) and tripotassium phosphate (K$_3$PO$_4$; 52.3 g) were added to DMF (200 ml) under a nitrogen atmosphere, and the mixture was stirred at 70° C. trans-4-Chloromethylpentylcyclohexane (52) (10.0 g) was added thereto and the mixture was stirred at 70° C. for 7 hours. The reaction mixture obtained was cooled to 30° C., and then solid materials were filtered out. Toluene (200 ml) and water (200 ml) were added and mixed thereto. The mixture was allowed to stand until it had separated into organic and aqueous phases, and an extractive operation into an organic phase was carried out. The organic phase obtained was fractionated, washed with brine, and then dried over anhydrous magnesium sulfate. Then, the solvent was distilled off under reduced pressure, and the residue obtained was purified with a fractional operation by means of column chromatography using toluene as the eluent and silica gel as the stationary phase powder. The product was further purified by recrystallization from Solmix A-11, and dried, giving 13.9 g of 2,3-difluoro-4-(trans-4-pentylcyclohexylmethoxy)benzene (58). The yield based on the compound (52) was 95.1%.

Second Step:

The compound (58) (13.9 g) and THF (200 ml) were put in a reaction vessel under a nitrogen atmosphere, and cooled to −74° C. sec-Butyllithium (1.00 M, in a n-hexane and cyclohexane solution; 51.6 ml) was added dropwise thereto in the temperature range of −74° C. to −70° C., and the mixture was stirred for another 2 hours. Subsequently, trimethyl borate (5.6 g) in a THF solution (50 ml) was added dropwise thereto in the temperature range of −74° C. to −65° C., and the mixture was stirred for 8 hours while allowing the temperature to come to 25° C. The reaction mixture obtained was poured into a vessel containing an aqueous 1N—HCl solution (100 ml) and ice-water (500 ml), and mixed. Then, ethyl acetate (300 ml) was added thereto and the mixture was allowed to be separated into organic and aqueous phases, and an extractive operation was carried out. The organic phase obtained was fractionated, washed with water, a saturated aqueous solution of sodium hydrogencarbonate and brine, and then dried over anhydrous magnesium sulfate. Then, the solvent was distilled off under reduced pressure, giving 14.2 g of 2,3-difluoro-4-(trans-4-pentylcyclohexylmethoxy)phenylboronic acid (59). The yield based on the compound (58) was 89.0%.

Third Step:

4-Ethoxy-4'-bromo-2,3-difluoro-1,1'-biphenyl (3) (3.0 g), 2,3-difluoro 4-(trans-4-pentylcyclohexylmethoxy)phenylboronic acid (59) (3.6 g), potassium carbonate (4.0 g), Pd(Ph$_3$P)$_2$Cl$_2$ (0.2 g), toluene (100 ml), Solmix A-11 (100 ml), and water (100 ml) were put in a reaction vessel under a nitrogen atmosphere, and heated under reflux for 2 hours. The reaction mixture was cooled to 25° C., and then poured into water (500 ml) and toluene (500 ml), and mixed. Subsequently, the mixture was allowed to stand until it had separated into two phases of organic and aqueous phases, and an extractive operation into an organic phase was carried out. The organic phase obtained was fractionated, washed with water, and then dried over anhydrous magnesium sulfate. The solution obtained was concentrated under reduced pressure, and the residue obtained was purified with a fractional operation by means of column chromatography using toluene as the eluent and silica gel as the stationary phase powder. The residue was further purified by means of recrystallization from a mixed solvent of ethyl acetate/Solmix A-11 (volume ratio; ethyl acetate: Solmix A-11=2:1), and dried, giving 0.5 g of 1-ethoxy-2,3,2'',3'''-tetrafluoro-4''-(trans-4-pentylcyclohexylmethoxy)-1,1'-terphenyl (No. 3923). The yield based on the compound (59) was 9.9%.

The chemical shift δ (ppm) in $^1$H-NMR analysis was described below, and the compound obtained was identified as 1-ethoxy-2,3,2'',3'''-tetrafluoro-4''-(trans-4-pentylcyclohexylmethoxy)-1,1'-terphenyl (No. 3923). The solvent for measurement was CDCl$_3$.

Chemical shift δ (ppm); 7.57 (s, 4H), 7.13 (qd, 2H), 6.81 (qd, 2H), 4.17 (q, 2H), 3.88 (d, 2H), 1.96-1.90 (m, 2H), 1.86-1.77 (m, 3H), 1.48 (t, 3H), 1.35-1.17 (m, 9H), 1.08 (qd, 2H), 1.01-0.92 (m, 2H), and 0.89 (t, 3H).

The transition temperature of the obtained compound (No. 3923) was as follows.

Transition temperature: C 186.3 N 251.3 I.

Example 22

The compounds (No. 1) to (No. 4040) shown below can be synthesized by synthetic methods similar to those described in Examples 1 to 21. Attached data were measured in accordance with the methods described above.

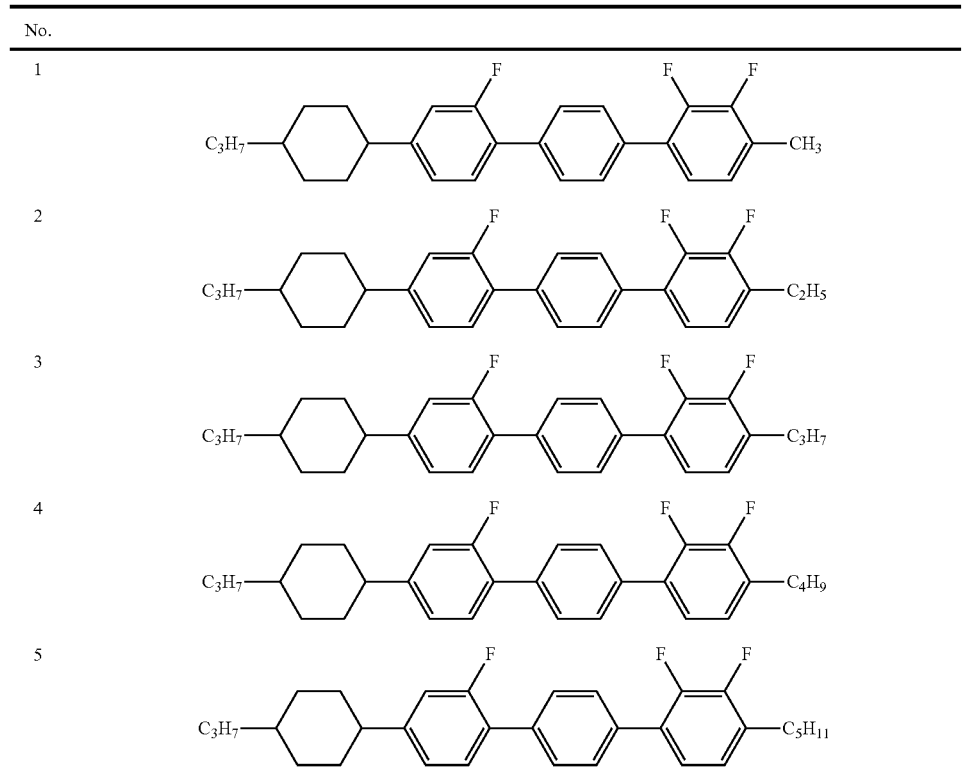

-continued
| No. | |
|---|---|
| 6 | 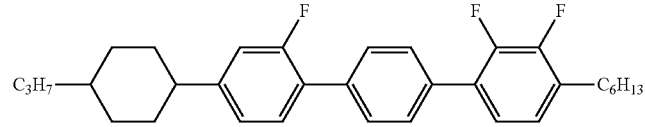 |
| 7 | 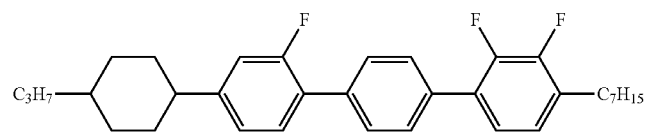 |
| 8 | 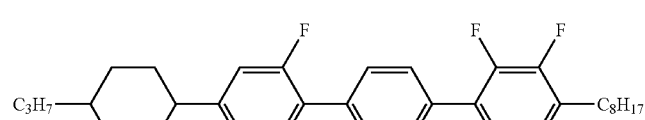 |
| 9 | 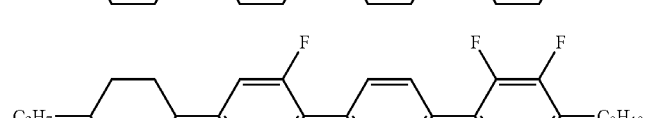 |
| 10 | 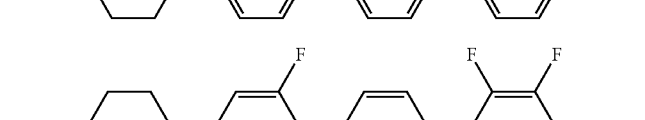 |
| 11 | 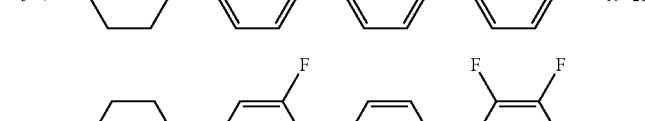 |
| 12 | 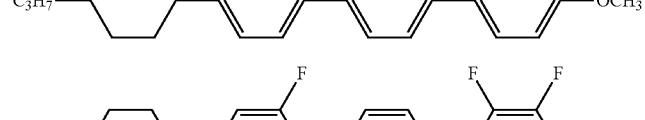<br>C 118.1 N 304.9 I<br>$T_{NI}$; 238.6° C., $\Delta\varepsilon$; -7.22, $\Delta n$; 0.271 |
| 13 | 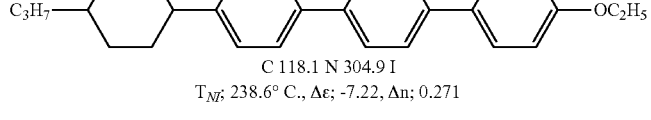 |
| 14 | 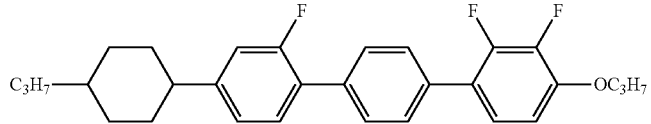 |
| 15 | 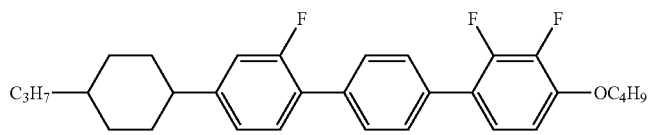 |
| 16 | 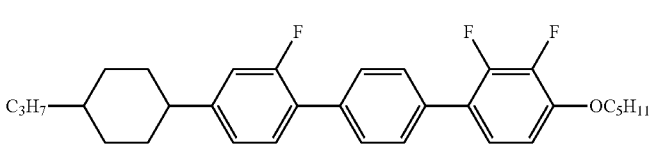 |

| No. | |
|---|---|
| 17 | 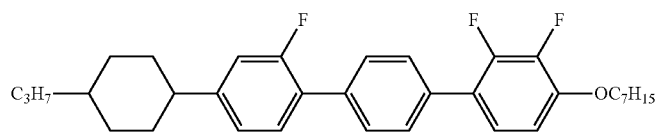 |
| 18 | 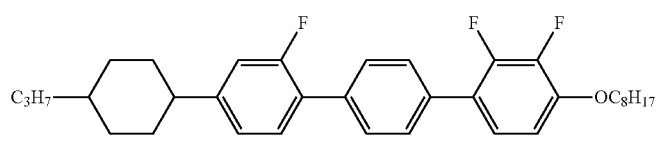 |
| 19 | 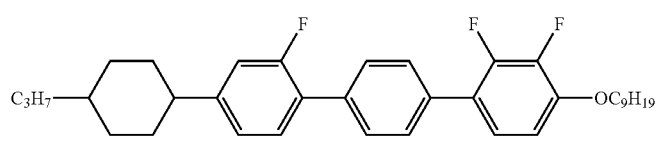 |
| 20 | 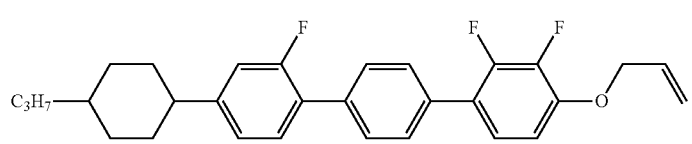 |
| 21 | 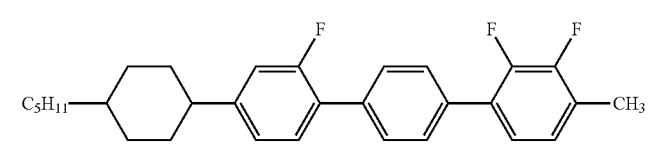 |
| 22 | 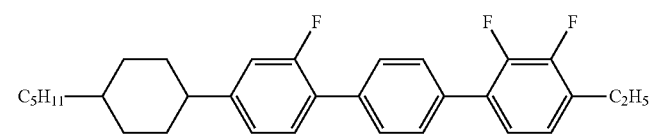 |
| 23 | 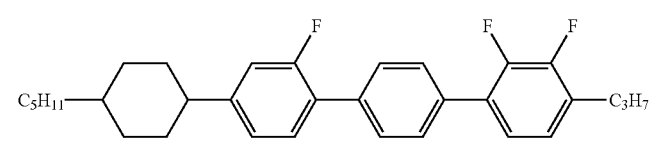 |
| 24 | 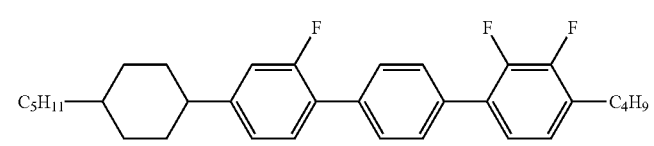 |
| 25 | 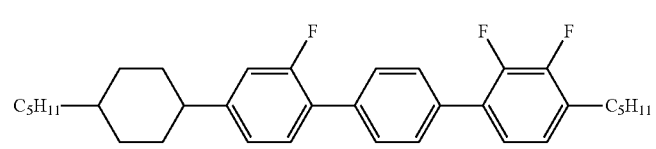 |
| 26 | 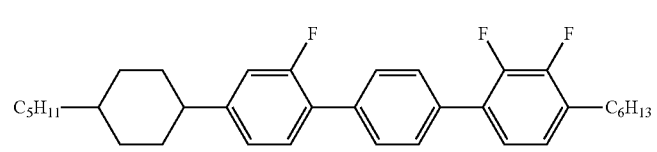 |
| 27 | 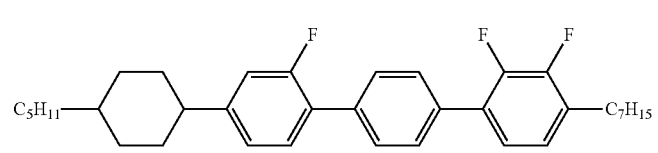 |

-continued
| No. | |
|---|---|
| 28 | 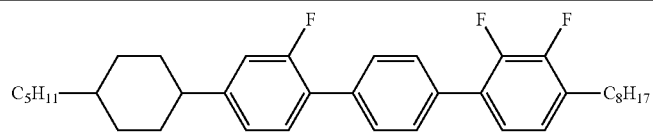 |
| 29 | 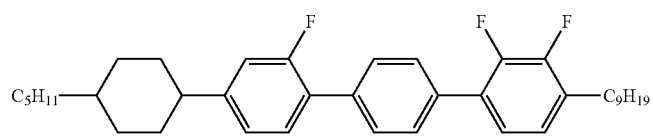 |
| 30 | 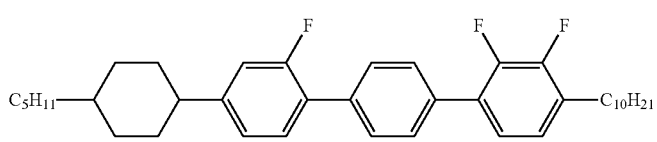 |
| 31 | 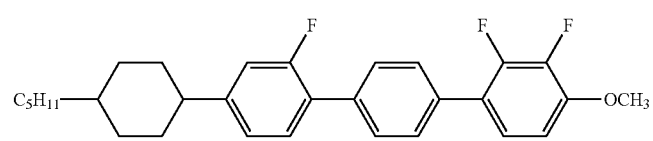 |
| 32 | 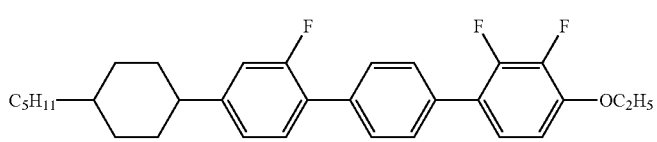
C 107.8 N 299.3 I
$T_{NI}$; 238.6° C., Δε; -5.54, Δn; 0.257 |
| 33 | 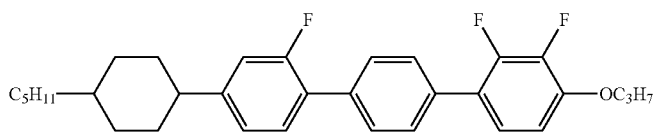 |
| 34 | 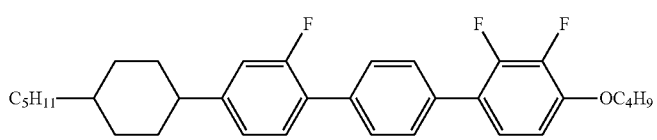 |
| 35 | 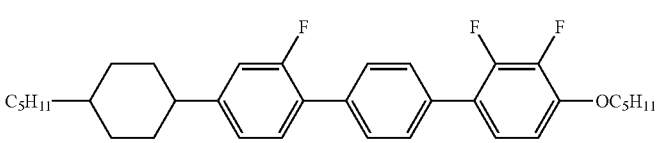 |
| 36 | 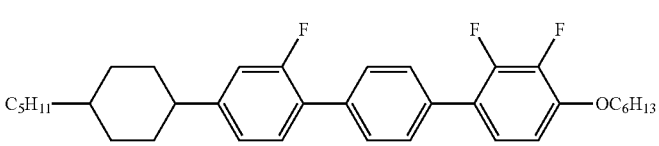 |
| 37 | 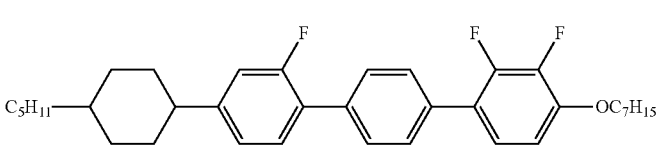 |
| 38 | 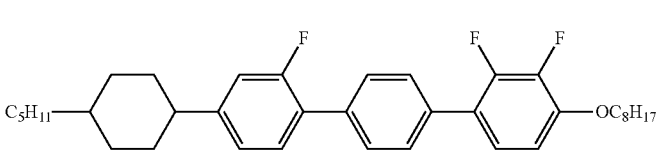 |

-continued
| No. | |
|---|---|
| 39 | 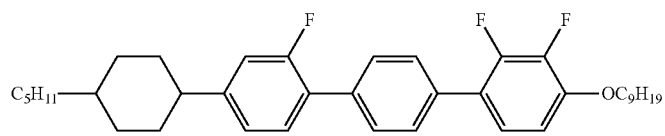 |
| 40 | 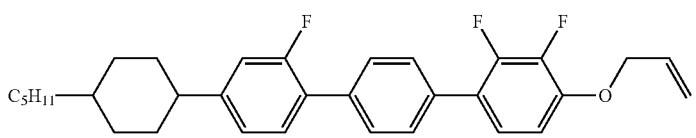 |
| 41 | 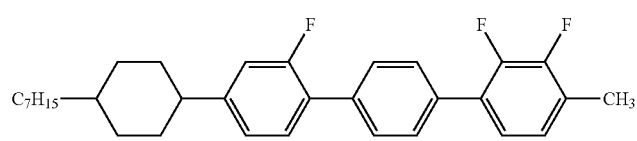 |
| 42 | 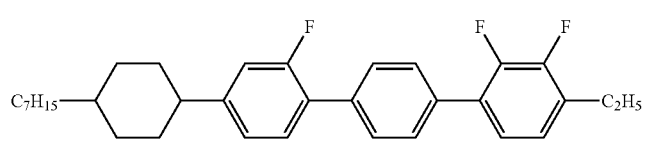 |
| 43 | 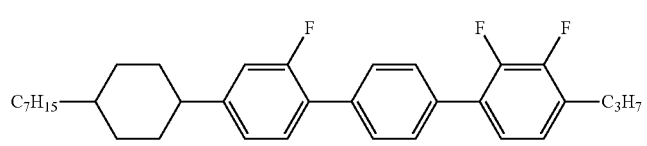 |
| 44 | 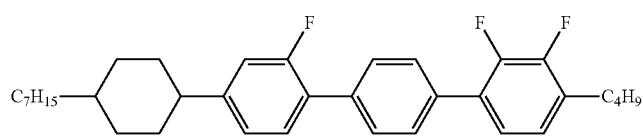 |
| 45 | 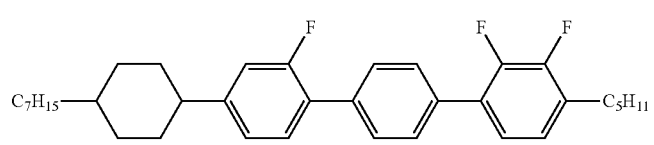 |
| 46 | 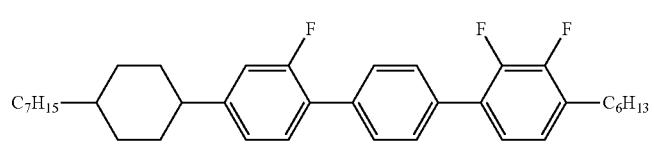 |
| 47 | 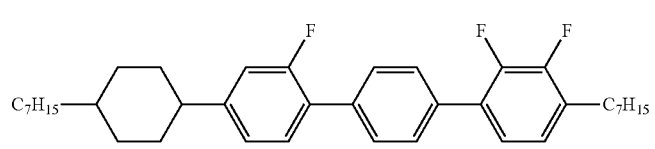 |
| 48 | 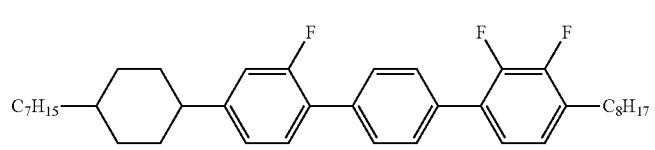 |
| 49 | 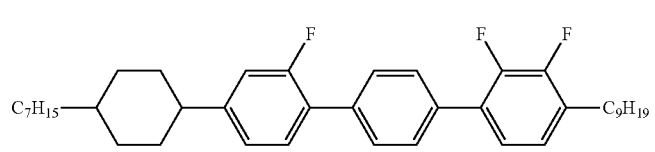 |

-continued
| No. | |
|---|---|
| 50 | 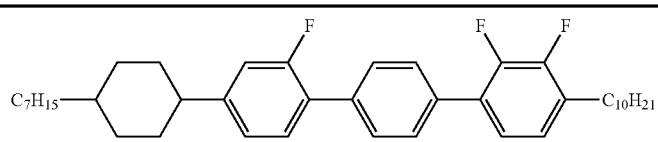 |
| 51 | 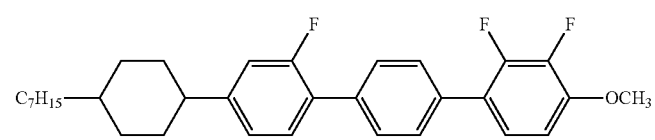 |
| 52 | 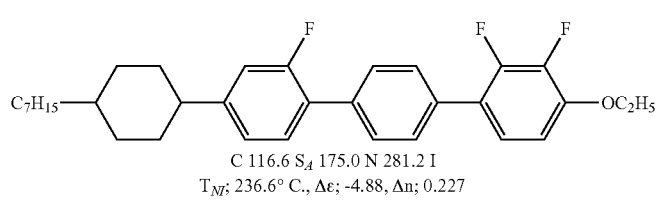
C 116.6 S$_A$ 175.0 N 281.2 I
T$_{NI}$; 236.6° C., Δε; -4.88, Δn; 0.227 |
| 53 | 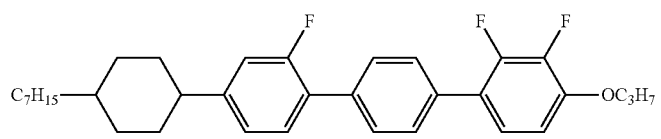 |
| 54 | 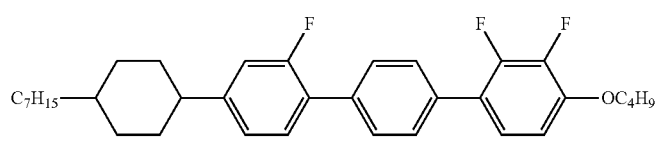 |
| 55 | 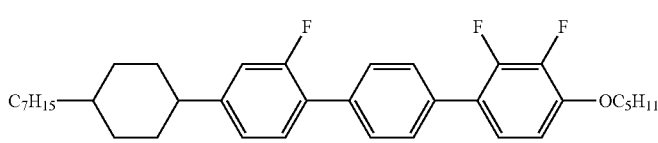 |
| 56 | 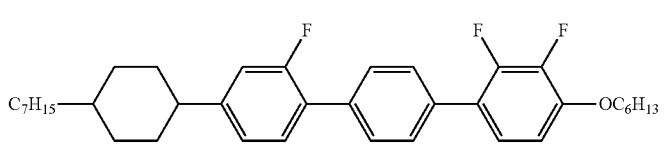 |
| 57 | 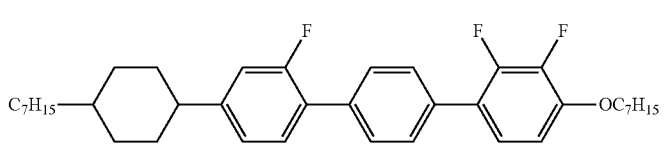 |
| 58 | 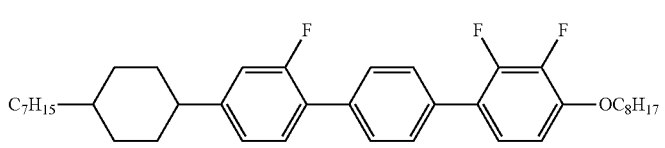 |
| 59 | 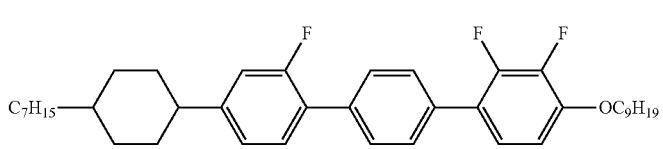 |
| 60 | 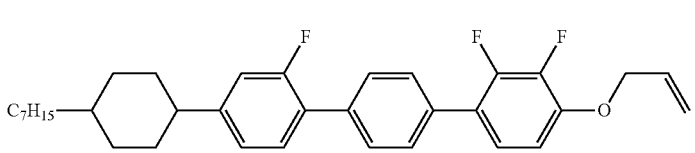 |

-continued
| No. | |
|---|---|
| 61 | 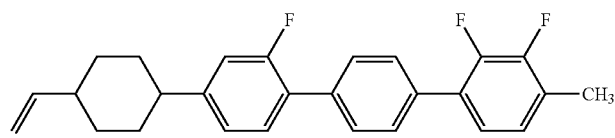 |
| 62 | 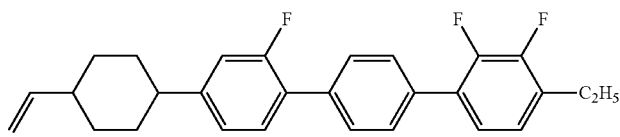 |
| 63 | 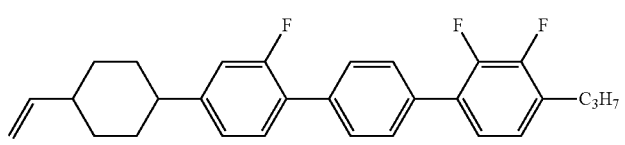 |
| 64 | 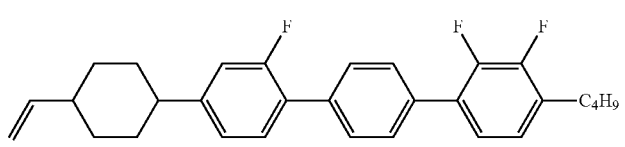 |
| 65 | 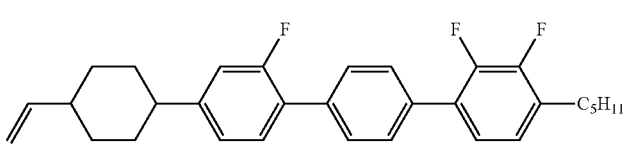 |
| 66 | 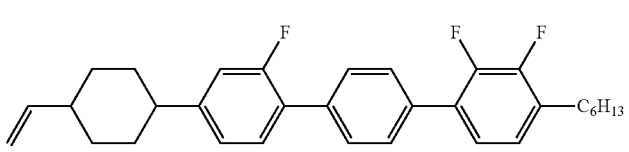 |
| 67 | 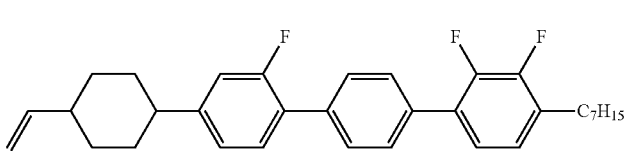 |
| 68 | 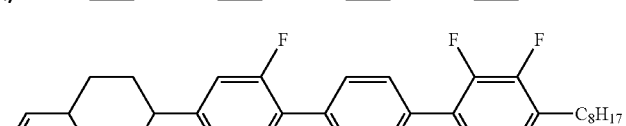 |
| 69 | 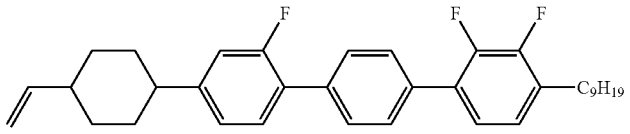 |
| 70 |  |
| 71 | 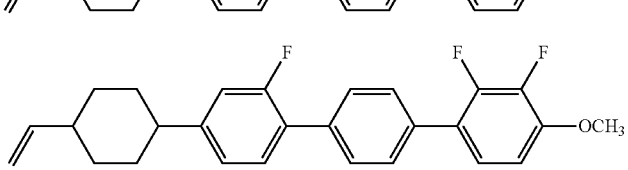 |

-continued
| No. | |
|---|---|
| 72 | 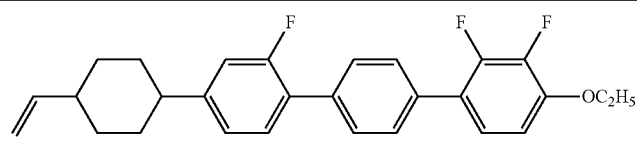 C 127.6 N 302.8 I $T_{NI}$; 238.6 ° C., Δε; -5.6, Δn; 0.227 |
| 73 | 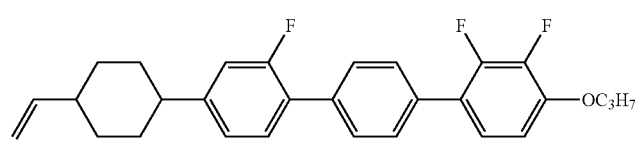 |
| 74 | 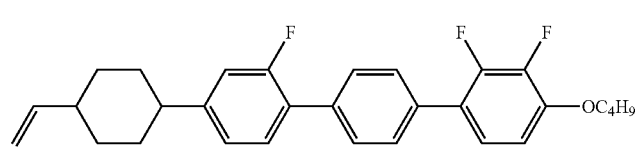 |
| 75 | 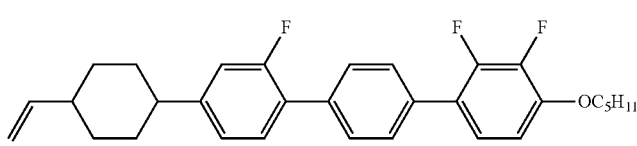 |
| 76 | 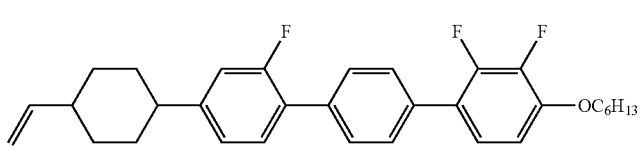 |
| 77 | 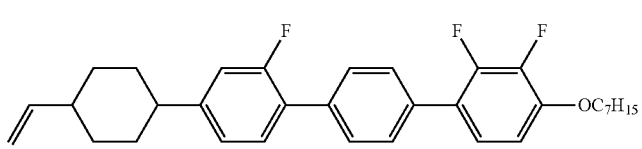 |
| 78 | 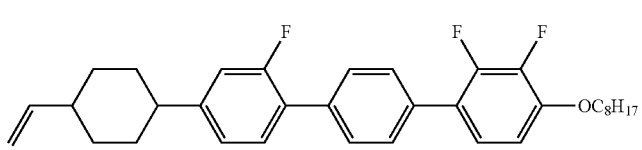 |
| 79 | 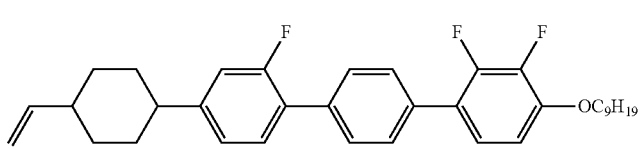 |
| 80 | 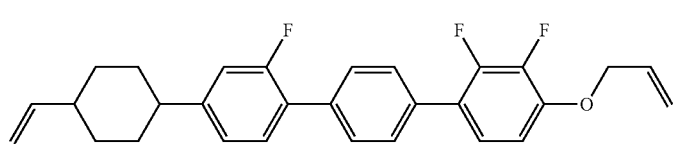 |
| 81 | 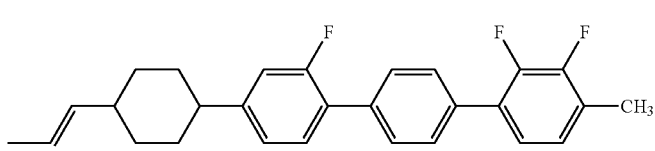 |

-continued
| No. | |
|---|---|
| 82 | 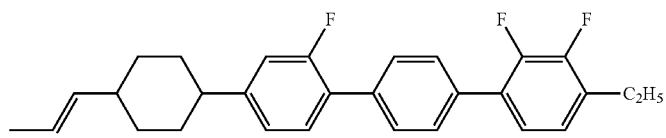 |
| 83 | 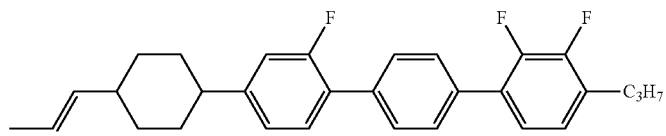 |
| 84 | 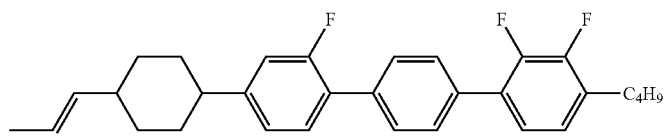 |
| 85 | 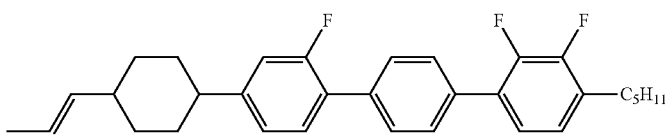 |
| 86 | 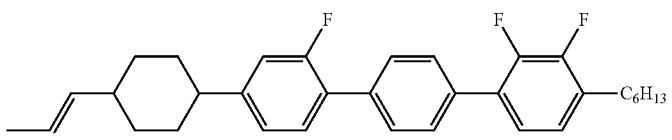 |
| 87 | 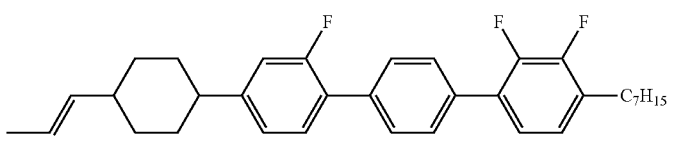 |
| 88 | 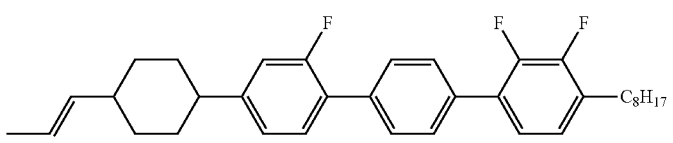 |
| 89 | 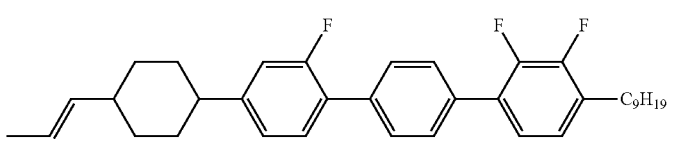 |
| 90 | 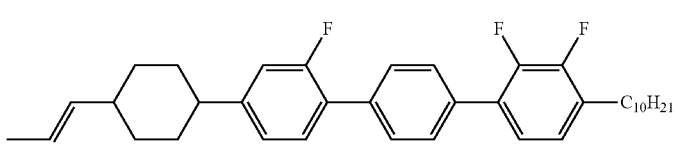 |
| 91 | 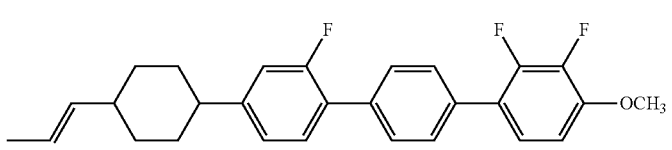 |
| 92 | 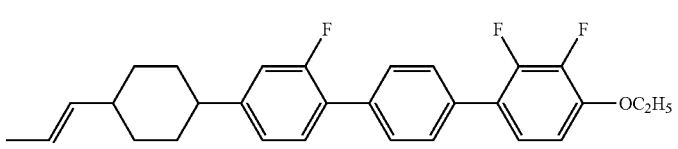 |

-continued
| No. | |
|---|---|
| 93 | 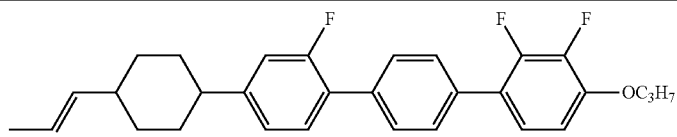 |
| 94 | 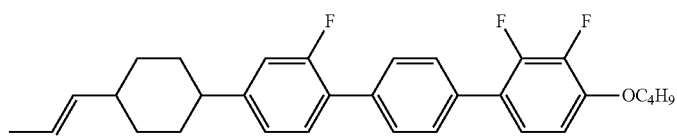 |
| 95 | 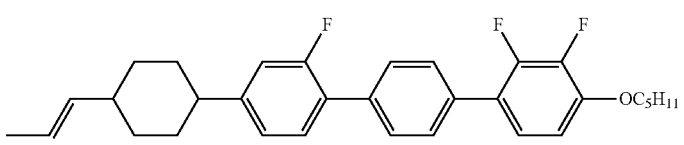 |
| 96 | 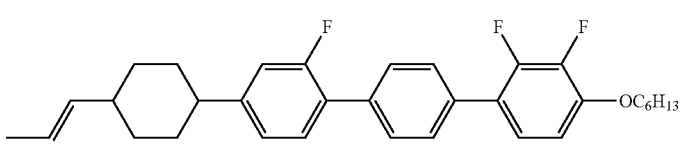 |
| 97 | 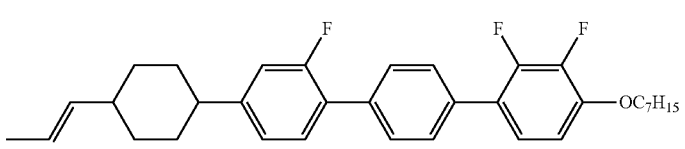 |
| 98 | 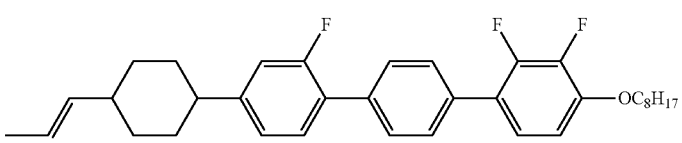 |
| 99 | 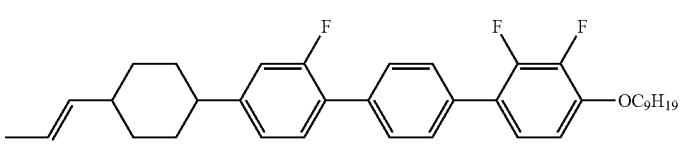 |
| 100 | 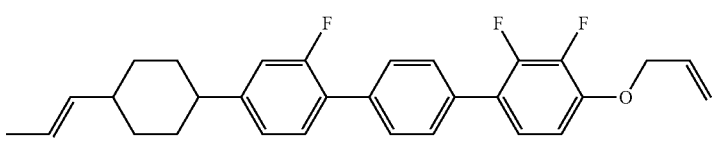 |
| 101 | 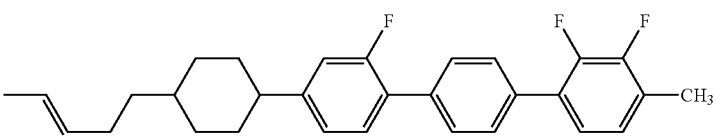 |
| 102 | 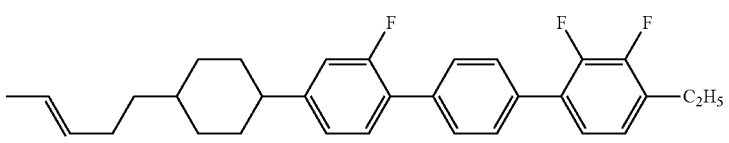 |
| 103 | 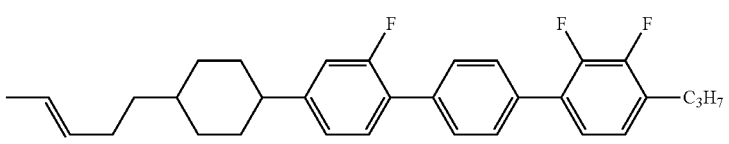 |

-continued
| No. |
|---|
| 104 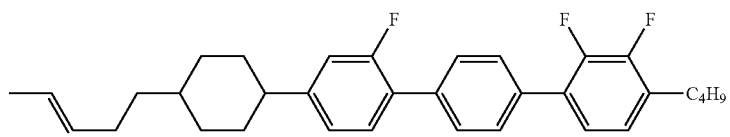 |
| 105 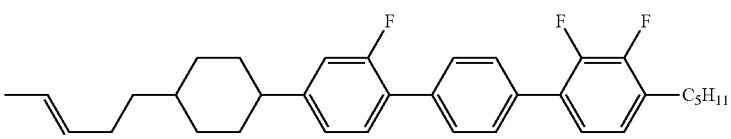 |
| 106 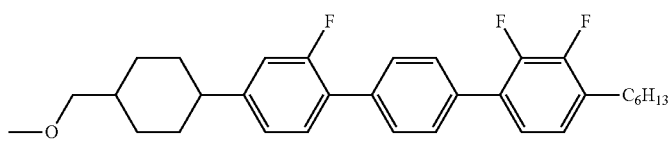 |
| 107 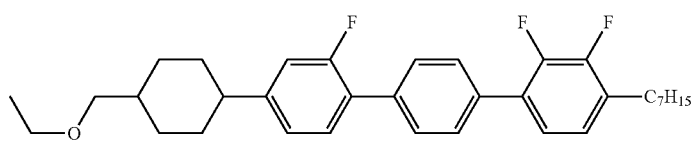 |
| 108 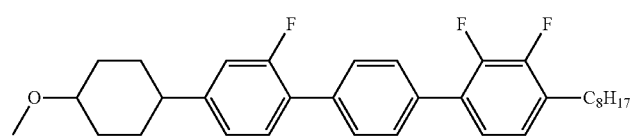 |
| 109 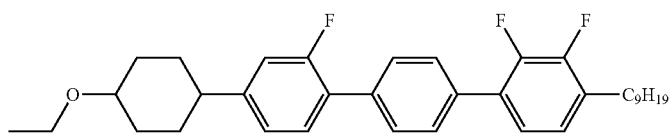 |
| 110 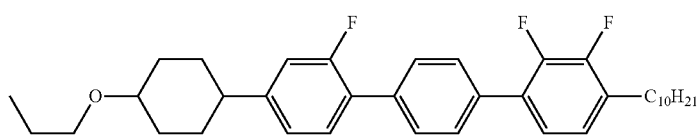 |
| 111 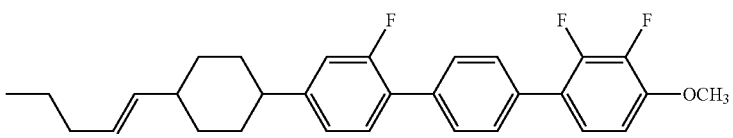 |
| 112 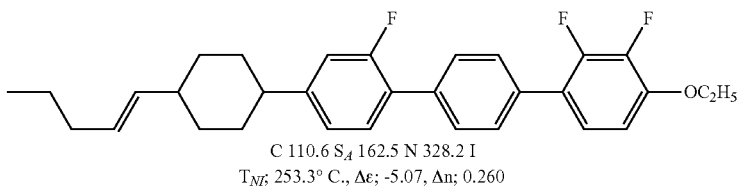<br>C 110.6 S$_A$ 162.5 N 328.2 I<br>T$_{NI}$; 253.3° C., Δε; -5.07, Δn; 0.260 |
| 113 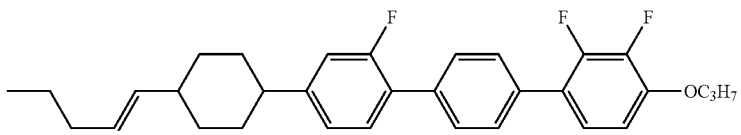 |

-continued
| No. | |
|---|---|
| 114 | 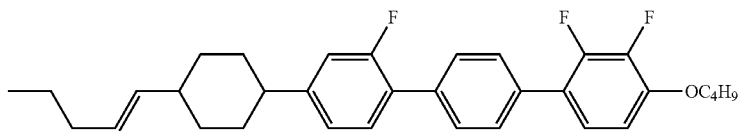 |
| 115 | 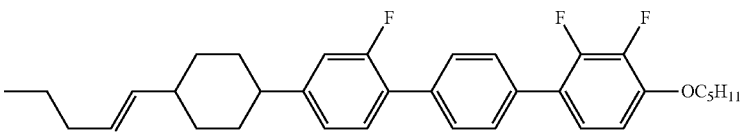 |
| 116 | 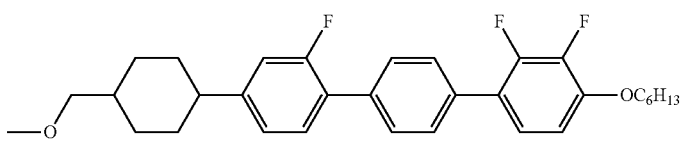 |
| 117 | 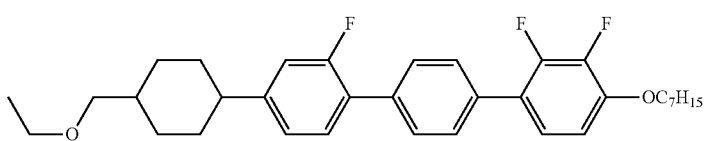 |
| 118 | 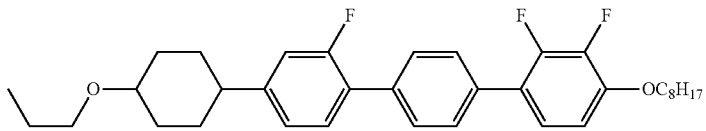 |
| 119 | 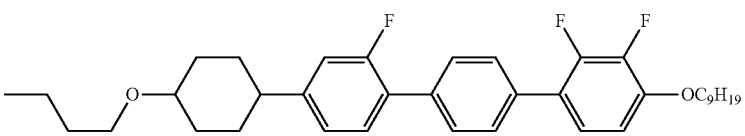 |
| 120 | 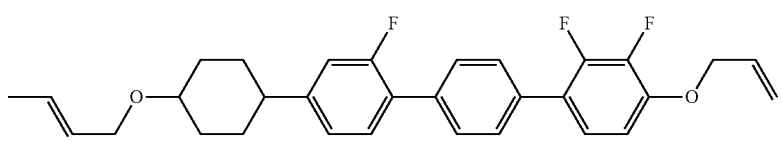 |
| 121 | 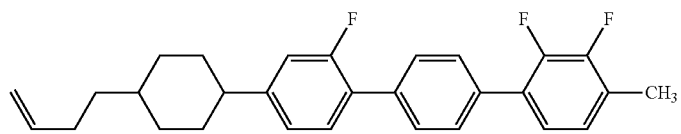 |
| 122 | 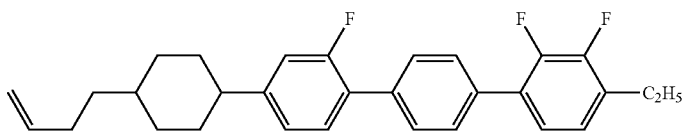 |
| 123 | 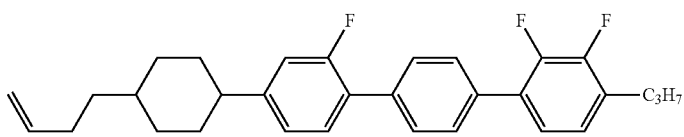 |
| 124 | 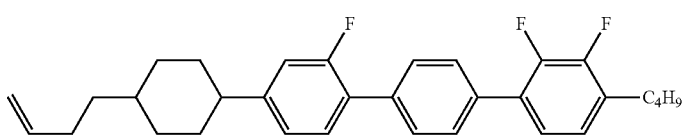 |

-continued
| No. | |
|---|---|
| 125 | 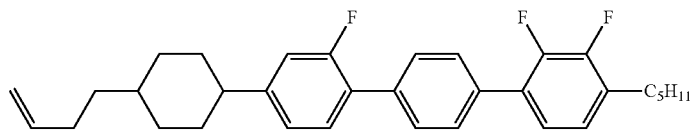 |
| 126 | 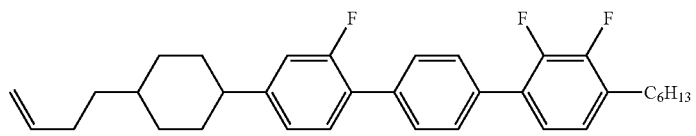 |
| 127 | 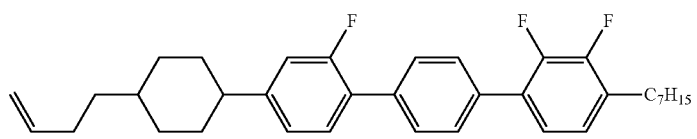 |
| 128 | 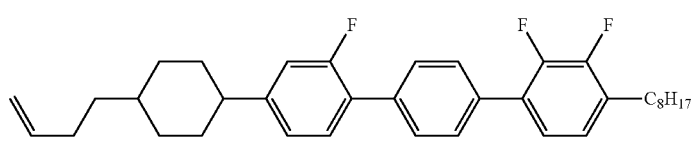 |
| 129 | 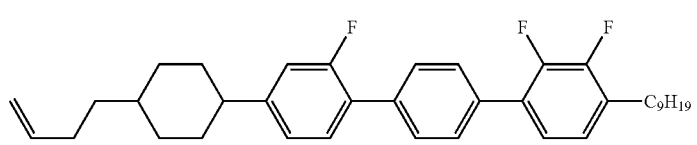 |
| 130 | 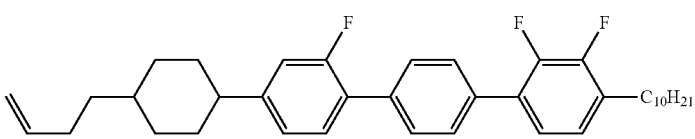 |
| 131 | 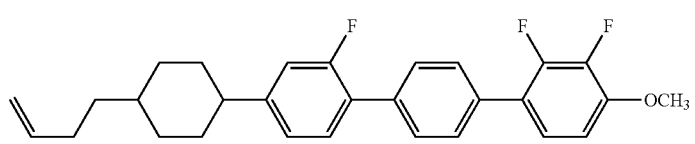 |
| 132 | 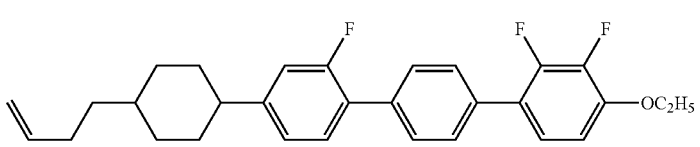 |
| 133 | 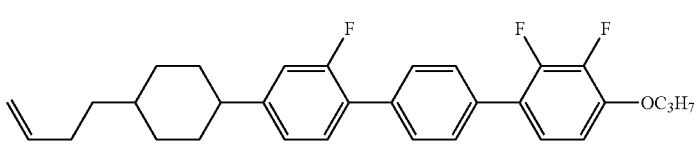 |
| 134 | 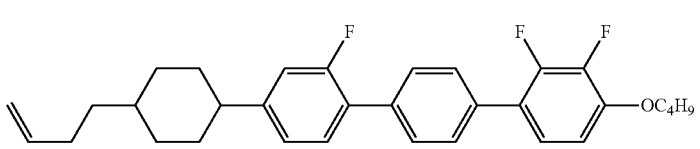 |
| 135 | 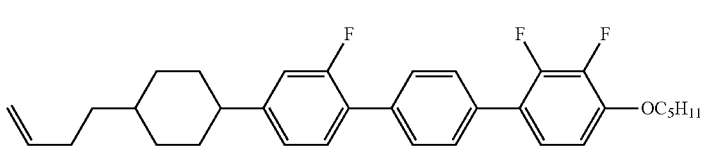 |

-continued
| No. | |
|---|---|
| 136 | 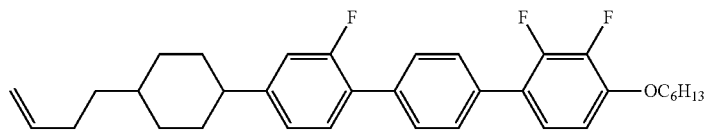 |
| 137 | 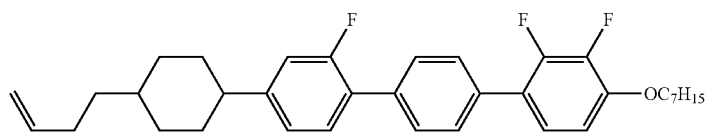 |
| 138 | 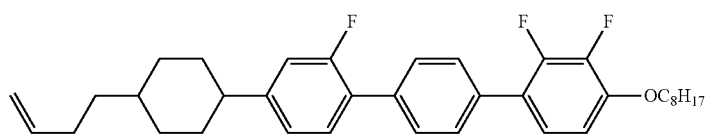 |
| 139 | 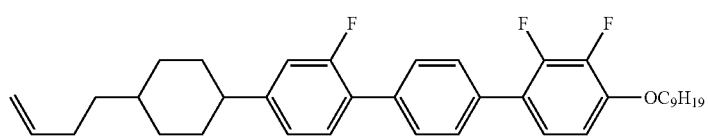 |
| 140 | 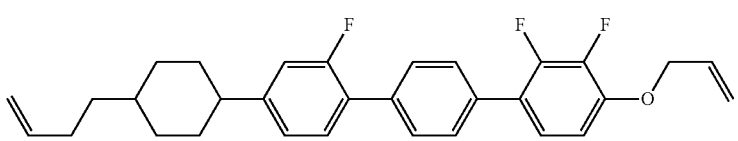 |
| 141 | 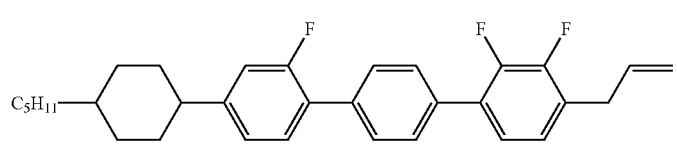 |
| 142 | 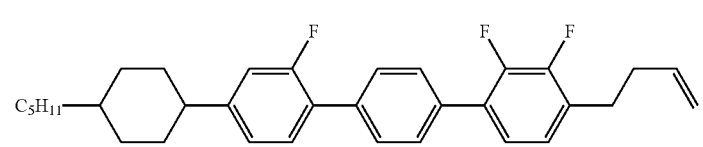 |
| 143 | 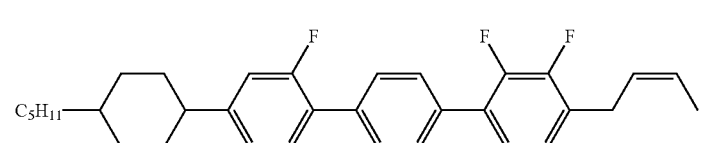 |
| 144 | 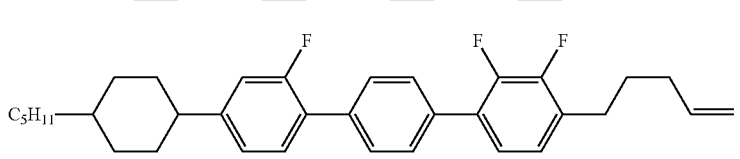 |
| 145 | 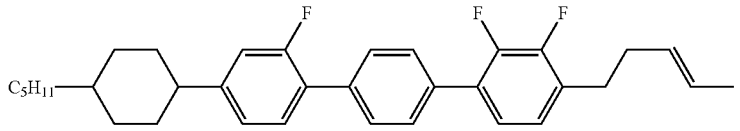 |
| 146 | 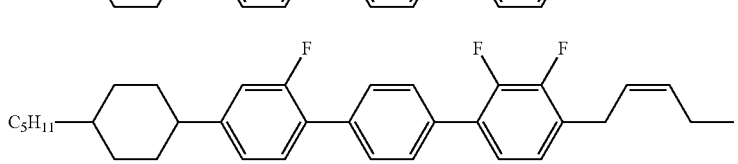 |

| No. |
|---|
| 147 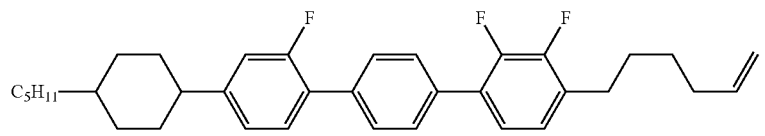 |
| 148 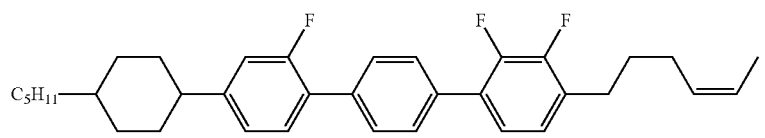 |
| 149 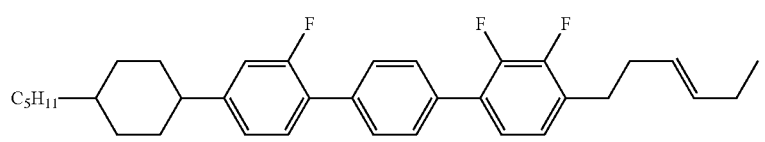 |
| 150 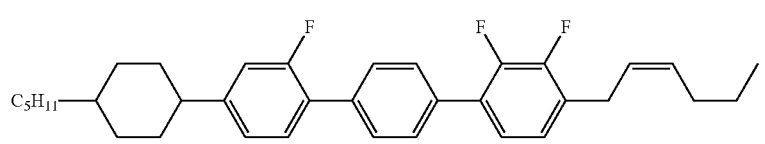 |
| 151 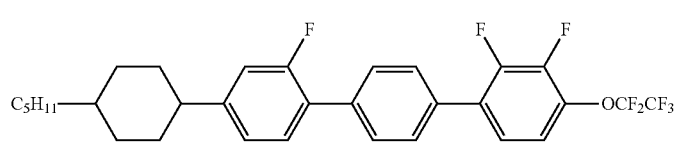 |
| 152 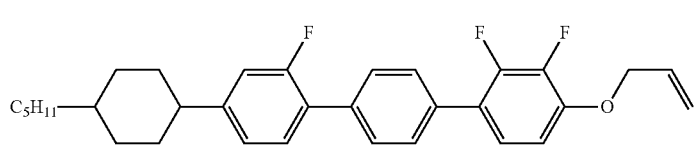 |
| 153 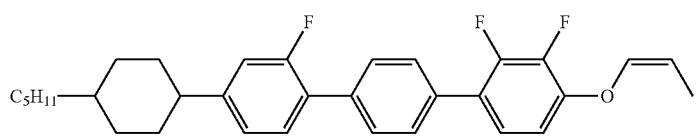 |
| 154 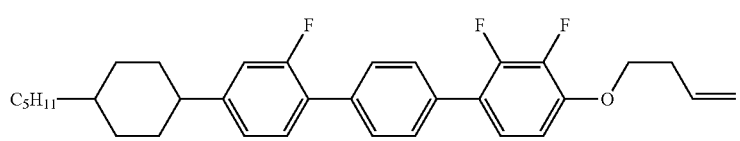 |
| 155 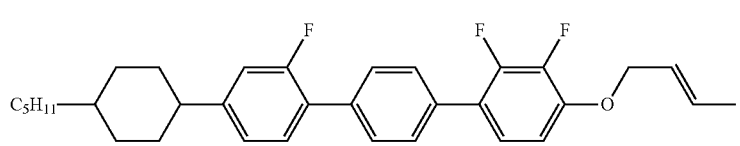 |
| 156 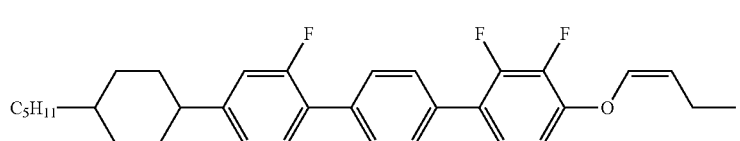 |
| 157 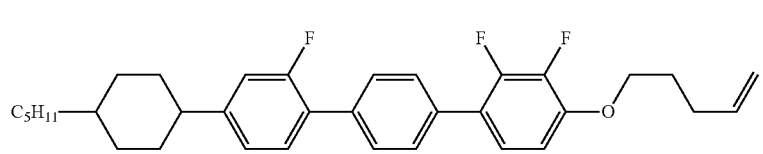 |

| No. | |
|---|---|
| 158 | 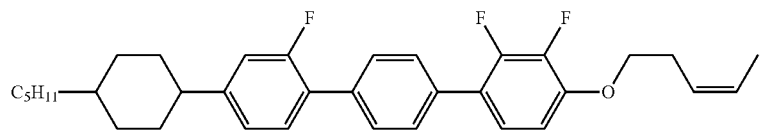 |
| 159 | 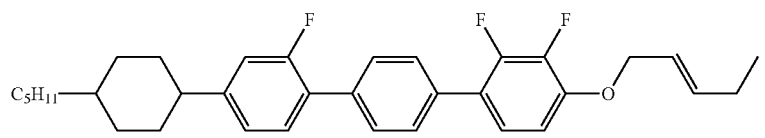 |
| 160 | 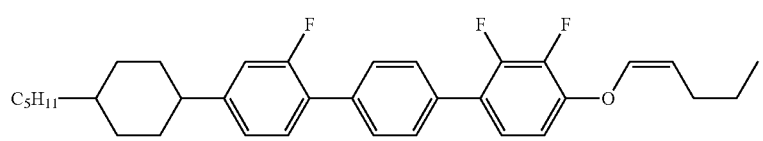 |
| 161 | 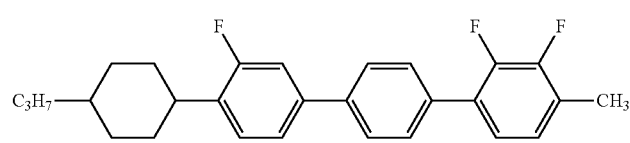 |
| 162 | 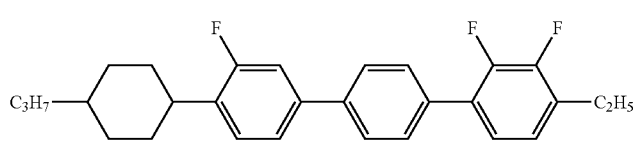 |
| 163 | 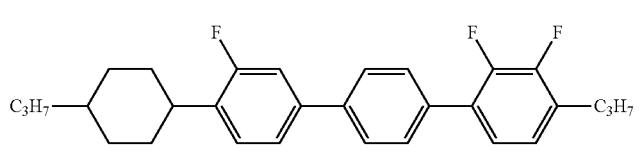 |
| 164 | 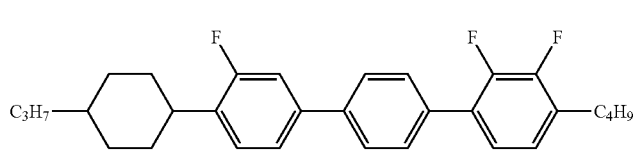 |
| 165 | 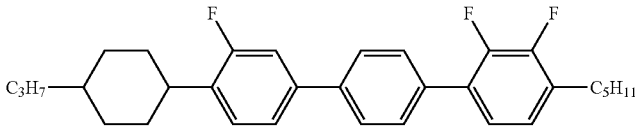 |
| 166 | 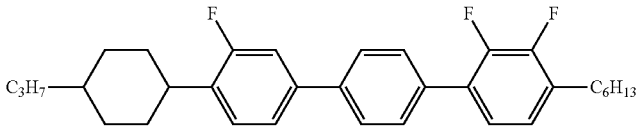 |
| 167 |  |
| 168 | 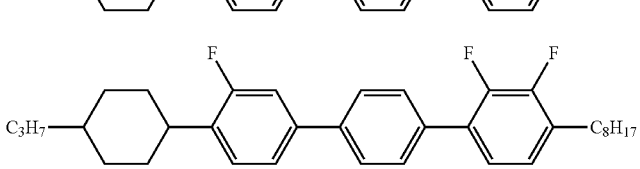 |

| No. | |
|---|---|
| 169 | 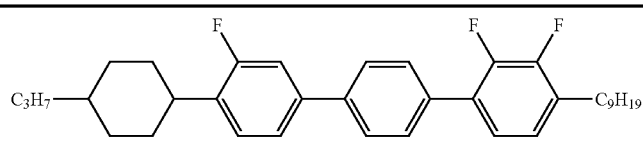 |
| 170 | 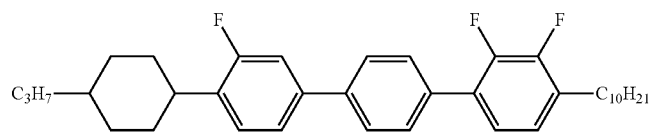 |
| 171 | 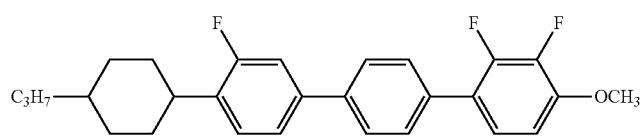 |
| 172 |  C 129.1 N 311.7 I $T_{NI}$; 246.6° C., Δε; -6.62, Δn; 0.271 |
| 173 | 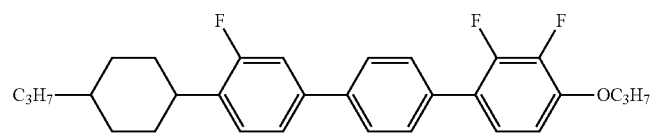 |
| 174 | 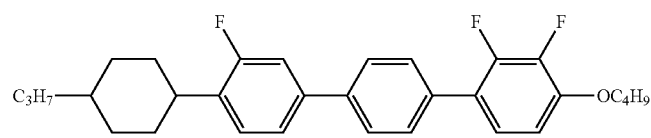 |
| 175 | 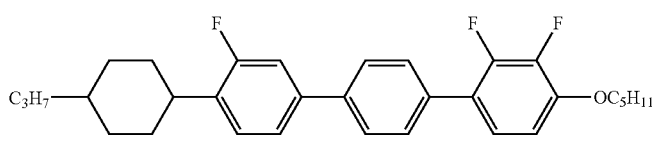 |
| 176 | 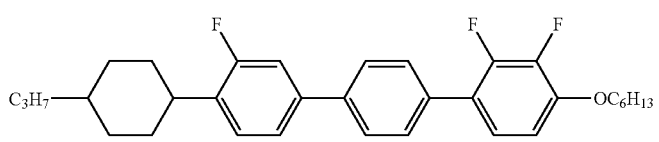 |
| 177 | 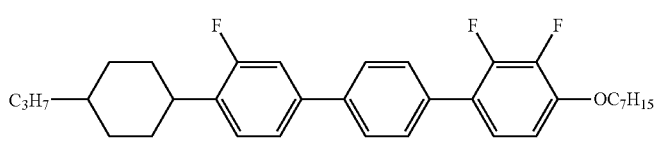 |
| 178 | 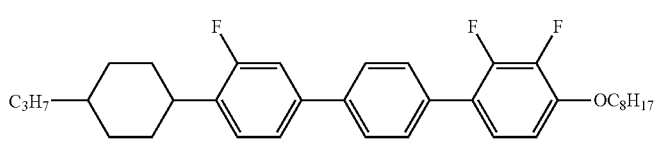 |
| 179 | 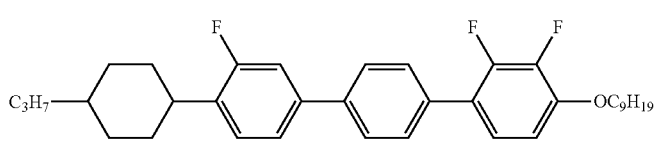 |

-continued
| No. | |
|---|---|
| 180 | 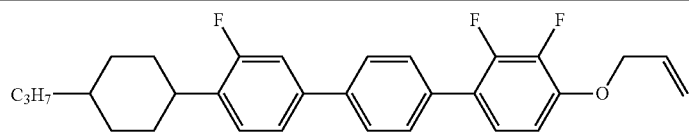 |
| 181 | 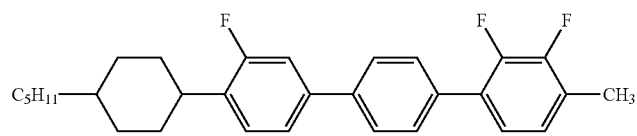 |
| 182 | 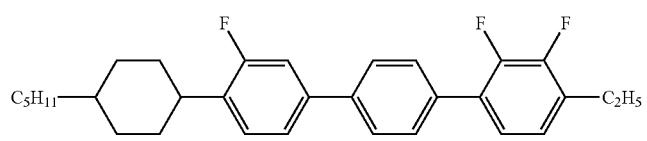 |
| 183 | 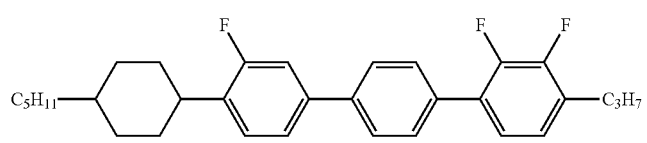 |
| 184 | 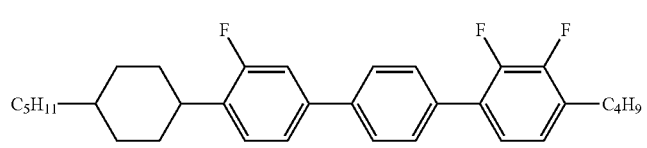 |
| 185 | 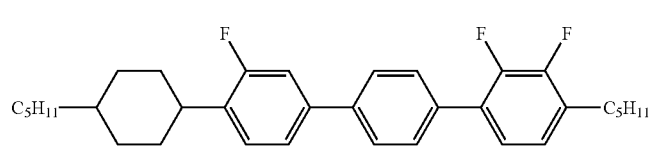 |
| 186 | 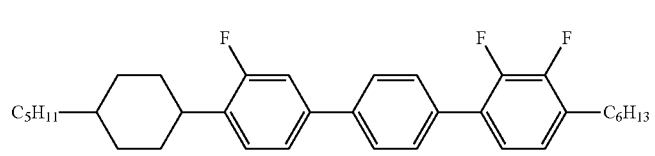 |
| 187 | 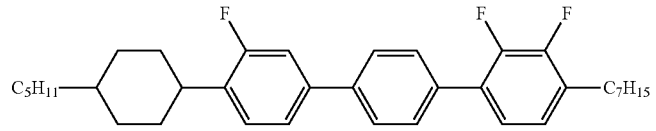 |
| 188 | 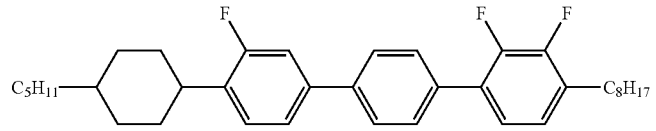 |
| 189 | 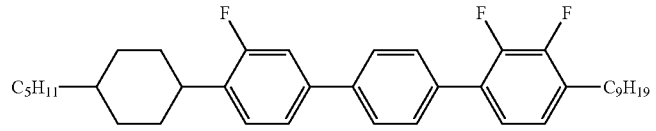 |
| 190 | 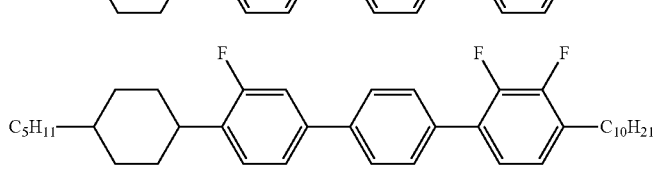 |

-continued
| No. | |
|---|---|
| 191 | 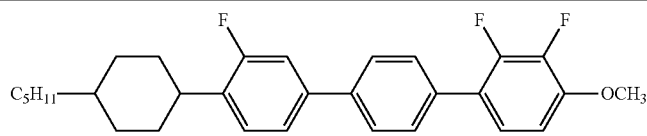 |
| 192 | 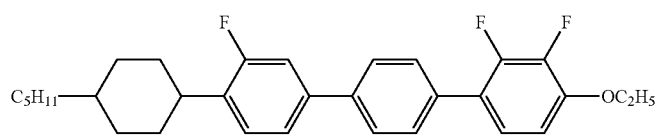 |
| 193 | 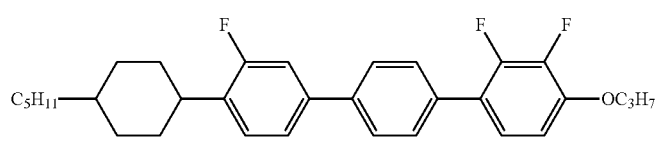 |
| 194 | 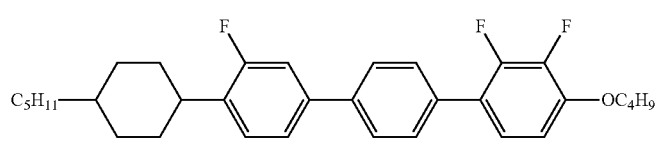 |
| 195 | 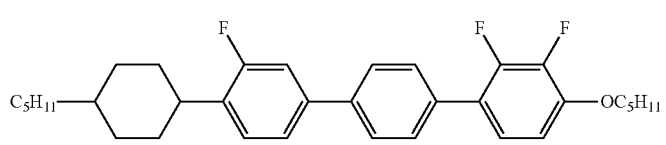 |
| 196 | 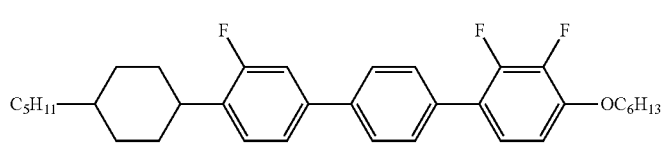 |
| 197 | 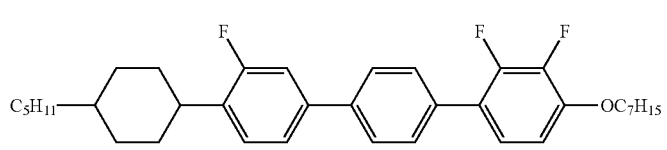 |
| 198 | 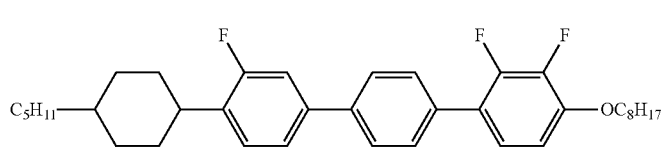 |
| 199 | 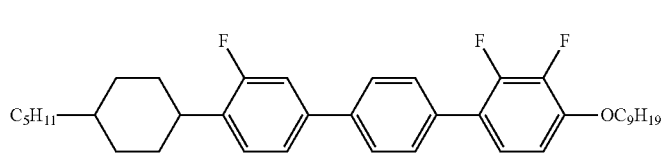 |
| 200 | 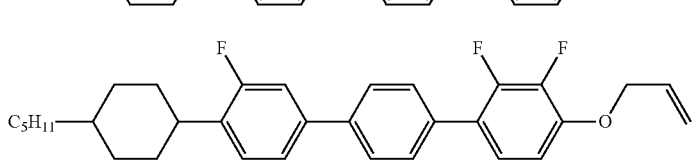 |
| 201 | 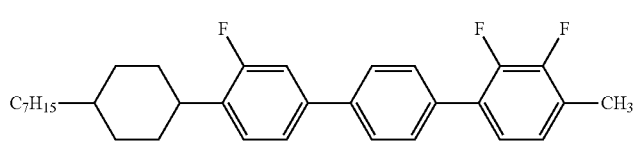 |

-continued
| No. | |
|---|---|
| 202 | 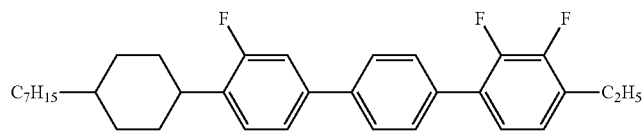 |
| 203 | 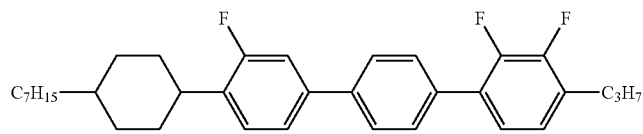 |
| 204 | 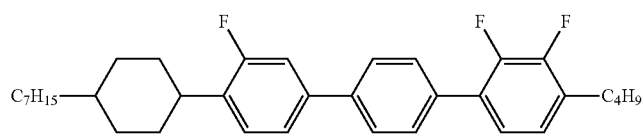 |
| 205 | 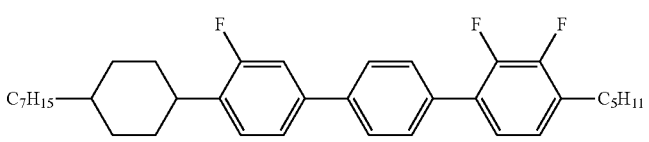 |
| 206 | 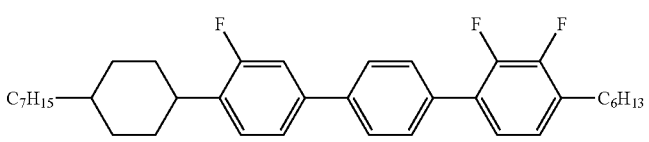 |
| 207 | 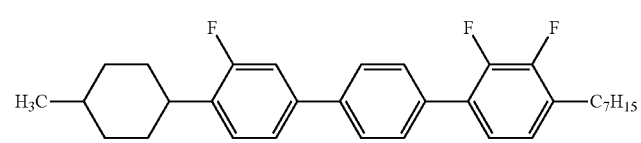 |
| 208 | 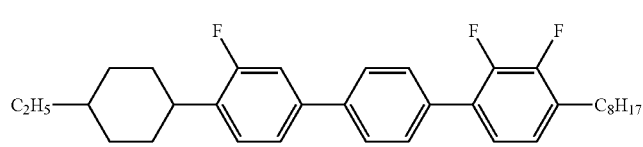 |
| 209 | 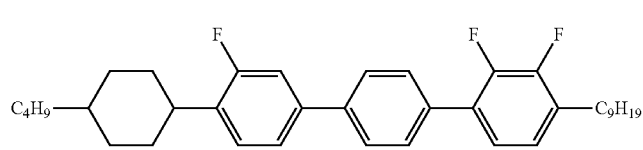 |
| 210 | 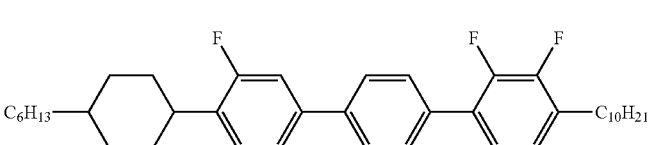 |
| 211 | 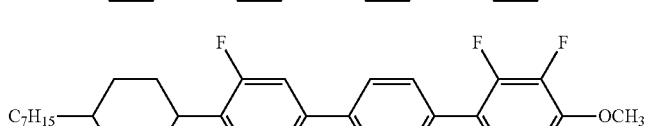 |
| 212 | 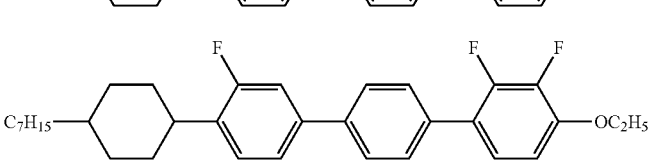 |

-continued
| No. | |
|---|---|
| 213 | 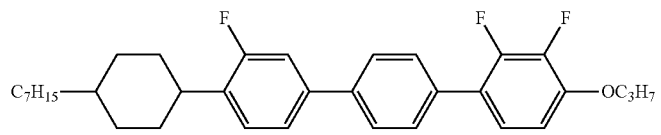 |
| 214 | 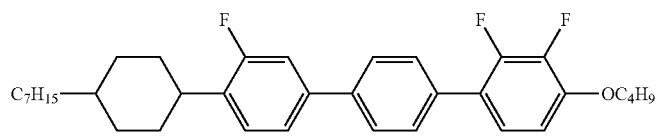 |
| 215 | 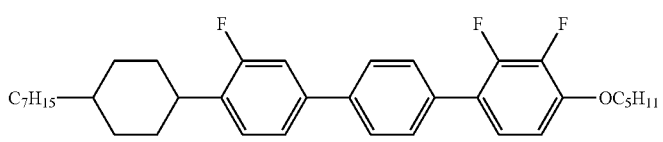 |
| 216 | 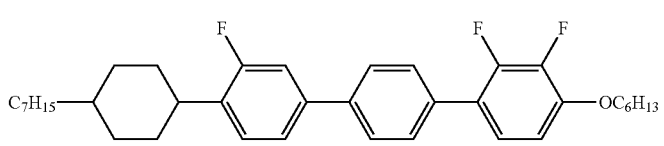 |
| 217 | 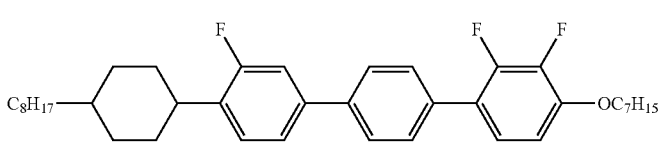 |
| 218 | 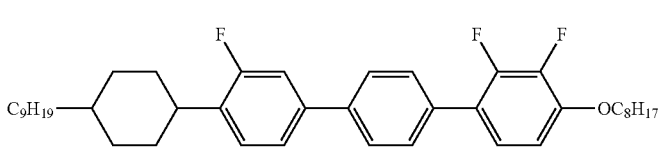 |
| 219 | 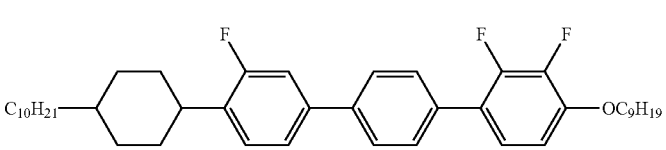 |
| 220 | 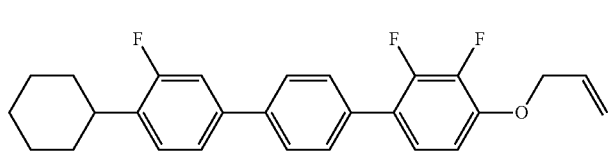 |
| 221 | 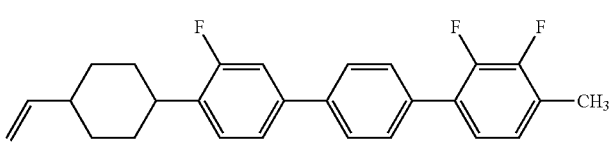 |
| 222 | 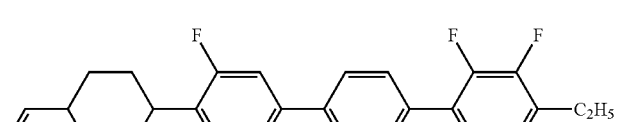 |
| 223 | 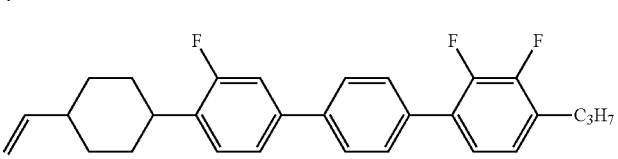 |

-continued
| No. | |
|---|---|
| 224 | 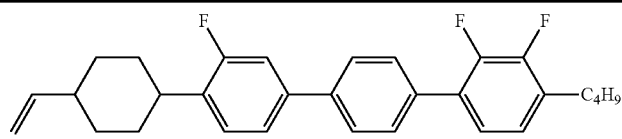 |
| 225 | 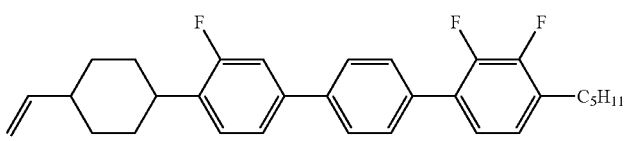 |
| 226 | 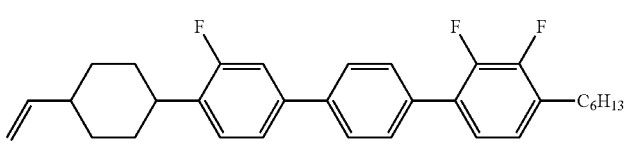 |
| 227 | 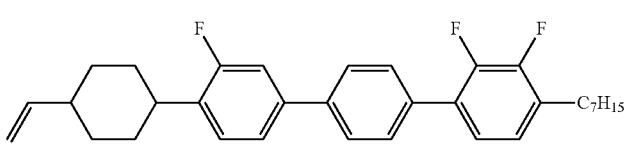 |
| 228 | 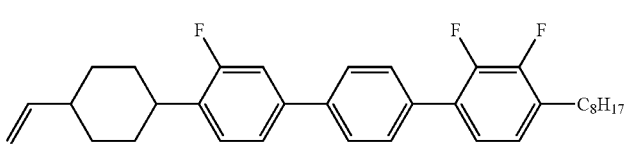 |
| 229 | 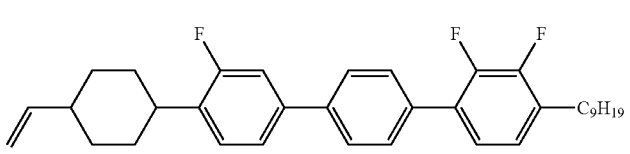 |
| 230 | 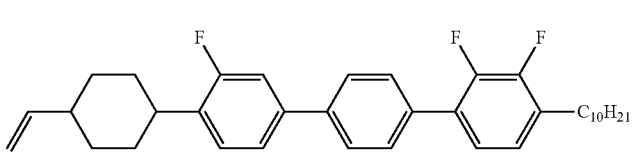 |
| 231 | 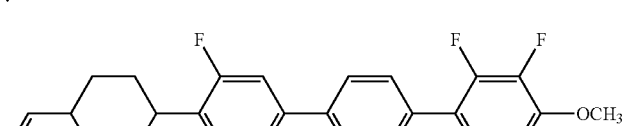 |
| 232 | 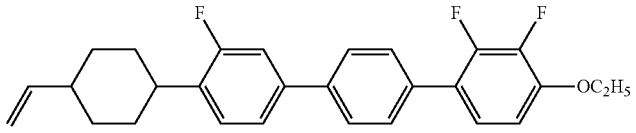 |
| 233 | 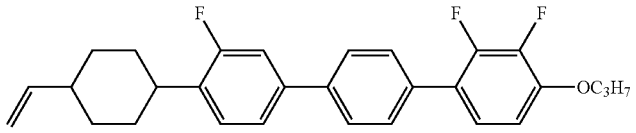 |
| 234 | 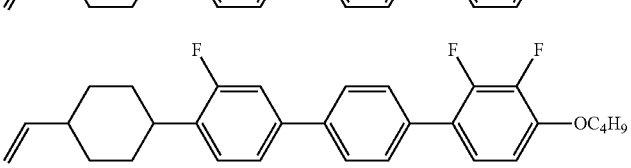 |

-continued
| No. | |
|---|---|
| 235 | 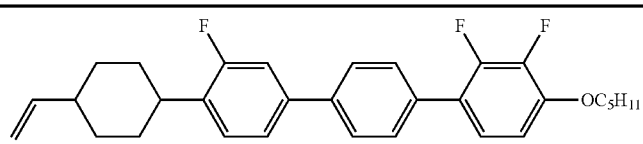 |
| 236 | 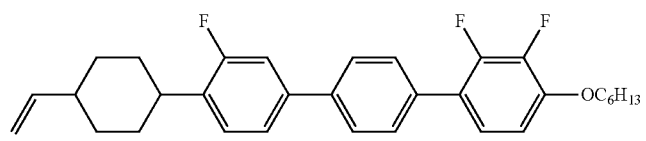 |
| 237 | 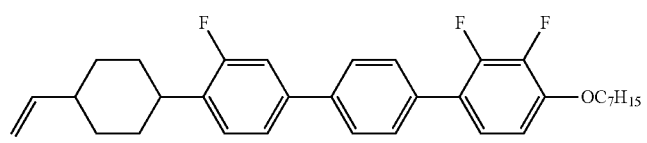 |
| 238 | 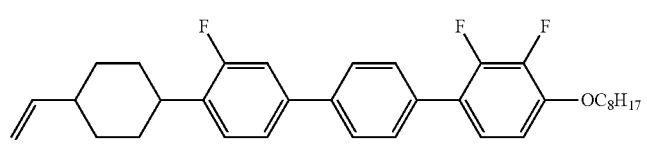 |
| 239 | 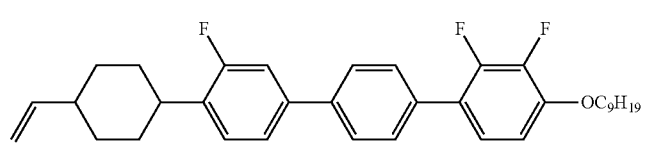 |
| 240 | 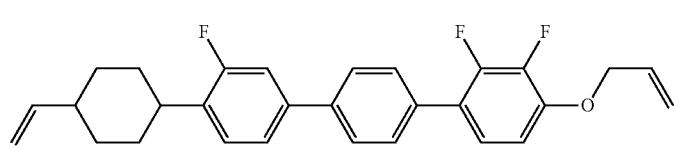 |
| 241 | 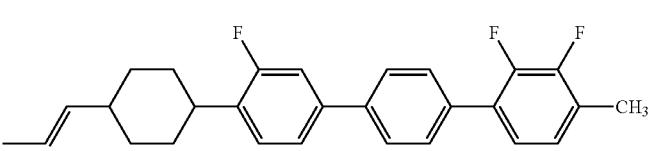 |
| 242 | 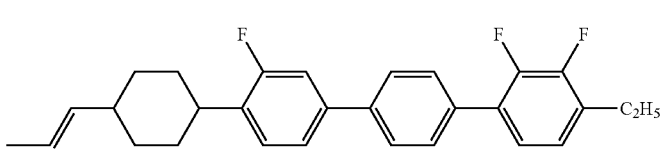 |
| 243 | 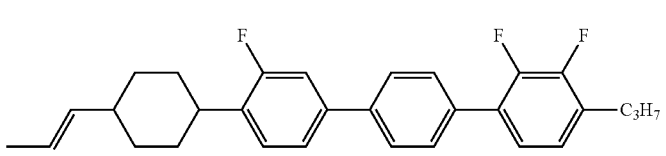 |
| 244 | 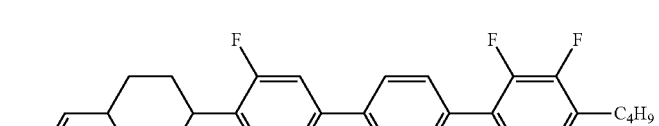 |
| 245 | 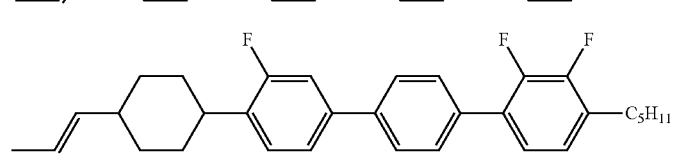 |

-continued
| No. | |
|---|---|
| 246 | 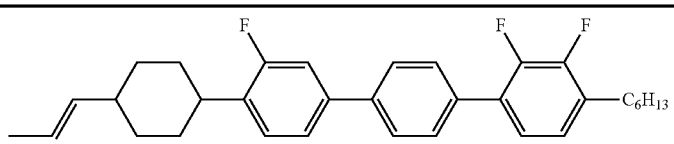 |
| 247 | 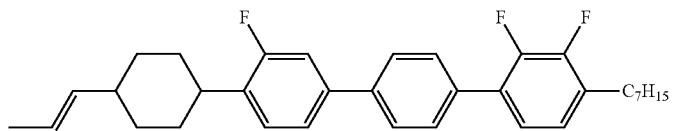 |
| 248 | 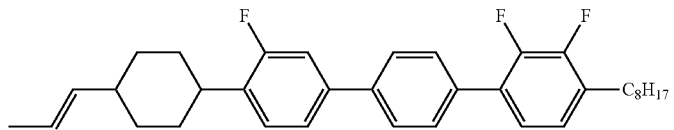 |
| 249 | 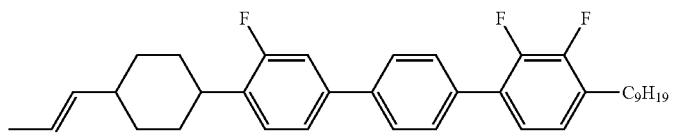 |
| 250 | 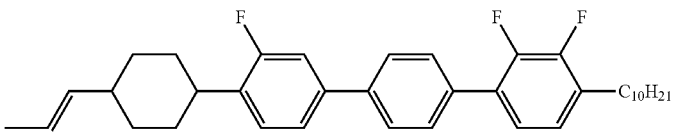 |
| 251 | 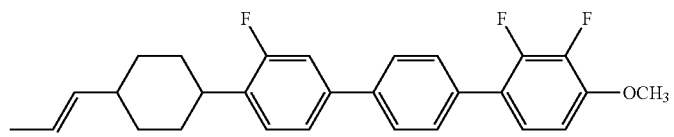 |
| 252 | 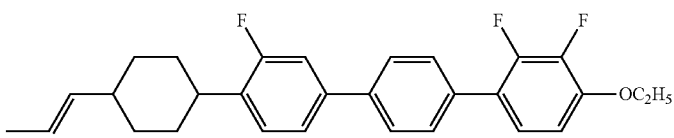 |
| 253 | 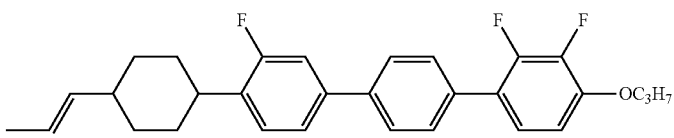 |
| 254 | 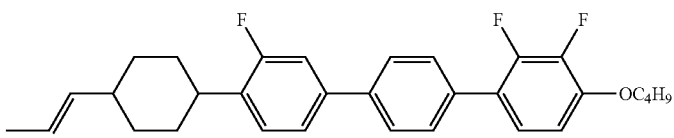 |
| 255 | 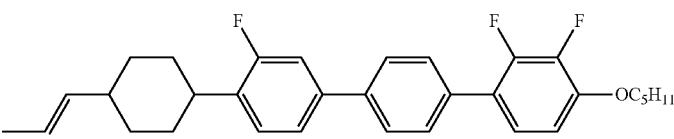 |
| 256 | 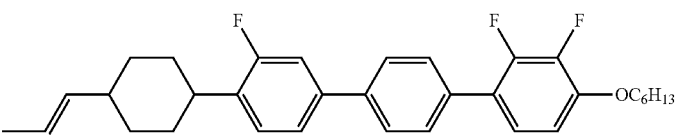 |

-continued
| No. | |
|---|---|
| 257 | 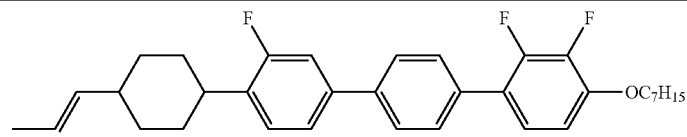 |
| 258 | 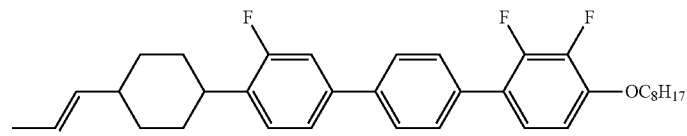 |
| 259 | 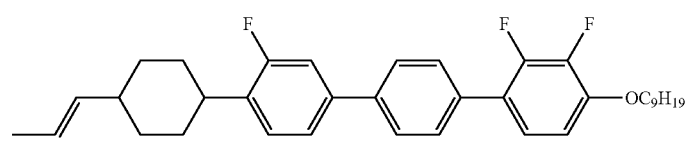 |
| 260 | 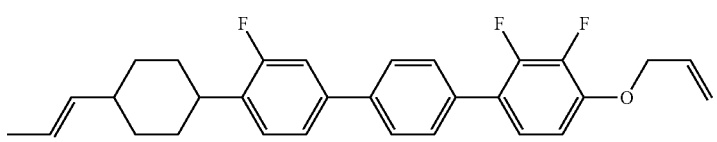 |
| 261 | 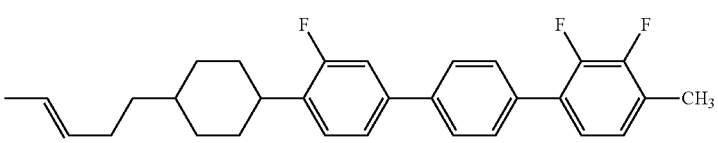 |
| 262 | 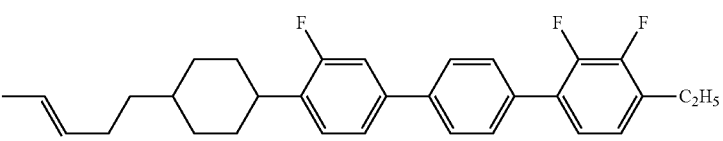 |
| 263 | 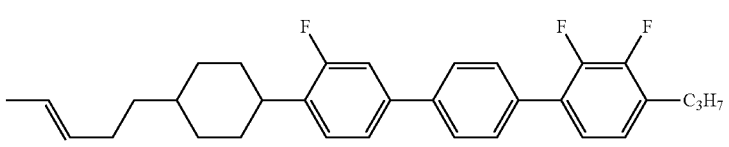 |
| 264 | 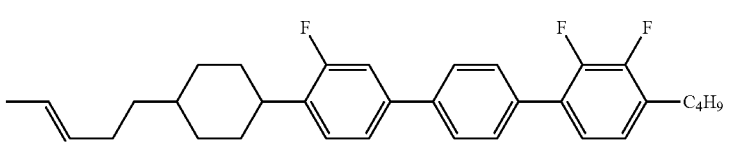 |
| 265 | 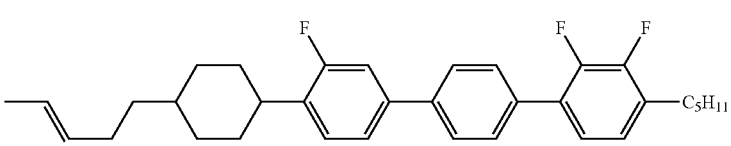 |
| 266 | 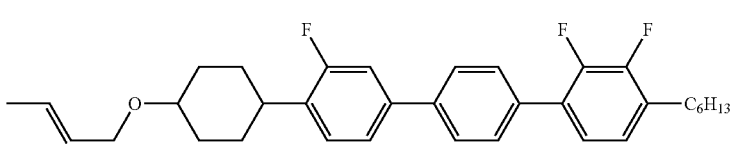 |
| 267 | 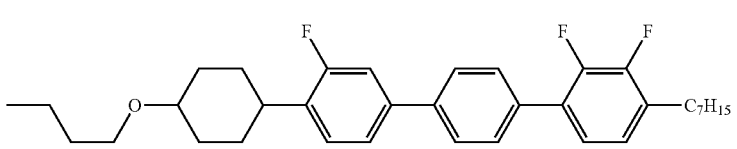 |

| No. | |
|---|---|
| 268 | 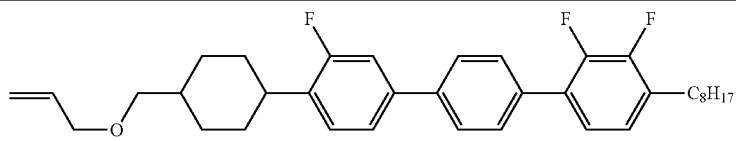 |
| 269 | 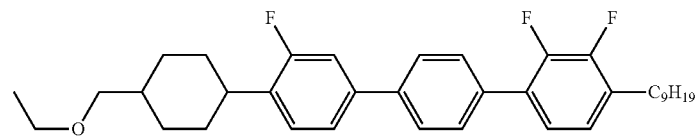 |
| 270 | 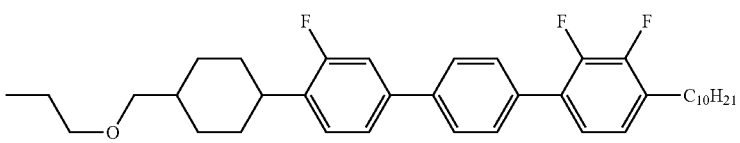 |
| 271 | 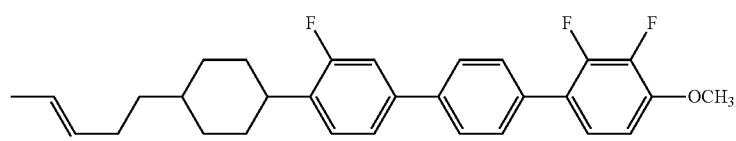 |
| 272 | 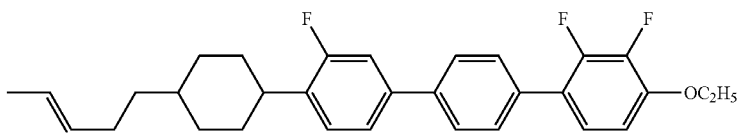 |
| 273 | 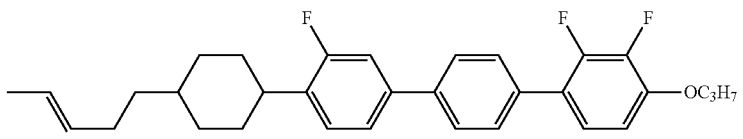 |
| 274 | 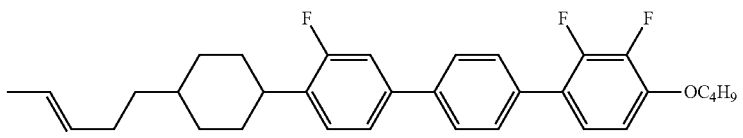 |
| 275 | 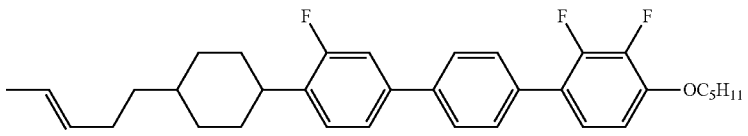 |
| 276 | 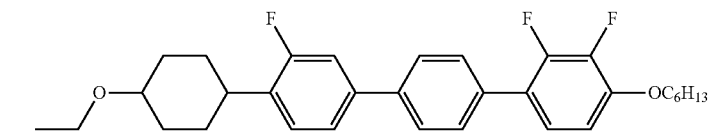 |
| 277 | 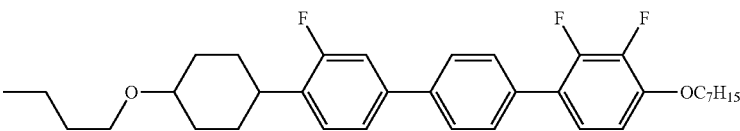 |
| 278 | 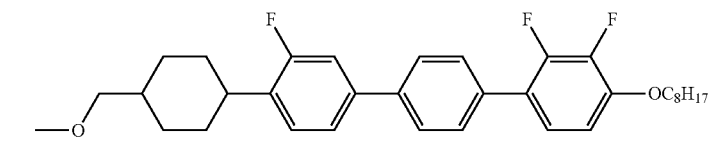 |

| No. | |
|---|---|
| 279 | 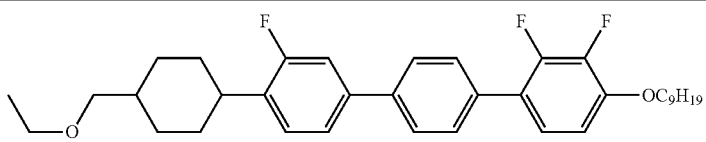 |
| 280 | 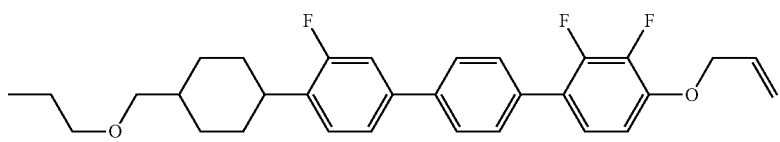 |
| 281 | 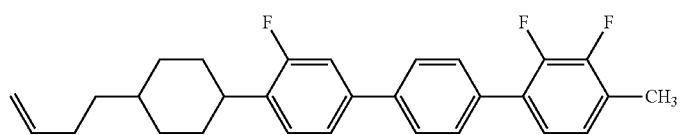 |
| 282 | 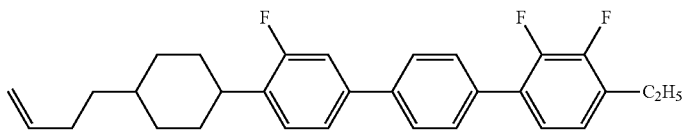 |
| 283 | 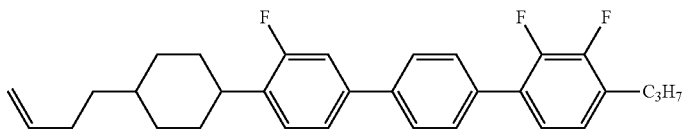 |
| 284 | 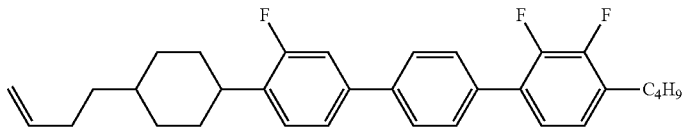 |
| 285 | 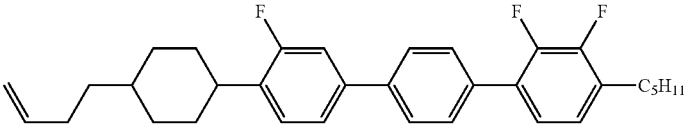 |
| 286 | 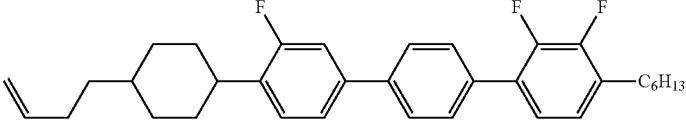 |
| 287 | 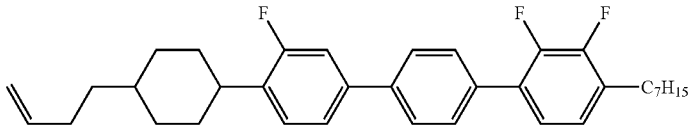 |
| 288 | 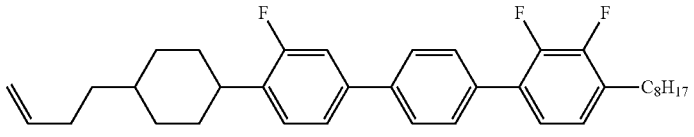 |
| 289 | 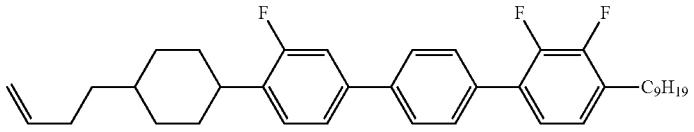 |

| No. | |
|---|---|
| 290 | 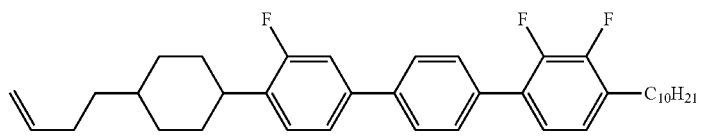 |
| 291 | 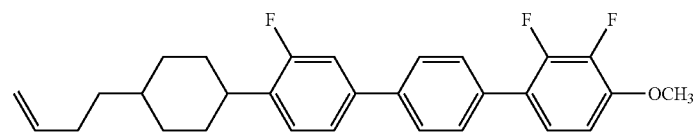 |
| 292 | 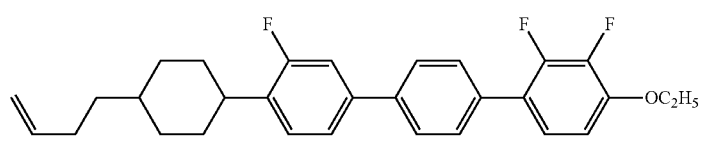 |
| 293 | 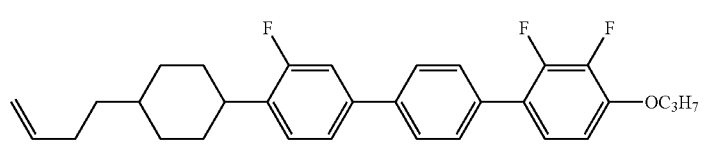 |
| 294 | 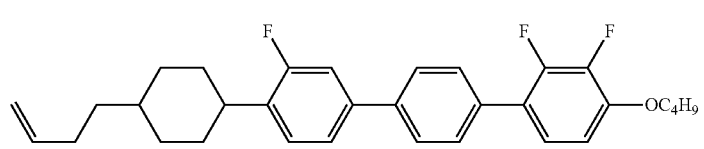 |
| 295 | 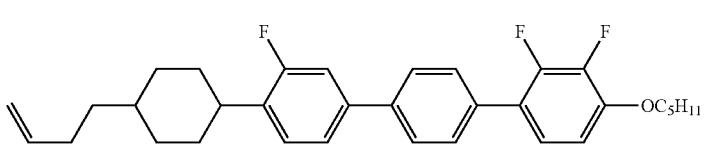 |
| 296 | 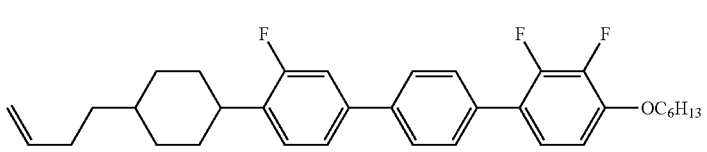 |
| 297 | 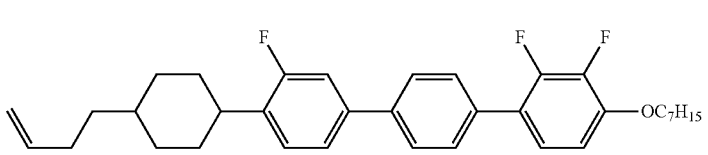 |
| 298 | 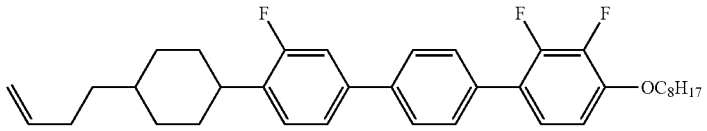 |
| 299 | 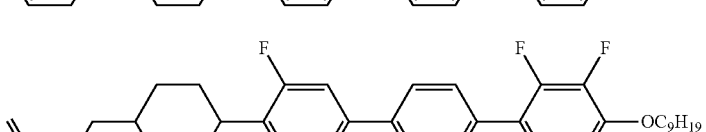 |
| 300 | 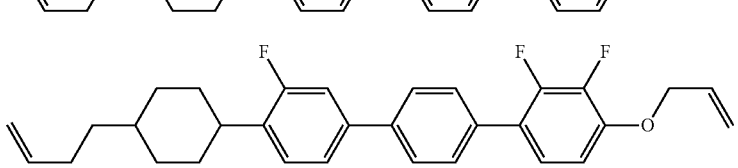 |

-continued
| No. | |
|---|---|
| 301 | 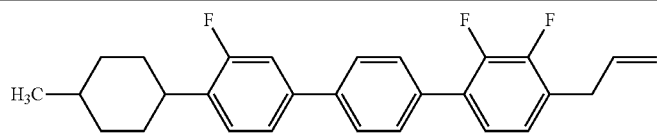 |
| 302 | 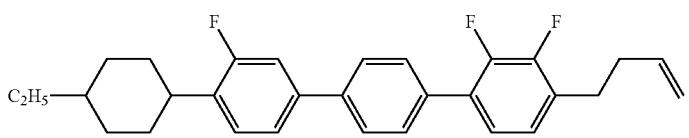 |
| 303 | 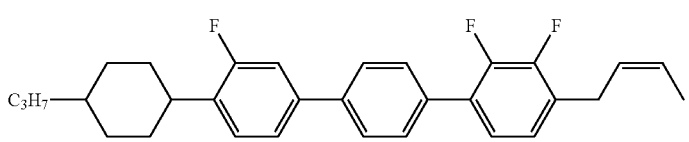 |
| 304 | 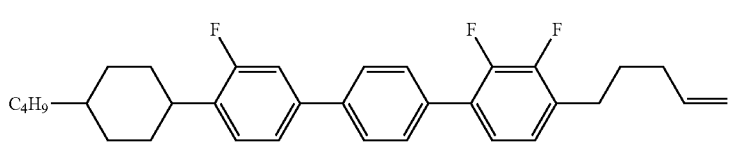 |
| 305 | 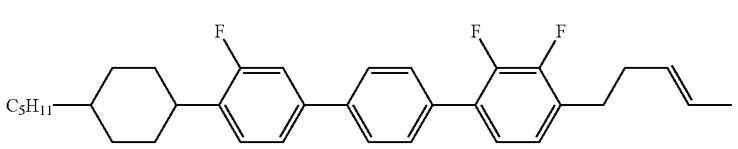 |
| 306 | 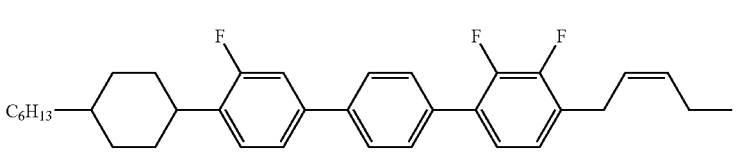 |
| 307 | 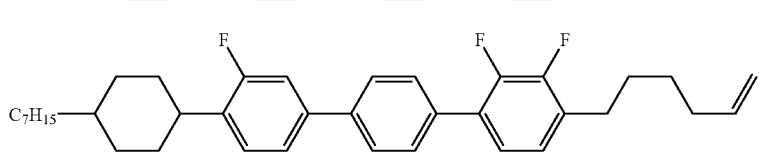 |
| 308 | 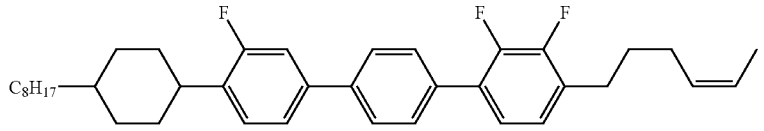 |
| 309 | 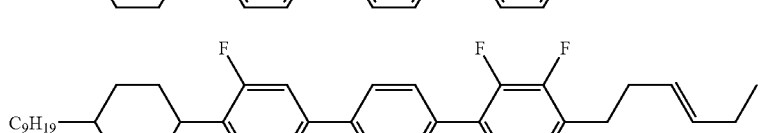 |
| 310 | 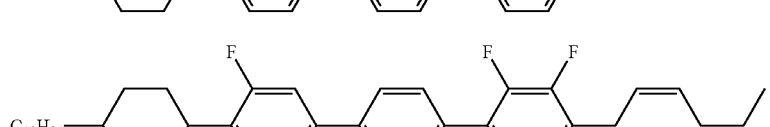 |
| 311 | 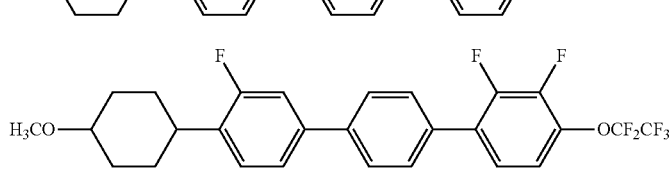 |

| No. | |
|---|---|
| 312 | 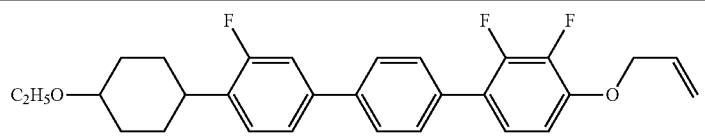 |
| 313 | 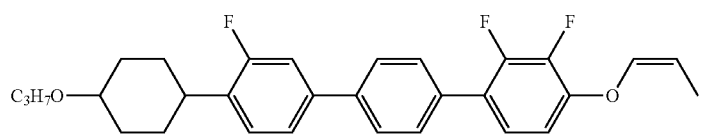 |
| 314 | 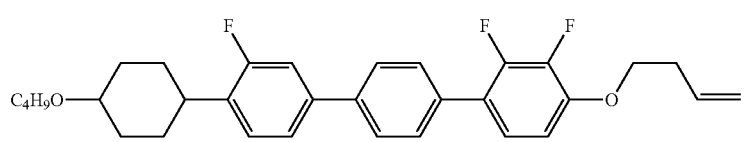 |
| 315 | 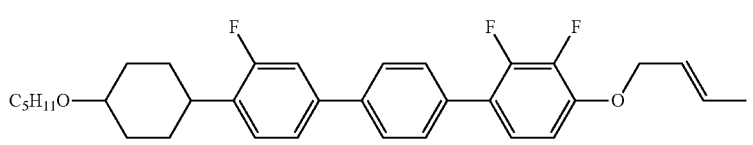 |
| 316 | 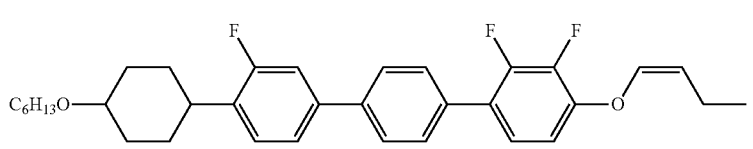 |
| 317 | 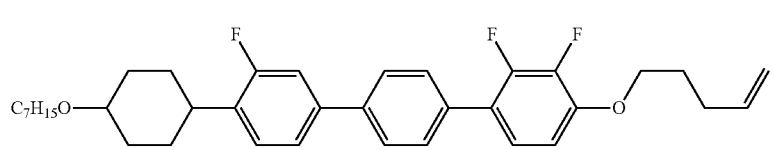 |
| 318 | 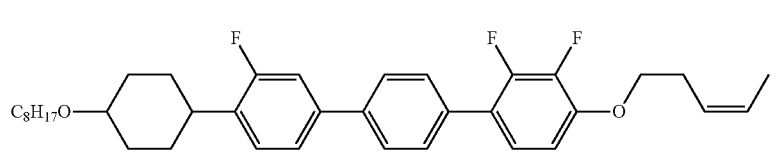 |
| 319 | 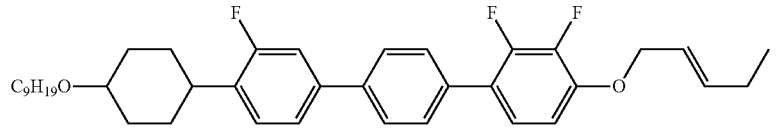 |
| 320 | 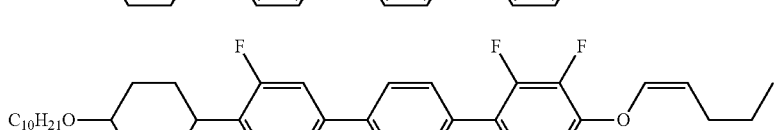 |
| 321 | 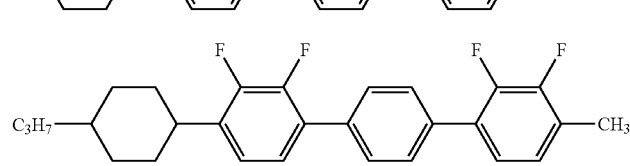 |
| 322 | 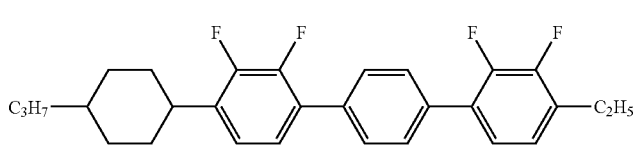 |

| No. | |
|---|---|
| 323 | 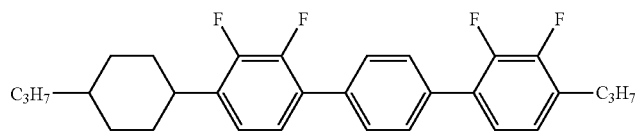 |
| 324 | 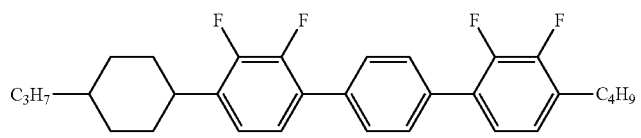 |
| 325 | 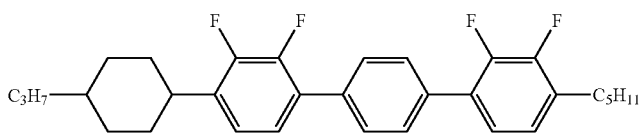 |
| 326 | 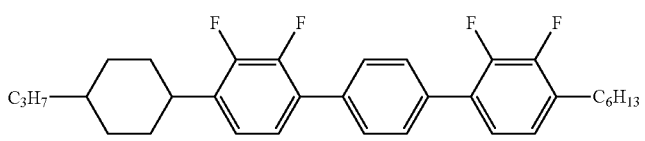 |
| 327 | 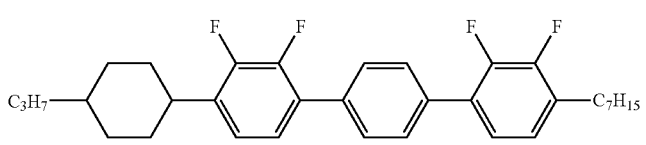 |
| 328 | 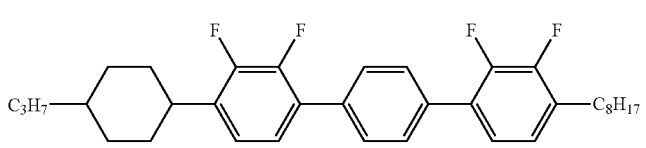 |
| 329 | 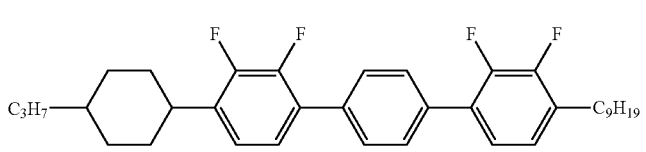 |
| 330 | 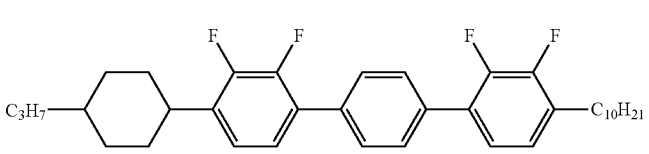 |
| 331 | 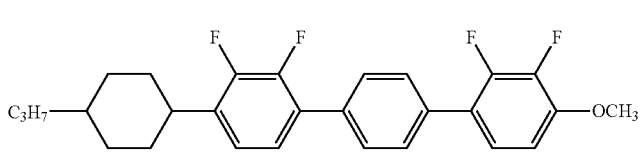 |
| 332 | 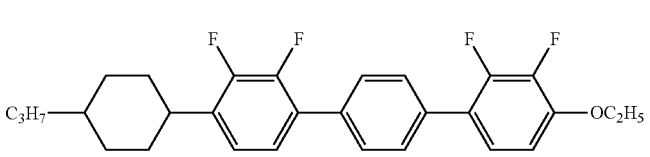 |
| 333 | 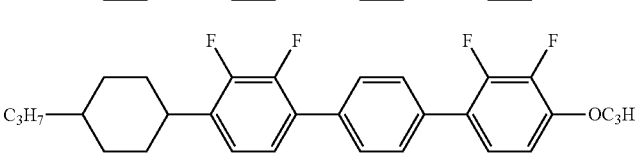 |

-continued
| No. | |
|---|---|
| 334 | 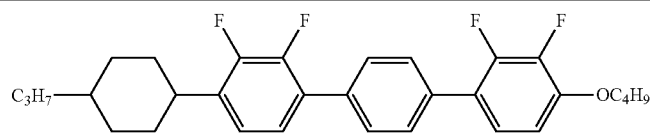 |
| 335 | 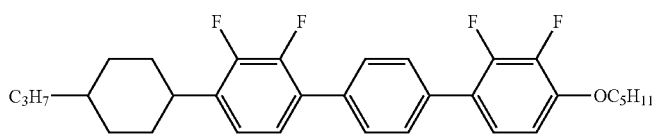 |
| 336 | 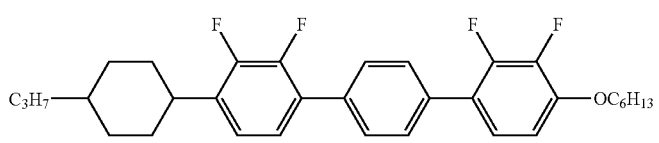 |
| 337 | 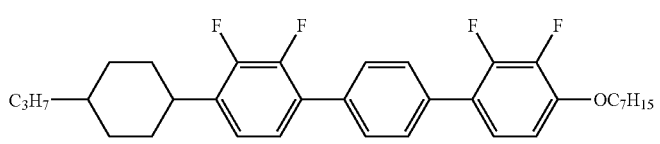 |
| 338 | 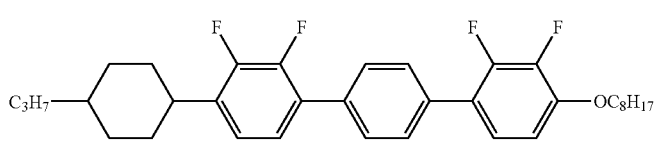 |
| 339 | 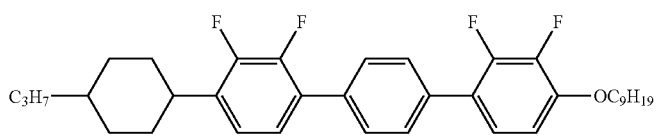 |
| 340 | 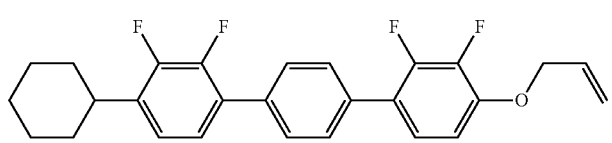 |
| 341 | 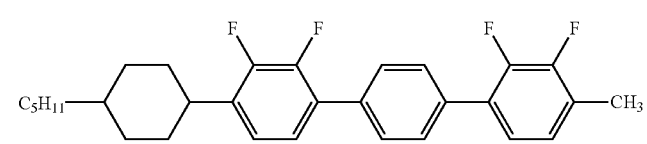 |
| 342 | 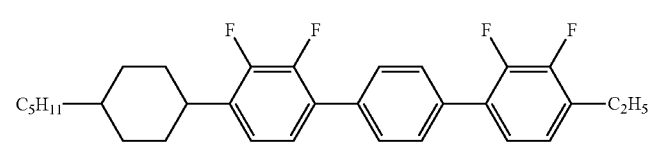 |
| 343 | 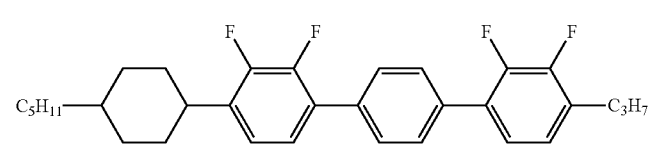 |
| 344 | 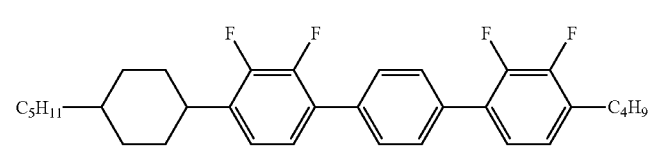 |

| No. | |
|---|---|
| 345 | 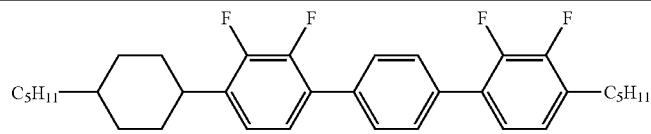 |
| 346 | 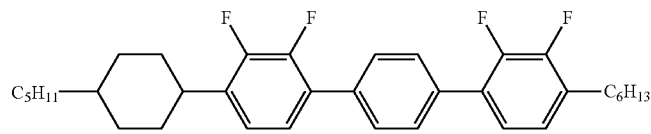 |
| 347 | 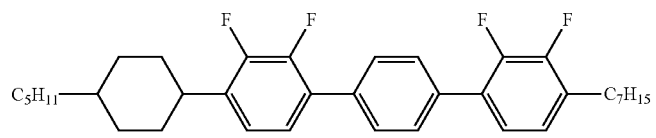 |
| 348 | 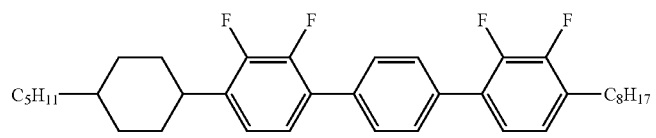 |
| 349 | 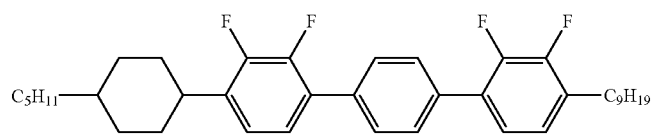 |
| 350 | 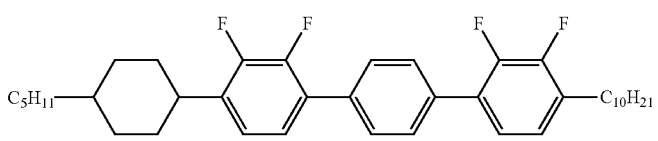 |
| 351 | 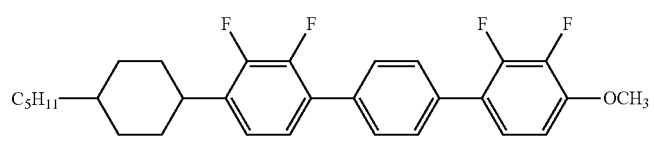 |
| 352 | 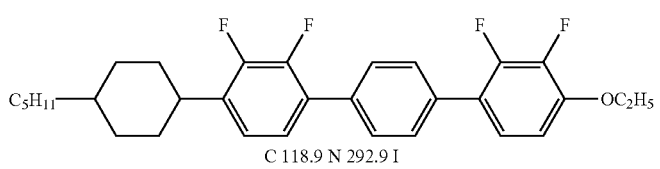 <br> C 118.9 N 292.9 I <br> $T_{NI}$; 228.6° C., $\Delta\varepsilon$; −6.14, $\Delta n$; 0.207 |
| 353 | 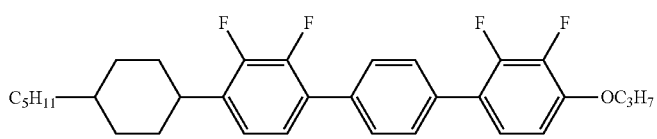 |
| 354 | 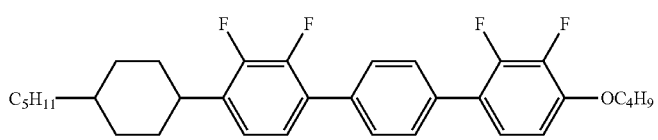 |
| 355 | 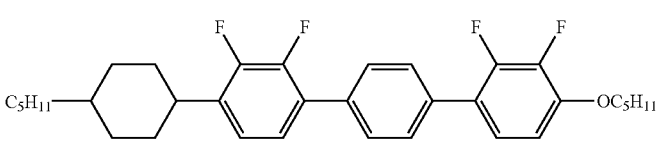 |

-continued
| No. | |
|---|---|
| 356 | 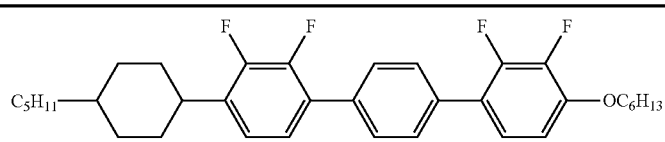 |
| 357 | 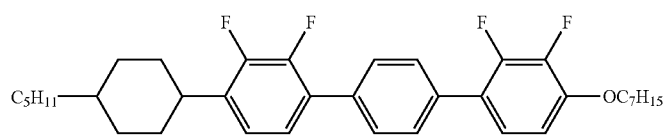 |
| 358 | 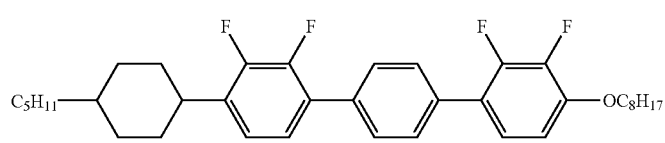 |
| 359 | 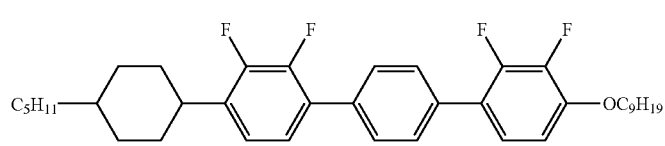 |
| 360 | 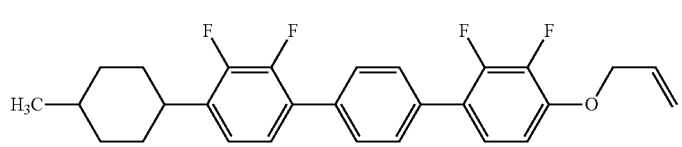 |
| 361 | 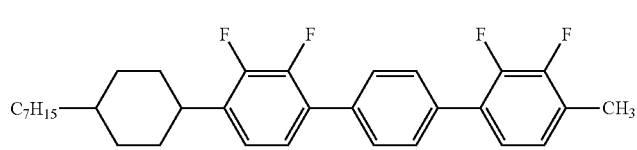 |
| 362 | 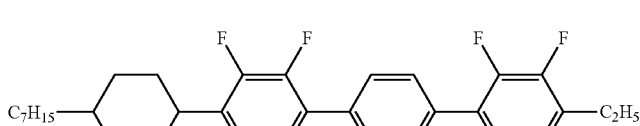 |
| 363 | 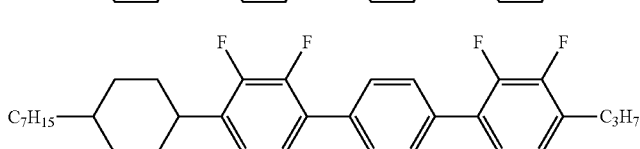 |
| 364 | 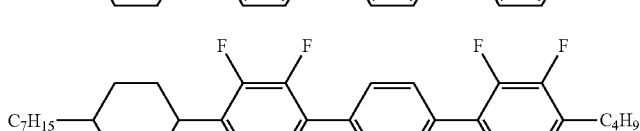 |
| 365 | 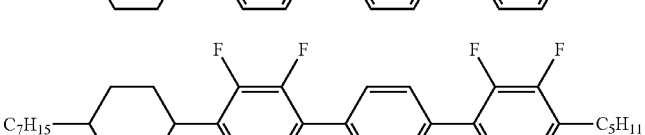 |
| 366 | 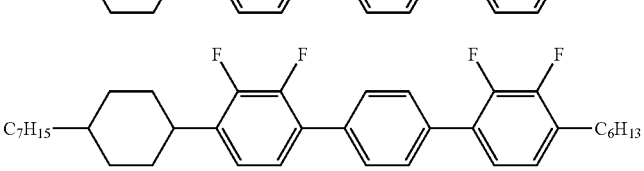 |

-continued
| No. | |
|---|---|
| 367 | 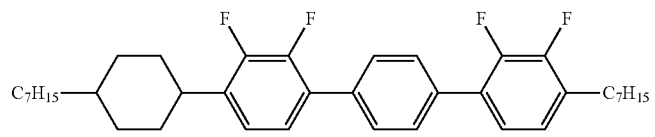 |
| 368 | 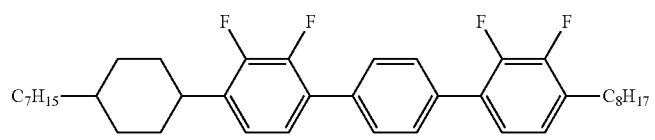 |
| 369 | 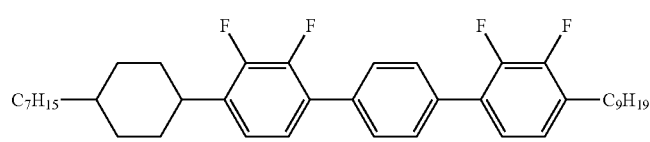 |
| 370 | 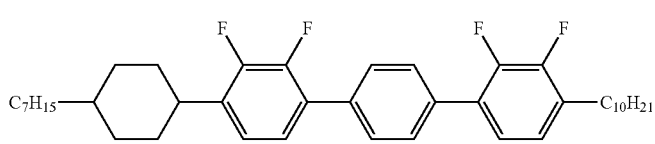 |
| 371 | 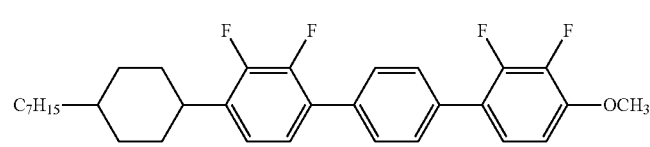 |
| 372 | 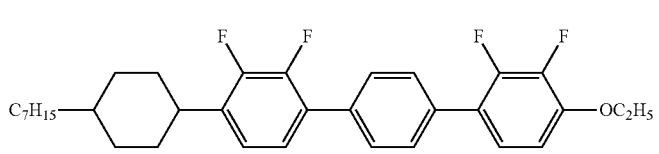 |
| 373 | 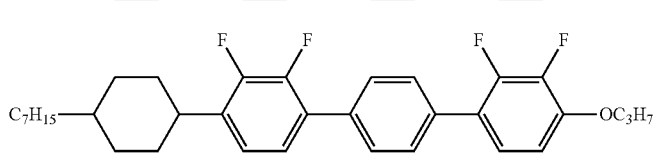 |
| 374 | 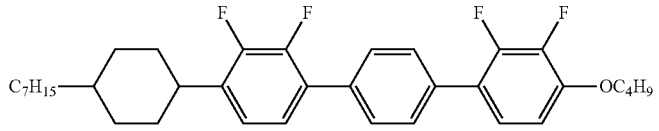 |
| 375 | 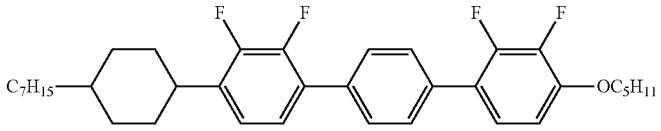 |
| 376 |  |
| 377 | 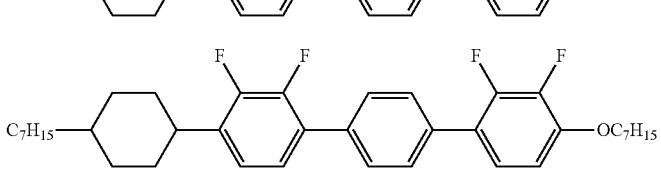 |

-continued
| No. | |
|---|---|
| 378 | 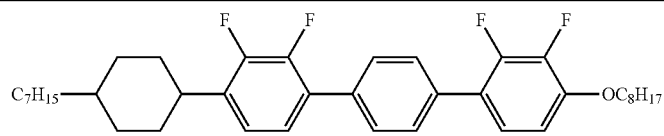 |
| 379 | 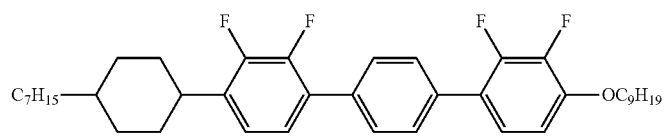 |
| 380 | 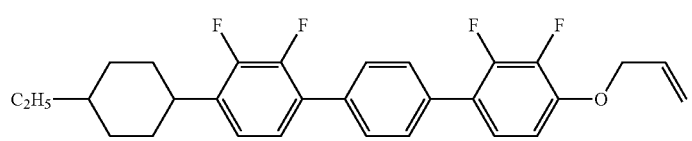 |
| 381 | 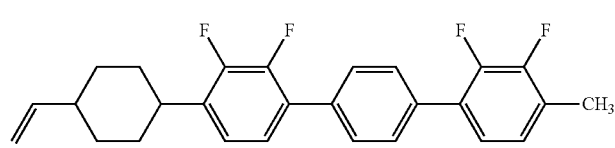 |
| 382 | 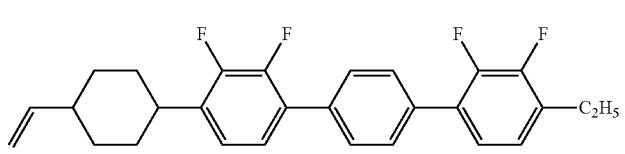 |
| 383 | 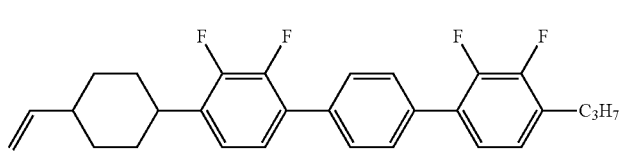 |
| 384 | 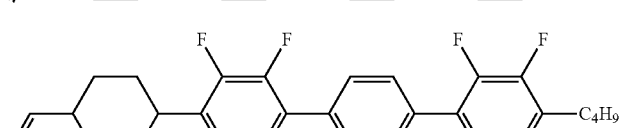 |
| 385 | 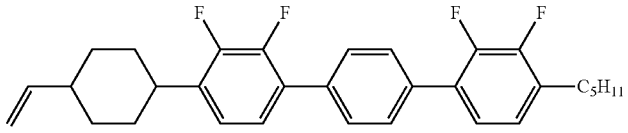 |
| 386 | 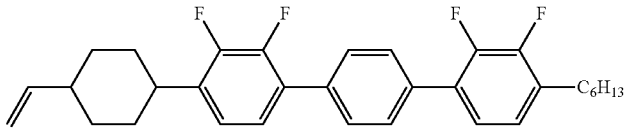 |
| 387 | 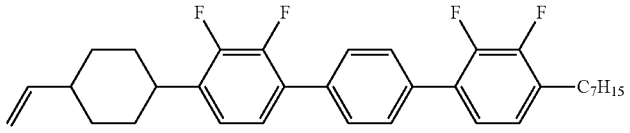 |
| 388 | 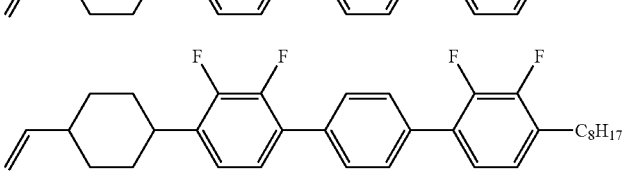 |

| No. | |
|---|---|
| 389 | 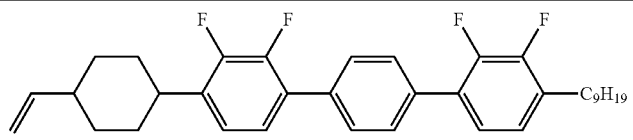 |
| 390 | 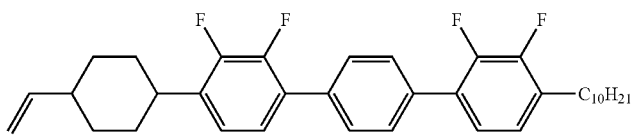 |
| 391 | 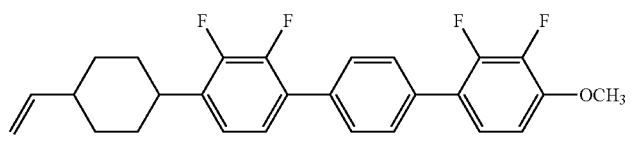 |
| 392 | 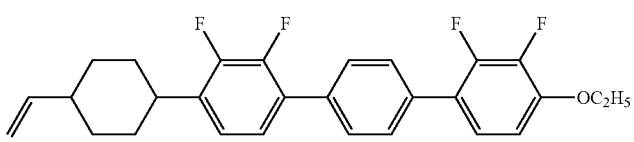 |
| 393 | 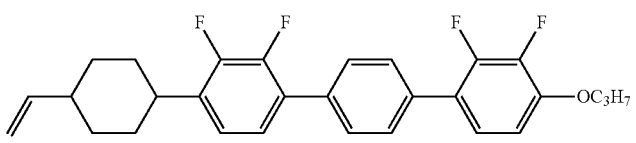 |
| 394 | 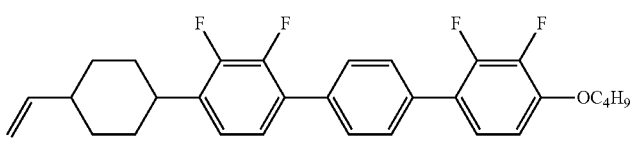 |
| 395 | 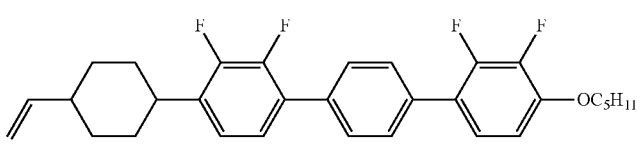 |
| 396 | 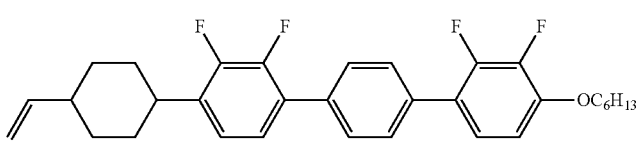 |
| 397 | 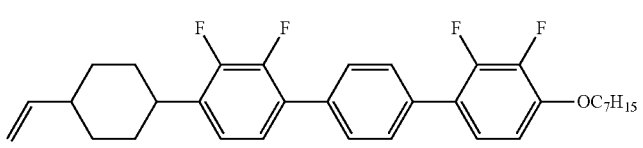 |
| 398 | 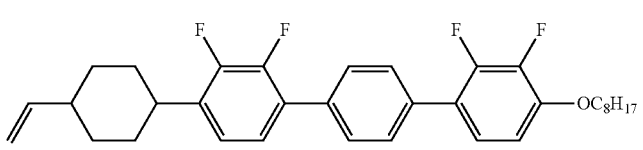 |
| 399 | 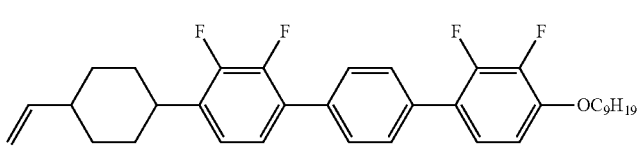 |

-continued
| No. | |
|---|---|
| 400 | 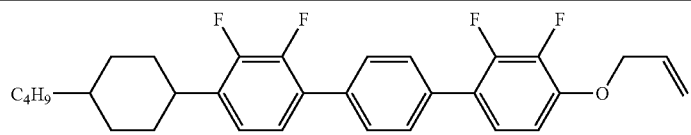 |
| 401 | 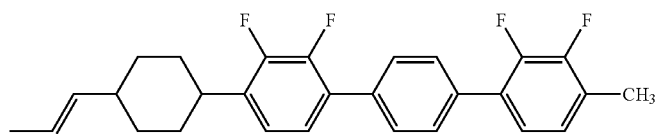 |
| 402 | 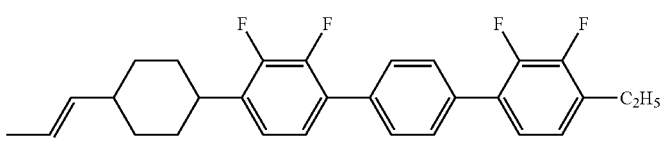 |
| 403 | 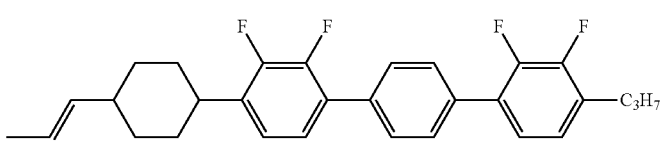 |
| 404 | 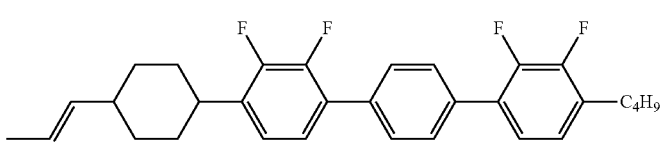 |
| 405 | 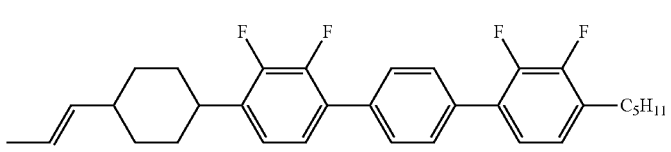 |
| 406 | 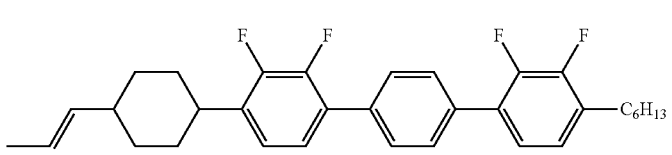 |
| 407 | 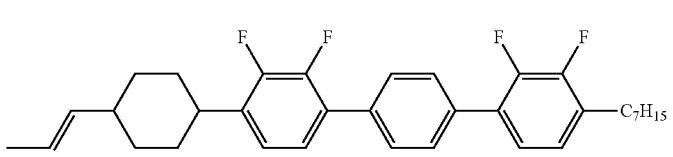 |
| 408 | 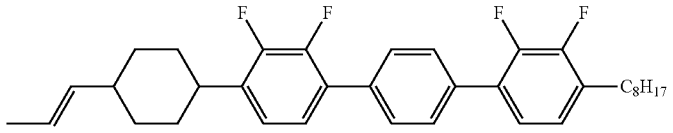 |
| 409 | 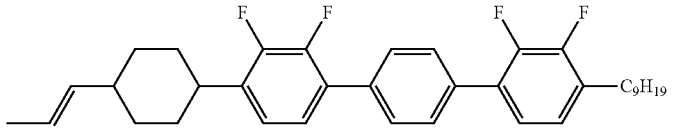 |
| 410 | 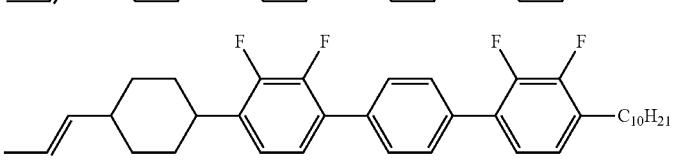 |

-continued
| No. | |
|---|---|
| 411 | 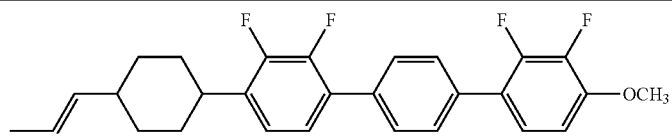 |
| 412 | 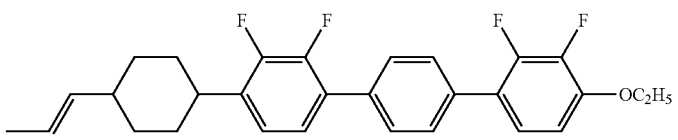 |
| 413 | 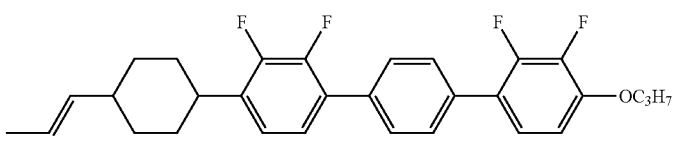 |
| 414 | 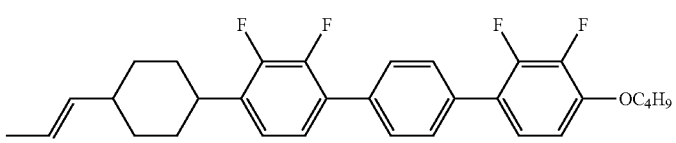 |
| 415 | 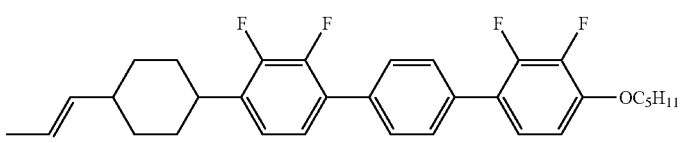 |
| 416 | 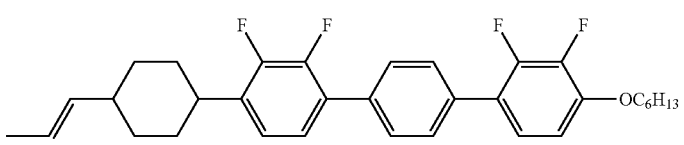 |
| 417 | 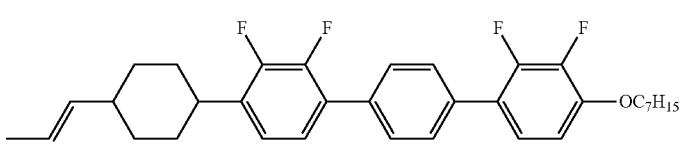 |
| 418 | 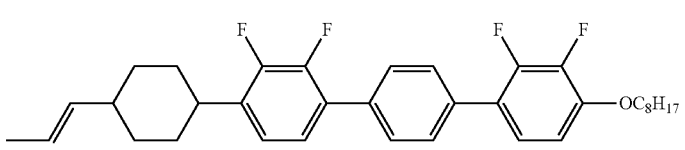 |
| 419 | 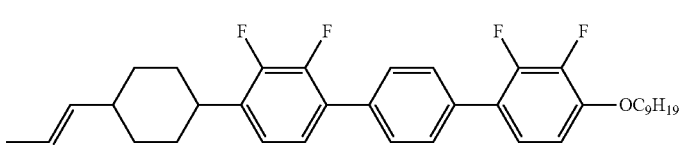 |
| 420 | 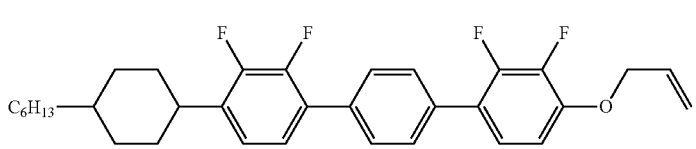 |
| 421 | 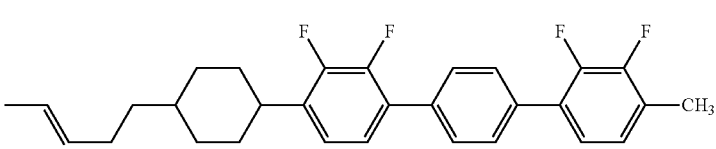 |

| No. | |
|---|---|
| 422 | 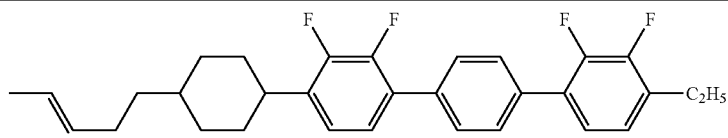 |
| 423 | 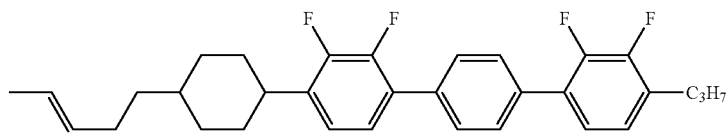 |
| 424 | 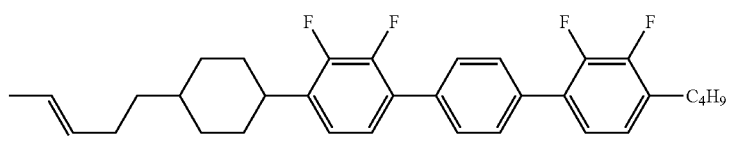 |
| 425 | 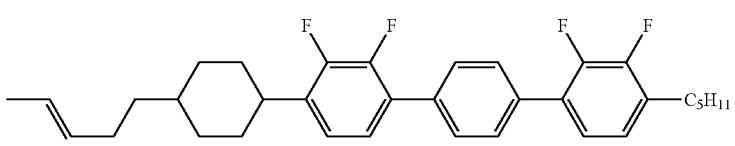 |
| 426 | 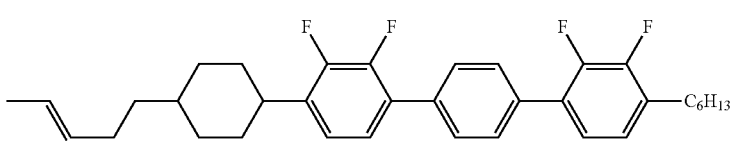 |
| 427 | 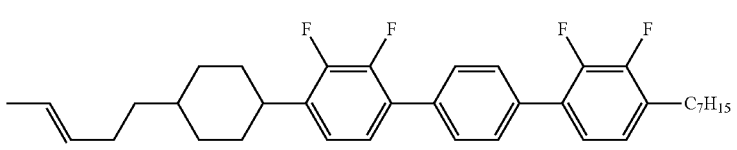 |
| 428 | 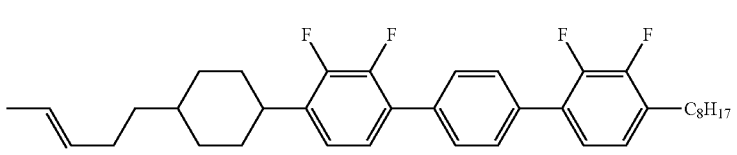 |
| 429 | 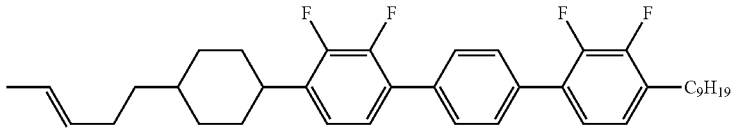 |
| 430 | 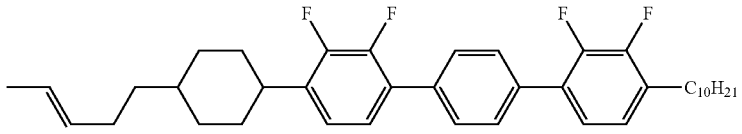 |
| 431 |  |
| 432 | 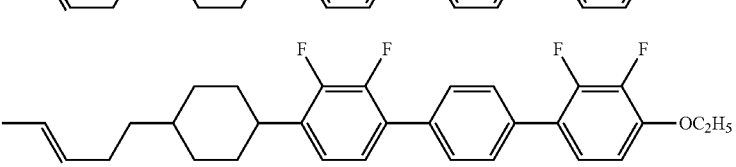 |

| No. | |
|---|---|
| 433 | 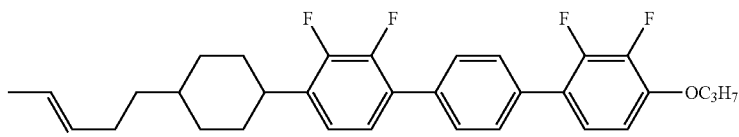 |
| 434 | 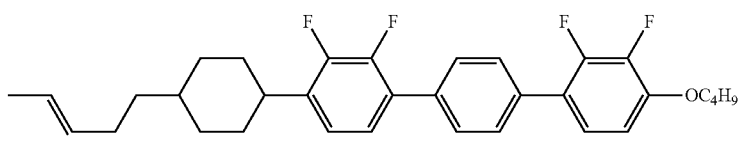 |
| 435 | 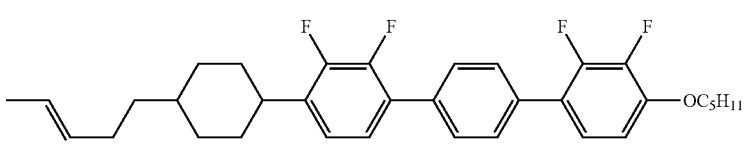 |
| 436 | 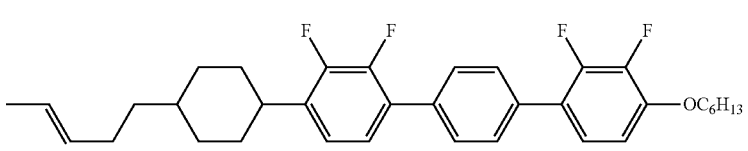 |
| 437 | 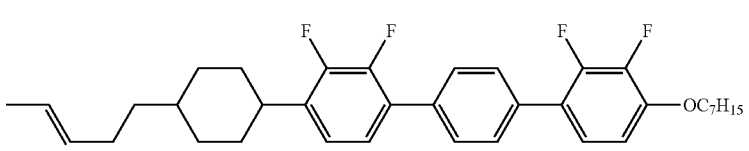 |
| 438 | 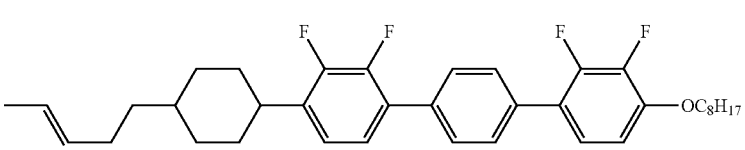 |
| 439 | 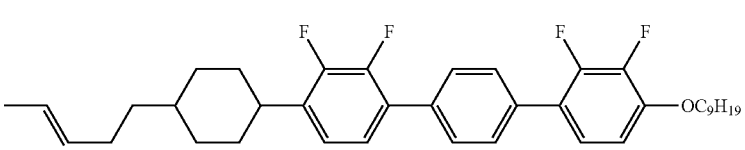 |
| 440 | 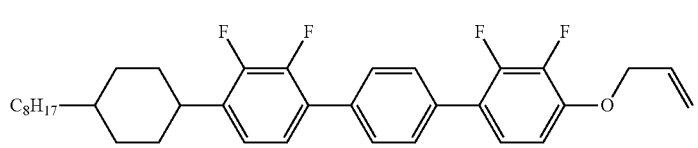 |
| 441 | 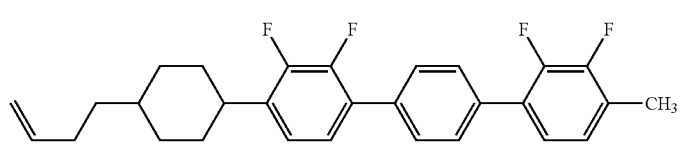 |
| 442 | 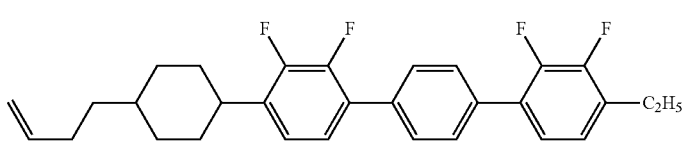 |
| 443 | 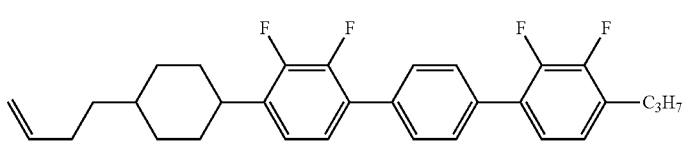 |

| No. | |
|---|---|
| 444 | 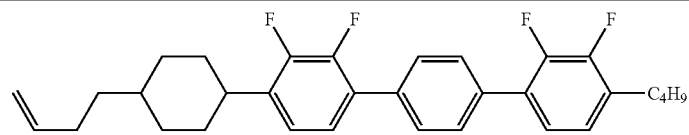 |
| 445 | 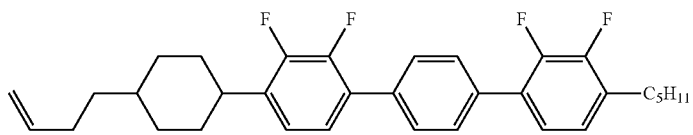 |
| 446 | 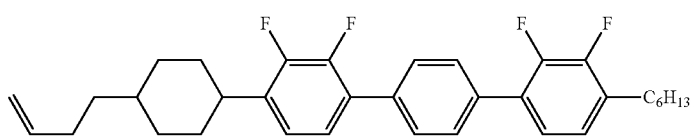 |
| 447 | 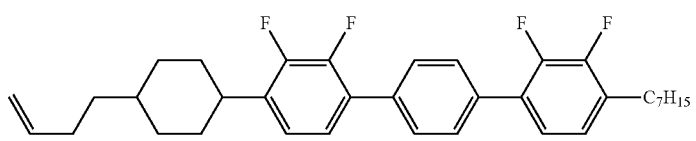 |
| 448 | 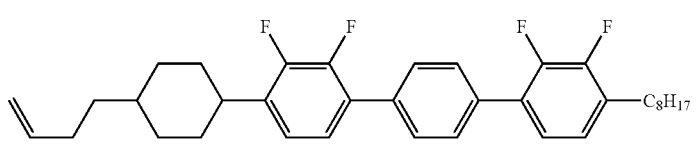 |
| 449 | 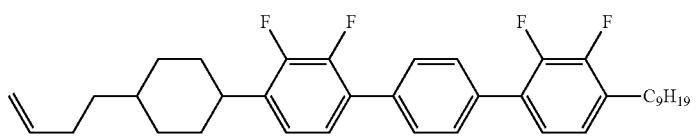 |
| 450 | 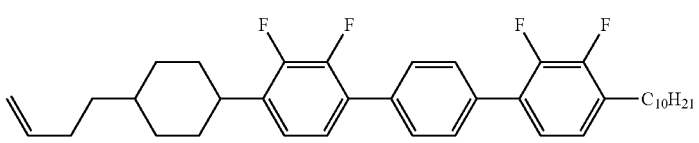 |
| 451 | 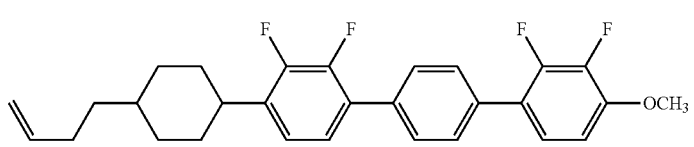 |
| 452 | 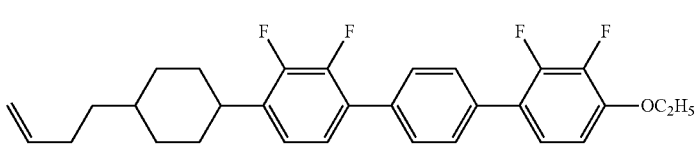 |
| 453 | 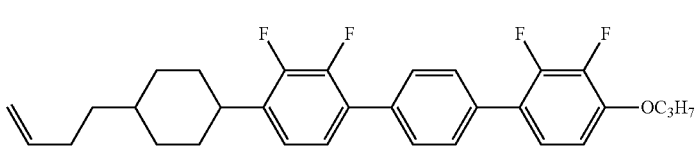 |
| 454 | 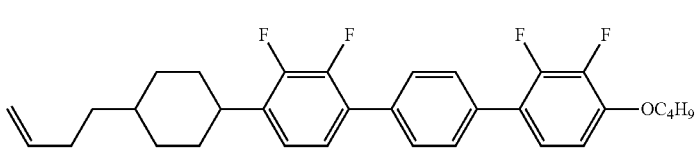 |

| No. |
|---|
| 455 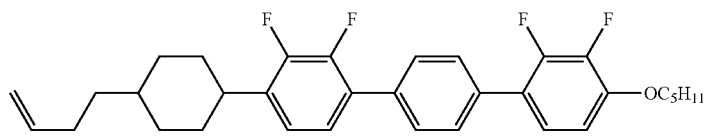 |
| 456 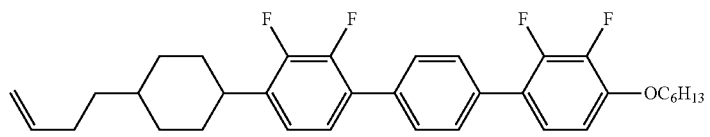 |
| 457 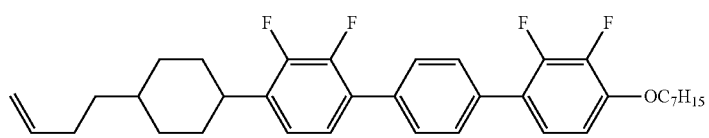 |
| 458 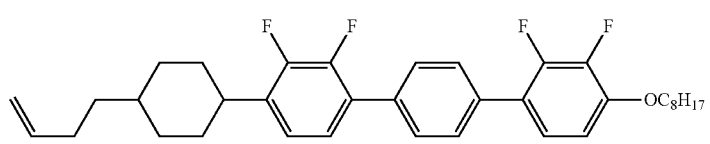 |
| 459 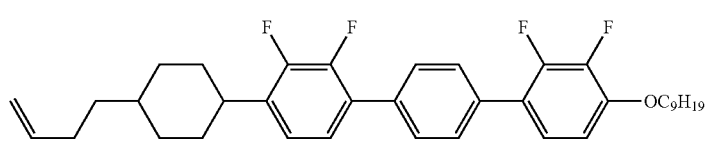 |
| 460 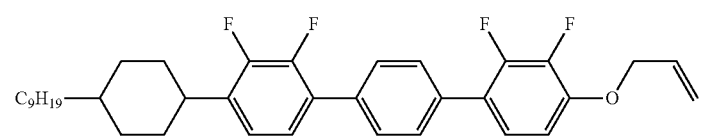 |
| 461 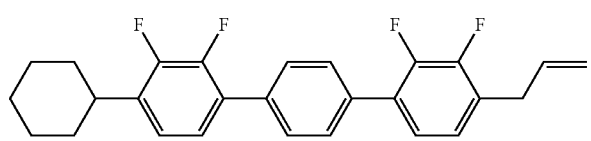 |
| 462 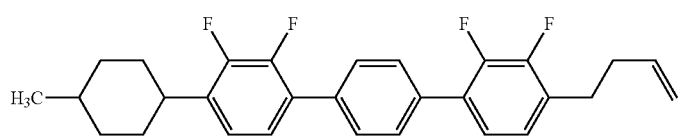 |
| 463 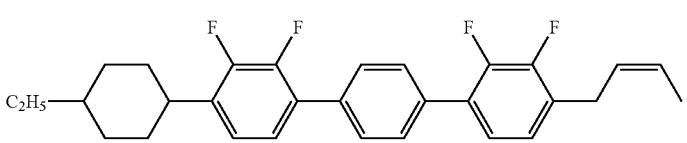 |
| 464 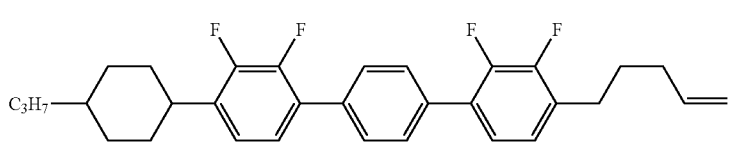 |
| 465 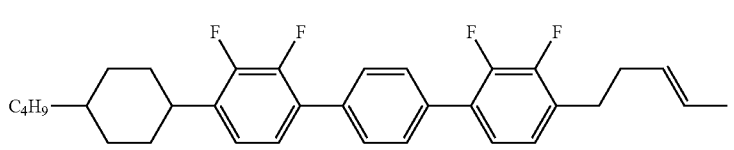 |

-continued
| No. | |
|---|---|
| 466 | 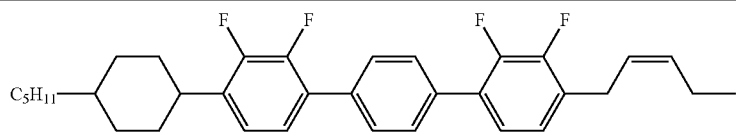 |
| 467 | 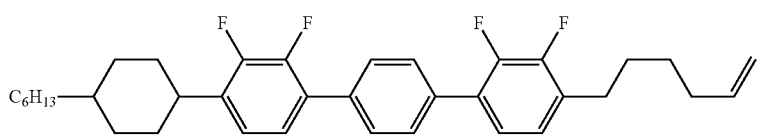 |
| 468 | 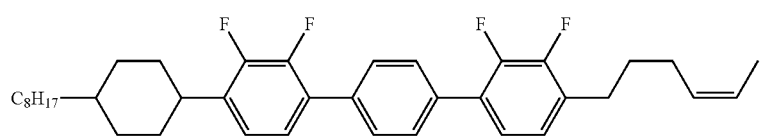 |
| 469 | 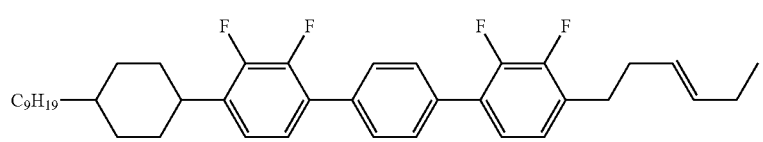 |
| 470 |  |
| 471 | 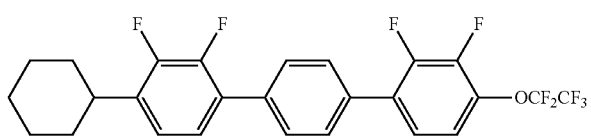 |
| 472 | 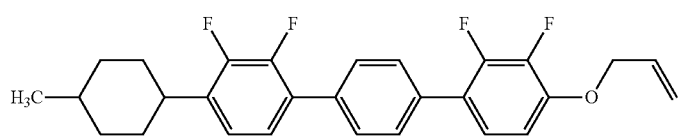 |
| 473 | 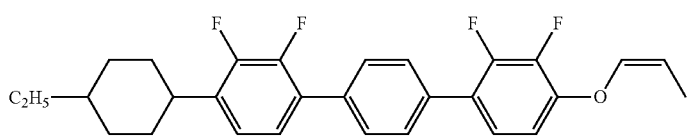 |
| 474 | 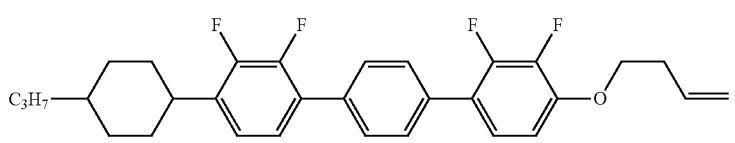 |
| 475 | 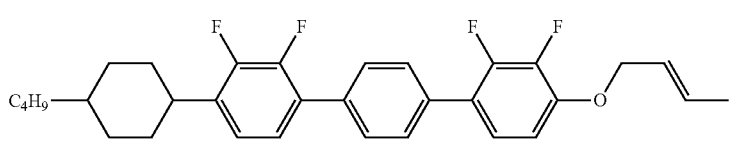 |
| 476 | 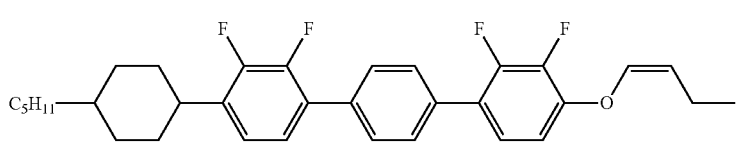 |

| No. | |
|---|---|
| 477 | 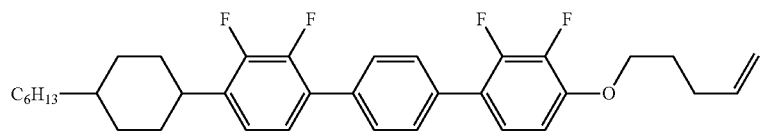 |
| 478 | 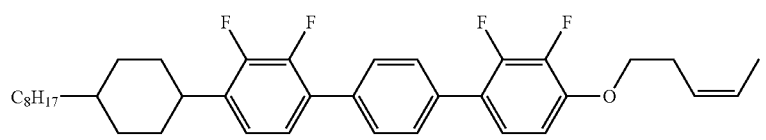 |
| 479 | 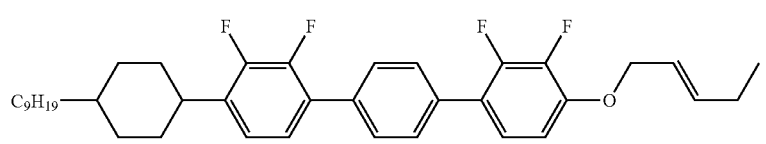 |
| 480 | 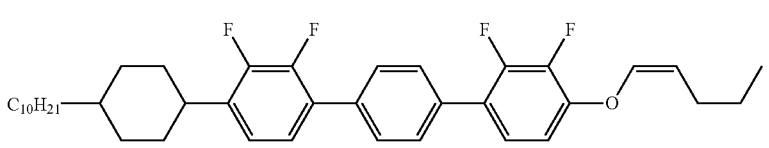 |
| 481 | 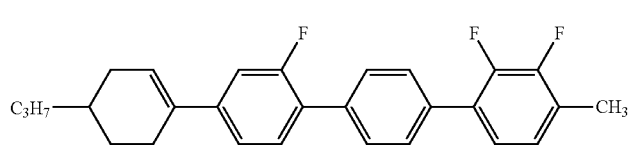 |
| 482 | 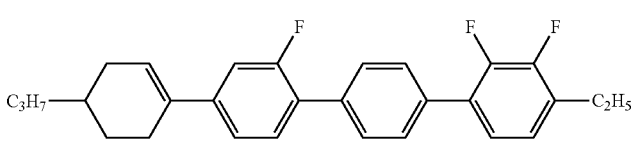 |
| 483 | 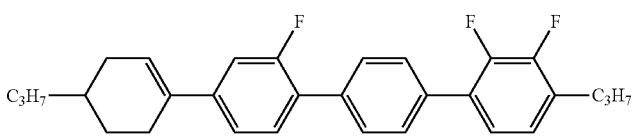 |
| 484 | 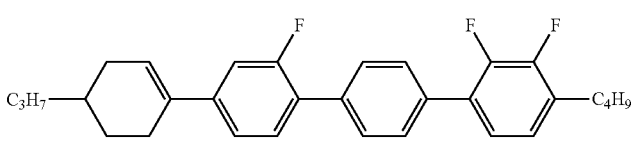 |
| 485 | 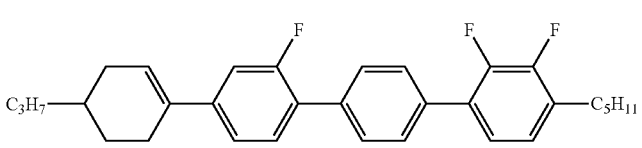 |
| 486 | 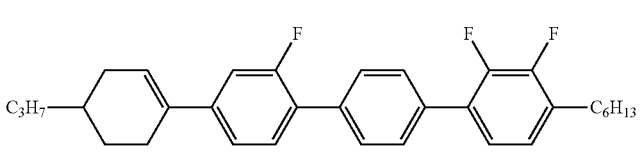 |
| 487 | 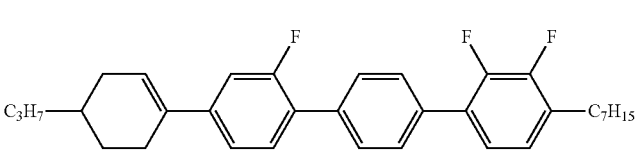 |

| No. | |
|---|---|
| 488 | 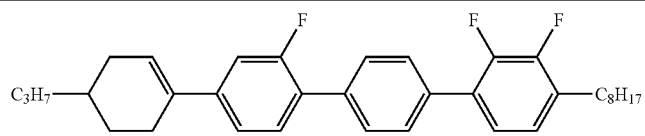 |
| 489 | 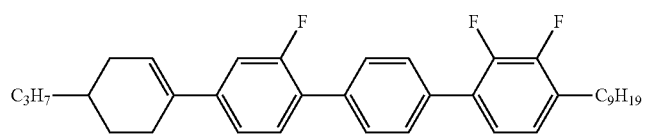 |
| 490 | 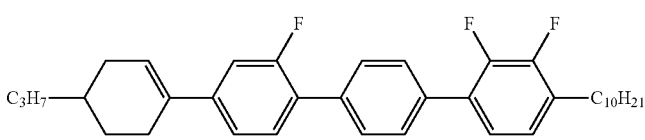 |
| 491 | 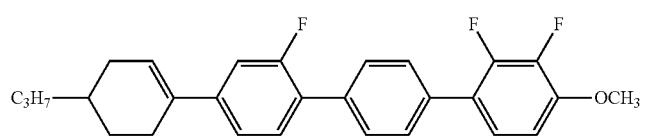 |
| 492 | 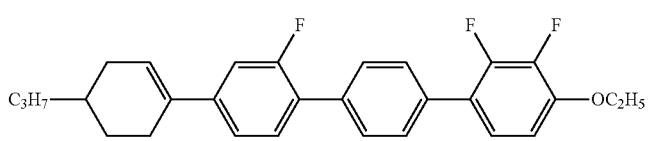<br>C 117.6 N 294.9 I<br>$T_{NI}$; 252.6° C., Δε; -6.29, Δn; 0.307 |
| 493 | 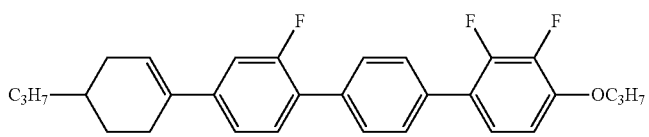 |
| 494 | 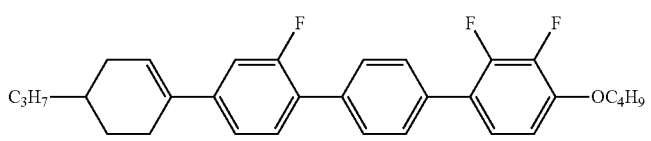 |
| 495 | 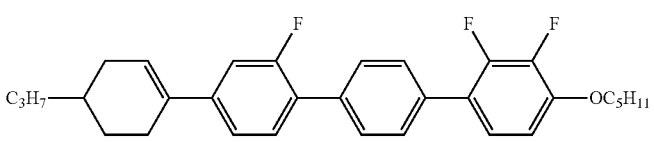 |
| 496 | 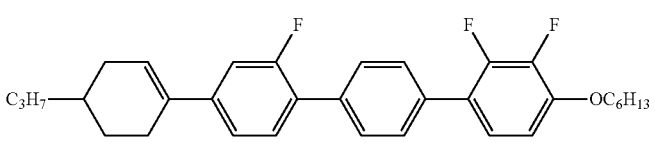 |
| 497 | 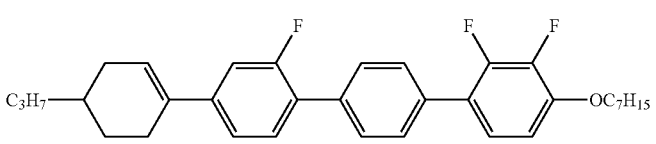 |
| 498 | 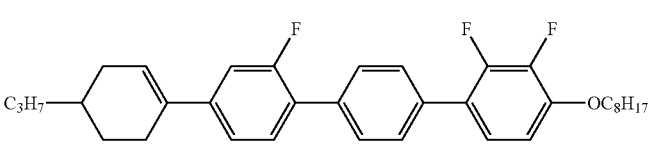 |

-continued
| No. | |
|---|---|
| 499 | 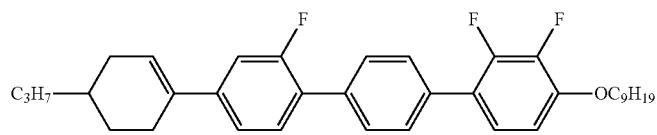 |
| 500 | 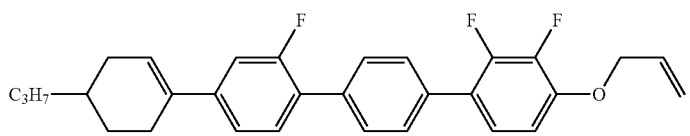 |
| 501 | 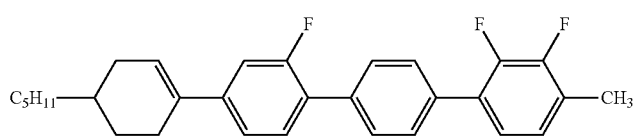 |
| 502 | 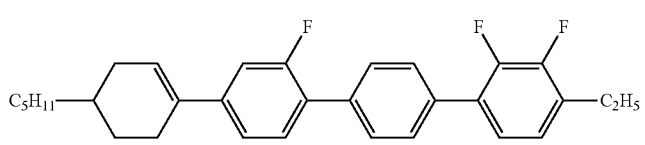 |
| 503 |  |
| 504 |  |
| 505 | 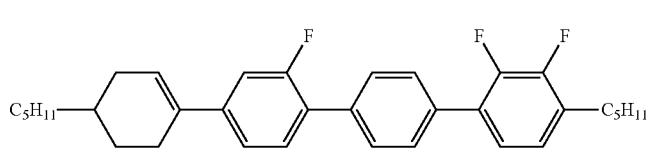 |
| 506 |  |
| 507 | 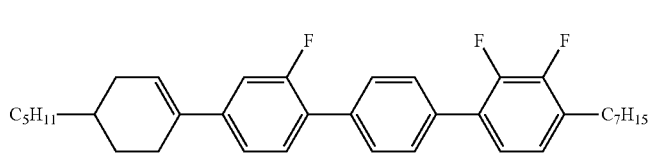 |
| 508 | 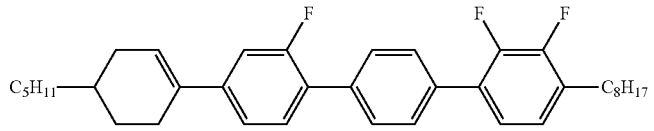 |
| 509 | 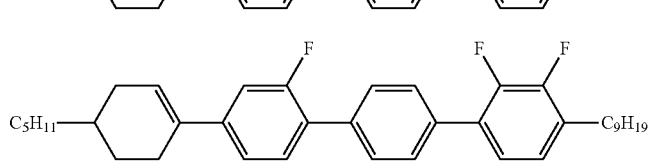 |

-continued
| No. | |
|---|---|
| 510 | 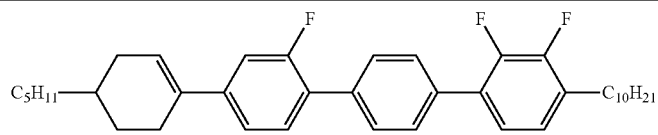 |
| 511 | 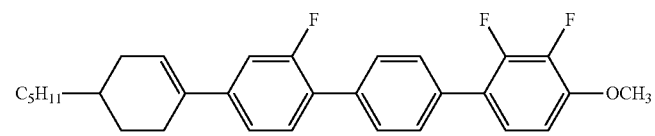 |
| 512 | 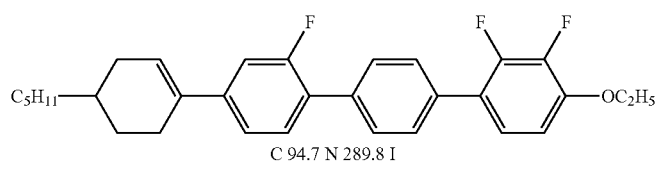
C 94.7 N 289.8 I
$T_{NI}$; 250.6° C., Δε; -6.43, Δn; 02.87 |
| 513 | 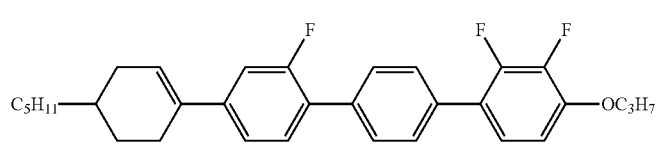 |
| 514 | 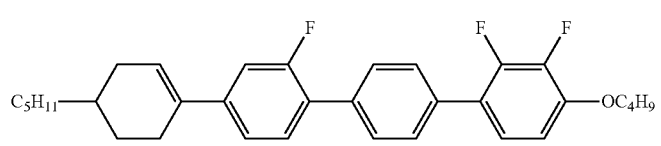 |
| 515 | 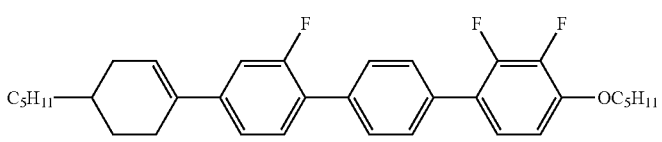 |
| 516 | 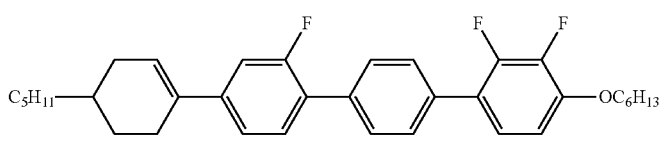 |
| 517 | 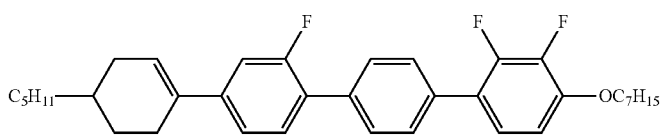 |
| 518 | 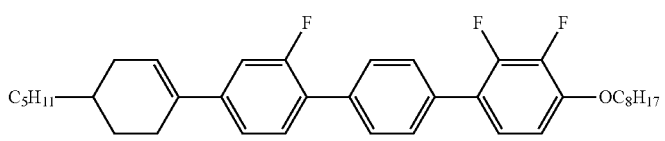 |
| 519 | 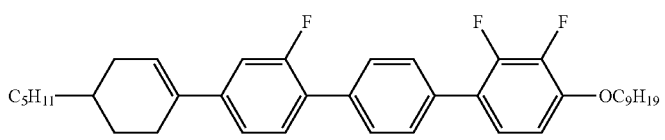 |
| 520 | 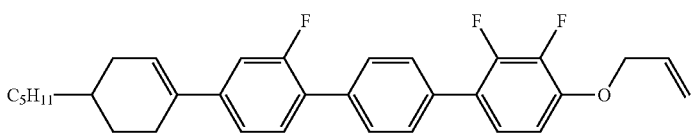 |

-continued

| No. | |
|---|---|
| 521 | C7H15–[cyclohexene]–[Ph(F)]–[Ph]–[Ph(F,F)]–CH3 |
| 522 | C7H15–[cyclohexene]–[Ph(F)]–[Ph]–[Ph(F,F)]–C2H5 |
| 523 | C7H15–[cyclohexene]–[Ph(F)]–[Ph]–[Ph(F,F)]–C3H7 |
| 524 | C7H15–[cyclohexene]–[Ph(F)]–[Ph]–[Ph(F,F)]–C4H9 |
| 525 | C7H15–[cyclohexene]–[Ph(F)]–[Ph]–[Ph(F,F)]–C5H11 |
| 526 | C7H15–[cyclohexene]–[Ph(F)]–[Ph]–[Ph(F,F)]–C6H13 |
| 527 | C7H15–[cyclohexene]–[Ph(F)]–[Ph]–[Ph(F,F)]–C7H15 |
| 528 | C7H15–[cyclohexene]–[Ph(F)]–[Ph]–[Ph(F,F)]–C8H17 |
| 529 | C7H15–[cyclohexene]–[Ph(F)]–[Ph]–[Ph(F,F)]–C9H19 |
| 530 | C7H15–[cyclohexene]–[Ph(F)]–[Ph]–[Ph(F,F)]–C10H21 |
| 531 | C7H15–[cyclohexene]–[Ph(F)]–[Ph]–[Ph(F,F)]–OCH3 |

-continued
| No. | |
|---|---|
| 532 | 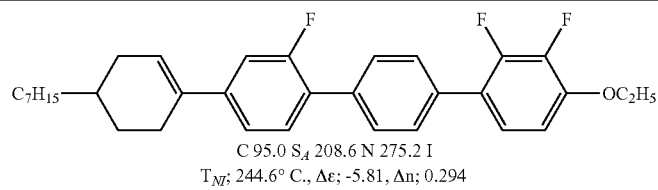<br>C 95.0 S$_A$ 208.6 N 275.2 I<br>T$_{NI}$; 244.6° C., Δε; -5.81, Δn; 0.294 |
| 533 | 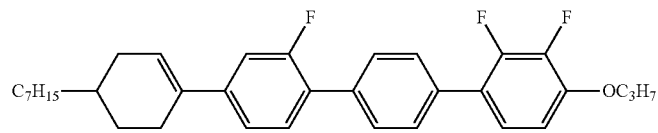 |
| 534 |  |
| 535 | 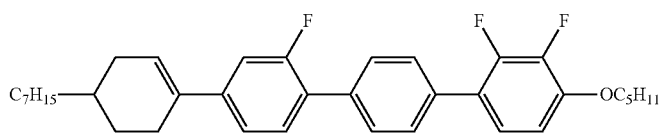 |
| 536 | 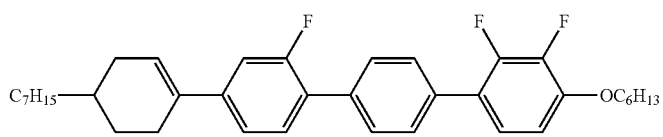 |
| 537 | 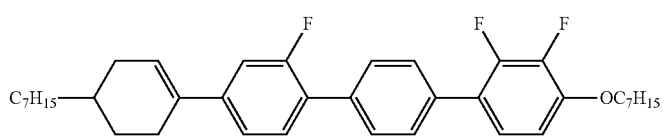 |
| 538 | 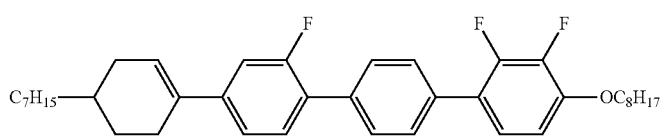 |
| 539 | 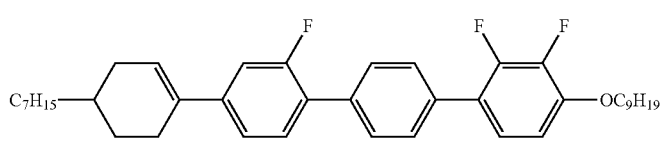 |
| 540 | 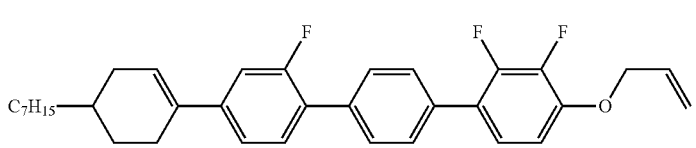 |
| 541 | 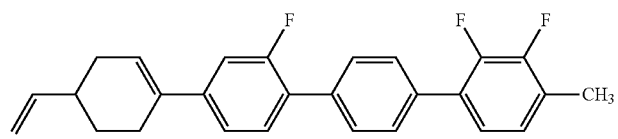 |
| 542 | 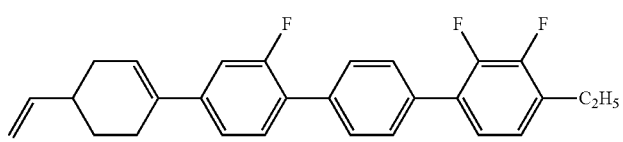 |

-continued
| No. | |
|---|---|
| 543 | 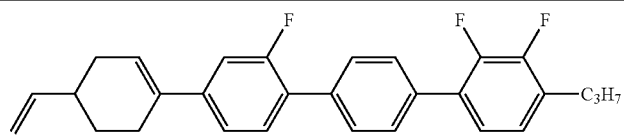 |
| 544 | 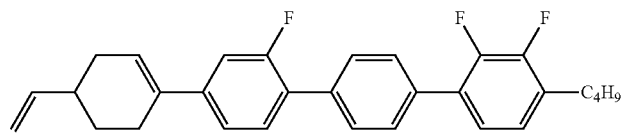 |
| 545 | 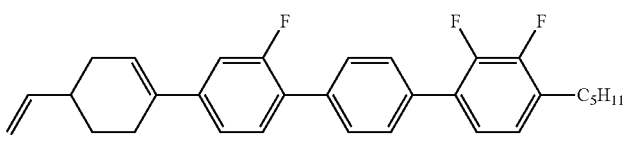 |
| 546 | 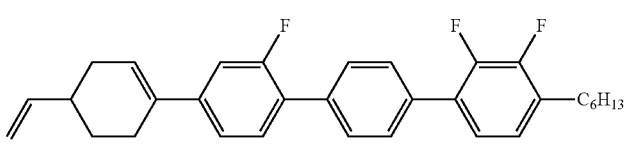 |
| 547 | 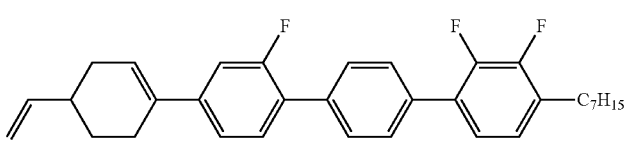 |
| 548 | 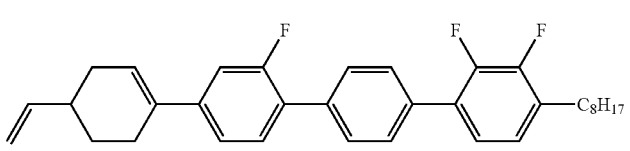 |
| 549 | 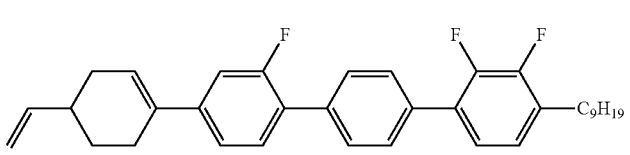 |
| 550 |  |
| 551 | 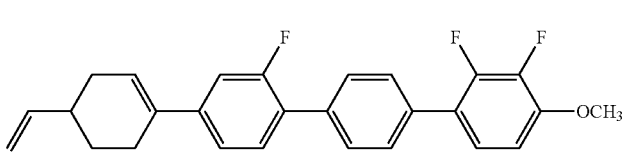 |
| 552 | 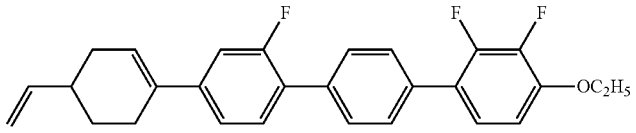 |
| 553 | 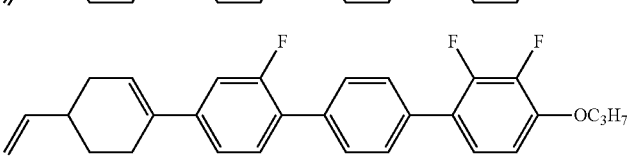 |

| No. | |
|---|---|
| 554 | 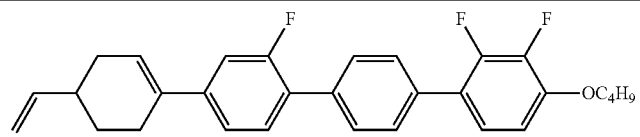 |
| 555 | 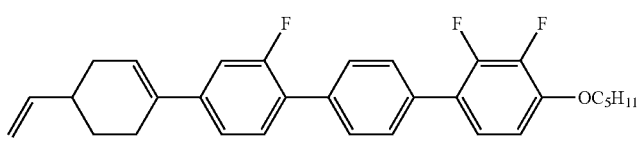 |
| 556 | 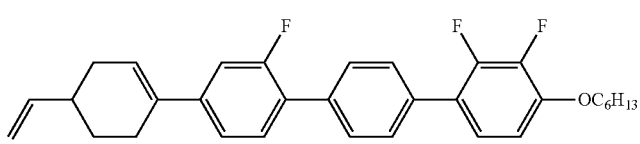 |
| 557 | 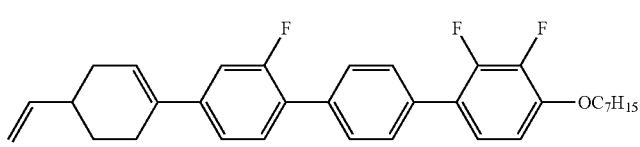 |
| 558 | 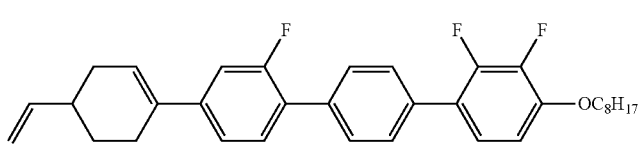 |
| 559 | 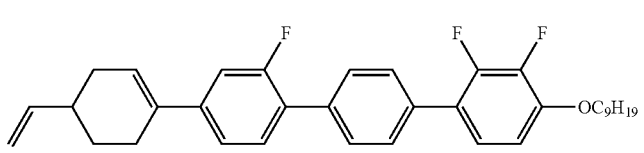 |
| 560 | 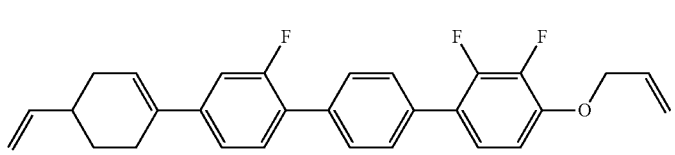 |
| 561 | 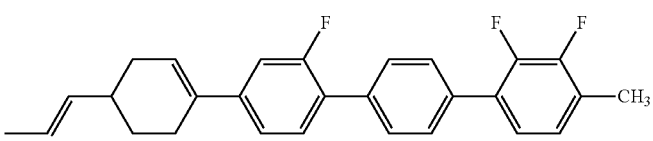 |
| 562 | 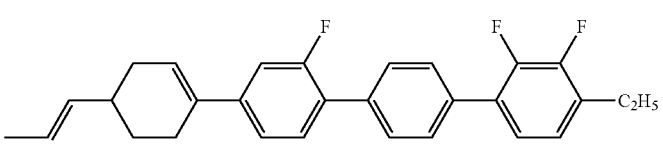 |
| 563 | 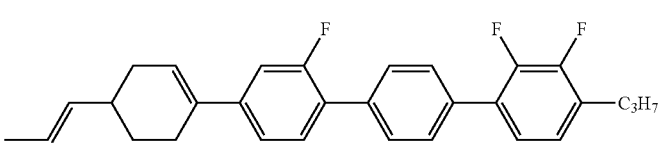 |
| 564 | 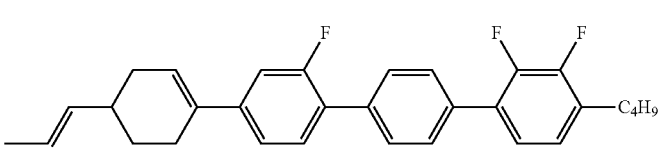 |

| No. | |
|---|---|
| 565 | (structure with vinyl-cyclohexene—C₆H₃F—C₆H₄—C₆H₂F₂—C₅H₁₁) |
| 566 | (structure with vinyl-cyclohexene—C₆H₃F—C₆H₄—C₆H₂F₂—C₆H₁₃) |
| 567 | (structure with vinyl-cyclohexene—C₆H₃F—C₆H₄—C₆H₂F₂—C₇H₁₅) |
| 568 | (structure with vinyl-cyclohexene—C₆H₃F—C₆H₄—C₆H₂F₂—C₈H₁₇) |
| 569 | (structure with vinyl-cyclohexene—C₆H₃F—C₆H₄—C₆H₂F₂—C₉H₁₉) |
| 570 | (structure with vinyl-cyclohexene—C₆H₃F—C₆H₄—C₆H₂F₂—C₁₀H₂₁) |
| 571 | (structure with vinyl-cyclohexene—C₆H₃F—C₆H₄—C₆H₂F₂—OCH₃) |
| 572 | (structure with vinyl-cyclohexene—C₆H₃F—C₆H₄—C₆H₂F₂—OC₂H₅) |
| 573 | (structure with vinyl-cyclohexene—C₆H₃F—C₆H₄—C₆H₂F₂—OC₃H₇) |
| 574 | (structure with vinyl-cyclohexene—C₆H₃F—C₆H₄—C₆H₂F₂—OC₄H₉) |
| 575 | (structure with vinyl-cyclohexene—C₆H₃F—C₆H₄—C₆H₂F₂—OC₅H₁₁) |

-continued
| No. | |
|---|---|
| 576 | 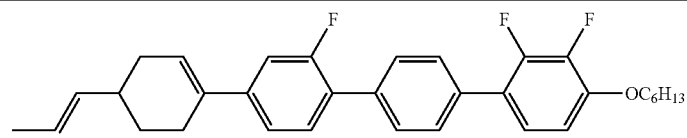 |
| 577 | 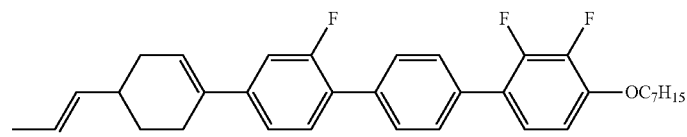 |
| 578 | 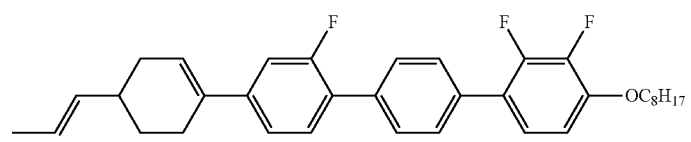 |
| 579 | 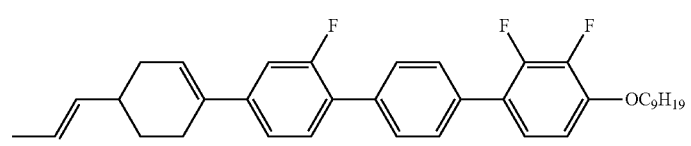 |
| 580 | 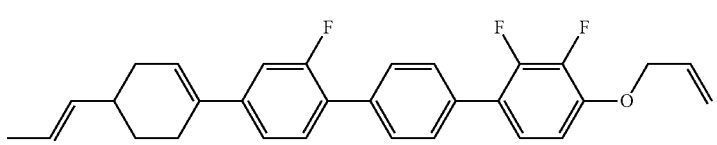 |
| 581 | 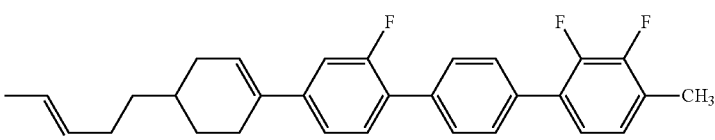 |
| 582 | 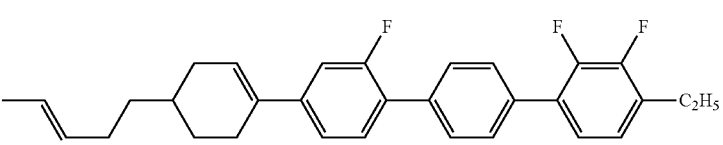 |
| 583 | 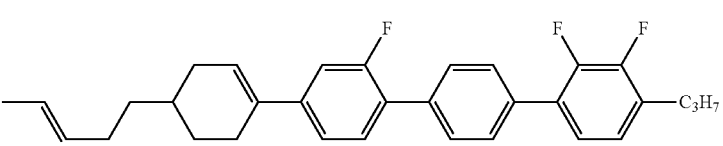 |
| 584 | 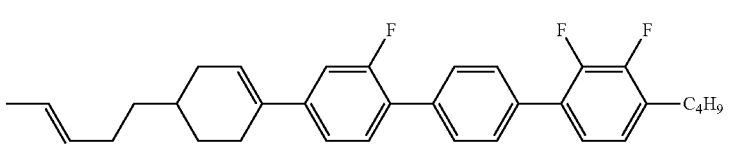 |
| 585 | 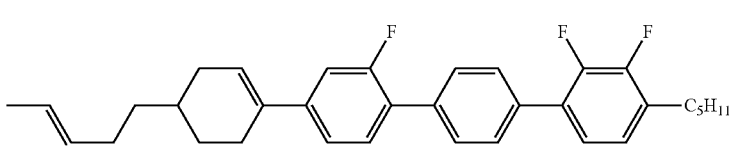 |
| 586 | 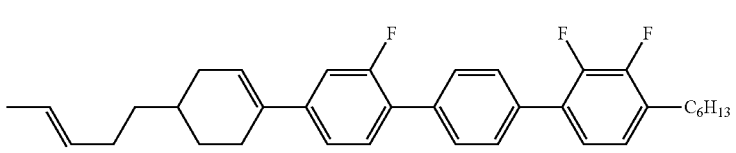 |

-continued
| No. | |
|---|---|
| 587 | 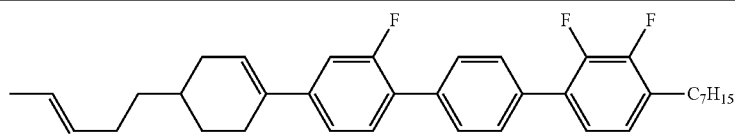 |
| 588 | 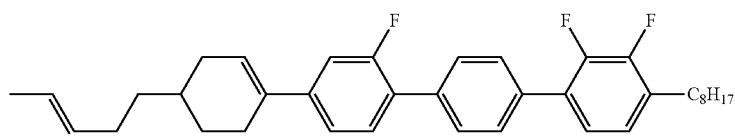 |
| 589 | 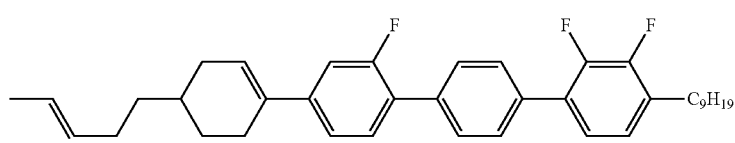 |
| 590 | 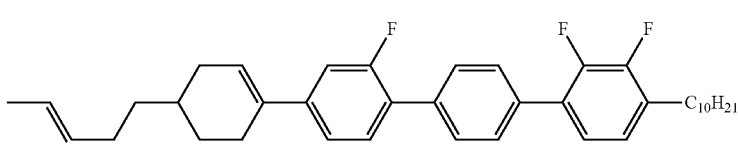 |
| 591 | 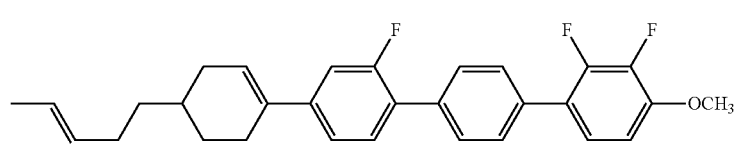 |
| 592 | 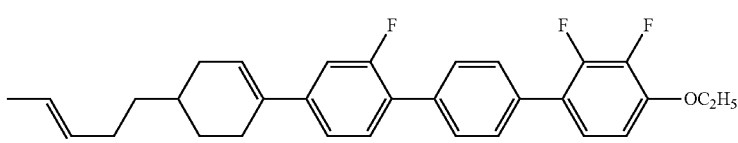 |
| 593 | 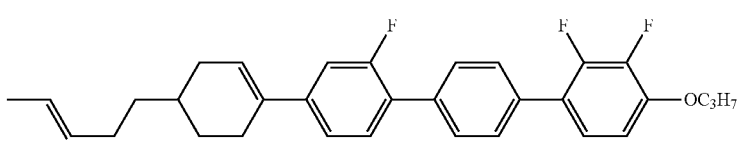 |
| 594 | 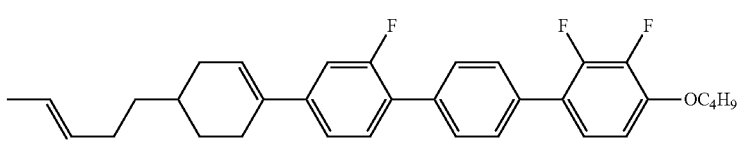 |
| 595 | 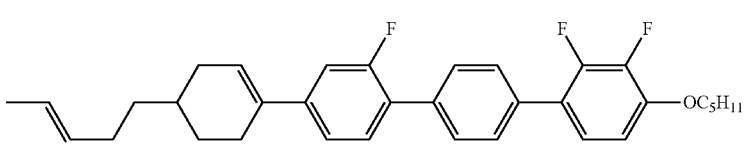 |
| 596 | 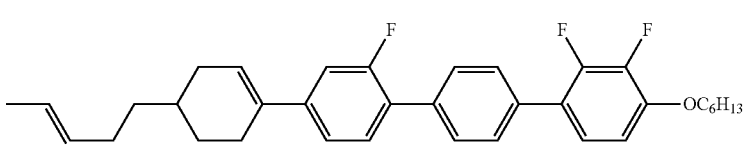 |
| 597 | 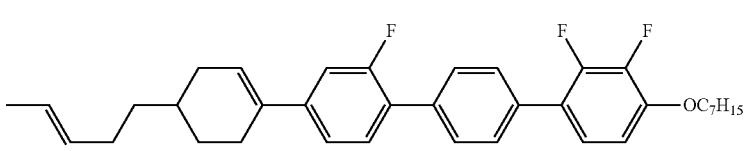 |

-continued
| No. |
|---|
| 598 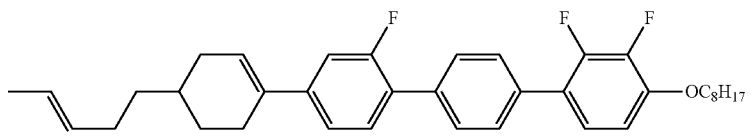 |
| 599 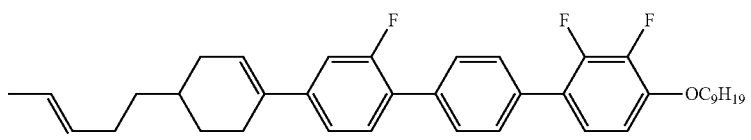 |
| 600 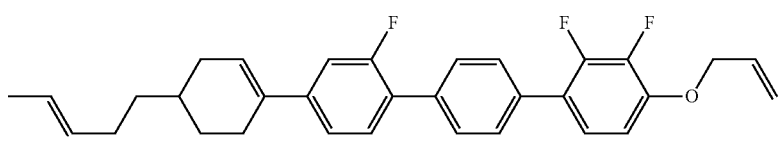 |
| 601 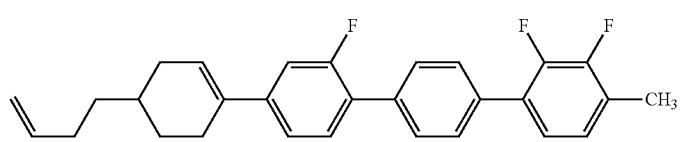 |
| 602 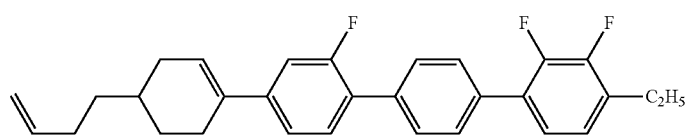 |
| 603 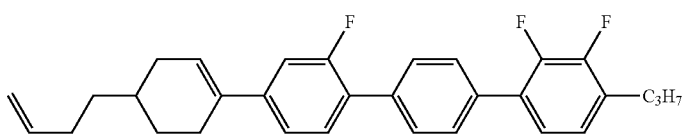 |
| 604 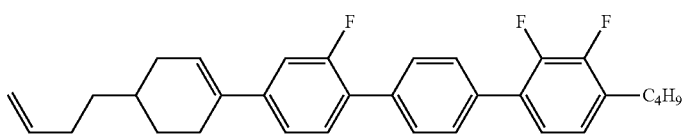 |
| 605 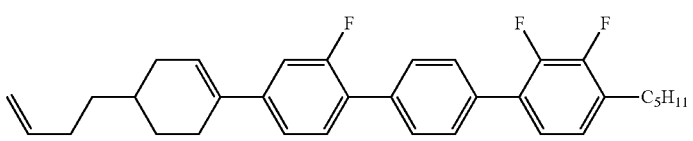 |
| 606 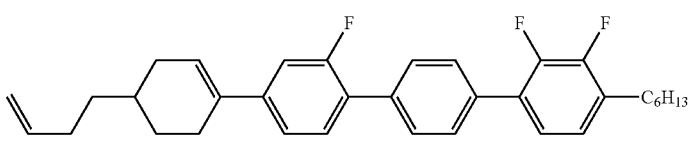 |
| 607 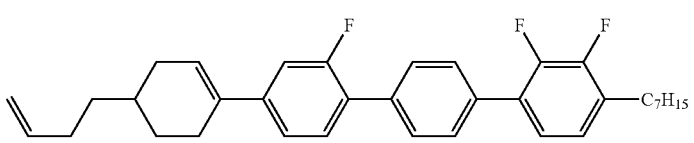 |
| 608 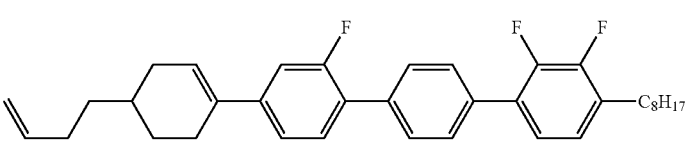 |

| No. |
|---|
| 609 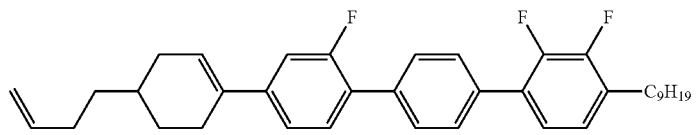 |
| 610 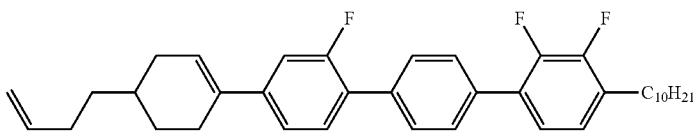 |
| 611 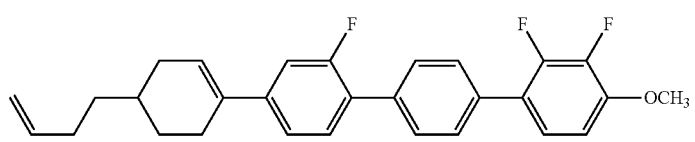 |
| 612 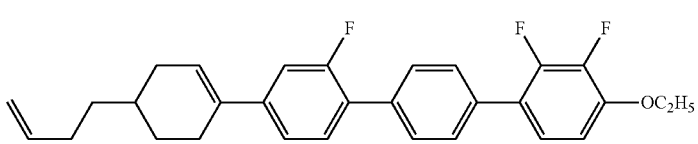 |
| 613 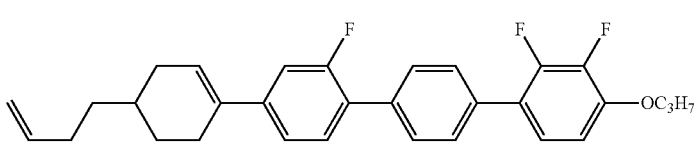 |
| 614 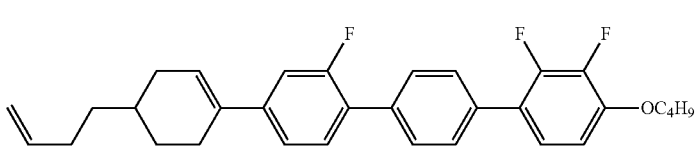 |
| 615 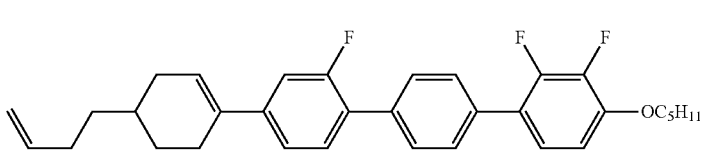 |
| 616 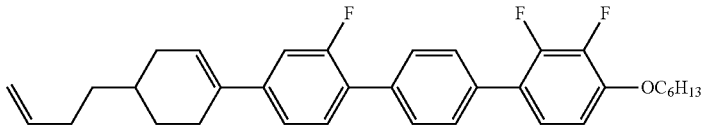 |
| 617  |
| 618  |
| 619 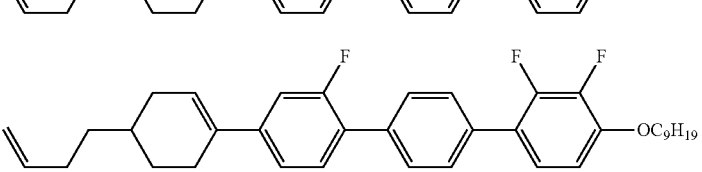 |

| No. | |
|---|---|
| 620 | 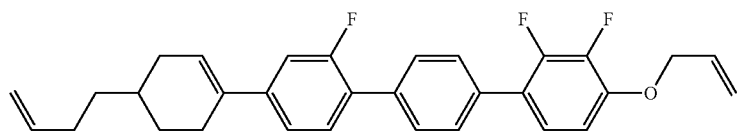 |
| 621 | 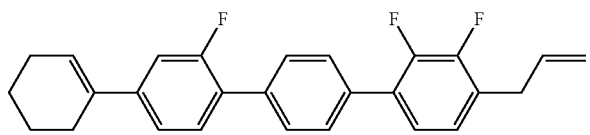 |
| 622 | 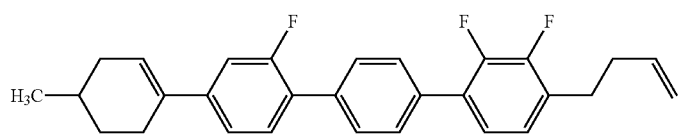 |
| 623 | 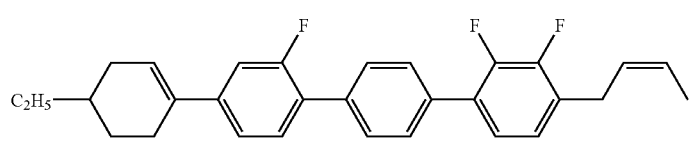 |
| 624 | 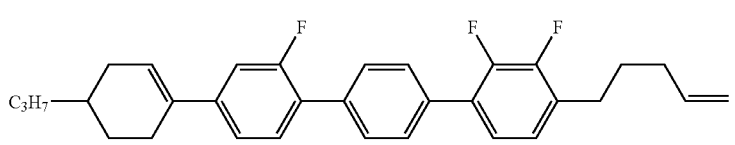 |
| 625 | 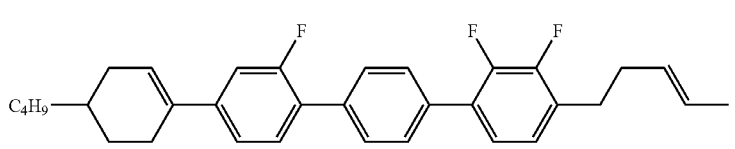 |
| 626 | 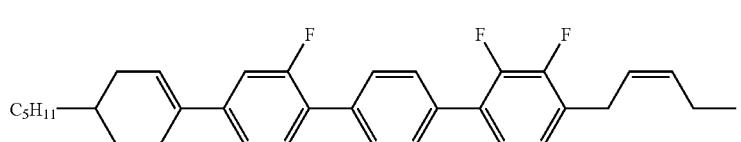 |
| 627 | 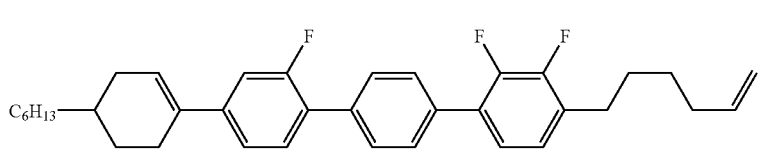 |
| 628 | 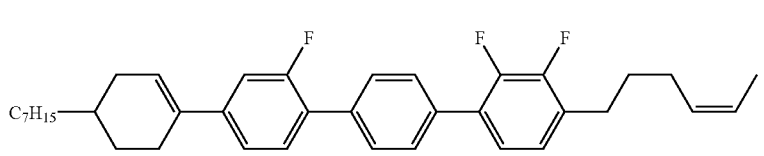 |
| 629 | 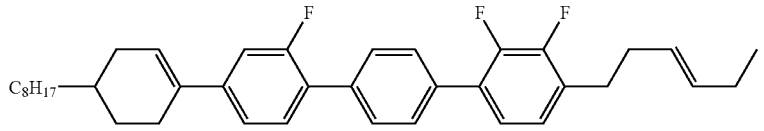 |
| 630 | 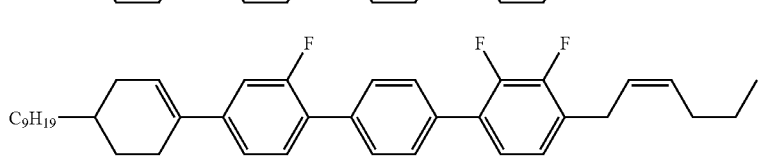 |

-continued
| No. | |
|---|---|
| 631 | 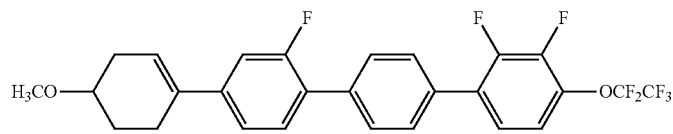 |
| 632 | 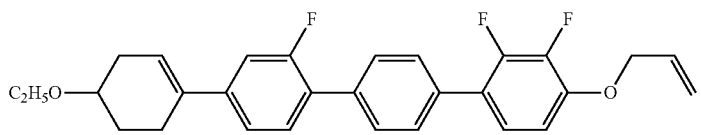 |
| 633 | 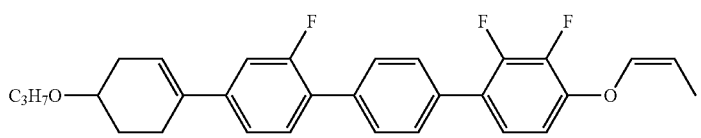 |
| 634 | 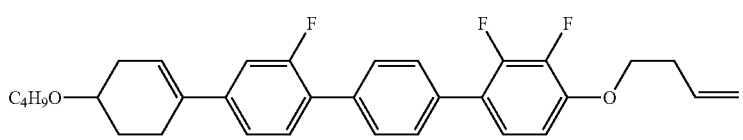 |
| 635 | 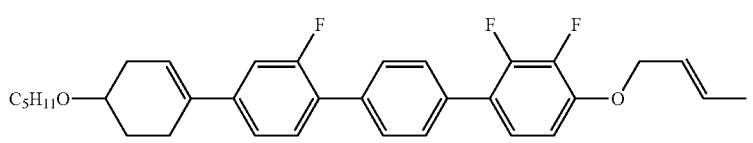 |
| 636 | 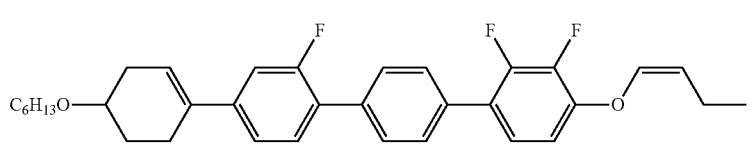 |
| 637 | 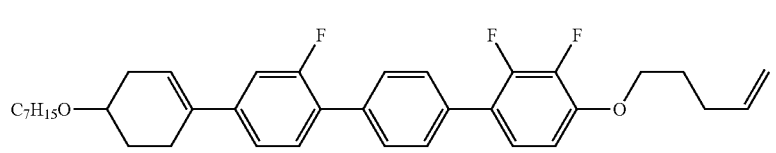 |
| 638 | 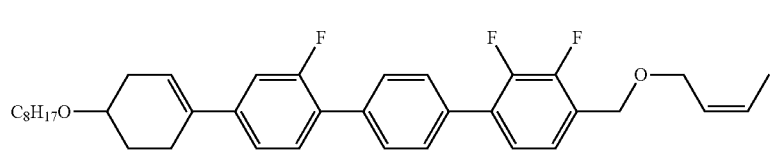 |
| 639 | 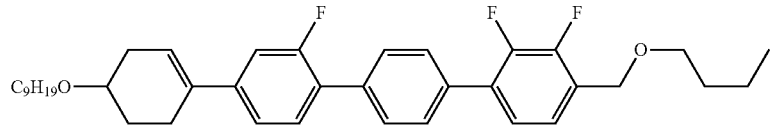 |
| 640 | 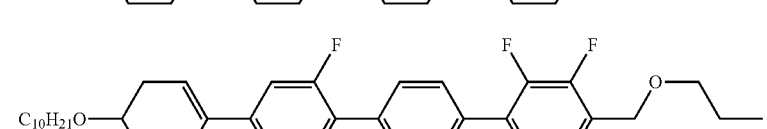 |
| 621 | 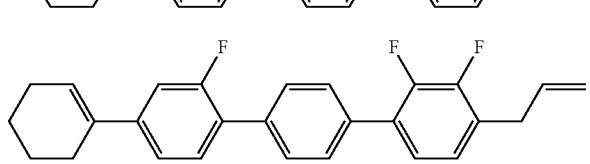 |

-continued
| No. | |
|---|---|
| 622 | 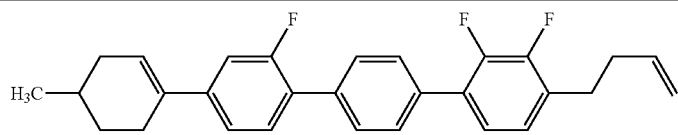 |
| 623 | 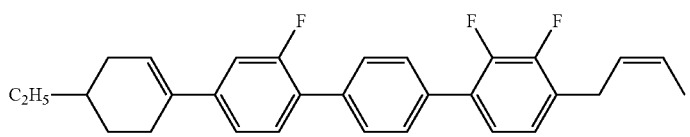 |
| 624 | 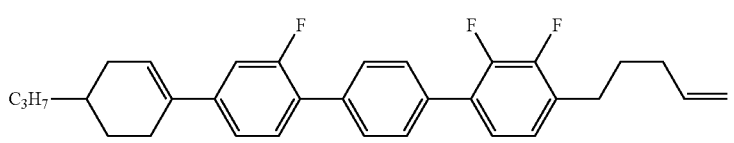 |
| 625 | 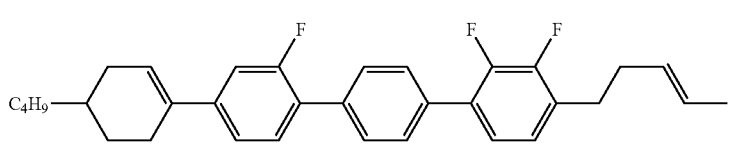 |
| 626 | 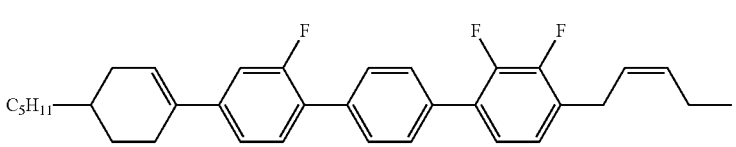 |
| 627 | 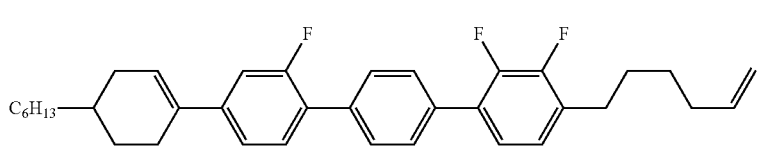 |
| 628 | 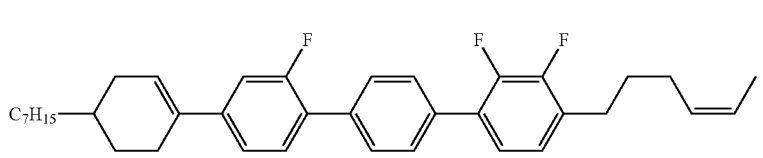 |
| 629 | 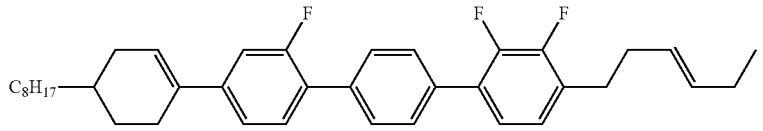 |
| 630 | 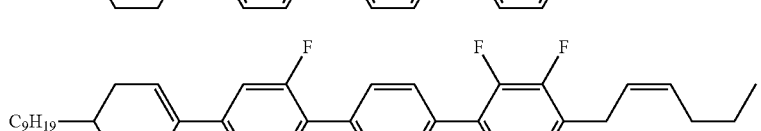 |
| 631 | 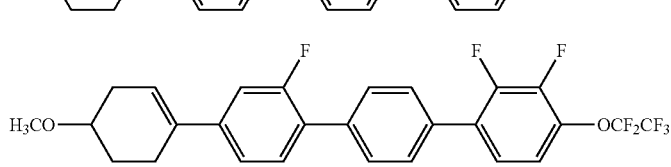 |
| 632 | 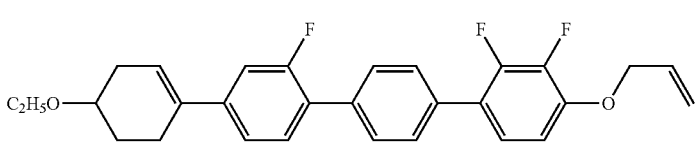 |

| No. | |
|---|---|
| 633 | 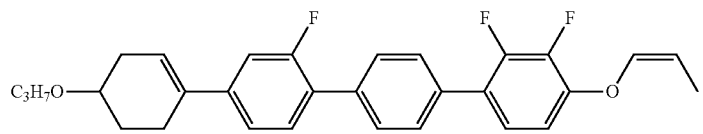 |
| 634 | 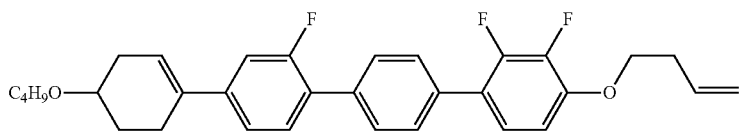 |
| 635 | 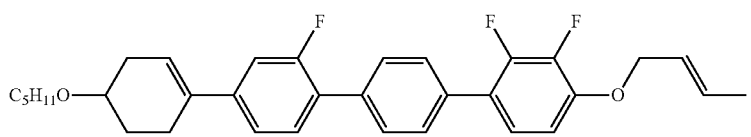 |
| 636 | 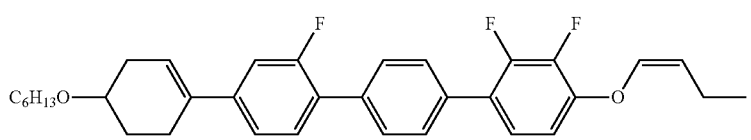 |
| 637 | 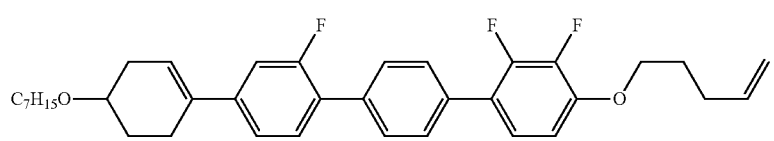 |
| 638 | 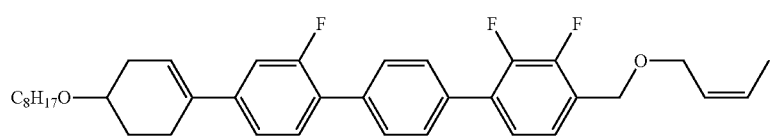 |
| 639 | 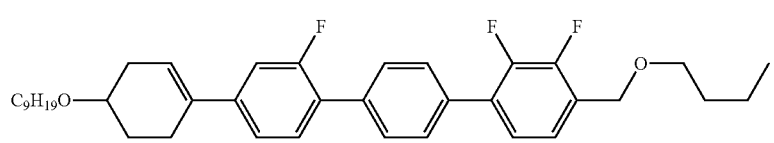 |
| 640 | 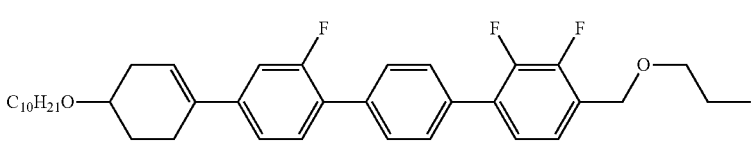 |
| 641 | 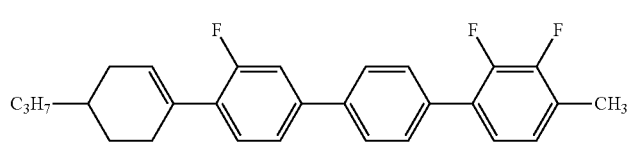 |
| 642 | 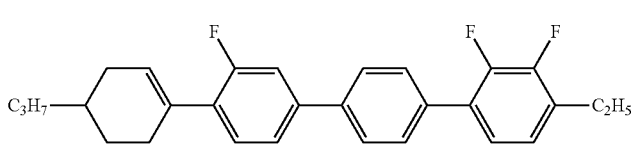 |
| 643 | 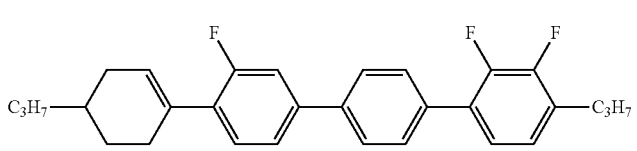 |

| No. | |
|---|---|
| 644 | 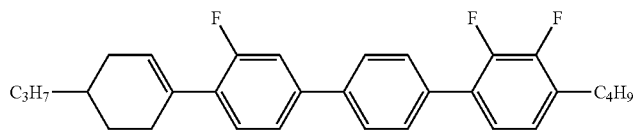 |
| 645 | 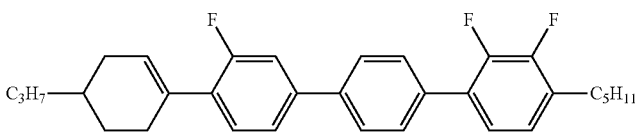 |
| 646 | 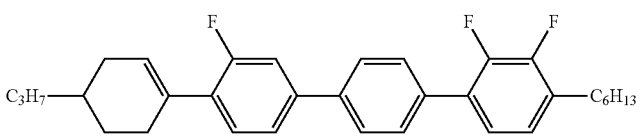 |
| 647 | 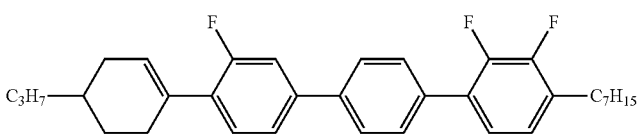 |
| 648 | 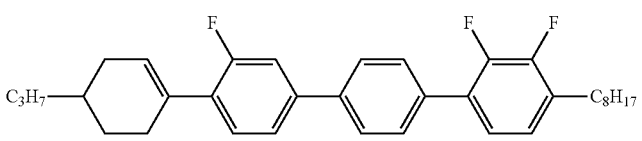 |
| 649 | 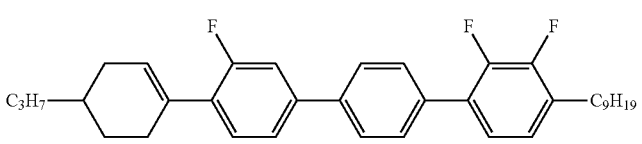 |
| 650 | 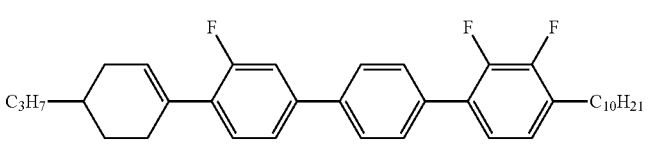 |
| 651 | 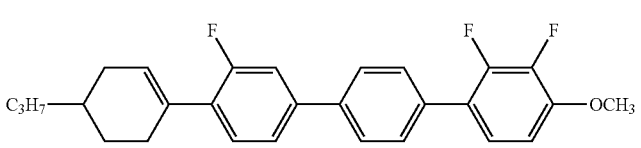 |
| 652 | 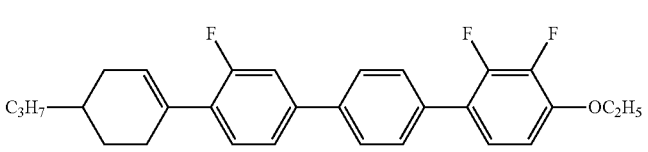<br>C 102.1 SA 136.8 N 299.0 I<br>$T_{NI}$; 247.6° C., $\Delta\varepsilon$; -5.12, $\Delta n$; 0.298 |
| 653 | 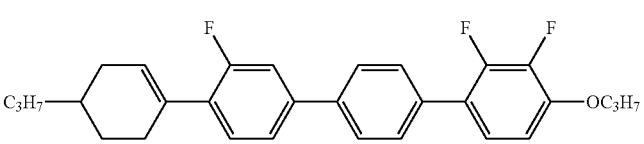 |
| 654 | 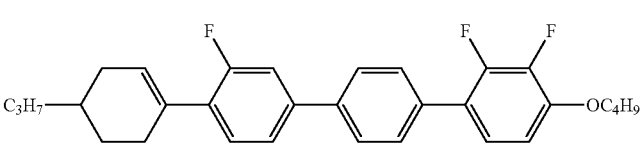 |

| No. | |
|---|---|
| 655 | 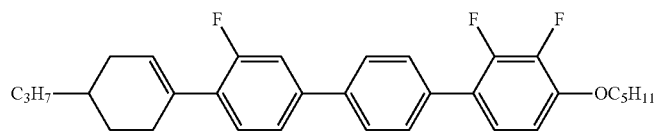 |
| 656 | 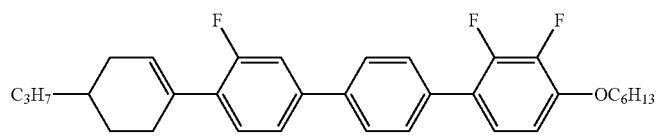 |
| 657 | 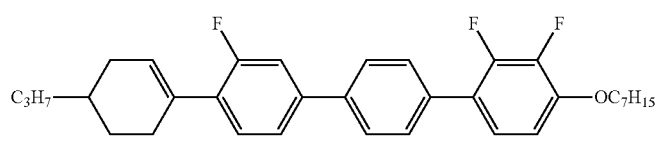 |
| 658 | 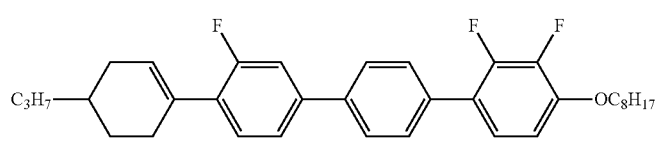 |
| 659 | 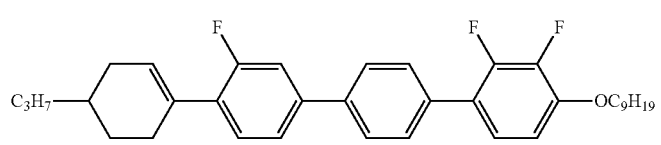 |
| 660 | 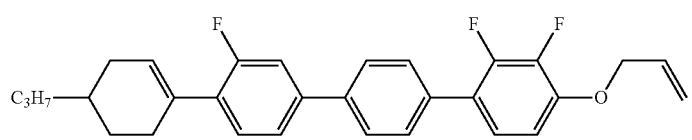 |
| 661 | 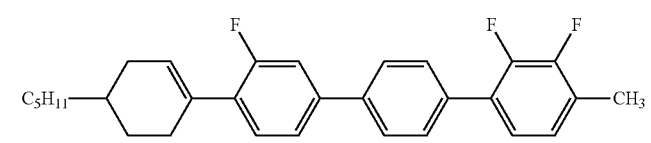 |
| 662 | 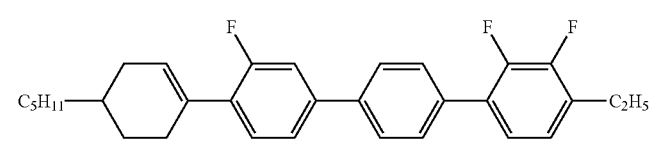 |
| 663 | 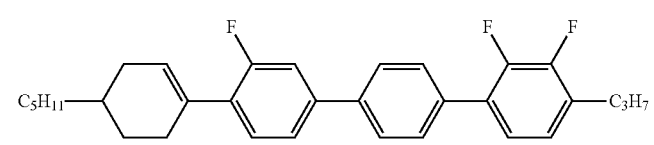 |
| 664 | 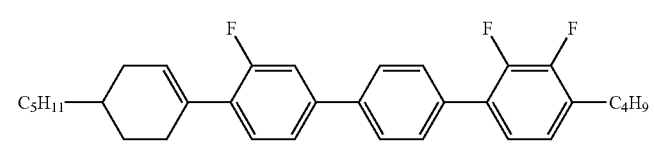 |
| 665 | 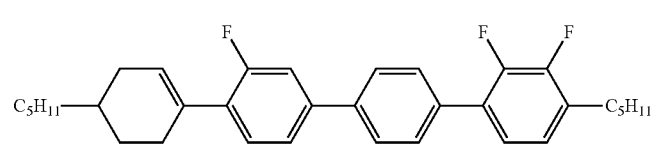 |

| No. | |
|---|---|
| 666 | 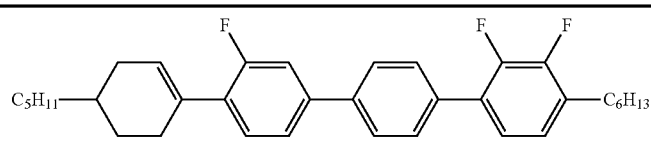 |
| 667 | 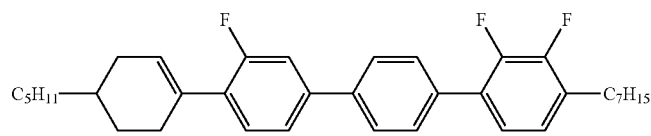 |
| 668 | 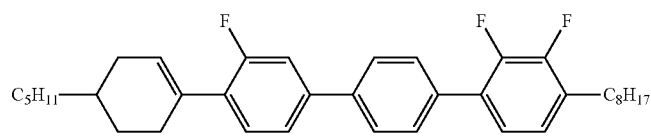 |
| 669 | 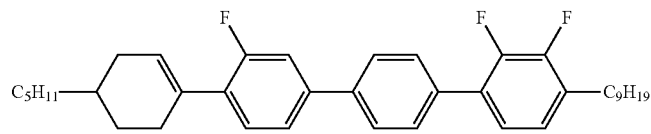 |
| 670 | 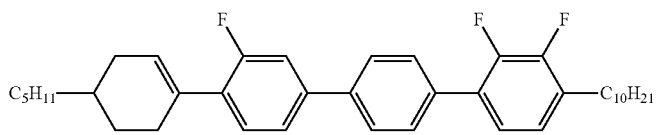 |
| 671 | 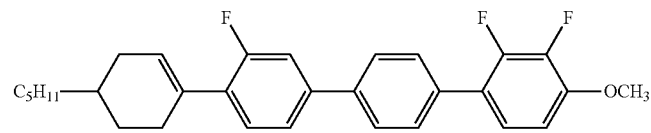 |
| 672 | 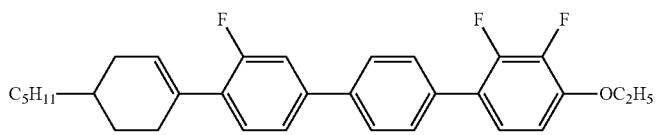<br>C 88.3 SA 196.9 N 287.3 I<br>$T_{NI}$; 245.3° C., Δε; -5.23, Δn; 0.294 |
| 673 | 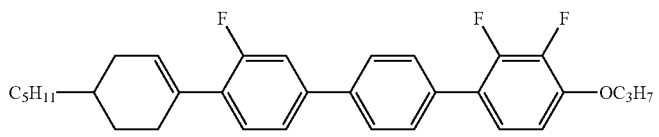 |
| 674 | 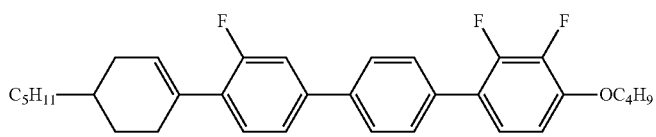 |
| 675 | 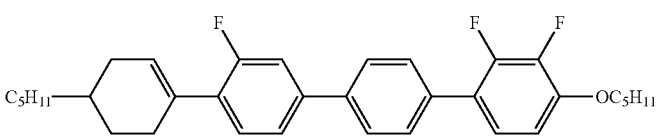 |
| 676 | 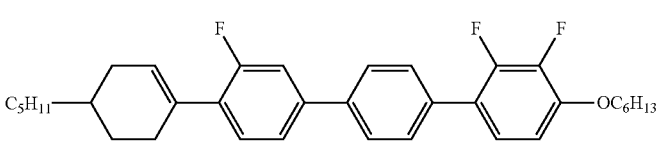 |

-continued
| No. | |
|---|---|
| 677 | 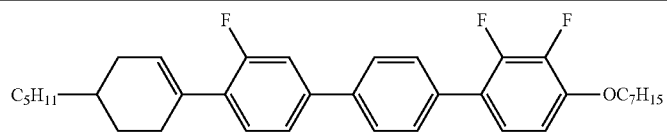 |
| 678 |  |
| 679 | 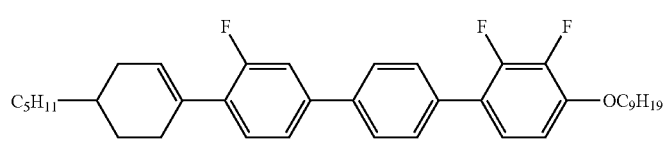 |
| 680 | 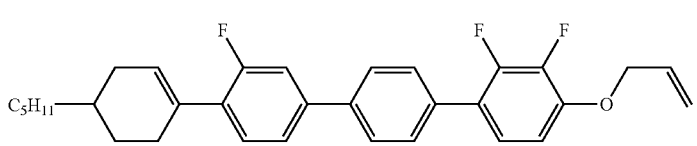 |
| 681 | 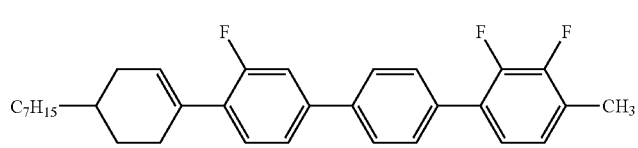 |
| 682 | 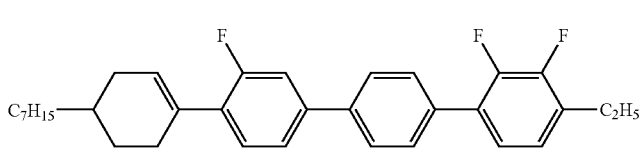 |
| 683 | 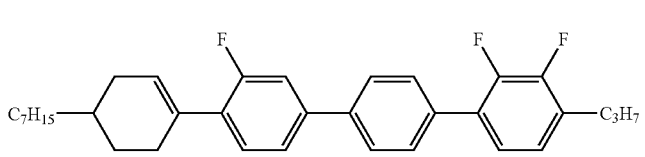 |
| 684 | 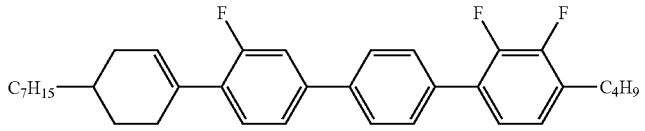 |
| 685 | 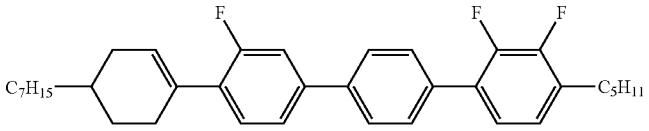 |
| 686 | 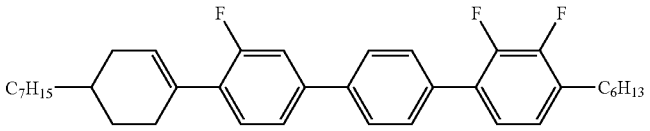 |
| 687 | 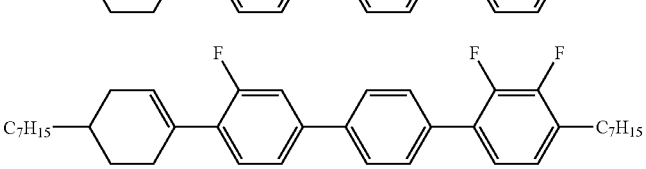 |

| No. | |
|---|---|
| 688 | 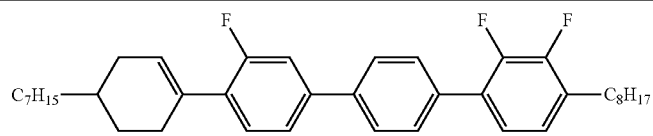 |
| 689 | 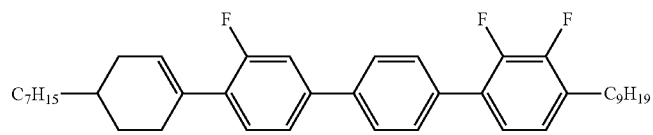 |
| 690 | 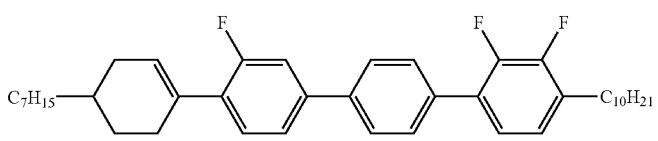 |
| 691 | 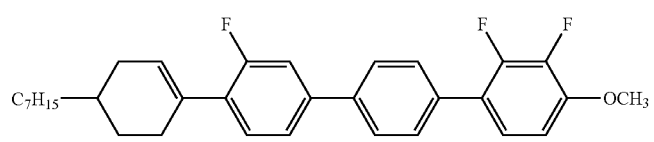 |
| 692 | 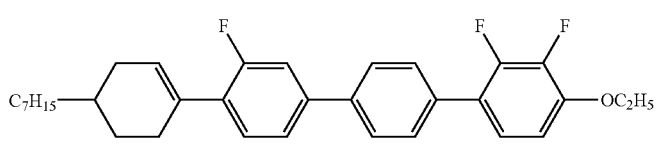 |
| 693 | 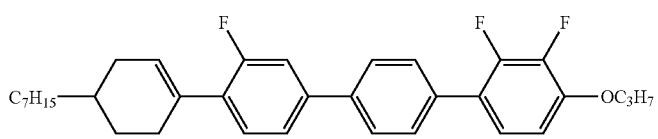 |
| 694 | 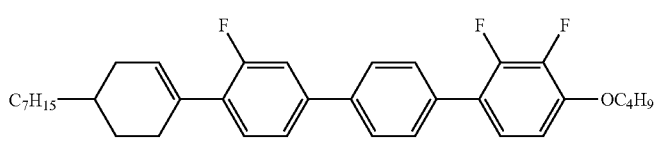 |
| 695 | 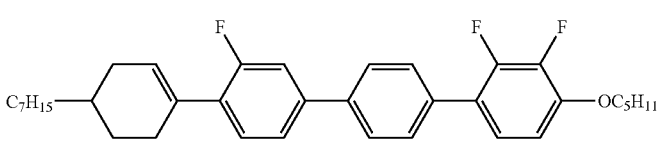 |
| 696 | 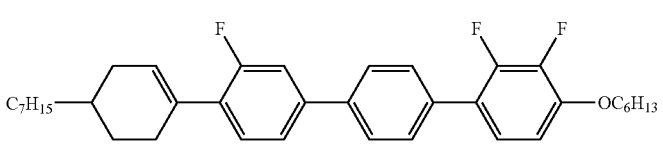 |
| 697 | 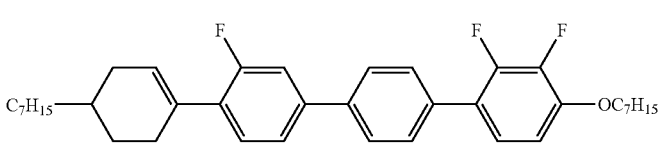 |
| 698 | 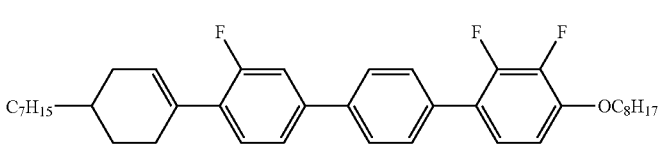 |

| No. | |
|---|---|
| 699 | 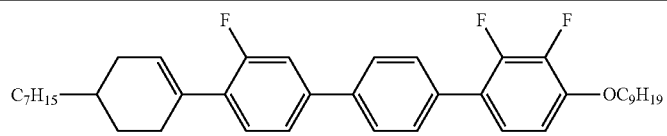 |
| 700 | 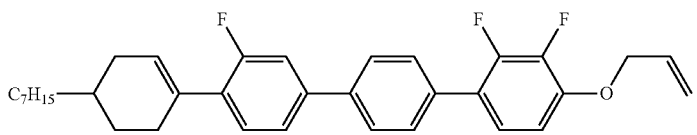 |
| 701 | 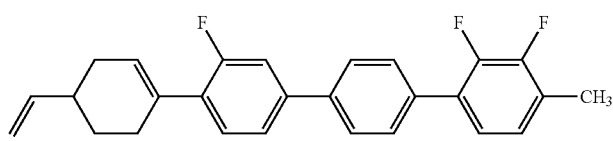 |
| 702 | 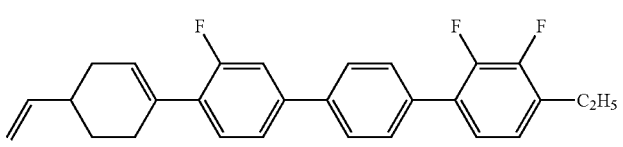 |
| 703 | 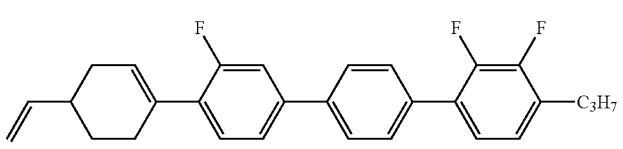 |
| 704 | 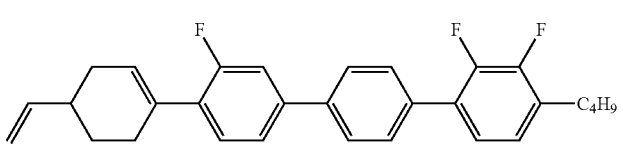 |
| 705 | 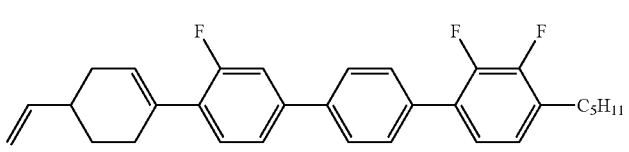 |
| 706 | 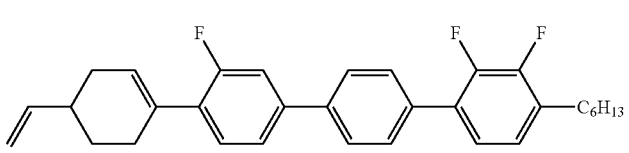 |
| 707 | 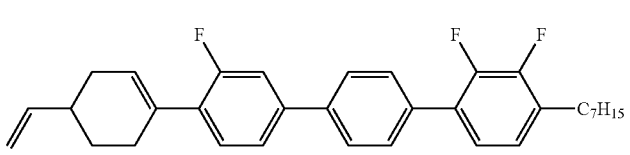 |
| 708 | 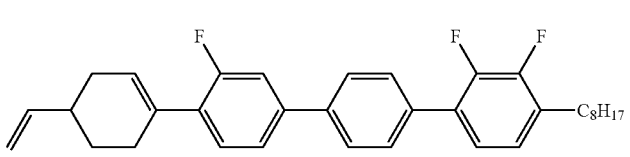 |
| 709 | 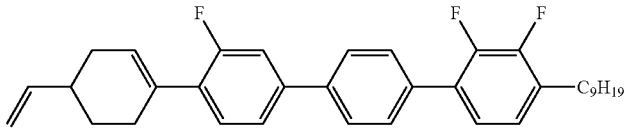 |

| No. | |
|---|---|
| 710 | 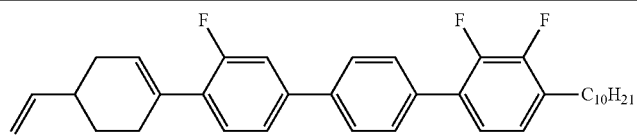 |
| 711 | 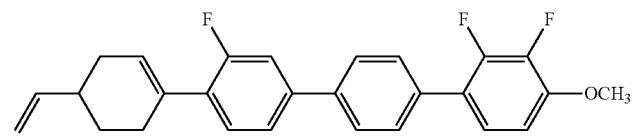 |
| 712 | 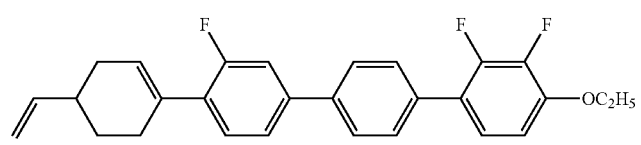 |
| 713 | 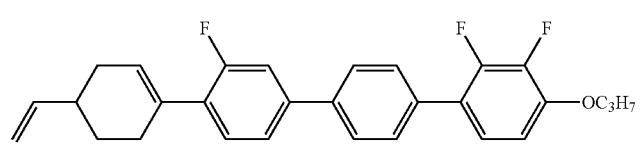 |
| 714 | 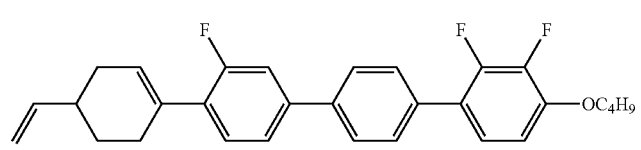 |
| 715 | 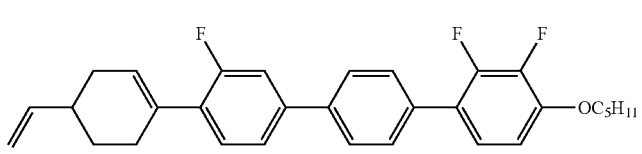 |
| 716 | 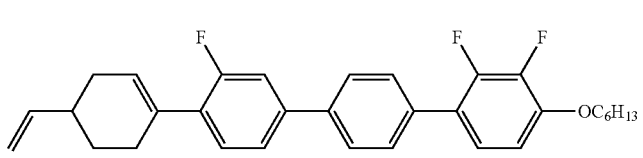 |
| 717 | 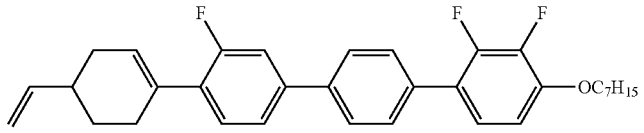 |
| 718 | 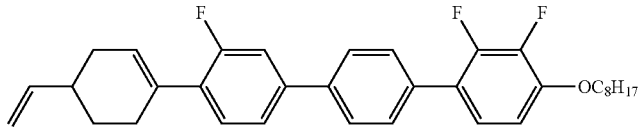 |
| 719 | 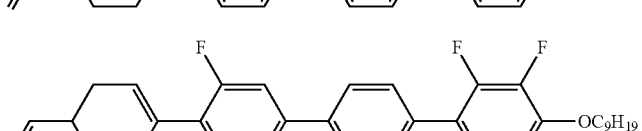 |
| 720 | 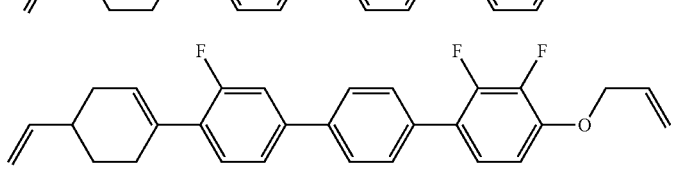 |

| No. | |
|---|---|
| 721 | 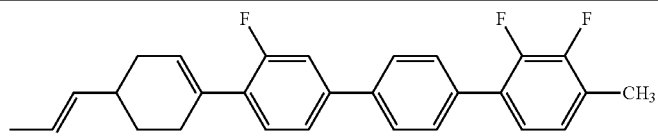 |
| 722 | 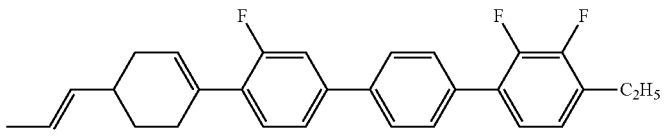 |
| 723 | 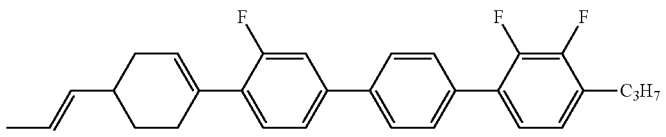 |
| 724 | 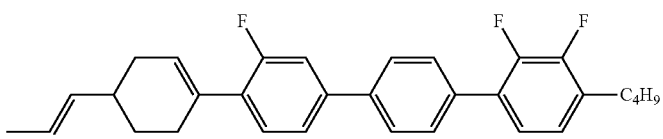 |
| 725 | 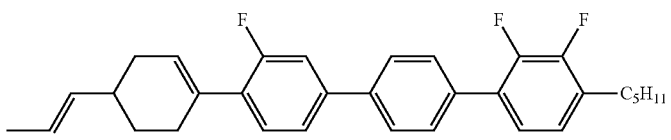 |
| 726 | 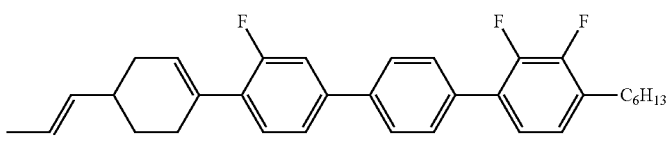 |
| 727 | 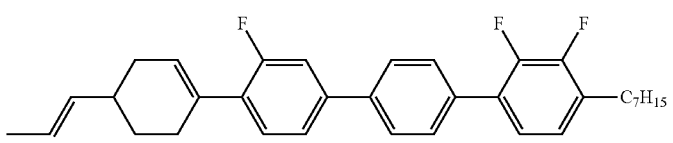 |
| 728 | 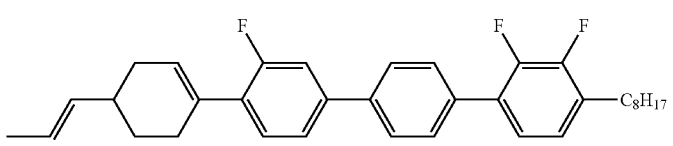 |
| 729 | 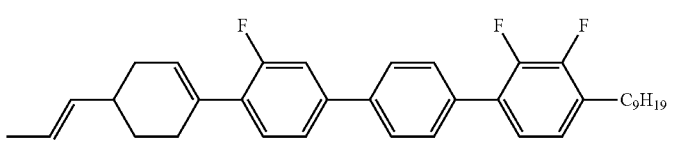 |
| 730 | 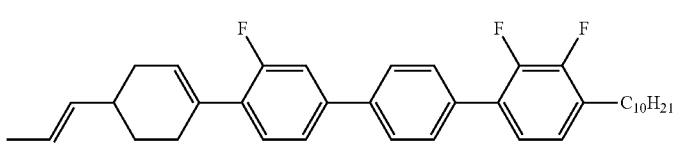 |
| 731 | 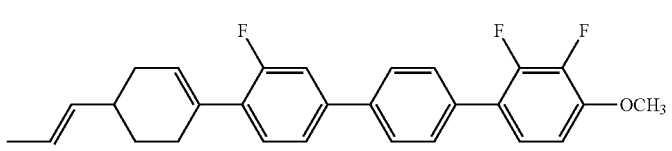 |

| No. | |
|---|---|
| 732 | 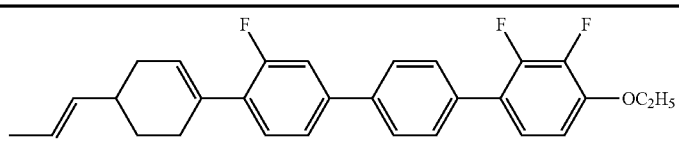 |
| 733 | 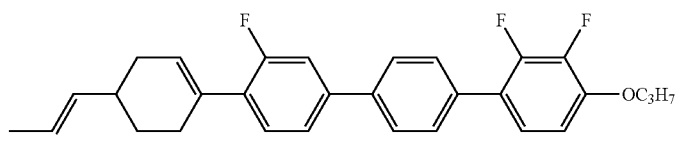 |
| 734 | 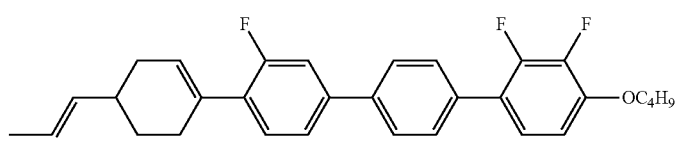 |
| 735 | 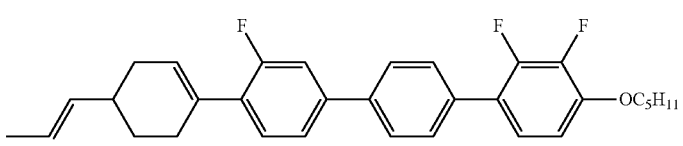 |
| 736 | 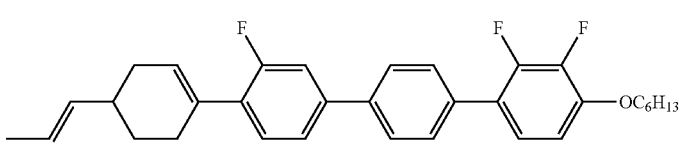 |
| 737 | 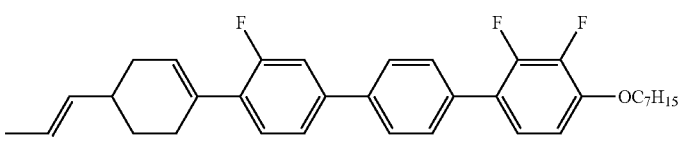 |
| 738 | 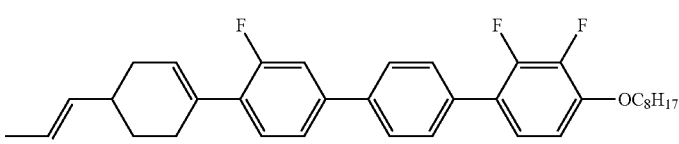 |
| 739 | 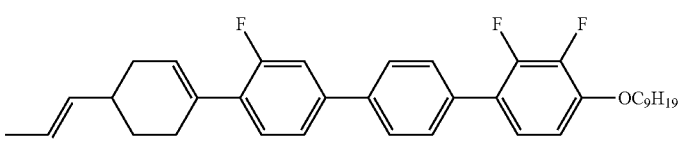 |
| 740 | 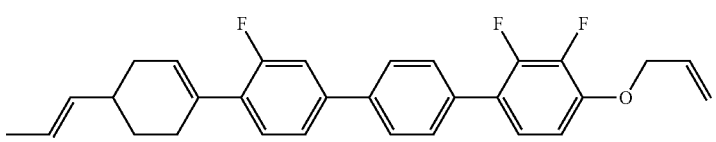 |
| 741 | 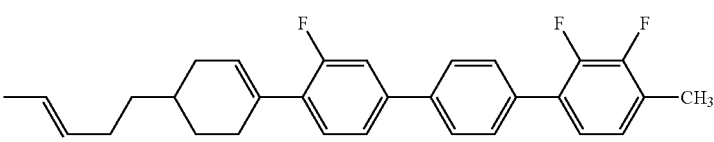 |
| 742 | 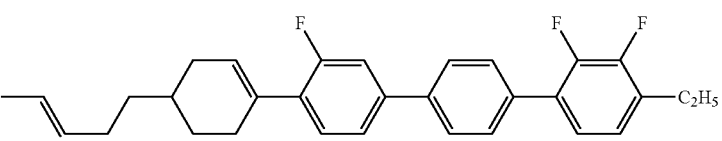 |

| No. | |
|---|---|
| 743 | 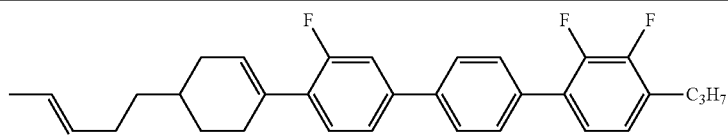 |
| 744 | 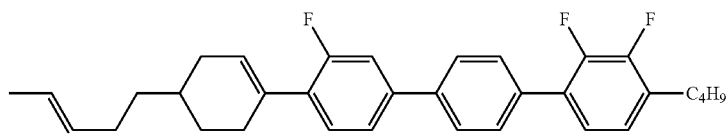 |
| 745 | 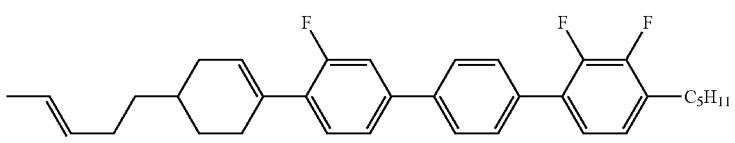 |
| 746 | 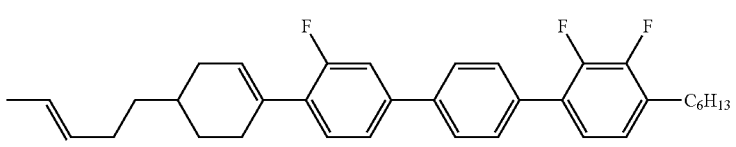 |
| 747 | 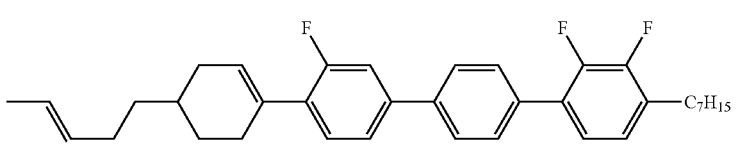 |
| 748 | 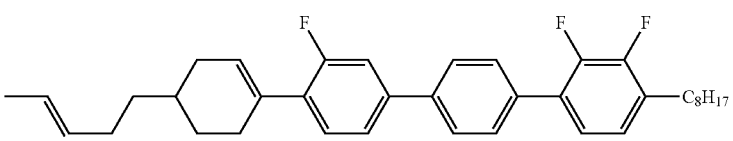 |
| 749 | 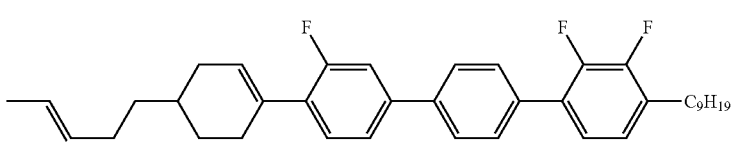 |
| 750 | 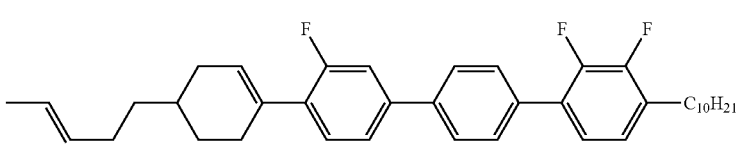 |
| 751 | 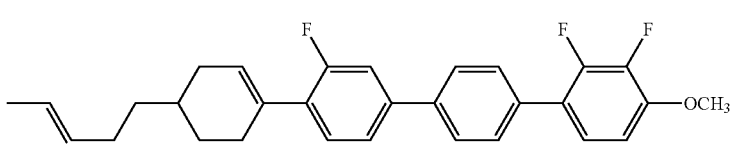 |
| 752 | 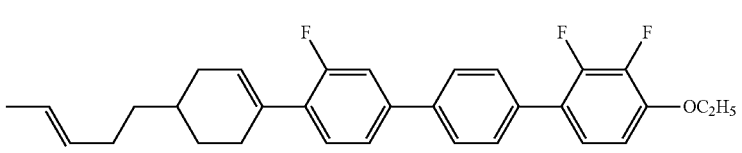 |
| 753 | 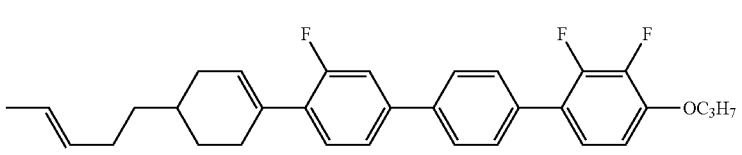 |

| No. | |
|---|---|
| 754 | 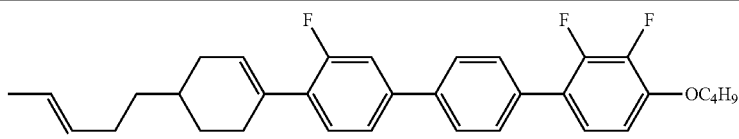 |
| 755 | 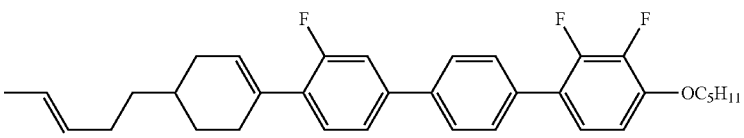 |
| 756 | 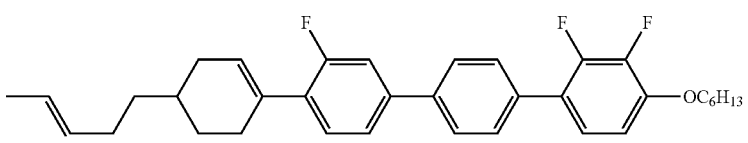 |
| 757 | 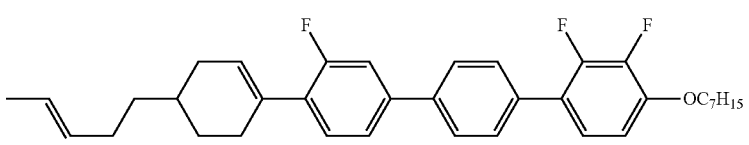 |
| 758 | 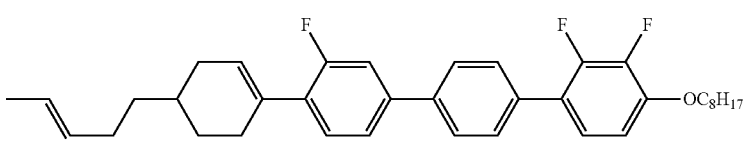 |
| 759 | 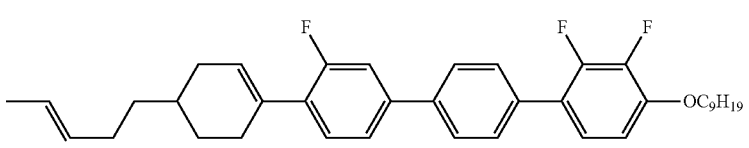 |
| 760 | 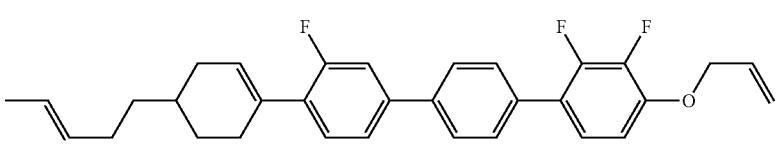 |
| 761 | 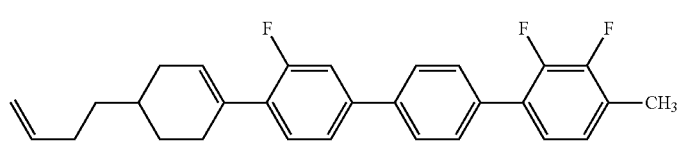 |
| 762 | 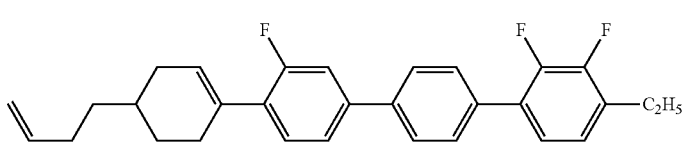 |
| 763 | 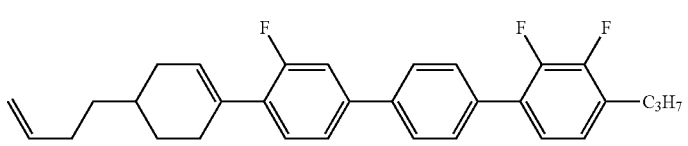 |
| 764 | 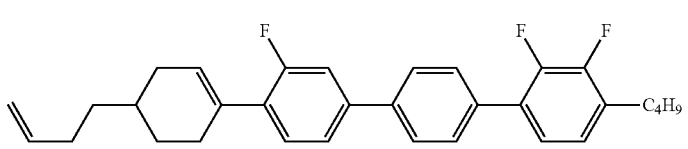 |

| No. | |
|---|---|
| 765 | 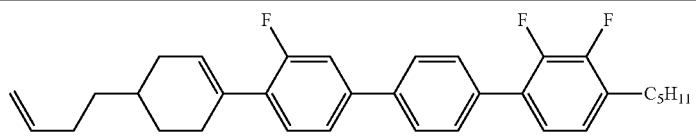 |
| 766 | 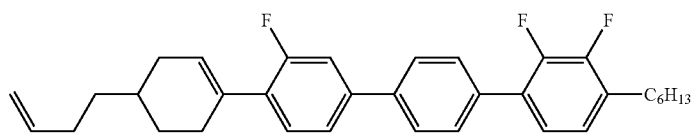 |
| 767 | 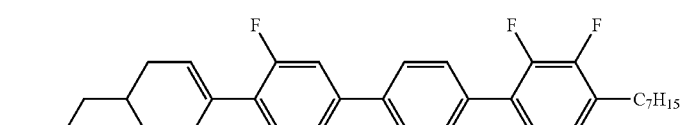 |
| 768 | 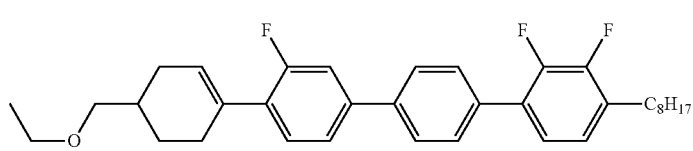 |
| 769 | 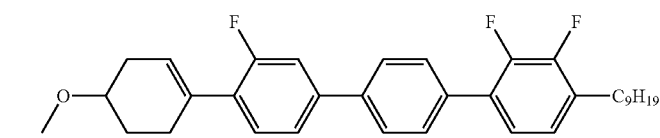 |
| 770 | 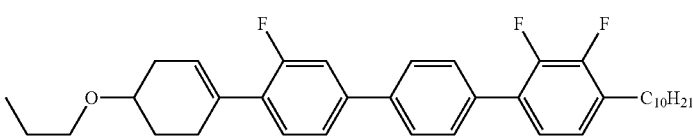 |
| 771 | 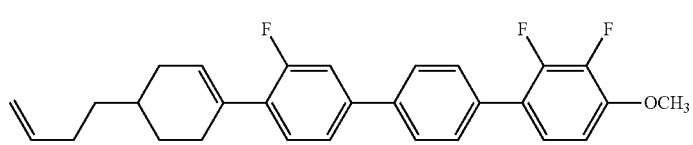 |
| 772 | 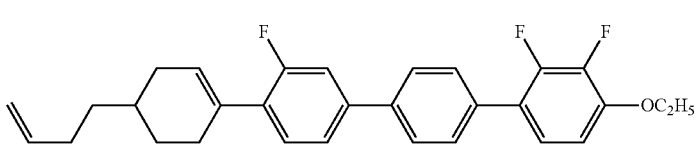 |
| 773 | 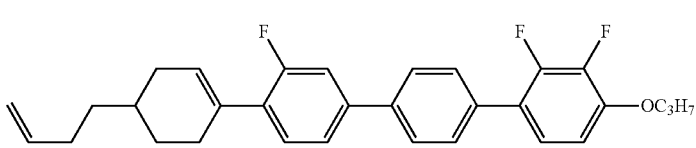 |
| 774 | 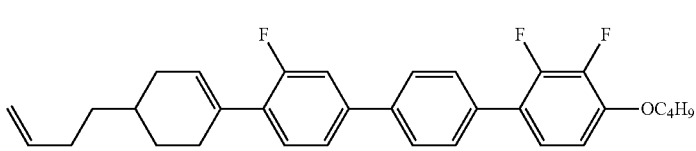 |
| 775 | 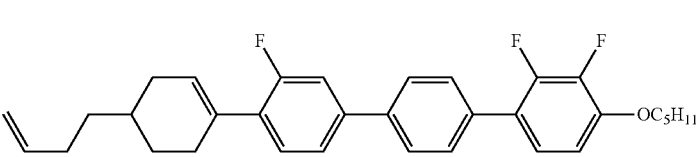 |

| No. | |
|---|---|
| 776 | 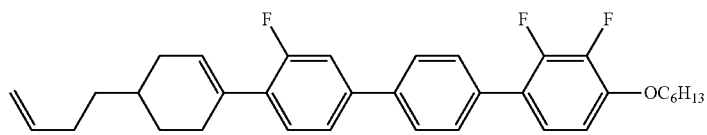 |
| 777 | 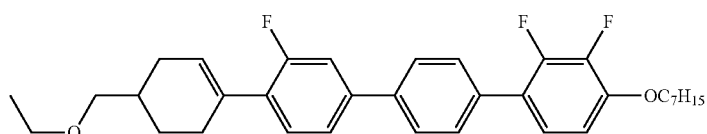 |
| 778 | 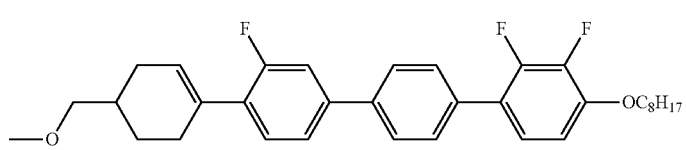 |
| 779 | 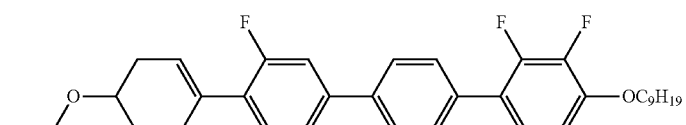 |
| 780 | 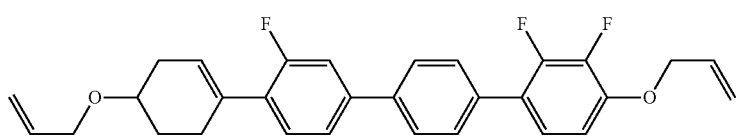 |
| 781 | 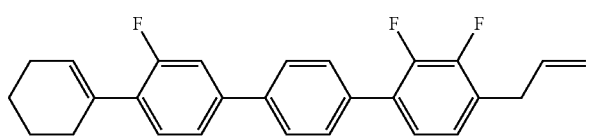 |
| 782 | 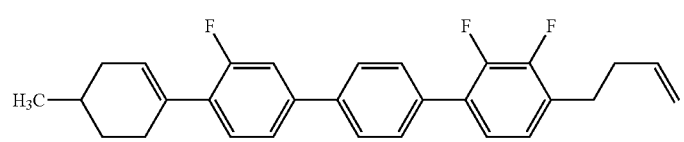 |
| 783 | 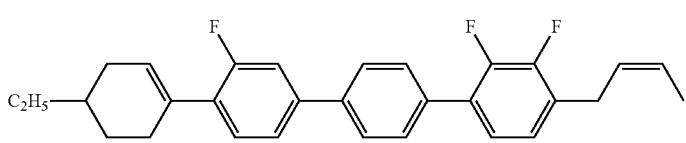 |
| 784 | 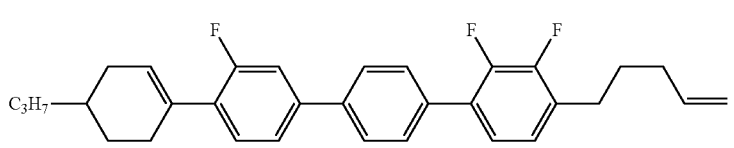 |
| 785 | 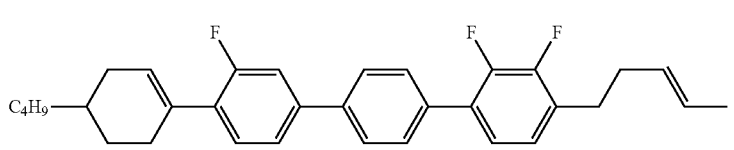 |
| 786 | 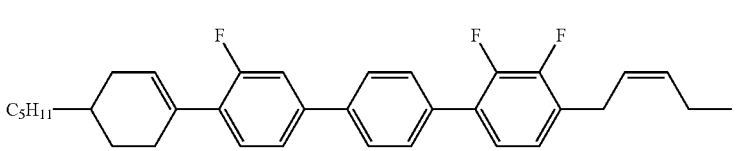 |

| No. | |
|---|---|
| 787 | 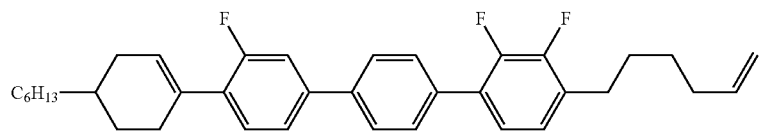 |
| 788 | 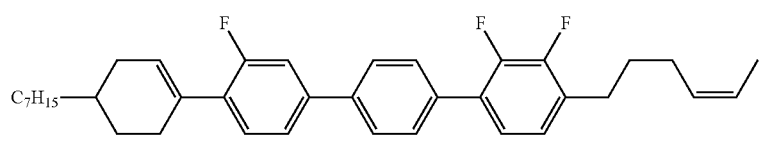 |
| 789 | 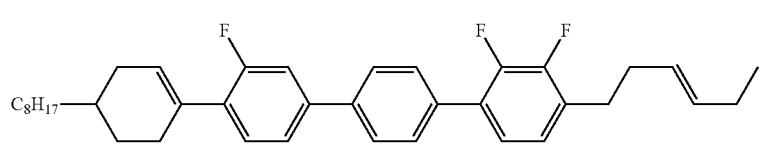 |
| 790 | 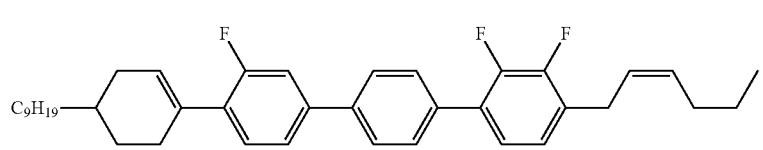 |
| 791 | 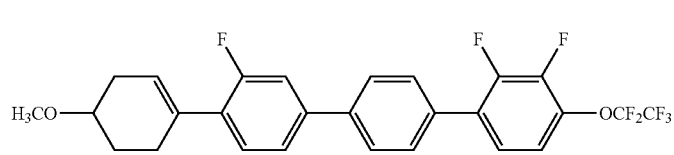 |
| 792 | 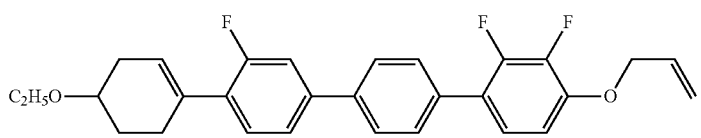 |
| 793 | 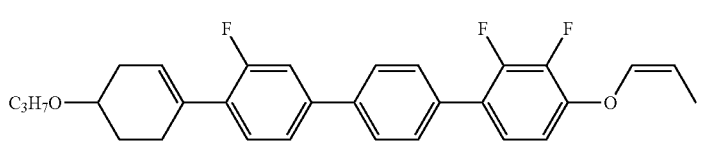 |
| 794 | 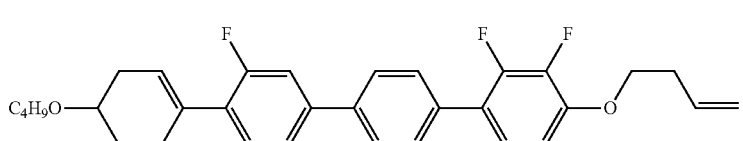 |
| 795 | 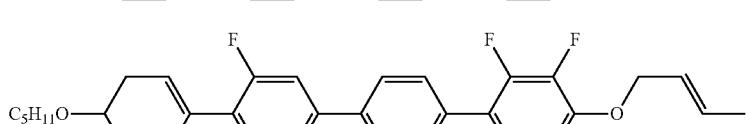 |
| 796 | 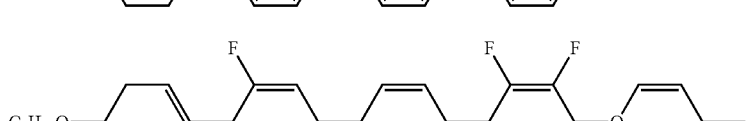 |
| 797 | 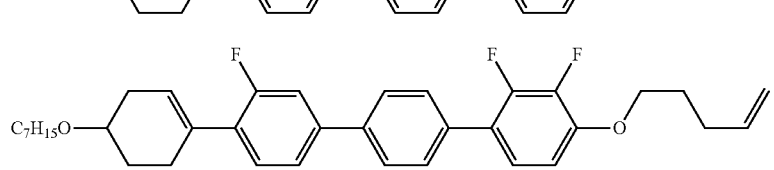 |

-continued
| No. | |
|---|---|
| 798 |  |
| 799 |  |
| 800 | 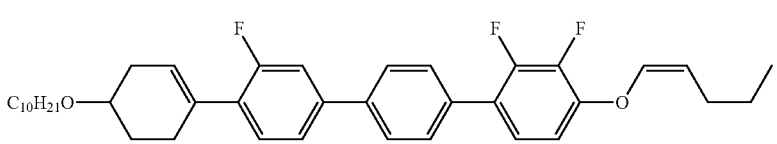 |
| 801 | 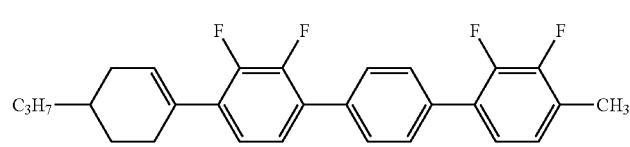 |
| 802 | 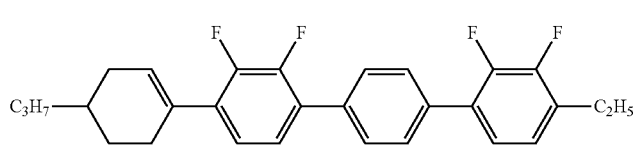 |
| 803 | 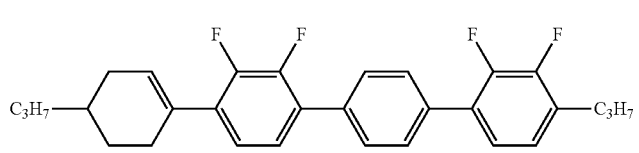 |
| 804 | 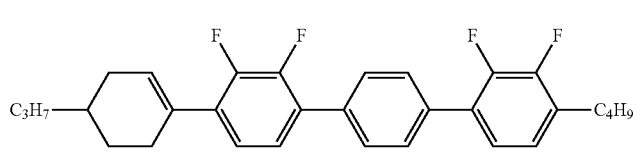 |
| 805 | 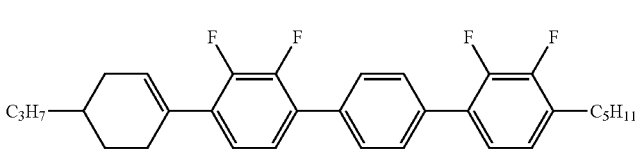 |
| 806 | 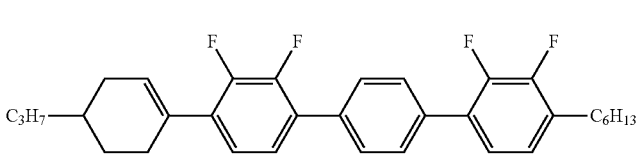 |
| 807 | 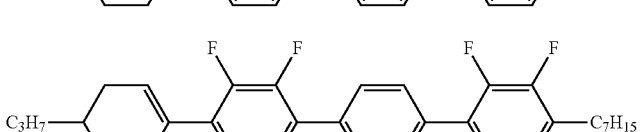 |
| 808 | 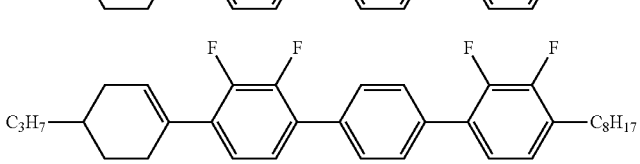 |

| No. | |
|---|---|
| 809 | 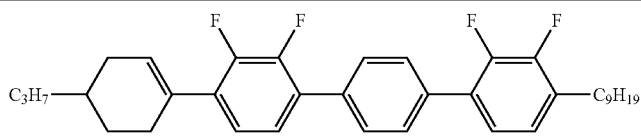 |
| 810 | 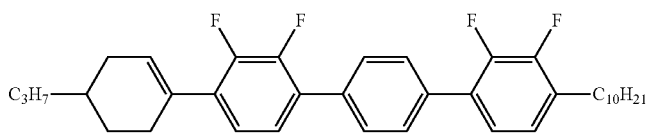 |
| 811 | 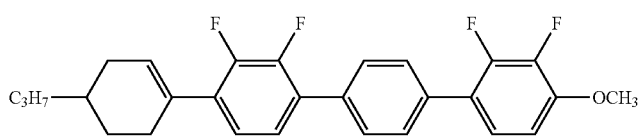 |
| 812 | 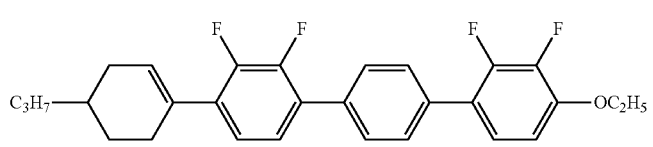 |
| 813 | 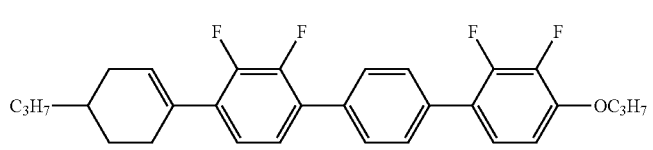 |
| 814 | 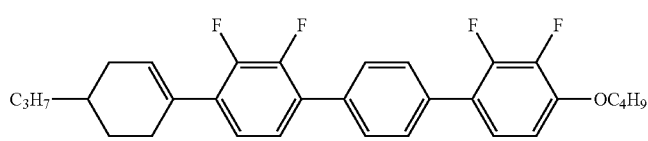 |
| 815 | 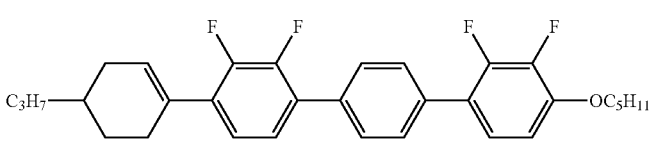 |
| 816 | 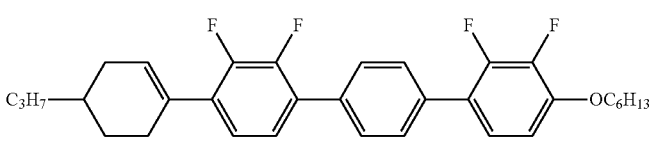 |
| 817 | 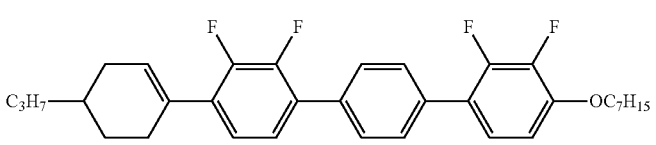 |
| 818 | 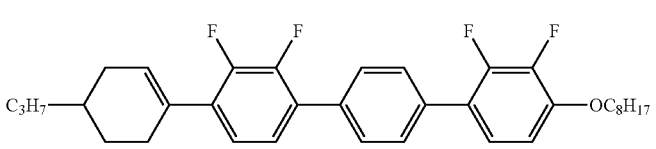 |
| 819 | 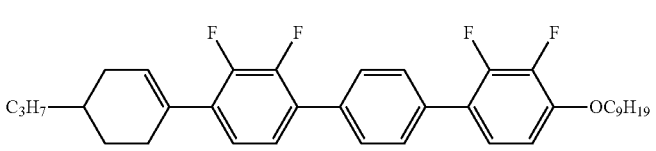 |

| No. | |
|---|---|
| 820 | 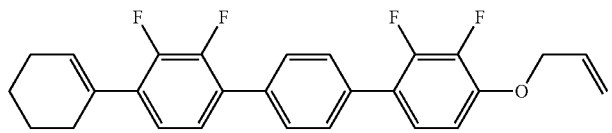 |
| 821 | 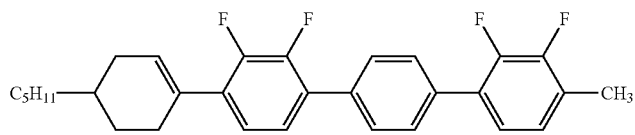 |
| 822 | 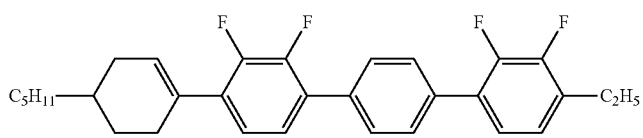 |
| 823 | 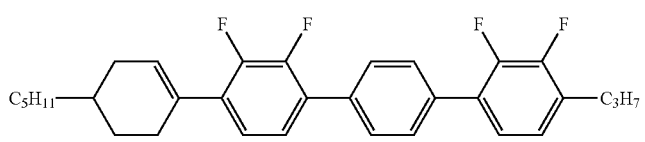 |
| 824 | 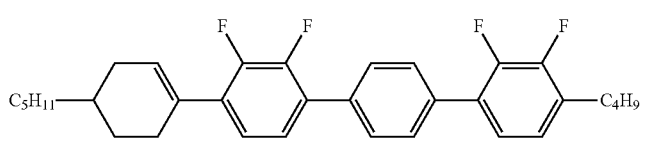 |
| 825 | 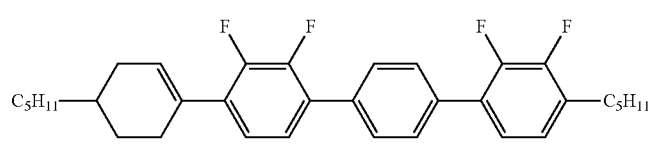 |
| 826 | 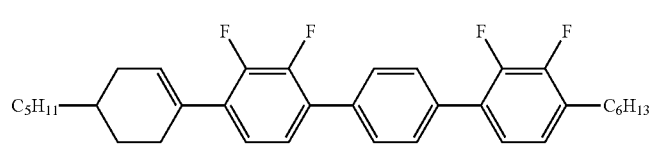 |
| 827 | 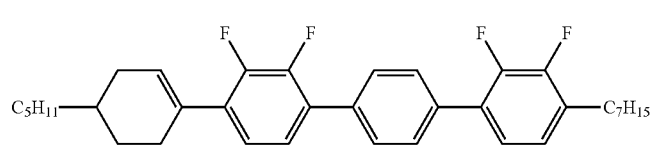 |
| 828 | 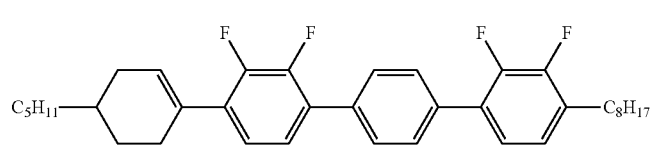 |
| 829 | 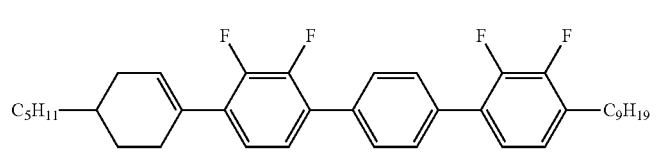 |
| 830 | 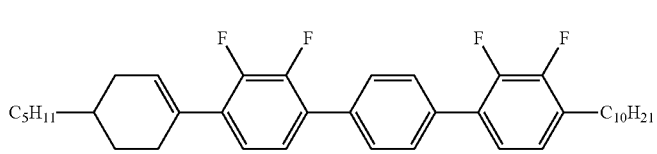 |

-continued
| No. | |
|---|---|
| 831 | 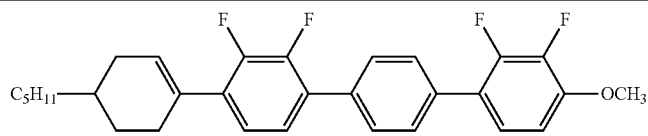 |
| 832 | 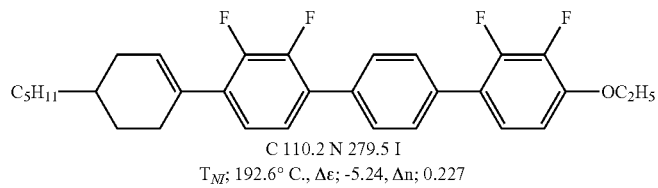
C 110.2 N 279.5 I
$T_{NI}$; 192.6° C., Δε; -5.24, Δn; 0.227 |
| 833 | 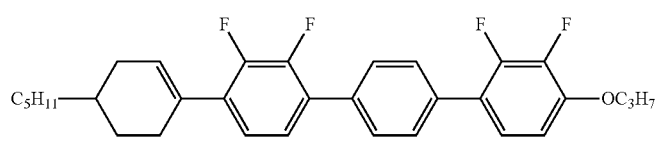 |
| 834 | 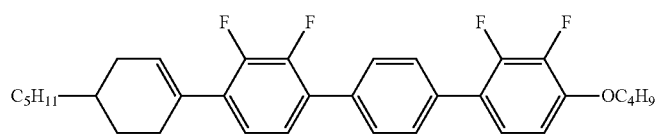 |
| 835 | 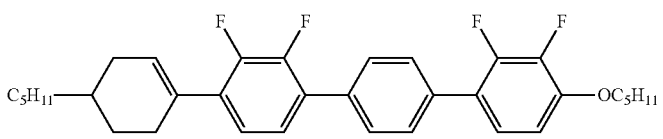 |
| 836 | 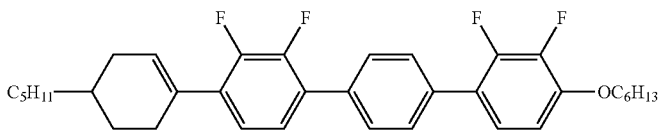 |
| 837 | 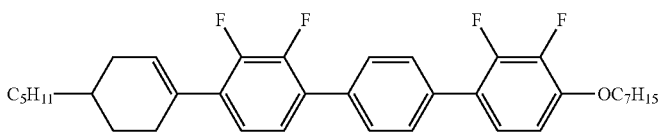 |
| 838 | 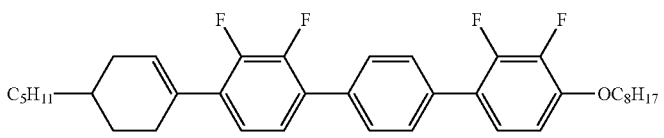 |
| 839 | 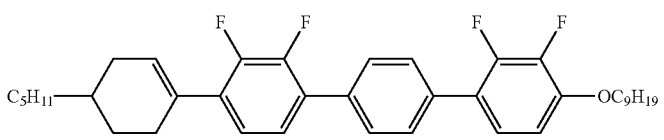 |
| 840 | 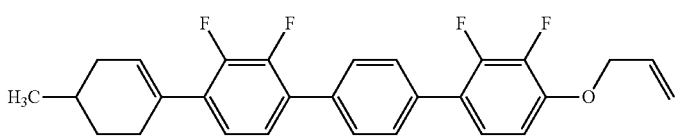 |
| 841 | 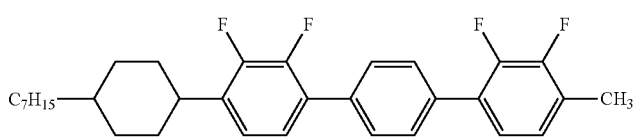 |

| No. | |
|---|---|
| 842 | 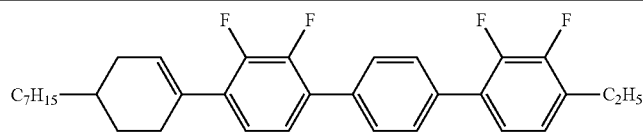 |
| 843 | 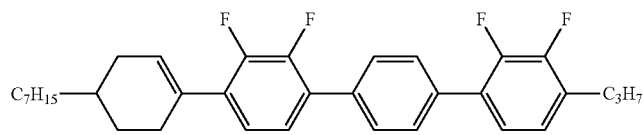 |
| 844 | 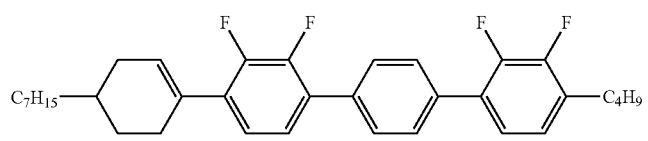 |
| 845 | 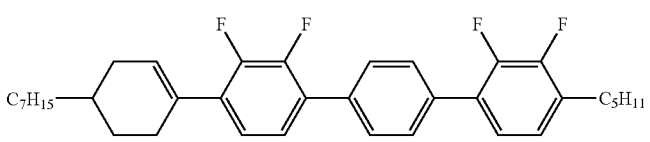 |
| 846 | 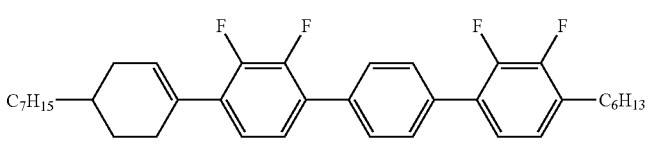 |
| 847 | 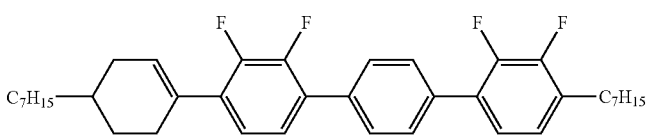 |
| 848 | 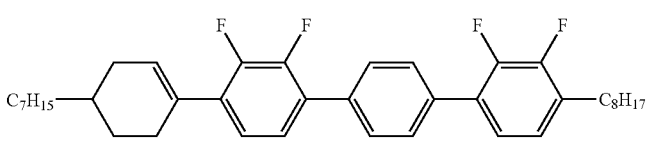 |
| 849 | 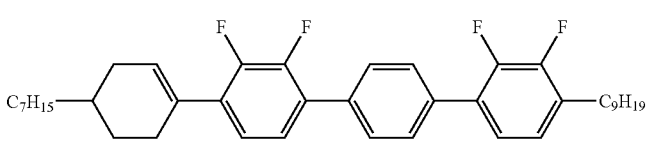 |
| 850 | 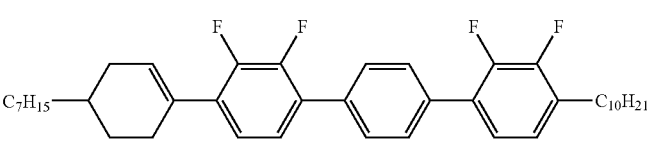 |
| 851 | 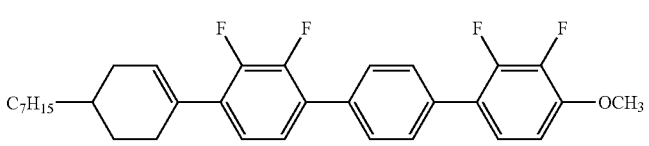 |
| 852 | 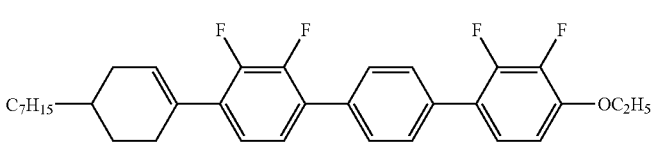 |

| No. | |
|---|---|
| 853 | 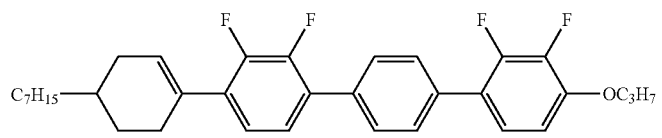 |
| 854 | 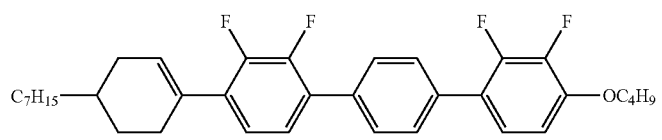 |
| 855 | 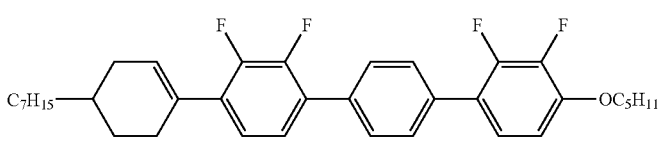 |
| 856 | 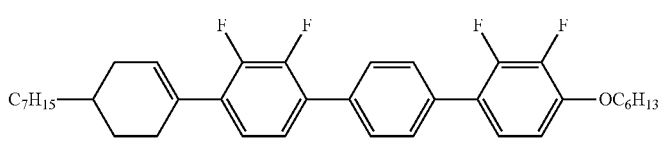 |
| 857 | 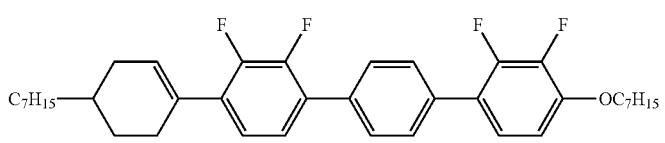 |
| 858 | 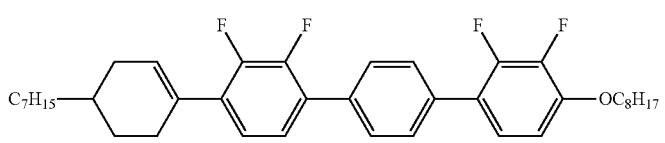 |
| 859 | 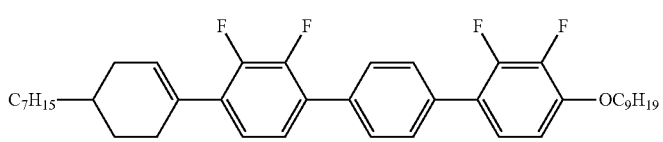 |
| 860 | 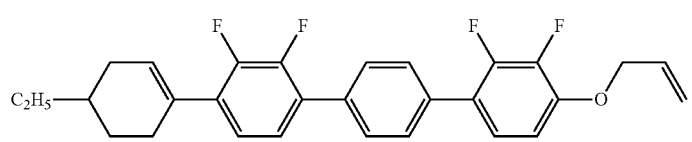 |
| 861 | 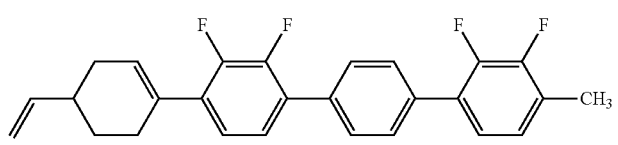 |
| 862 | 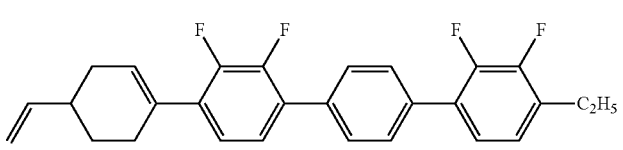 |
| 863 | 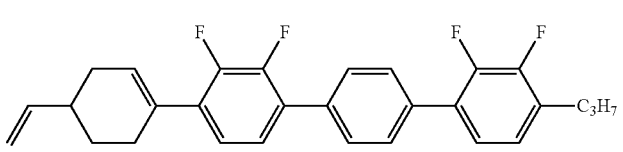 |

-continued
| No. | |
|---|---|
| 864 | 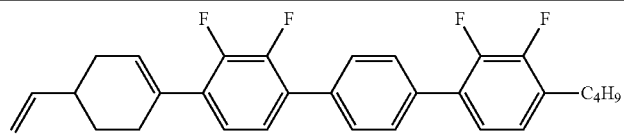 |
| 865 | 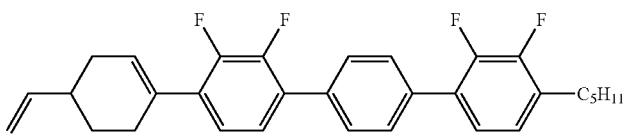 |
| 866 | 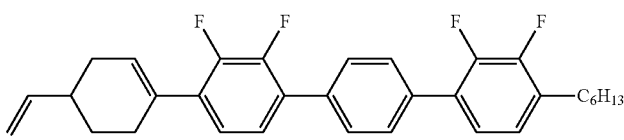 |
| 867 | 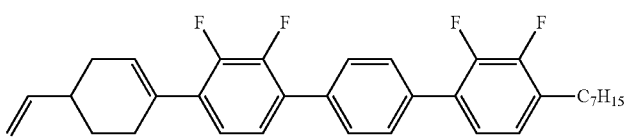 |
| 868 | 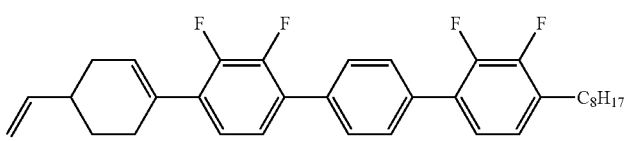 |
| 869 | 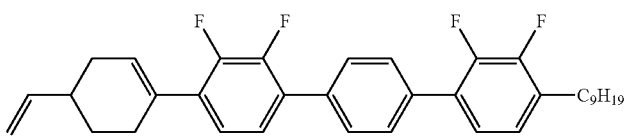 |
| 870 | 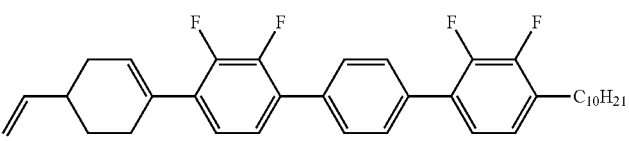 |
| 871 | 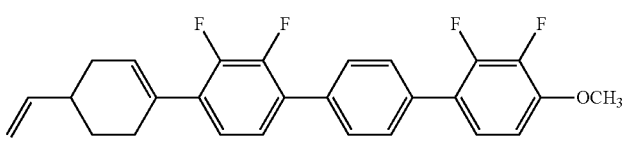 |
| 872 | 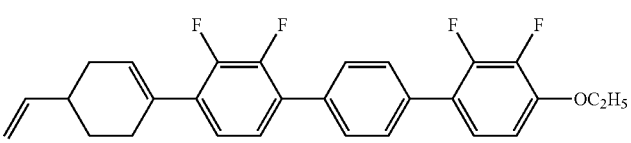 |
| 873 | 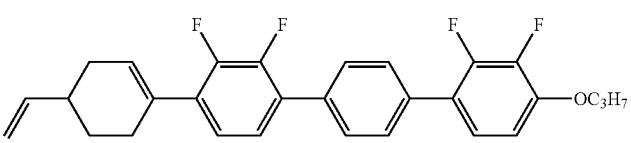 |
| 874 | 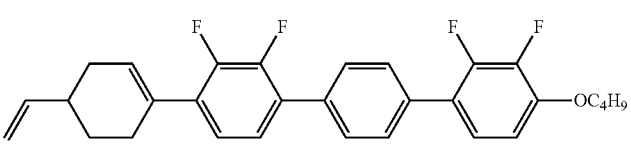 |

| No. | |
|---|---|
| 875 | 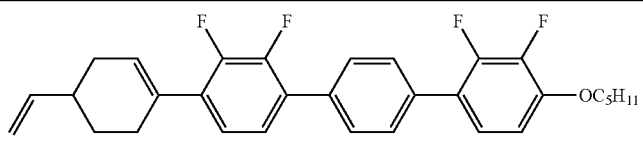 |
| 876 | 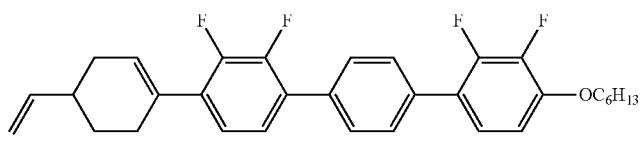 |
| 877 | 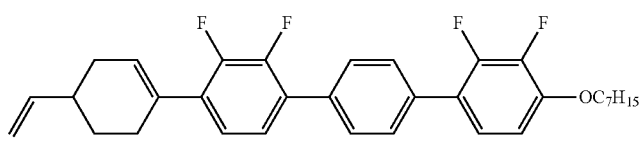 |
| 878 | 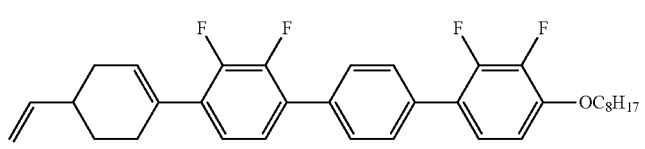 |
| 879 | 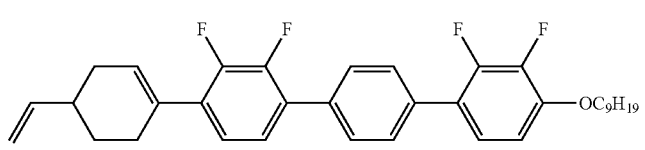 |
| 880 | 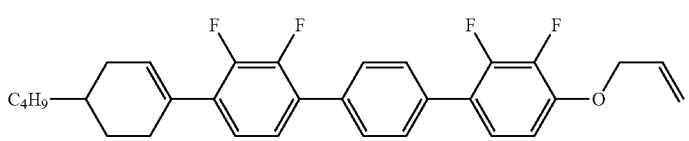 |
| 881 | 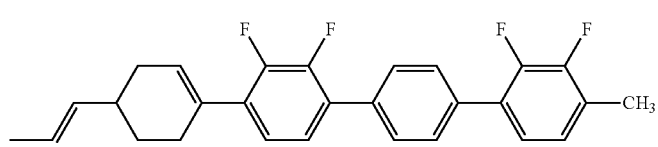 |
| 882 | 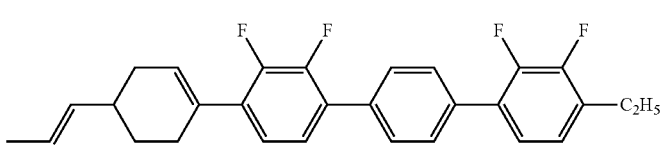 |
| 883 | 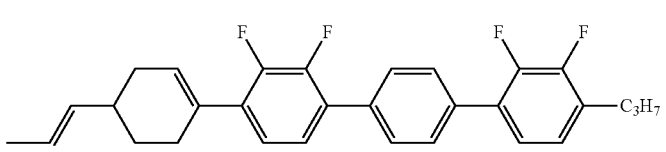 |
| 887 | 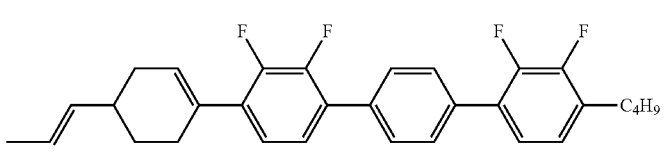 |
| 885 | 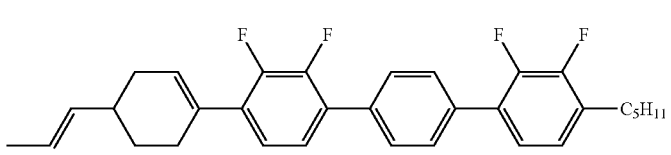 |

-continued
| No. | |
|---|---|
| 886 | 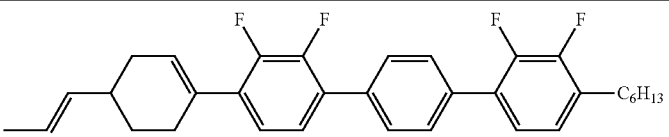 C6H13 |
| 887 | 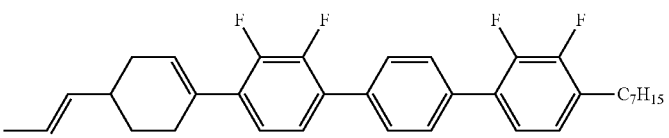 C7H15 |
| 888 | 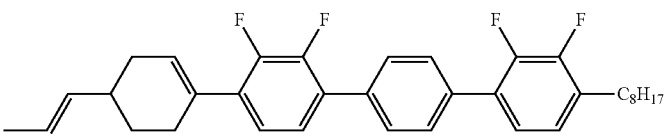 C8H17 |
| 889 | 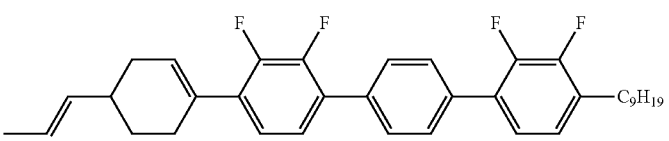 C9H19 |
| 890 | 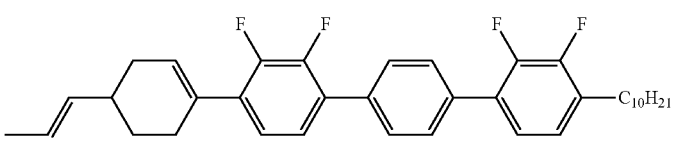 C10H21 |
| 891 | 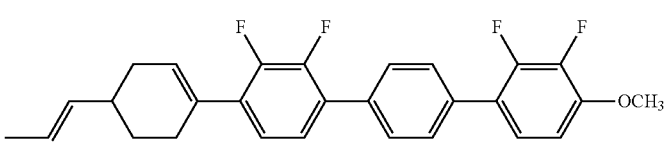 OCH3 |
| 892 | 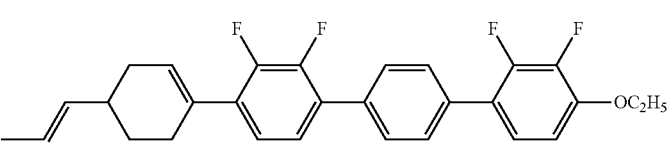 OC2H5 |
| 893 | 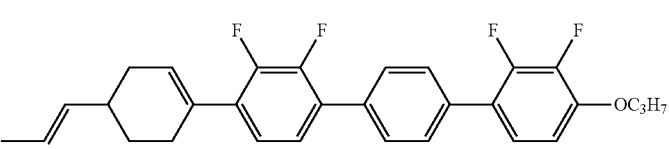 OC3H7 |
| 894 | 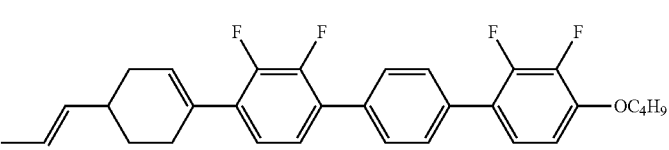 OC4H9 |
| 895 | 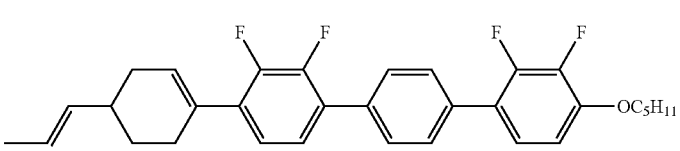 OC5H11 |
| 896 | 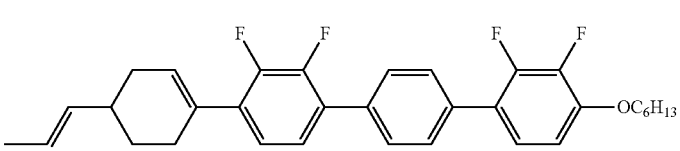 OC6H13 |

| No. | |
|---|---|
| 897 | 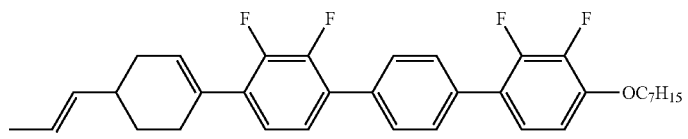 |
| 898 | 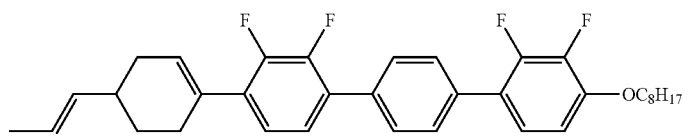 |
| 899 | 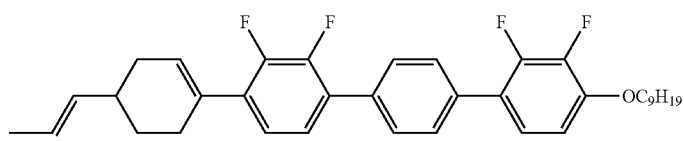 |
| 900 | 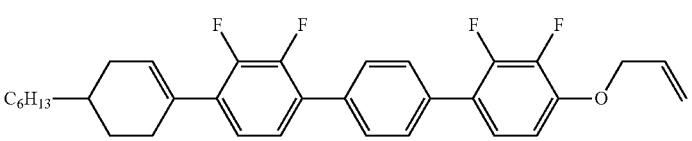 |
| 901 | 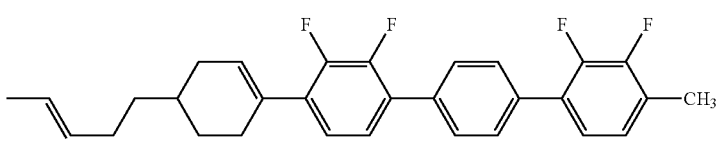 |
| 902 | 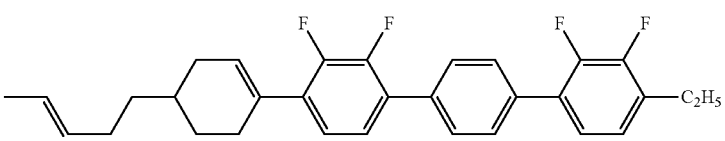 |
| 903 | 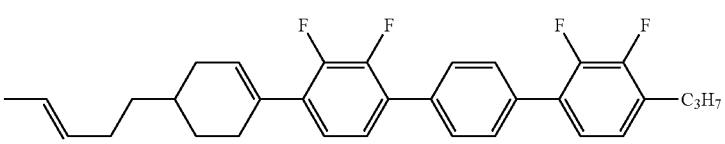 |
| 904 | 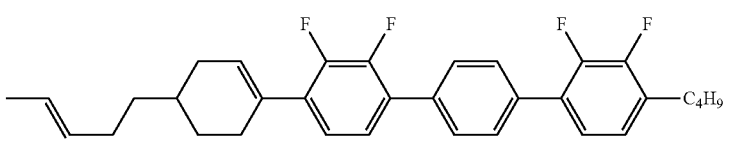 |
| 905 | 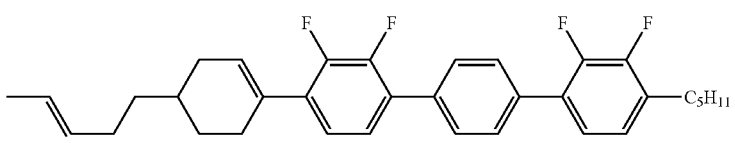 |
| 906 | 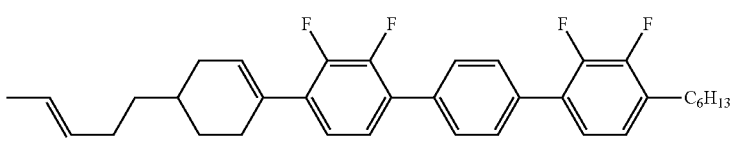 |
| 907 | 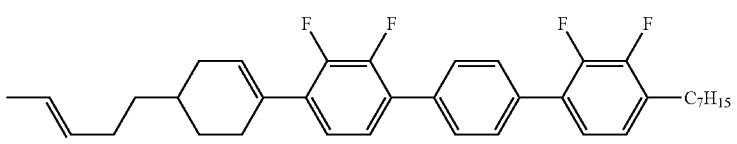 |

| No. |
|---|
| 908 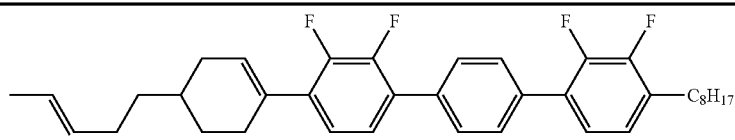 |
| 909 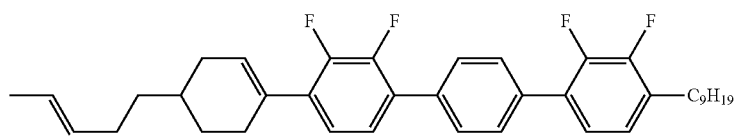 |
| 910 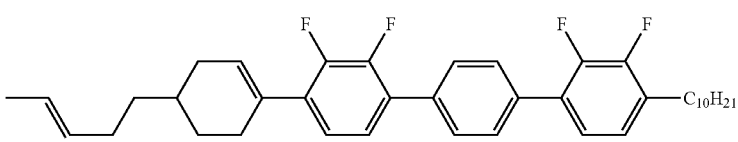 |
| 911 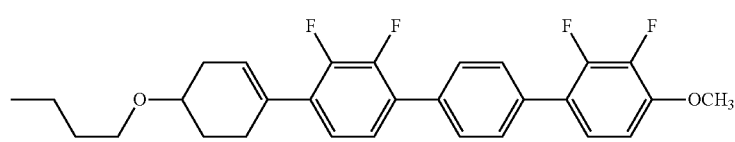 |
| 912 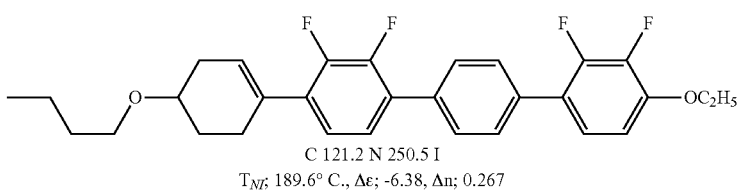 <br> C 121.2 N 250.5 I <br> $T_{NI}$; 189.6° C., Δε; -6.38, Δn; 0.267 |
| 913 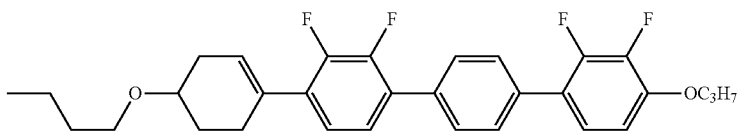 |
| 914  |
| 915 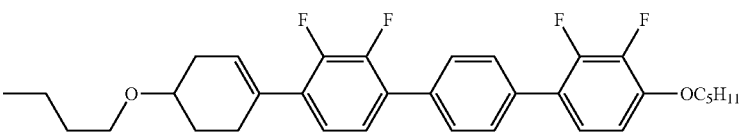 |
| 916 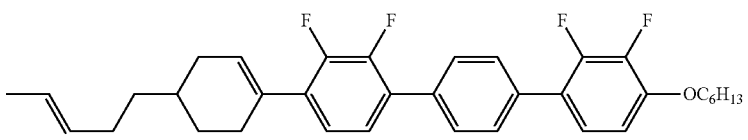 |
| 917 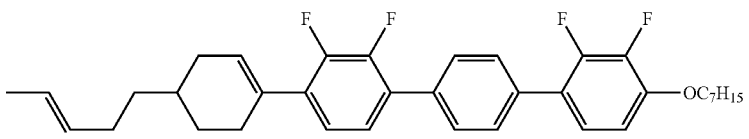 |
| 918 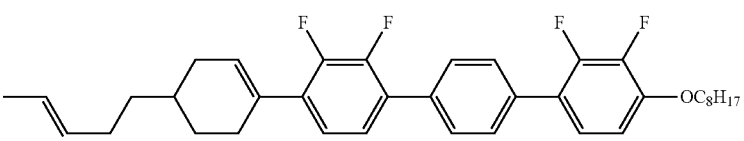 |

| No. | |
|---|---|
| 919 | 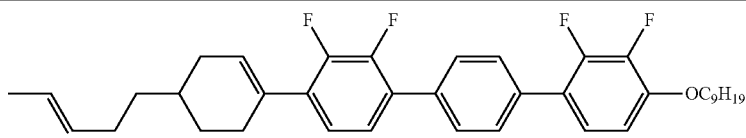 |
| 920 | 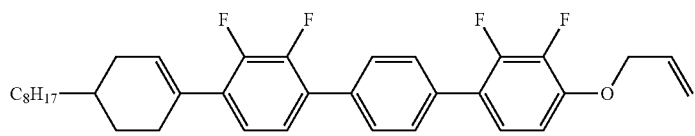 |
| 921 | 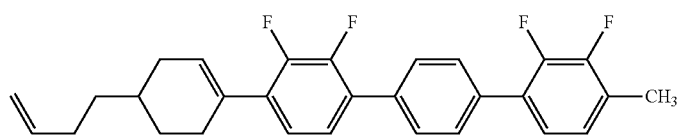 |
| 922 | 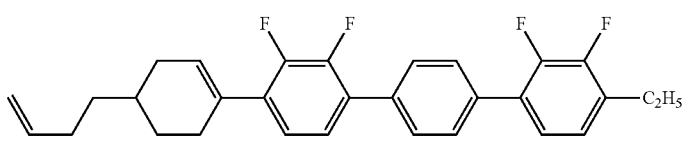 |
| 923 | 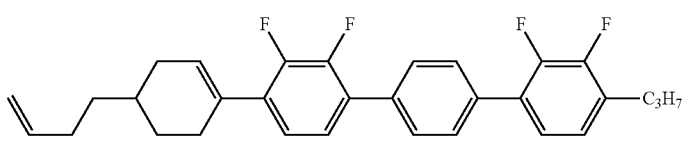 |
| 924 | 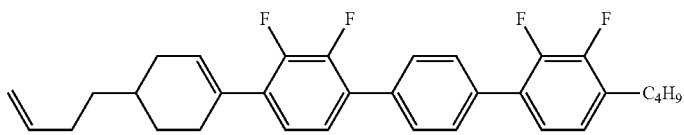 |
| 925 | 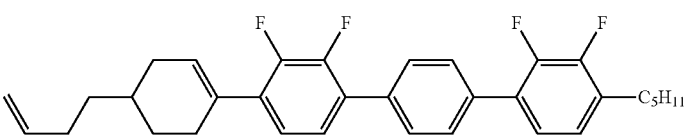 |
| 926 | 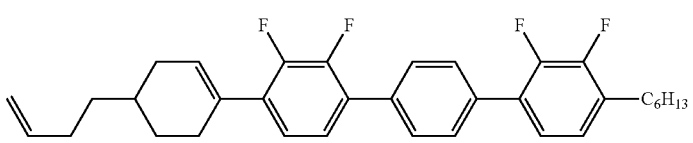 |
| 927 | 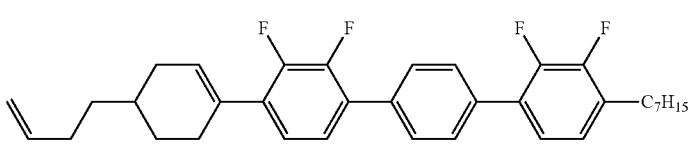 |
| 928 | 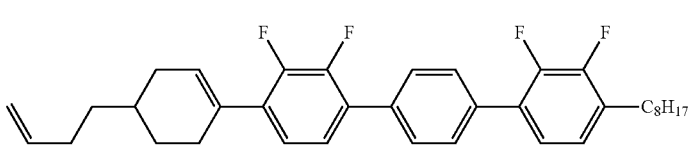 |
| 929 | 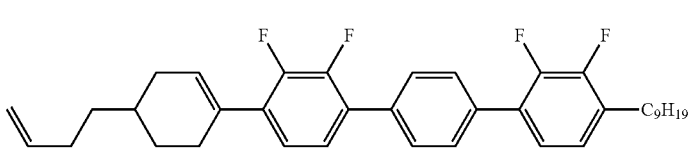 |

| No. | |
|---|---|
| 930 | 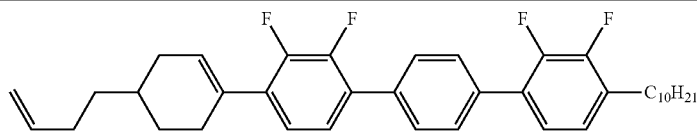 |
| 931 | 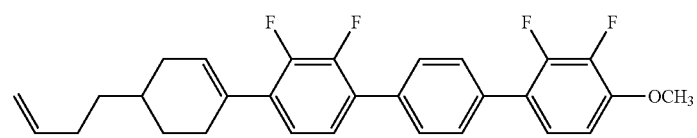 |
| 932 | 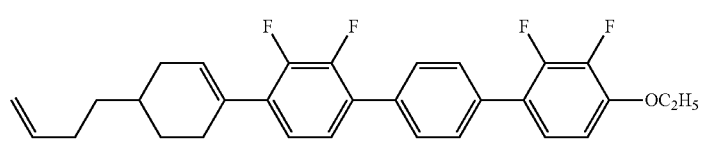 |
| 933 | 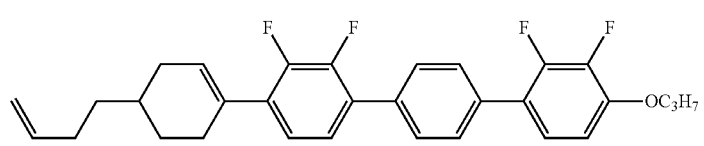 |
| 934 | 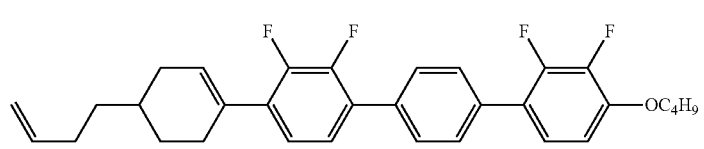 |
| 935 | 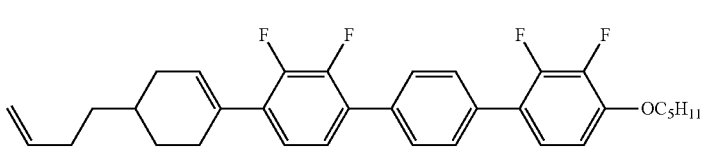 |
| 936 | 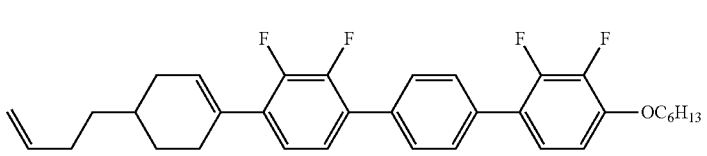 |
| 937 | 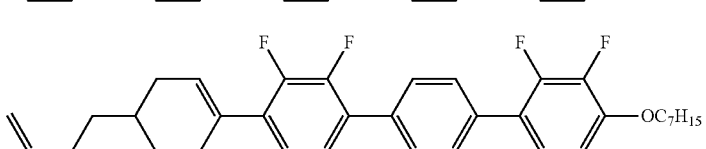 |
| 938 | 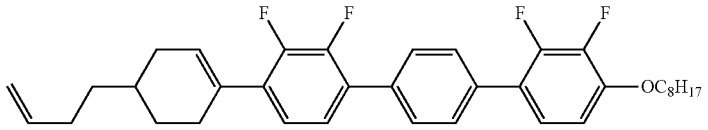 |
| 939 | 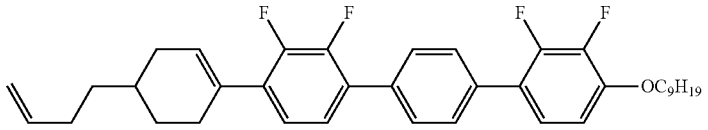 |
| 940 | 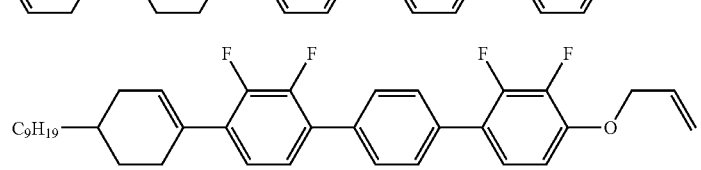 |

| No. | |
|---|---|
| 941 | 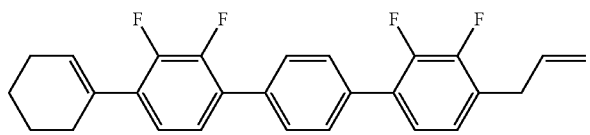 |
| 942 | 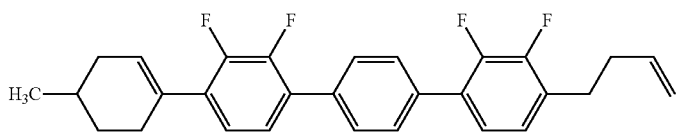 |
| 943 | 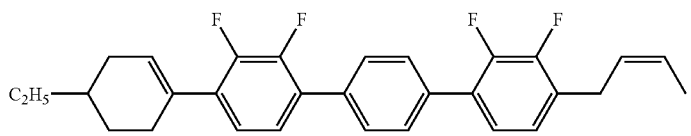 |
| 944 | 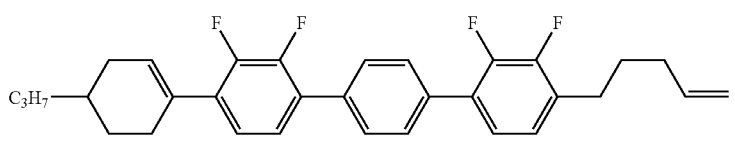 |
| 945 | 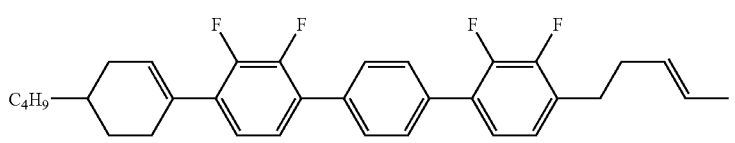 |
| 946 | 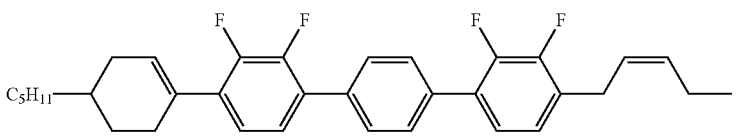 |
| 947 | 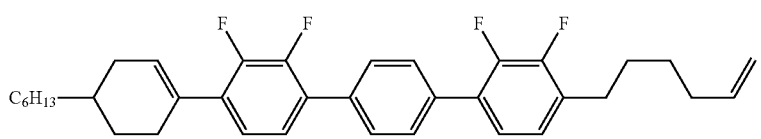 |
| 948 | 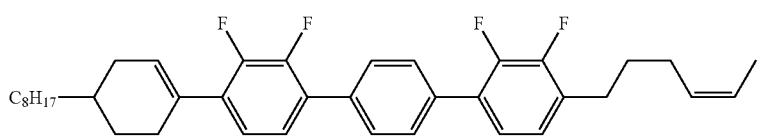 |
| 949 | 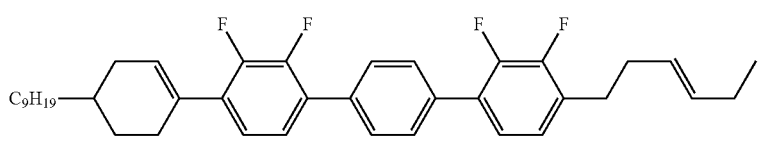 |
| 950 | 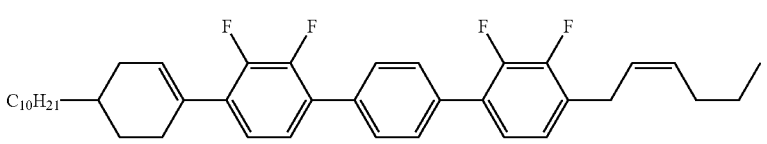 |
| 951 | 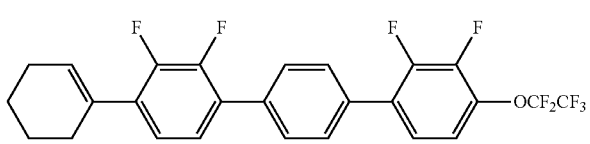 |

| No. | |
|---|---|
| 952 | 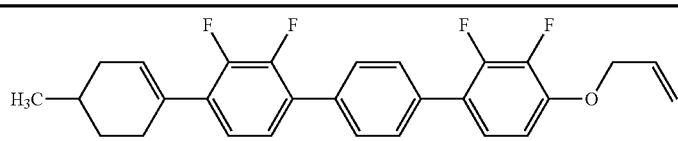 |
| 953 | 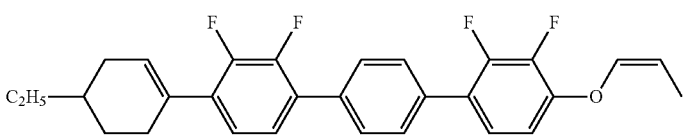 |
| 954 | 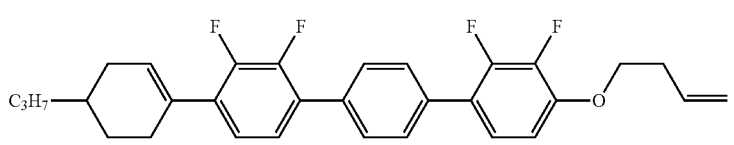 |
| 955 | 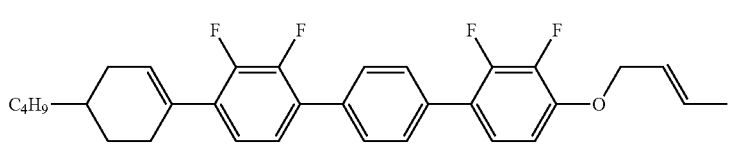 |
| 956 | 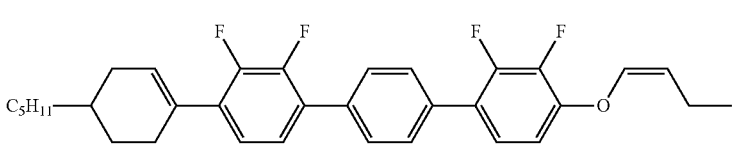 |
| 957 | 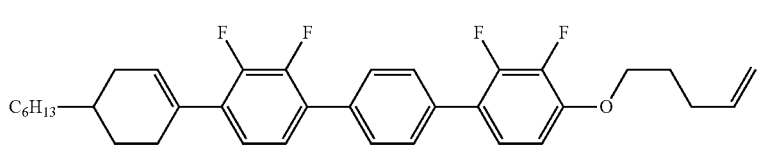 |
| 958 | 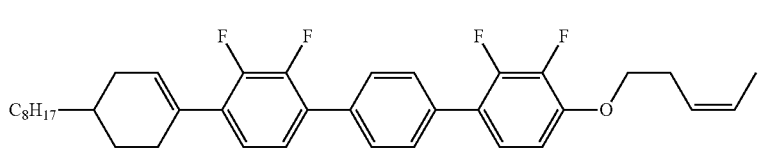 |
| 959 | 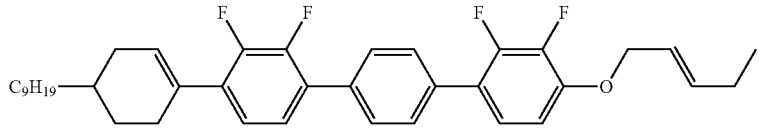 |
| 960 | 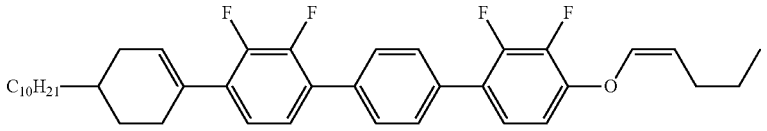 |
| 961 | 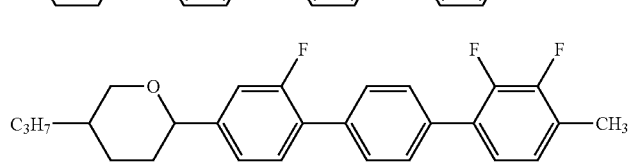 |
| 962 | 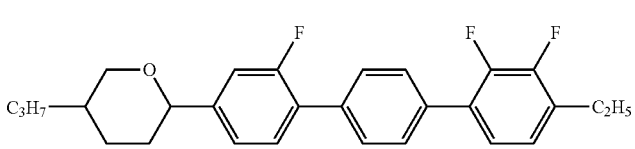 |

| No. | |
|---|---|
| 963 | 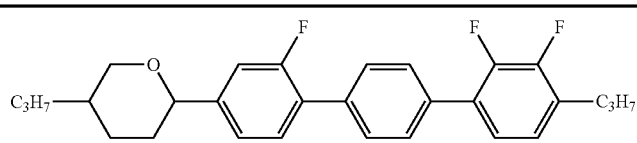 |
| 964 | 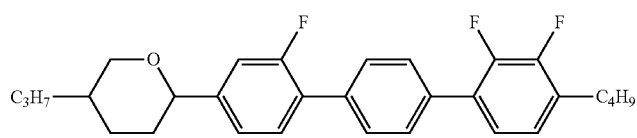 |
| 965 | 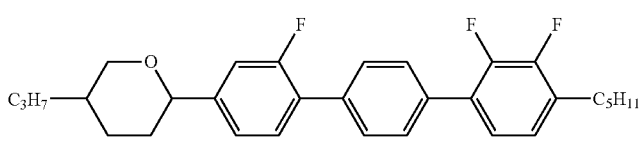 |
| 966 | 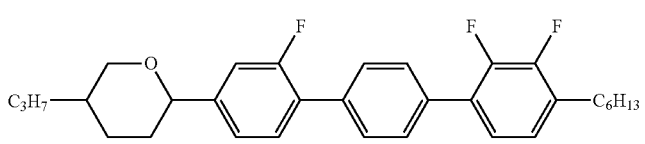 |
| 967 | 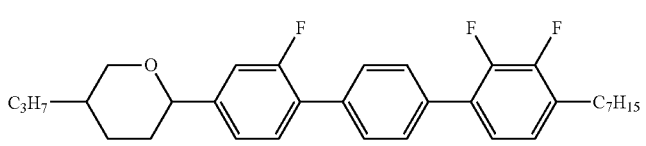 |
| 968 | 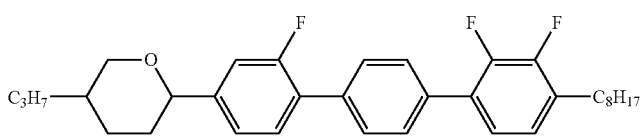 |
| 969 | 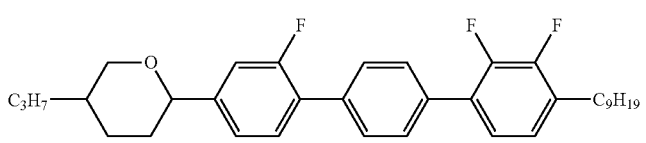 |
| 970 | 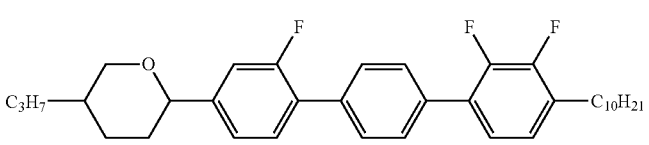 |
| 971 | 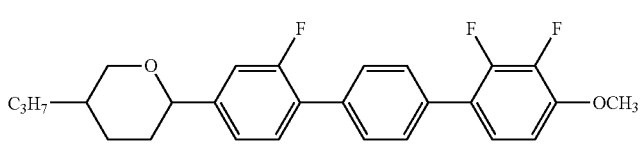 |
| 972 | 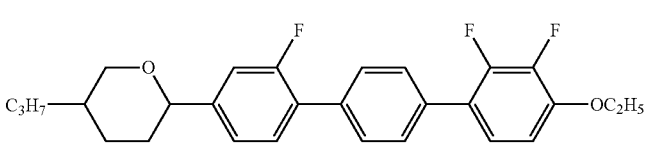 |
| 973 | 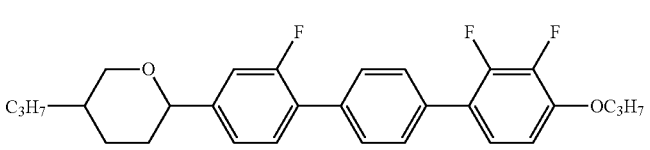 |

-continued
| No. |
|---|
| 974 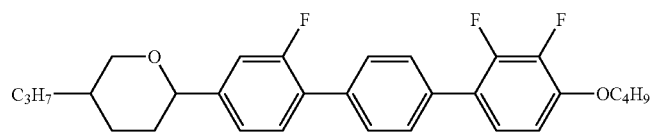 |
| 975 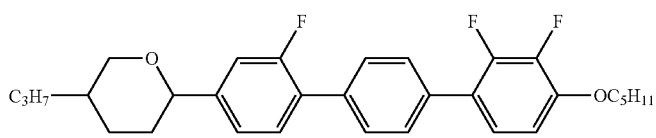 |
| 976 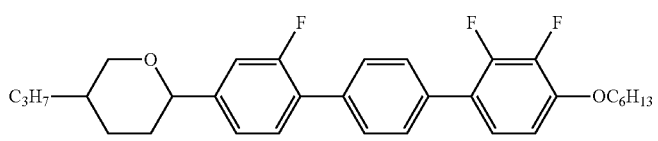 |
| 977 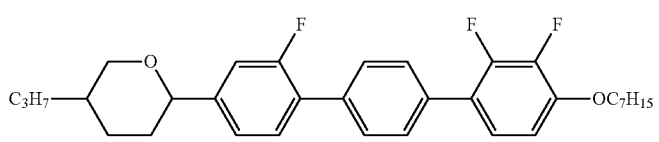 |
| 978 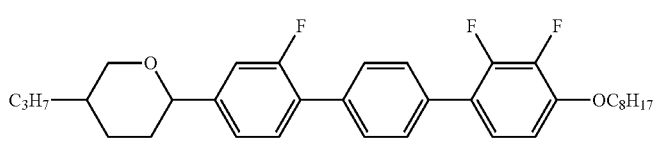 |
| 979 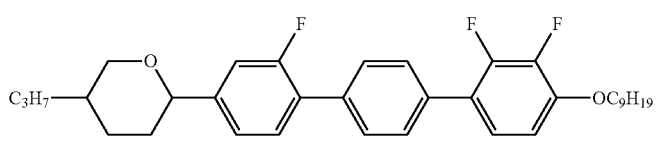 |
| 980 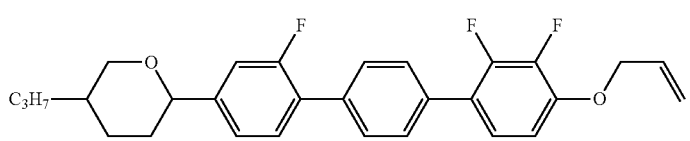 |
| 981 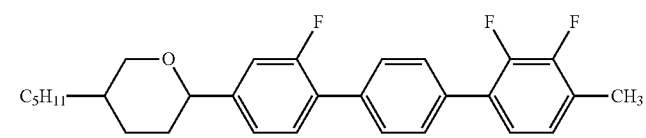 |
| 982 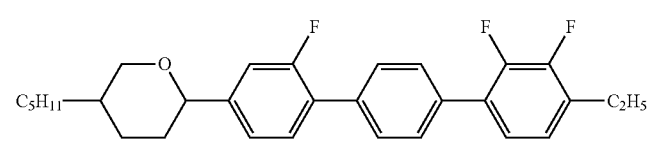 |
| 983 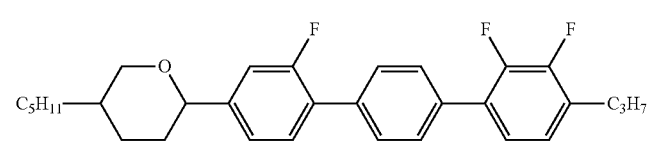 |
| 984 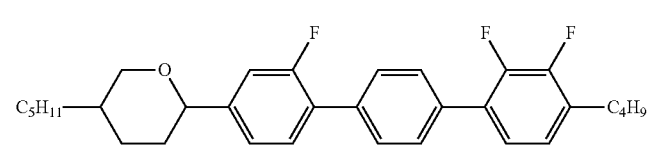 |

-continued
| No. | |
|---|---|
| 985 | 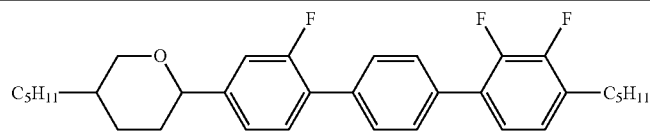 |
| 986 | 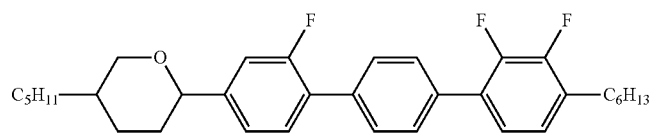 |
| 987 | 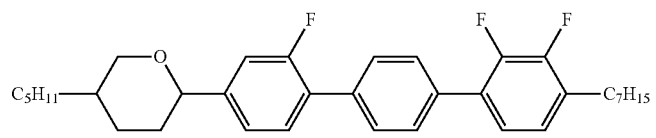 |
| 988 | 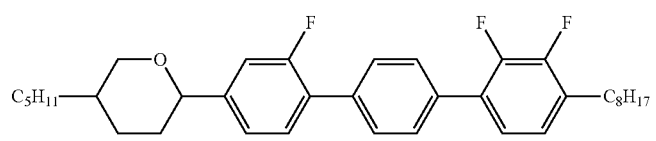 |
| 989 | 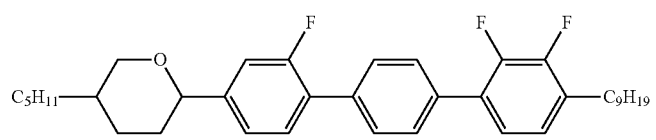 |
| 990 | 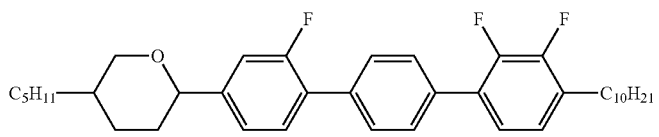 |
| 991 | 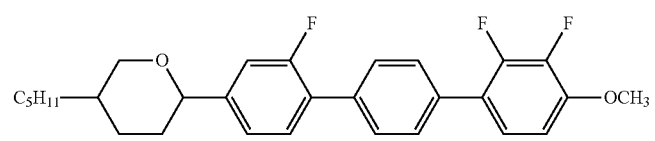 |
| 992 | 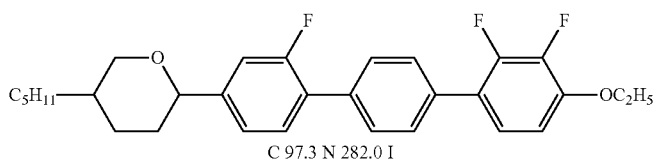 C 97.3 N 282.0 I  $T_{NI}$; 232.6° C., Δε ; -4.62, Δn; 0.247 |
| 993 | 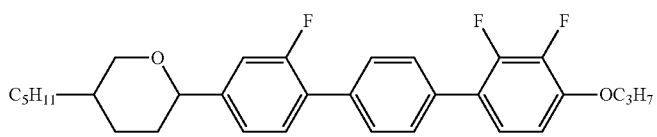 |
| 994 | 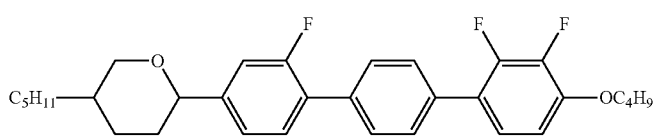 |
| 995 | 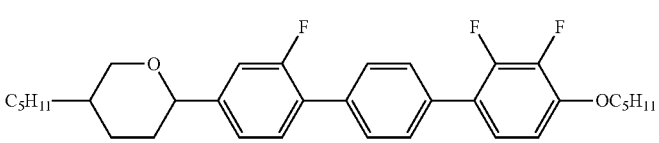 |

| No. | |
|---|---|
| 996 | 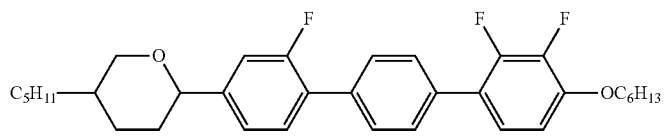 |
| 997 | 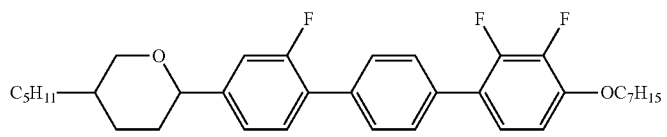 |
| 998 | 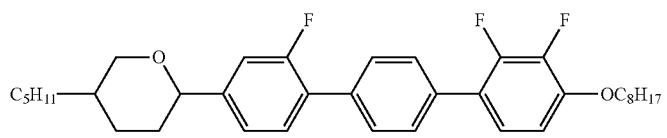 |
| 999 |  |
| 1000 | 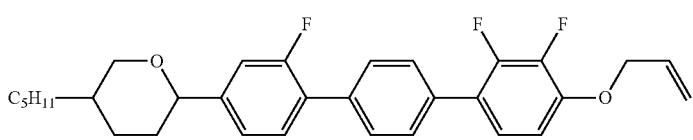 |
| 1001 | 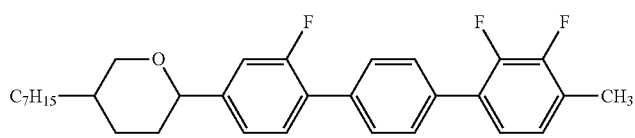 |
| 1002 |  |
| 1003 | 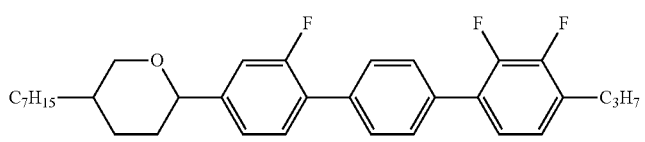 |
| 1004 | 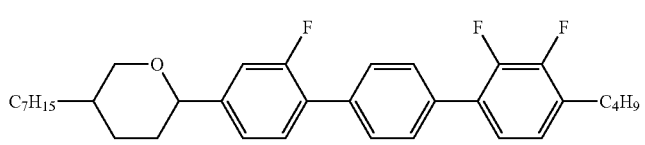 |
| 1005 | 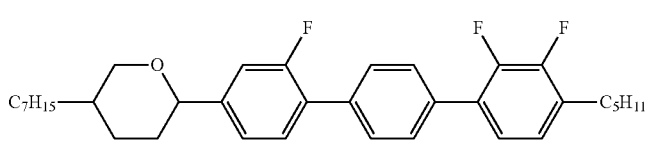 |
| 1006 | 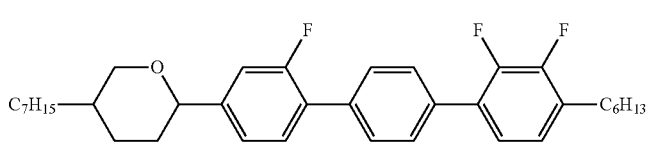 |

| No. | |
|---|---|
| 1007 | 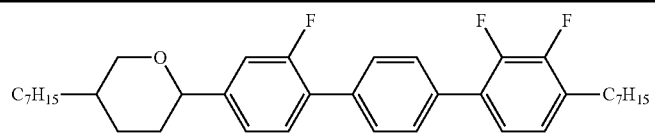 |
| 1008 | 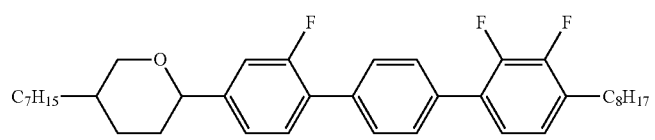 |
| 1009 | 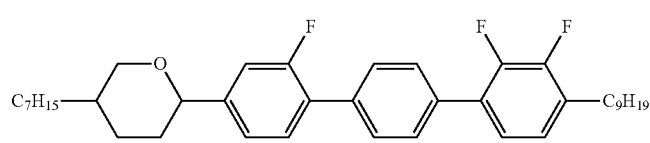 |
| 1010 | 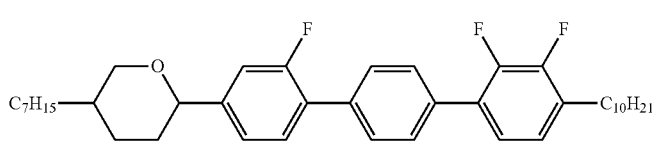 |
| 1011 | 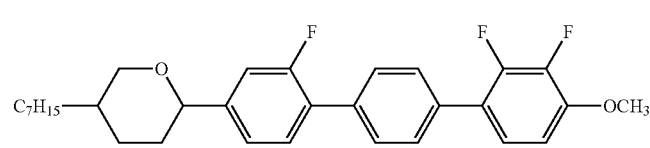 |
| 1012 | 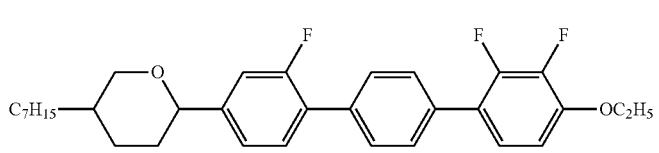 |
| 1013 | 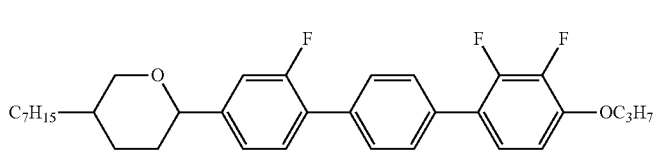 |
| 1014 | 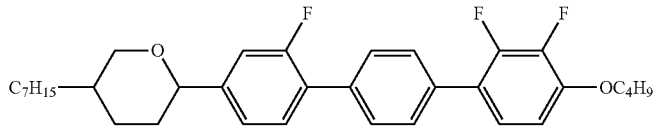 |
| 1015 | 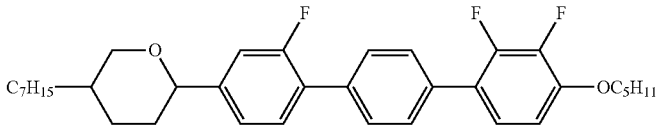 |
| 1016 |  |
| 1017 | 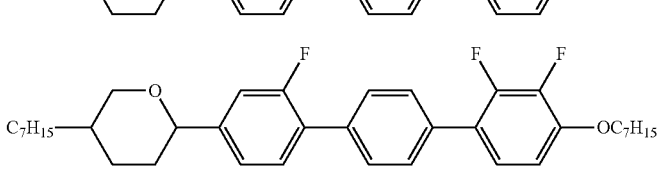 |

| No. | |
|---|---|
| 1018 | 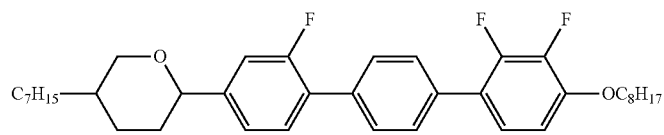 |
| 1019 | 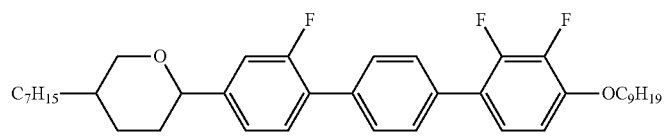 |
| 1020 | 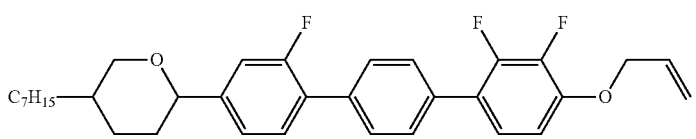 |
| 1021 | 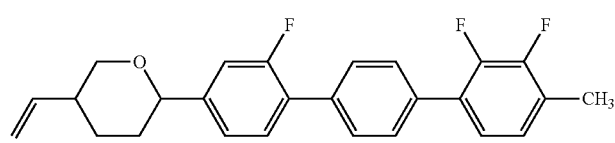 |
| 1022 | 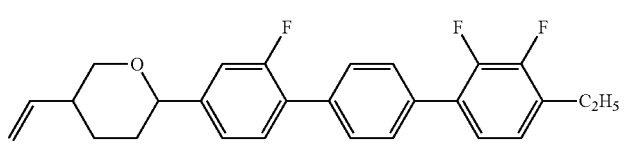 |
| 1023 | 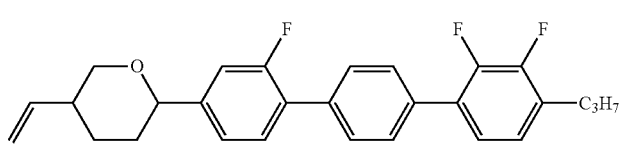 |
| 1024 | 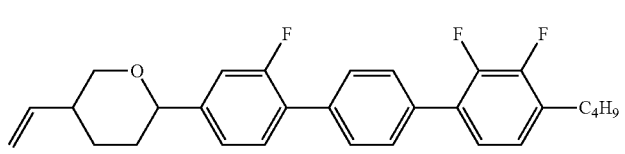 |
| 1025 | 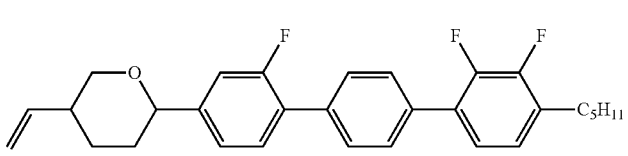 |
| 1026 | 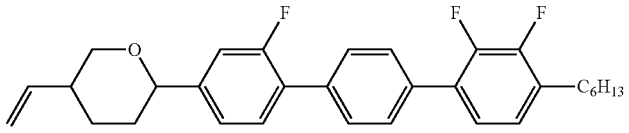 |
| 1027 | 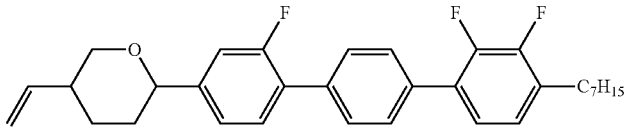 |
| 1028 | 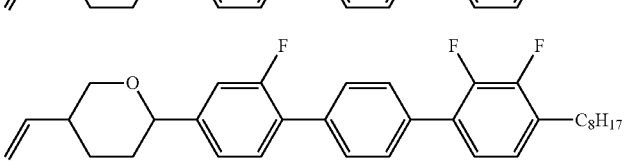 |

| No. | |
|---|---|
| 1029 | 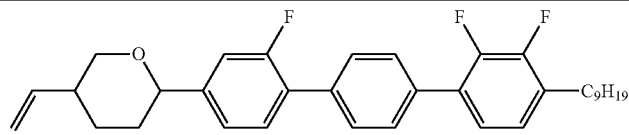 |
| 1030 | 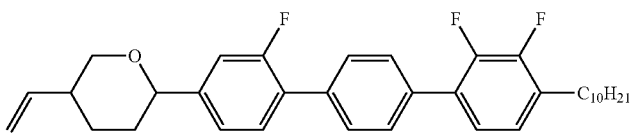 |
| 1031 | 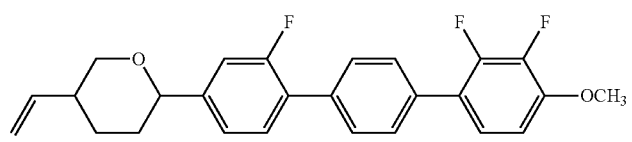 |
| 1032 | 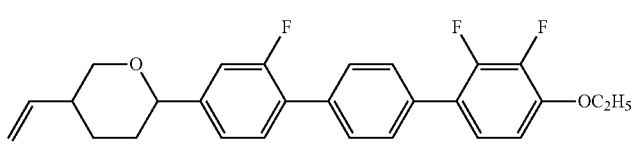 |
| 1033 | 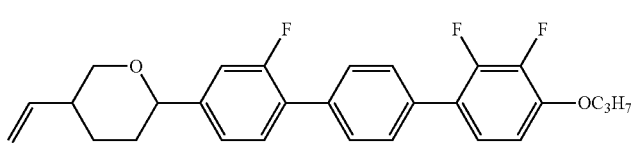 |
| 1034 | 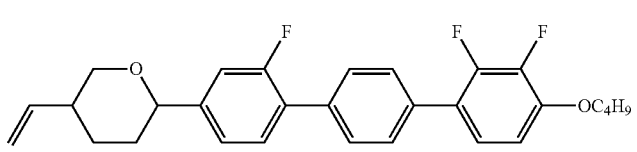 |
| 1035 | 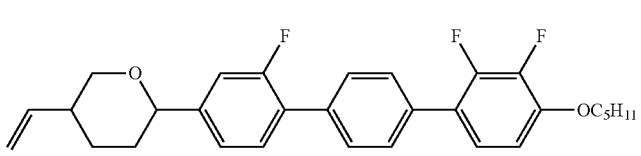 |
| 1036 | 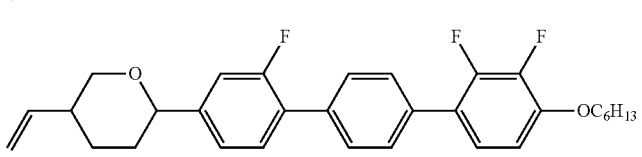 |
| 1037 | 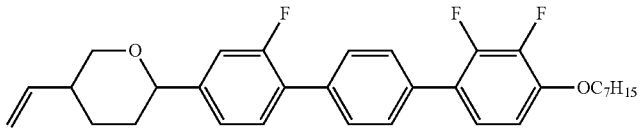 |
| 1038 | 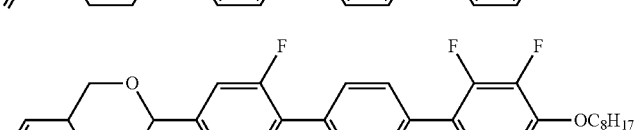 |
| 1039 | 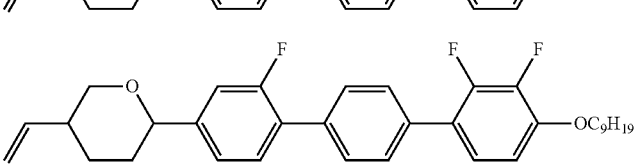 |

| No. |
|---|
| 1040 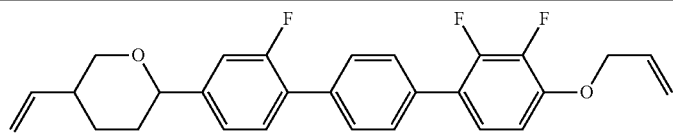 |
| 1041 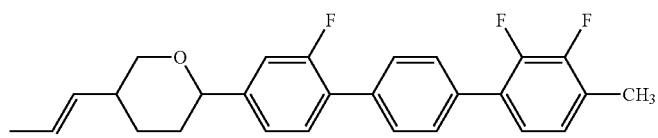 |
| 1042 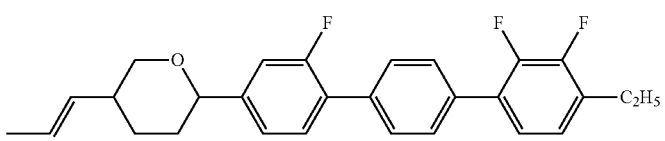 |
| 1043 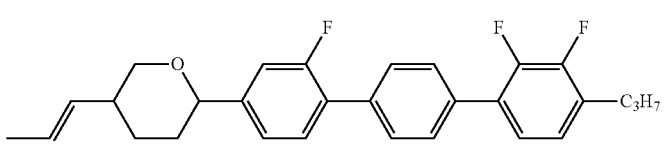 |
| 1044 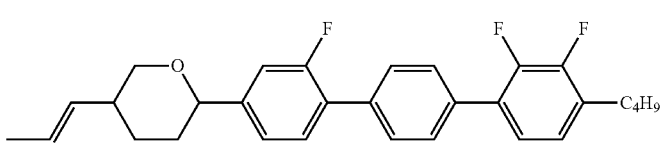 |
| 1045 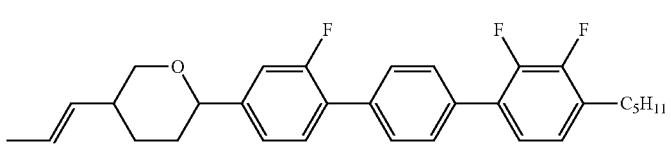 |
| 1046 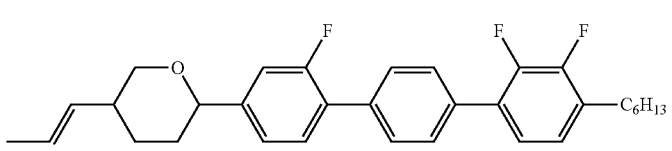 |
| 1047 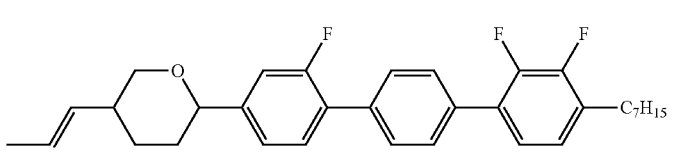 |
| 1048 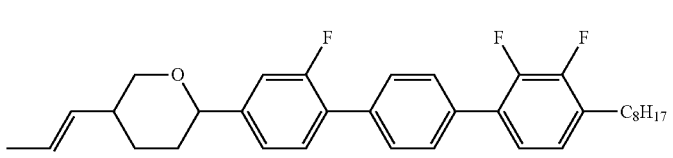 |
| 1049 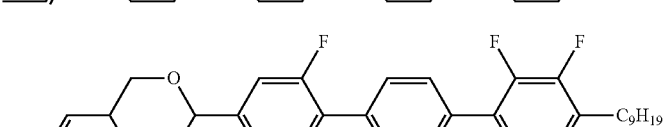 |
| 1050 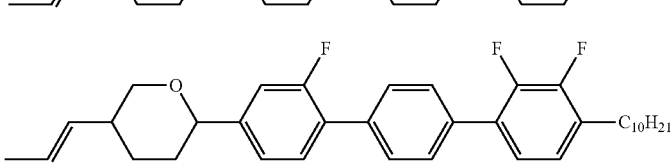 |

| No. | |
|---|---|
| 1051 | 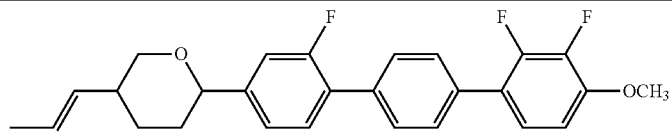 |
| 1052 | 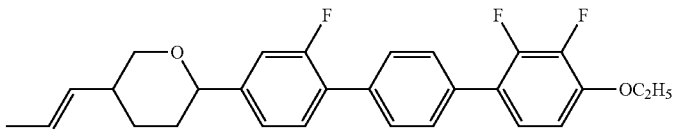 |
| 1053 | 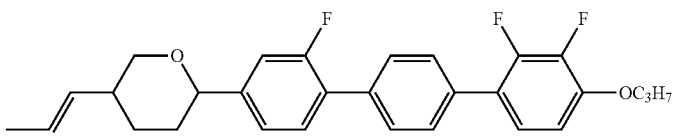 |
| 1054 | 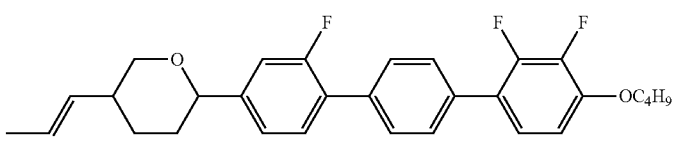 |
| 1055 | 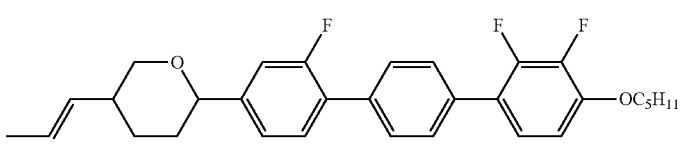 |
| 1056 | 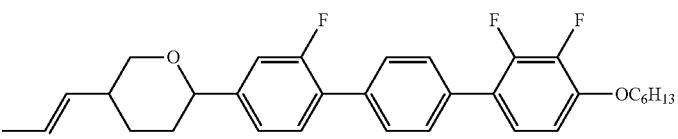 |
| 1057 | 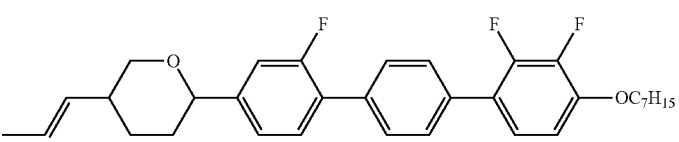 |
| 1058 | 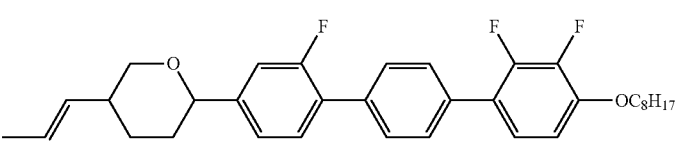 |
| 1059 | 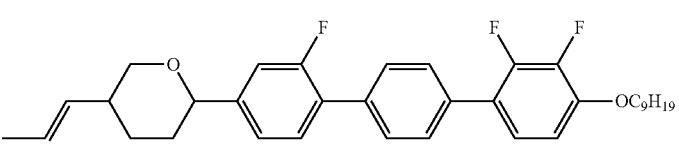 |
| 1060 | 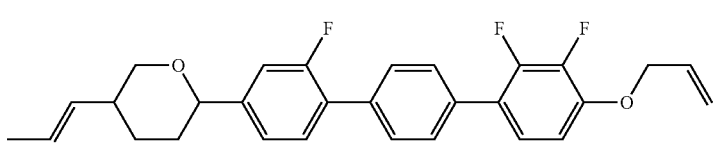 |
| 1061 | 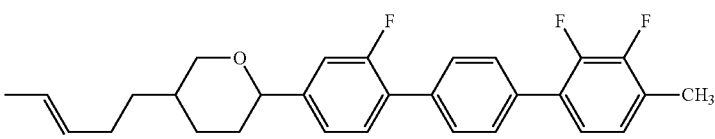 |

-continued
| No. | |
|---|---|
| 1062 | 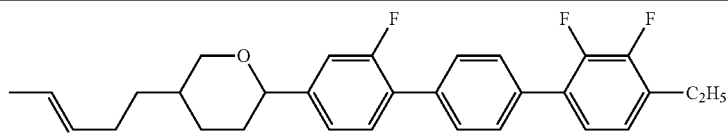 |
| 1063 | 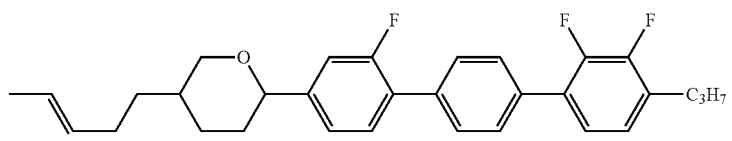 |
| 1064 | 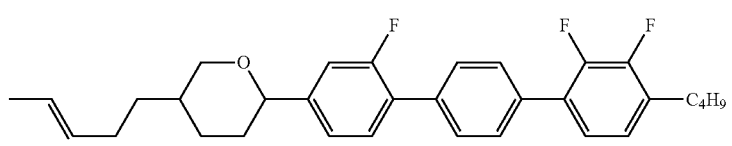 |
| 1065 | 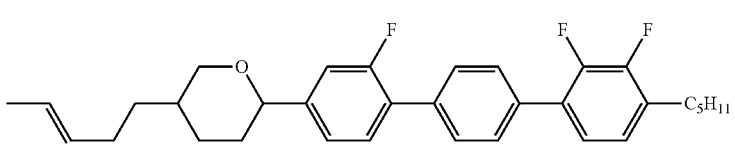 |
| 1066 | 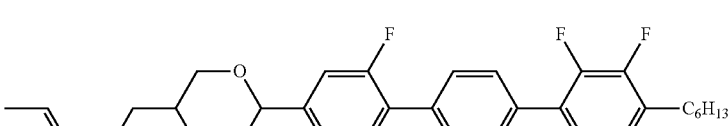 |
| 1067 | 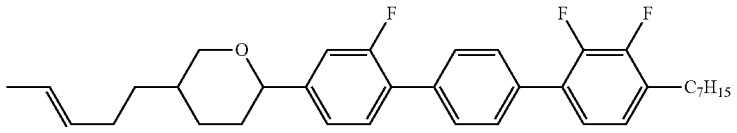 |
| 1068 | 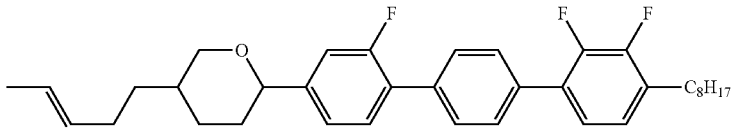 |
| 1069 | 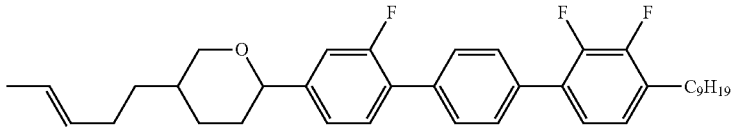 |
| 1070 |  |
| 1071 |  |
| 1072 | 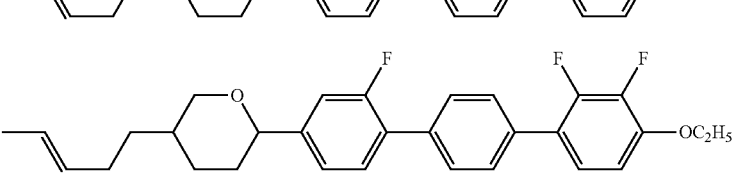 |

| No. |
|---|
| 1073 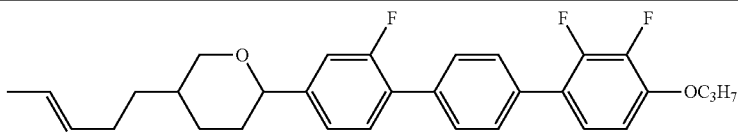 |
| 1074 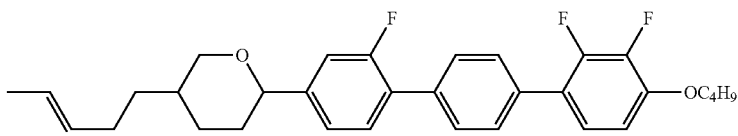 |
| 1075 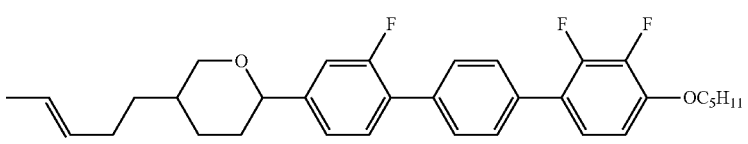 |
| 1076 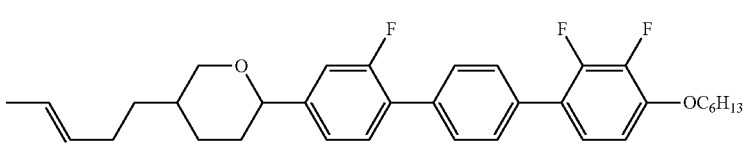 |
| 1077 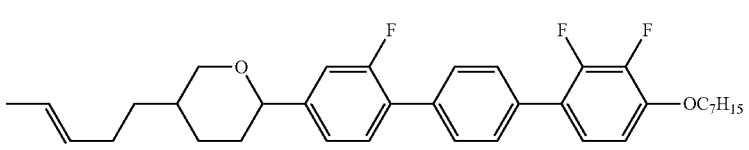 |
| 1078 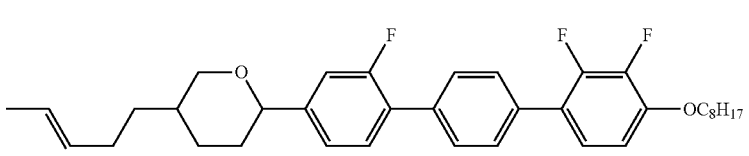 |
| 1079 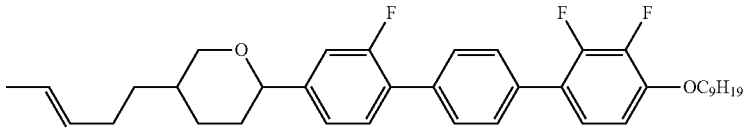 |
| 1080 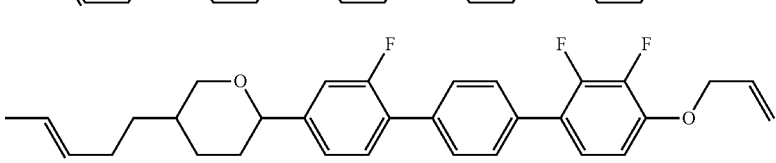 |
| 1081 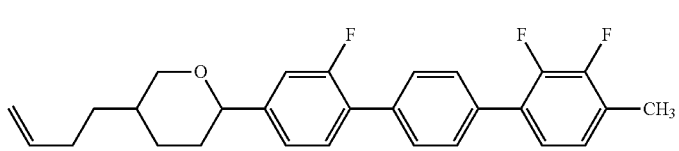 |
| 1082 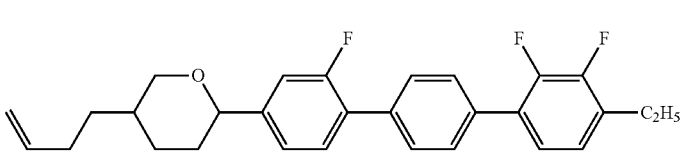 |
| 1083 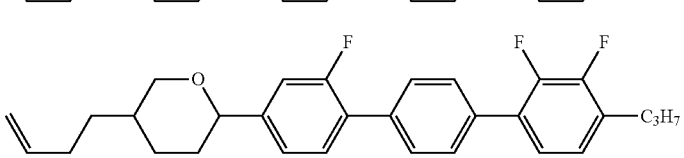 |

| No. |
|---|
| 1084 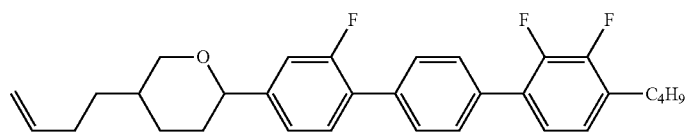 |
| 1085 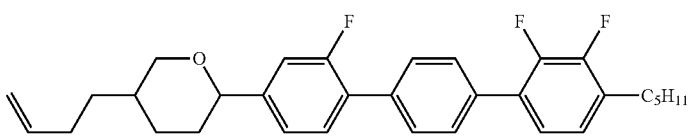 |
| 1086 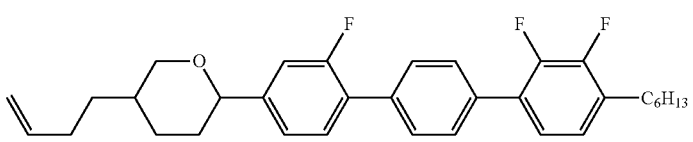 |
| 1087 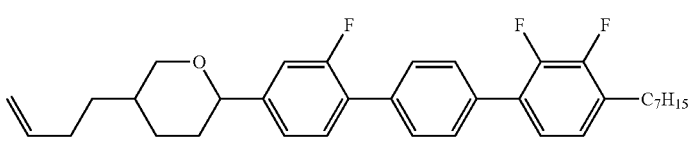 |
| 1088 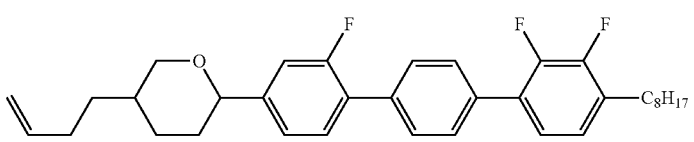 |
| 1089 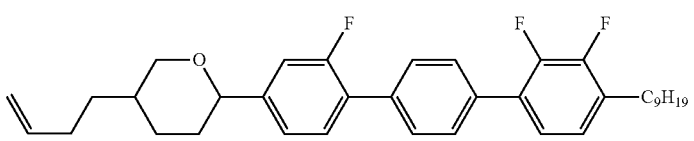 |
| 1090 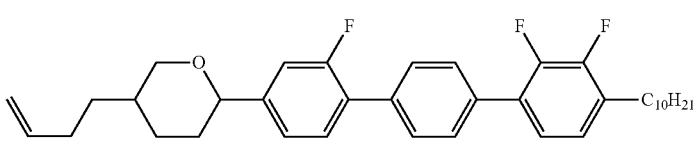 |
| 1091 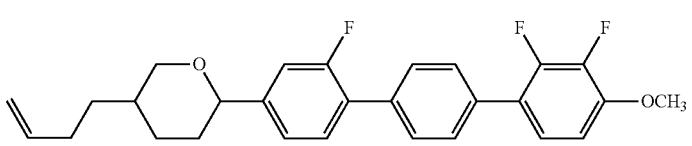 |
| 1092  |
| 1093 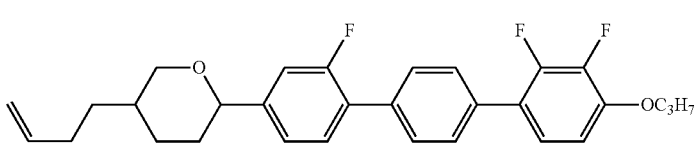 |
| 1094 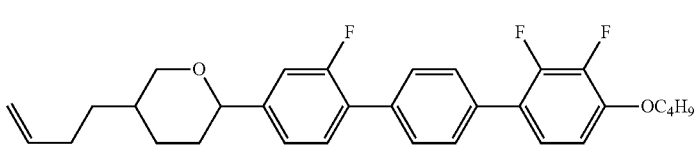 |

| No. | |
|---|---|
| 1095 | 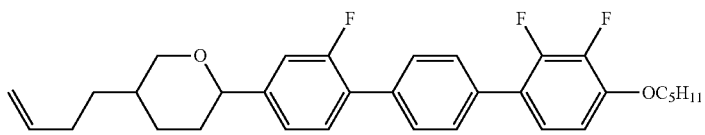 |
| 1096 | 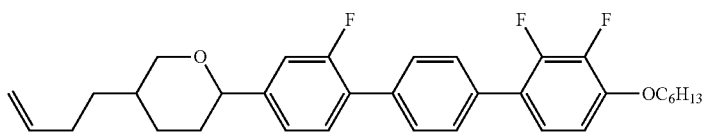 |
| 1097 | 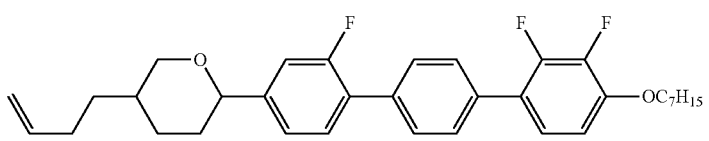 |
| 1098 | 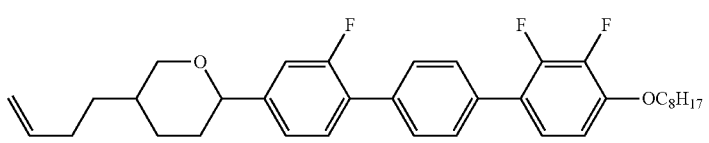 |
| 1099 | 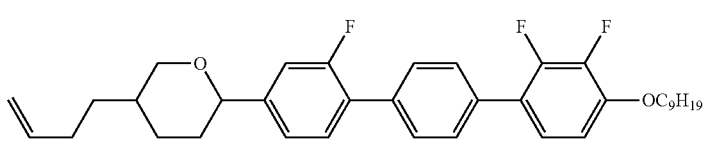 |
| 1100 | 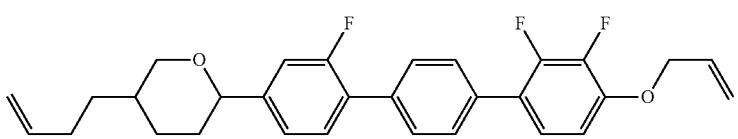 |
| 1101 | 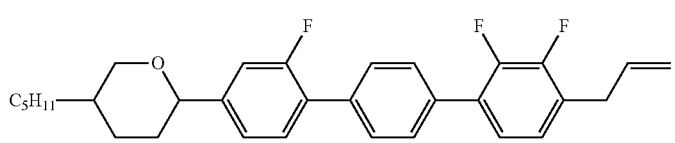 |
| 1102 | 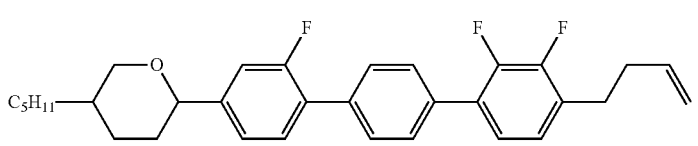 |
| 1103 | 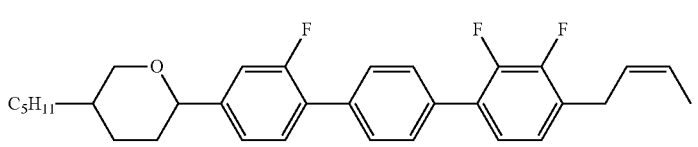 |
| 1104 | 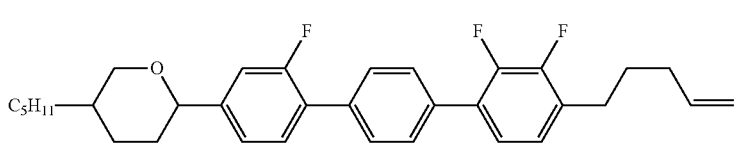 |
| 1105 | 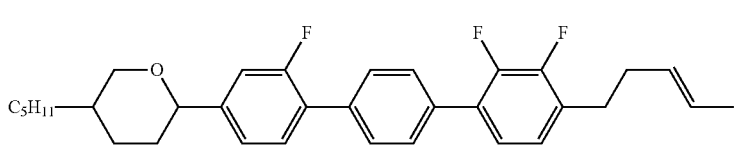 |

| No. | |
|---|---|
| 1106 | 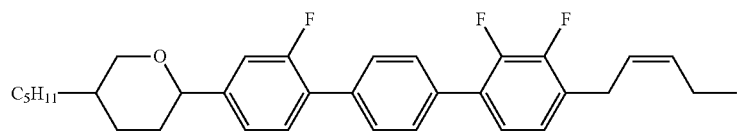 |
| 1107 | 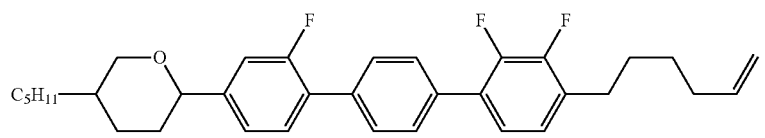 |
| 1108 | 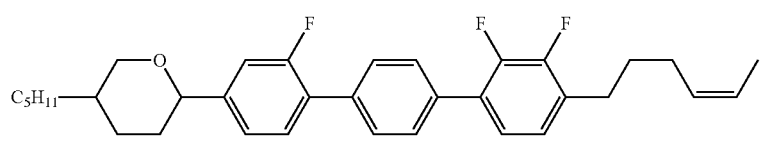 |
| 1109 | 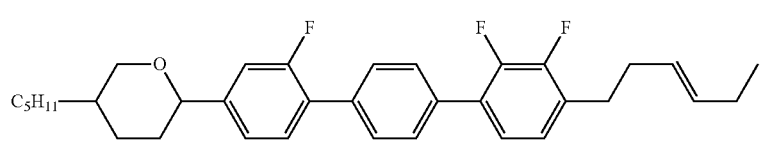 |
| 1110 | 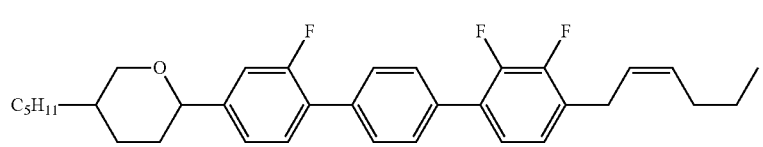 |
| 1111 | 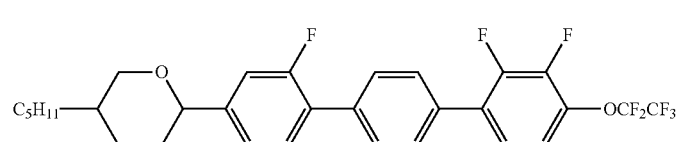 |
| 1112 | 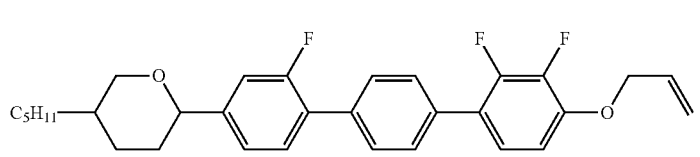 |
| 1113 | 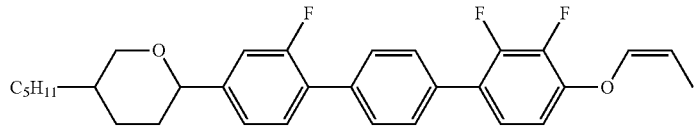 |
| 1114 | 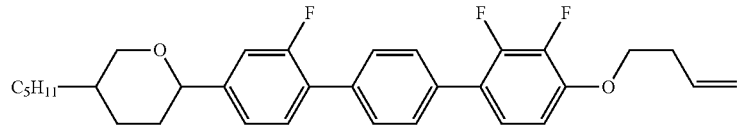 |
| 1115 |  |
| 1116 | 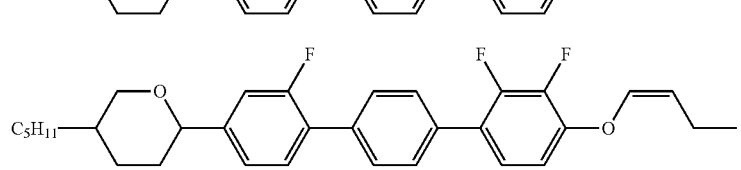 |

| No. | |
|---|---|
| 1117 | 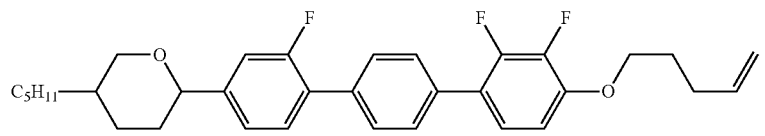 |
| 1118 | 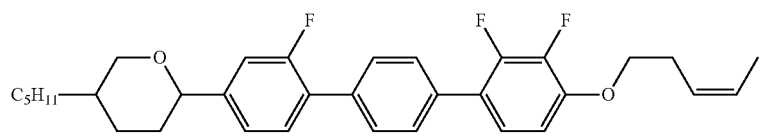 |
| 1119 | 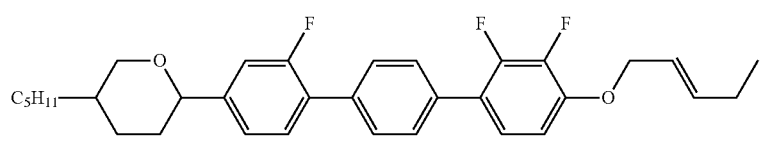 |
| 1120 | 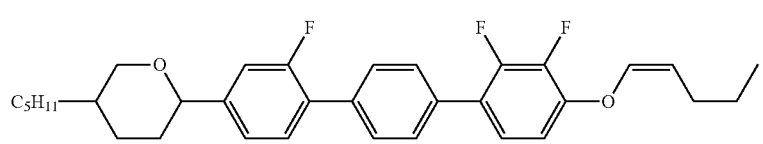 |
| 1121 | 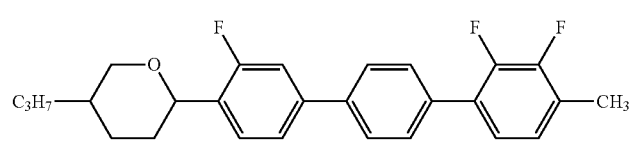 |
| 1122 | 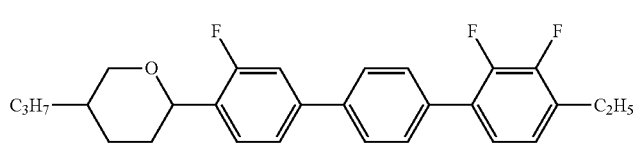 |
| 1123 | 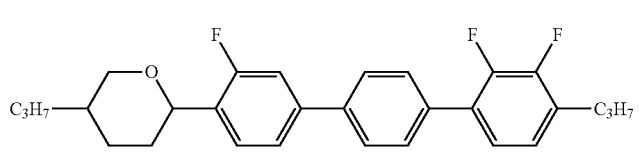 |
| 1124 | 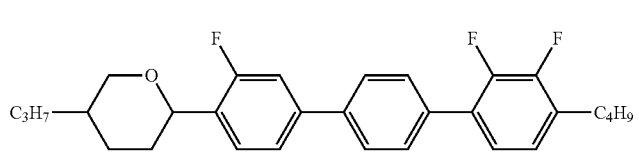 |
| 1125 | 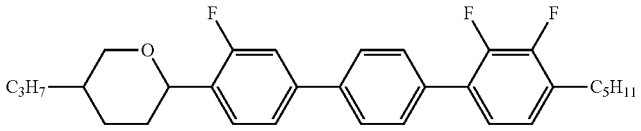 |
| 1126 |  |
| 1127 | 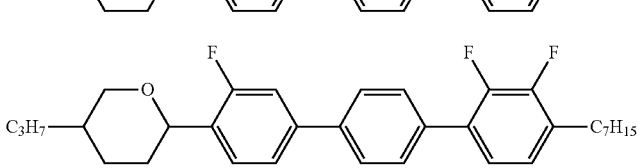 |

| No. | |
|---|---|
| 1128 | 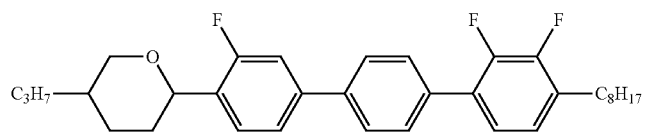 |
| 1129 | 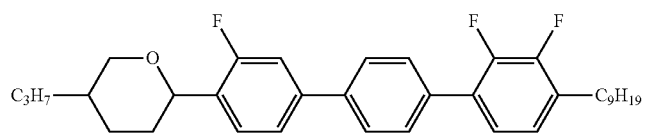 |
| 1130 | 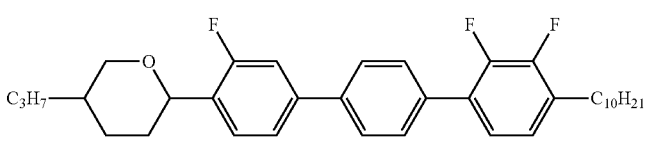 |
| 1131 | 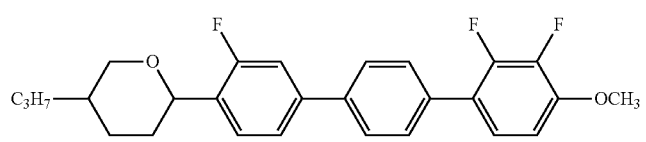 |
| 1132 | 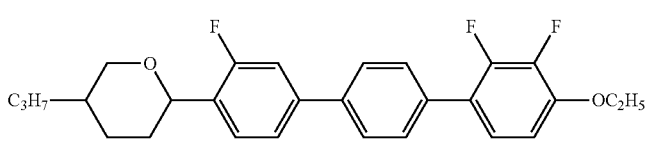 |
| 1133 | 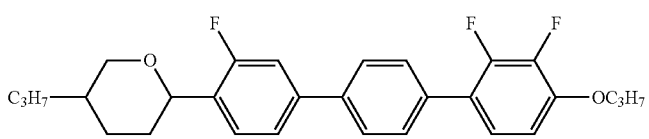 |
| 1134 | 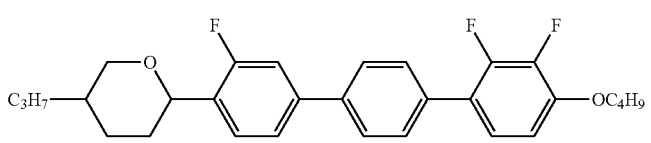 |
| 1135 | 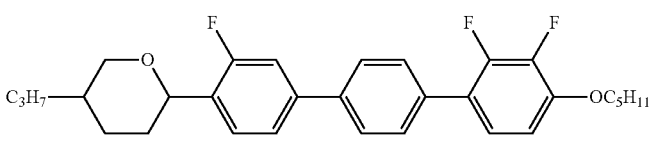 |
| 1136 | 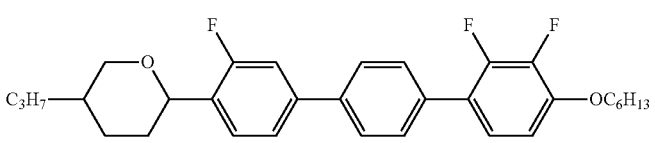 |
| 1137 | 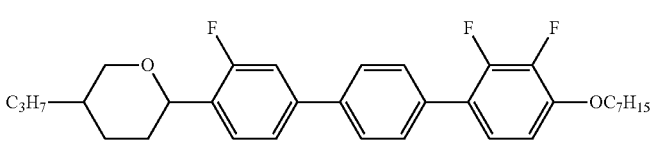 |
| 1138 | 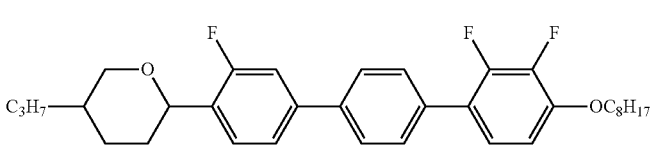 |

| No. | |
|---|---|
| 1139 | 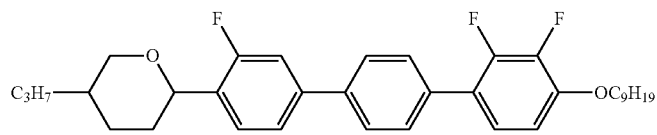 |
| 1140 | 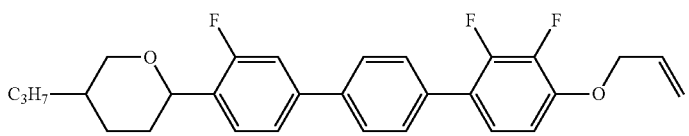 |
| 1141 | 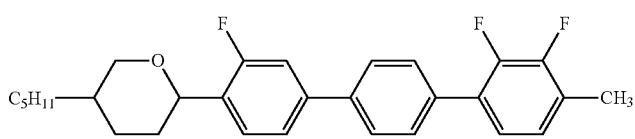 |
| 1142 | 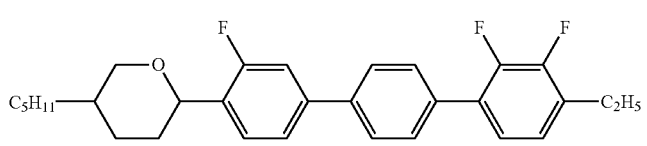 |
| 1143 | 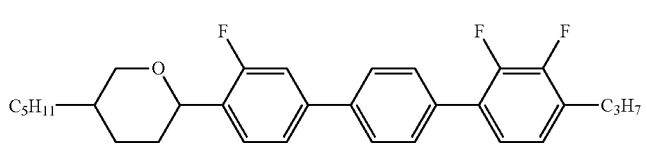 |
| 1144 | 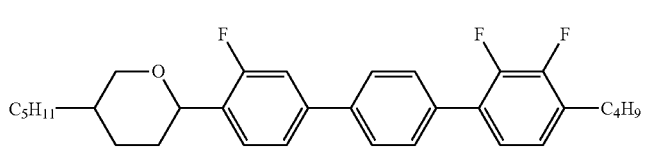 |
| 1145 | 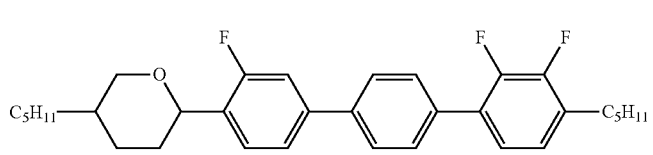 |
| 1146 | 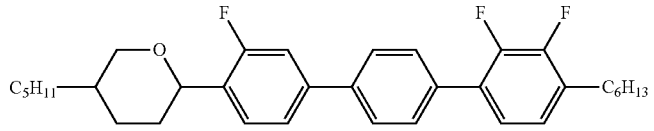 |
| 1147 | 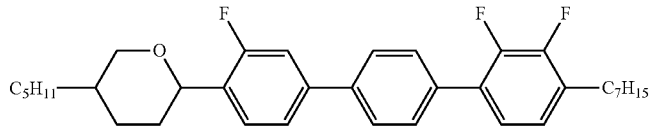 |
| 1148 |  |
| 1149 | 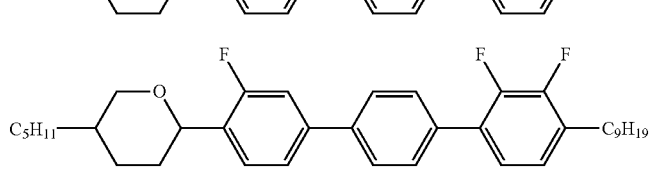 |

| No. | |
|---|---|
| 1150 | 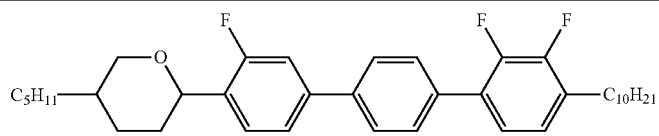 |
| 1151 | 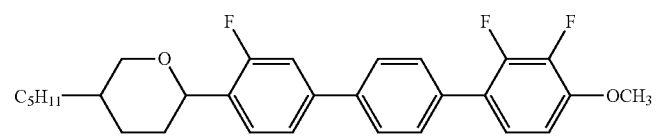 |
| 1152 | 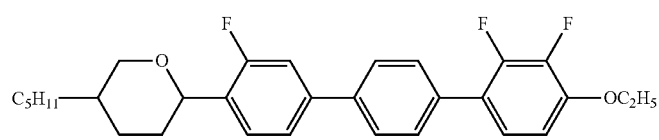<br>C 89.1 N 278.3 I<br>$T_{NI}$; 224.6° C., $\Delta\epsilon$; -4.28, $\Delta n$; 0.257 |
| 1153 | 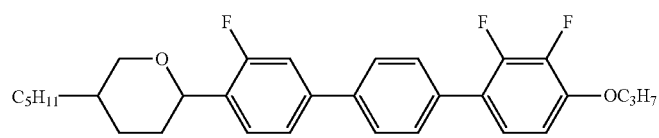 |
| 1154 | 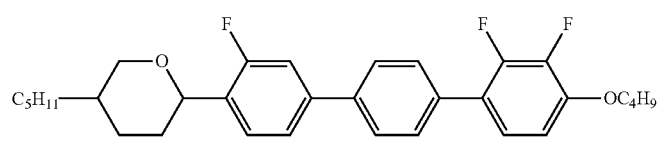 |
| 1155 | 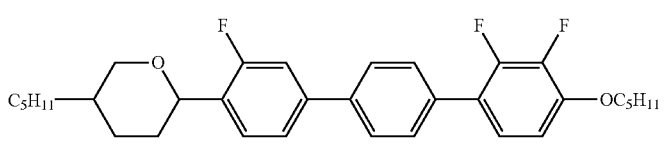 |
| 1156 | 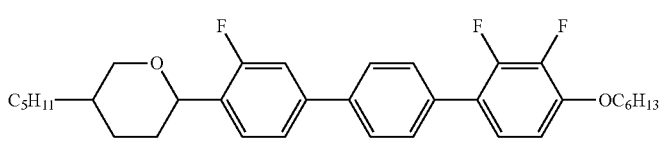 |
| 1157 | 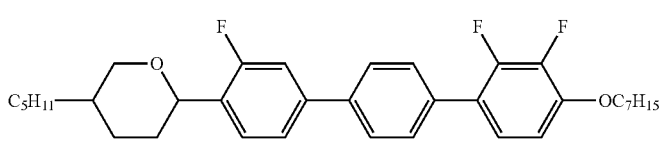 |
| 1158 | 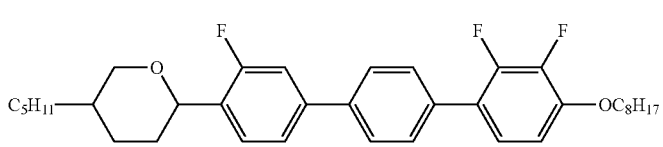 |
| 1159 | 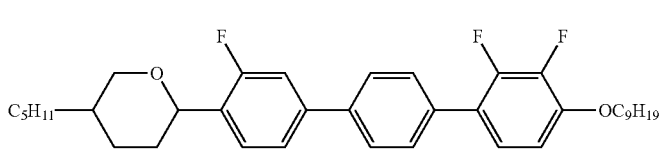 |
| 1160 | 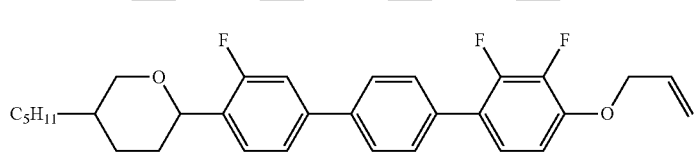 |

| No. | |
|---|---|
| 1161 | C7H15–[tetrahydropyran]–[C6H3(F)]–[C6H4]–[C6H2(F)(F)]–CH3 |
| 1162 | C7H15–[tetrahydropyran]–[C6H3(F)]–[C6H4]–[C6H2(F)(F)]–C2H5 |
| 1163 | C7H15–[tetrahydropyran]–[C6H3(F)]–[C6H4]–[C6H2(F)(F)]–C3H7 |
| 1164 | C7H15–[tetrahydropyran]–[C6H3(F)]–[C6H4]–[C6H2(F)(F)]–C4H9 |
| 1165 | C7H15–[tetrahydropyran]–[C6H3(F)]–[C6H4]–[C6H2(F)(F)]–C5H11 |
| 1166 | C7H15–[tetrahydropyran]–[C6H3(F)]–[C6H4]–[C6H2(F)(F)]–C6H13 |
| 1167 | C7H15–[tetrahydropyran]–[C6H3(F)]–[C6H4]–[C6H2(F)(F)]–C7H15 |
| 1168 | C7H15–[tetrahydropyran]–[C6H3(F)]–[C6H4]–[C6H2(F)(F)]–C8H17 |
| 1169 | C7H15–[tetrahydropyran]–[C6H3(F)]–[C6H4]–[C6H2(F)(F)]–C9H19 |
| 1170 | C7H15–[tetrahydropyran]–[C6H3(F)]–[C6H4]–[C6H2(F)(F)]–C10H21 |
| 1171 | C7H15–[tetrahydropyran]–[C6H3(F)]–[C6H4]–[C6H2(F)(F)]–OCH3 |

| No. | |
|---|---|
| 1172 | 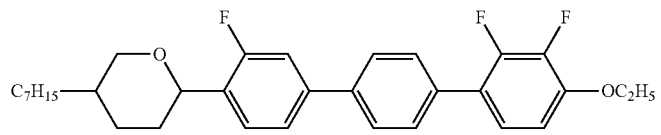 |
| 1173 | 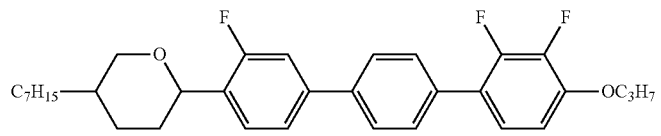 |
| 1174 |  |
| 1175 | 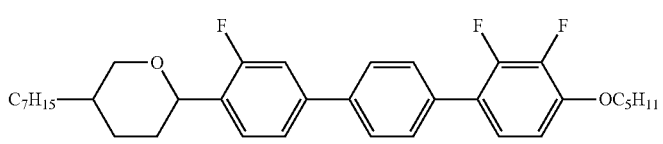 |
| 1176 | 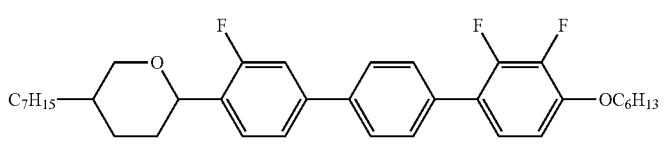 |
| 1177 | 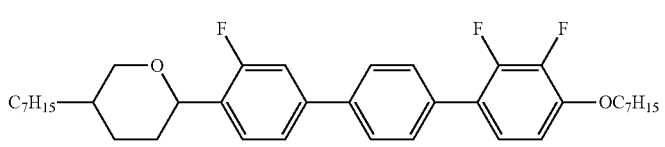 |
| 1178 | 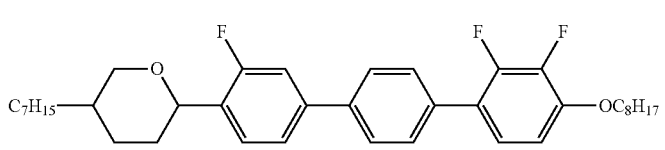 |
| 1179 | 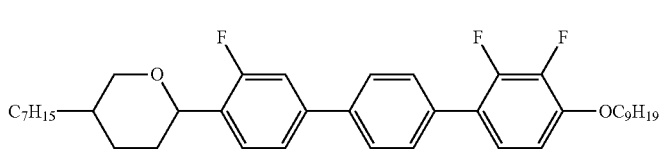 |
| 1180 | 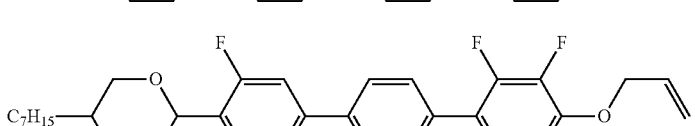 |
| 1181 | 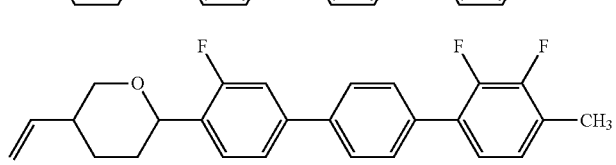 |
| 1182 | 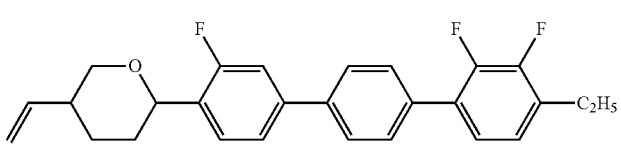 |

| No. | |
|---|---|
| 1183 | 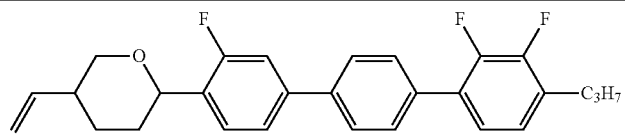 |
| 1184 | 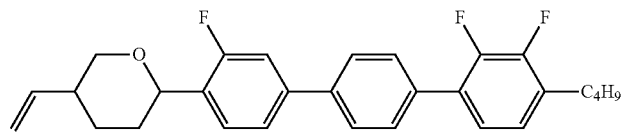 |
| 1185 | 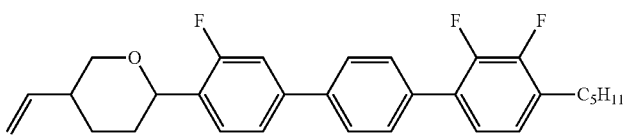 |
| 1186 | 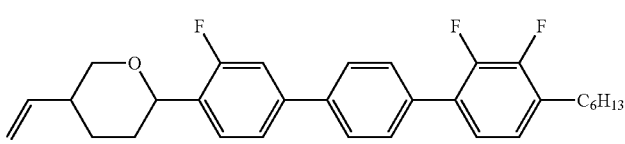 |
| 1187 | 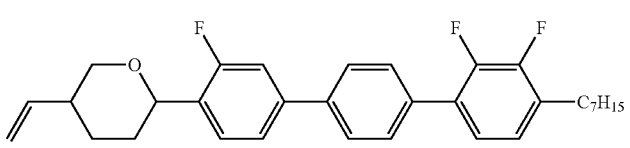 |
| 1188 | 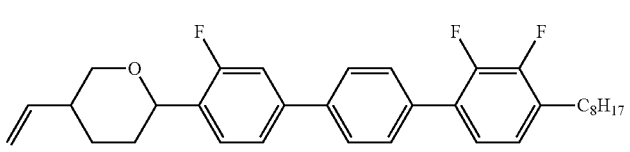 |
| 1189 | 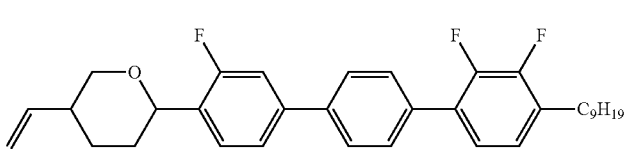 |
| 1190 | 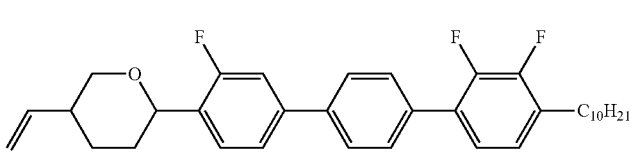 |
| 1191 | 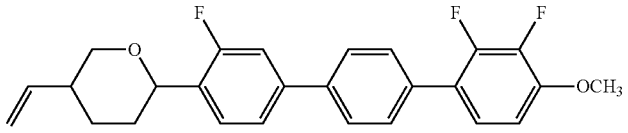 |
| 1192 | 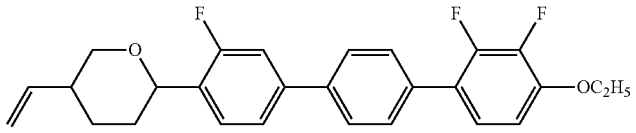 |
| 1193 | 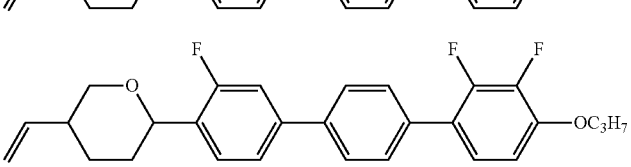 |

-continued
| No. | |
|---|---|
| 1194 | 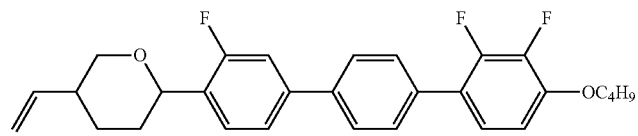 |
| 1195 | 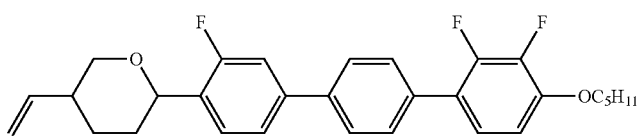 |
| 1196 | 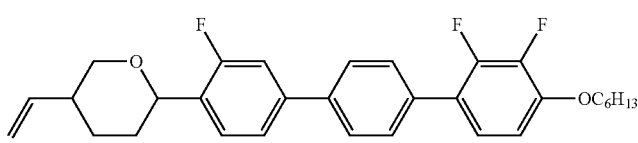 |
| 1197 | 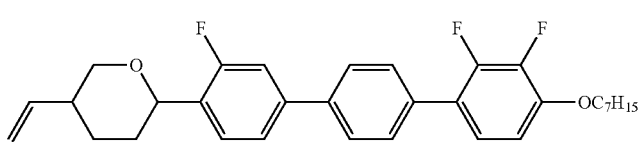 |
| 1198 | 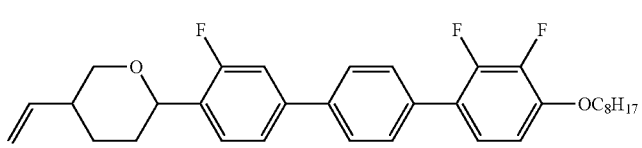 |
| 1199 | 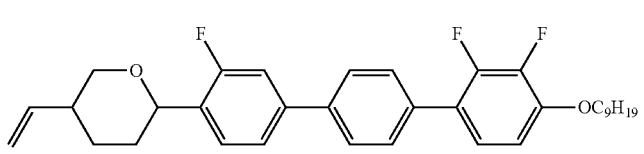 |
| 1200 | 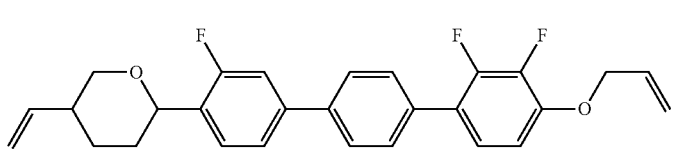 |
| 1201 | 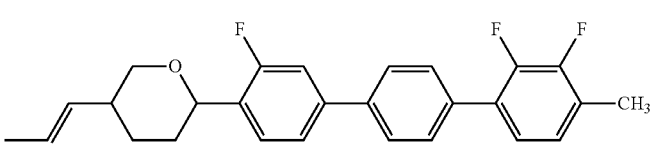 |
| 1202 | 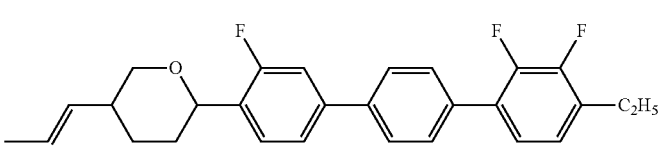 |
| 1203 | 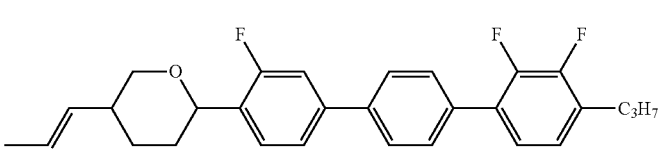 |
| 1204 | 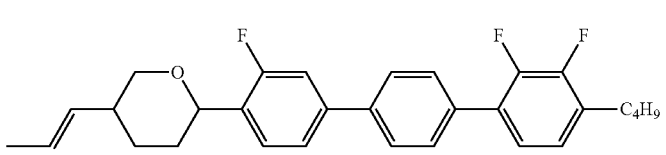 |

-continued
| No. | |
|---|---|
| 1205 | 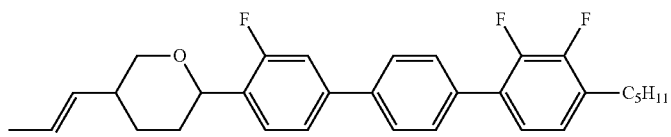 |
| 1206 | 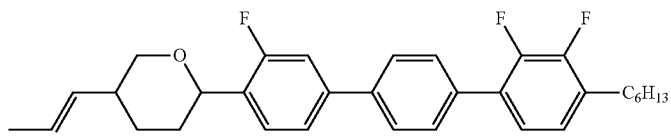 |
| 1207 | 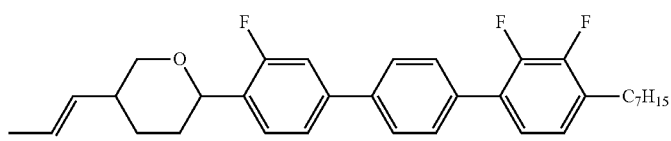 |
| 1208 | 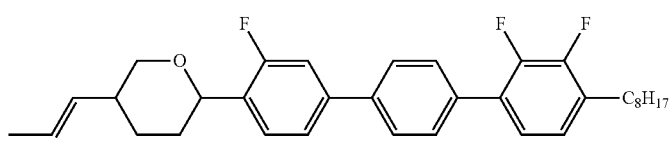 |
| 1209 | 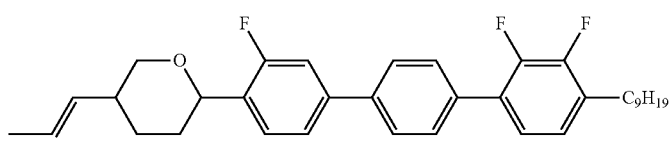 |
| 1210 | 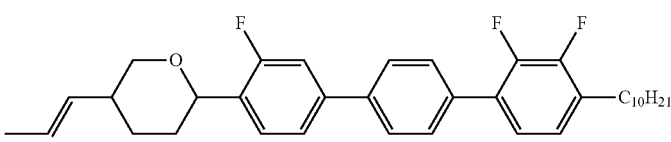 |
| 1211 | 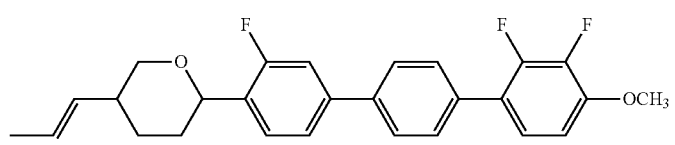 |
| 1212 | 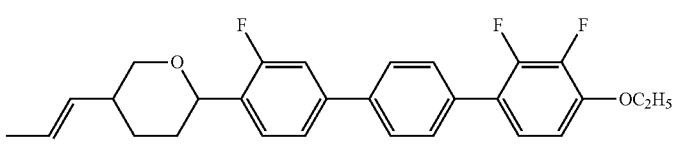 |
| 1213 | 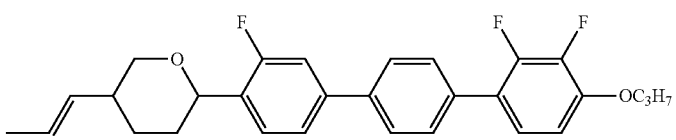 |
| 1214 | 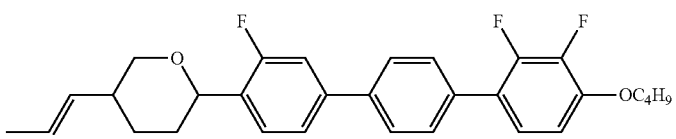 |
| 1215 | 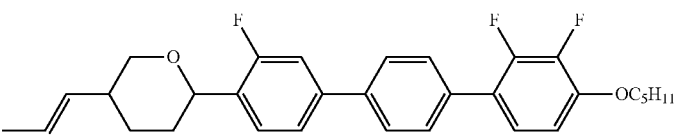 |

| No. | |
|---|---|
| 1216 | 3-F,4-(5-(prop-1-enyl)tetrahydropyran-2-yl)-2',3'-difluoro-4'-hexyloxy-[1,1':4',1''-terphenyl] — OC₆H₁₃ |
| 1217 | heptyloxy analog — OC₇H₁₅ |
| 1218 | octyloxy analog — OC₈H₁₇ |
| 1219 | nonyloxy analog — OC₉H₁₉ |
| 1220 | allyloxy analog |
| 1221 | 5-(but-2-enyl) pyran; terphenyl with CH₃ |
| 1222 | C₂H₅ |
| 1223 | C₃H₇ |
| 1224 | C₄H₉ |
| 1225 | C₅H₁₁ |
| 1226 | C₆H₁₃ |

(Structural formulas for compounds 1216–1226 shown; each is a 2-(2-fluoro-4-[2',3'-difluoro-4''-R-[1,1':4',1''-terphenyl]-4-yl])-5-alkenyl-tetrahydro-2H-pyran derivative with the following terminal R groups:
- 1216: OC₆H₁₃ (5-propenyl pyran)
- 1217: OC₇H₁₅ (5-propenyl pyran)
- 1218: OC₈H₁₇ (5-propenyl pyran)
- 1219: OC₉H₁₉ (5-propenyl pyran)
- 1220: O-CH₂-CH=CH₂ (5-propenyl pyran)
- 1221: CH₃ (5-but-2-enyl pyran)
- 1222: C₂H₅ (5-but-2-enyl pyran)
- 1223: C₃H₇ (5-but-2-enyl pyran)
- 1224: C₄H₉ (5-but-2-enyl pyran)
- 1225: C₅H₁₁ (5-but-2-enyl pyran)
- 1226: C₆H₁₃ (5-but-2-enyl pyran))

-continued
| No. | |
|---|---|
| 1227 | 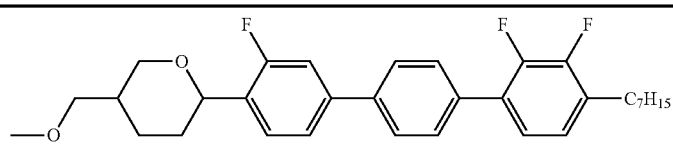 |
| 1228 | 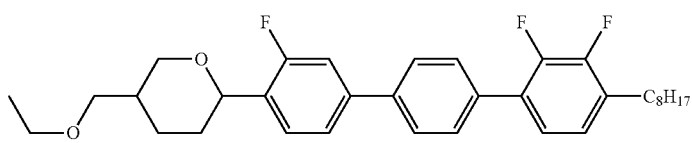 |
| 1229 | 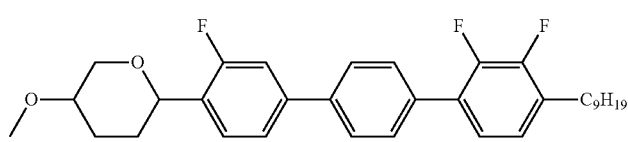 |
| 1230 | 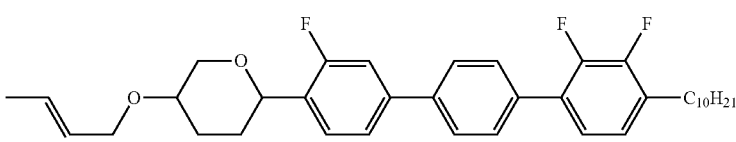 |
| 1231 | 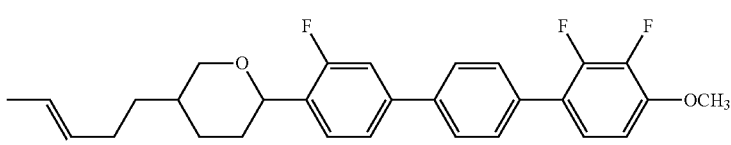 |
| 1232 | 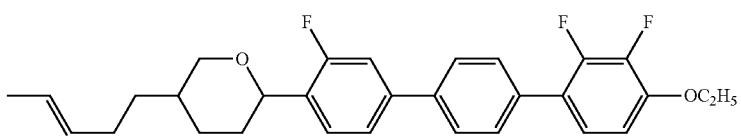 |
| 1233 | 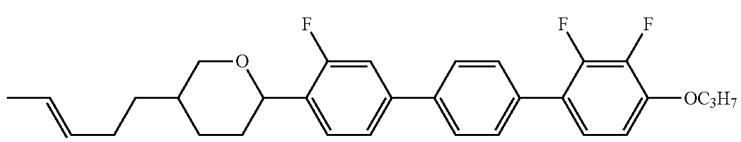 |
| 1234 | 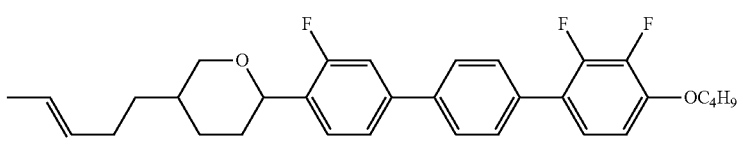 |
| 1235 | 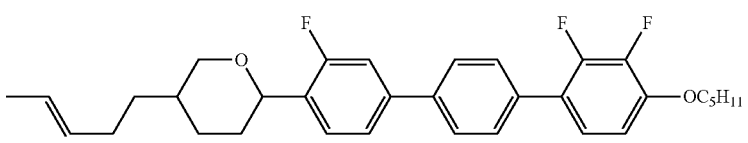 |
| 1236 | 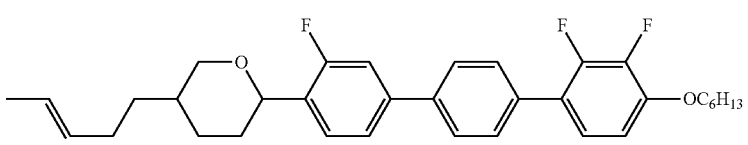 |
| 1237 | 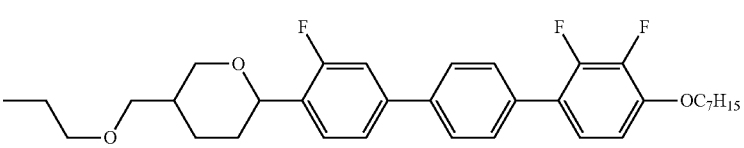 |

-continued
| No. | |
|---|---|
| 1238 | 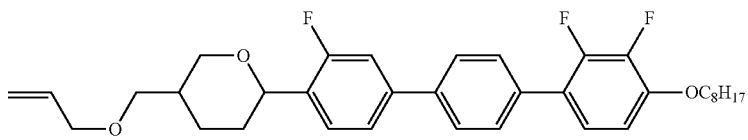 |
| 1239 | 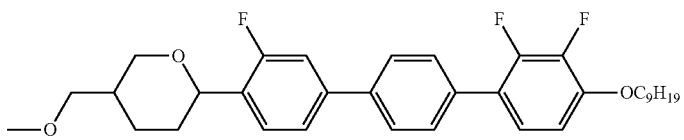 |
| 1240 | 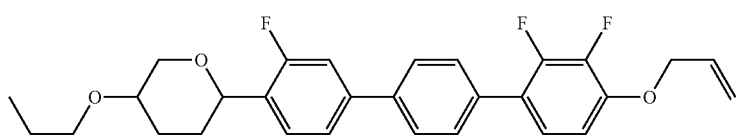 |
| 1241 | 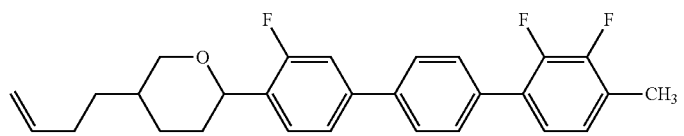 |
| 1242 | 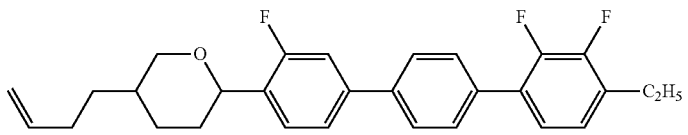 |
| 1243 | 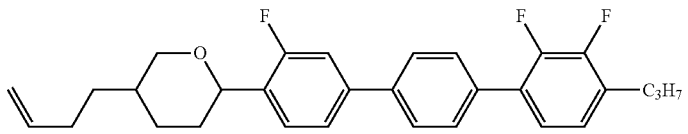 |
| 1244 | 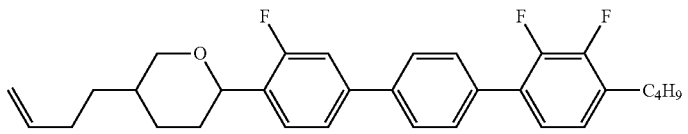 |
| 1245 | 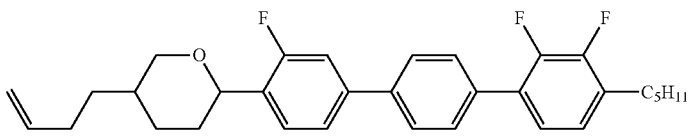 |
| 1246 | 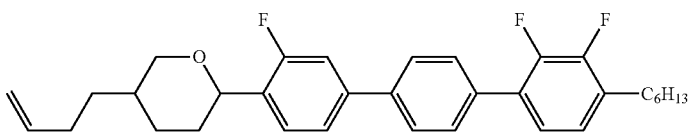 |
| 1247 | 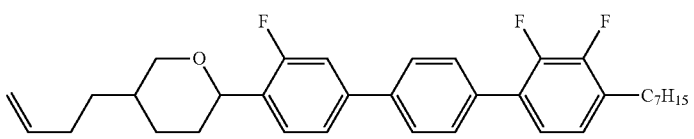 |
| 1248 | 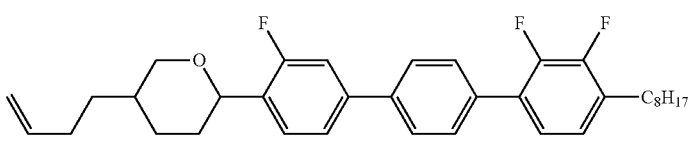 |

-continued
| No. | |
|---|---|
| 1249 | 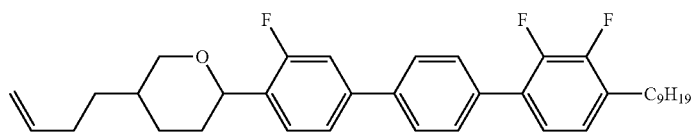 |
| 1250 | 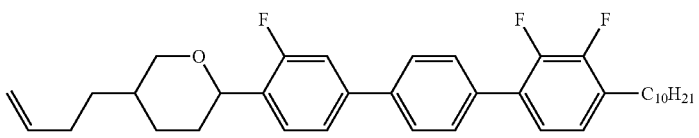 |
| 1251 | 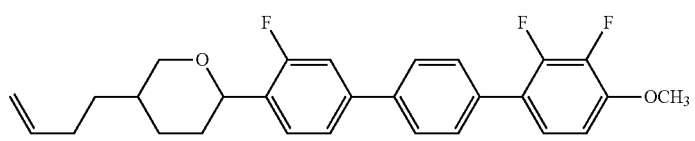 |
| 1252 | 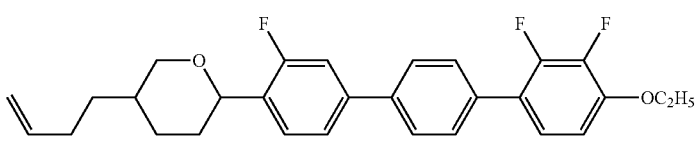 |
| 1253 | 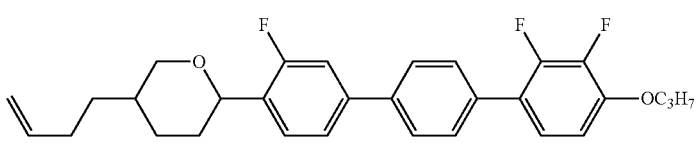 |
| 1254 | 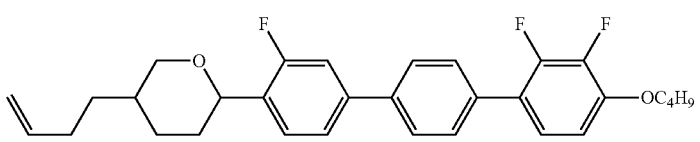 |
| 1255 | 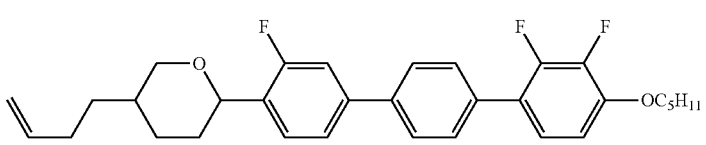 |
| 1256 | 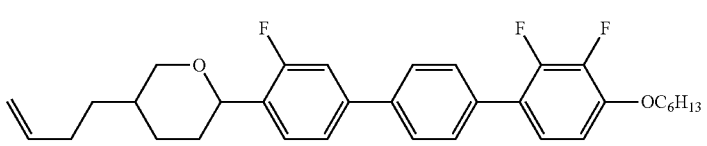 |
| 1257 | 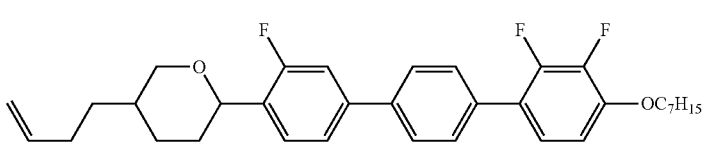 |
| 1258 | 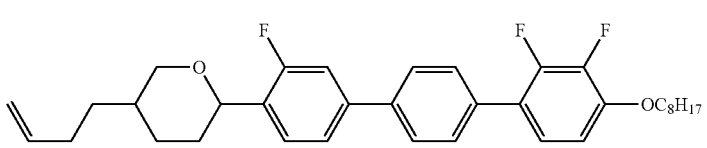 |
| 1259 | 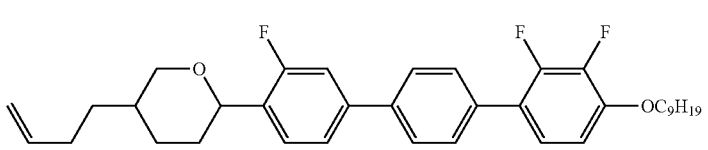 |

| No. | |
|---|---|
| 1260 | 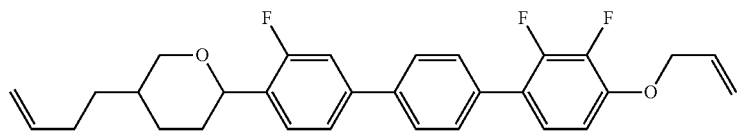 |
| 1261 | 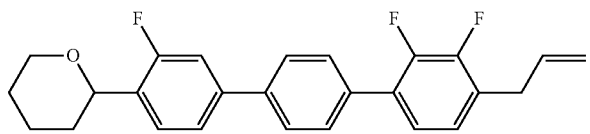 |
| 1262 | 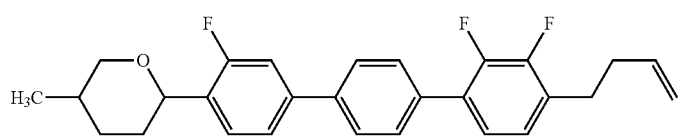 |
| 1263 | 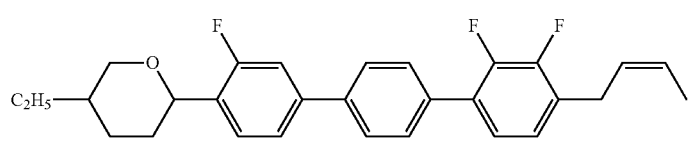 |
| 1264 | 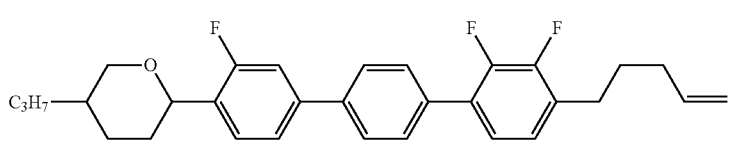 |
| 1265 | 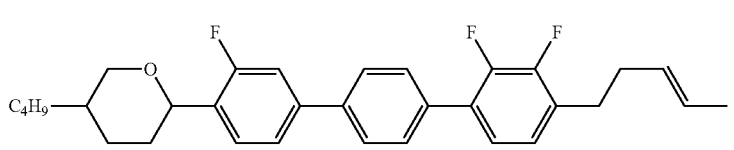 |
| 1266 | 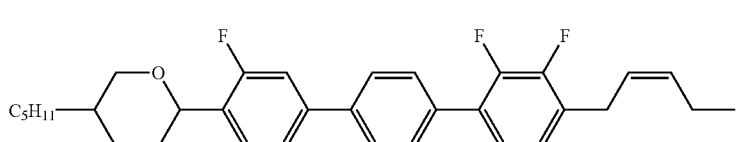 |
| 1267 | 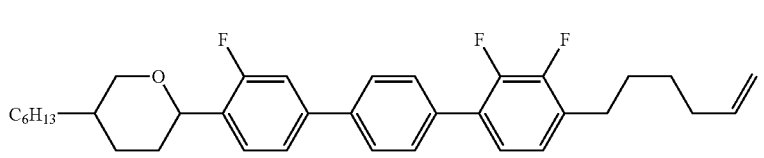 |
| 1268 | 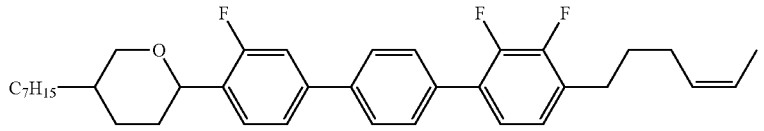 |
| 1269 | 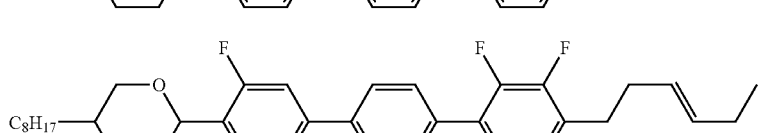 |
| 1270 | 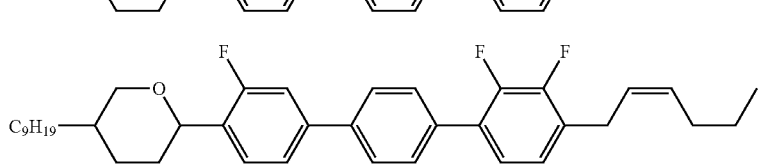 |

| No. |
|---|
| 1271 |
| 1272 |
| 1273 |
| 1274 |
| 1275 |
| 1276 |
| 1277 |
| 1278 |
| 1279 |
| 1280 |
| 1281 |

| No. | |
|---|---|
| 1282 | 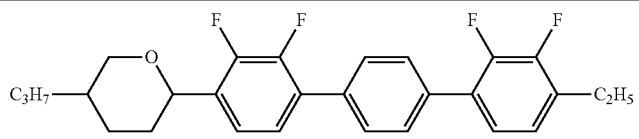 |
| 1283 |  |
| 1284 |  |
| 1285 | 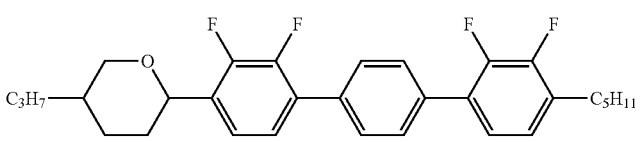 |
| 1286 | 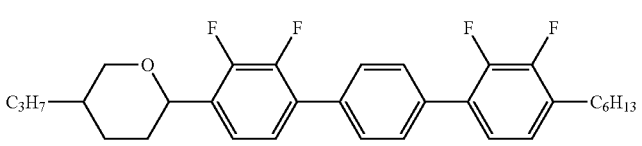 |
| 1287 | 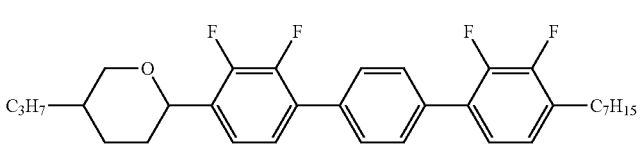 |
| 1288 | 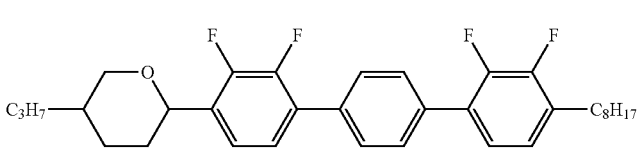 |
| 1289 | 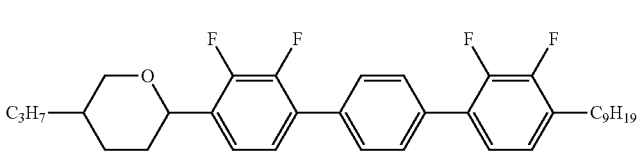 |
| 1290 | 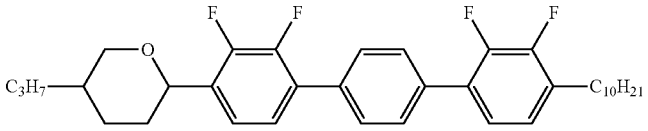 |
| 1291 | 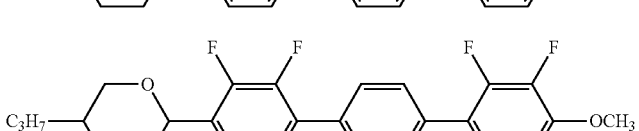 |
| 1292 | 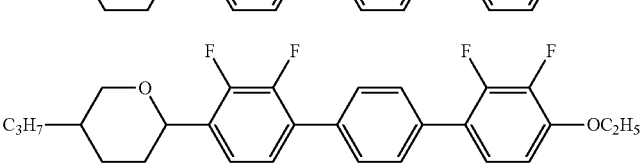 |

-continued
| No. | |
|---|---|
| 1293 | 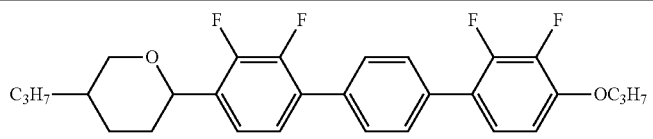 |
| 1294 | 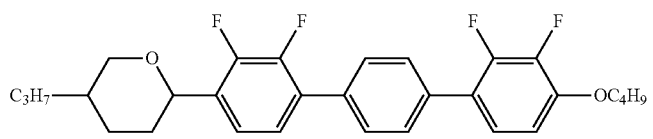 |
| 1295 | 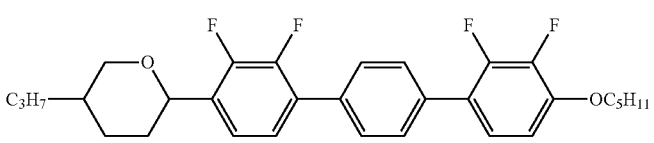 |
| 1296 | 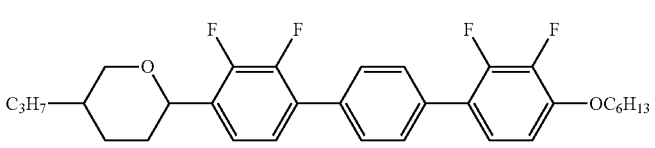 |
| 1297 | 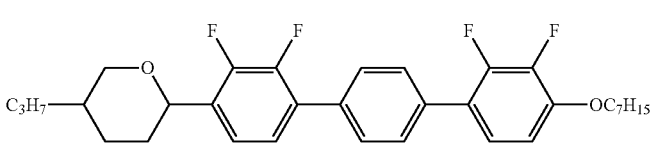 |
| 1298 | 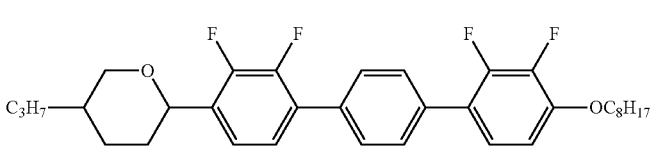 |
| 1299 | 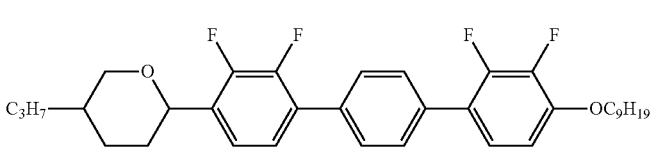 |
| 1300 | 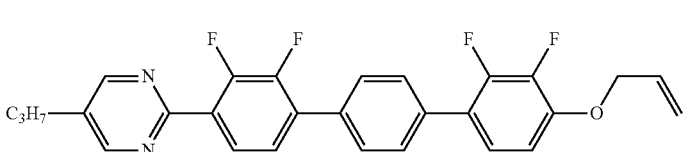 |
| 1301 | 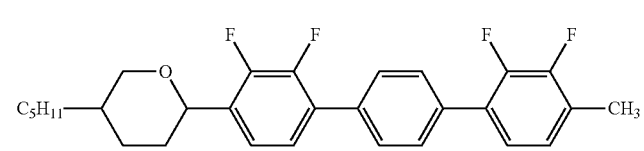 |
| 1302 | 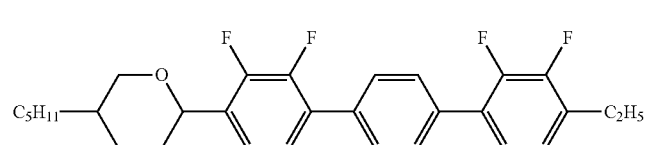 |
| 1303 | 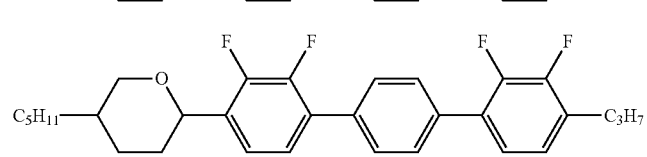 |

| No. | |
|---|---|
| 1304 | 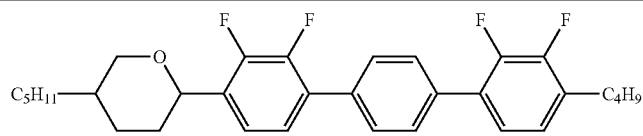 |
| 1305 | 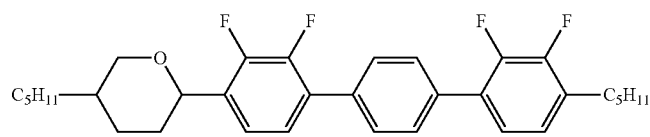 |
| 1306 | 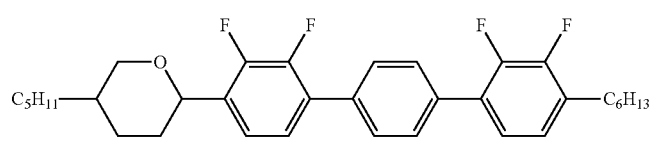 |
| 1307 | 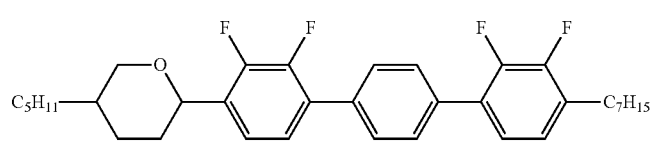 |
| 1308 | 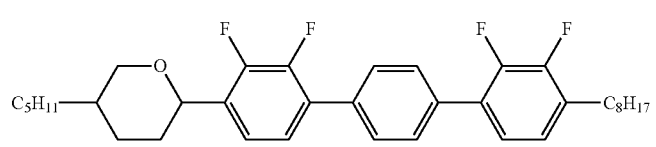 |
| 1309 | 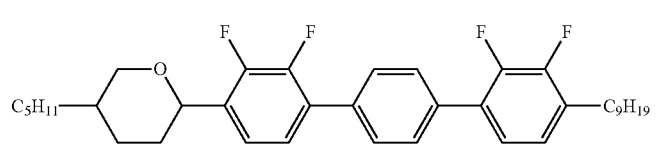 |
| 1310 | 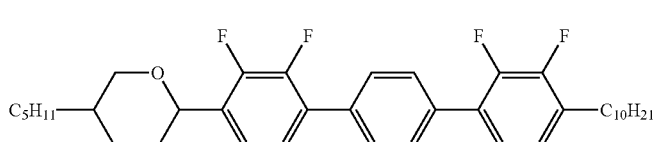 |
| 1311 | 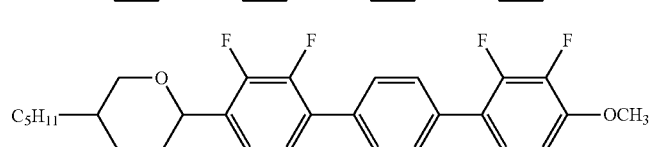 |
| 1312 | 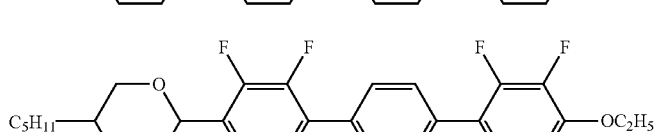 |
| 1313 | 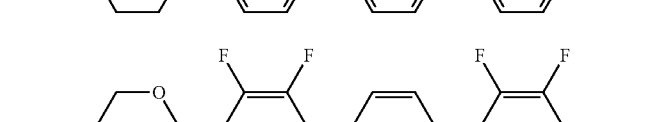 |
| 1314 | 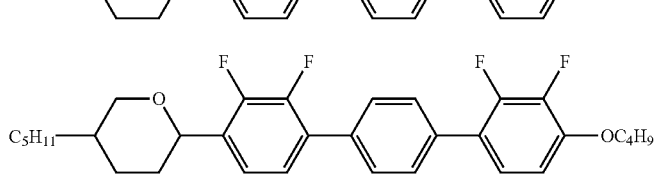 |

| No. | |
|---|---|
| 1315 | 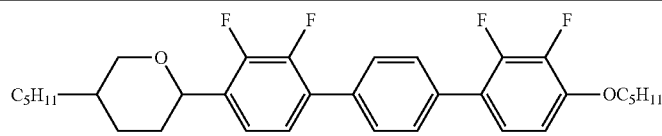 |
| 1316 | 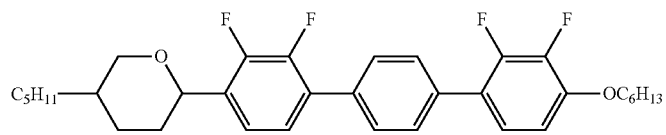 |
| 1317 | 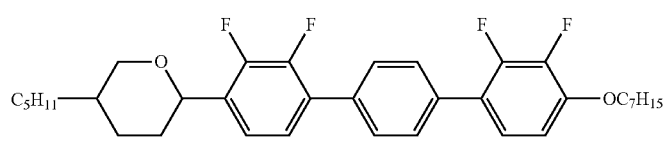 |
| 1318 | 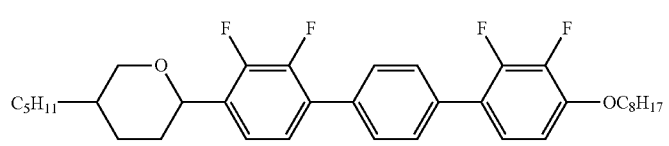 |
| 1319 | 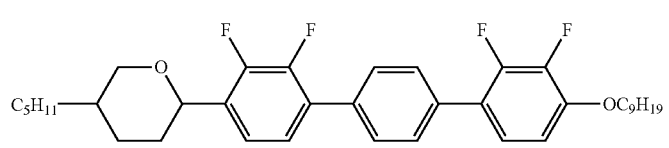 |
| 1320 | 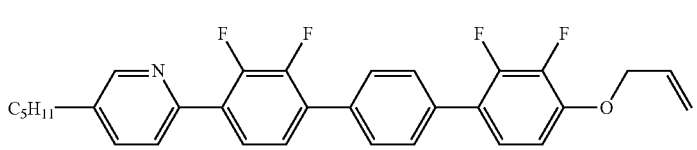 |
| 1321 | 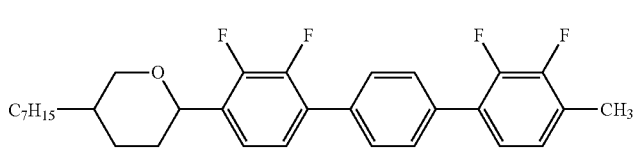 |
| 1322 | 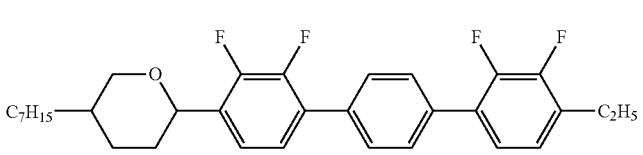 |
| 1323 | 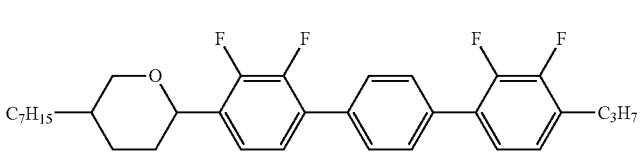 |
| 1324 | 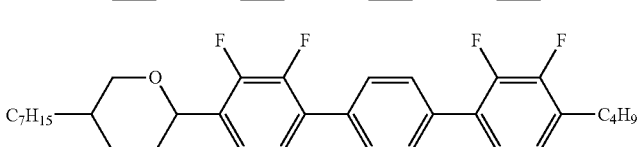 |
| 1325 | 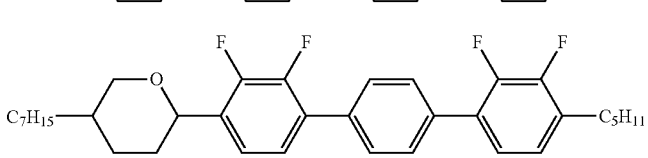 |

-continued
| No. | |
|---|---|
| 1326 |  |
| 1327 |  |
| 1328 | 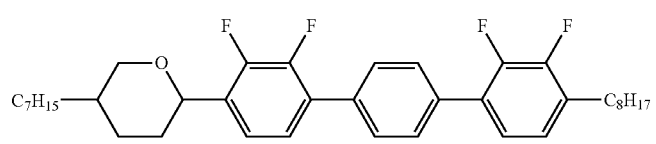 |
| 1329 | 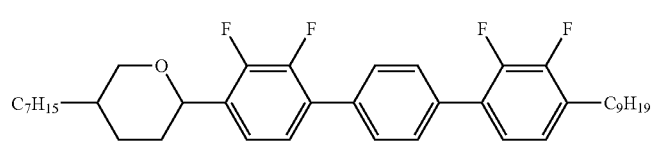 |
| 1330 | 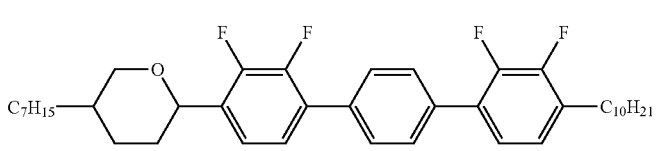 |
| 1331 | 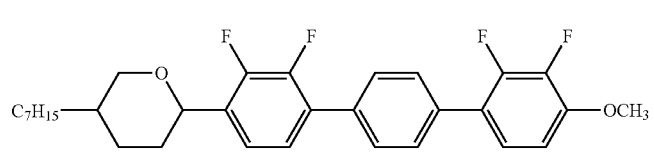 |
| 1332 | 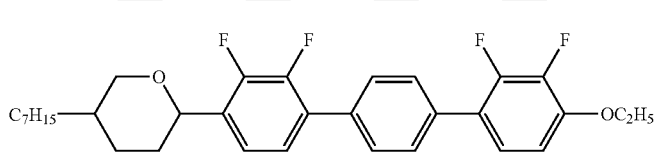 |
| 1333 | 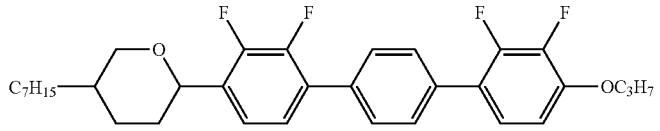 |
| 1334 |  |
| 1335 |  |
| 1336 | 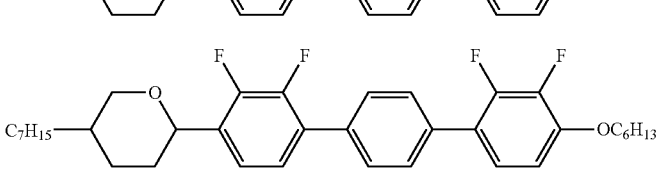 |

-continued
| No. | |
|---|---|
| 1337 | 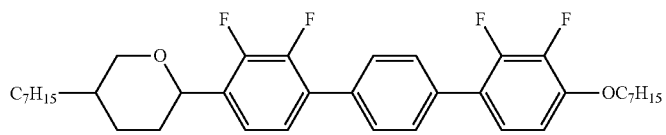 |
| 1338 | 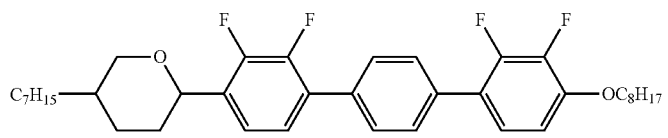 |
| 1339 | 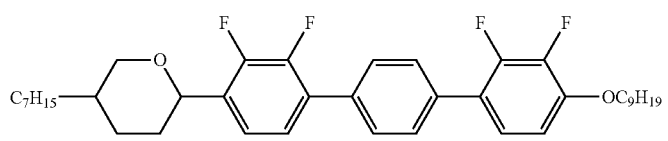 |
| 1340 | 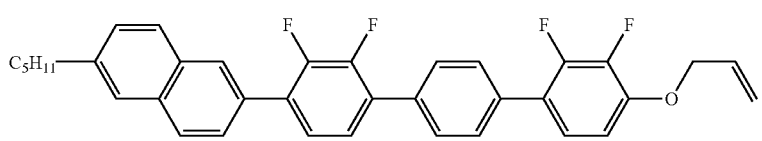 |
| 1341 | 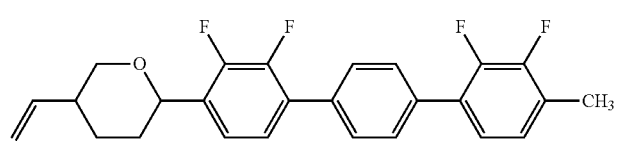 |
| 1342 | 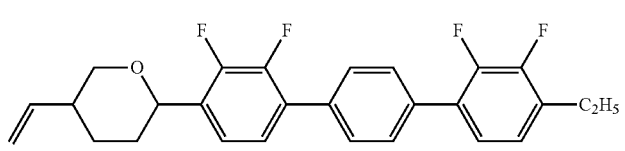 |
| 1343 | 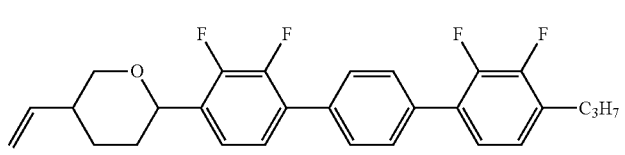 |
| 1344 | 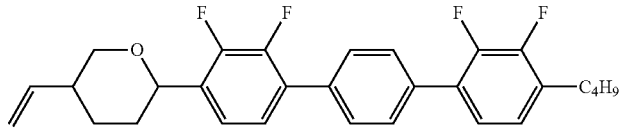 |
| 1345 | 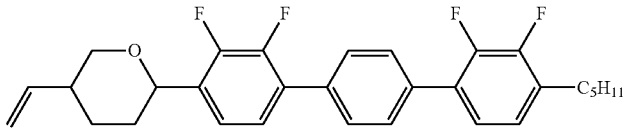 |
| 1346 | 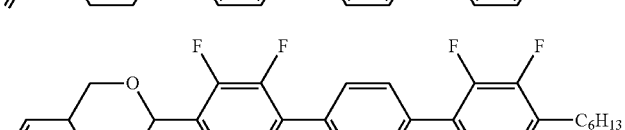 |
| 1347 | 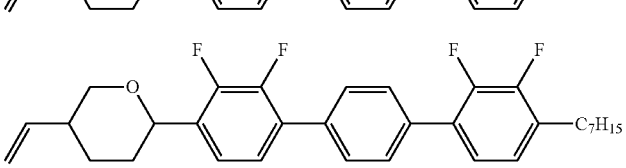 |

| No. | |
|---|---|
| 1348 | 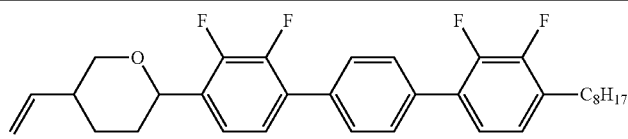 |
| 1349 | 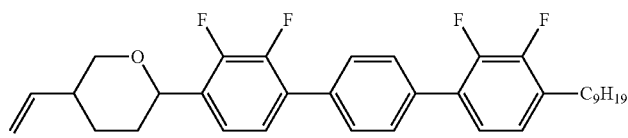 |
| 1350 | 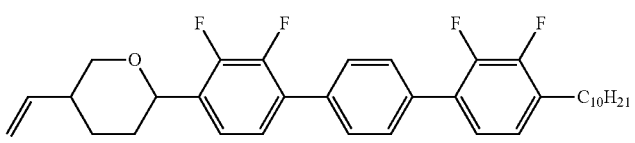 |
| 1351 | 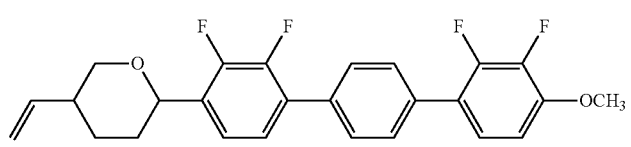 |
| 1352 | 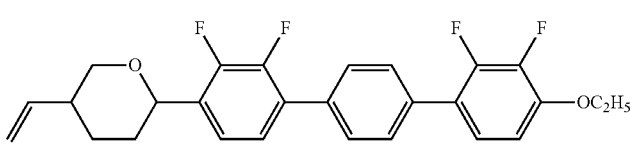 |
| 1353 | 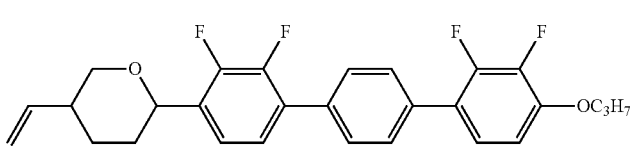 |
| 1354 | 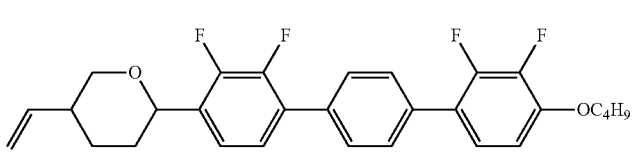 |
| 1355 | 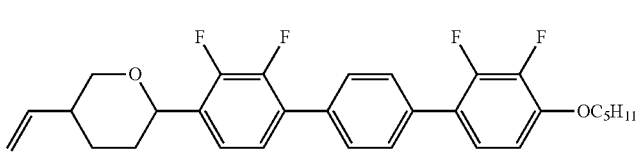 |
| 1356 | 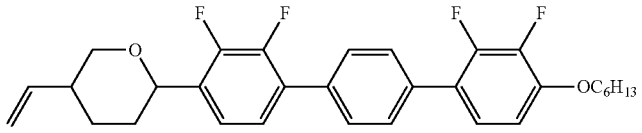 |
| 1357 | 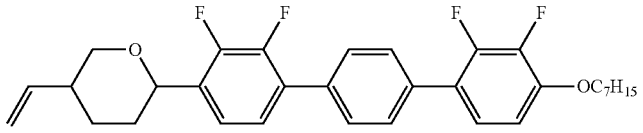 |
| 1358 | 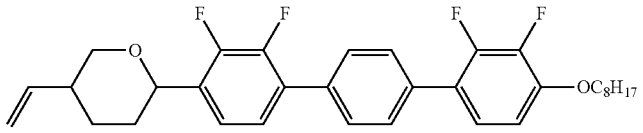 |

-continued
| No. | |
|---|---|
| 1359 | 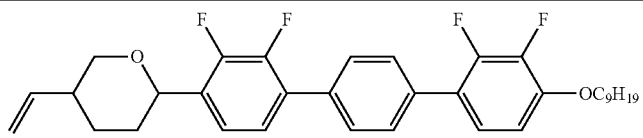 |
| 1360 | 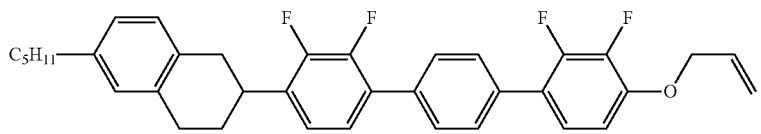 |
| 1361 | 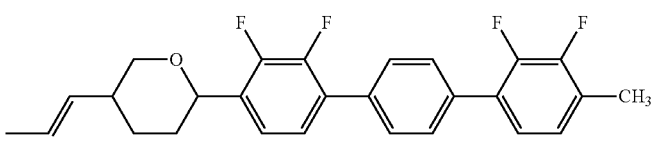 |
| 1362 | 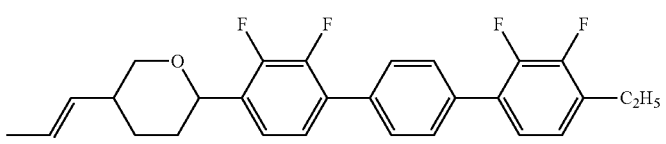 |
| 1363 | 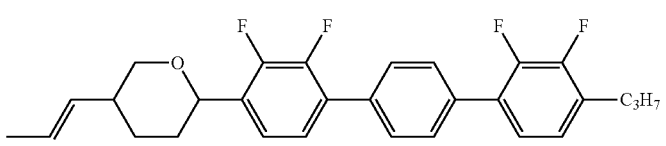 |
| 1364 | 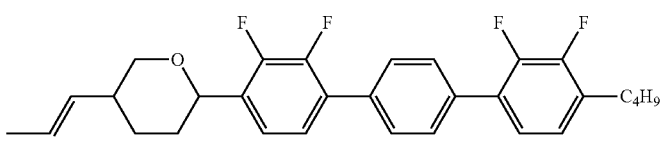 |
| 1365 | 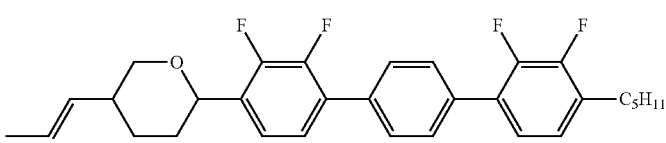 |
| 1366 | 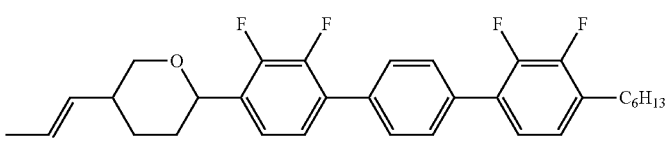 |
| 1367 | 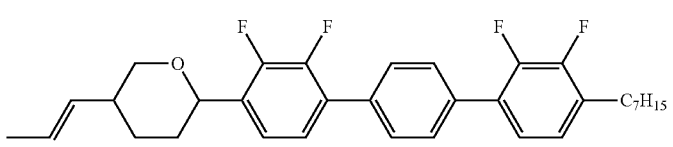 |
| 1368 | 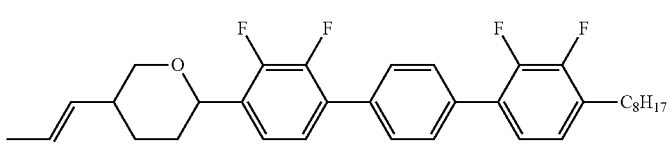 |
| 1369 | 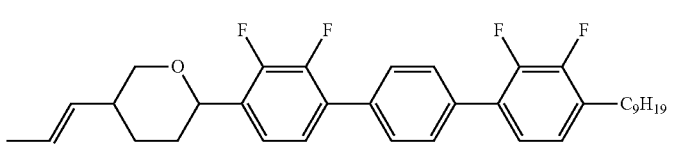 |

| No. | |
|---|---|
| 1370 | 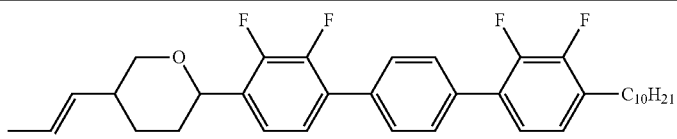 |
| 1371 | 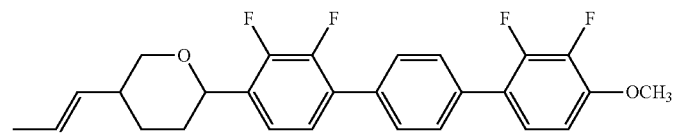 |
| 1372 | 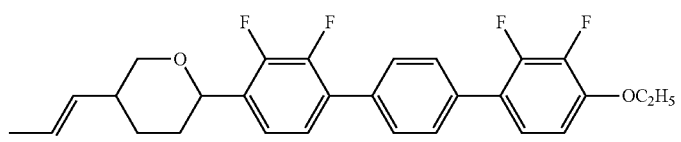 |
| 1373 | 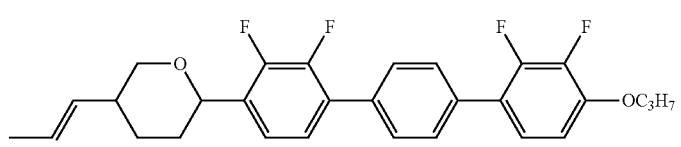 |
| 1374 | 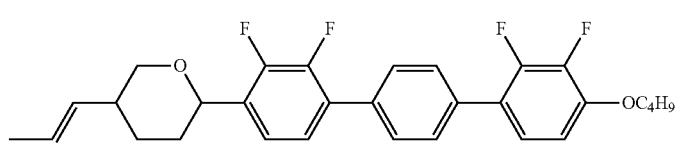 |
| 1375 | 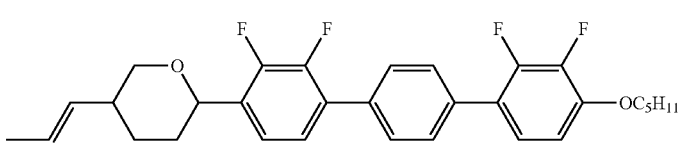 |
| 1376 | 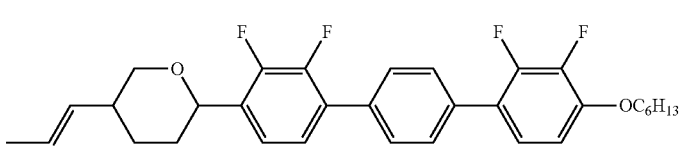 |
| 1377 | 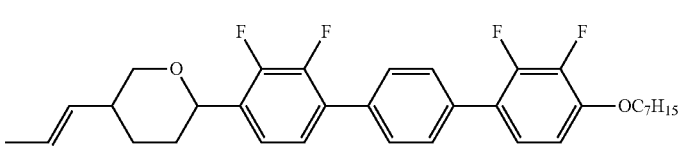 |
| 1378 | 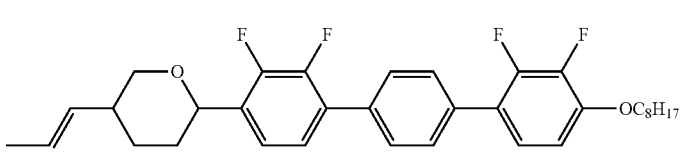 |
| 1379 | 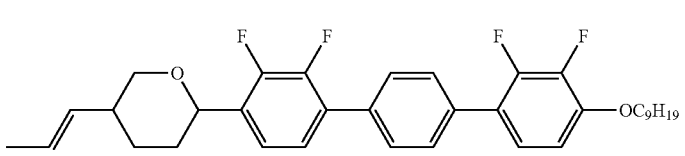 |
| 1380 | 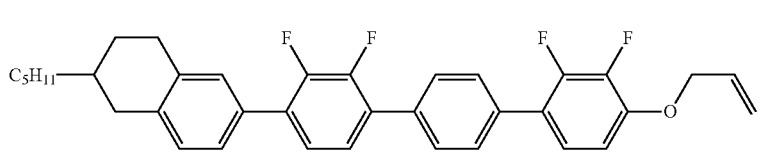 |

-continued
| No. | |
|---|---|
| 1381 | 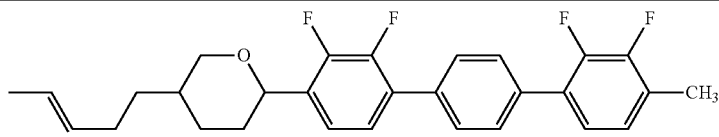 |
| 1382 | 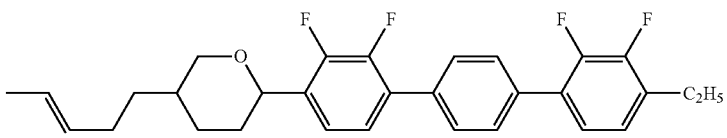 |
| 1383 | 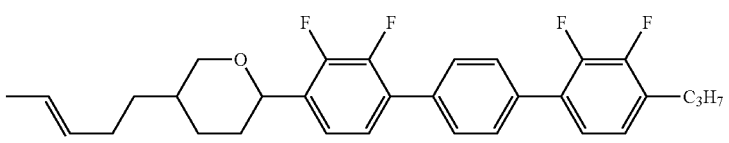 |
| 1384 | 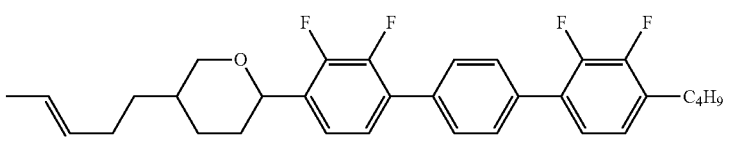 |
| 1385 | 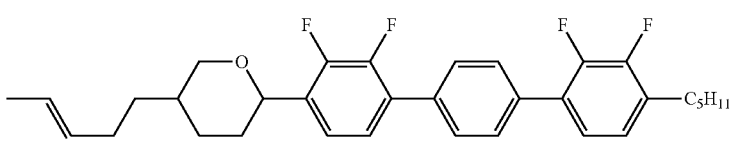 |
| 1386 | 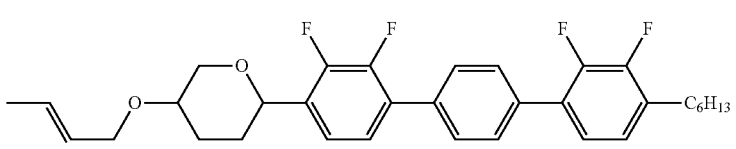 |
| 1387 | 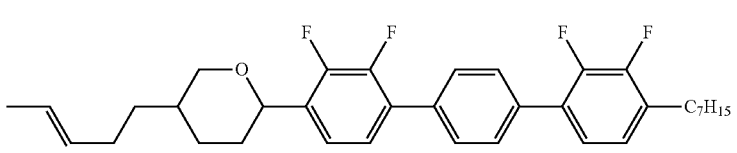 |
| 1388 | 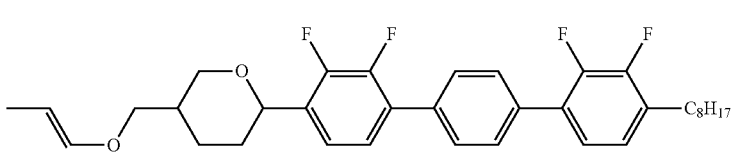 |
| 1389 | 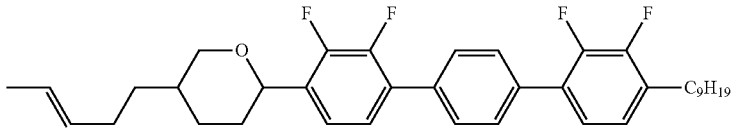 |
| 1390 | 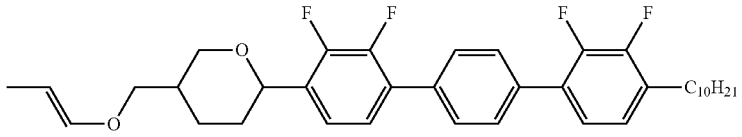 |
| 1391 | 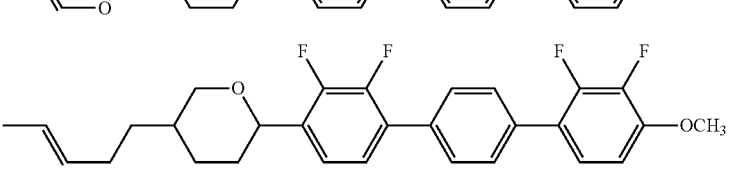 |

-continued
| No. | |
|---|---|
| 1392 | 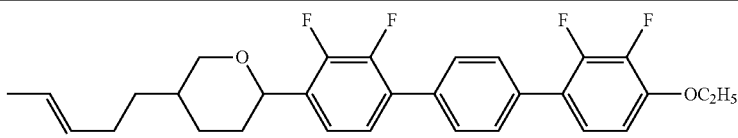 |
| 1393 | 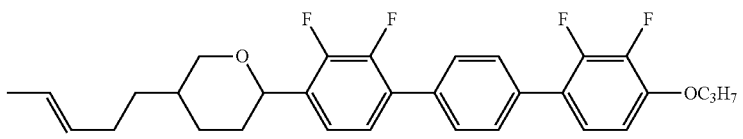 |
| 1394 | 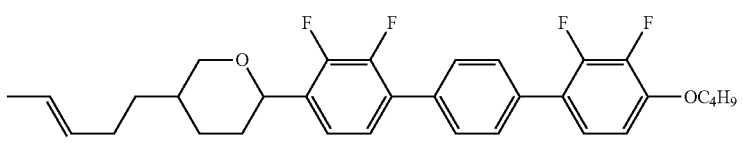 |
| 1395 | 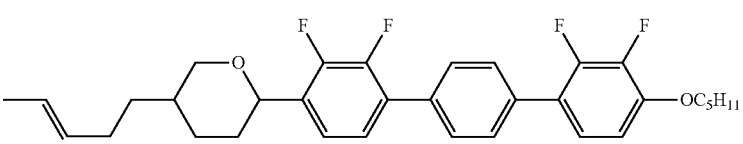 |
| 1396 | 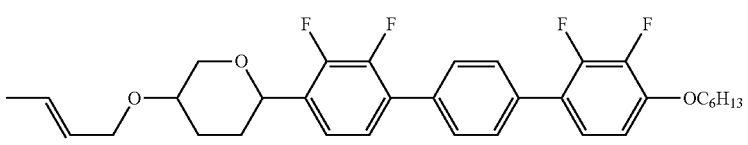 |
| 1397 | 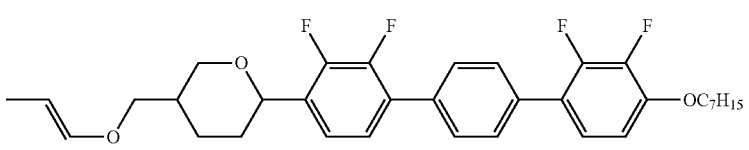 |
| 1398 | 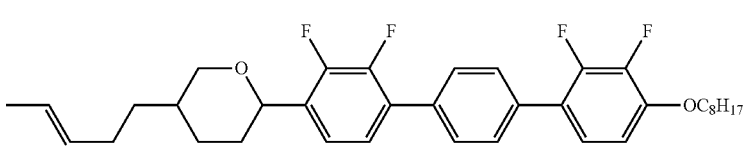 |
| 1399 | 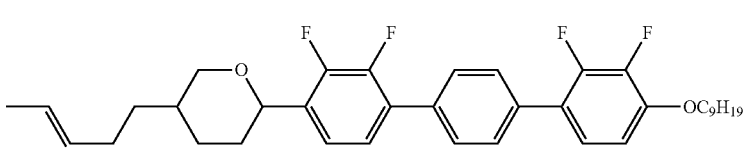 |
| 1400 | 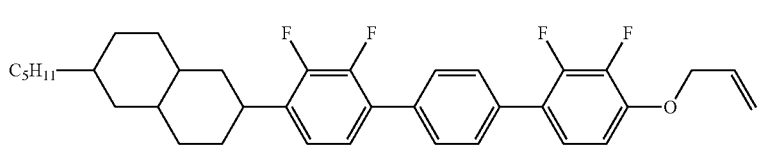 |
| 1401 | 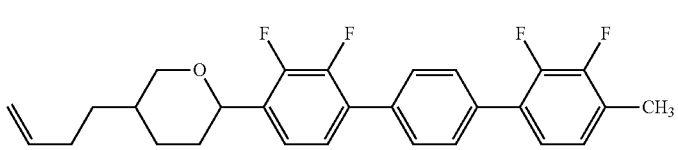 |
| 1402 | 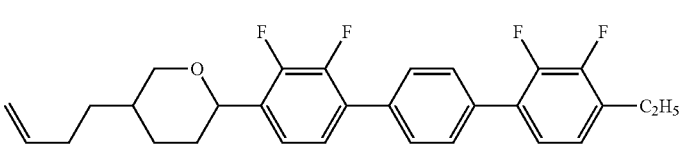 |

| No. | |
|---|---|
| 1403 | 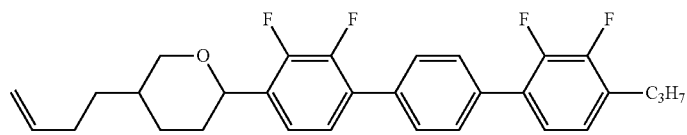 |
| 1404 | 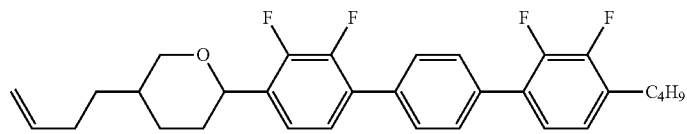 |
| 1405 | 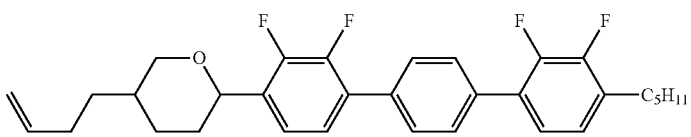 |
| 1406 | 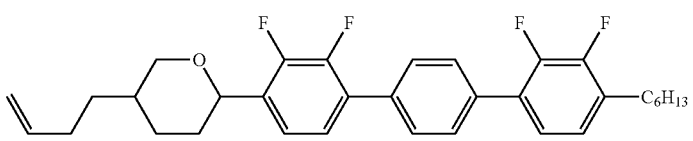 |
| 1407 | 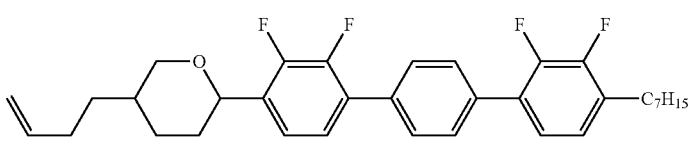 |
| 1408 | 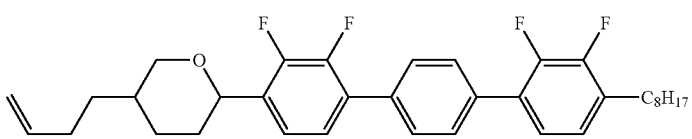 |
| 1409 | 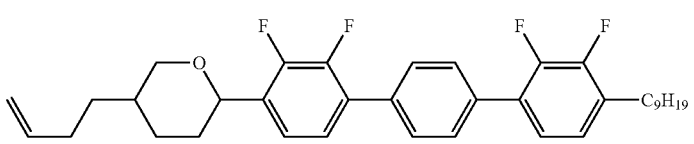 |
| 1410 | 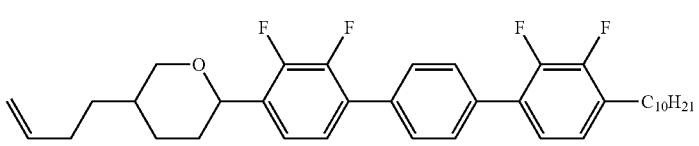 |
| 1411 | 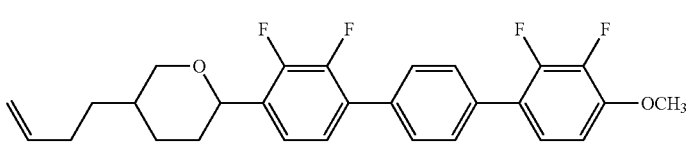 |
| 1412 | 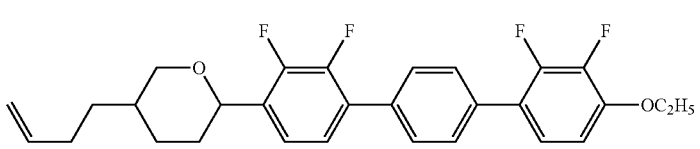 |
| 1413 | 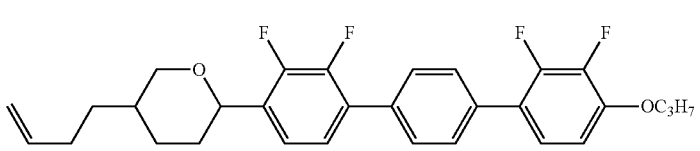 |

| No. | |
|---|---|
| 1414 | (structure with tetrahydropyran-allyl, difluorophenyl-phenyl-difluorophenyl-OC₄H₉) |
| 1415 | (structure with tetrahydropyran-allyl, difluorophenyl-phenyl-difluorophenyl-OC₅H₁₁) |
| 1416 | (structure with tetrahydropyran-allyl, difluorophenyl-phenyl-difluorophenyl-OC₆H₁₃) |
| 1417 | (structure with tetrahydropyran-allyl, difluorophenyl-phenyl-difluorophenyl-OC₇H₁₅) |
| 1418 | (structure with tetrahydropyran-allyl, difluorophenyl-phenyl-difluorophenyl-OC₈H₁₇) |
| 1419 | (structure with tetrahydropyran-allyl, difluorophenyl-phenyl-difluorophenyl-OC₉H₁₉) |
| 1420 | (pyridine-butenyl, difluorophenyl-phenyl-difluorophenyl-O-allyl) |
| 1421 | (tetrahydropyran, difluorophenyl-phenyl-difluorophenyl-allyl) |
| 1422 | (H₃C-tetrahydropyran, difluorophenyl-phenyl-difluorophenyl-butenyl) |
| 1423 | (C₂H₅-tetrahydropyran, difluorophenyl-phenyl-difluorophenyl-butenyl) |
| 1424 | (C₃H₇-tetrahydropyran, difluorophenyl-phenyl-difluorophenyl-pentenyl) |

| No. | |
|---|---|
| 1425 | 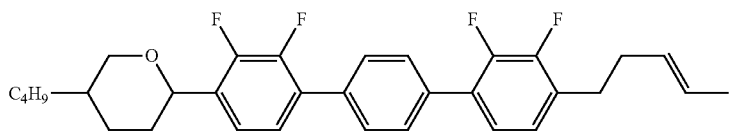 |
| 1426 | 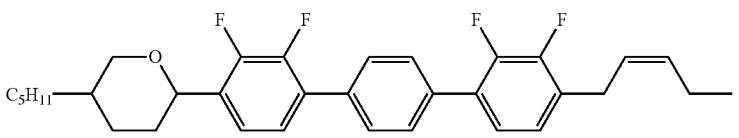 |
| 1427 | 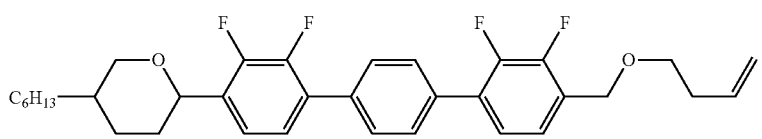 |
| 1428 | 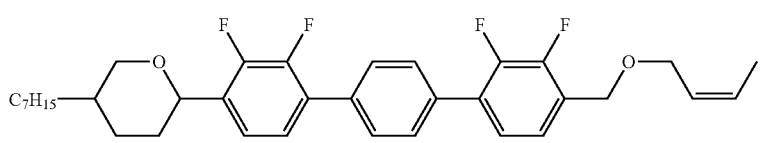 |
| 1429 | 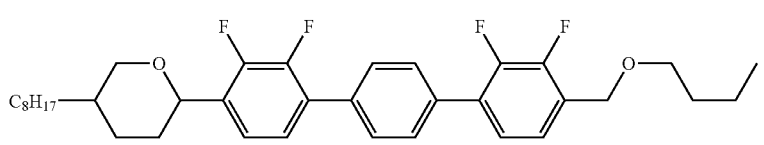 |
| 1430 | 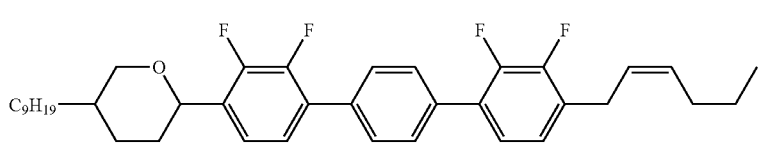 |
| 1431 | 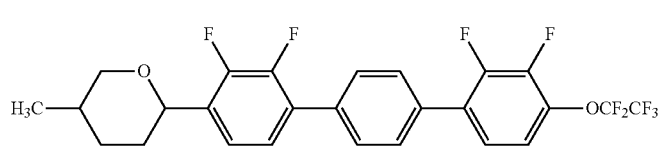 |
| 1432 | 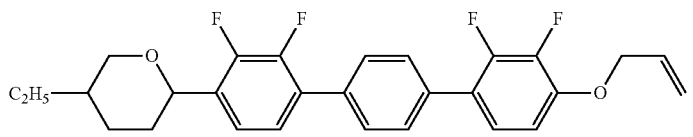 |
| 1433 | 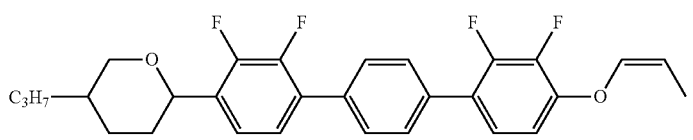 |
| 1434 | 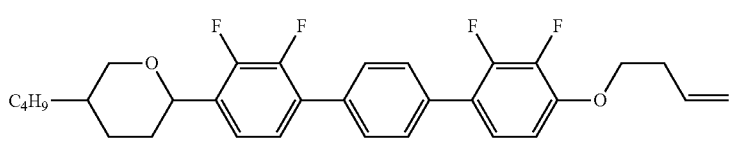 |
| 1435 | 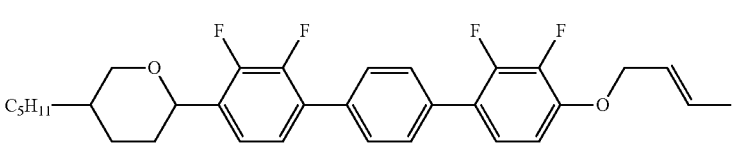 |

| No. | |
|---|---|
| 1436 | C₆H₁₃–[tetrahydropyran-O]–[C₆H₂(F)(F)]–[C₆H₄]–[C₆H₂(F)(F)]–O–CH₂–CH=CH–CH₃ |
| 1437 | C₇H₁₅–[tetrahydropyran-O]–[C₆H₂(F)(F)]–[C₆H₄]–[C₆H₂(F)(F)]–O–CH₂–CH₂–CH=CH₂ |
| 1438 | C₈H₁₇–[tetrahydropyran-O]–[C₆H₂(F)(F)]–[C₆H₄]–[C₆H₂(F)(F)]–O–CH₂–CH=CH–CH₃ |
| 1439 | C₉H₁₉–[tetrahydropyran-O]–[C₆H₂(F)(F)]–[C₆H₄]–[C₆H₂(F)(F)]–O–CH₂–CH=CH–CH₃ |
| 1440 | C₁₀H₂₁–[pyrimidine]–[C₆H₂(F)(F)]–[C₆H₄]–[C₆H₂(F)(F)]–O–CH₂–CH=CH–CH₃ |
| 1441 | C₃H₇–[tetrahydropyran-O]–[C₆H₃(F)]–[C₆H₄]–[C₆H₂(F)(F)]–CH₃ |
| 1442 | C₃H₇–[tetrahydropyran-O]–[C₆H₃(F)]–[C₆H₄]–[C₆H₂(F)(F)]–C₂H₅ |
| 1443 | C₃H₇–[tetrahydropyran-O]–[C₆H₃(F)]–[C₆H₄]–[C₆H₂(F)(F)]–C₃H₇ |
| 1444 | C₃H₇–[tetrahydropyran-O]–[C₆H₃(F)]–[C₆H₄]–[C₆H₂(F)(F)]–C₄H₉ |
| 1445 | C₃H₇–[tetrahydropyran-O]–[C₆H₃(F)]–[C₆H₄]–[C₆H₂(F)(F)]–C₅H₁₁ |
| 1446 | C₃H₇–[tetrahydropyran-O]–[C₆H₃(F)]–[C₆H₄]–[C₆H₂(F)(F)]–C₆H₁₃ |

-continued
| No. | |
|---|---|
| 1447 | 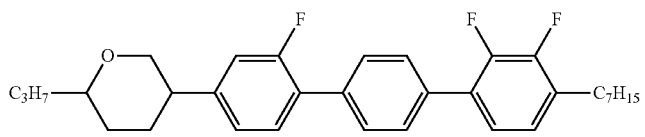 |
| 1448 | 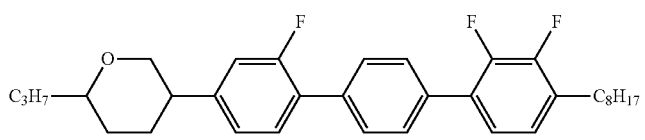 |
| 1449 | 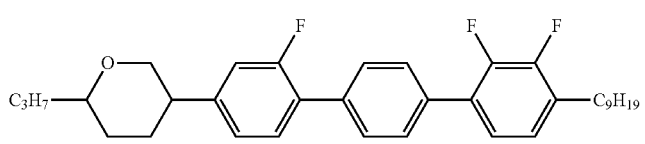 |
| 1450 | 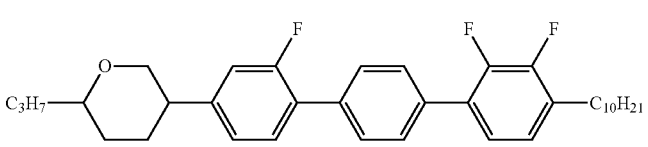 |
| 1451 | 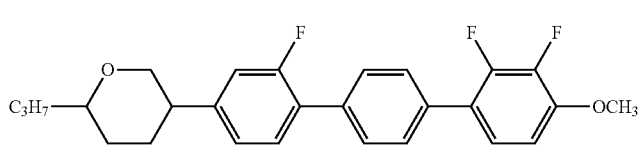 |
| 1452 | 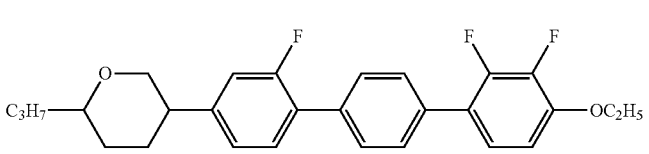 |
| 1453 | 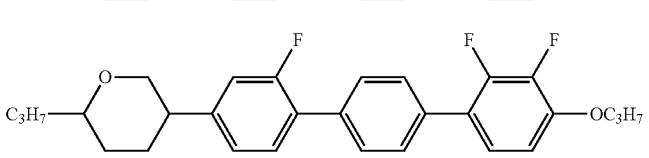 |
| 1454 | 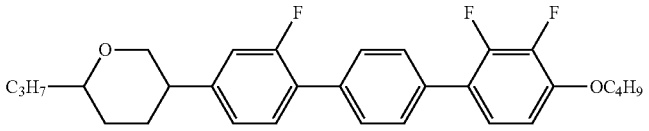 |
| 1455 |  |
| 1456 |  |
| 1457 | 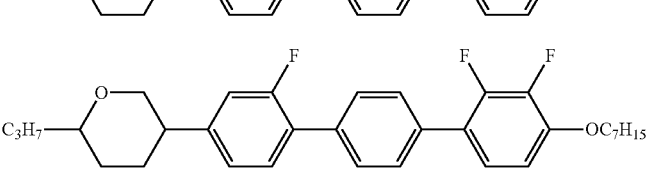 |

-continued
| No. |
|---|
| 1458 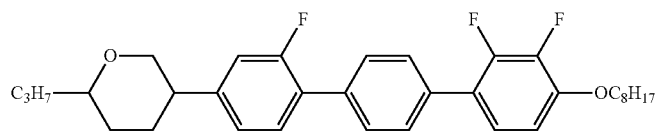 |
| 1459 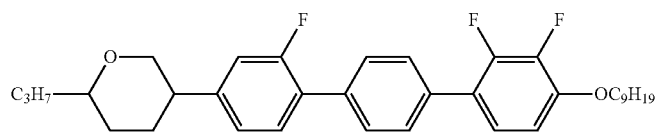 |
| 1460 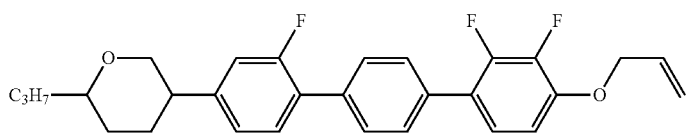 |
| 1461 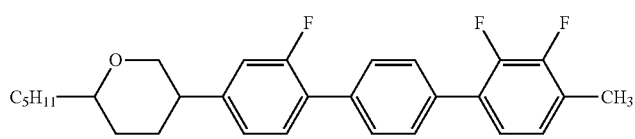 |
| 1462 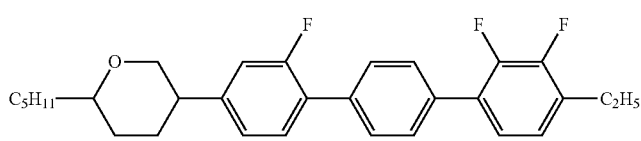 |
| 1463 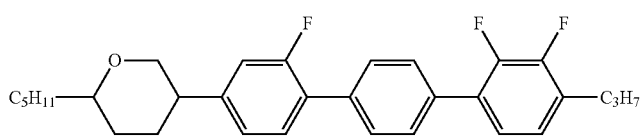 |
| 1464 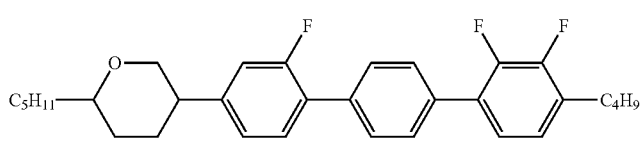 |
| 1465 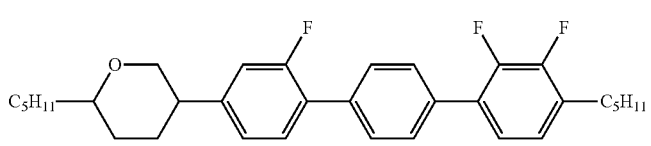 |
| 1466 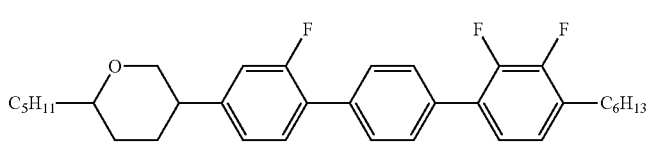 |
| 1467 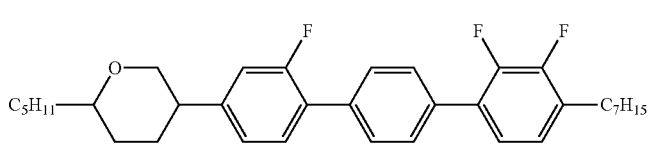 |
| 1468 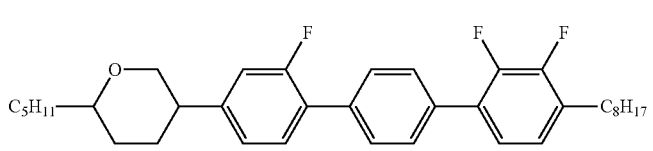 |

| No. | |
|---|---|
| 1469 | 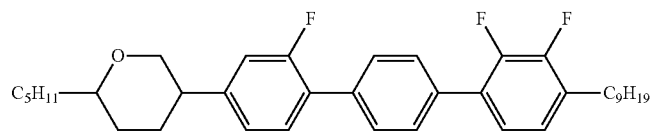 |
| 1470 | 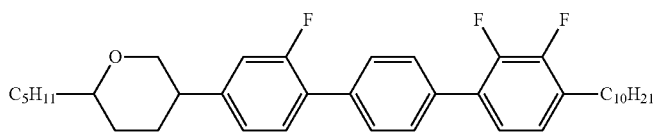 |
| 1471 | 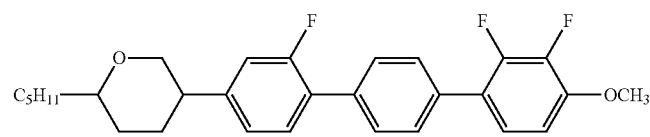 |
| 1472 | 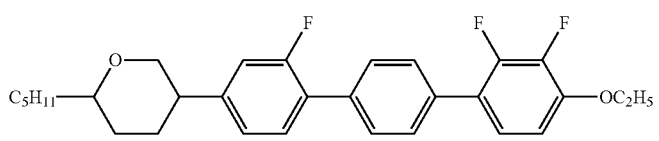 |
| 1473 | 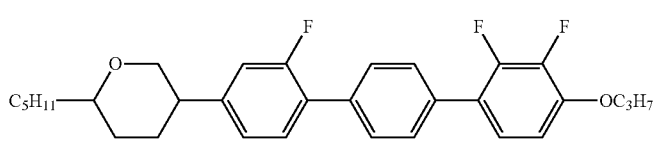 |
| 1474 | 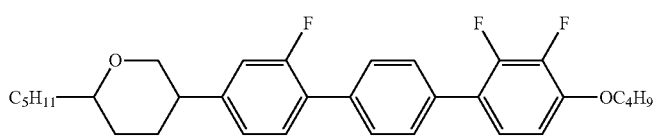 |
| 1475 | 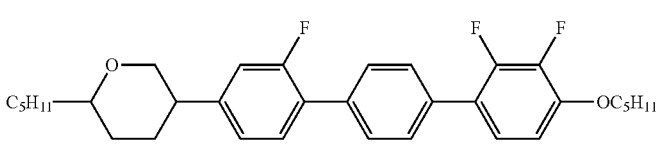 |
| 1476 | 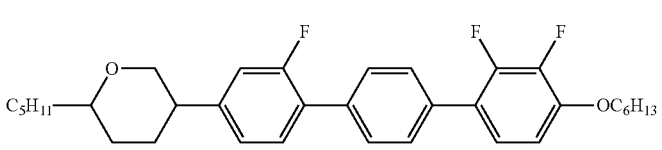 |
| 1477 | 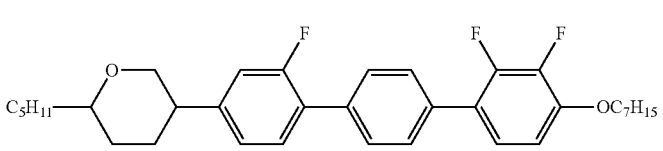 |
| 1478 | 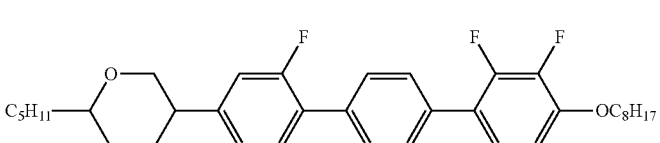 |
| 1479 | 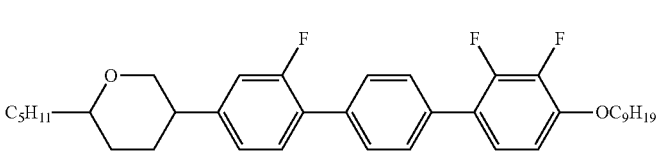 |

| No. | |
|---|---|
| 1480 | 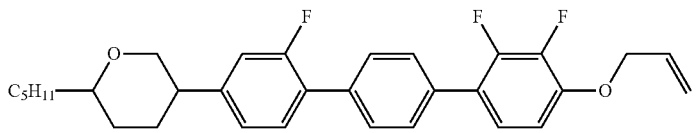 |
| 1481 | 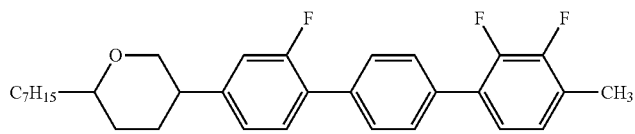 |
| 1482 | 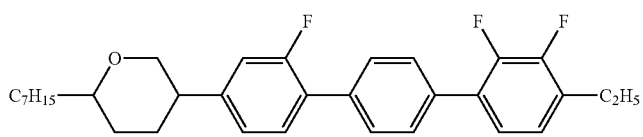 |
| 1483 | 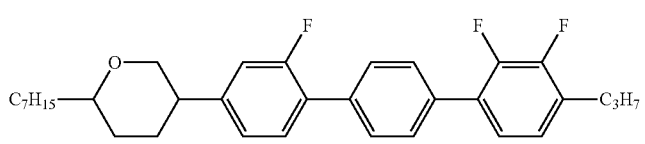 |
| 1484 | 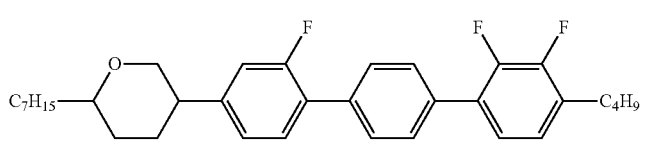 |
| 1485 | 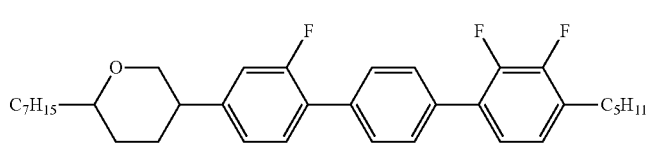 |
| 1486 | 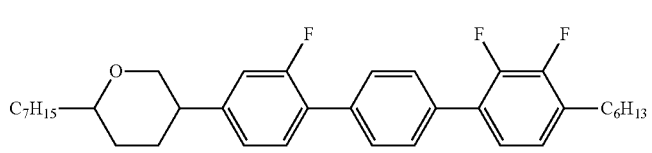 |
| 1487 | 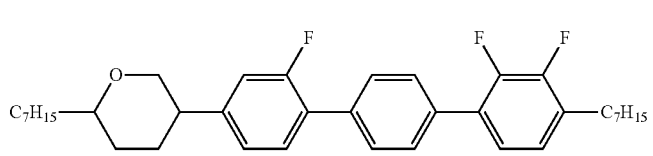 |
| 1488 | 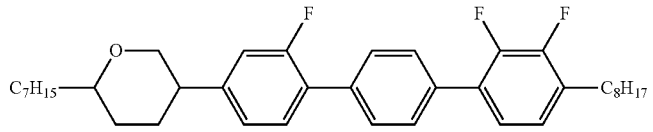 |
| 1489 | 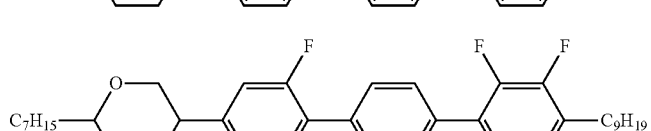 |
| 1490 | 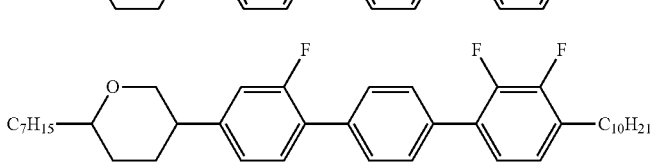 |

| No. |
|---|
| 1491 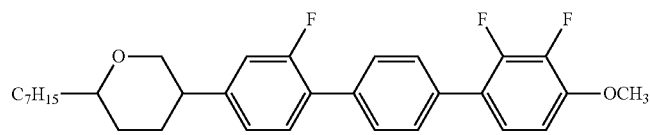 |
| 1492 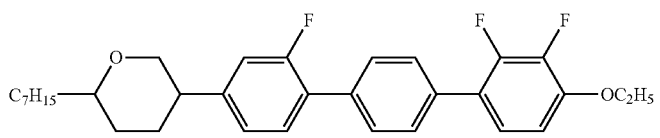 |
| 1493 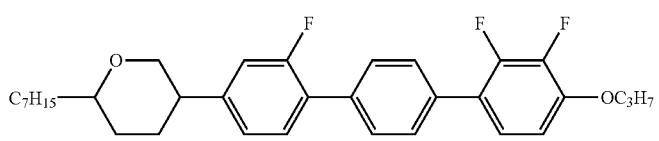 |
| 1494 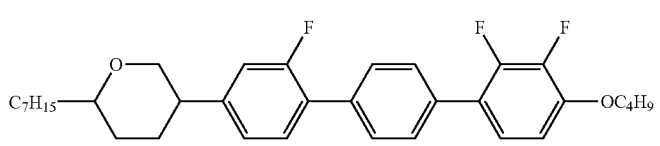 |
| 1495 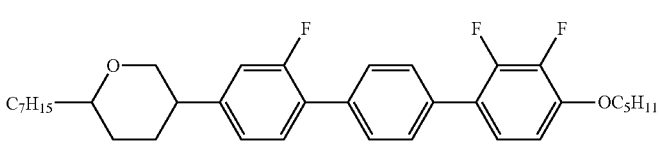 |
| 1496 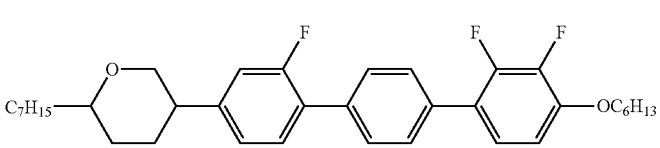 |
| 1497 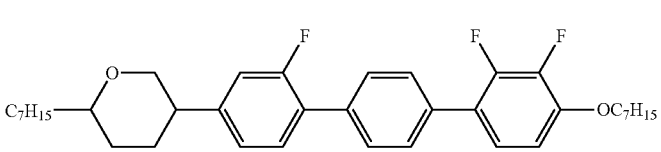 |
| 1498 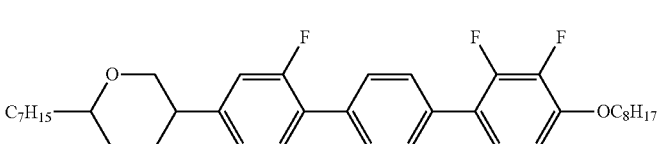 |
| 1499 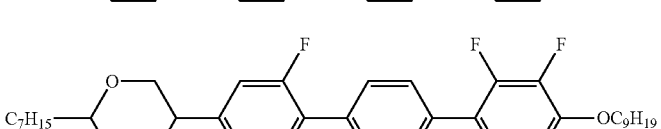 |
| 1500 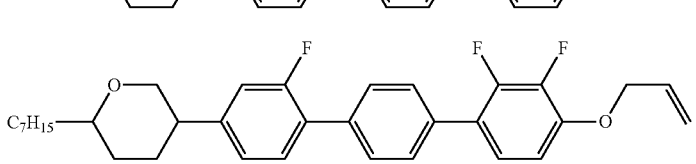 |
| 1501 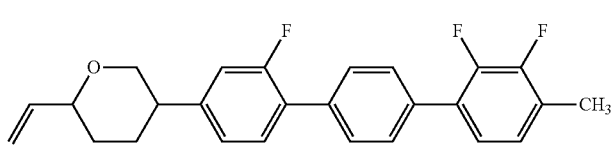 |

-continued
| No. |  |
|---|---|
| 1502 | 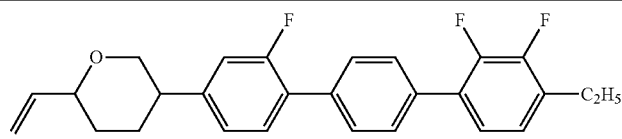 |
| 1503 | 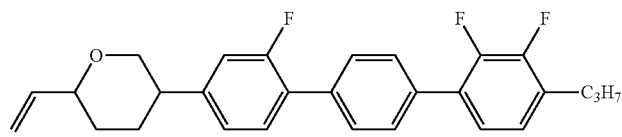 |
| 1504 | 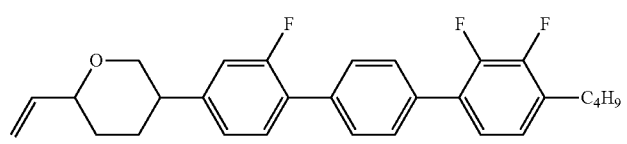 |
| 1505 | 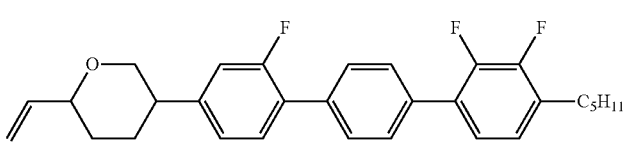 |
| 1506 | 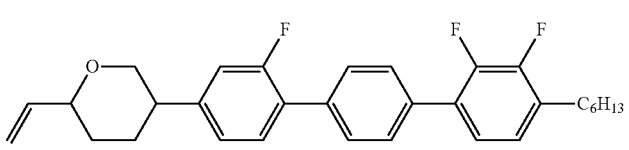 |
| 1507 | 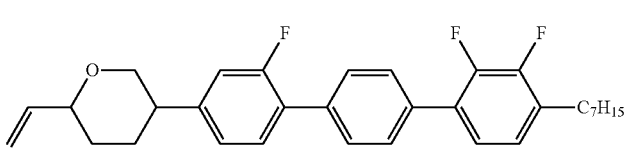 |
| 1508 | 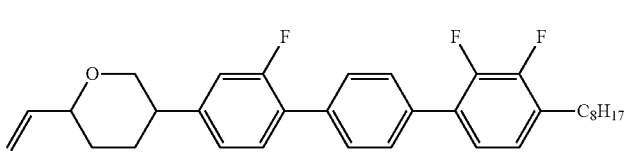 |
| 1509 | 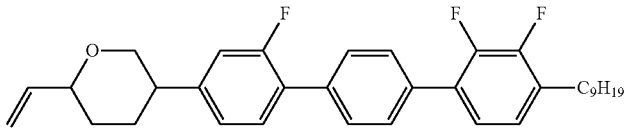 |
| 1510 | 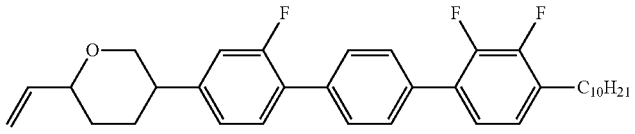 |
| 1511 |  |
| 1512 | 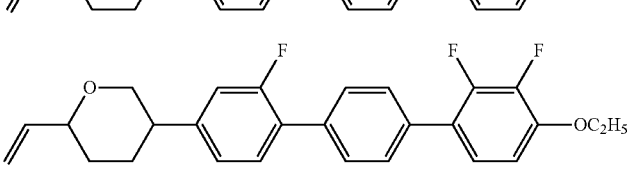 |

| No. | |
|---|---|
| 1513 | 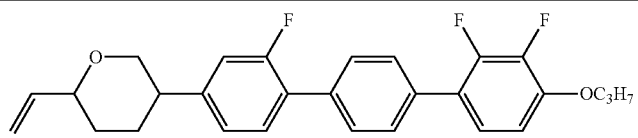 |
| 1514 | 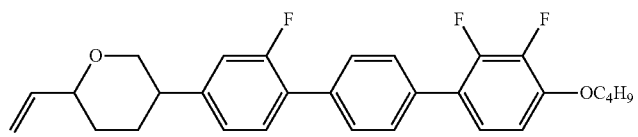 |
| 1515 | 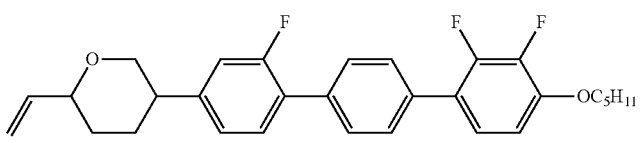 |
| 1516 | 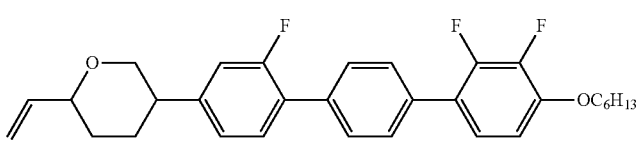 |
| 1517 | 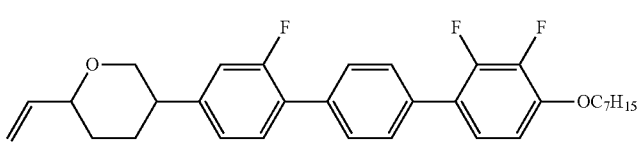 |
| 1518 | 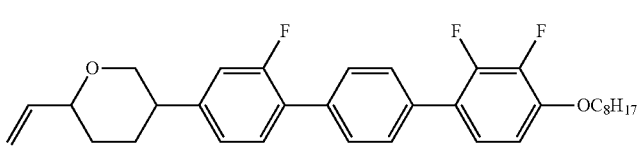 |
| 1519 | 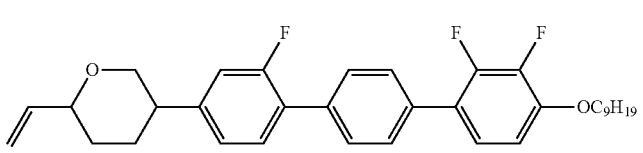 |
| 1520 | 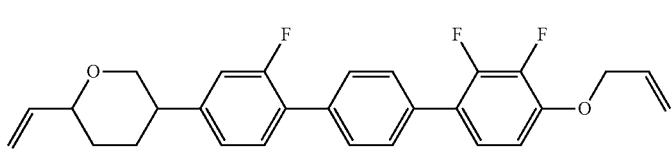 |
| 1521 | 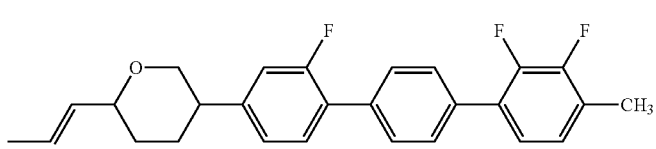 |
| 1522 | 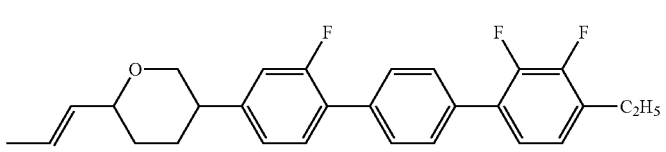 |
| 1523 | 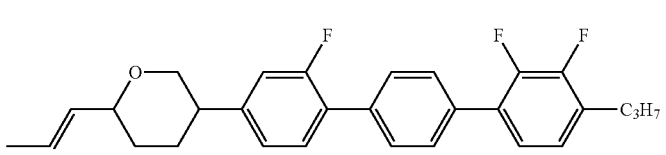 |

-continued
| No. | |
|---|---|
| 1524 | 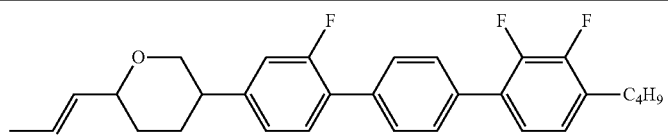 |
| 1525 | 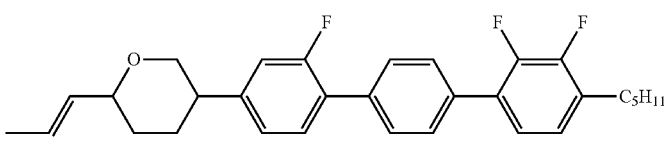 |
| 1526 | 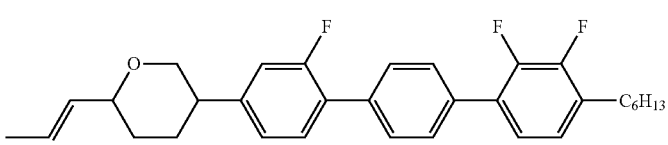 |
| 1527 | 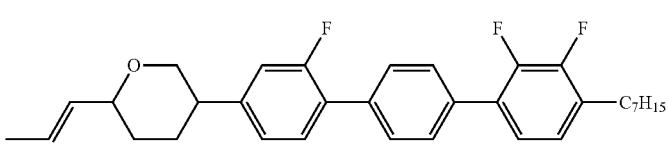 |
| 1528 | 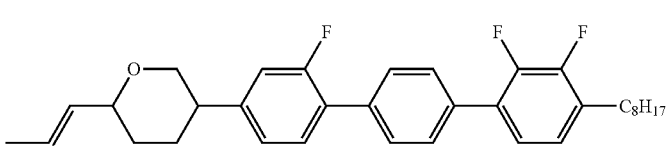 |
| 1529 | 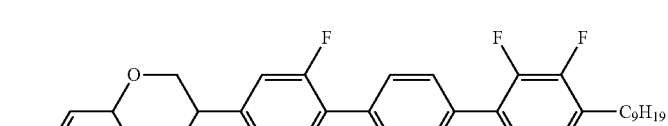 |
| 1530 | 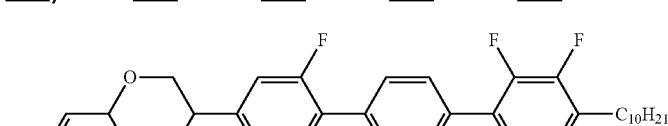 |
| 1531 | 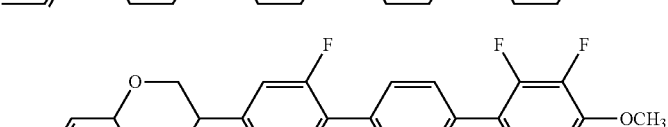 |
| 1532 | 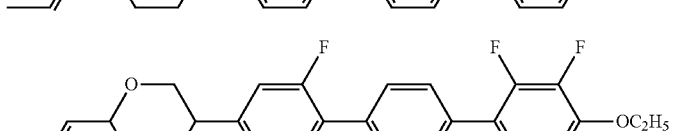 |
| 1533 | 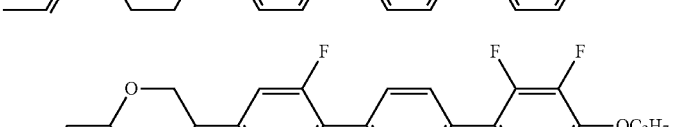 |
| 1534 | 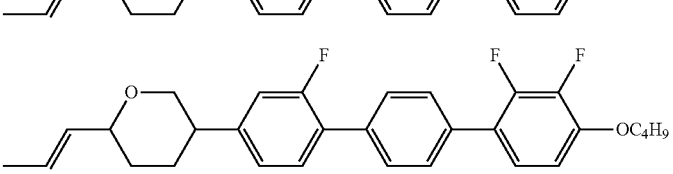 |

| No. | |
|---|---|
| 1535 | 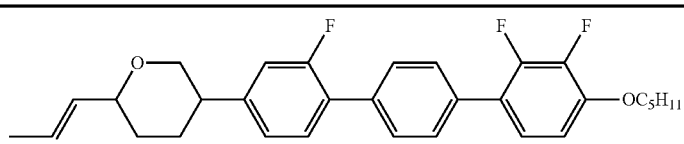 |
| 1536 | 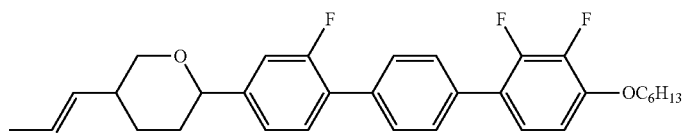 |
| 1537 | 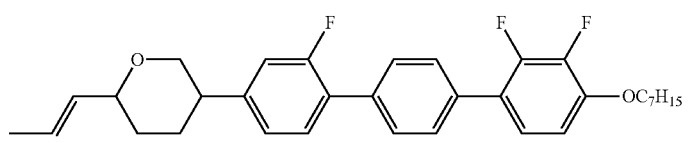 |
| 1538 | 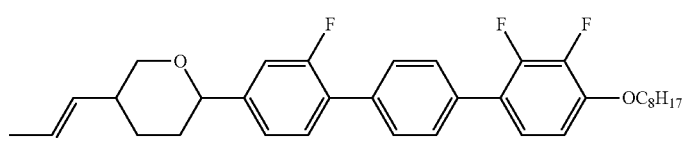 |
| 1539 | 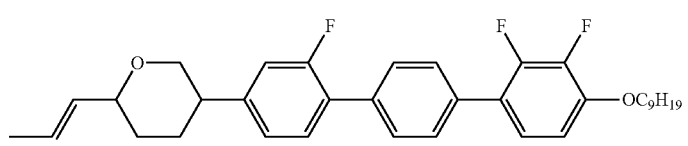 |
| 1540 | 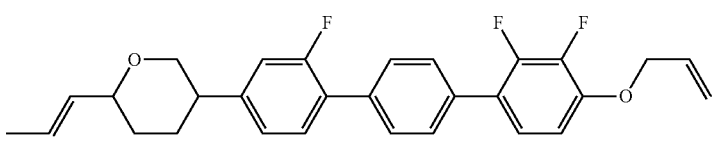 |
| 1541 | 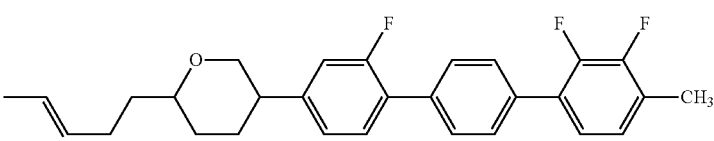 |
| 1542 | 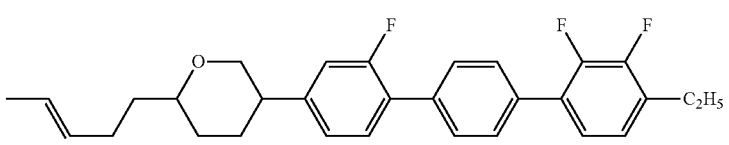 |
| 1543 | 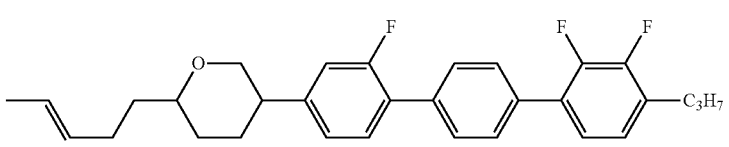 |
| 1544 | 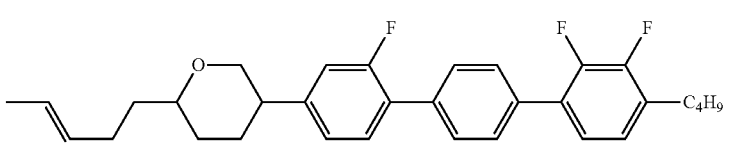 |
| 1545 | 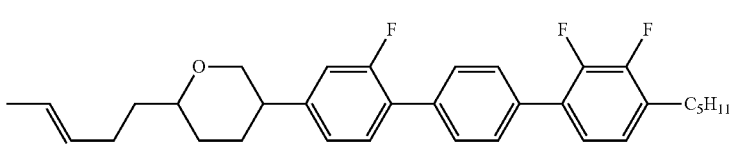 |

| No. | |
|---|---|
| 1546 | 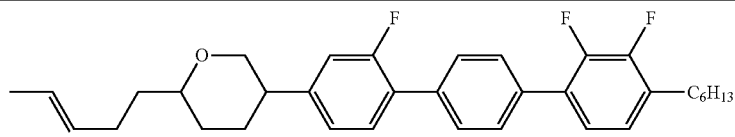 |
| 1547 | 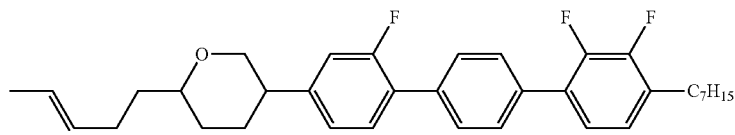 |
| 1548 | 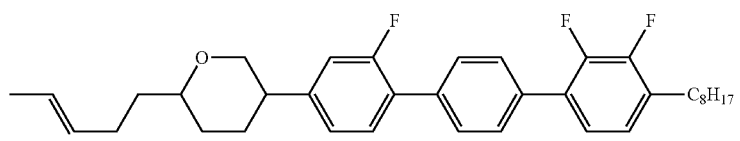 |
| 1549 | 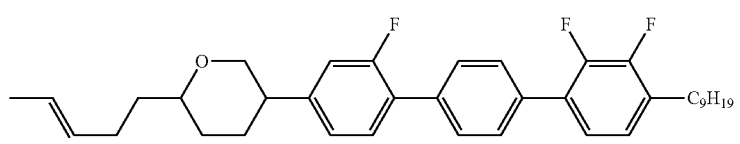 |
| 1550 |  |
| 1551 | 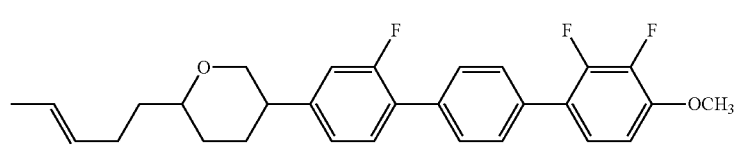 |
| 1552 | 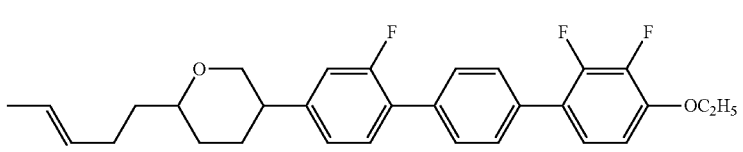 |
| 1553 | 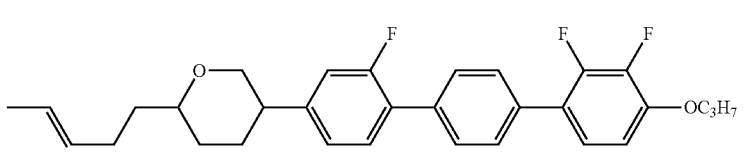 |
| 1554 | 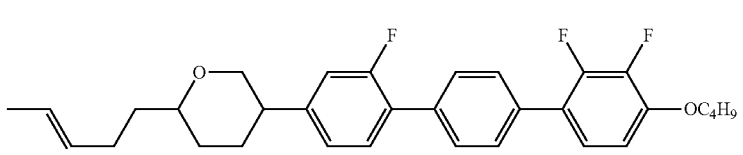 |
| 1555 | 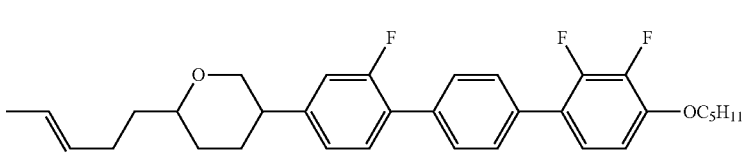 |
| 1556 | 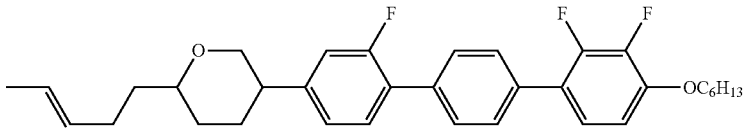 |

| No. |
|---|
| 1557 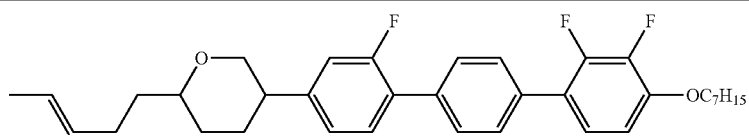 |
| 1558 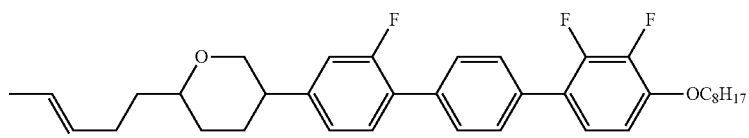 |
| 1559 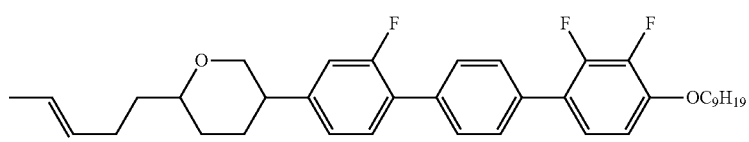 |
| 1560 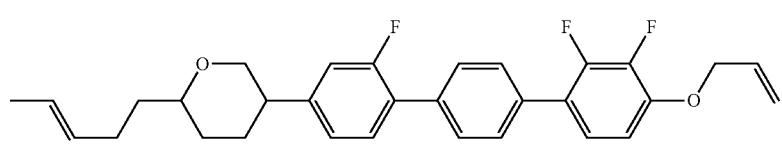 |
| 1561 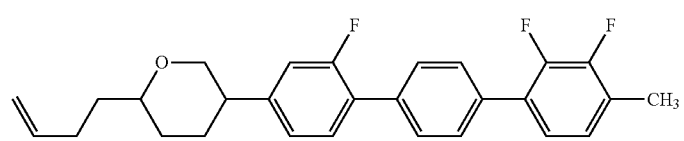 |
| 1562 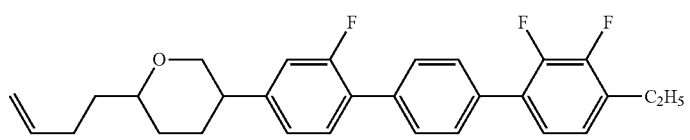 |
| 1563 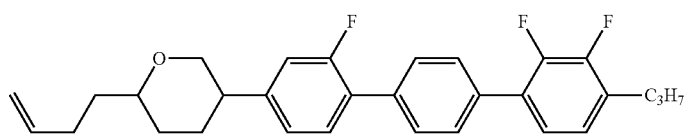 |
| 1564 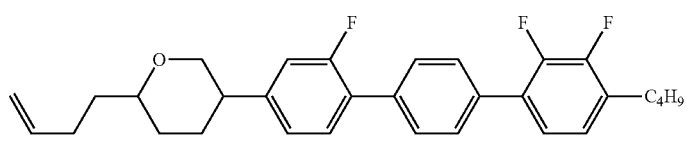 |
| 1565 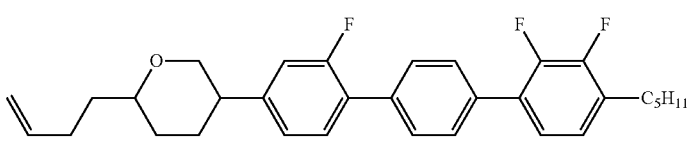 |
| 1566 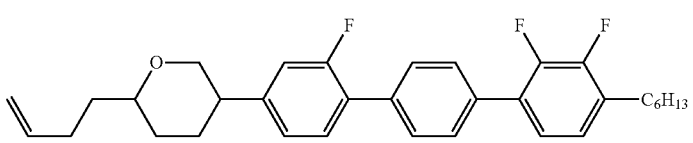 |
| 1567 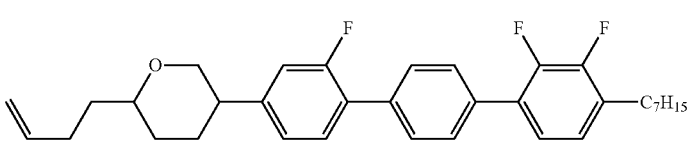 |

-continued
| No. |
|---|
| 1568 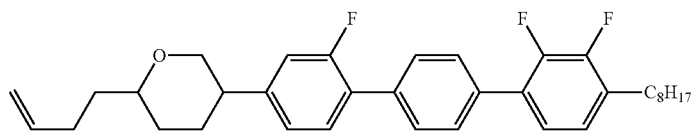 |
| 1569  |
| 1570 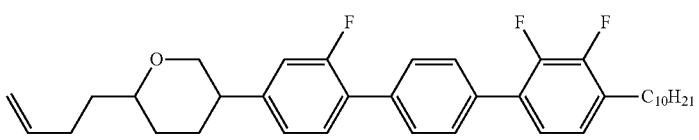 |
| 1571 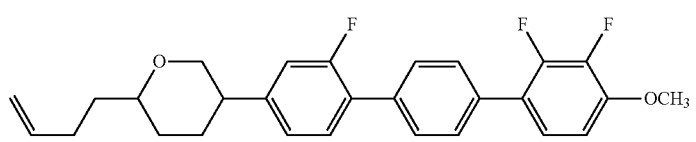 |
| 1572 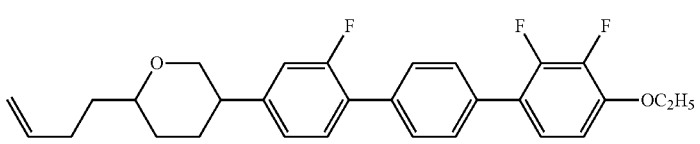 |
| 1573 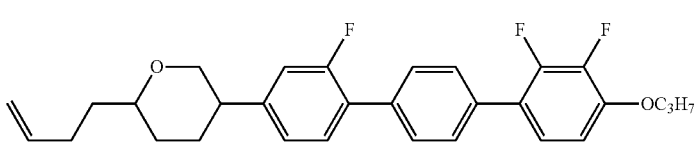 |
| 1574 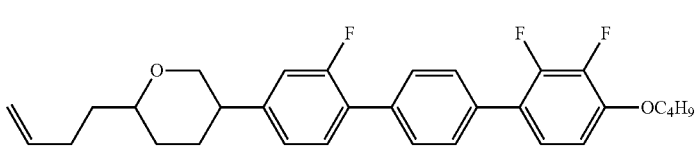 |
| 1575 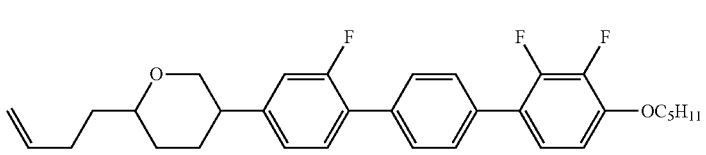 |
| 1576 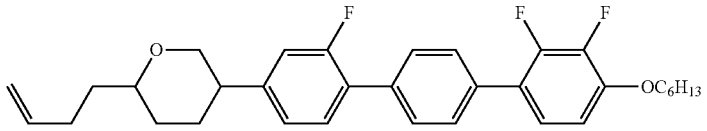 |
| 1577 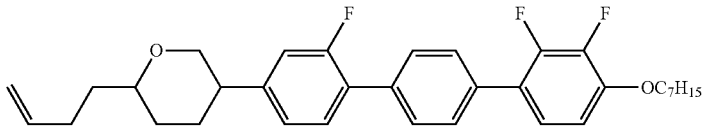 |
| 1578 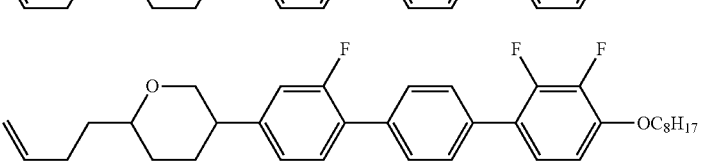 |

-continued
| No. | |
|---|---|
| 1579 | 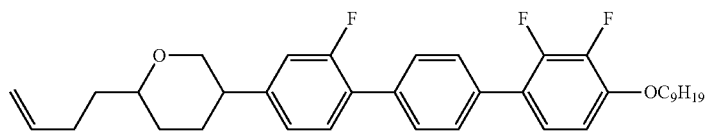 |
| 1580 | 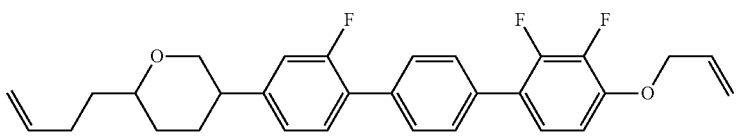 |
| 1581 | 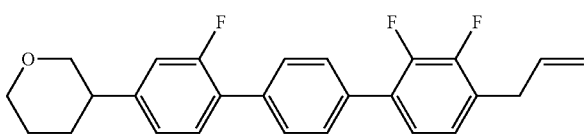 |
| 1582 | 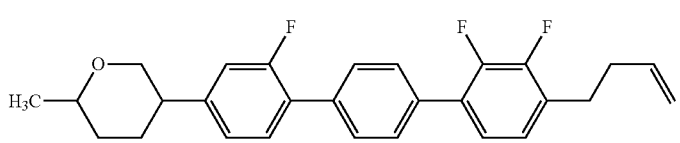 |
| 1583 |  |
| 1584 |  |
| 1585 | 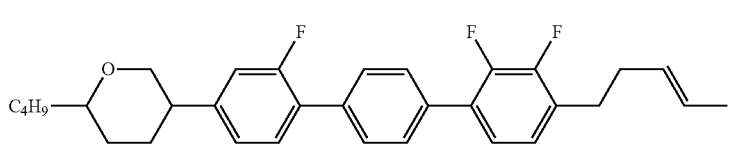 |
| 1586 |  |
| 1587 | 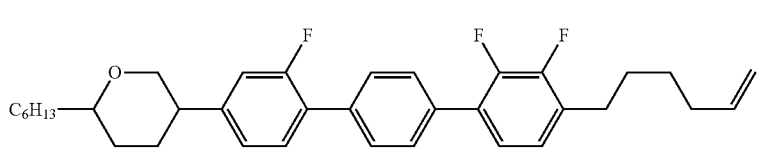 |
| 1588 | 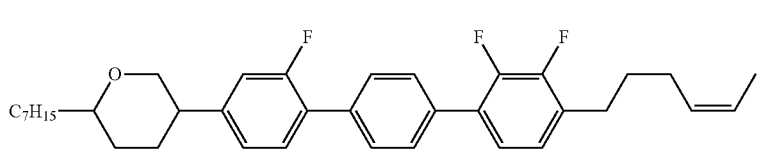 |
| 1589 | 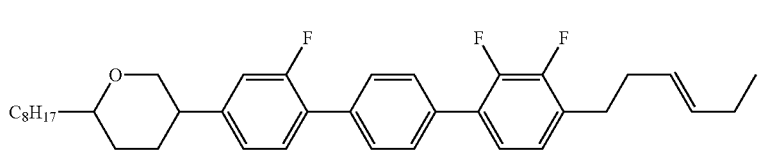 |

| No. |
|---|
| 1590 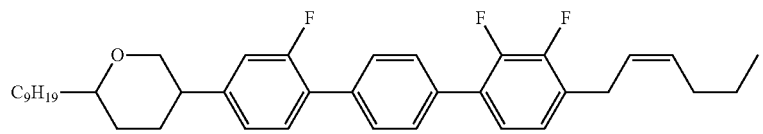 |
| 1591 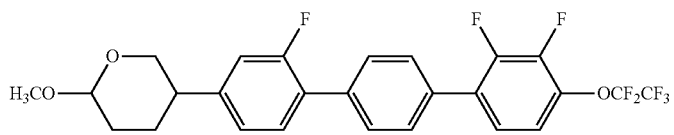 |
| 1592 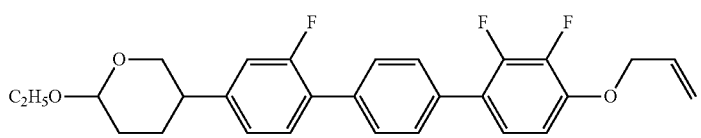 |
| 1593 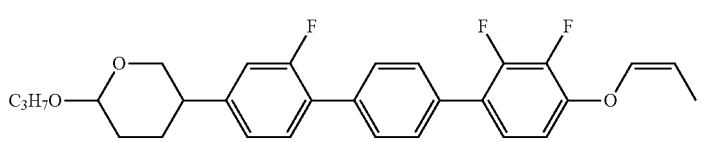 |
| 1594 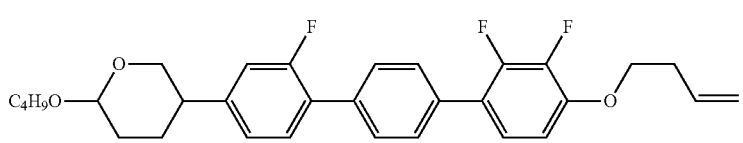 |
| 1595 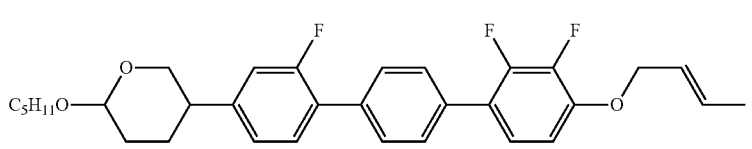 |
| 1596 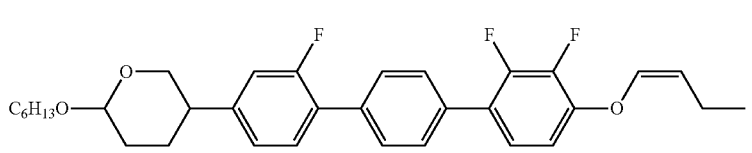 |
| 1597 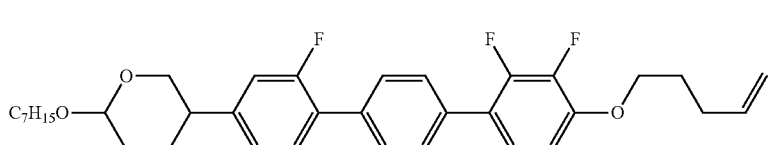 |
| 1598 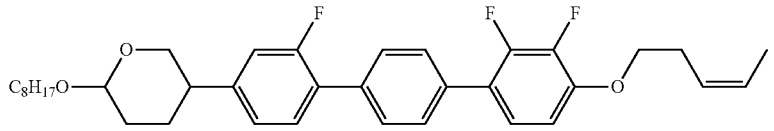 |
| 1599 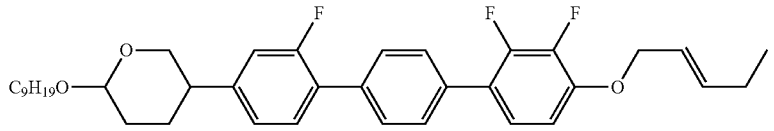 |
| 1600 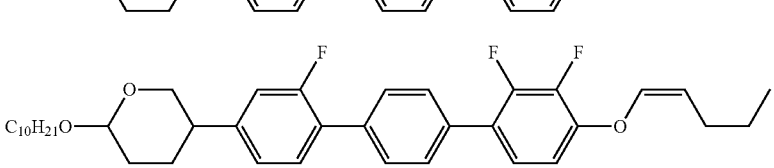 |

| No. | |
|---|---|
| 1601 | 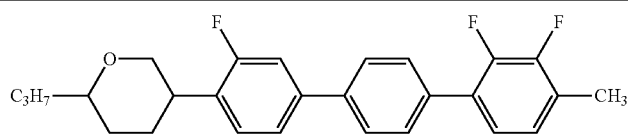 |
| 1602 | 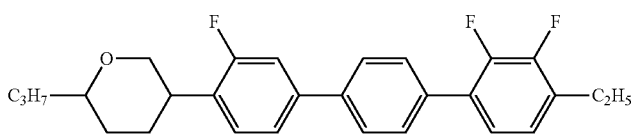 |
| 1603 | 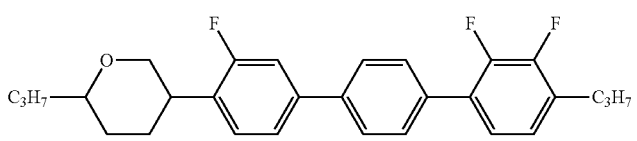 |
| 1604 |  |
| 1605 | 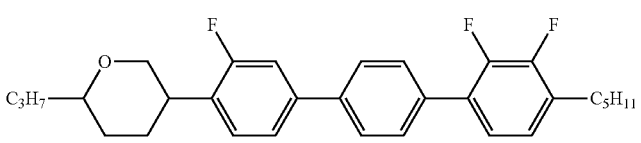 |
| 1606 | 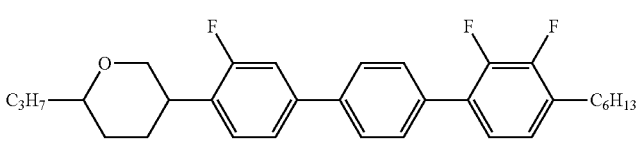 |
| 1607 | 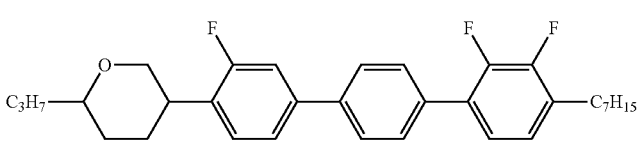 |
| 1608 | 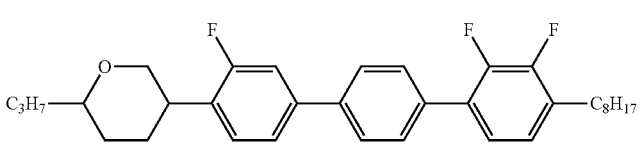 |
| 1609 | 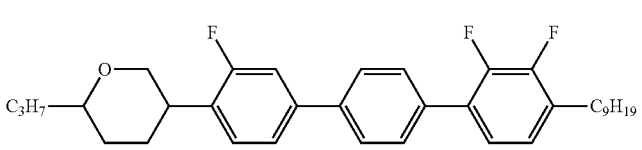 |
| 1610 | 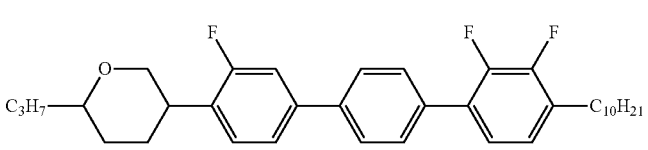 |
| 1611 | 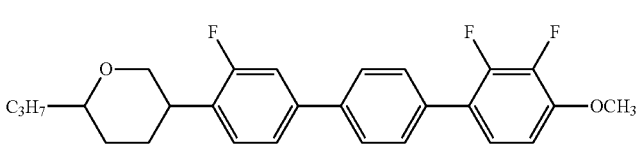 |

| No. | |
|---|---|
| 1612 | 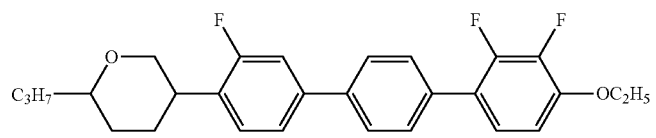 |
| 1613 | 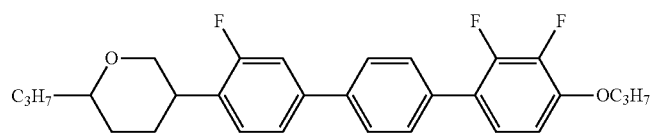 |
| 1614 | 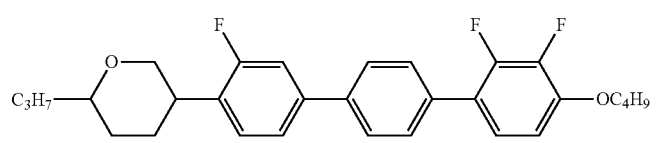 |
| 1615 | 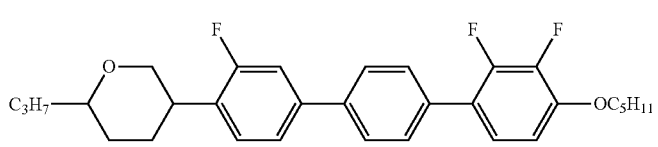 |
| 1616 | 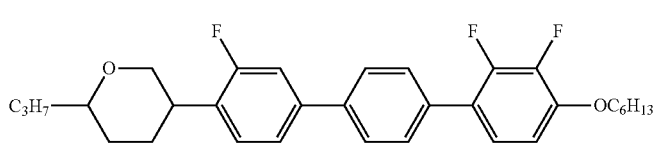 |
| 1617 | 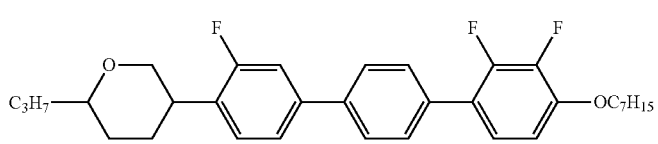 |
| 1618 | 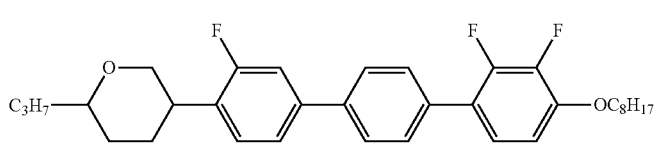 |
| 1619 | 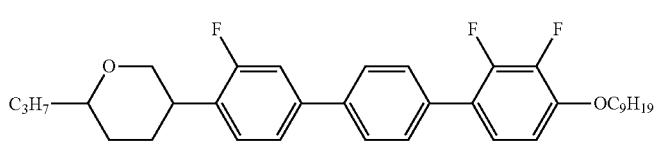 |
| 1620 | 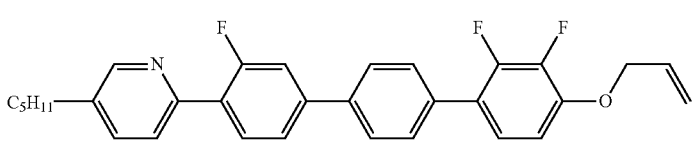 |
| 1621 | 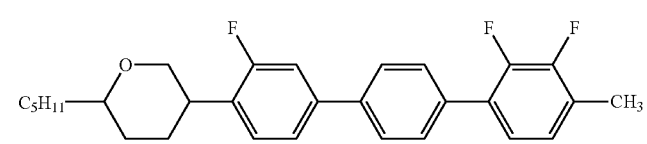 |
| 1622 | 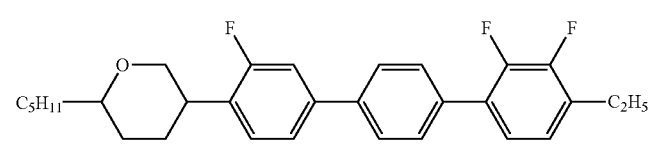 |

| No. | |
|---|---|
| 1623 | 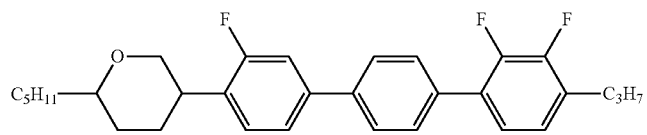 |
| 1624 | 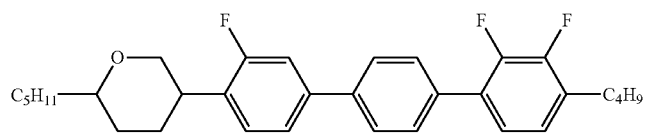 |
| 1625 | 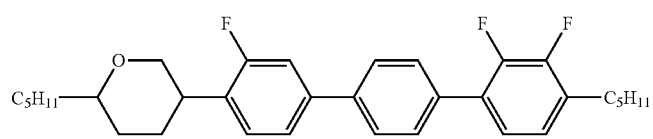 |
| 1626 | 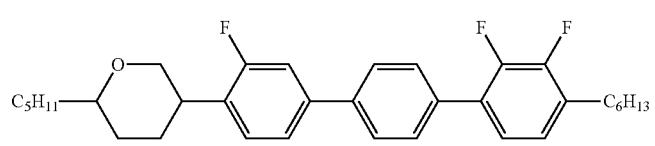 |
| 1627 | 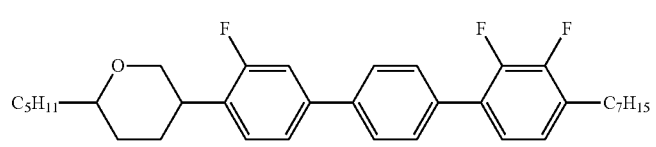 |
| 1628 | 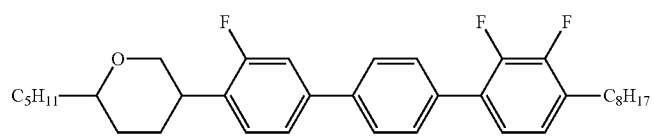 |
| 1629 | 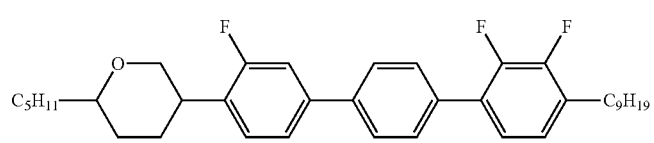 |
| 1630 |  |
| 1631 | 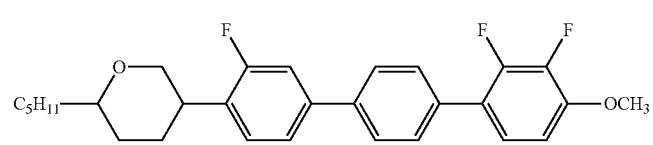 |
| 1632 | 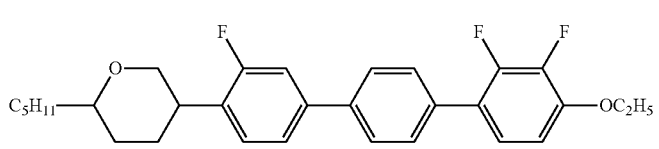 |
| 1633 | 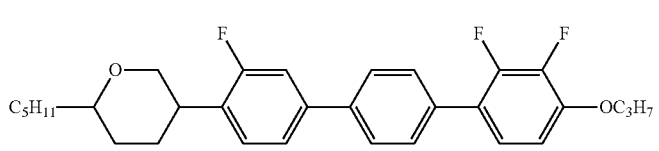 |

-continued
| No. | |
|---|---|
| 1634 | 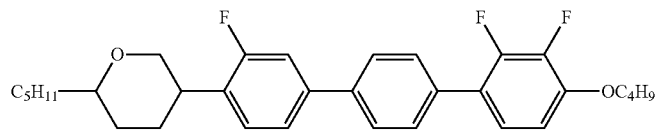 |
| 1635 | 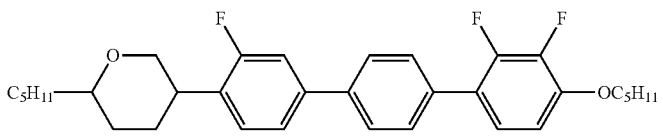 |
| 1636 | 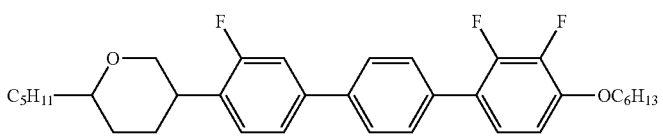 |
| 1637 | 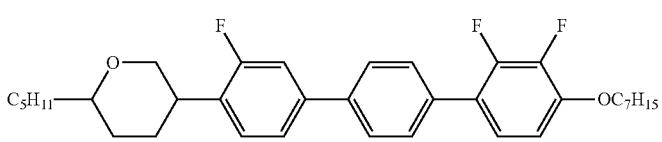 |
| 1638 | 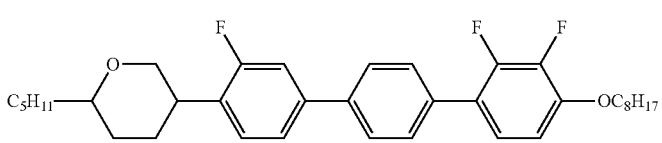 |
| 1639 | 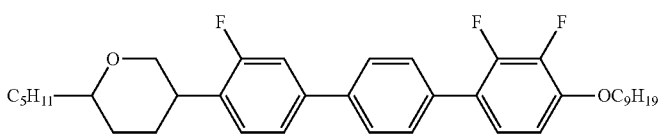 |
| 1640 | 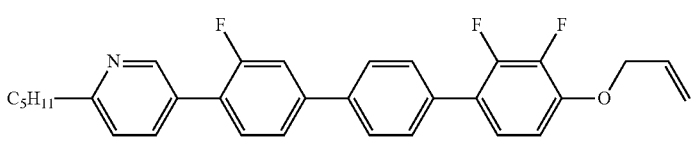 |
| 1641 | 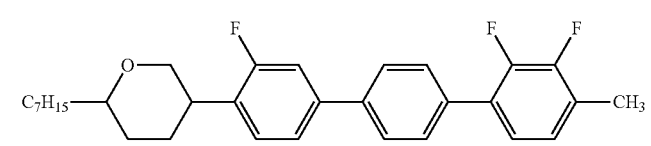 |
| 1642 | 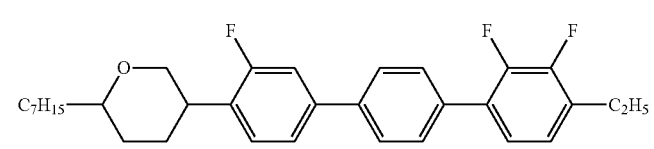 |
| 1643 | 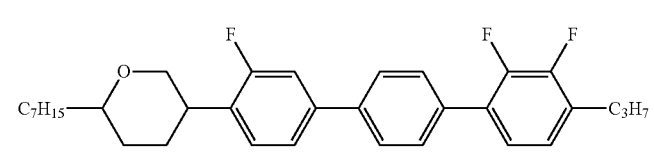 |
| 1644 | 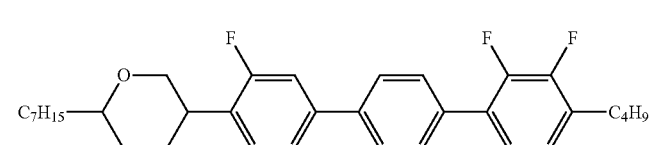 |

| No. | |
|---|---|
| 1645 | 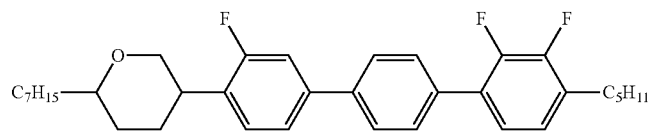 |
| 1646 | 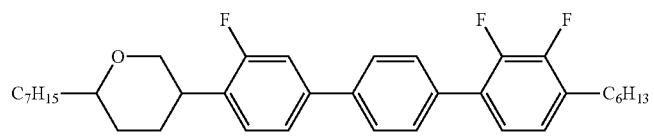 |
| 1647 | 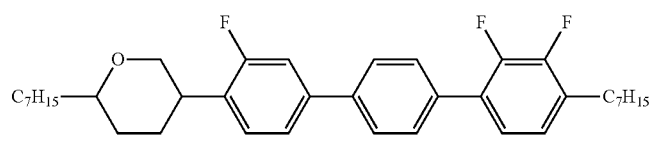 |
| 1648 | 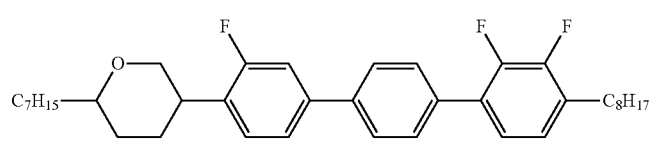 |
| 1649 | 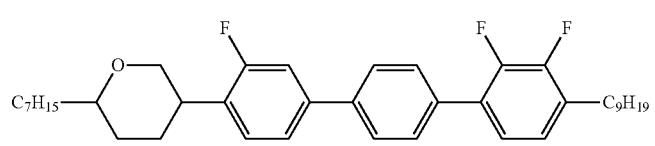 |
| 1650 | 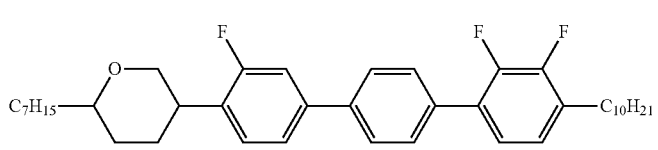 |
| 1651 | 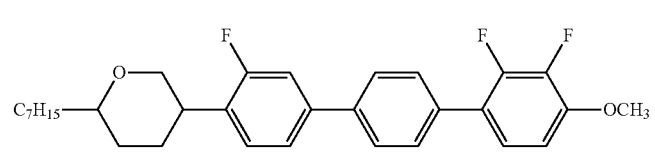 |
| 1652 | 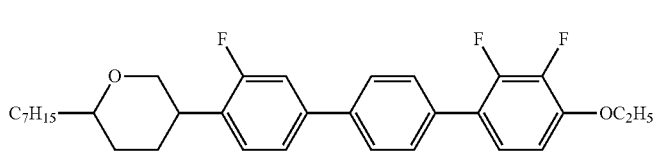 |
| 1653 | 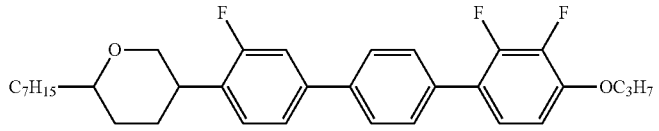 |
| 1654 | 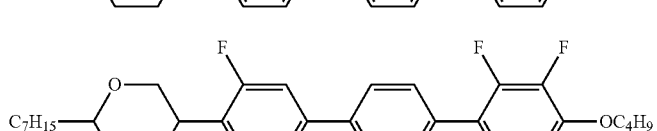 |
| 1655 | 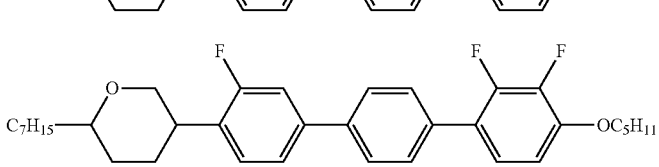 |

| No. | |
|---|---|
| 1656 | 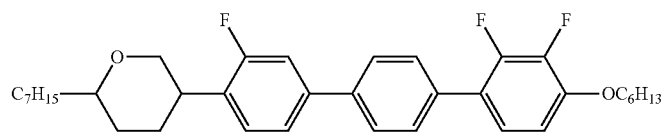 |
| 1657 | 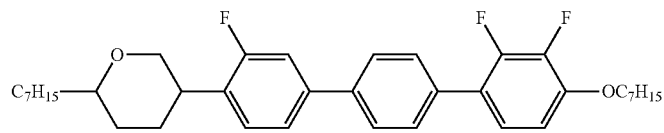 |
| 1658 | 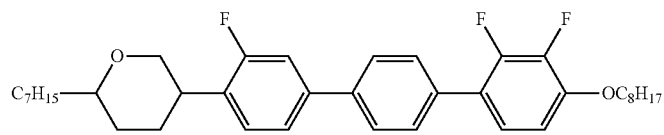 |
| 1659 | 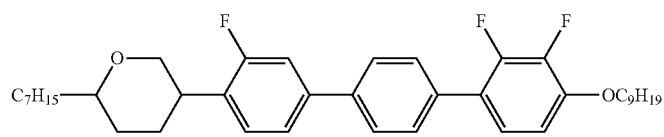 |
| 1660 | 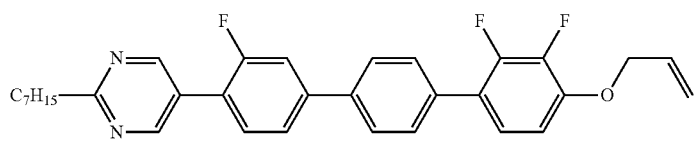 |
| 1661 | 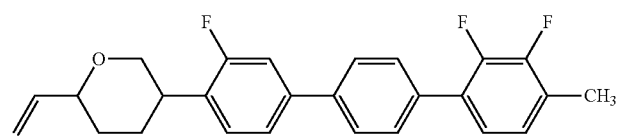 |
| 1662 | 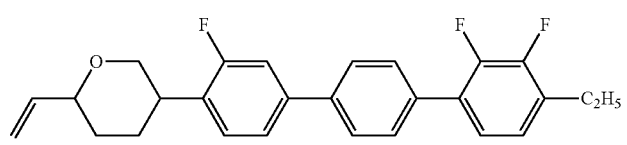 |
| 1663 | 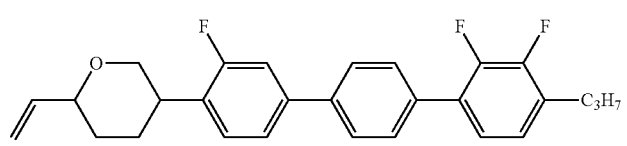 |
| 1664 | 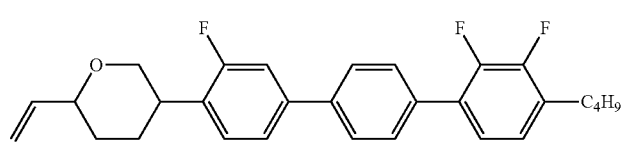 |
| 1665 |  |
| 1666 | 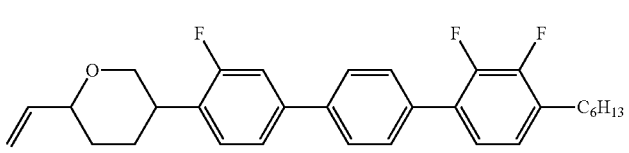 |

-continued
| No. | |
|---|---|
| 1667 | 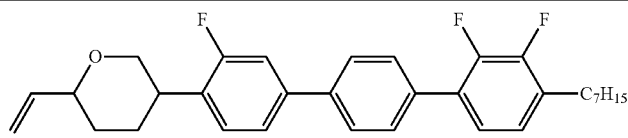 —C7H15 |
| 1668 | 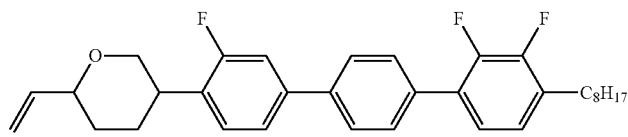 —C8H17 |
| 1669 | 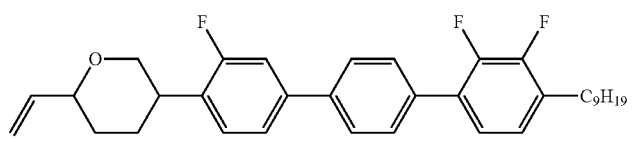 —C9H19 |
| 1670 | 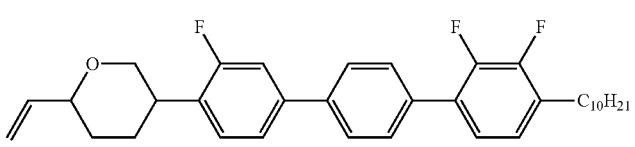 —C10H21 |
| 1671 | 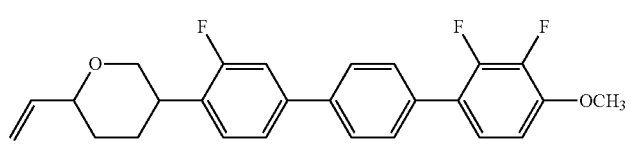 —OCH3 |
| 1672 | 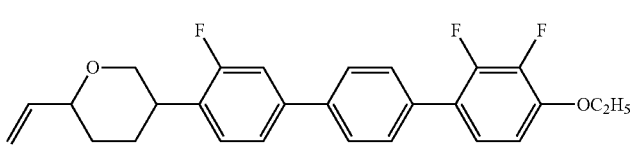 —OC2H5 |
| 1673 | 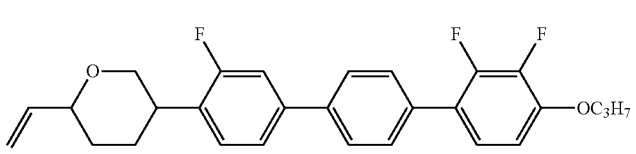 —OC3H7 |
| 1674 | 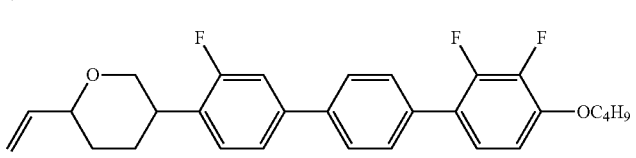 —OC4H9 |
| 1675 | 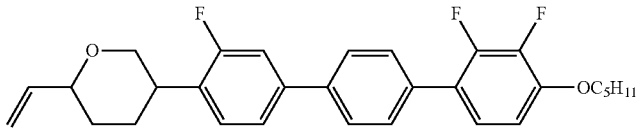 —OC5H11 |
| 1676 | 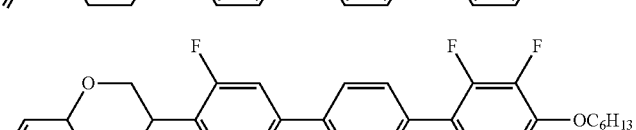 —OC6H13 |
| 1677 | 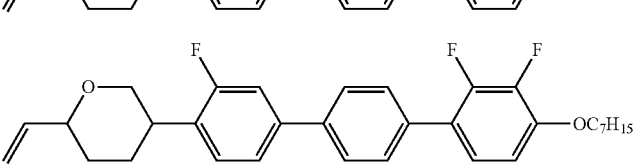 —OC7H15 |

| No. | |
|---|---|
| 1678 | 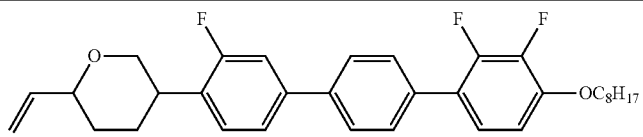 |
| 1679 | 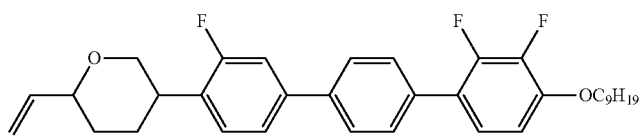 |
| 1680 | 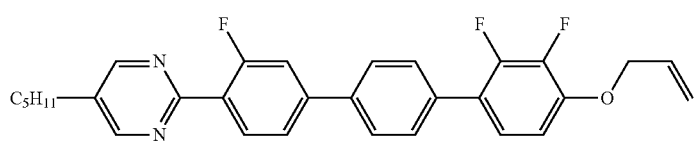 |
| 1681 | 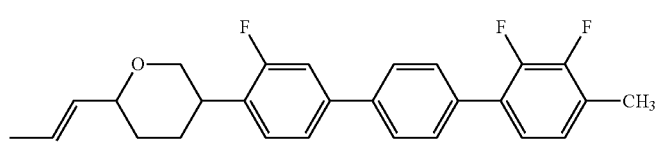 |
| 1682 | 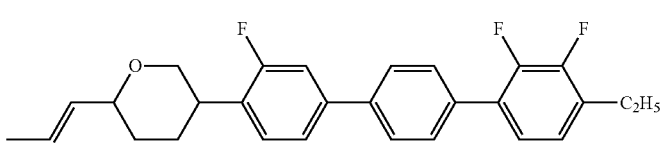 |
| 1683 | 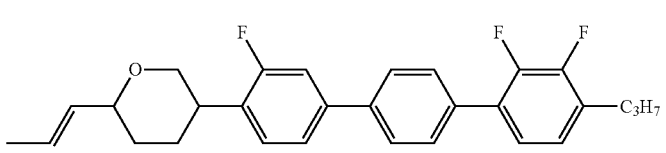 |
| 1684 | 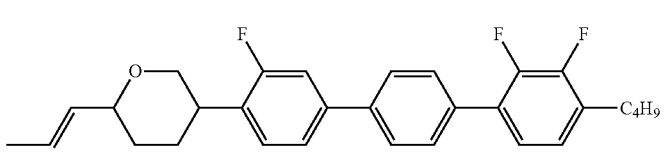 |
| 1685 | 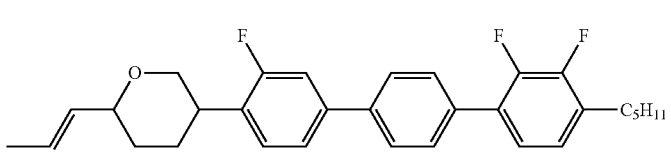 |
| 1686 | 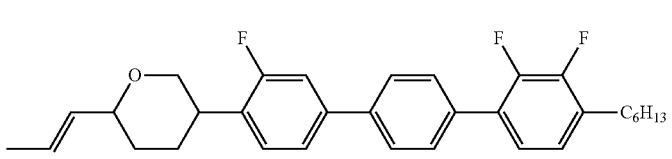 |
| 1687 | 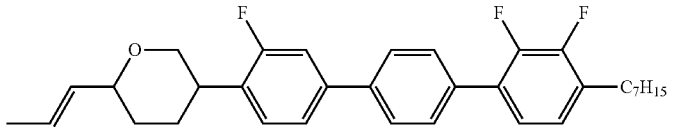 |
| 1688 | 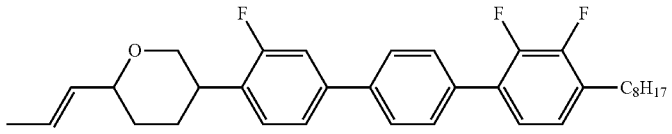 |

| No. | |
|---|---|
| 1689 | 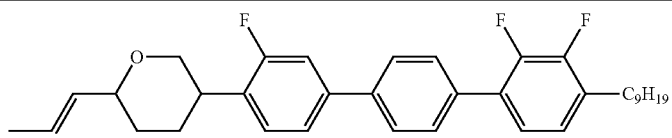 |
| 1690 | 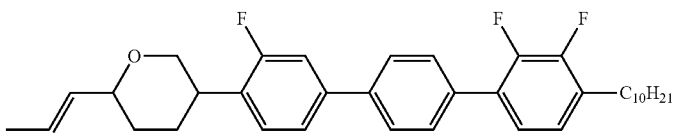 |
| 1691 | 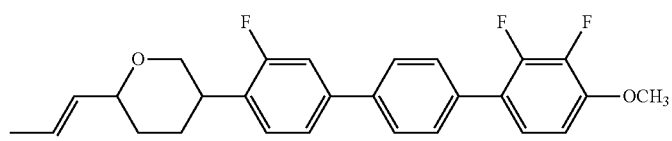 |
| 1692 | 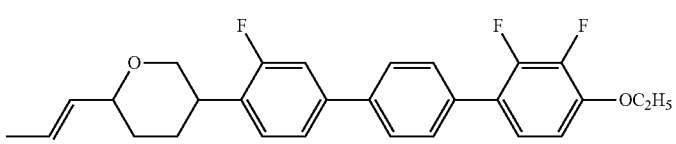 |
| 1693 | 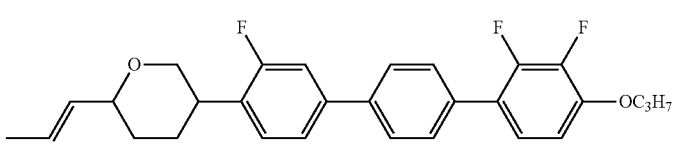 |
| 1694 | 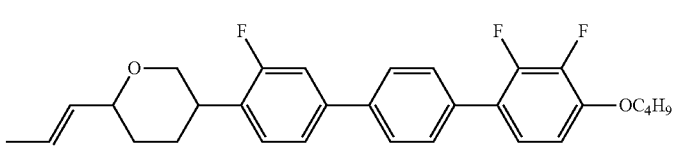 |
| 1695 | 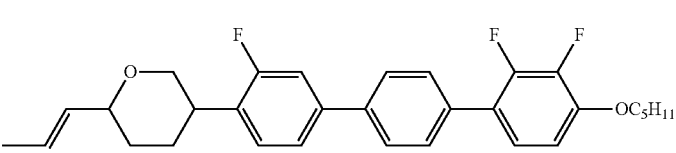 |
| 1696 | 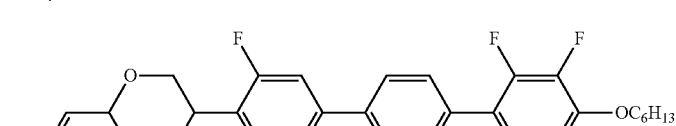 |
| 1697 | 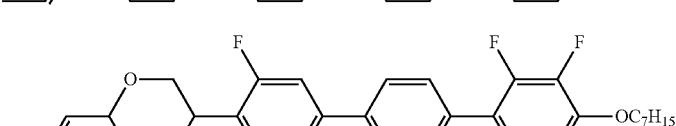 |
| 1698 | 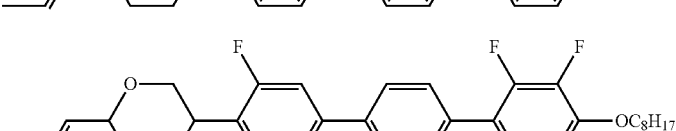 |
| 1699 | 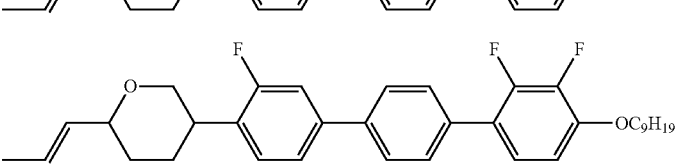 |

| No. | |
|---|---|
| 1700 | 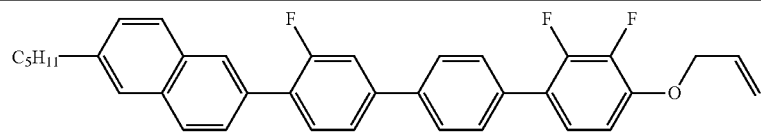 |
| 1701 | 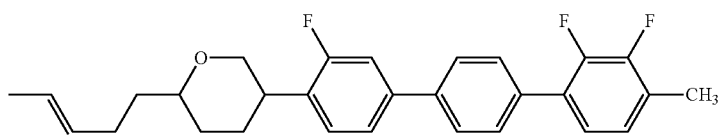 |
| 1702 | 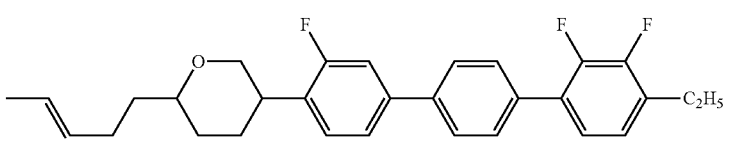 |
| 1703 | 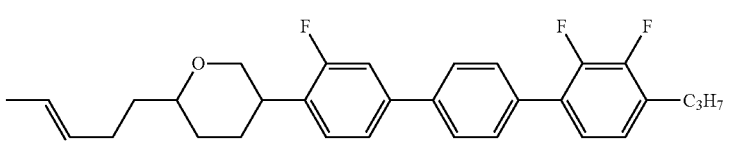 |
| 1704 | 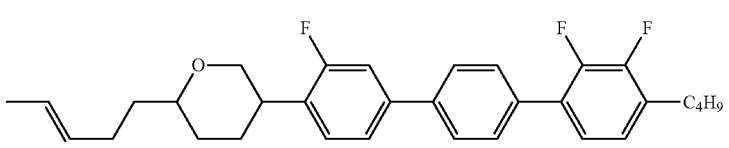 |
| 1705 | 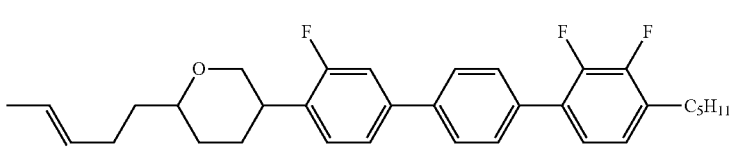 |
| 1706 | 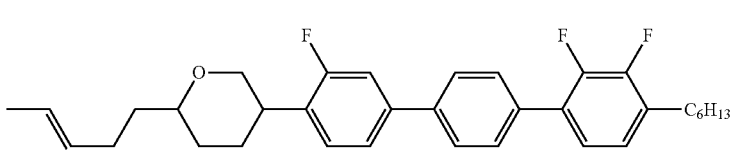 |
| 1707 | 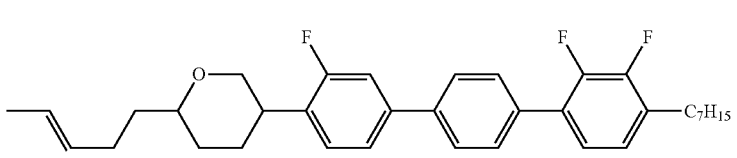 |
| 1708 | 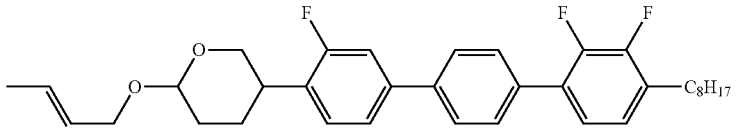 |
| 1709 | 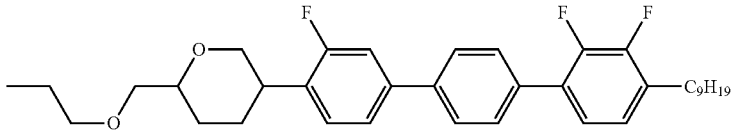 |
| 1710 | 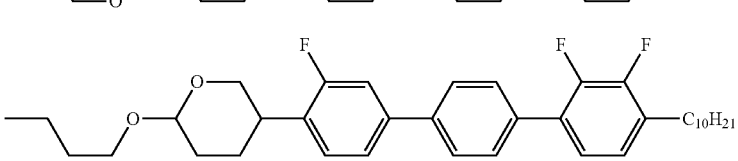 |

-continued
| No. | |
|---|---|
| 1711 | 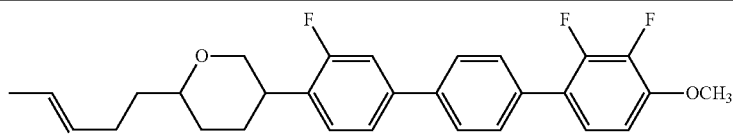 |
| 1712 | 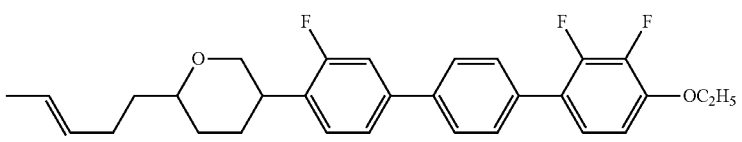 |
| 1713 | 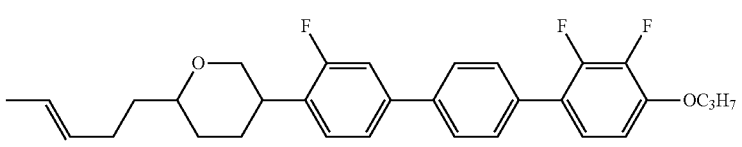 |
| 1714 | 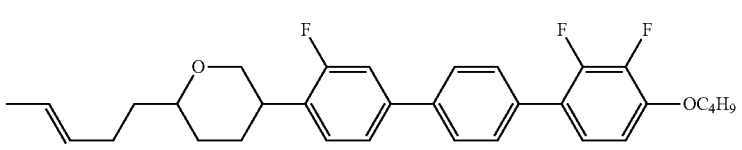 |
| 1715 | 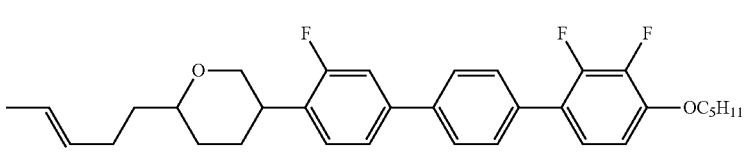 |
| 1716 | 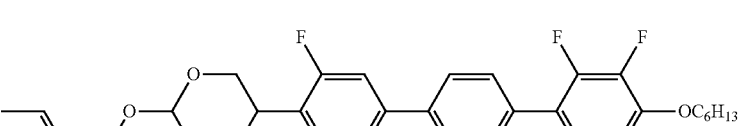 |
| 1717 | 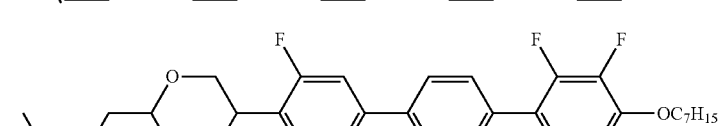 |
| 1718 | 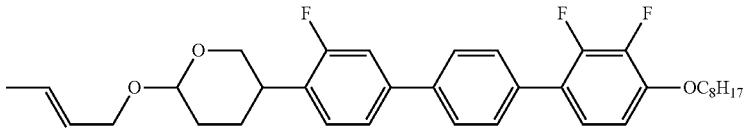 |
| 1719 | 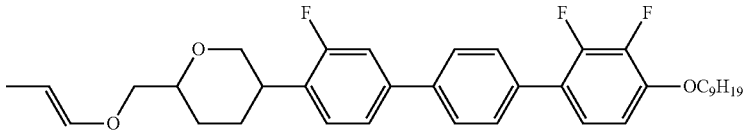 |
| 1720 | 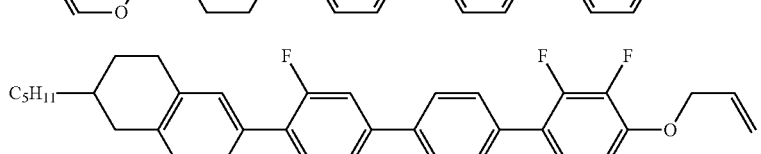 |
| 1721 | 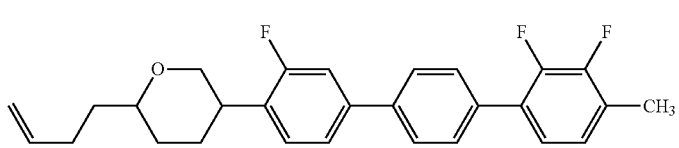 |

-continued
| No. | |
|---|---|
| 1722 | 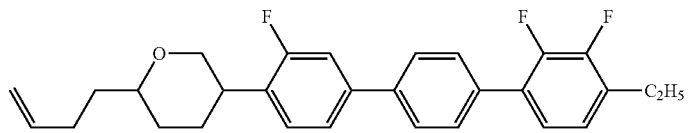 |
| 1723 | 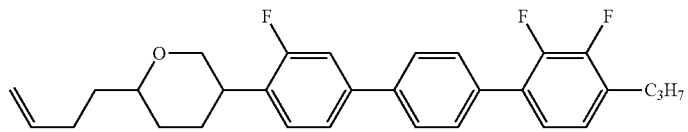 |
| 1724 | 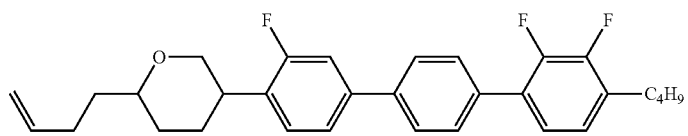 |
| 1725 | 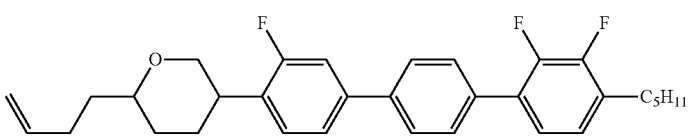 |
| 1726 | 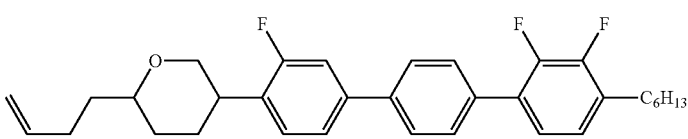 |
| 1727 | 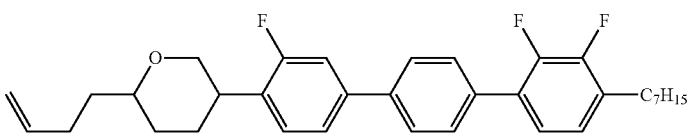 |
| 1728 | 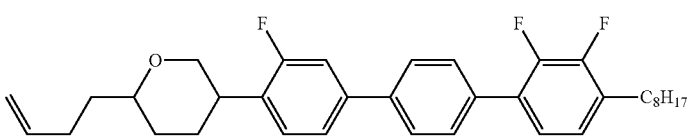 |
| 1729 | 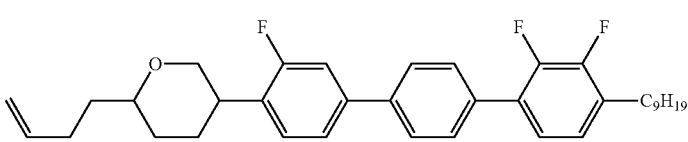 |
| 1730 | 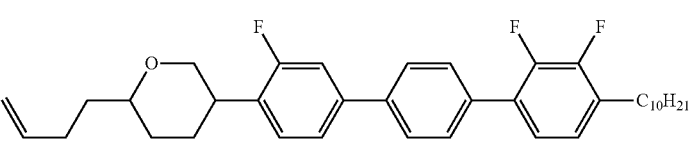 |
| 1731 | 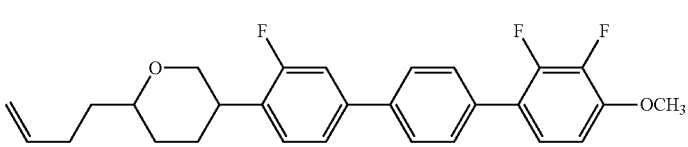 |
| 1732 | 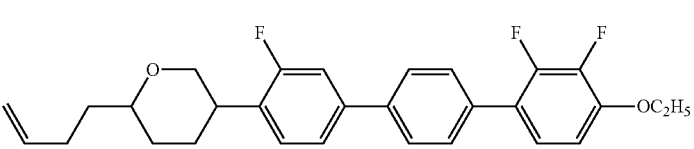 |

-continued
| No. | |
|---|---|
| 1733 | 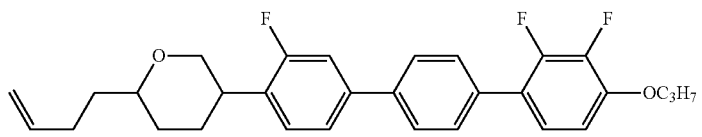 |
| 1734 | 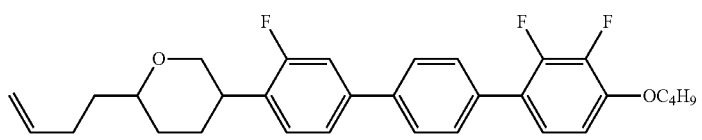 |
| 1735 | 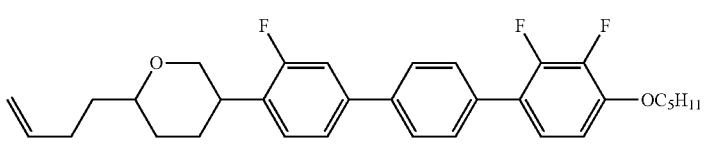 |
| 1736 | 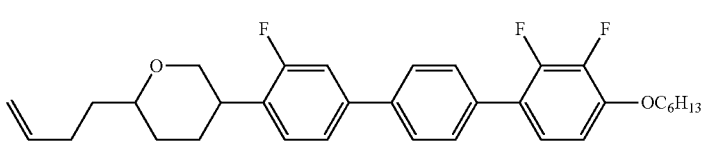 |
| 1737 | 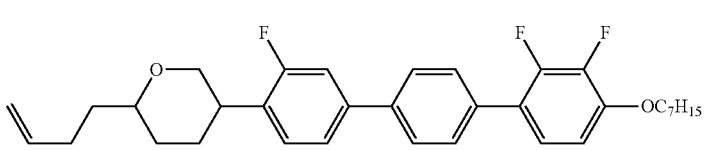 |
| 1738 | 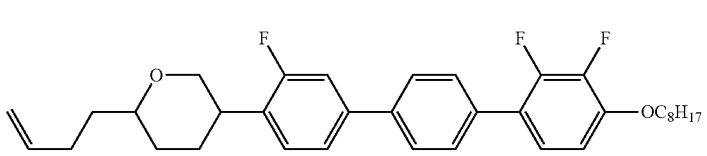 |
| 1739 | 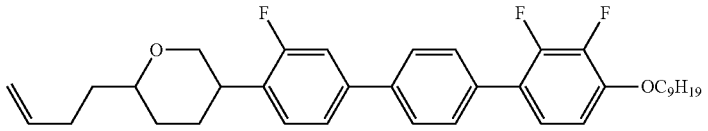 |
| 1740 | 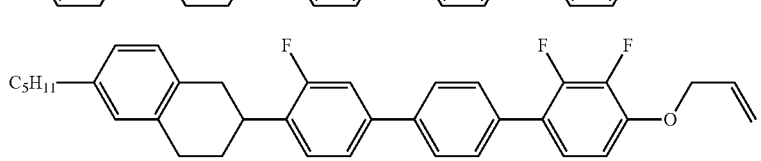 |
| 1741 | 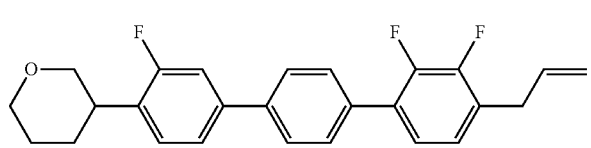 |
| 1742 | 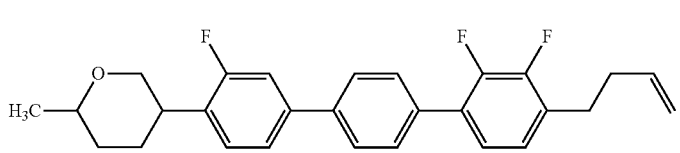 |
| 1743 | 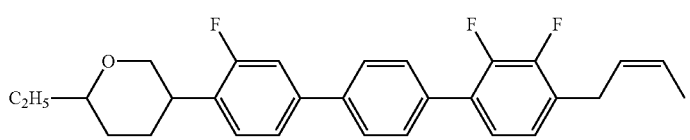 |

| No. |
|---|
| 1744 |
| 1745 |
| 1746 |
| 1747 |
| 1748 |
| 1749 |
| 1750 |
| 1751 |
| 1752 |
| 1753 |
| 1754 |

| No. |
|---|
| 1755 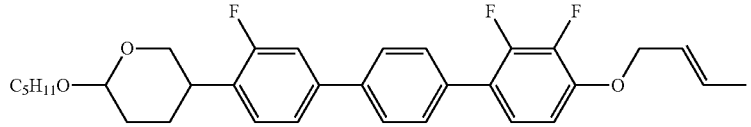 |
| 1756 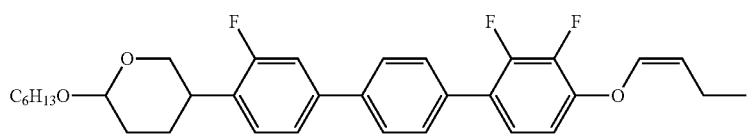 |
| 1757 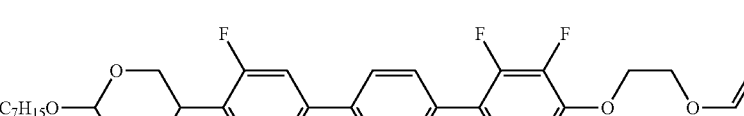 |
| 1758 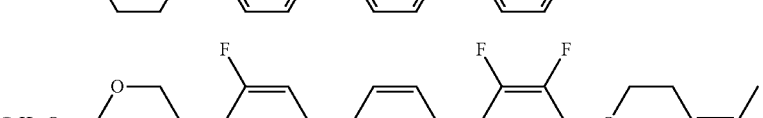 |
| 1759 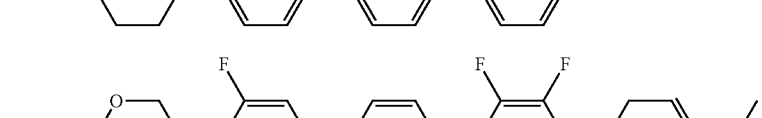 |
| 1760 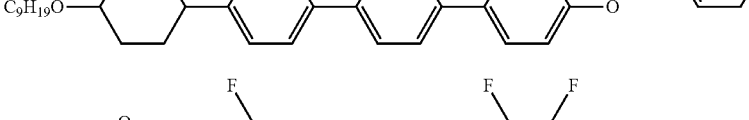 |
| 1761 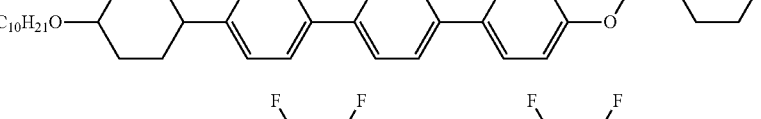 |
| 1762 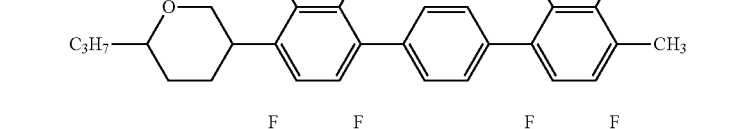 |
| 1763 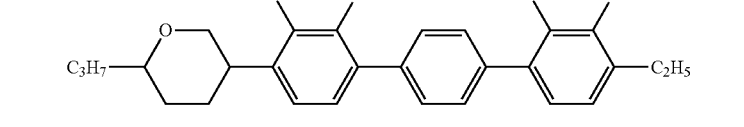 |
| 1764 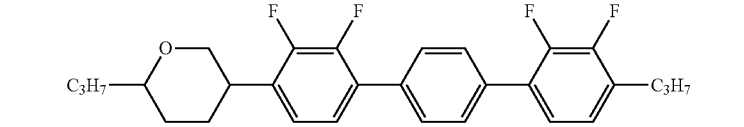 |
| 1765 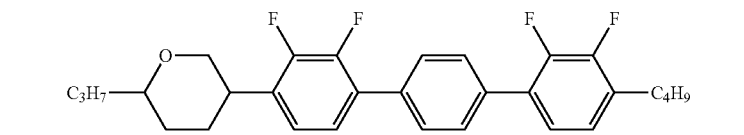 |

| No. | |
|---|---|
| 1766 | C3H7—[tetrahydropyran]—[C6H2F2]—[C6H4]—[C6H2F2]—C6H13 |
| 1767 | C3H7—[tetrahydropyran]—[C6H2F2]—[C6H4]—[C6H2F2]—C7H15 |
| 1768 | C3H7—[tetrahydropyran]—[C6H2F2]—[C6H4]—[C6H2F2]—C8H17 |
| 1769 | C3H7—[tetrahydropyran]—[C6H2F2]—[C6H4]—[C6H2F2]—C9H19 |
| 1770 | C3H7—[tetrahydropyran]—[C6H2F2]—[C6H4]—[C6H2F2]—C10H21 |
| 1771 | C3H7—[tetrahydropyran]—[C6H2F2]—[C6H4]—[C6H2F2]—OCH3 |
| 1772 | C3H7—[tetrahydropyran]—[C6H2F2]—[C6H4]—[C6H2F2]—OC2H5 |
| 1773 | C3H7—[tetrahydropyran]—[C6H2F2]—[C6H4]—[C6H2F2]—OC3H7 |
| 1774 | C3H7—[tetrahydropyran]—[C6H2F2]—[C6H4]—[C6H2F2]—OC4H9 |
| 1775 | C3H7—[tetrahydropyran]—[C6H2F2]—[C6H4]—[C6H2F2]—OC5H11 |
| 1776 | C3H7—[tetrahydropyran]—[C6H2F2]—[C6H4]—[C6H2F2]—OC6H13 |

-continued
| No. | |
|---|---|
| 1777 | 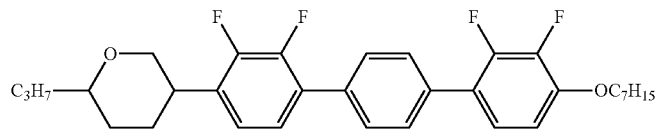 |
| 1778 | 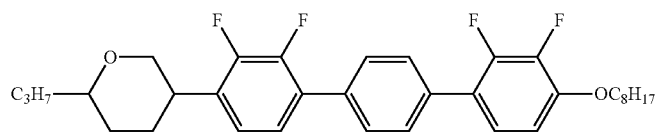 |
| 1779 | 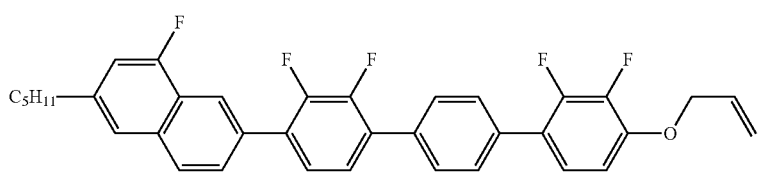 |
| 1780 | 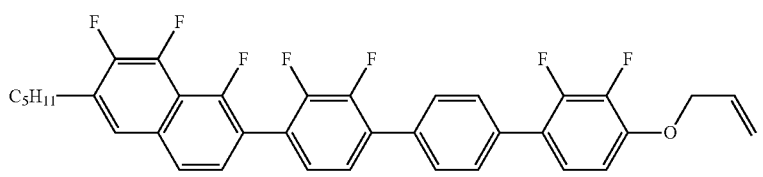 |
| 1781 | 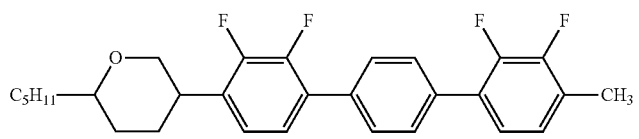 |
| 1782 | 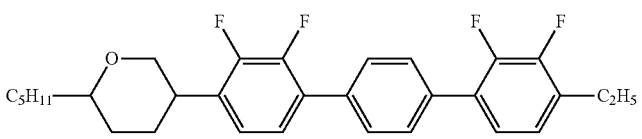 |
| 1783 | 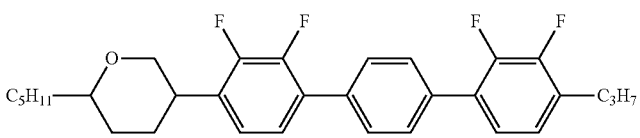 |
| 1784 | 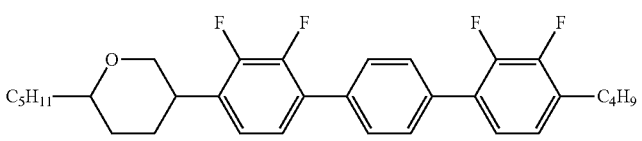 |
| 1785 | 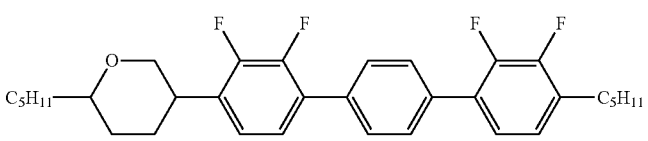 |
| 1786 | 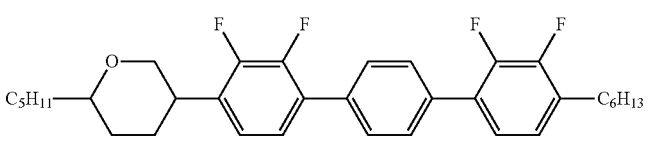 |

| No. | |
|---|---|
| 1787 | 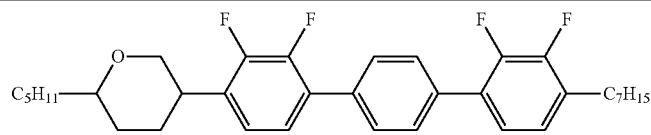 |
| 1788 | 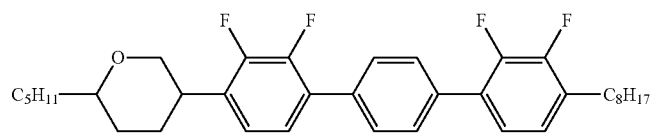 |
| 1789 | 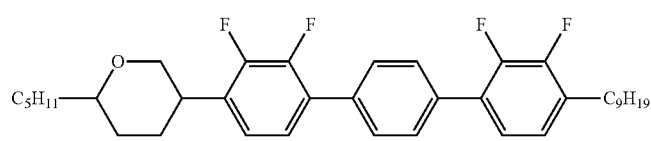 |
| 1790 | 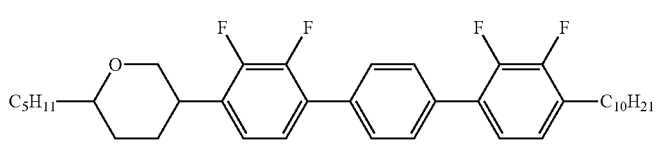 |
| 1791 | 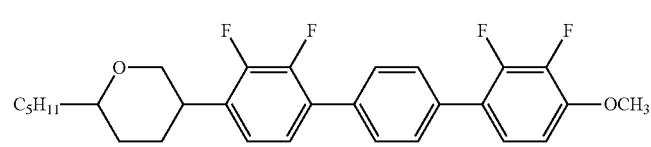 |
| 1792 | 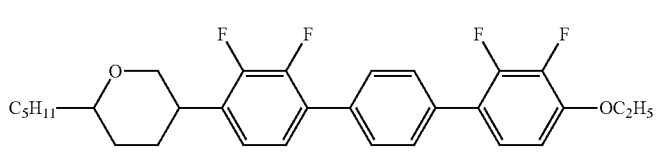 |
| 1793 | 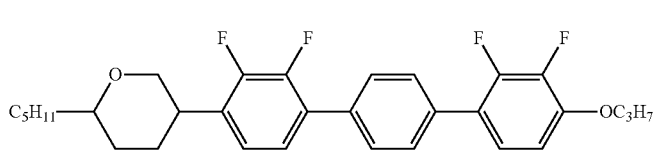 |
| 1794 | 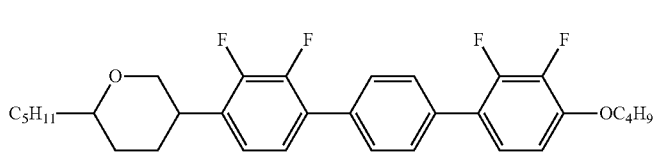 |
| 1795 | 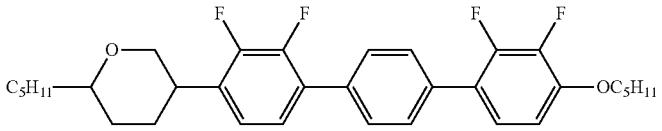 |
| 1796 | 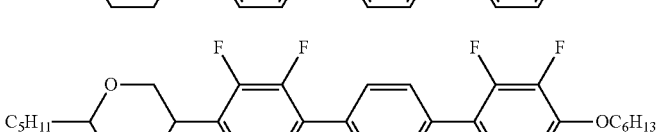 |
| 1797 | 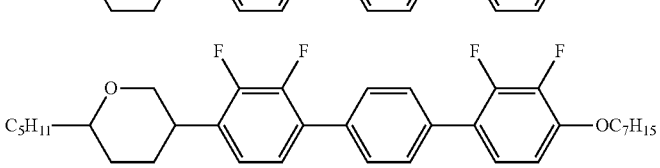 |

| No. | |
|---|---|
| 1798 | 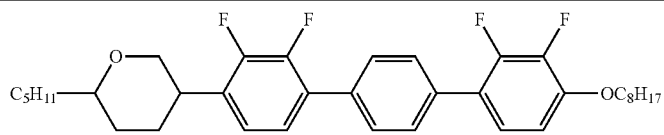 |
| 1799 | 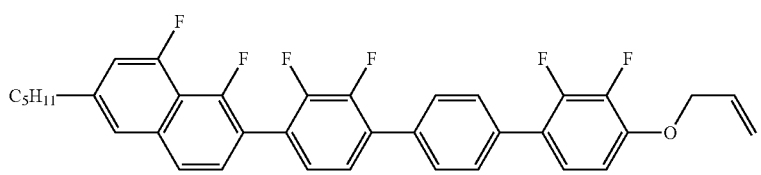 |
| 1800 | 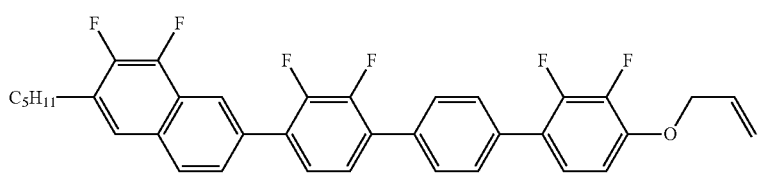 |
| 1801 | 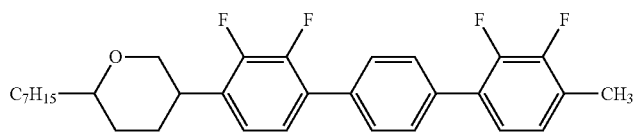 |
| 1802 | 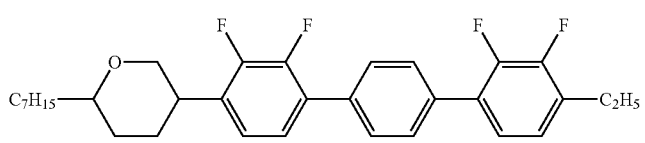 |
| 1803 | 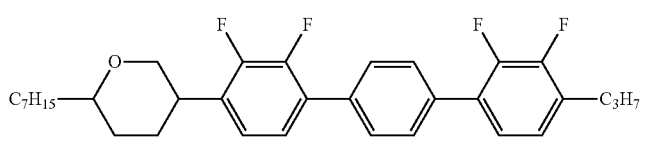 |
| 1804 | 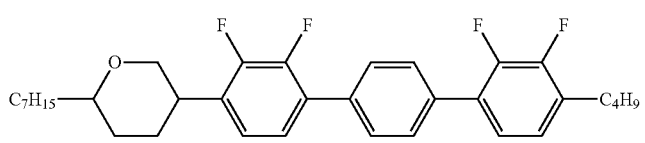 |
| 1805 | 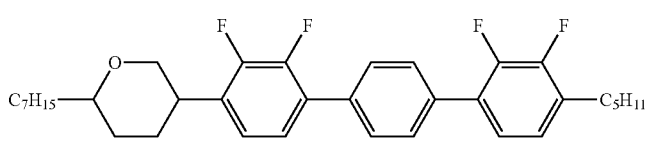 |
| 1806 | 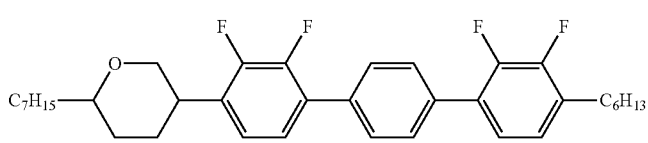 |
| 1807 | 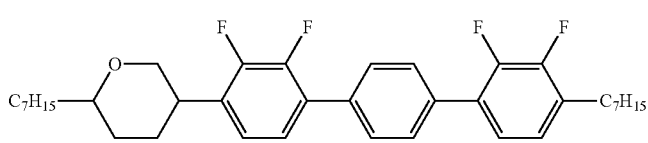 |
| 1808 | 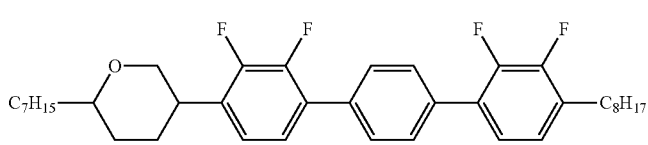 |

| No. | |
|---|---|
| 1809 | 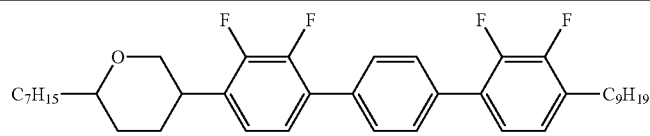 |
| 1810 | 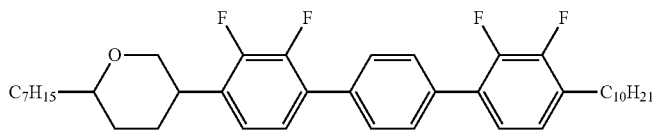 |
| 1811 | 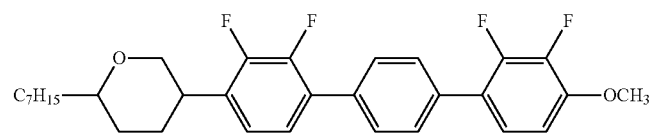 |
| 1812 | 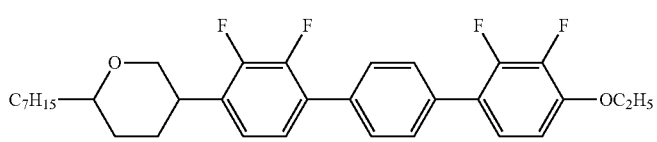 |
| 1813 | 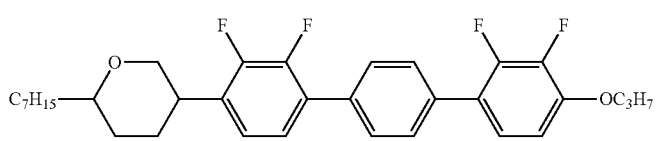 |
| 1814 | 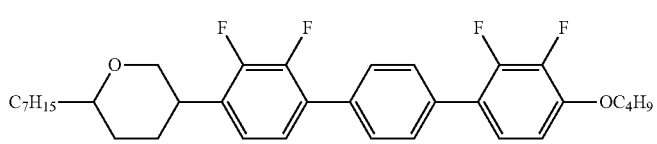 |
| 1815 | 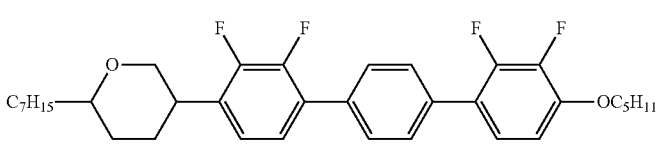 |
| 1816 | 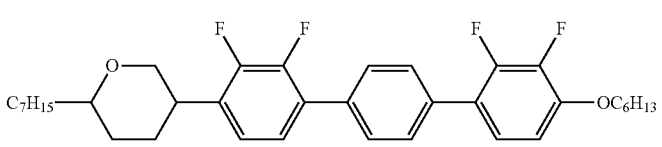 |
| 1817 | 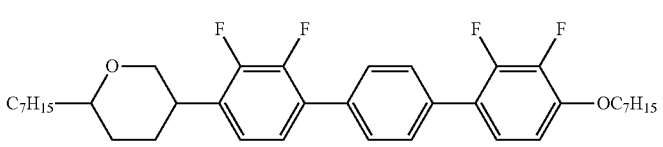 |
| 1818 | 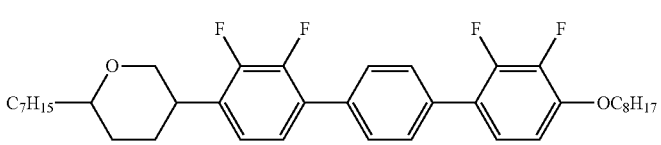 |
| 1819 | 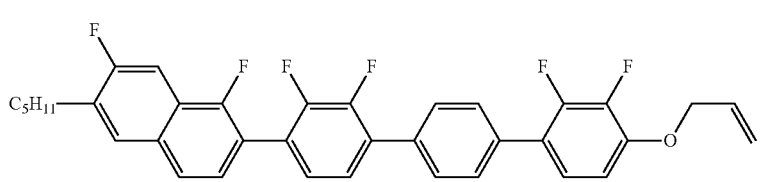 |

-continued
| No. | |
|---|---|
| 1820 | 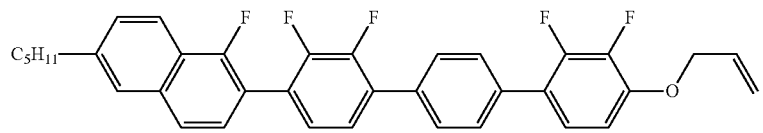 |
| 1821 | 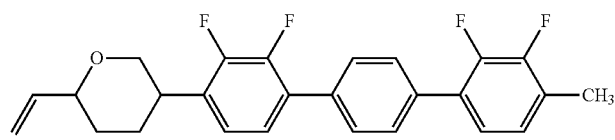 |
| 1822 | 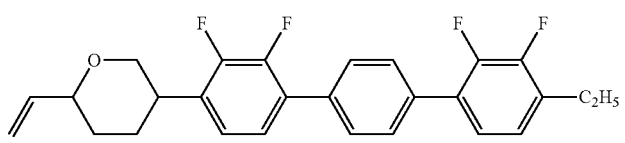 |
| 1823 | 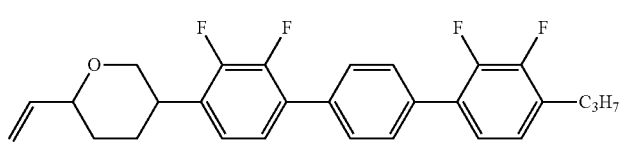 |
| 1824 | 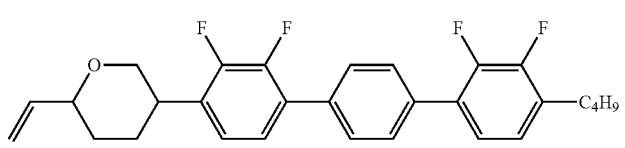 |
| 1825 | 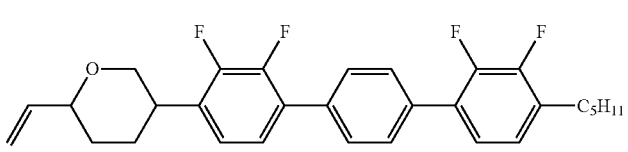 |
| 1826 | 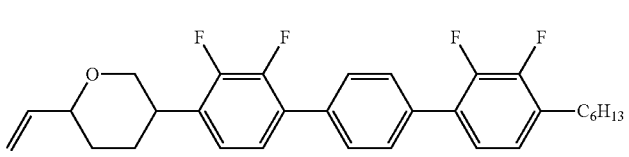 |
| 1827 | 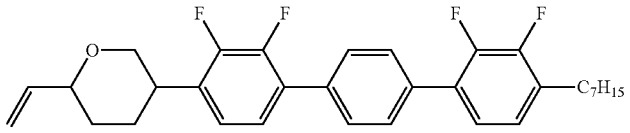 |
| 1828 | 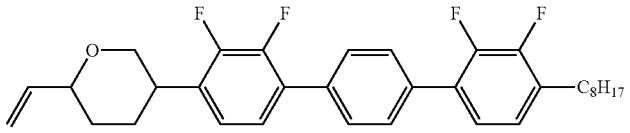 |
| 1829 | 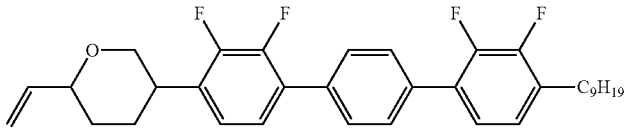 |
| 1830 | 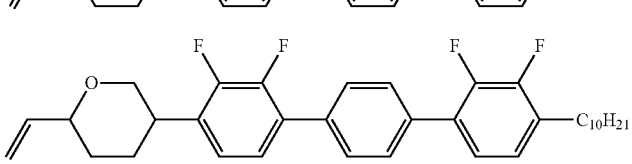 |

-continued
| No. | |
|---|---|
| 1831 | 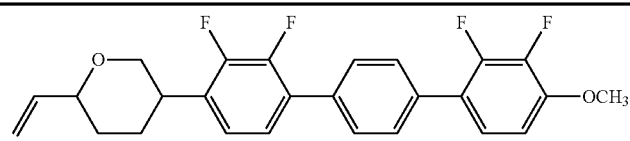 |
| 1832 | 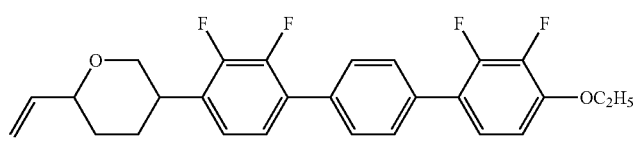 |
| 1833 | 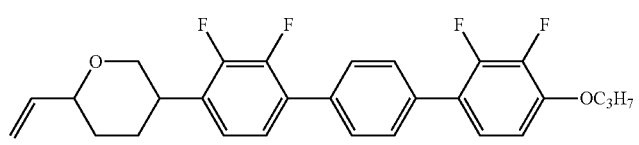 |
| 1834 | 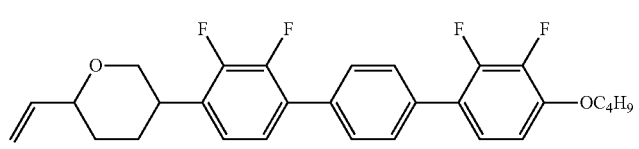 |
| 1835 | 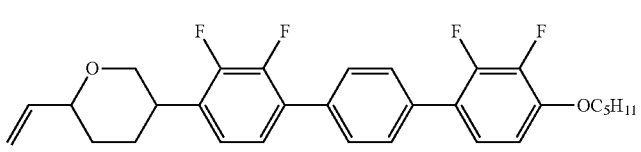 |
| 1836 | 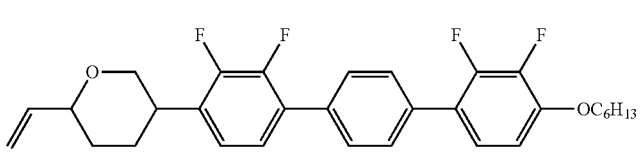 |
| 1837 | 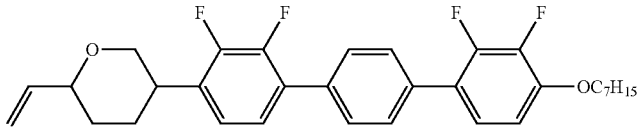 |
| 1838 | 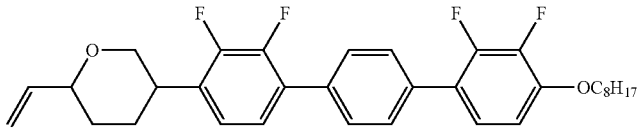 |
| 1839 | 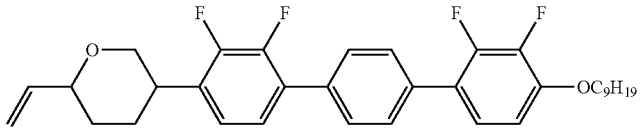 |
| 1840 | 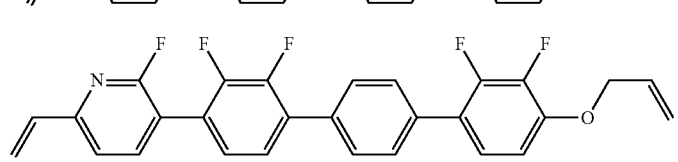 |
| 1841 | 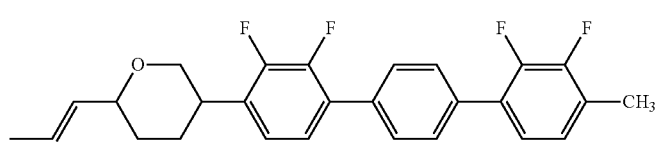 |

-continued
| No. | |
|---|---|
| 1842 | 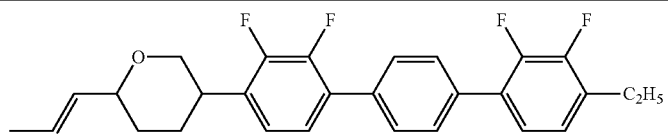 |
| 1843 | 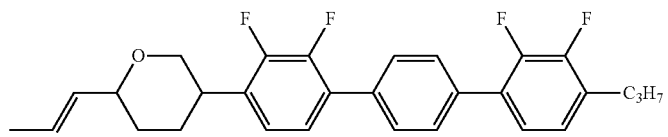 |
| 1844 | 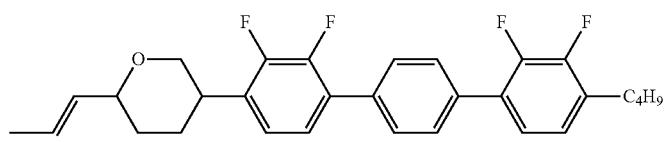 |
| 1845 | 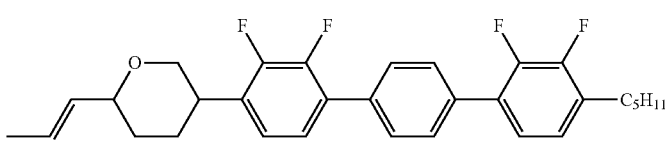 |
| 1846 | 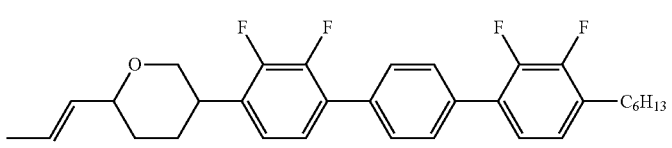 |
| 1847 | 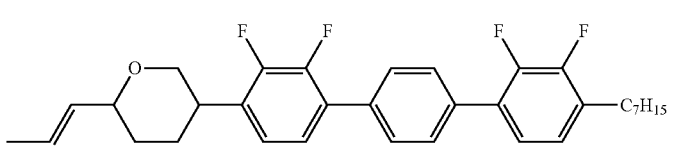 |
| 1848 | 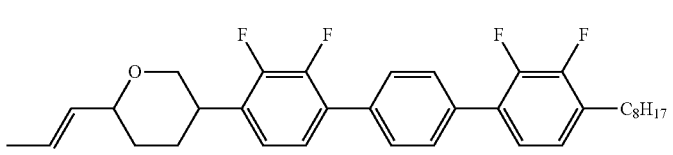 |
| 1849 | 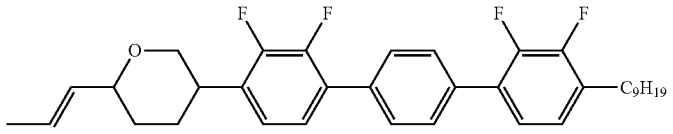 |
| 1850 | 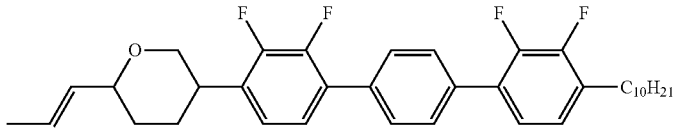 |
| 1851 | 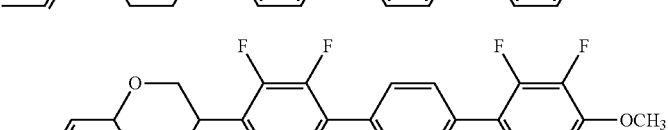 |
| 1852 | 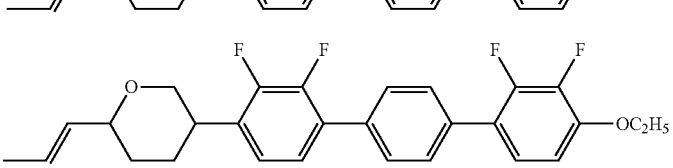 |

| No. | |
|---|---|
| 1853 | 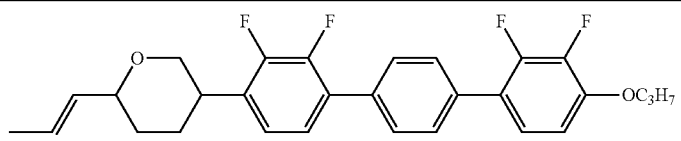 |
| 1854 | 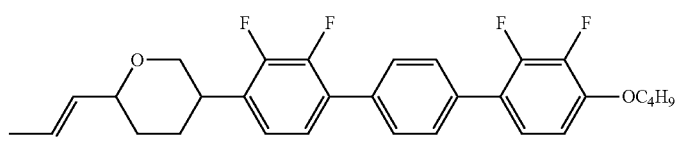 |
| 1855 | 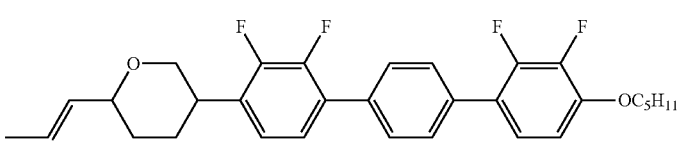 |
| 1856 | 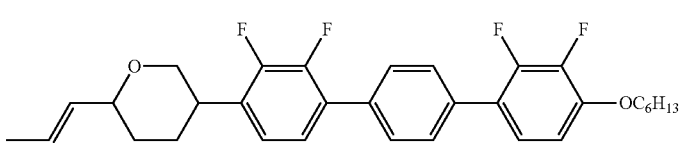 |
| 1857 | 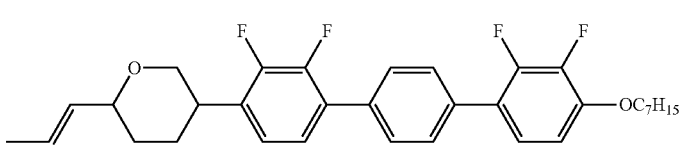 |
| 1858 | 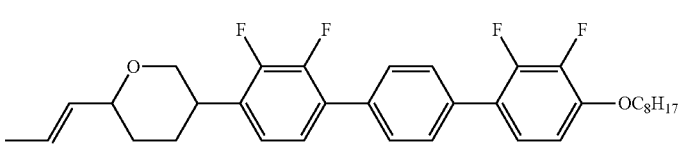 |
| 1859 | 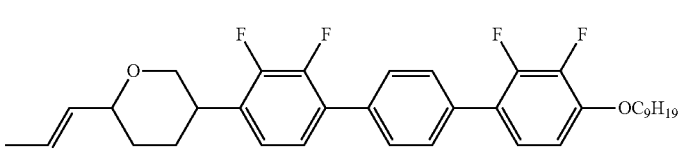 |
| 1860 | 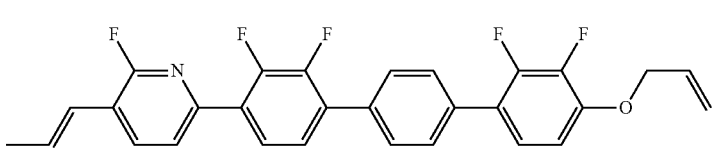 |
| 1861 | 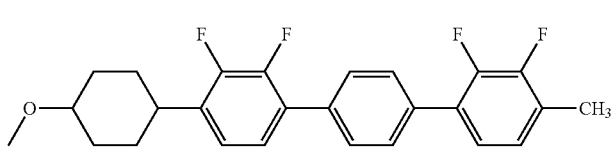 |
| 1862 | 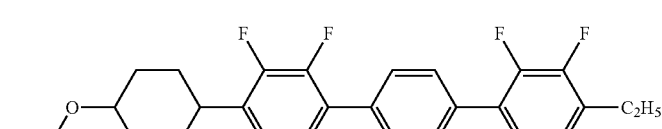 |
| 1863 | 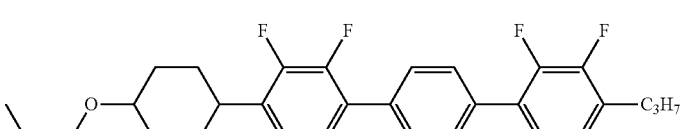 |

| No. | |
|---|---|
| 1864 | 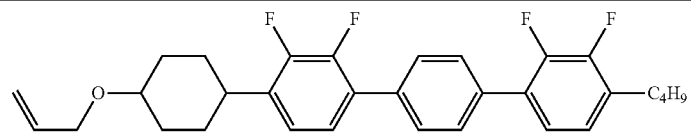 |
| 1865 | 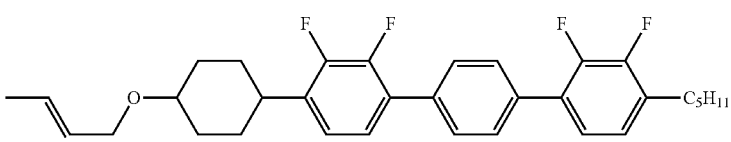 |
| 1866 | 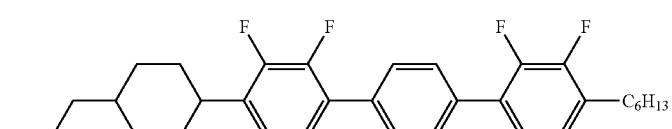 |
| 1867 | 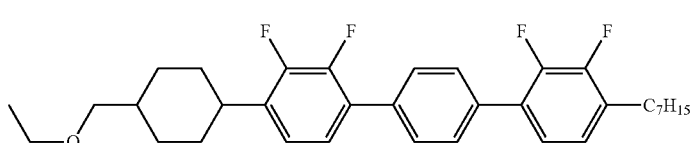 |
| 1868 | 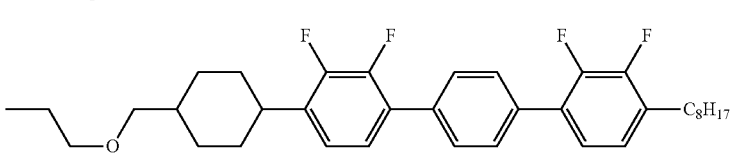 |
| 1869 | 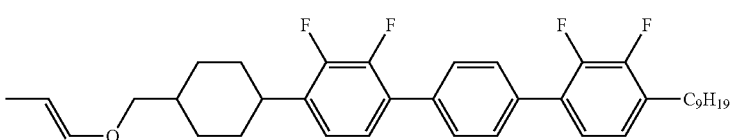 |
| 1870 | 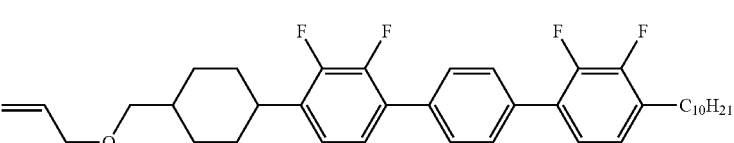 |
| 1871 | 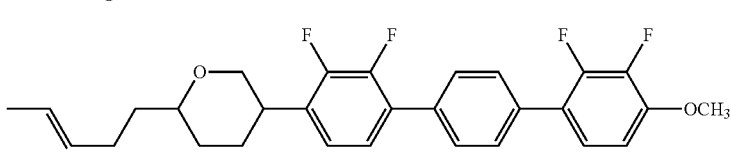 |
| 1872 | 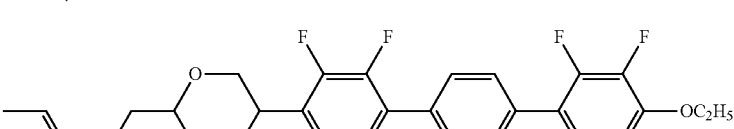 |
| 1873 | 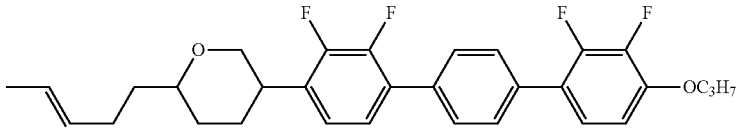 |
| 1874 | 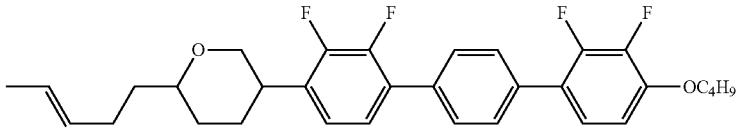 |

| No. |
|---|
| 1875 |
| 1876 |
| 1877 |
| 1878 |
| 1879 |
| 1880 |
| 1881 |
| 1882 |
| 1883 |
| 1884 |

| No. | |
|---|---|
| 1885 | 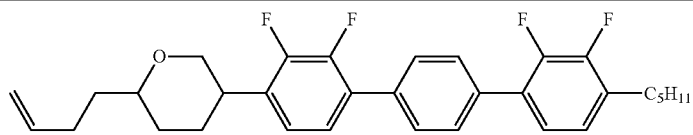 |
| 1886 | 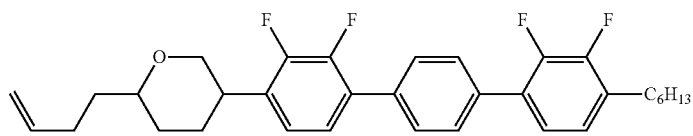 |
| 1887 | 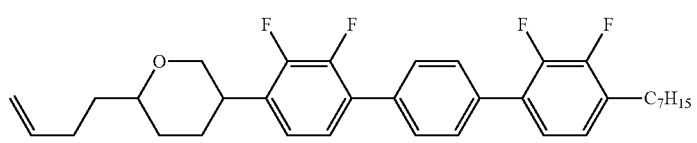 |
| 1888 | 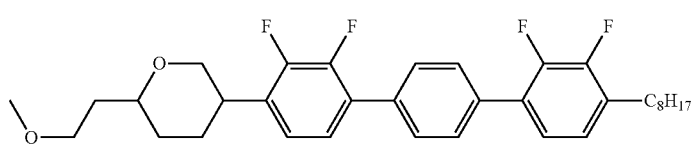 |
| 1889 | 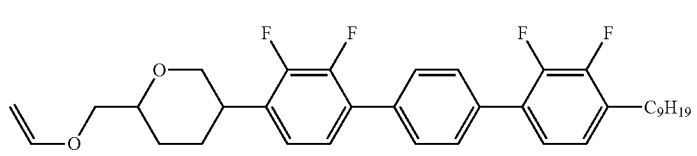 |
| 1890 | 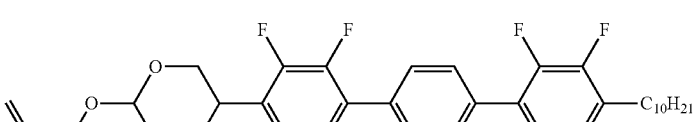 |
| 1891 | 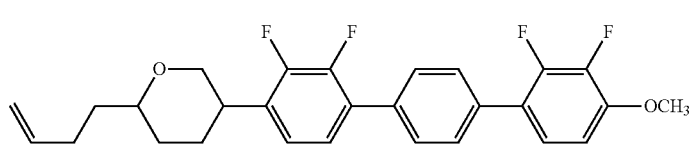 |
| 1892 | 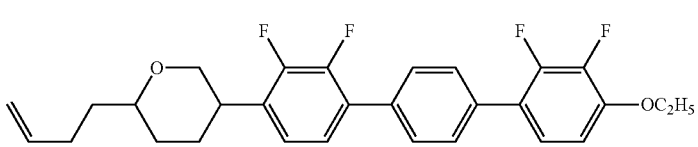 |
| 1893 | 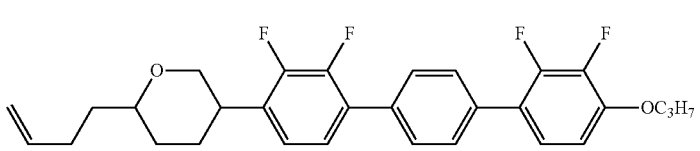 |
| 1894 | 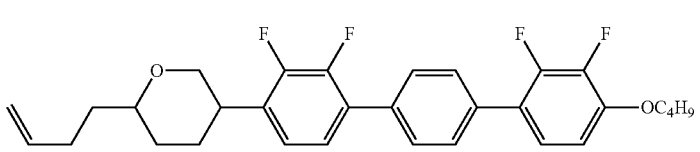 |
| 1895 | 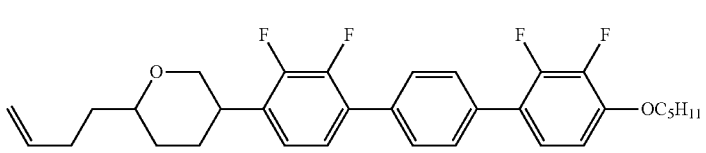 |

| No. | |
|---|---|
| 1896 | 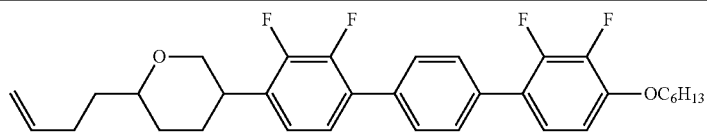 |
| 1897 | 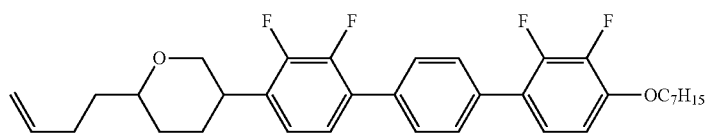 |
| 1898 | 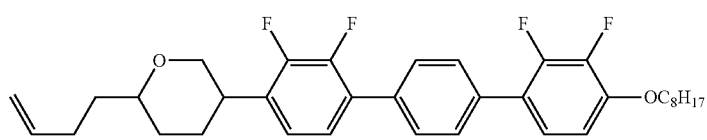 |
| 1899 | 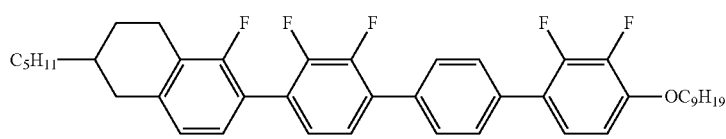 |
| 1900 | 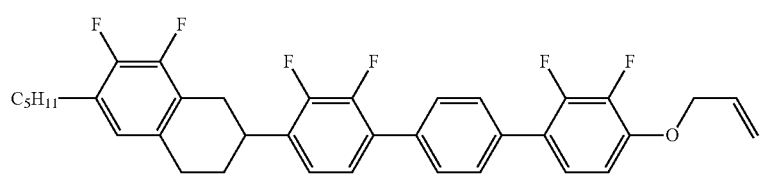 |
| 1901 | 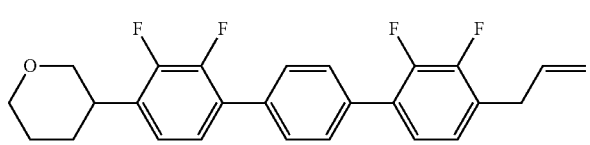 |
| 1902 | 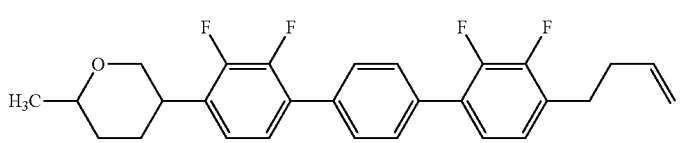 |
| 1903 | 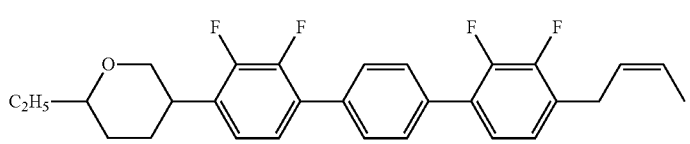 |
| 1904 | 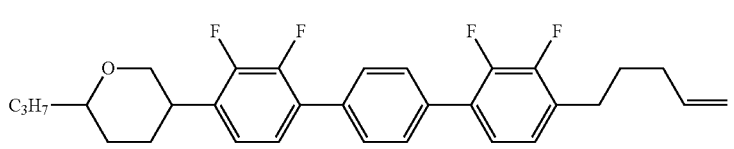 |
| 1905 | 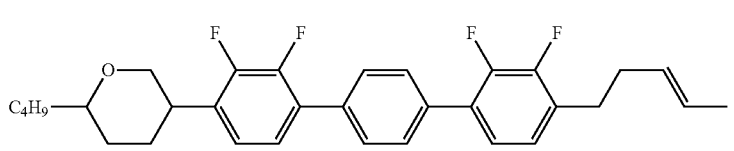 |
| 1906 | 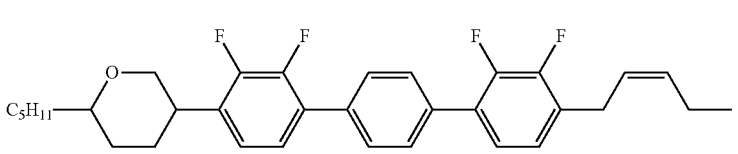 |

| No. |
|---|
| 1907 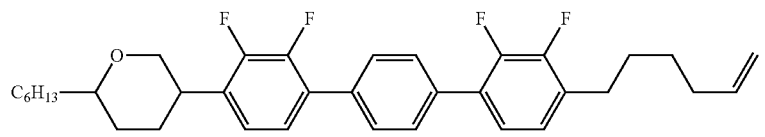 |
| 1908 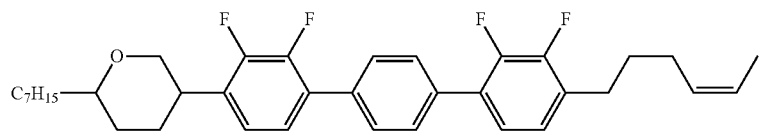 |
| 1909 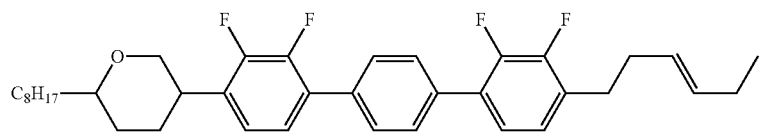 |
| 1910 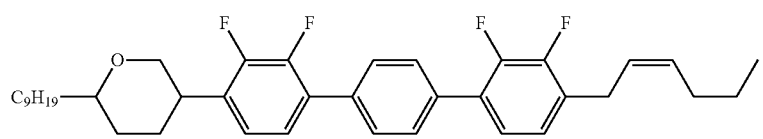 |
| 1911 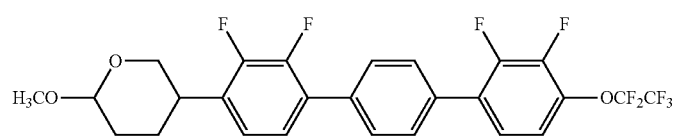 |
| 1912 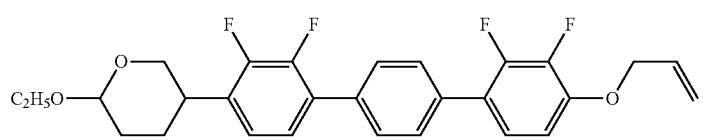 |
| 1913 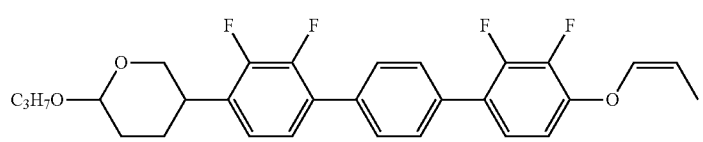 |
| 1914 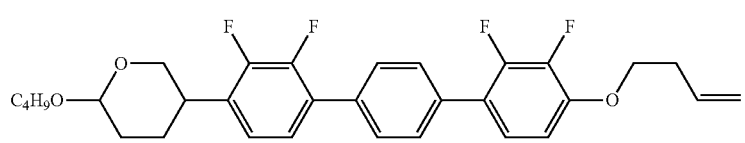 |
| 1915 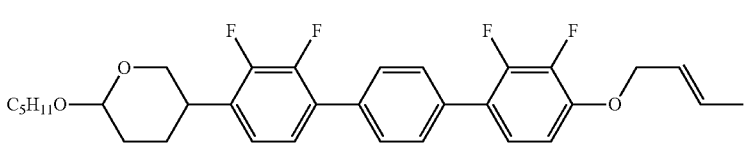 |
| 1916 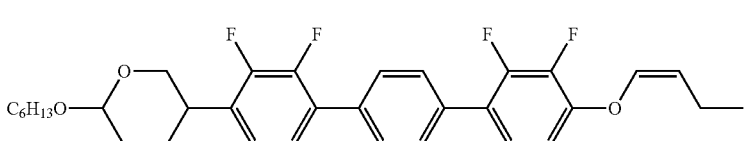 |
| 1917 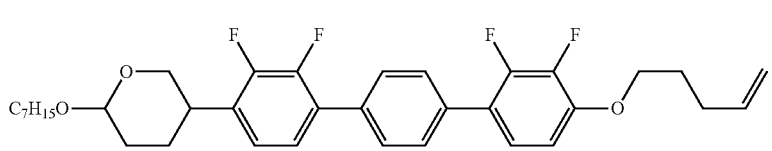 |

| No. | |
|---|---|
| 1918 | 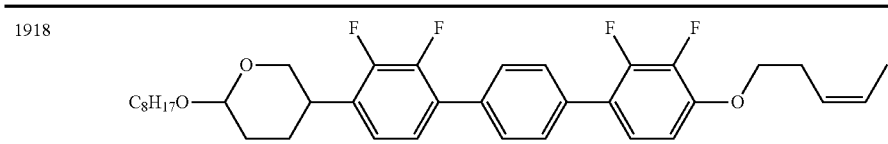 |
| 1919 | 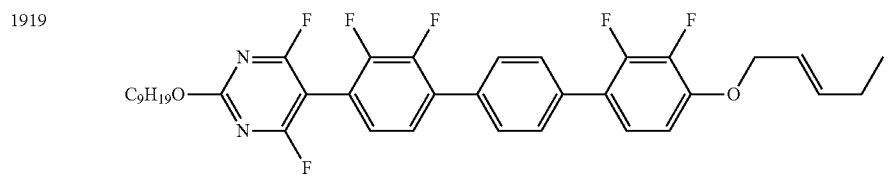 |
| 1920 | 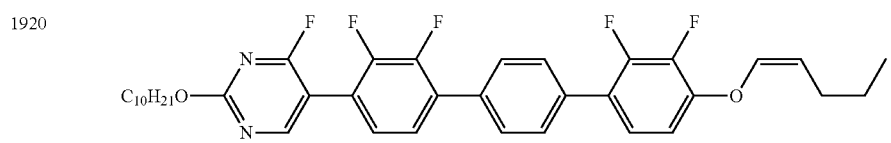 |
| 1921 | 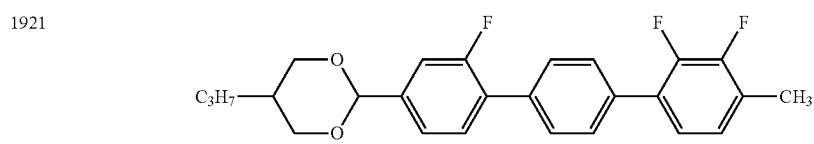 |
| 1922 | 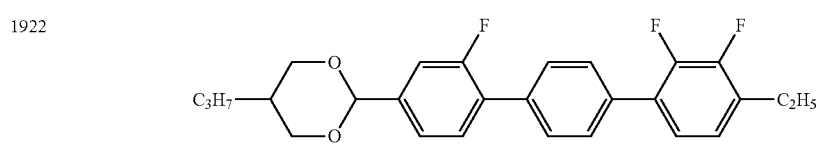 |
| 1923 | 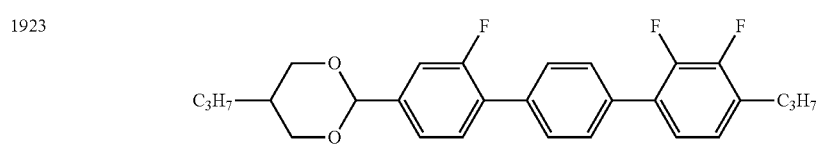 |
| 1924 | 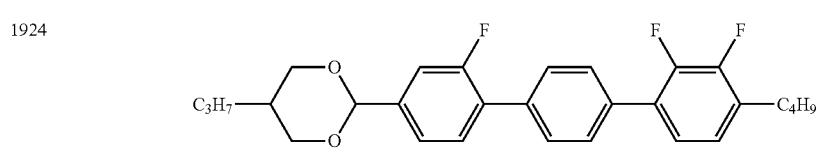 |
| 1925 | 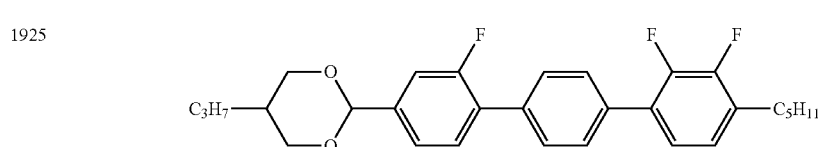 |
| 1926 | 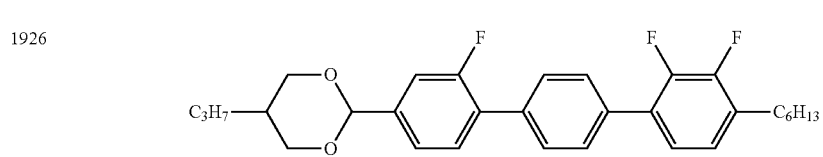 |
| 1927 | 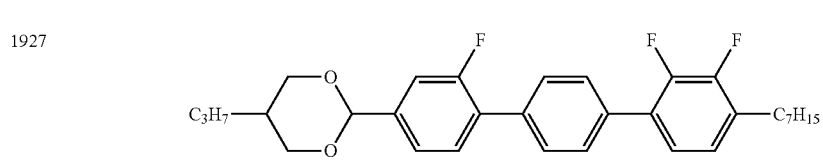 |

-continued
| No. | |
|---|---|
| 1928 | 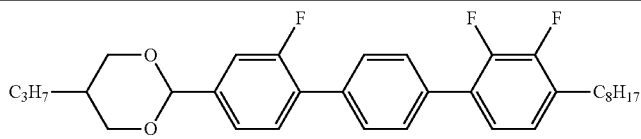 |
| 1929 | 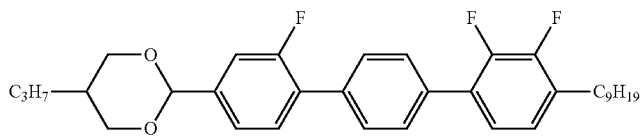 |
| 1930 | 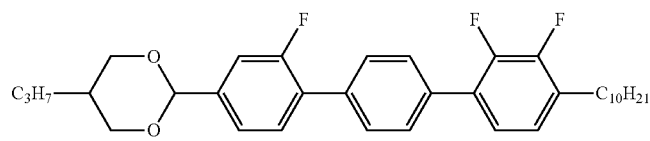 |
| 1931 | 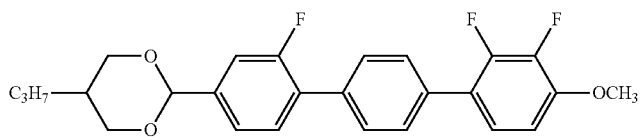 |
| 1932 | 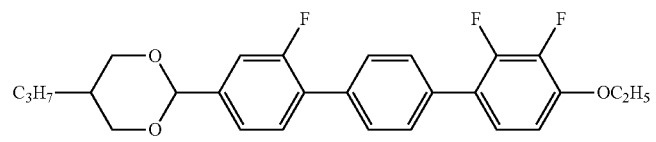 |
| 1933 | 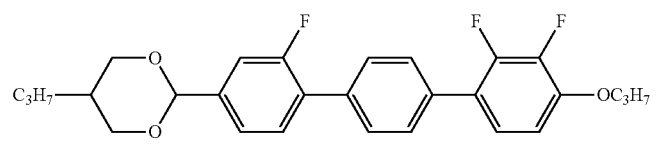 |
| 1934 | 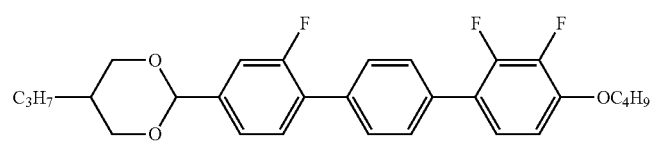 |
| 1935 | 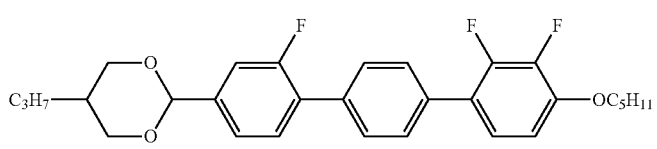 |
| 1936 | 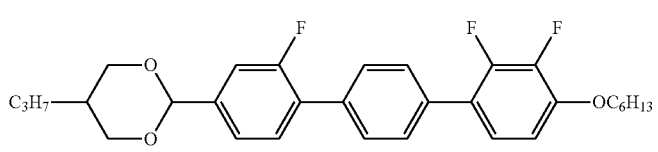 |
| 1937 | 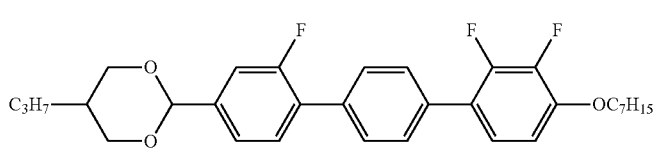 |
| 1938 | 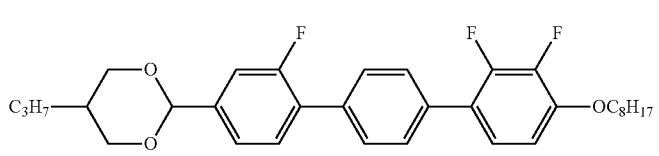 |

-continued
| No. | |
|---|---|
| 1939 | 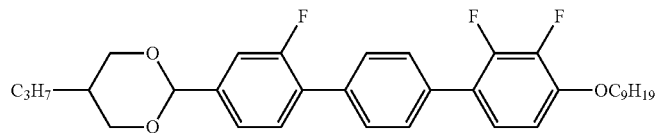 |
| 1940 | 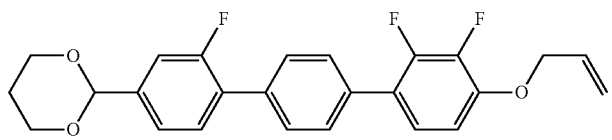 |
| 1941 | 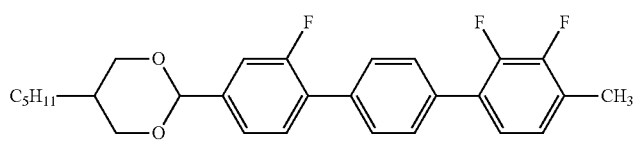 |
| 1942 | 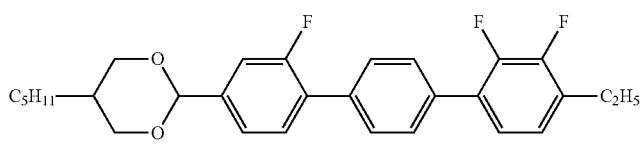 |
| 1943 | 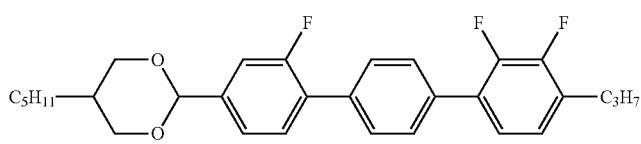 |
| 1944 | 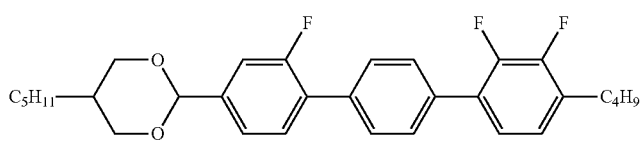 |
| 1945 | 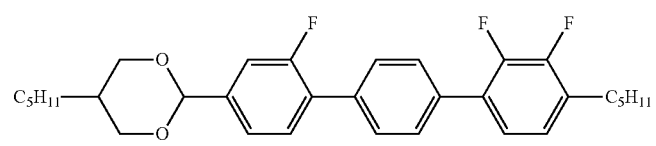 |
| 1946 | 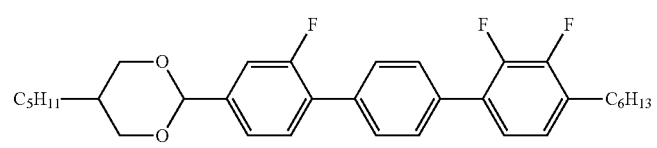 |
| 1947 | 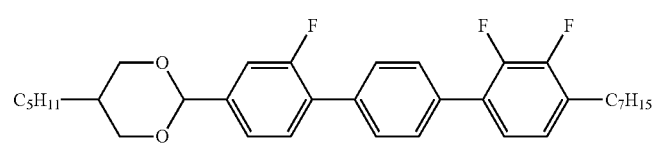 |
| 1948 | 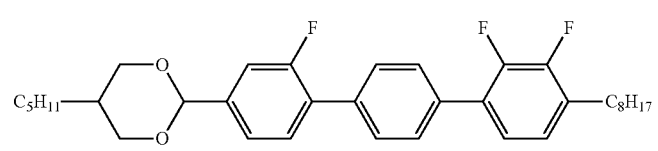 |

| No. | |
|---|---|
| 1949 | 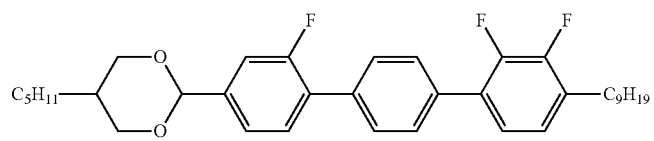 |
| 1950 | 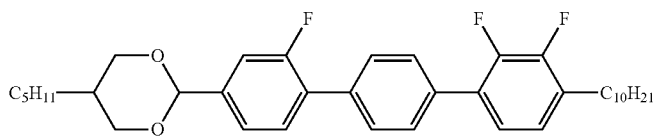 |
| 1951 | 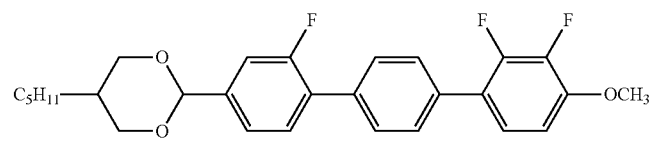 |
| 1952 | 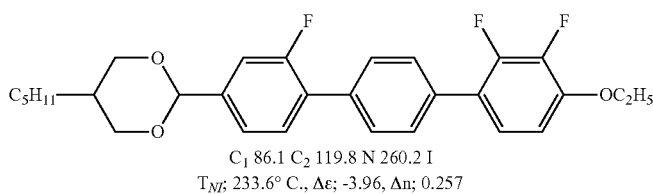<br>$C_1$ 86.1 $C_2$ 119.8 N 260.2 I<br>$T_{NI}$; 233.6° C., Δε; -3.96, Δn; 0.257 |
| 1953 | 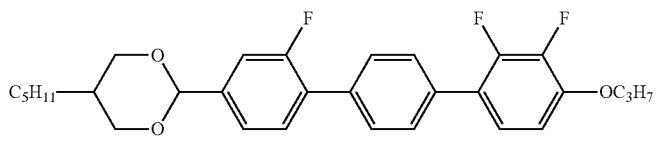 |
| 1954 | 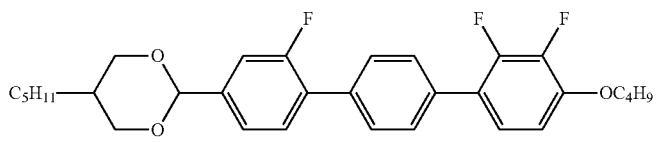 |
| 1955 | 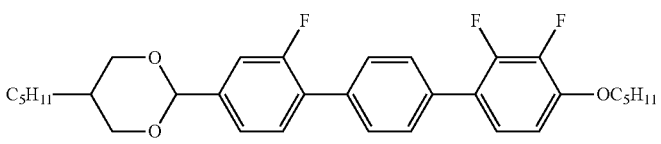 |
| 1956 | 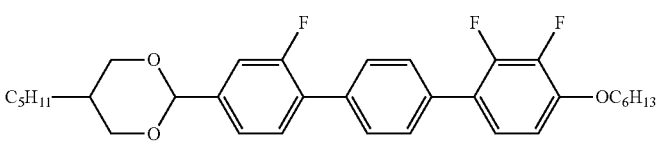 |
| 1957 | 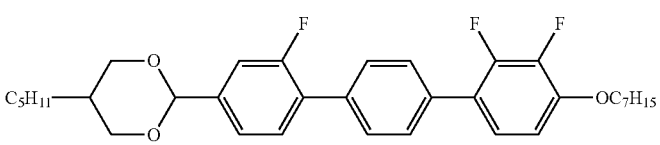 |
| 1958 | 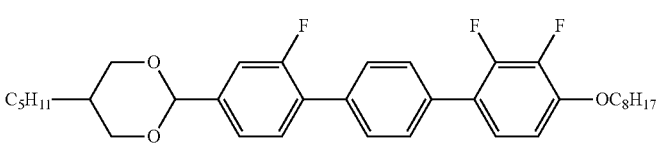 |

| No. | |
|---|---|
| 1959 | 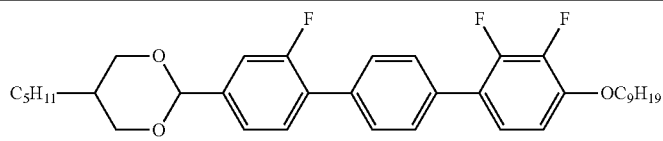 |
| 1960 | 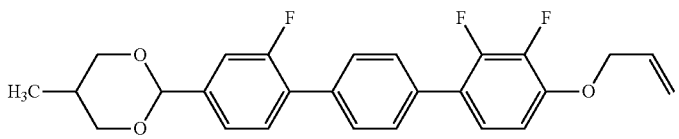 |
| 1961 | 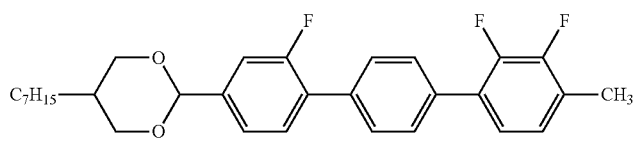 |
| 1962 | 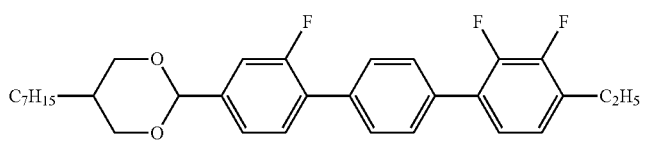 |
| 1963 | 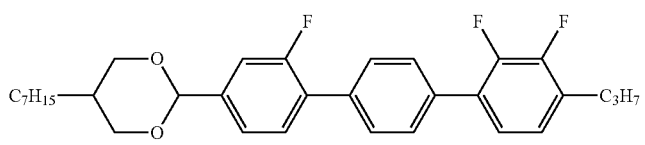 |
| 1964 | 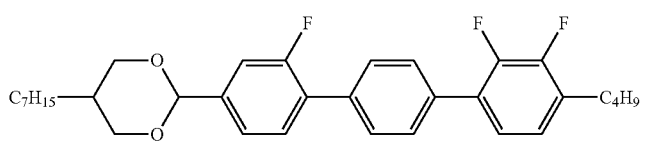 |
| 1965 | 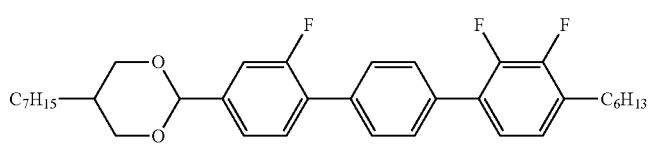 |
| 1966 | 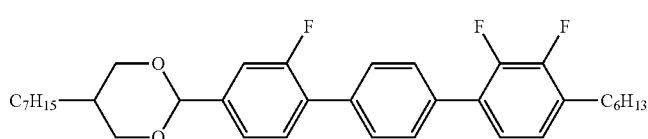 |
| 1967 | 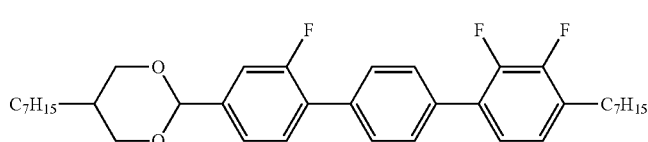 |
| 1968 | 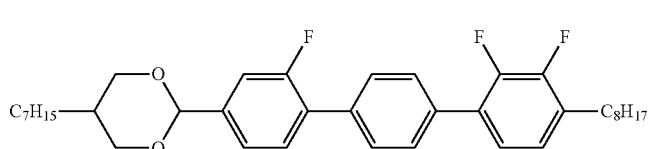 |
| 1969 |  |

| No. |
|---|
| 1970 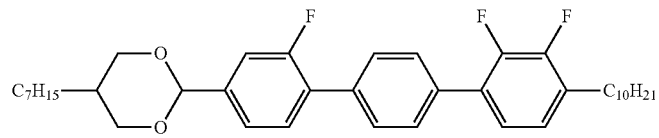 |
| 1971 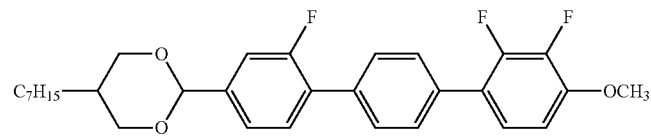 |
| 1972 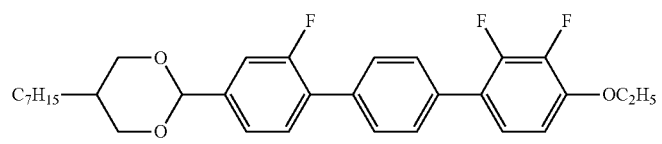 |
| 1973 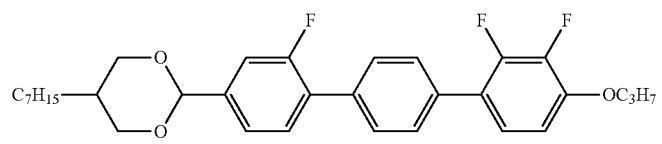 |
| 1974 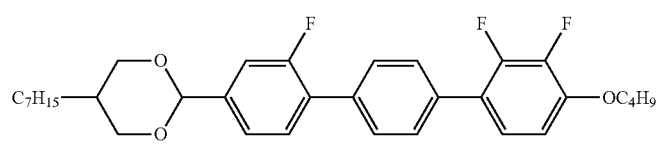 |
| 1975 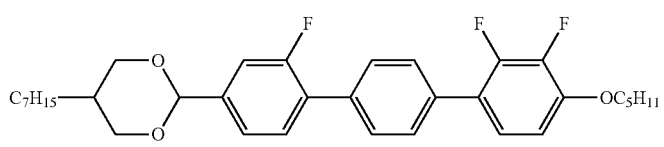 |
| 1976 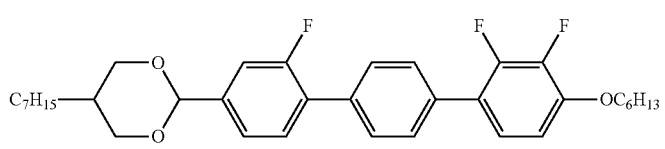 |
| 1977 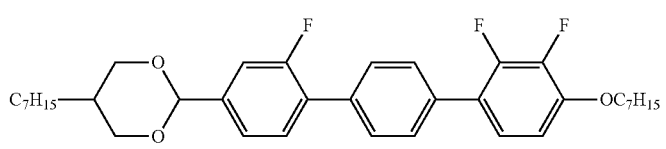 |
| 1978 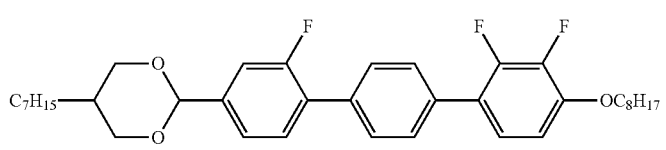 |
| 1979 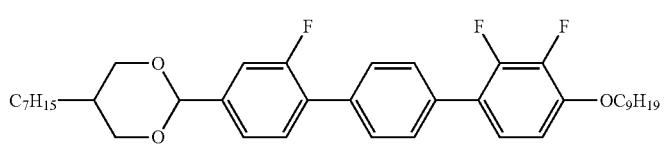 |

| No. | |
|---|---|
| 1980 | 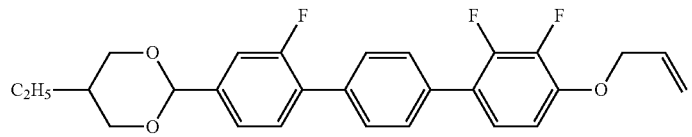 |
| 1981 | 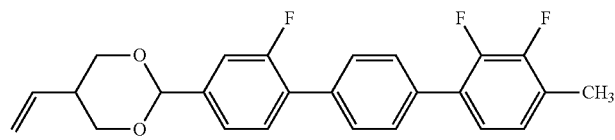 |
| 1982 | 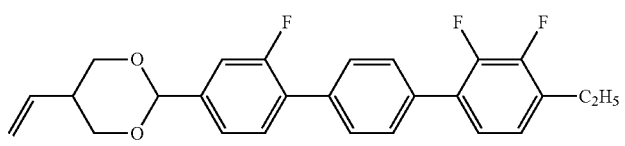 |
| 1983 | 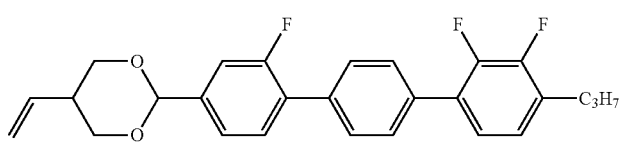 |
| 1984 | 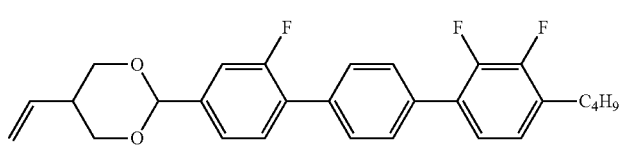 |
| 1985 | 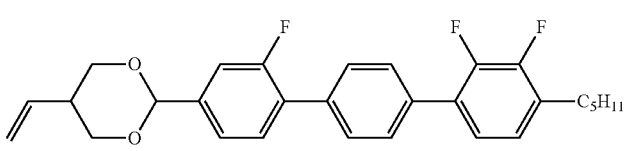 |
| 1986 | 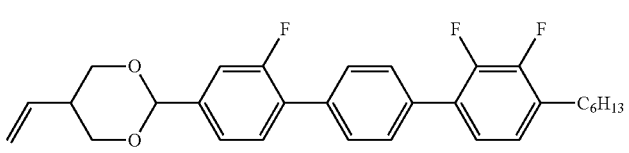 |
| 1987 | 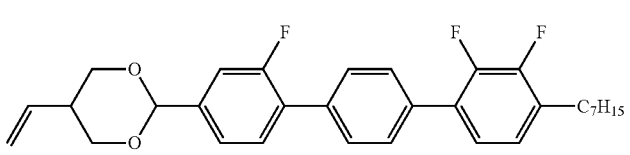 |
| 1988 | 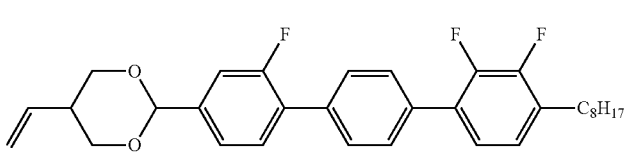 |
| 1989 | 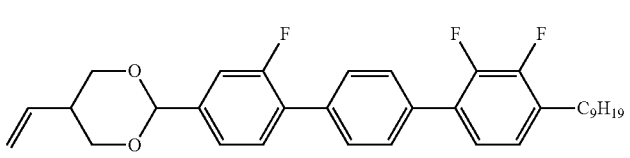 |

-continued
| No. | |
|---|---|
| 1990 | 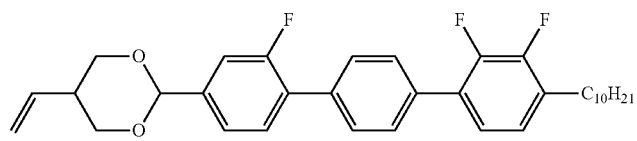 |
| 1991 | 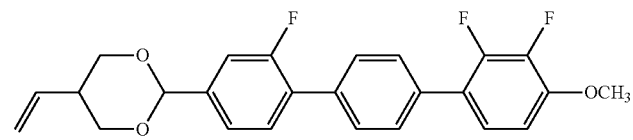 |
| 1992 | 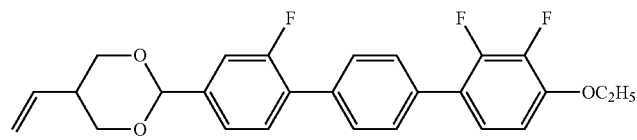 |
| 1993 | 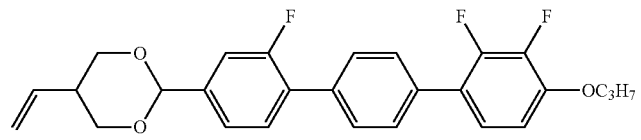 |
| 1994 | 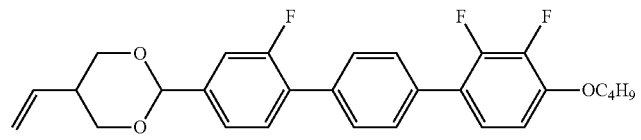 |
| 1995 | 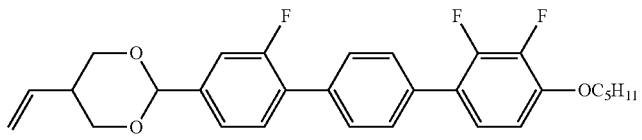 |
| 1996 | 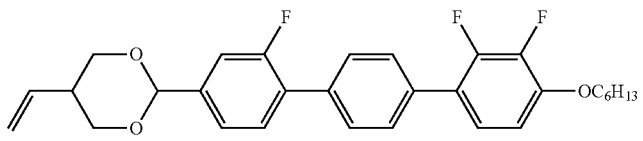 |
| 1997 | 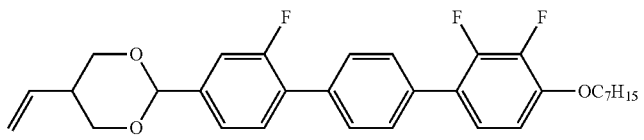 |
| 1998 | 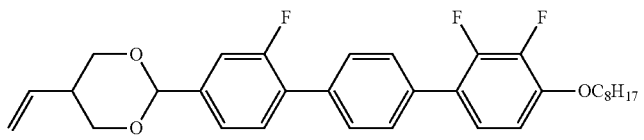 |
| 1999 | 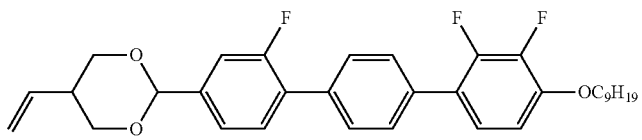 |

-continued
| No. | |
|---|---|
| 2000 | 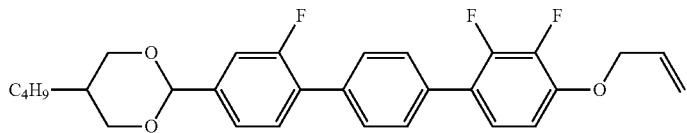 |
| 2001 | 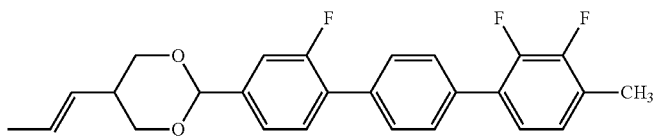 |
| 2002 | 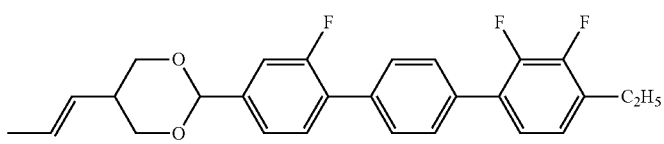 |
| 2003 | 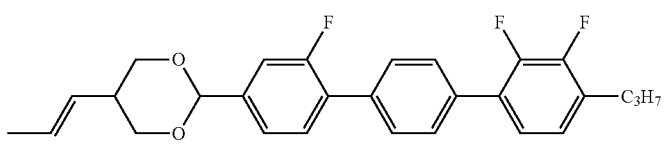 |
| 2004 | 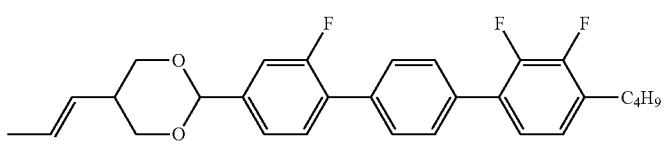 |
| 2005 | 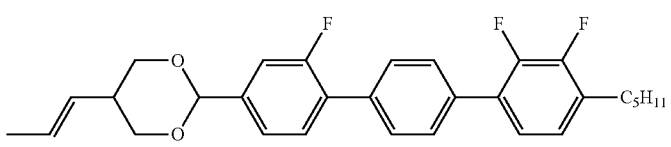 |
| 2006 | 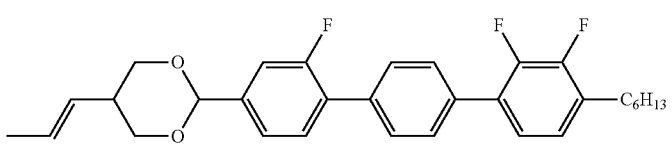 |
| 2007 | 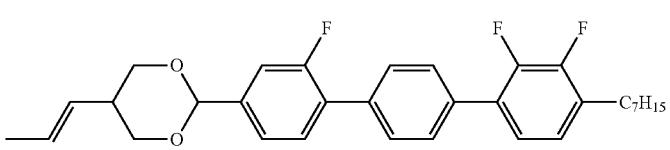 |
| 2008 | 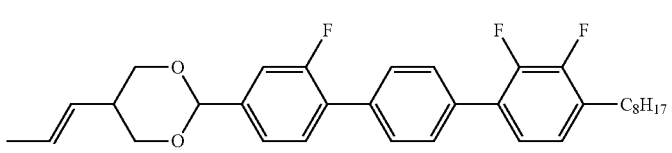 |
| 2009 | 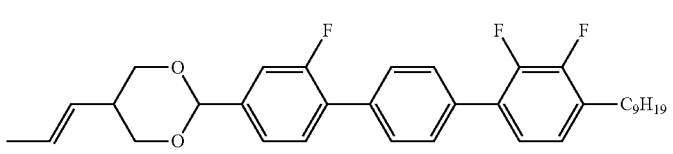 |

| No. | |
|---|---|
| 2010 | 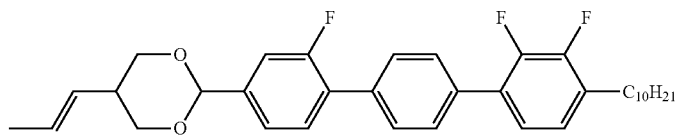 |
| 2011 | 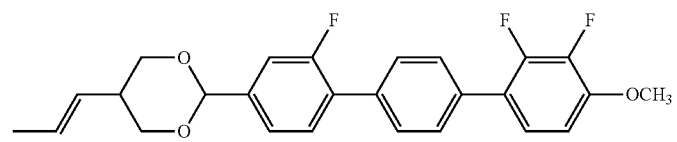 |
| 2012 | 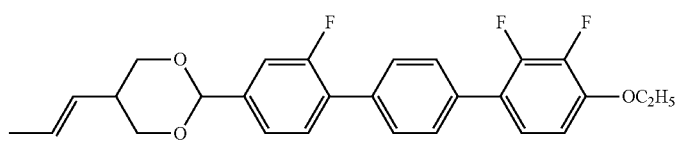 |
| 2013 | 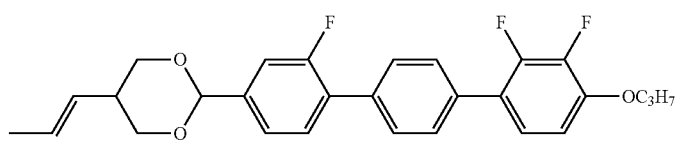 |
| 2014 | 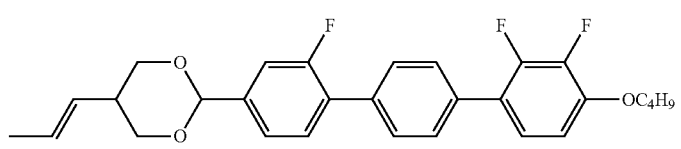 |
| 2015 | 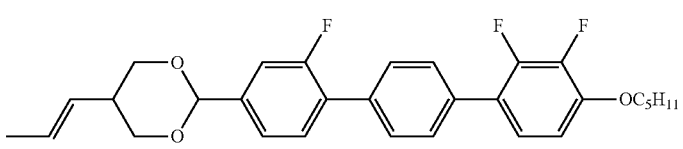 |
| 2016 | 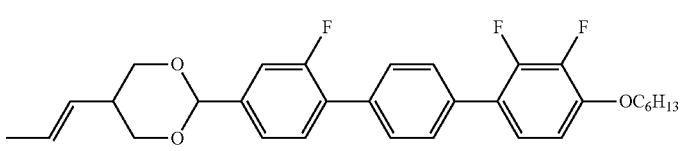 |
| 2017 | 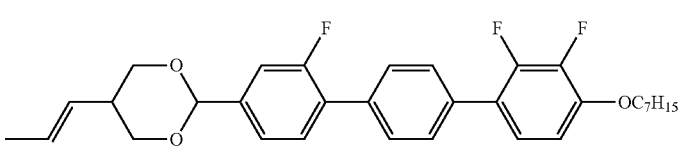 |
| 2018 | 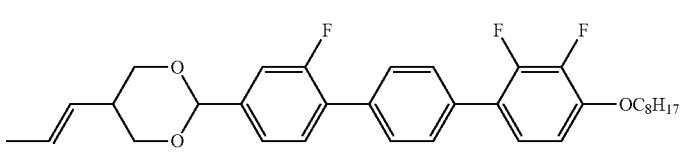 |
| 2019 | 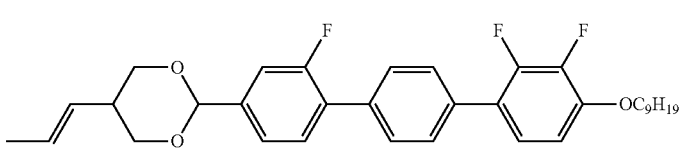 |

| No. |
|---|
| 2020 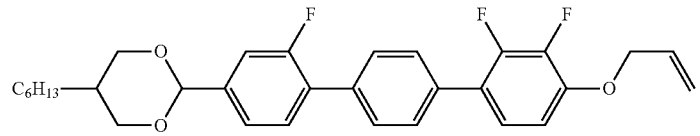 |
| 2021 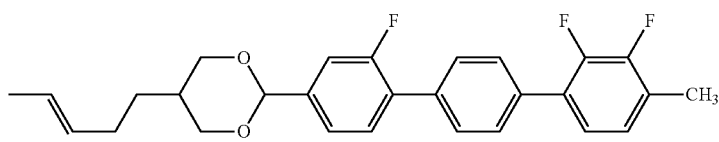 |
| 2022 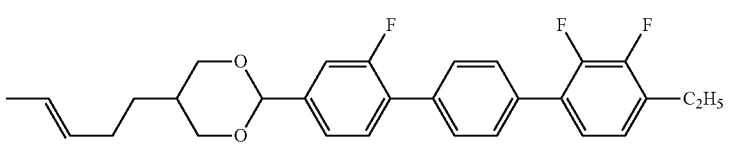 |
| 2023 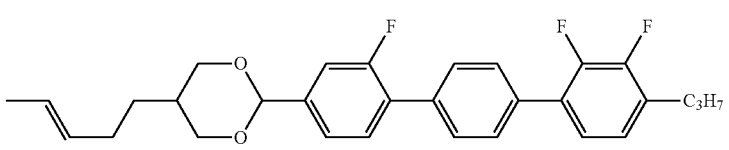 |
| 2024 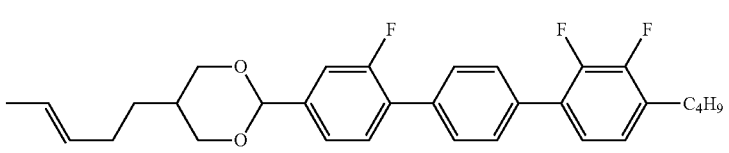 |
| 2025 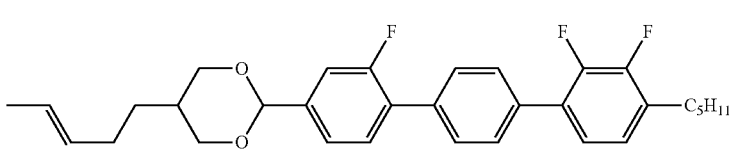 |
| 2026 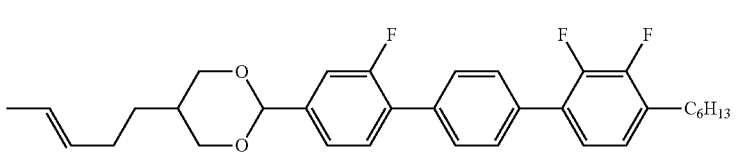 |
| 2027 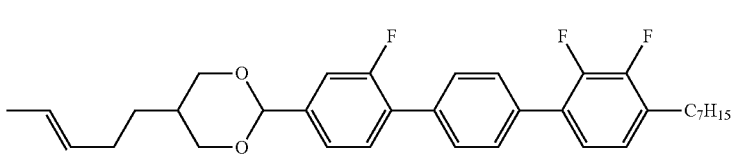 |
| 2028 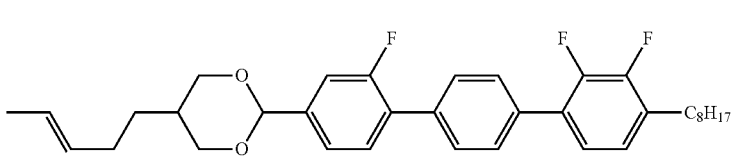 |
| 2029 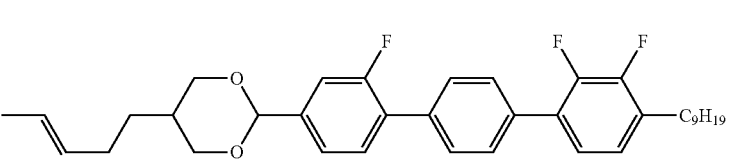 |

| No. | |
|---|---|
| 2030 | 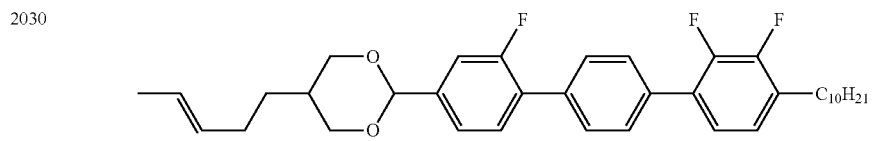 |
| 2031 | 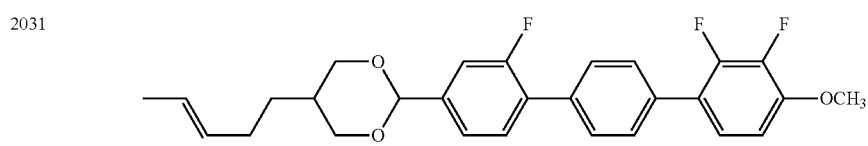 |
| 2032 | 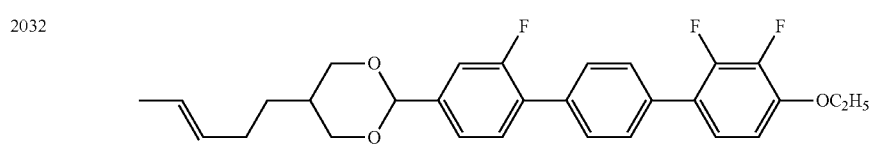 |
| 2033 | 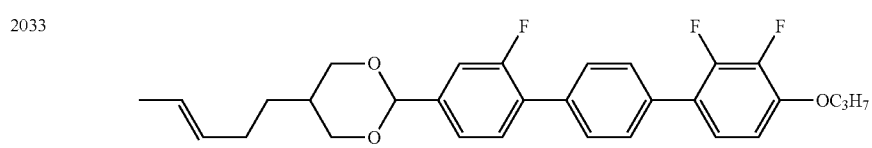 |
| 2034 | 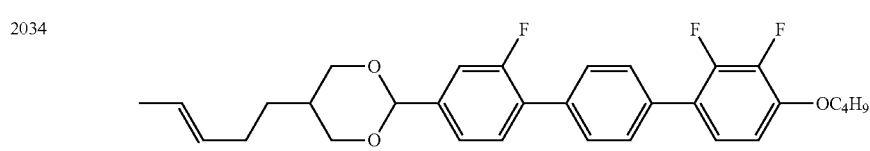 |
| 2035 | 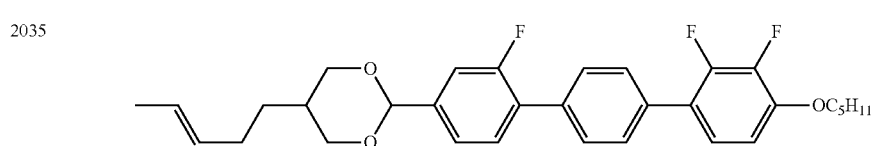 |
| 2036 | 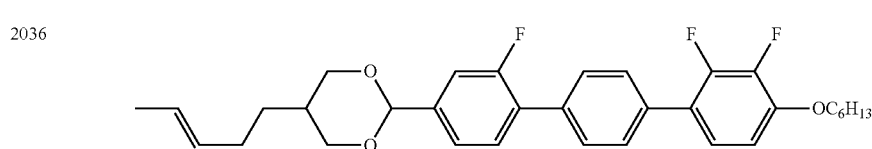 |
| 2037 | 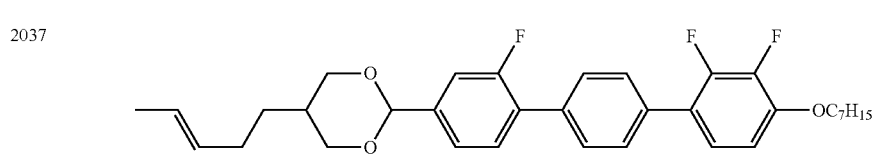 |
| 2038 | 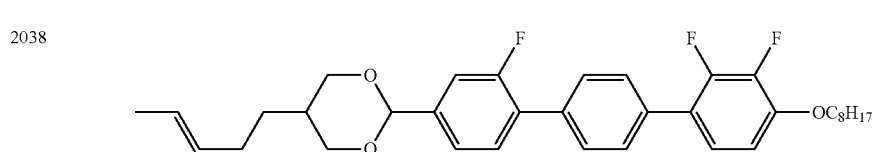 |
| 2039 | 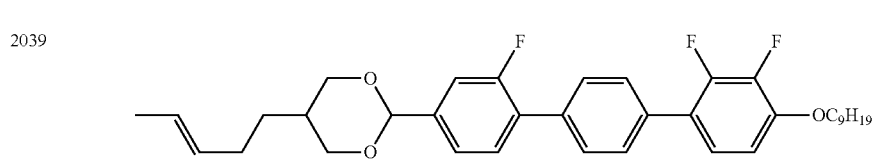 |

-continued
| No. | |
|---|---|
| 2040 | 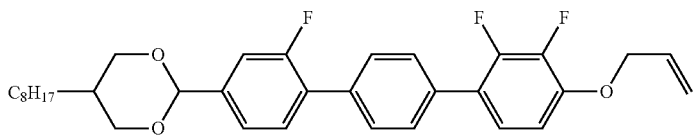 |
| 2041 | 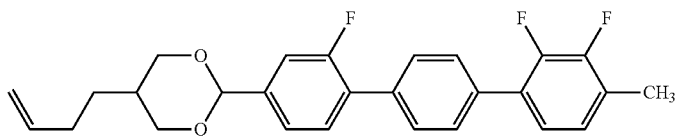 |
| 2042 | 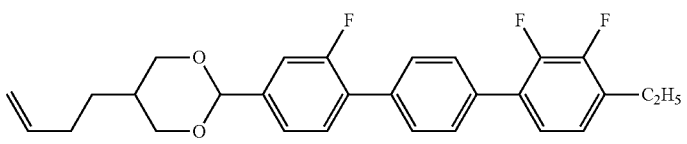 |
| 2043 | 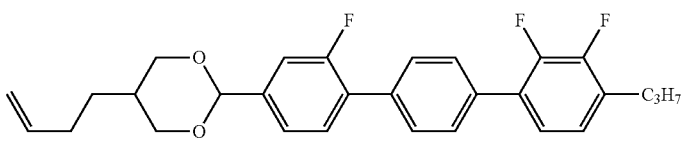 |
| 2044 | 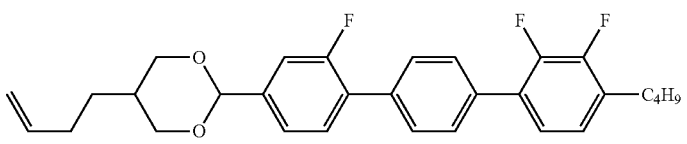 |
| 2045 | 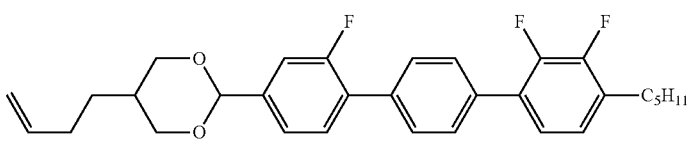 |
| 2046 | 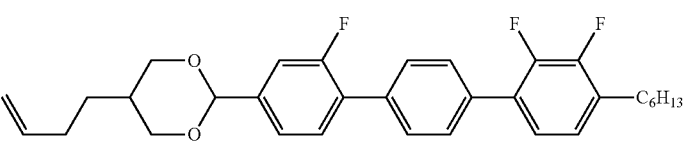 |
| 2047 | 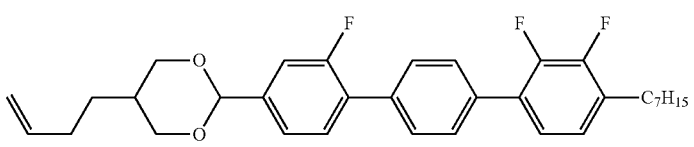 |
| 2048 | 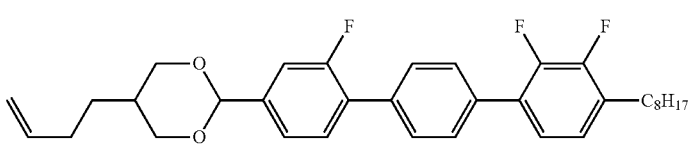 |
| 2049 | 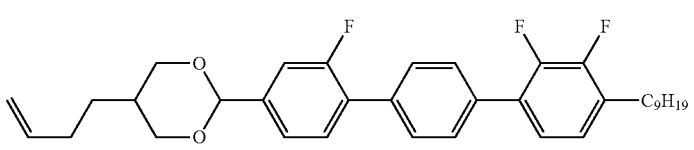 |

-continued
| No. | |
|---|---|
| 2050 | 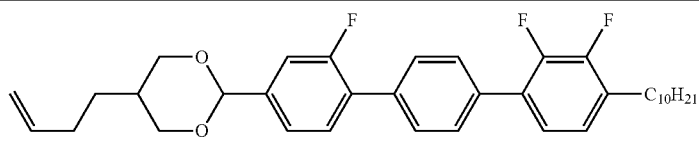 |
| 2051 | 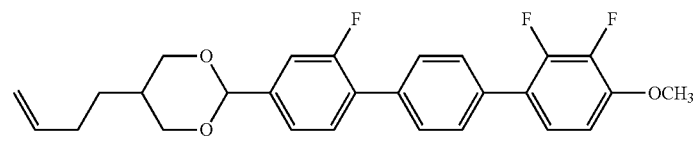 |
| 2052 | 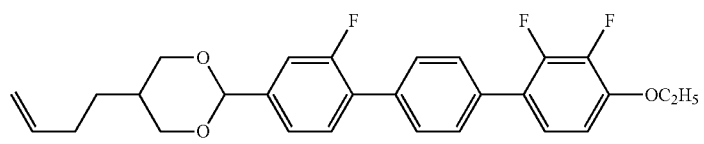 |
| 2053 | 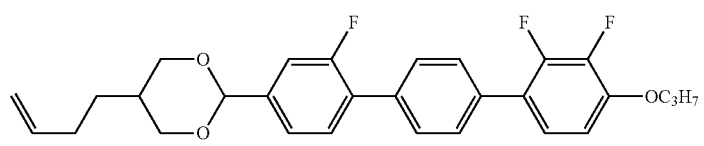 |
| 2054 | 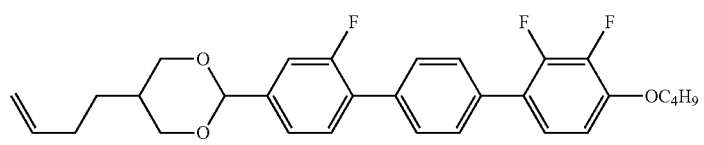 |
| 2055 | 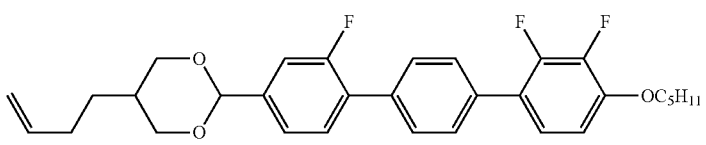 |
| 2056 | 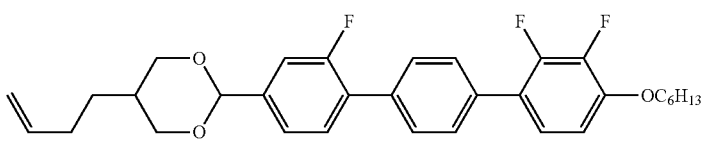 |
| 2057 | 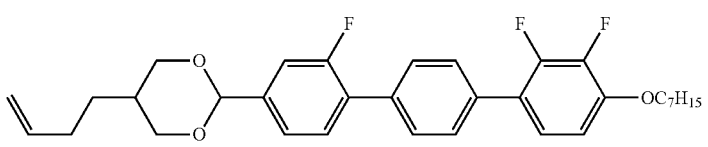 |
| 2058 | 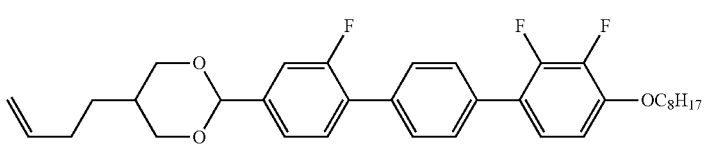 |
| 2059 | 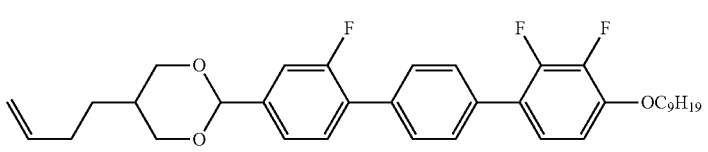 |
| 2060 | 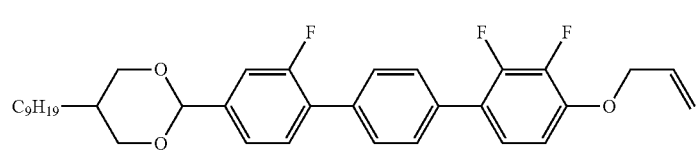 |

| No. |
|---|
| 2061 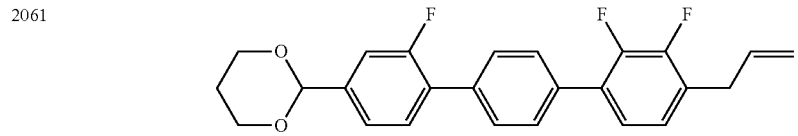 |
| 2062 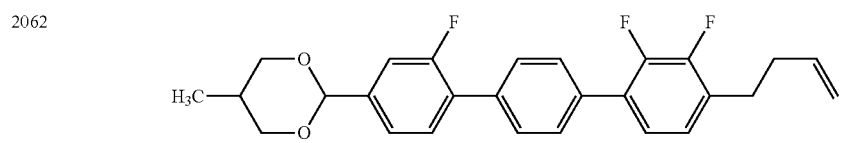 |
| 2063 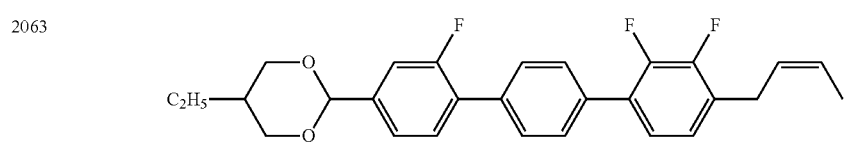 |
| 2064 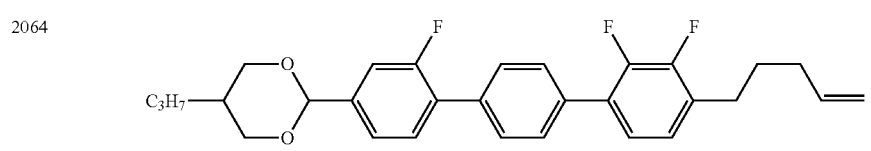 |
| 2065  |
| 2066 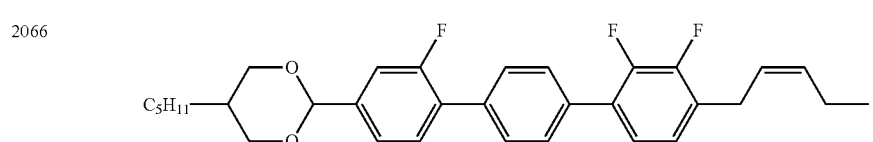 |
| 2067 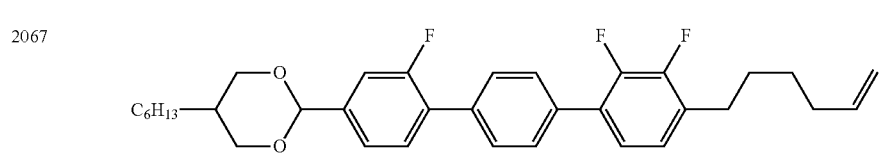 |
| 2068 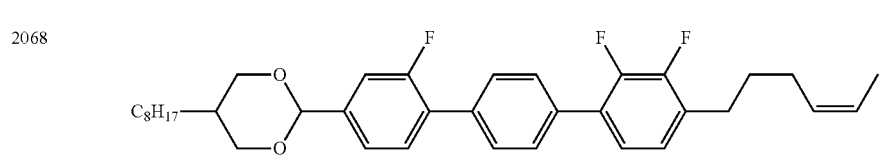 |
| 2069 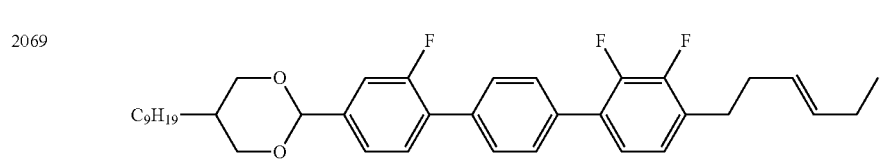 |
| 2070 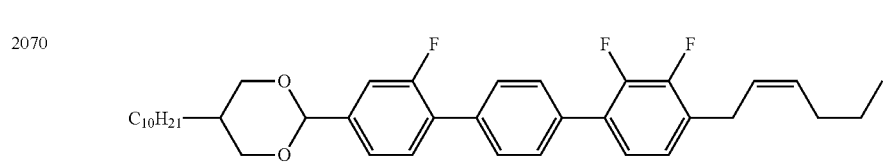 |

| No. | |
|---|---|
| 2071 | 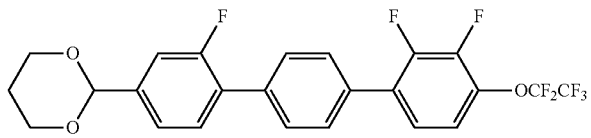 |
| 2072 | 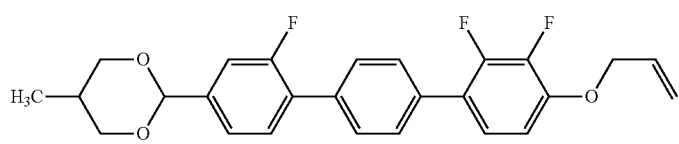 |
| 2073 | 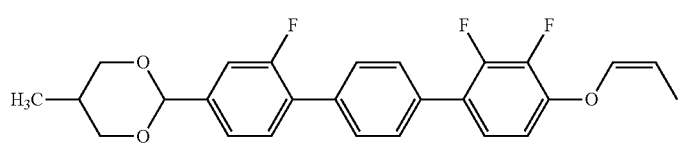 |
| 2074 | 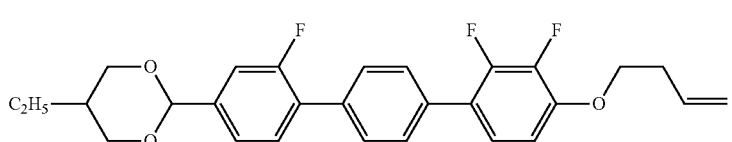 |
| 2075 | 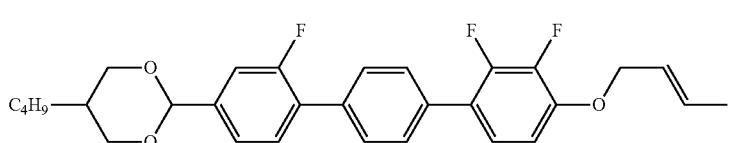 |
| 2076 | 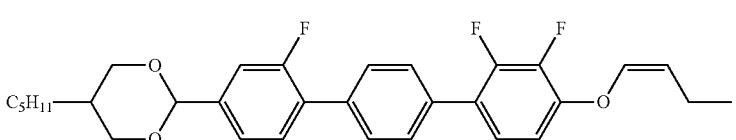 |
| 2077 | 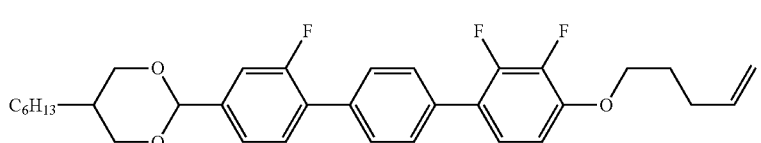 |
| 2078 | 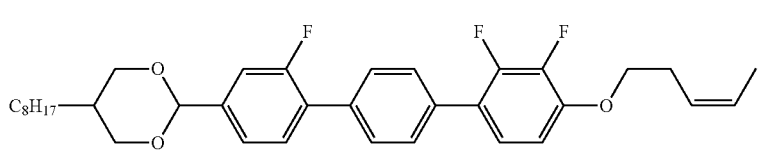 |
| 2079 | 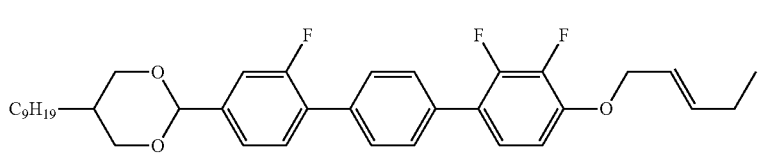 |
| 2080 | 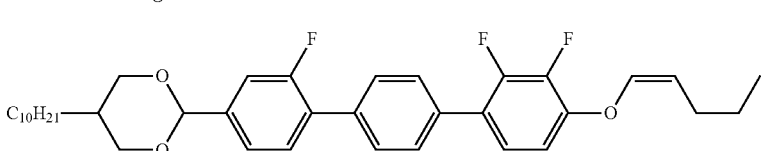 |
| 2081 | 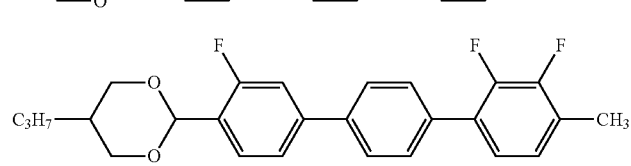 |

-continued

| No. | |
|---|---|
| 2082 | C₃H₇–[1,3-dioxane]–[3-F-phenyl]–[phenyl]–[2,3-diF-phenyl]–C₂H₅ |
| 2083 | C₃H₇–[1,3-dioxane]–[3-F-phenyl]–[phenyl]–[2,3-diF-phenyl]–C₃H₇ |
| 2084 | C₃H₇–[1,3-dioxane]–[3-F-phenyl]–[phenyl]–[2,3-diF-phenyl]–C₄H₉ |
| 2085 | C₃H₇–[1,3-dioxane]–[3-F-phenyl]–[phenyl]–[2,3-diF-phenyl]–C₅H₁₁ |
| 2086 | C₃H₇–[1,3-dioxane]–[3-F-phenyl]–[phenyl]–[2,3-diF-phenyl]–C₆H₁₃ |
| 2087 | C₃H₇–[1,3-dioxane]–[3-F-phenyl]–[phenyl]–[2,3-diF-phenyl]–C₇H₁₅ |
| 2088 | C₃H₇–[1,3-dioxane]–[3-F-phenyl]–[phenyl]–[2,3-diF-phenyl]–C₈H₁₇ |
| 2089 | C₃H₇–[1,3-dioxane]–[3-F-phenyl]–[phenyl]–[2,3-diF-phenyl]–C₉H₁₉ |
| 2090 | C₃H₇–[1,3-dioxane]–[3-F-phenyl]–[phenyl]–[2,3-diF-phenyl]–C₁₀H₂₁ |
| 2091 | C₃H₇–[1,3-dioxane]–[3-F-phenyl]–[phenyl]–[2,3-diF-phenyl]–OCH₃ |

-continued
| No. | |
|---|---|
| 2092 | 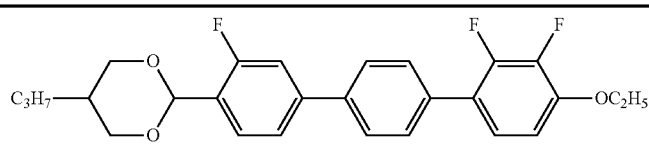 |
| 2093 | 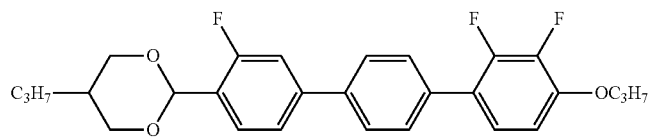 |
| 2094 | 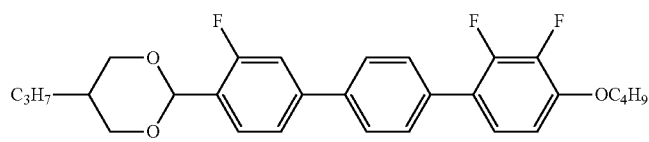 |
| 2095 | 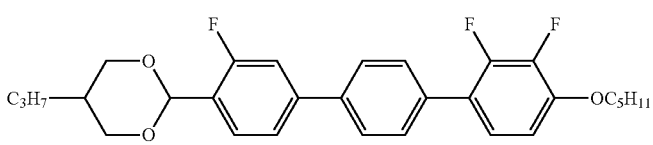 |
| 2096 | 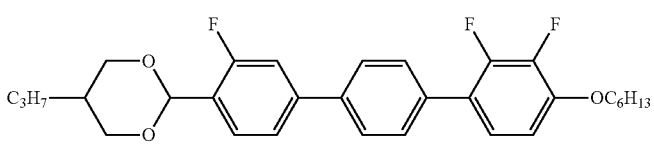 |
| 2097 | 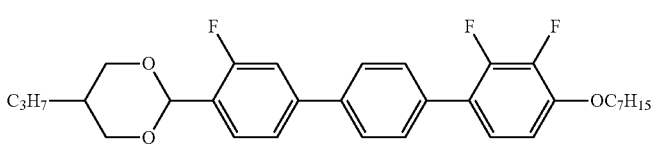 |
| 2098 | 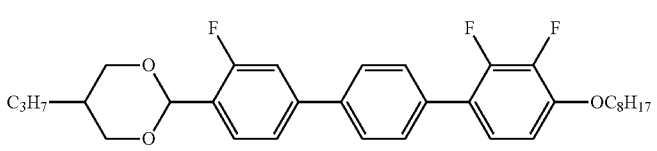 |
| 2099 | 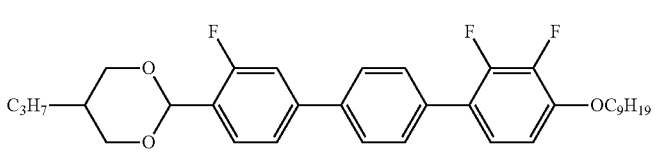 |
| 2100 | 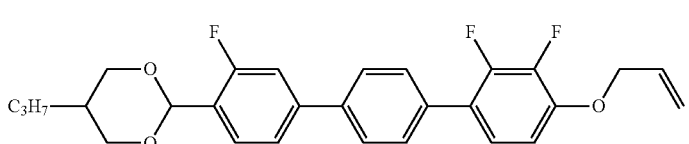 |
| 2101 | 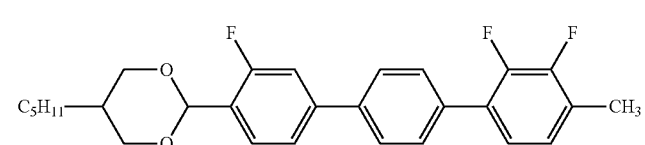 |
| 2102 | 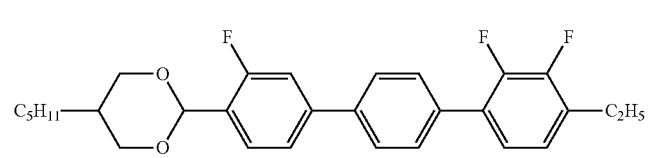 |

-continued
| No. | |
|---|---|
| 2013 | 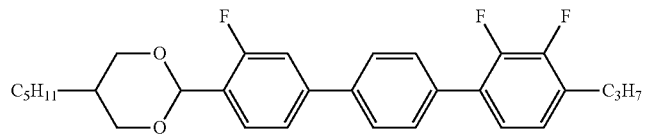 |
| 2104 | 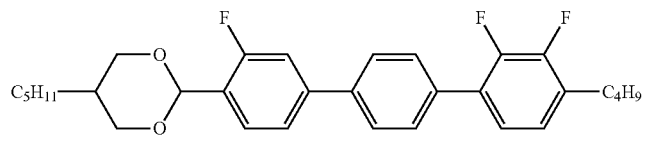 |
| 2105 | 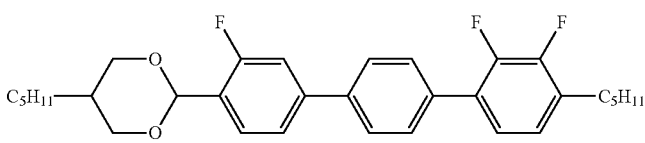 |
| 2106 | 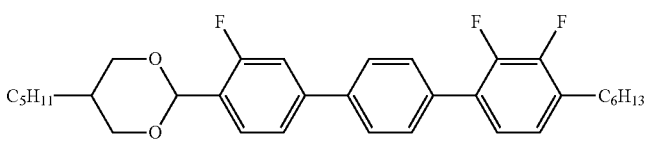 |
| 2107 | 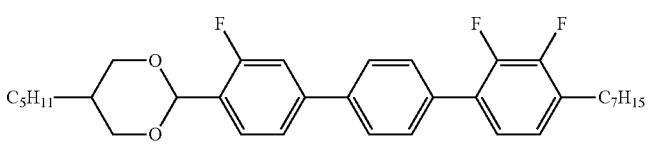 |
| 2108 | 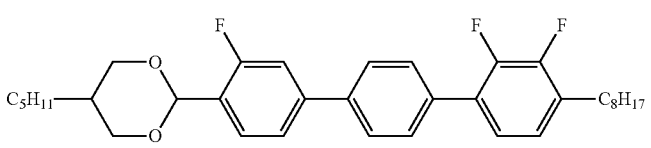 |
| 2109 | 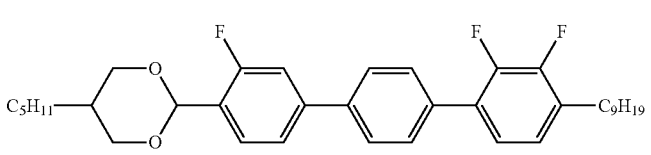 |
| 2110 | 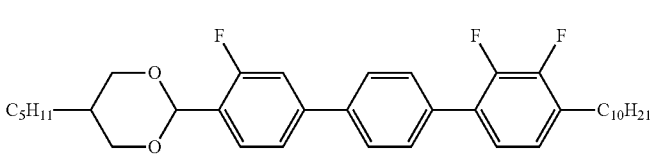 |
| 2111 | 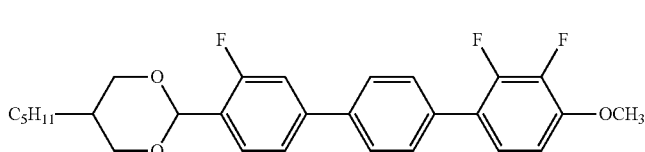 |
| 2112 | 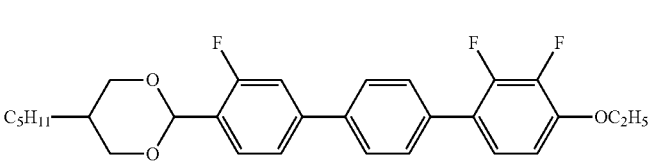 |

| No. | |
|---|---|
| 2113 | 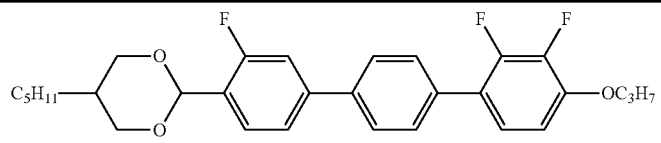 |
| 2114 | 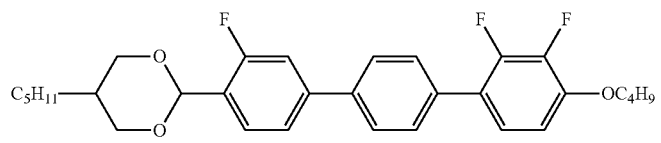 |
| 2115 | 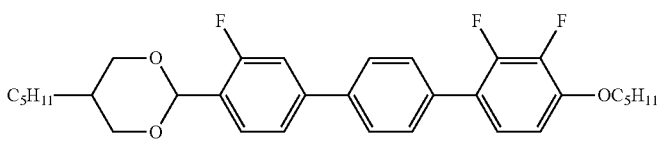 |
| 2116 | 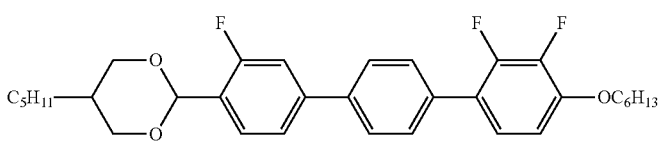 |
| 2117 | 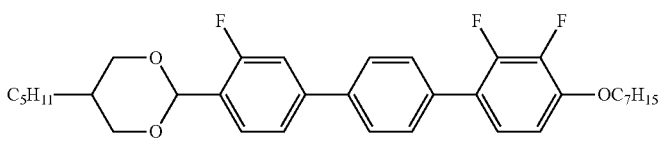 |
| 2118 | 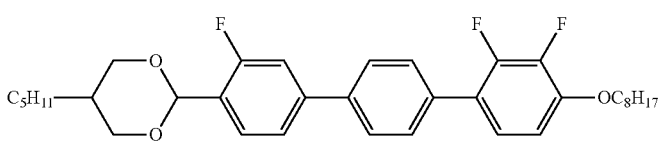 |
| 2119 | 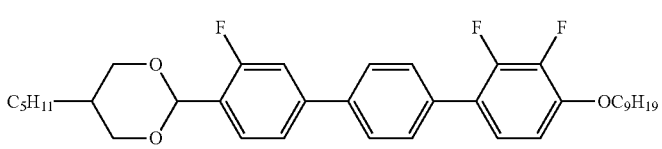 |
| 2120 | 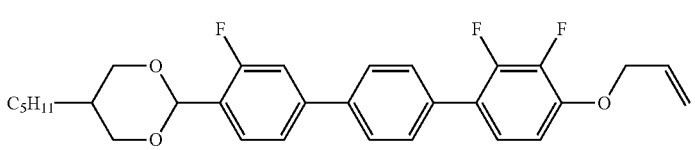 |
| 2121 | 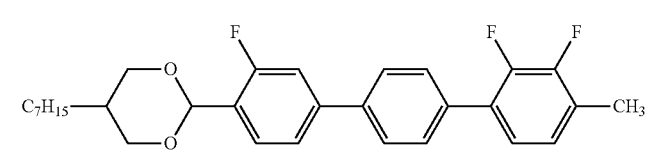 |
| 2122 | 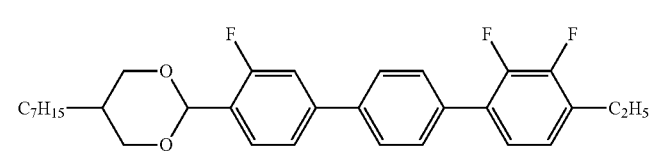 |
| 2123 | 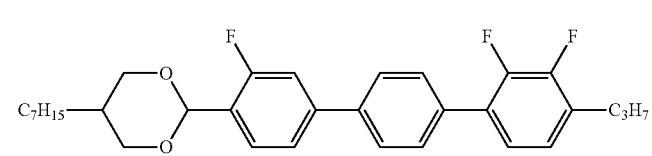 |

| No. | |
|---|---|
| 2124 | 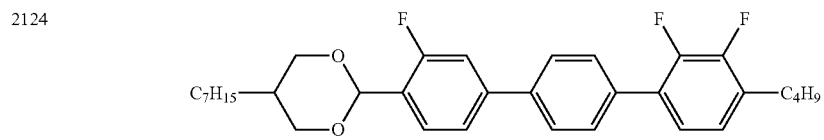 |
| 2125 | 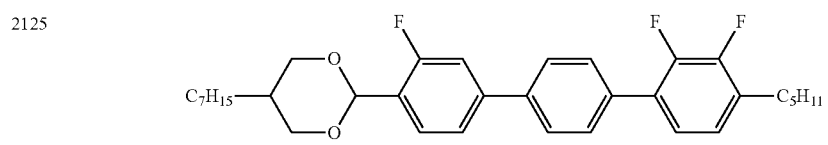 |
| 2126 | 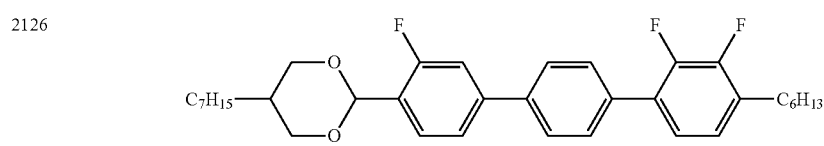 |
| 2127 | 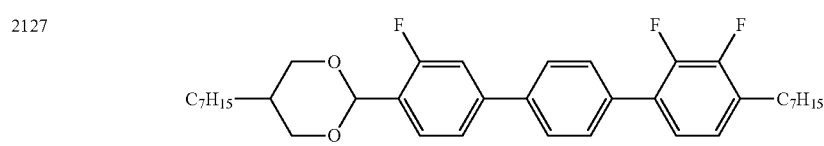 |
| 2128 | 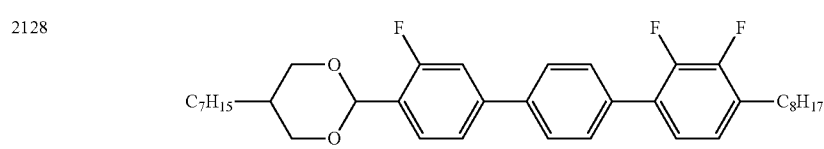 |
| 2129 | 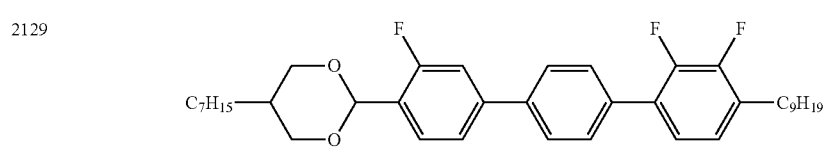 |
| 2130 | 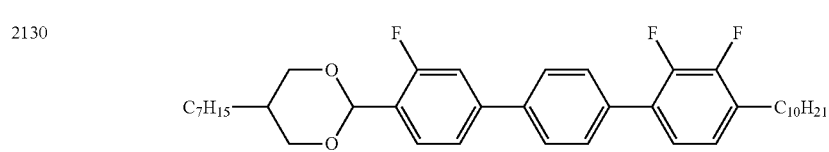 |
| 2131 | 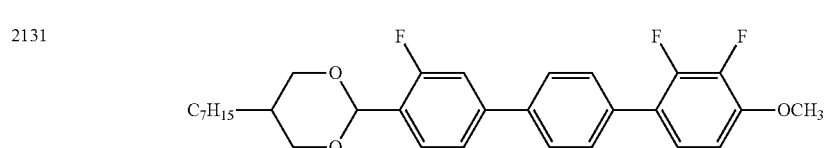 |
| 2132 | 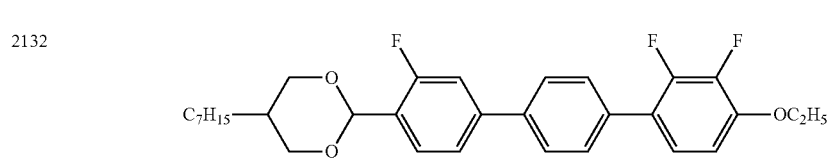 |
| 2133 | 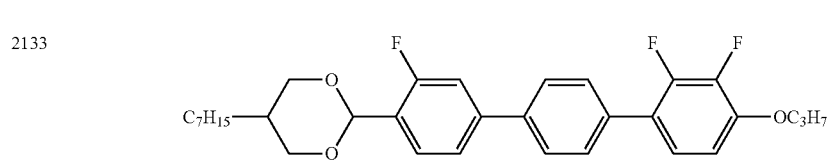 |

-continued
| No. | |
|---|---|
| 2134 | 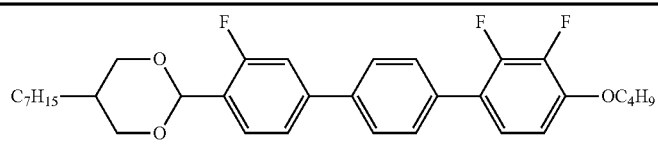 |
| 2135 | 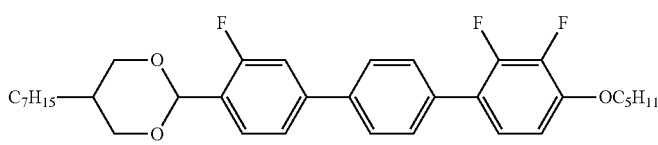 |
| 2136 | 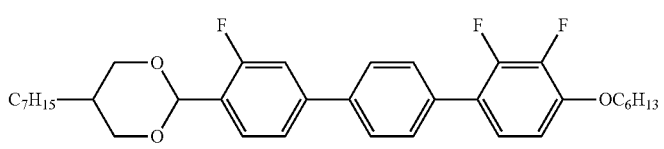 |
| 2137 | 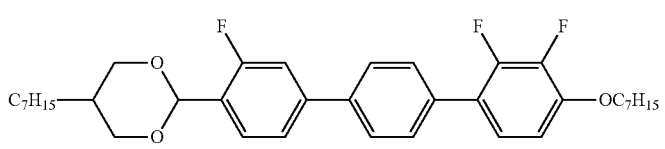 |
| 2138 | 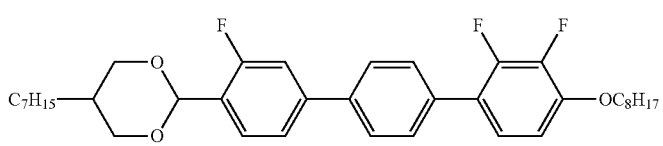 |
| 2139 | 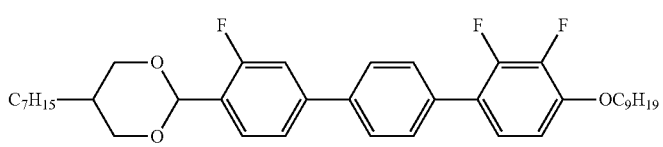 |
| 2140 | 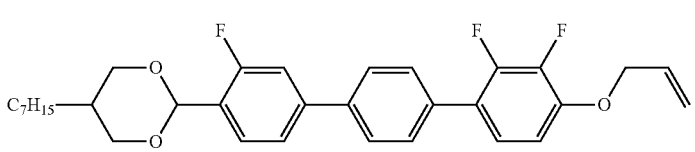 |
| 2141 | 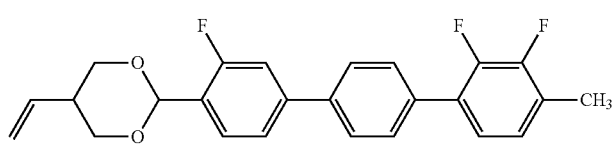 |
| 2142 | 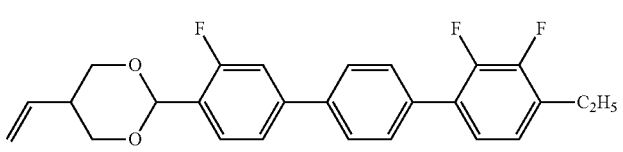 |
| 2143 | 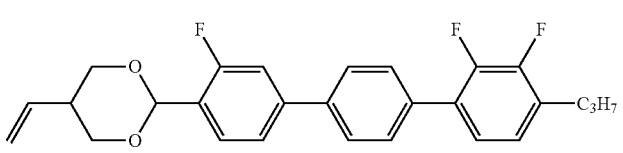 |
| 2144 | 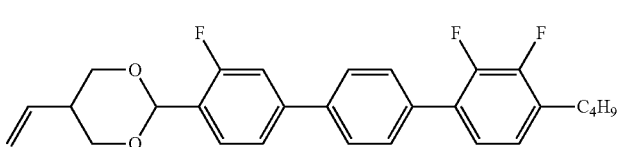 |

| No. | |
|---|---|
| 2145 | 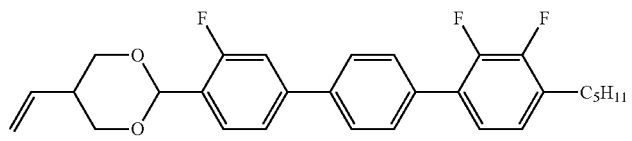 |
| 2146 | 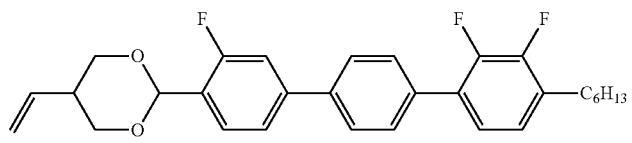 |
| 2147 | 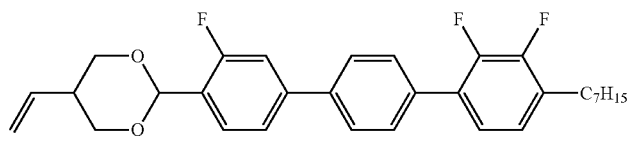 |
| 2148 | 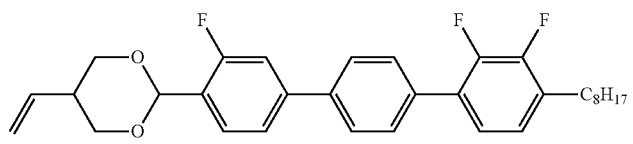 |
| 2149 | 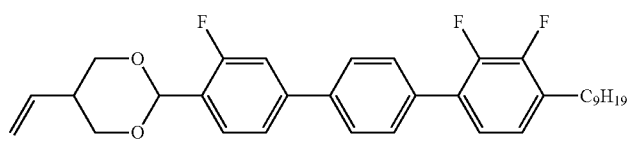 |
| 2150 | 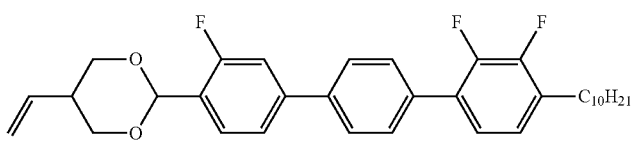 |
| 2151 | 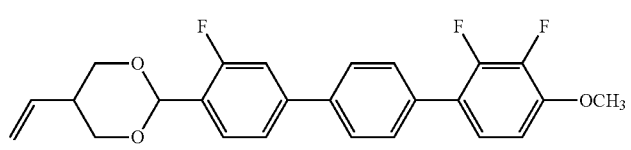 |
| 2152 | 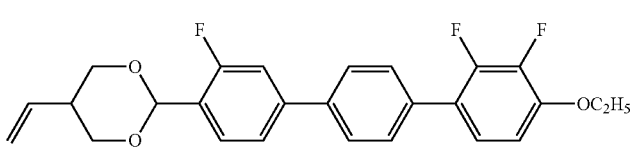 |
| 2153 | 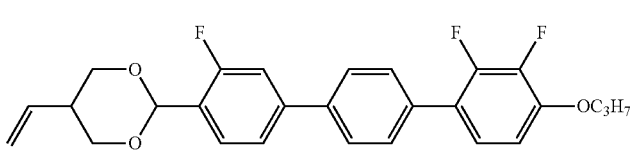 |
| 2154 | 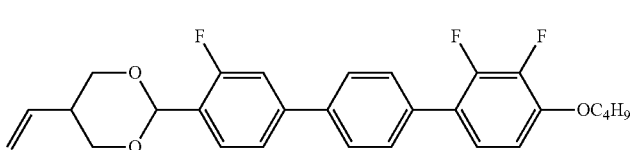 |

| No. | |
|---|---|
| 2155 | 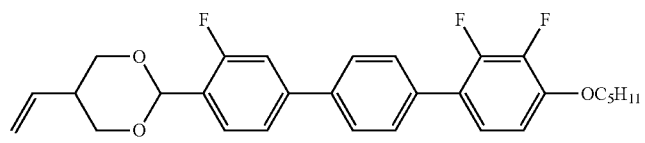 |
| 2156 | 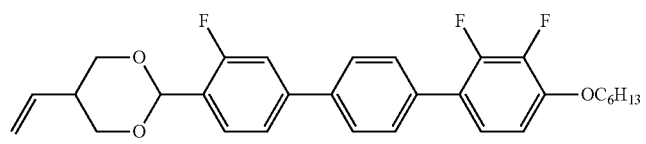 |
| 2157 | 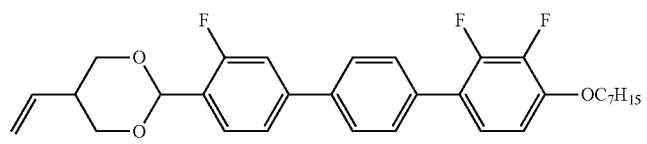 |
| 2158 | 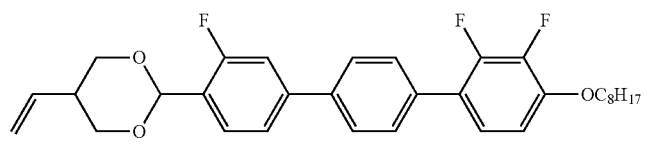 |
| 2159 | 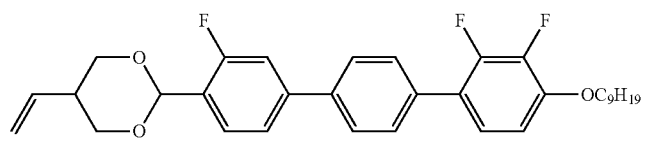 |
| 2160 | 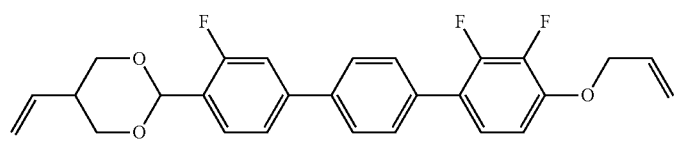 |
| 2161 | 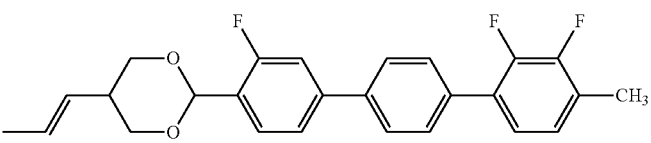 |
| 2162 | 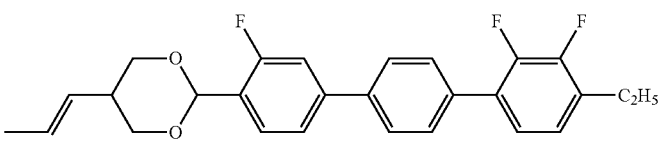 |
| 2163 | 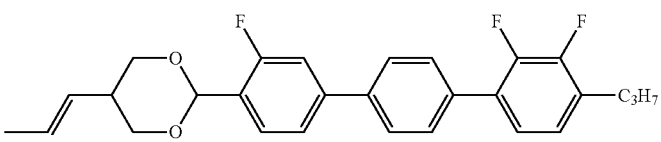 |
| 2164 | 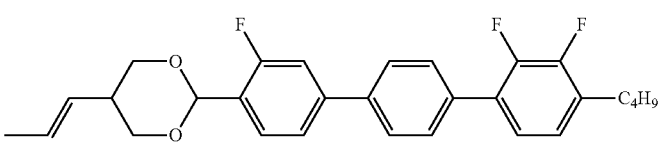 |

| No. | |
|---|---|
| 2165 | 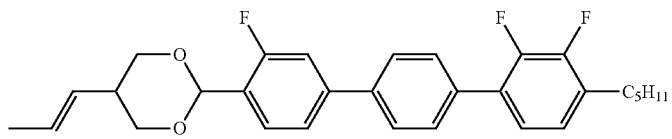 |
| 2166 | 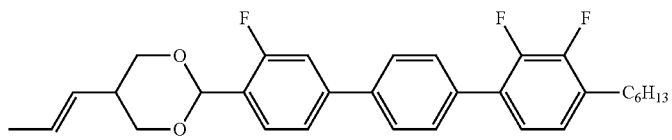 |
| 2167 | 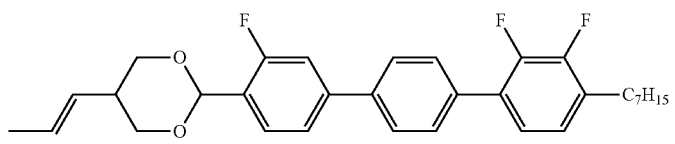 |
| 2168 | 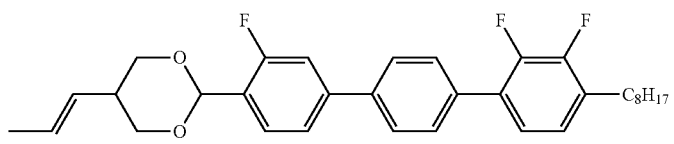 |
| 2169 | 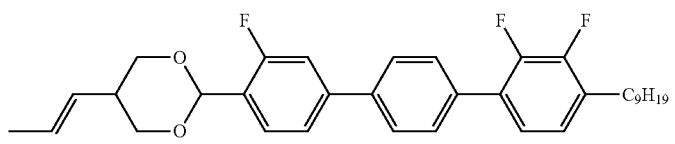 |
| 2170 | 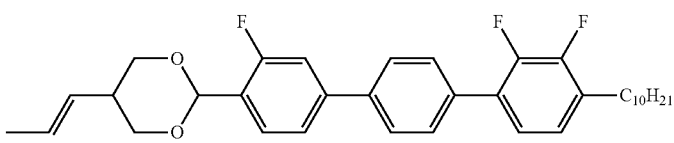 |
| 2171 | 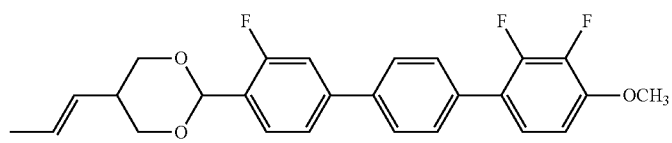 |
| 2172 | 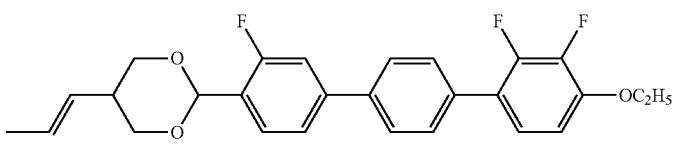 |
| 2173 |  |
| 2174 | 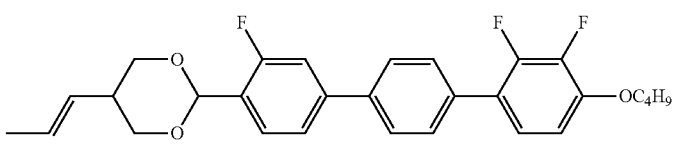 |

| No. | |
|---|---|
| 2175 | 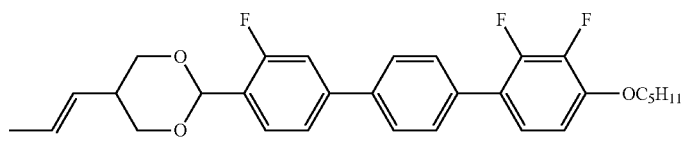 |
| 2176 | 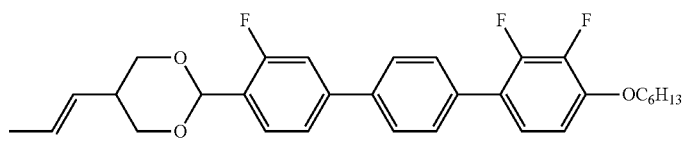 |
| 2177 | 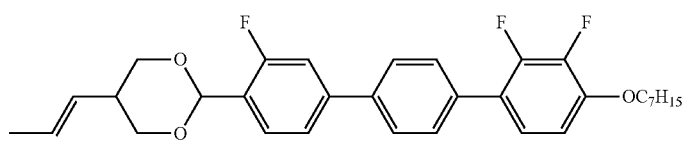 |
| 2178 | 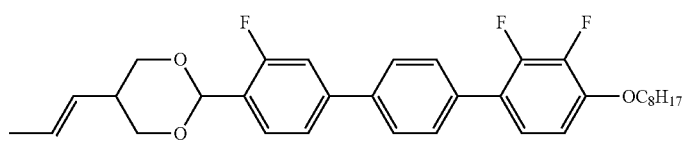 |
| 2179 | 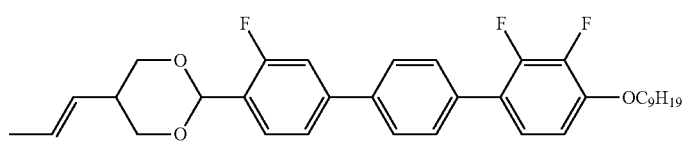 |
| 2180 | 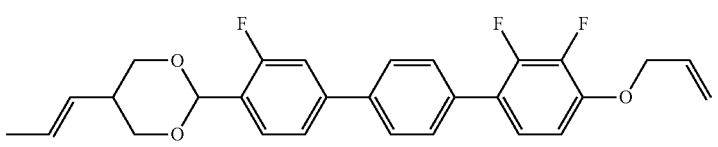 |
| 2181 | 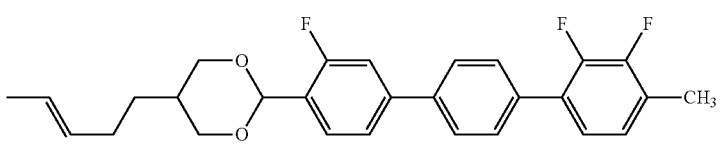 |
| 2182 | 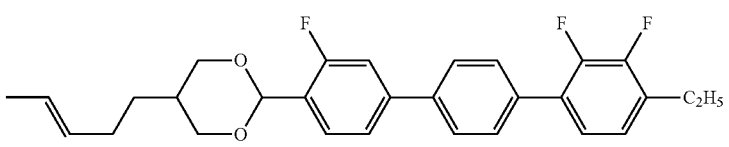 |
| 2183 | 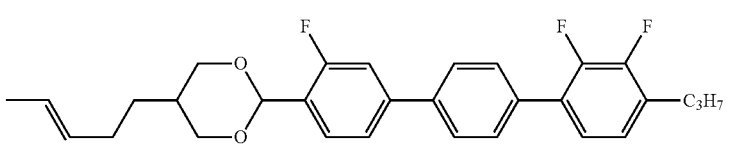 |
| 2184 | 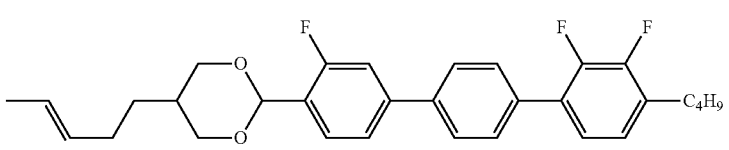 |

-continued
| No. | |
|---|---|
| 2185 | 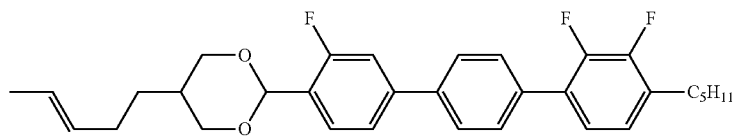 |
| 2186 | 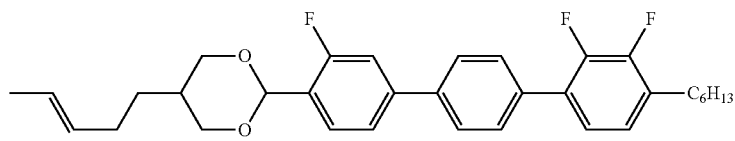 |
| 2187 | 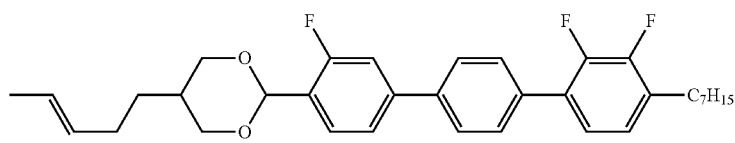 |
| 2188 | 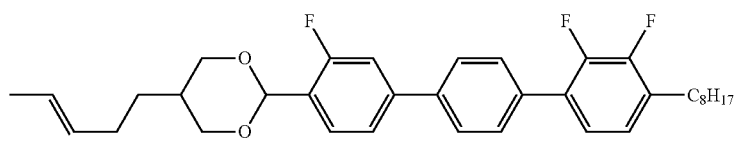 |
| 2189 | 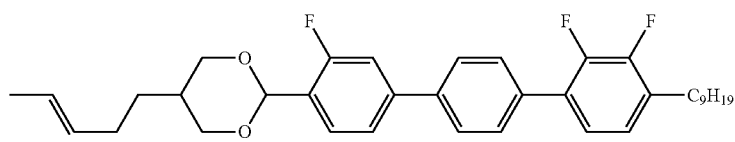 |
| 2190 | 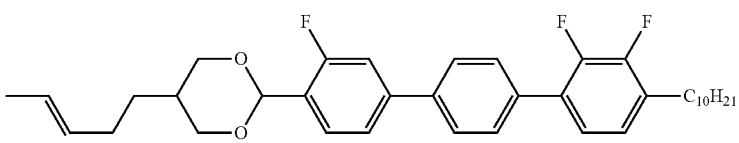 |
| 2191 | 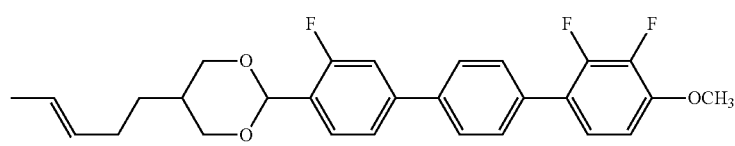 |
| 2192 | 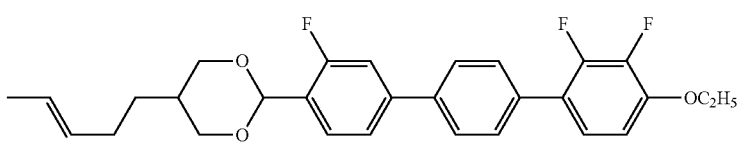 |
| 2193 | 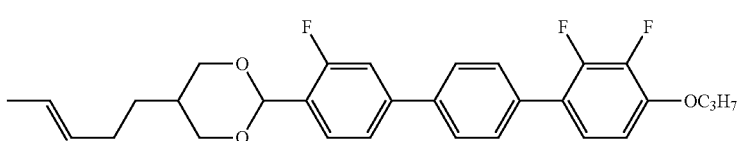 |
| 2194 | 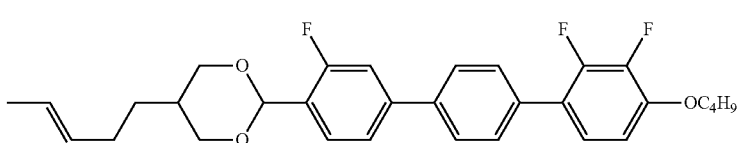 |

| No. | |
|---|---|
| 2195 | 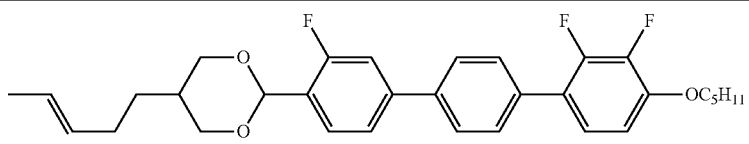 |
| 2196 | 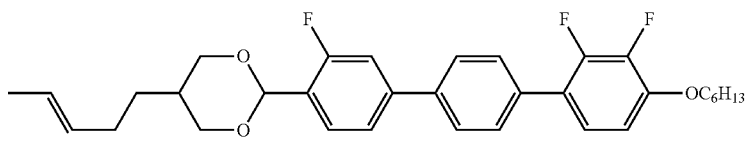 |
| 2197 | 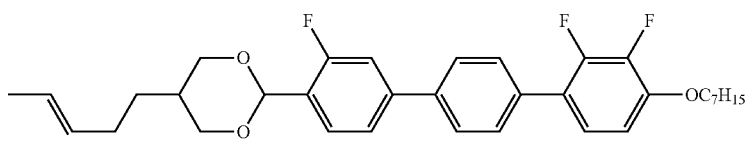 |
| 2198 | 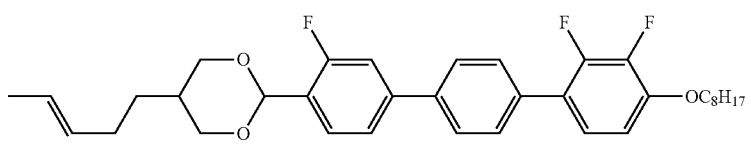 |
| 2199 | 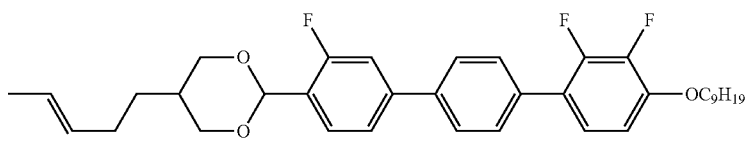 |
| 2200 | 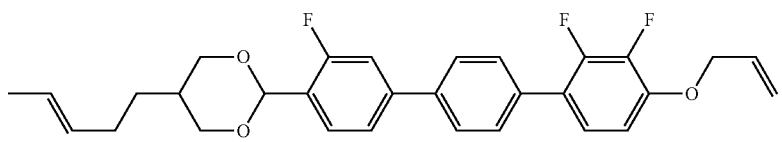 |
| 2201 | 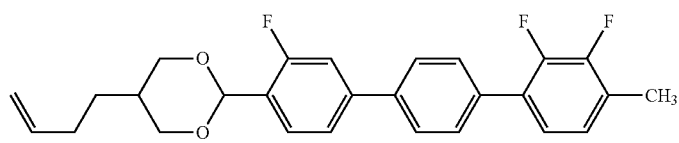 |
| 2202 | 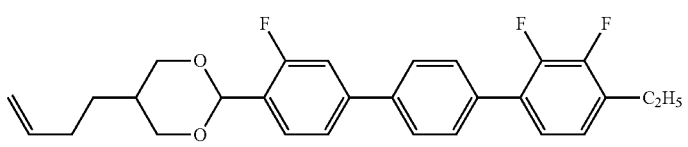 |
| 2203 | 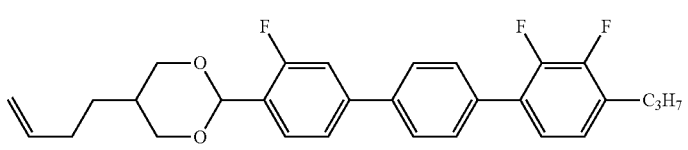 |
| 2204 | 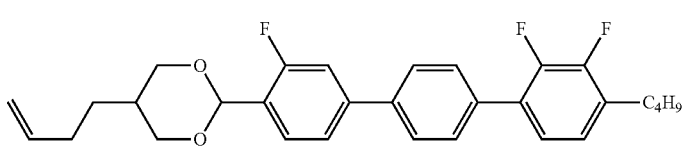 |
| 2205 | 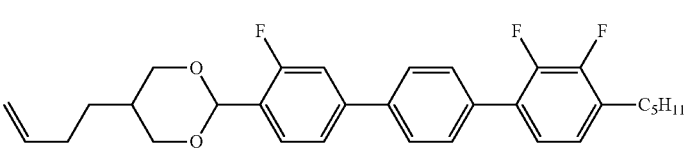 |

| No. | |
|---|---|
| 2206 | 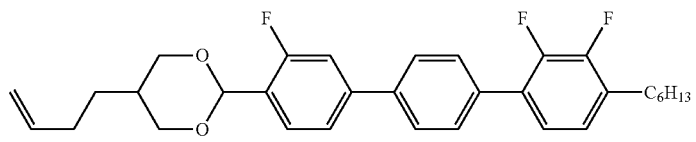 |
| 2207 | 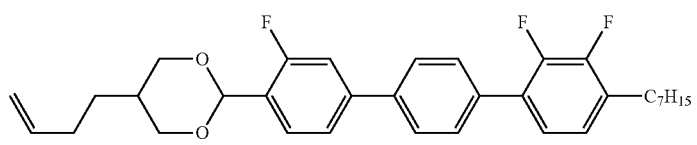 |
| 2208 | 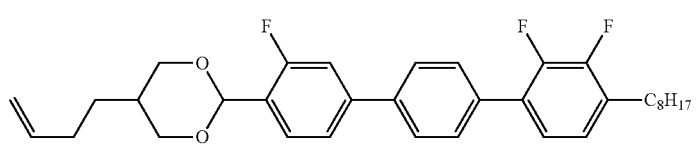 |
| 2209 | 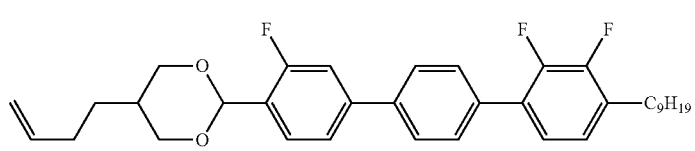 |
| 2210 | 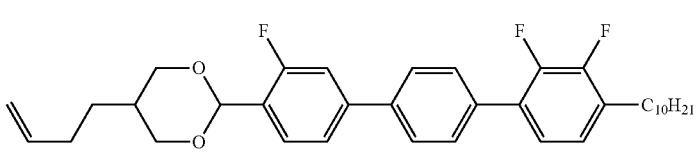 |
| 2211 | 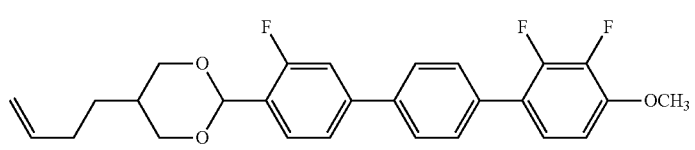 |
| 2212 | 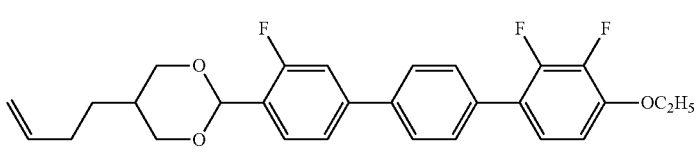 |
| 2213 | 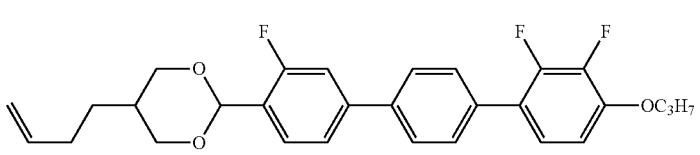 |
| 2214 | 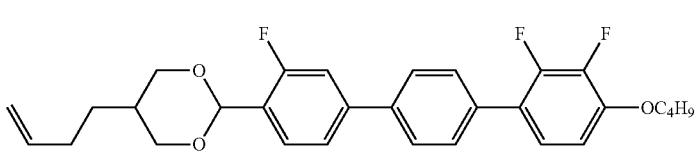 |
| 2215 | 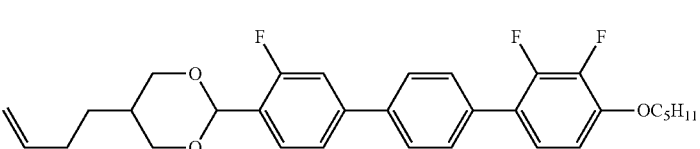 |

-continued
| No. | |
|---|---|
| 2216 | 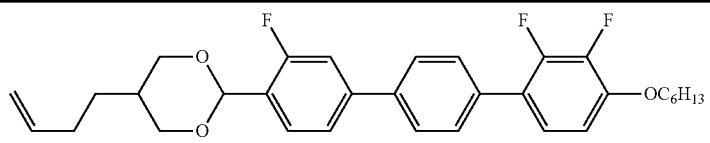 |
| 2217 | 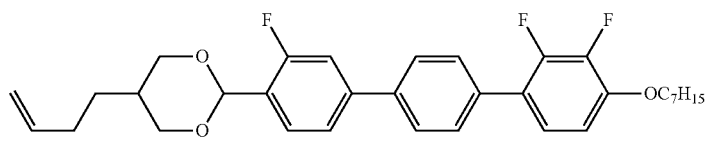 |
| 2218 | 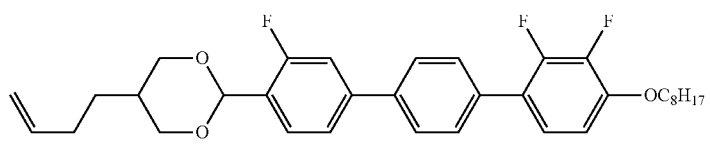 |
| 2219 | 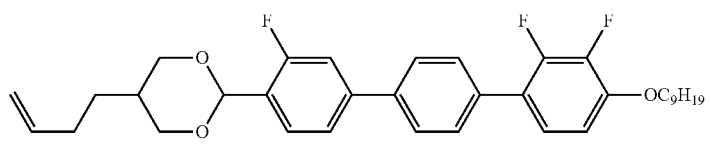 |
| 2220 | 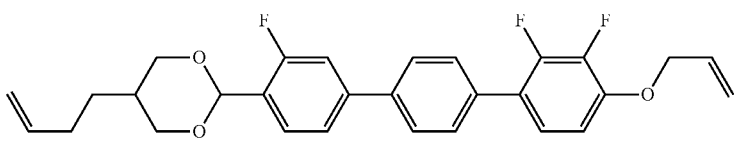 |
| 2221 | 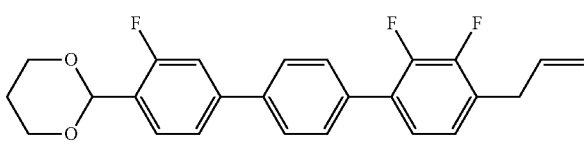 |
| 2222 | 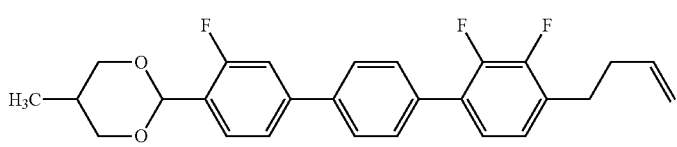 |
| 2223 | 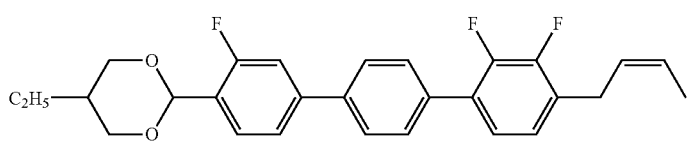 |
| 2224 | 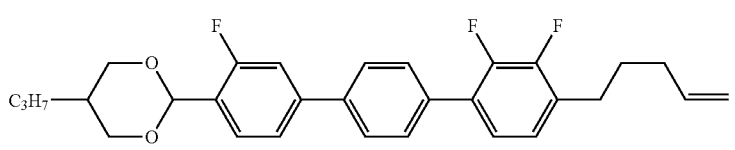 |
| 2225 |  |
| 2226 | 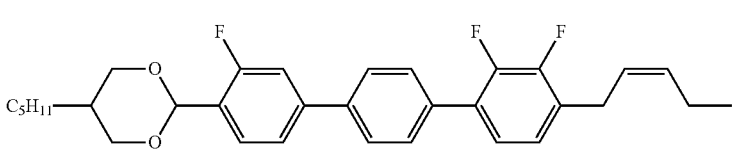 |

| No. | |
|---|---|
| 2227 | 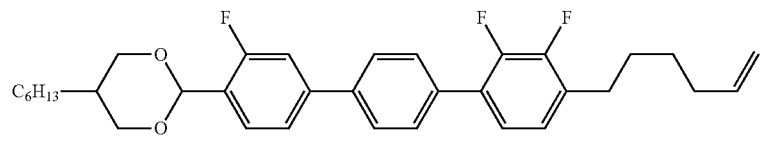 |
| 2228 | 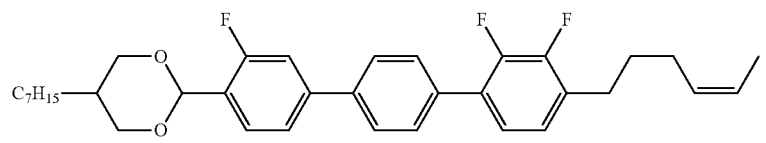 |
| 2229 | 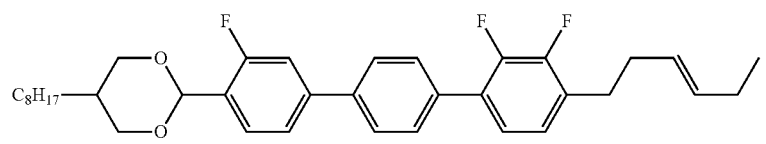 |
| 2230 | 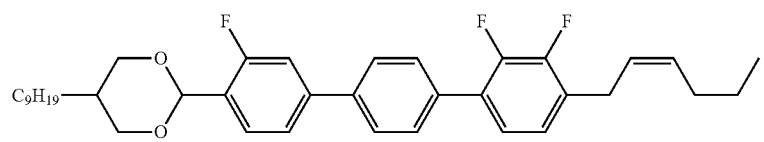 |
| 2231 | 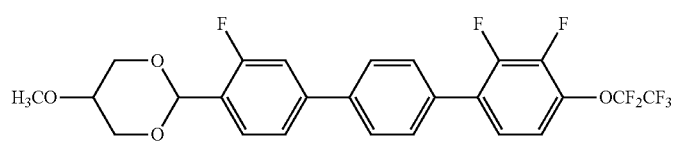 |
| 2232 | 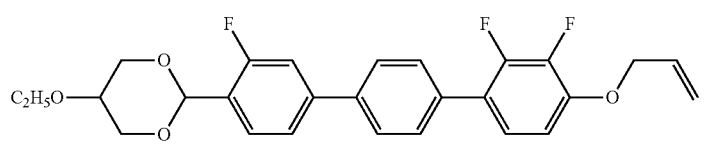 |
| 2233 | 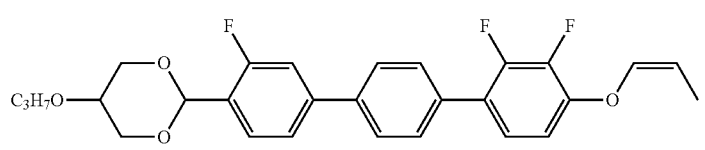 |
| 2234 | 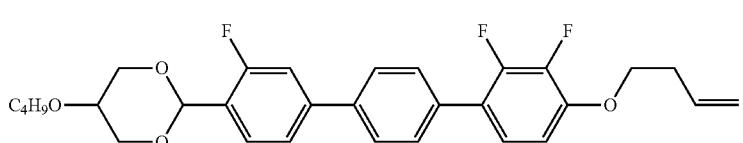 |
| 2235 | 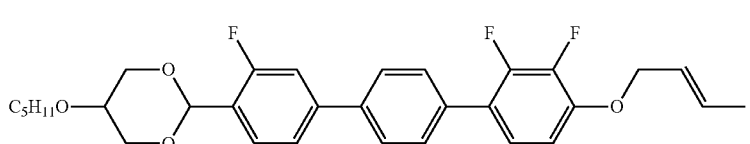 |
| 2236 | 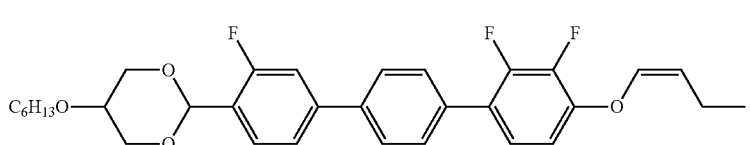 |

| No. | |
|---|---|
| 2237 | 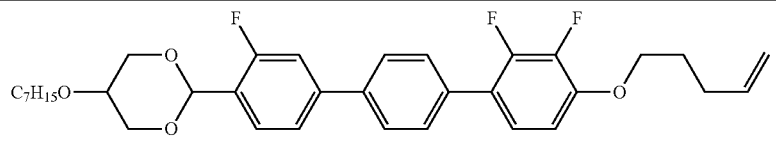 |
| 2238 | 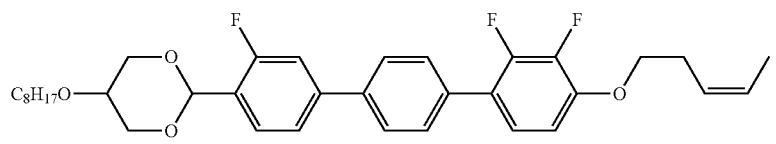 |
| 2239 | 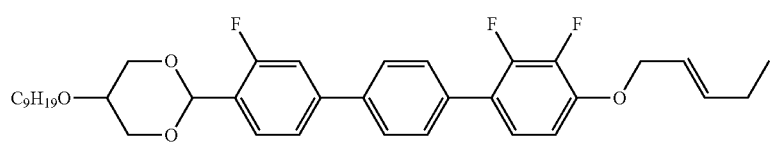 |
| 2240 | 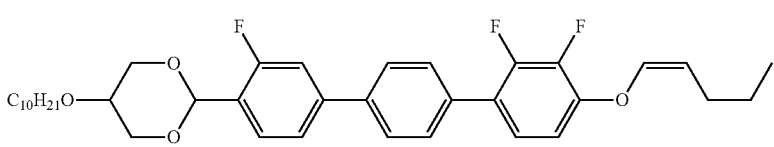 |
| 2241 | 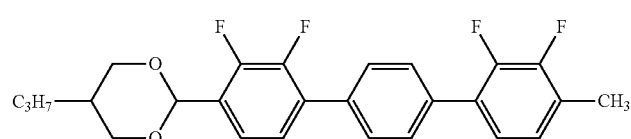 |
| 2242 | 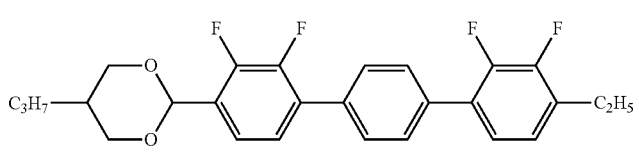 |
| 2243 | 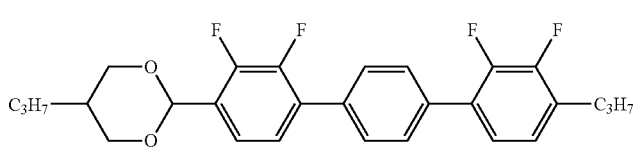 |
| 2244 | 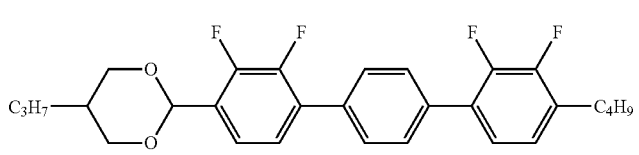 |
| 2245 | 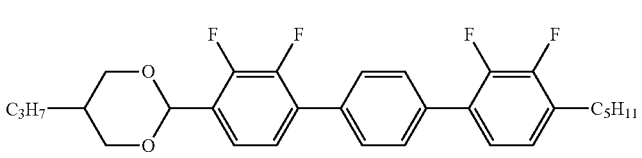 |
| 2246 | 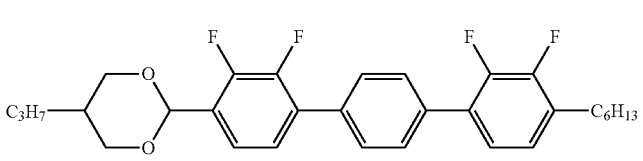 |
| 2247 | 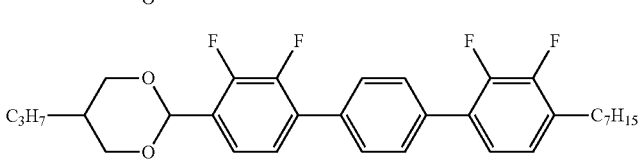 |

-continued
| No. | |
|---|---|
| 2248 | 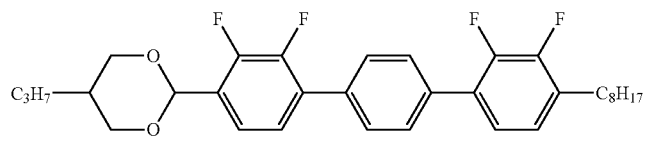 |
| 2249 | 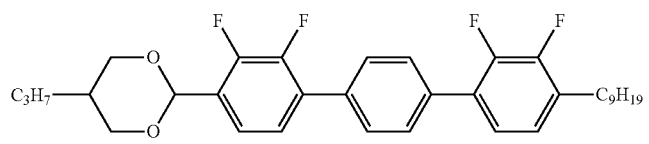 |
| 2250 | 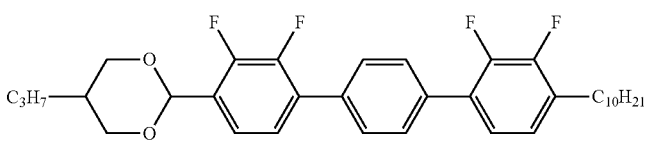 |
| 2251 | 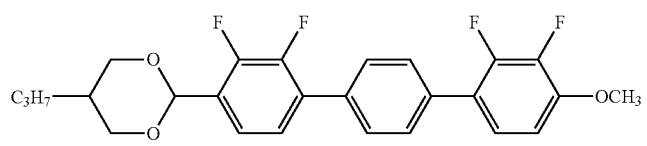 |
| 2252 | 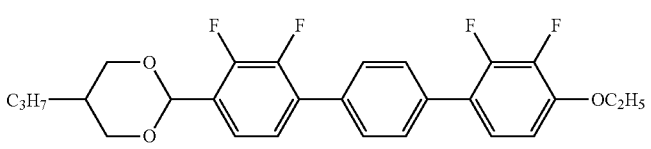 |
| 2253 | 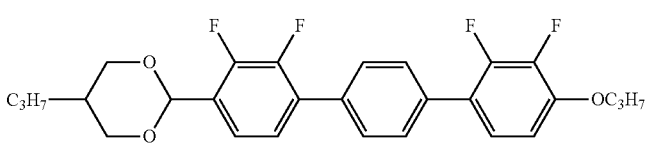 |
| 2254 | 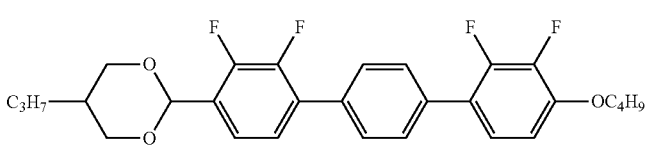 |
| 2255 | 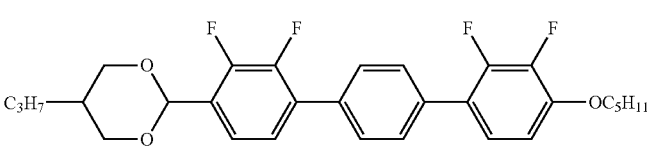 |
| 2256 | 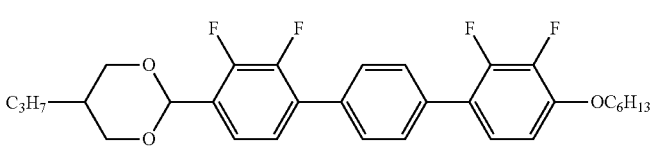 |
| 2257 | 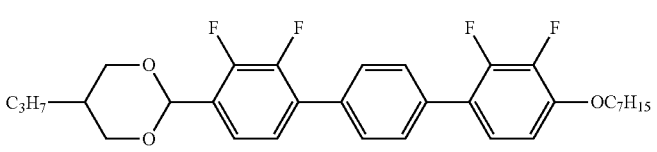 |

-continued
| No. | |
|---|---|
| 2258 | 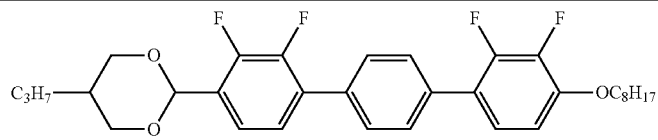 |
| 2259 | 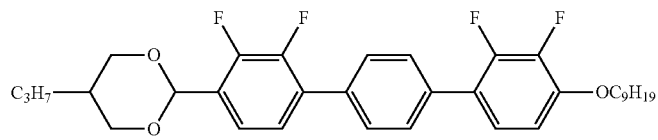 |
| 2260 | 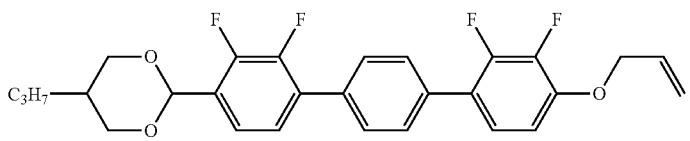 |
| 2261 | 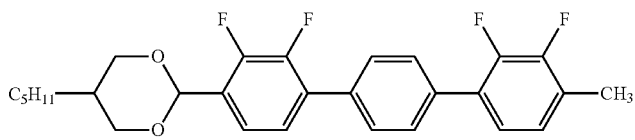 |
| 2262 | 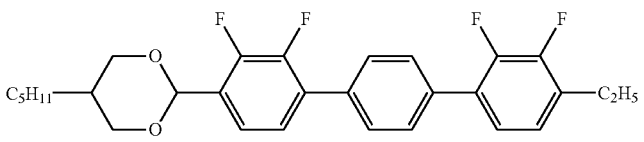 |
| 2263 | 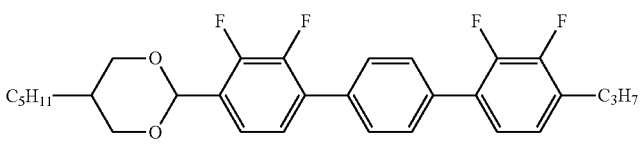 |
| 2264 | 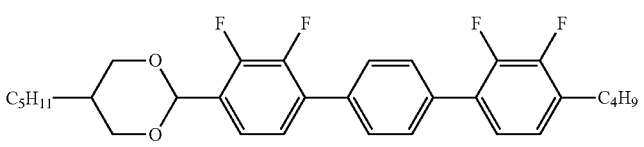 |
| 2265 | 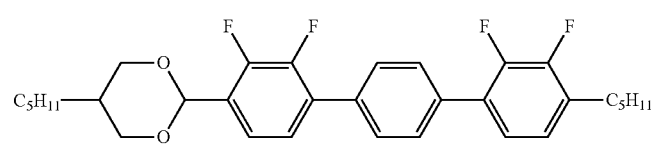 |
| 2266 | 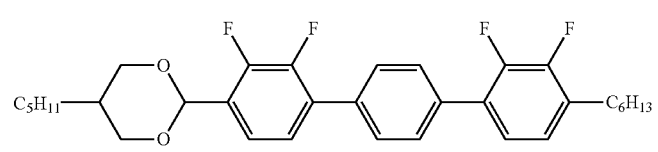 |
| 2267 | 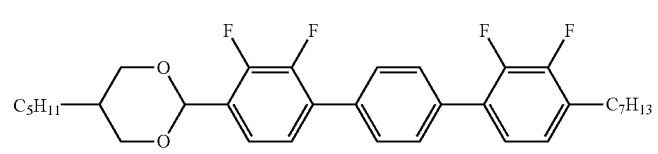 |
| 2268 | 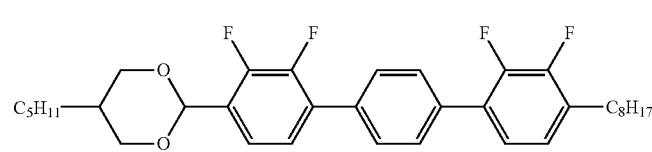 |

| No. | |
|---|---|
| 2269 | 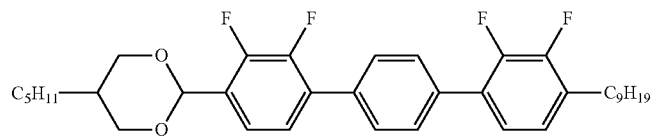 |
| 2270 | 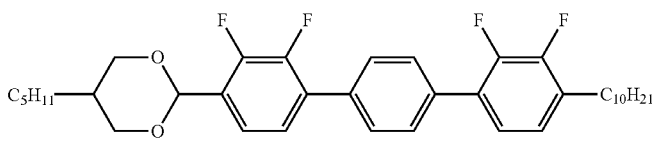 |
| 2271 | 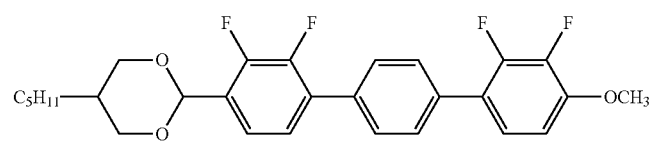 |
| 2272 | 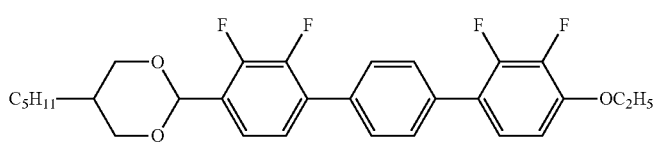 |
| 2273 | 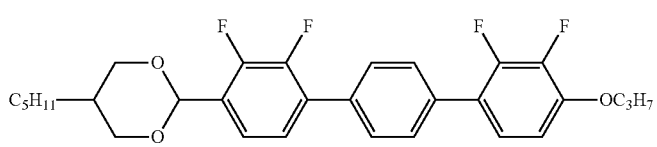 |
| 2274 | 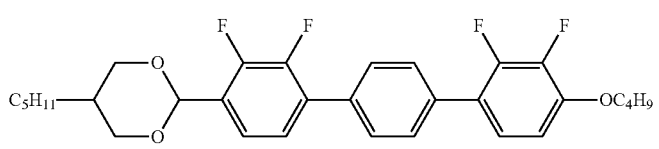 |
| 2275 | 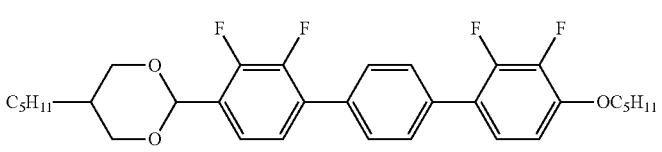 |
| 2276 | 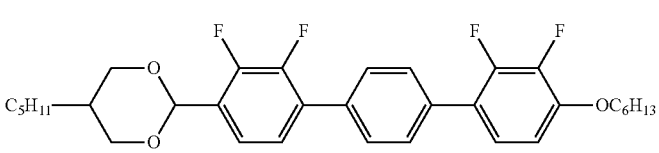 |
| 2277 | 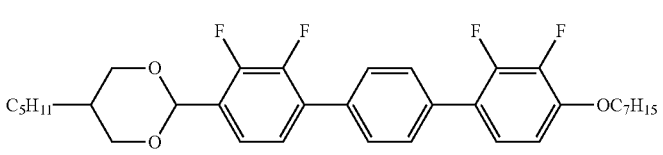 |
| 2278 | 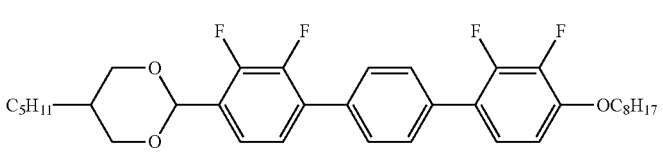 |

| No. | |
|---|---|
| 2279 | 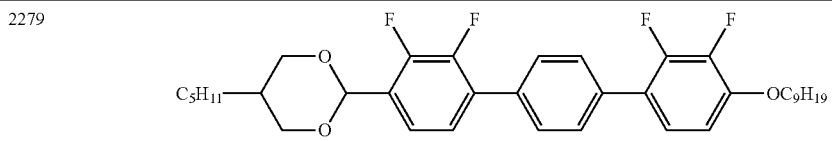 |
| 2280 | 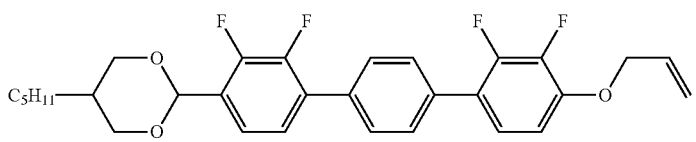 |
| 2281 | 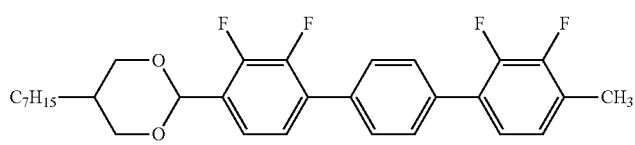 |
| 2282 | 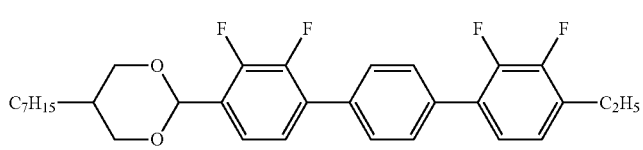 |
| 2283 | 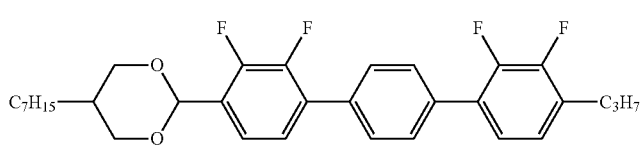 |
| 2284 | 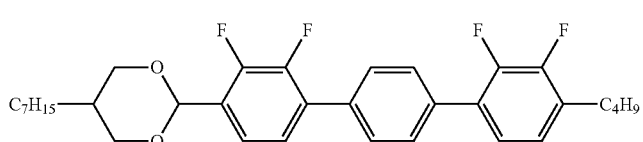 |
| 2285 | 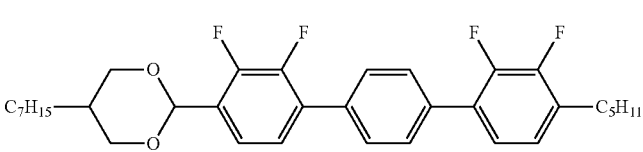 |
| 2286 | 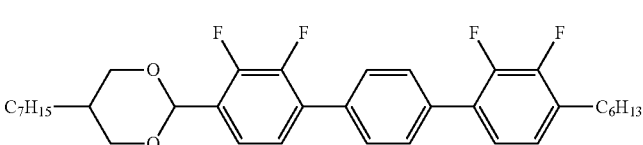 |
| 2287 | 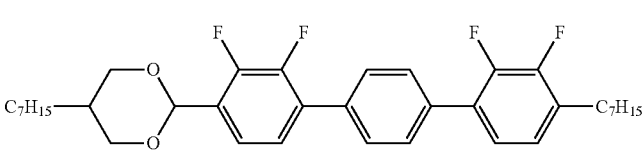 |
| 2288 | 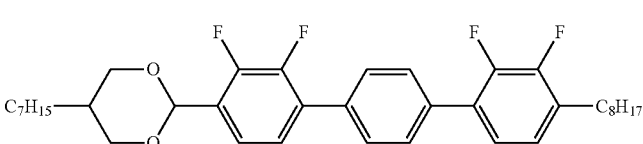 |
| 2289 | 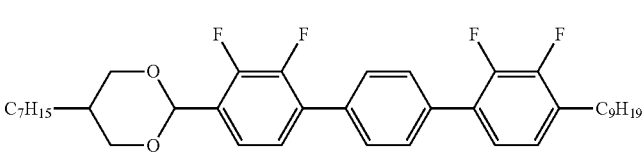 |

| No. | |
|---|---|
| 2290 | 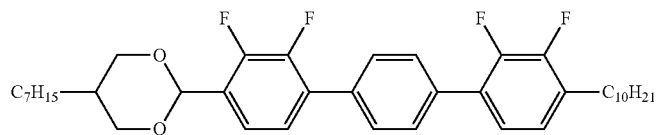 |
| 2291 | 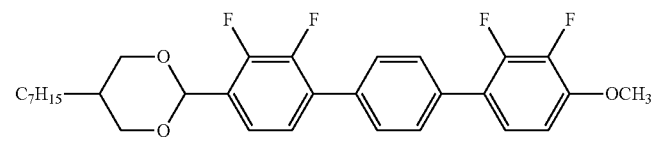 |
| 2292 | 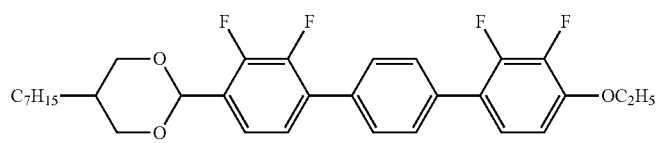 |
| 2293 | 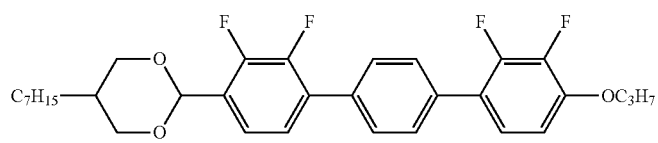 |
| 2294 | 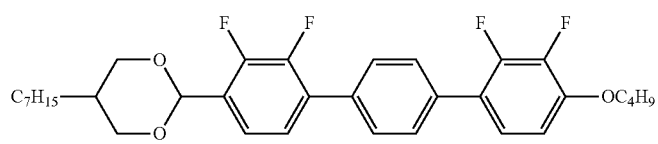 |
| 2295 | 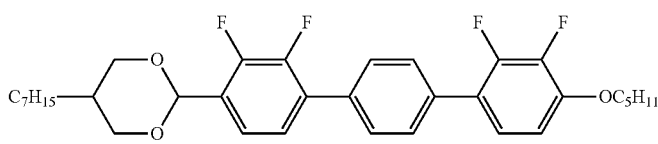 |
| 2296 | 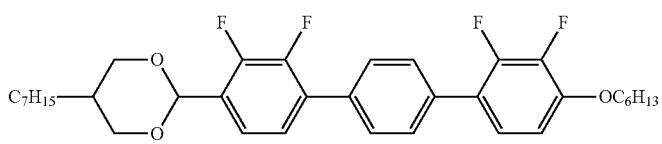 |
| 2297 | 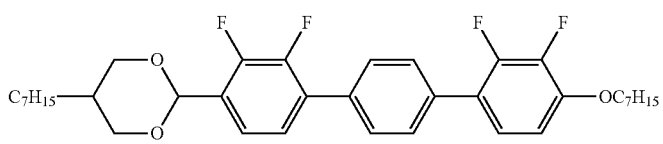 |
| 2298 | 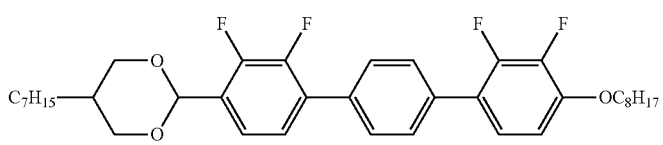 |
| 2299 | 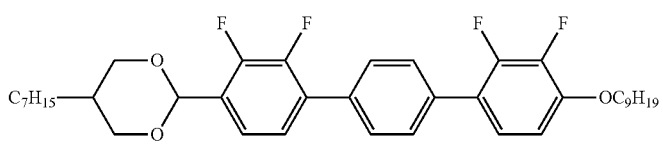 |

| No. | |
|---|---|
| 2300 | 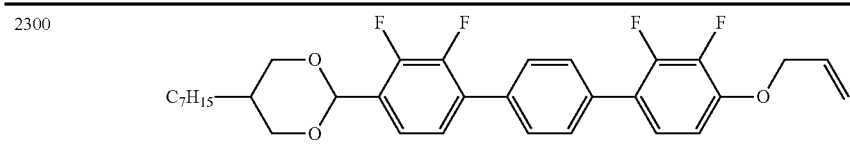 |
| 2301 | 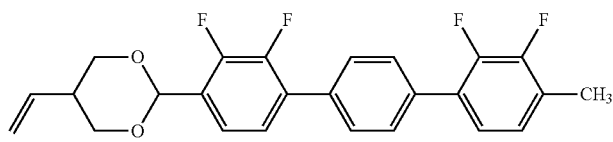 |
| 2302 | 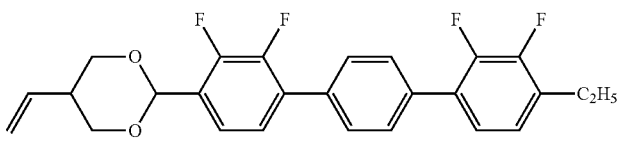 |
| 2303 | 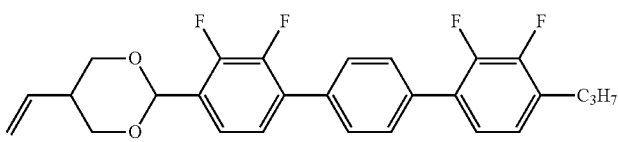 |
| 2304 | 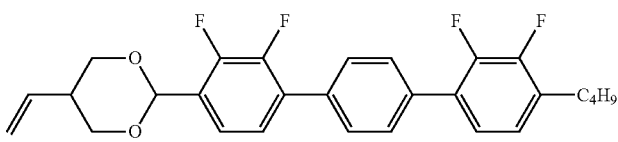 |
| 2305 | 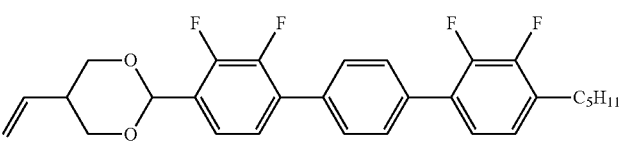 |
| 2306 | 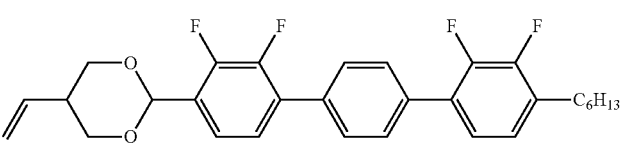 |
| 2307 | 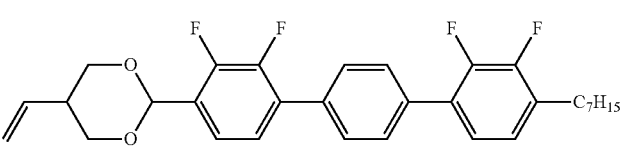 |
| 2308 | 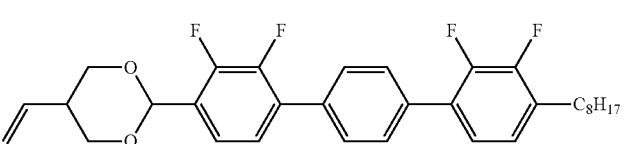 |
| 2309 | 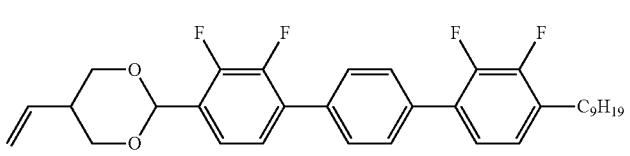 |
| 2310 | 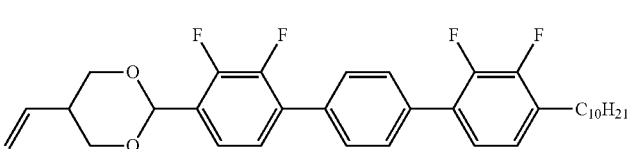 |

-continued
| No. | |
|---|---|
| 2311 | 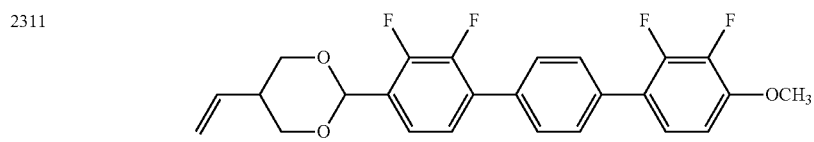 |
| 2312 | 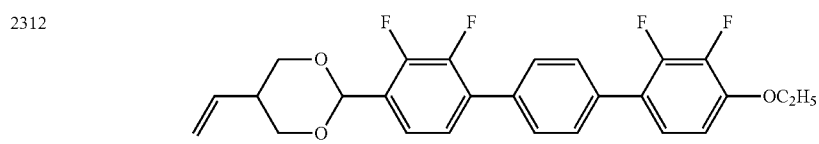 |
| 2313 | 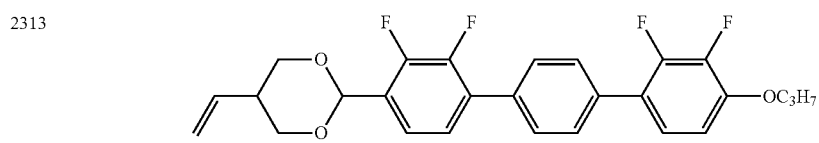 |
| 2314 | 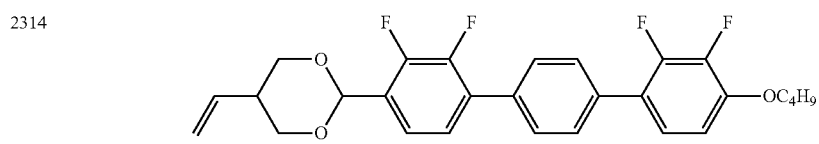 |
| 2315 | 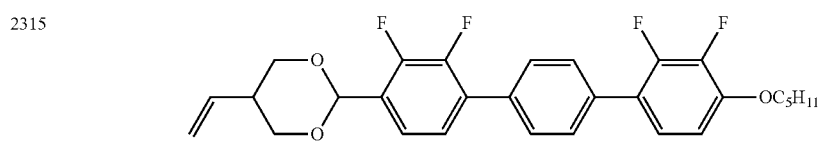 |
| 2316 | 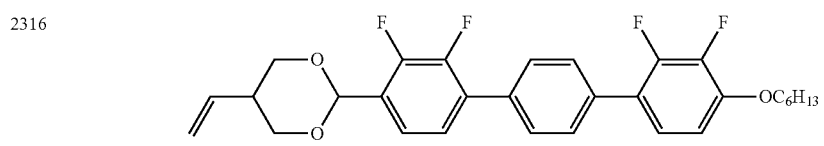 |
| 2317 | 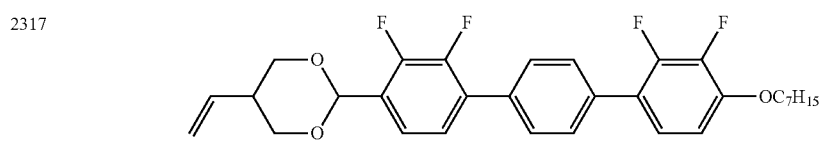 |
| 2318 | 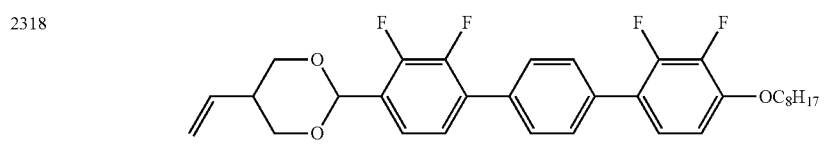 |
| 2319 | 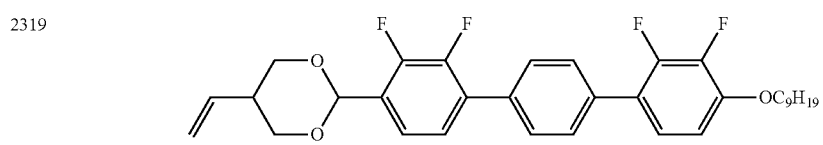 |
| 2320 | 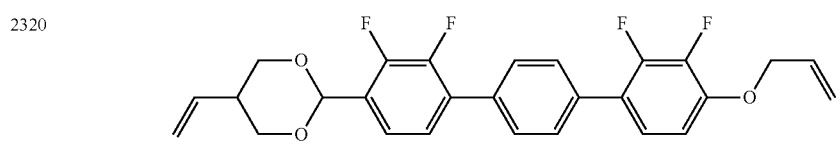 |

| No. | |
|---|---|
| 2321 | 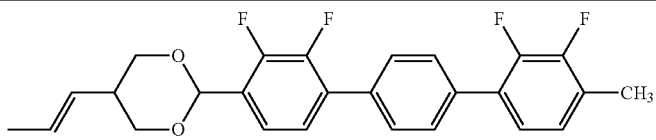 |
| 2322 | 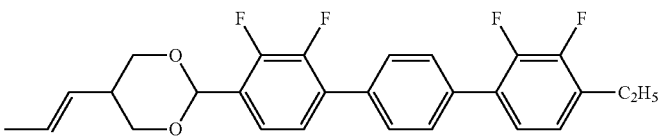 |
| 2323 | 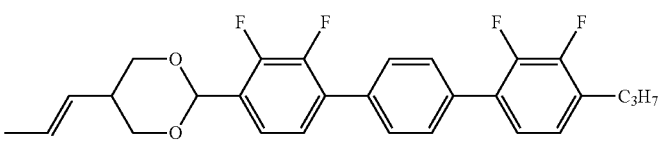 |
| 2324 | 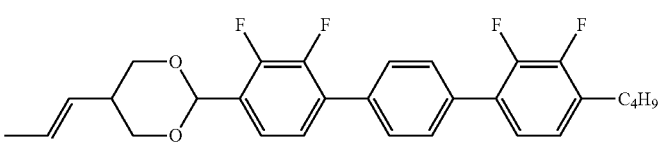 |
| 2325 | 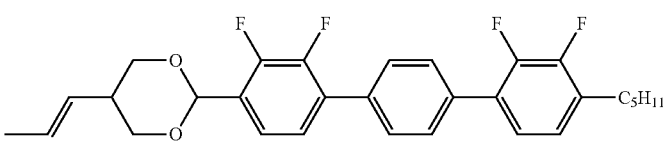 |
| 2326 | 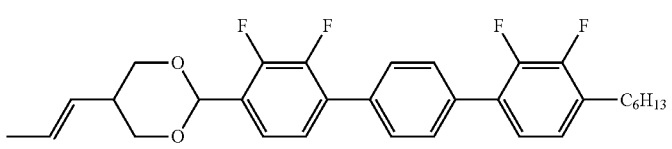 |
| 2327 | 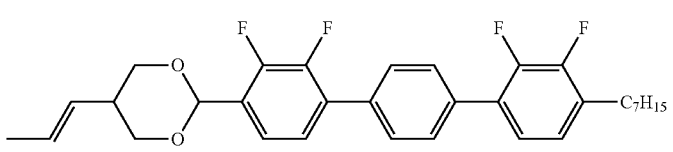 |
| 2328 | 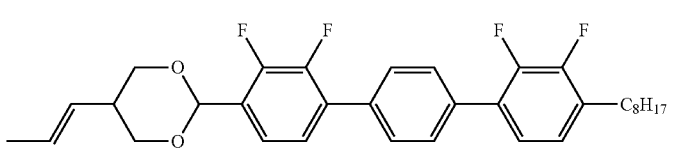 |
| 2329 | 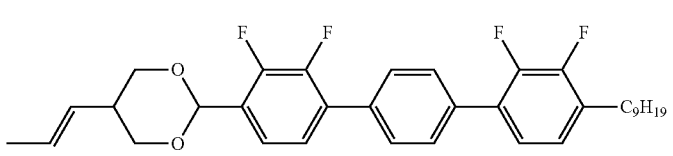 |
| 2330 | 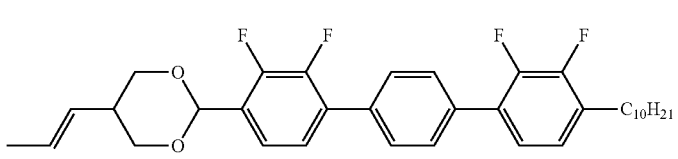 |
| 2331 | 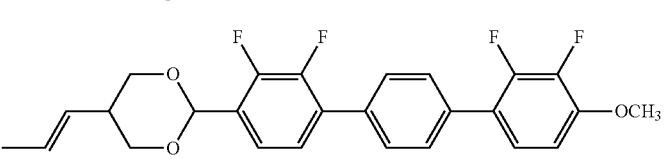 |

| No. |
|---|
| 2332 |
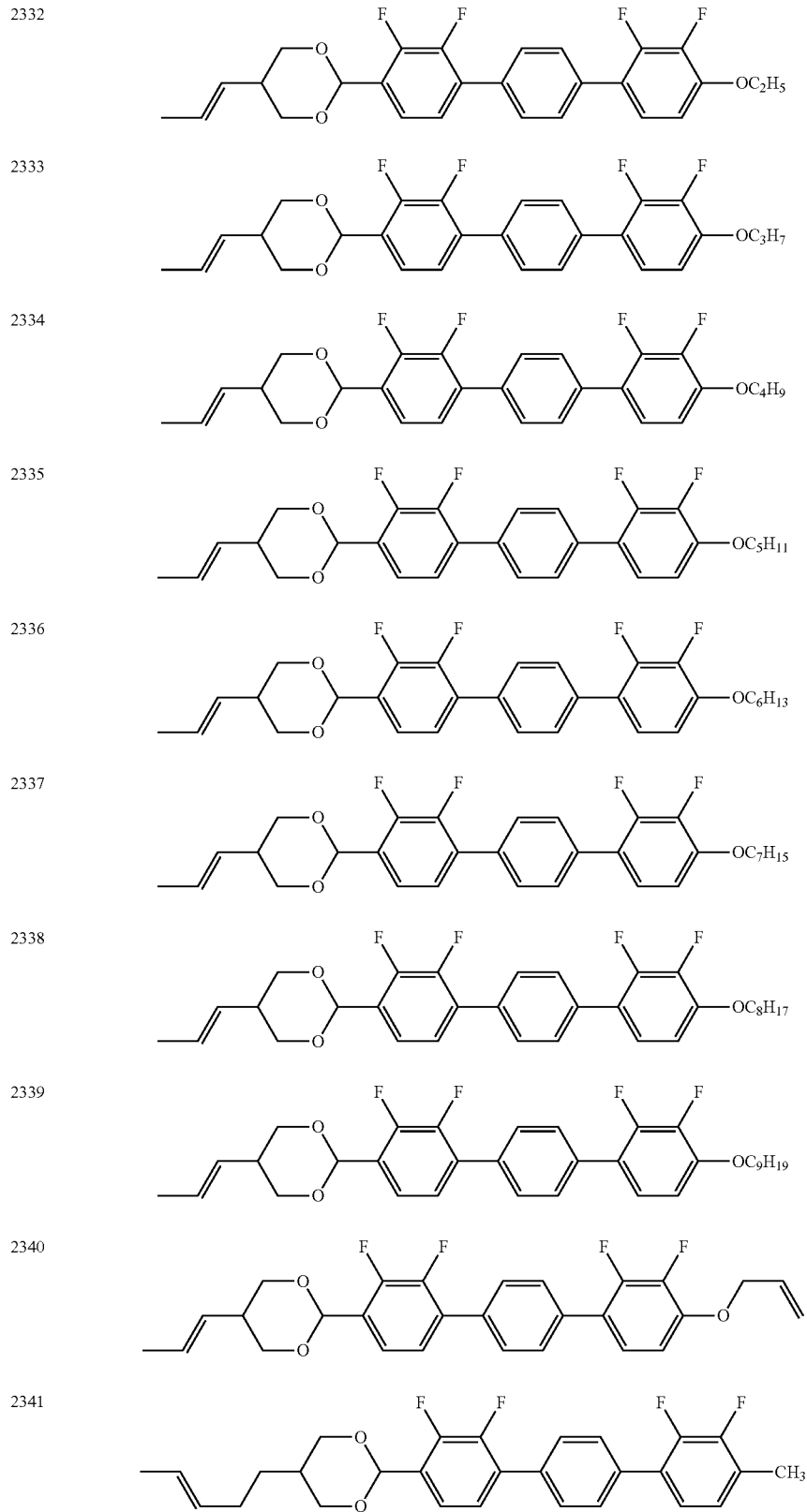
| 2333 |
| 2334 |
| 2335 |
| 2336 |
| 2337 |
| 2338 |
| 2339 |
| 2340 |
| 2341 |

| No. | |
|---|---|
| 2342 | 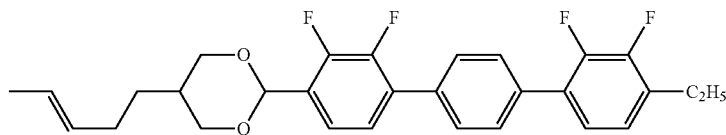 |
| 2343 | 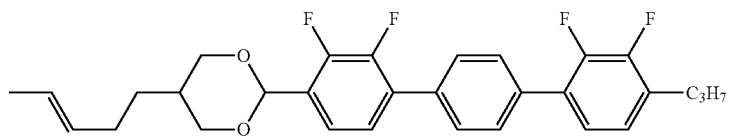 |
| 2344 | 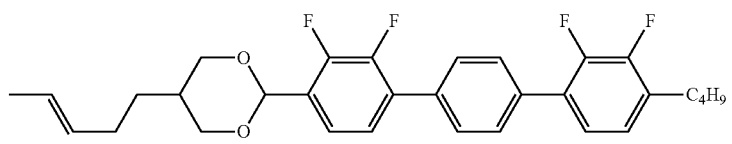 |
| 2345 | 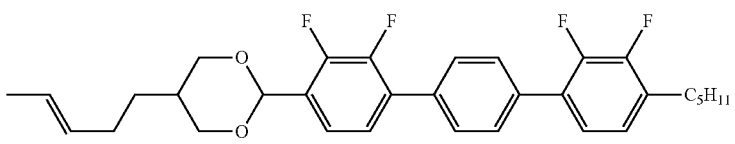 |
| 2346 | 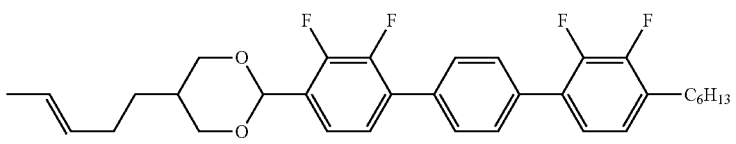 |
| 2347 | 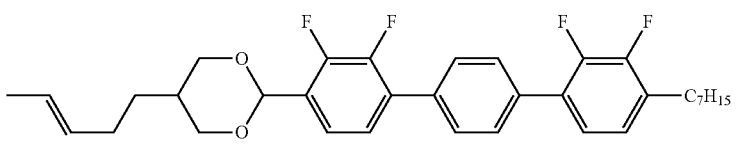 |
| 2348 | 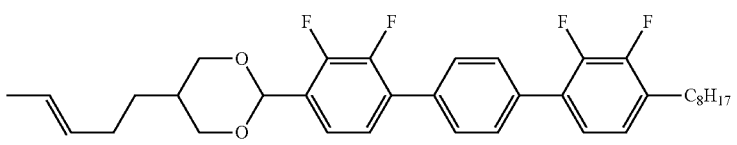 |
| 2349 | 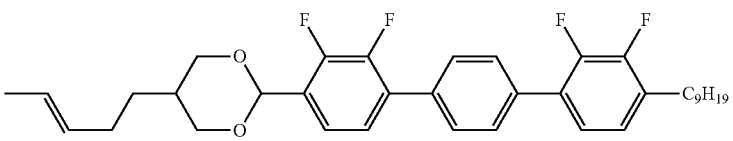 |
| 2350 | 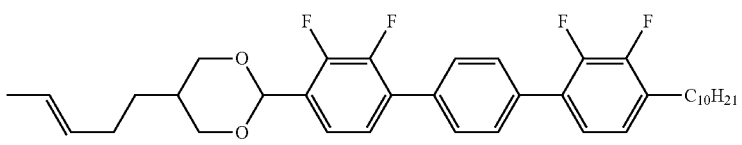 |
| 2351 | 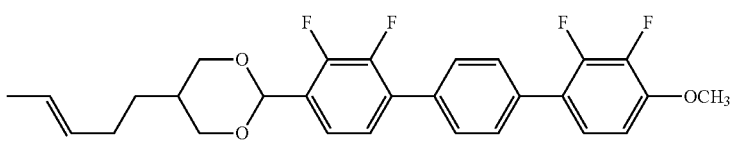 |

| No. | |
|---|---|
| 2352 | 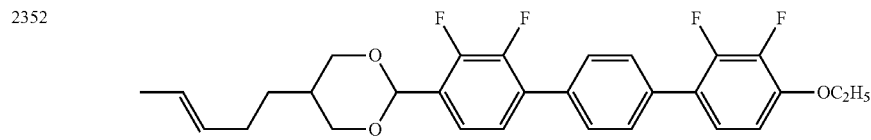 |
| 2353 | 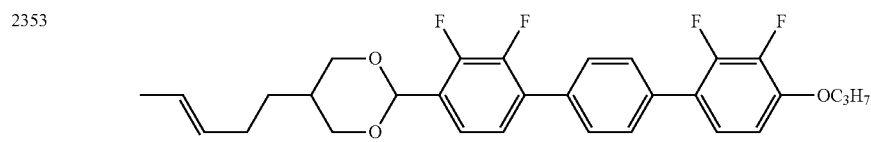 |
| 2354 | 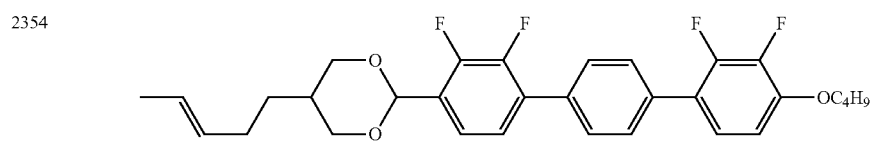 |
| 2355 | 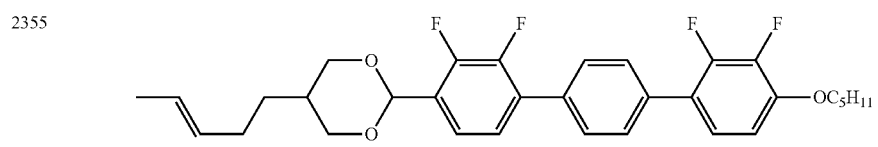 |
| 2356 | 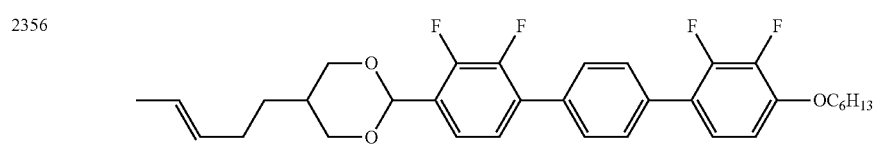 |
| 2357 | 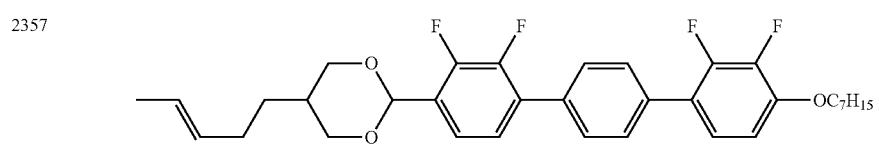 |
| 2358 | 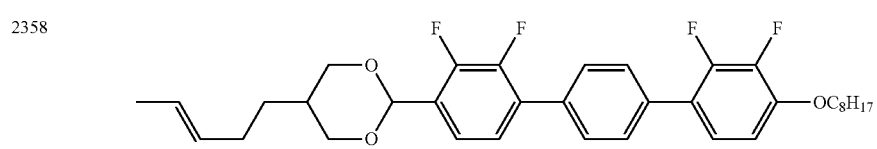 |
| 2359 | 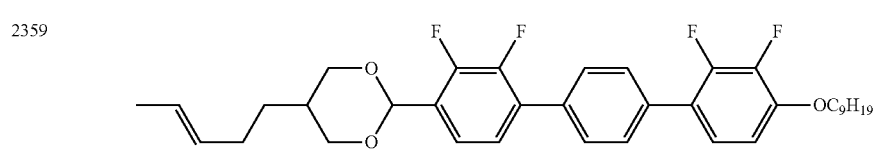 |
| 2360 | 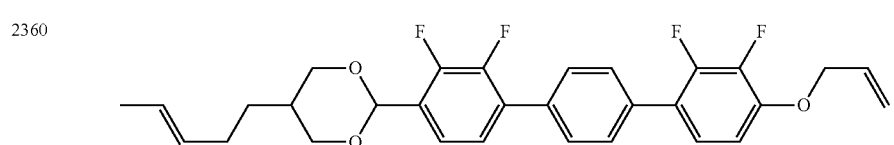 |
| 2361 | 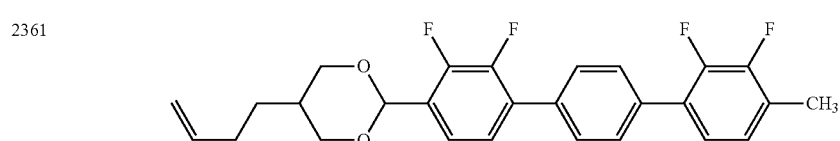 |

| No. | |
|---|---|
| 2362 | 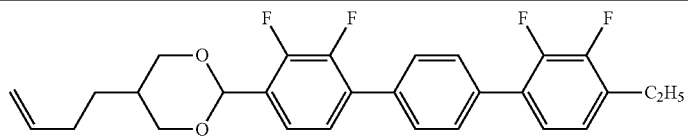 |
| 2363 | 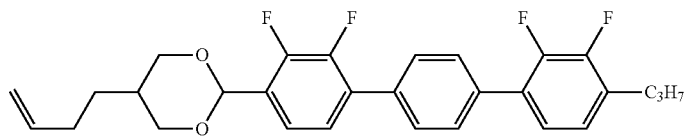 |
| 2364 | 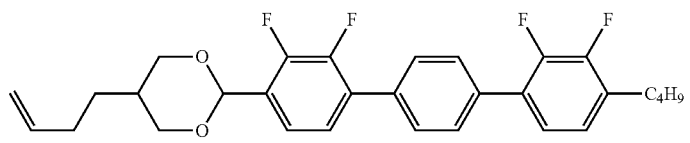 |
| 2365 | 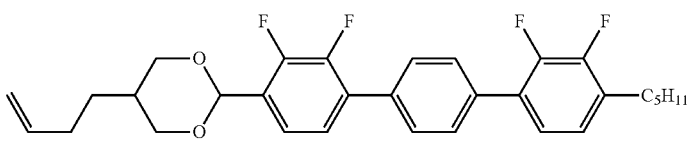 |
| 2366 | 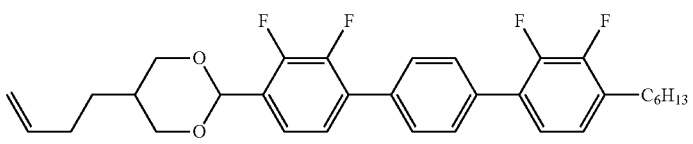 |
| 2367 | 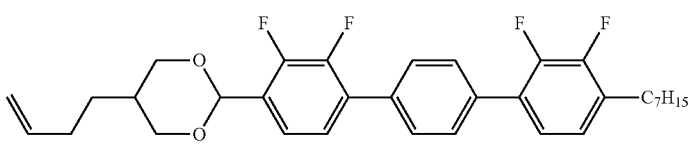 |
| 2368 | 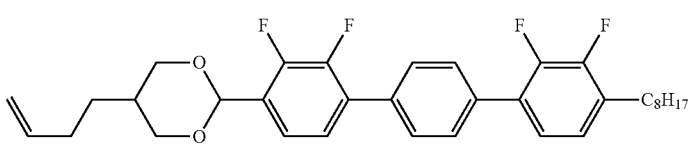 |
| 2369 | 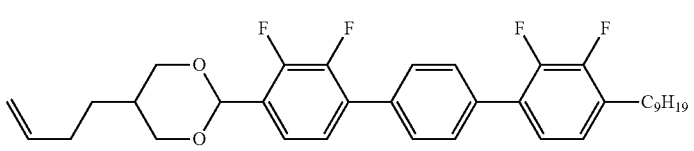 |
| 2370 | 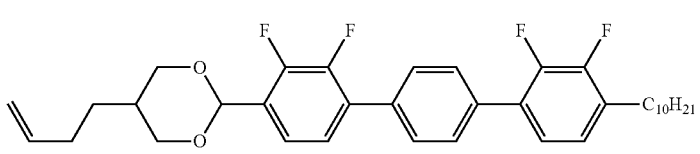 |
| 2371 | 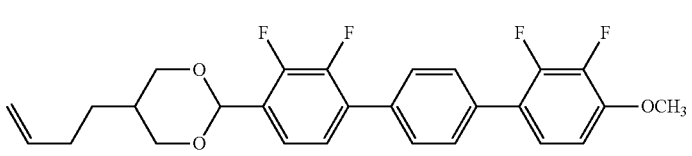 |
| 2372 | 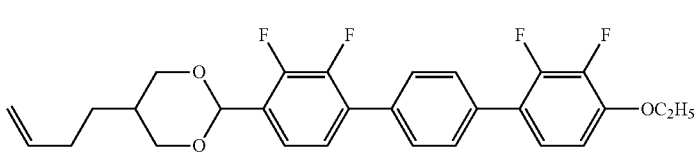 |

| No. | |
|---|---|
| 2373 | 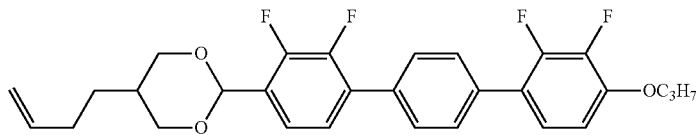 |
| 2374 | 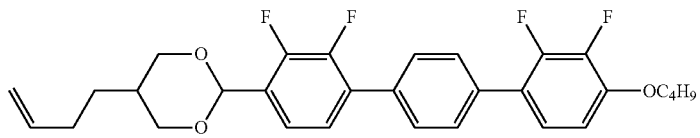 |
| 2375 | 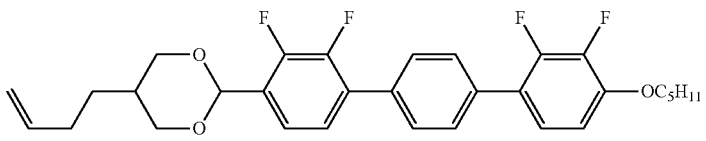 |
| 2376 | 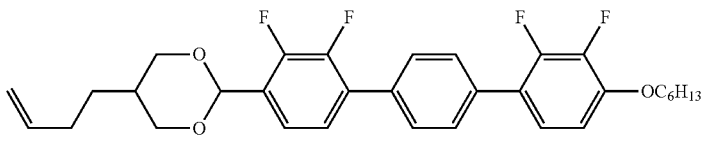 |
| 2377 | 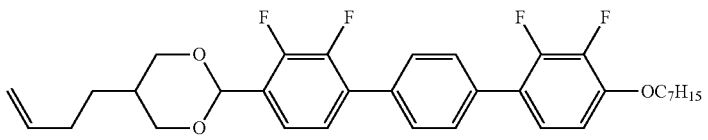 |
| 2378 | 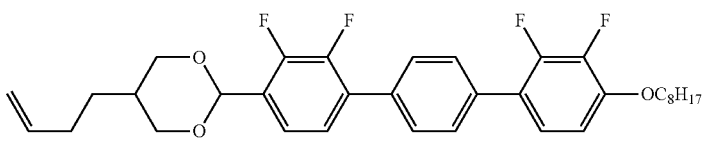 |
| 2379 | 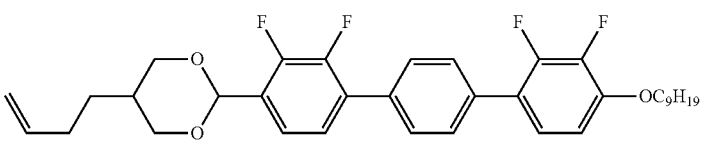 |
| 2380 | 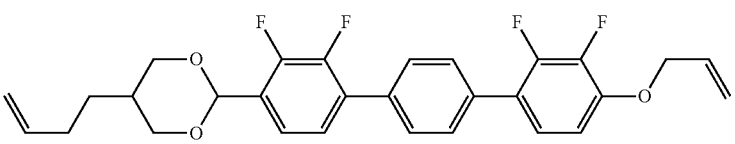 |
| 2381 | 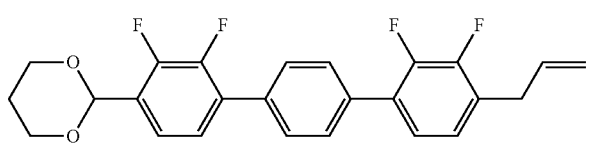 |
| 2382 | 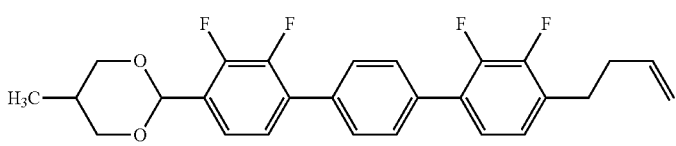 |

| No. | |
|---|---|
| 2383 | 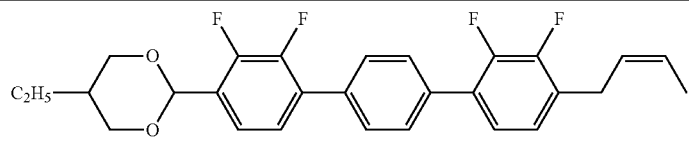 |
| 2384 | 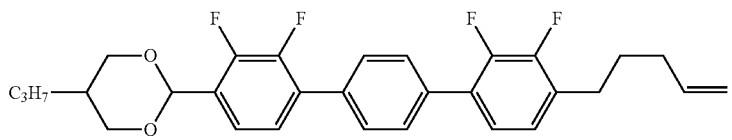 |
| 2385 | 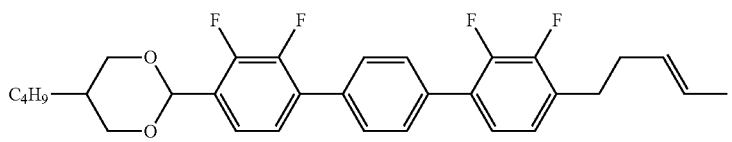 |
| 2386 | 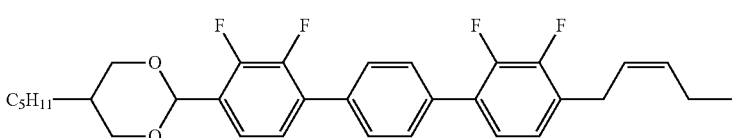 |
| 2387 | 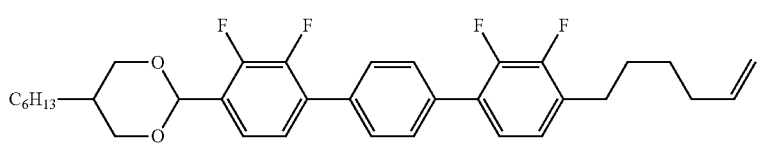 |
| 2388 | 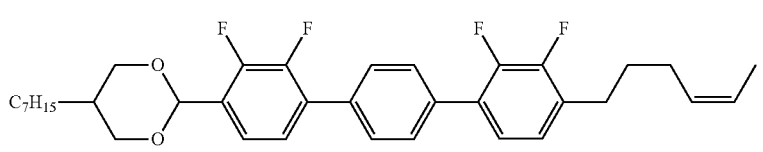 |
| 2389 | 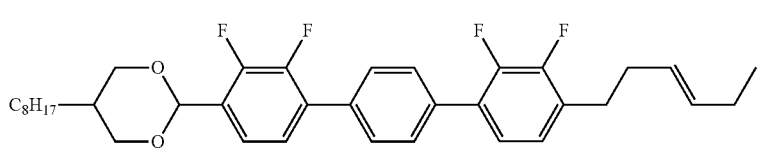 |
| 2390 | 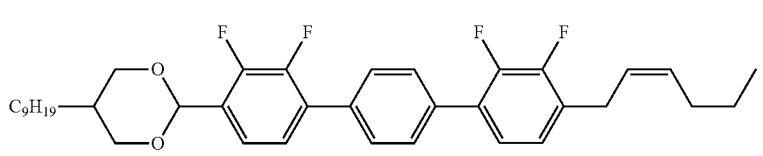 |
| 2391 | 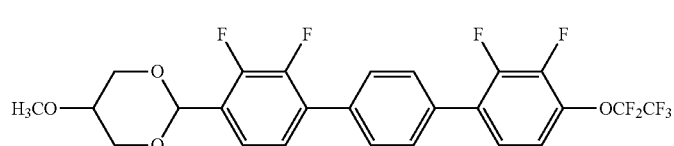 |
| 2392 | 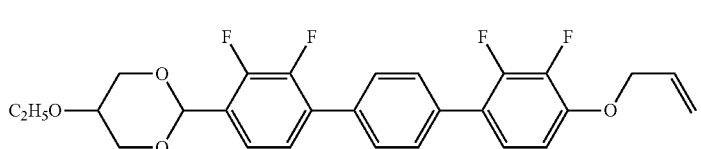 |
| 2393 | 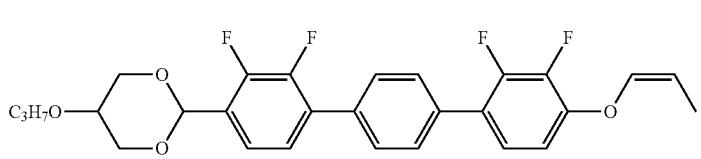 |

-continued
| No. | |
|---|---|
| 2394 | 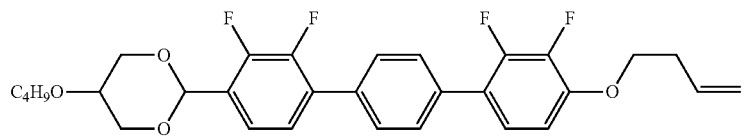 |
| 2395 | 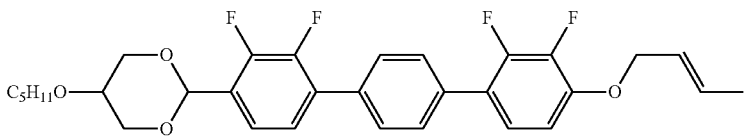 |
| 2396 | 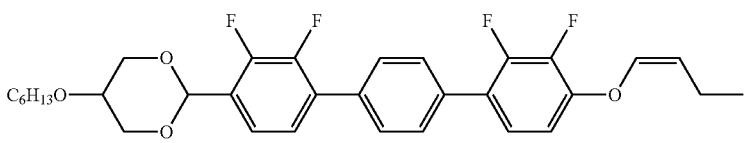 |
| 2397 | 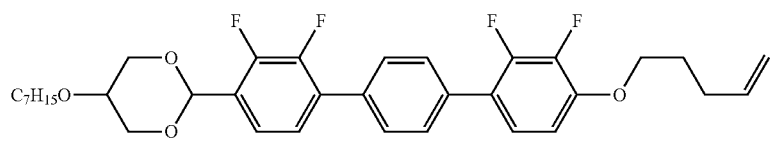 |
| 2398 | 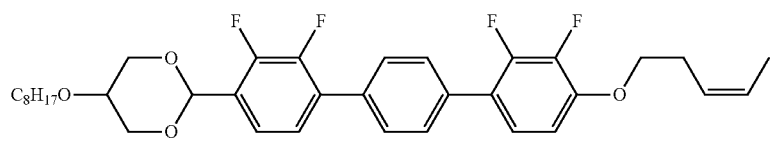 |
| 2399 | 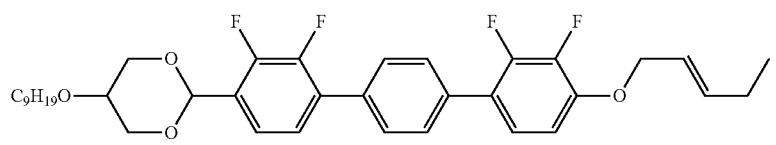 |
| 2400 | 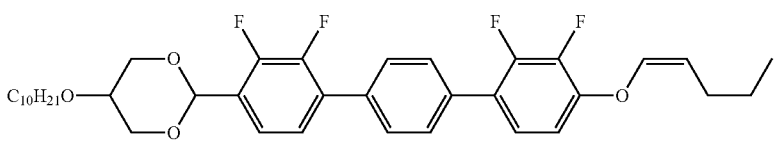 |
| 2401 | 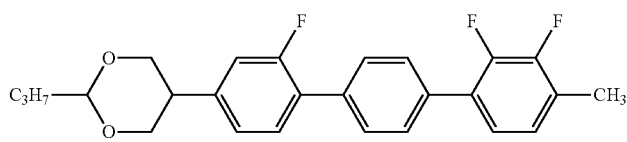 |
| 2402 | 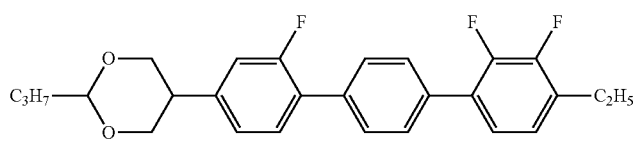 |
| 2403 | 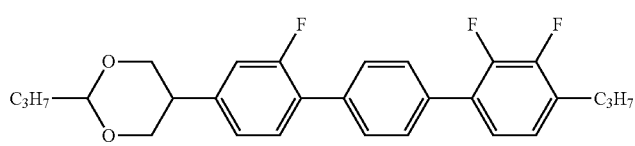 |

| No. | |
|---|---|
| 2404 | 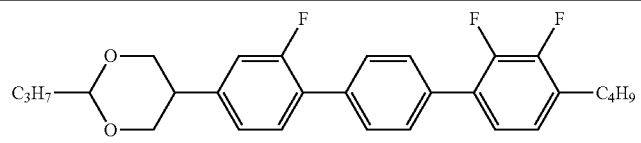 |
| 2405 | 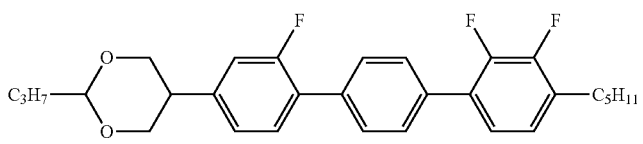 |
| 2406 | 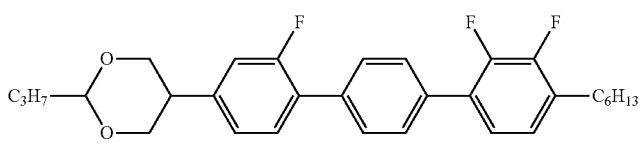 |
| 2407 | 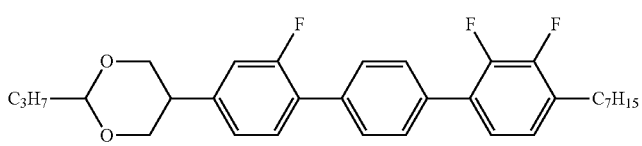 |
| 2408 | 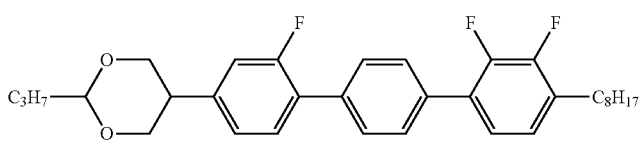 |
| 2409 | 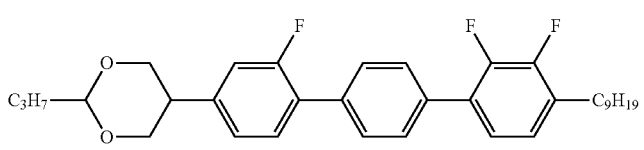 |
| 2410 | 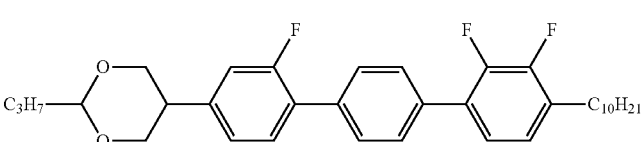 |
| 2411 | 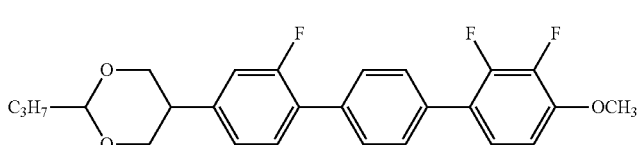 |
| 2412 | 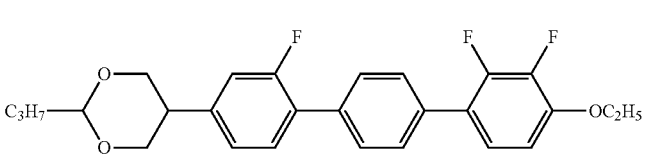 |
| 2413 | 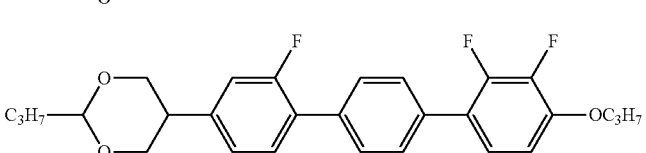 |
| 2414 | 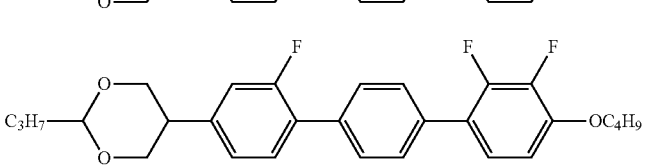 |

| No. | |
|---|---|
| 2415 | 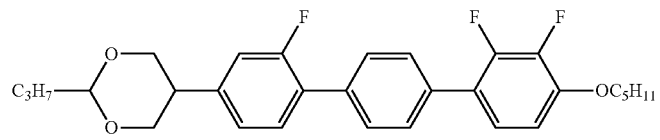 |
| 2416 | 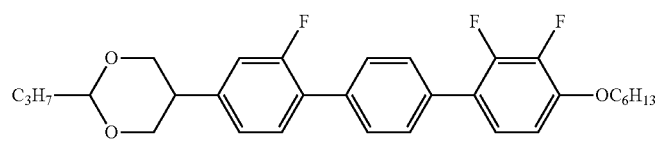 |
| 2417 | 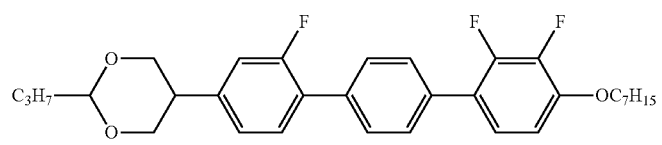 |
| 2418 | 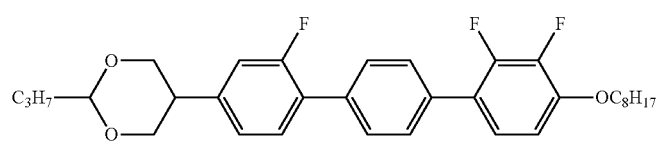 |
| 2419 | 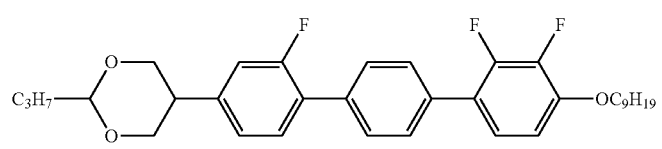 |
| 2420 | 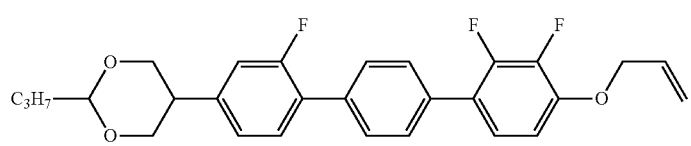 |
| 2421 | 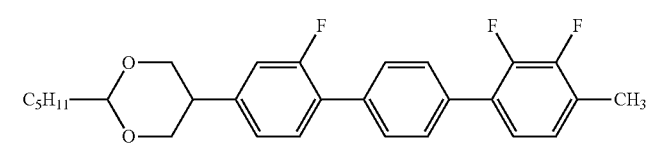 |
| 2422 | 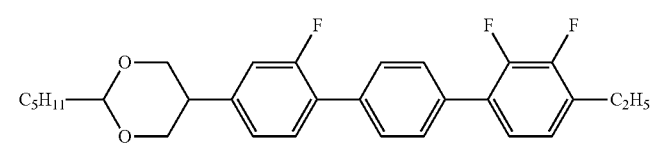 |
| 2423 | 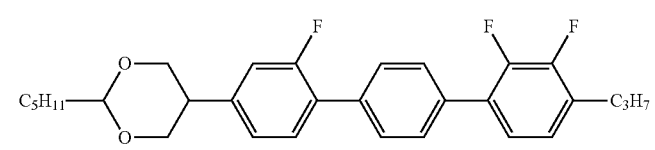 |
| 2424 | 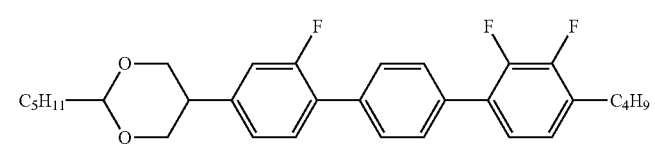 |

| No. | |
|---|---|
| 2425 | 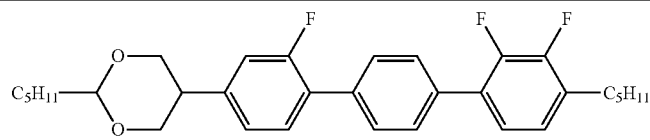 |
| 2426 | 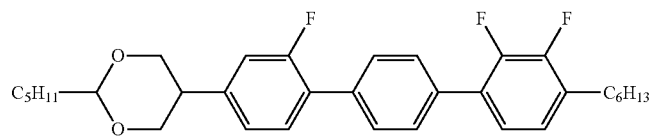 |
| 2427 | 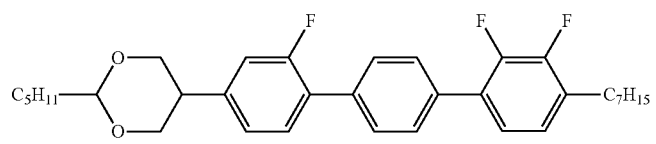 |
| 2428 | 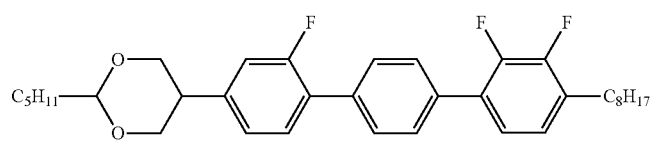 |
| 2429 | 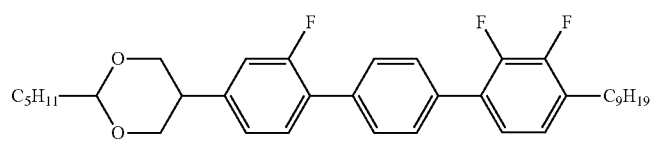 |
| 2430 | 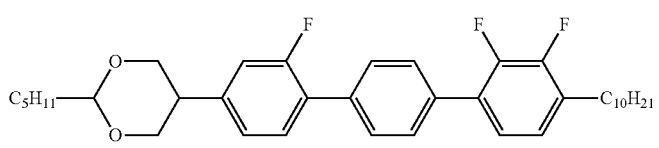 |
| 2431 | 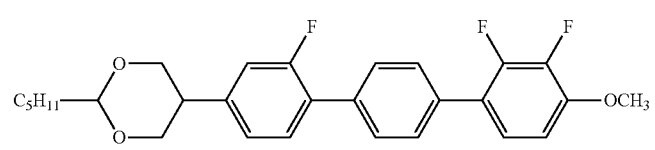 |
| 2432 | 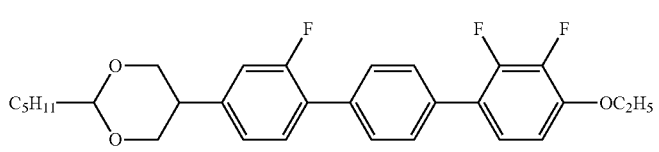 |
| 2433 | 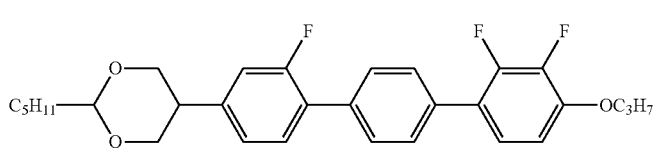 |
| 2434 | 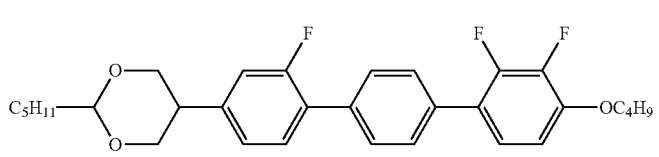 |
| 2435 | 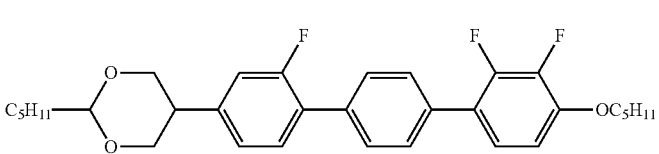 |

| No. | |
|---|---|
| 2436 | 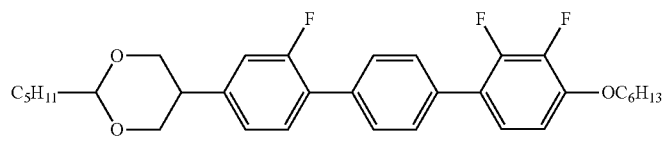 |
| 2437 | 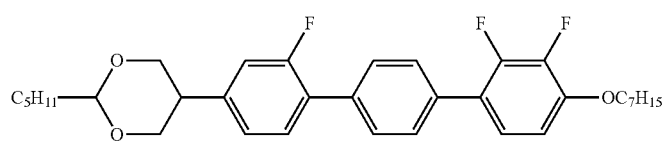 |
| 2438 | 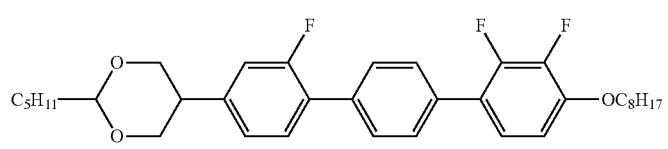 |
| 2439 | 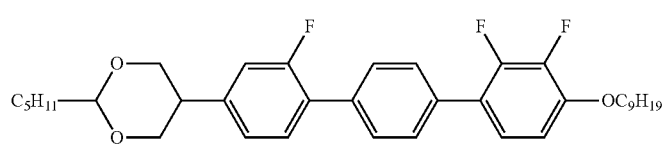 |
| 2440 | 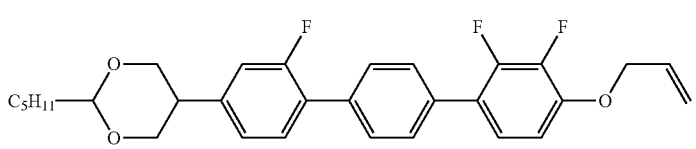 |
| 2441 | 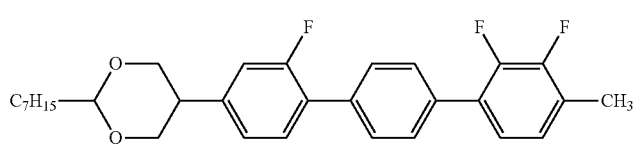 |
| 2442 | 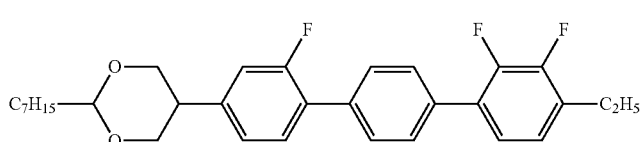 |
| 2443 | 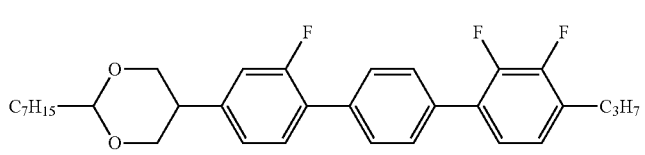 |
| 2444 | 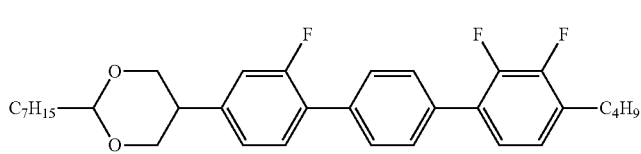 |
| 2445 | 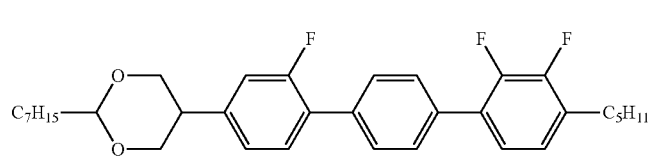 |

| No. | |
|---|---|
| 2446 | 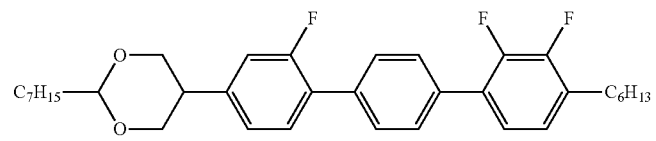 |
| 2447 | 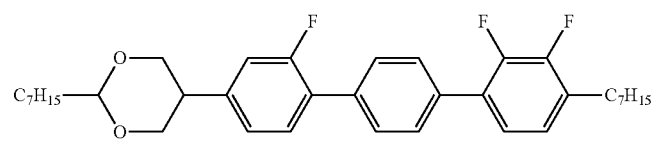 |
| 2448 | 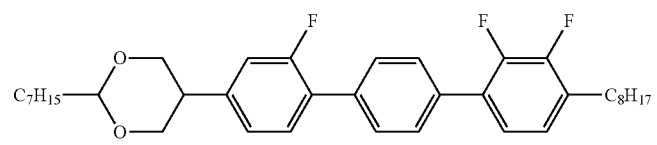 |
| 2449 | 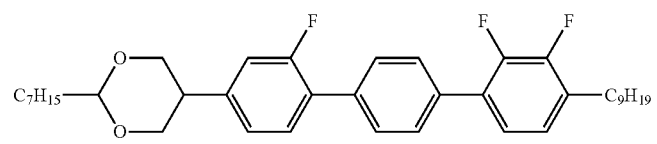 |
| 2450 | 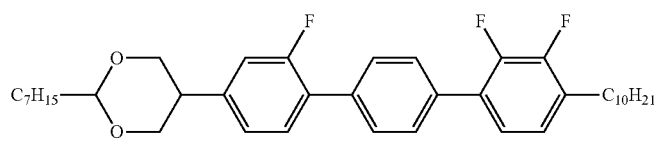 |
| 2451 | 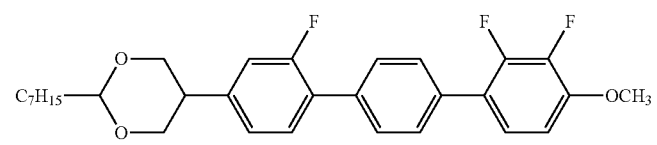 |
| 2452 | 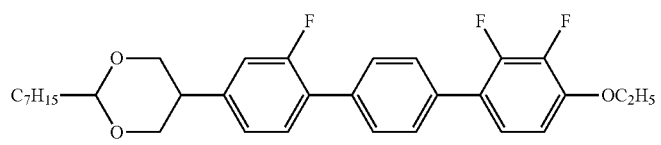 |
| 2453 | 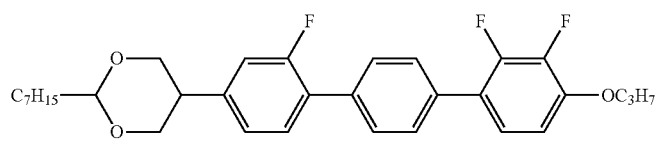 |
| 2454 | 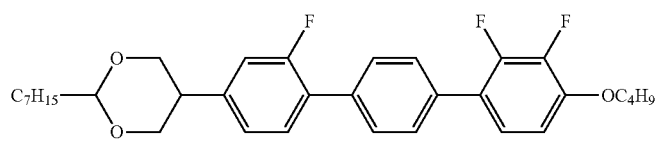 |
| 2455 | 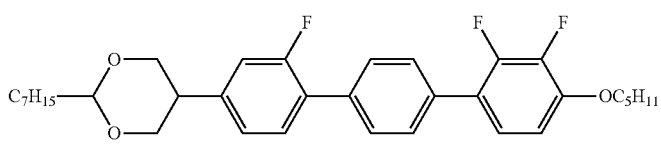 |

| No. | |
|---|---|
| 2456 | 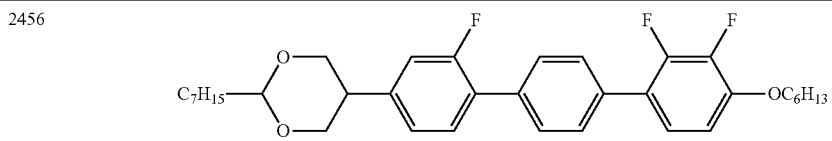 |
| 2457 | 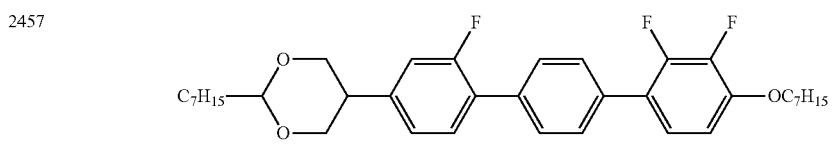 |
| 2458 | 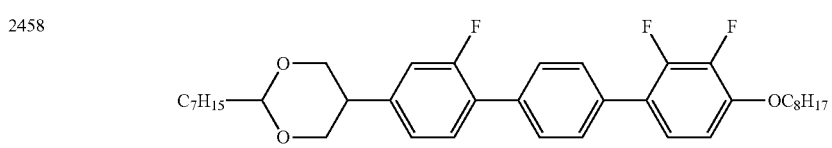 |
| 2459 | 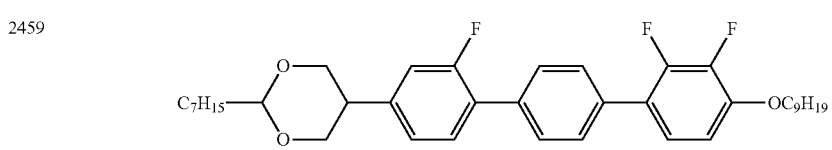 |
| 2460 | 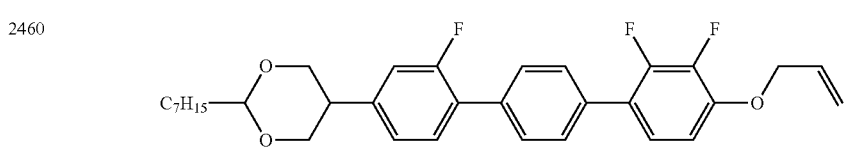 |
| 2461 | 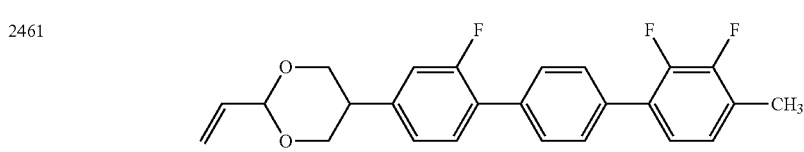 |
| 2462 | 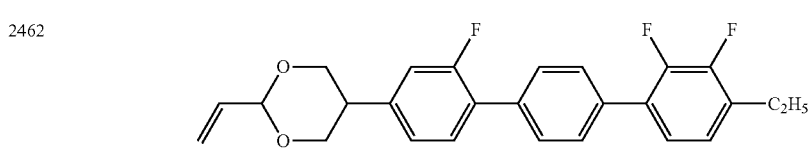 |
| 2463 | 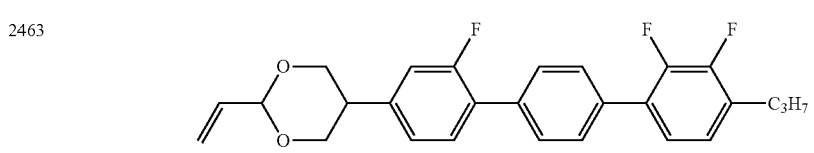 |
| 2464 | 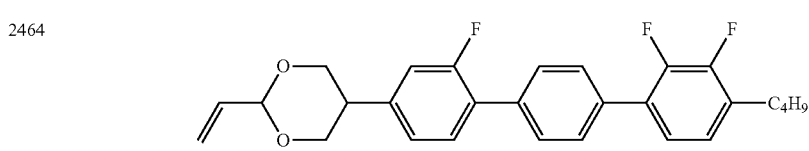 |
| 2465 | 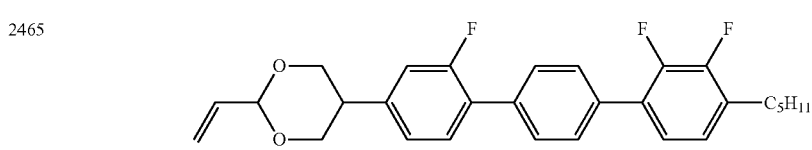 |
| 2466 | 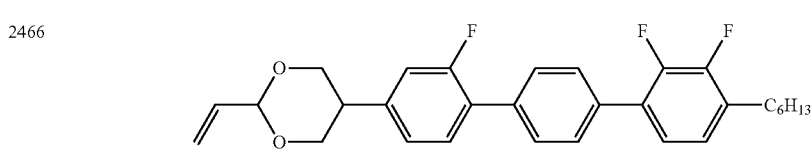 |

| No. | |
|---|---|
| 2467 | 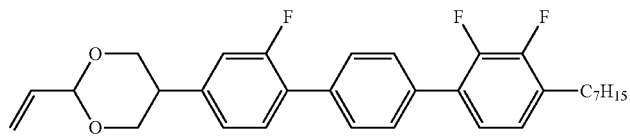 |
| 2468 | 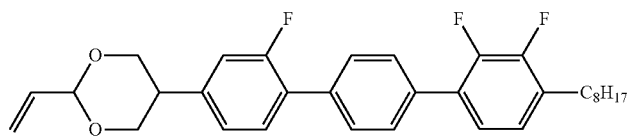 |
| 2469 | 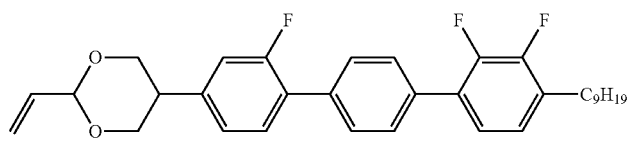 |
| 2470 | 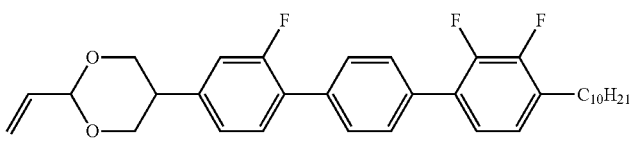 |
| 2471 | 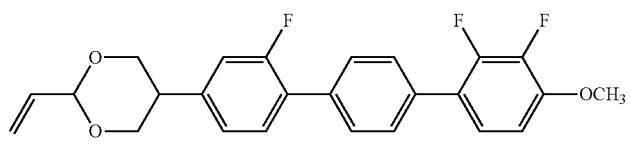 |
| 2472 | 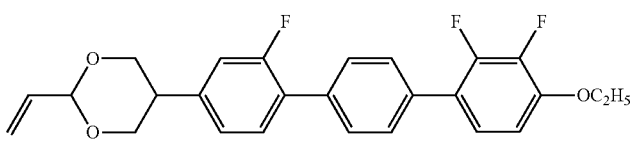 |
| 2473 | 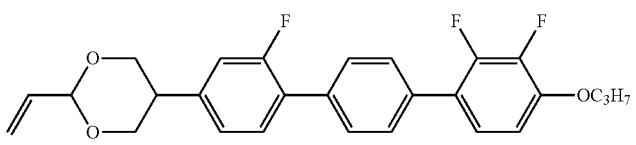 |
| 2474 | 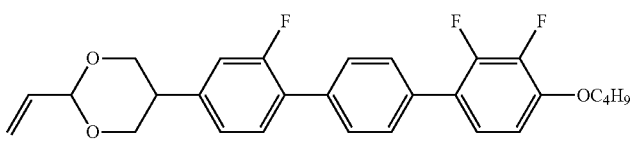 |
| 2475 | 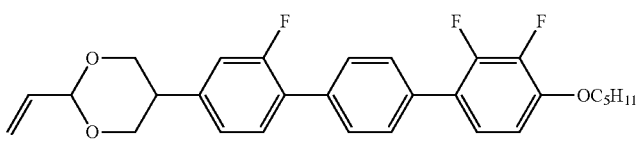 |
| 2476 | 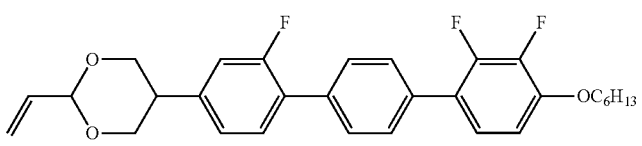 |

| No. | |
|---|---|
| 2477 | 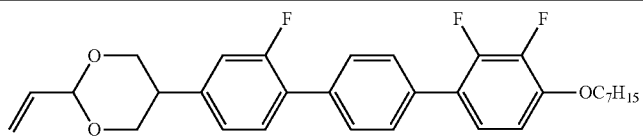 |
| 2478 | 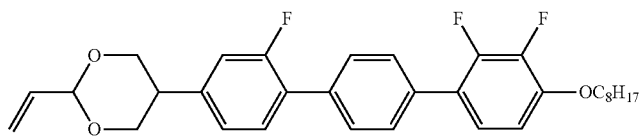 |
| 2479 | 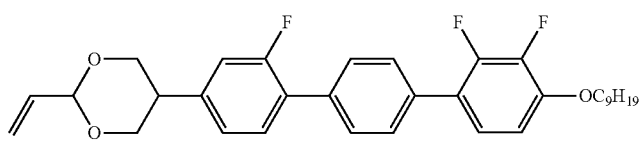 |
| 2480 | 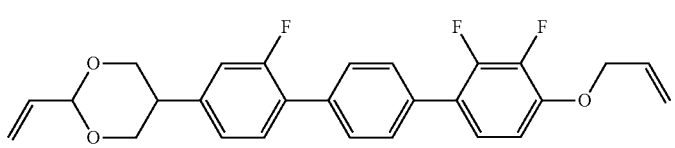 |
| 2481 | 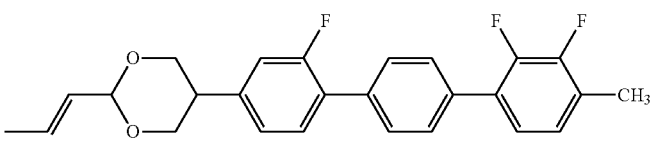 |
| 2482 | 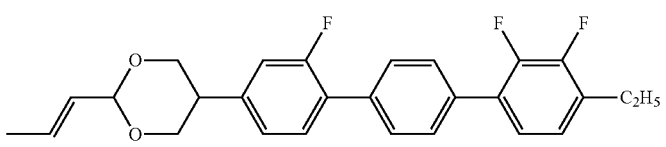 |
| 2483 | 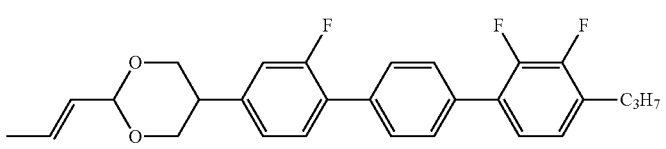 |
| 2484 | 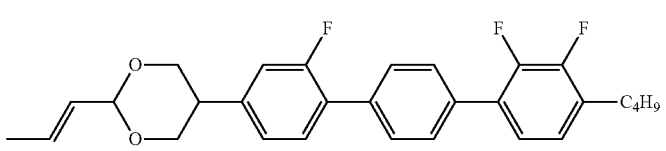 |
| 2485 | 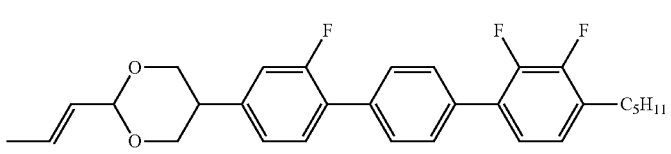 |
| 2486 | 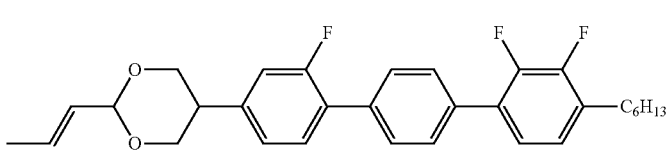 |
| 2487 | 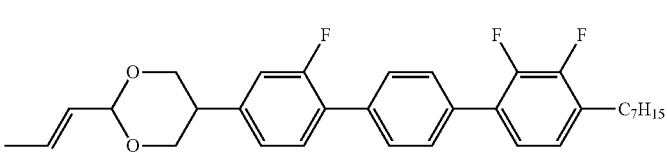 |

| No. | |
|---|---|
| 2488 | 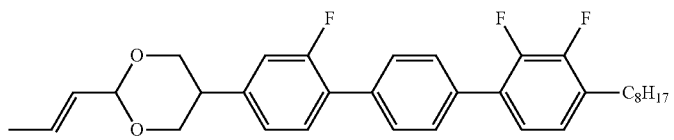 |
| 2489 | 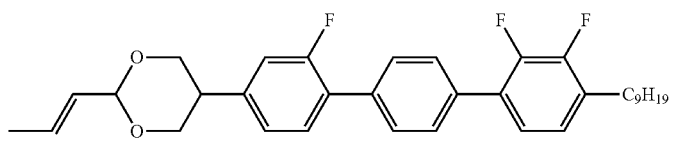 |
| 2490 | 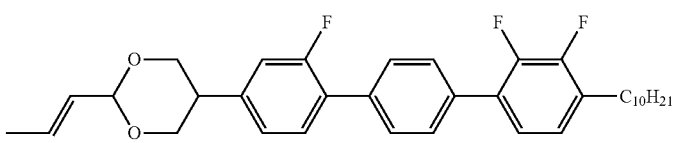 |
| 2491 | 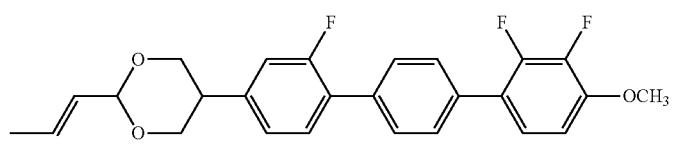 |
| 2492 | 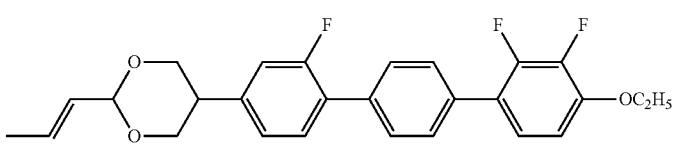 |
| 2493 | 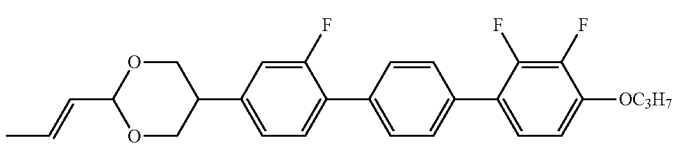 |
| 2494 | 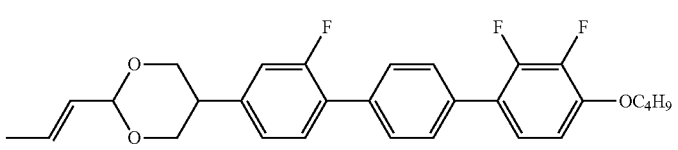 |
| 2495 | 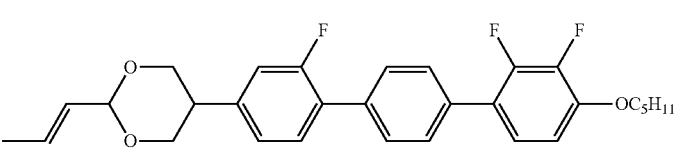 |
| 2496 | 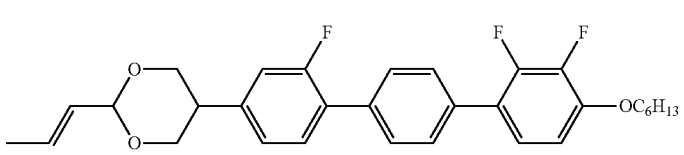 |
| 2497 | 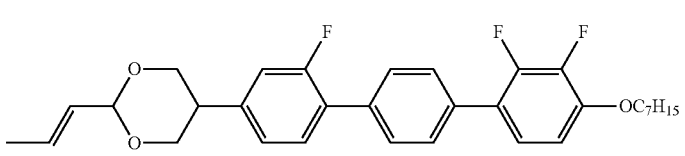 |

| No. | |
|---|---|
| 2498 | 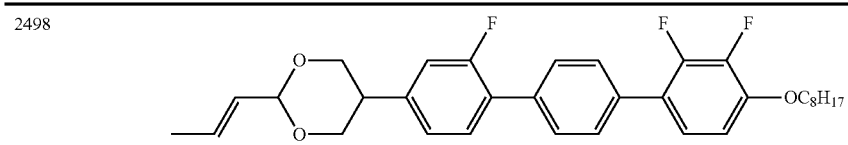 |
| 2499 | 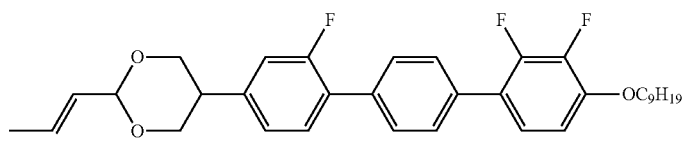 |
| 2500 | 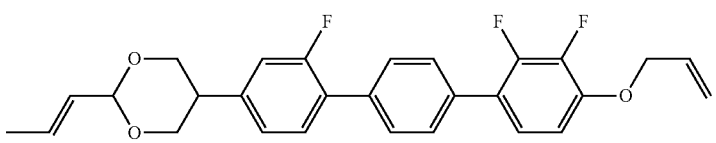 |
| 2501 | 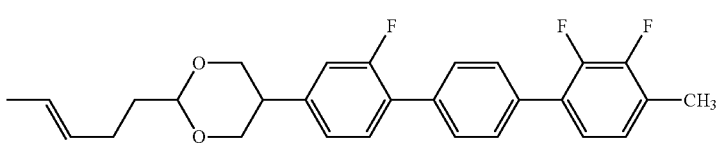 |
| 2502 | 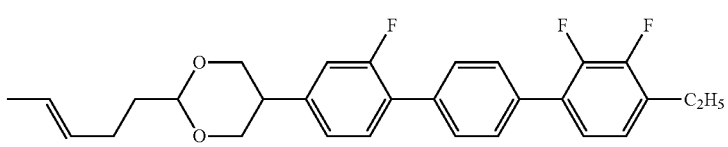 |
| 2503 | 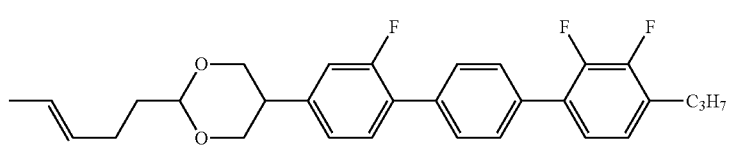 |
| 2504 | 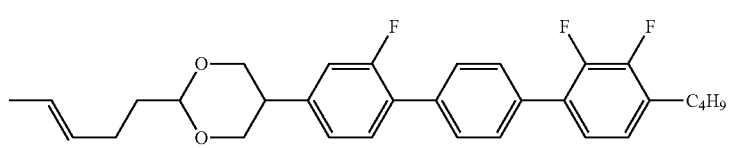 |
| 2505 | 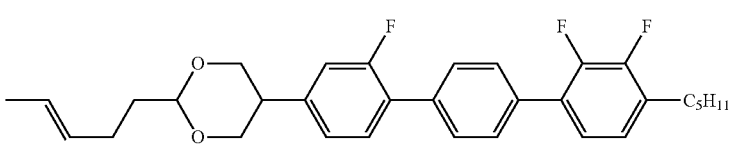 |
| 2506 | 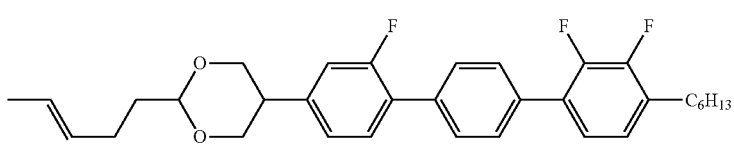 |
| 2507 | 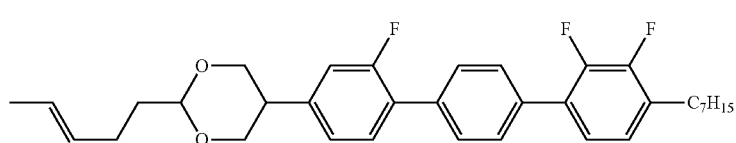 |
| 2508 | 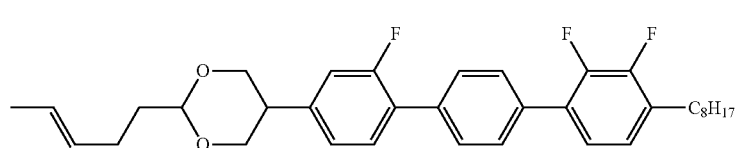 |

-continued
| No. | |
|---|---|
| 2509 | 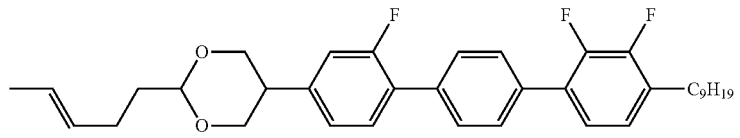 |
| 2510 | 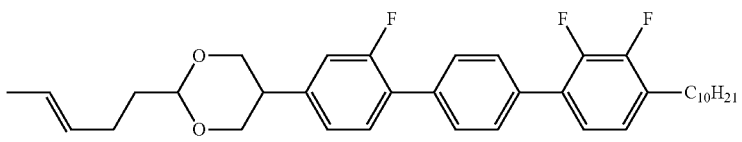 |
| 2511 | 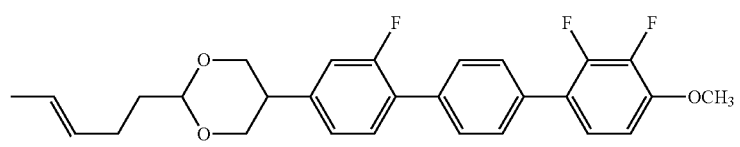 |
| 2512 | 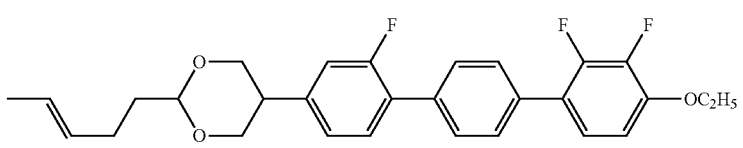 |
| 2513 | 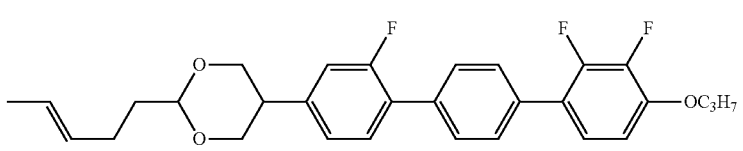 |
| 2514 | 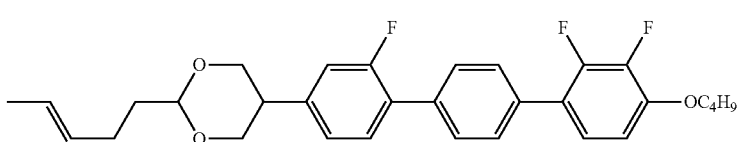 |
| 2515 | 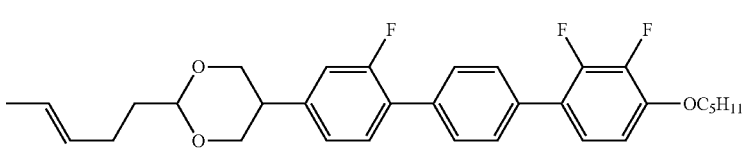 |
| 2516 | 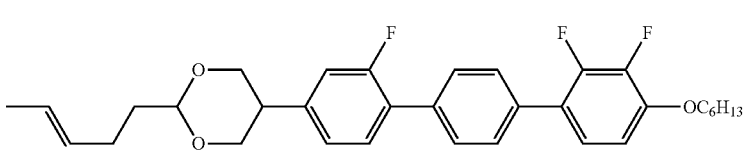 |
| 2517 | 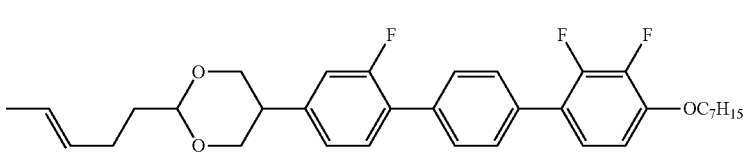 |
| 2518 | 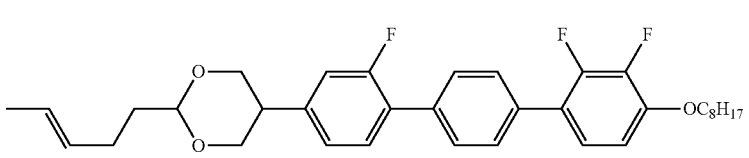 |

-continued
| No. | |
|---|---|
| 2519 | 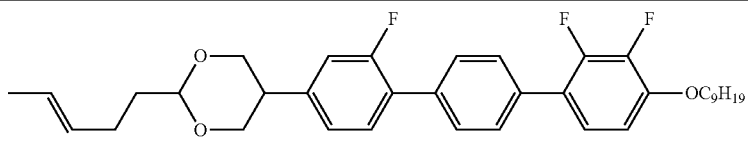 |
| 2520 | 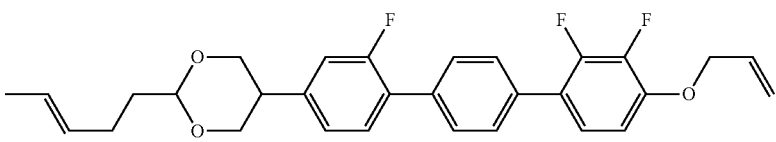 |
| 2521 | 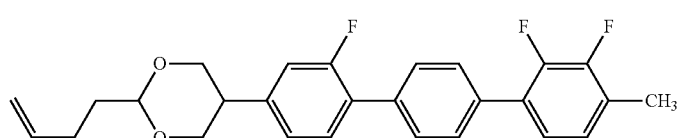 |
| 2522 | 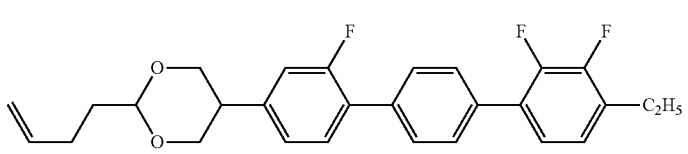 |
| 2523 | 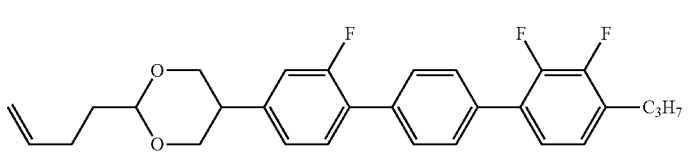 |
| 2524 | 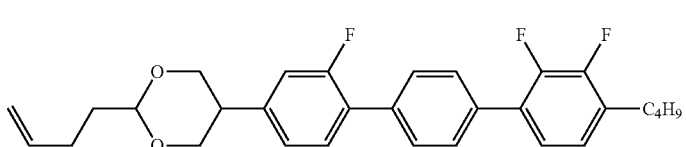 |
| 2525 | 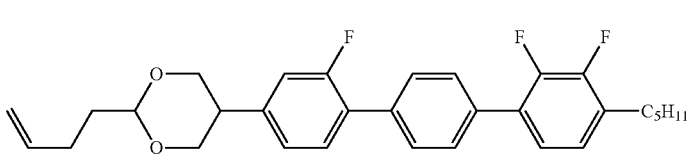 |
| 2526 | 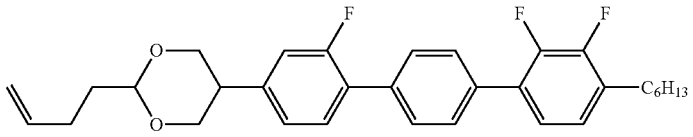 |
| 2527 | 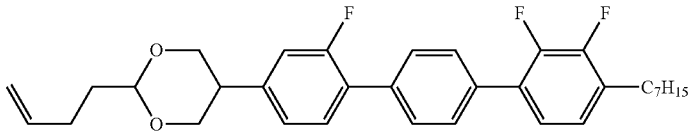 |
| 2528 | 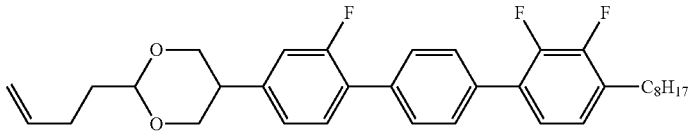 |
| 2529 | 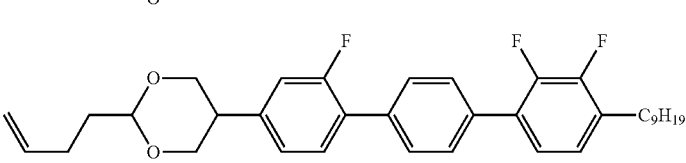 |

| No. | |
|---|---|
| 2530 | 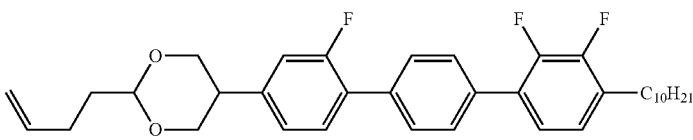 |
| 2531 | 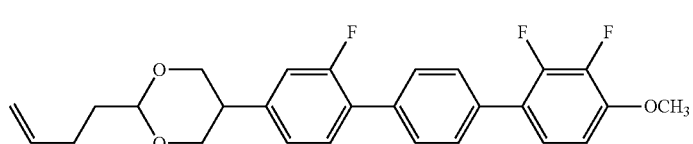 |
| 2532 | 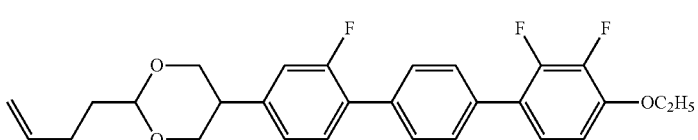 |
| 2533 | 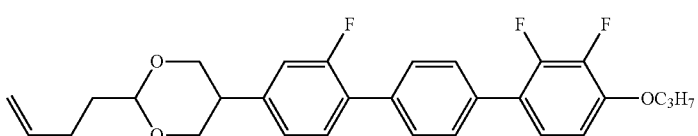 |
| 2534 | 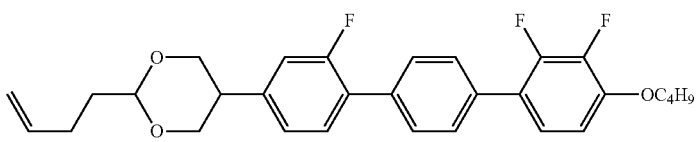 |
| 2535 | 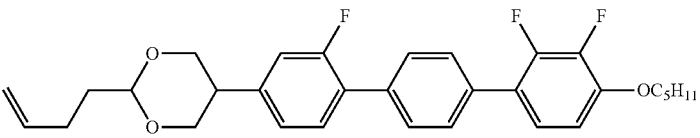 |
| 2536 | 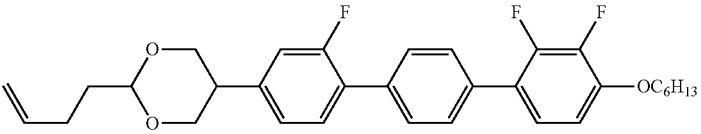 |
| 2537 | 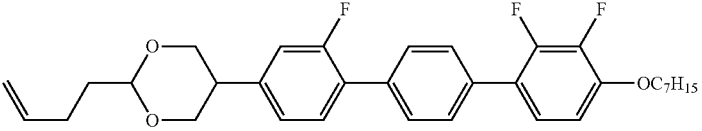 |
| 2538 | 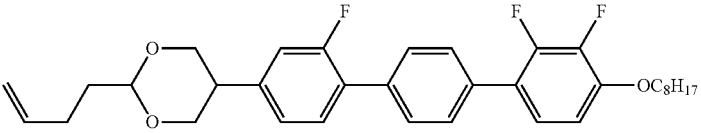 |
| 2539 | 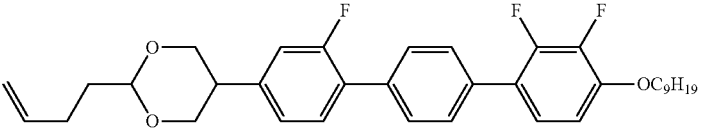 |

| No. | |
|---|---|
| 2540 | 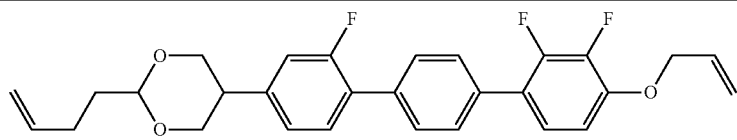 |
| 2541 | 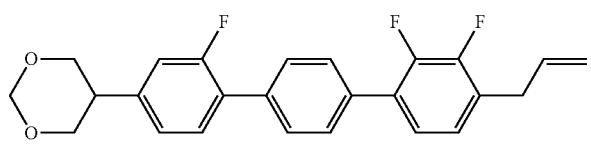 |
| 2542 | 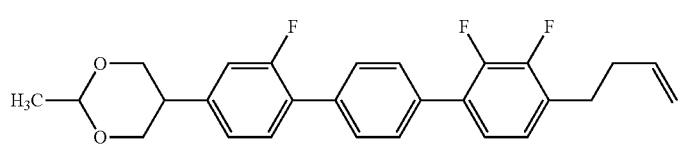 |
| 2543 | 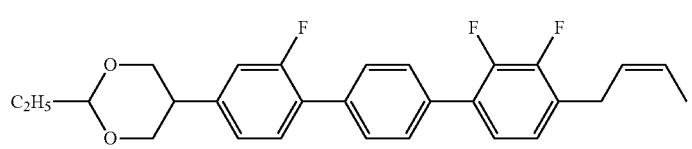 |
| 2544 | 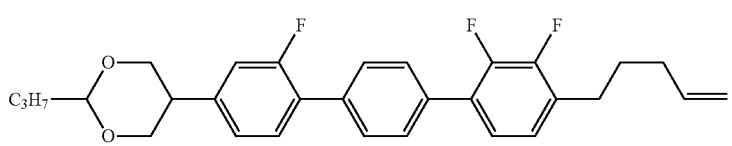 |
| 2545 | 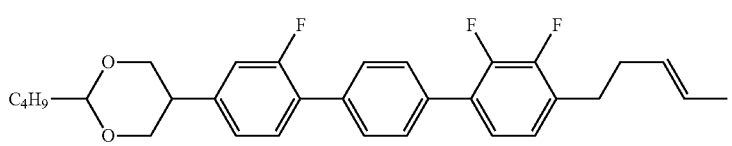 |
| 2546 | 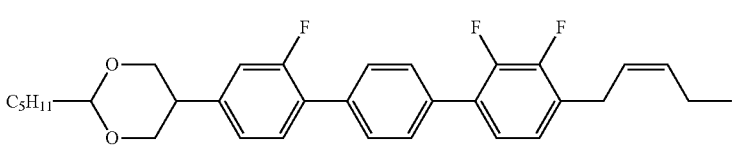 |
| 2547 | 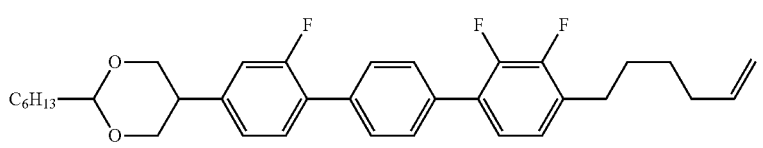 |
| 2548 | 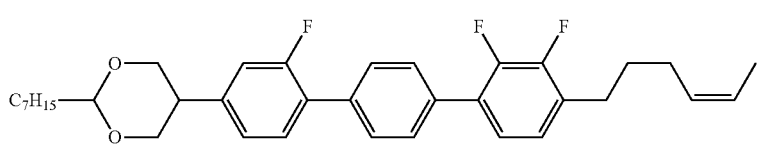 |
| 2549 | 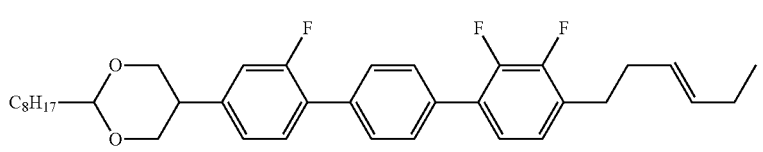 |
| 2550 | 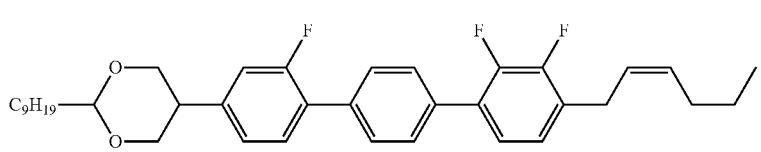 |

| No. | |
|---|---|
| 2551 | |
| 2552 | |
| 2553 | |
| 2554 | |
| 2555 | |
| 2556 | |
| 2557 | |
| 2558 | |
| 2559 | |
| 2560 | |

| No. | |
|---|---|
| 2561 | 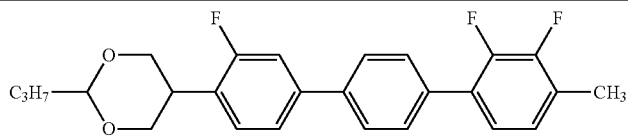 |
| 2562 | 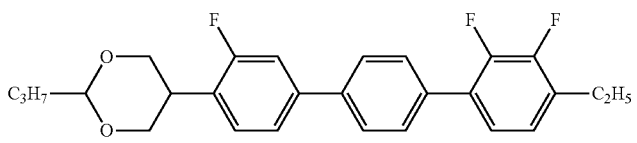 |
| 2563 | 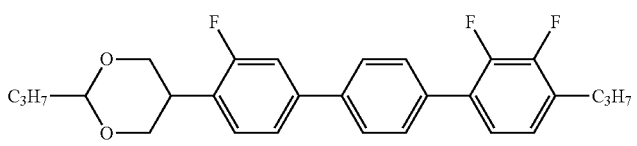 |
| 2564 | 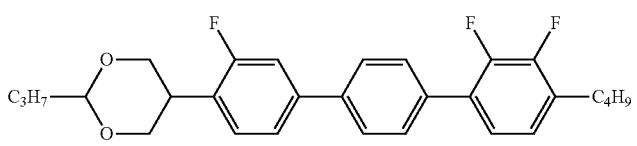 |
| 2565 | 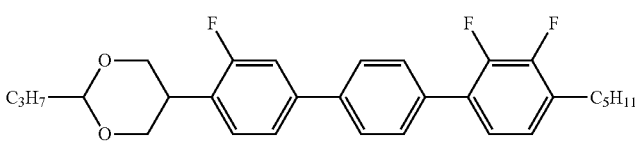 |
| 2566 | 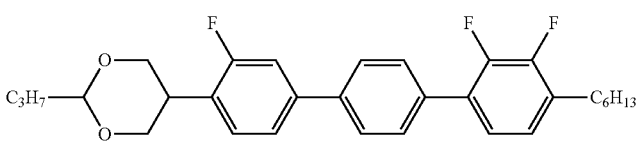 |
| 2567 | 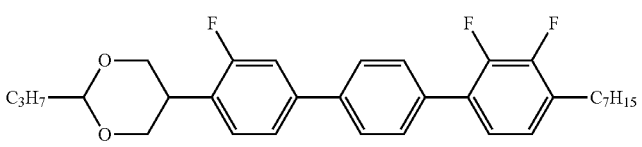 |
| 2568 | 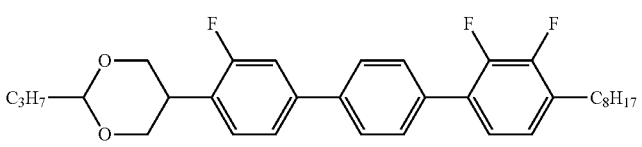 |
| 2569 | 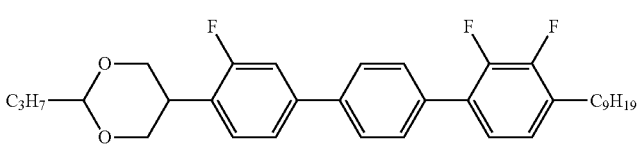 |
| 2570 |  |
| 2571 | 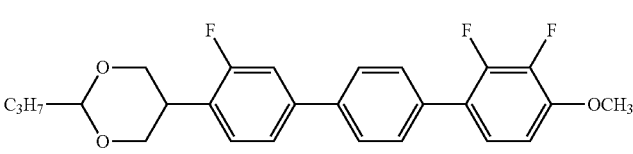 |

-continued
| No. |
|---|
| 2572  |
| 2573  |
| 2574  |
| 5275  |
| 2576  |
| 5277 |
| 2578  |
| 2579  |
| 2580 |
| 2581  |

| No. | |
|---|---|
| 2582 |  |
| 2583 |  |
| 2584 |  |
| 2585 |  |
| 2586 | |
| 2587 |  |
| 2588 | |
| 2589 | |
| 2590 | |
| 2591 |  |

-continued
| No. | |
|---|---|
| 2592 | 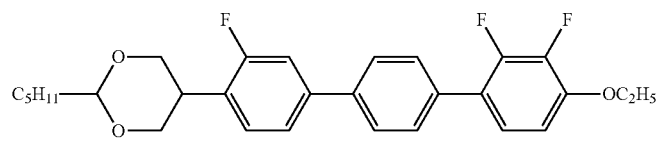 |
| 2593 | 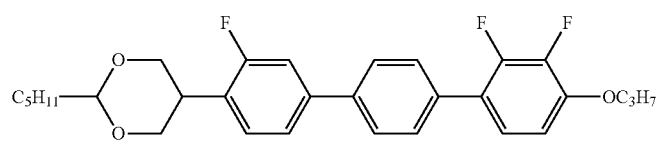 |
| 2594 | 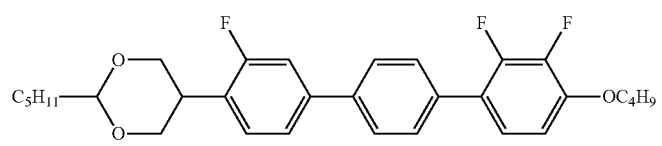 |
| 2595 | 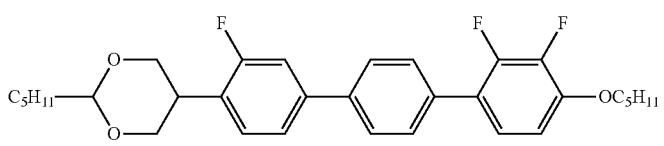 |
| 2596 | 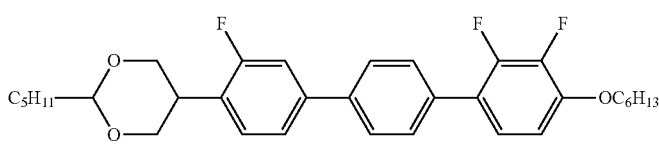 |
| 2597 | 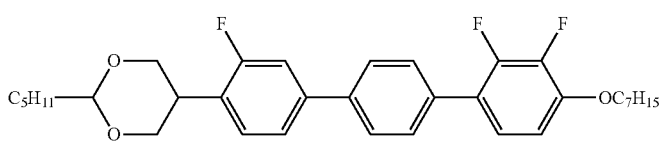 |
| 2598 | 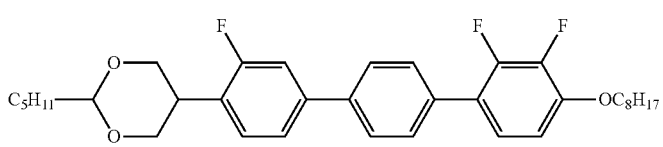 |
| 2599 | 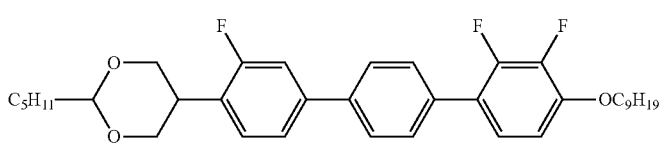 |
| 2600 | 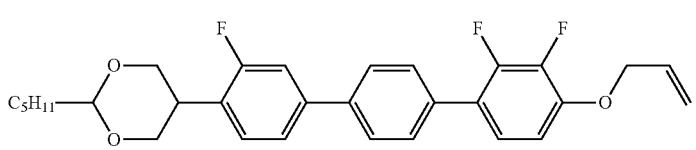 |
| 2601 | 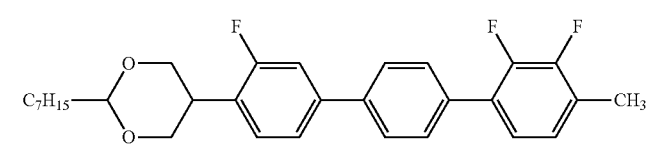 |

| No. | |
|---|---|
| 2602 | 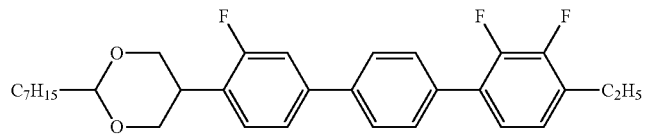 |
| 2603 | 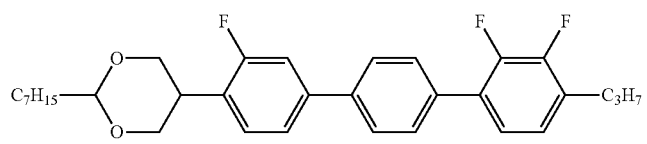 |
| 2604 | 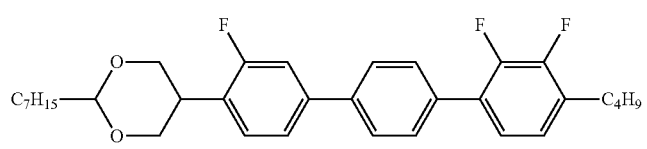 |
| 2605 | 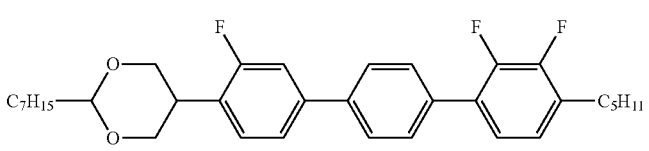 |
| 2606 |  |
| 2607 | 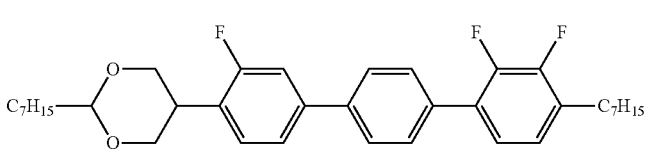 |
| 2608 | 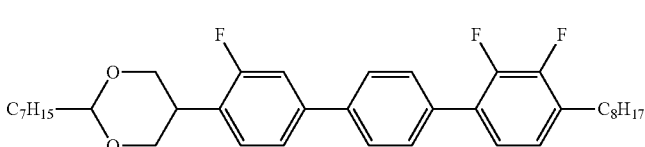 |
| 2609 | 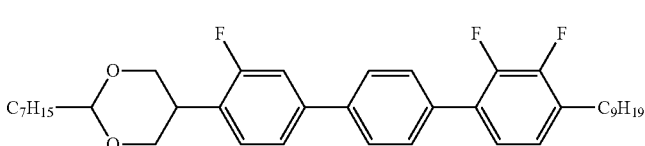 |
| 2610 | 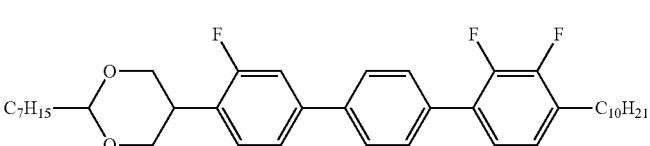 |
| 2611 | 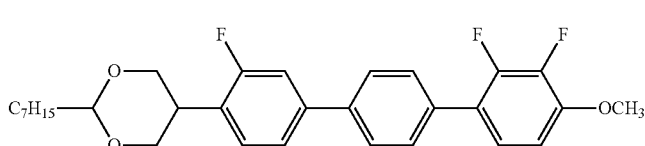 |

| No. | |
|---|---|
| 2612 | 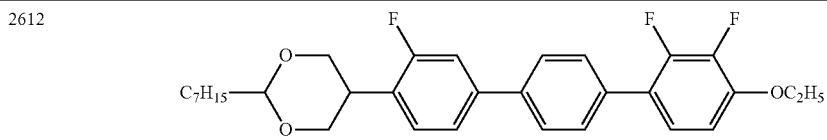 |
| 2613 | 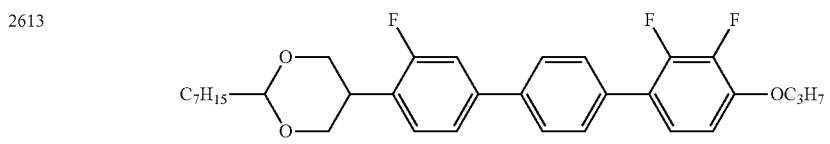 |
| 2614 | 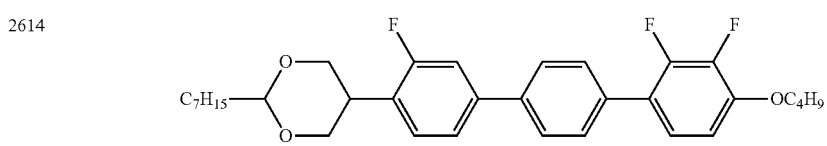 |
| 2615 | 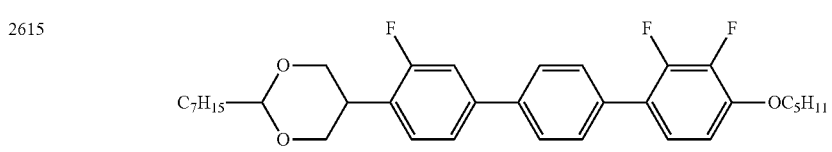 |
| 2616 | 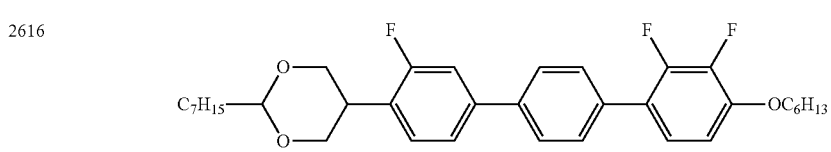 |
| 2617 | 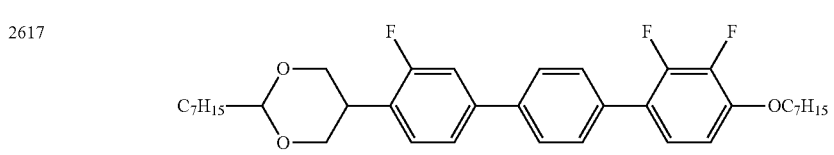 |
| 2618 | 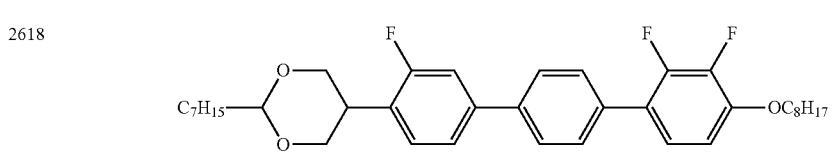 |
| 2619 | 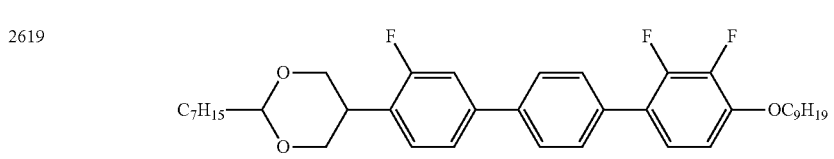 |
| 2620 | 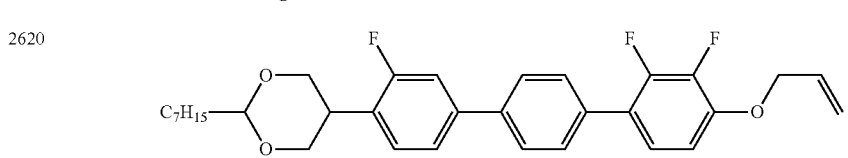 |
| 2621 | 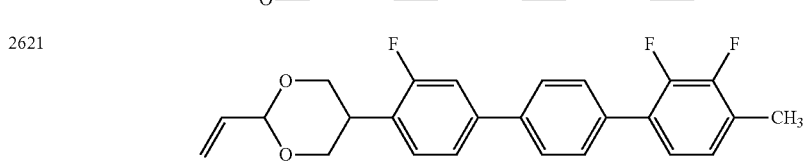 |
| 2622 | 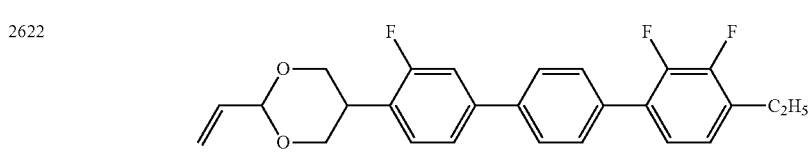 |

| No. |
|---|
| 2623 |
| 2624 |
| 2625 |
| 2626 |
| 2627 |
| 2628 |
| 2629 |
| 2630 |
| 2631 |
| 2632 |

-continued
| No. | |
|---|---|
| 2633 | 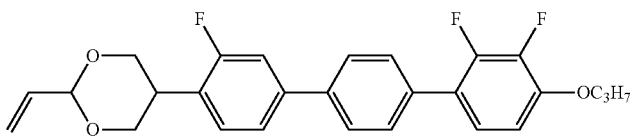 |
| 2634 | 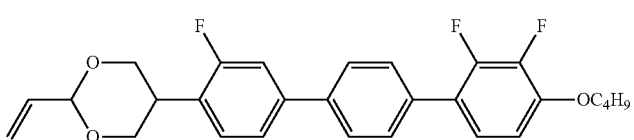 |
| 2635 | 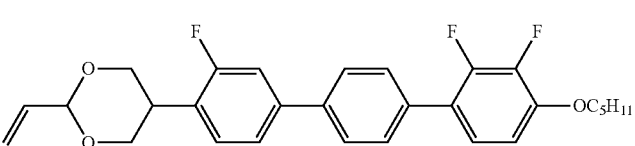 |
| 2636 | 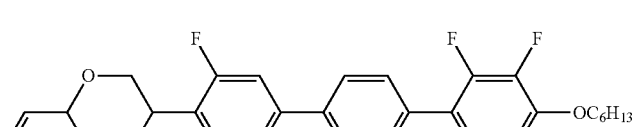 |
| 2637 | 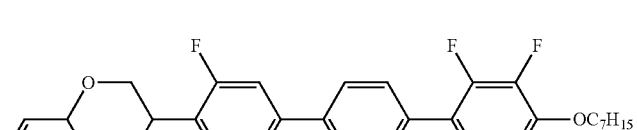 |
| 2638 | 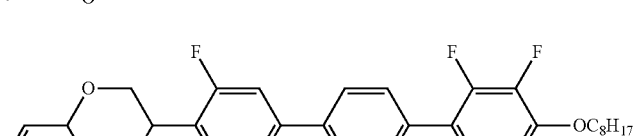 |
| 2639 |  |
| 2640 | 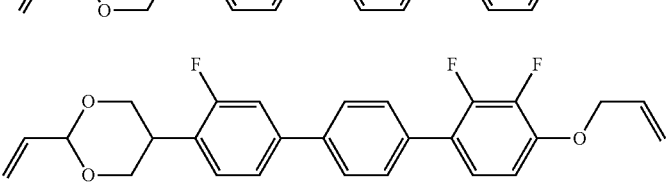 |
| 2641 | 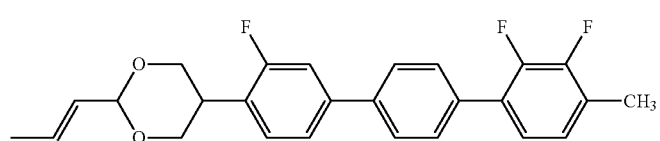 |
| 2642 | 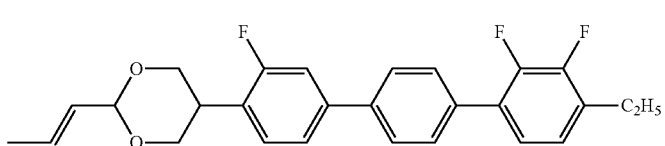 |

| No. | |
|---|---|
| 2643 | 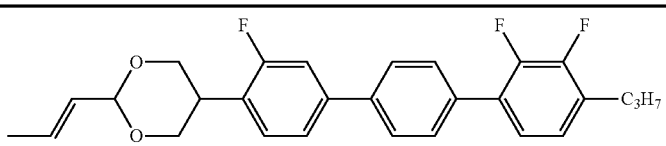 |
| 2644 | 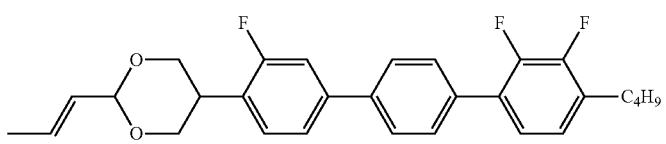 |
| 2645 | 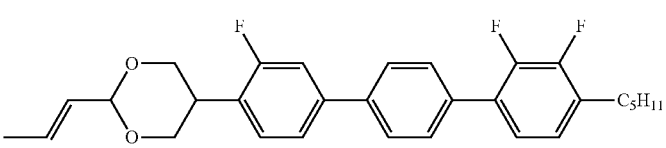 |
| 2646 | 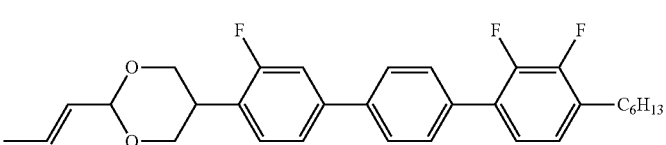 |
| 2647 | 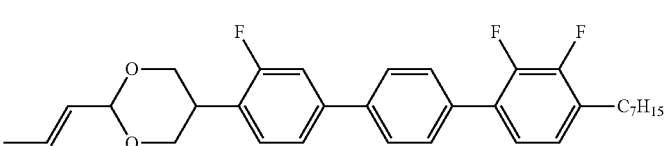 |
| 2648 | 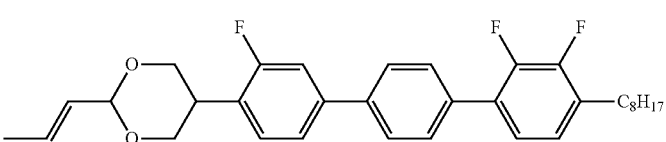 |
| 2649 | 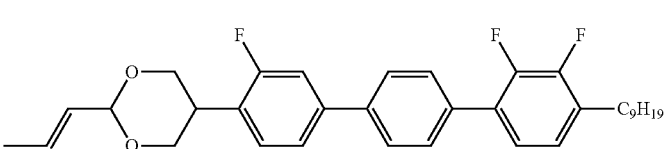 |
| 2650 | 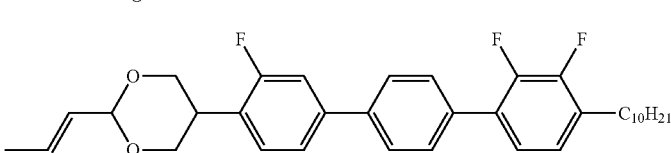 |
| 2651 | 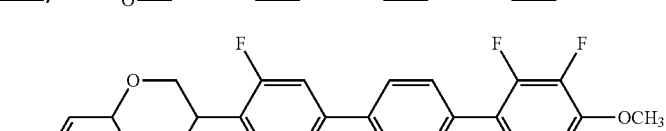 |
| 2652 | 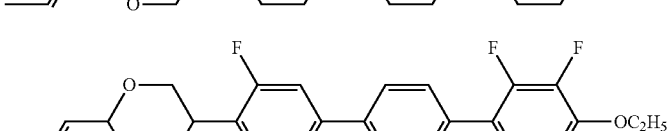 |
| 2653 | 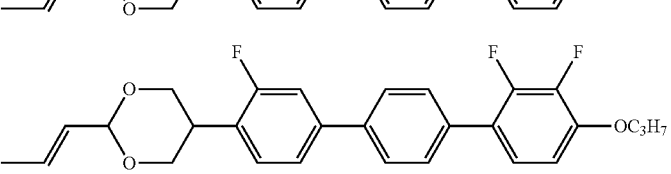 |

-continued
| No. | |
|---|---|
| 2654 | 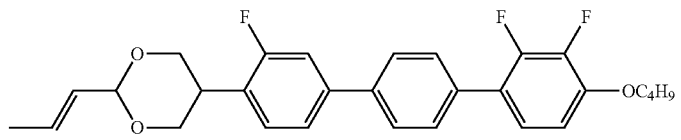 |
| 2655 | 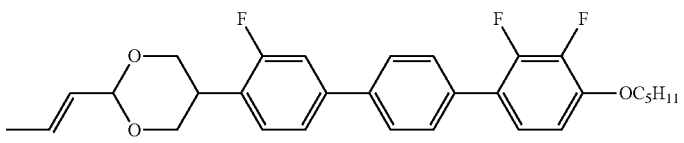 |
| 2656 | 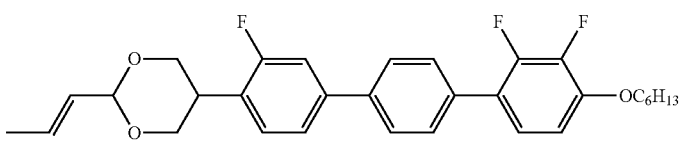 |
| 2657 |  |
| 2658 | 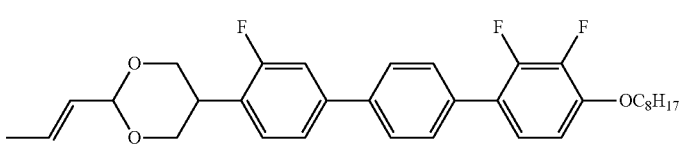 |
| 2659 | 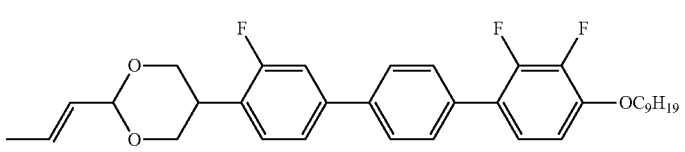 |
| 2660 | 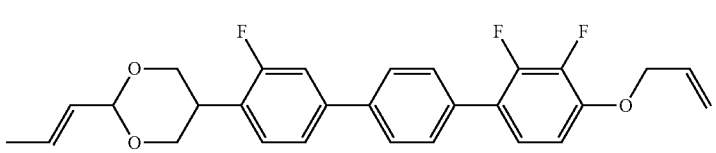 |
| 2661 | 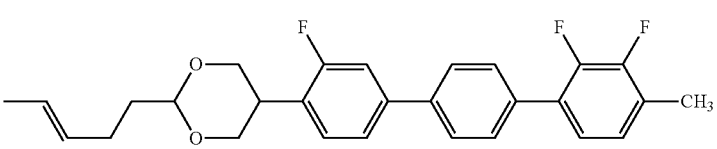 |
| 2662 | 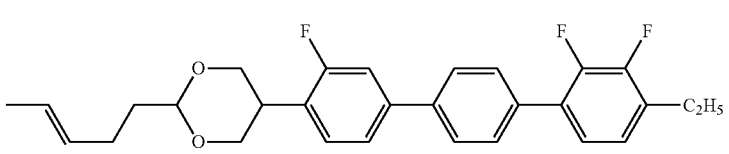 |
| 2663 | 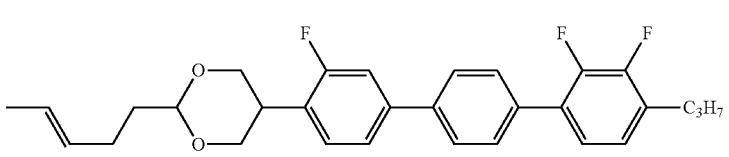 |

| No. | |
|---|---|
| 2664 | 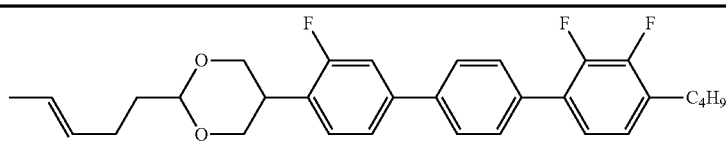 |
| 2665 | 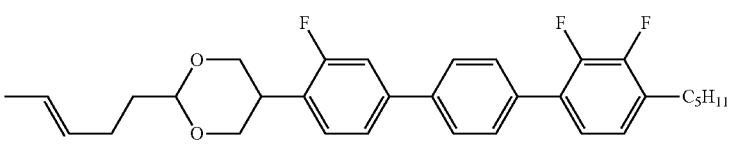 |
| 2666 | 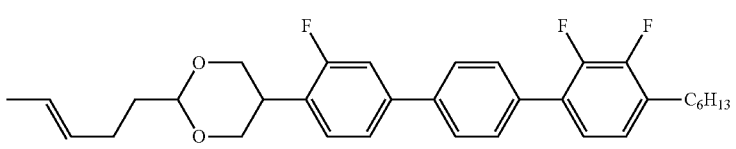 |
| 2667 | 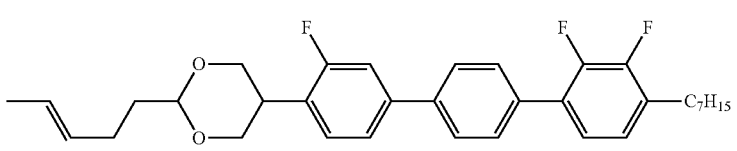 |
| 2668 | 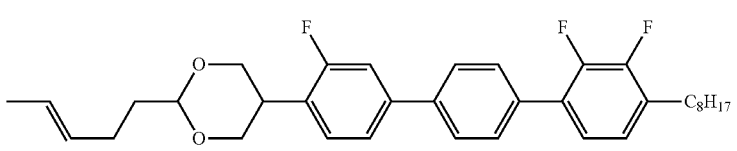 |
| 2669 | 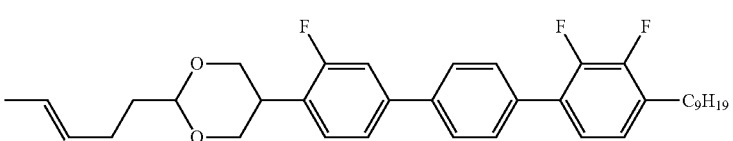 |
| 2670 | 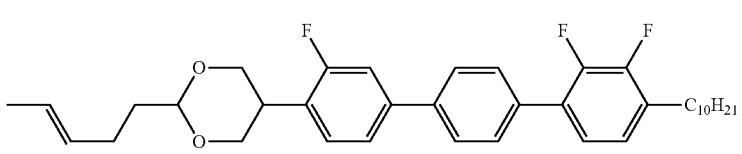 |
| 2671 | 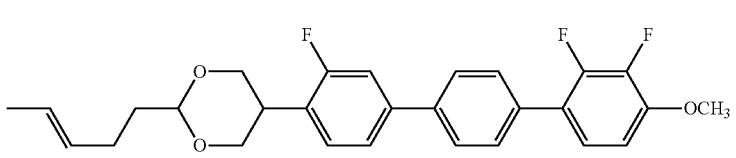 |
| 2672 | 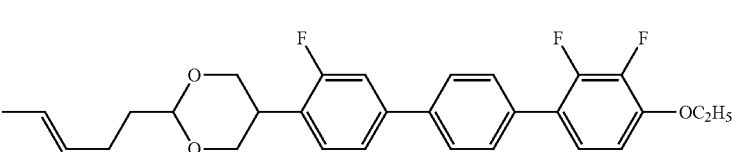 |
| 2673 | 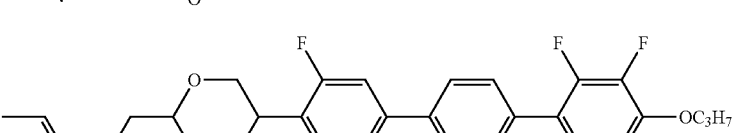 |
| 2674 | 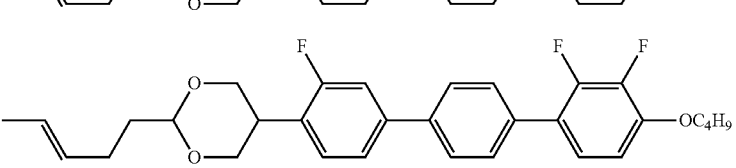 |

-continued
| No. | |
|---|---|
| 2675 | 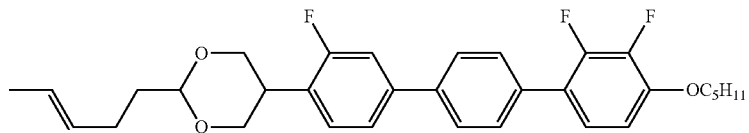 |
| 2676 | 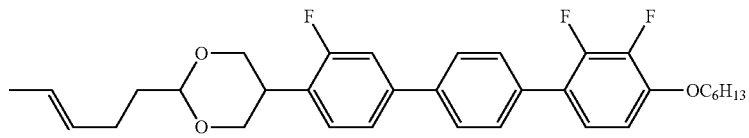 |
| 2677 | 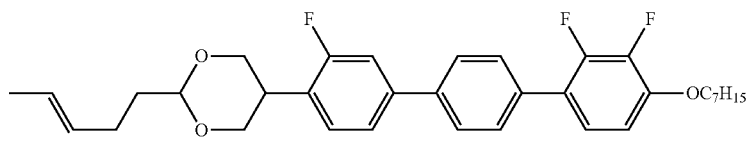 |
| 2678 | 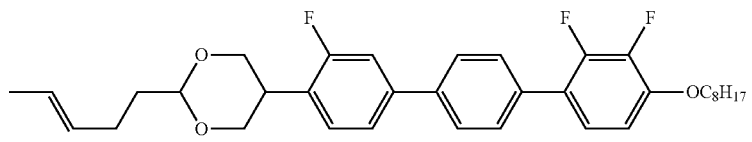 |
| 2679 | 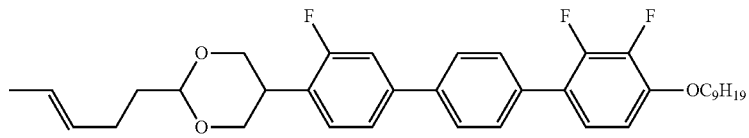 |
| 2680 | 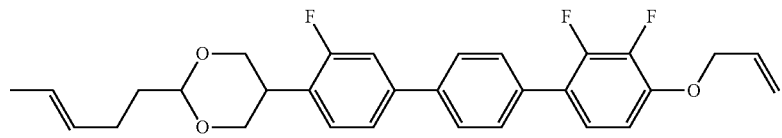 |
| 2681 | 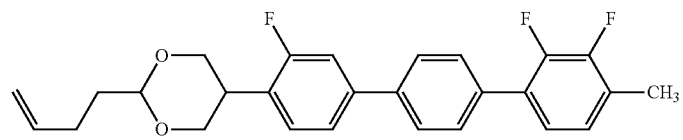 |
| 2682 |  |
| 2683 | 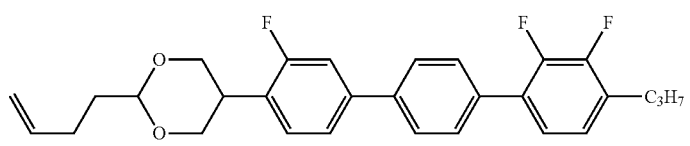 |
| 2684 | 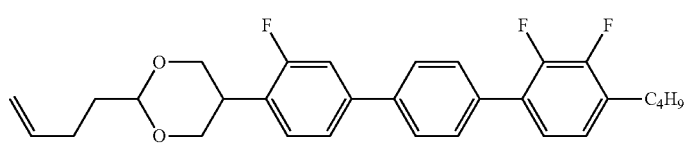 |

| No. | |
|---|---|
| 2685 | 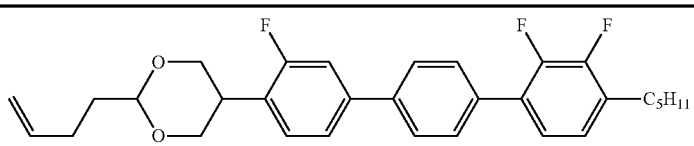 |
| 2686 | 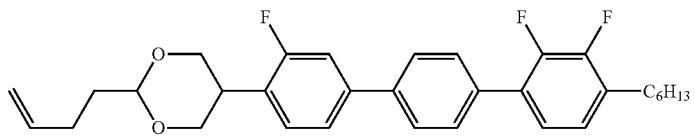 |
| 2687 | 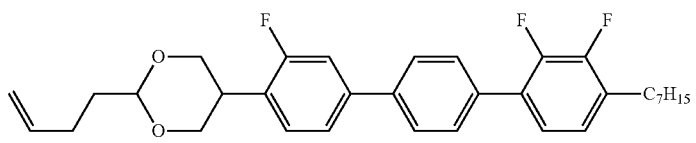 |
| 2688 | 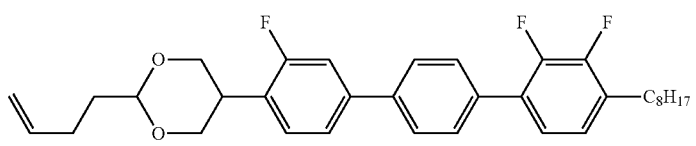 |
| 2689 | 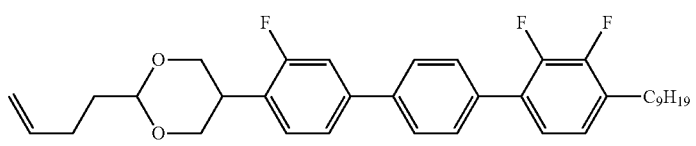 |
| 2690 | 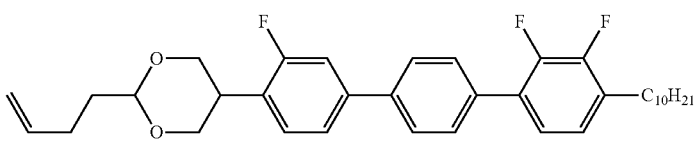 |
| 2691 | 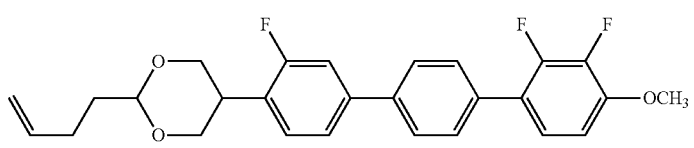 |
| 2692 | 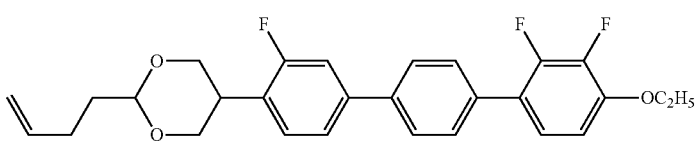 |
| 2693 | 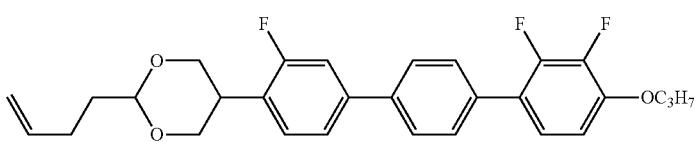 |
| 2694 | 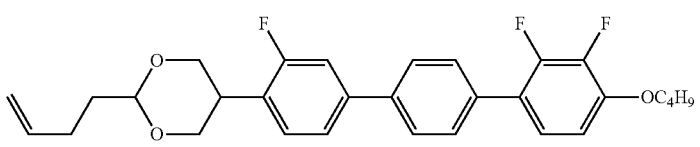 |
| 2695 | 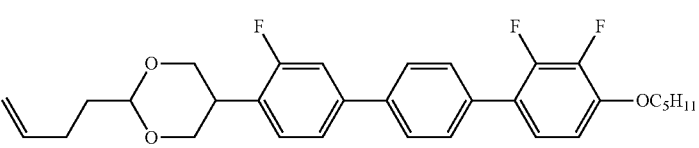 |

| No. | |
|---|---|
| 2696 | 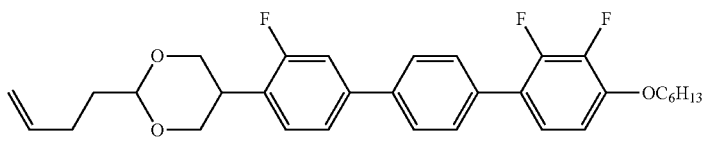 |
| 2697 | 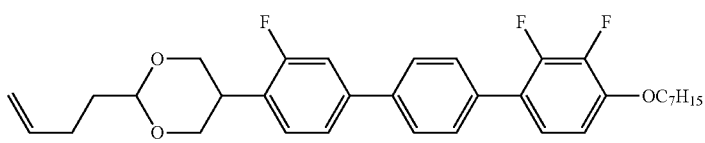 |
| 2698 | 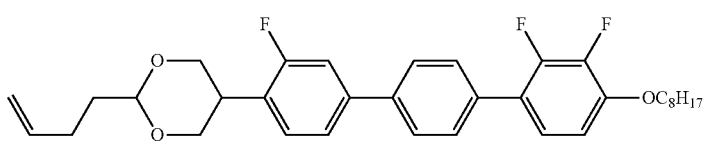 |
| 2699 | 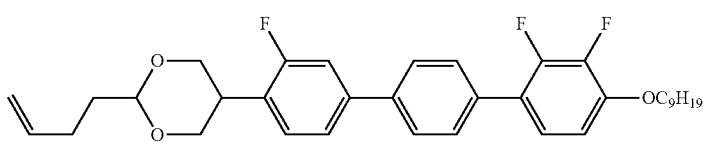 |
| 2700 | 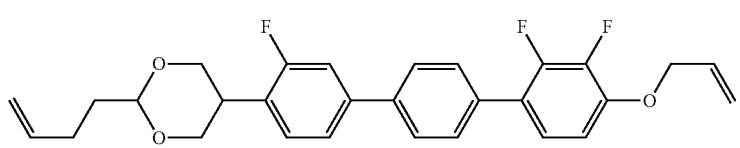 |
| 2701 | 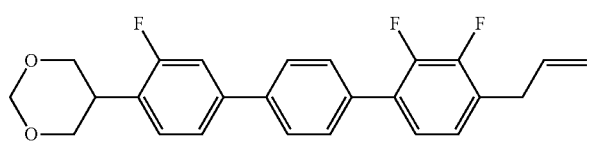 |
| 2702 | 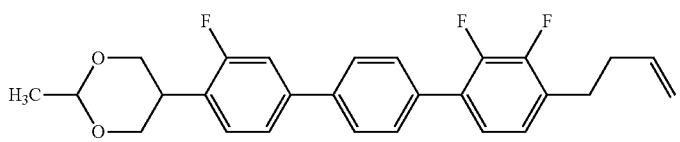 |
| 2703 | 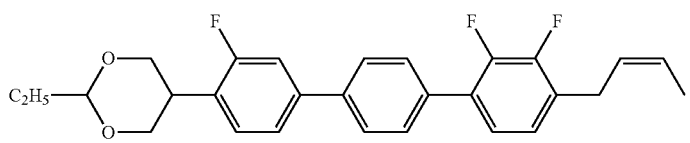 |
| 2704 | 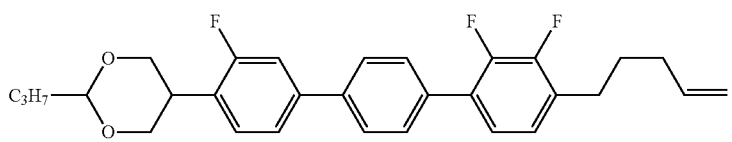 |
| 2705 | 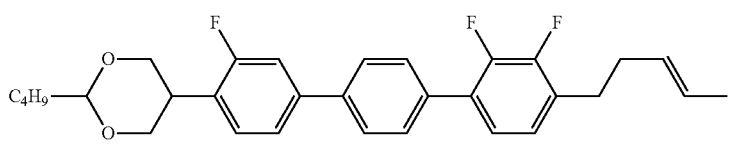 |

-continued
| No. | |
|---|---|
| 2706 | 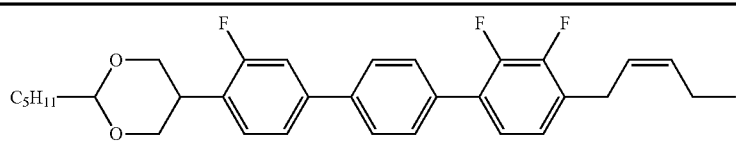 |
| 2707 | 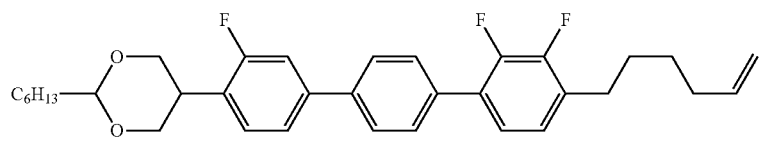 |
| 2708 | 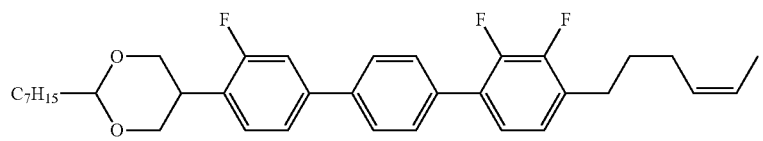 |
| 2709 | 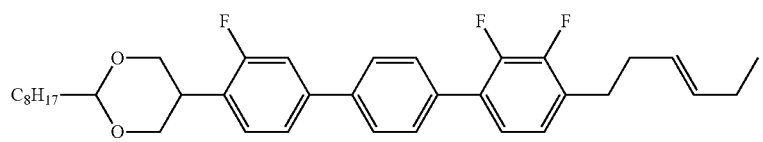 |
| 2710 | 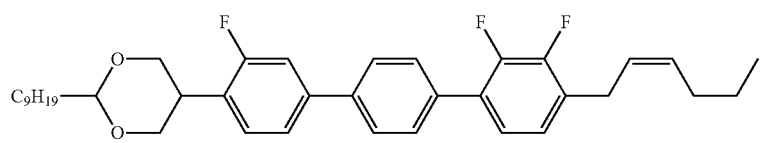 |
| 2711 | 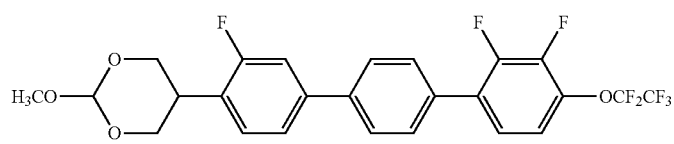 |
| 2712 | 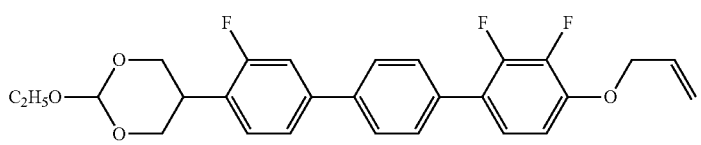 |
| 2713 | 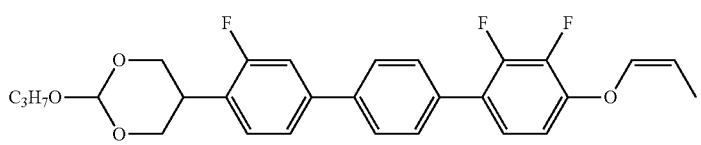 |
| 2714 | 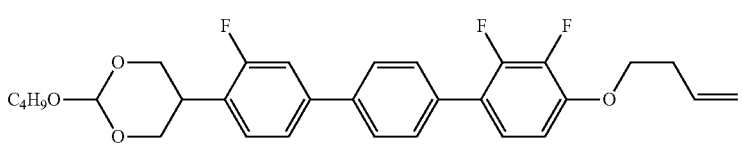 |
| 2715 | 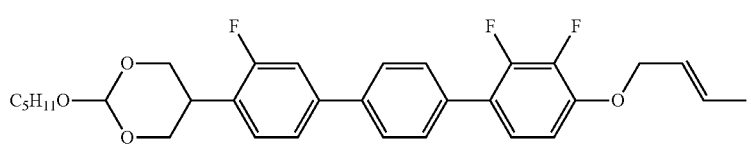 |
| 2716 | 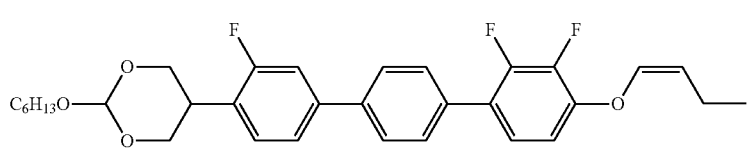 |

-continued
| No. | |
|---|---|
| 2717 | 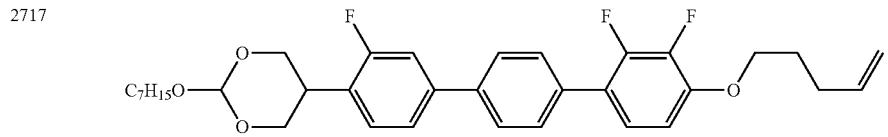 |
| 2718 | 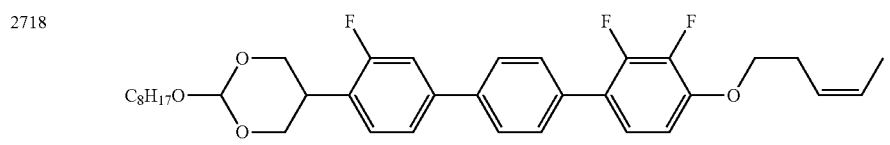 |
| 2719 | 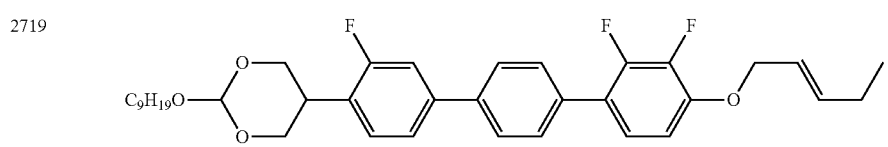 |
| 2720 | 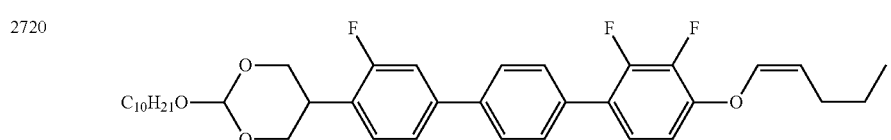 |
| 2721 | 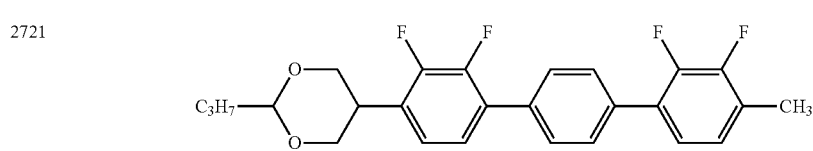 |
| 2722 | 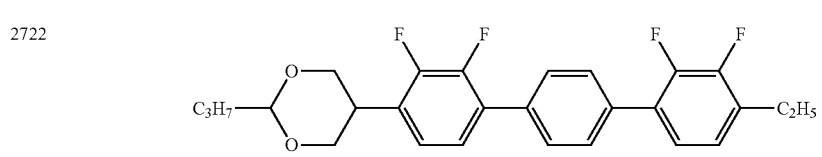 |
| 2723 | 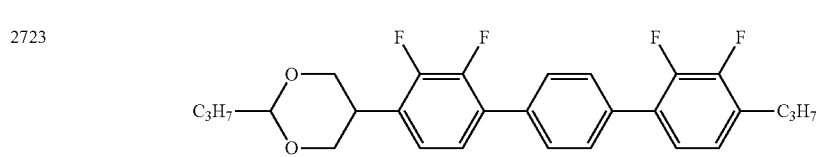 |
| 2724 | 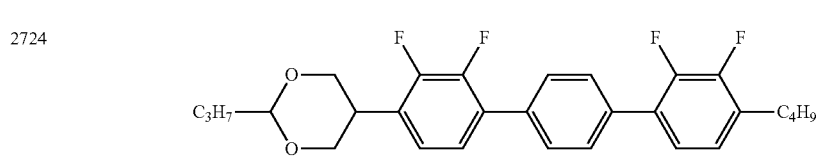 |
| 2725 | 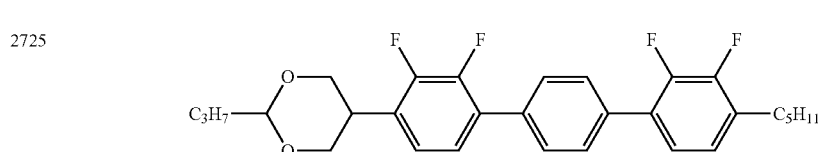 |
| 2726 | 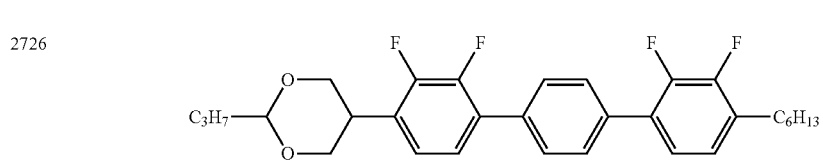 |

| No. | |
|---|---|
| 2727 | 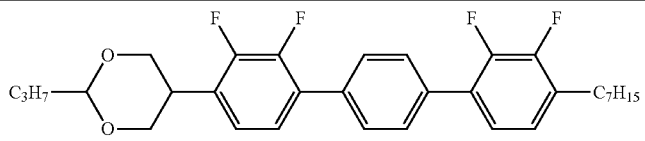 |
| 2728 | 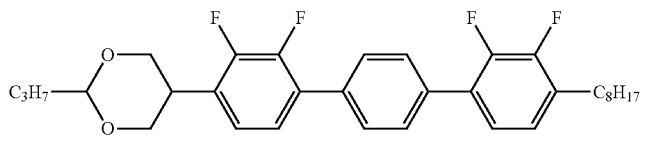 |
| 2729 | 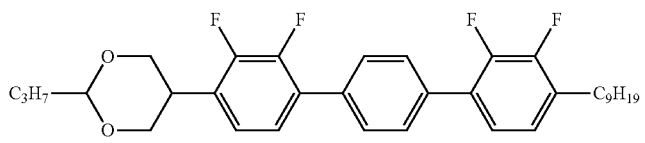 |
| 2730 | 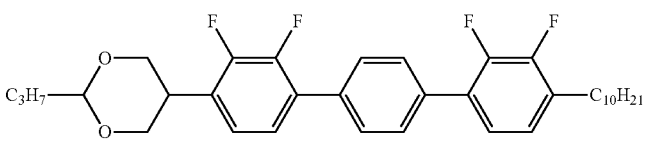 |
| 2731 | 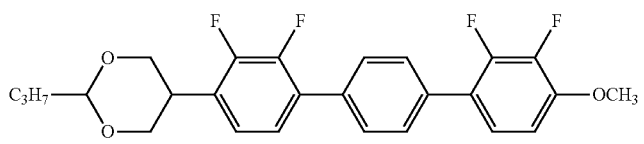 |
| 2732 | 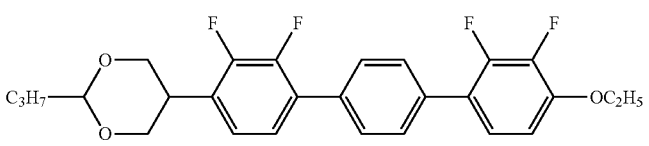 |
| 2733 | 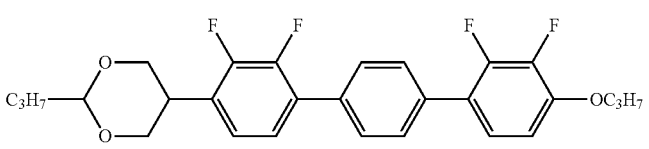 |
| 2734 | 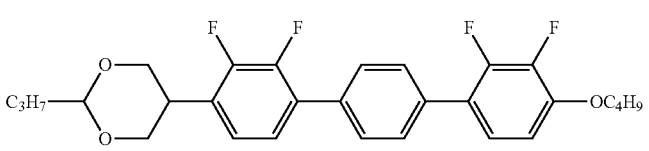 |
| 2735 | 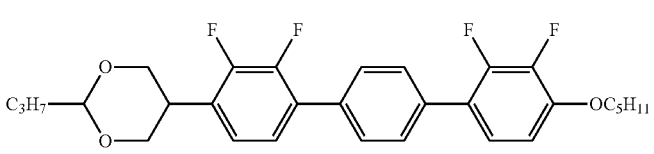 |
| 2736 | 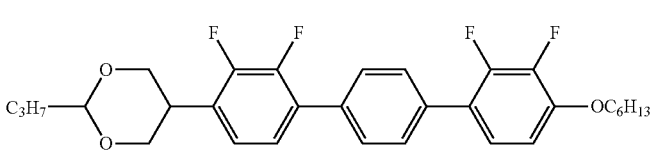 |
| 2737 | 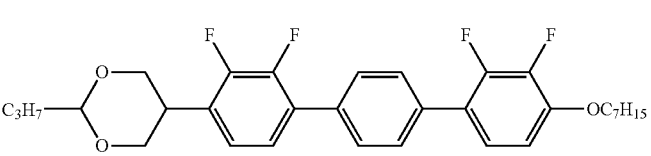 |

-continued
| No. |
|---|
| 2738  |
| 2739  |
| 2740 |
| 2741 |
| 2742 |
| 2743 |
| 2744  |
| 2745  |
| 2746  |
| 2747 |

| No. | |
|---|---|
| 2748 | 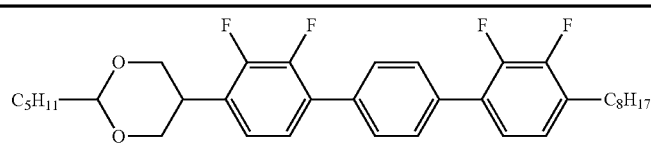 |
| 2749 | 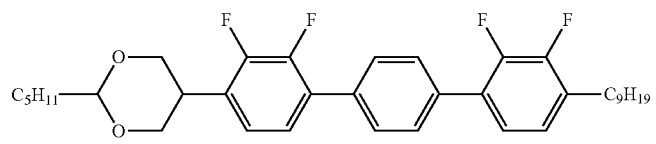 |
| 2750 | 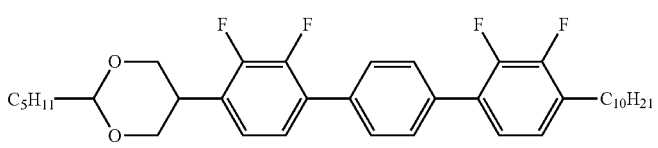 |
| 2751 | 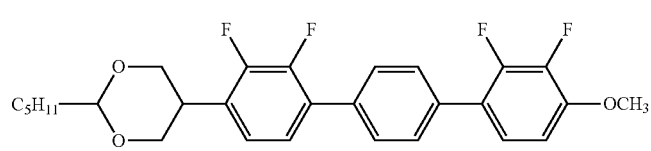 |
| 2752 | 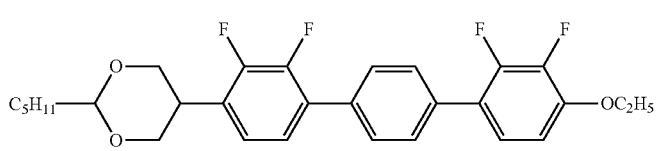 |
| 2753 | 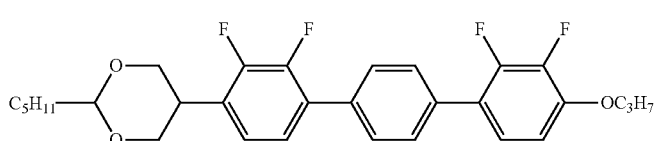 |
| 2754 | 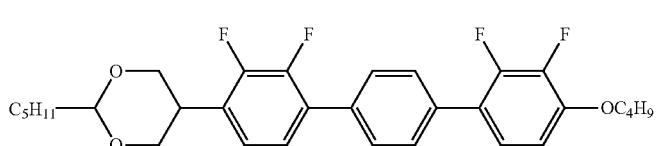 |
| 2755 | 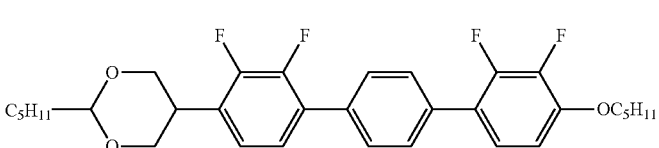 |
| 2756 | 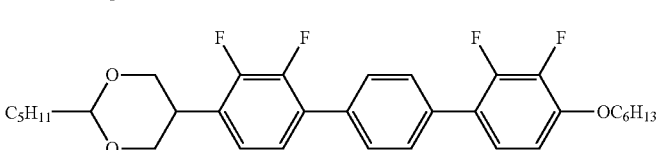 |
| 2757 | 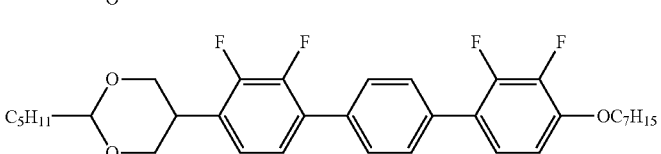 |
| 2758 | 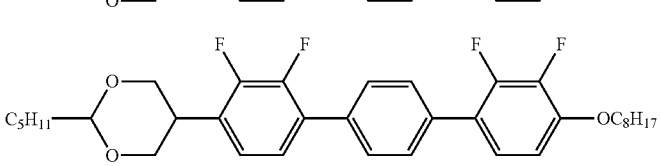 |

-continued
| No. | |
|---|---|
| 2759 |  |
| 2760 |  |
| 2761 | |
| 2762 |  |
| 2763 | |
| 2764 | |
| 2765 | |
| 2766 |  |
| 2767 | |
| 2768 | |

-continued

| No. | |
|---|---|
| 2769 | C7H15—[dioxane]—[C6H2F2]—[C6H4]—[C6H2F2]—C9H19 |
| 2770 | C7H15—[dioxane]—[C6H2F2]—[C6H4]—[C6H2F2]—C10H21 |
| 2771 | C7H15—[dioxane]—[C6H2F2]—[C6H4]—[C6H2F2]—OCH3 |
| 2772 | C7H15—[dioxane]—[C6H2F2]—[C6H4]—[C6H2F2]—OC2H5 |
| 2773 | C7H15—[dioxane]—[C6H2F2]—[C6H4]—[C6H2F2]—OC3H7 |
| 2774 | C7H15—[dioxane]—[C6H2F2]—[C6H4]—[C6H2F2]—OC4H9 |
| 2775 | C7H15—[dioxane]—[C6H2F2]—[C6H4]—[C6H2F2]—OC5H11 |
| 2776 | C7H15—[dioxane]—[C6H2F2]—[C6H4]—[C6H2F2]—OC6H13 |
| 2777 | C7H15—[dioxane]—[C6H2F2]—[C6H4]—[C6H2F2]—OC7H15 |
| 2778 | C7H15—[dioxane]—[C6H2F2]—[C6H4]—[C6H2F2]—OC8H17 |

-continued
| No. | |
|---|---|
| 2779 | 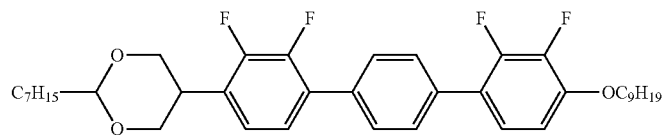 |
| 2780 | 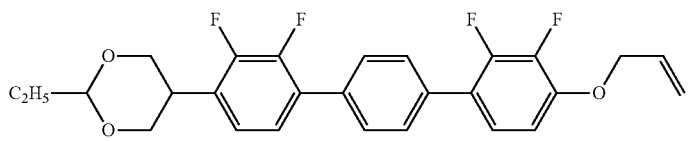 |
| 2781 | 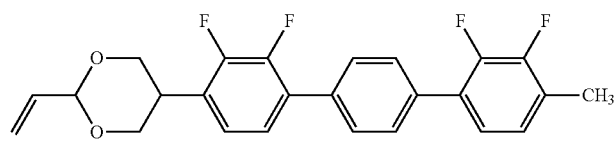 |
| 2782 | 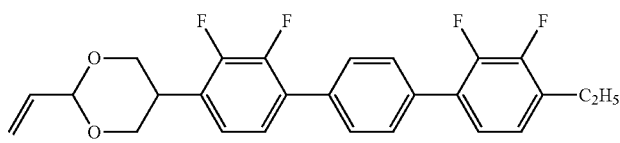 |
| 2783 | 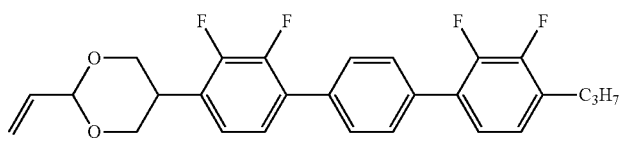 |
| 2784 | 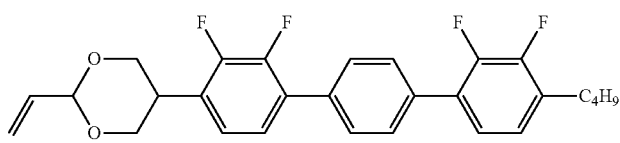 |
| 2785 | 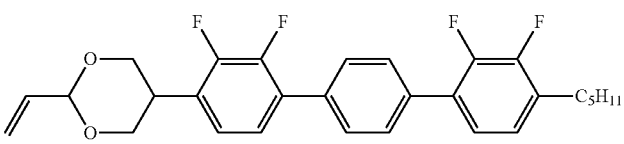 |
| 2786 | 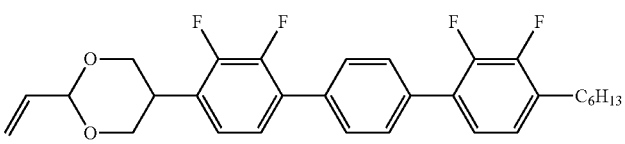 |
| 2787 | 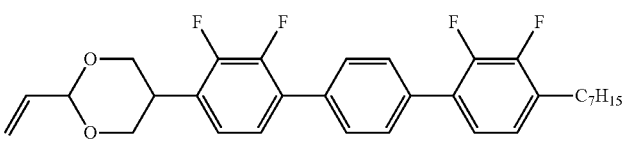 |
| 2788 | 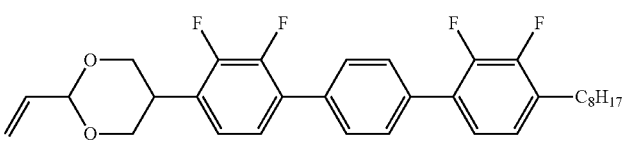 |

| No. | |
|---|---|
| 2789 | 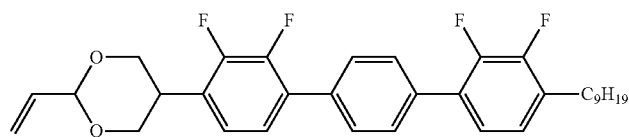 |
| 2790 | 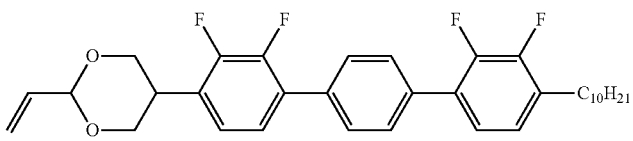 |
| 2791 | 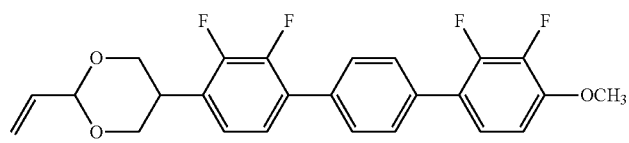 |
| 2792 | 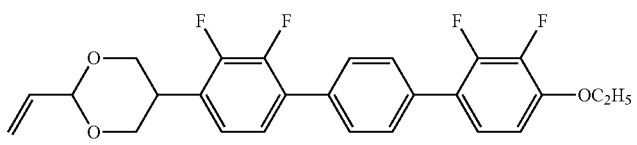 |
| 2793 | 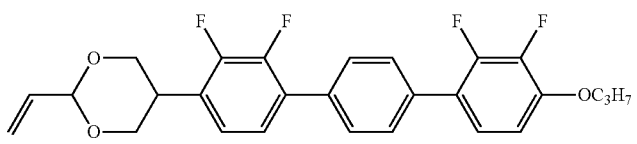 |
| 2794 | 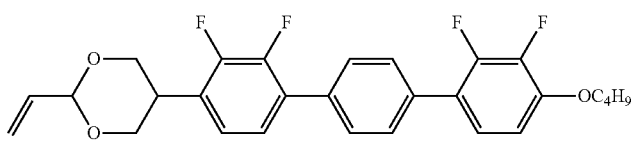 |
| 2795 | 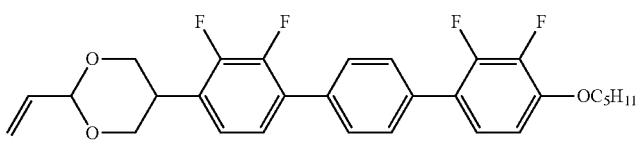 |
| 2796 | 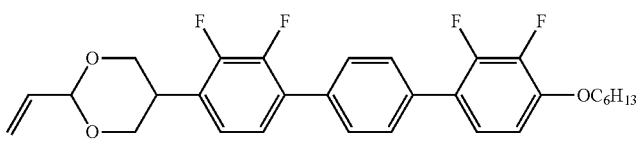 |
| 2797 | 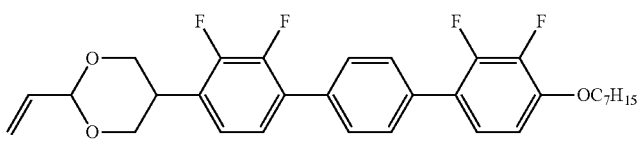 |
| 2798 | 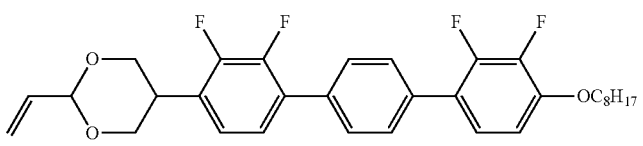 |

| No. | |
|---|---|
| 2799 | 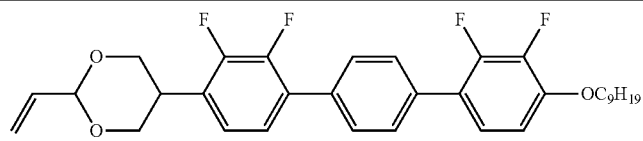 |
| 2800 | 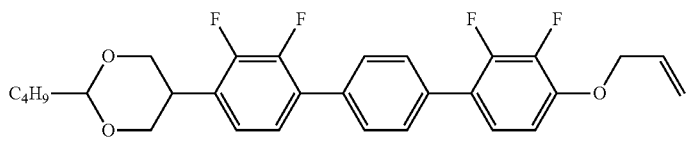 |
| 2801 | 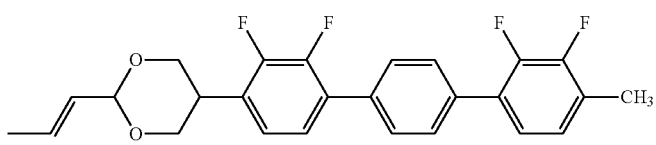 |
| 2802 | 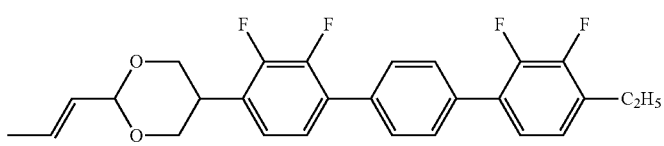 |
| 2803 | 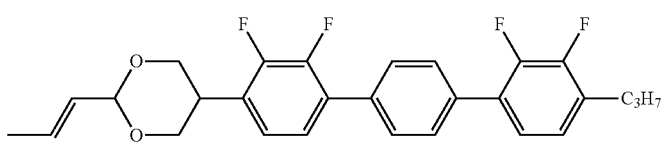 |
| 2804 | 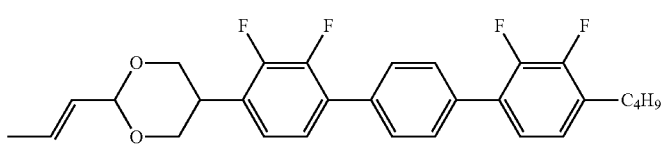 |
| 2805 | 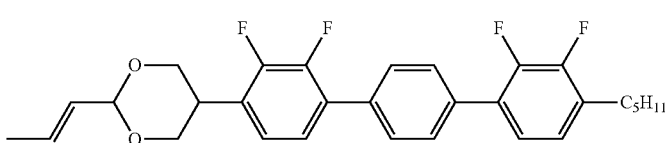 |
| 2806 | 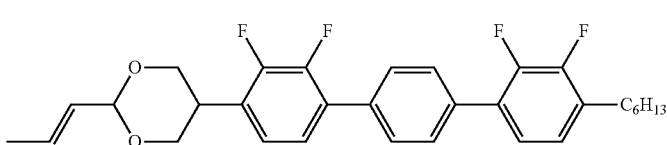 |
| 2807 | 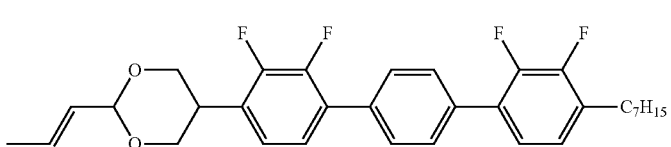 |
| 2808 | 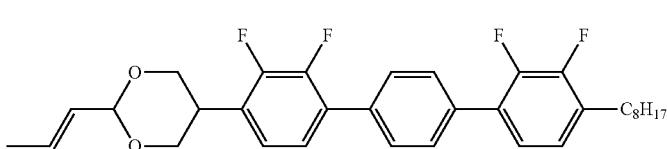 |
| 2809 | 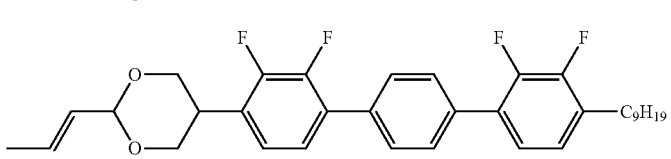 |

| No. | |
|---|---|
| 2810 | (structure with C₁₀H₂₁) |
| 2811 | (structure with OCH₃) |
| 2812 | (structure with OC₂H₅) |
| 2813 | (structure with OC₃H₇) |
| 2814 | (structure with OC₄H₉) |
| 2815 | (structure with OC₅H₁₁) |
| 2816 | (structure with OC₆H₁₃) |
| 2817 | (structure with OC₇H₁₅) |
| 2818 | (structure with OC₈H₁₇) |
| 2819 | (structure with OC₉H₁₉) |

| No. | |
|---|---|
| 2820 | 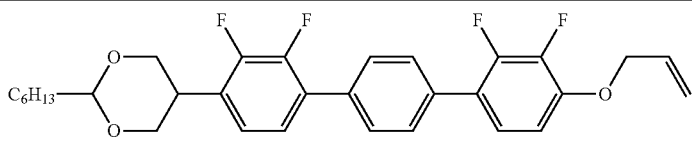 |
| 2821 | 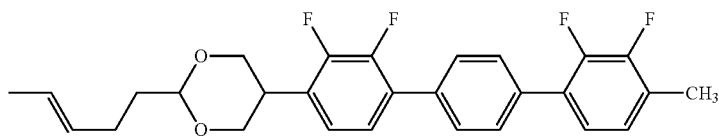 |
| 2822 | 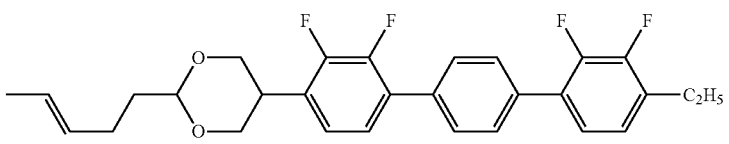 |
| 2823 | 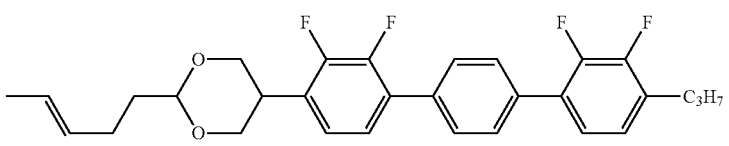 |
| 2824 | 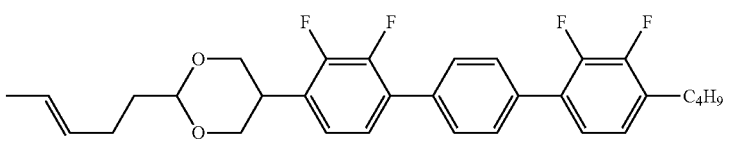 |
| 2825 | 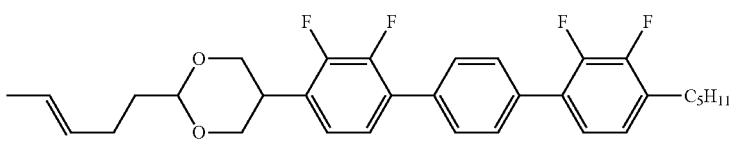 |
| 2826 | 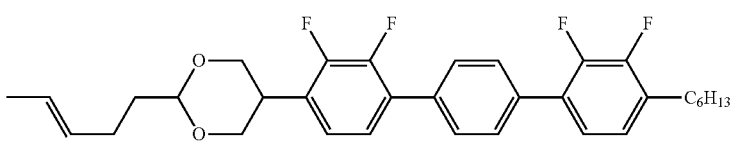 |
| 2827 | 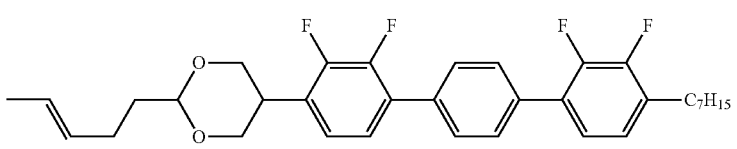 |
| 2828 | 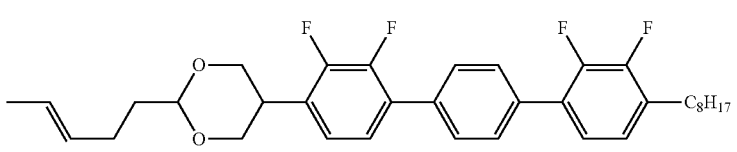 |
| 2829 | 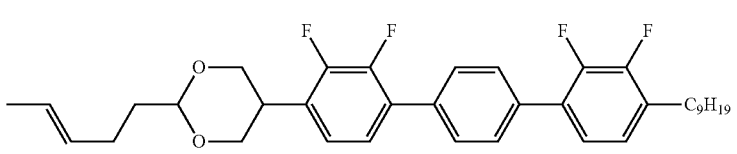 |
| 2830 | 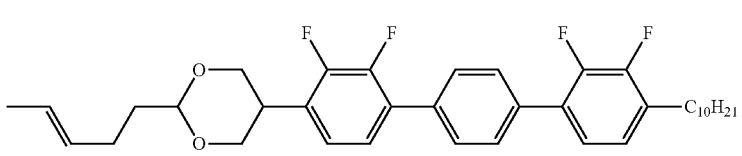 |

-continued
| No. |
|---|
| 2831 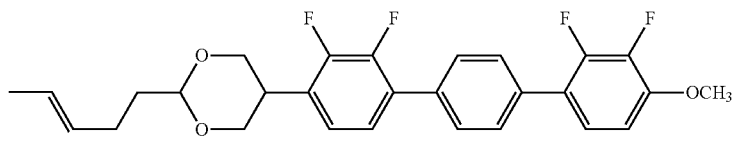 |
| 2832 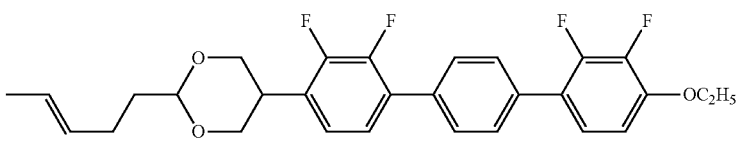 |
| 2833 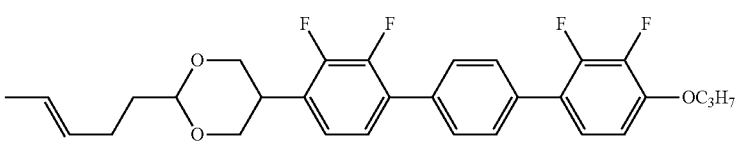 |
| 2834 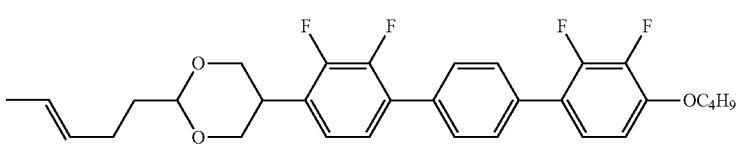 |
| 2835 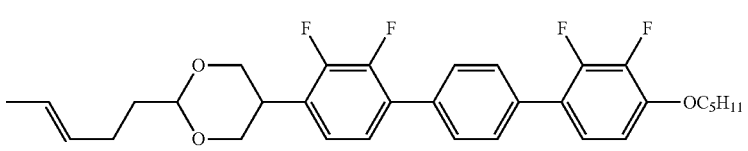 |
| 2836 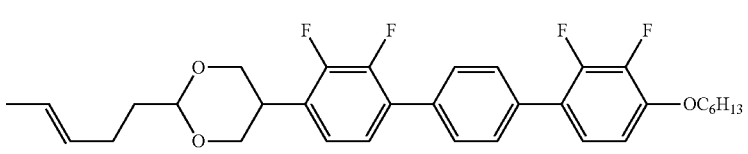 |
| 2837 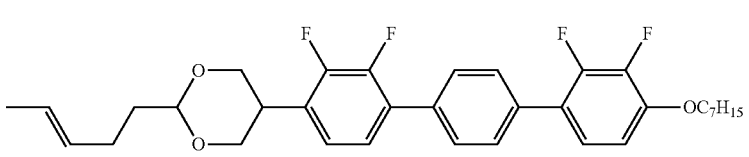 |
| 2838 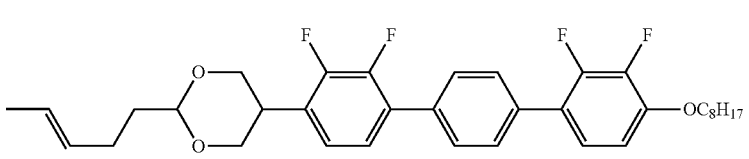 |
| 2839 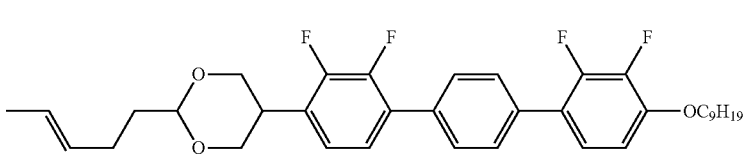 |
| 2840 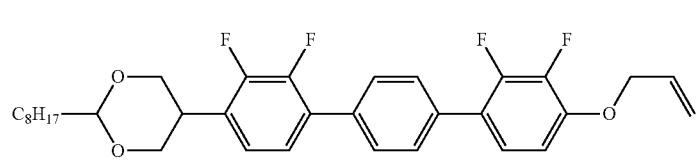 |

| No. | |
|---|---|
| 2841 | 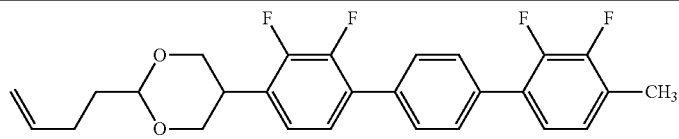 |
| 2842 | 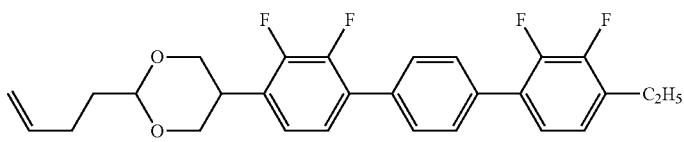 |
| 2843 | 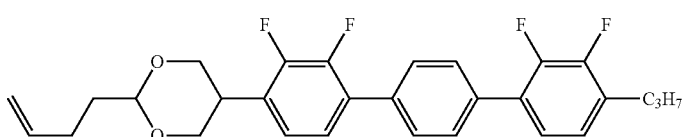 |
| 2844 | 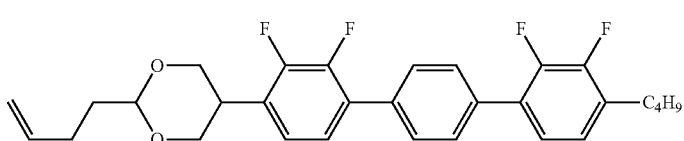 |
| 2845 | 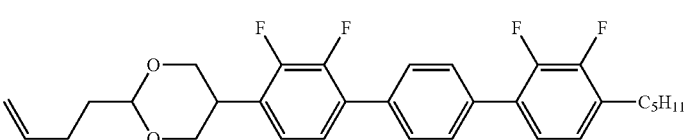 |
| 2846 | 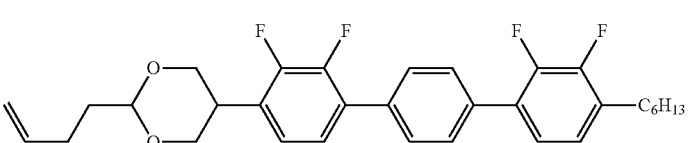 |
| 2847 | 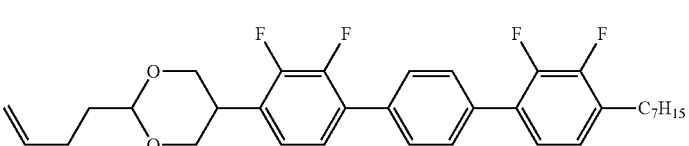 |
| 2848 | 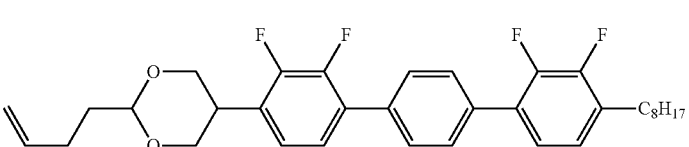 |
| 2849 | 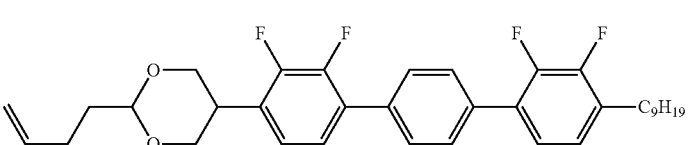 |
| 2850 | 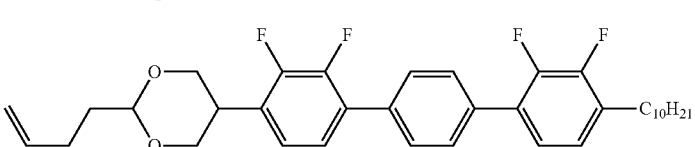 |
| 2851 | 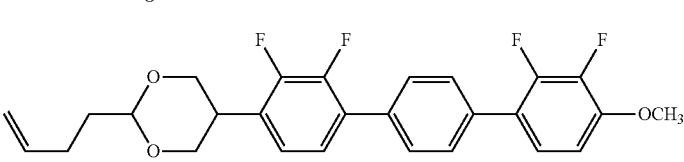 |

| No. |
|---|
| 2852 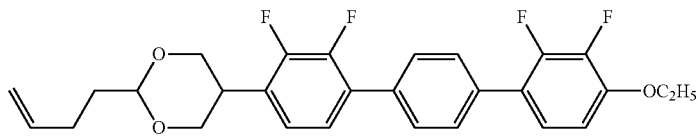 |
| 2853 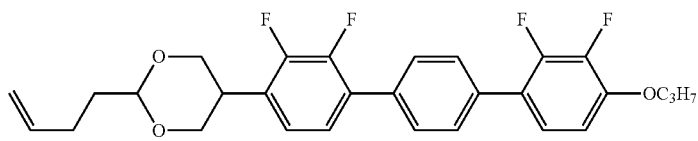 |
| 2854 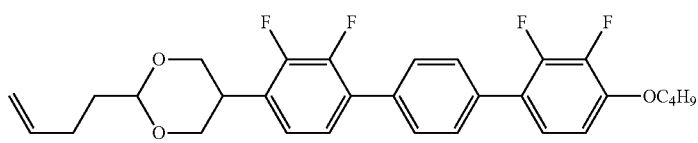 |
| 2855 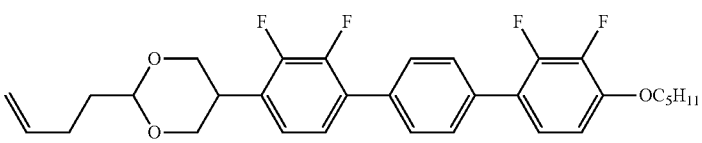 |
| 2856 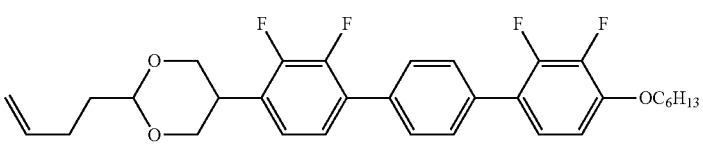 |
| 2857 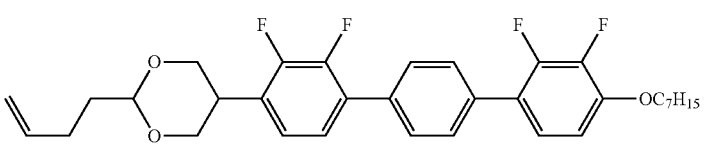 |
| 2858 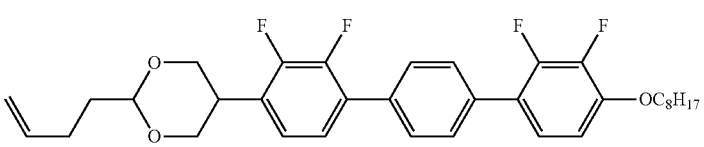 |
| 2859 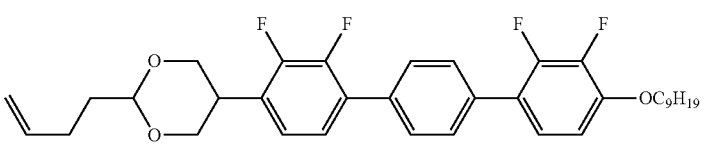 |
| 2860 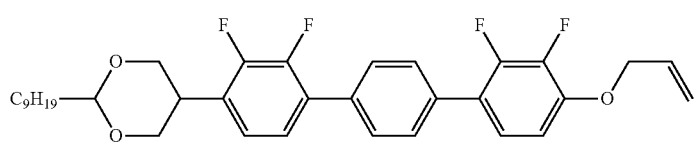 |
| 2861 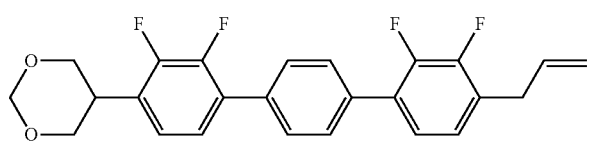 |

| No. | |
|---|---|
| 2862 | 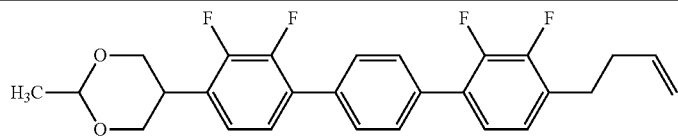 |
| 2863 | 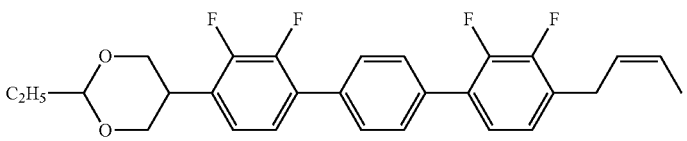 |
| 2864 | 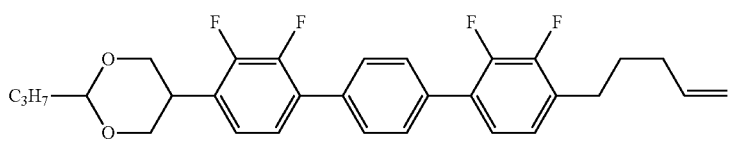 |
| 2865 | 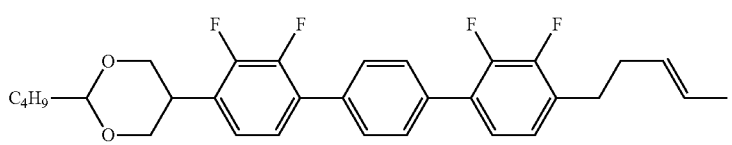 |
| 2866 | 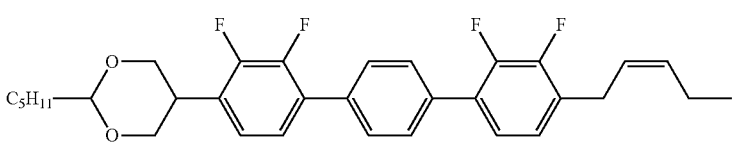 |
| 2867 | 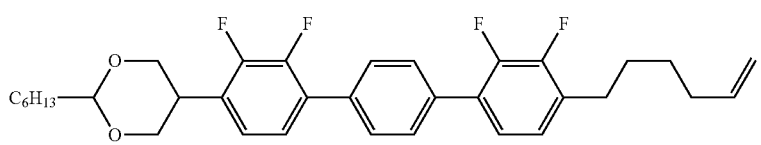 |
| 2868 | 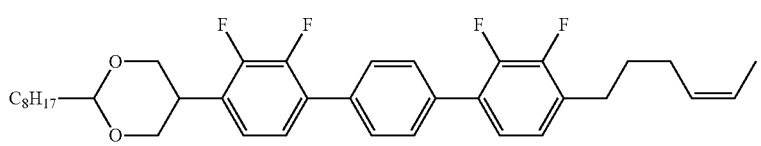 |
| 2869 | 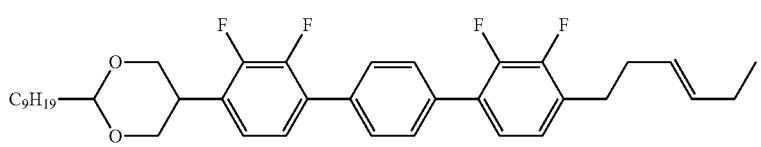 |
| 2870 | 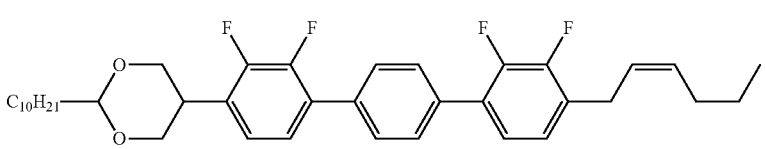 |
| 2871 | 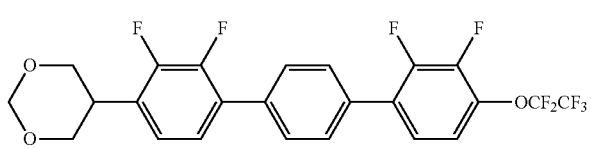 |
| 2872 | 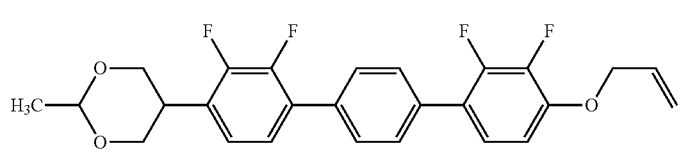 |

-continued
| No. | |
|---|---|
| 2873 | 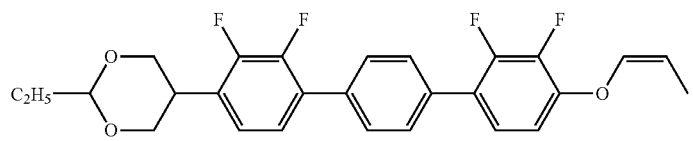 |
| 2874 | 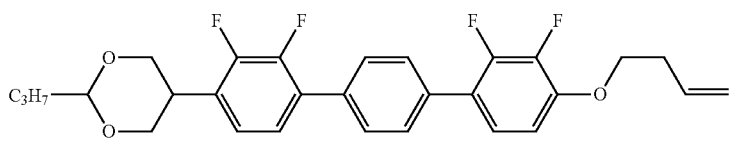 |
| 2875 | 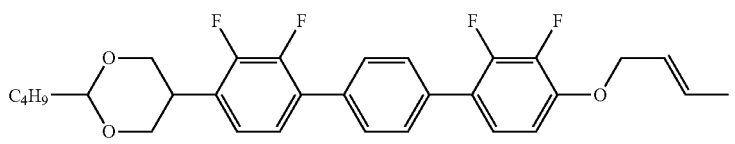 |
| 2876 | 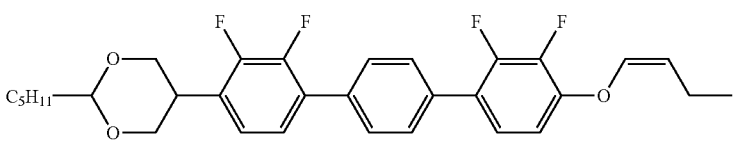 |
| 2877 | 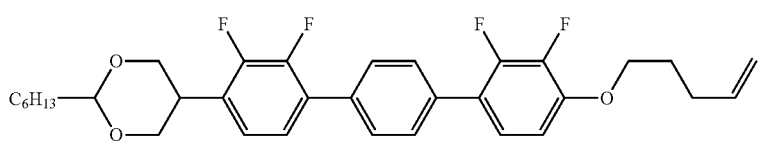 |
| 2878 | 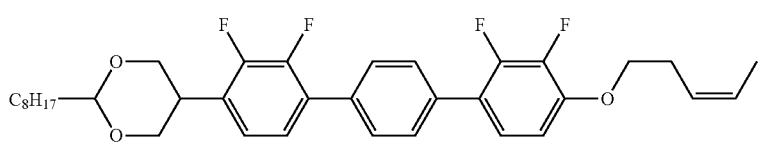 |
| 2879 | 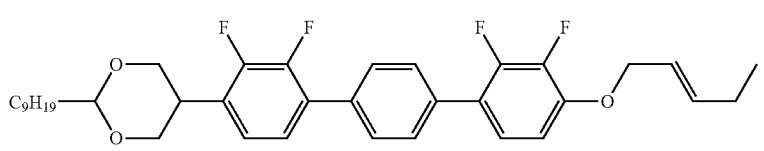 |
| 2880 | 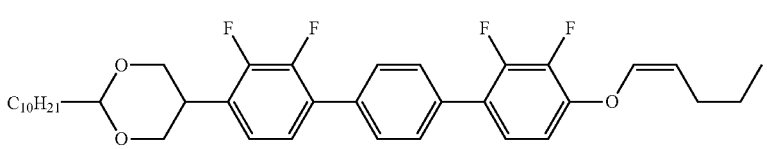 |
| 2881 | 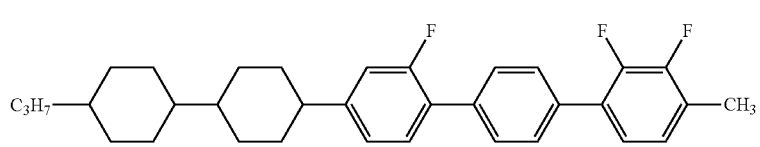 |
| 2882 | 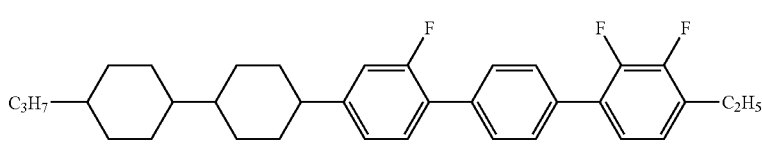 |

-continued
| No. | |
|---|---|
| 2883 | 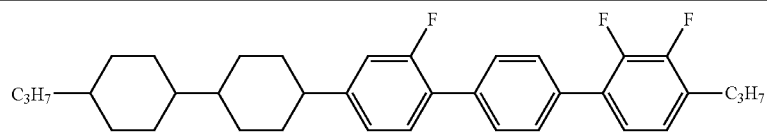 |
| 2884 | 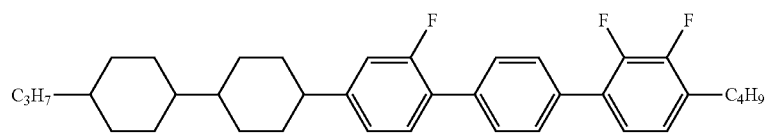 |
| 2885 | 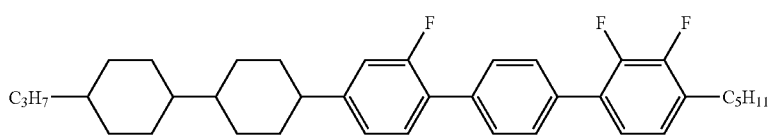 |
| 2886 | 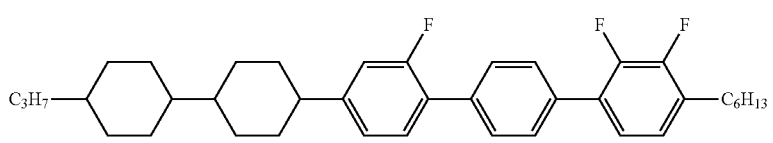 |
| 2887 | 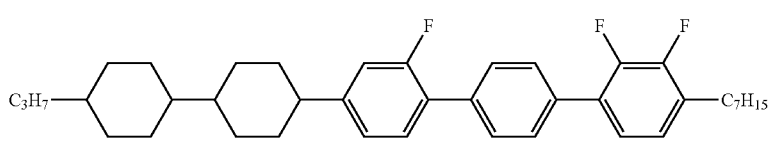 |
| 2888 | 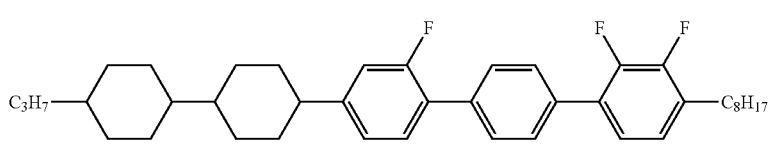 |
| 2889 | 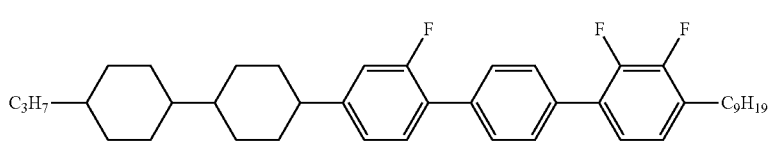 |
| 2890 | 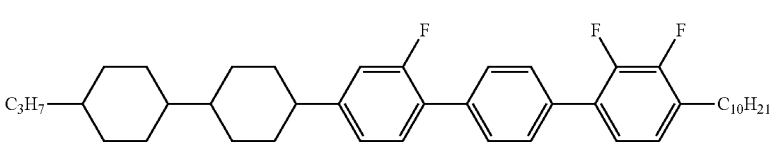 |
| 2891 | 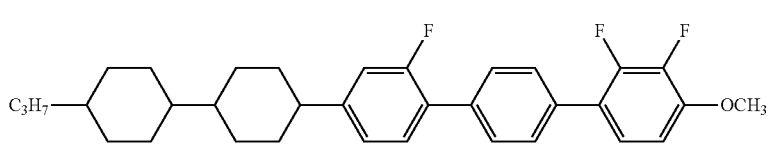 |
| 2892 | 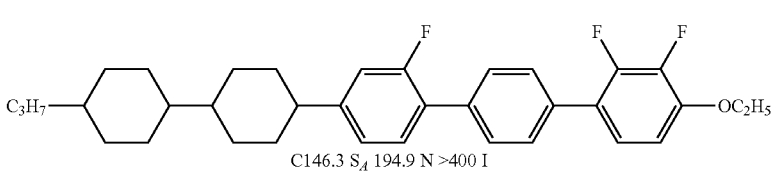<br>C146.3 $S_A$ 194.9 N >400 I |
| 2893 | 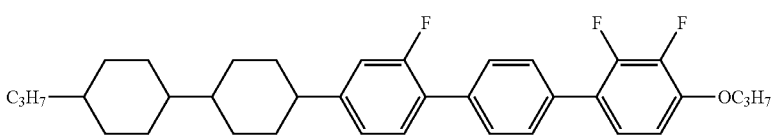 |

| No. | |
|---|---|
| 2894 | 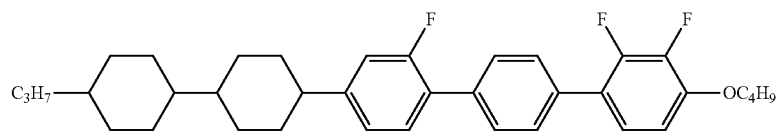 |
| 2895 | 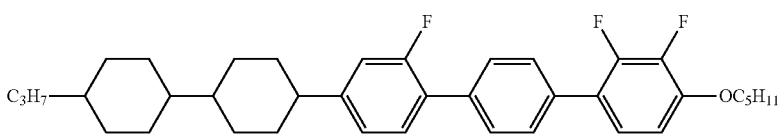 |
| 2896 | 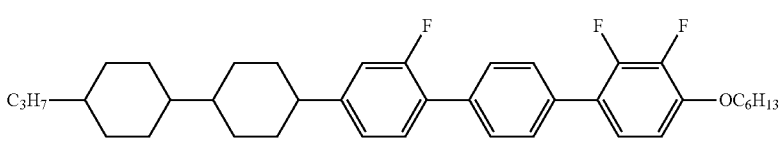 |
| 2897 | 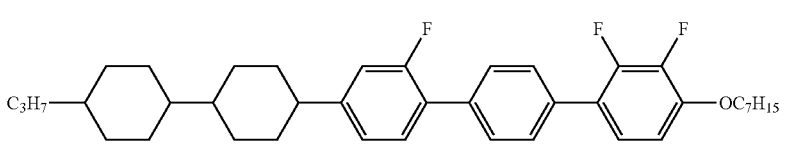 |
| 2898 | 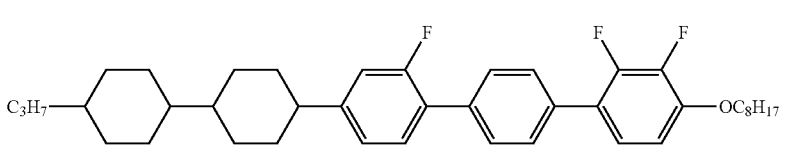 |
| 2899 | 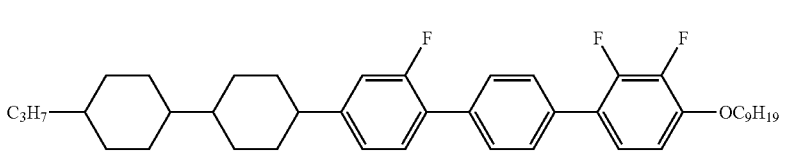 |
| 2900 | 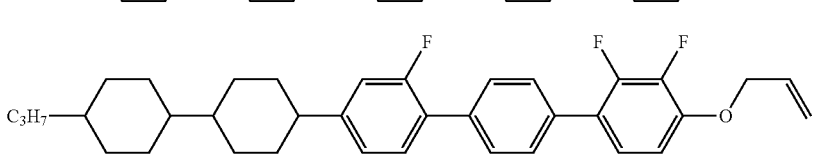 |
| 2901 | 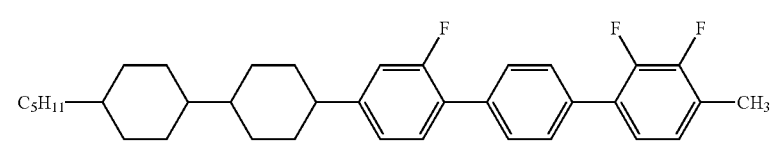 |
| 2902 | 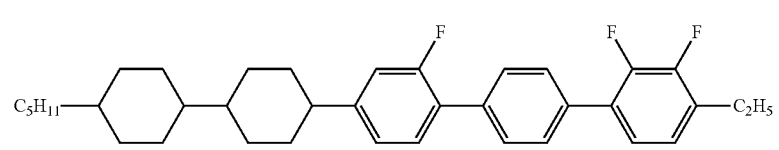 |
| 2903 | 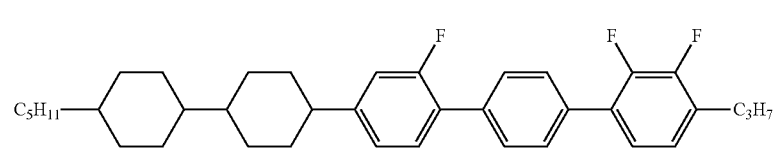 |
| 2904 | 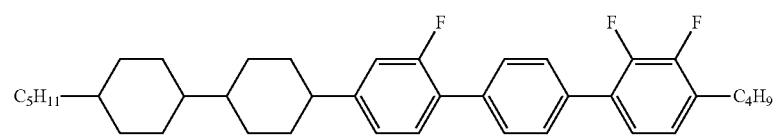 |

| No. | |
|---|---|
| 2905 | 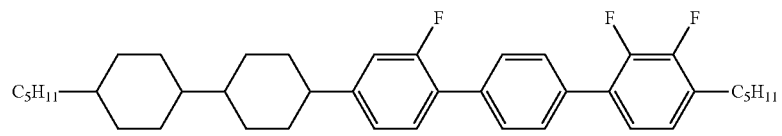 |
| 2906 | 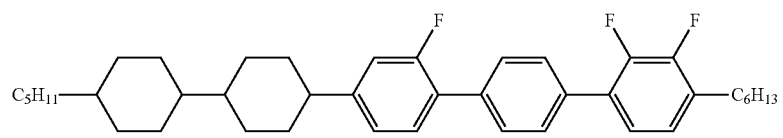 |
| 2907 | 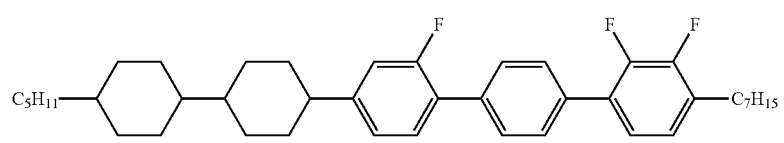 |
| 2908 | 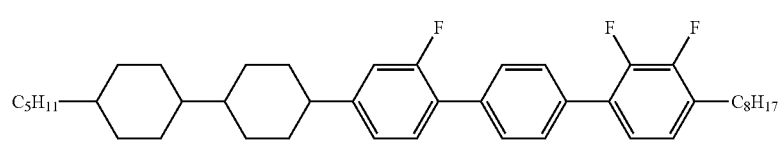 |
| 2909 | 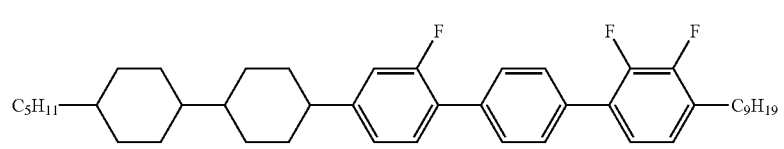 |
| 2910 | 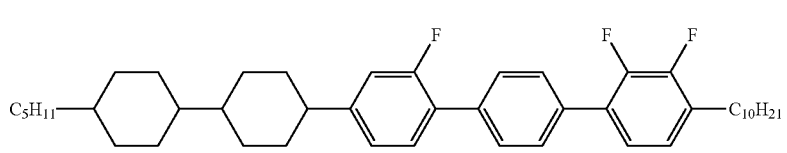 |
| 2911 | 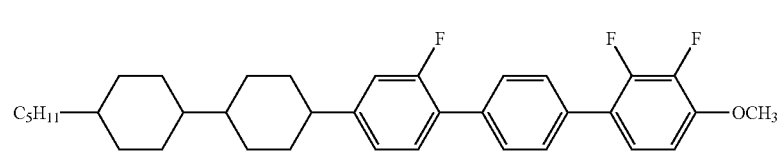 |
| 2912 | 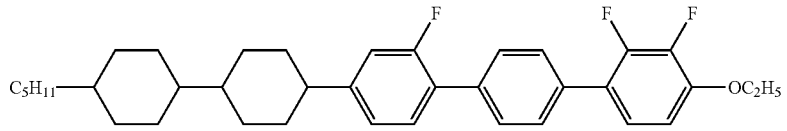 |
| 2913 |  |
| 2914 |  |
| 2915 | 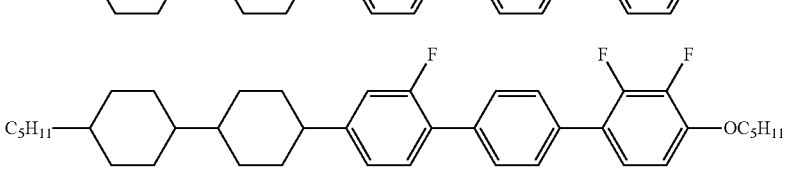 |

-continued

| No. |
|---|
| 2916 through 2926: chemical structures (not transcribable as text) |

| No. | |
|---|---|
| 2927 | 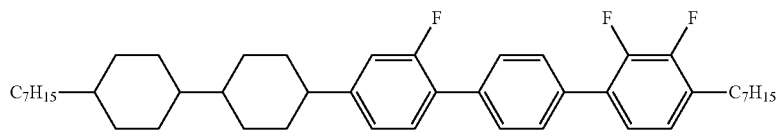 |
| 2928 | 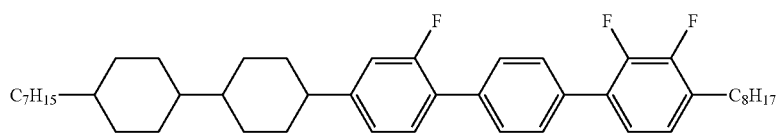 |
| 2929 | 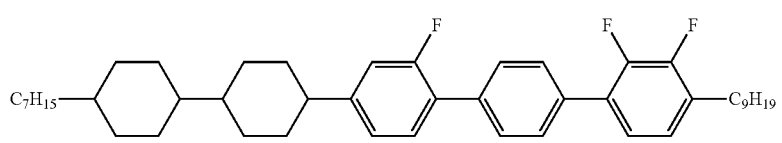 |
| 2930 | 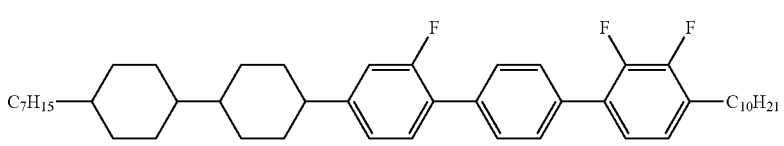 |
| 2931 | 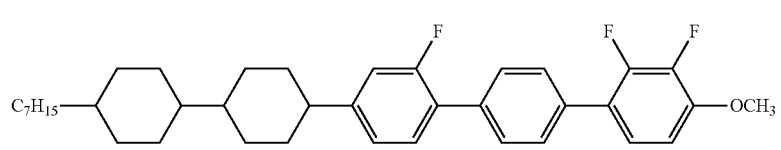 |
| 2932 | 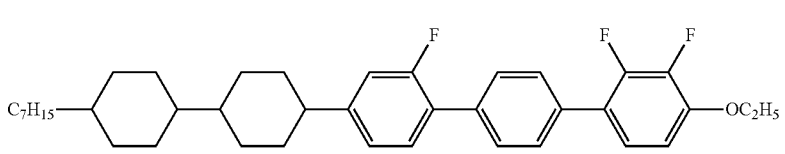 |
| 2933 | 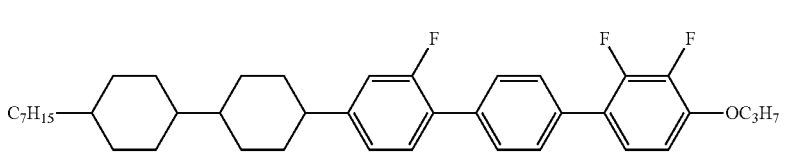 |
| 2934 | 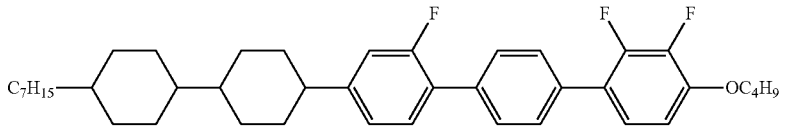 |
| 2935 |  |
| 2936 |  |
| 2937 | 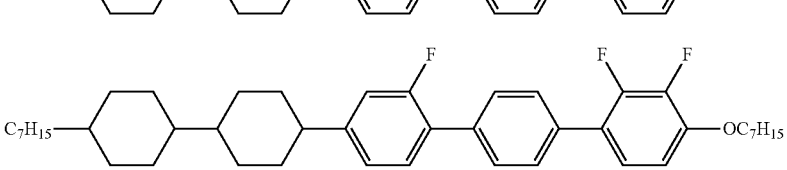 |

| No. | |
|---|---|
| 2938 | 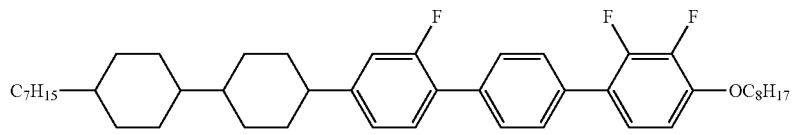 |
| 2939 | 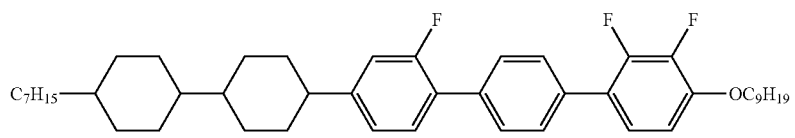 |
| 2940 | 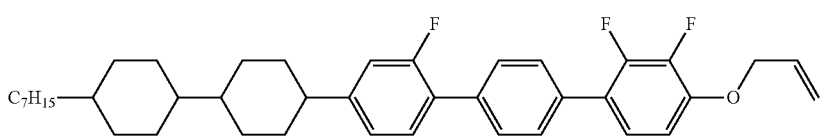 |
| 2941 | 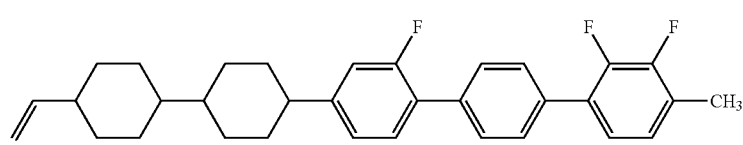 |
| 2942 | 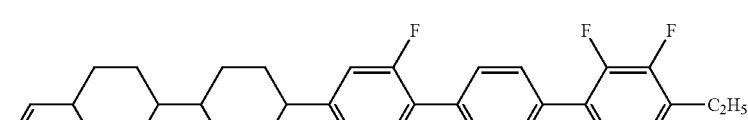 |
| 2943 | 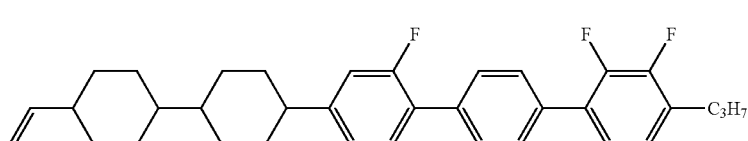 |
| 2944 | 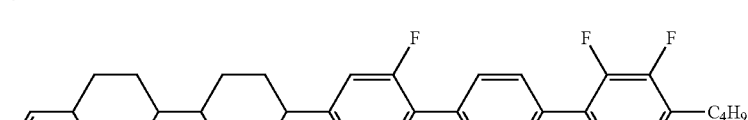 |
| 2945 | 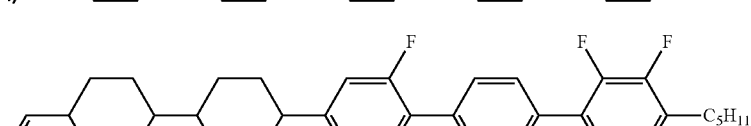 |
| 2946 | 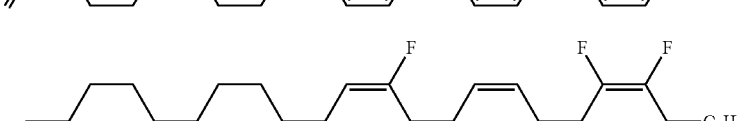 |
| 2947 | 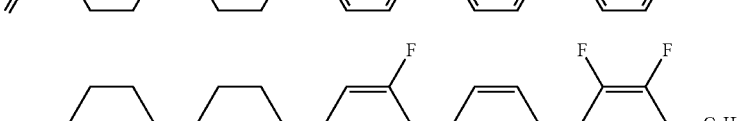 |
| 2948 | 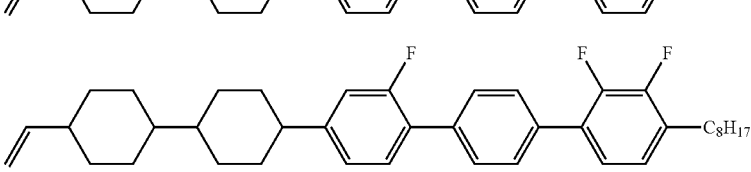 |

| No. | |
|---|---|
| 2949 | 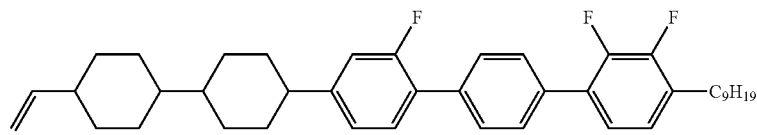 |
| 2950 | 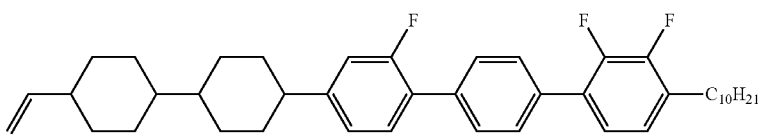 |
| 2951 | 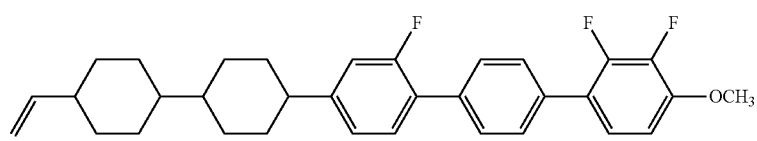 |
| 2952 | 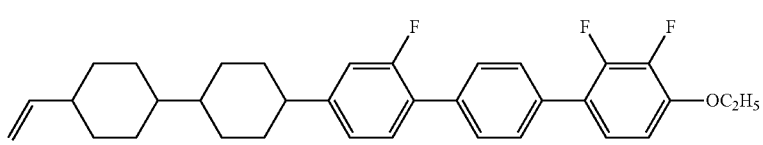 |
| 2953 | 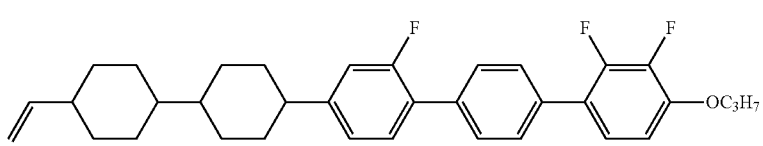 |
| 2954 | 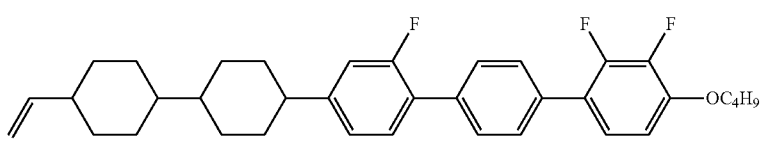 |
| 2955 | 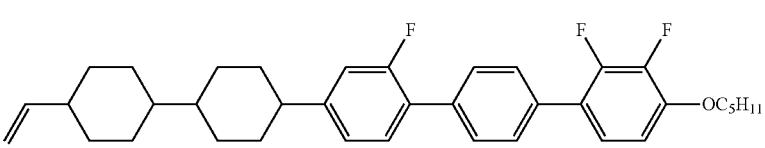 |
| 2956 | 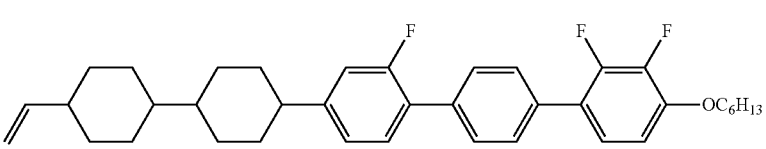 |
| 2957 | 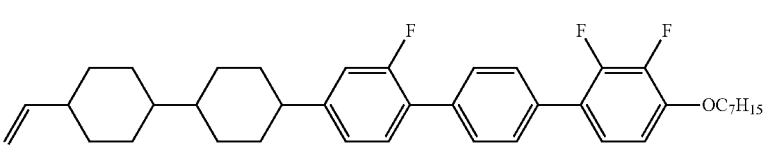 |
| 2958 | 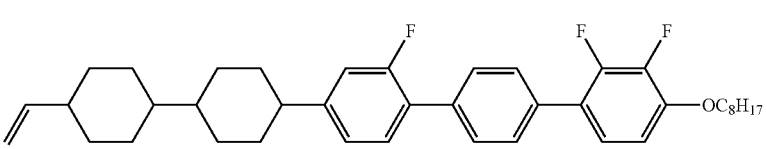 |
| 2959 | 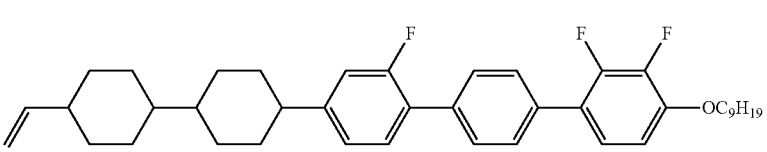 |

-continued
| No. | |
|---|---|
| 2960 | 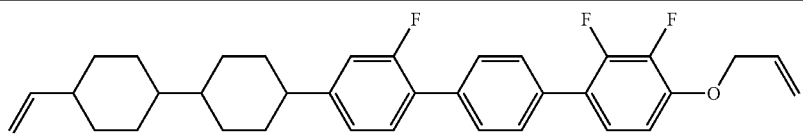 |
| 2961 | 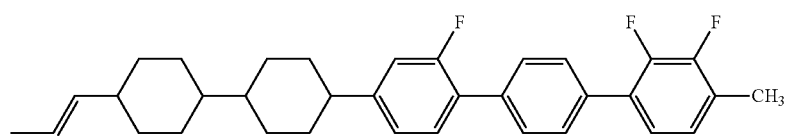 |
| 2962 | 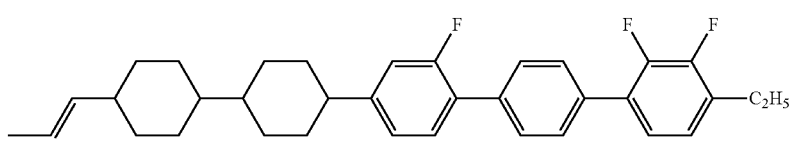 |
| 2963 | 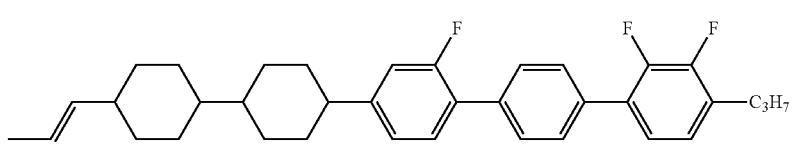 |
| 2964 | 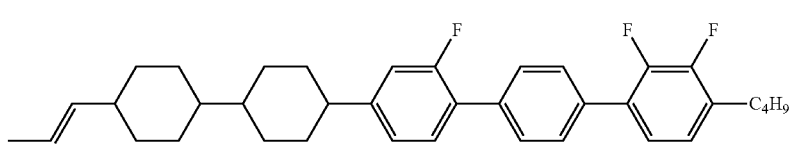 |
| 2965 | 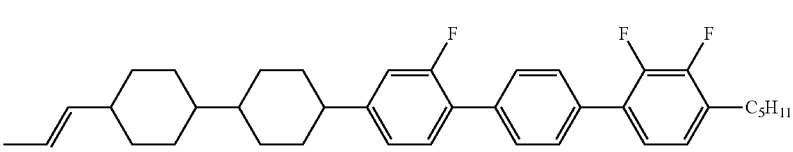 |
| 2966 | 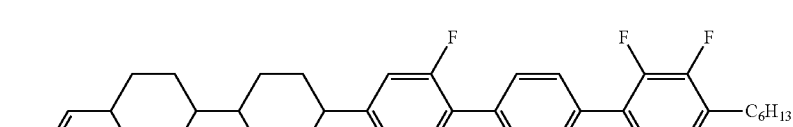 |
| 2967 | 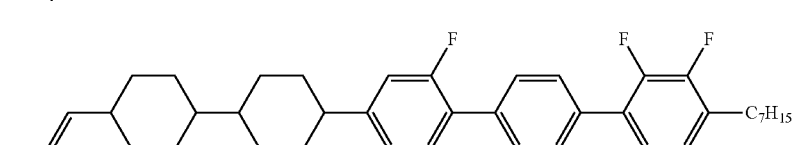 |
| 2968 | 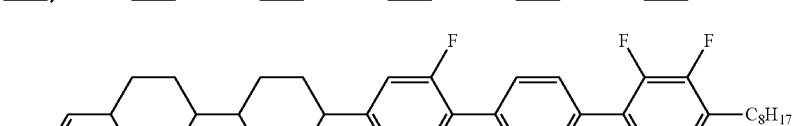 |
| 2969 | 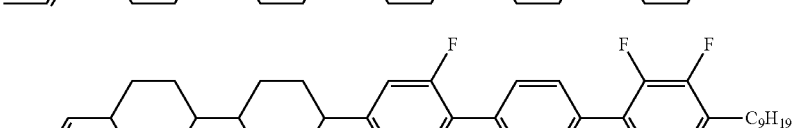 |
| 2970 | 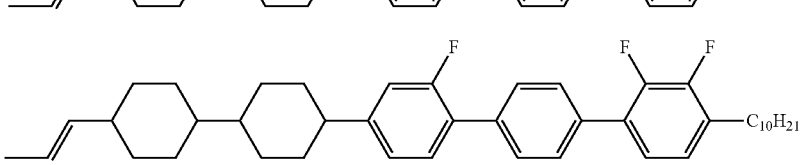 |

-continued
| No. | |
|---|---|
| 2971 | 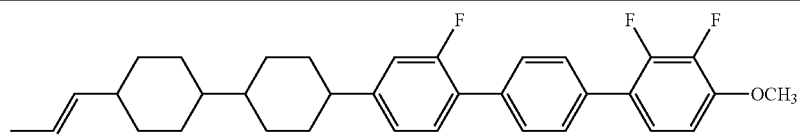 |
| 2972 | 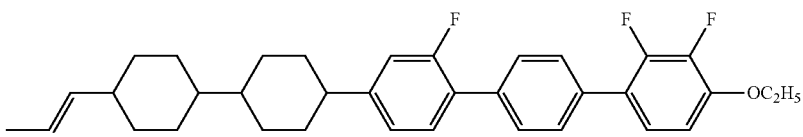 |
| 2973 | 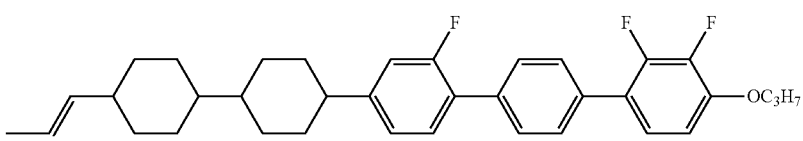 |
| 2974 | 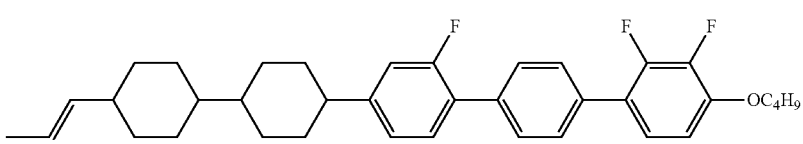 |
| 2975 | 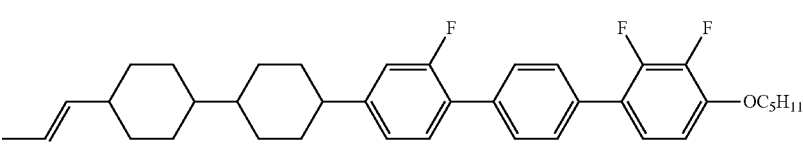 |
| 2976 | 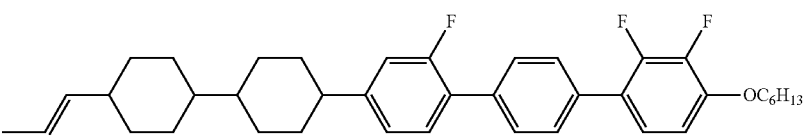 |
| 2977 | 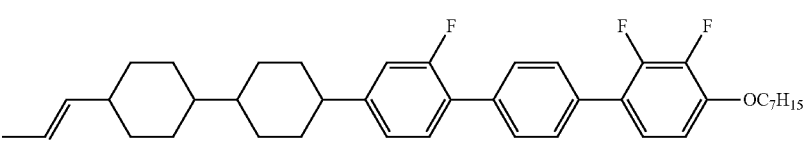 |
| 2978 | 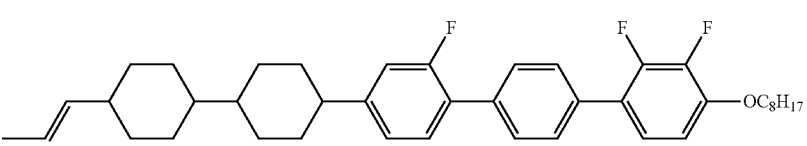 |
| 2979 | 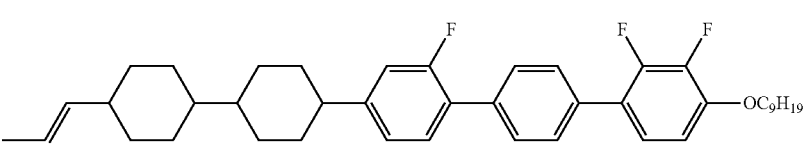 |
| 2980 | 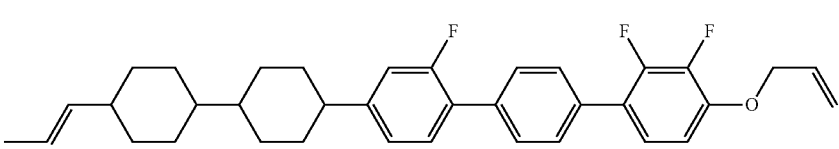 |
| 2981 | 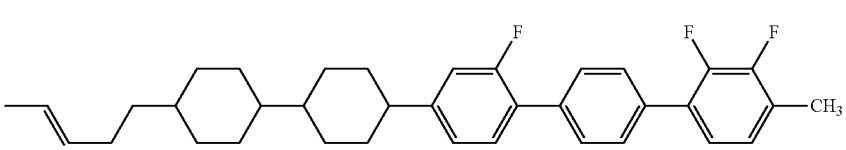 |

-continued
| No. | |
|---|---|
| 2982 | 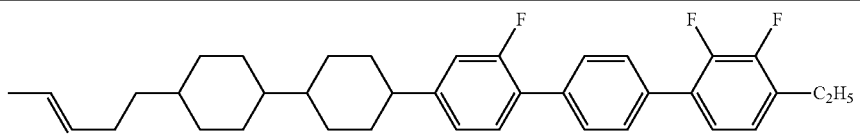 |
| 2983 | 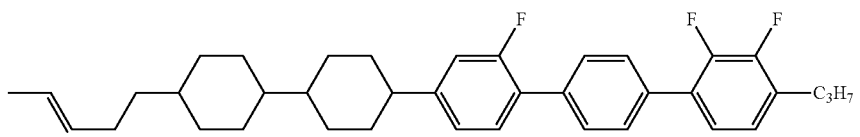 |
| 2984 | 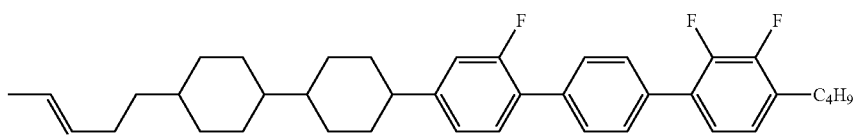 |
| 2985 | 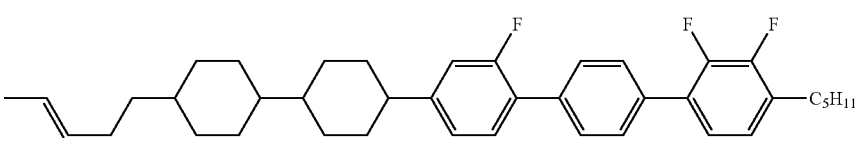 |
| 2986 | 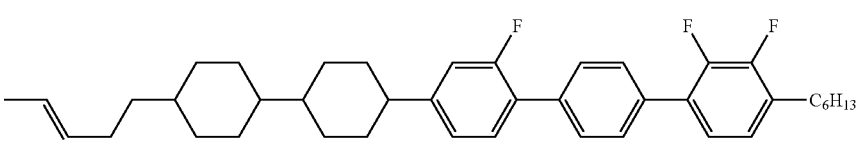 |
| 2987 | 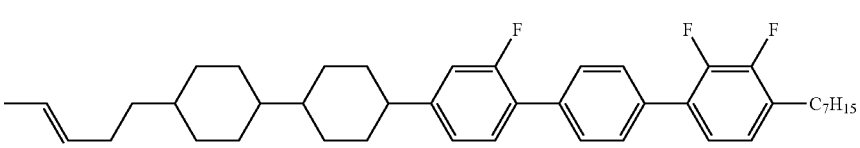 |
| 2988 | 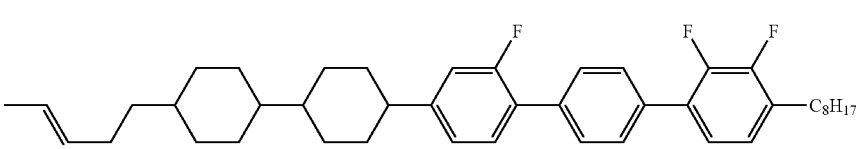 |
| 2989 | 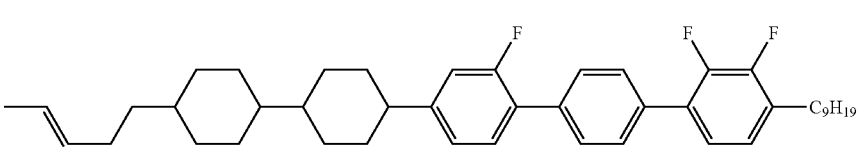 |
| 2990 | 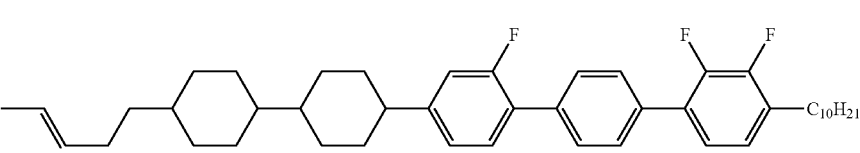 |
| 2991 | 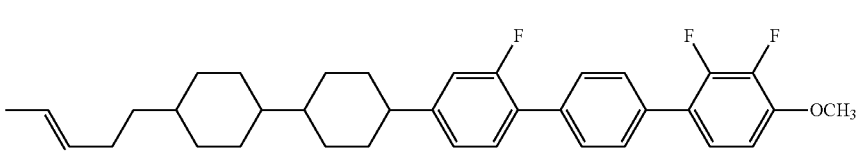 |
| 2992 | 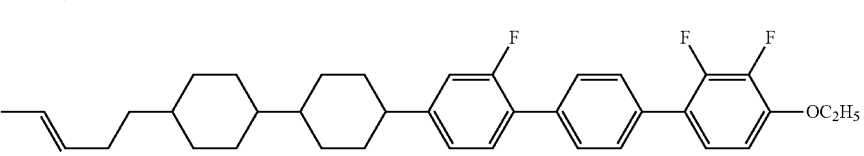 |

| No. |
|---|
| 2993 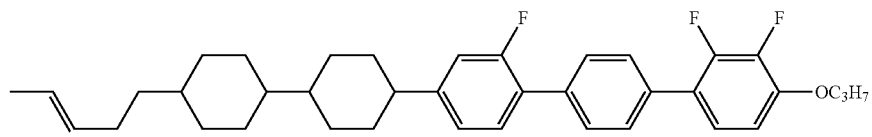 |
| 2994 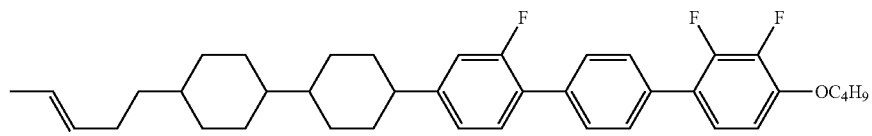 |
| 2995 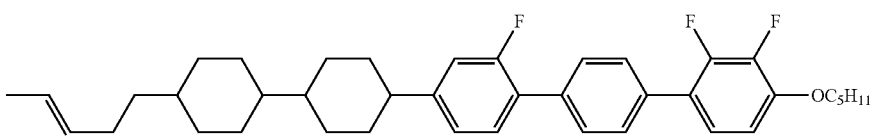 |
| 2996 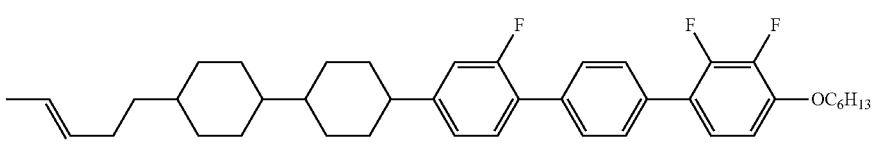 |
| 2997 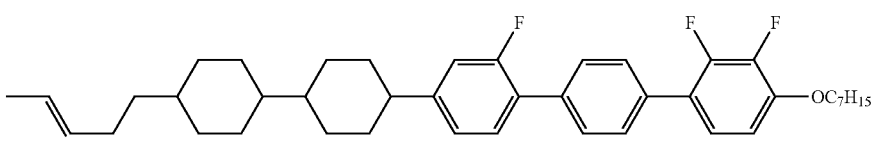 |
| 2998 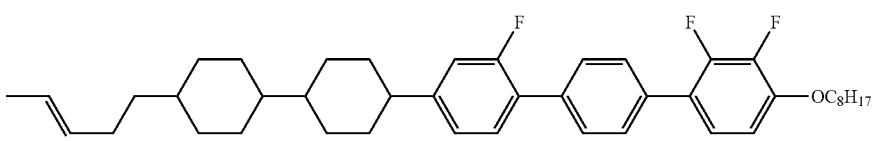 |
| 2999 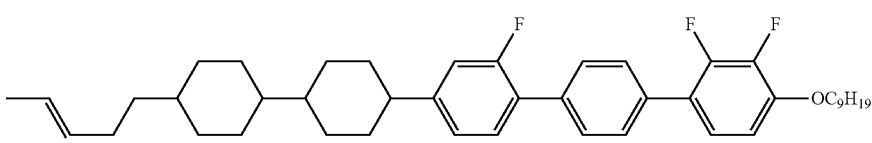 |
| 3000 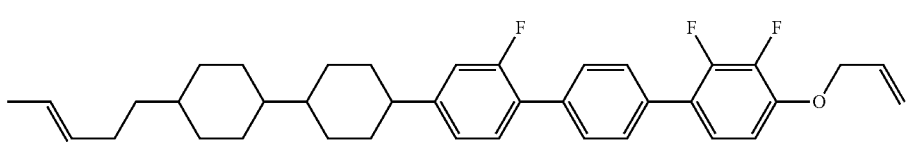 |
| 3001 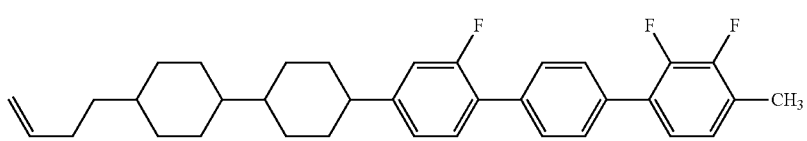 |
| 3002 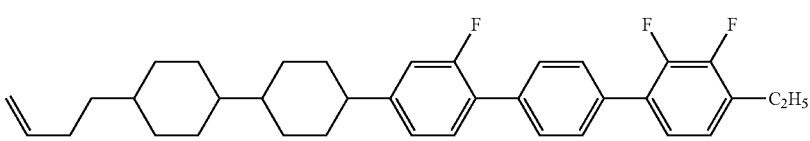 |
| 3003 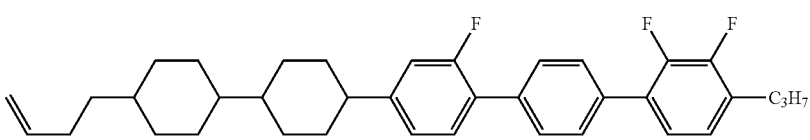 |

-continued
| No. | |
|---|---|
| 3004 | 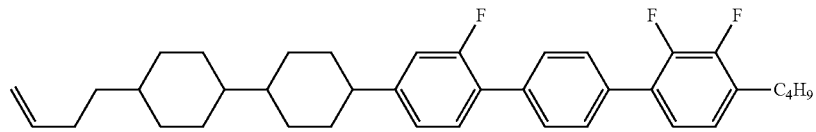 |
| 3005 | 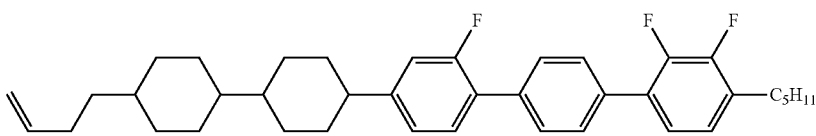 |
| 3006 | 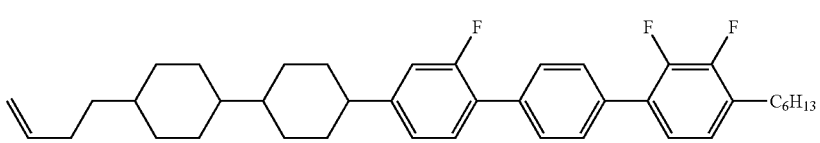 |
| 3007 | 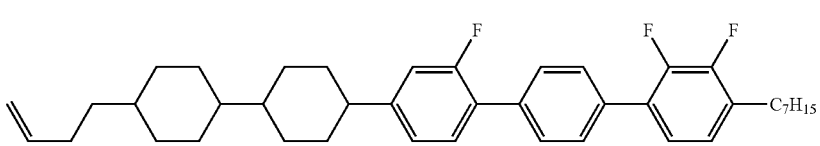 |
| 3008 | 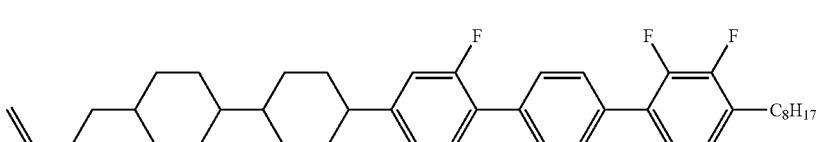 |
| 3009 | 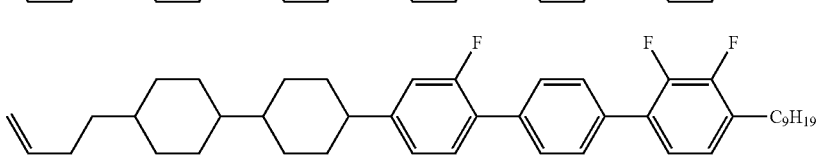 |
| 3010 | 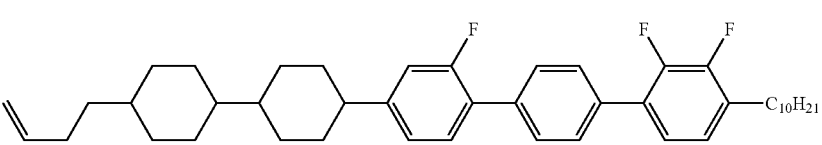 |
| 3011 | 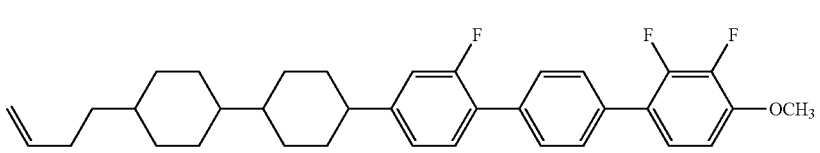 |
| 3012 | 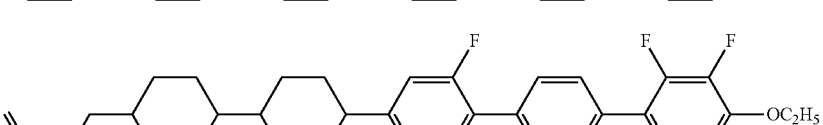 |
| 3013 | 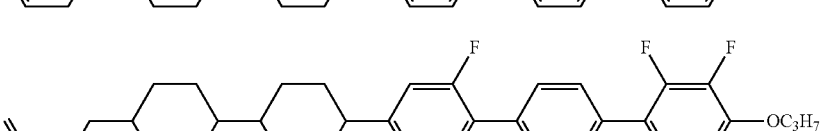 |
| 3014 |  |

-continued
| No. | |
|---|---|
| 3015 | 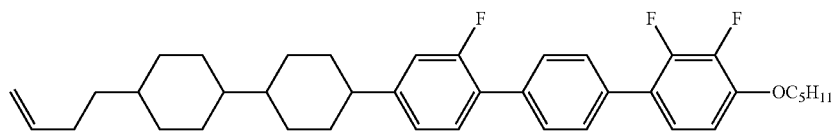 |
| 3016 | 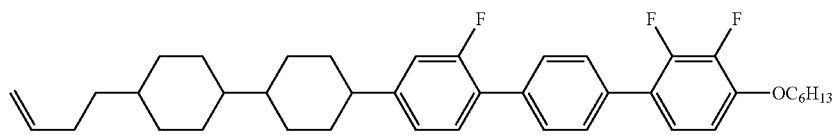 |
| 3017 | 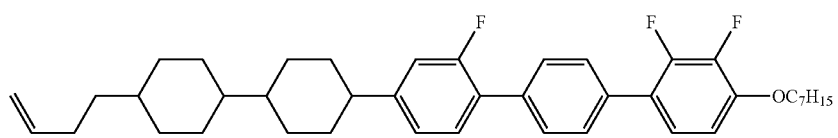 |
| 3018 | 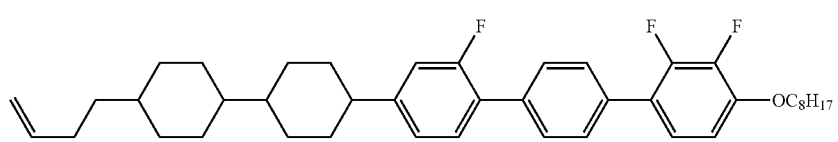 |
| 3019 | 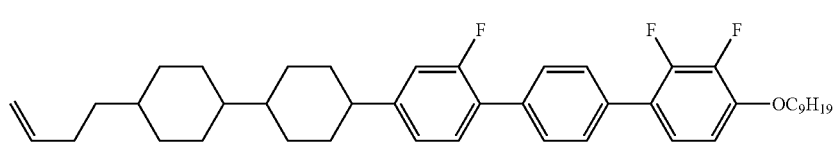 |
| 3020 | 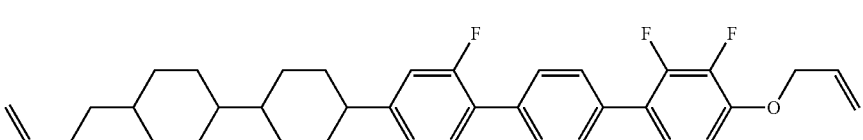 |
| 3021 | 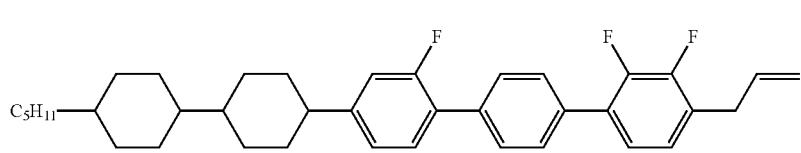 |
| 3022 | 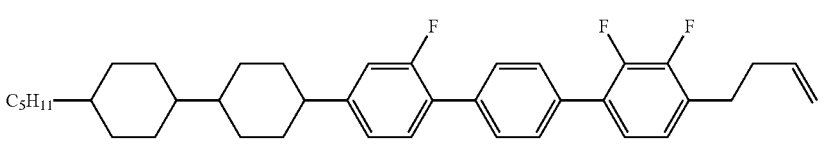 |
| 3023 | 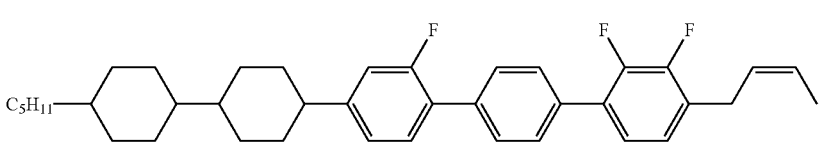 |
| 3024 | 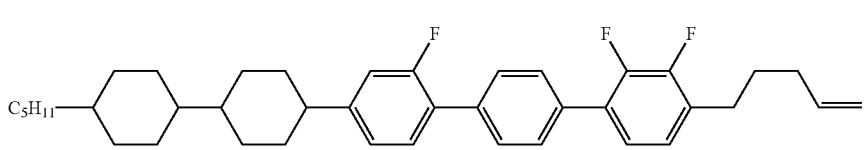 |
| 3025 | 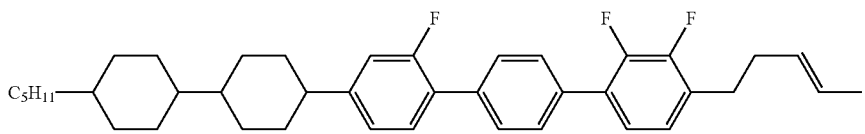 |

| No. | |
|---|---|
| 3026 | 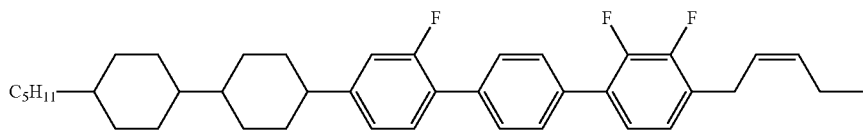 |
| 3027 | 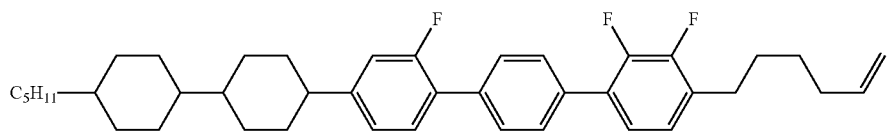 |
| 3028 | 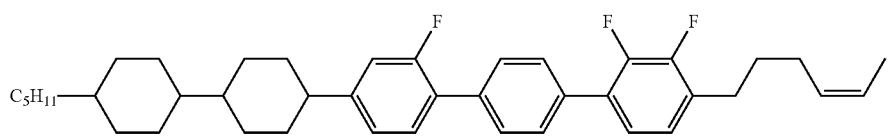 |
| 3029 | 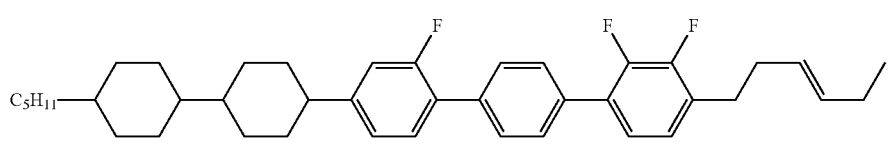 |
| 3030 | 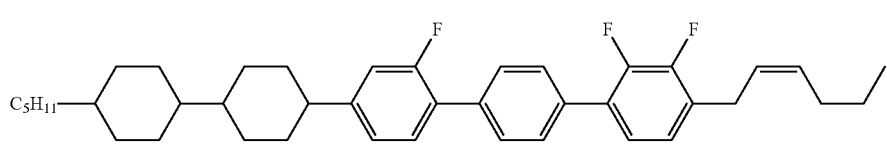 |
| 3031 | 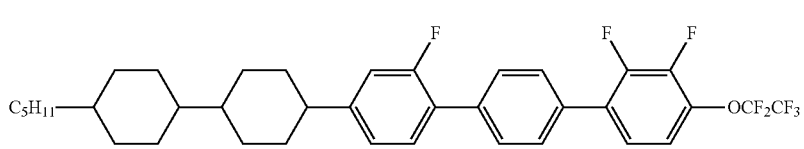 |
| 3032 | 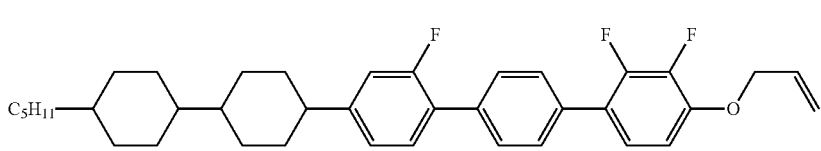 |
| 3033 | 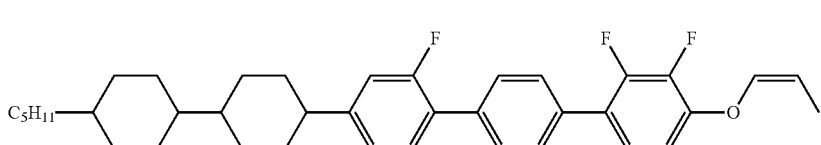 |
| 3034 | 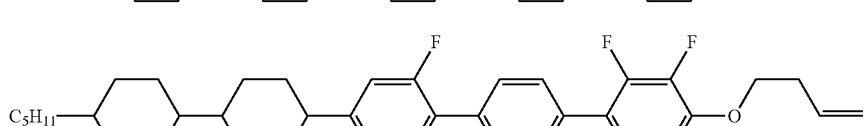 |
| 3035 | 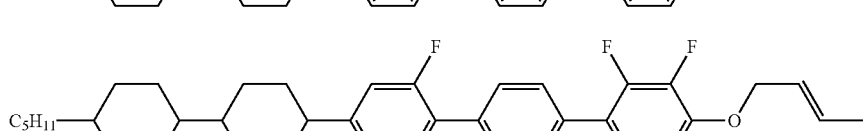 |
| 3036 | 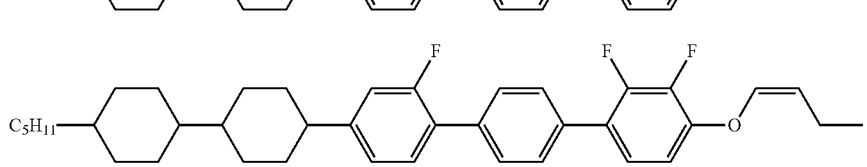 |

| No. |
|---|
| 3037 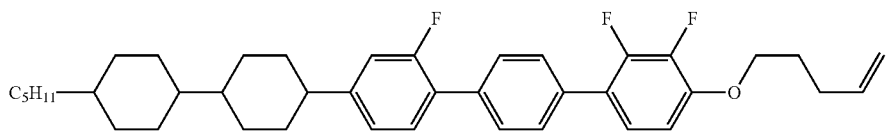 |
| 3038 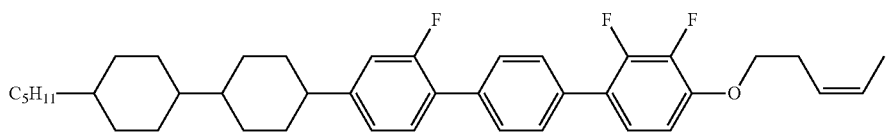 |
| 3039 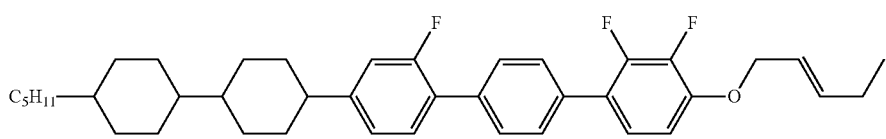 |
| 3040 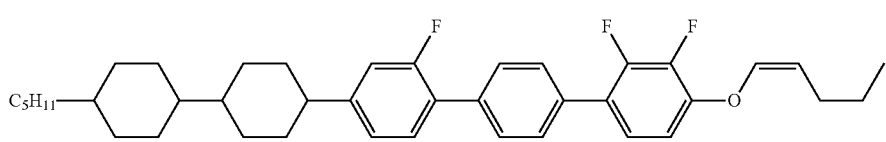 |
| 3041 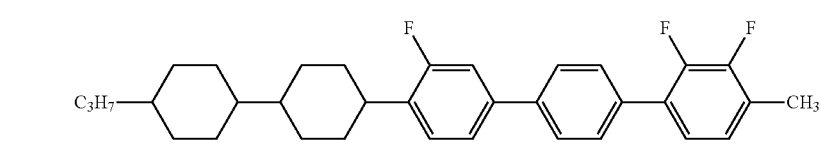 |
| 3042 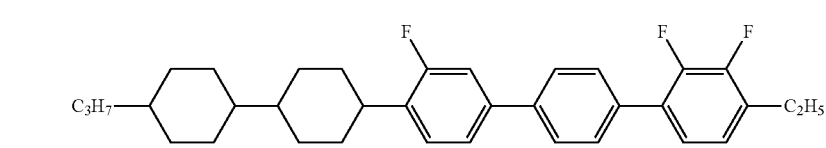 |
| 3043 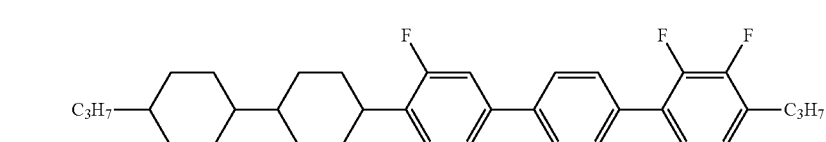 |
| 3044 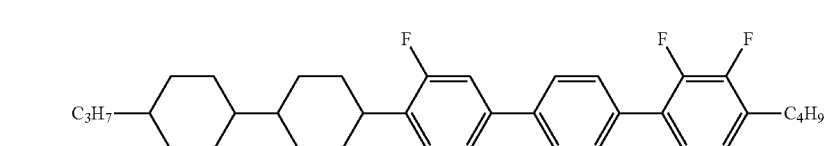 |
| 3045 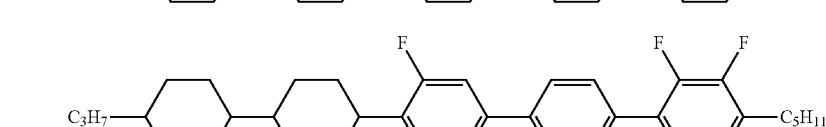 |
| 3046 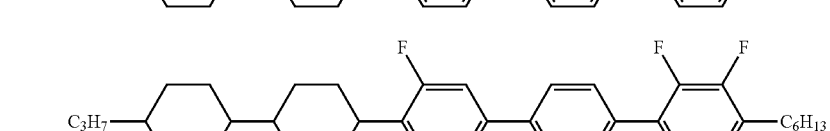 |
| 3047 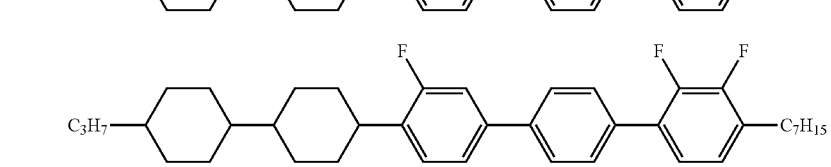 |

| No. | |
|---|---|
| 3048 | 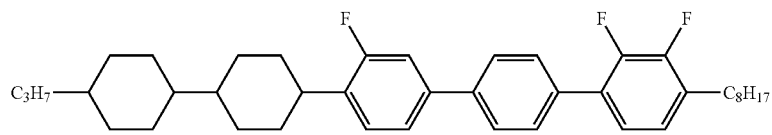 |
| 3049 | 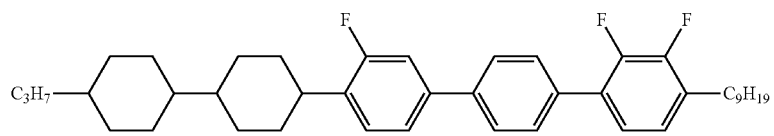 |
| 3050 | 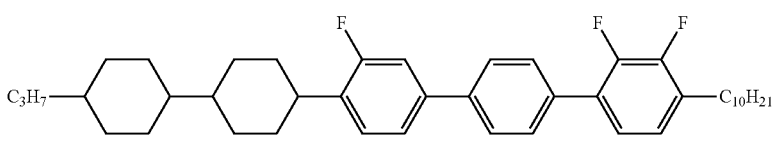 |
| 3051 | 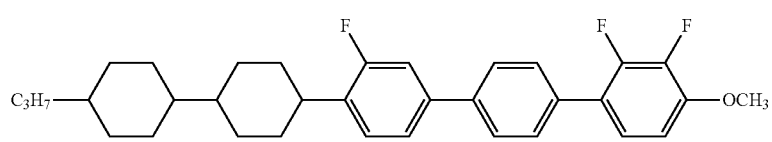 |
| 3052 | 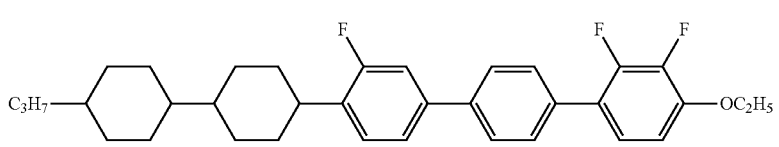 |
| 3053 | 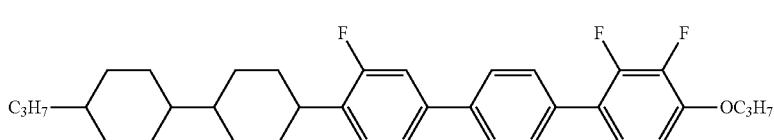 |
| 3054 | 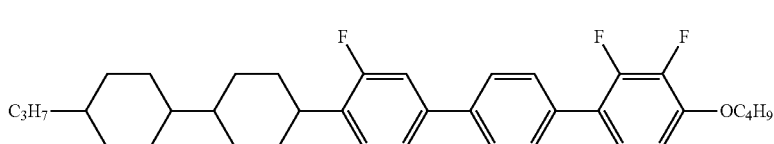 |
| 3055 | 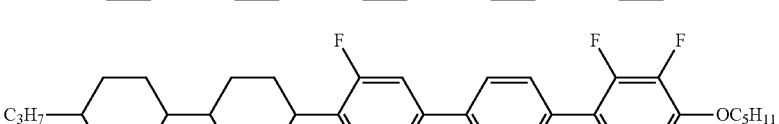 |
| 3056 | 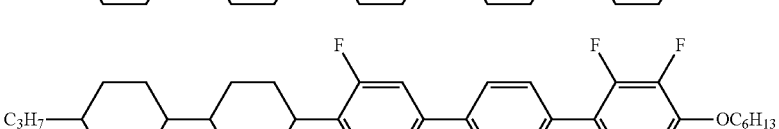 |
| 3057 |  |
| 3058 | 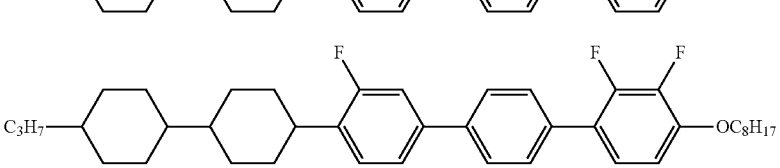 |

| No. | |
|---|---|
| 3059 | 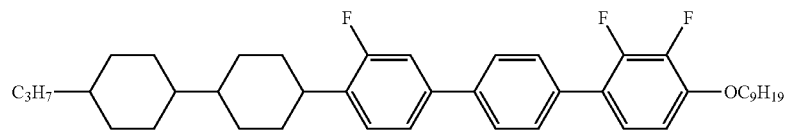 |
| 3060 | 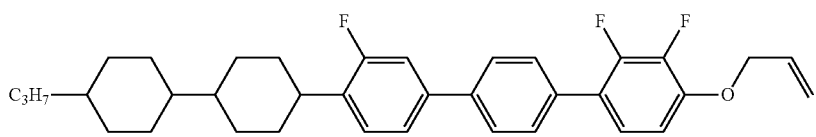 |
| 3061 | 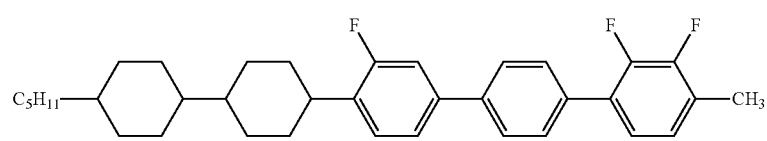 |
| 3062 | 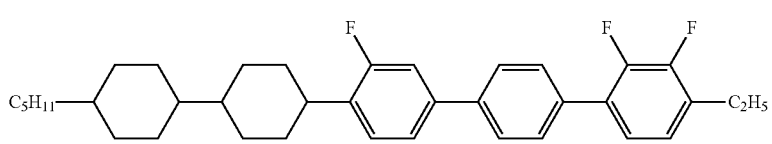 |
| 3063 | 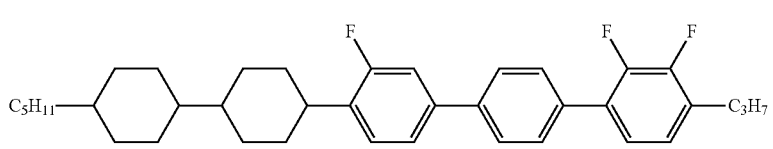 |
| 3064 | 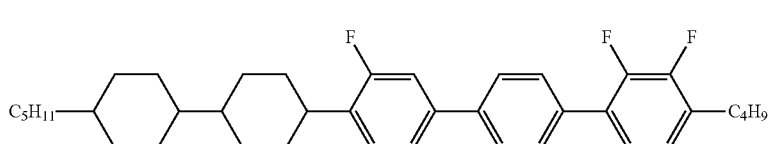 |
| 3065 | 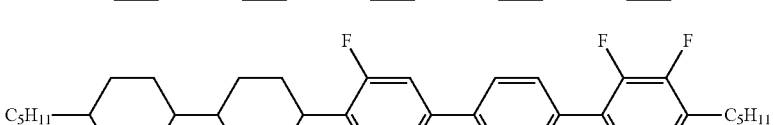 |
| 3066 | 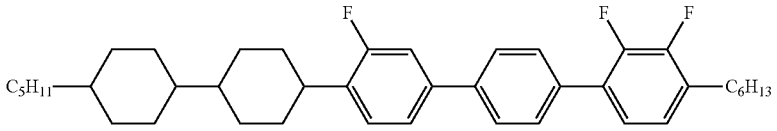 |
| 3067 |  |
| 3068 | 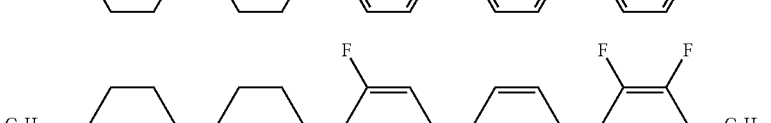 |
| 3069 | 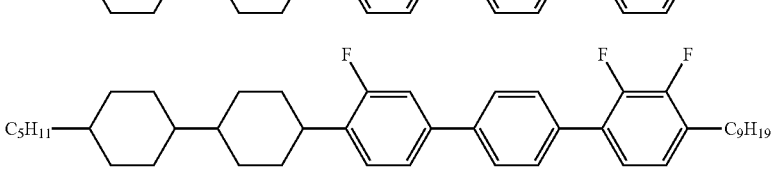 |

| No. | |
|---|---|
| 3070 | 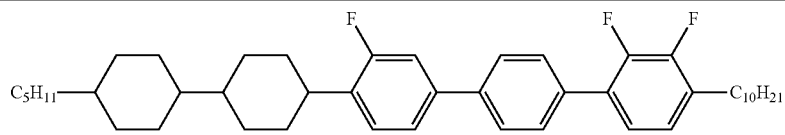 |
| 3071 | 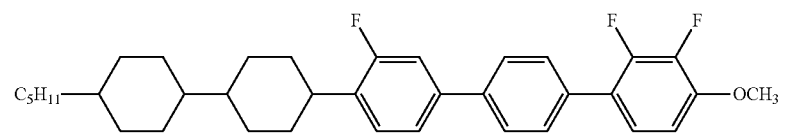 |
| 3072 | 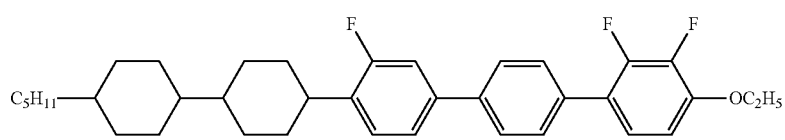 |
| 3073 | 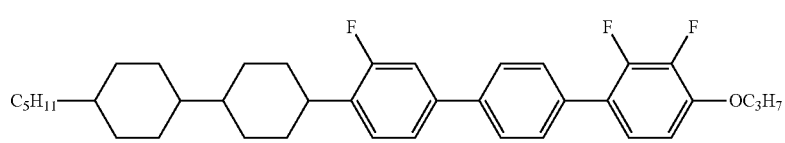 |
| 3074 | 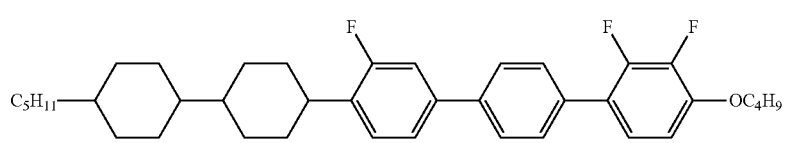 |
| 3075 | 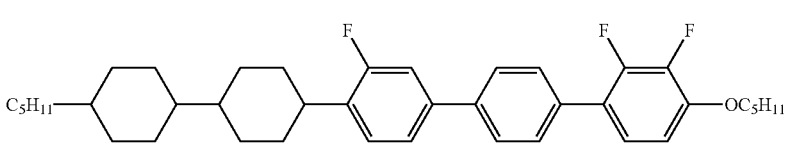 |
| 3076 | 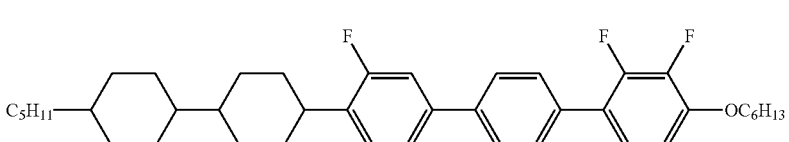 |
| 3077 | 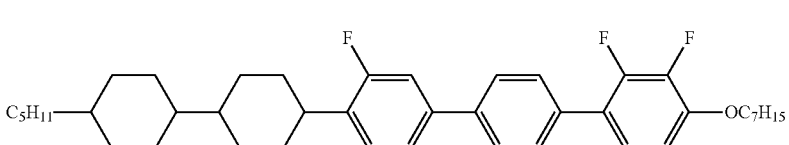 |
| 3078 | 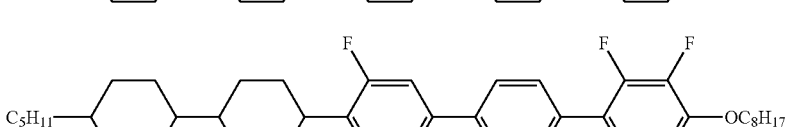 |
| 3079 | 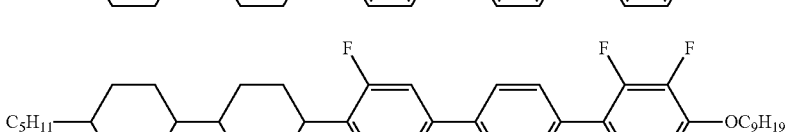 |
| 3080 | 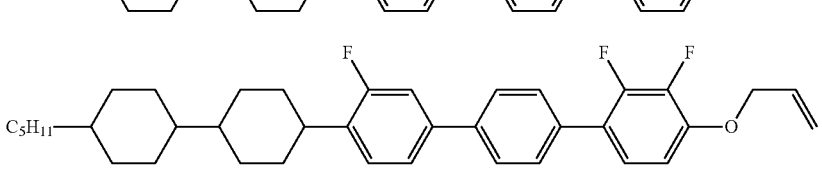 |

-continued
| No. | |
|---|---|
| 3081 | 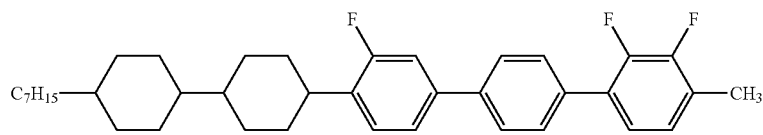 |
| 3082 | 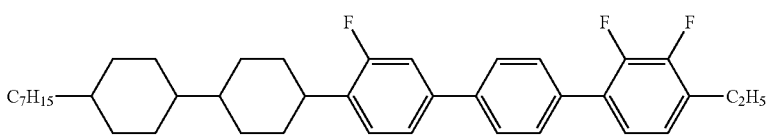 |
| 3083 | 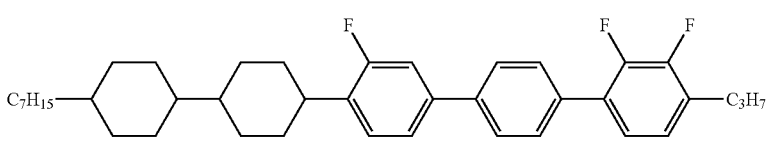 |
| 3084 | 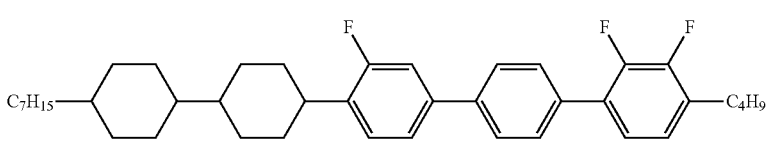 |
| 3085 | 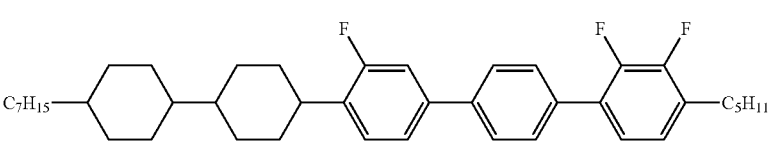 |
| 3086 | 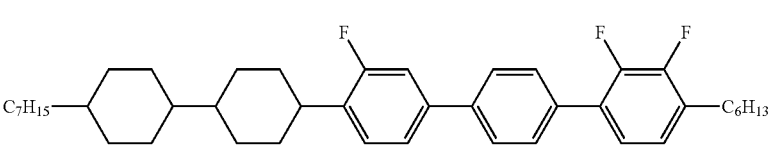 |
| 3087 | 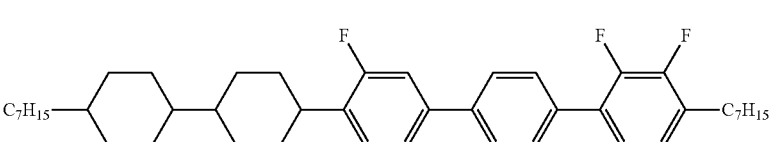 |
| 3088 | 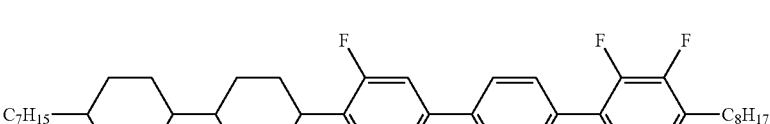 |
| 3089 | 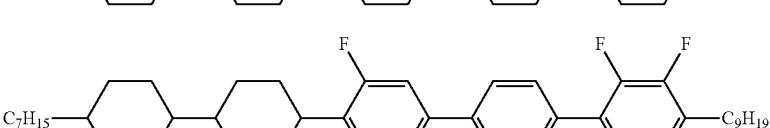 |
| 3090 | 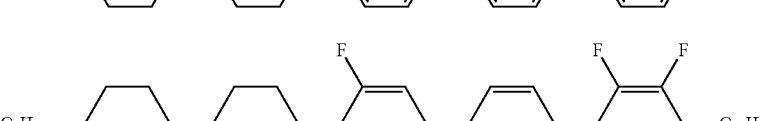 |
| 3091 | 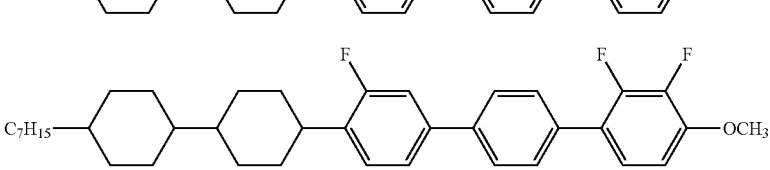 |

-continued
| No. | |
|---|---|
| 3092 | 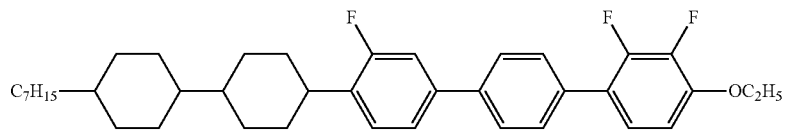 |
| 3093 | 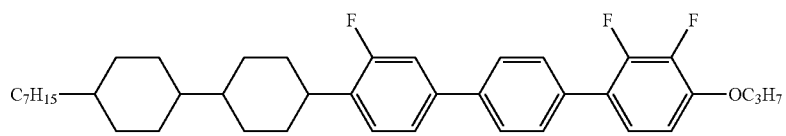 |
| 3094 | 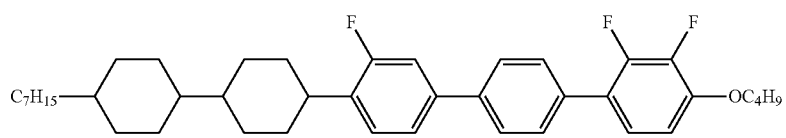 |
| 3095 | 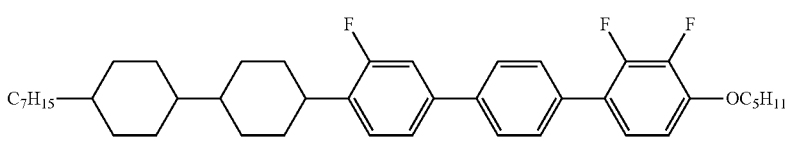 |
| 3096 | 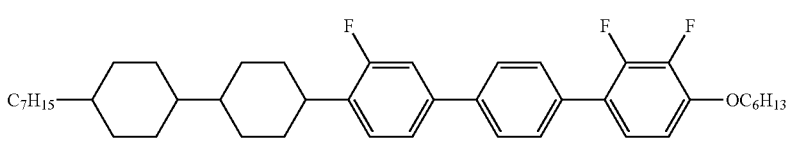 |
| 3097 | 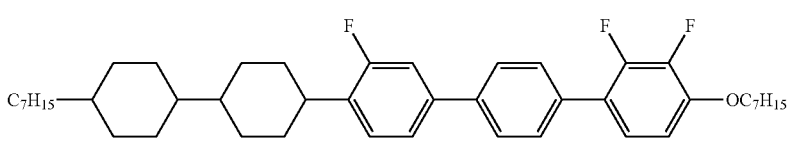 |
| 3098 | 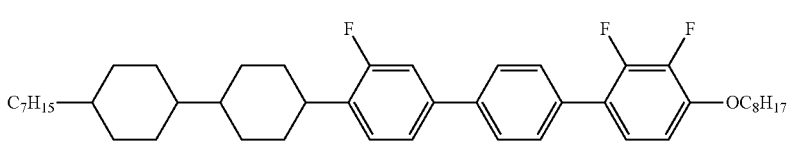 |
| 3099 | 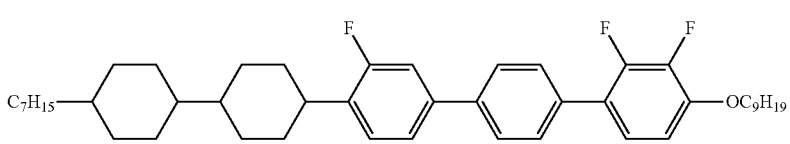 |
| 3100 | 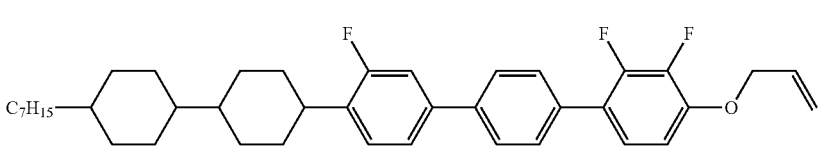 |
| 3101 | 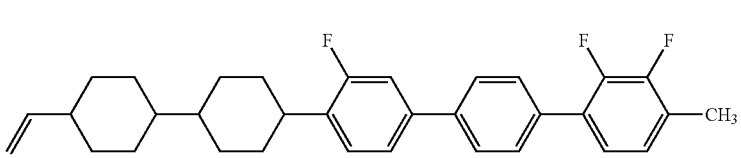 |
| 3102 | 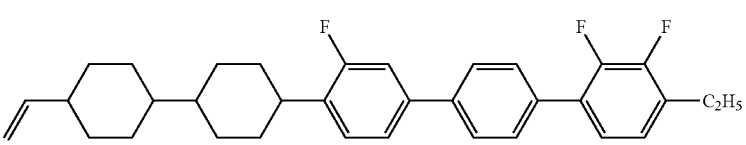 |

| No. | |
|---|---|
| 3103 | 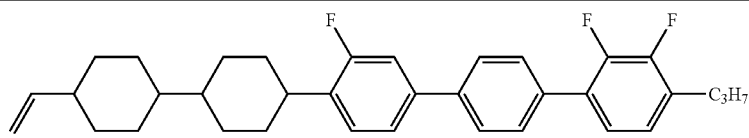 |
| 3104 | 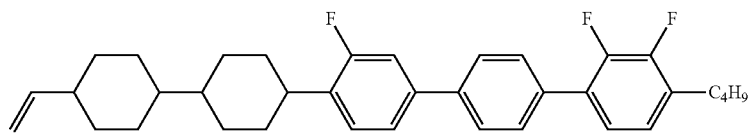 |
| 3105 | 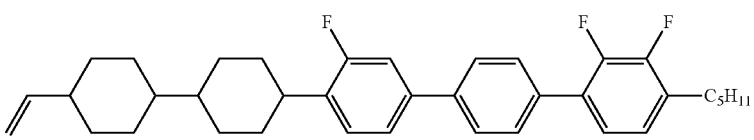 |
| 3106 | 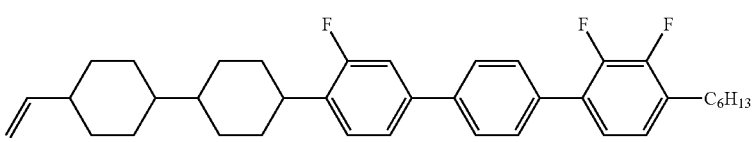 |
| 3107 | 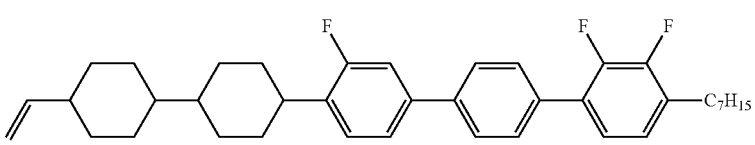 |
| 3108 | 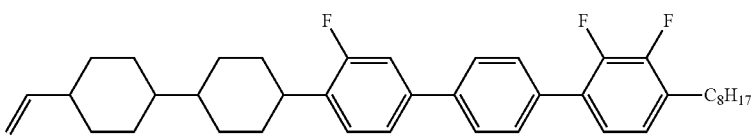 |
| 3109 | 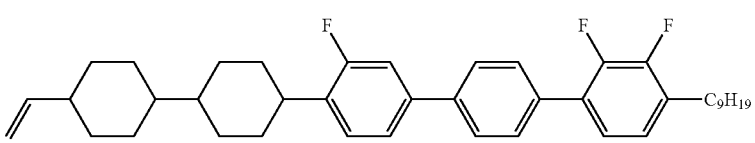 |
| 3110 | 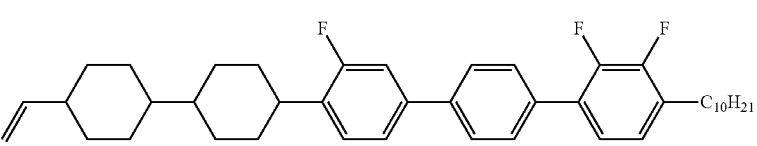 |
| 3111 | 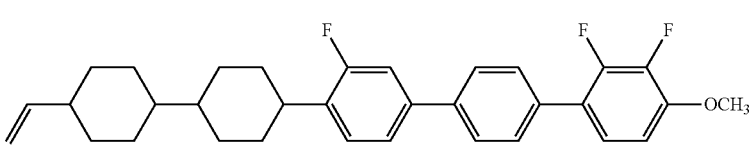 |
| 3112 | 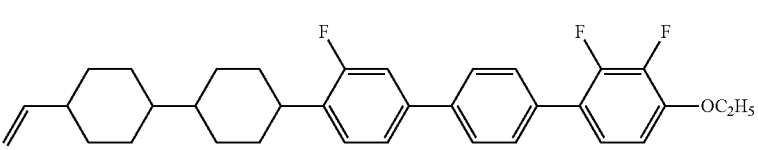 |
| 3113 | 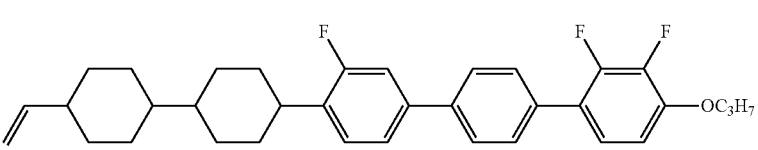 |

-continued
| No. | |
|---|---|
| 3114 | 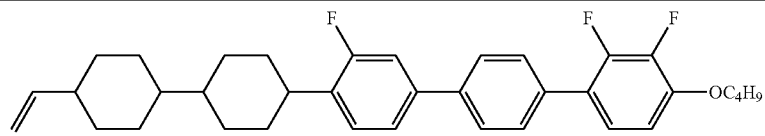 OC₄H₉ |
| 3115 | 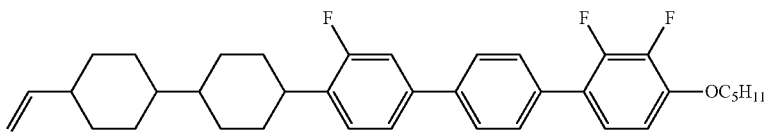 OC₅H₁₁ |
| 3116 | 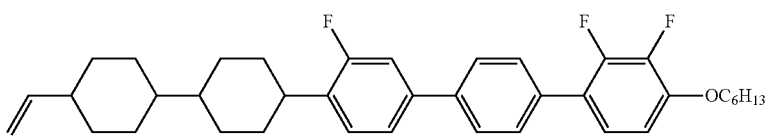 OC₆H₁₃ |
| 3117 | 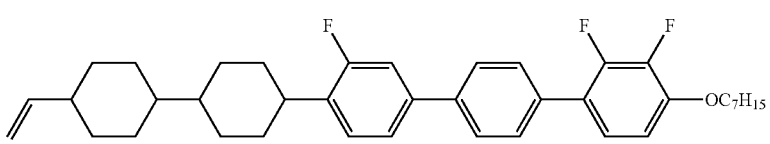 OC₇H₁₅ |
| 3118 | 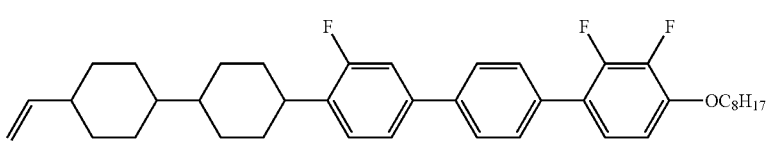 OC₈H₁₇ |
| 3119 | 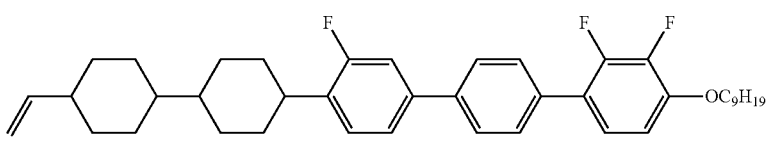 OC₉H₁₉ |
| 3120 | 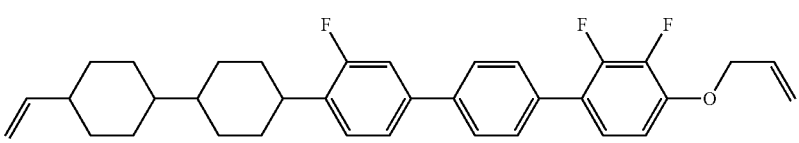 |
| 3121 | 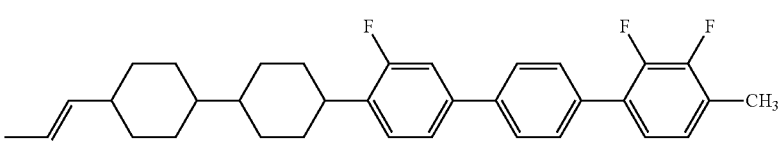 CH₃ |
| 3122 | 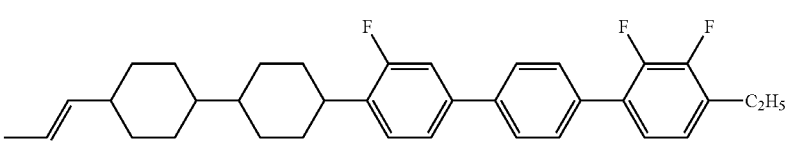 C₂H₅ |
| 3123 | 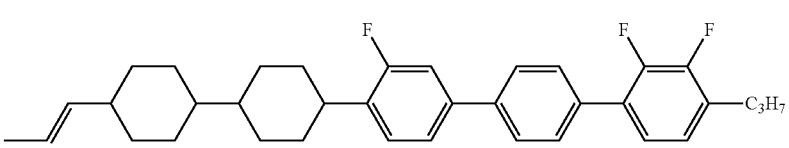 C₃H₇ |
| 3124 | 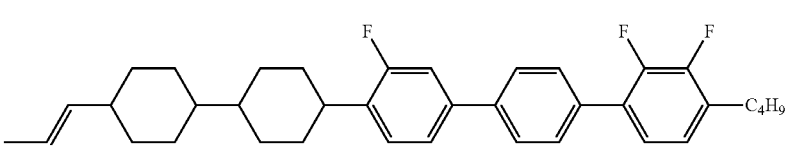 C₄H₉ |

| No. | |
|---|---|
| 3125 | 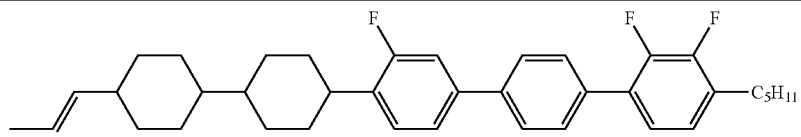 |
| 3126 | 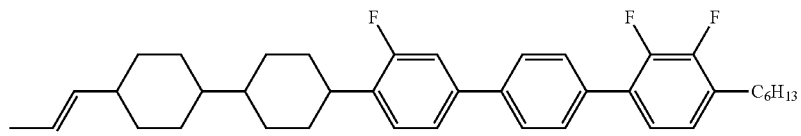 |
| 3127 | 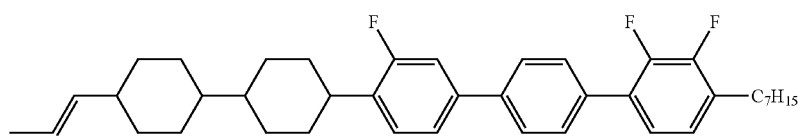 |
| 3128 | 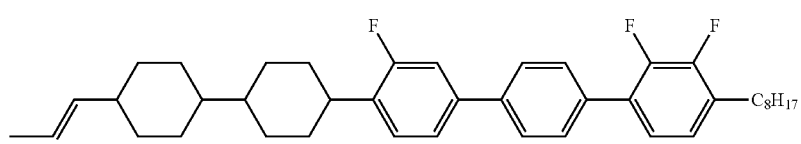 |
| 3129 | 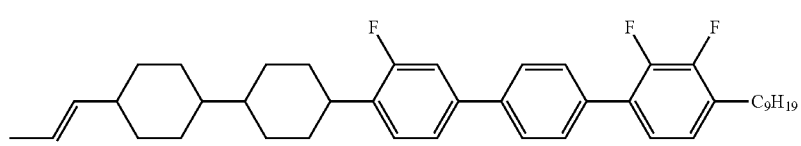 |
| 3130 | 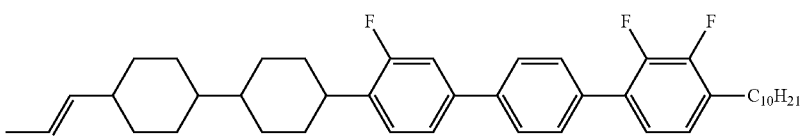 |
| 3131 | 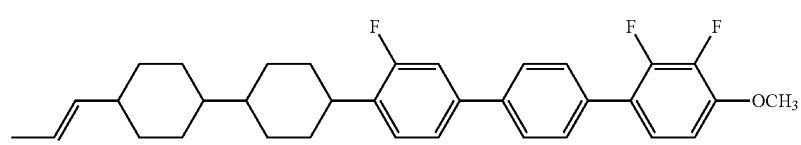 |
| 3132 | 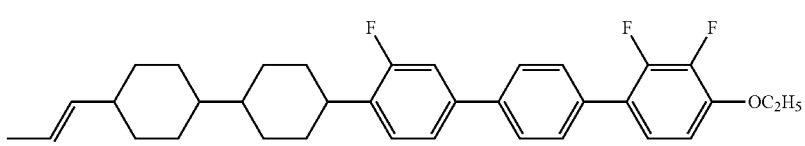 |
| 3133 | 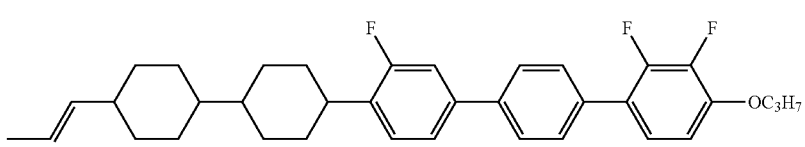 |
| 3134 | 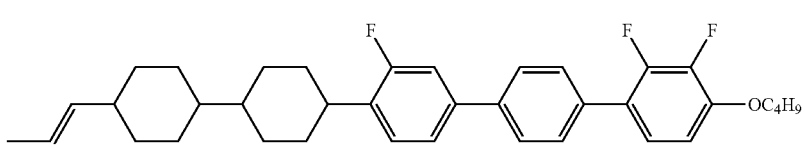 |
| 3135 | 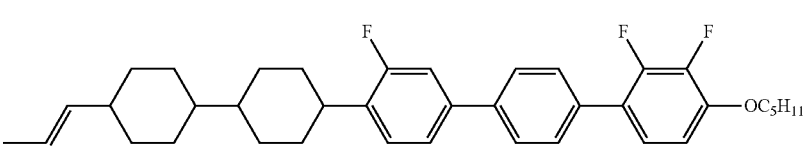 |

-continued
| No. | |
|---|---|
| 3136 | 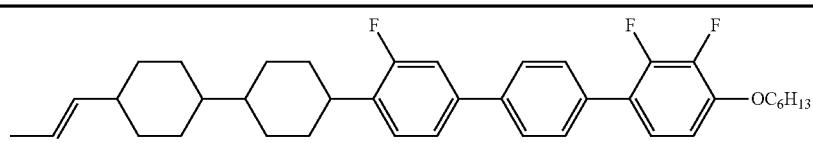 |
| 3137 | 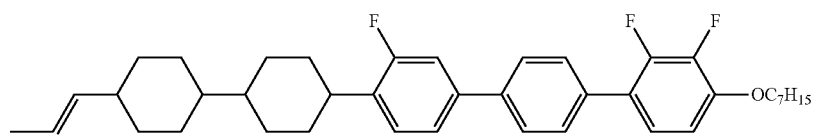 |
| 3138 | 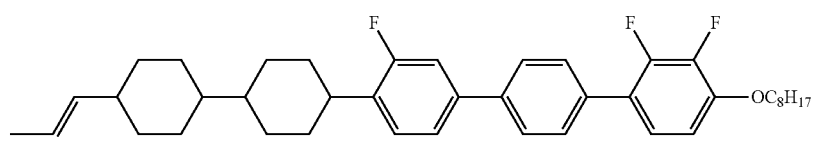 |
| 3139 |  |
| 3140 | 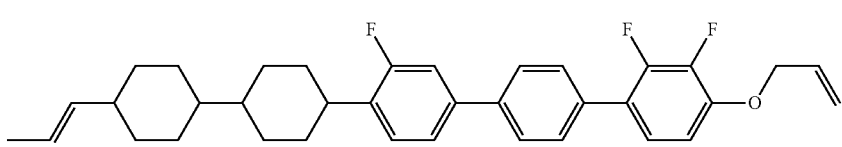 |
| 3141 | 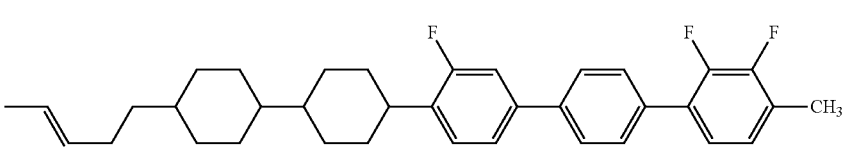 |
| 3142 | 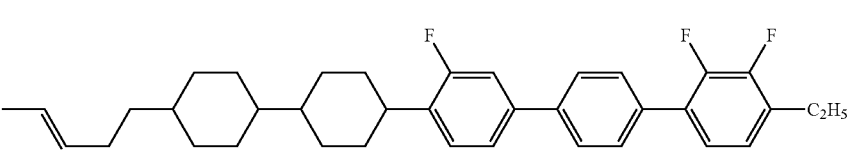 |
| 3143 | 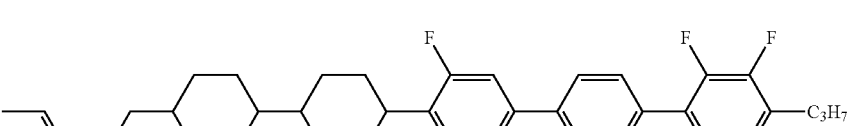 |
| 3144 | 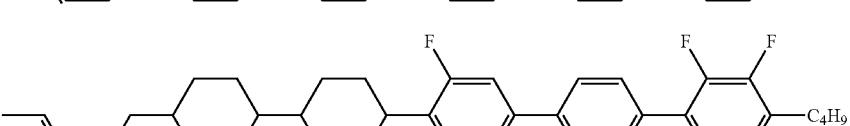 |
| 3145 | 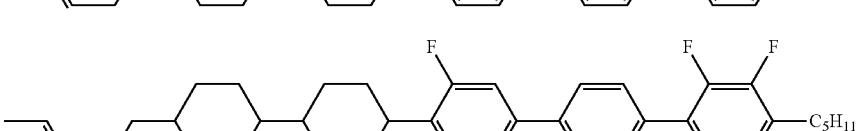 |
| 3146 | 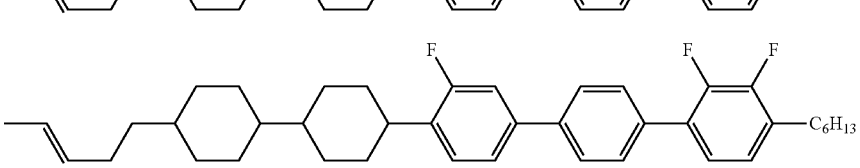 |

| No. | |
|---|---|
| 3147 | 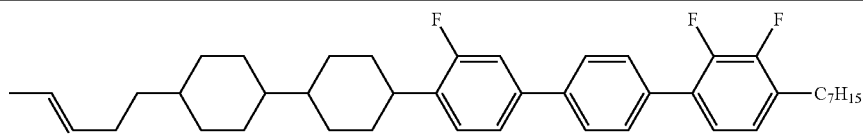 |
| 3148 | 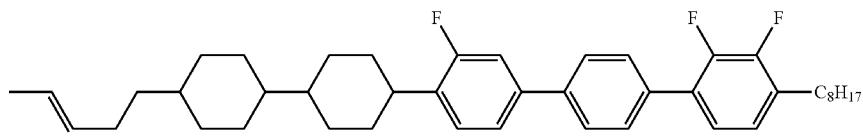 |
| 3149 | 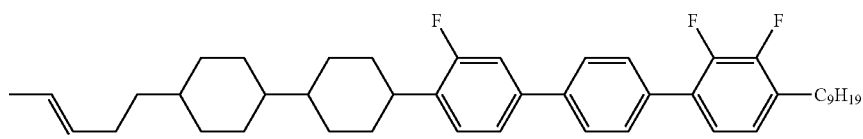 |
| 3150 | 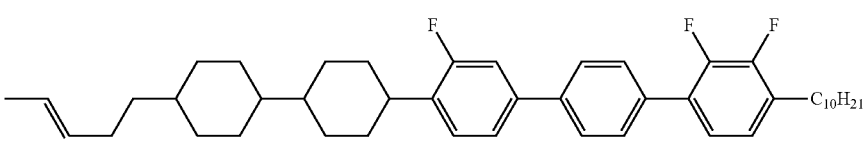 |
| 3151 | 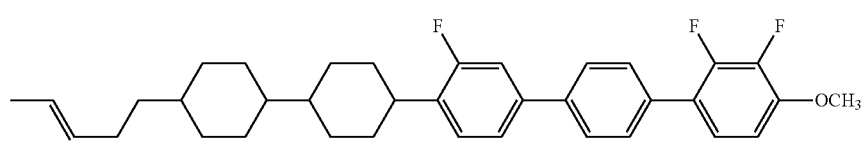 |
| 3152 | 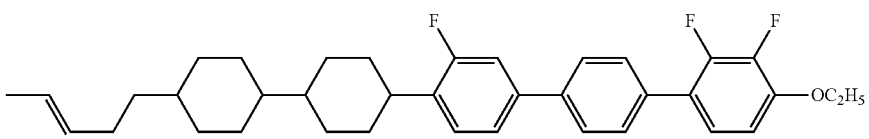 |
| 3153 | 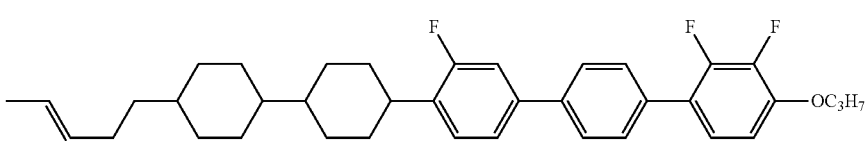 |
| 3154 | 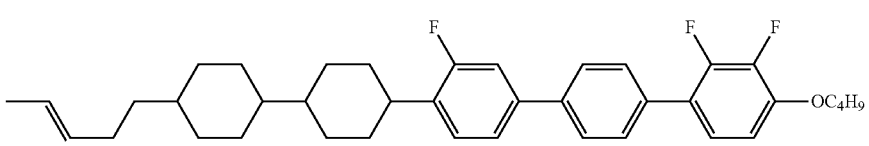 |
| 3155 | 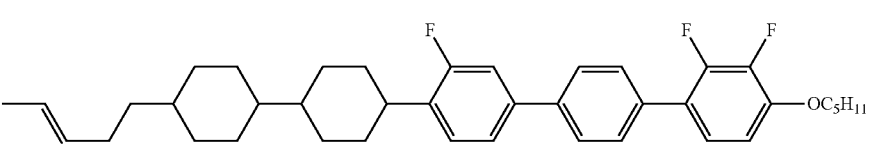 |
| 3156 | 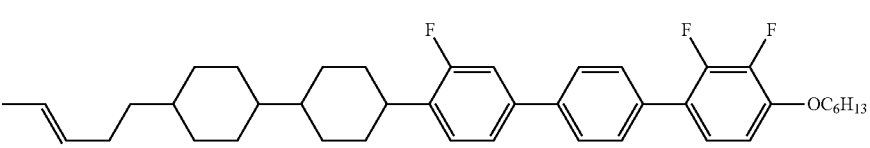 |
| 3157 | 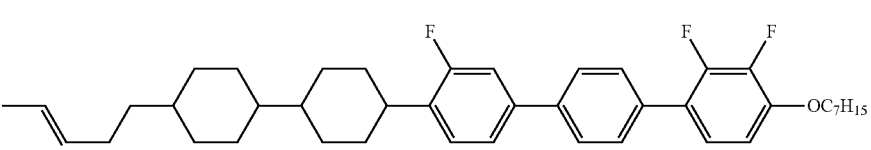 |

| No. | |
|---|---|
| 3158 | 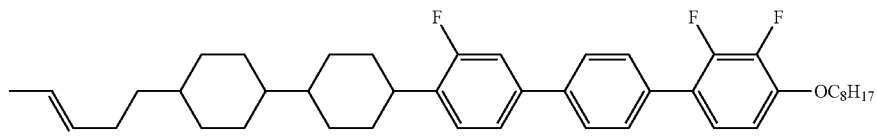 |
| 3159 | 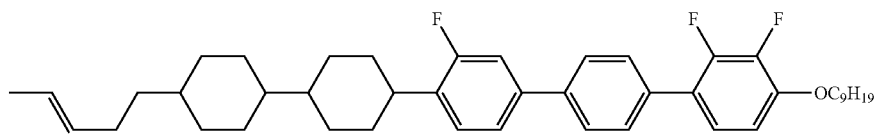 |
| 3160 | 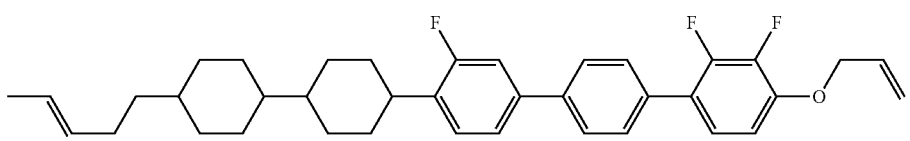 |
| 3161 | 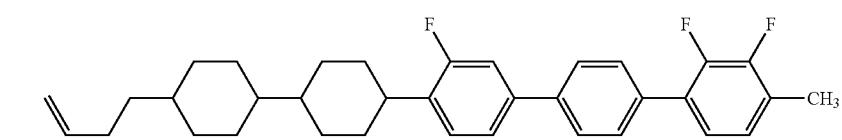 |
| 3162 | 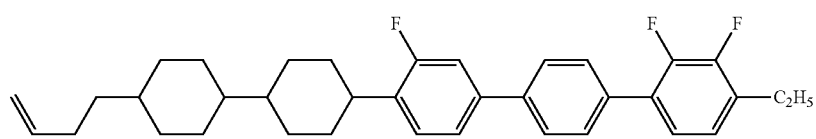 |
| 3163 | 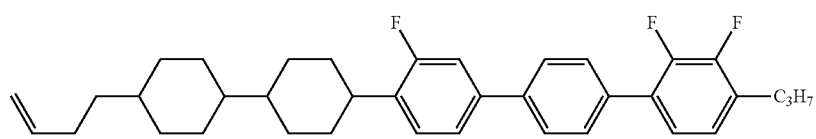 |
| 3164 | 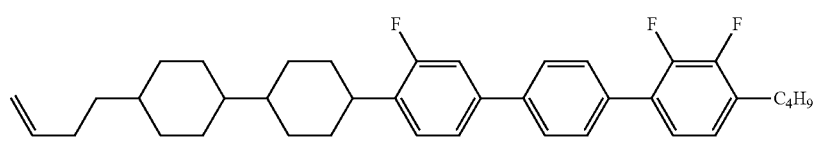 |
| 3165 | 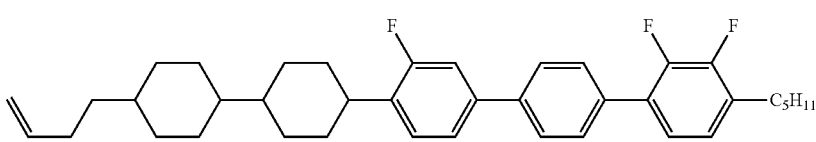 |
| 3166 | 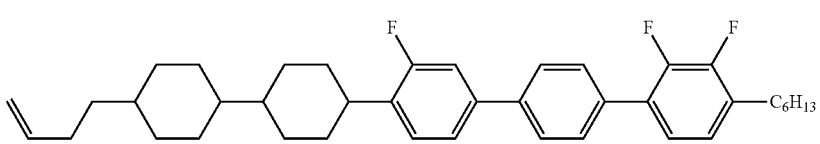 |
| 3167 | 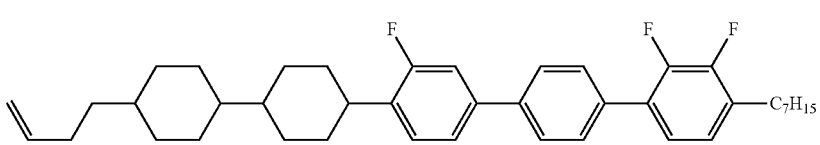 |
| 3168 | 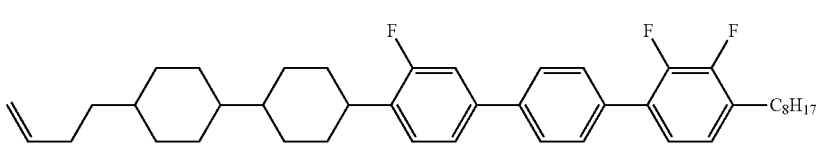 |

| No. |
|---|
| 3169 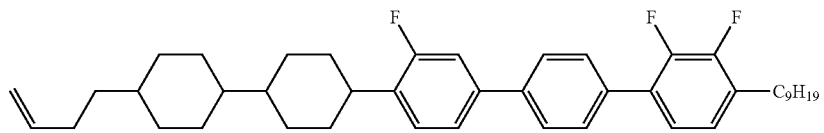 |
| 3170 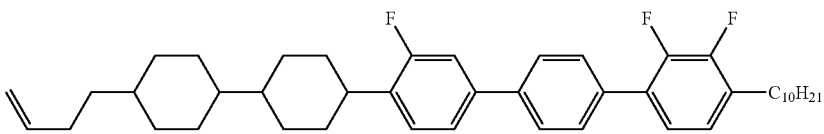 |
| 3171 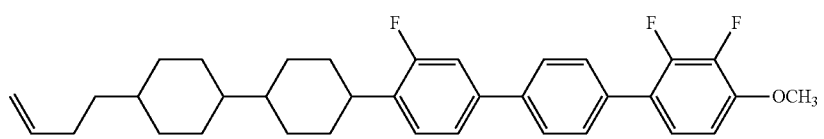 |
| 3172 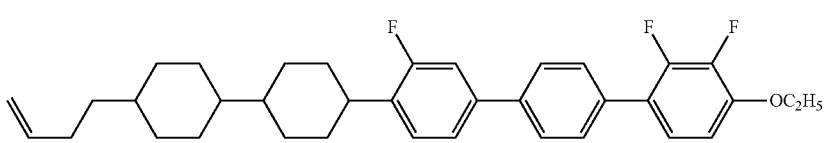 |
| 3173 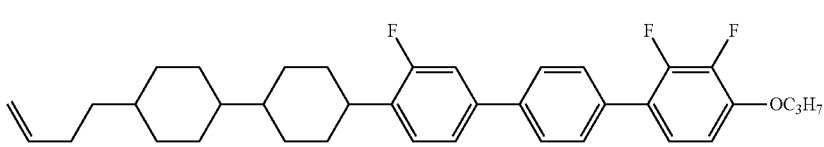 |
| 3174 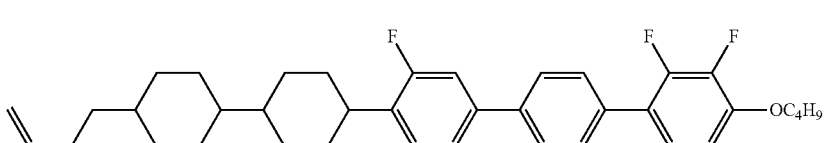 |
| 3175 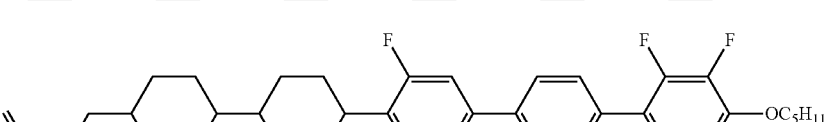 |
| 3176 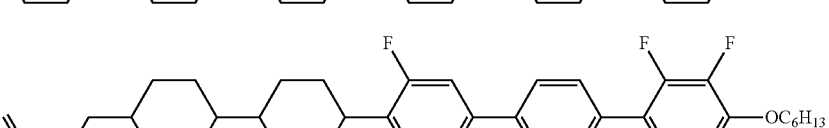 |
| 3177 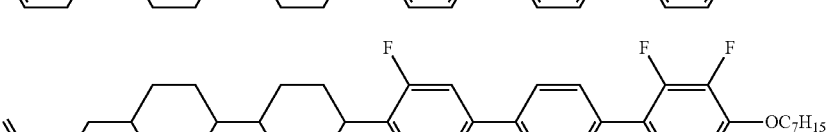 |
| 3178 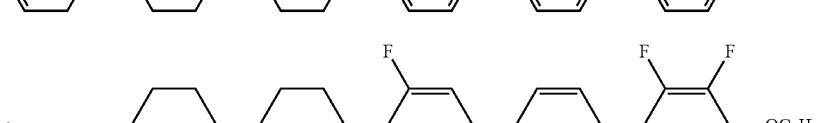 |
| 3179 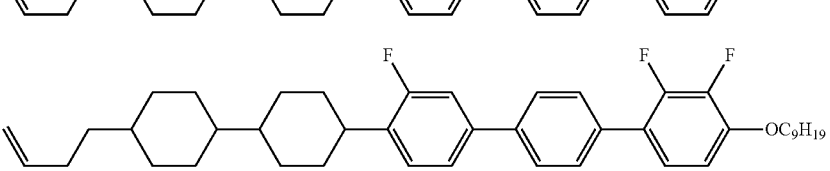 |

| No. |
| --- |
| 3180 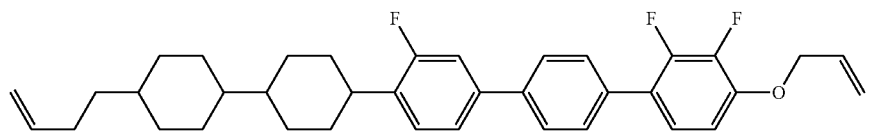 |
| 3181 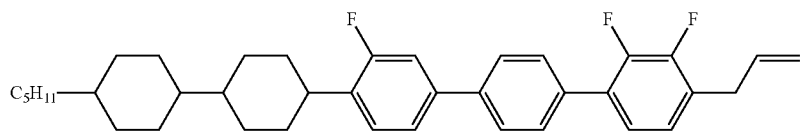 |
| 3182 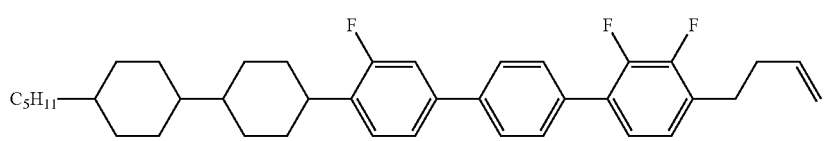 |
| 3183 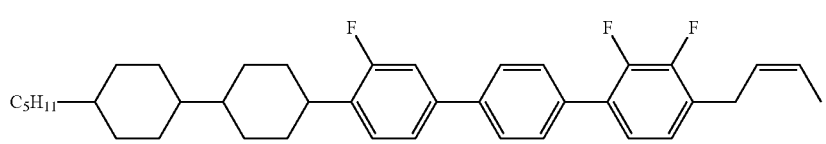 |
| 3184 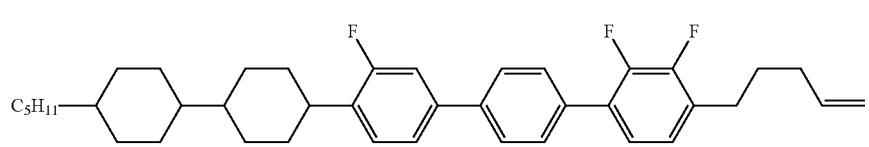 |
| 3185 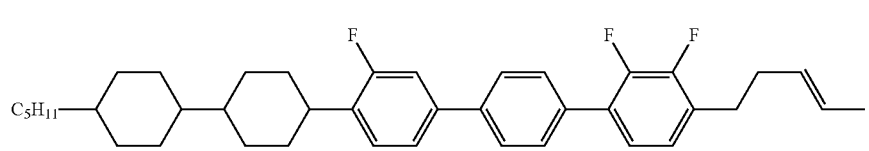 |
| 3186 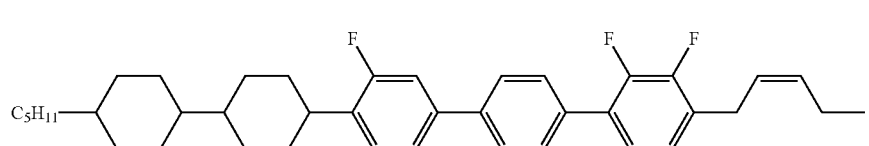 |
| 3187 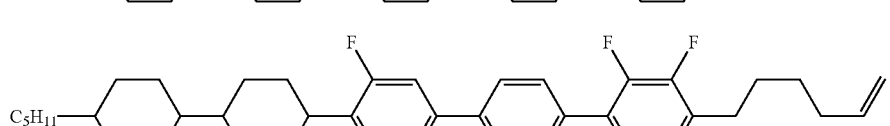 |
| 3188 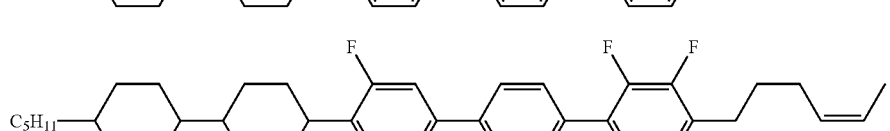 |
| 3189 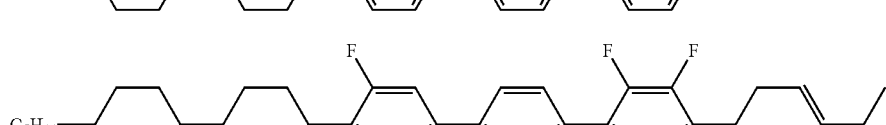 |
| 3190 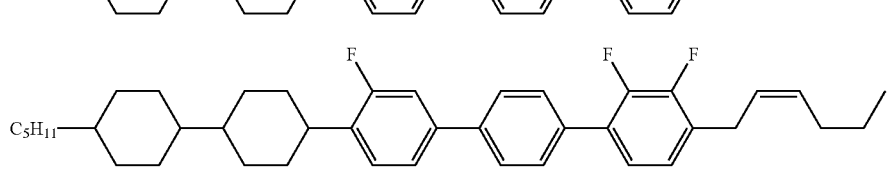 |

-continued
| No. | |
|---|---|
| 3191 | 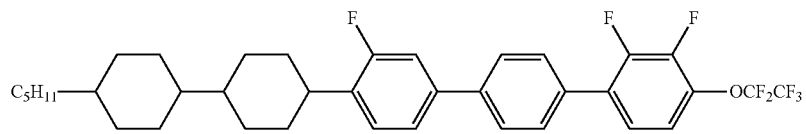 |
| 3192 | 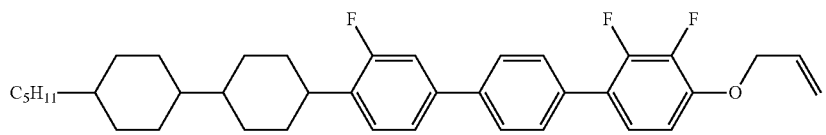 |
| 3193 | 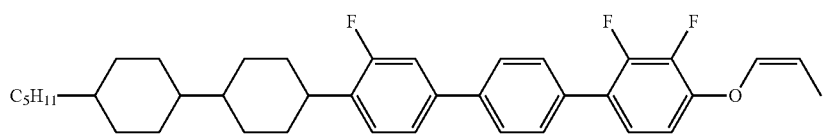 |
| 3194 | 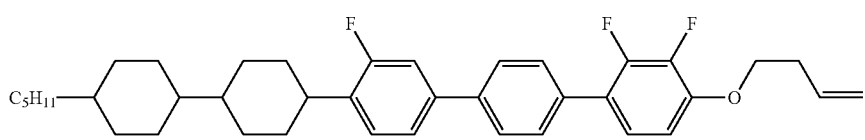 |
| 3195 | 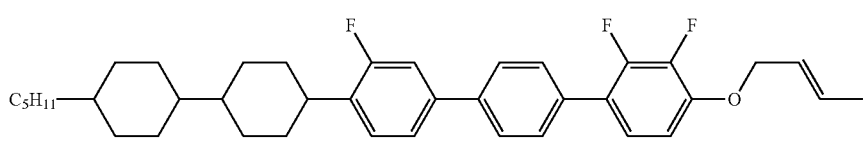 |
| 3196 | 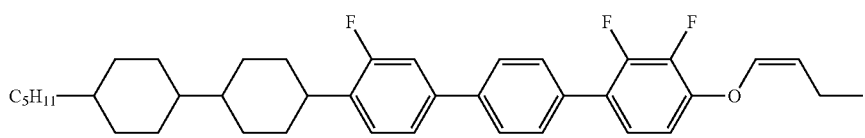 |
| 3197 | 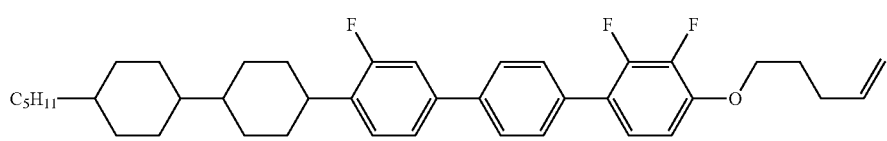 |
| 3198 | 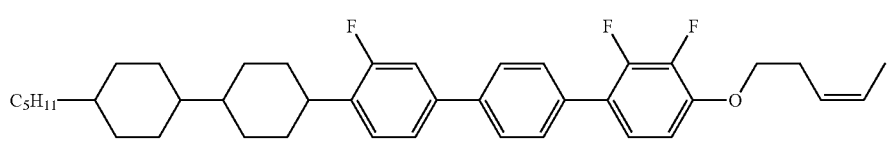 |
| 3199 | 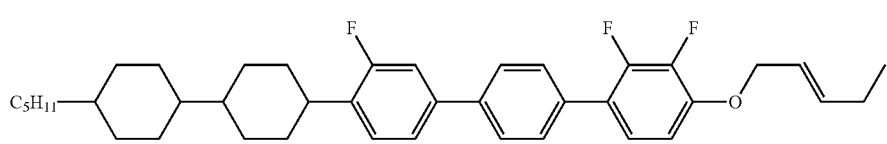 |
| 3200 | 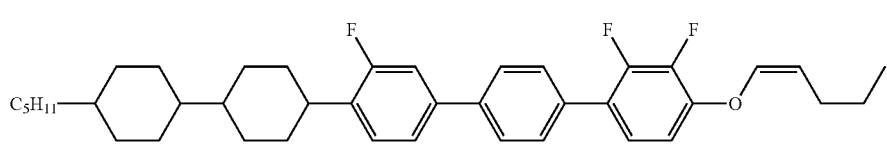 |
| 3201 | 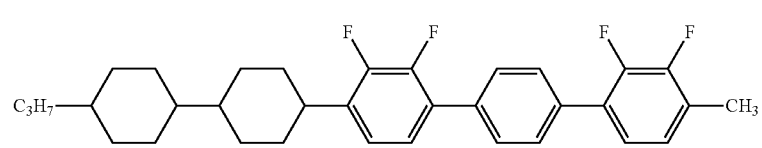 |

-continued
| No. | |
|---|---|
| 3202 | 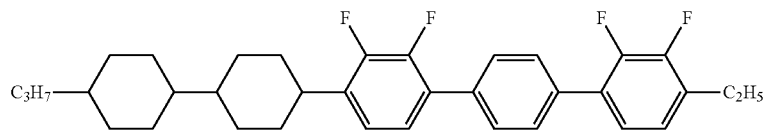 |
| 3203 | 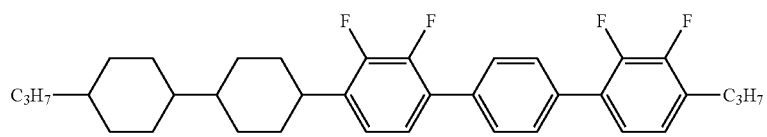 |
| 3204 | 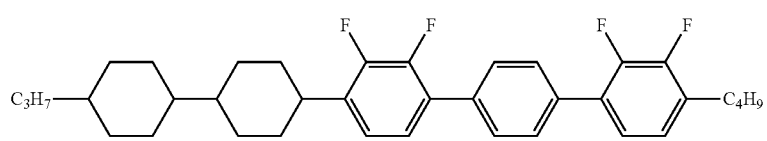 |
| 3205 | 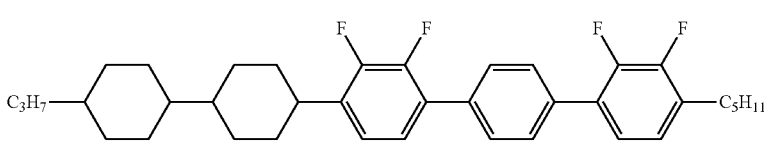 |
| 3206 | 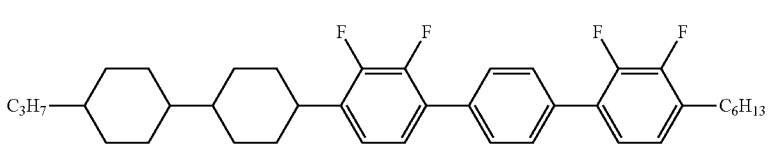 |
| 3207 | 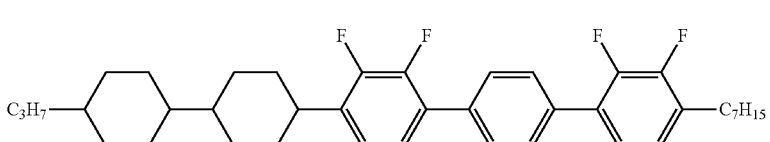 |
| 3208 | 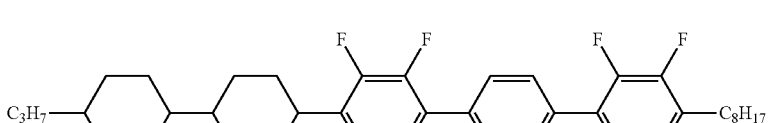 |
| 3209 | 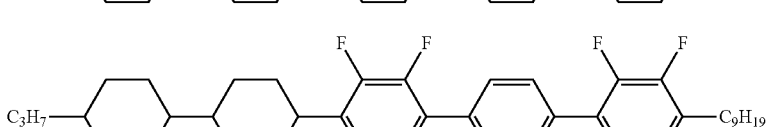 |
| 3210 | 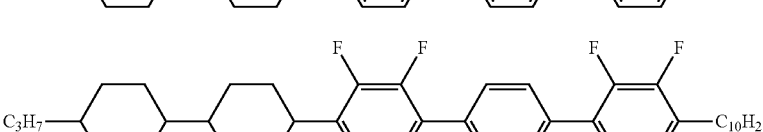 |
| 3211 | 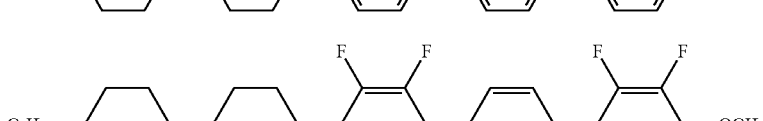 |
| 3212 | 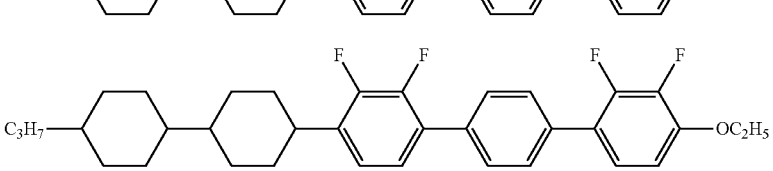 |

| No. | |
|---|---|
| 3213 | 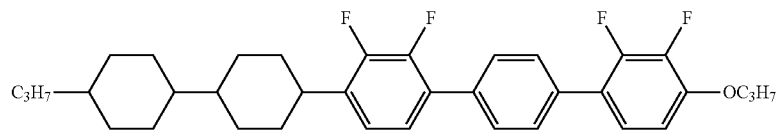 |
| 3214 | 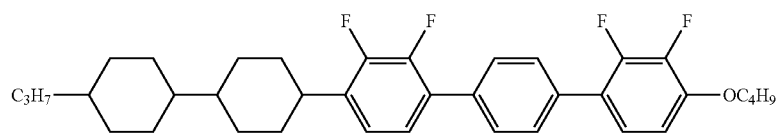 |
| 3215 | 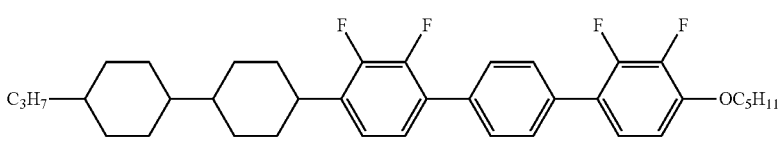 |
| 3216 | 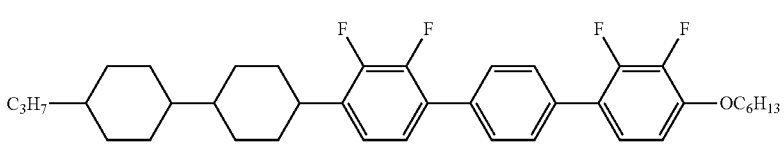 |
| 3217 | 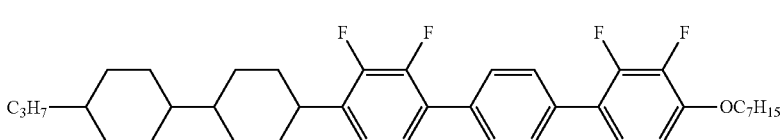 |
| 3218 | 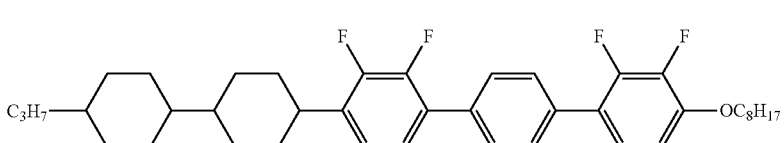 |
| 3219 | 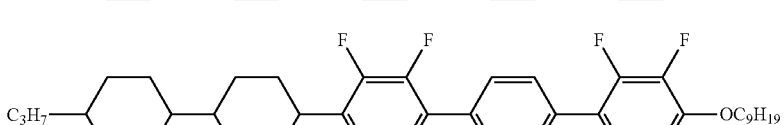 |
| 3220 | 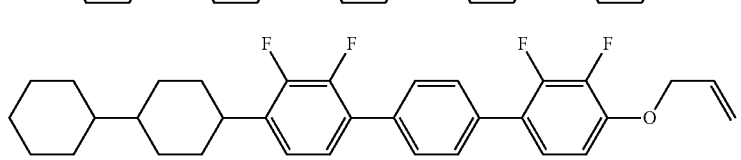 |
| 3221 | 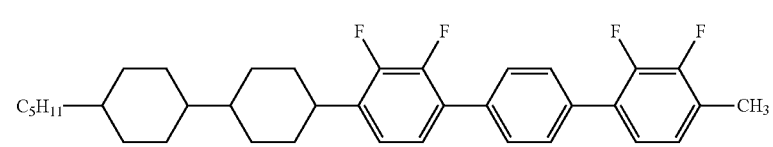 |
| 3222 | 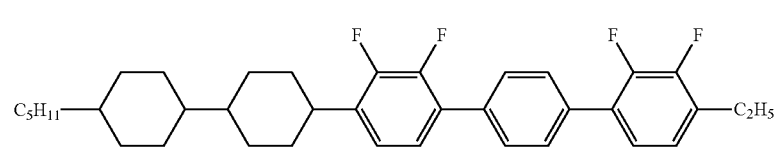 |
| 3223 | 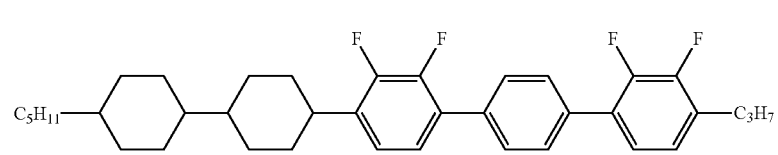 |

| No. | |
|---|---|
| 3224 | 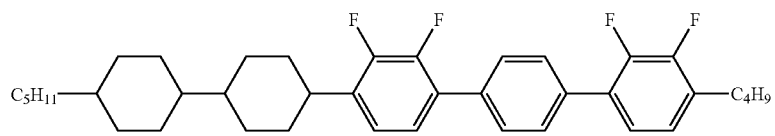 |
| 3225 | 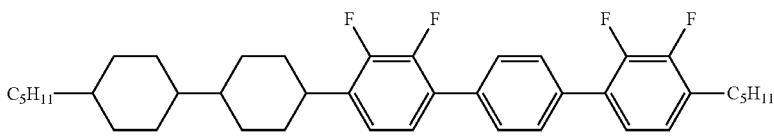 |
| 3226 | 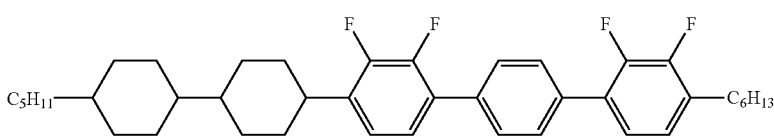 |
| 3227 | 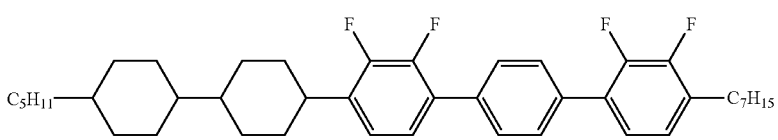 |
| 3228 | 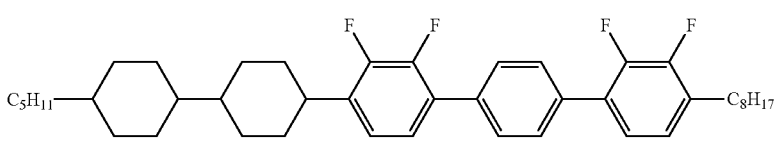 |
| 3229 | 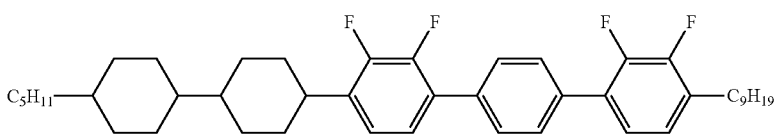 |
| 3230 | 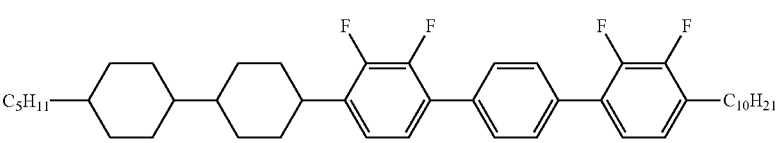 |
| 3231 | 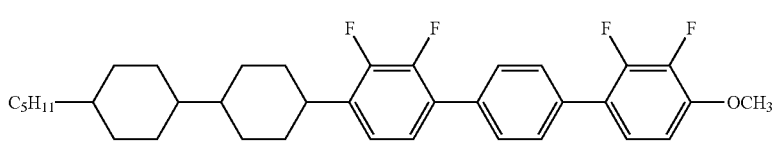 |
| 3232 |  |
| 3233 | 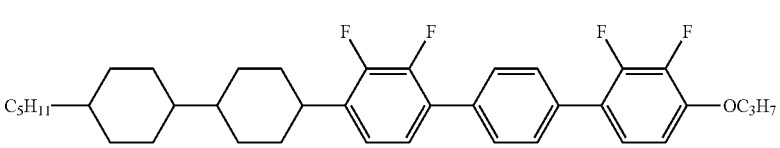 |
| 3234 | 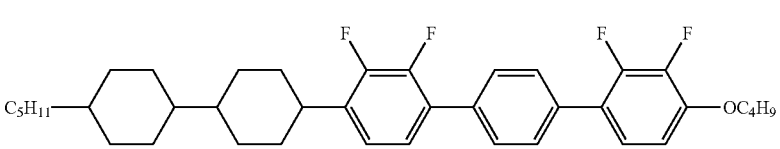 |

| No. | |
|---|---|
| 3235 | 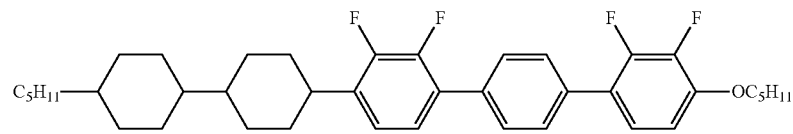 |
| 3236 | 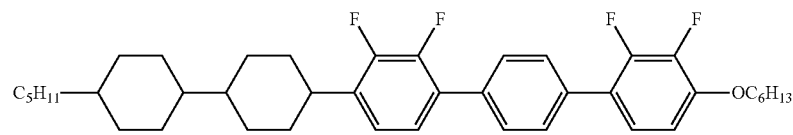 |
| 3237 | 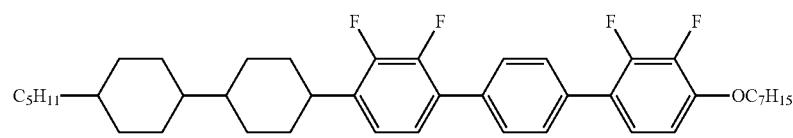 |
| 3238 | 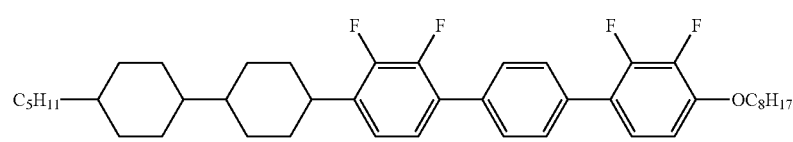 |
| 3239 | 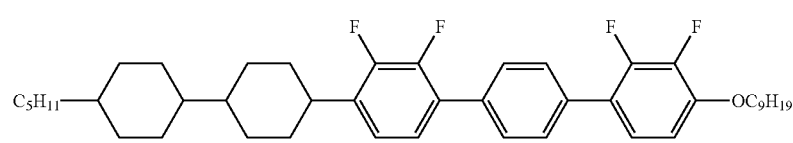 |
| 3240 | 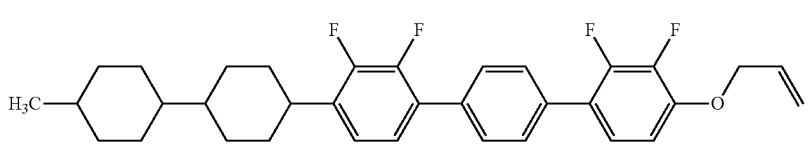 |
| 3241 | 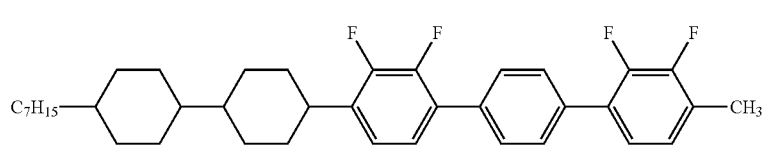 |
| 3242 | 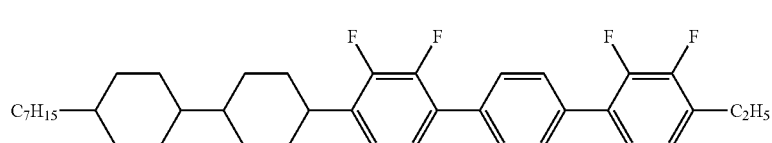 |
| 3243 | 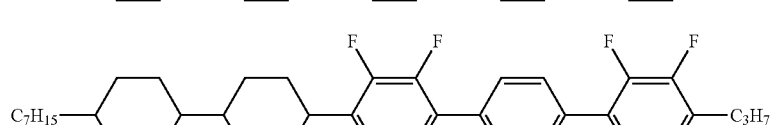 |
| 3244 | 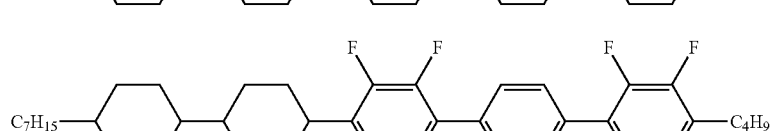 |
| 3245 | 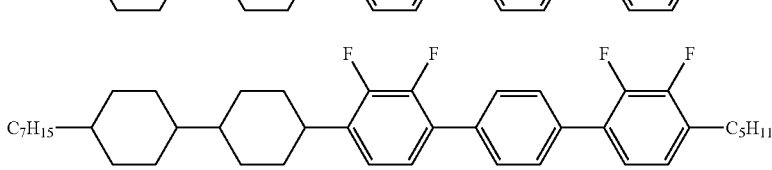 |

-continued
| No. | |
|---|---|
| 3246 | 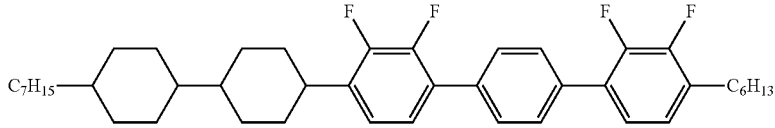 |
| 3247 | 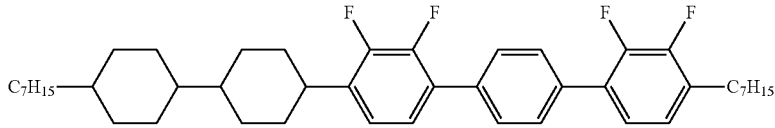 |
| 3248 | 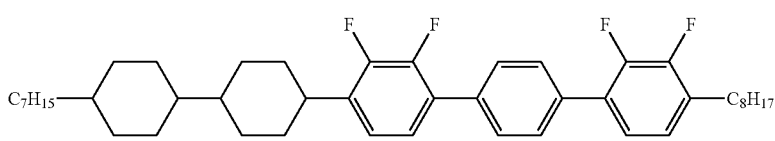 |
| 3249 | 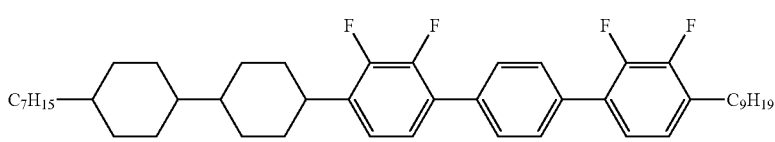 |
| 3250 |  |
| 3251 | 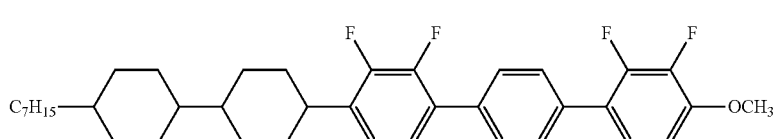 |
| 3252 | 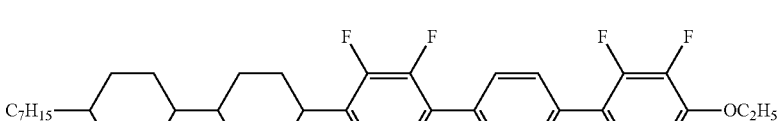 |
| 3253 | 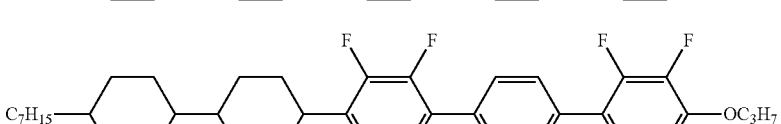 |
| 3254 | 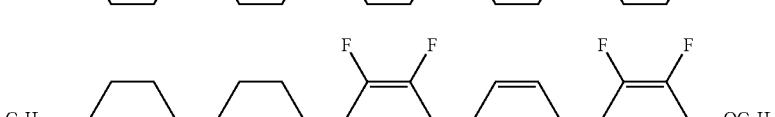 |
| 3255 | 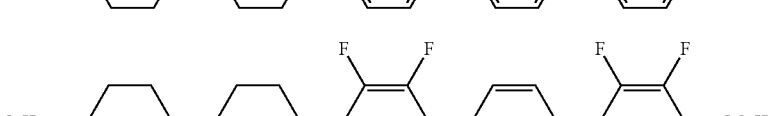 |
| 3256 | 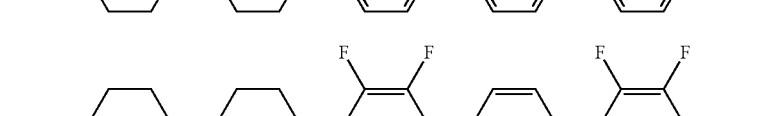 |

| No. | |
|---|---|
| 3257 | 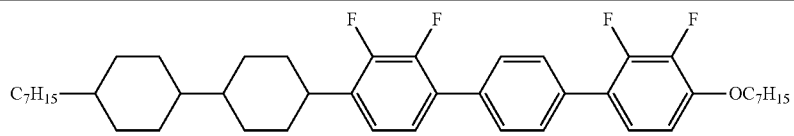 |
| 3258 | 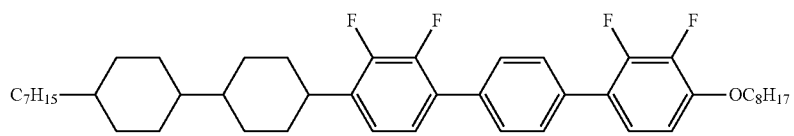 |
| 3259 | 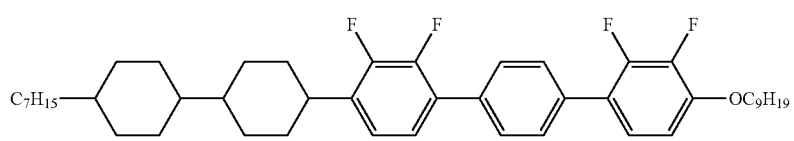 |
| 3260 | 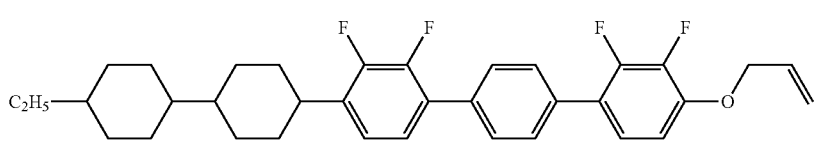 |
| 3261 | 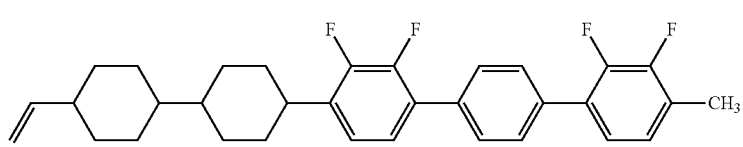 |
| 3262 | 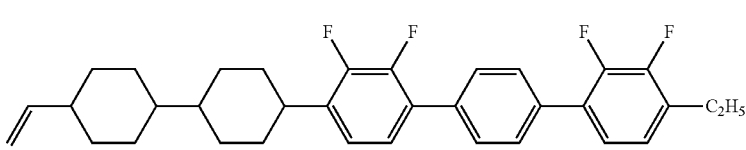 |
| 3263 | 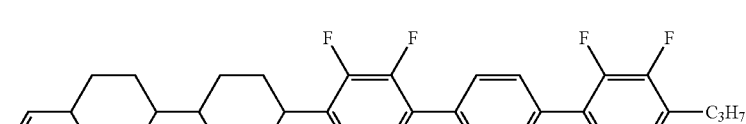 |
| 3264 | 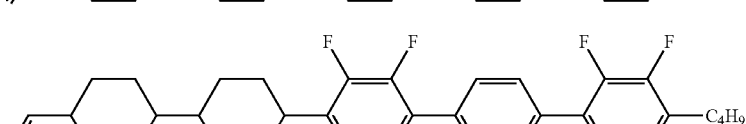 |
| 3265 | 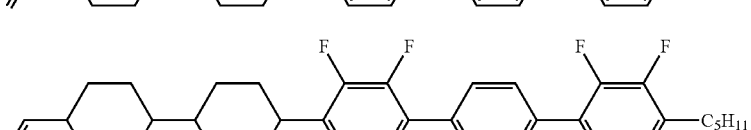 |
| 3266 | 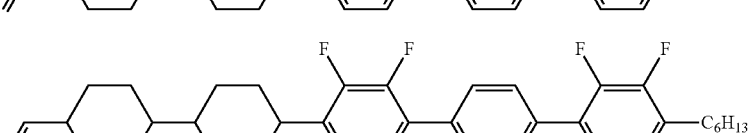 |
| 3267 | 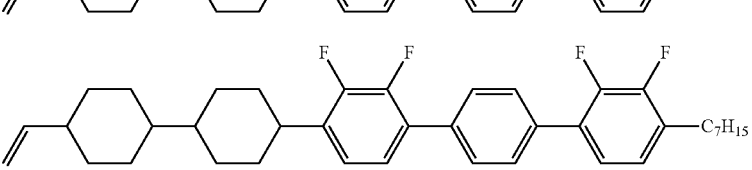 |

| No. | |
|---|---|
| 3268 | 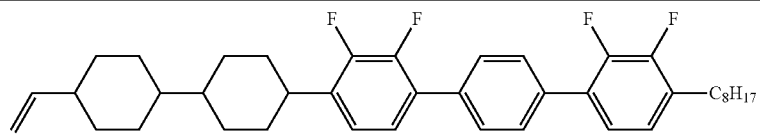 |
| 3269 | 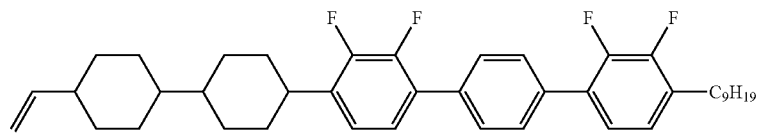 |
| 3270 | 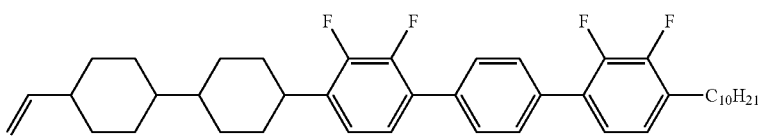 |
| 3271 | 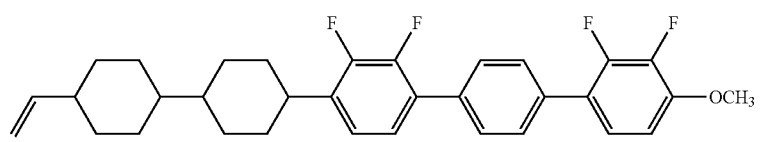 |
| 3272 | 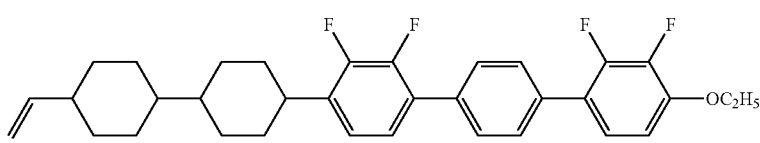 |
| 3273 | 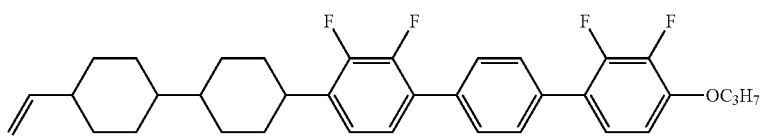 |
| 3274 | 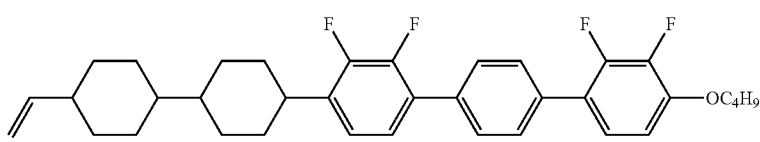 |
| 3275 | 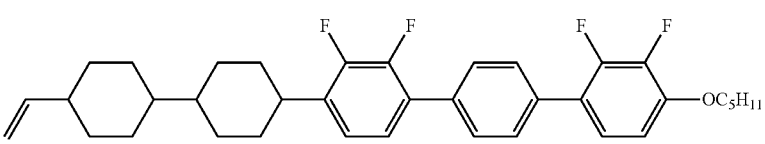 |
| 3276 | 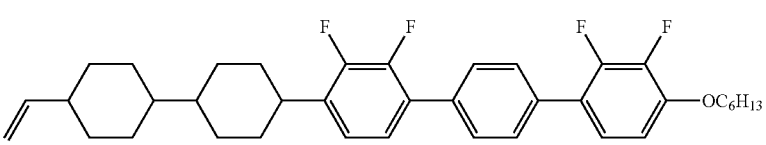 |
| 3277 | 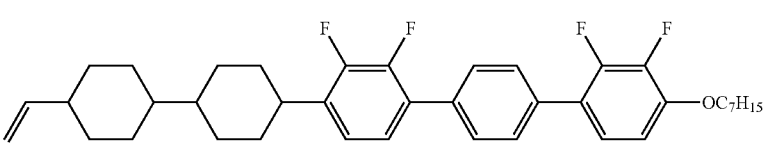 |
| 3278 | 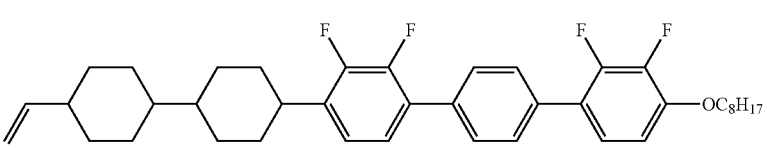 |

| No. |
|---|
| 3279 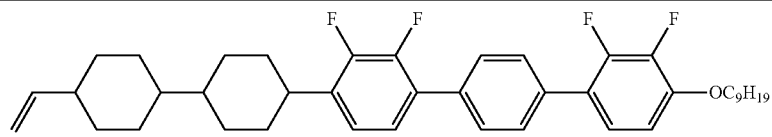 |
| 3280 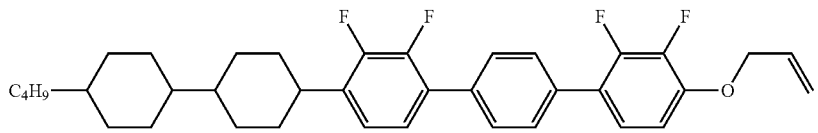 |
| 3281 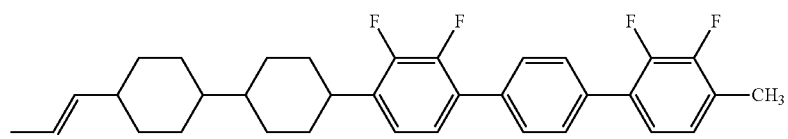 |
| 3282 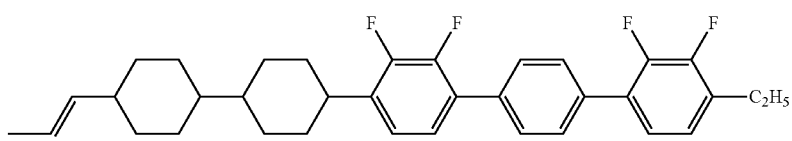 |
| 3283 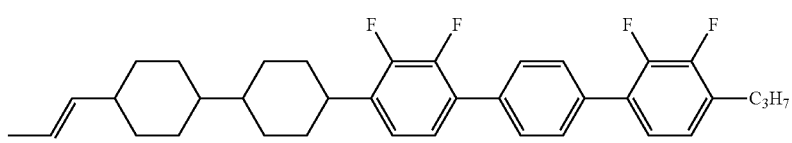 |
| 3284 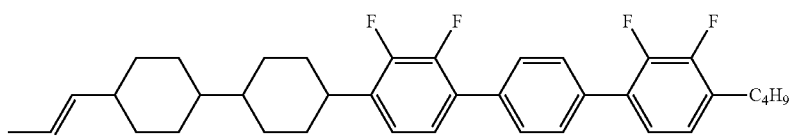 |
| 3285 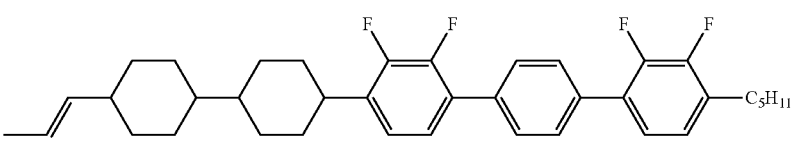 |
| 3286 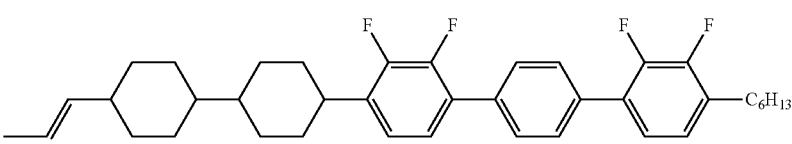 |
| 3287 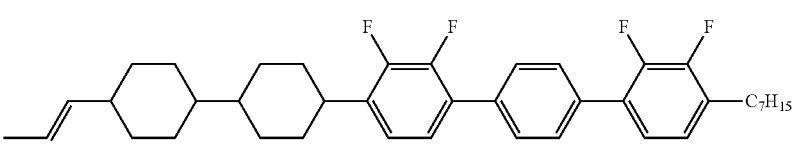 |
| 3288  |
| 3289 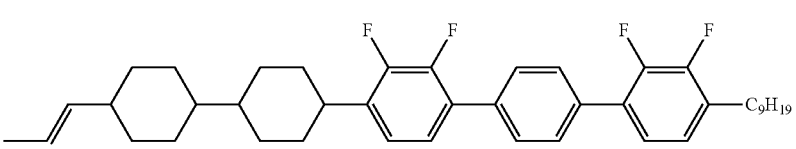 |

-continued
| No. | |
|---|---|
| 3290 | 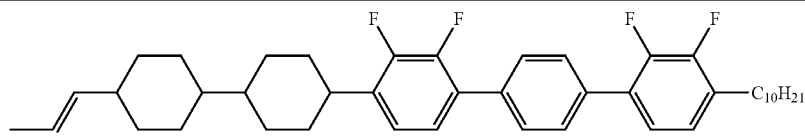 |
| 3291 | 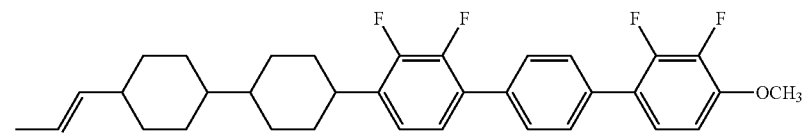 |
| 3292 | 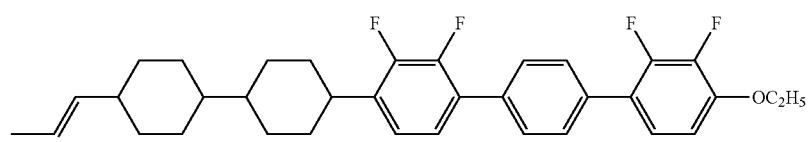 |
| 3293 | 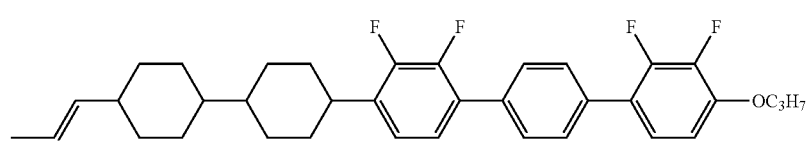 |
| 3294 | 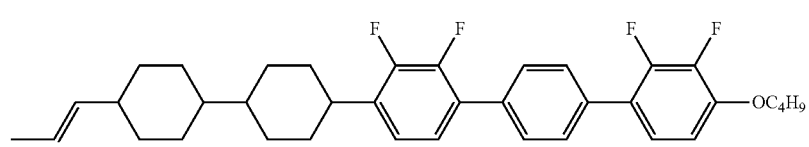 |
| 3295 | 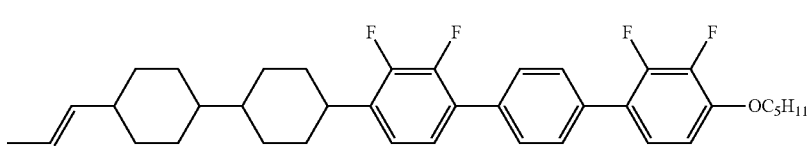 |
| 3296 | 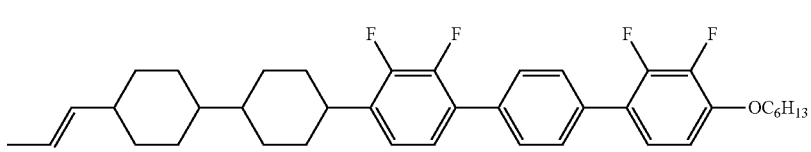 |
| 3297 | 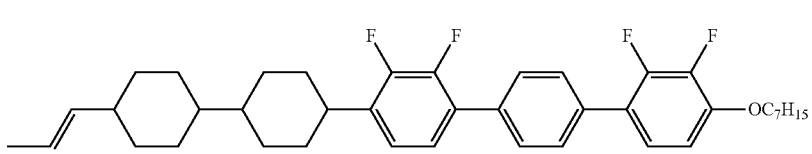 |
| 3298 | 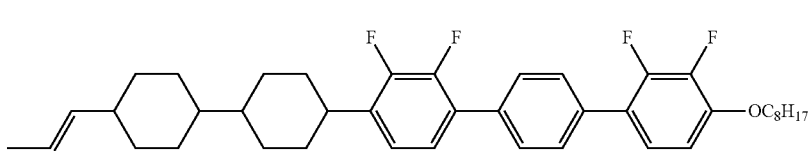 |
| 3299 | 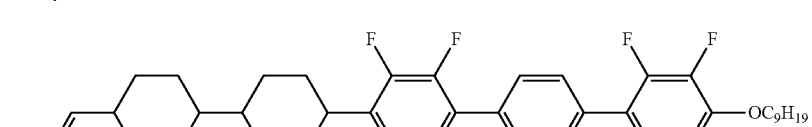 |
| 3300 | 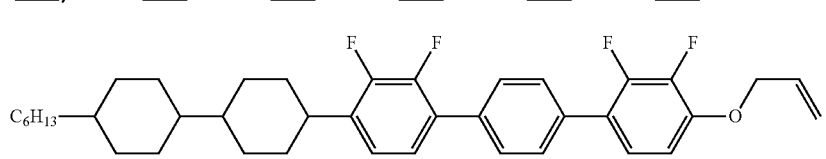 |

| No. | |
|---|---|
| 3301 | 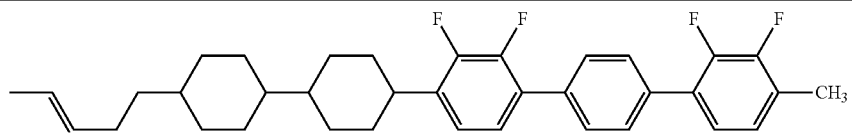 |
| 3302 | 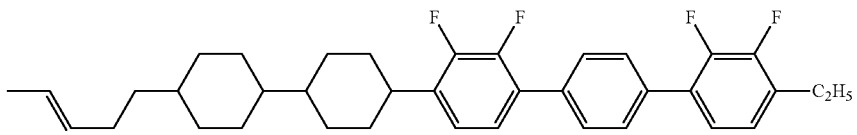 |
| 3303 | 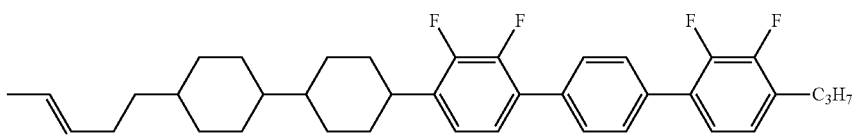 |
| 3304 | 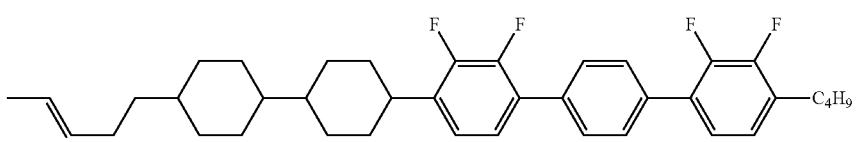 |
| 3305 | 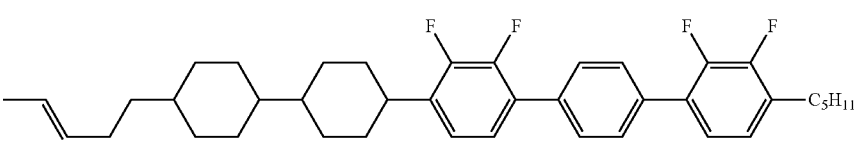 |
| 3306 | 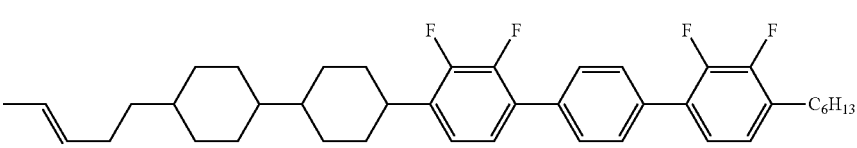 |
| 3307 | 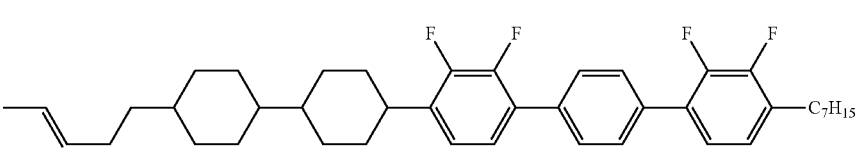 |
| 3308 | 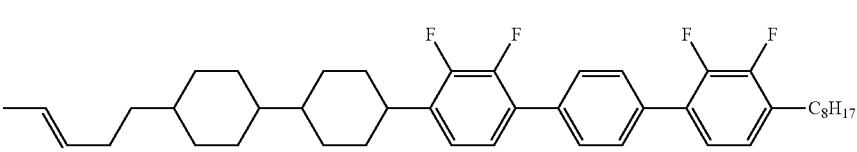 |
| 3309 | 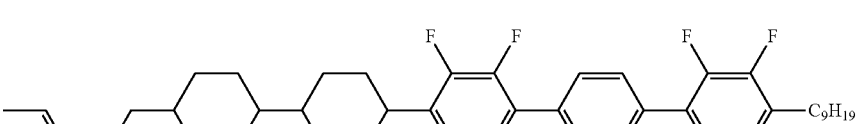 |
| 3310 | 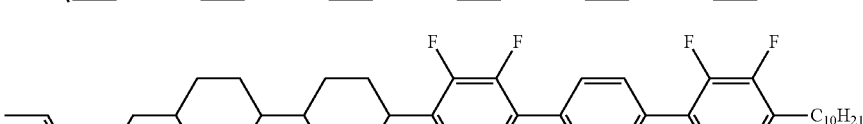 |
| 3311 | 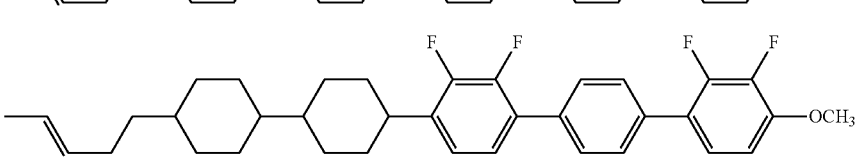 |

| No. | |
|---|---|
| 3312 | 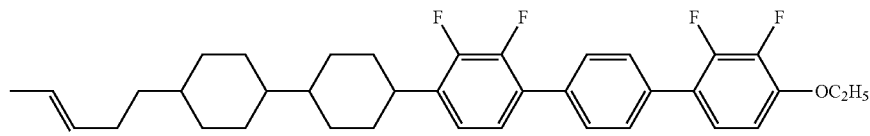 |
| 3313 | 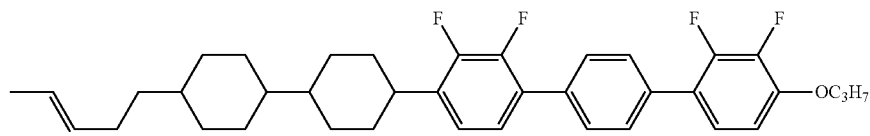 |
| 3314 | 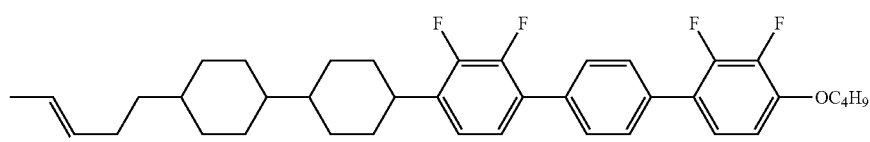 |
| 3315 | 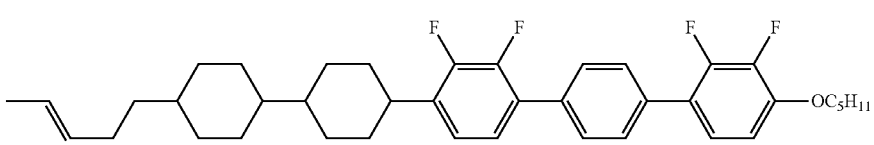 |
| 3316 | 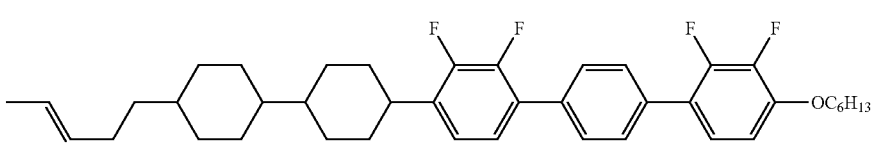 |
| 3317 | 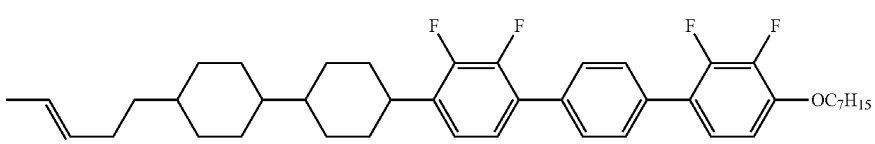 |
| 3318 | 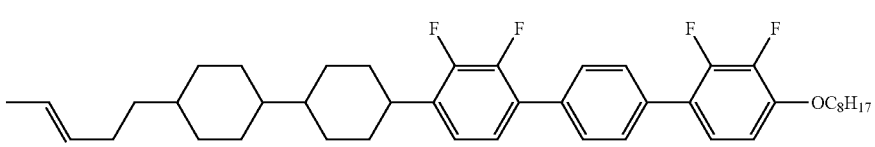 |
| 3319 | 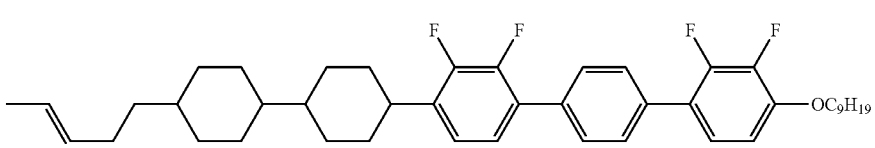 |
| 3320 | 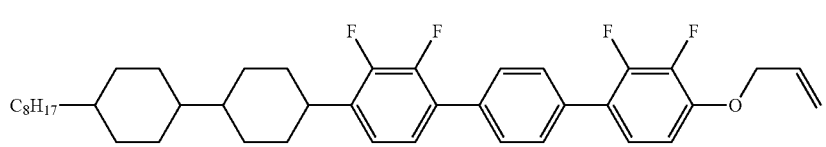 |
| 3321 | 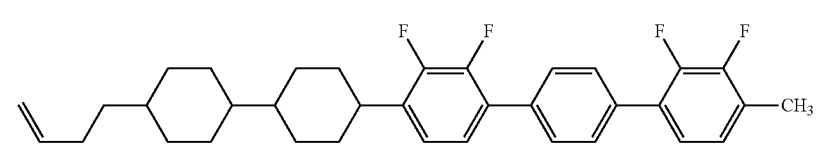 |
| 3322 | 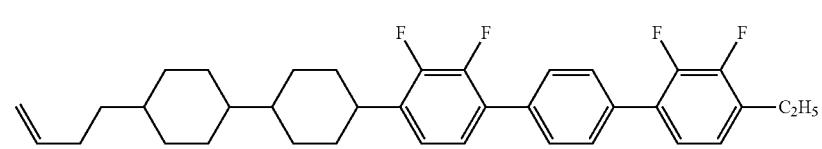 |

-continued
| No. | |
|---|---|
| 3323 | 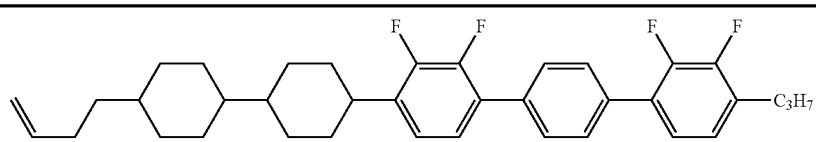 C₃H₇ |
| 3324 | 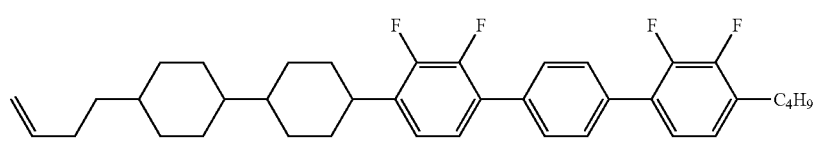 C₄H₉ |
| 3325 | 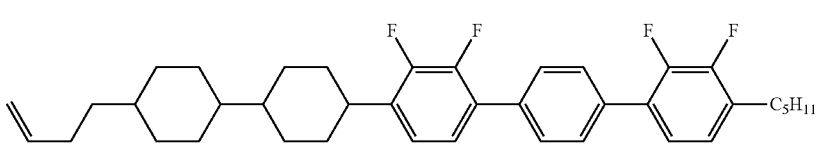 C₅H₁₁ |
| 3326 | 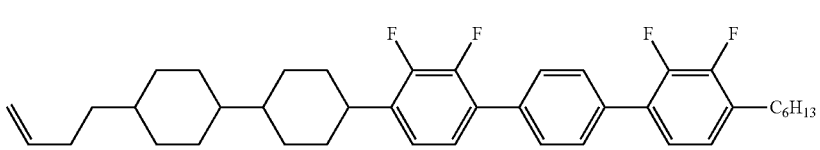 C₆H₁₃ |
| 3327 | 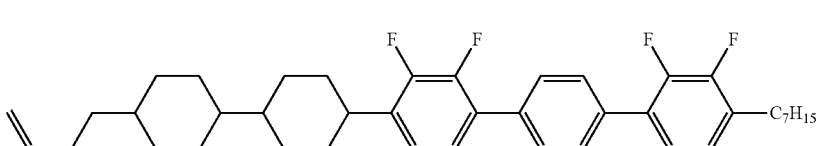 C₇H₁₅ |
| 3328 | 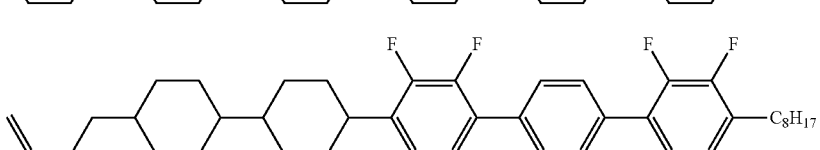 C₈H₁₇ |
| 3329 | 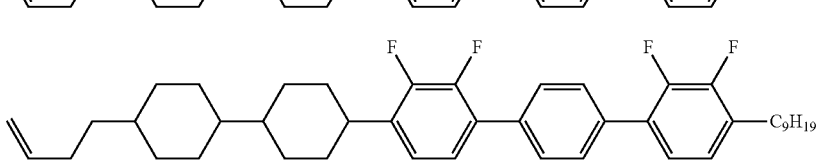 C₉H₁₉ |
| 3330 | 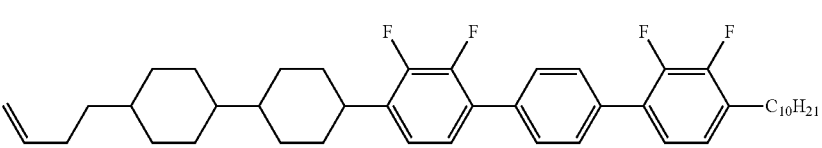 C₁₀H₂₁ |
| 3331 | 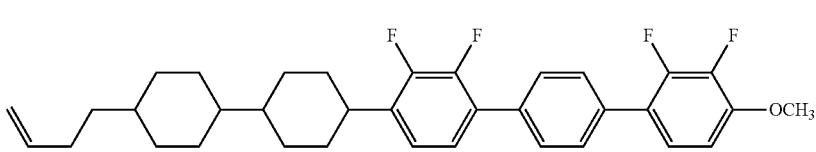 OCH₃ |
| 3332 | 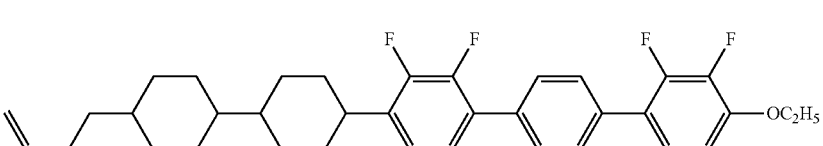 OC₂H₅ |
| 3333 | 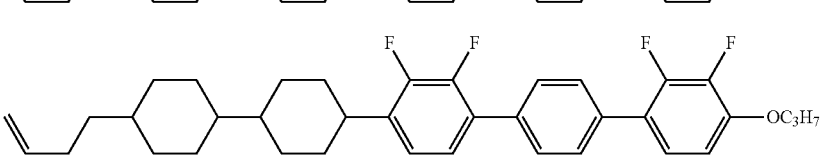 OC₃H₇ |

| No. | |
|---|---|
| 3334 | 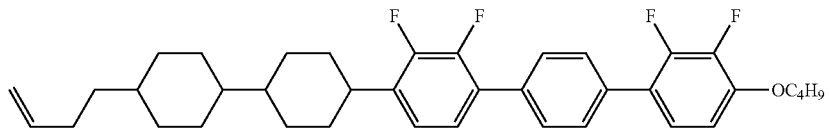 |
| 3335 | 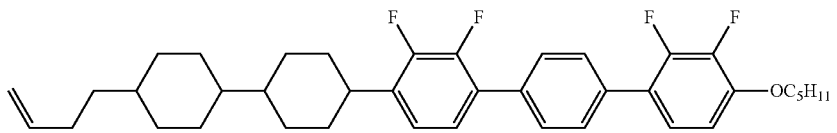 |
| 3336 | 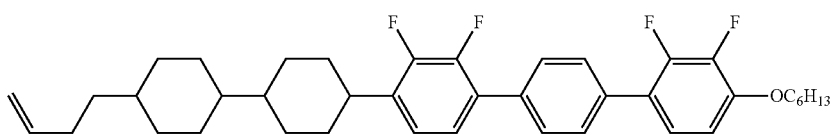 |
| 3337 | 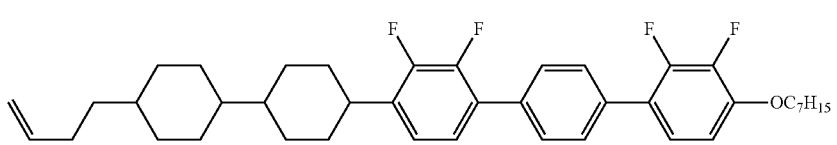 |
| 3338 | 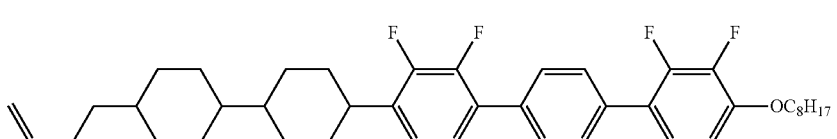 |
| 3339 | 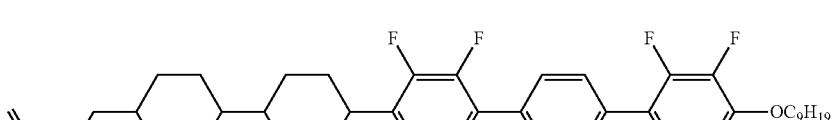 |
| 3340 | 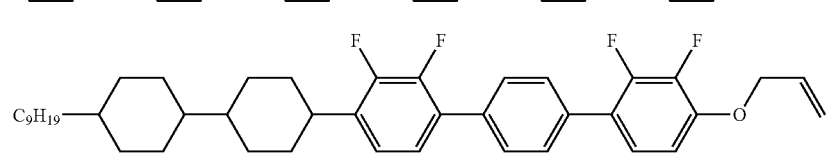 |
| 3341 | 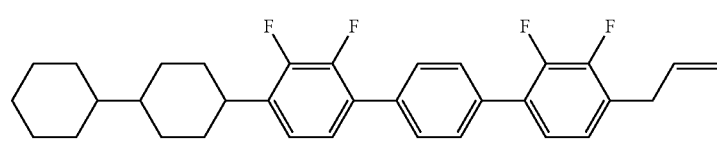 |
| 3342 | 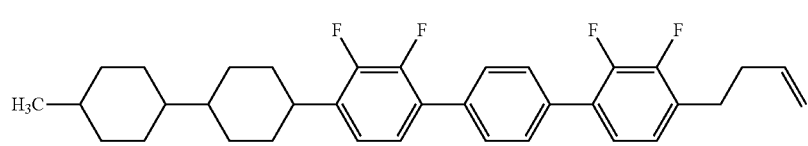 |
| 3343 | 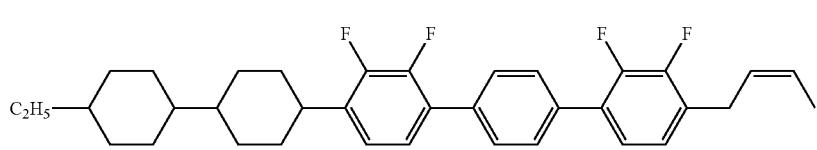 |
| 3344 | 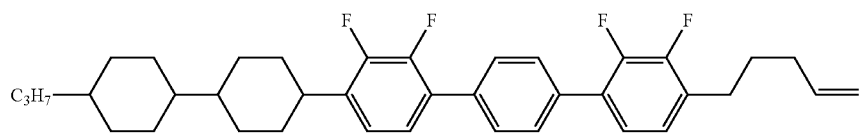 |

| No. | |
|---|---|
| 3345 | C4H9-[Cy]-[Cy]-[Ph(F,F)]-[Ph]-[Ph(F,F)]-CH2CH2CH=CHCH3 |
| 3346 | C5H11-[Cy]-[Cy]-[Ph(F,F)]-[Ph]-[Ph(F,F)]-CH2CH=CHCH2CH3 |
| 3347 | C6H13-[Cy]-[Cy]-[Ph(F,F)]-[Ph]-[Ph(F,F)]-CH2CH2CH2CH=CH2 |
| 3348 | C8H17-[Cy]-[Cy]-[Ph(F,F)]-[Ph]-[Ph(F,F)]-CH2CH2CH=CHCH3 |
| 3349 | C9H19-[Cy]-[Cy]-[Ph(F,F)]-[Ph]-[Ph(F,F)]-CH2CH2CH=CHCH3 |
| 3350 | C10H21-[Cy]-[Cy]-[Ph(F,F)]-[Ph]-[Ph(F,F)]-CH2CH=CHCH2CH3 |
| 3351 | [Cy]-[Cy]-[Ph(F,F)]-[Ph]-[Ph(F,F)]-OCF2CF3 |
| 3352 | H3C-[Cy]-[Cy]-[Ph(F,F)]-[Ph]-[Ph(F,F)]-O-CH2CH=CH2 |
| 3353 | C2H5-[Cy]-[Cy]-[Ph(F,F)]-[Ph]-[Ph(F,F)]-O-CH=CHCH3 |
| 3354 | C3H7-[Cy]-[Cy]-[Ph(F,F)]-[Ph]-[Ph(F,F)]-O-CH2CH2CH=CH2 |
| 3355 | C4H9-[Cy]-[Cy]-[Ph(F,F)]-[Ph]-[Ph(F,F)]-O-CH2CH=CHCH3 |

| No. |
|---|
| 3356 |
| 3357 |
| 3358 |
| 3359 |
| 3360 |
| 3361 |
| 3362 |
| 3363 |
| 3364 |
| 3365 |
| 3366 |

| No. | |
|---|---|
| 3367 | 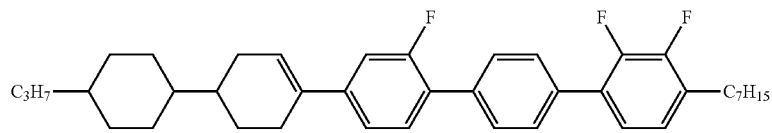 |
| 3368 | 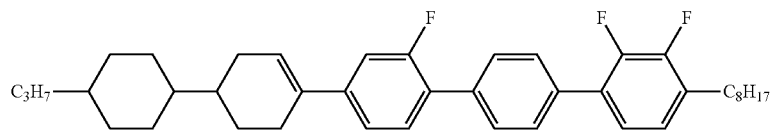 |
| 3369 | 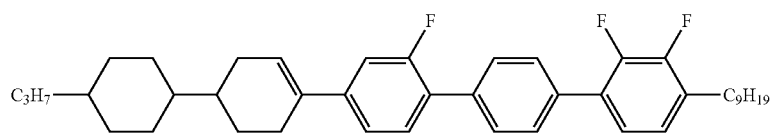 |
| 3370 | 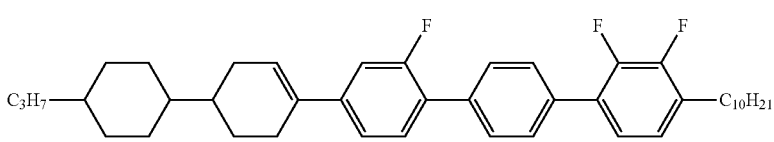 |
| 3371 | 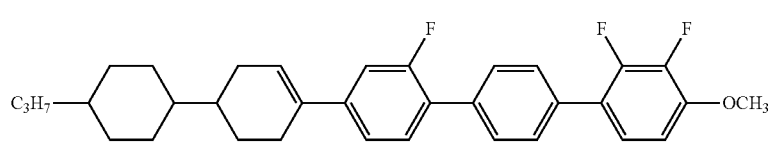 |
| 3372 | 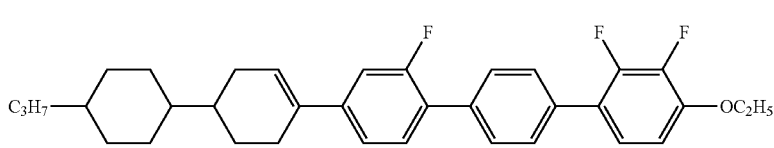 |
| 3373 | 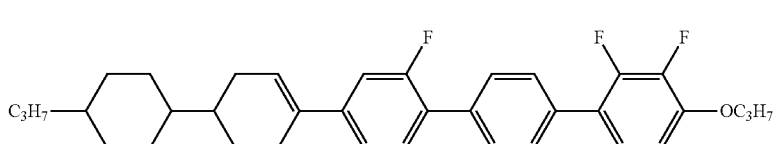 |
| 3374 | 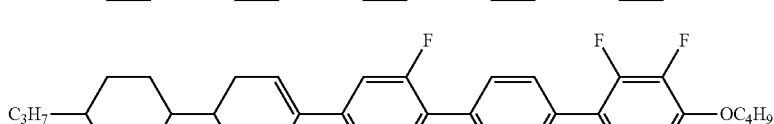 |
| 3375 | 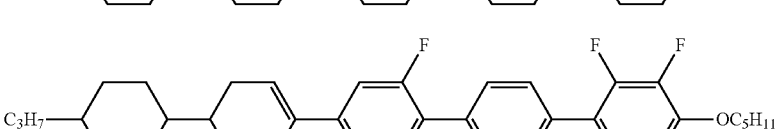 |
| 3376 | 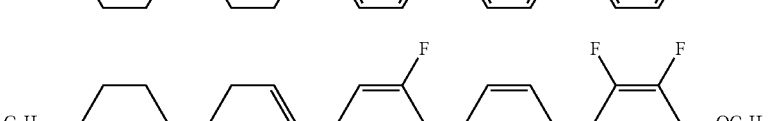 |
| 3377 | 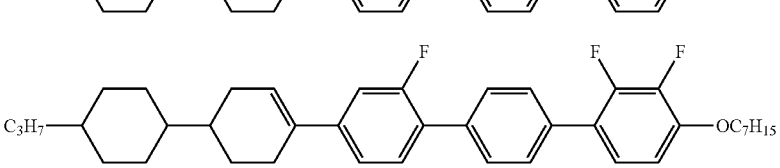 |

| No. | |
|---|---|
| 3378 | 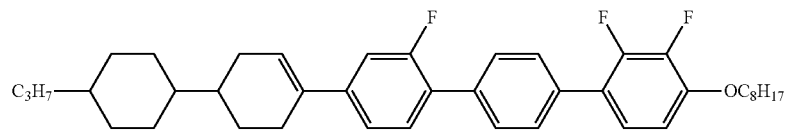 |
| 3379 | 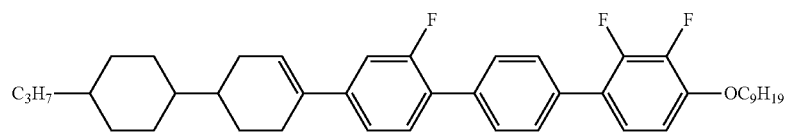 |
| 3380 | 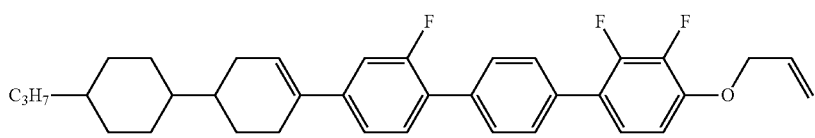 |
| 3381 | 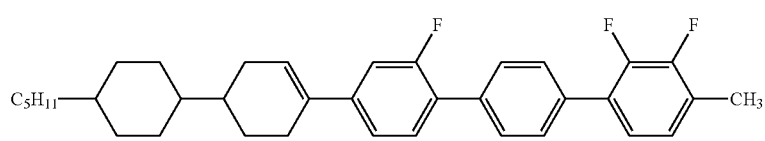 |
| 3382 | 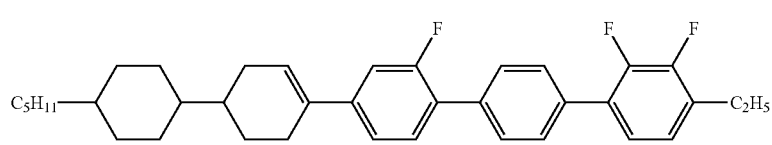 |
| 3383 | 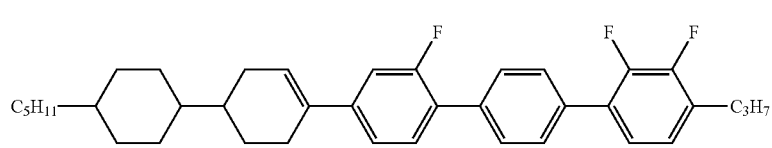 |
| 3384 | 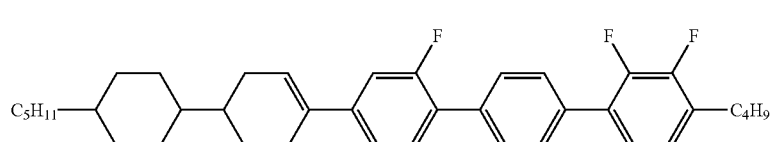 |
| 3385 | 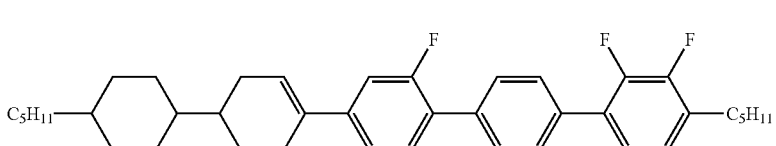 |
| 3386 | 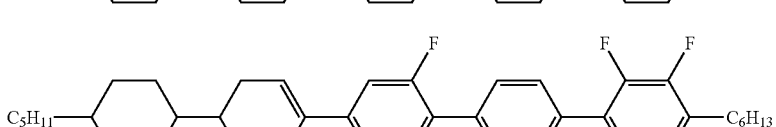 |
| 3387 | 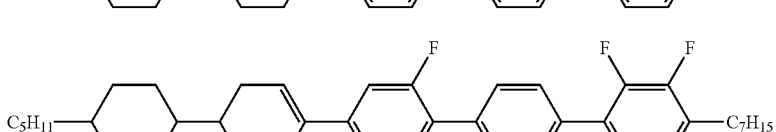 |
| 3388 | 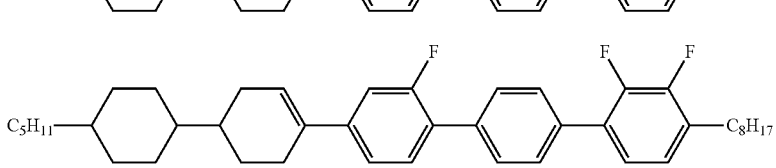 |

| No. | |
|---|---|
| 3389 | 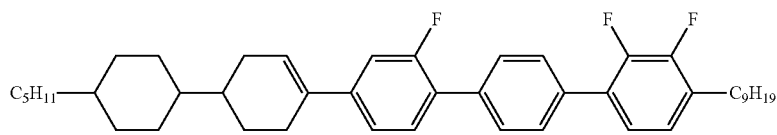 |
| 3390 | 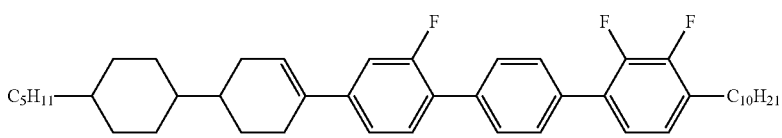 |
| 3391 | 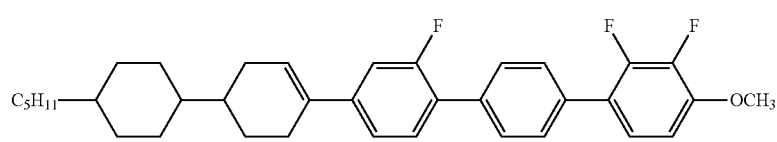 |
| 3392 | 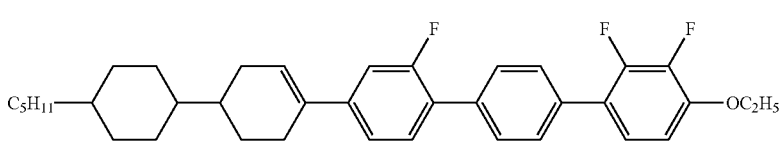 |
| 3393 | 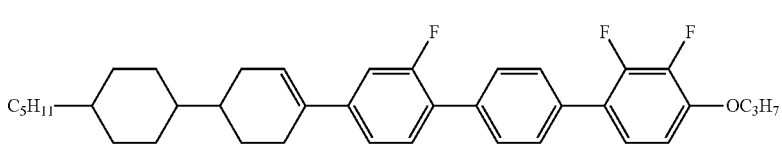 |
| 3394 | 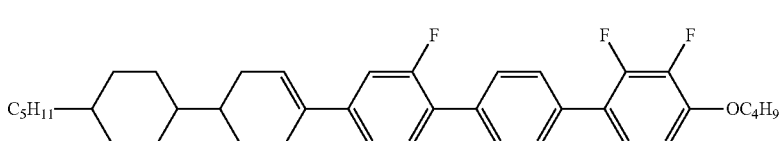 |
| 3395 | 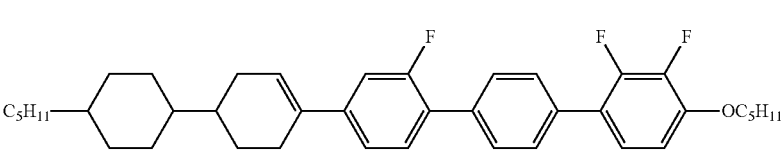 |
| 3396 | 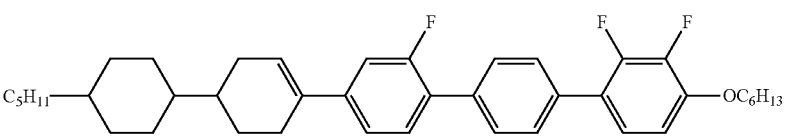 |
| 3397 | 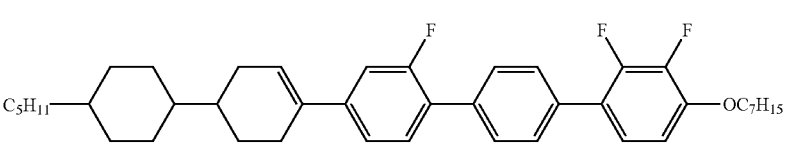 |
| 3398 | 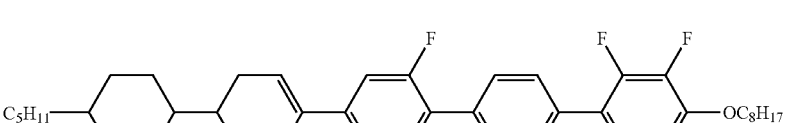 |
| 3399 | 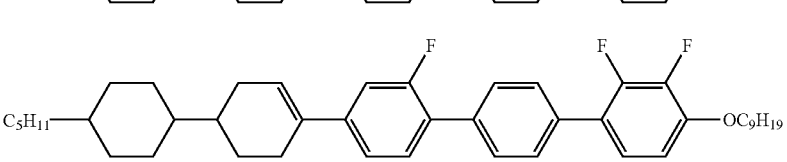 |

| No. | |
|---|---|
| 3400 | 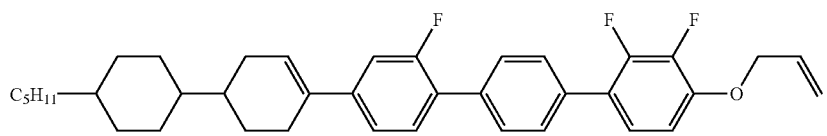 |
| 3401 | 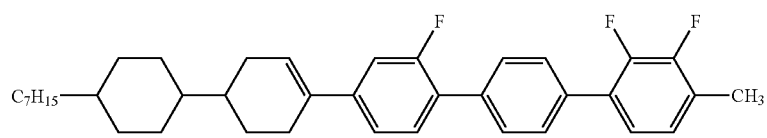 |
| 3402 | 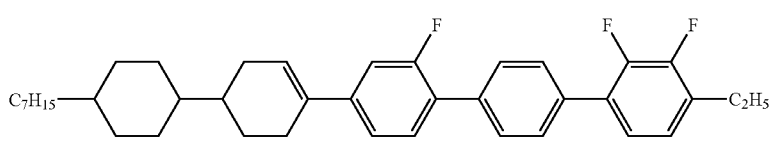 |
| 3403 | 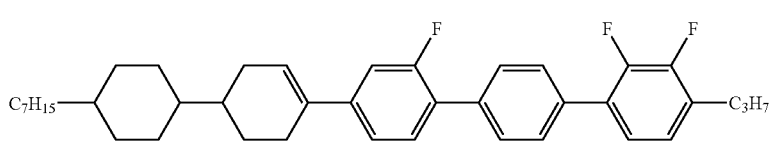 |
| 3404 | 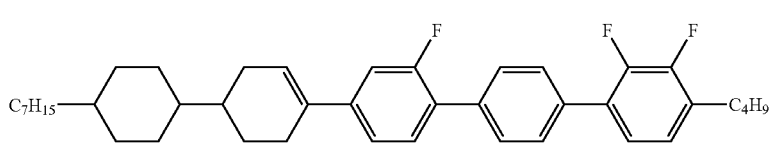 |
| 3405 | 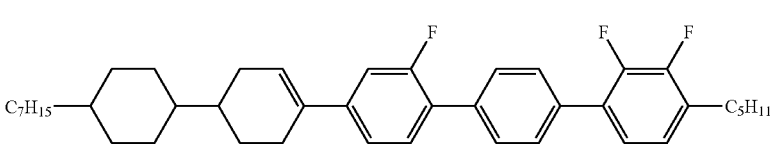 |
| 3406 | 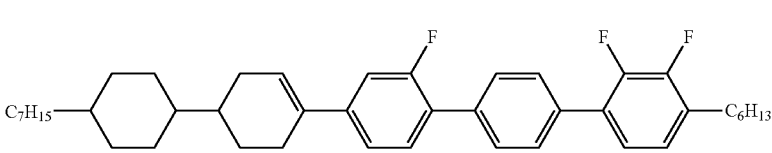 |
| 3407 | 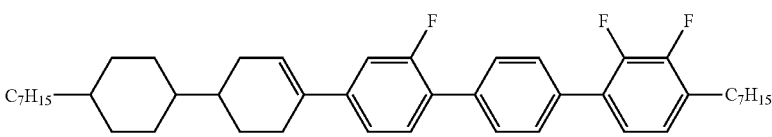 |
| 3408 | 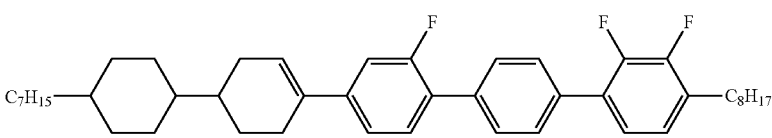 |
| 3409 | 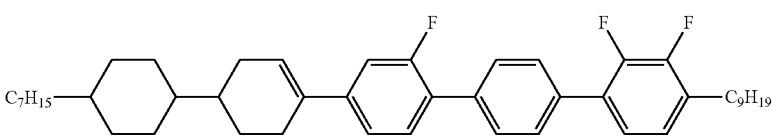 |
| 3410 | 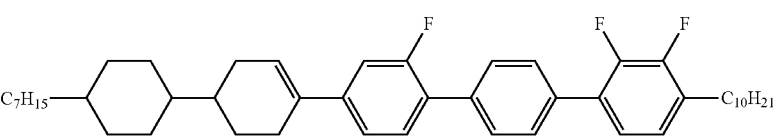 |

| No. | |
|---|---|
| 3411 | 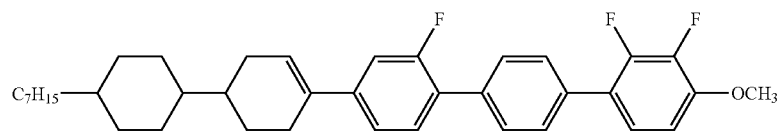 |
| 3412 | 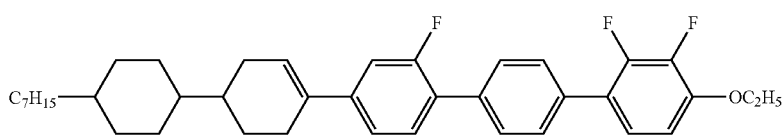 |
| 3413 | 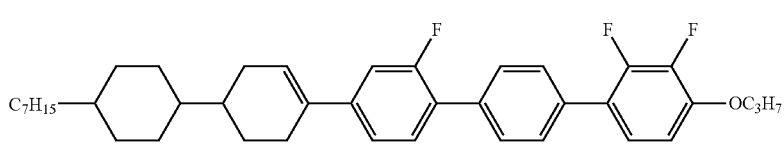 |
| 3414 | 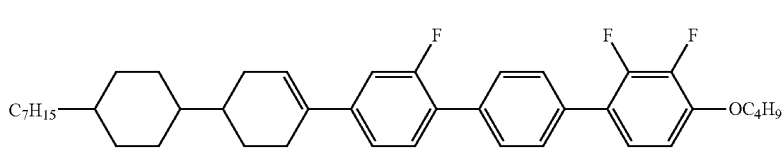 |
| 3415 | 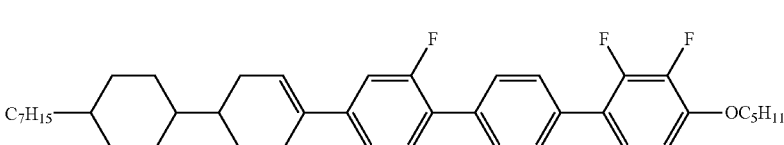 |
| 3416 | 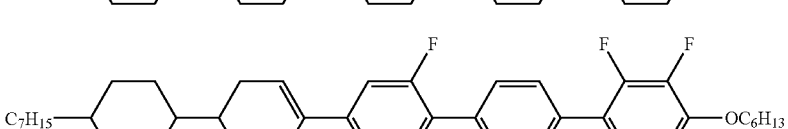 |
| 3417 | 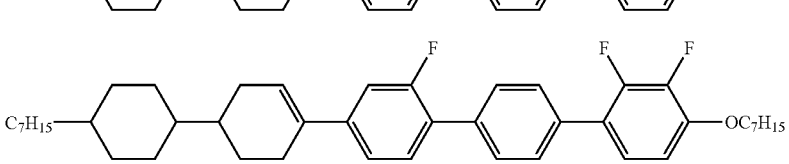 |
| 3418 | 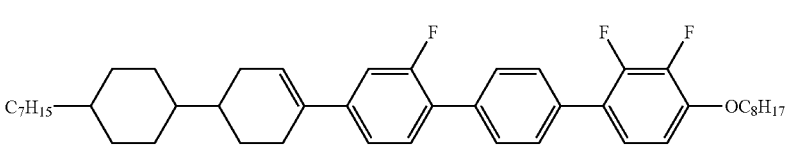 |
| 3419 | 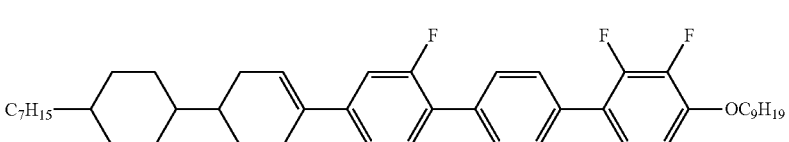 |
| 3420 | 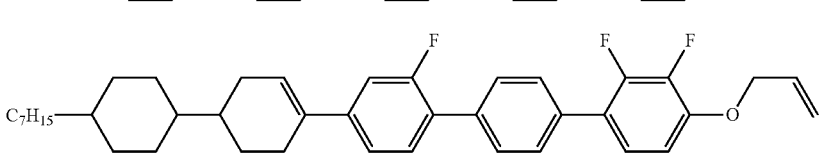 |
| 3421 | 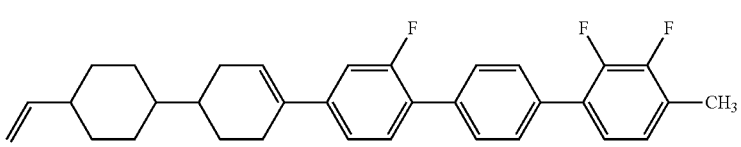 |

| No. | |
|---|---|
| 3422 | 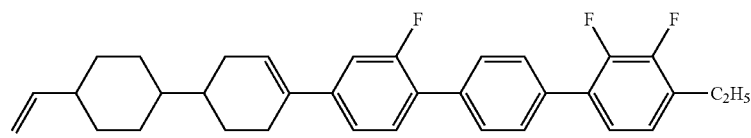 |
| 3423 | 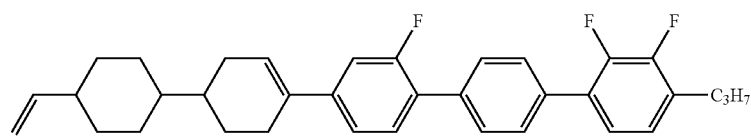 |
| 3424 | 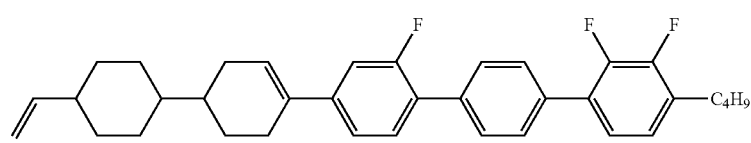 |
| 3425 | 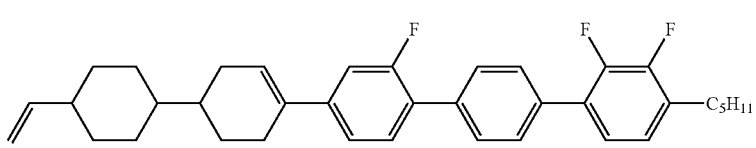 |
| 3426 | 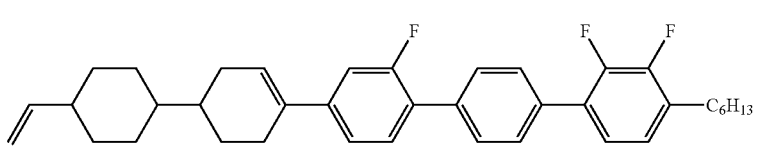 |
| 3427 | 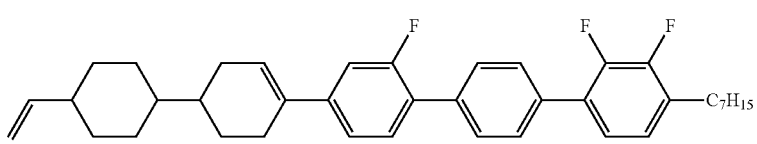 |
| 3428 | 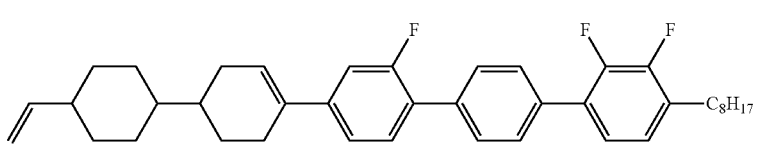 |
| 3429 | 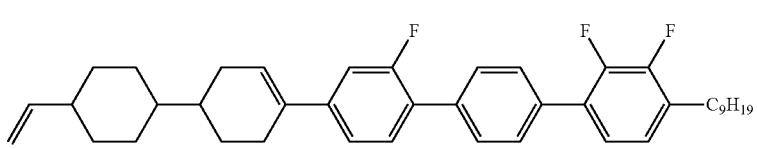 |
| 3430 | 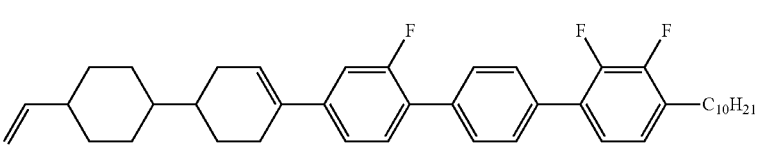 |
| 3431 | 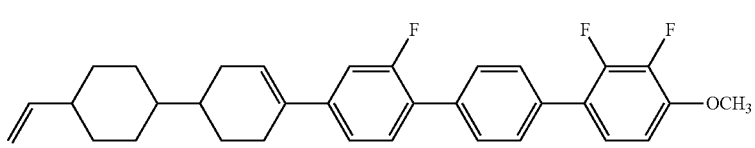 |
| 3432 | 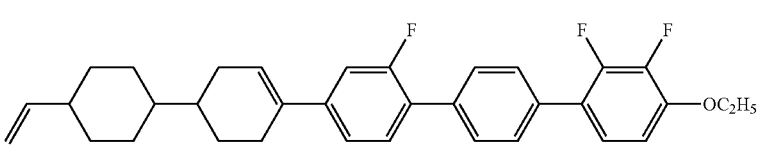 |

-continued
| No. | |
|---|---|
| 3433 | 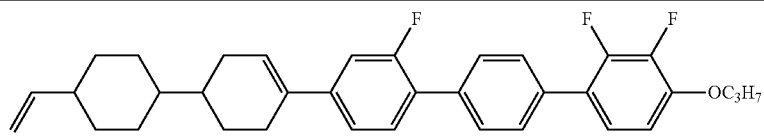 |
| 3434 | 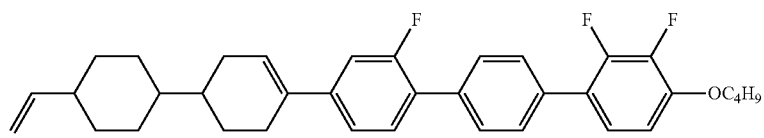 |
| 3435 | 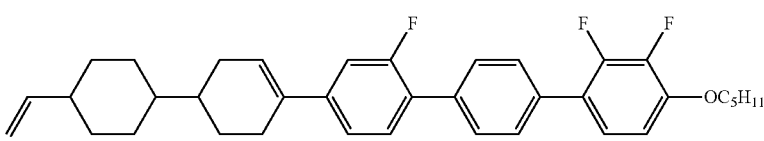 |
| 3436 | 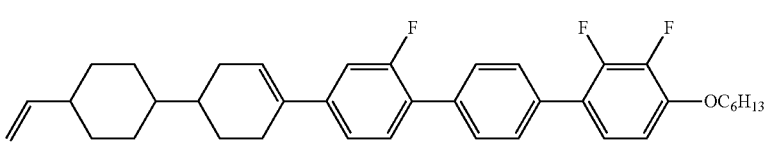 |
| 3437 | 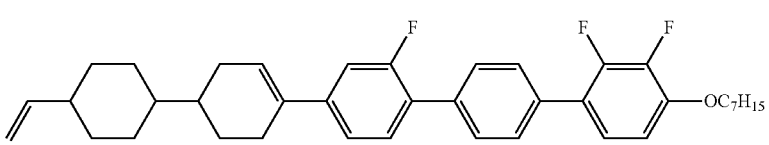 |
| 3438 | 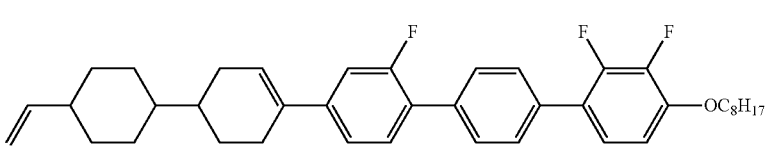 |
| 3439 | 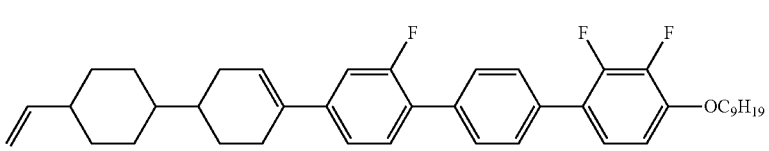 |
| 3440 | 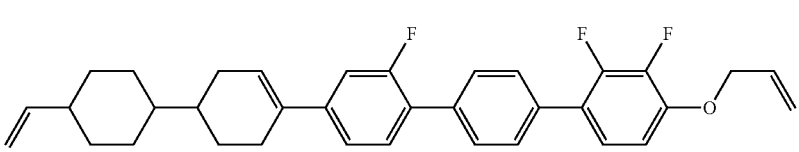 |
| 3441 | 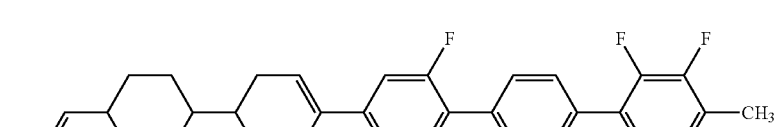 |
| 3442 | 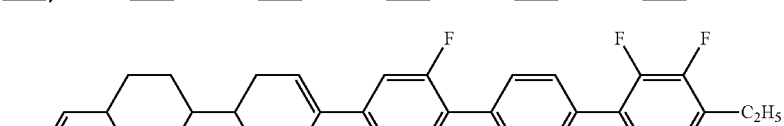 |
| 3443 | 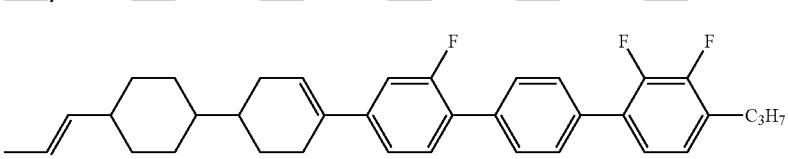 |

-continued
| No. |
|---|
| 3444 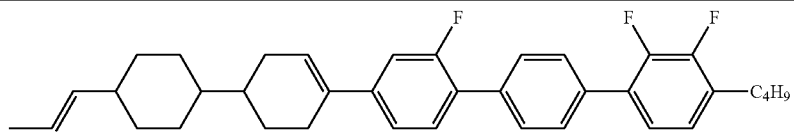 |
| 3445 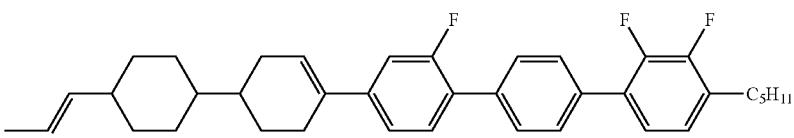 |
| 3446 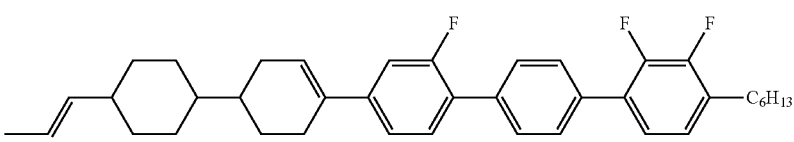 |
| 3447 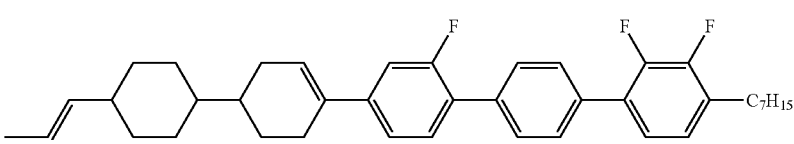 |
| 3448 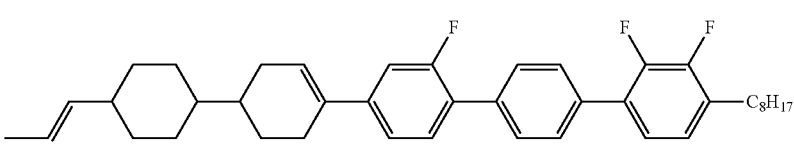 |
| 3449 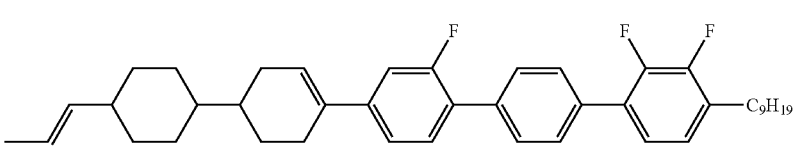 |
| 3450 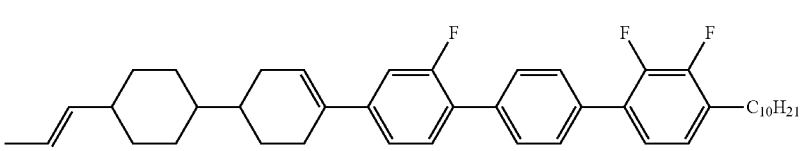 |
| 3451 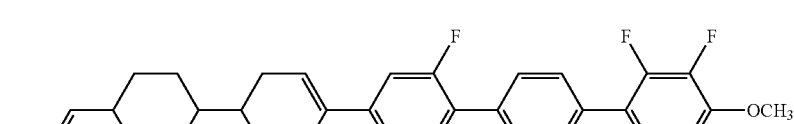 |
| 3452 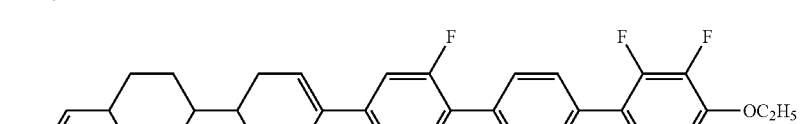 |
| 3453 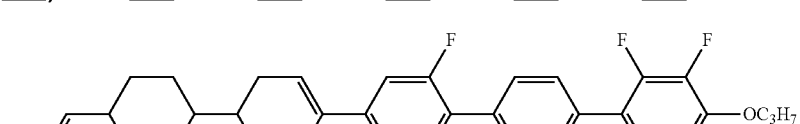 |
| 3454 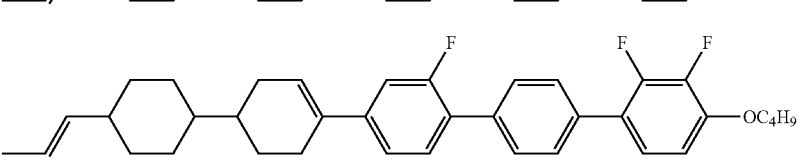 |

| No. | |
|---|---|
| 3455 | 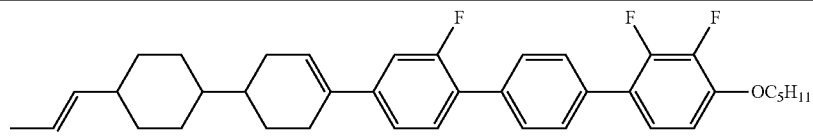 |
| 3456 | 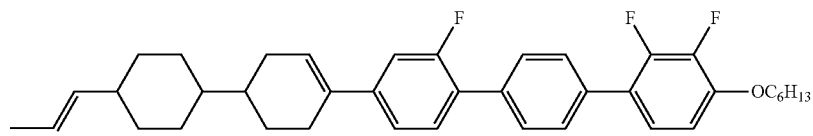 |
| 3457 | 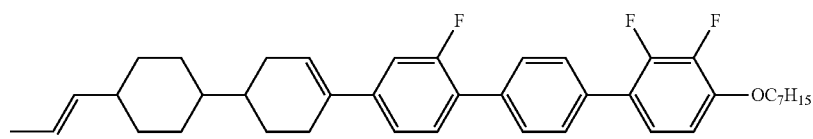 |
| 3458 | 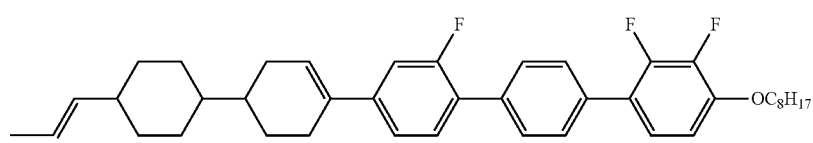 |
| 3459 | 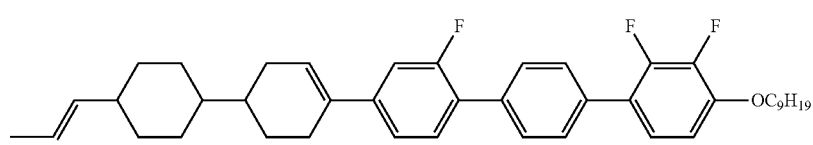 |
| 3460 | 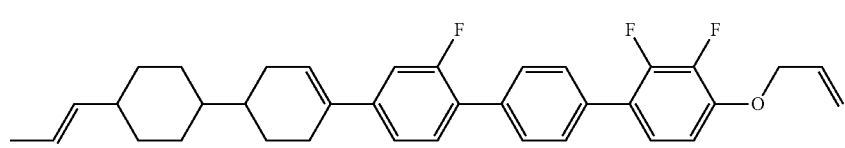 |
| 3461 | 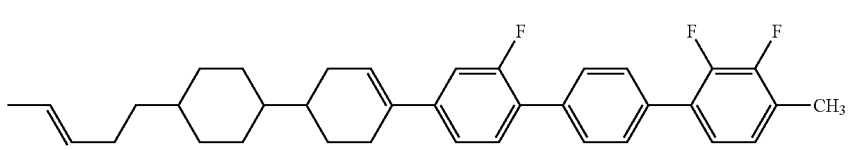 |
| 3462 | 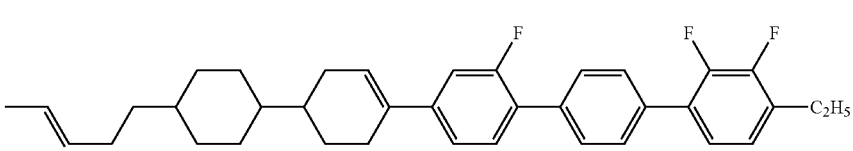 |
| 3463 | 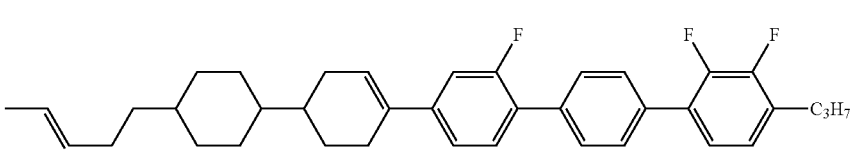 |
| 3464 | 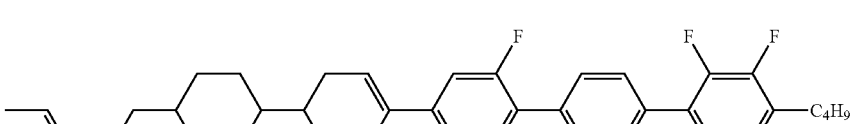 |
| 3465 | 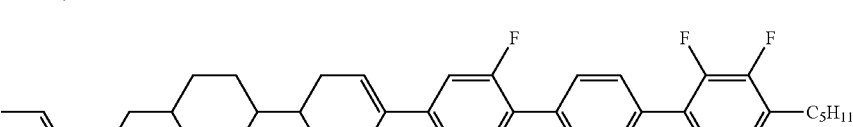 |

| No. | |
|---|---|
| 3466 | 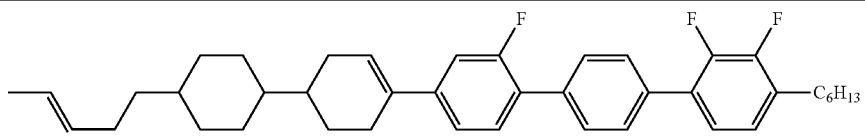 |
| 3467 | 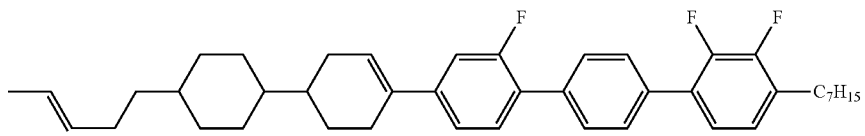 |
| 3468 | 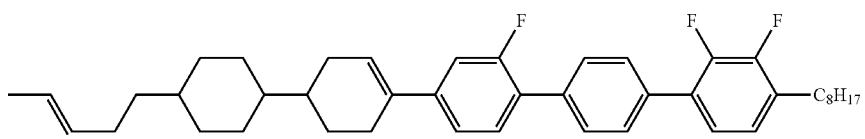 |
| 3469 | 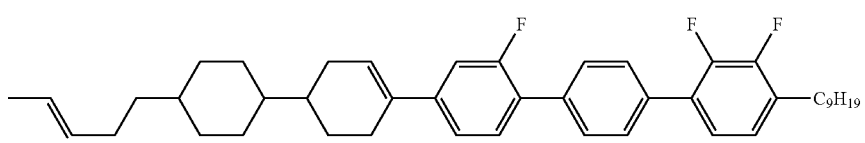 |
| 3470 | 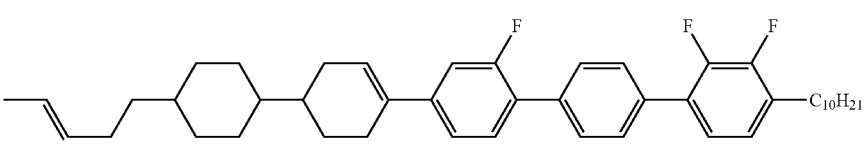 |
| 3471 | 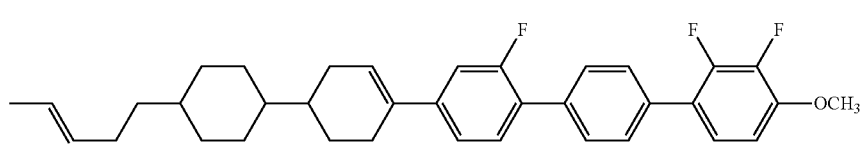 |
| 3472 | 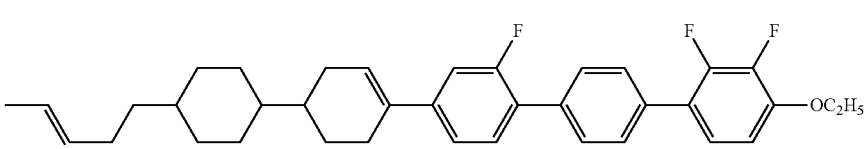 |
| 3473 | 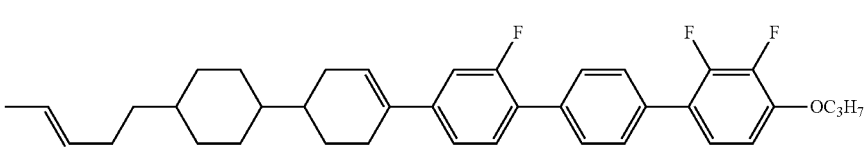 |
| 3474 | 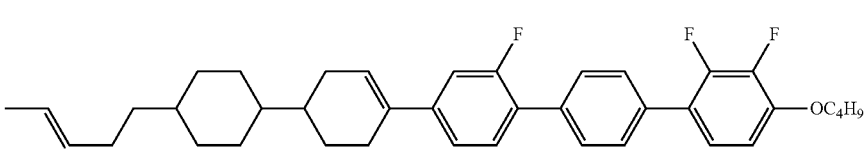 |
| 3475 | 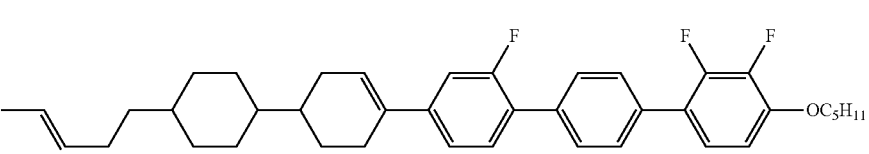 |
| 3476 | 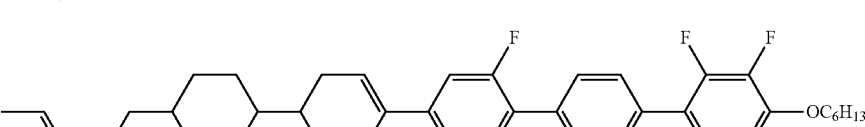 |

-continued
| No. | |
|---|---|
| 3477 | 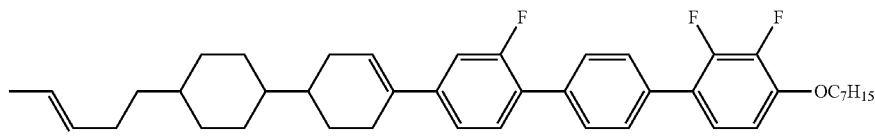 |
| 3478 | 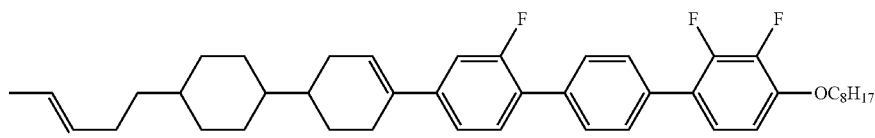 |
| 3479 | 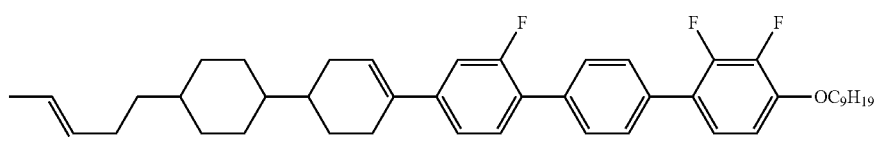 |
| 3480 | 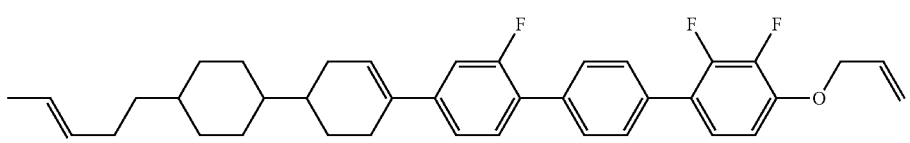 |
| 3481 | 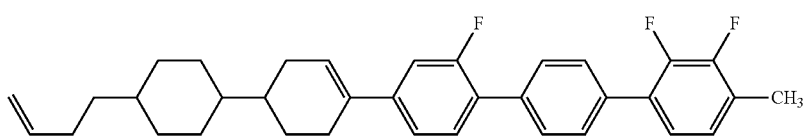 |
| 3482 | 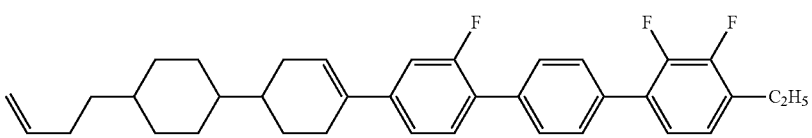 |
| 3483 | 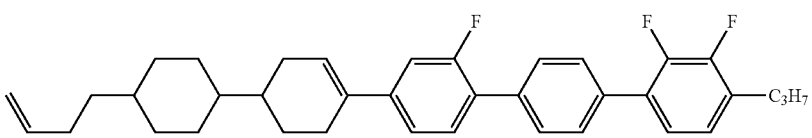 |
| 3484 | 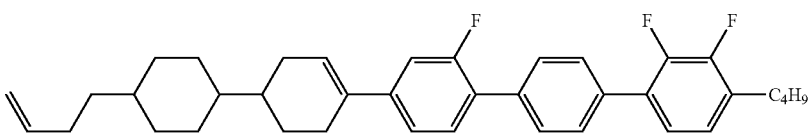 |
| 3485 | 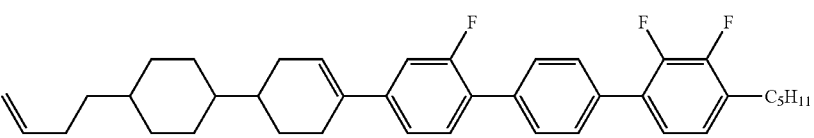 |
| 3486 | 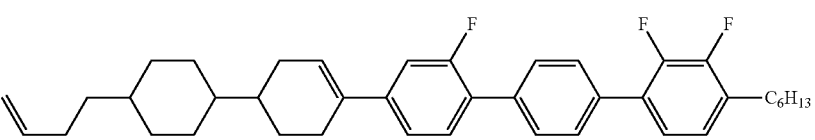 |
| 3487 | 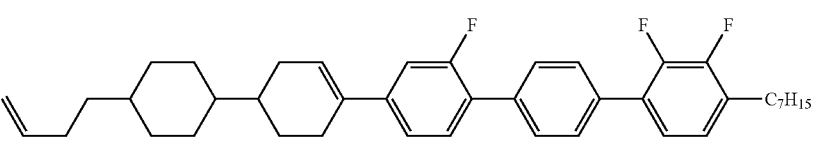 |

| No. |
|---|
| 3488 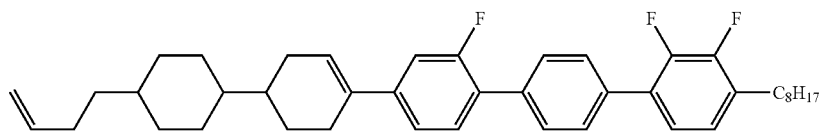 |
| 3489 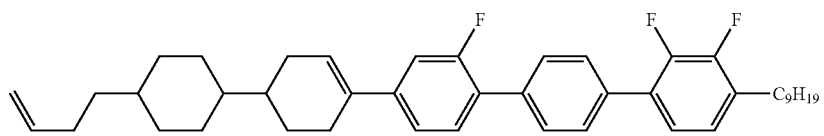 |
| 3490 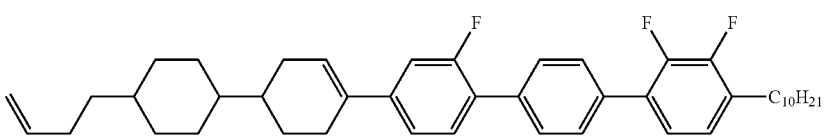 |
| 3491 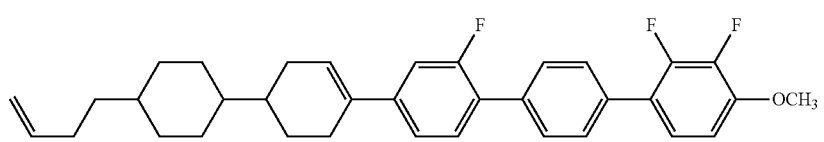 |
| 3492 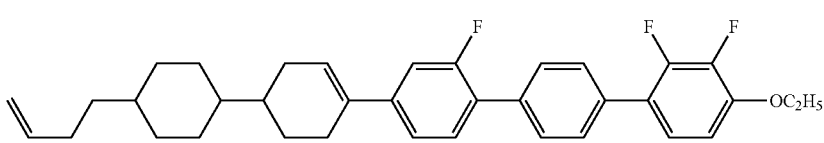 |
| 3493 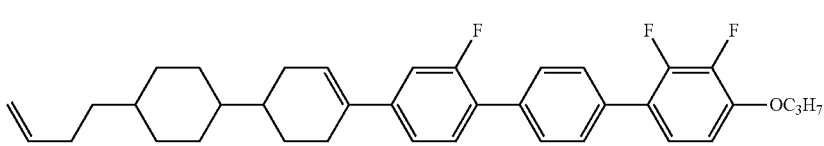 |
| 3494 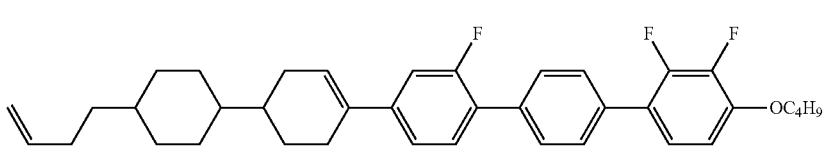 |
| 3495 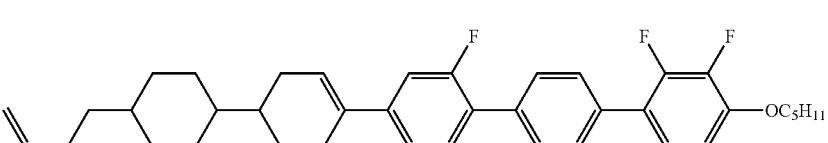 |
| 3496 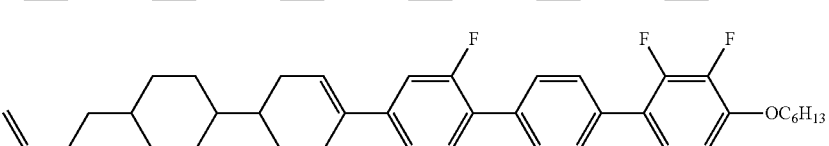 |
| 3497 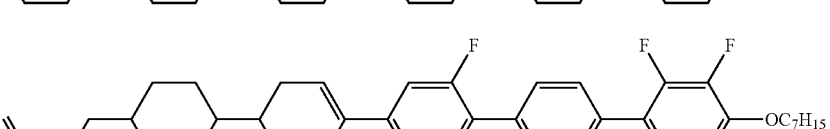 |
| 3498 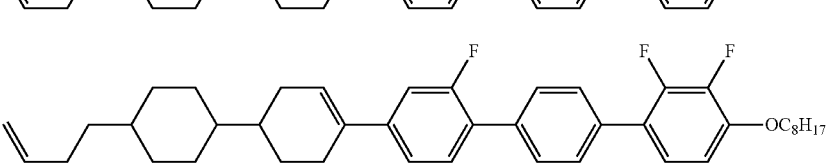 |

| No. |
|---|
| 3499 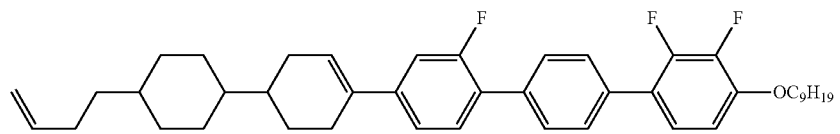 |
| 3500 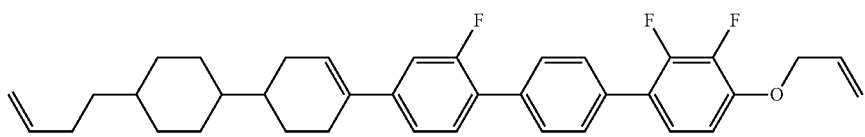 |
| 3501 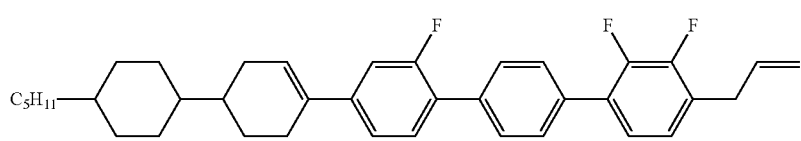 |
| 3502 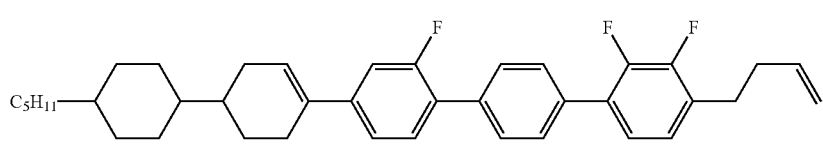 |
| 3503 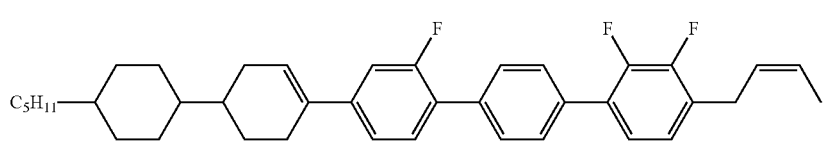 |
| 3504 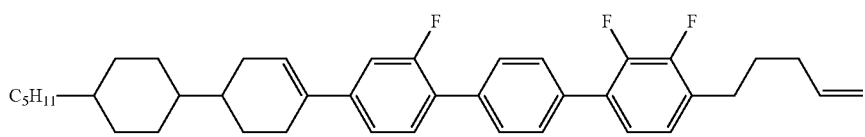 |
| 3505 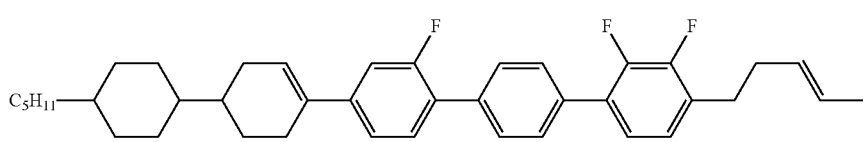 |
| 3506 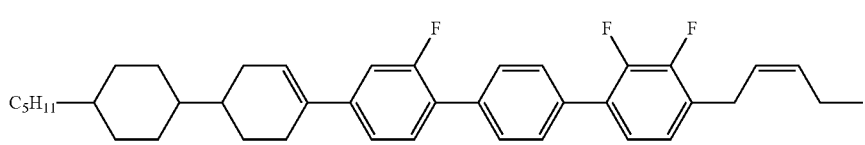 |
| 3507 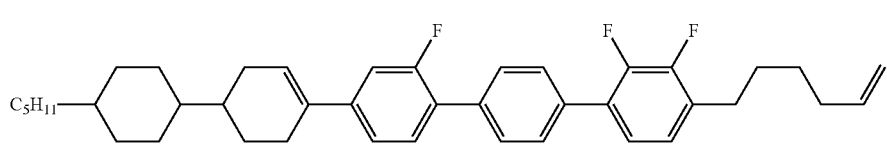 |
| 3508 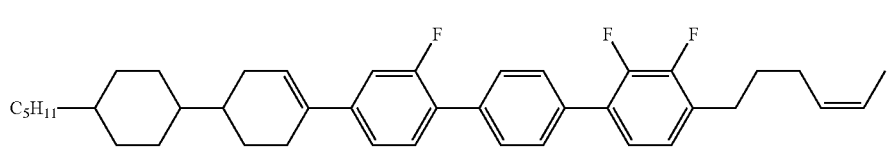 |
| 3509 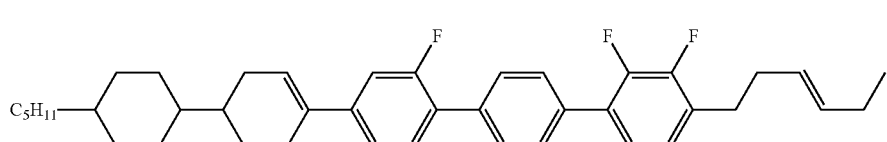 |

| No. |
|---|
| 3510 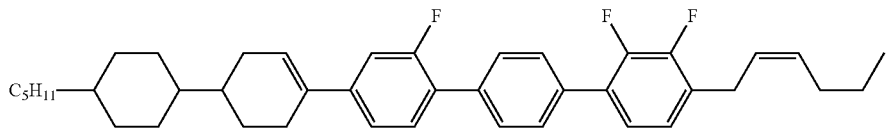 |
| 3511 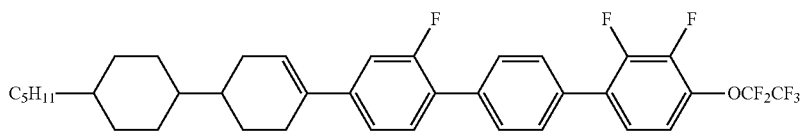 |
| 3512 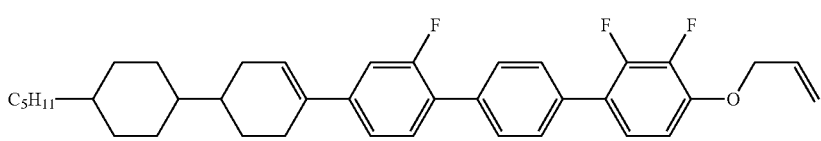 |
| 3513 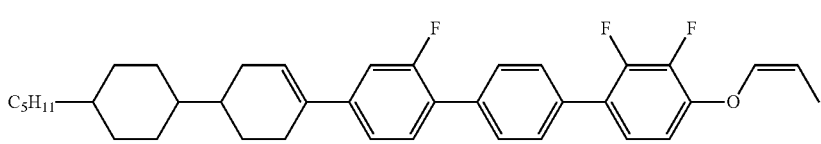 |
| 3514 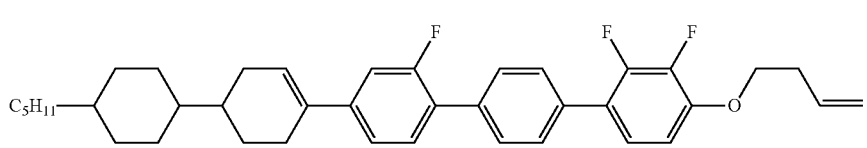 |
| 3515 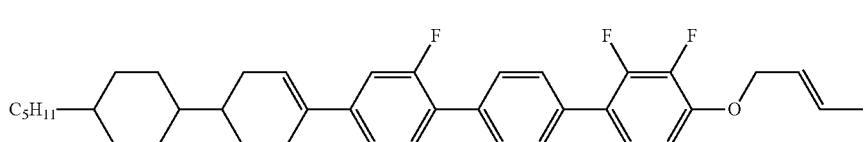 |
| 3516 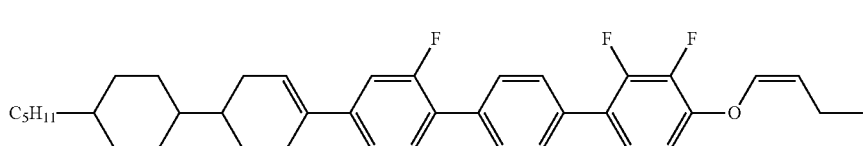 |
| 3517 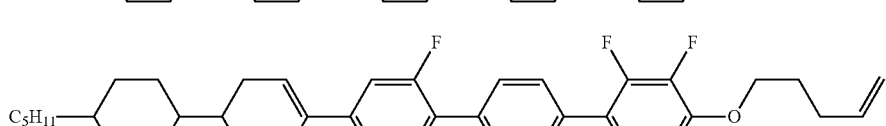 |
| 3518 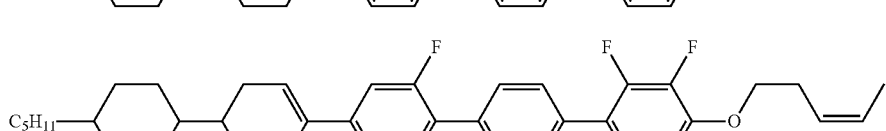 |
| 3519 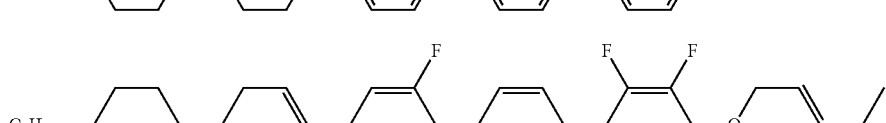 |
| 3520 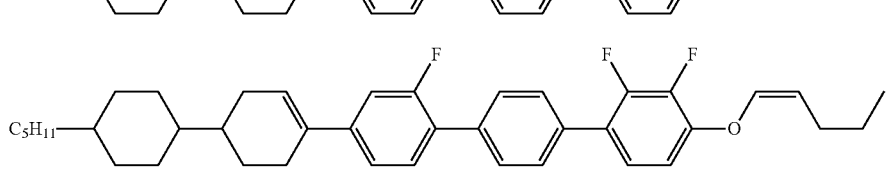 |

| No. | |
|---|---|
| 3521 | 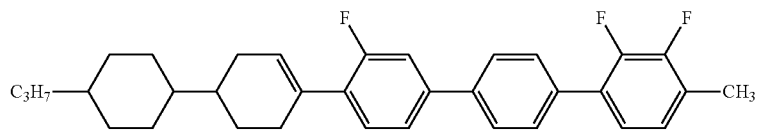 |
| 3522 | 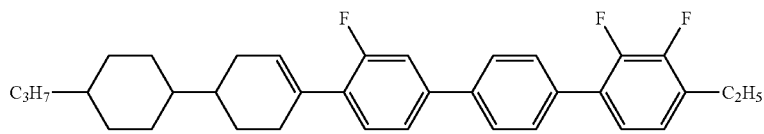 |
| 3523 | 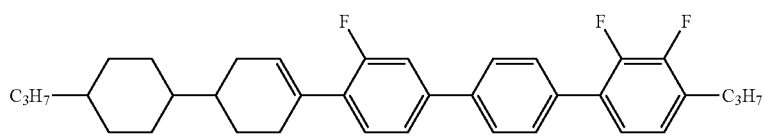 |
| 3524 | 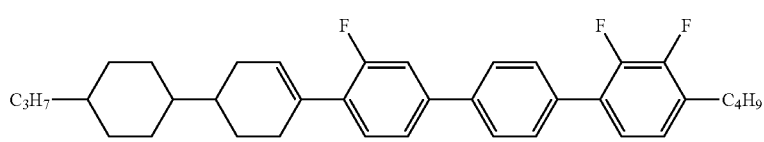 |
| 3525 | 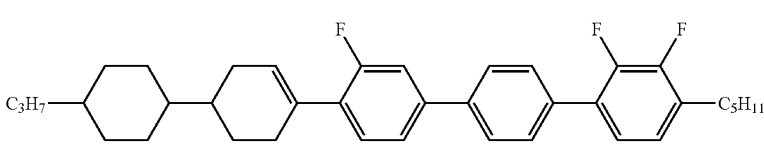 |
| 3526 | 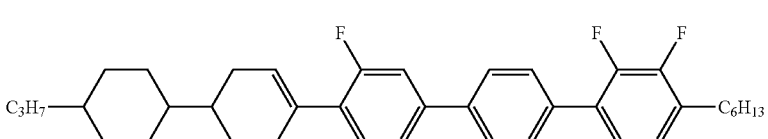 |
| 3527 | 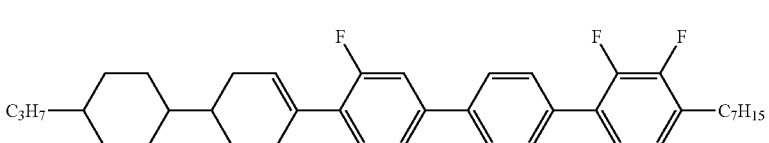 |
| 3528 | 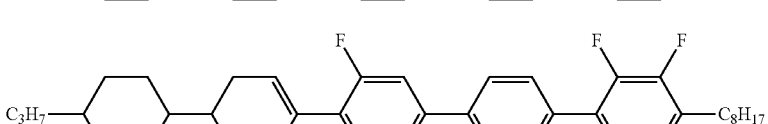 |
| 3529 | 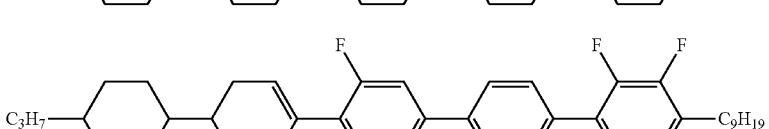 |
| 3530 | 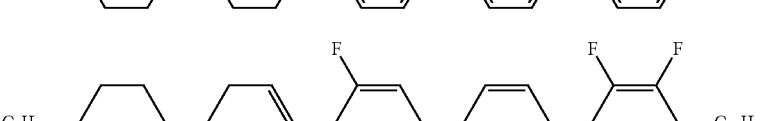 |
| 3531 | 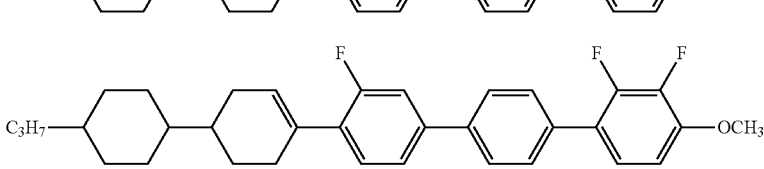 |

| No. | |
|---|---|
| 3532 | 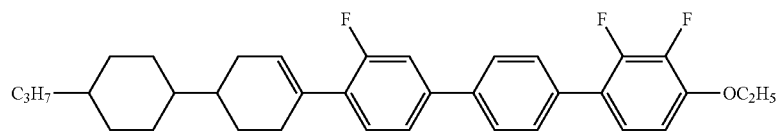 |
| 3533 | 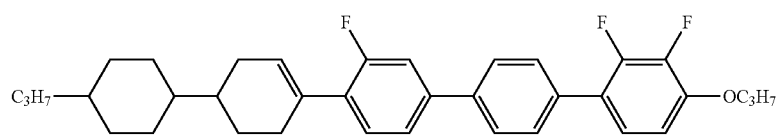 |
| 3534 | 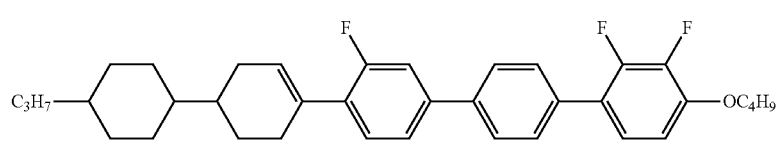 |
| 3535 | 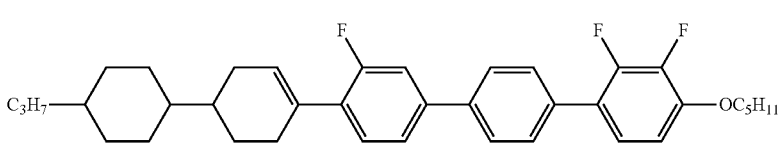 |
| 3536 | 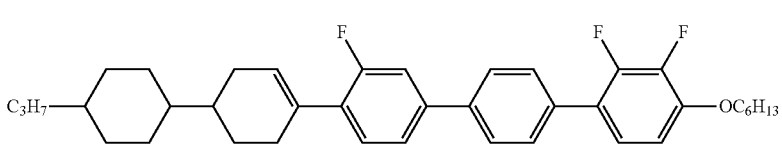 |
| 3537 | 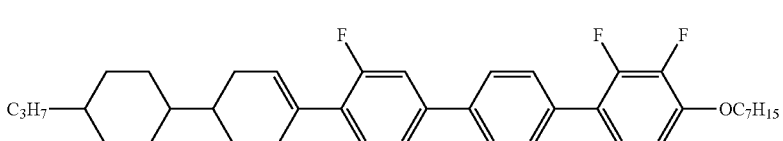 |
| 3538 | 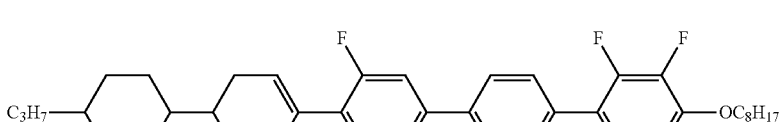 |
| 3539 | 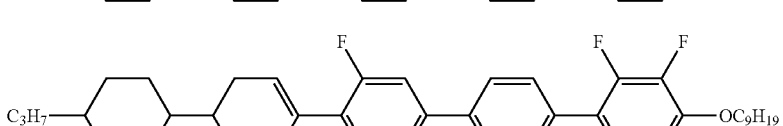 |
| 3540 | 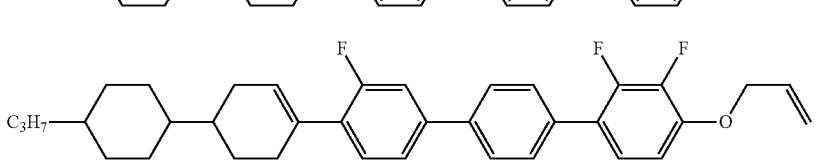 |
| 3541 | 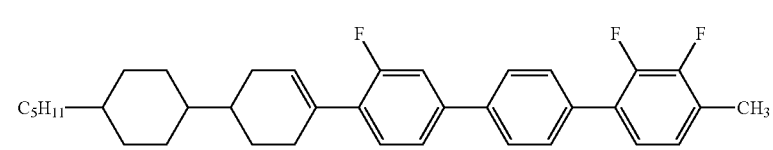 |
| 3542 | 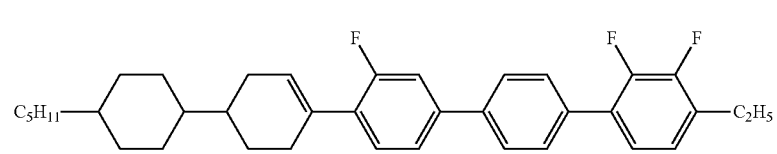 |

| No. | |
|---|---|
| 3543 | 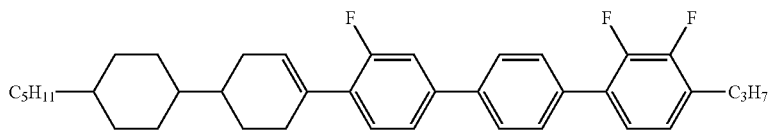 |
| 3544 | 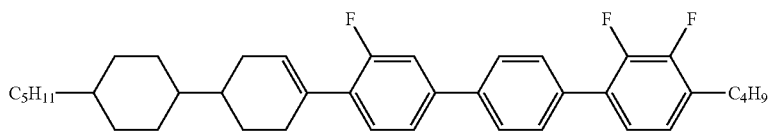 |
| 3545 | 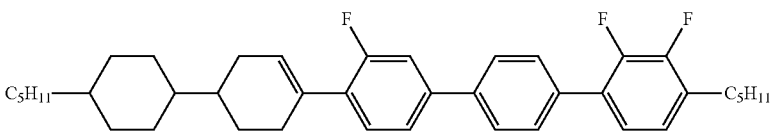 |
| 3546 | 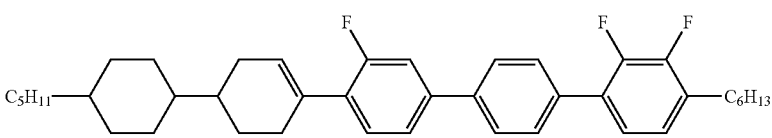 |
| 3547 | 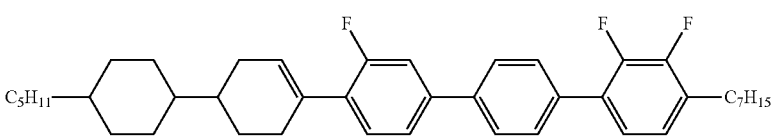 |
| 3548 | 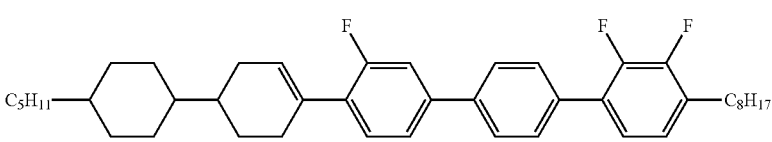 |
| 3549 | 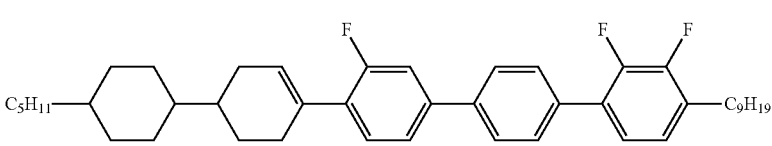 |
| 3550 | 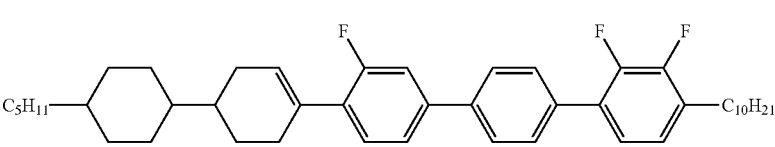 |
| 3551 | 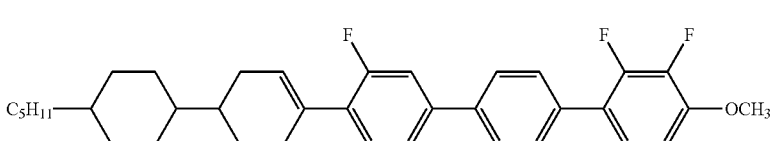 |
| 3552 | 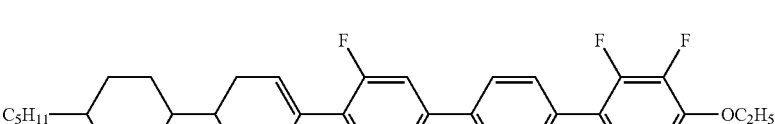 |
| 3553 | 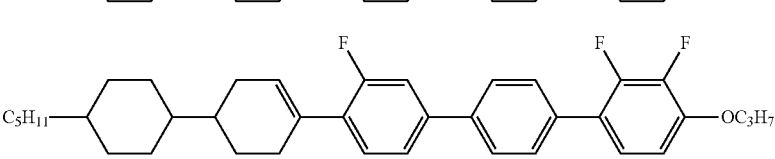 |

| No. | |
|---|---|
| 3554 | 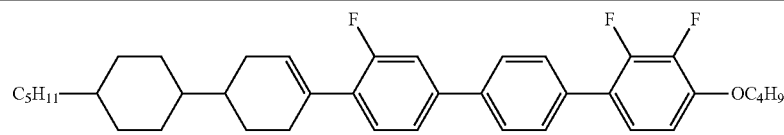 |
| 3555 | 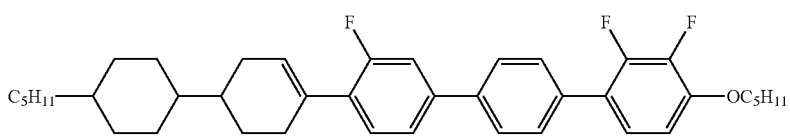 |
| 3556 | 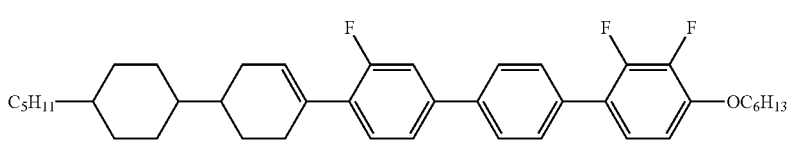 |
| 3557 | 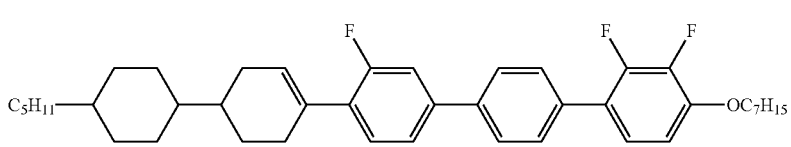 |
| 3558 | 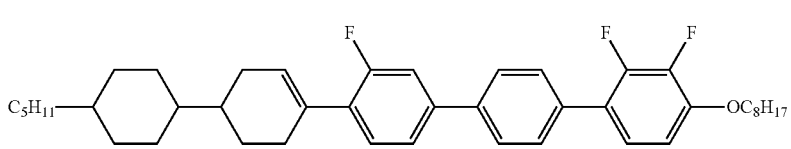 |
| 3559 | 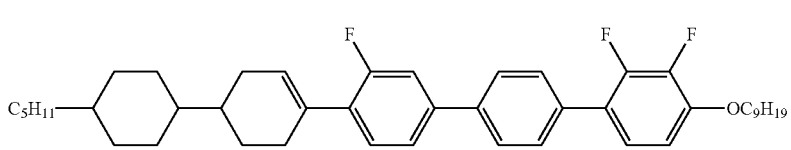 |
| 3560 | 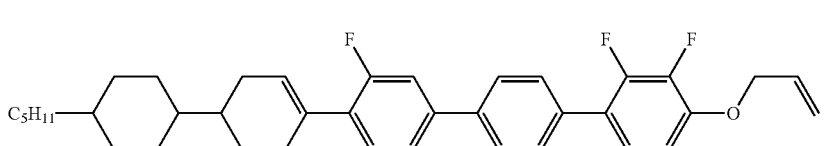 |
| 3561 | 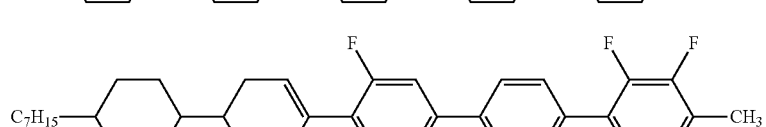 |
| 3562 | 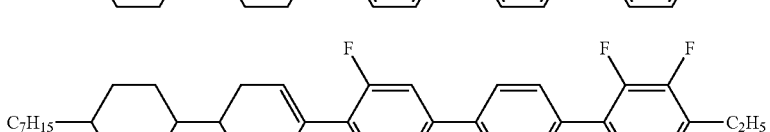 |
| 3563 | 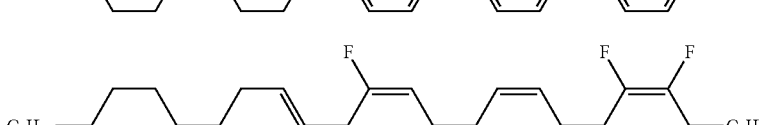 |
| 3564 | 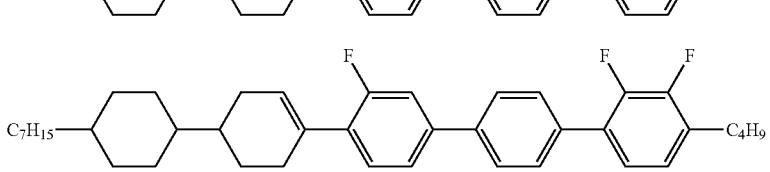 |

| No. | |
|---|---|
| 3565 | 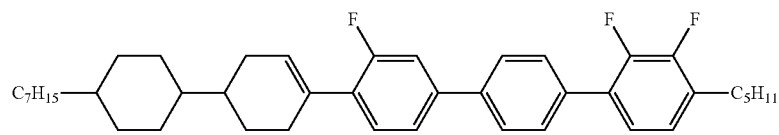 |
| 3566 | 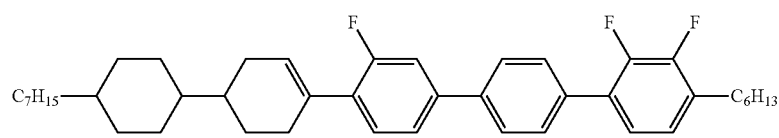 |
| 3567 | 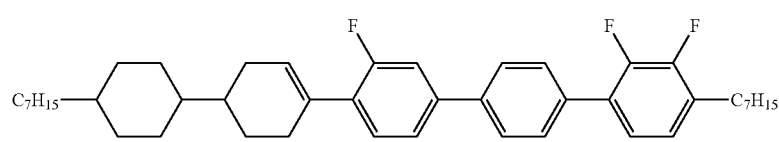 |
| 3568 | 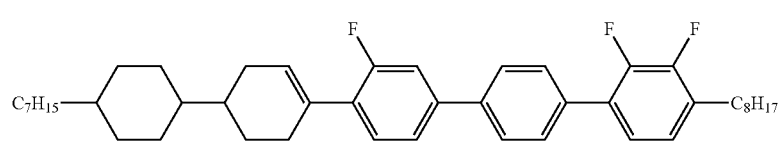 |
| 3569 | 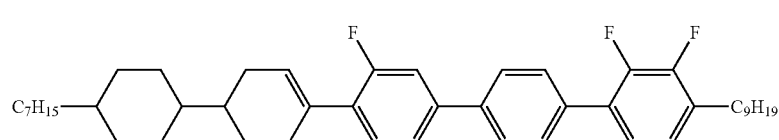 |
| 3570 | 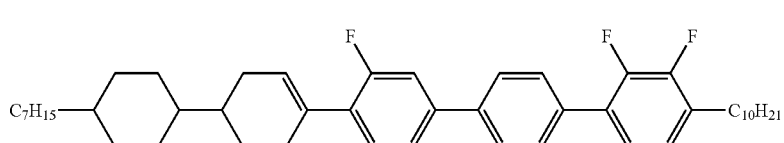 |
| 3571 | 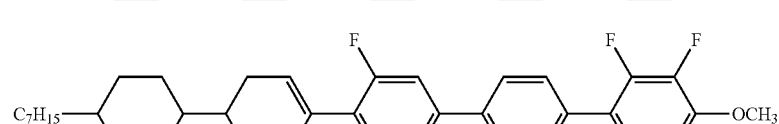 |
| 3572 | 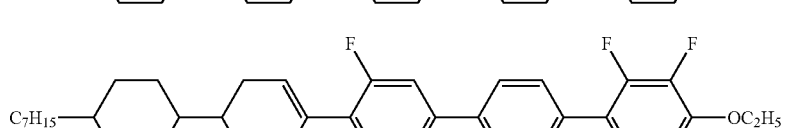 |
| 3573 | 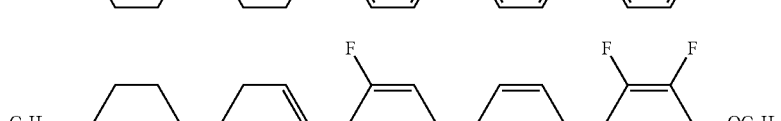 |
| 3574 | 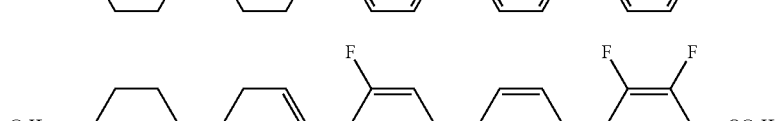 |
| 3575 | 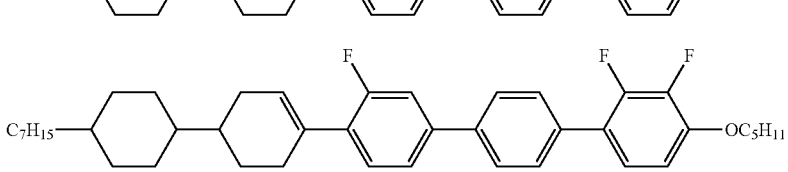 |

| No. | |
|---|---|
| 3576 | C7H15—[Cy]—[Cy]—[Ph(F)]—[Ph]—[Ph(F,F)]—OC6H13 |
| 3577 | C7H15—[Cy]—[Cy]—[Ph(F)]—[Ph]—[Ph(F,F)]—OC7H15 |
| 3578 | C7H15—[Cy]—[Cy]—[Ph(F)]—[Ph]—[Ph(F,F)]—OC8H17 |
| 3579 | C7H15—[Cy]—[Cy]—[Ph(F)]—[Ph]—[Ph(F,F)]—OC9H19 |
| 3580 | C7H15—[Cy]—[Cy]—[Ph(F)]—[Ph]—[Ph(F,F)]—O-CH2-CH=CH2 |
| 3581 | CH2=CH—[Cy]—[Cy]—[Ph(F)]—[Ph]—[Ph(F,F)]—CH3 |
| 3582 | CH2=CH—[Cy]—[Cy]—[Ph(F)]—[Ph]—[Ph(F,F)]—C2H5 |
| 3583 | CH2=CH—[Cy]—[Cy]—[Ph(F)]—[Ph]—[Ph(F,F)]—C3H7 |
| 3584 | CH2=CH—[Cy]—[Cy]—[Ph(F)]—[Ph]—[Ph(F,F)]—C4H9 |
| 3585 | CH2=CH—[Cy]—[Cy]—[Ph(F)]—[Ph]—[Ph(F,F)]—C5H11 |
| 3586 | CH2=CH—[Cy]—[Cy]—[Ph(F)]—[Ph]—[Ph(F,F)]—C6H13 |

| No. | |
|---|---|
| 3587 | 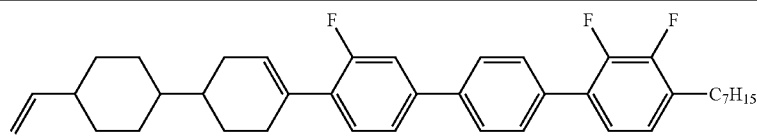 |
| 3588 | 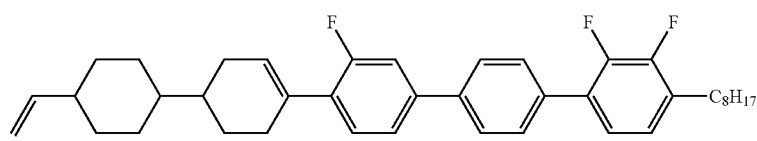 |
| 3589 | 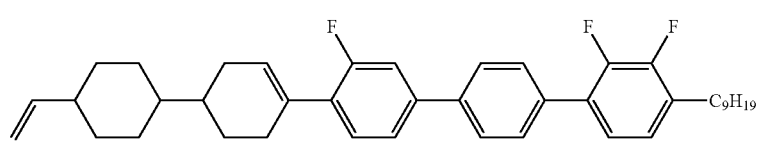 |
| 3590 | 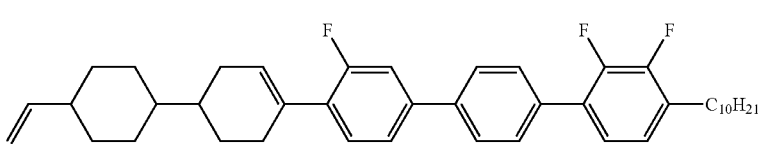 |
| 3591 | 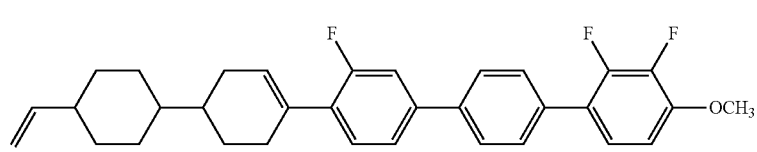 |
| 3592 | 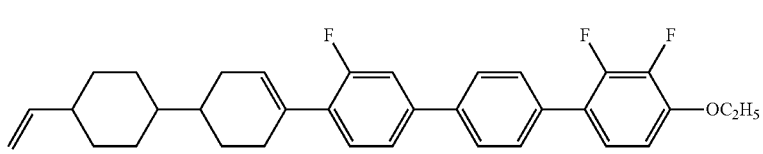 |
| 3593 | 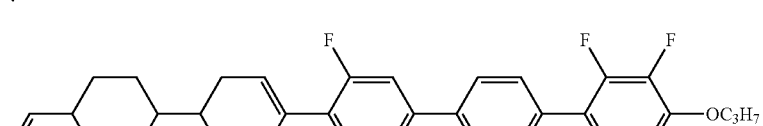 |
| 3594 | 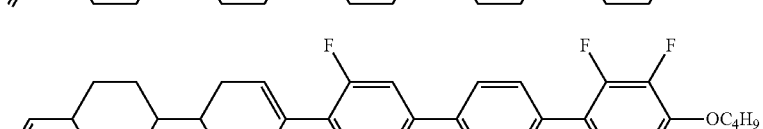 |
| 3595 | 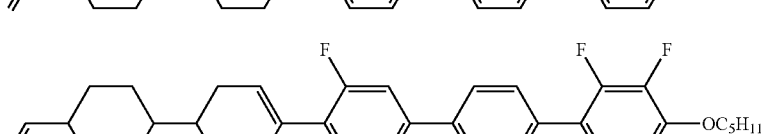 |
| 3596 | 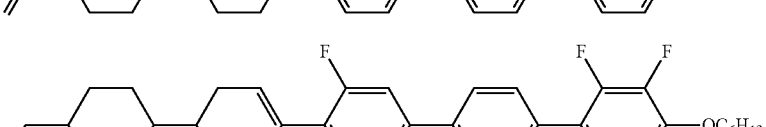 |
| 3597 | 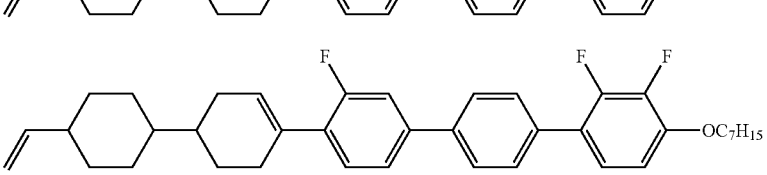 |

| No. | |
|---|---|
| 3598 | 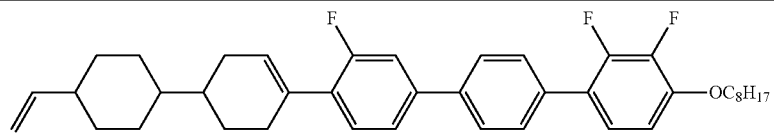 |
| 3599 | 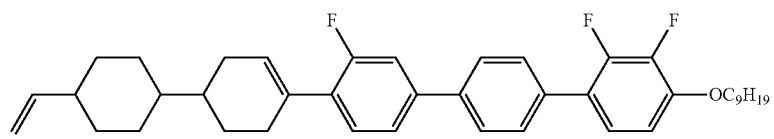 |
| 3600 | 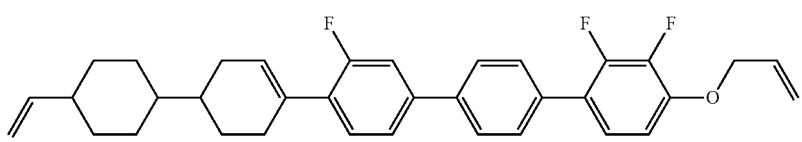 |
| 3601 | 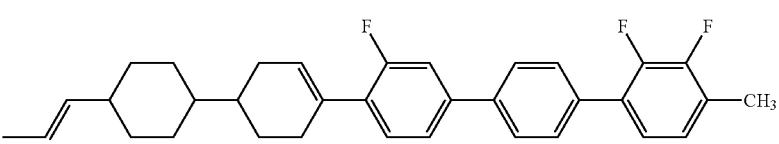 |
| 3602 | 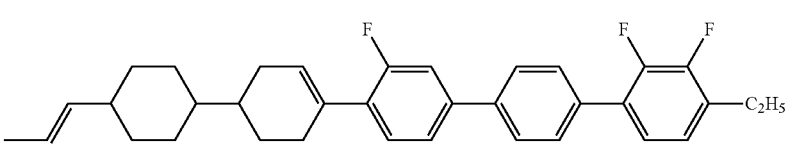 |
| 3603 | 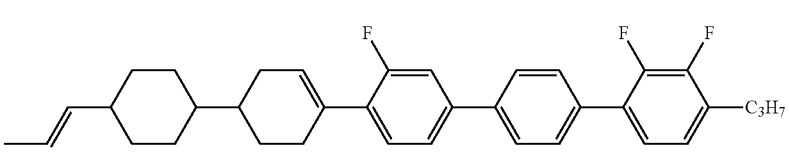 |
| 3604 | 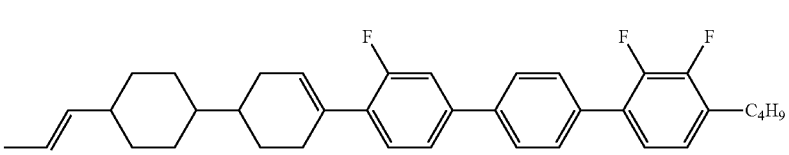 |
| 3605 | 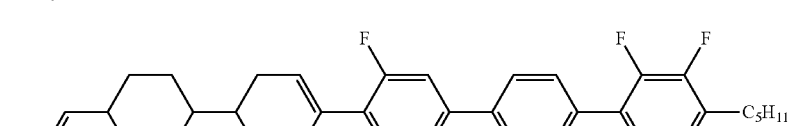 |
| 3606 | 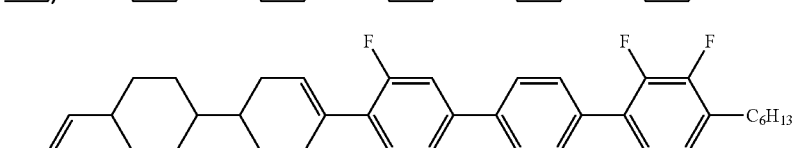 |
| 3607 | 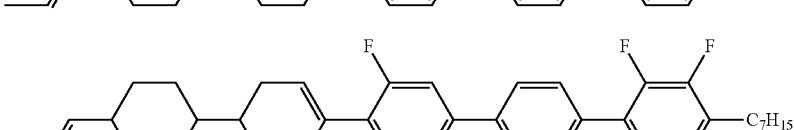 |
| 3608 | 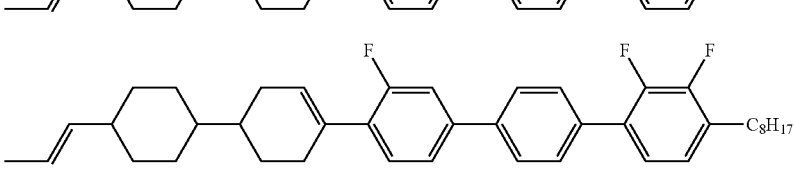 |

| No. | |
|---|---|
| 3609 | 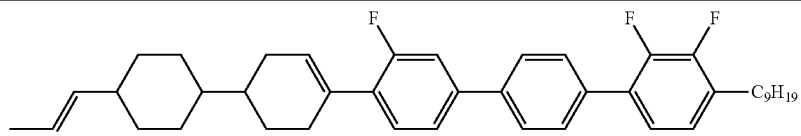 |
| 3610 | 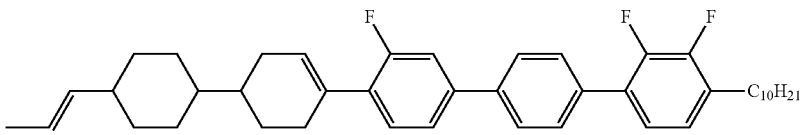 |
| 3611 | 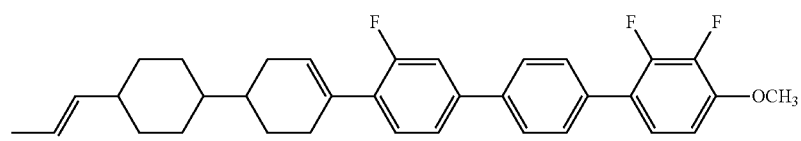 |
| 3612 | 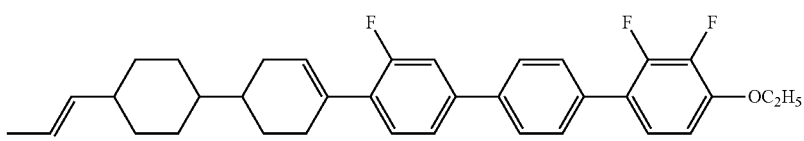 |
| 3613 | 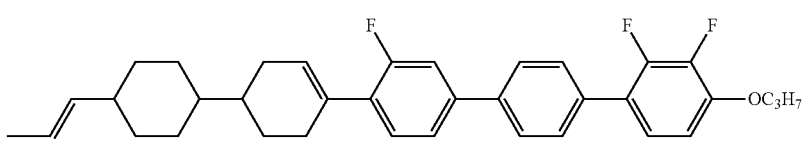 |
| 3614 | 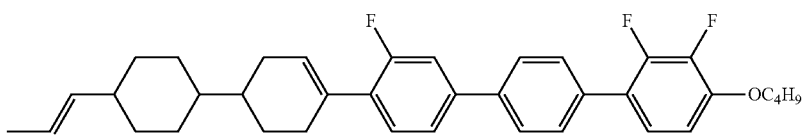 |
| 3615 | 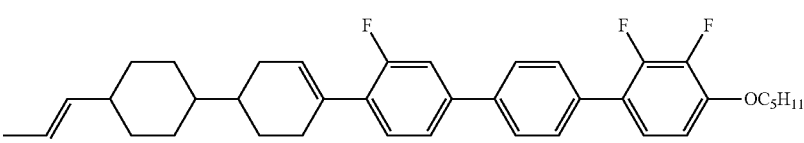 |
| 3616 | 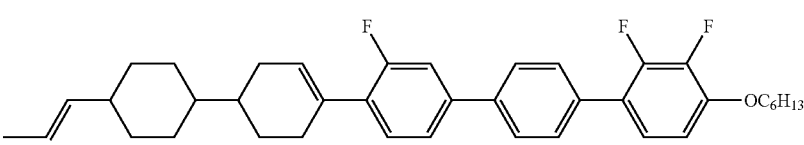 |
| 3617 | 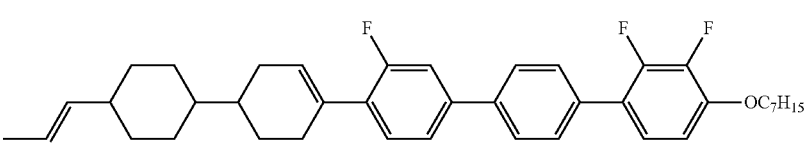 |
| 3618 | 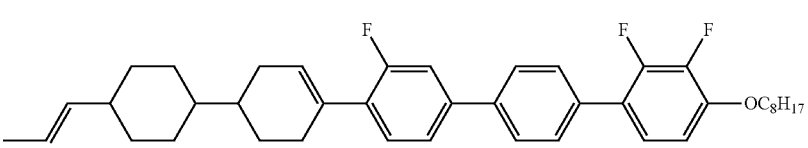 |
| 3619 | 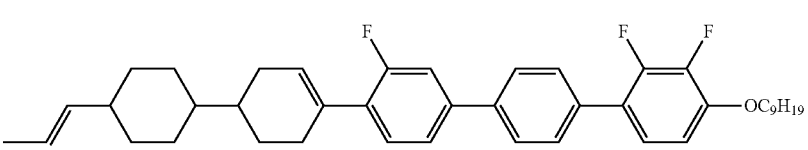 |

| No. | |
|---|---|
| 3620 | 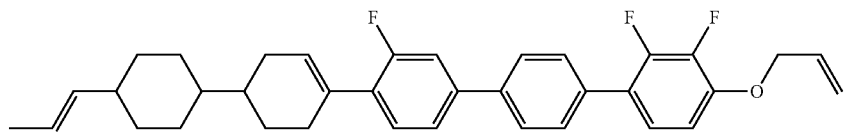 |
| 3621 | 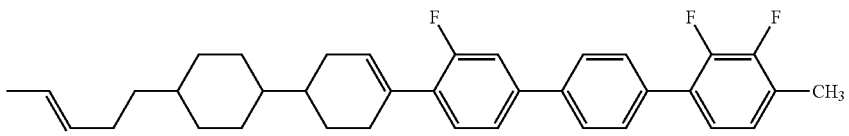 |
| 3622 | 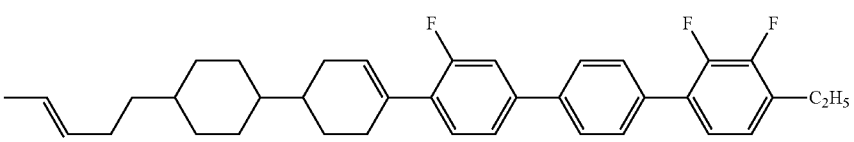 |
| 3623 | 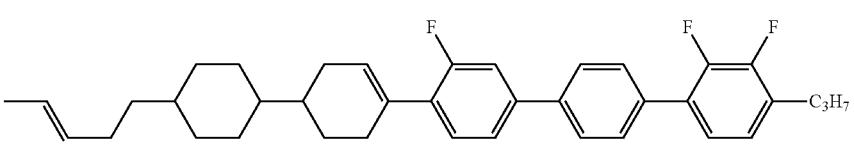 |
| 3624 | 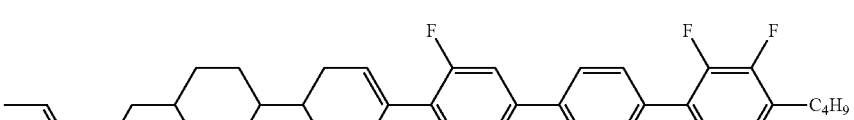 |
| 3625 | 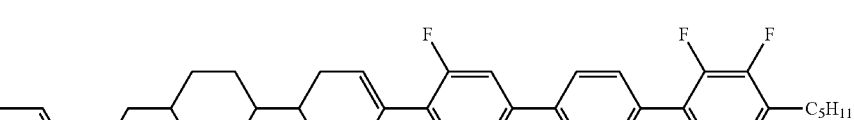 |
| 3626 | 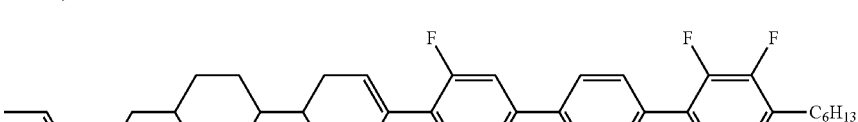 |
| 3627 | 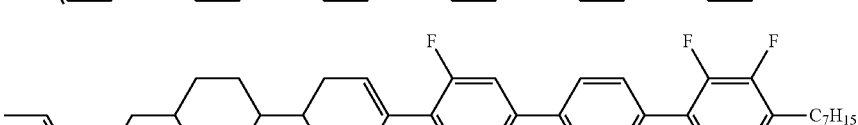 |
| 3628 | 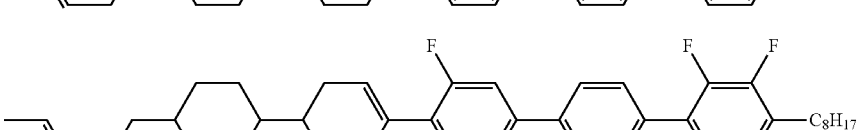 |
| 3629 | 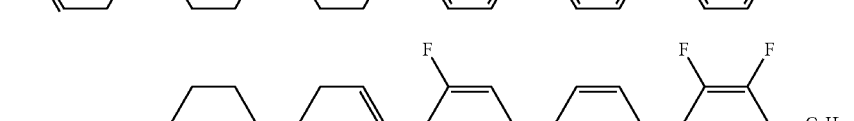 |
| 3630 | 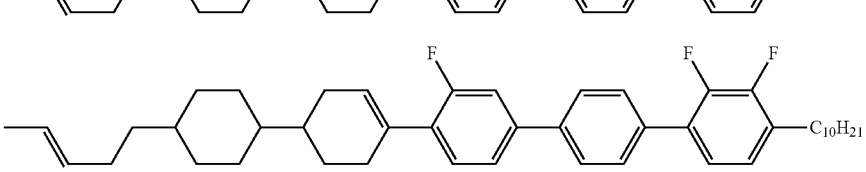 |

-continued
| No. | |
|---|---|
| 3631 | 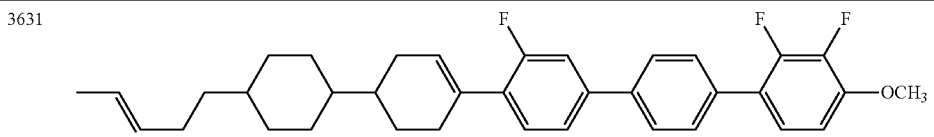 |
| 3632 | 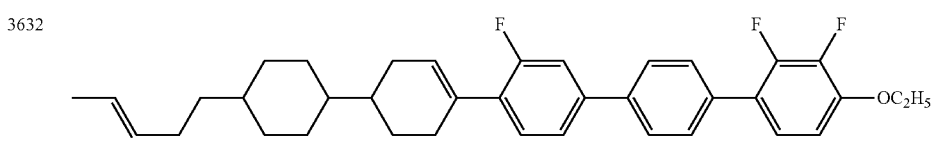 |
| 3633 | 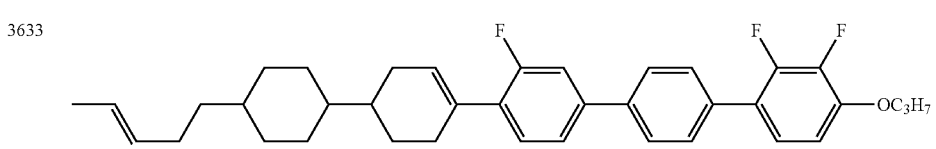 |
| 3634 | 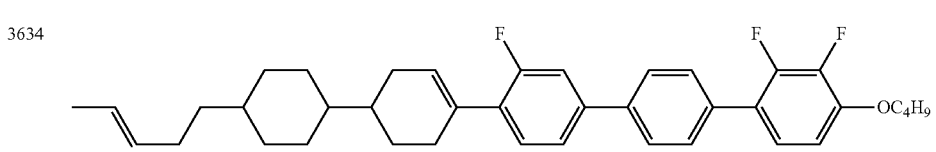 |
| 3635 | 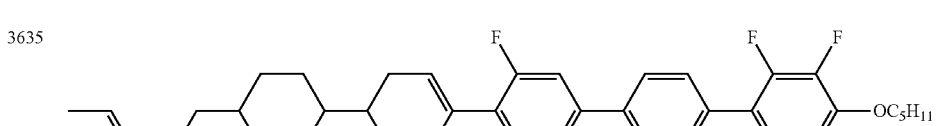 |
| 3636 | 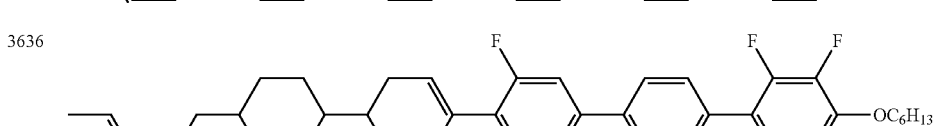 |
| 3637 | 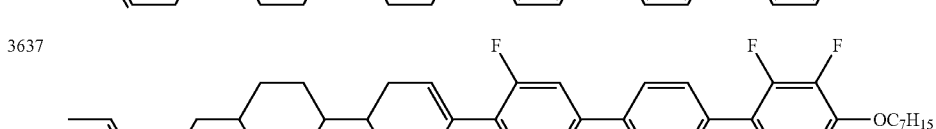 |
| 3638 | 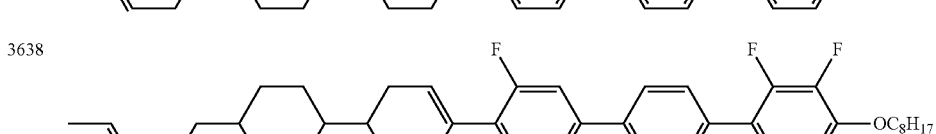 |
| 3639 | 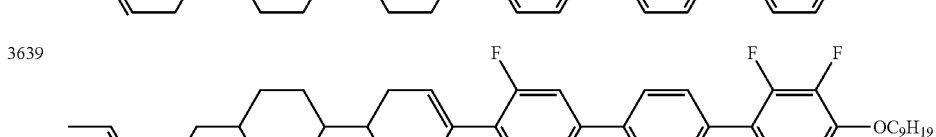 |
| 3640 | 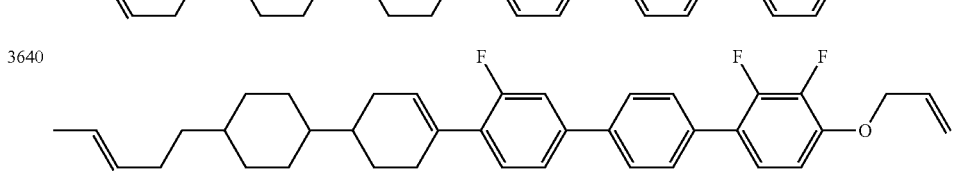 |
| 3641 | 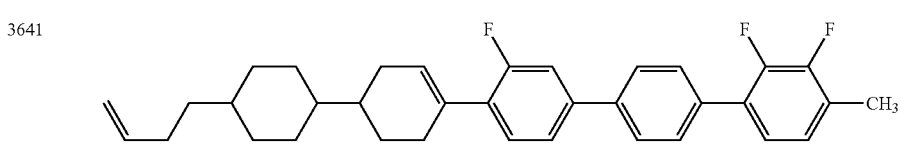 |

| No. | |
|---|---|
| 3642 | 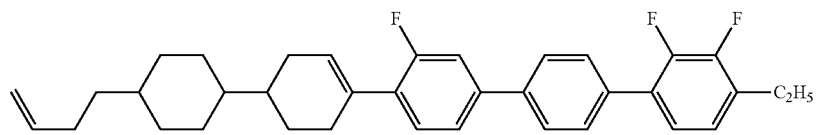 |
| 3643 | 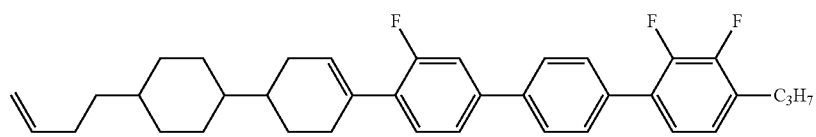 |
| 3644 | 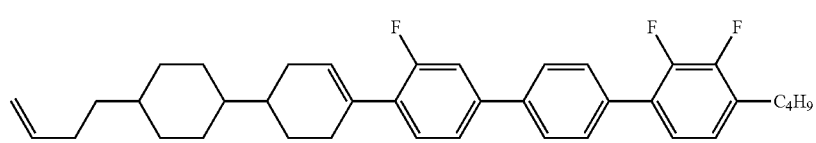 |
| 3645 | 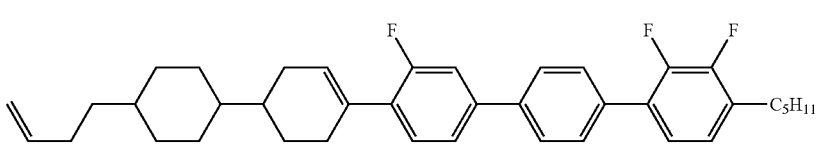 |
| 3646 | 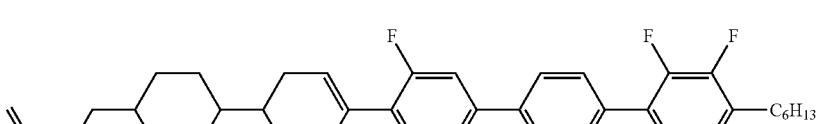 |
| 3647 | 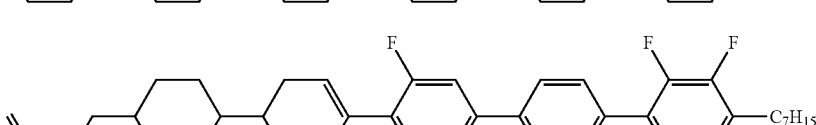 |
| 3648 | 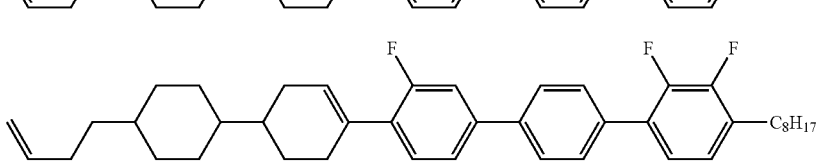 |
| 3649 | 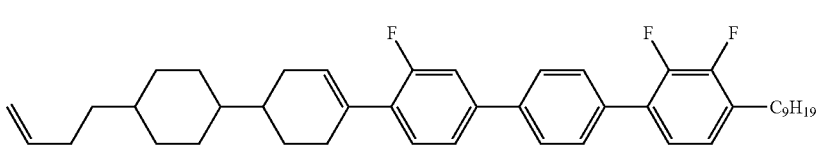 |
| 3650 | 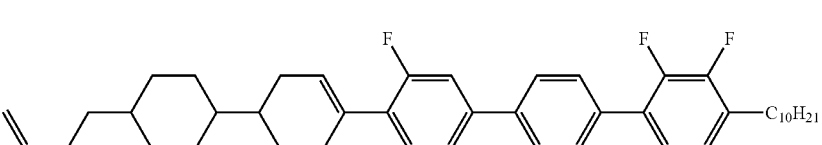 |
| 3651 |  |
| 3652 | 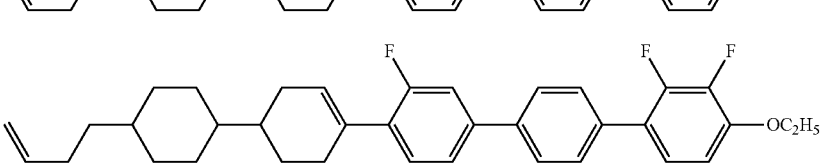 |

-continued
| No. |
|---|
| 3653 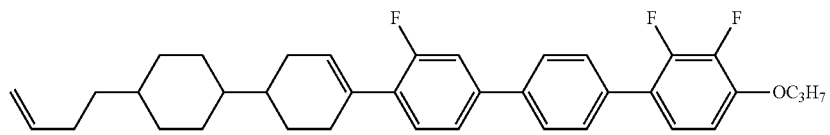 |
| 3654 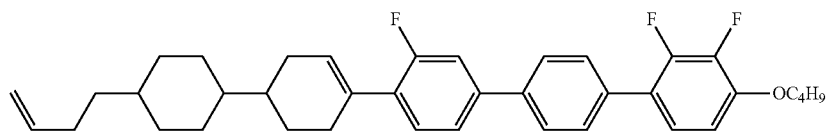 |
| 3655 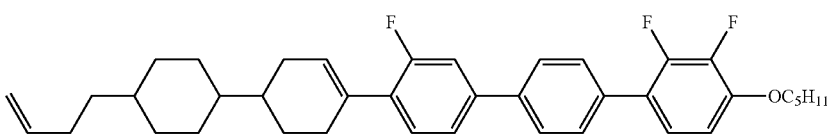 |
| 3656 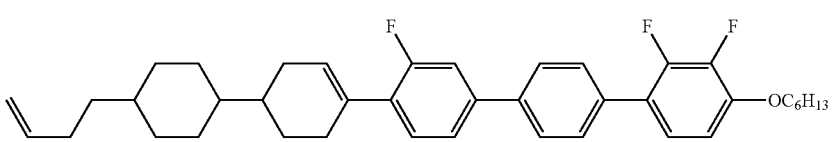 |
| 3657 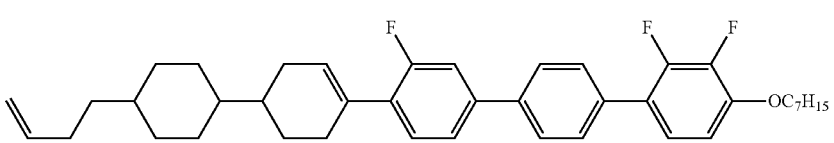 |
| 3658 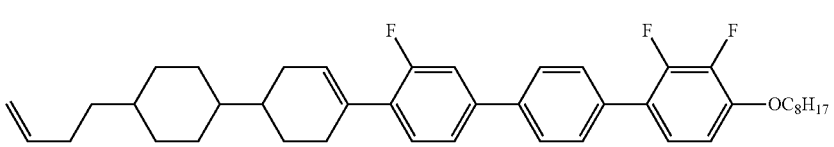 |
| 3659 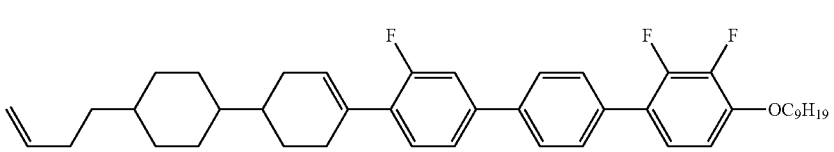 |
| 3660 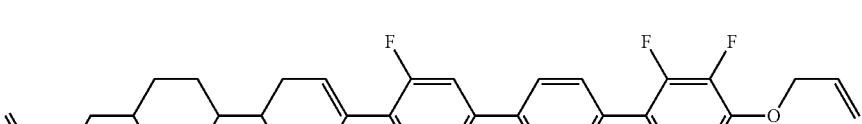 |
| 3661 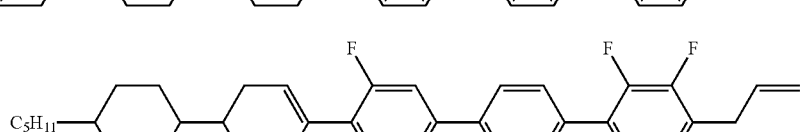 |
| 3662 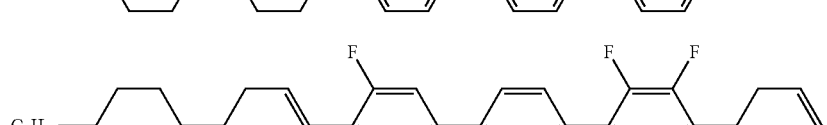 |
| 3663 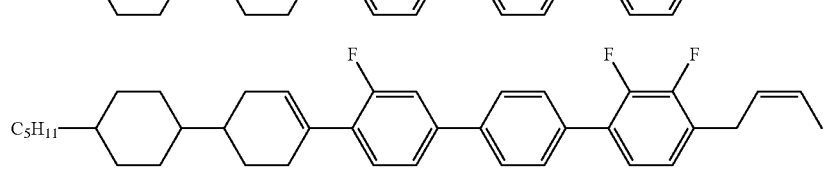 |

| No. | |
|---|---|
| 3664 | C5H11-[Cy]-[Cy]-[C6H3(F)]-[C6H4]-[C6H2(F)(F)]-CH2CH2CH=CH2 |
| 3665 | C5H11-[Cy]-[Cy]-[C6H3(F)]-[C6H4]-[C6H2(F)(F)]-CH2CH=CHCH3 (E) |
| 3666 | C5H11-[Cy]-[Cy]-[C6H3(F)]-[C6H4]-[C6H2(F)(F)]-CH2CH=CHCH3 (Z) |
| 3667 | C5H11-[Cy]-[Cy]-[C6H3(F)]-[C6H4]-[C6H2(F)(F)]-(CH2)3CH=CH2 |
| 3668 | C5H11-[Cy]-[Cy]-[C6H3(F)]-[C6H4]-[C6H2(F)(F)]-CH2CH2CH=CHCH3 (Z) |
| 3669 | C5H11-[Cy]-[Cy]-[C6H3(F)]-[C6H4]-[C6H2(F)(F)]-CH2CH=CHC2H5 (E) |
| 3670 | C5H11-[Cy]-[Cy]-[C6H3(F)]-[C6H4]-[C6H2(F)(F)]-CH2CH=CHC2H5 (Z) |
| 3671 | C5H11-[Cy]-[Cy]-[C6H3(F)]-[C6H4]-[C6H2(F)(F)]-OCF2CF3 |
| 3672 | C5H11-[Cy]-[Cy]-[C6H3(F)]-[C6H4]-[C6H2(F)(F)]-OCH2CH=CH2 |
| 3673 | C5H11-[Cy]-[Cy]-[C6H3(F)]-[C6H4]-[C6H2(F)(F)]-OCH=CHCH3 |
| 3674 | C5H11-[Cy]-[Cy]-[C6H3(F)]-[C6H4]-[C6H2(F)(F)]-OCH2CH2CH=CH2 |

| No. |
|---|
| 3675 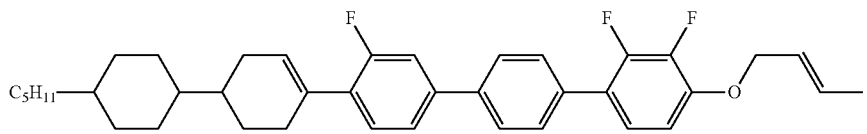 |
| 3676 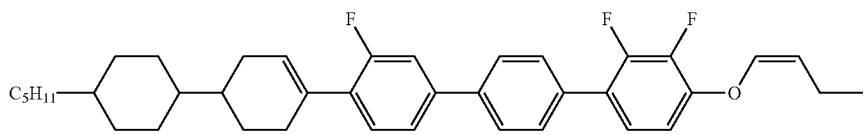 |
| 3677 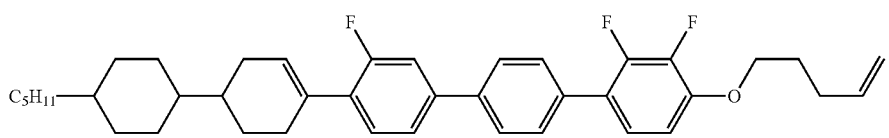 |
| 3678 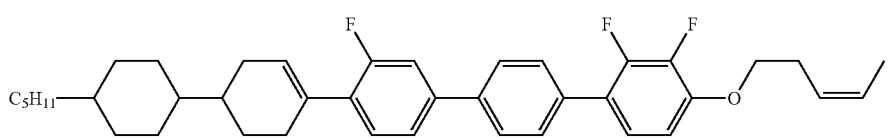 |
| 3679 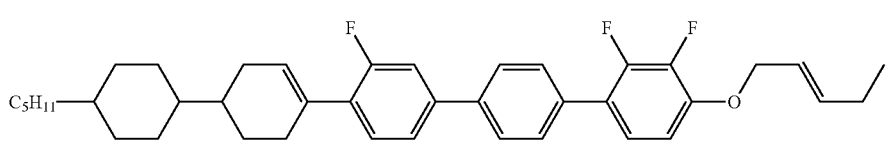 |
| 3680 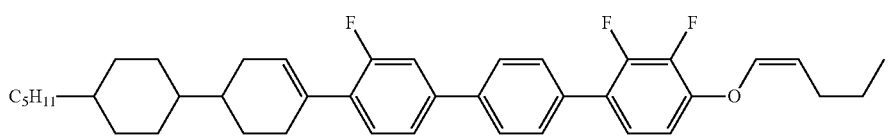 |
| 3681 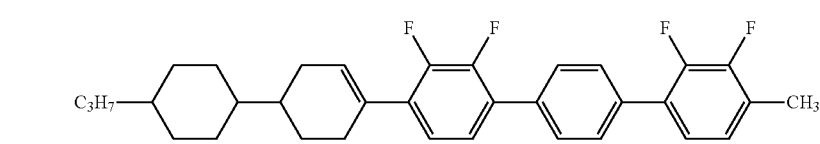 |
| 3682 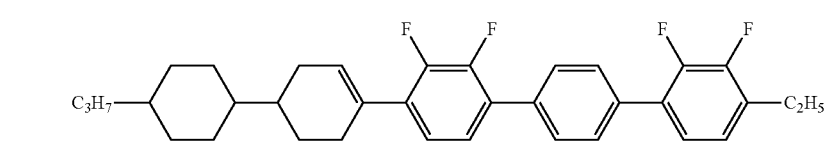 |
| 3683 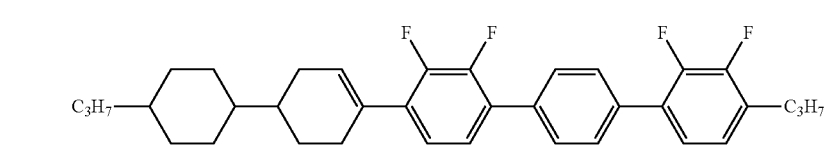 |
| 3684 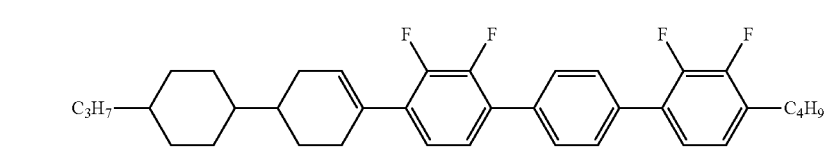 |
| 3685 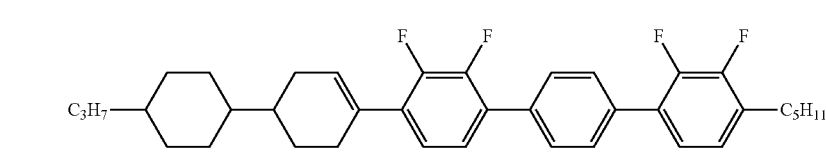 |

| No. | |
|---|---|
| 3686 | 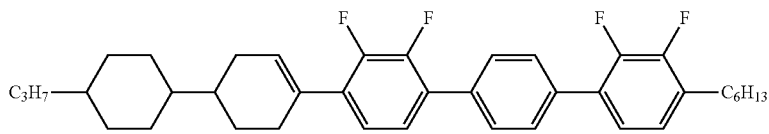 |
| 3687 | 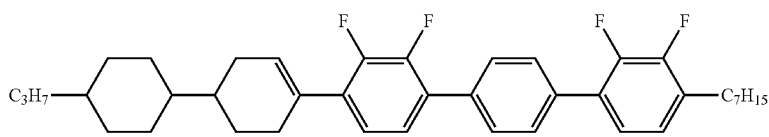 |
| 3688 | 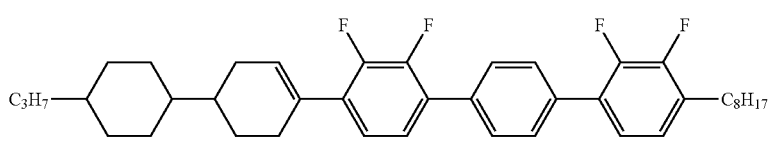 |
| 3689 | 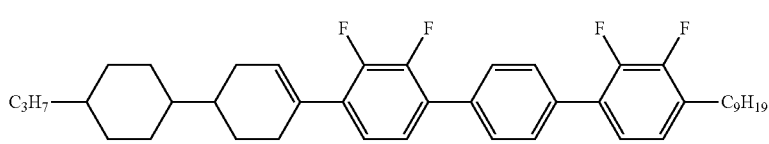 |
| 3690 |  |
| 3691 | 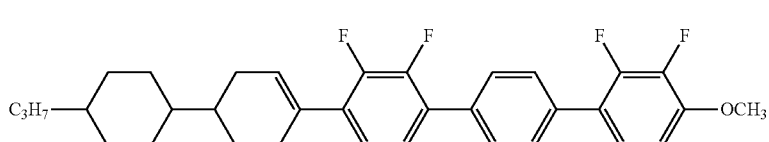 |
| 3692 | 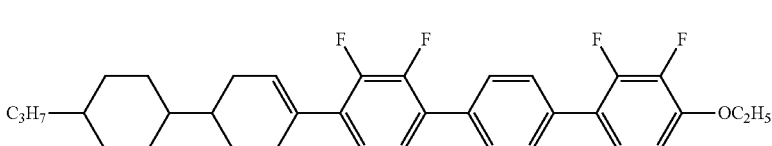 |
| 3693 | 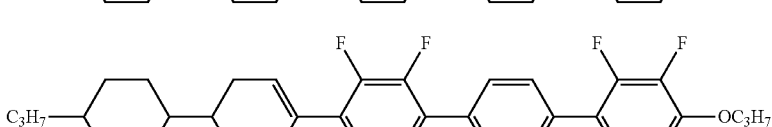 |
| 3694 | 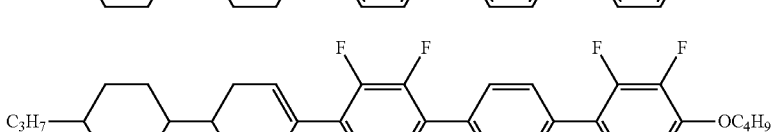 |
| 3695 | 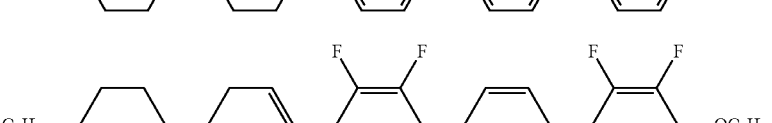 |
| 3696 | 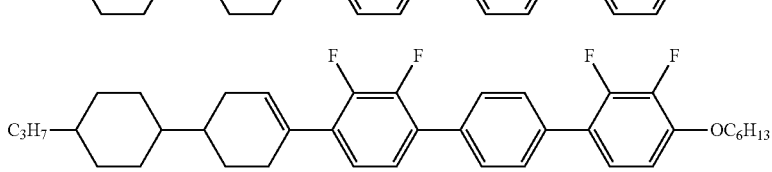 |

-continued
| No. | |
|---|---|
| 3697 | 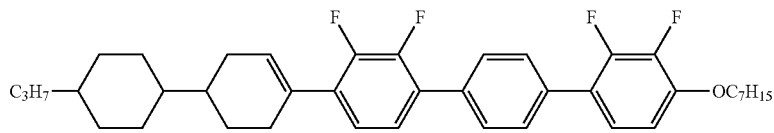 |
| 3698 | 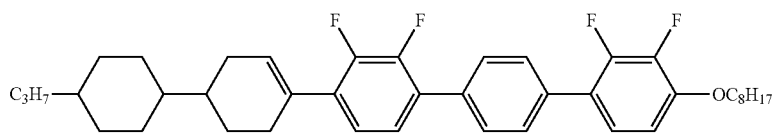 |
| 3699 | 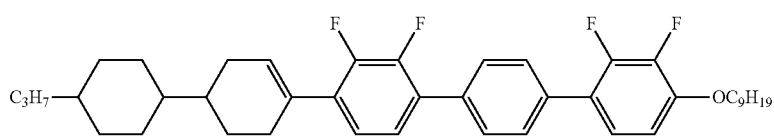 |
| 3700 | 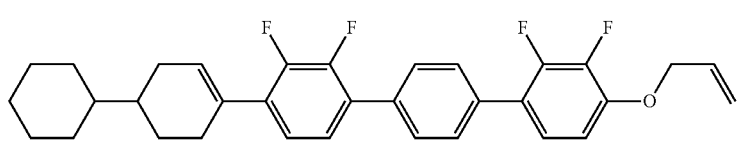 |
| 3701 | 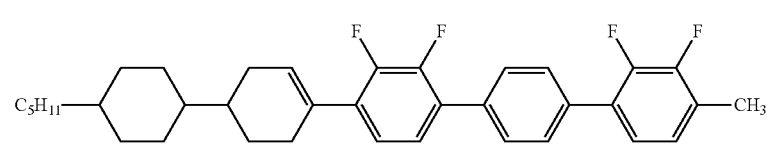 |
| 3702 | 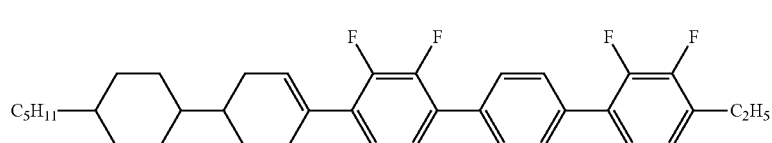 |
| 3703 | 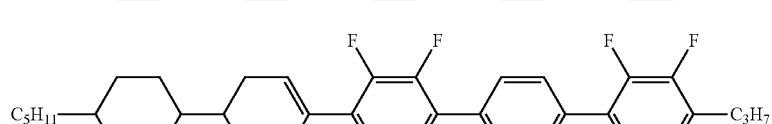 |
| 3704 | 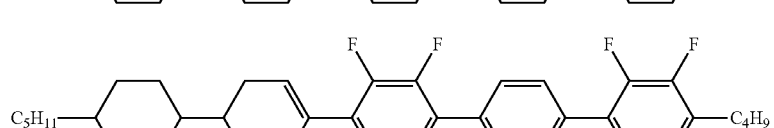 |
| 3705 | 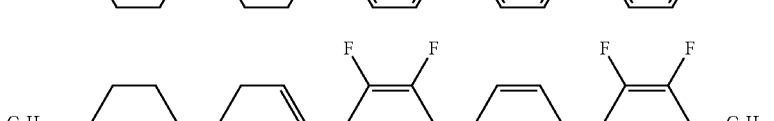 |
| 3706 | 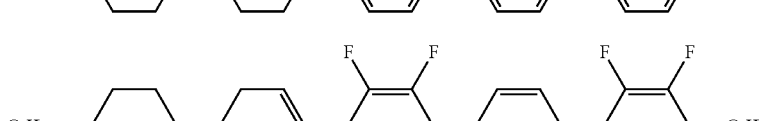 |
| 3707 | 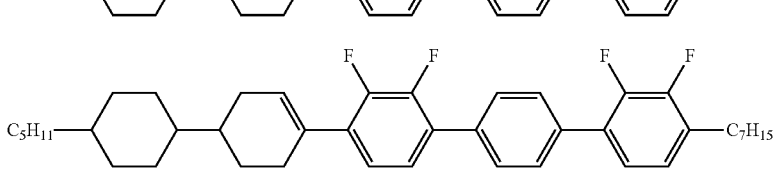 |

| No. | |
|---|---|
| 3708 | 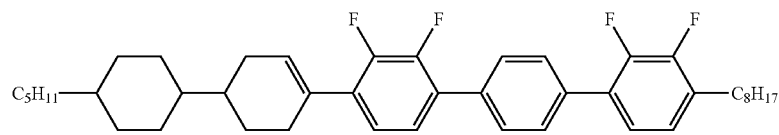 |
| 3709 |  |
| 3710 | 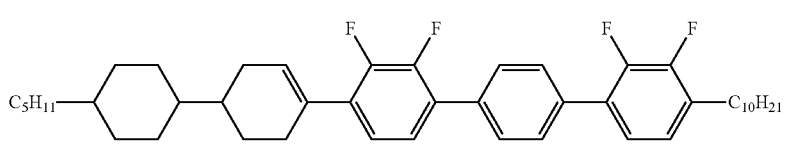 |
| 3711 | 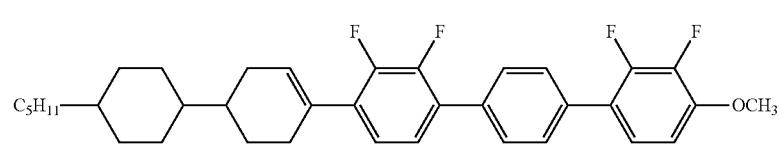 |
| 3712 | 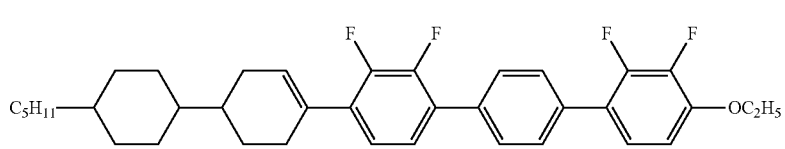 |
| 3713 | 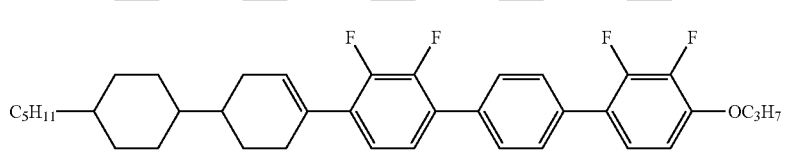 |
| 3714 | 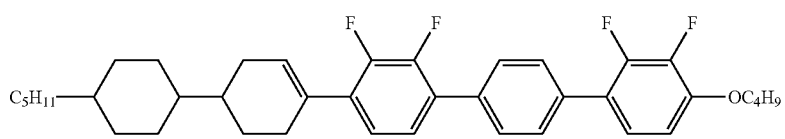 |
| 3715 | 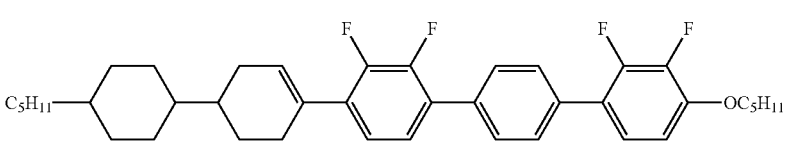 |
| 3716 | 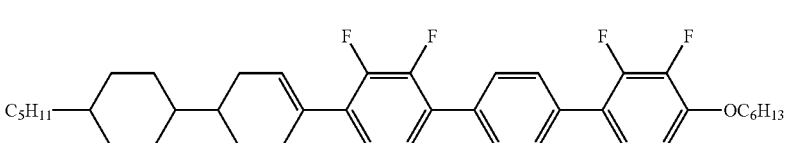 |
| 3717 | 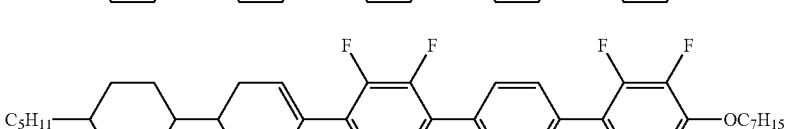 |
| 3718 | 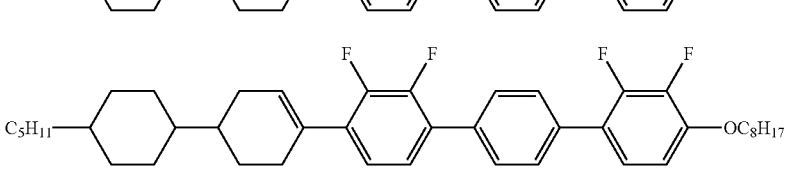 |

-continued
| No. | |
|---|---|
| 3719 | 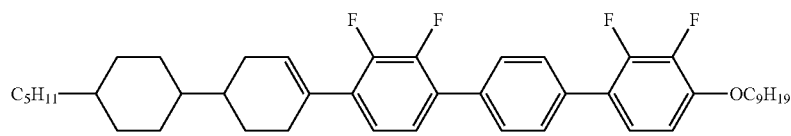 |
| 3720 | 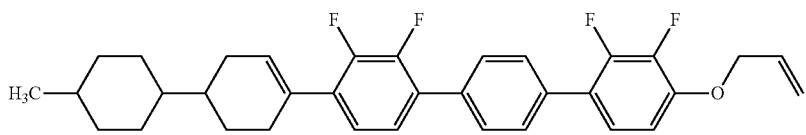 |
| 3721 | 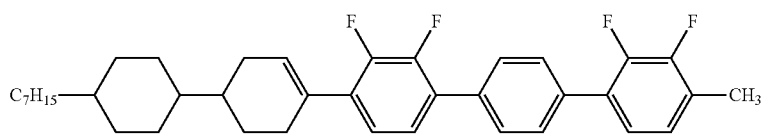 |
| 3722 | 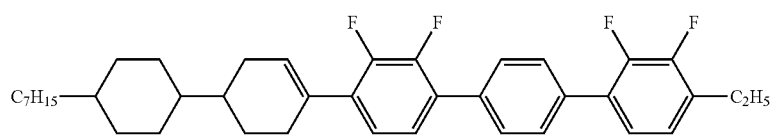 |
| 3723 |  |
| 3724 |  |
| 3725 | 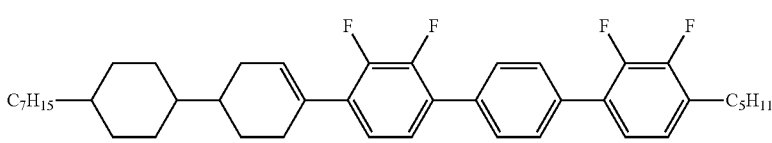 |
| 3726 |  |
| 3727 | 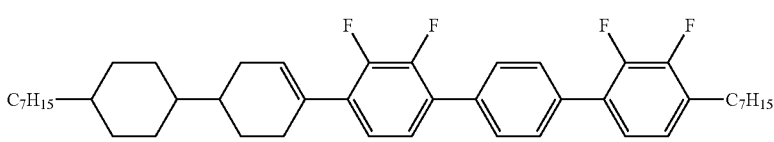 |
| 3728 | 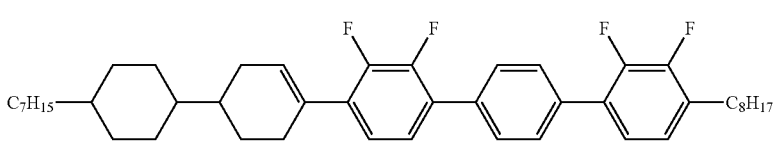 |
| 3729 | 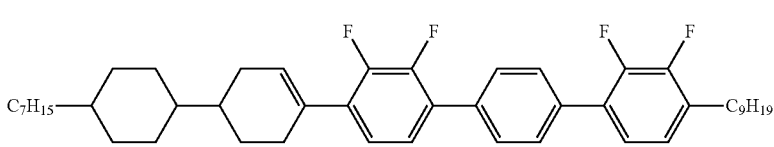 |

-continued
| No. | |
|---|---|
| 3730 |  |
| 3731 | 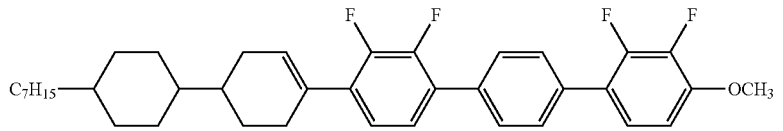 |
| 3732 | 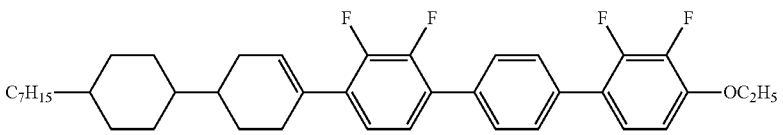 |
| 3733 | 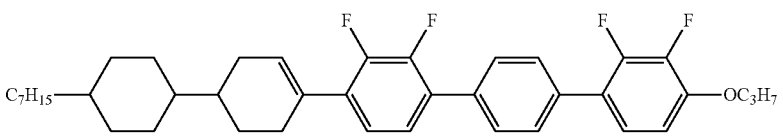 |
| 3734 | 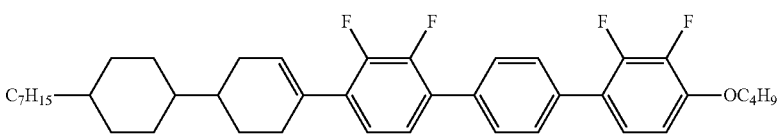 |
| 3735 |  |
| 3736 |  |
| 3737 |  |
| 3738 |  |
| 3739 | 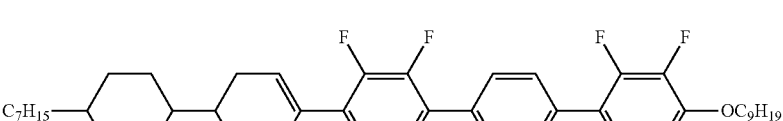 |
| 3740 | 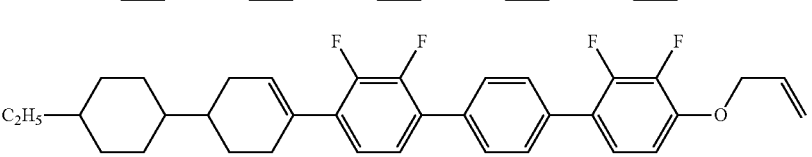 |

| No. | |
|---|---|
| 3741 | 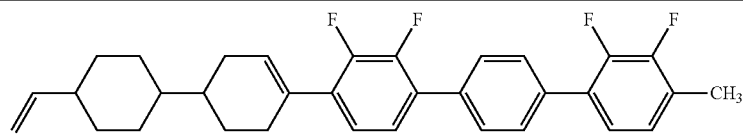 |
| 3742 | 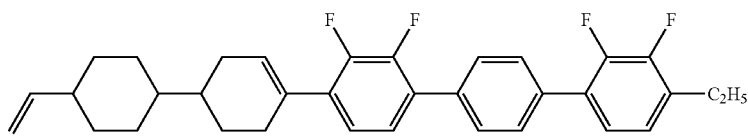 |
| 3743 | 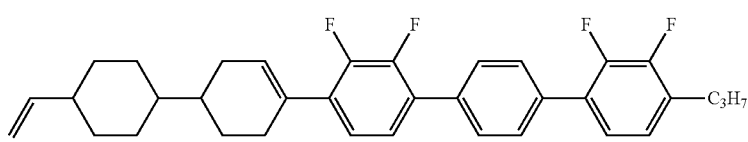 |
| 3744 |  |
| 3745 | 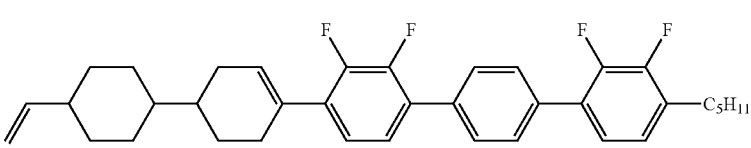 |
| 3746 | 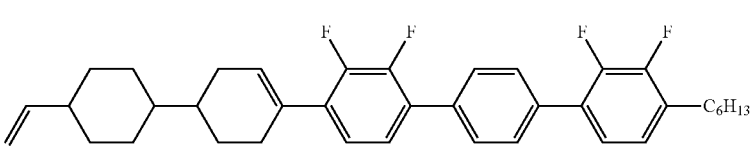 |
| 3747 | 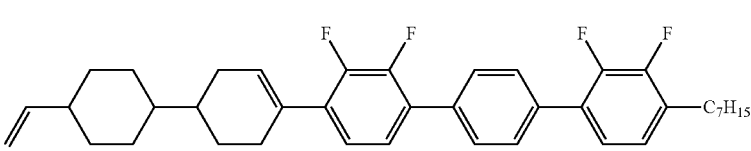 |
| 3748 | 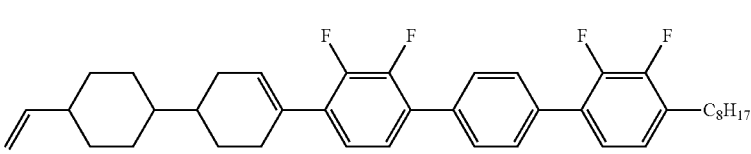 |
| 3749 | 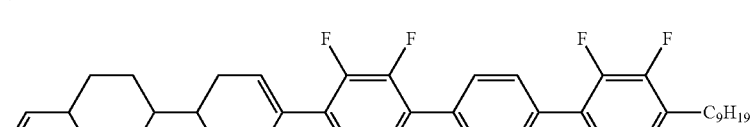 |
| 3750 | 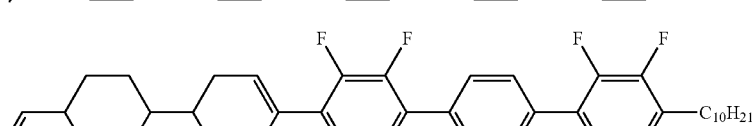 |
| 3751 | 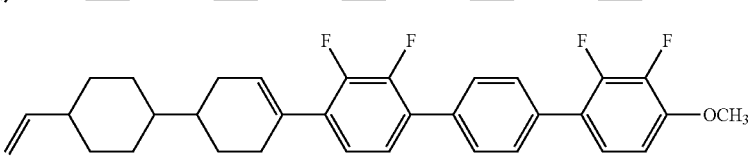 |

-continued
| No. | |
|---|---|
| 3752 | 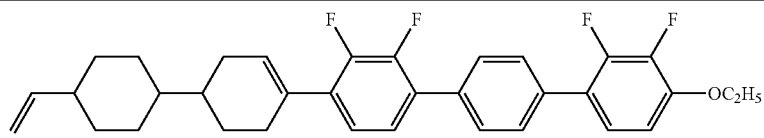 |
| 3753 | 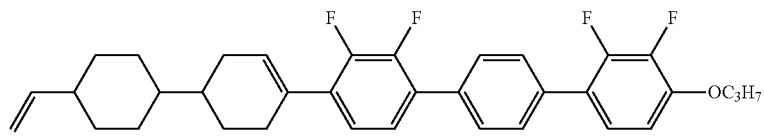 |
| 3754 | 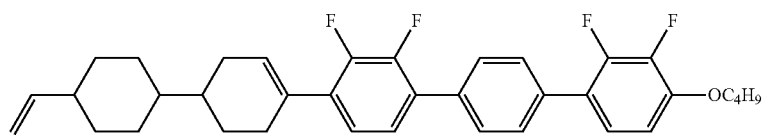 |
| 3755 | 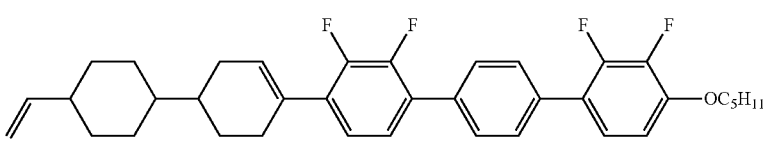 |
| 3756 | 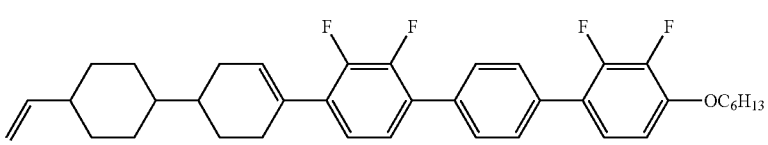 |
| 3757 | 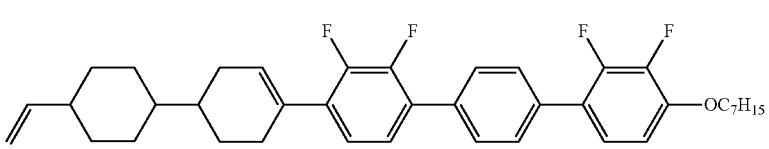 |
| 3758 | 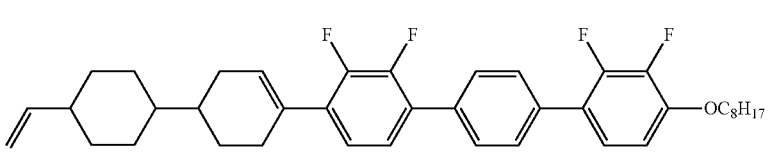 |
| 3759 | 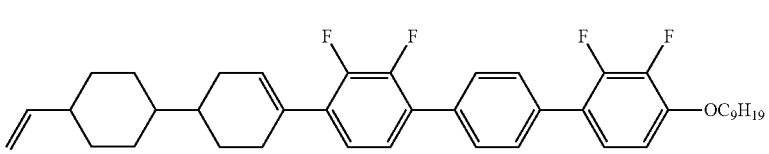 |
| 3760 | 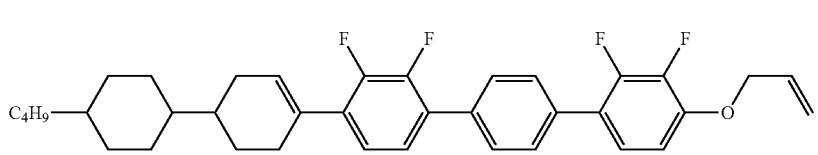 |
| 3761 | 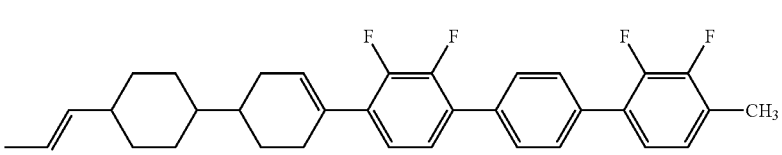 |
| 3762 | 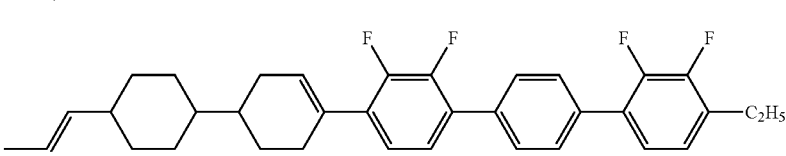 |

-continued
| No. | |
|---|---|
| 3763 | 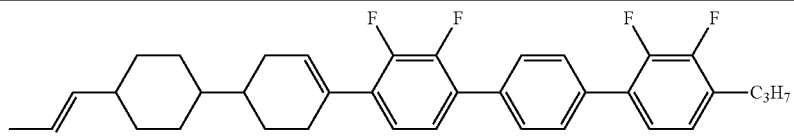 |
| 3764 | 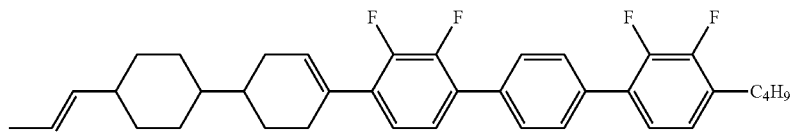 |
| 3765 | 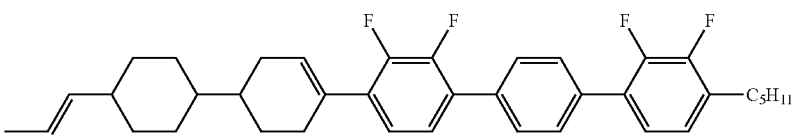 |
| 3766 | 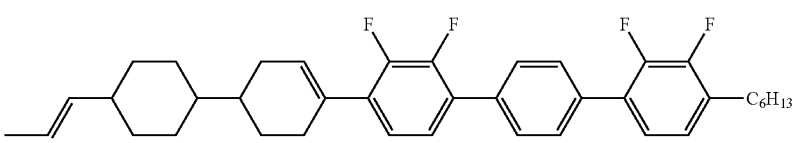 |
| 3767 | 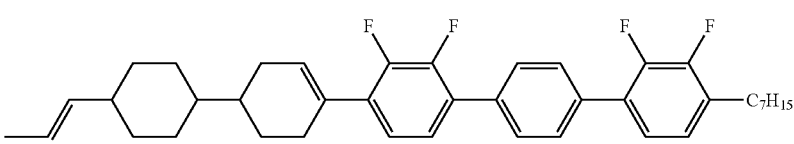 |
| 3768 | 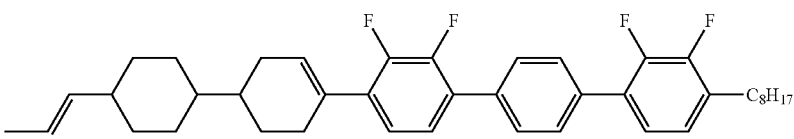 |
| 3769 | 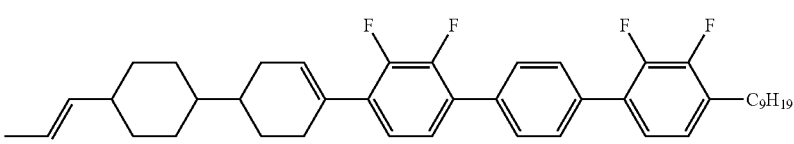 |
| 3770 |  |
| 3771 | 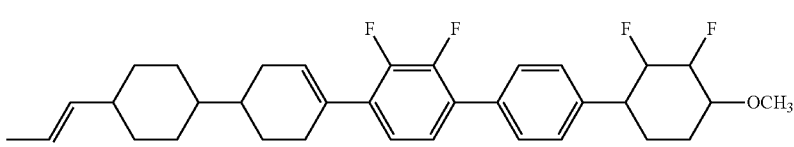 |
| 3772 | 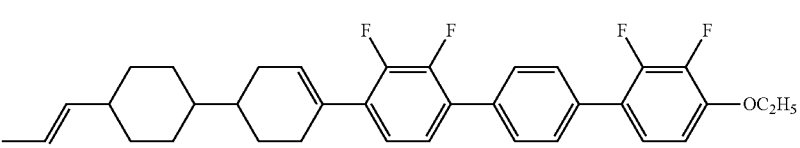 |
| 3773 | 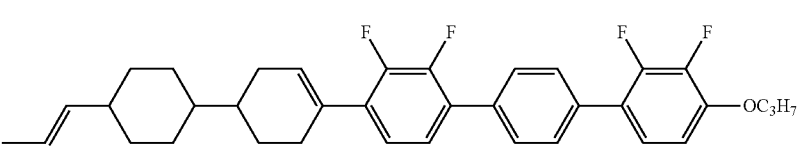 |

-continued
| No. | |
|---|---|
| 3774 | 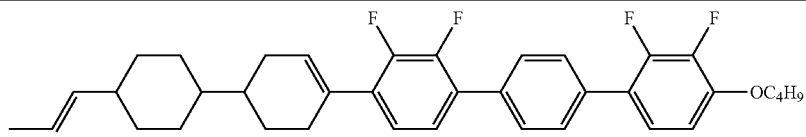 |
| 3775 | 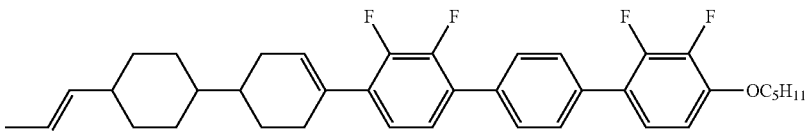 |
| 3776 | 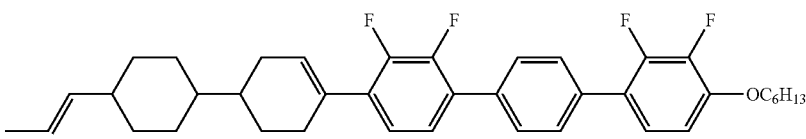 |
| 3777 | 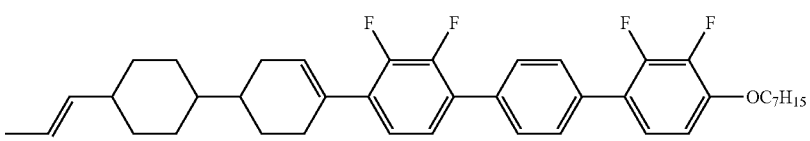 |
| 3778 | 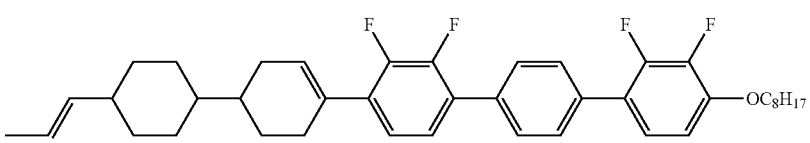 |
| 3779 | 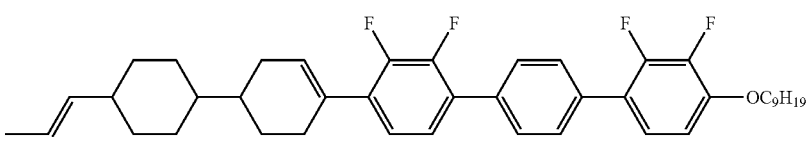 |
| 3780 | 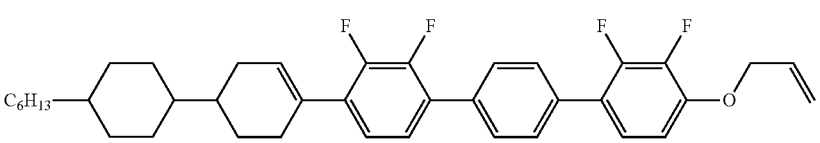 |
| 3781 | 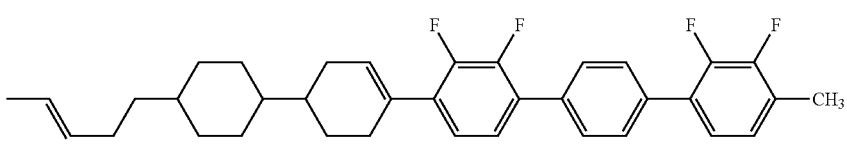 |
| 3782 | 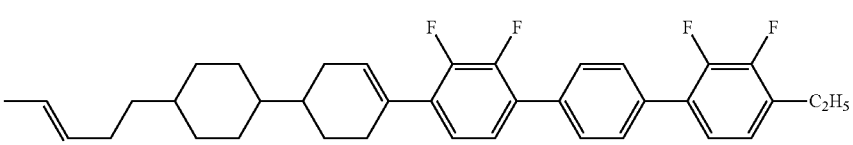 |
| 3783 | 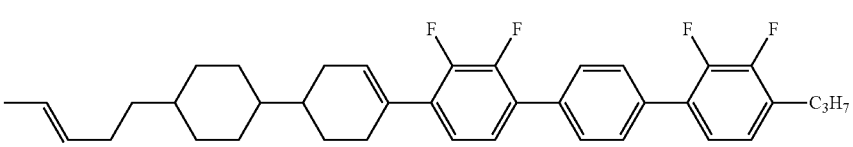 |
| 3784 | 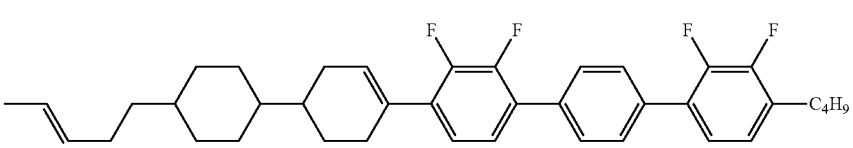 |

| No. | |
|---|---|
| 3785 | 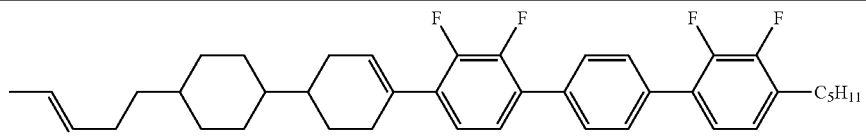 |
| 3786 | 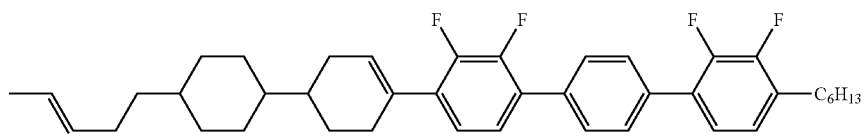 |
| 3787 | 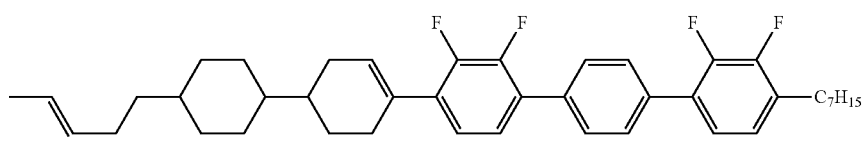 |
| 3788 | 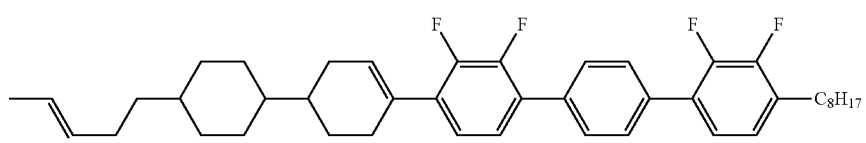 |
| 3789 | 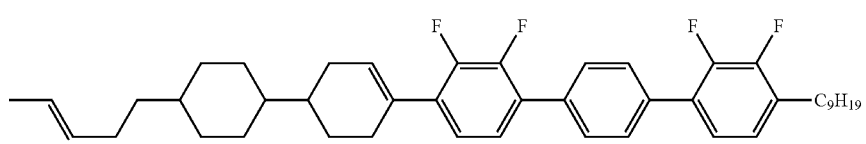 |
| 3790 | 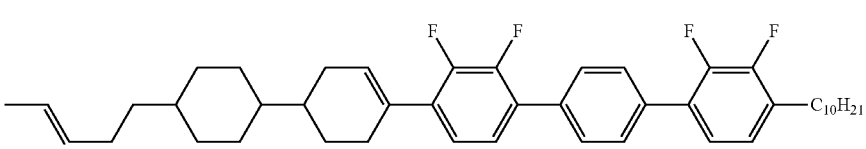 |
| 3791 | 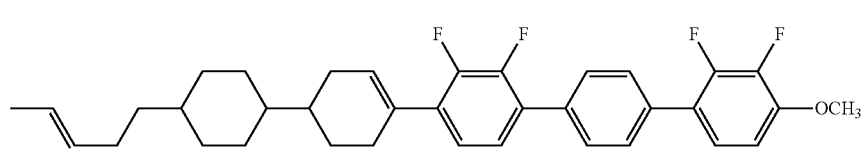 |
| 3792 | 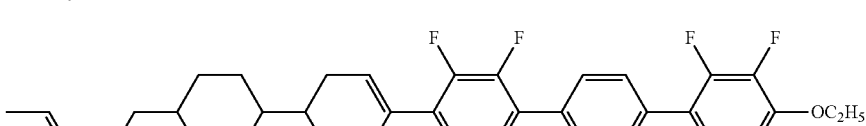 |
| 3793 | 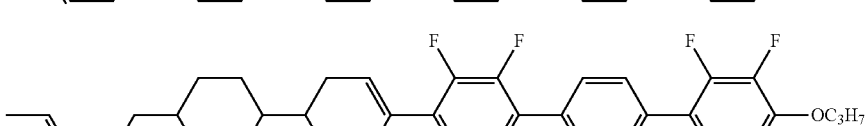 |
| 3794 | 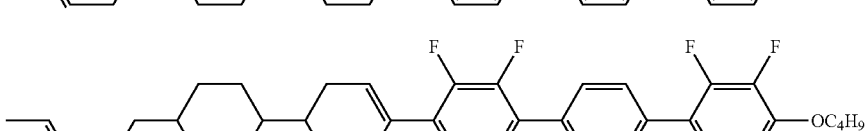 |
| 3795 | 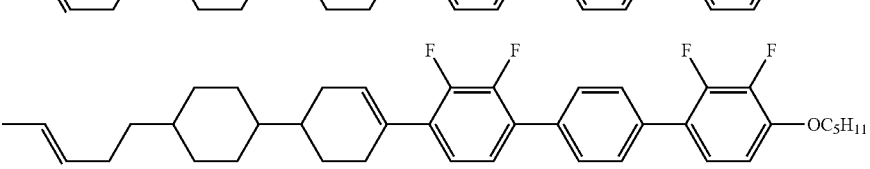 |

-continued
| No. | |
|---|---|
| 3796 | 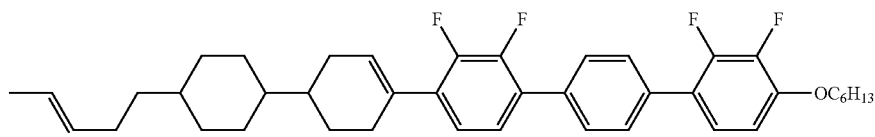 |
| 3797 | 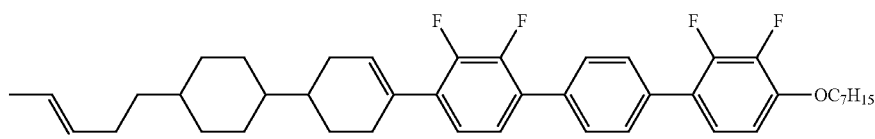 |
| 3798 | 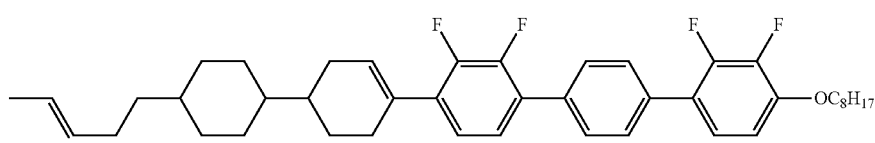 |
| 3799 | 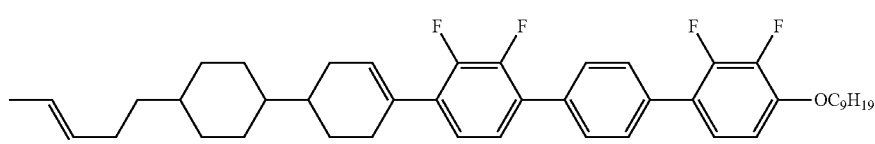 |
| 3800 | 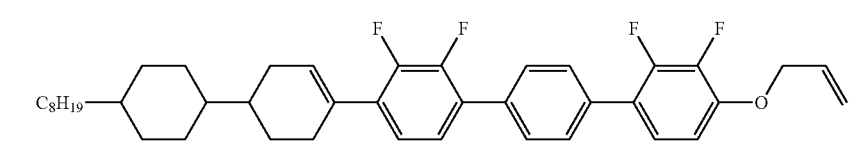 |
| 3801 | 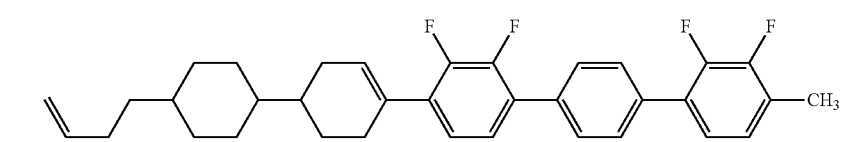 |
| 3802 | 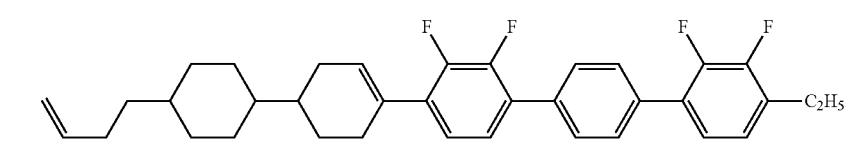 |
| 3803 | 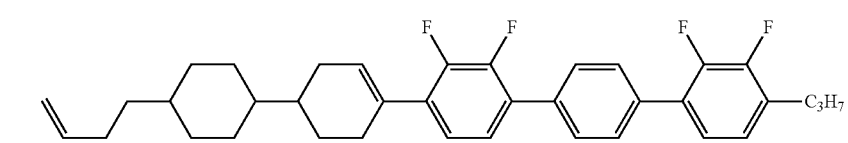 |
| 3804 | 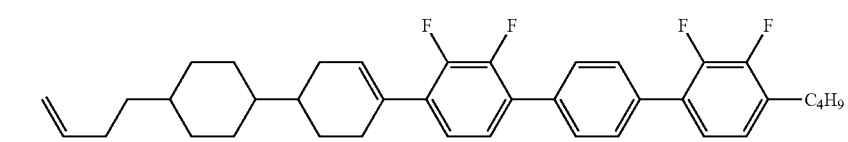 |
| 3805 | 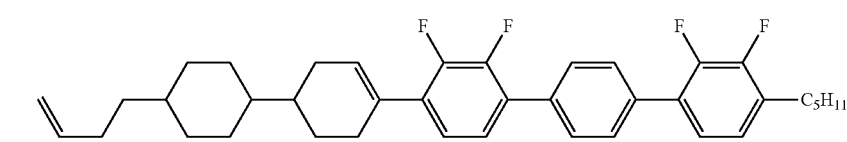 |
| 3806 | 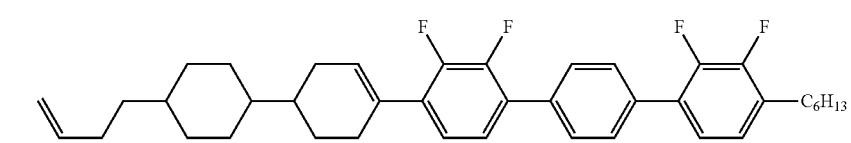 |

-continued
| No. |
|---|
| 3807 | 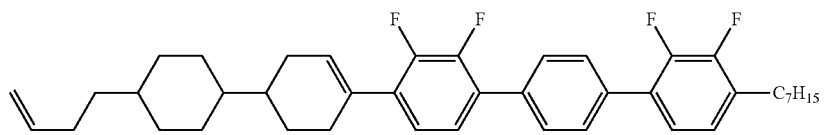
| 3808 | 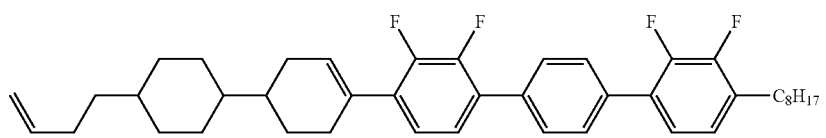
| 3809 | 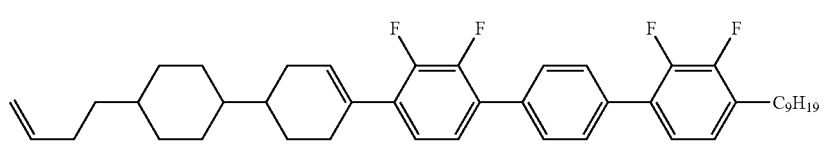
| 3810 | 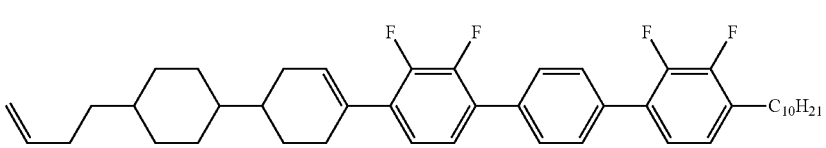
| 3811 | 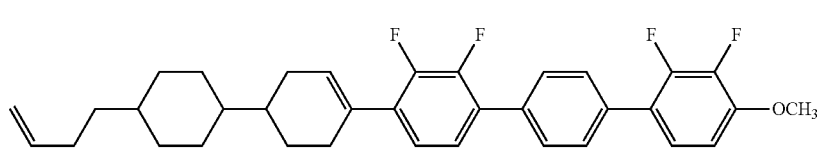
| 3812 | 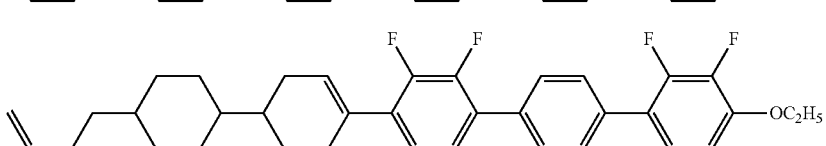
| 3813 | 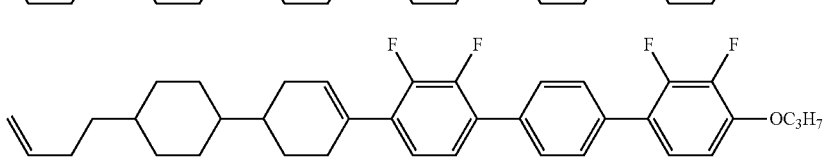
| 3814 | 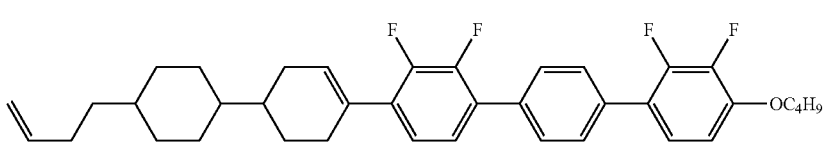
| 3815 | 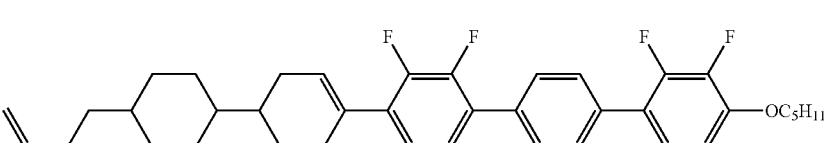
| 3816 | 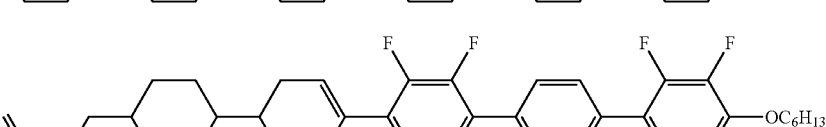
| 3817 | 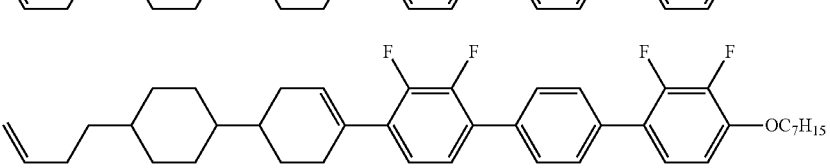

| No. |
| --- |
| 3818 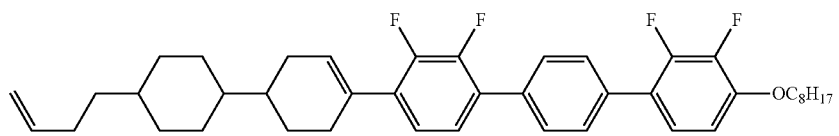 |
| 3819 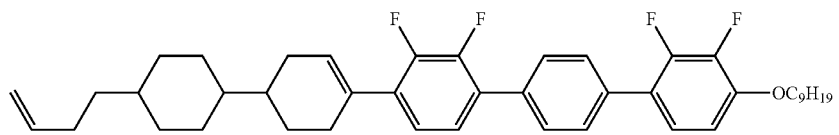 |
| 3820 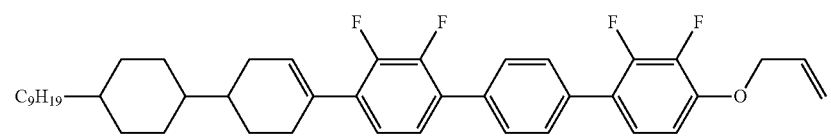 |
| 3821 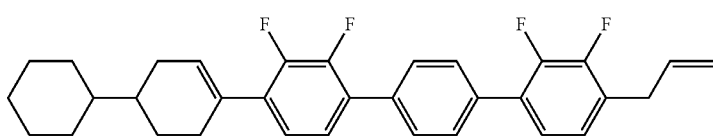 |
| 3822 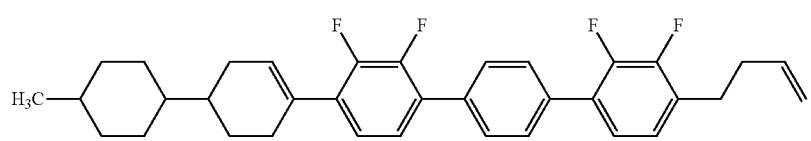 |
| 3823 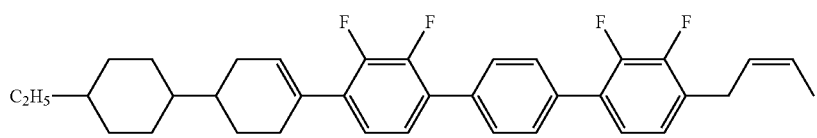 |
| 3824 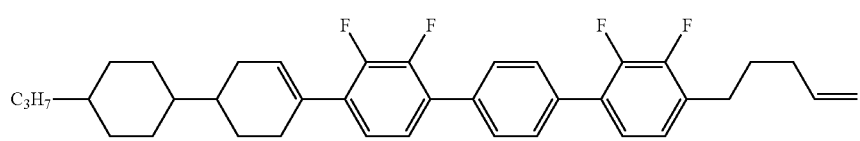 |
| 3825 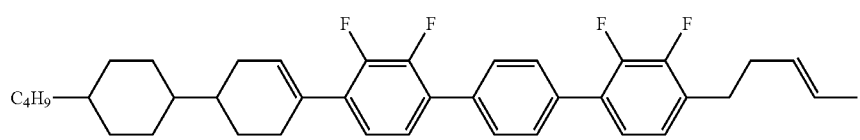 |
| 3826 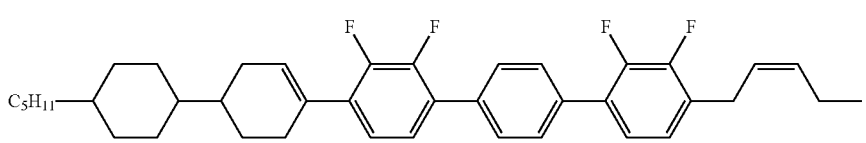 |
| 3827 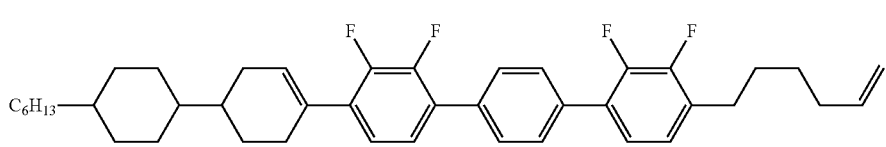 |
| 3828 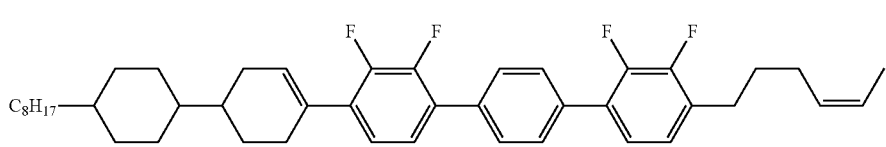 |

-continued

| No. |
|---|
| 3829 |
| 3830 |
| 3831 |
| 3832 |
| 3833 |
| 3834 |
| 3835 |
| 3836 |
| 3837 |
| 3838 |
| 3839 |

-continued
| No. | |
|---|---|
| 3840 | 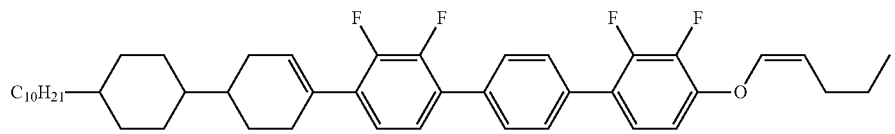 |
| 3841 | 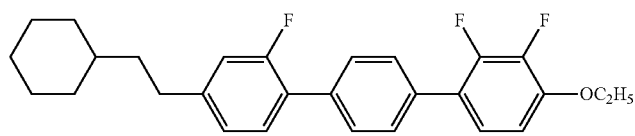 |
| 3842 | 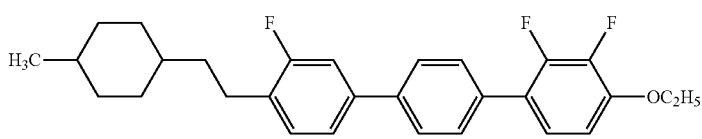 |
| 3843 | 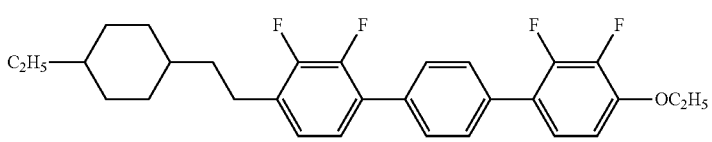 |
| 3844 | 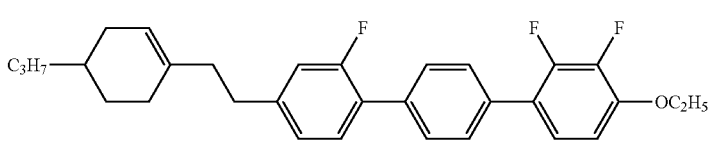 |
| 3845 | 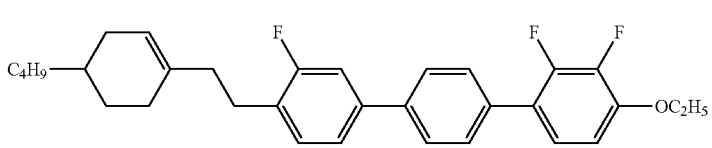 |
| 3846 | 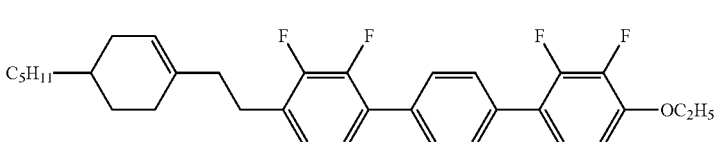 |
| 3847 | 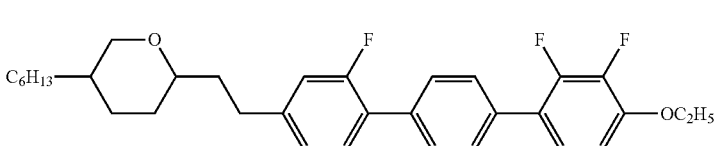 |
| 3848 | 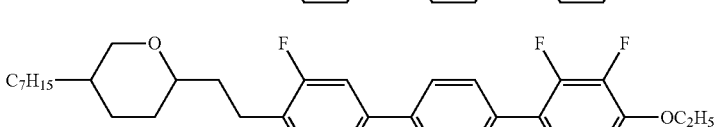 |
| 3849 | 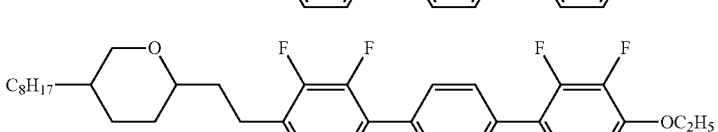 |
| 3850 | 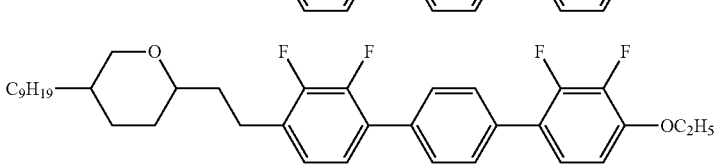 |

-continued
| No. |
|---|
| 3851 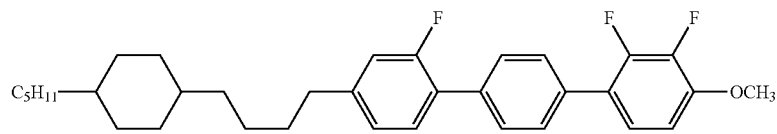 |
| 3852 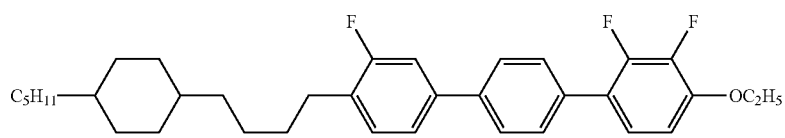 |
| 3853 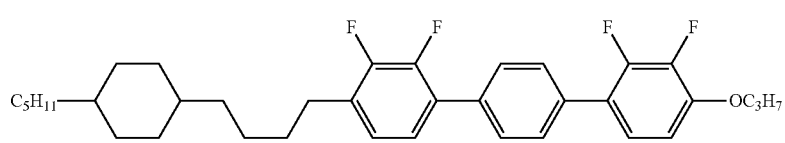 |
| 3854 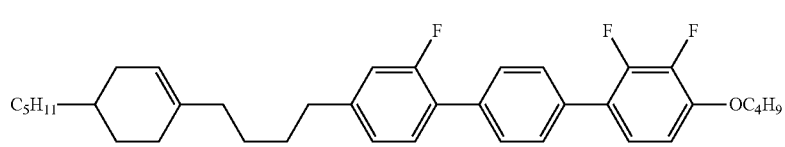 |
| 3855 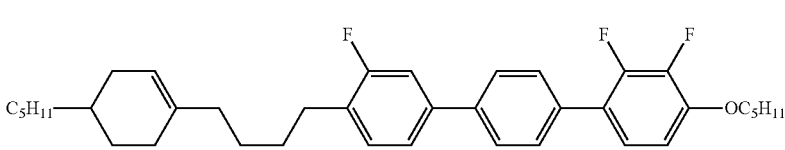 |
| 3856 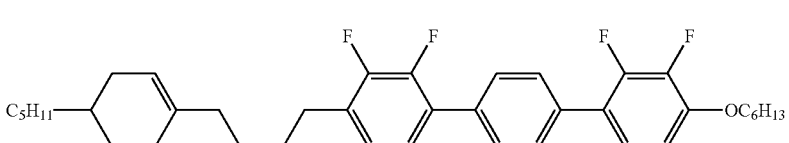 |
| 3857 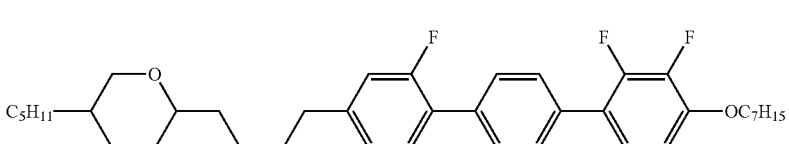 |
| 3858 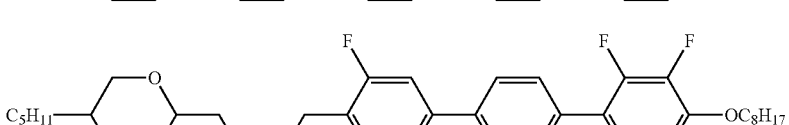 |
| 3859 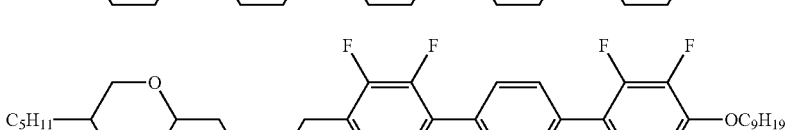 |
| 3860 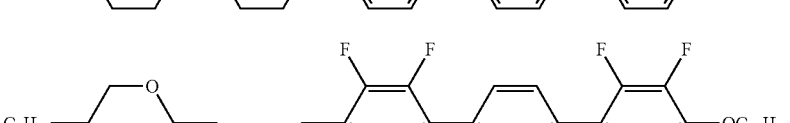 |
| 3861 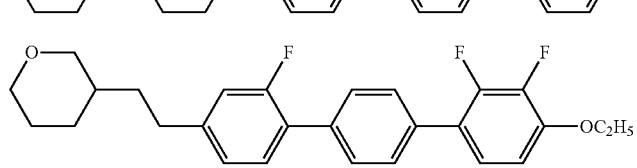 |

-continued
| No. | |
|---|---|
| 3862 | 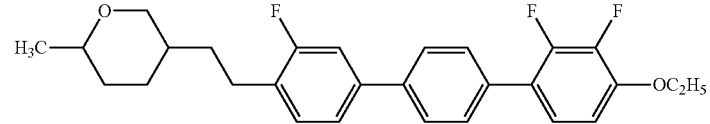 |
| 3863 | 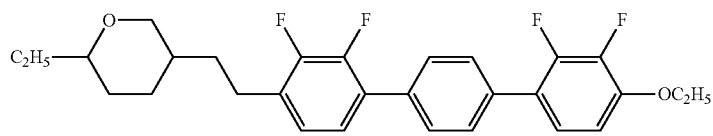 |
| 3864 | 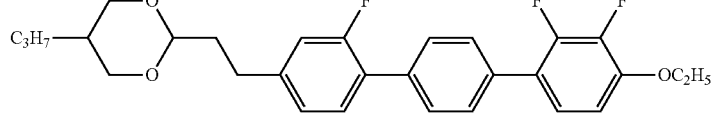 |
| 3865 | 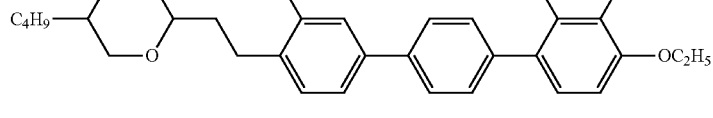 |
| 3866 | 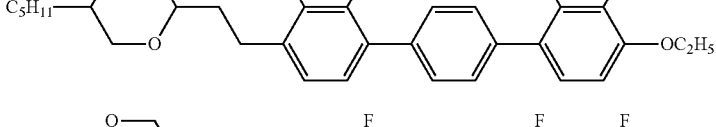 |
| 3867 | 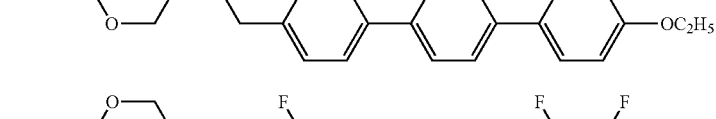 |
| 3868 | 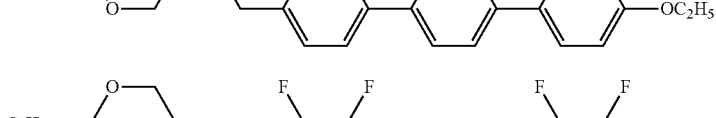 |
| 3869 | 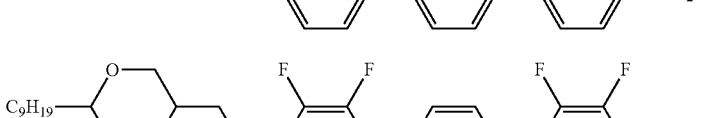 |
| 3870 | 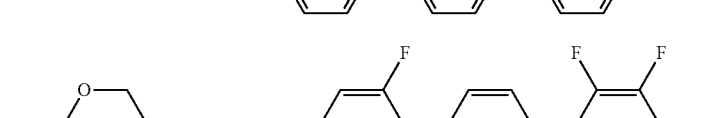 |
| 3871 | 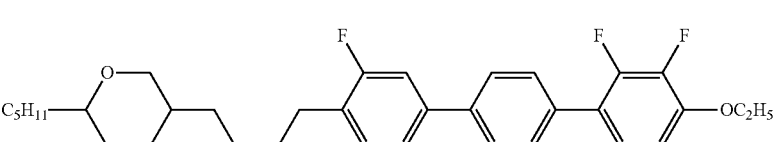 |
| 3872 |  |

| No. | |
|---|---|
| 3873 | 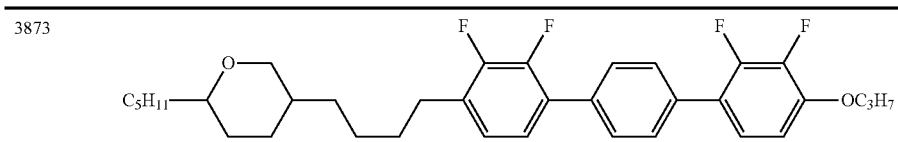 |
| 3874 | 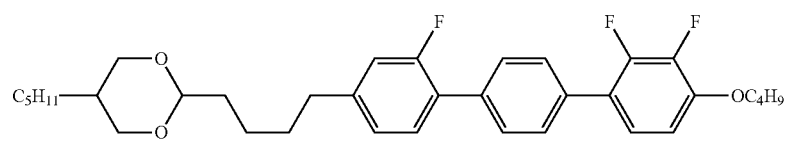 |
| 3875 | 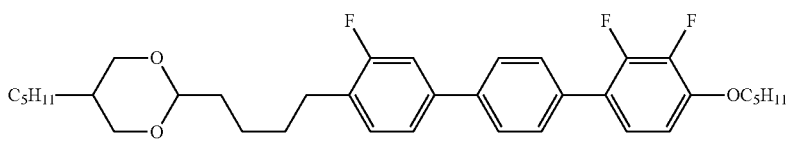 |
| 3876 | 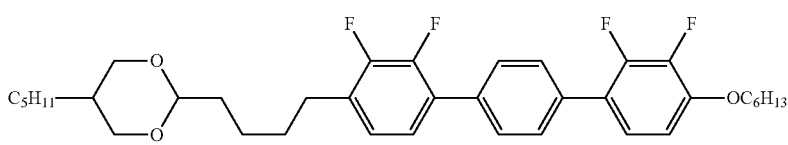 |
| 3877 | 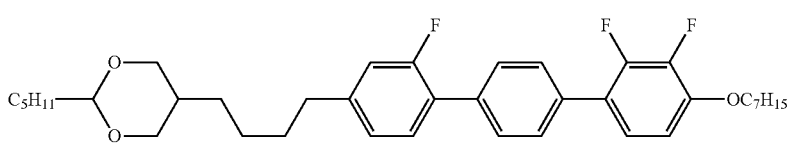 |
| 3878 | 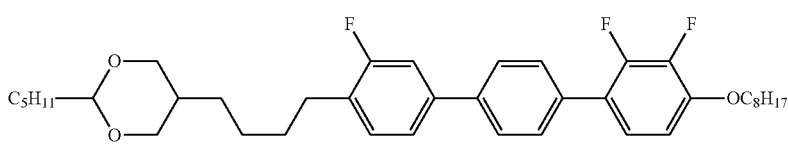 |
| 3879 | 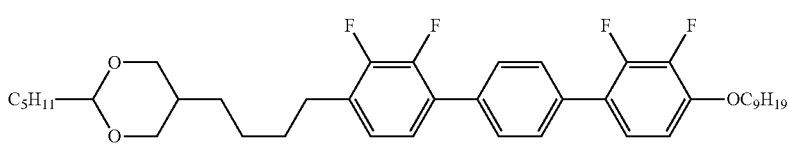 |
| 3880 | 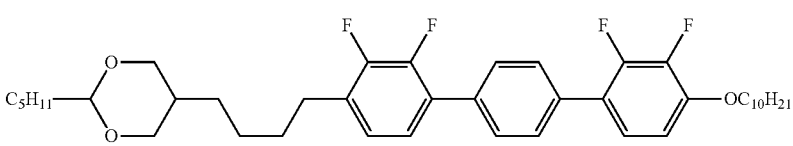 |
| 3881 | 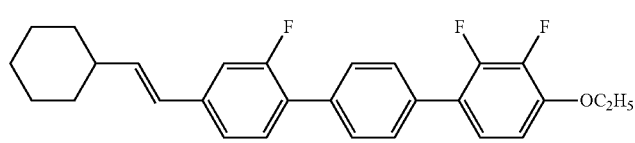 |
| 3882 | 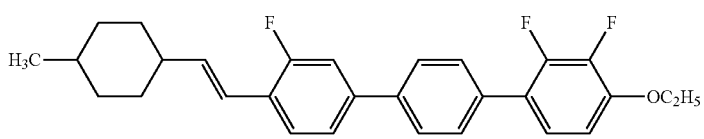 |
| 3883 | 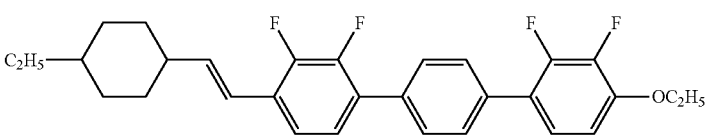 |

| No. | |
|---|---|
| 3884 | 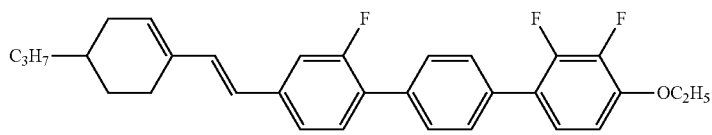 |
| 3885 | 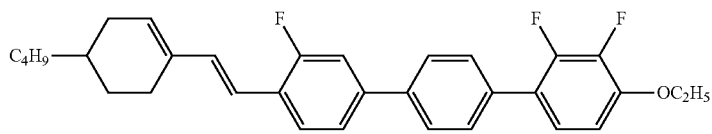 |
| 3886 | 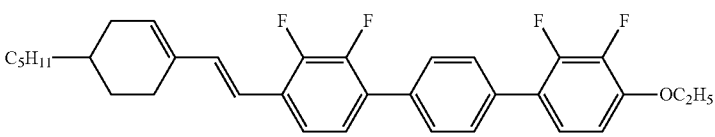 |
| 3887 | 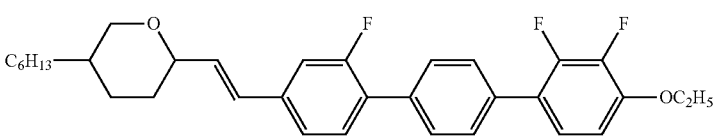 |
| 3888 | 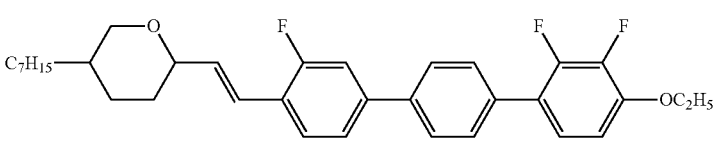 |
| 3889 | 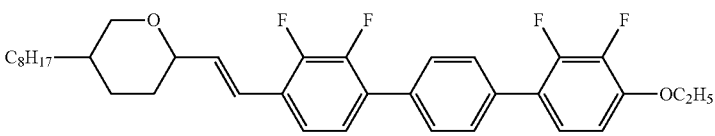 |
| 3890 | 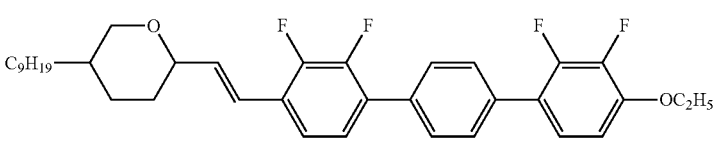 |
| 3891 | 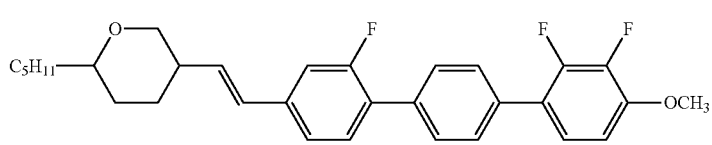 |
| 3892 | 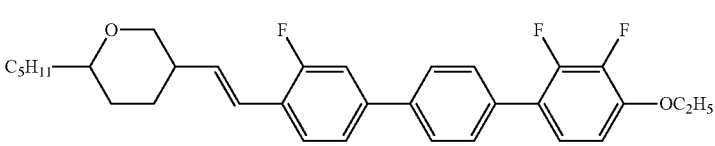 |
| 3893 | 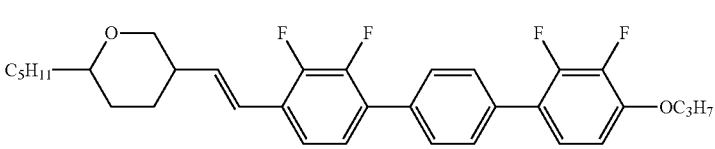 |
| 3894 | 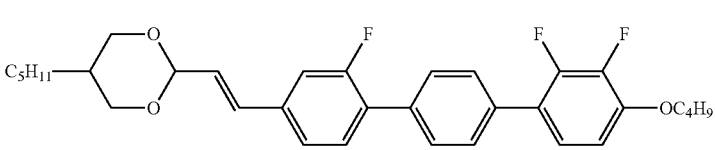 |

| No. |
|---|
| 3895 |
| 3896 |
| 3897 |
| 3898 |
| 3899 |
| 3900 |
| 3901 |
| 3902 |
| 3903 |
| 3904 |
| 3905 |

| No. |  |
|---|---|
| 3906 | 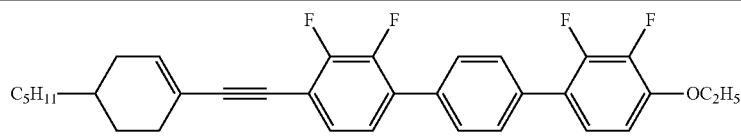 |
| 3907 | 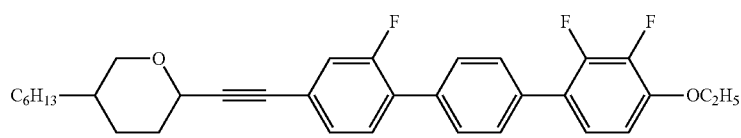 |
| 3908 | 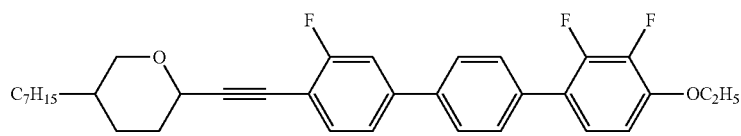 |
| 3909 | 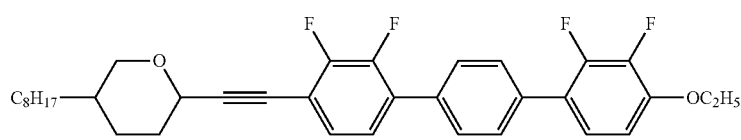 |
| 3910 | 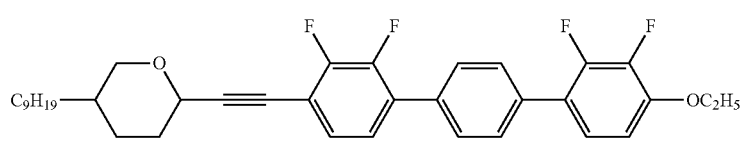 |
| 3911 | 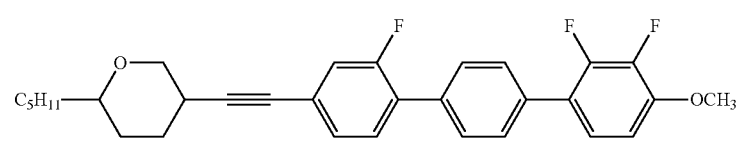 |
| 3912 | 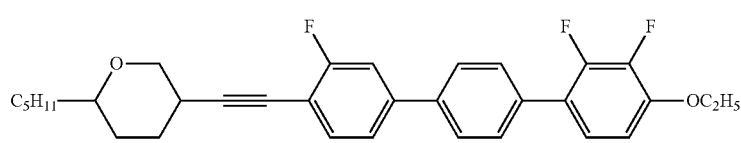 |
| 3913 | 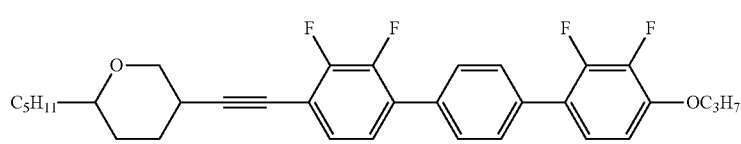 |
| 3914 | 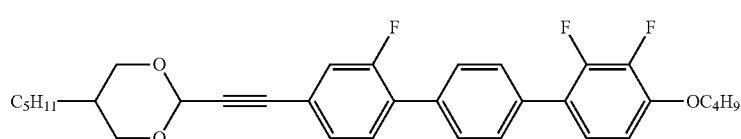 |
| 3915 | 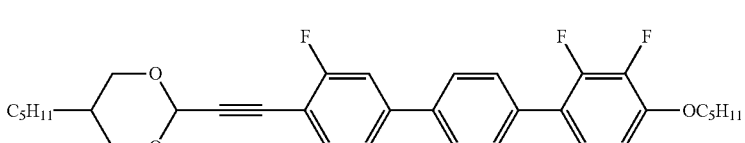 |
| 3916 | 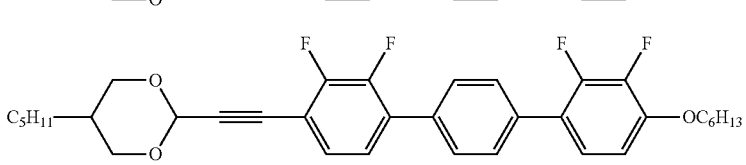 |

| No. | |
|---|---|
| 3917 | 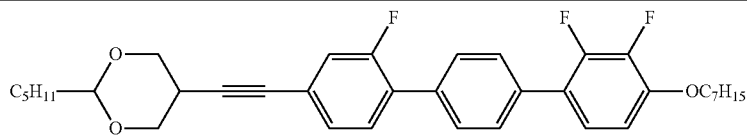 |
| 3918 | 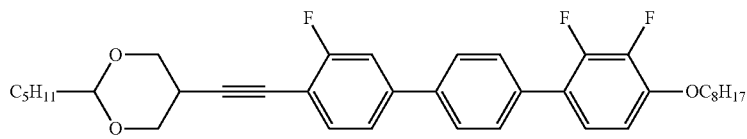 |
| 3919 | 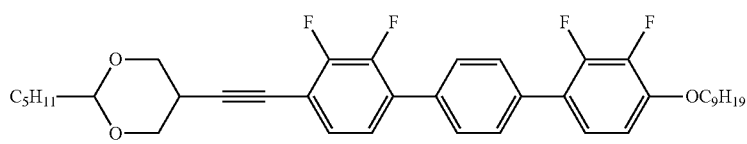 |
| 3920 | 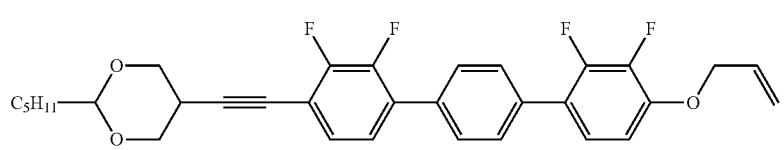 |
| 3921 | 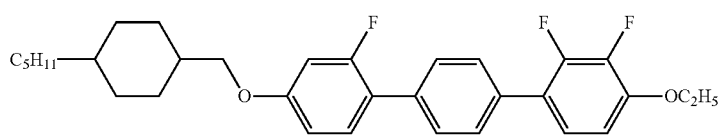 |
| 3922 | 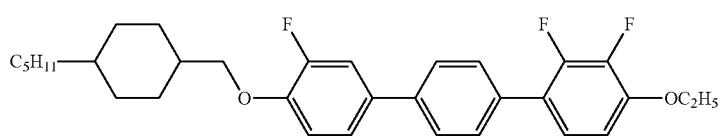 |
| 3923 | 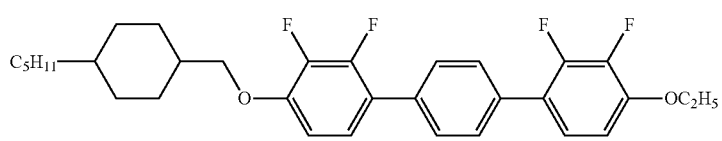 |
| 3924 | 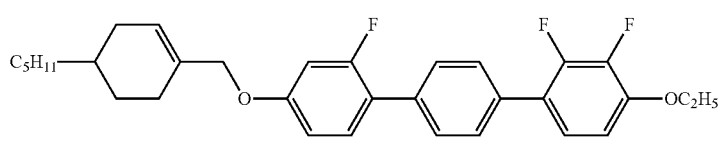 |
| 3925 | 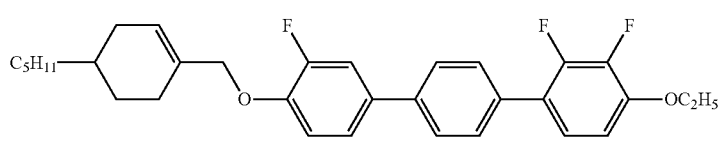 |
| 3926 | 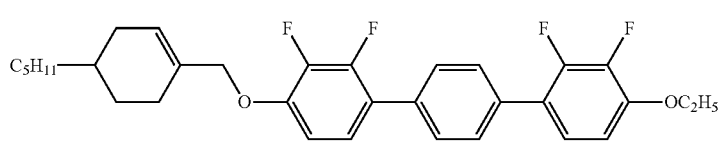 |
| 3927 | 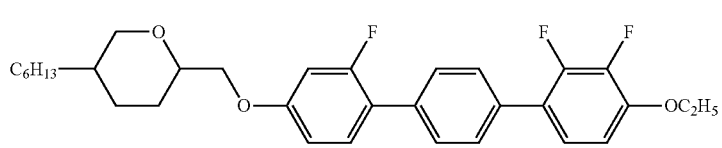 |

-continued
| No. | |
|---|---|
| 3928 | 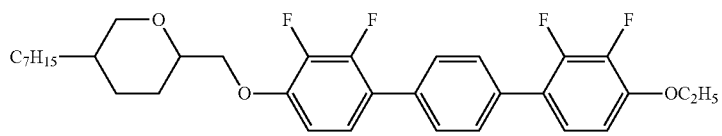 |
| 3929 | 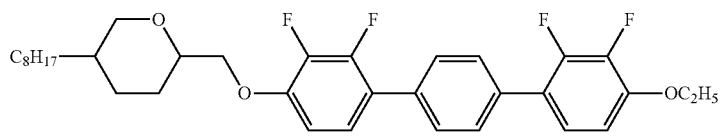 |
| 3930 | 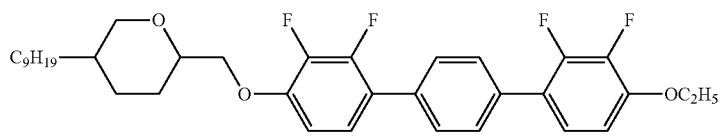 |
| 3931 | 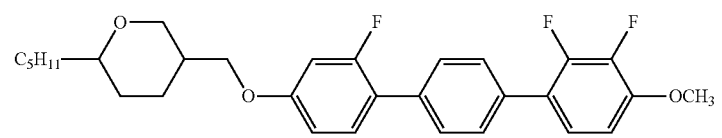 |
| 3932 | 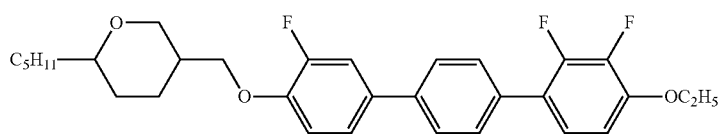 |
| 3933 | 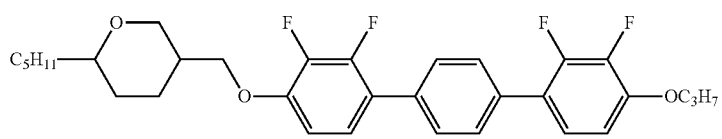 |
| 3934 | 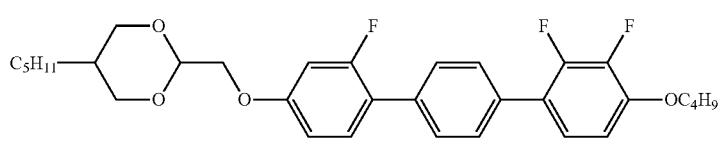 |
| 3935 | 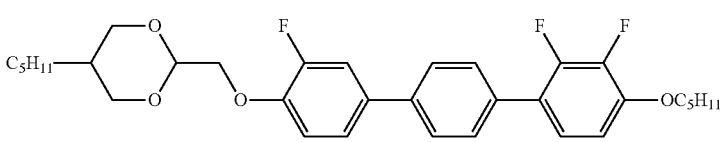 |
| 3936 | 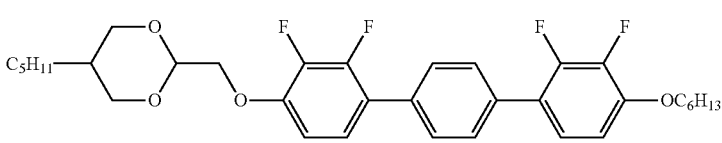 |
| 3937 | 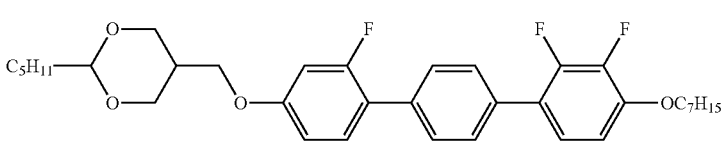 |
| 3938 | 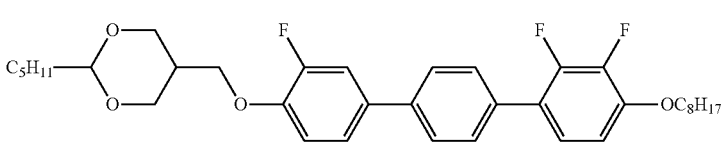 |

| No. | |
|---|---|
| 3939 | 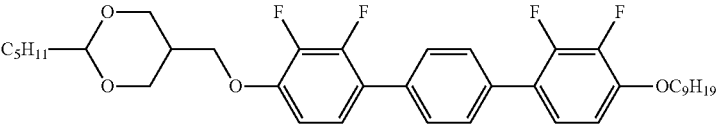 |
| 3940 | 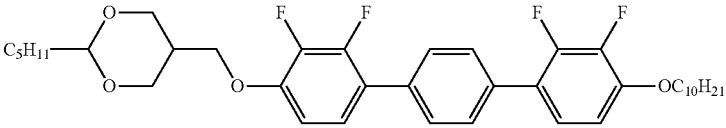 |
| 3941 | 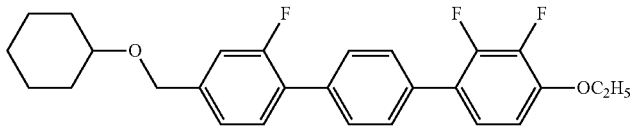 |
| 3942 | 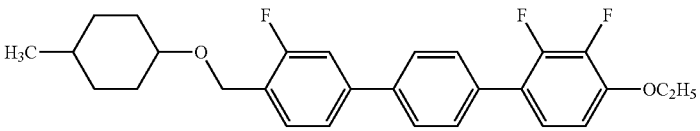 |
| 3943 | 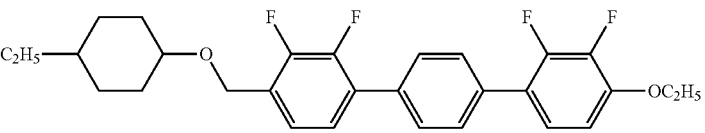 |
| 3944 | 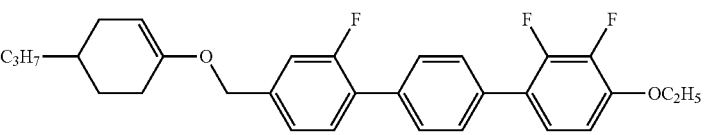 |
| 3945 | 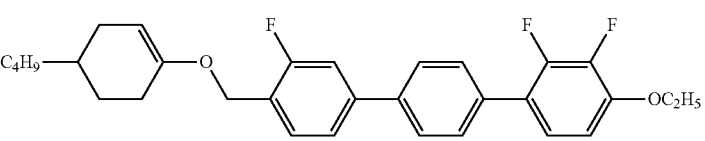 |
| 3946 | 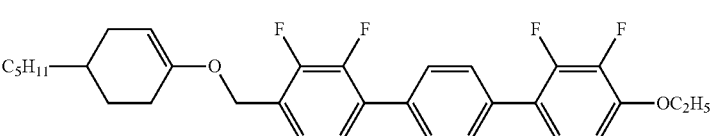 |
| 3947 | 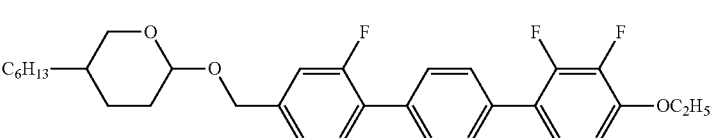 |
| 3948 | 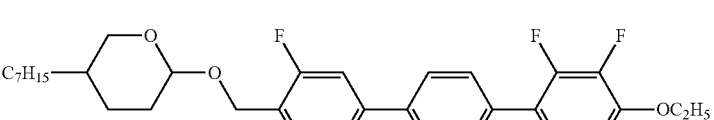 |
| 3949 | 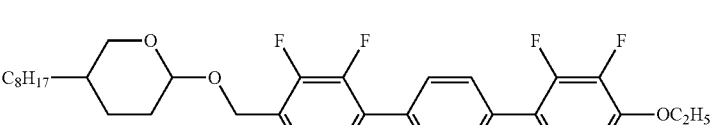 |

| No. | |
|---|---|
| 3950 | C9H19—[tetrahydropyran]—O—CH2—[C6H2(F)(F)]—[C6H4]—[C6H2(F)(F)]—OC2H5 |
| 3951 | C5H11—[tetrahydropyran]—O—[C6H3(F)]—[C6H4]—[C6H2(F)(F)]—OCH3 |
| 3952 | C5H11—[tetrahydropyran]—O—[C6H3(F)]—[C6H4]—[C6H2(F)(F)]—OC2H5 |
| 3953 | C5H11—[tetrahydropyran]—O—[C6H2(F)(F)]—[C6H4]—[C6H2(F)(F)]—OC3H7 |
| 3954 | C5H11—[1,3-dioxane]—O—CH2—[C6H3(F)]—[C6H4]—[C6H2(F)(F)]—OC4H9 |
| 3955 | C5H11—[1,3-dioxane]—O—CH2—[C6H3(F)]—[C6H4]—[C6H2(F)(F)]—OC5H11 |
| 3956 | C5H11—[1,3-dioxane]—O—CH2—[C6H2(F)(F)]—[C6H4]—[C6H2(F)(F)]—OC6H13 |
| 3957 | C5H11—[1,3-dioxane]—O—CH2—[C6H3(F)]—[C6H4]—[C6H2(F)(F)]—OC7H15 |
| 3958 | C5H11—[1,3-dioxane]—O—CH2—[C6H3(F)]—[C6H4]—[C6H2(F)(F)]—OC8H17 |
| 3959 | C5H11—[1,3-dioxane]—O—CH2—[C6H2(F)(F)]—[C6H4]—[C6H2(F)(F)]—OC9H19 |
| 3960 | C5H11—[1,3-dioxane]—O—CH2—[C6H2(F)(F)]—[C6H4]—[C6H2(F)(F)]—OC10H21 |

| No. | |
|---|---|
| 3961 | (structure) |
| 3962 | (structure) |
| 3963 | (structure) |
| 3964 | (structure) |
| 3965 | (structure) |
| 3966 | (structure) |
| 3967 | (structure) |
| 3968 | (structure) |
| 3969 | (structure) |
| 3970 | (structure) |
| 3971 | (structure) |

| No. | |
|---|---|
| 3972 | 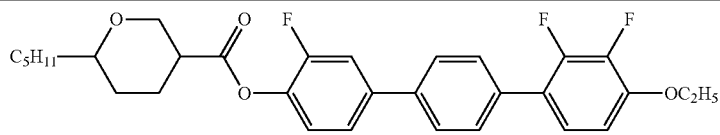 |
| 3973 | 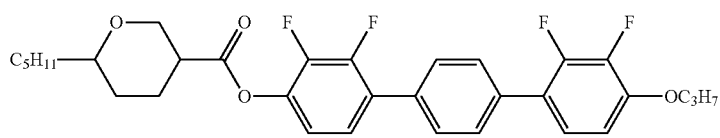 |
| 3974 | 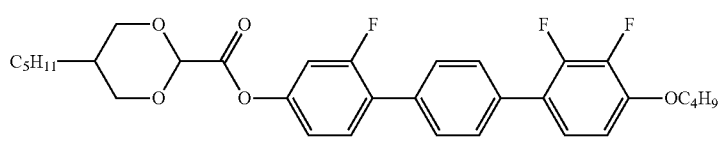 |
| 3975 | 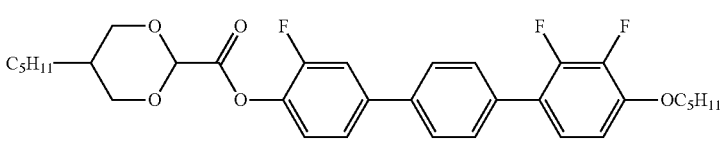 |
| 3976 | 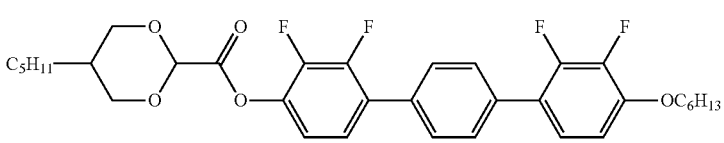 |
| 3977 | 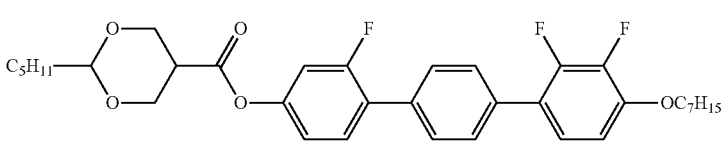 |
| 3978 | 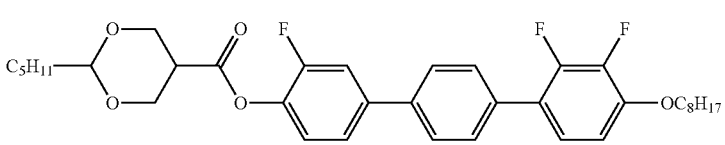 |
| 3979 | 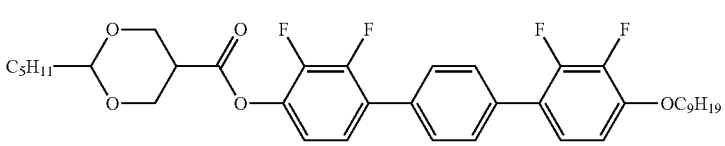 |
| 3980 | 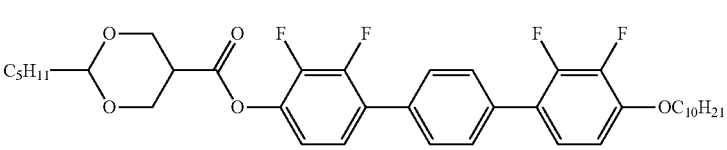 |
| 3981 | 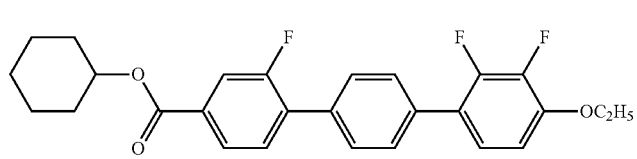 |
| 3982 | 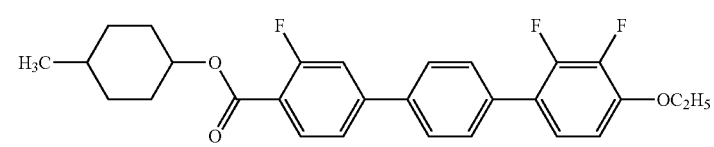 |

-continued
| No. | |
|---|---|
| 3983 | 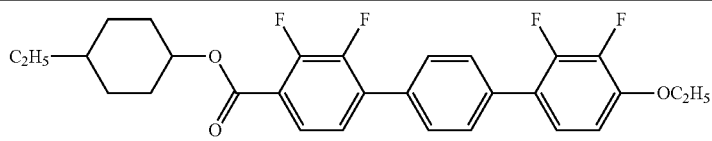 |
| 3984 | 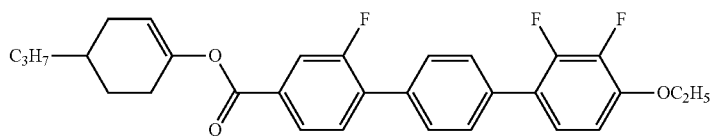 |
| 3985 | 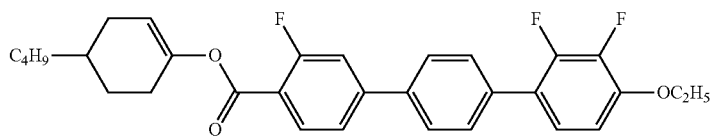 |
| 3986 | 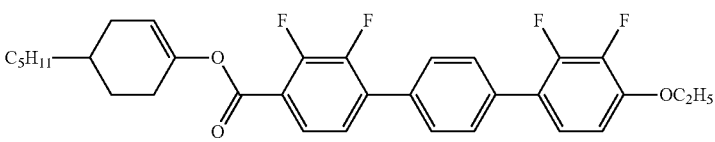 |
| 3987 | 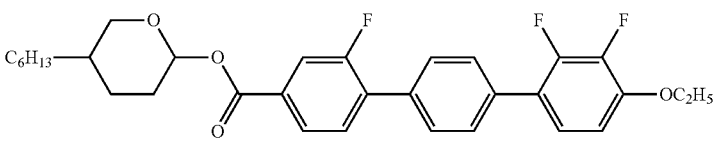 |
| 3988 | 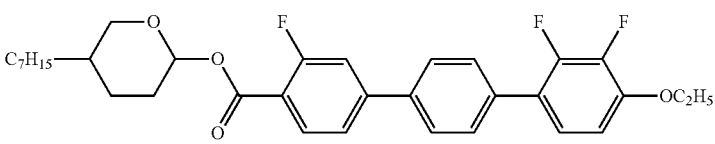 |
| 3989 | 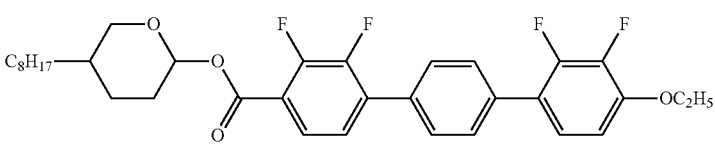 |
| 3990 | 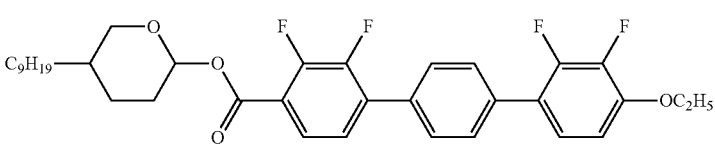 |
| 3991 | 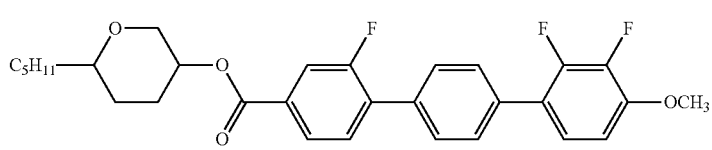 |
| 3992 | 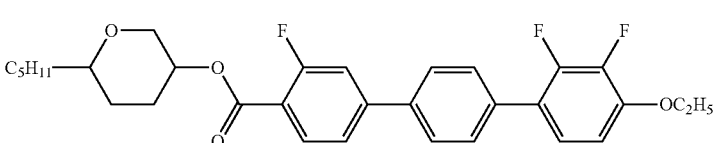 |
| 3993 | 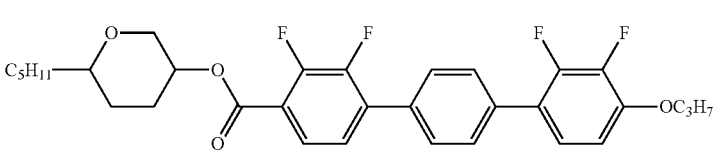 |

| No. | |
|---|---|
| 3994 | 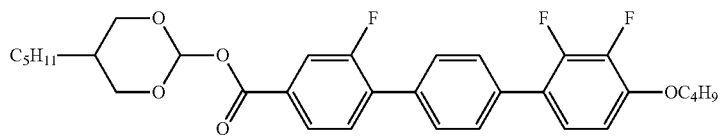 |
| 3995 | 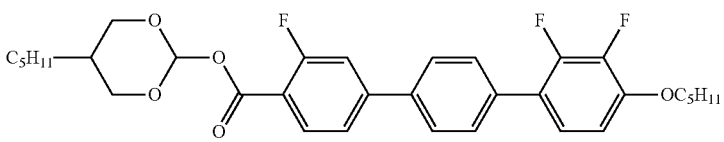 |
| 3996 | 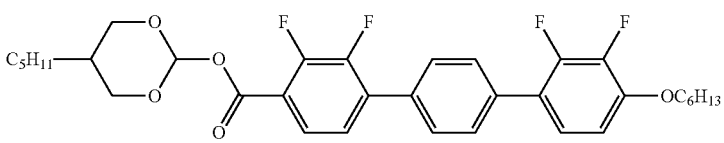 |
| 3997 | 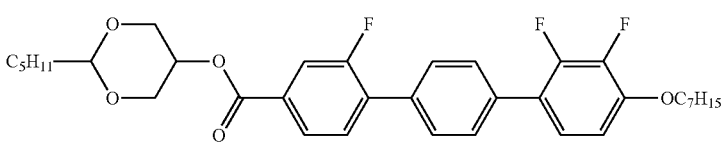 |
| 3998 | 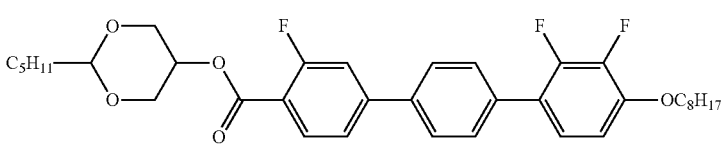 |
| 3999 | 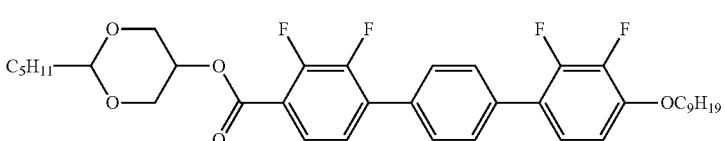 |
| 4000 | 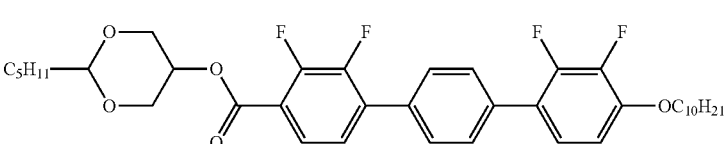 |
| 4001 | 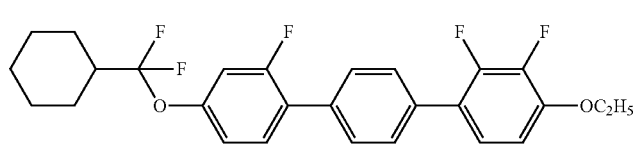 |
| 4002 | 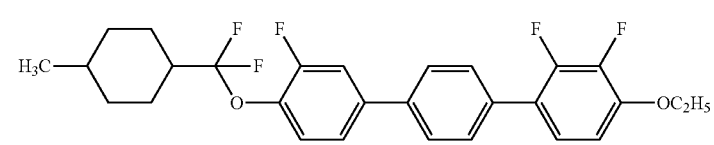 |
| 4003 | 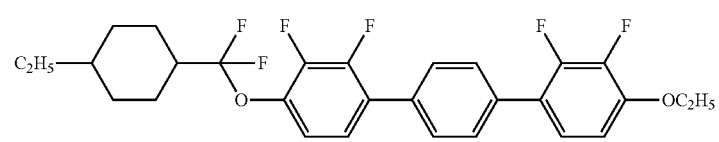 |
| 4004 | 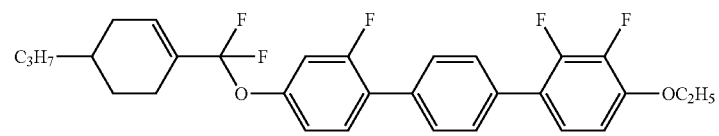 |

| No. | |
|---|---|
| 4005 | 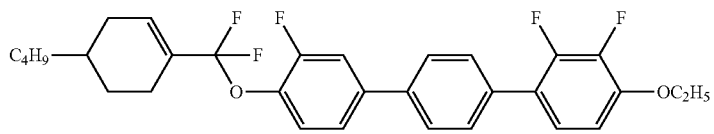 |
| 4006 | 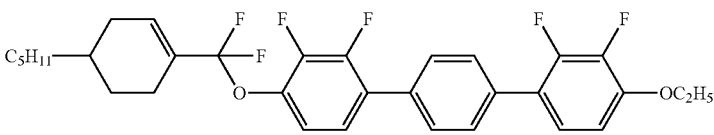 |
| 4007 | 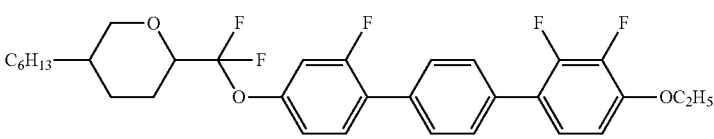 |
| 4008 | 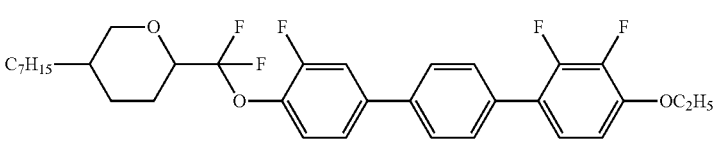 |
| 4009 | 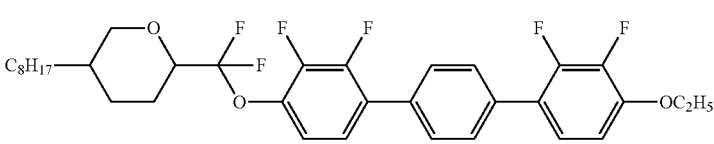 |
| 4010 | 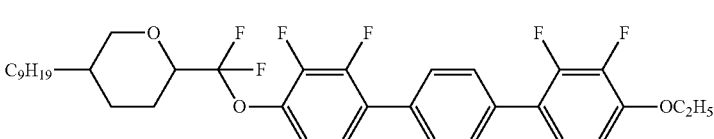 |
| 4011 | 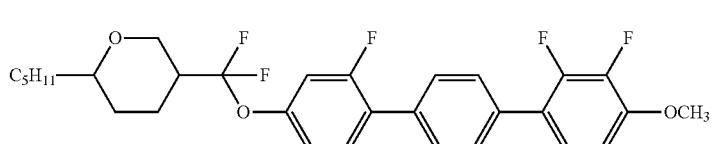 |
| 4012 | 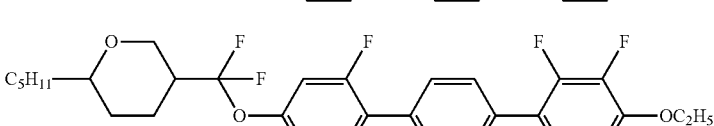 |
| 4013 | 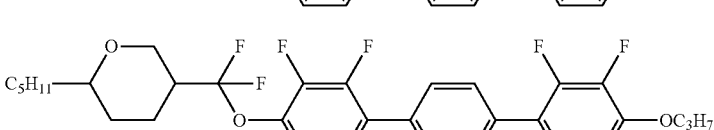 |
| 4014 | 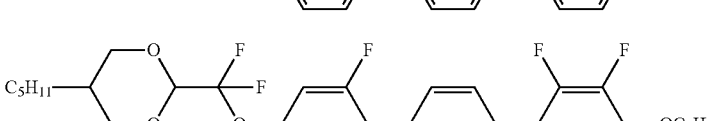 |
| 4015 | 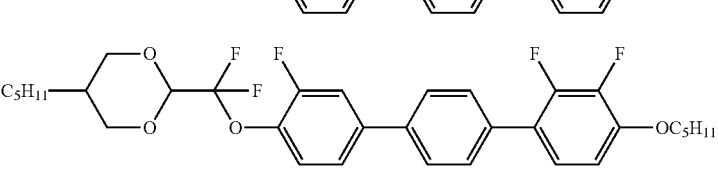 |

| No. | |
|---|---|
| 4016 | 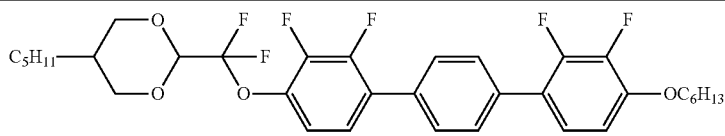 |
| 4017 | 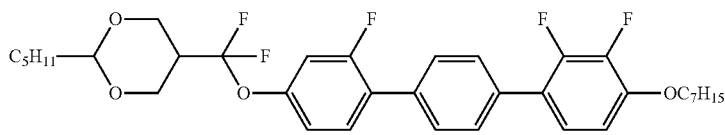 |
| 4018 | 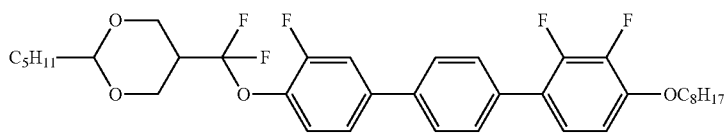 |
| 4019 | 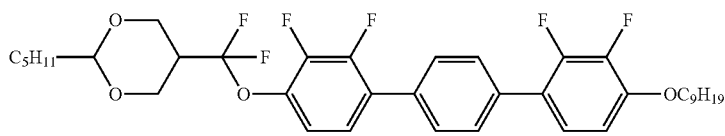 |
| 4020 | 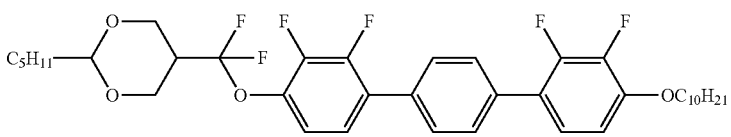 |
| 4021 | 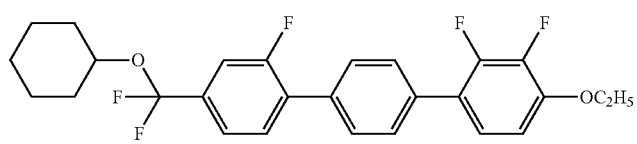 |
| 4022 | 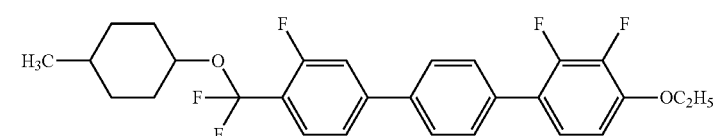 |
| 4023 | 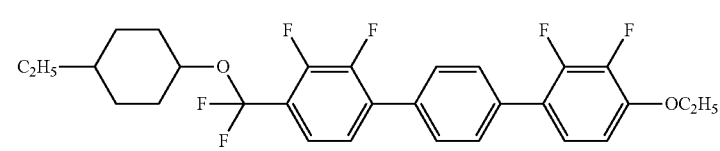 |
| 4024 | 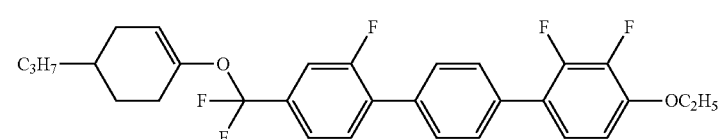 |
| 4025 | 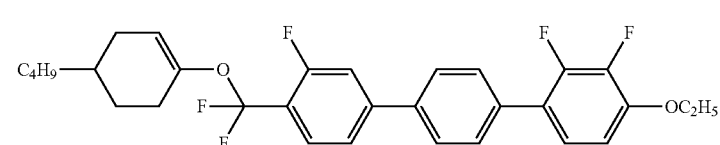 |
| 4026 | 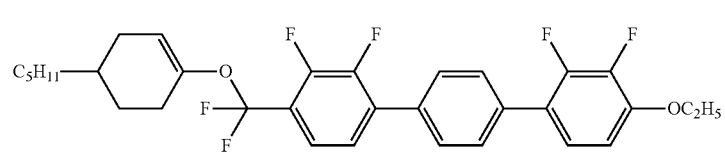 |

| No. | |
|---|---|
| 4027 | 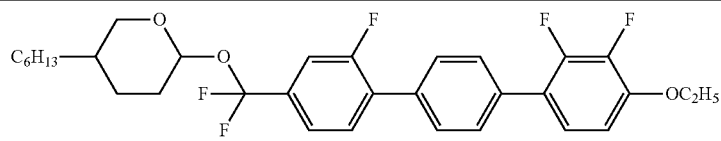 |
| 4028 | 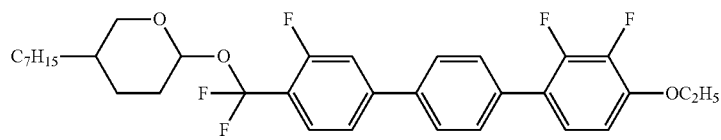 |
| 4029 | 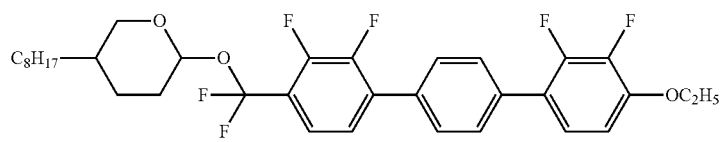 |
| 4030 | 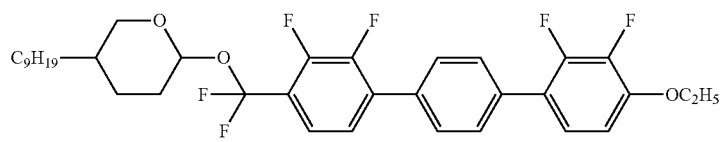 |
| 4031 | 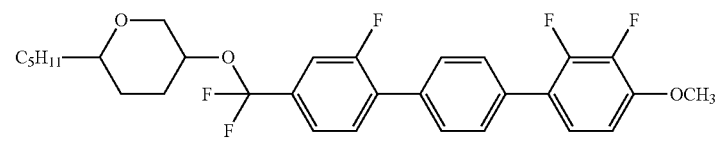 |
| 4032 | 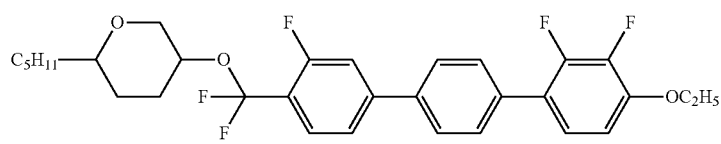 |
| 4033 | 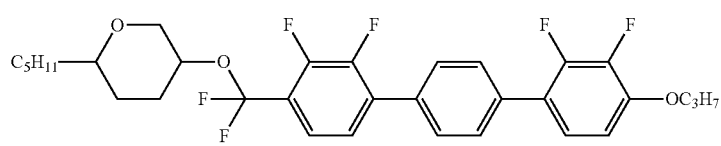 |
| 4034 | 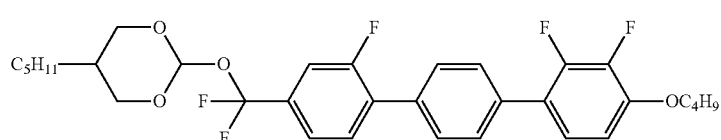 |
| 4035 | 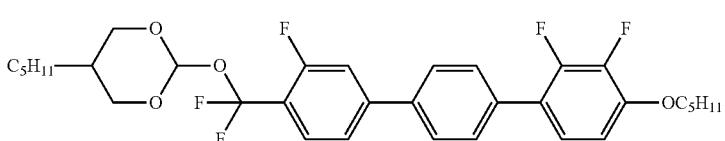 |
| 4036 | 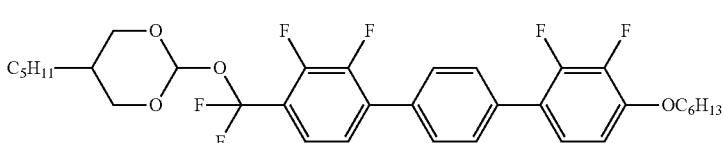 |
| 4037 | 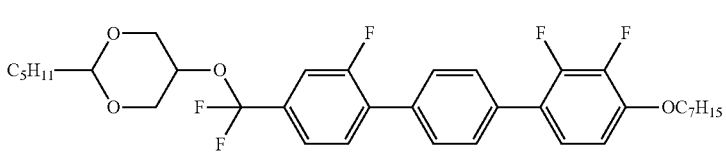 |

-continued

| No. | |
|---|---|
| 4038 | 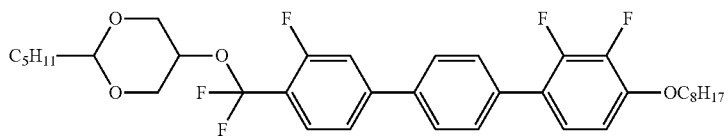 |
| 4039 | 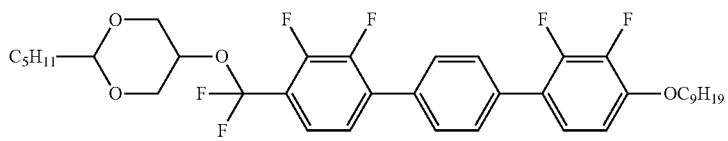 |
| 4040 | 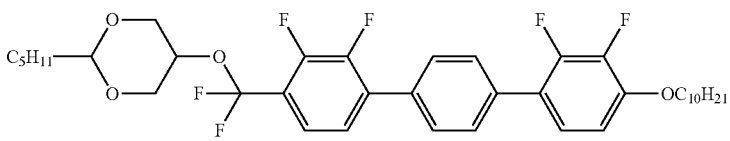 |

Comparative Example 1

For a comparative example, 4-(2,3-difluoro-4-ethoxy-1,1'-biphenylethyl)-trans-4-propyl-(2-fluorophenyl)cyclohexane (E) was synthesized.

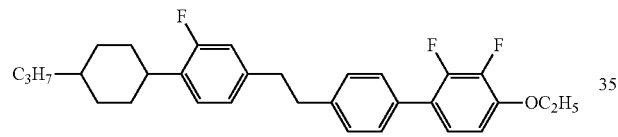

(E)

The chemical shift δ (ppm) in $^1$H-NMR analysis was described below, and the compound obtained was identified as 4-(2,3-difluoro-4-ethoxy-1,1'-biphenylethyl)-trans-4-propyl-(2-fluorophenyl)cyclohexane (E). The solvent for measurement was CDCl$_3$.

Chemical shift δ (ppm); 7.43 (d, 2H), 7.26 (t, 3H), 7.14 (t, 1H), 7.09 (td, 1H), 6.93 (d, 1H), 6.86 (d, 1H), 6.79 (t, 1H), 4.15 (q, 2H), 2.93 (m, 4H), 2.79 (tt, 1H), 1.85 (m, 4H), 1.53-1.41 (m, 5H), 1.39-1.18 (m, 5H), 1.12-1.02 (m, 2H), and 0.90 (t, 3H).

The transition temperature of the compound (E) was as follows.

Transition temperature: C 81.5 N 209.5 I.

Five compounds referred to as the mother liquid crystals (i), which was described above, were mixed and the mother liquid crystals (i) having a nematic phase was prepared. The physical properties of the mother liquid crystals (i) were as follows.

Maximum temperature $(T_{NI})$=74.6° C.;
Viscosity $(\eta_{20})$=18.9 mPa·s;
Optical anisotropy (Δn)=0.087;
Dielectric anisotropy (Δ∈)=−1.3.

The liquid crystal composition (ii) consisting of 85% by weight of the mother liquid crystals (i) and 15% by weight of synthesized 4-(2,3-difluoro-4-ethoxy-1,1'-biphenylethyl)-trans-4-propyl-(2-fluorophenyl)cyclohexane (E) was prepared. Extrapolated values on the physical properties of the comparative example compound (E) were calculated on the basis of measurement on the physical property-values of the liquid crystal composition (ii) obtained and the extrapolation of the measured values. The values were as follows.

Maximum temperature $(T_{NI})$=195.3° C.;
Optical anisotropy (Δn)=0.207;
Dielectric anisotropy (Δ∈)=−4.76.

Example 23

Physical Properties of the Liquid Crystal Compound (No. 672)

The liquid crystal composition (iii) consisting of 85% by weight of the mother liquid crystals (i) and 15% by weight of 4-ethoxy-2,3-difluoro-1,1'-biphenylbenzoic acid-trans-4-pentylcyclohexyl-2,3-difluorophenyl ester (No. 672) obtained in Example 9 was prepared. Extrapolated values on the physical properties of the comparative example compound (No. 672) were calculated on the basis of measurement on the physical property-values of the liquid crystal composition (iii) obtained and the extrapolation of the measured values. The values were as follows.

Maximum temperature $(T_{NI})$=245.3° C.;
Optical anisotropy (Δn)=0.294;
Dielectric anisotropy (Δ∈)=−5.23;

From these results, it was found the liquid crystal compound (No. 672) had a low melting point and a high maximum temperature $(T_{NI})$, a large optical anisotropy (Δn), and a large negative dielectric anisotropy (Δ∈).

Moreover, the compound (No. 672) was found to have a high maximum temperature $(T_{NI})$, a large optical anisotropy (Δn), and a large negative dielectric anisotropy (Δ∈) as compared with those of the comparative example compound (E).

Comparative Example 2

For a comparative example, 4-ethoxy-4'''-propyl-2'',2,3-trifluoro-1,1',4',1'',4'',1'''-quaterphenyl (F) having benzene rings only as rings was synthesized.

(F)

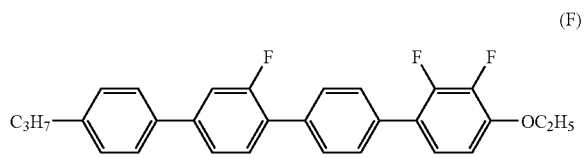

The chemical shift δ (ppm) in ¹H-NMR analysis was described below, and the compound obtained was identified as 4-ethoxy-4'''-propyl-2'',2,3-trifluoro-1,1',4',1'',4'',1'''-quaterphenyl (F). The solvent for measurement was CDCl$_3$.

Chemical shift δ (ppm); 7.67 (d, 2H), 7.61 (d, 2H), 7.54 (m, 3H), 7.46 (dd, 1H), 7.40 (dd, 1H), 7.28 (d, 2H), 7.16 (td, 1H), 6.82 (td, 1H), 4.17 (q, 2H), 2.65 (t, 2H), 1.69 (sextet, 2H), 1.49 (t, 3H), and 0.98 (t, 3H).

The transition temperature of the compound (F) was as follows.

Transition temperature: C 148.6 N 325.5 I.

The liquid crystal composition (iv) consisting of 95% by weight of the mother liquid crystals (i) and 5% by weight of 4-ethoxy-4'''-propyl-2'',2,3-trifluoro-1,1',4',1'',4'',1'''-quaterphenyl (F) was prepared. Extrapolated values on the physical properties of the comparative example compound (F) were calculated on the basis of measurement on the physical property-values of the liquid crystal composition (iv) obtained and the extrapolation of the measured values. The values were as follows.

Maximum temperature ($T_{NI}$)=248.6° C.;
Dielectric anisotropy (Δ∈)=−4.86;
Viscosity (η)=82.6 mPa·s.

Moreover, the elastic constant $K_{33}$ of the liquid crystal composition (iv) was 15.18 pN.

Physical Properties of the Liquid Crystal Compound (No. 12):

The liquid crystal composition (v) consisting of 95% by weight of the mother liquid crystals (i) and 5% by weight of 4-ethoxy-2,3-difluoro-2''-fluoro-4''-(trans-4-propyl-cyclohexyl)-1,1'-terphenyl (No. 12) obtained in Example 1 was prepared. Extrapolated values on the physical properties of the comparative example compound (No. 12) were calculated on the basis of measurement on the physical property-values of the liquid crystal composition (v) obtained and the extrapolation of the measured values. The values were as follows.

Maximum temperature ($T_{NI}$)=238.6° C.;
Dielectric anisotropy (Δ∈)=−7.22;
Viscosity (η)=73.5 mPa·s.

Moreover, the elastic constant $K_{33}$ of the liquid crystal composition (v) was 17.07 pN.

From these results, it was found the liquid crystal compound (No. 12) had a low melting point, a high maximum temperature ($T_{NI}$), a large optical anisotropy (Δn), and a large negative dielectric anisotropy (Δ∈).

Moreover, the compound (No. 12) was found to have a large negative dielectric anisotropy (Δ∈), a low melting point, a low viscosity (η), and a large elastic constant $K_{33}$, although the maximum temperature ($T_{NI}$) was nearly equivalent to, as compared with those of the comparative example compound (F).

Comparative Example 3

For a comparative example, 4-ethoxy-2,3-difluoro-4''-(trans-4-pentyl-cyclohexyl)-1,1'-terphenyl (G) was synthesized.

(G)

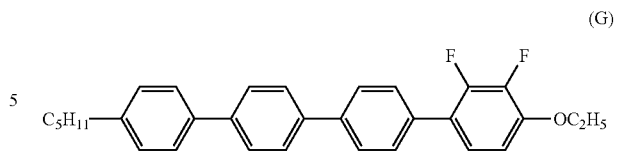

The chemical shift δ (ppm) in ¹H-NMR analysis was described below, and the compound obtained was identified as 4-ethoxy-2,3-difluoro-4''-(trans-4-pentyl-cyclohexyl)-1,1'-terphenyl (G). The solvent for measurement was CDCl$_3$.

Chemical shift δ (ppm); 7.65 (d, 2H), 7.56 (m, 4H), 7.30 (d, 2H), 7.14 (td, 1H), 6.81 (t, 1H), 4.17 (q, 2H), 2.52 (tt, 1H), 1.97-1.85 (m, 4H), 1.54-1.44 (m, 5H), 1.38-1.20 (m, 9H), 1.12-1.02 (m, 2H), and 0.90 (t, 3H).

The transition temperature of the compound (G) was as follows.

Transition temperature: $C_1$ 83.9 $C_2$ 95.4 $S_B$ 158.5 $S_A$ 255.6 N 324.9 I.

The liquid crystal composition (vi) consisting of 90% by weight of the mother liquid crystals (i) and 10% by weight of 4-ethoxy-2,3-difluoro-4''-(trans-4-pentyl-cyclohexyl)-1,1'-terphenyl (G) was prepared. Extrapolated values on the physical properties of the comparative example compound (G) were calculated on the basis of measurement on the physical property-values of the liquid crystal composition (vi) obtained and the extrapolation of the measured values. The values were as follows.

Maximum temperature ($T_{NI}$)=263.6° C.;
Dielectric anisotropy (Δ∈)=−5.18.

Moreover, the elastic constant $K_{33}$ of the liquid crystal composition (vi) was 17.88 pN.

Comparative Example 4

For a comparative example, a compound having benzene rings only as rings, 4-ethoxy-4'''-pentyl-2'',2,3-trifluoro-1,1',4',1'',4'',1'''-quaterphenyl (H) was synthesized.

(H)

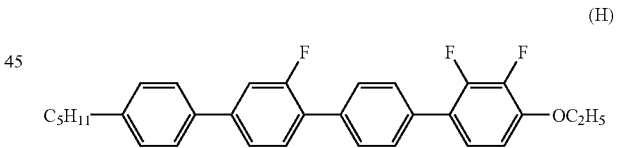

The chemical shift δ (ppm) in ¹H-NMR analysis was described below, and the compound obtained was identified as 4-ethoxy-4'''-pentyl-2'',2,3-trifluoro-1,1',4',1'',4'',1'''-quaterphenyl (H). The solvent for measurement was CDCl$_3$.

Chemical shift δ (ppm); 7.67 (d, 2H), 7.60 (d, 2H), 7.54 (m, 3H), 7.46 (dd, 1H), 7.40 (dd, 1H), 7.28 (d, 2H), 7.15 (td, 1H), 6.82 (t, 1H), 4.17 (q, 2H), 2.66 (t, 2H), 1.68 (m, 2H), 1.49 (t, 3H), 1.40-1.32 (m, 4H), and 0.91 (t, 3H).

The transition temperature of the compound (H) was as follows.

Transition temperature: C 129.0 $S_A$ 163.7 N 303.9 I.

The liquid crystal composition (vii) consisting of 90% by weight of mother liquid crystals (i) and 10% by weight of 4-ethoxy-4'''-pentyl-2'',2,3-trifluoro-1,1',4',1'',4'',1'''-quaterphenyl (H) was prepared. Extrapolated values on the physical properties of the comparative example compound (H) were calculated on the basis of measurement on the physical property-values of the liquid crystal composition (vii) obtained and the extrapolation of the measured values. The values were as follows.

Maximum temperature $(T_{NI})$=242.4° C.;
dielectric constant anisotropy $(\Delta\in)$=−5.35.

Moreover, the elastic constant $K_{33}$ of the liquid crystal composition (v) was 17.20 pN.

Example 25

Physical Properties of the Liquid Crystal Compound (No. 32)

For a comparative example, the liquid crystal composition (viii) consisting of 90% by weight of the mother liquid crystals (i) and 10% by weight of 4-ethoxy-2,3,2"-trifluoro-4"'-(trans-4-pentyl-cyclohexyl)-1,1'-terphenyl (No. 32) obtained in Example 4 was prepared. Extrapolated values on the physical properties of the comparative example compound (No. 32) were calculated on the basis of measurement on the physical property-values of the liquid crystal composition (viii) obtained and the extrapolation of the measured values. The values were as follows.

Maximum temperature $(T_{NI})$=238.6° C.;
Dielectric anisotropy $(\Delta\in)$=−5.54;

Moreover, the elastic constant $K_{33}$ of the liquid crystal composition (viii) was 18.07 pN.

From these results, it was found the liquid crystal compound (No. 32) had a high maximum temperature $(T_{NI})$, a large negative dielectric anisotropy $(\Delta\in)$, a large elastic constant $K_{33}$.

Moreover, the compound (No. 32) was found to have a large negative dielectric anisotropy $(\Delta\in)$ and a large elastic constant $K_{33}$, although the maximum temperature $(T_{NI})$ was nearly equivalent to, as compared with those of the comparative example compound.

The compound (No. 32) was found to have a low melting point, a large negative dielectric anisotropy $(\Delta\in)$, and a large elastic constant $K_{33}$, although the maximum temperature (TNI) was nearly equivalent to, as compared with those of the comparative example compound (H).

Examples of Liquid Crystal Compositions

Hereinafter, the liquid crystal compositions obtained by means of the invention will be explained in detail on the basis of examples. Liquid crystal compounds used in the examples are expressed as symbols according to the notations in Table 1 below. In Table 1, 1,4-cyclohexylene has a trans-configuration. The ratio (percentage) of each compound means a weight percentage (% by weight) based on the total weight of the liquid crystal composition, unless otherwise indicated. Characteristic values of the liquid crystal composition obtained are shown in the last part of each example.

A number descried next to the name of a liquid crystal compound in each example corresponds to that of the formula of the liquid crystal compound used for the first to third components of the invention described above. When a symbol "-" is given only instead of the number of a formula, it means other compound which is different from that of the components.

The notations using symbols for compounds is shown below.

TABLE 1

Notation using symbols for compounds
R—$(A_1)$—$Z_1$—...—$Z_n$—$(A_n)$—R'

| 1) Left-Terminal Groups R— | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |

| 2) Right-Terminal Groups —R' | Symbol |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —CH=$CF_2$ | —VFF |
| —$COOCH_3$ | -EMe |

| 3) Bonding Groups —$Z_n$— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |

| 4) Ring Structures —$A_n$— | Symbol |
|---|---|
| 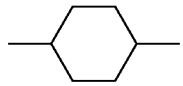 | H |

TABLE 1-continued
| | |
|---|---|
| (cyclohexene) | Ch |
| (tetrahydropyran, 2,5) | Dh |
| (tetrahydropyran, 2,5 alt) | dh |
| (1,3-dioxane) | G |
| (1,3-dioxane alt) | g |
| (benzene) | B |
| (2-F benzene) | B (2F) |
| (3-F benzene) | B (3F) |
| (2,3-diF benzene) | B (2F, 3F) |
| (2-F, 3-Cl benzene) | B (2F, 3Cl) |
| (2-Cl, 3-F benzene) | B (2Cl, 3F) |
5) Examples of Notation
Example 1. 5-HB (3F) BB (2F, 3F)-O2
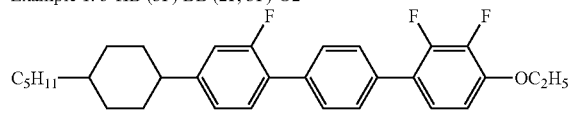

TABLE 1-continued

Example 2. 5-ChB (2F) BB (2F, 3F)-O2

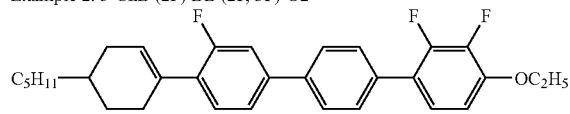

Example 3. 5-HBB ( 3F) B-3

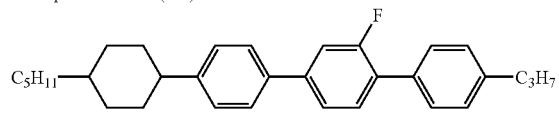

Example 4. 5-HBB (2F, 3F)-O2

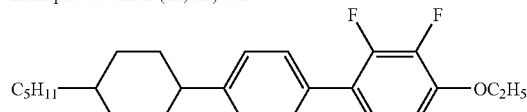

Physical property-values were measured according to the following methods. Many of these measurement methods were described in the Standard of Electric Industries Association of Japan, EIAJ-ED-2521A, or those with some modifications.

(1) Maximum Temperature of Nematic Phase (NI; ° C.)

A sample was put on a hot plate in a melting point apparatus equipped with a polarizing microscope, and heated at the rate of 1° C. per minute. A temperature was measured when part of sample changed from a nematic phase to an isotropic liquid. Hereinafter, the maximum temperature of a nematic phase may be abbreviated to "maximum temperature."

(2) Minimum Temperature of Nematic Phase (TC; ° C.)

Samples having a nematic phase were respectively kept in freezers at 0° C., -10° C., -20° C., -30° C., and -40° C. for ten days, and then liquid crystal phases were observed. For example, when a sample still remained in a nematic phase at -20° C., and changed to crystals (or a smectic phase) at -30° C., $T_c$ was expressed as -20° C. Hereinafter, the minimum temperature of a nematic phase may be abbreviated to "minimum temperature."

(3) Optical Anisotropy (Δn; Measured at 25° C.)

The optical anisotropy was measured by use of an Abbe refractometer with a polarizing plate attached to the ocular, using light at a wavelength of 589 nm. The surface of a main prism was rubbed in one direction, and then a sample was dropped onto the main prism. A refractive index (n∥) when the direction of polarization was parallel to that of rubbing and a refractive index (n⊥) when the direction of polarization was perpendicular to that of rubbing were measured. The value (Δn) of optical anisotropy was calculated from the formula of Δn=n∥-n⊥.

(4) Viscosity (η; Measured at 20° C.; mPa·s)

An E type viscometer was used for measurement.

(5) Dielectric Anisotropy (Δ∈; measured at 25° C.)

An ethanol (20 mL) solution of octadecyltriethoxysilane (0.16 mL) was applied to well-washed glass substrates. The glass substrates were rotated with a spinner, and then heated at 150° C. for 1 hour. A VA device in which a distance (cell gap) was 20 μm was assembled from the two glass substrates.

A polyimide alignment film was prepared on glass substrates in a similar manner. After a rubbing-treatment to the alignment film obtained on the glass substrates, a TN device in which a distance between the two glass substrates was 9 μm and the twist angle was 80 degrees was assembled.

A sample (a liquid crystal composition, or a mixture of a liquid crystal compound and mother liquid crystals) was put in the VA device obtained, applied with a voltage of 0.5 V (1 kHz, sine waves), and then a dielectric constant (∈∥) in a major axis direction of the liquid crystal molecules was measured.

The sample (the liquid crystal composition, or the mixture of the liquid crystal compound and the mother liquid crystals) was put in the TN device obtained, applied with a voltage of 0.5 V (1 kHz, sine waves), and then the dielectric constant (∈⊥) in a minor axis direction of liquid crystal molecules was measured. The value of dielectric anisotropy was calculated from the equation of Δ∈=∈∥-∈⊥. A composition in which this value is negative has a negative dielectric anisotropy.

(6) Voltage Holding Ratio (VHR; Measured at 25° C. and 100° C.;%)

A TN device was prepared by putting a sample in a cell which has a polyimide alignment film and a distance between two glass substrates (cell gap) of 6 μm. The TN device was charged at 25° C. by applying pulse voltage (60 microseconds at 5V). The waveforms of the voltage applied to the TN device were observed with a cathode ray oscilloscope and an area between a voltage curve and a horizontal axis in a unit period (16.7 milliseconds) was measured. An area was similarly measured based on the waveform of the applied voltage after the TN device had been removed. The value of the voltage holding ratio (%) was calculated from the equation: (voltage holding ratio)=(value of the area in the presence of a TN device)/(value of the area in the absence of TN device)×100.

The voltage holding ratio thus obtained was referred to as "VHR-1". Then, the TN device was heated at 100° C. for 250 hours. After the TN device had been allowed to come to 25° C., the voltage holding ratio was measured by a method similar to that described above. The voltage holding ratio obtained after the heating test was referred to as "VHR-2."

The heating test means an acceleration test and was used as a test corresponding to a long-term durability test for the TN device.

Example 26

| | |
|---|---|
| 3-HB(3F)BB(2F, 3F)-O2 | 5% |
| 5-HB(3F)BB(2F, 3F)-O2 | 5% |
| 7-HB(3F)BB(2F, 3F)-O2 | 5% |
| 2-HH-5 | 5% |
| 3-HH-4 | 10% |
| 3-HH-5 | 6% |
| 5-HB-O2 | 10% |
| V-HHB-1 | 10% |
| 3-H2B(2F, 3F)-O2 | 5% |
| 5-H2B(2F, 3F)-O2 | 10% |
| 2-HBB(2F, 3F)-O2 | 5% |
| 3-HBB(2F, 3F)-O2 | 12% |
| 5-HBB(2F, 3F)-O2 | 12% |

NI = 112.0° C.; TC ≦ −20° C.; Δn = 0.129; η = 26.4 mPa·s; Δε = −3.2.

Example 27

| | |
|---|---|
| 3-HB(2F)BB(2F, 3F)-O2 | 5% |
| 5-HB(2F)BB(2F, 3F)-O2 | 5% |
| 3-HH-4 | 5% |
| 3-HH-5 | 5% |
| 3-HH-O1 | 10% |
| 3-HB-O2 | 10% |
| V2-HHB-1 | 15% |
| 5-H2B(2F, 3F)-O2 | 10% |
| 5-HHB(2F, 3F)-O2 | 10% |
| 2-HBB(2F, 3F)-O2 | 5% |
| 3-HBB(2F, 3F)-O2 | 10% |
| 5-HBB(2F, 3F)-O2 | 10% |

NI = 113.1° C.; TC ≦ −20° C.; Δn = 0.121; η = 25.4 mPa·s; Δε = −3.1.

Example 28

| | |
|---|---|
| 3-ChB(3F)BB(2F, 3F)-O2 | 5% |
| 5-ChB(3F)BB(2F, 3F)-O2 | 5% |
| 7-ChB(3F)BB(2F, 3F)-O2 | 5% |
| 3-HH-4 | 10% |
| 3-HH-5 | 5% |
| 5-HB-3 | 10% |
| 3-HB-O2 | 10% |
| 5-HB-O2 | 10% |
| 3-H2B(2F, 3F)-O2 | 6% |
| 5-HHB(2F, 3F)-O2 | 10% |
| 3-HBB(2F, 3F)-O2 | 12% |
| 5-HBB(2F, 3F)-O2 | 12% |

Example 29

| | |
|---|---|
| 3-ChB(2F)BB(2F, 3F)-O2 | 5% |
| 5-ChB(2F)BB(2F, 3F)-O2 | 5% |
| 3-HH-4 | 10% |
| 3-HH-5 | 6% |
| 3-HB-O1 | 9% |
| 3-HHB-1 | 6% |
| 3-HHB-3 | 10% |
| 3-HB(2F, 3F)-O2 | 10% |
| 3-H2B(2F, 3F)-O2 | 5% |
| 5-H2B(2F, 3F)-O2 | 5% |
| 2-HBB(2F, 3F)-O2 | 5% |
| 3-HBB(2F, 3F)-O2 | 12% |
| 5-HBB(2F, 3F)-O2 | 12% |

Example 30

| | |
|---|---|
| 5-dhB(3F)BB(2F, 3F)-O2 | 5% |
| 5-dhB(2F)BB(2F, 3F)-O2 | 5% |
| 2-HH-3 | 5% |
| 2-H2H-3 | 5% |
| 3-HB-O1 | 10% |
| V-HHB-1 | 8% |
| 3-HBB-2 | 5% |
| 3-HB(2F, 3F)-O2 | 4% |
| 3-H2B(2F, 3F)-O2 | 10% |
| 2-HBB(2F, 3F)-O2 | 3% |
| 3-HBB(2F, 3F)-O2 | 12% |
| 5-HBB(2F, 3F)-O2 | 12% |
| 3-HBB(2F, 3Cl)-O2 | 8% |
| 3-HBB(2Cl, 3F)-O2 | 8% |

Example 31

| | |
|---|---|
| 5-gB(3F)BB(2F, 3F)-O2 | 5% |
| 5-GB(3F)BB(2F, 3F)-O2 | 5% |
| 3-HH-4 | 10% |
| 3-HB-O2 | 15% |
| 2-BBB(2F)-3 | 5% |
| 2-BBB(2F)-5 | 5% |
| 5-HHEBH-3 | 5% |
| 5-HHEBH-5 | 3% |
| 5-HB(2F, 3F)-O2 | 5% |
| 3-H2B(2F, 3F)-O2 | 7% |
| 5-H2B(2F, 3F)-O2 | 10% |
| V-HHB(2F, 3F)-O2 | 12% |
| 5-HHB(2F, 3F)-O2 | 13% |

A pitch measured when 0.25 part of the optically active compound (Op-05) was added to 100 parts of compositions described just above was 60.9 μm.

Example 32

| | |
|---|---|
| 5-gB(2F)BB(2F, 3F)-O2 | 5% |
| 5-GB(2F)BB(2F, 3F)-O2 | 5% |
| 2-HH-5 | 5% |
| 3-HH-4 | 10% |
| 3-HH-5 | 5% |
| 1V-HBB-2 | 5% |
| 2-BB(3F)B-3 | 5% |
| 2-BB(3F)B-5 | 5% |
| 3-HB(2F, 3F)-O2 | 10% |
| 5-HB(2F, 3F)-O2 | 10% |
| 3-HH2B(2F, 3F)-O2 | 12% |
| 5-HH2B(2F, 3F)-O2 | 12% |
| 3-HBB(2F, 3F)-O2 | 5% |
| 5-HBB(2F, 3F)-O2 | 6% |

Example 33

| | |
|---|---|
| 5-HB(2F, 3F)BB(2F, 3F)-O2 | 5% |
| 5-ChB(2F, 3F)BB(2F, 3F)-O2 | 5% |
| 3-HH-4 | 10% |
| V-HHB-1 | 6% |
| V2-BB(3F)B-1 | 5% |
| 3-HHEH-3 | 5% |
| 3-HHEH-5 | 5% |
| 3-HB(2F, 3F)-O2 | 10% |
| 5-HB(2F, 3F)-O2 | 10% |
| 5-HB(2F, 3Cl)-O2 | 5% |
| 3-HB(2Cl, 3F)-O2 | 5% |
| 5-HHB(2F, 3F)-O2 | 5% |
| 3-HH2B(2F, 3F)-O2 | 12% |
| 5-HH2B(2F, 3F)-O2 | 12% |

Example 34

| | |
|---|---|
| V-HB(3F)BB(2F, 3F)-O2 | 5% |
| 3V-HB(3F)BB(2F, 3F)-O2 | 5% |
| V2-HB(3F)BB(2F, 3F)-O2 | 5% |
| 3-HH-4 | 12% |
| 3-HB-O1 | 10% |
| 3-HBB-2 | 5% |
| 1V-HBB-2 | 5% |
| 3-HBBH-5 | 5% |
| 1O1-HBBH-4 | 5% |
| 3-HB(2F, 3F)-O2 | 10% |
| 3-H2B(2F, 3F)-O2 | 3% |
| 5-H2B(2F, 3F)-O2 | 10% |
| 3-HB(2F, 3Cl)-O2 | 3% |
| 3-HB(2Cl, 3F)-O2 | 3% |
| 3-HBB(2F, 3F)-O2 | 4% |
| 5-HBB(2F, 3F)-O2 | 5% |
| 2-BB(2F, 3F)B-3 | 5% |

Example 35

| | |
|---|---|
| V-HB(2F)BB(2F, 3F)-O2 | 5% |
| 3V-HB(2F)BB(2F, 3F)-O2 | 5% |
| V2-HB(2F)BB(2F, 3F)-O2 | 5% |
| 2-HH-3 | 10% |
| 3-HH-4 | 8% |
| 5-HB-O2 | 12% |
| 5-HBB(3F)B-2 | 5% |
| 5-HBB(3F)B-3 | 5% |
| 3-HB(2F, 3F)-O2 | 10% |
| 3-H2B(2F, 3F)-O2 | 10% |
| 2-HHB(2F, 3F)-1 | 5% |
| 3-HHB(2F, 3Cl)-O2 | 5% |
| 3-HHB(2Cl, 3F)-O2 | 5% |
| 3-HBB(2F, 3Cl)-O2 | 5% |
| 3-HBB(2Cl, 3F)-O2 | 5% |

Example 36

| | |
|---|---|
| 5-DhB(3F)BB(2F, 3F)-O2 | 5% |
| 5-DhB(2F)BB(2F, 3F)-O2 | 5% |
| 2-HH-3 | 16% |
| 3-HH-4 | 10% |
| 3-HHEBH-3 | 5% |
| 3-HHEBH-5 | 5% |
| 5-HB(2F, 3F)-O2 | 5% |
| V-HB(2F, 3F)-O2 | 5% |
| 5-H2B(2F, 3F)-O2 | 10% |
| 2-HBB(2F, 3F)-O2 | 6% |
| 3-HBB(2F, 3F)-O2 | 10% |
| 5-HBB(2F, 3F)-O2 | 10% |
| 2-BB(2F, 3F)B-3 | 8% |

Example 37

| | |
|---|---|
| 3-HB(3F)BB(2F, 3F)-O2 | 5% |
| 7-HB(3F)BB(2F, 3F)-O2 | 5% |
| 3-HH-4 | 10% |
| 5-HB-3 | 5% |
| 3-HB-O1 | 10% |
| 2-BB(3F)B-3 | 5% |
| 5-HBB(3F)B-2 | 5% |
| 3-H2B(2F, 3F)-O2 | 10% |
| 5-H2B(2F, 3F)-O2 | 10% |
| V-HHB(2F, 3F)-O2 | 5% |
| 3-HHB(2F, 3F)-O2 | 10% |
| 5-HHB(2F, 3F)-O2 | 10% |
| 5-HBB(2F, 3F)-O2 | 10% |

INDUSTRIAL APPLICABILITY

The liquid crystal compound of the invention has stability to heat, light and so forth, a wide temperature range of a nematic phase, a small viscosity, a suitable optical anisotropy, and a suitable elastic constant $K_{33}$, and further has a suitable and negative dielectric anisotropy and an excellent compatibility with other liquid crystal compounds. Hence, the composition containing this liquid crystal compound can be used for a liquid crystal panel which has performances of, for example, an improvement of a response speed, an improvement of contrast, and a decrease in driving voltage.

What is claimed is:

1. A compound represented by formula (a-1):

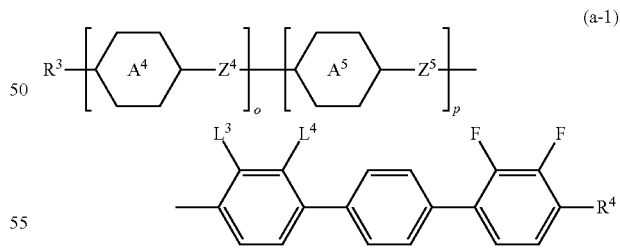

wherein
$R^3$ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;
$R^4$ is alkoxy having 1 to 9 carbons or alkenyloxy having 2 to 9 carbons;
rings $A^4$ and $A^5$ are each independently trans-1,4-cyclohexylene, cyclohexene-1,4-diyl, 1,3-dioxane-2,5-diyl, tetrahydropyran-2,5-diyl, pyrimidine-2,5-diyl, or pyridine-2,5-diyl;

L³ and L⁴ are each independently hydrogen or fluorine, and at least one of L³ and L⁴ is fluorine;

Z⁴ and Z⁵ are each independently a single bond, —(CH₂)₂—, —(CH₂)₄—, —CH=CH—, —C≡C—, —CH₂O—, —OCH₂—, —COO—, or —OCO—; and o and p are each independently 0 or 1, and o+p is 1 or 2.

2. The compound according to claim 1, which is represented by formula (a-2):

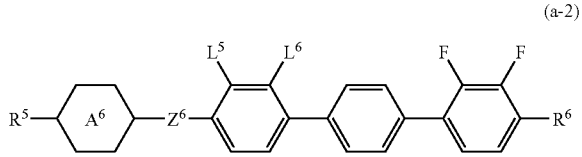

(a-2)

wherein

R⁵ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

R⁶ is alkoxy having 1 to 9 carbons or alkenyloxy having 2 to 9 carbons;

ring A⁶ is trans-1,4-cyclohexylene, cyclohexene-1,4-diyl, 1,3-dioxane-2,5-diyl, or tetrahydropyran-2-5-diyl;

L⁵ and L⁶ are each independently hydrogen or fluorine, and at least one of L⁵ and L⁶ is fluorine; and Z⁶ is a single bond, —(CH₂)₂—, —CH₂O—, —OCH₂—, —COO—, or —OCO—.

3. The compound according to claim 1, which is represented by formula (a-3):

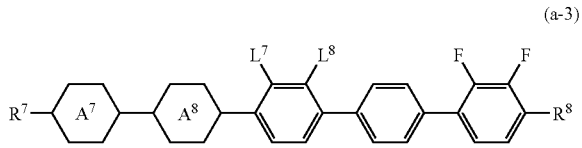

(a-3)

wherein

R⁷ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

R⁸ is alkoxy having 1 to 9 carbons or alkenyloxy having 2 to 9 carbons;

rings A⁷ and A⁸ are each independently trans-1,4-cyclohexylene, cyclohexene-1,4-diyl, 1,3-dioxane-2,5-diyl, or tetrahydropyran-2,5-diyl; and L⁷ and L⁸ are simultaneously fluorine, or one of L⁷ and L⁸ is hydrogen and the other is fluorine.

4. The compound according to claim 2, which is represented by formulas (a-4) to (a-6):

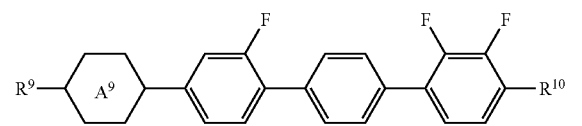

(a-4)

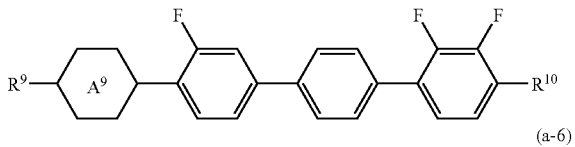

(a-5)

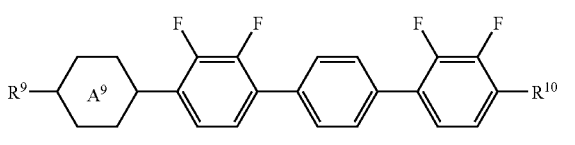

(a-6)

wherein

R⁹ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

R¹⁰ is alkoxy having 1 to 9 carbons or alkenyloxy having 2 to 9 carbons; and ring A⁹ is trans-1,4-cyclohexylene, cyclohexene-1,4-diyl, 1,3-dioxane-2,5-diyl, or tetrahydropyran-2,5-diyl.

5. The compound according to claim 4, which is represented by formulas (a-7) to (a-9):

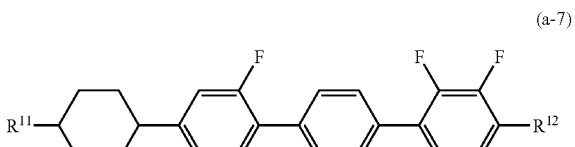

(a-7)

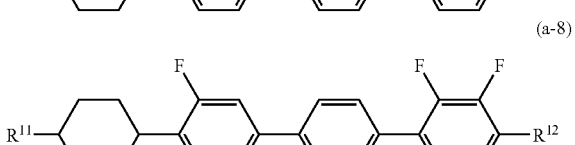

(a-8)

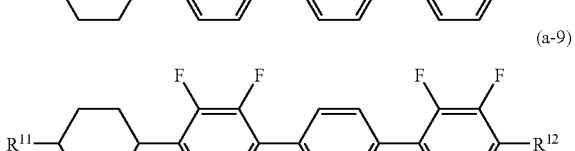

(a-9)

wherein R¹¹ is alkyl having 1 to 10 carbons, alkenyl having 2 to 10 carbons, or alkoxy having 1 to 9 carbons; and R¹² is alkoxy having 1 to 9 carbons or alkenyloxy having 2 to 9 carbons.

6. The compound according to claim 4, which is represented by formulas (a-10) to (a-12):

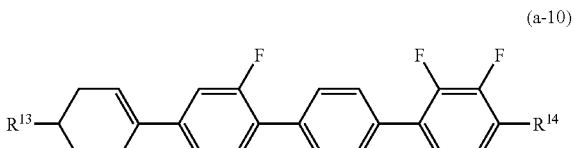

(a-10)

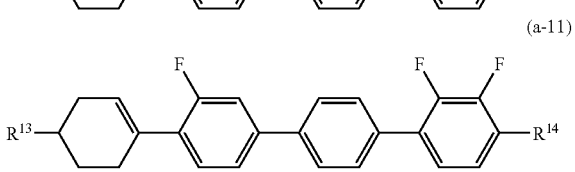

(a-11)

(a-12)

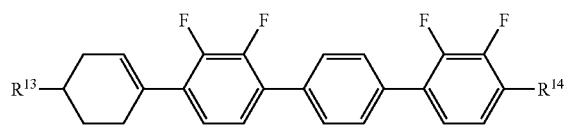

wherein $R^{13}$ is alkyl having 1 to 10 carbons, alkenyl having 2 to 10 carbons, or alkoxy having 1 to 9 carbons; and $R^{14}$ is alkoxy having 1 to 9 carbons or alkenyloxy having 2 to 9 carbons.

7. The compound according to claim 4, which is represented by formulas (a-13) to (a-18):

(a-13)
(a-14)
(a-15)
(a-16)
(a-17)
(a-18)

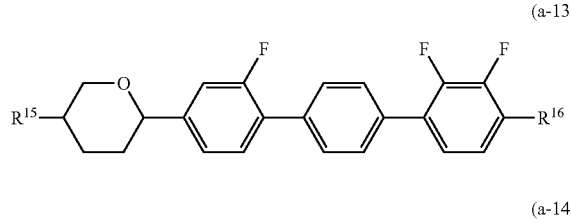

wherein $R^{15}$ is alkyl having 1 to 10 carbons, alkenyl having 2 to 10 carbons, or alkoxy having 1 to 9 carbons; and $R^{16}$ is alkoxy having 1 to 9 carbons or alkenyloxy having 2 to 9 carbons.

8. The compound according to claim 4, which is represented by formulas (a-19) to (a-24):

(a-19)
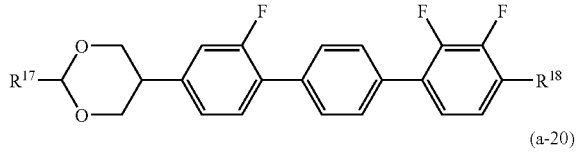

(a-20)
(a-21)
(a-22)
(a-23)
(a-24)

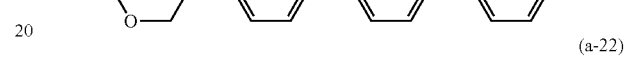
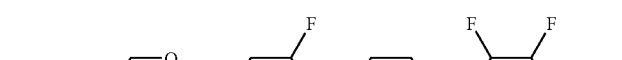
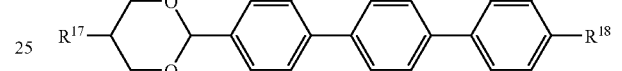
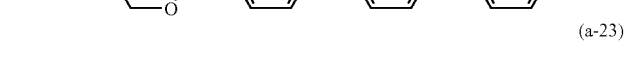
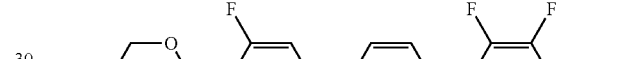

wherein $R^{17}$ is alkyl having 1 to 10 carbons, alkenyl having 2 to 10 carbons or alkoxy having 1 to 9 carbons; and $R^{18}$ is alkoxy having 1 to 9 carbons or alkenyloxy having 2 to 9 carbons.

9. A liquid crystal composition which has a negative dielectric anisotropy, comprising a first component which is at least one compound selected from compounds according to claim 1, and a second component which is at least one compound selected from the group of compounds represented by formula (e-1), formula (e-2), and formula (e-3):

(e-1)
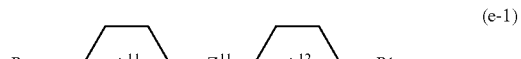

(e-2)
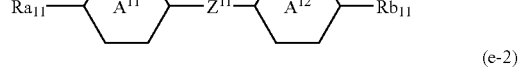

(e-3)
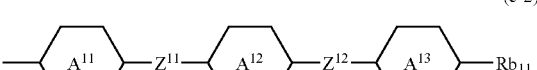

wherein

Ra$_{11}$ and Rb$_{11}$ are each independently alkyl having 1 to 10 carbons, and in the alkyl, —CH$_2$— may be nonadjacently replaced by —O—, —(CH$_2$)$_2$— may be nonadjacently replaced by —CH=CH—, and hydrogen may be replaced by fluorine;

ring A$^{11}$, ring A$^{12}$, ring A$^{13}$, and ring A$^{14}$ are each independently trans-1,4-cyclohexylene, 1,4-phenylene, 2-fluoro-1,4-phenylene, 3-fluoro-1,4-phenylene, pyrimidine-2,5-diyl, 1,3-dioxane-2,5-diyl, or tetrahydropyran-2,5-diyl; and, Z$^{11}$, Z$^{12}$, and Z$^{13}$ are each independently a single bond, —CH$_2$—CH$_2$—, —CH=CH—, —C≡C—, —COO—, or —CH$_2$O—.

10. A liquid crystal composition which has a negative dielectric anisotropy, comprising a first component which is at least one compound selected from the group of compounds according to claim 4, and a second component which is at least one compound selected from the group of compounds represented by formula (e-1), formula (e-2), and formula (e-3).

11. The liquid crystal composition according to claim 10, wherein the content ratio of the first component is in the range of 5% to 60% by weight and the content ratio of the second component is in the range of 40% to 95% by weight, based on the total weight of the liquid crystal composition.

12. The liquid crystal composition according to claim 9, comprising, in addition to the first component and the second component, a third component which is at least one compound selected from the group of compounds represented by formulas (g-1) to (g-6):

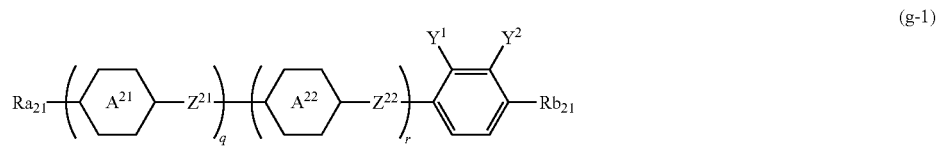
(g-1)

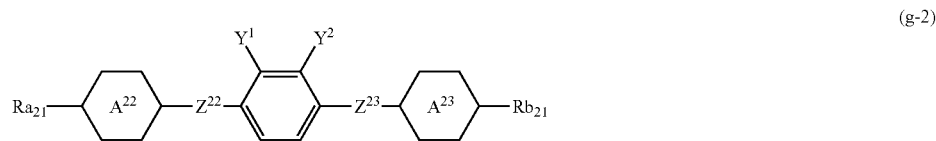
(g-2)

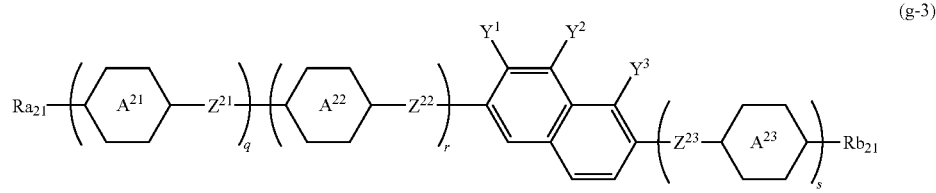
(g-3)

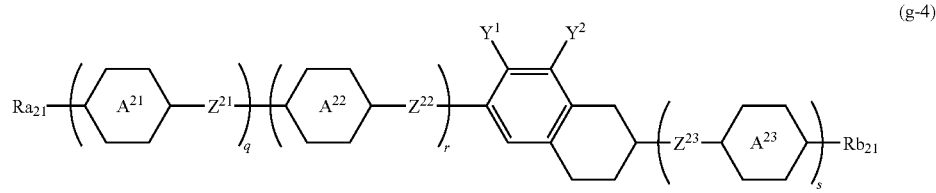
(g-4)

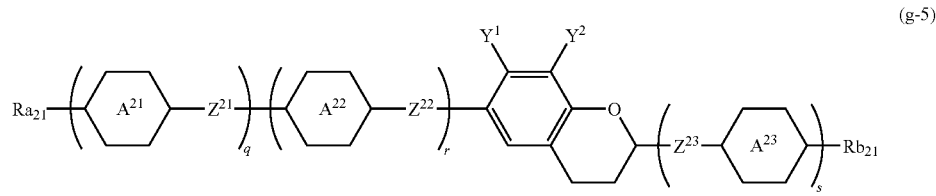
(g-5)

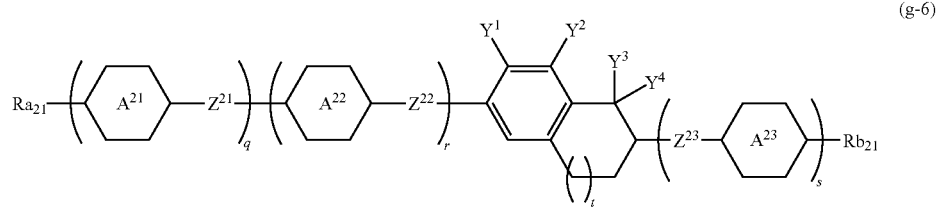
(g-6)

wherein

Ra$_{21}$ and Rb$_{21}$ are each independently hydrogen or alkyl having 1 to 10 carbons, and in the alkyl, —CH$_2$— may be nonadjacently replaced by —O—, and —(CH$_2$)$_2$— may be nonadjacently replaced by —CH=CH—, and hydrogen may be replaced by fluorine;

ring A$^{21}$, ring A$^{22}$, and ring A$^{23}$ are each independently trans-1,4-cyclohexylene, 1,4-phenylene, 2-fluoro-1,4-phenylene, 3-fluoro-1,4-phenylene, 2,3-difluoro-1,4-phenylene, pyrimidine-2,5-diyl, 1,3-dioxane-2,5-diyl, or tetrahydropyran-2,5-diyl;

Z$^{21}$, Z$^{22}$, and Z$^{23}$ are each independently a single bond, —CH$_2$—CH$_2$—, —CH=CH—, —C≡C—, —OCF$_2$—, —CF$_2$O—, —OCF$_2$CH$_2$CH$_2$—, —CH$_2$CH$_2$CF$_2$O—, —COO—, —OCO—, —OCH$_2$—, or —CH$_2$O—;

Y$^1$, Y$^2$, Y$^3$, and Y$^4$ are each independently fluorine or chlorine;

q, r, and s are each independently 0, 1 or 2, q+r is 1 or 2, q+r+s is 1, 2 or 3; and t is 0, 1 or 2.

13. The liquid crystal composition according to claim 9, comprising, in addition to the first component and the second component, a third component which is at least one compound selected from the group of compounds represented by formulas (h-1) to (h-7),

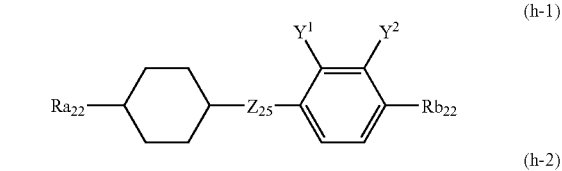
(h-1)

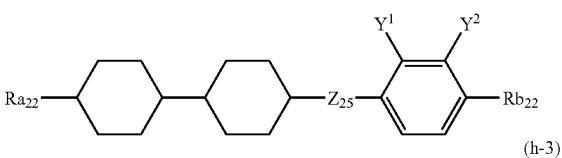
(h-2)

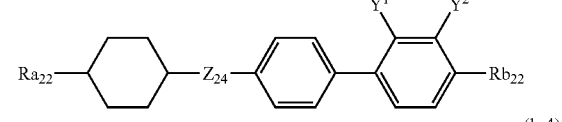
(h-3)

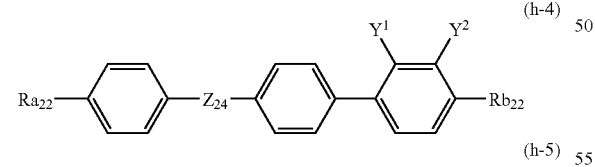
(h-4)

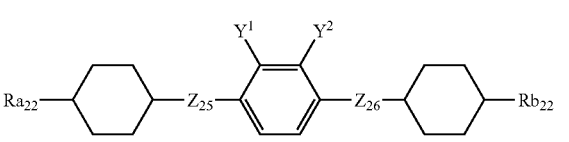
(h-5)

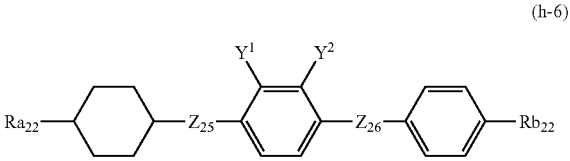
(h-6)

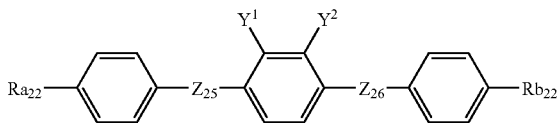
(h-7)

wherein

Ra$_{22}$ and Rb$_{22}$ are each independently a straight-chain alkyl having 1 to 8 carbons, a straight-chain alkenyl having 2 to 8 carbons, or alkoxy having 1 to 7 carbons; Z$^{24}$, Z$^{25}$, and Z$^{26}$ are a single bond, —CH$_2$CH$_2$—, —CH$_2$O—, or —OCH$_2$—; and Y$^1$ and Y$^2$ are simultaneously fluorine, or one of Y$^1$ and Y$^2$ is fluorine and the other is chlorine.

14. A liquid crystal composition which has a negative dielectric anisotropy, comprising a first component, a second component, and a third component, wherein the first component is at least one compound selected from the group of compounds represented by formulas (a-4) to (a-6),

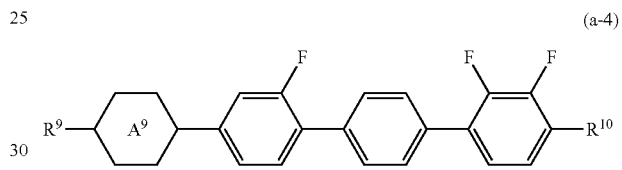
(a-4)

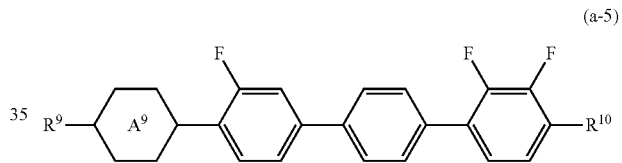
(a-5)

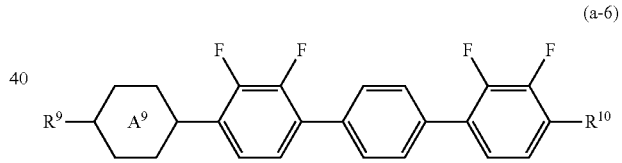
(a-6)

wherein

R$^9$ is alkyl having 1 to 10 carbons, alkenyl having 2 to 10 carbons, alkoxy having 1 to 9 carbons, alkoxyalkyl having 2 to 9 carbons, or alkenyloxy having 2 to 9 carbons;

R$^{10}$ is alkoxy having 1 to 9 carbons or alkenyloxy having 2 to 9 carbons; and ring A$^9$ is trans-1,4-cyclohexylene cyclohexene-1,4-diyl, 1,3-dioxane-2,5-diyl, or tetrahydropyran-2,5-diyl;

the second component is at least one compound selected from the group of compounds represented by formula (e-1), formula (e-2), and formula (e-3),

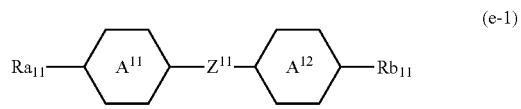
(e-1)

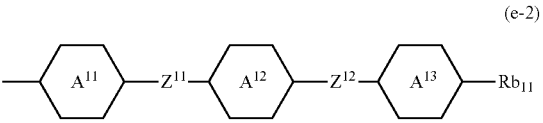
(e-2)

(e-3)

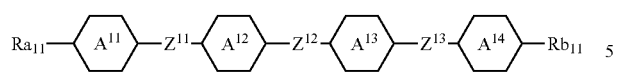

wherein $Ra_{11}$ and $Rb_{11}$ are each independently 1 to 10 carbons, and in the alkyl, —CH$_2$— may be nonadjacent replaced by —O—, —(CH$_2$)$_2$— may be nonadjacently replaced by —CH=CH—, and hydrogen may be replaced by fluorine;

ring $A^{11}$, ring $A^{12}$, ring $A^{13}$, and ring $A^{14}$ are each independently trans-1,4-cyclohexylene, 1,4-phenylene, 2-fluoro-1,4-phenylene, 3-fluoro-1,4-phenylene, pyrimidine-2,5-diyl, 1,3-dioxane-2,5-diyl, or tetrahydropyran-2,5-diyl; and, $Z^{11}$, $Z^{12}$, and $Z^{13}$ are each independently a single bond, —CH$_2$—CH$_2$—, —CH=CH—, —C≡C—, —COO—, or —CH$_2$O—; and the third component is at least one compound selected from the group of compounds represented by formulas (h-1) to (h-7), (h-1)

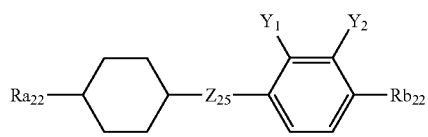

(h-2)

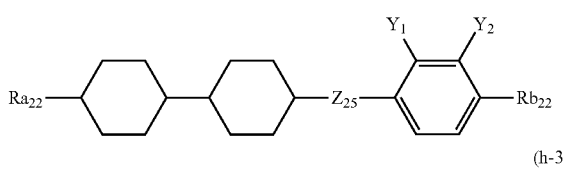

(h-3)

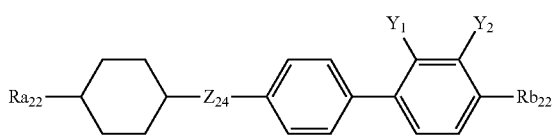

(h-4)

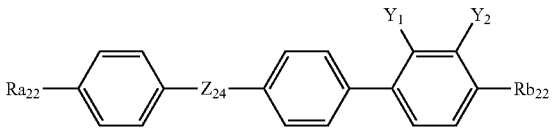

(h-5)

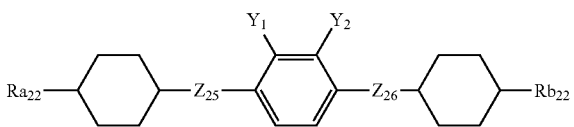

(h-6)

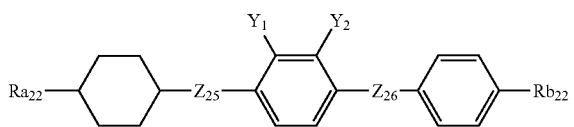

(h-7)

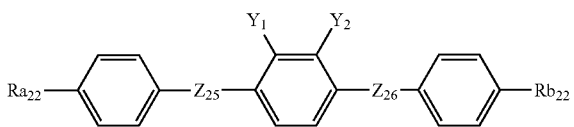

wherein $Ra_{22}$ and $Rb_{22}$ are each independently a straight-chain alkyl having 1 to 8 carbons, a straight-chain alkenyl having 2 to 8 carbons, or alkoxy having 1 to 7 carbons; $Z^{24}$, $Z^{25}$, and $Z^{26}$ are a single bond, —CH$_2$CH$_2$—, —CH$_2$O—, or —OCH$_2$—; and $Y^1$ and $Y^2$ are simultaneously fluorine, or one of $Y^1$ and $Y^2$ is fluorine and the other is chlorine.

15. The liquid crystal composition according to claim 14, wherein the content ratio of the first component is in the range of 5% to 60% by weight, the content ratio of the second component is in the range of 20% to 75% by weight, and the content ratio of the third component is in the range of 20% to 75% by weight, based on the total weight of the liquid crystal composition.

16. A liquid crystal display device comprising the liquid crystal composition according to claim 9.

17. The liquid crystal display device according to claim 16, wherein the operation mode thereof is a VA mode or a IPS mode, and the driving mode thereof is an active matrix mode.

* * * * *